US008546370B2

(12) United States Patent
Okram et al.

(10) Patent No.: US 8,546,370 B2
(45) Date of Patent: Oct. 1, 2013

(54) COMPOUNDS AND COMPOSITIONS AS KINASE INHIBITORS

(75) Inventors: Barun Okram, San Diego, CA (US); Tetsuo Uno, San Diego, CA (US); Qiang Ding, San Diego, CA (US); Yahua Liu, San Diego, CA (US); Yunho Jin, San Diego, CA (US); Qihui Jin, San Diego, CA (US); Xu Wu, San Deigo, CA (US); Jianwei Che, San Diego, CA (US); S. Frank Yan, Shanghai (CN); Xueshi Hao, San Diego, CA (US)

(73) Assignee: IRM LLC, Hamilton (BM)

( * ) Notice: Subject to any disclaimer, the term of this patent is extended or adjusted under 35 U.S.C. 154(b) by 358 days.

(21) Appl. No.: 12/865,339

(22) PCT Filed: Jan. 27, 2009

(86) PCT No.: PCT/US2009/032148

§ 371 (c)(1),
(2), (4) Date: Jul. 29, 2010

(87) PCT Pub. No.: WO2009/097287

PCT Pub. Date: Aug. 6, 2009

(65) Prior Publication Data

US 2011/0003798 A1 Jan. 6, 2011

Related U.S. Application Data

(60) Provisional application No. 61/025,665, filed on Feb. 1, 2008, provisional application No. 61/053,091, filed on May 14, 2008.

(51) Int. Cl.
*A61K 31/33* (2006.01)

(52) U.S. Cl.
USPC .......... 514/183

(58) Field of Classification Search
USPC .......... 514/183
See application file for complete search history.

(56) References Cited

U.S. PATENT DOCUMENTS

| | | | |
|---|---|---|---|
| 5,654,307 | A | 8/1997 | Bridges et al. |
| 2007/0142402 | A1 | 6/2007 | Ding et al. |
| 2007/0219195 | A1 | 9/2007 | Goldstein et al. |

FOREIGN PATENT DOCUMENTS

| | | |
|---|---|---|
| WO | WO03057695 | 7/2003 |
| WO | WO2004041823 | 5/2004 |
| WO | WO2005011597 | 2/2005 |
| WO | WO2005034869 | 4/2005 |
| WO | WO2006112666 | 10/2006 |
| WO | WO2007136465 | 11/2007 |
| WO | WO2008123755 | 10/2008 |

OTHER PUBLICATIONS

Cywin CL et al., Discovery and SAR of Novel [1,6]Naphthyridines as Potent Inhibitors of Spleen Tyrosine Kinase (SYK), Bioorganic & Medicinal Chemistry Letters, (2003) 1415-1418, vol. 13.

Jang M, et al., Development of Synthetic Strategies for the Construction of Pyrido[4,3-d]-pyrimidine Libraries—the Discovery of a New Class of PDE-4 Inhibitors, Eur. J. Org. Chem., (2006), 4257-4269.

Liu JL et al., Synthesis and Structure of 2-Substituted Thieno[3',2':5,6]pyrido-[4,3-d]pyrimidin-4(3H)-one Derivatives, Helvetica Chimica Acta, (2007), 999-1005, vol. 90.

Williams EJ et al., Synthesis of a 5-alkoxypyrido[4,3-d]pyrimidin-4(3H)-one derivative via a regioselective Meisenheimer N-oxide rearrangement, Tetrahedron Letters, (2004), 3737-3739, vol. 45.

Jang M et al., Regioselective cross-coupling reactions and nucleophilic aromatic substitutions on a 5,7-dichloropyrido(4,3-d)pyrimidine scaffold, Tetrahedron Letters, (2006), 8917-8920, vol. 47.

Andoux J. et al., First functionalization by metallation of the pyridine moiety of pyridopyrimidin-4(3H)-ones. Diazines. Part 36, Tetrahedron, (2004) 4107--4123, vol. 60.

*Primary Examiner* — Brandon Fetterolf
*Assistant Examiner* — Christopher R Stone
(74) *Attorney, Agent, or Firm* — Daniel E. Raymond; Genomics Institute of the Novartis Research Foundation

(57) ABSTRACT

The invention provides a novel class of 2,7-naphthyridin derivatives; pharmaceutical compositions comprising such compounds and methods of using such compounds to treat or prevent diseases or disorders associated with abnormal or deregulated kinase activity, particularly Syk, ZAP70, KDR, FMS, FLT3, c-Kit, RET, TrkA, TrkB, TrkC-GR-1R, Alk, c-FMS, or combinations thereof.

25 Claims, No Drawings

COMPOUNDS AND COMPOSITIONS AS KINASE INHIBITORS

CROSS-REFERENCE TO RELATED APPLICATIONS

This application is a 371 U.S. national phase application of international application number PCT/US2009/032148 filed 27 Jan. 2009, which application claims the benefit of priority under 35 U.S.C. §119(e) to U.S. Provisional Patent Application No. 61/025,665, filed Feb. 1, 2008 and U.S. Provisional Patent Application No. 61/053,091, filed May 14, 2008. The disclosure of these applications is incorporated herein by reference in their entirety and for all purposes.

FIELD OF THE INVENTION

The invention relates to protein kinase inhibitors, and methods of using such compounds.

BACKGROUND OF THE INVENTION

Protein kinases (PK) are a large set of structurally related phosphoryl transferases having highly conserved structures and catalytic functions. Protein kinases are enzymatic components of the signal transduction pathways which catalyze the transfer of the terminal phosphate from ATP to the hydroxy group of tyrosine, serine and/or threonine residues of proteins, and are therefore categorized into families by the substrates they phosphorylate: Protein Tyrosine Kinases (PTK), and Protein Serine/Threonine Kinases.

Protein kinases play a critical role in the control of cell growth and differentiation and are responsible for the control of a wide variety of cellular signal transduction processes, wherein protein kinases are key mediators of cellular signals leading to the production of growth factors and cytokines. The overexpression or inappropriate expression of normal or mutant protein kinases plays a significant role in the development of many diseases and disorders including, central nervous system disorders such as Alzheimer's, inflammatory disorders such as arthritis, bone diseases such as osteoporosis, metabolic disorders such as diabetes, blood vessel proliferative disorders such as angiogenesis, autoimmune diseases such as rheumatoid arthritis, ocular diseases, cardiovascular disease, atherosclerosis, cancer, thrombosis, psoriasis, restenosis, schizophrenia, pain sensation, transplant rejection and infectious diseases such as viral, and fungal infections.

Examples of protein-tyrosine kinases include, but are not limited to, Irk, IGFR-1, Zap-70, Bmx, Btk, CHK (Csk homologous kinase), CSK (C-terminal Src Kinase), Itk-1, Src (c-Src, Lyn, Fyn, Lck, Syk, Hck, Yes, Blk, Fgr and Frk), Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met-1 or c-MET), PDGFR (.alpha. and .beta.), Tie-1, Tie-2 (also Tek-1 or Tek), VEGFR1 (also FLT-1), VEGFR2 (also KDR), FLT-3, FLT-4, c-KIT, JAK1, JAK2, JAK3, TYK2, LOK, RET, TRKA, PYK2, ALK (Anaplastic Lymphoma Kinase), EPHA (1-8), EPHB (1-6), RON, Fes, Fer or EPHB4 (also EPHB4-1).

Examples of protein-serine/threonine kinases include, but are not limited to, Ark, ATM (1-3), CamK (1-IV), CamKK, Chk1 and 2 (Checkpoint kinases), CK1, CK2, Erk, IKK-1 (also IKK-ALPHA or CHUK), IKK-2 (also IKK-BETA), Ilk, Jnk (1-3), LimK (1 and 2), MLK3Raf (A, B, and C), CDK (1-10), PKC (including all PKC subtypes), Plk (1-3), NIK, Pak (1-3), PDK1, PKR, RhoK, RIP, RIP-2, GSK3 (.alpha. and .beta.), PKA, P38, Erk (1-3), PKB (including all PKB subtypes) (also AKT-1, AKT-2, AKT-3 or AKT3-1), IRAK1, FRK, SGK, TAK1 or Tp1-2 (also COT).

SUMMARY OF THE INVENTION

The invention provides compounds and pharmaceutical compositions thereof, which are useful as protein kinase inhibitors.

In one aspect, the present invention provides compounds having Formula (I), and the pharmaceutically acceptable salts, pharmaceutically acceptable solvates (e.g. hydrates), the N-oxide derivatives, prodrug derivatives, protected derivatives, individual isomers and mixture of isomers thereof:

(I)

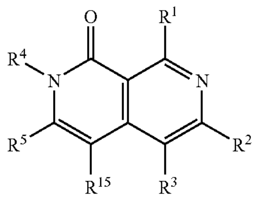

wherein:

$R^1$ is —$NR^6R^7$, $(CH_2)_nR^{19}$, $L^3R^{19}$, $R^{20}$, $C_6$-$C_{14}$aryl, $C_3$-$C_8$cycloalkyl, $C_2$-$C_{14}$heterocycloalkyl or $C_3$-$C_{13}$heteroaryl, wherein the $C_6$-$C_{14}$aryl, $C_3$-$C_8$cycloalkyl, $C_2$-$C_{14}$heterocycloalkyl and $C_3$-$C_{13}$heteroaryl of $R^1$ is optionally substituted with 1 to 3 substituents independently selected from halogen, nitro, cyano, $C_1$-$C_6$alkyl, $C_1$-$C_6$alkoxy, $C_1$-$C_6$alkylthio, hydroxyl-$C_1$-$C_6$alkyl, halo-substituted-$C_1$-$C_6$alkyl, halo-substituted-$C_1$-$C_6$alkoxy, $C_3$-$C_{12}$cycloalkyl, $C_2$-$C_{14}$heterocycloalkyl, $C_6$-$C_{14}$aryl, $C_3$-$C_{13}$heteroaryl, —$X^2S(O)_{0-2}R^{17}$, —$X^2S(O)_{0-2}X^2R^{19}$, —$X^2NR^{17}R^{17}$, —$X^2R^{17}C(O)R^{17}$, —$X^2C(O)NR^{17}R^{17}$, —$X^2NR^{17}C(O)R^{19}$, —$X^2C(O)NR^{17}R^{19}$, —$X^2C(O)R^{19}$, —$X^2NR^{17}X^2R^{19}$ and —$X^2OX^2R^{19}$; wherein, $X^2$ is a bond or $C_1$-$C_4$alkylene;

$L^3$ is a bond, $C_1$-$C_6$alkyl or $C_1$-$C_6$alkoxy; wherein the $C_1$-$C_6$alkyl and $C_1$-$C_6$alkoxy groups of $L^3$ are optionally substituted with 1 to 3 substituents independently selected from halogen, —CN, —$C_1$-$C_6$alkyl, $C_1$-$C_6$alkoxy, —$OR^{13}$, —$C(O)R^{13}$, $^-OC(O)R^{13}$, —$C(O)OR^{13}$, —$N(R^{12})_2$, —$C(O)N(R^{12})_2$, —$N(R^{12})C(O)R^{13}$, $C_2$-$C_{14}$heterocycloalkyl, —$S(O)_2R^{13}$, —$S(O)_2$ $N(R^{12})_2$, $R^{13}$, —$(C(R^{12})_2)_nR^{13}$, —$(C(R^{12})_2)_n$ $R^{14}$, halo-substituted $C_1$-$C_6$alkyl and halo-substituted $C_1$-$C_6$alkoxy;

$R^{17}$ is H or $C_1$-$C_6$alkyl; and $R^{19}$ is $R^{20}$, $C_3$-$C_{12}$cycloalkyl, $C_2$-$C_{14}$heterocycloalkyl, $C_6$-$C_{14}$aryl or $C_3$-$C_{13}$heteroaryl, wherein the $C_6$-$C_{14}$aryl, $C_3$-$C_{13}$heteroaryl, $C_3$-$C_{12}$cycloalkyl and $C_2$-$C_{14}$heterocycloalkyl of $R^{19}$ are optionally substituted with 1 to 3 radicals independently selected from halogen, nitro, cyano, $C_1$-$C_6$alkyl, $C_1$-$C_6$alkoxy, $C_1$-$C_6$alkylthio, hydroxyl-$C_1$-$C_6$alkyl, halo-substituted-$C_1$-$C_6$alkyl, and halo-substituted-$C_1$-$C_6$alkoxy;

$R^2$ and $R^3$ are independently selected from H, $(CH_2)_nR^{11}$, —$C(O)R^{12}$, —$CR^{12}$═$NOCR^{12}$, —$NR^8R^{10}$, halogen, $R^{20}$, $C_1$-$C_6$alkyl, $C_2$-$C_6$alkenyl, $C_2$-$C_6$alkynyl, $C_1$-$C_6$alkoxy, $C_1$-$C_6$alkylthio, hydroxyl-$C_1$-$C_6$alkyl, halo-substituted-$C_1$-$C_6$alkyl, and halo-substituted-$C_1$-$C_6$alkoxy, $C_6$-$C_{14}$aryl, $C_3$-$C_{13}$heteroaryl and $C_2$-$C_{14}$heterocycloalkyl, wherein the $C_6$-$C_{14}$aryl, $C_2$-$C_6$alkenyl, $C_2$-$C_6$alkynyl, $C_3$-$C_{13}$heteroaryl, and $C_2$-$C_{14}$heterocycloalkyl of $R^2$ and $R^3$ are optionally substituted with 1 to 3 substituents independently selected from halogen, —CN, —$NO_2$, —$OR^{12}$, —$OR^{10}$, =O, —$C(O)OR^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$NR^{12}C(O)N(R^{12})_2$, —$NHS(O)_2R^{13}$, —$(CR^{12}R^{12})_nR^{11}$, —$SR^8$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, $S(O)_2N(R^{11})_2$, —$S(O)_2N(R^{12})_2$, $R^{12}$, $R^{10}$, —$OR^{13}$, —$C(O)R^{13}$, $^-OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl and halo-substituted $C_1$-$C_6$alkoxy;

$R^4$ is H, $C_1$-$C_6$alkyl or —$(CR^{12}R^{12})_nR^{11}$;

$R^5$ is H or $C_1$-$C_6$alkyl;

$R^6$ is $C_6$-$C_{14}$aryl, $C_3$-$C_{13}$heteroaryl, $C_2$-$C_{14}$heterocycloalkyl, $C_1$-$C_6$alkyl, $C_3$-$C_8$cycloalkyl, halo-substituted $C_1$-$C_6$alkyl, —$(CH_2)_nR^9$, $R^{20}$, -$L^3R^9$ or —$Y^1$-$L^1$-$R^{14}$, wherein, $Y^1$ is arylene, heteroarylene or heterocycloalkylene, and $L^1$- is a bond, —O—, —C(O)—, —$C(O)N(R^{11})$—, —$(C(R^{12})_2)_n$— or —$O(CH_2)_n$—;

and wherein the $C_6$-$C_{14}$aryl, $C_3$-$C_{13}$heteroaryl, $C_1$-$C_6$alkyl, halo-substituted $C_1$-$C_6$alkyl, $C_2$-$C_{14}$heterocycloalkyl and $C_3$-$C_8$cycloalkyl of $R^6$ and $Y^1$ are optionally substituted with 1 to 3 substituents independently selected from, halogen, —CN, —$OR^{12}$, —$OR^{10}$, —$C(O)R^{12}$, —$OC(O)R^{12}$, —$C(O)OR^{12}$, $N(R^{11})_2$, —$N(R^{12})_2$, —$N(R^{12}R^{10})$, —$N(R^{12}R^{11})$, —$(CR^{12}R^{12})_nR^{11}$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, —$(CH_2)_nR^{14}$, —$O(CH_2)_nR^{14}$, $(CH_2)_nR^{16}$, —$S(O)_2R^{12}$, —$S(O)^2N(R^{11})^2$, —$S(O)_2N(R^{12})_2$, $R^{12}$, $R^{10}$, —$OR^{13}$, —$C(O)R^{13}$, $^-OC(O)R^{13}$, —$C(O)OR^{13}$, —$S(O)_2R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

$R^7$ is H or $C_1$-$C_6$ alkyl;

$R^8$ is H or $C_1$-$C_6$ alkyl;

$R^9$ is $R^{20}$, $C_6$-$C_{14}$aryl, $C_3$-$C_{13}$heteroaryl, $C_2$-$C_{14}$heterocycloalkyl, $C_3$-$C_8$cycloalkyl or $Y^2$-$L^2$-$R^{14}$, wherein, $Y^2$ is bond, arylene, heteroarylene or heterocycloalkylene, and $L^2$- is a bond, —O—, or —$O(CH_2)_n$—;

and wherein the $C_6$-$C_{14}$aryl, $C_3$-$C_{13}$heteroaryl, $C_3$-$C_8$cycloalkyl and $C_2$-$C_{14}$heterocycloalkyl of $R^9$ and $Y^2$ are optionally substituted with 1 to 3 substituents independently selected from halogen, —CN, =O, —$OR^{12}$, —$C(O)R^{12}$, —$OC(O)R^{12}$, —$C(O)OR^{12}$, —$N(R^{11})_2$, —$N(R^{12})_2$, $N(R^{12}R^{10})$, —$N(R^{12}R^{11})$, —$(CR^{12}R^{12})_nR^{11}$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, $^-OC(O)R^{13}$, —$C(O)OR^{13}$, —$S(O)_2R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_r$. $C_6$alkoxy;

$R^{10}$ is halo-substituted $C_1$-$C_6$alkyl, $C_6$-$C_{14}$aryl, $C_3$-$C_{13}$heteroaryl, $C_2$-$C_{14}$heterocycloalkyl, $C_3$-$C_8$cycloalkyl or —$(CH_2)_nR^{11}$, wherein the $C_6$-$C_{14}$aryl, $C_3$-$C_{13}$heteroaryl, $C_2$-$C_{14}$heterocycloalkyl and $C_3$-$C_8$cycloalkyl of $R^{10}$ are optionally substituted with 1 to 3 substituents independently selected from halogen, —CN, hydroxyl, —$OR^{12}$, —$OR^{10}$, —$C(O)R^{12}$, —$OC(O)R^{12}$, —$C(O)OR^{12}$, —$N(R^{11})_2$, —$N(R^{12})_2$, $N(R^{12}R^{10})$, —$N(R^{12}R^{11})$, —$(CR^{12}R^{12})_nR^{11}$, —$SR^8$, —$NR^{12}C(O)N(R^{12})_2$, —$C(O)N(R^{12}R^{10})_2$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_n$ $^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, $^-OC(O)R^{13}$, —$C(O)OR^{13}$, —$S(O)_2R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

$R^{11}$ is —$N(R^{12})_2$, —$OR^{13}$, $R^{20}$, —$C(O)N(R^{12})_2$, —$S(O)_2R^{13}$, —$S(O)^2$ $N(R^{12})_2$, $C_6$-$C_{14}$aryl, $C_3$-$C_{13}$heteroaryl, $C_1$-$C_6$alkyl, $C_3$-$C_8$cycloalkyl, or $C_2$-$C_{14}$heterocycloalkyl, wherein the $C_6$-$C_{14}$aryl, $C_3$-$C_{13}$heteroaryl, $C_1$-$C_6$alkyl, $C_3$-$C_8$cycloalkyl and $C_2$-$C_{14}$heterocycloalkyl of $R^{11}$ are optionally substituted with 1 to 3 substituents independently selected from halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$(CR^{12}R^{12})_nR^{11}$, —$SR^8$, —$NR^{12}C(O)N(R^{12})_2$, —$C(O)N(R^{12}R^{10})_2$, —$N(R^{12})C(O)R^{13}$, —$C(O)N(R^{11})_2$, —$C(O)N(R^{12})_2$, —$(CR^{12}R^{12})_n$ $R^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, $^-OC(O)R^{13}$, —$C(O)OR^{13}$, —$S(O)_2R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

each $R^u$ is independently selected from H, $C_1$-$C_6$alkyl, $C_2$-$C_6$alkene, halo-substituted $C_1$-$C_6$alkyl and $C_3$-$C_8$cycloalkyl, or each $R^u$ is independently a $C_1$-$C_6$alkyl that together with N they are attached to form a heterocycloalkyl;

$R^{13}$ is H, $C_1$-$C_6$ alkyl, $C_3$-$C_8$cycloalkyl, halo-substituted $C_1$-$C_6$ alkyl or $C_2$-$C_{14}$heterocycloalkyl;

$R^{14}$ is H, halogen, $OR^{13}$, $R^{20}$, —CN, —$S(O)_2N(R^{12})_2$, —$S(O)_2R^{13}$, —$C(O)N(R^{12})_2$, $N(R^{12})_2$, $C_1$-$C_6$alkyl, halo-substituted $C_1$-$C_6$alkyl, $C_6$-$C_{14}$aryl, heteroaryl or $C_2$-$C_{14}$heterocycloalkyl, wherein the $C_2$-$C_{14}$heterocycloalkyl, $C_6$-$C_{14}$aryl and $C_3$-$C_{13}$heteroaryl are optionally substituted with 1-3 substituents independently selected from halogen, —CN, $C_1$-$C_6$alkyl, $C_1$-$C_6$alkoxy, $C_3$-$C_8$cycloalkyl, —$OR^{13}$, —$C(O)R^{13}$, $^-OC(O)R^{13}$, —$C(O)OR^{13}$, —$N(R^{12})_2$, —$C(O)(C(R^{12})_2)_nR^{16}$, —$C(O)N(R^{12})_2$, heterocycloalkyl, —$S(O)_2R^{13}$, —$S(O)_2$ $N(R^{12})_2$, —$NHS(O)_2R^{13}$, $R^{13}$, $R^{10}$, —$(CH_2)_nR^{12}$, —$(CH_2)_nR^{13}$, —O—$(CH_2)_nR^{13}$, —$(C(R^{12})_2)_nR^{16}$, halo-substituted $C_1$-$C_6$alkyl and halo-substituted $C_1$-$C_6$alkoxy;

$R^{15}$ is H, $C_1$-$C_6$alkyl, $C_2$-$C_6$alkenyl, —CN, halogen, $R^{10}$, $R^{16}$ is H, halogen, $OR^{13}$, —$C(O)R^{13}$, —$OC(O)R^{13}$, —$C(O)OR^{13}$, —$N(R^{12})_2$, —CN, —$S(O)_2N(R^{12})_2$, —$S(O)_2R^{13}$, $C(O)N(R^{12})_2$, —$NR^{12}C(O)(R^{12})$, halo-substituted $C_1$-$C_6$alkyl, or $C_2$-$C_{14}$heterocycloalkyl;

$R^{20}$ is

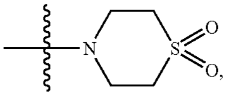
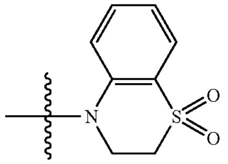 or
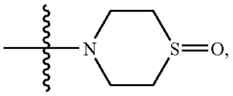

and each n is independently 1, 2, 3, 4, 5 or 6.

In certain embodiments of the compounds of Formulas (I) are compounds of Formula (Ia):

(Ia)

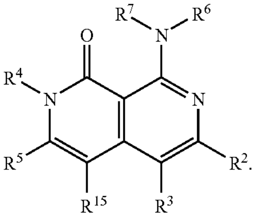

In certain embodiments of the compounds of Formulas (I) and Formula (Ia), $R^6$ is $C_6$-$C_{14}$aryl, $C_3$-$C_{13}$heteroaryl, $C_2$-$C_{14}$heterocycloalkyl or $C_3$-$C_8$cycloalkyl, wherein the $C_6$-$C_{14}$aryl, $C_3$-$C_{13}$heteroaryl $C_2$-$C_{14}$heterocycloalkyl and $C_3$-$C_8$cycloalkyl are optionally substituted with 1 to 3 substituents independently selected from halogen, —CN, —$OR^{12}$, $OR^{10}$, —C(O)$R^{12}$, —OC(O)$R^{12}$, —C(O)$OR^{12}$, —N$(R^{11})_2$, —N$(R^{12})_2$, —N$(R^{12}R^{10})$, —N$(R^{12}R^{11})$, —$(CR^{12}R^{12})_nR^{11}$, —$SR^8$, —$NR^{12}$C(O)N$(R^{12})_2$, —C(O)N$(R^{12}R^{10})$, —N$(R^{12})$C(O)$R^{13}$, —C(O)N$(R^{11})_2$, —C(O)N$(R^{12})_2$, —$(CR^{12}R^{12})_nR^{11}$, —$(CH_2)_nR^{12}$, —$(CH_2)_nR^{13}$, —O$(CH_2)_nR^{13}$, $(CH_2)_nR^{14}$, —O$(CH_2)_nR^{14}$, $(CH_2)_nR^{16}$, —S$(O)_2R^{12}$, —S$(O)_2$N$(R^{11})_2$, —S$(O)_2$N$(R^{12})_2$, $R^{12}$, $R^{10}$, $OR^{13}$, C(O)$R^{13}$, $^-$OC(O)$R^{13}$, —C(O)$OR^{13}$, —S$(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy. In other embodiments $R^6$ is

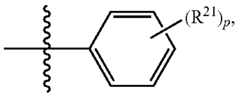
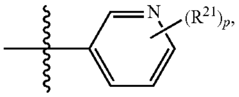
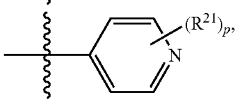
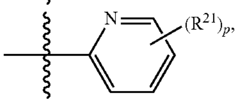
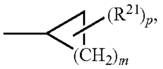
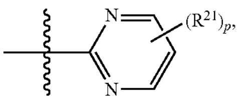
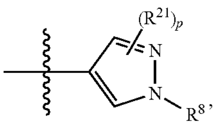
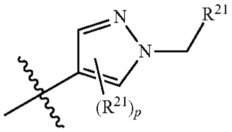

-continued

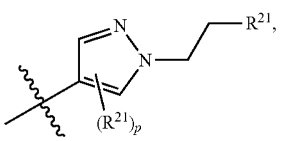
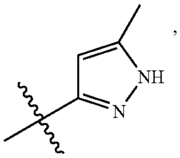
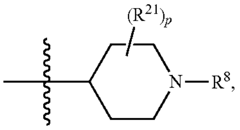
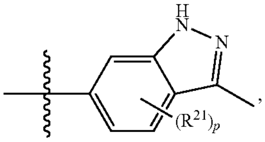
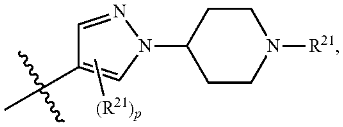
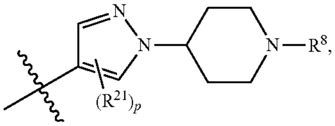
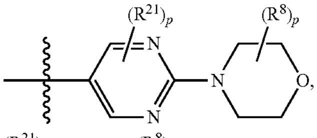
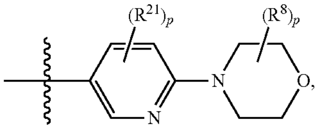
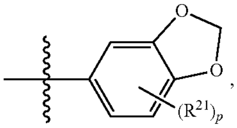
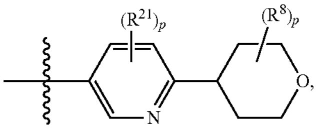
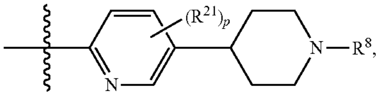
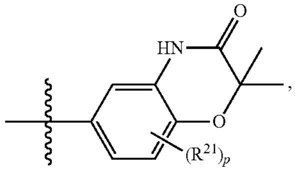
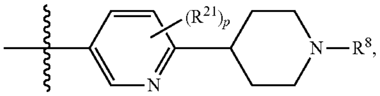
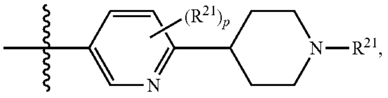
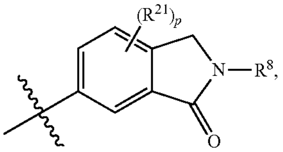
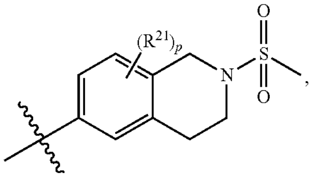

-continued

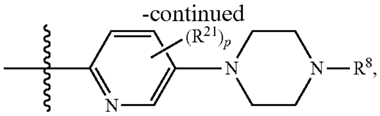

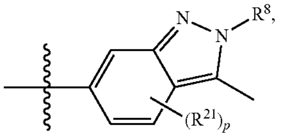

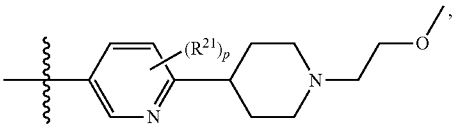

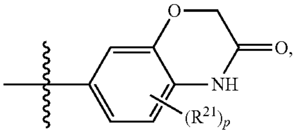

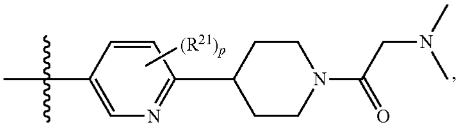

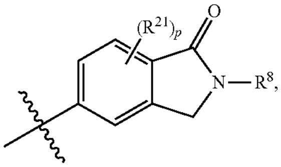

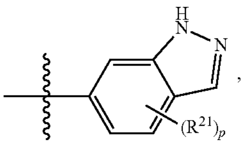

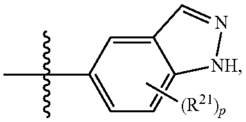

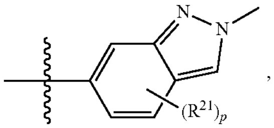

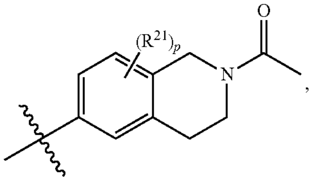

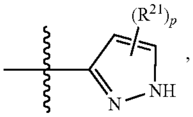

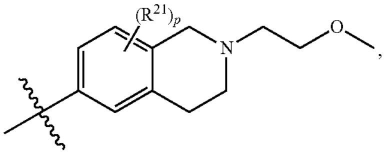

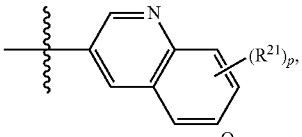

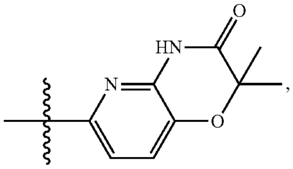

or

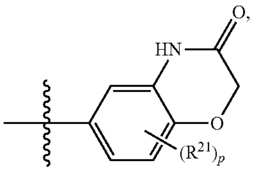

wherein, $R^{21}$ is halogen, —CN, —$OR^{12}$, —$OR^{10}$, —C(O)$R^{12}$, —OC(O)$R^{12}$, —C(O)O$R^{12}$, —N($R^{11}$)$_2$, —N($R^{12}$)$_2$, —N($R^{12}R^{16}$), —N($R^{12}R^{11}$), —$(CR^{12}R^{12})_nR^{11}$, —$NR^{12}$C(O)N($R^{12}$)$_2$, —C(O)N($R^{12}R^{16}$), —N($R^{12}$)C(O)$R^{13}$, —C(O)N($R^{11}$)$_2$, —C(O)N($R^{12}$)$_2$, —$(CR^{12}R^{12})_n$ $R^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_n$ $R^{16}$, —S(O)$_2R^{12}$, —S(O)$_2$N($R^{11}$)$_2$, —S(O)$_2$N($R^{12}$)$_2$, $R^{12}$, $R^{10}$, —$OR^{13}$, —C(O)$R^{13}$, $^{-}$OC(O)$R^{13}$, —C(O)O$R^{13}$, —S(O)$_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

$R^8$ is H or $C_1$-$C_6$ alkyl;

n is 1, 2, 3 or 4, and p is 0, 1, 2 or 3.

In other embodiments $R^6$ is

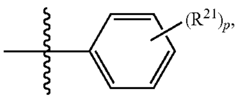

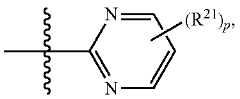

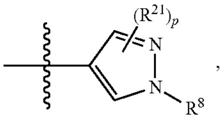

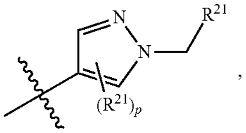

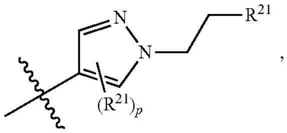

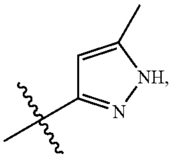

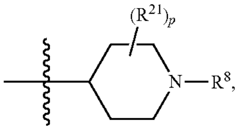

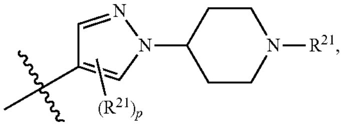

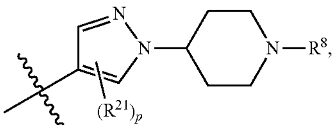

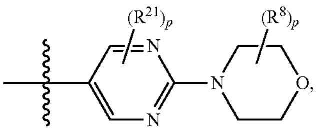

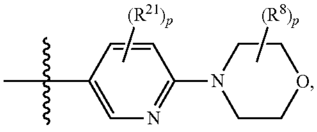

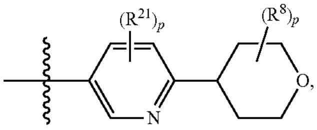

-continued

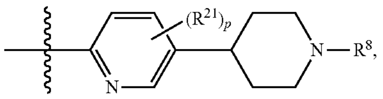

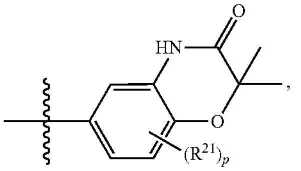

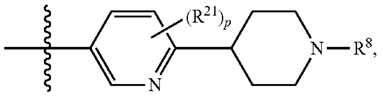

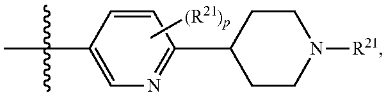

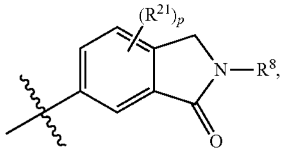

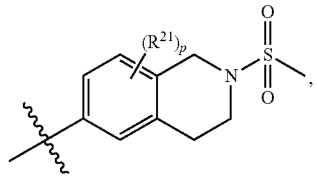

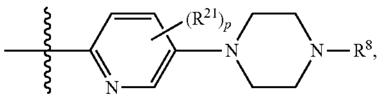

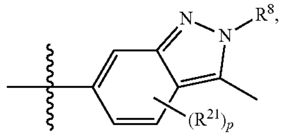

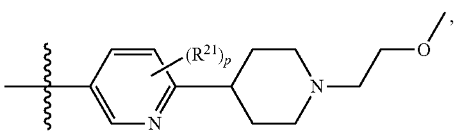

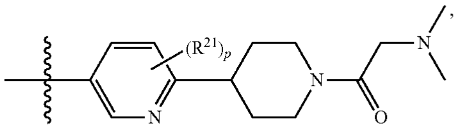

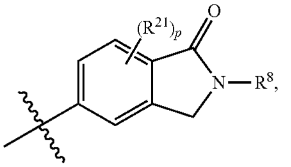

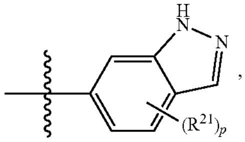

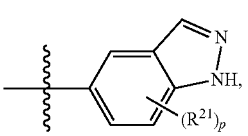

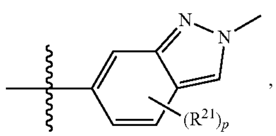

-continued

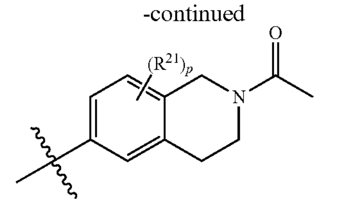

or

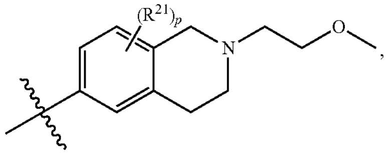

wherein:

$R^{21}$ is halogen, —CN, —$OR^{12}$, —$OR^{12}$, —$OR^{10}$, —C(O)$R^{12}$, —OC(O)$R^{12}$, —C(O)$OR^{12}$, —N$(R^{11})_2$, —N$(R^{12})_2$, —N($R^{12}R^{10}$), —N($R^{12}R^{11}$), —$(CR^{12}R^{12})_nR^{11}$, —$SR^8$, —$NR^{12}$C(O)N$(R^{12})_2$, —C(O)N($R^{12}R^{10}$), —N($R^{12}$)C(O)$R^{13}$, —C(O)N$(R^{11})_2$, —C(O)N$(R^{12})_2$, —$(CR^{12}R^{12})_nR^{11}$, —$(CH_2)_nR^{12}$, —$(CH_2)_nR^{13}$, —O$(CH_2)_nR^{13}$, $(CH_2)_nR^{14}$, —O$(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —C(O)$R^{13}$, $^{-}$OC(O)$R^{13}$, —C(O)$OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

$R^8$ is H or $C_1$-$C_6$ alkyl;

n is 1, 2, 3 or 4, and p is 0, 1, 2 or 3.

In other embodiments of the aforementioned $R^6$, $R^{21}$ is halogen, —CN, —$C_1$-$C_6$ alkyl, $C_1$-$C_6$alkoxy, —$OR^{13}$, —C(O)$R^{13}$, $^{-}$OC(O)$R^{13}$, —C(O)$OR^{13}$, —N$(R^{12})_2$, —C(O)N$(R^{12})_2$, $C_2$-$C_{14}$heterocycloalkyl, —$S(O)_2R^{13}$, —$S(O)_2N(R^{12})_2$, $R^{13}$, —$(CH_2)_nR^{13}$, —O$(CH_2)_nR^{13}$, —$(CH_2)_nR^{14}$, halo-substituted $C_1$-$C_6$ alkyl or halo-substituted $C_1$-$C_6$alkoxy.

In certain embodiments of the compounds of Formulas (I) and Formula (Ia), $R^6$ is —$(CH_2)_nR^9$, where $R^9$ is $C_6$-$C_{14}$aryl, $C_3$-$C_{13}$heteroaryl, $C_3$-$C_8$cycloalkyl or $C_2$-$C_{14}$heterocycloalkyl, wherein the $C_6$-$C_{14}$aryl, $C_3$-$C_{13}$heteroaryl, $C_3$-$C_8$cycloalkyl and $C_2$-$C_{14}$heterocycloalkyl are optionally substituted with 1 to 3 substituents independently selected from halogen, —CN, —$OR^{12}$, —$OR^{10}$, —C(O)$R^{12}$, —OC(O)$R^{12}$, —C(O)$OR^{12}$, —N$(R^{11})_2$, —N$(R^{12})_2$, —N($R^{12}R^{10}$), —N($R^{12}R^{11}$), —$(CR^{12}R^{12})_nR^{11}$, —$SR^8$, —$NR^{12}$C(O)N$(R^{12})_2$, —C(O)N($R^{12}R^{10}$), —N($R^{12}$)C(O)$R^{13}$, —C(O)N$(R^{11})_2$, —C(O)N$(R^{12})_2$, —$(CR^{12}R^{12})_nR^{11}$, —$(CH_2)_nR^{12}$, —$(CH_2)_nR^{13}$, —O$(CH_2)_nR^{13}$, $(CH_2)_nR^{14}$, —O$(CH_2)_nR^{14}$, $(CH_2)_nR^{16}$, —$S(O)_2R^{12}$, —$S(O)_2N(R^{11})_2$, —$S(O)_2N(R^{12})_2$, $OR^{13}$, —C(O)$R^{13}$, $^{-}$OC(O)$R^{13}$, —C(O)$OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy, and n is 1, 2, 3 or 4.

In certain embodiments of the compounds of Formulas (I) and Formula (Ia), $R^6$ is -$L^3R^9$, where $R^9$ is $C_6$-$C_{14}$aryl, $C_3$-$C_{13}$heteroaryl, $C_3$-$C_8$cycloalkyl or $C_2$-$C_{14}$heterocycloalkyl, wherein the $C_6$-$C_{14}$aryl, $C_3$-$C_{13}$heteroaryl, $C_3$-$C_8$cycloalkyl and $C_2$-$C_{14}$heterocycloalkyl are optionally substituted with 1 to 3 substituents independently selected from halogen, —CN, —$OR^{12}$, —$OR^{10}$, —C(O)$R^{12}$, —OC(O)$R^{12}$, —C(O)$OR^{12}$, —N$(R^{11})_2$, —N$(R^{12})_2$, —N($R^{12}R^{10}$), —N($R^{12}R^{11}$), —$(CR^{12}R^{12})_nR^{11}$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, $^-OC(O)R^{13}$, —$C(O)OR^{13}$, —$S(O)_2R^{13}$, —$R^{13}$, $C_2$-$C_{14}$ heterocycloalkyl, $C_1$-$C_6$alkoxy, hydroxyl-$C_1$-$C_6$alkyl, halo-substituted $C_1$-$C_6$alkyl or halo-substituted $C_1$-$C_6$alkoxy, and n is 1, 2, 3 or 4.

In other embodiments of the compounds of Formulas (I) and Formula (Ia), $L^3$ is a $C_1$-$C_6$alkyl or $C_1$-$C_6$alkoxy; wherein the $C_1$-$C_6$alkyl and $C_1$-$C_6$alkoxy groups of $L^3$ are optionally substituted with 1 to 3 substituents independently selected from halogen, —$C_1$-$C_6$alkyl, —$OR^{13}$, —$N(R^{12})_2$, halo-substituted $C_1$-$C_6$alkyl and halo-substituted $C_1$-$C_6$alkoxy. In other embodiments of such $L^3$, $R^{13}$ is H or $C_1$-$C_6$ alkyl.

In other embodiments of the aforementioned embodiments, $R^9$ is

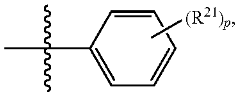 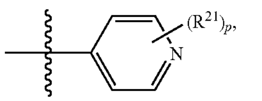

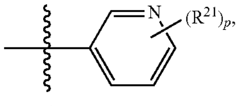 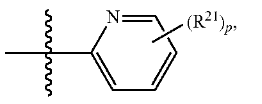

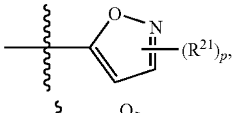 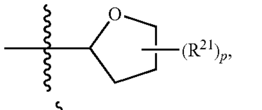

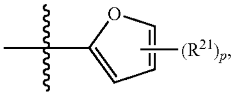 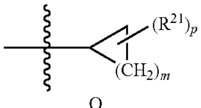,

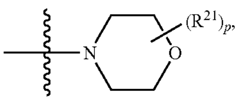 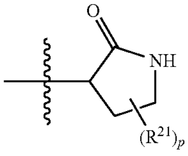 or

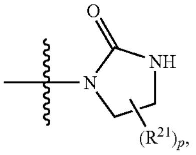

wherein:

$R^{21}$ is halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$(CR^{12}R^{12})_nR^{11}$, —$SR^8$, —$NR^{12}C(O)N(R^{12})_2$, —$C(O)N(R^{12}R^{10}$, —$N(R^{12})C(O)R^{13}$, —$C(O)N(R^{11})_2$, —$C(O)N(R^{12})_2$, —$(CR^{12}R^{12})_n$ $R^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_n$ $R^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, $^-OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

$R^8$ is H or $C_1$-$C_6$ alkyl;

n is 1, 2, 3 or 4;

m is 1, 2, 3 or 4, and p is 0, 1, 2 or 3.

In certain embodiments of such $R^9$, $R^{21}$ is halogen, —CN, —$C_1$-$C_6$ alkyl, $C_1$-$C_6$alkoxy, —$OR^{13}$, —$C(O)R^{13}$, $^-OC(O)R^{13}$, —$C(O)OR^{13}$, —$N(R^{12})_2$, —$C(O)N(R^{12})_2$, $C_2$-$C_{14}$heterocycloalkyl, —$S(O)_2R^{13}$, —$S(O)_2N(R^{12})_2$, $R^{13}$, —$(CH_2)_nR^{13}$, —$O(CH_2)_nR^{13}$, —$(CH_2)_nR^{14}$, halo-substituted $C_1$-$C_6$ alkyl or halo-substituted $C_1$-$C_6$alkoxy.

In certain embodiments of the compounds of Formulas (I) and Formula (Ia), $R^6$ is —$Y^1$-$L^1$-$R^{14}$, where $Y^1$ is arylene and $R^{14}$ is $C_2$-$C_{14}$heterocycloalkyl optionally substituted with 1-3 substituents independently selected from halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$(CR^{12}R^{12})_nR^{11}$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_n$ $R^{13}$, —$(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy, and n is 1, 2, 3 or 4. In certain embodiments of the compounds of Formulas (I) and Formula (Ia), $R^6$ is —$Y^1$-$L^1$-$R^{14}$, where $Y^1$ is phenylene and $R^{14}$ is heterocycloalkyl optionally substituted with 1-3 substituents independently selected from halogen, —CN, —$C_1$-$C_6$alkyl, $C_1$-$C_6$alkoxy, —$OR^{13}$, —$C(O)R^{13}$, —$OC(O)R^{13}$, —$C(O)OR^{13}$, —$N(R^{12})_2$, —$C(O)N(R^{12})_2$, $C_2$-$C_{14}$heterocycloalkyl, —$S(O)_2R^{13}$, —$S(O)_2$ $N(R^{12})_2$, $R^{13}$, —$(CH_2)_nR^{13}$, —$O(CH_2)_n$ $R^{13}$, —$(CH_2)_nR^{14}$, halo-substituted $C_1$-$C_6$ alkyl and halo-substituted $C_1$-$C_6$alkoxy.

In certain embodiments of the compounds of Formulas (I) and Formula (Ia), $R^6$ is —$(CH_2)_nR^9$ and $R^9$ is $Y^2$-$L^2$-$R^{14}$, wherein $Y^2$ is arylene and $R^{14}$ is $C_2$-$C_{14}$heterocycloalkyl optionally substituted with 1-3 substituents independently selected from halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$(CR^{12}R^{12})_nR^{11}$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy, and n is 1, 2, 3 or 4. In certain embodiments, $Y^2$ is phenylene.

In certain embodiments of the compounds of Formulas (I) and Formula (Ia), $R^6$ is $C_1$-$C_6$alkyl or halo-substituted $C_1$-$C_6$alkyl, wherein the $C_1$-$C_6$alkyl and halo-substituted $C_1$-$C_6$alkyl of $R^6$ are optionally substituted with 1 to 3 substituents independently selected from halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$(CR^{12}R^{12})_nR^{11}$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy, and n is 1, 2, 3 or 4.

In certain embodiments of the compounds of Formulas (I) and Formula (Ia), $R^2$ is H, $(CH_2)_nR^{11}$, —$C(O)R^{12}$, —$CR^{12}$=$NOCR^{12}$, halogen, $R^{20}$, $C_1$-$C_6$alkyl, $C_2$-$C_6$alkenyl, $C_2$-$C_6$alkynyl, $C_1$-$C_6$alkoxy, $C_1$-$C_6$alkylthio, hydroxyl-$C_1$-

$C_6$alkyl, halo-substituted-$C_1$-$C_6$alkyl, and halo-substituted-$C_1$-$C_6$alkoxy, $C_6$-$C_{14}$aryl, $C_3$-$C_{13}$heteroaryl and $C_2$-$C_{14}$heterocycloalkyl, wherein the $C_6$-$C_{14}$aryl, $C_2$-$C_6$alkenyl, $C_2$-$C_6$alkynyl, $C_3$-$C_{13}$heteroaryl, and $C_2$-$C_{14}$heterocycloalkyl of $R^2$ and $R^3$ are optionally substituted with 1 to 3 substituents independently selected from halogen, —CN, —$OR^{12}$, —$NO_2$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$(CR^{12}R^{12})_nR^{11}$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy, and n is 1, 2, 3 or 4.

In certain embodiments of the compounds of Formulas (I) and Formula (Ia), $R^2$ H, halogen, $R^{20}$,

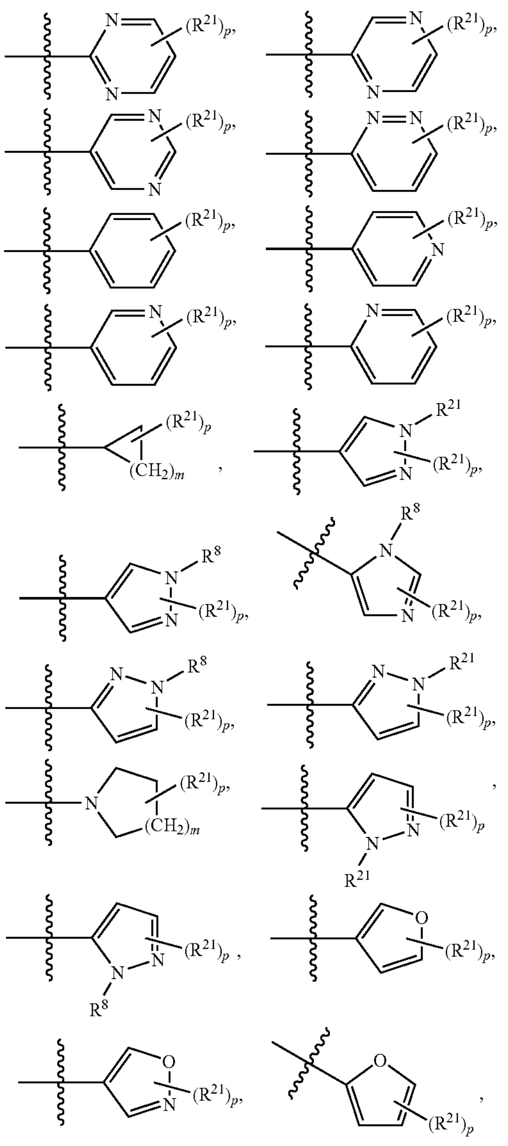

-continued

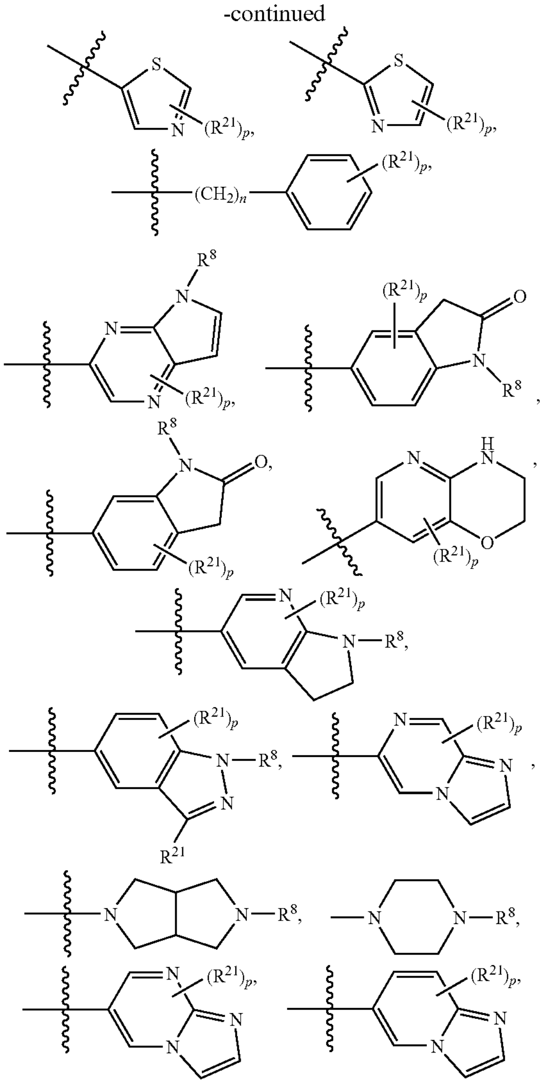

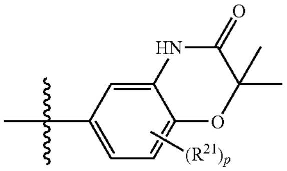

or

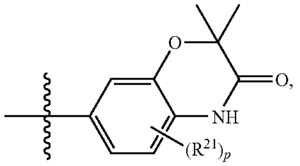

wherein:

$R^{21}$ is halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{16})$, —$N(R^{12}R^{11})$, —$(CR^{12}R^{12})_nR^{11}$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_n$ $R^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

$R^8$ is H or $C_1$-$C_6$ alkyl;

n is 1, 2, 3 or 4;

m is 1, 2, or 3 and p is 0, 1, 2 or 3.

In certain embodiments of such $R^2$, $R^{21}$ is —$OR^{12}$, —C(O)$R^{12}$, —$N(R^{12})_2$, —$(CH_2)_nR^{13}$, $R^{10}$, $C_2$-$C_{14}$ heterocycloalkyl, hydroxyl-$C_1$-$C_6$alkyl or halo-substituted $C_1$-$C_6$alkyl.

Also provided herein are compounds of Formulas (I) and Formula (Ia), wherein the compound of Formula (I) or Formula (Ia) are compounds of Formula (Ib):

(Ib)

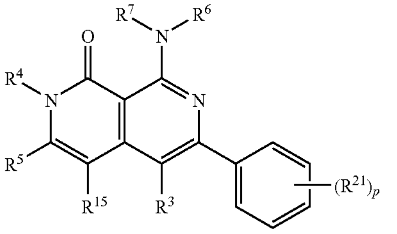

wherein, $R^{21}$ is halogen, —CN, —$OR^{12}$, —$OR^{10}$—C(O)$R^{12}$, —OC(O)$R^{12}$, —C(O)O$R^{12}$, —C(O)O$R^{12}$, —$N(R^{11})_2$, —$N(R^{12})_2$, —$N(R^{12}R^{10})$, —$N(R^{12}R^{11})$, —$(CR^{12}R^{12})_nR^{11}$, —$SR^8$, —$NR^{12}C(O)N(R^{12})_2$, —C(O)N($R^{12}R^{10}$), —$N(R^{12})C(O)R^{13}$, —C(O)N$(R^{11})_2$, —C(O)N$(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —C(O)$R^{13}$, -OC(O)$R^{13}$, —C(O)O$R^{13}$, —$S(O)_2R^{13}$, —$R^{13}$, $C_2$-$C_{14}$ heterocycloalkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

n is 1, 2, 3 or 4, and p is 0, 1, 2 or 3.

In certain embodiments of such compounds of Formula (Ib), $R^{21}$ is halogen, —CN, —$NO_2$, —$OR^{12}$, —C(O)$R^{12}$, —C(O)O$R^{12}$, —$N(R^{12})_2$, —$NR^{12}C(O)N(R^{12})_2$, —C(O)N($R^{12}R^{10}$), —C(O)N$(R^{12})_2$, —$(CR^{12}R^{12})_nR^{11}$, $(CH_2)_nR^{14}$, —$O(CH_2)_nR^{14}$, —$S(O)_2R^{12}$, —$S(O)_2N(R^{12})_2$, $C_2$-$C_{14}$ heterocycloalkyl, hydroxyl-$C_1$-$C_6$alkyl or halo-substituted $C_1$-$C_6$alkyl. In other embodiments of such compounds of Formula (Ib), each $R^{12}$ is independently selected from H, $C_1$-$C_6$alkyl and $C_3$-$C_8$cycloalkyl, or each $R^{12}$ is independently a $C_1$-$C_6$alkyl that together with N they are attached form a heterocycloalkyl. In other embodiments of such compounds of Formula (Ib), $R^{10}$ is $C_3$-$C_8$cycloalkyl or —$(CH_2)_{11}R^{11}$. In other embodiments of such compounds of Formula (Ib), $R^{11}$ is $C_3$-$C_8$cycloalkyl or $C_2$-$C_{14}$heterocycloalkyl. In other embodiments of such compounds of Formula (Ib), $R^{14}$ is —$OR^{13}$, —CN, $N(R^{12})_2$, halo-substituted $C_1$-$C_6$alkyl, $C_6$-$C_{14}$aryl, $C_3$-$C_{13}$heteroaryl or $C_2$-$C_{14}$heterocycloalkyl, wherein the $C_2$-$C_{14}$heterocycloalkyl, $C_6$-$C_{14}$aryl and $C_3$-$C_{13}$heteroaryl are optionally substituted with 1-3 substituents independently selected from halogen and $C_1$-$C_6$alkyl.

Also provided herein are compounds of Formulas (I) and Formula (Ia), wherein the compound of Formula (I) or Formula (Ia) are compounds of Formula (Ic):

(Ic)

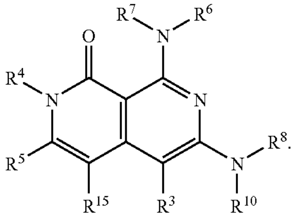

In certain embodiments of such compounds of Formula (Ic), $R^{10}$ is $C_6$-$C_{14}$aryl, $C_3$-$C_{13}$heteroaryl, $C_2$-$C_{14}$heterocycloalkyl, $C_3$-$C_8$cycloalkyl or —$(CH_2)_nR^{11}$, wherein the $C_6$-$C_{14}$aryl, $C_3$-$C_{13}$heteroaryl, $C_2$-$C_{14}$heterocycloalkyl and $C_3$-$C_8$cycloalkyl of $R^{10}$ are optionally substituted with 1 to 3 substituents independently selected from halogen, —CN, —$OR^{12}$, —$OR^{10}$, —C(O)$R^{12}$, —OC(O)$R^{12}$, —C(O)O$R^{12}$, —$N(R^{11})_2$, —$N(R^{12})_2$, —$N(R^{12}R^{10})$, —$N(R^{12}R^{11})$, —$(CR^{12}R^{12})_nR^{11}$, —$SR^8$, —$NR^{12}C(O)N(R^{12})_2$, —C(O)N($R^{12}R^{10}$), —$N(R^{12})C(O)R^{13}$, —C(O)N$(R^{11})_2$, —C(O)N$(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, C(O)$R^{13}$, —OC(O)$R^{13}$, —C(O)O$R^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy, and n is 1, 2, 3 or 4. In certain embodiments $R^{10}$ is

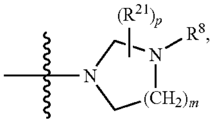
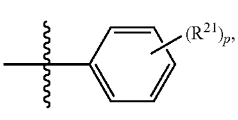
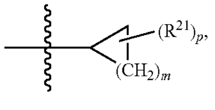
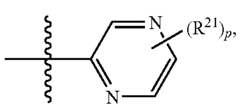
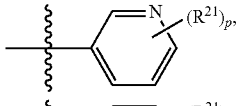
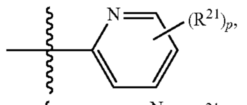
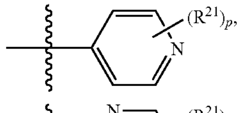
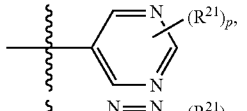
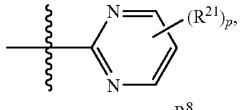
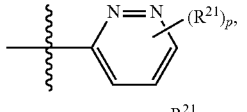
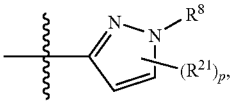
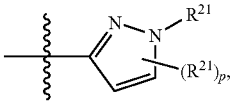
or
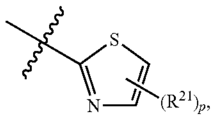

wherein:

$R^{21}$ is halogen, —CN, —$OR^{12}$, —$OR^{10}$, —C(O)$R^{12}$, —OC(O)$R^{12}$, —C(O)O$R^{12}$, —$N(R^{11})_2$, —$N(R^{12})_2$, —$N(R^{12}R^{10})$, —$N(R^{12}R^{11})$, —$(CR^{12}R^{12})_nR^{11}$, —$SR^8$, —$NR^{12}C(O)N(R^{12})_2$, —C(O)N($R^{12}R^{10}$), —$N(R^{12})C(O)R^{13}$, —C(O)N$(R^{11})_2$, —C(O)N$(R^{12})_2$, $-(CR^{12}R^{12})_n$ $R^{11}$, $-(CH_2)_nR^{12}$, $-(CH_2)_nR^{13}$, $-O(CH_2)_nR^{13}$, $(CH_2)_nR^{14}$, $-O(CH_2)_nR^{14}$, $(CH_2)_n$ $R^{16}$, $-S(O)_2R^{12}$, $-S(O)_2N(R^{11})_2$, $-S(O)_2N(R^{12})_2$, $R^{12}$, $R^{10}$, $-OR^{13}$, $-C(O)R^{13}$, $-OC(O)R^{13}$, $-C(O)OR^{13}$, $-S(O)_2R^{13}$, $-R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy; $R^8$ is H or $C_1$-$C_6$ alkyl; n is 1, 2, 3 or 4; m is 1, 2, or 3 and p is 0, 1, 2 or 3.

In certain embodiments of such compounds of Formula (Ic), $R^{10}$ is $-(CH_2)_nR^{11}$. In certain embodiments of such compounds of Formula (Ic), $R^{11}$ is $-N(R^{12})_2$, $-OR^{13}$, $-C(O)N(R^{12})_2$, $C_6$-$C_{14}$aryl, $C_3$-$C_{13}$heteroaryl, $C_1$-$C_6$alkyl, $C_3$-$C_8$cycloalkyl, or $C_2$-$C_{14}$heterocycloalkyl, wherein the $C_6$-$C_{14}$aryl, $C_3$-$C_{13}$heteroaryl, $C_2$-$C_{14}$heterocycloalkyl and $C_3$-$C_8$cycloalkyl of $R^{10}$ are optionally substituted with 1 to 3 substituents independently selected from halogen, $-CN$, $-OR^{12}$, $-OR^{10}$, $-C(O)R^{12}$, $-OC(O)R^{12}$, $-C(O)OR^{12}$, $-N(R^{11})_2$, $-N(R^{12})_2$, $-N(R^{12}R^{10})$, $-N(R^{12}R^{11})$, $-(CR^{12}R^{12})_nR^{11}$, $-SR^8$, $-NR^{12}C(O)N(R^{12})_2$, $-C(O)N(R^{12}R^{10})$, $-N(R^{12})C(O)R^{13}$, $-C(O)N(R^{11})_2$, $-C(O)N(R^{12})_2$, $-(CR^{12}R^{12})_nR^{11}$, $-(CH_2)_nR^{12}$, $-(CH_2)_nR^{13}$, $-O(CH_2)_nR^{13}$, $(CH_2)_nR^{14}$, $-O(CH_2)_nR^{14}$, $(CH_2)_nR^{16}$, $-S(O)_2R^{12}$, $-S(O)_2N(R^{11})_2$, $-S(O)_2N(R^{12})_2$, $-C(O)R^{13}$, $-OC(O)R^{13}$, $-C(O)OR^{13}$, $-S(O)_2R^{13}$, $-R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy, and n is 1, 2, 3 or 4.

In certain embodiments of such compounds of Formula (Ic), $R^{11}$ is $R^{11}$ is $-N(R^{12})_2$,

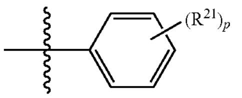
or
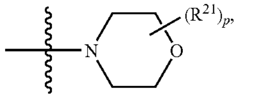

wherein:

$R^{21}$ is halogen, $-CN$, $-OR^{12}$, $-OR^{10}$, $-C(O)R^{12}$, $-OC(O)R^{12}$, $-C(O)OR^{12}$, $-N(R^{11})_2$, $-N(R^{12})_2$, $-N(R^{12}R^{10})$, $-N(R^{12}R^{11})$, $-(CR^{12}R^{12})_nR^{11}$, $-SR^8$, $-NR^{12}C(O)N(R^{12})_2$, $-C(O)N(R^{12}R^{10})$, $-N(R^{12})C(O)R^{13}$, $-C(O)N(R^{11})_2$, $-C(O)N(R^{12})_2$, $-(CR^{12}R^{12})_n$ $R^{11}$, $-(CH_2)_nR^{12}$, $-(CH_2)_nR^{13}$, $-O(CH_2)_nR^{13}$, $(CH_2)_nR^{14}$, $-O(CH_2)_nR^{14}$, $(CH_2)_n$ $R^{16}$, $-S(O)_2R^{12}$, $-S(O)_2N(R^{11})_2$, $-S(O)_2N(R^{12})_2$, $R^{12}$, $R^{10}$, $-OR^{13}$, $-C(O)R^{13}$, $-OC(O)R^{13}$, $-C(O)OR^{13}$, $-S(O)_2R^{13}$, $-R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy; n is 1, 2, 3 or 4, and p is 0, 1, 2 or 3

Also provided herein are compounds of Formulas (I) and Formula (Ia), wherein the compound of Formula (I) or Formula (Ia) are compounds of Formula (Id):

(Id)

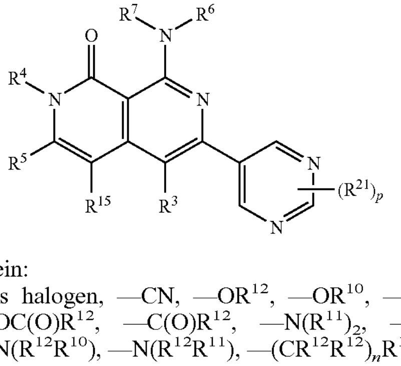

wherein:

$R^{21}$ is halogen, $-CN$, $-OR^{12}$, $-OR^{10}$, $-C(O)R^{12}$, $-OC(O)R^{12}$, $-C(O)R^{12}$, $-N(R^{11})_2$, $-N(R^{12})_2$, $-N(R^{12}R^{10})$, $-N(R^{12}R^{11})$, $-(CR^{12}R^{12})_nR^{11}$, $-SR^8$, $-NR^{12}C(O)N(R^{12})_2$, $-C(O)N(R^{12}R^{10})$, $-N(R^{12})C(O)R^{13}$, $-C(O)N(R^{11})_2$, $-C(O)N(R^{12})_2$, $-(CR^{12}R^{12})_n$ $R^{11}$, $-(CH_2)_nR^{12}$, $-(CH_2)_nR^{13}$, $-O(CH_2)_nR^{13}$, $(CH_2)_nR^{14}$, $-O(CH_2)_nR^{14}$, $(CH_2)_n$ $R^{16}$, $-S(O)_2R^{12}$, $-S(O)_2N(R^{11})_2$, $-S(O)_2N(R^{12})_2$, $R^{12}$, $R^{10}$, $-OR^{13}$, $-C(O)R^{13}$, $-OC(O)R^{13}$, $-C(O)OR^{13}$, $-S(O)_2R^{13}$, $-R^{13}$, $C_2$-$C_{14}$ heterocycloalkyl, $C_1$-$C_6$alkoxy, hydroxyl-$C_1$-$C_6$alkyl, halo-substituted $C_1$-$C_6$alkyl or halo-substituted $C_1$-$C_6$alkoxy; n is 1, 2, 3 or 4, and p is 0, 1, 2 or 3.

In certain embodiments of the aforementioned compounds, $R^{15}$ is H, halogen, $C_2$-$C_6$alkenyl, $-CN$,

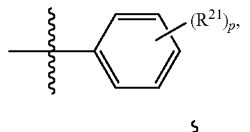
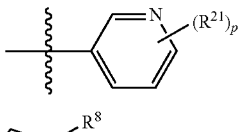
or
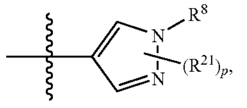

wherein:

$R^{21}$ is halogen, $-CN$, $-OR^{12}$, $-OR^{10}$, $-C(O)R^{12}$, $-OC(O)R^{12}$, $-C(O)OR^{12}$, $-N(R^{11})_2$, $-N(R^{12})_2$, $-N(R^{12}R^{10})$, $-N(R^{12}R^{11})$, $-(CR^{12}R^{12})_nR^{11}$, $-SR^8$, $-NR^{12}C(O)N(R^{12})_2$, $-C(O)N(R^{12}R^{10})$, $-N(R^{12})C(O)R^{13}$, $-NHS(O)_2R^{13}$, $-C(O)N(R^{11})_2$, $-C(O)N(R^{12})_2$, $-(CR^{12}R^{12})_nR^{12}$, $-(CH_2)_nR^{13}$, $-O(CH_2)_n$ $R^{13}$, $(CH_2)_nR^{14}$, $-O(CH_2)_nR^{14}$, $(CH_2)_nR^{16}$, $-S(O)_2$ $R^{12}$, $-S(O)_2N(R^{11})_2$, $-S(O)_2N(R^{12})_2$, $R^{12}$, $R^{10}$, $-OR^{13}$, $-C(O)R^{13}$, $^{-}OC(O)R^{13}$, $-C(O)OR^{13}$, $-S(O)_2R^{13}$, $-R^{13}$, $C_2$-$C_{14}$ heterocycloalkyl, $C_1$-$C_6$alkoxy, hydroxyl-$C_1$-$C_6$alkyl, halo-substituted $C_1$-$C_6$alkyl or halo-substituted $C_1$-$C_6$alkoxy, $R^8$ is H or $C_1$-$C_6$ alkyl; n is 1, 2, 3 or 4, and p is 0, 1, 2 or 3.

In certain embodiments of the aforementioned compounds, $R^{15}$ is H. In certain embodiments of the aforementioned compounds, $R^4$ is H.

Also provided herein are compounds of Formulas (I) and Formula (Ia), wherein the compound of Formula (I) or Formula (Ia) are compounds of Formula (Ie):

(Ie)

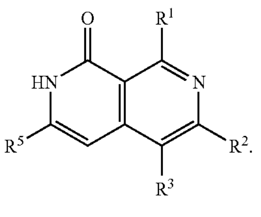

In certain embodiments of the aforementioned compounds, $R^3$ is H, $-CN$, halogen, $C_2$-$C_6$ alkenyl,

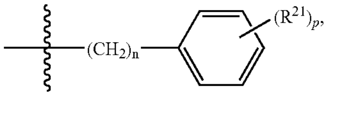

-continued

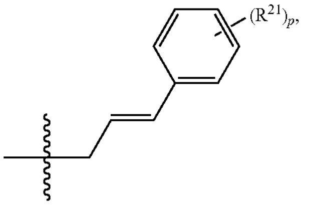,
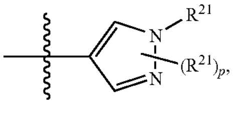,
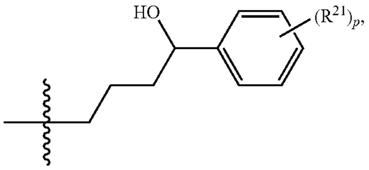,
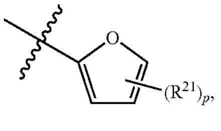, or
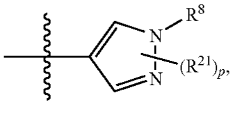, wherein:

$R^{21}$ is halogen, —CN, —$OR^{12}$, —$OR^{10}$—$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$(CR^{12}R^{12})_nR^{11}$, —$SR^8$, —$NR^{12}C(O)N(R^{12})_2$, —$C(O)N(R^{12}R^{10})$, —$N(R^{12}C(O)R^{13}$, —$C(O)N(R^{11})_2$, —$C(O)N(R^{12})_2$, —$(CR^{12}R^{12})_n$ $R^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_n$ $R^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy; n is 1, 2, 3 or 4, and p is 0, 1, 2 or 3.

In certain embodiments of the aforementioned compounds, The compound of any of claims 1-30, wherein $R^8$ is H. In certain embodiments of the aforementioned compounds, $R^3$ is H. In certain embodiments of the aforementioned compounds, $R^5$ is H. In certain embodiments of the aforementioned compounds, $R^2$ is H or halogen.

In another aspect, the present invention provides compounds of Formula (I) selected from: 7-chloro-5-(4-morpholinophenylamino)pyrido[4,3-d]pyrimidin-4(3H)-one, 3-(morpholin-4-yl)-N-(8-oxo-3-phenyl-7,8-dihydro-2,7-naphthyridin-1-yl)benzamide; 8-amino-6-phenyl-1,2-dihydro-2,7-naphthyridin-1-one; 8-{[3-(morpholin-4-yl)phenyl]amino}-6-phenyl-1,2-dihydro-2,7-naphthyridin-1-one; N-(8-oxo-3-phenyl-7,8-dihydro-2,7-naphthyridin-1-yl)oxane-4-carboxamide 6-[(dimethylamino)methyl]-8-{[3-(trifluoromethyl)phenyl]amino}-1,2-dihydro-2,7-naphthyridin-1-one; 6-[(dimethylamino)methyl]-8-{[3-(morpholin-4-yl)phenyl]amino}-1,2-dihydro-2,7-naphthyridin-1-one; 6-(2-phenylethyl)-8-{[3-(trifluoromethyl)phenyl]amino}-1,2-dihydro-2,7-naphthyridin-1-one; 8-{[3-(morpholin-4-yl)phenyl]amino}-6-(2-phenylethyl)-1,2-dihydro-2,7-naphthyridin-1-one; 6-[3-(trifluoromethyl)phenyl]-8-{[3-(trifluoromethyl)phenyl]amino}-1,2-dihydro-2,7-naphthyridin-1-one; 6-(2-aminoethyl)-8-{[3-(trifluoromethyl)phenyl]amino}-1,2-dihydro-2,7-naphthyridin-1-one; 6-(3-aminopropyl)-8-{[3-(trifluoromethyl)phenyl]amino}-1,2-dihydro-2,7-naphthyridin-1-one; 6-phenyl-8-{[3-(trifluoromethyl)phenyl]amino}-1,2-dihydro-2,7-naphthyridin-1-one; 8-{[4-(morpholin-4-yl)phenyl]amino}-6-phenyl-1,2-dihydro-2,7-naphthyridin-1-one; 6-(pyridin-3-yl)-8-{[3-(trifluoromethyl)phenyl]amino}-1,2-dihydro-2,7-naphthyridin-1-one; 2-[2-(8-amino-1-oxo-1,2-dihydro-2,7-naphthyridin-3-yl)ethyl]-2,3-dihydro-1H-isoindole-1,3-dione; 6-(3-aminopropyl)-8-{[4-(morpholin-4-yl)phenyl]amino}-1,2-dihydro-2,7-naphthyridin-1-one; 6-(3-aminopropyl)-8-{[3-(morpholin-4-yl)phenyl]amino}-1,2-dihydro-2,7-naphthyridin-1-one; 8-{[4-(4-methylpiperazin-1-yl)phenyl]amino}-6-phenyl-1,2-dihydro-2,7-naphthyridin-1-one; 8-({4-[3-(dimethylamino)propyl]phenyl}amino)-6-phenyl-1,2-dihydro-2,7-naphthyridin-1-one; 8-({4-[2-(morpholin-4-yl)ethyl]phenyl}amino)-6-phenyl-1,2-dihydro-2,7-naphthyridin-1-one; N-(3-methoxypropyl)-4-[(8-oxo-3-phenyl-7,8-dihydro-2,7-naphthyridin-1-yl)amino]benzene-1-sulfonamide; 6-phenyl-8-{[3-(trifluoro methoxy)phenyl]amino}-1,2-dihydro-2,7-naphthyridin-1-one; 6-(3-aminopropyl)-8-({4-[2-(morpholin-4-yl)ethyl]phenyl}amino)-1,2-dihydro-2,7-naphthyridin-1-one; 8-amino-3-(2-aminoethyl)-1,2-dihydro-2,7-naphthyridin-1-one; 6-(4-aminobutyl)-8-{[3-(trifluoromethyl)phenyl]amino}-1,2-dihydro-2,7-naphthyridin-1-one; 6-(4-aminobutyl)-8-{[3-(trifluoromethoxy)phenyl]amino}-1,2-dihydro-2,7-naphthyridin-1-one; 6-(3-aminopropyl)-8-{[4-methyl-3-(trifluoromethyl)phenyl]amino}-1,2-dihydro-2,7-naphthyridin-1-one; 8-{[3-(morpholin-4-yl)phenyl]amino}-6-(pyridin-3-yl)-1,2-dihydro-2,7-naphthyridin-1-one; 8-amino-3-(3-aminopropyl)-1,2-dihydro-2,7-naphthyridin-1-one; 6-phenyl-8-{[4-(trifluoromethoxy)phenyl]amino}-1,2-dihydro-2,7-naphthyridin-1-one; 6-(3-aminopropyl)-8-{[4-methoxy-3-(trifluoromethyl)phenyl]amino}-1,2-dihydro-2,7-naphthyridin-1-one; 6-(3-aminopropyl)-8-[(3,5-dimethoxyphenyl)amino]-1,2-dihydro-2,7-naphthyridin-1-one; 6-(3-aminopropyl)-8-[(3,4-dimethoxyphenyl)amino]-1,2-dihydro-2,7-naphthyridin-1-one; 6-(3-aminopropyl)-8-[(3-methoxyphenyl)amino]-1,2-dihydro-2,7-naphthyridin-1-one; 6-(3-aminopropyl)-8-{[3-fluoro-4-(piperazin-1-ylmethyl)phenyl]amino}-1,2-dihydro-2,7-naphthyridin-1-one; 8-[(3-bromophenyl)amino]-6-phenyl-1,2-dihydro-2,7-naphthyridin-1-one; 6-cyclohexyl-8-{[3-(trifluoromethyl)phenyl]amino}-1,2-dihydro-2,7-naphthyridin-1-one; 6-cyclohexyl-8-{[4-(4-methylpiperazin-1-yl)phenyl]amino}-1,2-dihydro-2,7-naphthyridin-1-one; 8-{[4-methoxyphenyl]amino}-6-phenyl-1,2-dihydro-2,7-naphthyridin-1-one; 6-phenyl-8-{[2-(trifluoromethoxy)phenyl]amino}-1,2-dihydro-2,7-naphthyridin-1-one; 8-{[4-(morpholin-4-yl)phenyl]amino}-6-[3-(trifluoromethyl)phenyl]-1,2-dihydro-2,7-naphthyridin-1-one; 6-[(2-aminoethyl)amino]-8-{[3-(trifluoromethyl)phenyl]amino}-1,2-dihydro-2,7-naphthyridin-1-one; 6-[(2-aminoethyl)amino]-8-{[4-(morpholin-4-yl)phenyl]amino}-1,2-dihydro-2,7-naphthyridin-1-one; 6-(3-aminopropyl)-8-{[4-(4-ethylpiperazin-1-yl)phenyl]amino}-1,2-dihydro-2,7-naphthyridin-1-one; 6-[(3R)-piperidin-3-ylamino]-8-{[3-(trifluoromethyl)phenyl]amino}-1,2-dihydro-2,7-naphthyridin-1-one; 8-{[4-(morpholin-4-yl)phenyl]amino}-6-[(3R)-piperidin-3-ylamino]-1,2-dihydro-2,7-naphthyridin-1-one; 6-(4-ethylpiperazin-1-yl)-8-{[4-(morpholin-4-yl)phenyl]amino}-1,2-dihydro-2,7-naphthyridin-1-one; 8-{[4-(morpholin-4-yl)phenyl]amino}-6-[(38)-piperidin-3-ylamino]-1,2-dihydro-2,7-naphthyridin-1-one; 8-{[4-(morpholin-4-yl)phenyl]amino}-6-[(38)-pyrrolidin-3-ylamino]-1,2-dihydro-2,7-naphthyridin-1-one; 6-{[(18,28)-2-aminocyclohexyl]amino}-8-{[4-(morpholin-4-yl)phenyl]amino}-1,2-dihydro-2,7-naphthyridin-1-one; 8-{[4-(morpholin-4-yl)phenyl]amino}-6-[(3R)-pyrrolidin-3-ylamino]-1,2-dihydro-2,7-naphthyridin-1-one; 6-{[(1S, 2R)-2-aminocyclohexyl]amino}-8-{[4-(morpholin-4-yl)phenyl]amino}-1,2-dihydro-2,7-naphthyridin-1-one; 8-{[4-(morpholin-4-yl)phenyl]amino}-6-(piperidin-3-yloxy)-1,2-dihydro-2,7-naphthyridin-1-one; 6-[(2-aminoethyl)amino]-8-{[4-(4-methylpiperazin-1-yl)phenyl]amino}-1,2-dihydro-2,7-naphthyridin-1-one; 8-{[4-(4-methylpiperazin-1-yl)phenyl]amino}-6-[(3S)-piperidin-3-ylamino]-1,2-dihydro-2,7-naphthyridin-1-one; 6-(benzylamino)-8-{[4-(4-methylpiperazin-1-yl)phenyl]amino}-1,2-dihydro-2,7-naphthyridin-1-one; 6-[(2-aminoethyl)amino]-8-{[4-(piperidin-4-yl)phenyl]amino}-1,2-dihydro-2,7-naphthyridin-1-one; tert-butyl 4-[4-({3-[(2-aminoethyl)amino]-8-oxo-7,8-dihydro-2,7-naphthyridin-1-yl}amino)phenyl]piperidine-1-carboxylate; 6-[(2-aminoethyl)amino]-8-({4-[(4-ethylpiperazin-1-yl)methyl]phenyl}amino)-1,2-dihydro-2,7-naphthyridin-1-one; 8-{[4-(4-methylpiperazin-1-yl)phenyl]amino}-6-(pyridin-3-yl)-1,2-dihydro-2,7-naphthyridin-1-one; 2-(1-{[4-(4-methylpiperazin-1-yl)phenyl]amino}-8-oxo-7,8-dihydro-2,7-naphthyridin-3-yl)benzamide; 8-{[4-(4-methylpiperazin-1-yl)phenyl]amino}-6-(1H-pyrazol-4-yl)-1,2-dihydro-2,7-naphthyridin-1-one; 6-{[(1S,2S)-2-aminocyclohexyl]amino}-8-{[4-(4-methylpiperazin-1-yl)phenyl]amino}-1,2-dihydro-2,7-naphthyridin-1-one; 6-[(2-aminoethyl)amino]-8-{[3-(4-methylpiperazin-1-yl)phenyl]amino}-1,2-dihydro-2,7-naphthyridin-1-one; 6-(3-aminopiperidin-1-yl)-8-{[4-(morpholin-4-yl)phenyl]amino}-1,2-dihydro-2,7-naphthyridin-1-one; 6-{[(3-chlorophenyl)methyl]amino}-8-{[4-(4-methylpiperazin-1-yl)phenyl]amino}-1,2-dihydro-2,7-naphthyridin-1-one; 6-[(3R)-3-aminopyrrolidin-1-yl]-8-{[4-(morpholin-4-yl)phenyl]amino}-1,2-dihydro-2,7-naphthyridin-1-one; 8-{[4-(piperidin-1-yl)phenyl]amino}-6-(pyridin-3-yl)-1,2-dihydro-2,7-naphthyridin-1-one; 6-[(2-aminoethyl)amino]-2-methyl-8-{[3-(trifluoromethyl)phenyl]amino}-1,2-dihydro-2,7-naphthyridin-1-one; 8-{[4-(morpholin-4-yl)phenyl]amino}-6-(pyridin-3-yl)-1,2-dihydro-2,7-naphthyridin-1-one; 8-{[4-(4-methylpiperazin-1-yl)phenyl]amino}-6-[1-(piperidin-4-yl)-1H-pyrazol-4-yl]-1,2-dihydro-2,7-naphthyridin-1-one; 6-(3-chlorophenyl)-8-{[4-(morpholin-4-yl)phenyl]amino}-1,2-dihydro-2,7-naphthyridin-1-one; 4-({3-[(2-aminoethyl)amino]-8-oxo-7,8-dihydro-2,7-naphthyridin-1-yl}amino)-N-(4-chlorophenyl)benzamide; 6-(3-methylphenyl)-8-{[4-(morpholin-4-yl)phenyl]amino}-1,2-dihydro-2,7-naphthyridin-1-one; tert-butyl 4-{4-[(8-oxo-3-phenyl-7,8-dihydro-2,7-naphthyridin-1-yl)amino]phenyl}piperidine-1-carboxylate; 6-phenyl-8-{[4-(piperidin-4-yl)phenyl]amino}-1,2-dihydro-2,7-naphthyridin-1-one; 6-(3-hydroxyphenyl)-8-{[4-(morpholin-4-yl)phenyl]amino}-1,2-dihydro-2,7-naphthyridin-1-one; 6-(3-methoxyphenyl)-8-{[4-(morpholin-4-yl)phenyl]amino}-1,2-dihydro-2,7-naphthyridin-1-one; 6-[(2-aminoethyl)amino]-8-{[2-methoxy-4-(4-methylpiperazin-1-yl)phenyl]amino}-1,2-dihydro-2,7-naphthyridin-1-one; 6-(6-methoxypyridin-3-yl)-8-{[4-(morpholin-4-yl)phenyl]amino}-1,2-dihydro-2,7-naphthyridin-1-one; 8-{[4-(morpholin-4-yl)phenyl]amino}-6-(1H-pyrazol-4-yl)-1,2-dihydro-2,7-naphthyridin-1-one; 6-(3,5-dimethyl-1H-pyrazol-4-yl)-8-{[4-(4-methylpiperazin-1-yl)phenyl]amino}-1,2-dihydro-2,7-naphthyridin-1-one; 2-(1-{[4-(4-methylpiperazin-1-yl)phenyl]amino}-8-oxo-7,8-dihydro-2,7-naphthyridin-3-yl)benzonitrile 6-(4-methoxypyridin-3-yl)-8-{[4-(4-methylpiperazin-1-yl)phenyl]amino}-1,2-dihydro-2,7-naphthyridin-1-one; 6-(6-aminopyridin-3-yl)-8-{[4-(4-methylpiperazin-1-yl)phenyl]amino}-1,2-dihydro-2,7-naphthyridin-1-one; 3-(1-{[4-(4-methylpiperazin-1-yl)phenyl]amino}-8-oxo-7,8-dihydro-2,7-naphthyridin-3-yl)benzamide; 8-{[4-(4-methylpiperazin-1-yl)phenyl]amino}-6-(pyrimidin-5-yl)-1,2-dihydro-2,7-naphthyridin-1-one; 6-(3,5-dimethyl-1,2-oxazol-4-yl)-8-{[4-(4-methylpiperazin-1-yl)phenyl]amino}-1,2-dihydro-2,7-naphthyridin-1-one; 6-(furan-3-yl)-8-{[4-(4-methylpiperazin-1-yl)phenyl]amino}-1,2-dihydro-2,7-naphthyridin-1-one; 6-(1-methyl-1H-pyrazol-4-yl)-8-{[4-(4-methylpiperazin-1-yl)phenyl]amino}-1,2-dihydro-2,7-naphthyridin-1-one; 4-[4-({3-[(2-aminoethyl)amino]-8-oxo-7,8-dihydro-2,7-naphthyridin-1-yl}amino)phenyl]-1,4-thiomorpholine-1,1-dione; 8-{[3-fluoro-4-(morpholin-4-yl)phenyl]amino}-6-phenyl-1,2-dihydro-2,7-naphthyridin-1-one; 4-{4-[(8-oxo-3-phenyl-7,8-dihydro-2,7-naphthyridin-1-yl)amino]phenyl}-1,4-thiomorpholine-1,1-dione; 6-(4-chlorophenyl)-8-{[4-(morpholin-4-yl)phenyl]amino}-1,2-dihydro-2,7-naphthyridin-1-one; 6-(2-chlorophenyl)-8-{[4-(morpholin-4-yl)phenyl]amino}-1,2-dihydro-2,7-naphthyridin-1-one; 6-(3,4-dichlorophenyl)-8-{[4-(morpholin-4-yl)phenyl]amino}-1,2-dihydro-2,7-naphthyridin-1-one; 6-(4-fluorophenyl)-8-{[4-(morpholin-4-yl)phenyl]amino}-1,2-dihydro-2,7-naphthyridin-1-one; 6-(2,4-dimethoxyphenyl)-8-{[4-(morpholin-4-yl)phenyl]amino}-1,2-dihydro-2,7-naphthyridin-1-one; 6-[3-(aminomethyl)phenyl]-8-{[4-(morpholin-4-yl)phenyl]amino}-1,2-dihydro-2,7-naphthyridin-1-one; 8-{[4-(morpholin-4-yl)phenyl]amino}-6-[4-(piperazin-1-yl)phenyl]-1,2-dihydro-2,7-naphthyridin-1-one; 8-{[4-(piperidin-4-yl)phenyl]amino}-6-(1H-pyrazol-4-yl)-1,2-dihydro-2,7-naphthyridin-1-one; 6-(1-methyl-1H-pyrazol-4-yl)-8-{[4-(piperidin-4-yl)phenyl]amino}-1,2-dihydro-2,7-naphthyridin-1-one; 8-{[4-(piperidin-4-yl)phenyl]amino}-6-(1H-pyrazol-3-yl)-1,2-dihydro-2,7-naphthyridin-1-one; 6-(3-hydroxyphenyl)-8-{[4-(piperidin-4-yl)phenyl]amino}-1,2-dihydro-2,7-naphthyridin-1-one; 6-(2-hydroxyphenyl)-8-{[4-(piperidin-4-yl)phenyl]amino}-1,2-dihydro-2,7-naphthyridin-1-one; 6-(6-hydroxypyridin-3-yl)-8-{[4-(piperidin-4-yl)phenyl]amino}-1,2-dihydro-2,7-naphthyridin-1-one; 6-(6-methoxypyridin-3-yl)-8-{[4-(piperidin-4-yl)phenyl]amino}-1,2-dihydro-2,7-naphthyridin-1-one; 8-{[4-(piperidin-4-yl)phenyl]amino}-6-(1-propyl-1H-pyrazol-4-yl)-1,2-dihydro-2,7-naphthyridin-1-one; 6-[1-(2-methylpropyl)-1H-pyrazol-4-yl]-8-{[4-(piperidin-4-yl)phenyl]amino}-1,2-dihydro-2,7-naphthyridin-1-one; 6-[1-(3-methylbutyl)-1H-pyrazol-4-yl]-8-{[4-(piperidin-4-yl)phenyl]amino}-1,2-dihydro-2,7-naphthyridin-1-one; 6-[1-(1,3-dioxolan-2-ylmethyl)-1H-pyrazol-4-yl]-8-{[4-(piperidin-4-yl)phenyl]amino}-1,2-dihydro-2,7-naphthyridin-1-one; 6-{1-[2-(morpholin-4-yl)ethyl]-1H-pyrazol-4-yl}-8-{[4-(piperidin-4-yl)phenyl]amino}-1,2-dihydro-2,7-naphthyridin-1-one; 6-(3-methyl-1H-pyrazol-4-yl)-8-{[4-(piperidin-4-yl)phenyl]amino}-1,2-dihydro-2,7-naphthyridin-1-one; 2-[4-(8-oxo-1-{[4-(piperidin-4-yl)phenyl]amino}-7,8-dihydro-2,7-naphthyridin-3-yl)-1H-pyrazol-1-yl]acetic acid 6-(3,5-dimethyl-1H-pyrazol-4-yl)-8-{[4-(piperidin-4-yl)phenyl]amino}-1,2-dihydro-2,7-naphthyridin-1-one; 8-({4-[1-(2-hydroxyethyl)piperidin-4-yl]phenyl}amino)-6-(1-methyl-1H-pyrazol-4-yl)-1,2-dihydro-2,7-naphthyridin-1-one; 8-({4-[1-(2-hydroxyethyl)piperidin-4-yl]phenyl}amino)-6-(3-hydroxyphenyl)-1,2-dihydro-2,7-naphthyridin-1-one; 8-({4-[1-(2-hydroxyethyl)piperidin-4-yl]phenyl}amino)-6-(6-methoxypyridin-3-yl)-1,2-dihydro-2,7-naphthyridin-1-one; 6-(1H-pyrazol-4-yl)-8-{[3-(trifluoromethyl)phenyl]amino}-1,2-dihydro-2,7-naphthyridin-1-one; 8-{[3-fluoro-4-(morpholin-4-yl)phenyl]amino}-6-[1-(piperidin-4-yl)-1H-pyrazol-4-yl]-1,2-dihydro-2,7-naphthyridin-1-one; 6-(1-benzyl-1H-pyrazol-4-yl)-8-{[3-fluoro-4-(morpholin-4-yl)phenyl]amino}-1,2-dihydro-2,7-naphthyridin-1-one; 8-[(4-fluorophenyl)amino]-5-[1-(piperidin-4-yl)-1H-pyrazol-4- yl]-1,2-dihydro-2,7-naphthyridin-1-one; 5-(1-methyl-1H-pyrazol-4-yl)-8-{[4-(morpholin-4-yl)phenyl]amino}-1,2-dihydro-2,7-naphthyridin-1-one; 8-[(4-fluorophenyl)amino]-5-(1-methyl-1H-pyrazol-4-yl)-1,2-dihydro-2,7-naphthyridin-1-one; 5-bromo-8-{[4-(morpholin-4-yl)phenyl]amino}-1,2-dihydro-2,7-naphthyridin-1-one; 8-{[4-(morpholin-4-yl)phenyl]amino}-1,2-dihydro-2,7-naphthyridin-1-one; 8-chloro-5-(pyridin-3-yl)-1,2-dihydro-2,7-naphthyridin-1-one; 6-(3,5-dimethyl-1H-pyrazol-4-yl)-8-{[4-(morpholin-4-yl)phenyl]amino}-1,2-dihydro-2,7-naphthyridin-1-one; 2-(1-{[4-(morpholin-4-yl)phenyl]amino}-8-oxo-7,8-dihydro-2,7-naphthyridin-3-yl)benzonitrile 5-(furan-3-yl)-8-{[4-(morpholin-4-yl)phenyl]amino}-1,2-dihydro-2,7-naphthyridin-1-one; 4-[(8-oxo-3-phenyl-7,8-dihydro-2,7-naphthyridin-1-yl)amino]-N-propylbenzamide; 4-({3-[(2-aminoethyl)amino]-8-oxo-7,8-dihydro-2,7-naphthyridin-1-yl}amino)-N-propylbenzamide; 4-(4-{[3-(4-methoxypyridin-3-yl)-8-oxo-7,8-dihydro-2,7-naphthyridin-1-yl]amino}phenyl)-1,4-thiomorpholine-1,1-dione; 6-[2-(3-fluorophenyl)pyrrolidin-1-yl]-8-{[4-(morpholin-4-yl)phenyl]amino}-1,2-dihydro-2,7-naphthyridin-1-one; 6-(4-methoxypyridin-3-yl)-8-{[4-(1-methylpiperidin-4-yl)phenyl]amino}-1,2-dihydro-2,7-naphthyridin-1-one; 4-[4-({3-[6-(morpholin-4-yl)pyridin-3-yl]-8-oxo-7,8-dihydro-2,7-naphthyridin-1-yl}amino)phenyl]-1,4-thiomorpholine-1,1-dione; 6-(4-methoxypyridin-3-yl)-8-{[4-(piperidin-1-yl)phenyl]amino}-1,2-dihydro-2,7-naphthyridin-1-one; 8-({4-[3-(dimethylamino)propyl]phenyl}amino)-6-(4-methoxypyridin-3-yl)-1,2-dihydro-2,7-naphthyridin-1-one; 8-{[4-(1-ethylpiperidin-4-yl)phenyl]amino}-6-(1-propyl-1H-pyrazol-4-yl)-1,2-dihydro-2,7-naphthyridin-1-one; 8-{[4-(1-ethylpiperidin-4-yl)phenyl]amino}-6-(3-methyl-1H-pyrazol-4-yl)-1,2-dihydro-2,7-naphthyridin-1-one; 6-[2-(3-fluorophenyl)pyrrolidin-1-yl]-8-{[4-(1-methylpiperidin-4-yl)phenyl]amino}-1,2-dihydro-2,7-naphthyridin-1-one; 2-[4-(1-{[4-(1-ethylpiperidin-4-yl)phenyl]amino}-8-oxo-7,8-dihydro-2,7-naphthyridin-3-yl)-1H-pyrazol-1-yl]acetic acid 8-{[4-(1-acetylpiperidin-4-yl)phenyl]amino}-6-[1-(2-methylpropyl)-1H-pyrazol-4-yl]-1,2-dihydro-2,7-naphthyridin-1-one; 8-[(5-methyl-1H-pyrazol-3-yl)amino]-6-phenyl-1,2-dihydro-2,7-naphthyridin-1-one; 8-{[4-(1-acetylpiperidin-4-yl)phenyl]amino}-6-[1-(3-methylbutyl)-1H-pyrazol-4-yl]-1,2-dihydro-2,7-naphthyridin-1-one; 8-{[4-(1-acetylpiperidin-4-yl)phenyl]amino}-6-{1-[2-(morpholin-4-yl)ethyl]-1H-pyrazol-4-yl}-1,2-dihydro-2,7-naphthyridin-1-one; 6-(6-aminopyridin-3-yl)-8-{[4-(morpholin-4-yl)phenyl]amino}-1,2-dihydro-2,7-naphthyridin-1-one; 6-(4-ethylpiperazin-1-yl)-8-{[4-(piperidin-4-yl)phenyl]amino}-1,2-dihydro-2,7-naphthyridin-1-one; 6-(piperazin-1-yl)-8-{[4-(piperidin-4-yl)phenyl]amino}-1,2-dihydro-2,7-naphthyridin-1-one; 6-(4-methylpiperazin-1-yl)-8-{[4-(piperidin-4-yl)phenyl]amino}-1,2-dihydro-2,7-naphthyridin-1-one; 8-{[4-(piperidin-4-yl)phenyl]amino}-6-(piperidin-4-ylamino)-1,2-dihydro-2,7-naphthyridin-1-one; 6-[4-(piperidin-1-yl)piperidin-1-yl]-8-{[4-(piperidin-4-yl)phenyl]amino}-1,2-dihydro-2,7-naphthyridin-1-one; 6-{[2-(morpholin-4-yl)ethyl]amino}-8-{[4-(piperidin-4-yl)phenyl]amino}-1,2-dihydro-2,7-naphthyridin-1-one; 6-(5-methoxypyridin-3-yl)-8-{[4-(1-methylpiperidin-4-yl)phenyl]amino}-1,2-dihydro-2,7-naphthyridin-1-one; 5-(6-aminopyridin-3-yl)-8-[(4-methoxyphenyl)amino]-1,2-dihydro-2,7-naphthyridin-1-one; 5-(6-aminopyridin-3-yl)-8-{[4-(morpholin-4-yl)phenyl]amino}-1,2-dihydro-2,7-naphthyridin-1-one; 5-(2-chloropyridin-3-yl)-8-{[4-(morpholin-4-yl)phenyl]amino}-1,2-dihydro-2,7-naphthyridin-1-one; 5-[4-(aminomethyl)phenyl]-8-{[4-(morpholin-4-yl)phenyl]amino}-1,2-dihydro-2,7-naphthyridin-1-one; 3-(1-{[4-(morpholin-4-yl)phenyl]amino}-8-oxo-7,8-dihydro-2,7-naphthyridin-4-yl)benzamide; 5-iodo-8-[(4-methoxyphenyl)amino]-1,2-dihydro-2,7-naphthyridin-1-one; 8-[(4-methoxyphenyl)amino]-5-(3-phenylprop-1-yn-1-yl)-1,2-dihydro-2,7-naphthyridin-1-one; 5-phenyl-8-(phenylamino)-1,2-dihydro-2,7-naphthyridin-1-one; 5-(2-chlorophenyl)-8-(phenylamino)-1,2-dihydro-2,7-naphthyridin-1-one; 5-(3-chlorophenyl)-8-(phenylamino)-1,2-dihydro-2,7-naphthyridin-1-one; 5-(4-chlorophenyl)-8-(phenylamino)-1,2-dihydro-2,7-naphthyridin-1-one; 5-(2-methoxyphenyl)-8-(phenylamino)-1,2-dihydro-2,7-naphthyridin-1-one; 5-(3-methoxyphenyl)-8-(phenylamino)-1,2-dihydro-2,7-naphthyridin-1-one; 5-(4-methoxyphenyl)-8-(phenylamino)-1,2-dihydro-2,7-naphthyridin-1-one; 5-(1-benzyl-1H-pyrazol-4-yl)-8-{[4-(morpholin-4-yl)phenyl]amino}-1,2-dihydro-2,7-naphthyridin-1-one; 8-(phenylamino)-5-[1-(piperidin-4-yl)-1H-pyrazol-4-yl]-1,2-dihydro-2,7-naphthyridin-1-one; 5-(1-benzyl-1H-pyrazol-4-yl)-8-(phenylamino)-1,2-dihydro-2,7-naphthyridin-1-one; 5-{1-[2-(morpholin-4-yl)ethyl]-1H-pyrazol-4-yl}-8-(phenylamino)-1,2-dihydro-2,7-naphthyridin-1-one; 5-[1-(1,3-dioxolan-2-ylmethyl)-1H-pyrazol-4-yl]-8-(phenylamino)-1,2-dihydro-2,7-naphthyridin-1-one; 5-(1-methyl-1H-pyrazol-4-yl)-8-(phenylamino)-1,2-dihydro-2,7-naphthyridin-1-one; 5-(furan-3-yl)-8-(phenylamino)-1,2-dihydro-2,7-naphthyridin-1-one; 5-[8-oxo-1-(phenylamino)-7,8-dihydro-2,7-naphthyridin-4-yl]furan-2-carb aldehyde 8-(phenylamino)-5-(pyridin-3-yl)-1,2-dihydro-2,7-naphthyridin-1-one; 6-[2-(2-chlorophenyl)phenyl]-8-{[4-(morpholin-4-yl)phenyl]amino}-1,2-dihydro-2,7-naphthyridin-1-one; 6-(2-chlorophenyl)-8-{[4-(piperidin-4-yl)phenyl]amino}-1,2-dihydro-2,7-naphthyridin-1-one; N-[2-(morpholin-4-yl)ethyl]-4-[(8-oxo-3-phenyl-7,8-dihydro-2,7-naphthyridin-1-yl)amino]benzamide; N,N-diethyl-4-[(8-oxo-3-phenyl-7,8-dihydro-2,7-naphthyridin-1-yl)amino]benzamide; 6-(1-methyl-1H-pyrazol-4-yl)-8-{[4-(1-methylpiperidin-4-yl)phenyl]amino}-1,2-dihydro-2,7-naphthyridin-1-one; 8-{[4-(1-ethylpiperidin-4-yl)phenyl]amino}-6-(1-methyl-1H-pyrazol-4-yl)-1,2-dihydro-2,7-naphthyridin-1-one; 8-[4-(1-acetylpiperidin-4-yl)phenyl]amino-6-(1-methyl-1H-pyrazol-4-yl)-1,2-dihydro-2,7-naphthyridin-1-one; 8-(phenylamino)-5-[3-(trifluoromethyl)phenyl]-1,2-dihydro-2,7-naphthyridin-1-one; 8-(phenylamino)-5-[4-(trifluoromethyl)phenyl]-1,2-dihydro-2,7-naphthyridin-1-one; 5-(6-aminopyridin-3-yl)-8-(phenylamino)-1,2-dihydro-2,7-naphthyridin-1-one; 5-[6-(morpholin-4-yl)pyridin-3-yl]-8-(phenylamino)-1,2-dihydro-2,7-naphthyridin-1-one; 8-(phenylamino)-5-[6-(piperazin-1-yl)pyridin-3-yl]-1,2-dihydro-2,7-naphthyridin-1-one; 5-[6-(4-methylpiperazin-1-yl)pyridin-3-yl]-8-(phenylamino)-1,2-dihydro-2,7-naphthyridin-1-one; 5-(3-aminophenyl)-8-(phenylamino)-1,2-dihydro-2,7-naphthyridin-1-one; 5-(4-aminophenyl)-8-(phenylamino)-1,2-dihydro-2,7-naphthyridin-1-one; 5-(3-fluorophenyl)-8-(phenylamino)-1,2-dihydro-2,7-naphthyridin-1-one; 5-(4-fluorophenyl)-8-(phenylamino)-1,2-dihydro-2,7-naphthyridin-1-one; 4-[8-oxo-1-(phenylamino)-7,8-dihydro-2,7-naphthyridin-4-yl]benzamide; 8-(phenylamino)-5-[(1E)-3-phenylprop-1-en-1-yl]-1,2-dihydro-2,7-naphthyridin-1-one; 5-[(E)-2-(2,4-difluorophenyl)ethenyl]-8-(phenylamino)-1,2-dihydro-2,7-naphthyridin-1-one; 5-[(E)-2-cyclohexylethenyl]-8-(phenylamino)-1,2-dihydro-2,7-naphthyridin-1-one; 8-(phenylamino)-5-[(E)-2-[3-(trifluoromethyl)phenyl]ethenyl]-1,2-dihydro-2,7-naphthyridin-1-one; 6-(4-tert-butylpiperidin-1-yl)-8-{[4-(1-methylpiperidin-4-yl)phenyl]amino}-

1,2-dihydro-2,7-naphthyridin-1-one; 6-[4-(2-hydroxypropan-2-yl)piperidin-1-yl]-8-{[4-(1-methylpiperidin-4-yl)phenyl]amino}-1,2-dihydro-2,7-naphthyridin-1-one; 3-[8-oxo-1-(phenylamino)-7,8-dihydro-2,7-naphthyridin-4-yl]benzonitrile 8-{[4-(1-methylpiperidin-4-yl)phenyl]amino}-6-[(2,2,2-trifluoroethyl)amino]-1,2-dihydro-2,7-naphthyridin-1-one; 6-(4-methylpiperidin-1-yl)-8-{[4-(1-methylpiperidin-4-yl)phenyl]amino}-1,2-dihydro-2,7-naphthyridin-1-one; 8-{[4-(morpholin-4-ylcarbonyl)phenyl]amino}-6-phenyl-1,2-dihydro-2,7-naphthyridin-1-one; 6-phenyl-8-{[4-(piperazin-1-ylcarbonyl)phenyl]amino}-1,2-dihydro-2,7-naphthyridin-1-one; 4-{[3-(4-methylpiperazin-1-yl)-8-oxo-7,8-dihydro-2,7-naphthyridin-1-yl]amino}-N-[2-(morpholin-4-yl)ethyl]benzamide; 4-({3-[(2-aminoethyl)amino]-8-oxo-7,8-dihydro-2,7-naphthyridin-1-yl}amino)-N-[2-(morpholin-4-yl)ethyl]benzamide; 4-{[3-(4-methoxypyridin-3-yl)-8-oxo-7,8-dihydro-2,7-naphthyridin-1-yl]amino}-N-[2-(morpholin-4-yl)ethyl]benzamide; 6-(2-methoxyphenyl)-8-{[4-(1-methylpiperidin-4-yl)phenyl]amino}-1,2-dihydro-2,7-naphthyridin-1-one; 6-(2-ethoxyphenyl)-8-{[4-(1-methylpiperidin-4-yl)phenyl]amino}-1,2-dihydro-2,7-naphthyridin-1-one; 8-{[4-(1-methylpiperidin-4-yl)phenyl]amino}-6-[2-(propan-2-yloxy)phenyl]-1,2-dihydro-2,7-naphthyridin-1-one; 6-(5-fluoro-2-methoxyphenyl)-8-{[4-(1-methylpiperidin-4-yl)phenyl]amino}-1,2-dihydro-2,7-naphthyridin-1-one; 6-(6-aminopyridin-3-yl)-8-{[5-(4-ethylpiperazin-1-yl)pyridin-2-yl]amino}-1,2-dihydro-2,7-naphthyridin-1-one; 6-(5-methoxypyridin-3-yl)-8-{[4-(piperidin-4-yl)phenyl]amino}-1,2-dihydro-2,7-naphthyridin-1-one; 6-(5-methoxypyridin-3-yl)-8-{[4-(piperidin-3-yl)phenyl]amino}-1,2-dihydro-2,7-naphthyridin-1-one; 6-(5-methoxypyridin-3-yl)-8-{[4-(1-methylpiperidin-3-yl)phenyl]amino}-1,2-dihydro-2,7-naphthyridin-1-one; 8-{[4-(1-methanesulfonylpiperidin-4-yl)phenyl]amino}-6-(5-methoxypyridin-3-yl)-1,2-dihydro-2,7-naphthyridin-1-one; 8-{[4-(1-acetylpiperidin-4-yl)phenyl]amino}-6-(5-methoxypyridin-3-yl)-1,2-dihydro-2,7-naphthyridin-1-one; 6-(3-aminopropyl)-8-({4-[(4-ethylpiperazin-1-yl)methyl]phenyl}amino)-1,2-dihydro-2,7-naphthyridin-1-one; 6-(5-methoxypyridin-3-yl)-8-({4-[2-(morpholin-4-yl)ethoxy]phenyl}amino)-1,2-dihydro-2,7-naphthyridin-1-one; 8-{[4-(morpholin-4-yl)phenyl]amino}-5-[1-(piperidin-4-yl)-1H-pyrazol-4-yl]-1,2-dihydro-2,7-naphthyridin-1-one; 5-{1-[2-(morpholin-4-yl)ethyl]-1H-pyrazol-4-yl}-8-{[4-(morpholin-4-yl)phenyl]amino}-1,2-dihydro-2,7-naphthyridin-1-one; 5-[(E)-2-(3-methoxyphenyl)ethenyl]-8-(phenylamino)-1,2-dihydro-2,7-naphthyridin-1-one; 4-(1-{[4-(1-methylpiperidin-4-yl)phenyl]amino}-8-oxo-7,8-dihydro-2,7-naphthyridin-3-yl)-1,4-thiomorpholine-1,1-dione; 6-(4-acetylpiperazin-1-yl)-8-{[4-(1-methylpiperidin-4-yl)phenyl]amino}-1,2-dihydro-2,7-naphthyridin-1-one; 8-{[4-(1-methylpiperidin-4-yl)phenyl]amino}-6-[4-(piperidin-1-yl)piperidin-1-yl]-1,2-dihydro-2,7-naphthyridin-1-one; 6-(4-hydroxypiperidin-1-yl)-8-{[4-(1-methylpiperidin-4-yl)phenyl]amino}-1,2-dihydro-2,7-naphthyridin-1-one; 8-{[4-(1-methylpiperidin-4-yl)phenyl]amino}-6-[4-(morpholin-4-yl)piperidin-1-yl]-1,2-dihydro-2,7-naphthyridin-1-one; 4-(1-{[4-(1-methylpiperidin-4-yl)phenyl]amino}-8-oxo-7,8-dihydro-2,7-naphthyridin-3-yl)-1,4-thiomorpholin-1-one; 6-(2-methoxypyridin-3-yl)-8-{[4-(1-methylpiperidin-4-yl)phenyl]amino}-1,2-dihydro-2,7-naphthyridin-1-one; N-ethyl-4-(4-{[3-(5-methoxypyridin-3-yl)-8-oxo-7,8-dihydro-2,7-naphthyridin-1-yl]amino}phenyl)piperidine-1-carboxamide 6-(5-methoxypyridin-3-yl)-8-({4-[1-(propan-2-yl)piperidin-4-yl]phenyl}amino)-1,2-dihydro-2,7-naphthyridin-1-one; 8-{[4-(1-cyclopentylpiperidin-4-yl)phenyl]amino}-6-(5-methoxypyridin-3-yl)-1,2-dihydro-2,7-naphthyridin-1-one; 8-({4-[1-(2-methanesulfonylethyl)piperidin-4-yl]phenyl}amino)-6-(5-methoxypyridin-3-yl)-1,2-dihydro-2,7-naphthyridin-1-one; 6-(5-methoxypyridin-3-yl)-8-({4-[1-(3-oxobutyl)piperidin-4-yl]phenyl}amino)-1,2-dihydro-2,7-naphthyridin-1-one; 3-[4-(4-{[3-(5-methoxypyridin-3-yl)-8-oxo-7,8-dihydro-2,7-naphthyridin-1-yl]amino}phenyl)piperidin-1-yl]propanenitrile 4-[(8-oxo-7,8-dihydro-2,7-naphthyridin-1-yl)amino]-N-phenylbenzamide; 4-{[4-(1-methyl-1H-pyrazol-4-yl)-8-oxo-7,8-dihydro-2,7-naphthyridin-1-yl]amino}-N-phenylbenzamide; 4-{[4-(1-methyl-1H-pyrazol-4-yl)-8-oxo-7,8-dihydro-2,7-naphthyridin-1-yl]amino}-N-propylbenzamide; 4-{[3-(4-methylpyridin-3-yl)-8-oxo-7,8-dihydro-2,7-naphthyridin-1-yl]amino}-N-propylbenzamide; 4-{[3-(5-methoxypyridin-3-yl)-8-oxo-7,8-dihydro-2,7-naphthyridin-1-yl]amino}-N-methylbenzamide; N-(2-hydroxyethyl)-4-{[3-(5-methoxypyridin-3-yl)-8-oxo-7,8-dihydro-2,7-naphthyridin-1-yl]amino}benzamide; 4-{[3-(cyclopropylamino)-8-oxo-7,8-dihydro-2,7-naphthyridin-1-yl]amino}-N-propylbenzamide; 8-({4-[3-(dimethylamino)propyl]phenyl}amino)-6-(5-methoxypyridin-3-yl)-1,2-dihydro-2,7-naphthyridin-1-one; 8-[(4-fluorophenyl)amino]-5-(furan-3-yl)-1,2-dihydro-2,7-naphthyridin-1-one; 8-{[4-(morpholin-4-yl)phenyl]amino}-6-[(2,2,2-trifluoroethyl)amino]-1,2-dihydro-2,7-naphthyridin-1-one; N-cyclopropyl-4-{[3-(5-methoxypyridin-3-yl)-8-oxo-7,8-dihydro-2,7-naphthyridin-1-yl]amino}benzamide; 8-{[4-(1-acetylpiperidin-4-yl)phenyl]amino}-6-chloro-1,2-dihydro-2,7-naphthyridin-1-one; 8-{[4-(1-acetylpiperidin-4-yl)phenyl]amino}-6-(1H-indazol-5-yl)-1,2-dihydro-2,7-naphthyridin-1-one; 8-{[4-(1-acetylpiperidin-4-yl)phenyl]amino}-6-(1H-indol-6-yl)-1,2-dihydro-2,7-naphthyridin-1-one; 8-{[4-(1-acetylpiperidin-4-yl)phenyl]amino}-6-(1H-indol-5-yl)-1,2-dihydro-2,7-naphthyridin-1-one; 8-{[4-(1-acetylpiperidin-4-yl)phenyl]amino}-6-(3-fluoropyridin-4-yl)-1,2-dihydro-2,7-naphthyridin-1-one; 8-{[4-(1-acetylpiperidin-4-yl)phenyl]amino}-6-(6-fluoropyridin-3-yl)-1,2-dihydro-2,7-naphthyridin-1-one; 8-{[4-(1-acetylpiperidin-4-yl)phenyl]amino}-6-(2-methoxypyridin-4-yl)-1,2-dihydro-2,7-naphthyridin-1-one; 8-{[4-(1-acetylpiperidin-4-yl)phenyl]amino}-6-(6-fluoro-5-methylpyridin-3-yl)-1,2-dihydro-2,7-naphthyridin-1-one; 5-bromo-6-(1-methyl-1H-pyrazol-4-yl)-8-{[4-(piperidin-4-yl)phenyl]amino}-1,2-dihydro-2,7-naphthyridin-1-one; 6-(3-hydroxypiperidin-1-yl)-8-{[4-(1-methylpiperidin-4-yl)phenyl]amino}-1,2-dihydro-2,7-naphthyridin-1-one; 6-(4,4-difluoropiperidin-1-yl)-8-{[4-(1-methylpiperidin-4-yl)phenyl]amino}-1,2-dihydro-2,7-naphthyridin-1-one; 8-{[4-(1-methylpiperidin-4-yl)phenyl]amino}-6-[3-(trifluoromethyl)piperidin-1-yl]-1,2-dihydro-2,7-naphthyridin-1-one; 6-[4-(hydroxymethyl)piperidin-1-yl]-8-{[4-(1-methylpiperidin-4-yl)phenyl]amino}-1,2-dihydro-2,7-naphthyridin-1-one; 4-({8-oxo-3-[(3R)-piperidin-3-ylamino]-7,8-dihydro-2,7-naphthyridin-1-yl}amino)benzamide; 6-(3-methoxyphenyl)-8-{[4-(1-methylpiperidin-4-yl)phenyl]amino}-1,2-dihydro-2,7-naphthyridin-1-one; 8-{[4-(1-methylpiperidin-4-yl)phenyl]amino}-6-[3-(trifluoromethoxy)phenyl]-1,2-dihydro-2,7-naphthyridin-1-one; 8-{[4-(1-methylpiperidin-4-yl)phenyl]amino}-6-[2-(morpholin-4-yl)pyrimidin-5-yl]-1,2-dihydro-2,7-naphthyridin-1-one; 8-{[4-(1-methylpiperidin-4-yl)phenyl]amino}-6-(pyrimidin-5-yl)-1,2-dihydro-2,7-naphthyridin-1-one; 8-({4-[1-(ethanesulfonyl)piperidin-4-yl]phenyl}amino)-6-(5-methoxypyridin-3-yl)-1,2-dihydro-2,7-naphthyridin-1-one; ethyl 3-[4-(4-{[3-(5-methoxypyridin-3-yl)-8-oxo-7,8-dihydro-2,7-naphthyridin-1-yl]amino}phenyl)piperidin-1-yl] propanoate 6-(3,3-difluoropiperidin-1-yl)-8-{[4-(1-methylpiperidin-4-yl)phenyl]amino}-1,2-dihydro-2,7-naphthyridin-1-one; 8-{[4-(1-methylpiperidin-4-yl)phenyl]amino}-6-[2-(trifluoromethyl)pyrrolidin-1-yl]-1,2-dihydro-2,7-naphthyridin-1-one; 8-{[4-(1-methylpiperidin-4-yl)phenyl]amino}-6-[4-(trifluoromethyl)piperidin-1-yl]-1,2-dihydro-2,7-naphthyridin-1-one; 8-{[4-(1-methylpiperidin-4-yl)phenyl]amino}-6-[(2S)-2-(trifluoromethyl)pyrrolidin-1-yl]-1,2-dihydro-2,7-naphthyridin-1-one; 6-(3,3-difluoropyrrolidin-1-yl)-8-{[4-(1-methylpiperidin-4-yl)phenyl]amino}-1,2-dihydro-2,7-naphthyridin-1-one; 6-(3-fluoropiperidin-1-yl)-8-{[4-(1-methylpiperidin-4-yl)phenyl]amino}-1,2-dihydro-2,7-naphthyridin-1-one; 4-bromo-6-(4-ethylpiperazin-1-yl)-8-{[4-(morpholin-4-yl)phenyl]amino}-1,2-dihydro-2,7-naphthyridin-1-one; 6-[(3S)-3-fluoropyrrolidin-1-yl]-8-{[4-(1-methylpiperidin-4-yl)phenyl]amino}-1,2-dihydro-2,7-naphthyridin-1-one; 4-chloro-6-(4-ethylpiperazin-1-yl)-8-{[4-(morpholin-4-yl)phenyl]amino}-1,2-dihydro-2,7-naphthyridin-1-one; 6-(4-ethylpiperazin-1-yl)-4-iodo-8-{[4-(morpholin-4-yl)phenyl]amino}-1,2-dihydro-2,7-naphthyridin-1-one; 5-(1-methyl-1H-pyrazol-4-yl)-8-{[4-(morpholin-4-ylcarbonyl)phenyl]amino}-1,2-dihydro-2,7-naphthyridin-1-one; 5-iodo-6-(1-methyl-1H-pyrazol-4-yl)-8-{[4-(piperidin-4-yl)phenyl]amino}-1,2-dihydro-2,7-naphthyridin-1-one; 5-chloro-6-(1-methyl-1H-pyrazol-4-yl)-8-{[4-(piperidin-4-yl)phenyl]amino}-1,2-dihydro-2,7-naphthyridin-1-one; 5-{1-[(4-fluorophenyl)amino]-8-oxo-7,8-dihydro-2,7-naphthyridin-4-yl}furan-2-carbonitrile 6-(2-aminopyrimidin-5-yl)-8-{[4-(1-methylpiperidin-4-yl)phenyl]amino}-1,2-dihydro-2,7-naphthyridin-1-one; 6-(2,4-dimethoxypyrimidin-5-yl)-8-{[4-(1-methylpiperidin-4-yl)phenyl]amino}-1,2-dihydro-2,7-naphthyridin-1-one; 8-{[4-(1-methylpiperidin-4-yl)phenyl]amino}-6-[4-(propan-2-yl)pyrimidin-5-yl]-1,2-dihydro-2,7-naphthyridin-1-one; 6-(5-methanesulfonylpyridin-3-yl)-8-{[4-(1-methylpiperidin-4-yl)phenyl]amino}-1,2-dihydro-2,7-naphthyridin-1-one; ethyl 5-(1-{[4-(1-methylpiperidin-4-yl)phenyl]amino}-8-oxo-7,8-dihydro-2,7-naphthyridin-3-yl)pyridine-3-carboxylate; 8-{[4-(1-methylpiperidin-4-yl)phenyl]amino}-6-[5-(morpholin-4-yl)pyrazin-2-yl]-1,2-dihydro-2,7-naphthyridin-1-one; 8-{[4-(1-methylpiperidin-4-yl)phenyl]amino}-6-(4-methylpyridin-3-yl)-1,2-dihydro-2,7-naphthyridin-1-one; 8-{[4-(1-methanesulfonylpiperidin-4-yl)phenyl]amino}-6-[1-(2-methylpropyl)-1H-pyrazol-4-yl]-1,2-dihydro-2,7-naphthyridin-1-one; 8-{[4-(1-methanesulfonylpiperidin-4-yl)phenyl]amino}-6-(2-methoxyphenyl)-1,2-dihydro-2,7-naphthyridin-1-one; 8-{[4-(1-methanesulfonylpiperidin-4-yl)phenyl]amino}-6-phenyl-1,2-dihydro-2,7-naphthyridin-1-one; 6-(6-fluoropyridin-3-yl)-8-{[4-(1-methanesulfonylpiperidin-4-yl)phenyl]amino}-1,2-dihydro-2,7-naphthyridin-1-one; 8-{[4-(piperidin-4-yl)phenyl]amino}-6-(1,3,5-trimethyl-1H-pyrazol-4-yl)-1,2-dihydro-2,7-naphthyridin-1-one; 8-{[4-(1-methanesulfonylpiperidin-4-yl)phenyl]amino}-6-(1-methyl-1H-pyrazol-4-yl)-1,2-dihydro-2,7-naphthyridin-1-one; 6-[1-(1-methanesulfonylpiperidin-4-yl)-1H-pyrazol-4-yl]-8-{[4-(morpholin-4-yl)phenyl]amino}-1,2-dihydro-2,7-naphthyridin-1-one; 6-[1-(1-acetylpiperidin-4-yl)-1H-pyrazol-4-yl]-8-{[4-(morpholin-4-yl)phenyl]amino}-1,2-dihydro-2,7-naphthyridin-1-one; N,2-dimethyl-2-(4-{[8-oxo-3-(pyrimidin-5-yl)-7,8-dihydro-2,7-naphthyridin-1-yl]amino}phenyl)propanamide 4-{[8-oxo-3-(pyrimidin-5-yl)-7,8-dihydro-2,7-naphthyridin-1-yl]amino}-N-propylbenzamide; 8-{[4-(4-hydroxypiperidin-1-yl)phenyl]amino}-6-(pyrimidin-5-yl)-1,2-dihydro-2,7-naphthyridin-1-one; N-cyclopentyl-4-{[8-oxo-3-(pyrimidin-5-yl)-7,8-dihydro-2,7-naphthyridin-1-yl]amino}benzamide; 4-({8-oxo-3-[(2,2,2-trifluoroethyl)amino]-7,8-dihydro-2,7-naphthyridin-1-yl}amino)-N-propylbenzamide; N,2-dimethyl-2-[4-({8-oxo-3-[(2,2,2-trifluoroethyl)amino]-7,8-dihydro-2,7-naphthyridin-1-yl}amino)phenyl]propanamide 8-[(4-fluorophenyl)amino]-5-(3-phenylpropyl)-1,2-dihydro-2,7-naphthyridin-1-one; 6-(4-ethylpiperazin-1-yl)-8-{[4-(morpholin-4-yl)phenyl]amino}-1-oxo-1,2-dihydro-2,7-naphthyridine-4-carbonitrile 1-(benzylamino)-8-oxo-7,8-dihydro-2,7-naphthyridine-4-carbonitrile 6-(4-methylpyridin-3-yl)-8-{[4-(morpholin-4-yl)phenyl]amino}-1,2-dihydro-2,7-naphthyridin-1-one; 6-chloro-8-{[4-(pyridin-3-yl)phenyl]amino}-1,2-dihydro-2,7-naphthyridin-1-one; 6-chloro-8-[(4-{2H,3H-imidazo[2,1-b][1,3]thiazol-6-yl}phenyl)amino]-1,2-dihydro-2,7-naphthyridin-1-one; 6-chloro-8-{[4-(1H-imidazol-4-yl)phenyl]amino}-1,2-dihydro-2,7-naphthyridin-1-one; 6-chloro-8-{[4-(1,3-oxazol-4-yl)phenyl]amino}-1,2-dihydro-2,7-naphthyridin-1-one; 6-(5-methanesulfonylpyridin-3-yl)-8-{[4-(pyridin-3-yl)phenyl]amino}-1,2-dihydro-2,7-naphthyridin-1-one; 8-[(4-{2H,3H-imidazo[2,1-b][1,3]thiazol-6-yl}phenyl)amino]-6-(5-methanesulfonylpyridin-3-yl)-1,2-dihydro-2,7-naphthyridin-1-one; 8-{[4-(1H-imidazol-4-yl)phenyl]amino}-6-(5-methanesulfonylpyridin-3-yl)-1,2-dihydro-2,7-naphthyridin-1-one; 8-{[4-(1-acetylpiperidin-4-yl)phenyl]amino}-6-(6-methoxypyridin-3-yl)-1,2-dihydro-2,7-naphthyridin-1-one; 5-(1-{[4-(1-acetylpiperidin-4-yl)phenyl]amino}-8-oxo-7,8-dihydro-2,7-naphthyridin-3-yl)pyridine-3-carbonitrile 8-{[4-(1-acetylpiperidin-4-yl)phenyl]amino}-6-(6-methylpyridin-3-yl)-1,2-dihydro-2,7-naphthyridin-1-one; 8-{[4-(1-acetylpiperidin-4-yl)phenyl]amino}-6-[6-(piperidin-1-yl)pyridin-3-yl]-1,2-dihydro-2,7-naphthyridin-1-one; 6-[(2-aminoethyl)amino]-8-{[4-(oxan-4-yl)phenyl]amino}-1,2-dihydro-2,7-naphthyridin-1-one; 6-(4-ethylpiperazin-1-yl)-8-{[4-(oxan-4-yl)phenyl]amino}-1,2-dihydro-2,7-naphthyridin-1-one; 8-{[4-(oxan-4-yl)phenyl]amino}-6-[(3R)-piperidin-3-ylamino]-1,2-dihydro-2,7-naphthyridin-1-one; 6-(2-chlorophenyl)-8-{[4-(oxan-4-yl)phenyl]amino}-1,2-dihydro-2,7-naphthyridin-1-one; 6-(5-methoxypyridin-3-yl)-8-{[4-(oxan-4-yl)phenyl]amino}-1,2-dihydro-2,7-naphthyridin-1-one; 6-[1-(2-methylpropyl)-1H-pyrazol-4-yl]-8-{[4-(oxan-4-yl)phenyl]amino}-1,2-dihydro-2,7-naphthyridin-1-one; 6-[(3aS,6aS)-octahydropyrrolo[3,4-c]pyrrol-2-yl]-8-{[4-(morpholin-4-yl)phenyl]amino}-1,2-dihydro-2,7-naphthyridin-1-one; 6-(4-ethylpiperazin-1-yl)-4-methyl-8-{[4-(morpholin-4-yl)phenyl]amino}-1,2-dihydro-2,7-naphthyridin-1-one; 8-[(4-fluorophenyl)amino]-5-(3-hydroxy-3-phenylpropyl)-1,2-dihydro-2,7-naphthyridin-1-one; 8-{[4-(1-cyclopropylpiperidin-4-yl)phenyl]amino}-6-(3,3-difluoropyrrolidin-1-yl)-1,2-dihydro-2,7-naphthyridin-1-one; 8-{[4-(1-cyclopropylpiperidin-4-yl)phenyl]amino}-6-[4-(2-hydroxypropan-2-yl)piperidin-1-yl]-1,2-dihydro-2,7-naphthyridin-1-one; N-cyclopentyl-4-({8-oxo-3-[(2,2,2-trifluoro ethyl)amino]-7,8-dihydro-2,7-naphthyridin-1-yl}amino)benzamide; 6-(2-methylpyrimidin-5-yl)-8-{[4-(morpholin-4-yl)phenyl]amino}-1,2-dihydro-2,7-naphthyridin-1-one; 6-[2-(dimethylamino)pyrimidin-5-yl]-8-{[4-(morpholin-4-yl)phenyl]amino}-1,2-dihydro-2,7-naphthyridin-1-one; 5-(1-{[4-(morpholin-4-yl)phenyl]amino}-8-oxo-7,8-dihydro-2,7-naphthyridin-3-yl)pyridine-3-carbonitrile N-methyl-4-{[8-oxo-3-(pyrimidin-5-yl)-7,8-dihydro-2,7-naphthyridin-1-yl]amino}benzamide; 4-{[3-(2,6-dimethylpyridin-3-yl)-8-oxo-7,8-dihydro-2,7-naphthyridin-1-yl]amino}-N-methylbenzamide; 4-({3-[2-(dimethylamino)pyrimidin-5-yl]-8-oxo-7,8-dihydro-2,7-naphthyridin-1-yl}amino)-N-methylbenzamide; 8-({4-[2-(morpholin-4-yl)ethoxy]

phenyl}amino)-6-[4-(propan-2-yl)pyrimidin-5-yl]-1,2-dihydro-2,7-naphthyridin-1-one; 2-(4-{[3-(5-methanesulfonylpyridin-3-yl)-8-oxo-7,8-dihydro-2,7-naphthyridin-1-yl]amino}phenyl)-N,2-dimethylpropanamide 8-{[4-(1-acetylpiperidin-4-yl)phenyl]amino}-6-(3,3-difluoropyrrolidin-1-yl)-1,2-dihydro-2,7-naphthyridin-1-one; 6-chloro-8-[(2-methyl-1-oxo-2,3-dihydro-1H-isoindol-5-yl)amino]-1,2-dihydro-2,7-naphthyridin-1-one; 6-chloro-8-[(2-methyl-3-oxo-2,3-dihydro-1H-isoindol-5-yl)amino]-1,2-dihydro-2,7-naphthyridin-1-one; 6-(5-methoxypyridin-3-yl)-8-[(2-methyl-1-oxo-2,3-dihydro-1H-iso indol-5-yl)amino]-1,2-dihydro-2,7-naphthyridin-1-one; 6-(5-methoxypyridin-3-yl)-8-[(2-methyl-3-oxo-2,3-dihydro-1H-isoindol-5-yl)amino]-1,2-dihydro-2,7-naphthyridin-1-one; 3-{[3-(5-methoxypyridin-3-yl)-8-oxo-7,8-dihydro-2,7-naphthyridin-1-yl]amino}-N-methylbenzamide; 8-{[4-(1-acetylpiperidin-4-yl)phenyl]amino}-6-(2,6-difluoropyridin-3-yl)-1,2-dihydro-2,7-naphthyridin-1-one; 8-{[4-(1-acetylpiperidin-4-yl)phenyl]amino}-6-{imidazo[1,2-a]pyridin-6-yl}-1,2-dihydro-2,7-naphthyridin-1-one; 8-{[4-(1-acetylpiperidin-4-yl)phenyl]amino}-6-(5-fluoropyridin-3-yl)-1,2-dihydro-2,7-naphthyridin-1-one; 3-[(3-chloro-8-oxo-7,8-dihydro-2,7-naphthyridin-1-yl)amino]-N-methylbenzamide; 8-{[4-(1-acetylpiperidin-4-yl)phenyl]amino}-6-(6-fluoro-2-methylpyridin-3-yl)-1,2-dihydro-2,7-naphthyridin-1-one; 6-(5-methoxypyridin-3-yl)-8-{[4-(1,3-oxazol-4-yl)phenyl]amino}-1,2-dihydro-2,7-naphthyridin-1-one; 8-{[4-(1-acetylpiperidin-4-yl)phenyl]amino}-6-{1H-pyrrolo[2,3-b]pyridin-5-yl}-1,2-dihydro-2,7-naphthyridin-1-one; 5-(1-{[4-(1-acetylpiperidin-4-yl)phenyl]amino}-8-oxo-7,8-dihydro-2,7-naphthyridin-3-yl)pyridine-2-carbonitrile 6-(6-fluoro-2-methylpyridin-3-yl)-8-{[4-(1-methanesulfonylpiperidin-4-yl)phenyl]amino}-1,2-dihydro-2,7-naphthyridin-1-one; 6-(2,6-difluoropyridin-3-yl)-8-{[4-(1-methanesulfonylpiperidin-4-yl)phenyl]amino}-1,2-dihydro-2,7-naphthyridin-1-one; 5-(1-{[4-(1-acetylpiperidin-4-yl)phenyl]amino}-8-oxo-7,8-dihydro-2,7-naphthyridin-3-yl)-N-methylpyridine-2-carboxamide 6-chloro-8-{[4-(1-methanesulfonylpiperidin-3-yl)phenyl]amino}-1,2-dihydro-2,7-naphthyridin-1-one; 6-chloro-8-{[4-(1-methanesulfonylpyrrolidin-3-yl)phenyl]amino}-1,2-dihydro-2,7-naphthyridin-1-one; 6-chloro-8-{[4-(1-methylpyrrolidin-3-yl)phenyl]amino}-1,2-dihydro-2,7-naphthyridin-1-one; 4-chloro-6-(1-methyl-1H-pyrazol-4-yl)-8-{[4-(piperidin-4-yl)phenyl]amino}-1,2-dihydro-2,7-naphthyridin-1-one; 4-chloro-6-(5-methoxypyridin-3-yl)-8-{[4-(piperidin-4-yl)phenyl]amino}-1,2-dihydro-2,7-naphthyridin-1-one; 6-(3,3-difluoropyrrolidin-1-yl)-8-{[4-(1-methanesulfonylpiperidin-4-yl)phenyl]amino}-1,2-dihydro-2,7-naphthyridin-1-one; 4-({3-[4-(2-hydroxypropan-2-yl)piperidin-1-yl]-8-oxo-7,8-dihydro-2,7-naphthyridin-1-yl}amino)-N-methylbenzamide; 4-{[3-(1-methyl-1H-pyrazol-4-yl)-8-oxo-7,8-dihydro-2,7-naphthyridin-1-yl]amino}-N-propylbenzamide; 4-({3-[1-(2-methylpropyl)-1H-pyrazol-4-yl]-8-oxo-7,8-dihydro-2,7-naphthyridin-1-yl}amino)-N-propylbenzamide; 4-[(3-{1-[2-(morpholin-4-yl)ethyl]-1H-pyrazol-4-yl}-8-oxo-7,8-dihydro-2,7-naphthyridin-1-yl)amino]-N-propylbenzamide; 4-({8-oxo-3-[1-(piperidin-4-yl)-1H-pyrazol-4-yl]-7,8-dihydro-2,7-naphthyridin-1-yl}amino)-N-propylbenzamide; 4-{[3-(3-methyl-1H-pyrazol-4-yl)-8-oxo-7,8-dihydro-2,7-naphthyridin-1-yl]amino}-N-propylbenzamide; N-methyl-4-{[3-(1-methyl-1H-pyrazol-4-yl)-8-oxo-7,8-dihydro-2,7-naphthyridin-1-yl]amino}benzamide; N-methyl-4-{[3-(1-(2-methylpropyl)-1H-pyrazol-4-yl]-8-oxo-7,8-dihydro-2,7-naphthyridin-1-yl}amino)benzamide; N-methyl-4-[(3-{1-

[2-(morpholin-4-yl)ethyl]-1H-pyrazol-4-yl}-8-oxo-7,8-dihydro-2,7-naphthyridin-1-yl)amino]benzamide; N-methyl-4-({8-oxo-3-[1-(piperidin-4-yl)-1H-pyrazol-4-yl]-7,8-dihydro-2,7-naphthyridin-1-yl}amino)benzamide; N,2-dimethyl-2-[4-(8-oxo-1-{[4-(piperidin-4-yl)phenyl]amino}-7,8-dihydro-2,7-naphthyridin-3-yl)-1H-pyrazol-1-yl]propanamide N-ethyl-2-methyl-2-[4-(8-oxo-1-{[4-(piperidin-4-yl)phenyl]amino}-7,8-dihydro-2,7-naphthyridin-3-yl)-1H-pyrazol-1-yl]propanamide N,N,2-trimethyl-2-[4-(8-oxo-1-{[4-(piperidin-4-yl)phenyl]amino}-7,8-dihydro-2,7-naphthyridin-3-yl)-1H-pyrazol-1-yl]propanamide 6-{1-[2-methyl-1-oxo-1-(pyrrolidin-1-yl)propan-2-yl}-1H-pyrazol-4-yl]-8-{[4-(piperidin-4-yl)phenyl]amino}-1,2-dihydro-2,7-naphthyridin-1-one; 8-({4-[(4-ethylpiperazin-1-yl)methyl]phenyl}amino)-6-(5-methanesulfonylpyridin-3-yl)-1,2-dihydro-2,7-naphthyridin-1-one; 8-({4-[(4-ethylpiperazin-1-yl)methyl]phenyl}amino)-6-(pyrimidin-5-yl)-1,2-dihydro-2,7-naphthyridin-1-one; N-methyl-4-({8-oxo-3-[(2,2,2-trifluoroethyl)amino]-7,8-dihydro-2,7-naphthyridin-1-yl}amino)benzamide; N,N-dimethyl-4-{[8-oxo-3-(pyrimidin-5-yl)-7,8-dihydro-2,7-naphthyridin-1-yl]amino}benzamide; 4-{[3-(5-methanesulfonylpyridin-3-yl)-8-oxo-7,8-dihydro-2,7-naphthyridin-1-yl]amino}-N-methylbenzamide; 6-(2-aminopyrimidin-5-yl)-8-{[4-(morpholin-4-yl)phenyl]amino}-1,2-dihydro-2,7-naphthyridin-1-one; 6-(3-methanesulfonylphenyl)-8-{[4-(morpholin-4-yl)phenyl]amino}-1,2-dihydro-2,7-naphthyridin-1-one; 3-(1-{[4-(morpholin-4-yl)phenyl]amino}-8-oxo-7,8-dihydro-2,7-naphthyridin-3-yl)benzene-1-sulfonamide; N-methyl-4-{[3-(4-methylpyridin-3-yl)-8-oxo-7,8-dihydro-2,7-naphthyridin-1-yl]amino}benzamide; N-tert-butyl-5-(1-{[4-(morpholin-4-yl)phenyl]amino}-8-oxo-7,8-dihydro-2,7-naphthyridin-3-yl)pyridine-3-carboxamide N-tert-butyl-5-(1-{[4-(morpholin-4-yl)phenyl]amino}-8-oxo-7,8-dihydro-2,7-naphthyridin-3-yl)pyridine-3-carboxamide 8-{[4-(1-methanesulfonylpiperidin-4-yl)phenyl]amino}-6-(pyrimidin-5-yl)-1,2-dihydro-2,7-naphthyridin-1-one; 8-{[4-(1-methanesulfonylpiperidin-4-yl)phenyl]amino}-6-(2-methoxypyrimidin-5-yl)-1,2-dihydro-2,7-naphthyridin-1-one; 8-{[4-(1-methanesulfonylpiperidin-4-yl)phenyl]amino}-6-(4-methylpyridin-3-yl)-1,2-dihydro-2,7-naphthyridin-1-one; 8-{[4-(1-methanesulfonylpyrrolidin-3-yl)phenyl]amino}-6-(5-methoxypyridin-3-yl)-1,2-dihydro-2,7-naphthyridin-1-one; 6-(5-methoxypyridin-3-yl)-8-{[4-(1-methylpyrrolidin-3-yl)phenyl]amino}-1,2-dihydro-2,7-naphthyridin-1-one; 6-(2,6-dimethylpyridin-3-yl)-8-{[4-(1-methanesulfonylpiperidin-4-yl)phenyl]amino}-1,2-dihydro-2,7-naphthyridin-1-one; 8-{[4-(1-methanesulfonylpiperidin-4-yl)phenyl]amino}-6-{1-[2-(morpholin-4-yl)ethyl]-1H-pyrazol-4-yl}-1,2-dihydro-2,7-naphthyridin-1-one; 5-bromo-6-[1-(2-methylpropyl)-1H-pyrazol-4-yl]-8-{[4-(piperidin-4-yl)phenyl]amino}-1,2-dihydro-2,7-naphthyridin-1-one; 8-{[4-(1-acetylpiperidin-4-yl)phenyl]amino}-5-(3-hydroxy-3-phenylpropyl)-1,2-dihydro-2,7-naphthyridin-1-one; N-methyl-4-{[8-oxo-3-(2-oxopyrrolidin-1-yl)-7,8-dihydro-2,7-naphthyridin-1-yl]amino}benzamide; N-methyl-4-{[8-oxo-3-(2-oxopiperidin-1-yl)-7,8-dihydro-2,7-naphthyridin-1-yl]amino}benzamide; 8-{[4-(1-cyclopropylpiperidin-4-yl)phenyl]amino}-6-(2-oxopyrrolidin-1-yl)-1,2-dihydro-2,7-naphthyridin-1-one; 2-[(1-{[4-(morpholin-4-yl)phenyl]amino}-8-oxo-7,8-dihydro-2,7-naphthyridin-3-yl)amino]benzene-1-sulfonamide; 6-{[2-(difluoromethane)sulfonylphenyl]amino}-8-{[4-(morpholin-4-yl)phenyl]amino}-1,2-dihydro-2,7-naphthyridin-1-one; 6-(5-methoxypyridin-3-yl)-8-{[2-(propane-2-sulfonyl)phenyl]amino}-1,2-dihydro-2,7-naphthyridin-1-one; 4-{[3-(2,4- dimethoxypyrimidin-5-yl)-8-oxo-7,8-dihydro-2,7-naphthyridin-1-yl]amino}-N,2-dimethylbenzamide; 4-{[3-(5-methoxypyridin-3-yl)-8-oxo-7,8-dihydro-2,7-naphthyridin-1-yl]amino}-N,2-dimethylbenzamide; 8-{[4-(1-ethylpiperidin-4-yl)phenyl]amino}-6-(5-methanesulfonylpyridin-3-yl)-1,2-dihydro-2,7-naphthyridin-1-one; 8-{[4-(1-methanesulfonylpiperidin-3-yl)phenyl]amino}-6-(5-methoxypyridin-3-yl)-1,2-dihydro-2,7-naphthyridin-1-one; 5-chloro-6-(5-methoxypyridin-3-yl)-8-{[4-(piperidin-4-yl)phenyl]amino}-1,2-dihydro-2,7-naphthyridin-1-one; 8-[(4-{1-[2-(dimethylamino)acetyl]piperidin-4-yl}phenyl)amino]-6-[1-(2-methylpropyl)-1H-pyrazol-4-yl]-1,2-dihydro-2,7-naphthyridin-1-one; 8-{[4-(morpholin-4-yl)phenyl]amino}-6-[1-(pyridin-2-ylmethyl)-1H-pyrazol-4-yl]-1,2-dihydro-2,7-naphthyridin-1-one; 8-{[4-(piperidin-4-yl)phenyl]amino}-6-[1-(pyridin-2-ylmethyl)-1H-pyrazol-4-yl]-1,2-dihydro-2,7-naphthyridin-1-one; N-methyl-4-({8-oxo-3-[1-(pyridin-2-ylmethyl)-1H-pyrazol-4-yl]-7,8-dihydro-2,7-naphthyridin-1-yl}amino)benzamide; 8-{[4-(oxan-4-yl)phenyl]amino}-6-[1-(pyridin-2-ylmethyl)-1H-pyrazol-4-yl]-1,2-dihydro-2,7-naphthyridin-1-one; 8-({4-[1-(2-methanesulfonylethyl)piperidin-4-yl]phenyl}amino)-6-[1-(2-methylpropyl)-1H-pyrazol-4-yl]-1,2-dihydro-2,7-naphthyridin-1-one; 6-(3,3-difluoropiperidin-1-yl)-8-{[4-(oxan-4-yl)phenyl]amino}-1,2-dihydro-2,7-naphthyridin-1-one; 8-{[4-(1-methanesulfonylpyrrolidin-3-yl)phenyl]amino}-6-(1-methyl-1H-pyrazol-4-yl)-1,2-dihydro-2,7-naphthyridin-1-one; 8-({4-[1-(2-methanesulfonylacetyl)piperidin-4-yl]phenyl}amino)-6-[1-(2-methylpropyl)-1H-pyrazol-4-yl]-1,2-dihydro-2,7-naphthyridin-1-one; 6-[1-(3-methylbutyl)-1H-pyrazol-4-yl]-8-{[4-(oxan-4-yl)phenyl]amino}-1,2-dihydro-2,7-naphthyridin-1-one; 8-{[4-(morpholin-4-yl)phenyl]amino}-6-[5-(propane-2-sulfonyl)pyridin-3-yl]-1,2-dihydro-2,7-naphthyridin-1-one; 8-{[4-(piperidin-4-yl)phenyl]amino}-6-[5-(propane-2-sulfonyl)pyridin-3-yl]-1,2-dihydro-2,7-naphthyridin-1-one; N-methyl-4-{[8-oxo-3-(2-oxoazepan-1-yl)-7,8-dihydro-2,7-naphthyridin-1-yl]amino}benzamide; 6-(3,3-difluoropyrrolidin-1-yl)-8-{[4-(oxan-4-yl)phenyl]amino}-1,2-dihydro-2,7-naphthyridin-1-one; 8-{[4-(1-cyclopropylpiperidin-4-yl)phenyl]amino}-6-(3-methanesulfonylphenyl)-1,2-dihydro-2,7-naphthyridin-1-one; 8-({6-[(2R,6S)-2,6-dimethylmorpholin-4-yl]pyridin-3-yl}amino)-6-(3-methanesulfonylphenyl)-1,2-dihydro-2,7-naphthyridin-1-one; 2-{[1-({6-[(2R,6S)-2,6-dimethylmorpholin-4-yl]pyridin-3-yl}amino)-8-oxo-7,8-dihydro-2,7-naphthyridin-3-yl]amino}benzene-1-sulfonamide; 4-({8-oxo-3-[(2-sulfamoylphenyl)amino]-7,8-dihydro-2,7-naphthyridin-1-yl}amino)-N-propylbenzamide; N,2-dimethyl-4-({8-oxo-3-[(2-sulfamoylphenyl)amino]-7,8-dihydro-2,7-naphthyridin-1-yl}amino)benzamide; 2-[(8-oxo-1-{[4-(piperidin-4-yl)phenyl]amino}-7,8-dihydro-2,7-naphthyridin-3-yl)amino]benzene-1-sulfonamide; 2-[(1-{[4-(morpholin-4-yl)phenyl]amino}-8-oxo-7,8-dihydro-2,7-naphthyridin-3-yl)amino]benzamide; 6-[(4-fluoro-2-methylphenyl)amino]-8-{[4-(morpholin-4-yl)phenyl]amino}-1,2-dihydro-2,7-naphthyridin-1-one; 8-{[4-(morpholin-4-yl)phenyl]amino}-6-{[2-(propane-2-sulfonyl)phenyl]amino}-1,2-dihydro-2,7-naphthyridin-1-one; 6-(3-methanesulfonylphenyl)-8-{[4-(piperidin-4-yl)phenyl]amino}-1,2-dihydro-2,7-naphthyridin-1-one; 4-{[3-(3-methanesulfonylphenyl)-8-oxo-7,8-dihydro-2,7-naphthyridin-1-yl]amino}-N-propylbenzamide; N-ethyl-3-(1-{[4-(morpholin-4-yl)phenyl]amino}-8-oxo-7,8-dihydro-2,7-naphthyridin-3-yl)benzene-1-sulfonamide; 8-{[4-(1-methanesulfonylpyrrolidin-3-yl)phenyl]amino}-6-(pyrimidin-5-yl)-1,2-dihydro-2,7-naphthyridin-1-one; 3-{[3-(5-methoxypyridin-3-yl)-8-oxo-7,8-dihydro-2,7-naphthyridin-1-yl]amino}-N-methylbenzene-1-sulfonamide; 6-[5-(ethanesulfonyl)pyridin-3-yl]-8-{[4-(morpholin-4-yl)phenyl]amino}-1,2-dihydro-2,7-naphthyridin-1-one; 6-[5-(ethanesulfonyl)pyridin-3-yl]-8-{[4-(piperidin-4-yl)phenyl]amino}-1,2-dihydro-2,7-naphthyridin-1-one; 6-[5-(ethanesulfonyl)pyridin-3-yl]-8-{[4-(1-methanesulfonylpiperidin-4-yl)phenyl]amino}-1,2-dihydro-2,7-naphthyridin-1-one; 4-({3-[5-(ethanesulfonyl)pyridin-3-yl]-8-oxo-7,8-dihydro-2,7-naphthyridin-1-yl}amino)-N-methylbenzamide; 8-{[4-(1-methylpiperidin-4-yl)phenyl]amino}-6-[5-(propane-2-sulfonyl)pyridin-3-yl]-1,2-dihydro-2,7-naphthyridin-1-one; 6-[5-(ethanesulfonyl)pyridin-3-yl]-8-{[4-(1-methylpiperidin-4-yl)phenyl]amino}-1,2-dihydro-2,7-naphthyridin-1-one; 8-{[4-(1-methylpiperidin-4-yl)phenyl]amino}-6-[1-(2-methylpropyl)-1H-pyrazol-4-yl]-1,2-dihydro-2,7-naphthyridin-1-one; 2,2-dimethyl-6-(1-{[4-(morpholin-4-yl)phenyl]amino}-8-oxo-7,8-dihydro-2,7-naphthyridin-3-yl)-3,4-dihydro-2H-1,4-benzoxazin-3-one; 2,2-dimethyl-7-(1-{[4-(morpholin-4-yl)phenyl]amino}-8-oxo-7,8-dihydro-2,7-naphthyridin-3-yl)-3,4-dihydro-2H-1,4-benzoxazin-3-one; 7-[(1-{[4-(morpholin-4-yl)phenyl]amino}-8-oxo-7,8-dihydro-2,7-naphthyridin-3-yl)amino]-3,4-dihydro-2H-1,4-benzoxazin-3-one; 2,2-dimethyl-6-[(1-{[4-(morpholin-4-yl)phenyl]amino}-8-oxo-7,8-dihydro-2,7-naphthyridin-3-yl)amino]-3,4-dihydro-2H-1,4-benzoxazin-3-one; N-methyl-2-[(1-{[4-(morpholin-4-yl)phenyl]amino}-8-oxo-7,8-dihydro-2,7-naphthyridin-3-yl)amino]benzamide; 8-{[4-(1-methylpiperidin-4-yl)phenyl]amino}-6-(2-methylpyrimidin-5-yl)-1,2-dihydro-2,7-naphthyridin-1-one; 6-(2,3-dihydro-1H-indol-1-yl)-8-{[4-(morpholin-4-yl)phenyl]amino}-1,2-dihydro-2,7-naphthyridin-1-one; 6-(1-methyl-1H-pyrazol-4-yl)-8-{[3-methyl-4-(piperidin-4-yl)phenyl]amino}-1,2-dihydro-2,7-naphthyridin-1-one; 8-{[3-methyl-4-(piperidin-4-yl)phenyl]amino}-6-[1-(2-methylpropyl)-1H-pyrazol-4-yl]-1,2-dihydro-2,7-naphthyridin-1-one; 6-(5-methoxypyridin-3-yl)-8-{[3-methyl-4-(piperidin-4-yl)phenyl]amino}-1,2-dihydro-2,7-naphthyridin-1-one; 3-(1-{[3-methyl-4-(piperidin-4-yl)phenyl]amino}-8-oxo-7,8-dihydro-2,7-naphthyridin-3-yl)benzene-1-sulfonamide; 6-(3-methanesulfonylphenyl)-8-[4-(morpholin-4-yl)phenoxy]-1,2-dihydro-2,7-naphthyridin-1-one; 6-[2-(methylsulfanyl)pyrimidin-5-yl]-8-{[4-(piperidin-4-yl)phenyl]amino}-1,2-dihydro-2,7-naphthyridin-1-one; 6-(6-{[2-(morpholin-4-yl)ethyl]amino}pyridin-3-yl)-8-{[4-(piperidin-4-yl)phenyl]amino}-1,2-dihydro-2,7-naphthyridin-1-one; 6-(1-methyl-1H-pyrazol-4-yl)-8-{[6-(piperidin-4-yl)pyridin-3-yl]amino}-1,2-dihydro-2,7-naphthyridin-1-one; 6-(5-methoxypyridin-3-yl)-8-{[6-(piperidin-4-yl)pyridin-3-yl]amino}-1,2-dihydro-2,7-naphthyridin-1-one; 6-acetyl-8-{[4-(morpholin-4-yl)phenyl]amino}-1,2-dihydro-2,7-naphthyridin-1-one; 6-[(1E)-1-(methoxyimino)ethyl]-8-{[4-(morpholin-4-yl)phenyl]amino}-1,2-dihydro-2,7-naphthyridin-1-one; 2-[(1-{[4-(1-acetylpiperidin-4-yl)phenyl]amino}-8-oxo-7,8-dihydro-2,7-naphthyridin-3-yl)amino]benzene-1-sulfonamide; 2-[(1-{[4-(oxan-4-yl)phenyl]amino}-8-oxo-7,8-dihydro-2,7-naphthyridin-3-yl)amino]benzene-1-sulfonamide; 2-{[(1-[4-(1-methanesulfonylpiperidin-4-yl)phenyl]amino}-8-oxo-7,8-dihydro-2,7-naphthyridin-3-yl)amino]benzene-1-sulfonamide; 2-{[1-({4-[2-(morpholin-4-yl)ethoxy]phenyl}amino)-8-oxo-7,8-dihydro-2,7-naphthyridin-3-yl]amino}benzene-1-sulfonamide; tert-butyl 4-(4-{[8-oxo-3-(1,3,5-trimethyl-1H-pyrazol-4-yl)-7,8-dihydro-2,7-naphthyridin-1-yl]amino}phenyl)piperidine-1-carboxylate; 5-(8-oxo-1-{[4-(piperidin-4-yl)phenyl]amino}-7,8-dihydro- 2,7-naphthyridin-3-yl)pyridine-3-sulfonamide; 5-(1-{[4-(morpholin-4-yl)phenyl]amino}-8-oxo-7,8-dihydro-2,7-naphthyridin-3-yl)pyridine-3-sulfonamide; 5-(1-{[4-(1-ethylpiperidin-4-yl)phenyl]amino}-8-oxo-7,8-dihydro-2,7-naphthyridin-3-yl)pyridine-3-sulfonamide; 5-[1-({4-[1-(2-hydroxyethyl)piperidin-4-yl]phenyl}amino)-8-oxo-7,8-dihydro-2,7-naphthyridin-3-yl]pyridine-3-sulfonamide; 5-(1-{[4-(1-acetylpiperidin-4-yl)phenyl]amino}-8-oxo-7,8-dihydro-2,7-naphthyridin-3-yl)pyridine-3-sulfonamide; N-methyl-4-{[8-oxo-3-(5-sulfamoylpyridin-3-yl)-7,8-dihydro-2,7-naphthyridin-1-yl]amino}benzamide; 6-[2-(methylamino)pyrimidin-5-yl]-8-{[4-(piperidin-4-yl)phenyl]amino}-1,2-dihydro-2,7-naphthyridin-1-one; 6-(6-methylpyridin-2-yl)-8-{[4-(morpholin-4-yl)phenyl]amino}-1,2-dihydro-2,7-naphthyridin-1-one; 5-ethenyl-6-(1-methyl-1H-pyrazol-4-yl)-8-{[4-(piperidin-4-yl)phenyl]amino}-1,2-dihydro-2,7-naphthyridin-1-one; 6-(6-methylpyridin-2-yl)-8-{[4-(piperidin-4-yl)phenyl]amino}-1,2-dihydro-2,7-naphthyridin-1-one; 8-{[4-(piperidin-4-yl)phenyl]amino}-6-(pyridin-2-yl)-1,2-dihydro-2,7-naphthyridin-1-one; 4-(1-{[4-(morpholin-4-yl)phenyl]amino}-8-oxo-7,8-dihydro-2,7-naphthyridin-3-yl)-3,4-dihydro-2H-1,4-benzothiazine-1,1-dione; N-methyl-2-[(1-{[4-(morpholin-4-yl)phenyl]amino}-8-oxo-7,8-dihydro-2,7-naphthyridin-3-yl)amino]benzene-1-sulfonamide; N-ethyl-2-[(1-{[4-(morpholin-4-yl)phenyl]amino}-8-oxo-7,8-dihydro-2,7-naphthyridin-3-yl)amino]benzene-1-sulfonamide; 6-[(2-methanesulfonylphenyl)amino]-8-{[4-(morpholin-4-yl)phenyl]amino}-1,2-dihydro-2,7-naphthyridin-1-one; 2-[(1-{[4-(1-methylpiperidin-4-yl)phenyl]amino}-8-oxo-7,8-dihydro-2,7-naphthyridin-3-yl)amino]benzene-1-sulfonamide; 6-(2-aminopyrimidin-5-yl)-8-({3-[2-(morpholin-4-yl)ethoxy]phenyl}amino)-1,2-dihydro-2,7-naphthyridin-1-one; 2-({1-[(2,2-dimethyl-3-oxo-3,4-dihydro-2H-1,4-benzoxazin-6-yl)amino]-8-oxo-7,8-dihydro-2,7-naphthyridin-3-yl}amino)benzene-1-sulfonamide; 4-methoxy-2-[(1-{[4-(morpholin-4-yl)phenyl]amino}-8-oxo-7,8-dihydro-2,7-naphthyridin-3-yl)amino]benzene-1-sulfonamide; N,N,2-trimethyl-5-(1-{[4-(morpholin-4-yl)phenyl]amino}-8-oxo-7,8-dihydro-2,7-naphthyridin-3-yl)benzene-1-sulfonamide; 3-(1-{[4-(morpholin-4-yl)phenyl]amino}-8-oxo-7,8-dihydro-2,7-naphthyridin-3-yl)-N-(propan-2-yl)benzene-1-sulfonamide; N-cyclopropyl-3-(1-{[4-(morpholin-4-yl)phenyl]amino}-8-oxo-7,8-dihydro-2,7-naphthyridin-3-yl)benzene-1-sulfonamide; 8-{[4-(1-acetylpiperidin-4-yl)phenyl]amino}-6-(3-methanesulfonylphenyl)-1,2-dihydro-2,7-naphthyridin-1-one; 4-{[3-(3-methanesulfonylphenyl)-8-oxo-7,8-dihydro-2,7-naphthyridin-1-yl]oxy}benzonitrile 8-{[4-(1-ethylpiperidin-4-yl)phenyl]amino}-6-(3-methanesulfonylphenyl)-1,2-dihydro-2,7-naphthyridin-1-one; 6-(3-methanesulfonylphenyl)-8-{[4-(oxan-4-yl)phenyl]amino}-1,2-dihydro-2,7-naphthyridin-1-one; N-[3-(1-{[2-methoxy-5-methyl-4-(piperidin-4-yl)phenyl]amino}-8-oxo-7,8-dihydro-2,7-naphthyridin-3-yl)phenyl]methanesulfonamide; 2-hydroxy-N-[3-(1-{[4-(morpholin-4-yl)phenyl]amino}-8-oxo-7,8-dihydro-2,7-naphthyridin-3-yl)phenyl]ethane-1-sulfonamido 8-{[2-methoxy-5-methyl-4-(piperidin-4-yl)phenyl]amino}-6-(2-methoxypyridin-3-yl)-1,2-dihydro-2,7-naphthyridin-1-one; 6-(2,6-dimethoxypyridin-3-yl)-8-{[2-methoxy-5-methyl-4-(piperidin-4-yl)phenyl]amino}-1,2-dihydro-2,7-naphthyridin-1-one; 6-(4-methanesulfonylphenyl)-8-{[2-methoxy-5-methyl-4-(piperidin-4-yl)phenyl]amino}-1,2-dihydro-2,7-naphthyridin-1-one; 6-[2-(methylsulfanyl)pyrimidin-5-yl]-8-{[4-(morpholin-4-yl)phenyl]amino}-1,2-dihydro-2,7-naphthyridin-1-one; 6-[2-(methylamino)pyrimidin-5-yl]-8-{[4-(1-methylpiperidin-4-yl)phenyl]amino}-1,2-dihydro-2,7-naphthyridin-1-one; 6-(6-methoxypyridin-2-yl)-8-{[4-(piperidin-4-yl)phenyl]amino}-1,2-dihydro-2,7-naphthyridin-1-one; 6-(6-fluoropyridin-2-yl)-8-{[4-(piperidin-4-yl)phenyl]amino}-1,2-dihydro-2,7-naphthyridin-1-one; 8-{[4-(piperidin-4-yl)phenyl]amino}-6-(pyrimidin-2-yl)-1,2-dihydro-2,7-naphthyridin-1-one; 6-(2-ethyl-1,3-thiazol-4-yl)-8-{[4-(morpholin-4-yl)phenyl]amino}-1,2-dihydro-2,7-naphthyridin-1-one; 6-(5-methylpyridin-2-yl)-8-{[4-(piperidin-4-yl)phenyl]amino}-1,2-dihydro-2,7-naphthyridin-1-one; 6-(4-methylpyridin-2-yl)-8-{[4-(piperidin-4-yl)phenyl]amino}-1,2-dihydro-2,7-naphthyridin-1-one; 6-[2-(methylsulfanyl)pyrimidin-4-yl]-8-{[4-(piperidin-4-yl)phenyl]amino}-1,2-dihydro-2,7-naphthyridin-1-one; 2-(4-{[3-(2-aminopyrimidin-5-yl)-8-oxo-7,8-dihydro-2,7-naphthyridin-1-yl]amino}phenyl)-N,2-dimethylpropanamide 2-[(1-{[4-(morpholin-4-yl)phenyl]amino}-8-oxo-7,8-dihydro-2,7-naphthyridin-3-yl)amino]ethane-1-sulfonamide; 2-methyl-6-[(1-{[4-(morpholin-4-yl)phenyl]amino}-8-oxo-7,8-dihydro-2,7-naphthyridin-3-yl)amino]benzene-1-sulfonamide; N,N-dimethyl-2-[(1-{[4-(morpholin-4-yl)phenyl]amino}-8-oxo-7,8-dihydro-2,7-naphthyridin-3-yl)amino]benzene-1-sulfonamide; 2,2-dimethyl-6-(8-oxo-1-{[4-(piperidin-4-yl)phenyl]amino}-7,8-dihydro-2,7-naphthyridin-3-yl)-3,4-dihydro-2H-1,4-benzoxazin-3-one; N,2-dimethyl-2-[4-({8-oxo-3-[(2-sulfamoylphenyl)amino]-7,8-dihydro-2,7-naphthyridin-1-yl}amino)phenyl]propanamide 2-[(1-{[4-(1-cyclopropylpiperidin-4-yl)phenyl]amino}-8-oxo-7,8-dihydro-2,7-naphthyridin-3-yl)amino]-6-methylbenzene-1-sulfonamide; 6-(2-aminopyrimidin-5-yl)-8-{[4-(trifluoromethoxy)phenyl]amino}-1,2-dihydro-2,7-naphthyridin-1-one; 3-{[3-(2-aminopyrimidin-5-yl)-8-oxo-7,8-dihydro-2,7-naphthyridin-1-yl]amino}-N-methylbenzene-1-sulfonamide; 2,2-dimethyl-6-(1-{[4-(1-methylpiperidin-4-yl)phenyl]amino}-8-oxo-7,8-dihydro-2,7-naphthyridin-3-yl)-3,4-dihydro-2H-1,4-benzoxazin-3-one; N-methyl-3-({8-oxo-3-[(2-sulfamoylphenyl)amino]-7,8-dihydro-2,7-naphthyridin-1-yl}amino)benzene-1-sulfonamide; 6-[1-(2-methylpropyl)-1H-pyrazol-4-yl]-8-({3-[2-(morpholin-4-yl)ethoxy]phenyl}amino)-1,2-dihydro-2,7-naphthyridin-1-one; 6-(2-chlorophenyl)-8-({3-[2-(morpholin-4-yl)ethoxy]phenyl}amino)-1,2-dihydro-2,7-naphthyridin-1-one; N-ethoxy-4-{[3-(4-methylpyridin-3-yl)-8-oxo-7,8-dihydro-2,7-naphthyridin-1-yl]amino}benzamide; 2-[(1-{[4-(1-cyclopropylpiperidin-4-yl)phenyl]amino}-8-oxo-7,8-dihydro-2,7-naphthyridin-3-yl)amino]benzene-1-sulfonamide; 2-methyl-6-[(1-{[3-methyl-4-(piperidin-4-yl)phenyl]amino}-8-oxo-7,8-dihydro-2,7-naphthyridin-3-yl)amino]benzene-1-sulfonamide; 4-methyl-2-[(1-{[3-methyl-4-(piperidin-4-yl)phenyl]amino}-8-oxo-7,8-dihydro-2,7-naphthyridin-3-yl)amino]benzene-1-sulfonamide; 6-(1-methyl-1H-pyrazol-5-yl)-8-{[4-(morpholin-4-yl)phenyl]amino}-1,2-dihydro-2,7-naphthyridin-1-one; 6-(1-methyl-1H-pyrazol-3-yl)-8-{[4-(morpholin-4-yl)phenyl]amino}-1,2-dihydro-2,7-naphthyridin-1-one; 2-methoxy-5-(1-{[4-(morpholin-4-yl)phenyl]amino}-8-oxo-7,8-dihydro-2,7-naphthyridin-3-yl)benzene-1-sulfonamide; 2-methoxy-N-methyl-5-(1-{[4-(morpholin-4-yl)phenyl]amino}-8-oxo-7,8-dihydro-2,7-naphthyridin-3-yl)benzene-1-sulfonamide; tert-butyl 3-(4-{[3-(4-methanesulfonylphenyl)-8-oxo-7,8-dihydro-2,7-naphthyridin-1-yl]amino}phenyl)pyrrolidine-1-carboxylate; 6-(4-methanesulfonylphenyl)-8-{[4-(pyrrolidin-3-yl)phenyl]amino}-1,2-dihydro-2,7-naphthyridin-1-one; tert-butyl 4-(4-{[3-(4-methanesulfonylphenyl)-8-oxo-7,8-dihydro-2,7-naphthyridin-1-yl]amino}phenyl)piperidine-1-carboxylate; 6-(4-methanesulfonylphenyl)-8-{[4-(piperidin-4-yl)phenyl]amino}-1,2-dihydro-2,7-naphthyridin-1-one; 6-(2-methyl-1,3-thiazol-4-yl)-8-{[4-(morpholin-4-yl)phenyl]amino}-1,2-dihydro-2,7-naphthyridin-1-one; 6-(2-aminopyrimidin-5-yl)-8-({3-[2-(morpholin-4-yl)-2-oxoethoxy]phenyl}amino)-1,2-dihydro-2,7-naphthyridin-1-one; 6-(2-aminopyrimidin-5-yl)-8-({4-methyl-3-[2-(morpholin-4-yl)ethoxy]phenyl}amino)-1,2-dihydro-2,7-naphthyridin-1-one; 6-(2-aminopyrimidin-5-yl)-8-[(3-hydroxy-4-methylphenyl)amino]-1,2-dihydro-2,7-naphthyridin-1-one; 6-(2-aminopyrimidin-5-yl)-8-({4-[2-(morpholin-4-yl)ethoxy]phenyl}amino)-1,2-dihydro-2,7-naphthyridin-1-one; 3-{[3-(2-aminopyrimidin-5-yl)-8-oxo-7,8-dihydro-2,7-naphthyridin-1-yl]amino}-N-methylbenzamide; 6-(2-methylpyrimidin-5-yl)-8-({3-[2-(morpholin-4-yl)ethoxy]phenyl}amino)-1,2-dihydro-2,7-naphthyridin-1-one; 8-({4-methyl-3-[2-(morpholin-4-yl)ethoxy]phenyl}amino)-6-(2-methylpyrimidin-5-yl)-1,2-dihydro-2,7-naphthyridin-1-one; 6-(4-methylpyridin-3-yl)-8-({3-[2-(morpholin-4-yl)ethoxy]phenyl}amino)-1,2-dihydro-2,7-naphthyridin-1-one; 6-(2,6-dimethylpyridin-3-yl)-8-({3-[2-(morpholin-4-yl)ethoxy]phenyl}amino)-1,2-dihydro-2,7-naphthyridin-1-one; 8-{[4-(morpholin-4-yl)phenyl]amino}-6-(2-phenyl-1,3-thiazol-4-yl)-1,2-dihydro-2,7-naphthyridin-1-one; 6-(5-methanesulfonyl-4-methylpyridin-3-yl)-8-{[4-(morpholin-4-yl)phenyl]amino}-1,2-dihydro-2,7-naphthyridin-1-one; 6-(5-methanesulfonyl-4-methylpyridin-3-yl)-8-{[4-(morpholin-4-yl)phenyl]amino}-1,2-dihydro-2,7-naphthyridin-1-one; 6-(5-methanesulfonyl-4-methylpyridin-3-yl)-8-{[4-(piperidin-4-yl)phenyl]amino}-1,2-dihydro-2,7-naphthyridin-1-one; 6-(5-methanesulfonyl-4-methylpyridin-3-yl)-8-{[4-(1-methylpiperidin-4-yl)phenyl]amino}-1,2-dihydro-2,7-naphthyridin-1-one; 6-[3-(2-hydroxypropan-2-yl)phenyl]-8-{[4-(morpholin-4-yl)phenyl]amino}-1,2-dihydro-2,7-naphthyridin-1-one; 6-[4-(2-hydroxypropan-2-yl)phenyl]-8-{[4-(morpholin-4-yl)phenyl]amino}-1,2-dihydro-2,7-naphthyridin-1-one; 6-[3-methanesulfonyl-4-(morpholin-4-ylmethyl)phenyl]-8-{[4-(morpholin-4-yl)phenyl]amino}-1,2-dihydro-2,7-naphthyridin-1-one; 6-[3-methanesulfonyl-4-(pyrrolidin-1-ylmethyl)phenyl]-8-{[4-(morpholin-4-yl)phenyl]amino}-1,2-dihydro-2,7-naphthyridin-1-one; 6-(5-ethoxypyridin-3-yl)-8-{[4-(morpholin-4-yl)phenyl]amino}-1,2-dihydro-2,7-naphthyridin-1-one; 6-(6-amino-5-methoxypyridin-3-yl)-8-{[4-(morpholin-4-yl)phenyl]amino}-1,2-dihydro-2,7-naphthyridin-1-one; 6-(5-methylpyridin-3-yl)-8-{[4-(morpholin-4-yl)phenyl]amino}-1,2-dihydro-2,7-naphthyridin-1-one; 6-(3-methanesulfonyl-4-methylphenyl)-8-{[4-(morpholin-4-yl)phenyl]amino}-1,2-dihydro-2,7-naphthyridin-1-one; N-[5-(1-{[4-(morpholin-4-yl)phenyl]amino}-8-oxo-7,8-dihydro-2,7-naphthyridin-3-yl)pyridin-2-yl]acetamide 6-(4-methoxypyrimidin-5-yl)-8-{[4-(morpholin-4-yl)phenyl]amino}-1,2-dihydro-2,7-naphthyridin-1-one; 6-(6-amino-4-methylpyridin-3-yl)-8-{[4-(morpholin-4-yl)phenyl]amino}-1,2-dihydro-2,7-naphthyridin-1-one; 6-(6-amino-4-methylpyridin-3-yl)-8-{[4-(1-methylpiperidin-4-yl)phenyl]amino}-1,2-dihydro-2,7-naphthyridin-1-one; 6-(6-amino-5-methylpyridin-3-yl)-8-{[4-(morpholin-4-yl)phenyl]amino}-1,2-dihydro-2,7-naphthyridin-1-one; 6-(2-aminopyrimidin-5-yl)-8-({4-[2-(pyrrolidin-1-yl)ethoxy]phenyl}amino)-1,2-dihydro-2,7-naphthyridin-1-one; 2-methyl-6-[(1-{[4-(1-methylpiperidin-4-yl)phenyl]amino}-8-oxo-7,8-dihydro-2,7-naphthyridin-3-yl)amino]benzene-1-sulfonamide; N-methyl-2-[(1-{[4-(1-methylpiperidin-4-yl)phenyl]amino}-8-oxo-7,8-dihydro-2,7-naphthyridin-3-yl)amino]benzene-1-sulfonamide; 8-{[4-(1-ethylpiperidin-4-yl)phenyl]amino}-6-(4-methanesulfonylphenyl)-1,2-dihydro-2,7-naphthyridin-1-one; 8-{[4-(morpholin-4-yl)phenyl]amino}-6-(1H-pyrazol-5-yl)-1,2-dihydro-2,7-naphthyridin-1-one; 4-chloro-8-(1H-indazol-6-ylamino)-1,2-dihydro-2,7-naphthyridin-1-one; 4,6-dichloro-8-(1H-indazol-6-ylamino)-1,2-dihydro-2,7-naphthyridin-1-one; 8-{[4-(morpholin-4-yl)phenyl]amino}-6-(pyridin-2-yl)-1,2-dihydro-2,7-naphthyridin-1-one; 8-{[4-(morpholin-4-yl)phenyl]amino}-6-[5-(propan-2-yloxy)pyridin-3-yl]-1,2-dihydro-2,7-naphthyridin-1-one; 6-[5-methyl-6-(methylamino)pyridin-3-yl]-8-{[4-(morpholin-4-yl)phenyl]amino}-1,2-dihydro-2,7-naphthyridin-1-one; 4-methoxy-N-methyl-3-(1-{[4-(morpholin-4-yl)phenyl]amino}-8-oxo-7,8-dihydro-2,7-naphthyridin-3-yl)benzene-1-sulfonamide; 8-{[4-(morpholin-4-yl)phenyl]amino}-6-(1-propyl-1H-pyrazol-5-yl)-1,2-dihydro-2,7-naphthyridin-1-one; 8-{[4-(morpholin-4-yl)phenyl]amino}-6-[1-(2-phenylethyl)-1H-pyrazol-5-yl]-1,2-dihydro-2,7-naphthyridin-1-one; 8-{[4-(morpholin-4-yl)phenyl]amino}-6-[1-(propan-2-yl)-1H-pyrazol-5-yl]-1,2-dihydro-2,7-naphthyridin-1-one; 6-(1-benzyl-1H-pyrazol-5-yl)-8-{[4-(morpholin-4-yl)phenyl]amino}-1,2-dihydro-2,7-naphthyridin-1-one; 6-(1-tert-butyl-1H-pyrazol-5-yl)-8-{[4-(morpholin-4-yl)phenyl]amino}-1,2-dihydro-2,7-naphthyridin-1-one; 5-(1-{[4-(1-methylpiperidin-4-yl)phenyl]amino}-8-oxo-7,8-dihydro-2,7-naphthyridin-3-yl)pyridine-3-sulfonamide; 8-{[4-(morpholin-4-yl)phenyl]amino}-6-[5-(trifluoromethyl)pyridin-3-yl]-1,2-dihydro-2,7-naphthyridin-1-one; 8-{[4-(piperidin-4-yl)phenyl]amino}-6-[5-(trifluoromethyl)pyridin-3-yl]-1,2-dihydro-2,7-naphthyridin-1-one; 8-{[4-(1-methylpiperidin-4-yl)phenyl]amino}-6-[5-(trifluoromethyl)pyridin-3-yl]-1,2-dihydro-2,7-naphthyridin-1-one; 6-[2-(methylamino)pyrimidin-5-yl]-8-{[4-(morpholin-4-yl)phenyl]amino}-1,2-dihydro-2,7-naphthyridin-1-one; 6-(6-fluoropyridin-3-yl)-8-{[4-(morpholin-4-yl)phenyl]amino}-1,2-dihydro-2,7-naphthyridin-1-one; 6-(6-fluoropyridin-3-yl)-8-{[4-(piperidin-4-yl)phenyl]amino}-1,2-dihydro-2,7-naphthyridin-1-one; 6-[6-(methylamino)pyridin-3-yl]-8-{[4-(morpholin-4-yl)phenyl]amino}-1,2-dihydro-2,7-naphthyridin-1-one; 8-{[3-fluoro-4-(morpholin-4-yl)phenyl]amino}-1,2-dihydro-2,7-naphthyridin-1-one; 8-{[4-(morpholin-4-yl)-3-(trifluoromethyl)phenyl]amino}-1,2-dihydro-2,7-naphthyridin-1-one; 8-{[3-methyl-4-(morpholin-4-yl)phenyl]amino}-1,2-dihydro-2,7-naphthyridin-1-one; 6-(3,3-difluoropyrrolidin-1-yl)-8-({3-fluoro-4-[(2R)-2-methylmorpholin-4-yl]phenyl}amino)-1,2-dihydro-2,7-naphthyridin-1-one; 8-({3-fluoro-4-[(2R)-2-methylmorpholin-4-yl]phenyl}amino)-1,2-dihydro-2,7-naphthyridin-1-one; 6-(2-aminopyrimidin-5-yl)-8-({3-[2-(pyrrolidin-1-yl)ethoxy]phenyl}amino)-1,2-dihydro-2,7-naphthyridin-1-one; 6-(2-amino-4-methoxypyrimidin-5-yl)-8-{[4-(morpholin-4-yl)phenyl]amino}-1,2-dihydro-2,7-naphthyridin-1-one; 6-(2-aminopyrimidin-5-yl)-8-{[3-methyl-4-(morpholin-4-yl)phenyl]amino}-1,2-dihydro-2,7-naphthyridin-1-one; N,2-dimethyl-2-(4-{[3-(2-methylpyrimidin-5-yl)-8-oxo-7,8-dihydro-2,7-naphthyridin-1-yl]amino}phenyl)propanamide 2-methyl-6-{[8-oxo-1-({4-[2-(pyrrolidin-1-yl)ethoxy]phenyl}amino)-7,8-dihydro-2,7-naphthyridin-3-yl]amino}benzene-1-sulfonamide; 8-{[4-(morpholin-4-yl)phenyl]amino}-6-[5-(morpholin-4-ylmethyl)pyridin-3-yl]-1,2-dihydro-2,7-naphthyridin-1-one; 8-{[4-(morpholin-4-yl)phenyl]amino}-6-[5-(pyrrolidin-1-ylmethyl)pyridin-3-yl]-1,2-dihydro-2,7-naphthyridin-1-one; 6-(6-fluoropyridin-3-yl)-8-{[4-(1-methylpiperidin-4-yl)phenyl]amino}-1,2-dihydro-2,7-naphthyridin-1-one; 4-{[3-(6-fluoropyridin-3-yl)-8-oxo-7,8-dihydro-2,7-naphthyridin-1-yl]amino}-N- methylbenzamide; 6-[6-(methylamino)pyridin-3-yl]-8-{[4-(piperidin-4-yl)phenyl]amino}-1,2-dihydro-2,7-naphthyridin-1-one; 6-[6-(ethylamino)pyridin-3-yl]-8-{[4-(morpholin-4-yl)phenyl]amino}-1,2-dihydro-2,7-naphthyridin-1-one; 6-(3-methanesulfonyl-4-methoxyphenyl)-8-{[4-(morpholin-4-yl)phenyl]amino}-1,2-dihydro-2,7-naphthyridin-1-one; 6-(3-methanesulfonyl-4-methylphenyl)-8-{[4-(1-methylpiperidin-4-yl)phenyl]amino}-1,2-dihydro-2,7-naphthyridin-1-one; N-[5-(1-{[4-(1-methylpiperidin-4-yl)phenyl]amino}-8-oxo-7,8-dihydro-2,7-naphthyridin-3-yl)pyridin-2-yl]acetamide 8-({3-[2-(morpholin-4-yl)ethoxy]phenyl}amino)-6-[(2,2,2-trifluoroethyl)amino]-1,2-dihydro-2,7-naphthyridin-1-one; N-methyl-2-{[8-oxo-1-({4-[2-(pyrrolidin-1-yl)ethoxy]phenyl}amino)-7,8-dihydro-2,7-naphthyridin-3-yl]amino}benzene-1-sulfonamide; 6-(2-amino-4-methoxypyrimidin-5-yl)-8-({3-[2-(morpholin-4-yl)ethoxy]phenyl}amino)-1,2-dihydro-2,7-naphthyridin-1-one; 6-(2-aminopyrimidin-5-yl)-8-{[4-methyl-3-(methylamino)phenyl]amino}-1,2-dihydro-2,7-naphthyridin-1-one; 6-(2-methylpyrimidin-5-yl)-8-({4-[2-(morpholin-4-yl)ethoxy]phenyl}amino)-1,2-dihydro-2,7-naphthyridin-1-one; 8-{[4-(morpholin-4-yl)phenyl]amino}-6-(pyrazin-2-yl)-1,2-dihydro-2,7-naphthyridin-1-one; 6-(5-aminopyrazin-2-yl)-8-{[4-(morpholin-4-yl)phenyl]amino}-1,2-dihydro-2,7-naphthyridin-1-one; 6-(6-amino-2-methylpyridin-3-yl)-8-{[4-(morpholin-4-yl)phenyl]amino}-1,2-dihydro-2,7-naphthyridin-1-one; 2-[(1-{[4-(4-ethoxypiperidin-1-yl)-3-fluorophenyl]amino}-8-oxo-7,8-dihydro-2,7-naphthyridin-3-yl)amino]benzene-1-sulfonamide; 6-(3,3-difluoropyrrolidin-1-yl)-8-[4-(4-ethoxypiperidin-1-yl)-3-fluorophenyl)amino]-1,2-dihydro-2,7-naphthyridin-1-one; 8-{[4-(1-methylpiperidin-4-yl)phenyl]amino}-6-(6-methylpyridin-2-yl)-1,2-dihydro-2,7-naphthyridin-1-one; 8-{[4-(1-acetylpiperidin-4-yl)phenyl]amino}-6-(6-methylpyridin-2-yl)-1,2-dihydro-2,7-naphthyridin-1-one; 6-(3,3-difluoropyrrolidin-1-yl)-8-({6-[(2R)-2-methylmorpholin-4-yl]pyridin-3-yl}amino)-1,2-dihydro-2,7-naphthyridin-1-one; 2-[(1-{[3-methyl-4-(morpholin-4-yl)phenyl]amino}-8-oxo-7,8-dihydro-2,7-naphthyridin-3-yl)amino]benzene-1-sulfonamide; 6-(3,3-difluoropyrrolidin-1-yl)-8-{[5-methyl-6-(morpholin-4-yl)pyridin-3-yl]amino}-1,2-dihydro-2,7-naphthyridin-1-one; 6-(3,3-difluoropyrrolidin-1-yl)-8-{[3-methyl-4-(morpholin-4-yl)phenyl]amino}-1,2-dihydro-2,7-naphthyridin-1-one; 8-{[4-(1-methylpiperidin-4-yl)phenyl]amino}-6-(pyrazin-2-yl)-1,2-dihydro-2,7-naphthyridin-1-one; 6-(5-aminopyrazin-2-yl)-8-({3-fluoro-4-[(2R)-2-methylmorpholin-4-yl]phenyl}amino)-1,2-dihydro-2,7-naphthyridin-1-one; 4-{[3-(5-aminopyrazin-2-yl)-8-oxo-7,8-dihydro-2,7-naphthyridin-1-yl]amino}-N-propylbenzamide; 6-(6-methoxypyrazin-2-yl)-8-{[4-(morpholin-4-yl)phenyl]amino}-1,2-dihydro-2,7-naphthyridin-1-one; 6-(3-methoxypyrazin-2-yl)-8-{[4-(morpholin-4-yl)phenyl]amino}-1,2-dihydro-2,7-naphthyridin-1-one; 6-(2-amino-4-methoxypyrimidin-5-yl)-8-{[4-(1-methylpiperidin-4-yl)phenyl]amino}-1,2-dihydro-2,7-naphthyridin-1-one; 6-(2-aminopyrimidin-5-yl)-8-({4-[(2-methyl-1H-imidazol-1-yl)methyl]phenyl}amino)-1,2-dihydro-2,7-naphthyridin-1-one; 6-(2-aminopyrimidin-5-yl)-8-[(3-methoxy-4-phenylphenyl)amino]-1,2-dihydro-2,7-naphthyridin-1-one; 6-(2-aminopyrimidin-5-yl)-8-{[3-(4-methylpiperazin-1-yl)phenyl]amino}-1,2-dihydro-2,7-naphthyridin-1-one; 6-(2-aminopyrimidin-5-yl)-8-[(4-{2-[3-(dimethylamino)pyrrolidin-1-yl]ethyl}phenyl)amino]-1,2-dihydro-2,7-naphthyridin-1-one; 6-(1-butyl-1H-pyrazol-5-yl)-8-{[4-(morpholin-4-yl)phenyl]amino}-1,2-dihydro-2,7-naphthyridin-1-one; 6-[1-(2-hydroxyethyl)-1H-pyrazol-5-yl]-8-{[4-(morpholin-4-yl)phenyl]amino}-1,2-dihydro-2,7-naphthyridin-1-one; ethyl 2-[5-(1-{[4-(morpholin-4-yl)phenyl]amino}-8-oxo-7,8-dihydro-2,7-naphthyridin-3-yl)-1H-pyrazol-1-yl]acetate 6-(2-methylpyrimidin-4-yl)-8-{[4-(morpholin-4-yl)phenyl]amino}-1,2-dihydro-2,7-naphthyridin-1-one; 6-(6-methylpyridin-2-yl)-8-({4-[1-(2,2,2-trifluoroethyl)piperidin-4-yl]phenyl}amino)-1,2-dihydro-2,7-naphthyridin-1-one; 8-({4-[1-(2-hydroxyethyl)piperidin-4-yl]phenyl}amino)-6-(6-methylpyridin-2-yl)-1,2-dihydro-2,7-naphthyridin-1-one; 6-(6-methylpyridin-2-yl)-8-({4-[1-(propan-2-yl)piperidin-4-yl]phenyl}amino)-1,2-dihydro-2,7-naphthyridin-1-one; 8-{[4-(1-methanesulfonylpiperidin-4-yl)phenyl]amino}-6-(6-methylpyridin-2-yl)-1,2-dihydro-2,7-naphthyridin-1-one; 6-(2-amino-1,3-thiazol-4-yl)-8-{[4-(morpholin-4-yl)phenyl]amino}-1,2-dihydro-2,7-naphthyridin-1-one; 6-[2-(methylamino)-1,3-thiazol-4-yl]-8-{[4-(morpholin-4-yl)phenyl]amino}-1,2-dihydro-2,7-naphthyridin-1-one; 6-[6-(2-hydroxypropan-2-yl)pyridin-3-yl]-8-{[4-(morpholin-4-yl)phenyl]amino}-1,2-dihydro-2,7-naphthyridin-1-one; 6-(6-amino-5-methoxypyridin-3-yl)-8-({4-methyl-3-[2-(pyrrolidin-1-yl)ethoxy]phenyl}amino)-1,2-dihydro-2,7-naphthyridin-1-one; 6-(2-aminopyrimidin-5-yl)-8-({4-methyl-3-[2-(pyrrolidin-1-yl)ethoxy]phenyl}amino)-1,2-dihydro-2,7-naphthyridin-1-one; 8-({4-methyl-3-[2-(pyrrolidin-1-yl)ethoxy]phenyl}amino)-6-(pyrimidin-5-yl)-1,2-dihydro-2,7-naphthyridin-1-one; 6-[6-(2-hydroxypropan-2-yl)pyridin-3-yl]-8-{(4-methyl-3-[2-(pyrrolidin-1-yl)ethoxy]phenyl}amino)-1,2-dihydro-2,7-naphthyridin-1-one; 8-({4-methyl-3-[2-(pyrrolidin-1-yl)ethoxy]phenyl}amino)-6-(1H-pyrazol-3-yl)-1,2-dihydro-2,7-naphthyridin-1-one; 8-({4-methyl-3-[2-(pyrrolidin-1-yl)ethoxy]phenyl}amino)-6-[5-methyl-6-(methylamino)pyridin-3-yl]-1,2-dihydro-2,7-naphthyridin-1-one; 6-(2-methoxypyrimidin-5-yl)-8-({6-[(2R)-2-methylmorpholin-4-yl]pyridin-3-yl}amino)-1,2-dihydro-2,7-naphthyridin-1-one; 8-{[3-fluoro-4-(morpholin-4-yl)phenyl]amino}-6-(2-methoxypyrimidin-5-yl)-1,2-dihydro-2,7-naphthyridin-1-one; 8-(1H-indazol-6-ylamino)-6-(2-methoxypyrimidin-5-yl)-1,2-dihydro-2,7-naphthyridin-1-one; 8-({3-fluoro-4-[(2R)-2-methylmorpholin-4-yl]phenyl}amino)-6-(2-methoxypyrimidin-5-yl)-1,2-dihydro-2,7-naphthyridin-1-one; 6-(2-methoxypyrimidin-5-yl)-8-({5-methyl-6-[(2R)-2-methylmorpholin-4-yl]pyridin-3-yl}amino)-1,2-dihydro-2,7-naphthyridin-1-one; 8-{[4-(4-ethoxypiperidin-1-yl)-3-fluorophenyl]amino}-6-(2-methoxypyrimidin-5-yl)-1,2-dihydro-2,7-naphthyridin-1-one; 8-({6-[(2R)-2-methylmorpholin-4-yl]pyridin-3-yl}amino)-6-(pyrimidin-5-yl)-1,2-dihydro-2,7-naphthyridin-1-one; 8-({3-methyl-4-[(2R)-2-methylmorpholin-4-yl]phenyl}amino)-6-(pyrimidin-5-yl)-1,2-dihydro-2,7-naphthyridin-1-one; 4-{[3-(2-aminopyrimidin-5-yl)-8-oxo-7,8-dihydro-2,7-naphthyridin-1-yl]amino}-N-(1-methylpiperidin-4-yl)benzamide; N-(1-methylpiperidin-4-yl)-4-{[3-(2-methylpyrimidin-5-yl)-8-oxo-7,8-dihydro-2,7-naphthyridin-1-yl]amino}benzamide; 6-(2-aminopyrimidin-5-yl)-8-({4-[3-(dimethylamino)pyrrolidin-1-yl]phenyl}amino)-1,2-dihydro-2,7-naphthyridin-1-one; 8-({4-[3-(dimethylamino)pyrrolidin-1-yl]phenyl}amino)-6-(6-methoxypyrazin-2-yl)-1,2-dihydro-2,7-naphthyridin-1-one; 6-(2,4-dimethoxypyrimidin-5-yl)-8-{[4-(morpholin-4-yl)phenyl]amino}-1,2-dihydro-2,7-naphthyridin-1-one; N-methyl-3-{[3-(2-methylpyrimidin-5-yl)-8-oxo-7,8-dihydro-2,7-naphthyridin-1-yl]amino}benzene-1-sulfonamide; 2-methoxy-N-methyl-4-(1-{[4-(morpholin-4-yl)phenyl]amino}-8-oxo-7,8-dihydro-2,7-naphthyridin-3-yl)benzene-1-sulfonamide; 6-(6-hydrazinylpyridin-3-yl)-8-{[4-(morpholin-4-yl)phenyl]amino}-1,2-dihydro-2,7-naphthyridin-1-one; 6-[6-(4-methyl-1H-imidazol-1-yl)pyridin-2-yl]-8-{[4-(1-methylpiperidin-4-yl)phenyl]amino}-1,2-dihydro-2,7-naphthyridin-1-one; 8-{[4-(1-methylpiperidin-4-yl)phenyl]amino}-6-[6-(morpholin-4-ylmethyl)pyridin-3-yl]-1,2-dihydro-2,7-naphthyridin-1-one; 8-{[4-(morpholin-4-yl)phenyl]amino}-6-[6-(morpholin-4-ylmethyl)pyridin-3-yl]-1,2-dihydro-2,7-naphthyridin-1-one; 6-(2-methoxypyrimidin-5-yl)-8-({3-methyl-4-[(2R)-2-methylmorpholin-4-yl]phenyl}amino)-1,2-dihydro-2,7-naphthyridin-1-one; 6-hydroxy-8-({3-methyl-4-[(2R)-2-methylmorpholin-4-yl]phenyl}amino)-1,2-dihydro-2,7-naphthyridin-1-one; 8-({3-fluoro-4-[(2R)-2-methylmorpholin-4-yl]phenyl}amino)-6-(pyrimidin-5-yl)-1,2-dihydro-2,7-naphthyridin-1-one; 8-({5-methyl-6-[(2R)-2-methylmorpholin-4-yl]pyridin-3-yl}amino)-6-(pyrimidin-5-yl)-1,2-dihydro-2,7-naphthyridin-1-one; ethyl 4-(1-{[4-(morpholin-4-yl)phenyl]amino}-8-oxo-7,8-dihydro-2,7-naphthyridin-3-yl)-1,3-thiazole-2-carboxylate; 6-[2-(methanesulfonylmethyl)-1,3-thiazol-4-yl]-8-{[4-(morpholin-4-yl)phenyl]amino}-1,2-dihydro-2,7-naphthyridin-1-one; tert-butyl N-{2-[4-(1-{[4-(morpholin-4-yl)phenyl]amino}-8-oxo-7,8-dihydro-2,7-naphthyridin-3-yl)-1,3-thiazol-2-yl]ethyl}carbamate 6-[2-(2-aminoethyl)-1,3-thiazol-4-yl]-8-{[4-(morpholin-4-yl)phenyl]amino}-1,2-dihydro-2,7-naphthyridin-1-one; 6-(5-amino-6-methylpyridin-2-yl)-8-{[4-(1-methylpiperidin-4-yl)phenyl]amino}-1,2-dihydro-2,7-naphthyridin-1-one; 6-(5-amino-6-methylpyridin-2-yl)-8-{[4-(morpholin-4-yl)phenyl]amino}-1,2-dihydro-2,7-naphthyridin-1-one; 6-(2-amino-4-methylpyrimidin-5-yl)-8-{[4-(morpholin-4-yl)phenyl]amino}-1,2-dihydro-2,7-naphthyridin-1-one; 6-(2-amino-6-methylpyrimidin-4-yl)-8-{[4-(morpholin-4-yl)phenyl]amino}-1,2-dihydro-2,7-naphthyridin-1-one; 6-(6-amino-5-methylpyridin-3-yl)-8-({3-methyl-4-[(2R)-2-methylmorpholin-4-yl]phenyl}amino)-1,2-dihydro-2,7-naphthyridin-1-one; 6-(2-aminopyrimidin-5-yl)-2-methyl-8-{[4-(morpholin-4-yl)phenyl]amino}-1,2-dihydro-2,7-naphthyridin-1-one; 6-(2-aminopyrimidin-5-yl)-2-methyl-8-{methyl[4-(morpholin-4-yl)phenyl]amino}-1,2-dihydro-2,7-naphthyridin-1-one; 6-(6-amino-5-methylpyridin-3-yl)-8-({3-[2-(morpholin-4-yl)ethoxy]phenyl}amino)-1,2-dihydro-2,7-naphthyridin-1-one; 6-(2-aminopyrimidin-5-yl)-8-(morpholin-4-yl)-1,2-dihydro-2,7-naphthyridin-1-one; 6-(2-aminopyrimidin-5-yl)-8-[(1-methylpiperidin-4-yl)amino]-1,2-dihydro-2,7-naphthyridin-1-one; 6-(2-amino-4-methylpyrimidin-5-yl)-8-({4-[3-(dimethylamino)pyrrolidin-1-yl]phenyl}amino)-1,2-dihydro-2,7-naphthyridin-1-one; 6-(5-aminopyridin-2-yl)-8-{[4-(morpholin-4-yl)phenyl]amino}-1,2-dihydro-2,7-naphthyridin-1-one; 8-{[4-(morpholin-4-yl)phenyl]amino}-6-{5H-pyrrolo[2,3-b]pyrazin-2-yl}-1,2-dihydro-2,7-naphthyridin-1-one; 6-(5-aminopyridin-2-yl)-8-{[4-(1-methylpiperidin-4-yl)phenyl]amino}-1,2-dihydro-2,7-naphthyridin-1-one; 8-{[4-(1-methylpiperidin-4-yl)phenyl]amino}-6-{5H-pyrrolo[2,3-b]pyrazin-2-yl}-1,2-dihydro-2,7-naphthyridin-1-one; 6-(2,4-dimethyl-1,3-thiazol-5-yl)-8-{[4-(morpholin-4-yl)phenyl]amino}-1,2-dihydro-2,7-naphthyridin-1-one; 6-(2,4-dimethyl-1,3-thiazol-5-yl)-8-{[4-(1-methylpiperidin-4-yl)phenyl]amino}-1,2-dihydro-2,7-naphthyridin-1-one; 8-{[4-(piperidin-4-yl)phenyl]amino}-6-[4-(propane-2-sulfonyl)phenyl]-1,2-dihydro-2,7-naphthyridin-1-one; 6-[6-(4-methyl-1H-imidazol-1-yl)pyridin-2-yl]-8-{[4-(morpholin-4-yl)phenyl]amino}-1,2-dihydro-2,7-naphthyridin-1-one; N,N-dimethyl-4-(8-oxo-1-{[4-(piperidin-4-yl)phenyl]amino}-7,8-dihydro-2,7-naphthyridin-3-yl)benzene-1-sulfonamide; tert-butyl 4-[4-({8-oxo-3-[4-(propane-2-sulfonyl)phenyl]-7,8-dihydro-2,7-naphthyridin-1-yl}amino)phenyl]piperidine-1-carboxylate; tert-butyl 4-[4-({3-[4-(dimethylsulfamoyl)phenyl]-8-oxo-7,8-dihydro-2,7-naphthyridin-1-yl}amino)phenyl]piperidine-1-carboxylate; tert-butyl 4-(4-{[3-(3-methanesulfonylphenyl)-8-oxo-7,8-dihydro-2,7-naphthyridin-1-yl]amino}phenyl)piperidine-1-carboxylate; 6-(5-amino-6-methylpyrazin-2-yl)-8-{[4-(morpholin-4-yl)phenyl]amino}-1,2-dihydro-2,7-naphthyridin-1-one; 6-(6-aminopyrazin-2-yl)-8-{[4-(morpholin-4-yl)phenyl]amino}-1,2-dihydro-2,7-naphthyridin-1-one; 6-(6-methoxypyridazin-3-yl)-8-{[4-(morpholin-4-yl)phenyl]amino}-1,2-dihydro-2,7-naphthyridin-1-one; 8-({4-[1-(2-methanesulfonylethyl)piperidin-4-yl]phenyl}amino)-6-(4-methanesulfonylphenyl)-1,2-dihydro-2,7-naphthyridin-1-one; 6-(2-methoxypyrimidin-5-yl)-8-{[4-(morpholin-4-yl)phenyl]amino}-1,2-dihydro-2,7-naphthyridin-1-one; 6-(2-methoxypyrimidin-5-yl)-8-{[4-(1-methylpiperidin-4-yl)phenyl]amino}-1,2-dihydro-2,7-naphthyridin-1-one; 6-(1-methyl-1H-pyrazol-4-yl)-8-{[4-(morpholin-4-yl)phenyl]amino}-1,2-dihydro-2,7-naphthyridin-1-one; 6-(4-ethylpiperazin-1-yl)-8-{[4-(morpholin-4-yl)phenyl]amino}-4-phenyl-1,2-dihydro-2,7-naphthyridin-1-one; 8-{[4-(morpholin-4-yl)phenyl]amino}-4-phenyl-1,2-dihydro-2,7-naphthyridin-1-one; 4-(2-chlorophenyl)-8-{[4-(morpholin-4-yl)phenyl]amino}-1,2-dihydro-2,7-naphthyridin-1-one; 6-(1-methyl-1H-pyrazol-4-yl)-8-{methyl[4-(morpholin-4-yl)phenyl]amino}-1,2-dihydro-2,7-naphthyridin-1-one; 8-{[4-(1-acetylpiperidin-4-yl)phenyl]amino}-6-(2-aminopyrimidin-5-yl)-1,2-dihydro-2,7-naphthyridin-1-one; 8-{[4-(1-acetylpiperidin-4-yl)phenyl]amino}-6-(pyrimidin-5-yl)-1,2-dihydro-2,7-naphthyridin-1-one; 6-(2-aminopyrimidin-5-yl)-8-{[4-(1-methanesulfonylpyrrolidin-3-yl)phenyl]amino}-1,2-dihydro-2,7-naphthyridin-1-one; N-methyl-3-{[8-oxo-3-(pyrimidin-5-yl)-7,8-dihydro-2,7-naphthyridin-1-yl]amino}benzene-1-sulfonamide; 6-(2-aminopyrimidin-5-yl)-8-[(3-methoxyphenyl)amino]-1,2-dihydro-2,7-naphthyridin-1-one; 6-[6-(2-hydroxypropan-2-yl)pyridin-3-yl]-8-{[4-(1-methylpiperidin-4-yl)phenyl]amino}-1,2-dihydro-2,7-naphthyridin-1-one; 6-[5-methyl-6-(methylamino)pyridin-3-yl]-8-{[4-(1-methylpiperidin-4-yl)phenyl]amino}-1,2-dihydro-2,7-naphthyridin-1-one; 8-{[4-(1-methylpiperidin-4-yl)phenyl]amino}-6-[5-(propan-2-yloxy)pyridin-3-yl]-1,2-dihydro-2,7-naphthyridin-1-one; 4-methoxy-N-methyl-3-(1-{[4-(1-methylpiperidin-4-yl)phenyl]amino}-8-oxo-7,8-dihydro-2,7-naphthyridin-3-yl)benzene-1-sulfonamide; 6-[3-methanesulfonyl-4-(pyrrolidin-1-ylmethyl)phenyl]-8-{[4-(1-methylpiperidin-4-yl)phenyl]amino}-1,2-dihydro-2,7-naphthyridin-1-one; 6-[3-methanesulfonyl-4-(morpholin-4-ylmethyl)phenyl]-8-{[4-(1-methylpiperidin-4-yl)phenyl]amino}-1,2-dihydro-2,7-naphthyridin-1-one; 8-{[4-(1-methylpiperidin-4-yl)phenyl]amino}-6-[5-(morpholin-4-ylmethyl)pyridin-3-yl]-1,2-dihydro-2,7-naphthyridin-1-one; 8-{[4-(1-methylpiperidin-4-yl)phenyl]amino}-6-[5-(pyrrolidin-1-ylmethyl)pyridin-3-yl]-1,2-dihydro-2,7-naphthyridin-1-one; 8-{[4-(morpholin-4-yl)phenyl]amino}-6-[6-(propan-2-ylamino)pyridin-3-yl]-1,2-dihydro-2,7-naphthyridin-1-one; 6-(1-methyl-1H-imidazol-5-yl)-8-{[4-(morpholin-4-yl)phenyl]amino}-1,2-dihydro-2,7-naphthyridin-1-one; 6-(6-aminopyridin-3-yl)-2-methyl-8-{[4-(morpholin-4-yl)phenyl]amino}-1,2-dihydro-2,7-naphthyridin-1-one; 8-{[4-(morpholin-4-yl)phenyl]amino}-6-(1,3-thiazol-4-yl)-1,2-dihydro-2,7-naphthyridin-1-one; tert-butyl 6-{[3-(4-methanesulfonylphenyl)-8-oxo-7,8-dihydro-2,7-naphthyridin-1-yl]amino}-1,2,3,4-tetrahydroisoquinoline-2-carboxylate; 6-(4-methanesulfonylphenyl)-8-(1,2,3,4-tetrahydroisoquinolin-6-ylamino)-1,2-dihydro-2,7-naphthyridin-1-one; 8-{[4-(1-ethylpiperidin-4-yl)phenyl]amino}-6-[4-(propane-2- sulfonyl)phenyl]-1,2-dihydro-2,7-naphthyridin-1-one; 4-(1-{[4-(1-ethylpiperidin-4-yl)phenyl]amino}-8-oxo-7,8-dihydro-2,7-naphthyridin-3-yl)-N,N-dimethylbenzene-1-sulfonamide; 6-[6-(4-methyl-1H-imidazol-1-yl)pyridin-3-yl]-8-{[4-(morpholin-4-yl)phenyl]amino}-1,2-dihydro-2,7-naphthyridin-1-one; 8-[(2-ethyl-1,2,3,4-tetrahydroisoquinolin-6-yl)amino]-6-(4-methanesulfonylphenyl)-1,2-dihydro-2,7-naphthyridin-1-one; benzyl 4-{1-[(4-{1-[(tert-butoxy)carbonyl]piperidin-4-yl}phenyl)amino]-8-oxo-7,8-dihydro-2,7-naphthyridin-3-yl}piperazine-1-carboxylate; 8-({6-[(2R)-2-methylmorpholin-4-yl]pyridin-3-yl}amino)-6-(6-methylpyridin-2-yl)-1,2-dihydro-2,7-naphthyridin-1-one; 8-({3-methyl-4-[(2R)-2-methylmorpholin-4-yl]phenyl}amino)-6-(6-methylpyridin-2-yl)-1,2-dihydro-2,7-naphthyridin-1-one; 6-{[(1S,2R)-2-aminocyclohexyl]amino}-8-(1H-indazol-6-ylamino)-1,2-dihydro-2,7-naphthyridin-1-one; 6-(6-methoxypyrazin-2-yl)-8-({3-methyl-4-[(2R)-2-methylmorpholin-4-yl]phenyl}amino)-1,2-dihydro-2,7-naphthyridin-1-one; 6-(5-amino-6-methylpyrazin-2-yl)-8-({3-methyl-4-[(2R)-2-methylmorpholin-4-yl]phenyl}amino)-1,2-dihydro-2,7-naphthyridin-1-one; 6-(6-methoxypyrazin-2-yl)-8-({4-[2-(morpholin-4-yl)ethoxy]phenyl}amino)-1,2-dihydro-2,7-naphthyridin-1-one; 6-(2-aminopyrimidin-5-yl)-8-{[4-(2-methylpyridin-4-yl)phenyl]amino}-1,2-dihydro-2,7-naphthyridin-1-one; 8-{[4-(1-acetylpiperidin-4-yl)-3-methylphenyl]amino}-6-(6-amino-5-methylpyridin-3-yl)-1,2-dihydro-2,7-naphthyridin-1-one; 6-(2-aminopyrimidin-5-yl)-8-{[4-(4-methoxyphenyl)phenyl]amino}-1,2-dihydro-2,7-naphthyridin-1-one; 6-(2-amino-4-methylpyrimidin-5-yl)-2-methyl-8-{[4-(morpholin-4-yl)phenyl]amino}-1,2-dihydro-2,7-naphthyridin-1-one; 8-(1H-indazol-6-ylamino)-6-(6-methoxypyrazin-2-yl)-1,2-dihydro-2,7-naphthyridin-1-one; 6-(3-methanesulfinyl-2-methylphenyl)-8-{[4-(morpholin-4-yl)phenyl]amino}-1,2-dihydro-2,7-naphthyridin-1-one; 8-[(2-methanesulfonylethyl)({4-[1-(2-methanesulfonylethyl)piperidin-4-yl]phenyl})amino]-6-(4-methanesulfonylphenyl)-1,2-dihydro-2,7-naphthyridin-1-one; 8-{[4-(1-ethylpiperidin-4-yl)phenyl]amino}-6-(4-methanesulfonylpiperazin-1-yl)-1,2-dihydro-2,7-naphthyridin-1-one; 8-{[4-(1-ethylpiperidin-4-yl)-2-methoxy-5-methylphenyl]amino}-6-(4-methanesulfonylphenyl)-1,2-dihydro-2,7-naphthyridin-1-one; 8-{[4-(morpholin-4-yl)phenyl]amino}-6-(pyrimidin-5-yl)-1,2-dihydro-2,7-naphthyridin-1-one; 8-(1H-indazol-6-ylamino)-6-[5-(propan-2-yloxy)pyridin-3-yl]-1,2-dihydro-2,7-naphthyridin-1-one; 6-[6-(2-hydroxypropan-2-yl)pyridin-3-yl]-8-(1H-indazol-6-ylamino)-1,2-dihydro-2,7-naphthyridin-1-one; 8-(1H-indazol-6-ylamino)-6-[3-methanesulfonyl-4-(pyrrolidin-1-ylmethyl)phenyl]-1,2-dihydro-2,7-naphthyridin-1-one; 8-(1H-indazol-6-ylamino)-6-[3-methanesulfonyl-4-(morpholin-4-ylmethyl)phenyl]-1,2-dihydro-2,7-naphthyridin-1-one; 8-(1H-indazol-6-ylamino)-6-[6-(morpholin-4-ylmethyl)pyridin-3-yl]-1,2-dihydro-2,7-naphthyridin-1-one; 8-(1H-indazol-6-ylamino)-6-[5-(pyrrolidin-1-ylmethyl)pyridin-3-yl]-1,2-dihydro-2,7-naphthyridin-1-one; 3-(1-{[3-fluoro-4-(morpholin-4-yl)phenyl]amino}-8-oxo-7,8-dihydro-2,7-naphthyridin-3-yl)-4-methoxy-N-methylbenzene-1-sulfonamide; 4-(1-{[3-fluoro-4-(morpholin-4-yl)phenyl]amino}-8-oxo-7,8-dihydro-2,7-naphthyridin-3-yl)-2-methoxy-N-methylbenzene-1-sulfonamide; 6-[6-(2-hydroxypropan-2-yl)pyridin-3-yl]-8-({6-[(2R)-2-methylmorpholin-4-yl]pyridin-3-yl}amino)-1,2-dihydro-2,7-naphthyridin-1-one; 8-(1H-indazol-6-ylamino)-6-(6-methylpyridin-2-yl)-1,2-dihydro-2,7-naphthyridin-1-one; 6-[5-methyl-6-(methylamino)pyridin-3-yl]-8-({6-[(2R)-2-methylmorpholin-4-yl]pyridin-3-yl}amino)-1,2-dihydro-2,7-naphthyridin-1-one; 8-({6-[(2R)-2-methylmorpholin-4-yl]pyridin-3-yl}amino)-6-[2-(propan-2-yloxy)pyrimidin-5-yl]-1,2-dihydro-2,7-naphthyridin-1-one; 8-({3-methyl-4-[(2R)-2-methylmorpholin-4-yl]phenyl}amino)-6-[2-(propan-2-yloxy)pyrimidin-5-yl]-1,2-dihydro-2,7-naphthyridin-1-one; 8-({3-methyl-4-[(2R)-2-methylmorpholin-4-yl]phenyl}amino)-6-[5-methyl-6-(methylamino)pyridin-3-yl]-1,2-dihydro-2,7-naphthyridin-1-one; 6-(1H-indazol-6-yl)-8-({3-methyl-4-[(2R)-2-methylmorpholin-4-yl]phenyl}amino)-1,2-dihydro-2,7-naphthyridin-1-one; 8-benzyl-6-(pyrimidin-5-yl)-1,2-dihydro-2,7-naphthyridin-1-one; 8-[(4-methoxyphenyl)methyl]-6-(pyrimidin-5-yl)-1,2-dihydro-2,7-naphthyridin-1-one; 8-amino-6-(pyrimidin-5-yl)-1,2-dihydro-2,7-naphthyridin-1-one; 8-amino-6-(2-aminopyrimidin-5-yl)-1,2-dihydro-2,7-naphthyridin-1-one; 6-(4-methanesulfonylpiperazin-1-yl)-8-{[4-(piperidin-4-yl)phenyl]amino}-1,2-dihydro-2,7-naphthyridin-1-one; 8-({3-methyl-4-[(2R)-2-methylmorpholin-4-yl]phenyl}amino)-6-(2-oxo-2,3-dihydro-1H-indol-5-yl)-1,2-dihydro-2,7-naphthyridin-1-one; 8-({3-methyl-4-[(2R)-2-methylmorpholin-4-yl]phenyl}amino)-6-(2-oxo-2,3-dihydro-1H-indol-6-yl)-1,2-dihydro-2,7-naphthyridin-1-one; 6-[6-(methylamino)pyridin-2-yl]-8-{[4-(morpholin-4-yl)phenyl]amino}-1,2-dihydro-2,7-naphthyridin-1-one; 8-{[4-(morpholin-4-yl)phenyl]amino}-6-[6-(propylamino)pyridin-2-yl]-1,2-dihydro-2,7-naphthyridin-1-one; 6-(5-amino-6-methoxypyrazin-2-yl)-8-{[4-(morpholin-4-yl)phenyl]amino}-1,2-dihydro-2,7-naphthyridin-1-one; 8-{[4-(morpholin-4-yl)phenyl]amino}-6-[6-(propan-2-ylamino)pyridin-2-yl]-1,2-dihydro-2,7-naphthyridin-1-one; 6-{6-[(3-methoxypropyl)amino]pyridin-2-yl}-8-{[4-(morpholin-4-yl)phenyl]amino}-1,2-dihydro-2,7-naphthyridin-1-one; 6-[6-(dimethylamino)pyridin-2-yl]-8-{[4-(morpholin-4-yl)phenyl]amino}-1,2-dihydro-2,7-naphthyridin-1-one; 6-(4-ethylpiperazin-1-yl)-8-{methyl[6-(morpholin-4-yl)pyridin-3-yl]amino}-1,2-dihydro-2,7-naphthyridin-1-one; 4-(2,6-dimethylphenyl)-8-{[4-(morpholin-4-yl)phenyl]amino}-1,2-dihydro-2,7-naphthyridin-1-one; 2-methyl-6-(1-methyl-1H-pyrazol-4-yl)-8-{methyl[4-(morpholin-4-yl)phenyl]amino}-1,2-dihydro-2,7-naphthyridin-1-one; 6-(2-aminopyrimidin-5-yl)-8-{methyl[4-(morpholin-4-yl)phenyl]amino}-1,2-dihydro-2,7-naphthyridin-1-one; 6-(2-methyl-1,3-thiazol-4-yl)-8-({4-[2-(pyrrolidin-1-yl)ethoxy]phenyl}amino)-1,2-dihydro-2,7-naphthyridin-1-one; 6-(2-methyl-1,3-thiazol-4-yl)-8-({4-methyl-3-[2-(pyrrolidin-1-yl)ethoxy]phenyl}amino)-1,2-dihydro-2,7-naphthyridin-1-one; 4-[(1-{[4-(morpholin-4-yl)phenyl]amino}-8-oxo-7,8-dihydro-2,7-naphthyridin-3-yl)amino]pyridine-3-sulfonamide; 6-(6-methoxypyrazin-2-yl)-8-({3-methyl-4-[3-(4-methylpiperazin-1-yl)propoxy]phenyl}amino)-1,2-dihydro-2,7-naphthyridin-1-one; 2-(4-{[3-(6-amino-5-methylpyridin-3-yl)-8-oxo-7,8-dihydro-2,7-naphthyridin-1-yl]amino}phenyl)-N,2-dimethylpropanamide 8-[(4-{2-[3-(dimethylamino)pyrrolidin-1-yl]ethyl}phenyl)amino]-6-(6-methoxypyrazin-2-yl)-1,2-dihydro-2,7-naphthyridin-1-one; 8-[(4-hydroxy-3-methylphenyl)amino]-6-(6-methoxypyrazin-2-yl)-1,2-dihydro-2,7-naphthyridin-1-one; 6-(2-amino-6-methylpyrimidin-4-yl)-8-{[3-methyl-4-(morpholin-4-yl)phenyl]amino}-1,2-dihydro-2,7-naphthyridin-1-one; 6-(2-aminopyrimidin-5-yl)-2-methyl-8-{[4-(1-methylpiperidin-4-yl)phenyl]amino}-1,2-dihydro-2,7-naphthyridin-1-one; 4-(2,6-dichlorophenyl)-8-{[4-(morpholin-4-yl)phenyl]amino}-1,2-dihydro-2,7-naphthyridin-1-one; 6-(6-amino-5-methoxypyridin-3-yl)-8-[(4-methanesulfonylphenyl)amino]-1,2-dihydro-2,7- naphthyridin-1-one; 8-[(4-methanesulfonylphenyl)amino]-6-[6-(morpholin-4-ylmethyl)pyridin-3-yl]-1,2-dihydro-2,7-naphthyridin-1-one; 8-{[3-fluoro-4-(morpholin-4-yl)phenyl]amino}-6-{imidazo[1,2-a]pyridin-6-yl}-1,2-dihydro-2,7-naphthyridin-1-one; 8-{[3-fluoro-4-(morpholin-4-yl)phenyl]amino}-6-(6-methylpyridin-3-yl)-1,2-dihydro-2,7-naphthyridin-1-one; 6-(1H-indazol-6-yl)-8-{[4-(1-methylpiperidin-4-yl)phenyl]amino}-1,2-dihydro-2,7-naphthyridin-1-one; 6-{imidazo[1,2-a]pyridin-6-yl}-8-{[4-(1-methylpiperidin-4-yl)phenyl]amino}-1,2-dihydro-2,7-naphthyridin-1-one; 8-{[4-(1-methylpiperidin-4-yl)phenyl]amino}-6-{1H-pyrrolo[2,3-b]pyridin-5-yl}-1,2-dihydro-2,7-naphthyridin-1-one; 8-{[4-(1-methylpiperidin-4-yl)phenyl]amino}-6-(6-methylpyridin-3-yl)-1,2-dihydro-2,7-naphthyridin-1-one; 8-({3-methyl-4-[(2R)-2-methylmorpholin-4-yl]phenyl}amino)-6-(6-methylpyridin-3-yl)-1,2-dihydro-2,7-naphthyridin-1-one; 6-(6-fluoro-2-methylpyridin-3-yl)-8-{[4-(morpholin-4-yl)phenyl]amino}-1,2-dihydro-2,7-naphthyridin-1-one; 6-(6-fluoro-2-methylpyridin-3-yl)-8-{[3-fluoro-4-(morpholin-4-yl)phenyl]amino}-1,2-dihydro-2,7-naphthyridin-1-one; 6-(6-fluoro-2-methylpyridin-3-yl)-8-{[4-(1-methylpiperidin-4-yl)phenyl]amino}-1,2-dihydro-2,7-naphthyridin-1-one; 8-{[3-fluoro-4-(morpholin-4-yl)phenyl]amino}-6-(4-methylpyridin-3-yl)-1,2-dihydro-2,7-naphthyridin-1-one; 8-({3-methyl-4-[(2R)-2-methylmorpholin-4-yl]phenyl}amino)-6-(4-methylpyridin-3-yl)-1,2-dihydro-2,7-naphthyridin-1-one; 6-(6-aminopyridin-3-yl)-8-({3-methyl-4-[(2R)-2-methylmorpholin-4-yl]phenyl}amino)-1,2-dihydro-2,7-naphthyridin-1-one; 6-(6-methoxypyridin-3-yl)-8-({3-methyl-4-[(2R)-2-methylmorpholin-4-yl]phenyl}amino)-1,2-dihydro-2,7-naphthyridin-1-one; 6-(6-aminopyridin-3-yl)-8-{[3-fluoro-4-(morpholin-4-yl)phenyl]amino}-1,2-dihydro-2,7-naphthyridin-1-one; 6-(6-aminopyridin-3-yl)-8-{[4-(1-methylpiperidin-4-yl)phenyl]amino}-1,2-dihydro-2,7-naphthyridin-1-one; 6-(6-methoxypyridin-3-yl)-8-{[4-(1-methylpiperidin-4-yl)phenyl]amino}-1,2-dihydro-2,7-naphthyridin-1-one; 6-(6-methoxypyridin-2-yl)-8-{[4-(morpholin-4-yl)phenyl]amino}-1,2-dihydro-2,7-naphthyridin-1-one; 6-(2-aminopyrimidin-5-yl)-8-({3-methyl-4-[2-(pyrrolidin-1-yl)ethoxy]phenyl}amino)-1,2-dihydro-2,7-naphthyridin-1-one; 8-({3-methyl-4-[2-(pyrrolidin-1-yl)ethoxy]phenyl}amino)-6-(pyrimidin-5-yl)-1,2-dihydro-2,7-naphthyridin-1-one; 6-(3-methoxypyrazin-2-yl)-8-({4-[2-(morpholin-4-yl)ethoxy]phenyl}amino)-1,2-dihydro-2,7-naphthyridin-1-one; 6-(6-aminopyridin-3-yl)-8-({3-methyl-4-[2-(pyrrolidin-1-yl)ethoxy]phenyl}amino)-1,2-dihydro-2,7-naphthyridin-1-one; 6-(6-methoxypyridin-3-yl)-8-({3-methyl-4-[2-(pyrrolidin-1-yl)ethoxy]phenyl}amino)-1,2-dihydro-2,7-naphthyridin-1-one; 6-(6-amino-5-methylpyridin-3-yl)-8-({3-methyl-4-[2-(pyrrolidin-1-yl)ethoxy]phenyl}amino)-1,2-dihydro-2,7-naphthyridin-1-one; 8-{[3-fluoro-4-(morpholin-4-yl)phenyl]amino}-6-(6-methoxypyridin-2-yl)-1,2-dihydro-2,7-naphthyridin-1-one; 6-[6-(ethylamino)pyridin-2-yl]-8-{[4-(morpholin-4-yl)phenyl]amino}-1,2-dihydro-2,7-naphthyridin-1-one; 6-(4-ethylpiperazin-1-yl)-2-methyl-8-{methyl[4-(morpholin-4-yl)phenyl]amino}-1,2-dihydro-2,7-naphthyridin-1-one; 8-{[4-(1-ethylpiperidin-4-yl)phenyl]amino}-6-(furan-3-yl)-1,2-dihydro-2,7-naphthyridin-1-one; 8-(1H-indazol-5-ylamino)-6-(2-methoxypyrimidin-5-yl)-1,2-dihydro-2,7-naphthyridin-1-one; 8-{[4-(1-ethylpiperidin-4-yl)phenyl]amino}-6-(4-hydroxyphenyl)-1,2-dihydro-2,7-naphthyridin-1-one; 6-(pyrimidin-5-yl)-8-{[3-(trifluoromethyl)phenyl]methyl}-1,2-dihydro-2,7-naphthyridin-1-one; 6-[4-(dimethylamino)phenyl]-8-{[4-(1-ethylpiperidin-4-yl)phenyl]amino}-1,2-dihydro-2,7-naphthyridin-1-one; 8-{[4-(1-ethylpiperidin-4-yl)phenyl]amino}-6-(4-fluoro-2-methylphenyl)-1,2-dihydro-2,7-naphthyridin-1-one; 8-{[4-(1-ethylpiperidin-4-yl)phenyl]amino}-6-(4-fluoro-3-methoxyphenyl)-1,2-dihydro-2,7-naphthyridin-1-one; 6-[4-(benzyloxy)phenyl]-8-{[4-(1-ethylpiperidin-4-yl)phenyl]amino}-1,2-dihydro-2,7-naphthyridin-1-one; 6-(6-fluoropyridin-3-yl)-8-({6-[(2R)-2-methylmorpholin-4-yl]pyridin-3-yl}amino)-1,2-dihydro-2,7-naphthyridin-1-one; 6-[6-(methylamino)pyridin-3-yl]-8-({6-[(2R)-2-methylmorpholin-4-yl]pyridin-3-yl}amino)-1,2-dihydro-2,7-naphthyridin-1-one; 6-[6-(ethylamino)pyridin-3-yl]-8-({6-[(2R)-2-methylmorpholin-4-yl]pyridin-3-yl}amino)-1,2-dihydro-2,7-naphthyridin-1-one; 2-methyl-6-[2-(methylamino)pyrimidin-5-yl]-8-{[4-(morpholin-4-yl)phenyl]amino}-1,2-dihydro-2,7-naphthyridin-1-one; 8-({6-[(2R,6S)-2,6-dimethylmorpholin-4-yl]pyridin-3-yl}amino)-6-(6-methoxypyrazin-2-yl)-1,2-dihydro-2,7-naphthyridin-1-one; 6-(6-methoxypyrazin-2-yl)-8-({4-[2-(pyrrolidin-1-yl)ethoxy]phenyl}amino)-1,2-dihydro-2,7-naphthyridin-1-one; 6-(6-methoxypyrazin-2-yl)-8-{[4-(trifluoromethoxy)phenyl]amino}-1,2-dihydro-2,7-naphthyridin-1-one; 8-[(3-methoxy-4-phenylphenyl)amino]-6-(6-methoxypyrazin-2-yl)-1,2-dihydro-2,7-naphthyridin-1-one; 6-(6-methoxypyrazin-2-yl)-8-{[4-(2-methylpyridin-4-yl)phenyl]amino}-1,2-dihydro-2,7-naphthyridin-1-one; 6-(6-methoxypyrazin-2-yl)-8-{[3-methyl-4-(morpholin-4-yl)phenyl]amino}-1,2-dihydro-2,7-naphthyridin-1-one; 6-(6-amino-5-methylpyridin-3-yl)-8-[(4-{2-[3-(dimethylamino)pyrrolidin-1-yl]ethyl}phenyl)amino]-1,2-dihydro-2,7-naphthyridin-1-one; 6-(6-amino-5-methylpyridin-3-yl)-8-{[4-(2-methylpyridin-4-yl)phenyl]amino}-1,2-dihydro-2,7-naphthyridin-1-one; 6-(6-amino-5-methylpyridin-3-yl)-8-{[4-(4-hydroxypiperidin-1-yl)phenyl]amino}-1,2-dihydro-2,7-naphthyridin-1-one; 6-(6-amino-5-methylpyridin-3-yl)-8-{[3-methyl-4-(morpholin-4-yl)phenyl]amino}-1,2-dihydro-2,7-naphthyridin-1-one; 8-{[4-(1-acetylpiperidin-4-yl)-3-methylphenyl]amino}-6-(2-aminopyrimidin-5-yl)-1,2-dihydro-2,7-naphthyridin-1-one; 5-(1-{[4-(morpholin-4-yl)phenyl]amino}-8-oxo-7,8-dihydro-2,7-naphthyridin-3-yl)pyridine-2-sulfonamide; N-methyl-5-(1-{[4-(morpholin-4-yl)phenyl]amino}-8-oxo-7,8-dihydro-2,7-naphthyridin-3-yl)pyridine-2-sulfonamide; 6-(3-methoxypyrazin-2-yl)-8-({3-methyl-4-[2-(pyrrolidin-1-yl)ethoxy]phenyl}amino)-1,2-dihydro-2,7-naphthyridin-1-one; 8-[(3-methoxy-4-methylphenyl)amino]-6-(pyrimidin-5-yl)-1,2-dihydro-2,7-naphthyridin-1-one; 8-amino-2-methyl-6-(pyrimidin-5-yl)-1,2-dihydro-2,7-naphthyridin-1-one; 2-methyl-8-(methylamino)-6-(pyrimidin-5-yl)-1,2-dihydro-2,7-naphthyridin-1-one; 8-amino-6-(2-aminopyrimidin-5-yl)-2-methyl-1,2-dihydro-2,7-naphthyridin-1-one; 6-(2-aminopyrimidin-5-yl)-2-methyl-8-(methylamino)-1,2-dihydro-2,7-naphthyridin-1-one; 8-{[4-(1-ethylpiperidin-4-yl)phenyl]amino}-6-(2-methanesulfonylphenyl)-1,2-dihydro-2,7-naphthyridin-1-one; 6-(4-methanesulfonylphenyl)-8-{[3-(morpholin-4-yl)phenyl]amino}-1,2-dihydro-2,7-naphthyridin-1-one; 8-{[4-(1-ethylpiperidin-4-yl)phenyl]amino}-6-[2-(methylsulfanyl)phenyl]-1,2-dihydro-2,7-naphthyridin-1-one; 8-({4-[(4-ethylpiperazin-1-yl)methyl]phenyl}amino)-6-[(2-methylphenyl)amino]-1,2-dihydro-2,7-naphthyridin-1-one; 8-({4-[(4-ethylpiperazin-1-yl)methyl]phenyl}amino)-6-(3-methanesulfonylphenyl)-1,2-dihydro-2,7-naphthyridin-1-one; 8-({4-[(4-ethylpiperazin-1-yl)methyl]phenyl}amino)-6-(4-methanesulfonylphenyl)-1,2-dihydro-2,7-naphthyridin-1-one; 6-(3-methanesulfonylphenyl)-8-{[3-(morpholin-4-yl)phenyl]amino}-1,2-dihydro-2,7-naphthyridin-1-one; 8-{[4-(1-ethylpiperidin-4-yl)phenyl]

amino}-6-[(2-methylphenyl)amino]-1,2-dihydro-2,7-naphthyridin-1-one; 6-[4-(2-hydroxypropan-2-yl)phenyl]-8-(1H-indazol-5-ylamino)-1,2-dihydro-2,7-naphthyridin-1-one; 6-[6-(2-hydroxypropan-2-yl)pyridin-3-yl]-8-(1H-indazol-5-ylamino)-1,2-dihydro-2,7-naphthyridin-1-one; 8-(1H-indazol-5-ylamino)-6-[5-(propan-2-yloxy)pyridin-3-yl]-1,2-dihydro-2,7-naphthyridin-1-one; 6-(6-fluoropyridin-3-yl)-8-(1H-indazol-6-ylamino)-1,2-dihydro-2,7-naphthyridin-1-one; 8-(1H-indazol-6-ylamino)-6-[6-(methylamino)pyridin-3-yl]-1,2-dihydro-2,7-naphthyridin-1-one; 6-[6-(ethylamino)pyridin-3-yl]-8-(1H-indazol-6-ylamino)-1,2-dihydro-2,7-naphthyridin-1-one; 6-(2-aminopyrimidin-5-yl)-2-[2-(dimethylamino)ethyl]-8-{[4-(morpholin-4-yl)phenyl]amino}-1,2-dihydro-2,7-naphthyridin-1-one; 6-(2-methyl-1,3-thiazol-4-yl)-8-{[4-(trifluoromethoxy)phenyl]amino}-1,2-dihydro-2,7-naphthyridin-1-one; N-methyl-3-{[3-(2-methyl-1,3-thiazol-4-yl)-8-oxo-7,8-dihydro-2,7-naphthyridin-1-yl]amino}benzamide; 3-{[3-(2-methyl-1,3-thiazol-4-yl)-8-oxo-7,8-dihydro-2,7-naphthyridin-1-yl]amino}-N-propylbenzamide; 6-(2-methyl-1,3-thiazol-4-yl)-8-{[6-(piperidin-4-yl)pyridin-3-yl]amino}-1,2-dihydro-2,7-naphthyridin-1-one; 6-(2-methyl-1,3-thiazol-4-yl)-8-{[3-methyl-4-(piperidin-4-yl)phenyl]amino}-1,2-dihydro-2,7-naphthyridin-1-one; 8-({4-[(4-ethylpiperazin-1-yl)methyl]phenyl}amino)-6-(6-methoxypyrazin-2-yl)-1,2-dihydro-2,7-naphthyridin-1-one; N-(3-methoxypropyl)-4-{[3-(6-methoxypyrazin-2-yl)-8-oxo-7,8-dihydro-2,7-naphthyridin-1-yl]amino}benzene-1-sulfonamide; 6-(6-amino-5-methylpyridin-3-yl)-8-({4-[(2R,6S)-2,6-dimethylmorpholin-4-yl]phenyl}amino)-1,2-dihydro-2,7-naphthyridin-1-one; 6-(2-aminopyrimidin-5-yl)-2-methyl-8-{[3-(trifluoromethyl)phenyl]amino}-1,2-dihydro-2,7-naphthyridin-1-one; 6-(2-aminopyrimidin-5-yl)-2-methyl-8-({3-methyl-4-[2-(pyrrolidin-1-yl)ethoxy]phenyl}amino)-1,2-dihydro-2,7-naphthyridin-1-one; 6-(2-aminopyrimidin-5-yl)-2-ethyl-8-{[4-(morpholin-4-yl)phenyl]amino}-1,2-dihydro-2,7-naphthyridin-1-one; 6-(2-aminopyrimidin-5-yl)-2-methyl-8-({4-[2-(morpholin-4-yl)ethoxy]phenyl}amino)-1,2-dihydro-2,7-naphthyridin-1-one; 6-(2-aminopyrimidin-5-yl)-2-methyl-8-({3-[2-(morpholin-4-yl)ethoxy]phenyl}amino)-1,2-dihydro-2,7-naphthyridin-1-one; 6-(6-amino-5-methylpyridin-3-yl)-8-({3-chloro-4-[(2R,6S)-2,6-dimethylmorpholin-4-yl]phenyl}amino)-1,2-dihydro-2,7-naphthyridin-1-one; 8-({3-fluoro-4-[(2R)-2-methylmorpholin-4-yl]phenyl}amino)-6-(6-fluoropyridin-3-yl)-1,2-dihydro-2,7-naphthyridin-1-one; 8-({3-fluoro-4-[(2R)-2-methylmorpholin-4-yl]phenyl}amino)-6-[6-(methylamino)pyridin-3-yl]-1,2-dihydro-2,7-naphthyridin-1-one; 6-[6-(ethylamino)pyridin-3-yl]-8-({3-fluoro-4-[(2R)-2-methylmorpholin-4-yl]phenyl}amino)-1,2-dihydro-2,7-naphthyridin-1-one; 8-(1H-indazol-5-ylamino)-6-[3-methanesulfonyl-4-(pyrrolidin-1-ylmethyl)phenyl]-1,2-dihydro-2,7-naphthyridin-1-one; 8-(1H-indazol-5-ylamino)-6-[3-methanesulfonyl-4-(morpholin-4-ylmethyl)phenyl]-1,2-dihydro-2,7-naphthyridin-1-one; 8-(1H-indazol-5-ylamino)-6-[5-(morpholin-4-ylmethyl)pyridin-3-yl]-1,2-dihydro-2,7-naphthyridin-1-one; 8-(1H-indazol-5-ylamino)-6-[5-(pyrrolidin-1-ylmethyl)pyridin-3-yl]-1,2-dihydro-2,7-naphthyridin-1-one; 6-[4-(2-hydroxypropan-2-yl)phenyl]-8-(1H-indazol-6-ylamino)-1,2-dihydro-2,7-naphthyridin-1-one; 6-(2-aminopyrimidin-5-yl)-8-[(3-methoxy-4-methylphenyl)amino]-1,2-dihydro-2,7-naphthyridin-1-one; 2-(2-methanesulfonylethyl)-8-({4-[1-(2-methanesulfonylethyl)piperidin-4-yl]phenyl}amino)-6-(4-methanesulfonylphenyl)-1,2-dihydro-2,7-naphthyridin-1-one; 6-chloro-2-(2-methanesulfonylethyl)-8-({4-[1-(2-methanesulfonylethyl)piperidin-4-yl]phenyl}amino)-1,2-dihydro-2,7-naphthyridin-1-one; 6-chloro-8-{[4-(1-ethylpiperidin-4-yl)phenyl]amino}-2-(2-methanesulfonylethyl)-1,2-dihydro-2,7-naphthyridin-1-one; 8-{[4-(1-ethylpiperidin-4-yl)phenyl]amino}-2-(2-methanesulfonylethyl)-6-(4-methanesulfonylphenyl)-1,2-dihydro-2,7-naphthyridin-1-one; 2-(2-methanesulfonylethyl)-6-(4-methanesulfonylphenyl)-8-{[4-(piperidin-4-yl)phenyl]amino}-1,2-dihydro-2,7-naphthyridin-1-one; 6-chloro-2-(2-methanesulfonylethyl)-8-{[4-(piperidin-4-yl)phenyl]amino}-1,2-dihydro-2,7-naphthyridin-1-one; tert-butyl 4-(4-{[7-(2-methanesulfonylethyl)-3-(4-methanesulfonylphenyl)-8-oxo-7,8-dihydro-2,7-naphthyridin-1-yl]amino}phenyl)piperidine-1-carboxylate; tert-butyl 4-(4-{[3-chloro-7-(2-methanesulfonylethyl)-8-oxo-7,8-dihydro-2,7-naphthyridin-1-yl]amino}phenyl)piperidine-1-carboxylate; 6-(6-methoxypyridin-2-yl)-8-({3-methyl-4-[(2R)-2-methylmorpholin-4-yl]phenyl}amino)-1,2-dihydro-2,7-naphthyridin-1-one; 6-(6-methoxypyridin-2-yl)-8-({4-[2-(morpholin-4-yl)ethoxy]phenyl}amino)-1,2-dihydro-2,7-naphthyridin-1-one; 6-(3-methoxypyrazin-2-yl)-8-({3-methyl-4-[(2R)-2-methylmorpholin-4-yl]phenyl}amino)-1,2-dihydro-2,7-naphthyridin-1-one; 8-({3-fluoro-4-[(2R)-2-methylmorpholin-4-yl]phenyl}amino)-6-(6-methylpyridin-3-yl)-1,2-dihydro-2,7-naphthyridin-1-one; 8-({3-fluoro-4-[(2R)-2-methylmorpholin-4-yl]phenyl}amino)-6-(6-methoxypyridin-2-yl)-1,2-dihydro-2,7-naphthyridin-1-one; 8-({3-fluoro-4-[(2R)-2-methylmorpholin-4-yl]phenyl}amino)-6-(3-methoxypyrazin-2-yl)-1,2-dihydro-2,7-naphthyridin-1-one; 8-{[3-fluoro-4-(morpholin-4-yl)phenyl]amino}-6-(3-methoxypyrazin-2-yl)-1,2-dihydro-2,7-naphthyridin-1-one; 8-(1H-indazol-6-ylamino)-6-(pyrimidin-5-yl)-1,2-dihydro-2,7-naphthyridin-1-one; 6-(pyrimidin-5-yl)-8-[(2,2,2-trifluoroethyl)amino]-1,2-dihydro-2,7-naphthyridin-1-one; 6-(2-methoxypyrimidin-5-yl)-8-[(2,2,2-trifluoroethyl)amino]-1,2-dihydro-2,7-naphthyridin-1-one; 6-(2-aminopyrimidin-5-yl)-2-[2-(dimethylamino)ethyl]-8-[(3-methoxyphenyl)amino]-1,2-dihydro-2,7-naphthyridin-1-one; 6-(5-amino-4-methylpyridin-2-yl)-8-{[4-(morpholin-4-yl)phenyl]amino}-1,2-dihydro-2,7-naphthyridin-1-one; 6-(5-amino-6-methoxypyrazin-2-yl)-8-{[4-(piperidin-4-yl)phenyl]amino}-1,2-dihydro-2,7-naphthyridin-1-one; 6-(2-methoxypyrimidin-5-yl)-8-({6-[(2S)-2-methylmorpholin-4-yl]pyridin-3-yl}amino)-1,2-dihydro-2,7-naphthyridin-1-one; 8-({6-[(2S)-2-methylmorpholin-4-yl]pyridin-3-yl}amino)-6-(pyrimidin-5-yl)-1,2-dihydro-2,7-naphthyridin-1-one; 6-(2-aminopyrimidin-5-yl)-2-(2-methoxyethyl)-8-{[4-(morpholin-4-yl)phenyl]amino}-1,2-dihydro-2,7-naphthyridin-1-one; 2-[2-(dimethylamino)ethyl]-6-[2-(methylamino)pyrimidin-5-yl]-8-{[4-(morpholin-4-yl)phenyl]amino}-1,2-dihydro-2,7-naphthyridin-1-one; 8-{[4-(1-acetylpiperidin-4-yl)-3-methylphenyl]amino}-6-(2-aminopyrimidin-5-yl)-2-methyl-1,2-dihydro-2,7-naphthyridin-1-one; 6-(2-aminopyrimidin-5-yl)-8-{[3-methyl-4-(1-methylpiperidin-4-yl)phenyl]amino}-1,2-dihydro-2,7-naphthyridin-1-one; 8-{[3-methyl-4-(1-methylpiperidin-4-yl)phenyl]amino}-6-(6-methylpyridin-3-yl)-1,2-dihydro-2,7-naphthyridin-1-one; 6-(6-methoxypyridin-2-yl)-8-{[3-methyl-4-(1-methylpiperidin-4-yl)phenyl]amino}-1,2-dihydro-2,7-naphthyridin-1-one; 8-{[4-(1-acetylpiperidin-4-yl)-3-methylphenyl]amino}-6-(6-methoxypyridin-2-yl)-1,2-dihydro-2,7-naphthyridin-1-one; 8-{[4-(1-acetylpiperidin-4-yl)-3-methylphenyl]amino}-6-(3-methoxypyrazin-2-yl)-1,2-dihydro-2,7-naphthyridin-1-one; 8-{[4-(1-acetylpiperidin-4-yl)-3-methylphenyl]amino}-6-(6-methylpyridin-3-yl)-1,2-dihydro-2,7-naphthyridin-1-one; dimethoxypyrimidin-5- yl)-8-({3-methyl-4-[2-(pyrrolidin-1-yl)ethoxy]phenyl}amino)-1,2-dihydro-2,7-naphthyridin-1-one; 6-(2,4-dimethoxypyrimidin-5-yl)-8-({4-[2-(pyrrolidin-1-yl)ethoxy]phenyl}amino)-1,2-dihydro-2,7-naphthyridin-1-one; 6-(2,4-dimethoxypyrimidin-5-yl)-8-({4-[2-(morpholin-4-yl)ethoxy]phenyl}amino)-1,2-dihydro-2,7-naphthyridin-1-one; 6-(6-amino-5-methylpyridin-3-yl)-8-({4-[2-(4-ethylpiperazin-1-yl)ethyl]phenyl}amino)-1,2-dihydro-2,7-naphthyridin-1-one; 6-(2,4-dimethoxypyrimidin-5-yl)-8-({4-[2-(4-ethylpiperazin-1-yl)ethyl]phenyl}amino)-1,2-dihydro-2,7-naphthyridin-1-one; 8-({4-[2-(4-ethylpiperazin-1-yl)ethyl]phenyl}amino)-6-(6-methoxypyrazin-2-yl)-1,2-dihydro-2,7-naphthyridin-1-one; 6-(6-methoxypyrazin-2-yl)-8-({4-[2-(morpholin-4-yl)ethyl]phenyl}amino)-1,2-dihydro-2,7-naphthyridin-1-one; 6-(5-amino-6-methoxypyrazin-2-yl)-8-{[4-(1-methylpiperidin-4-yl)phenyl]amino}-1,2-dihydro-2,7-naphthyridin-1-one; 8-[{4-(1-acetylpiperidin-4-yl)phenyl]amino}-6-(5-amino-6-methoxypyrazin-2-yl)-1,2-dihydro-2,7-naphthyridin-1-one; 6-(6-aminopyridin-3-yl)-8-({4-[2-(morpholin-4-yl)ethyl]phenyl}amino)-1,2-dihydro-2,7-naphthyridin-1-one; 6-(6-aminopyridin-3-yl)-8-({4-[2-(4-ethylpiperazin-1-yl)ethyl]phenyl}amino)-1,2-dihydro-2,7-naphthyridin-1-one; 6-(6-aminopyridin-3-yl)-8-[(4-{2-[4-(morpholin-4-yl)piperidin-1-yl]ethyl}phenyl)amino]-1,2-dihydro-2,7-naphthyridin-1-one; 6-(6-aminopyridin-3-yl)-8-[(4-{2-[4-(2-methoxyethyl)piperazin-1-yl]ethyl}phenyl)amino]-1,2-dihydro-2,7-naphthyridin-1-one; 6-(6-aminopyridin-3-yl)-8-[(4-{2-[(2S)-2-(hydroxymethyl)pyrrolidin-1-yl]ethyl}phenyl)amino]-1,2-dihydro-2,7-naphthyridin-1-one; 6-(6-aminopyridin-3-yl)-8-({4-[(1-methylpiperidin-4-yl)oxy]phenyl}amino)-1,2-dihydro-2,7-naphthyridin-1-one; 8-({3-methyl-4-[(2S)-2-methylmorpholin-4-yl]phenyl}amino)-6-(pyrimidin-5-yl)-1,2-dihydro-2,7-naphthyridin-1-one; 6-(2-methoxypyrimidin-5-yl)-8-({3-methyl-4-[(2S)-2-methylmorpholin-4-yl]phenyl}amino)-1,2-dihydro-2,7-naphthyridin-1-one; 8-{[4-(morpholin-4-yl)phenyl]amino}-6-{6-[2-(pyrrolidin-1-yl)ethoxy]pyridin-2-yl}-1,2-dihydro-2,7-naphthyridin-1-one; 6-(2-ethoxypyrimidin-5-yl)-8-({3-methyl-4-[(2R)-2-methylmorpholin-4-yl]phenyl}amino)-1,2-dihydro-2,7-naphthyridin-1-one; 6-[6-(4-methylpiperazin-1-yl)pyridin-2-yl]-8-{[4-(morpholin-4-yl)phenyl]amino}-1,2-dihydro-2,7-naphthyridin-1-one; 8-{[4-(morpholin-4-yl)phenyl]amino}-6-[6-(morpholin-4-yl)pyridin-2-yl]-1,2-dihydro-2,7-naphthyridin-1-one; 8-{[4-(morpholin-4-yl)phenyl]amino}-6-[6-(pyrrolidin-1-yl)pyridin-2-yl]-1,2-dihydro-2,7-naphthyridin-1-one; 6-(2-ethoxypyrimidin-5-yl)-8-({6-[(2S)-2-methylmorpholin-4-yl]pyridin-3-yl}amino)-1,2-dihydro-2,7-naphthyridin-1-one; 6-(2-ethoxypyrimidin-5-yl)-8-({6-[(2R)-2-methylmorpholin-4-yl]pyridin-3-yl}amino)-1,2-dihydro-2,7-naphthyridin-1-one; 6-(2-ethoxypyrimidin-5-yl)-8-({3-methyl-4-[(2S)-2-methylmorpholin-4-yl]phenyl}amino)-1,2-dihydro-2,7-naphthyridin-1-one; 6-(6-aminopyridin-3-yl)-8-({[4-(morpholin-4-yl)phenyl]methyl}amino)-1,2-dihydro-2,7-naphthyridin-1-one; 8-{[3-methyl-4-(1-methylpiperidin-4-yl)phenyl]amino}-6-(pyrimidin-5-yl)-1,2-dihydro-2,7-naphthyridin-1-one; 6-(6-aminopyridin-3-yl)-8-({3-methyl-4-[(1-methylpiperidin-4-yl)oxy]phenyl}amino)-1,2-dihydro-2,7-naphthyridin-1-one; 6-(6-aminopyridin-3-yl)-8-{[4-(oxan-4-yloxy)phenyl]amino}-1,2-dihydro-2,7-naphthyridin-1-one; 6-[2-(methylamino)pyrimidin-5-yl]-8-({4-[2-(morpholin-4-yl)ethyl]phenyl}amino)-1,2-dihydro-2,7-naphthyridin-1-one; 6-[2-(methylamino)pyrimidin-5-yl]-8-[(4-{2-[4-(morpholin-4-yl)piperidin-1-yl]ethyl}phenyl)amino]-1,2-dihydro-2,7-naphthyridin-1-one; 6-[2-(methylamino)pyrimidin-5-yl]-8-({4-[(1-methylpiperidin-4-yl)oxy]phenyl}amino)-1,2-dihydro-2,7-naphthyridin-1-one; 8-({3-methyl-4-[(1-methylpiperidin-4-yl)oxy]phenyl}amino)-6-[2-(methylamino)pyrimidin-5-yl]-1,2-dihydro-2,7-naphthyridin-1-one; 6-[2-(methylamino)pyrimidin-5-yl]-8-{[4-(oxan-4-yloxy)phenyl]amino}-1,2-dihydro-2,7-naphthyridin-1-one; 6-[2-(methylamino)pyrimidin-5-yl]-8-({4-[1-(3,3,3-trifluoro-2-hydroxypropyl)piperidin-4-yl]phenyl}amino)-1,2-dihydro-2,7-naphthyridin-1-one; 6-(2-aminopyrimidin-5-yl)-2-(2-methoxyethyl)-8-[(3-methoxyphenyl)amino]-1,2-dihydro-2,7-naphthyridin-1-one; 6-(6-amino-5-methylpyridin-3-yl)-8-[(2,3-dimethyl-2H-indazol-6-yl)amino]-1,2-dihydro-2,7-naphthyridin-1-one; 6-(2-aminopyrimidin-5-yl)-8-[(2,3-dimethyl-2H-indazol-6-yl)amino]-2-methyl-1,2-dihydro-2,7-naphthyridin-1-one; 6-(2-aminopyrimidin-5-yl)-2-methyl-8-[(2-methyl-2H-indazol-6-yl)amino]-1,2-dihydro-2,7-naphthyridin-1-one; 6-(2-aminopyrimidin-5-yl)-8-({4-[(2R,6S)-2,6-dimethylmorpholin-4-yl]phenyl}amino)-2-methyl-1,2-dihydro-2,7-naphthyridin-1-one; 6-(2-aminopyrimidin-5-yl)-2-methyl-8-({4-[2-(morpholin-4-yl)ethyl]phenyl}amino)-1,2-dihydro-2,7-naphthyridin-1-one; 6-(2-aminopyrimidin-5-yl)-8-[(4-{2-[4-(dimethylamino)piperidin-1-yl]ethyl}phenyl)amino]-2-methyl-1,2-dihydro-2,7-naphthyridin-1-one; 8-({3-methyl-4-[(2R)-2-methylmorpholin-4-yl]phenyl}amino)-6-(2-methylpyrimidin-5-yl)-1,2-dihydro-2,7-naphthyridin-1-one; 6-(2-methyl-1,3-thiazol-4-yl)-8-({6-[(2R)-2-methylmorpholin-4-yl]pyridin-3-yl}amino)-1,2-dihydro-2,7-naphthyridin-1-one; 6-(2-methyl-1,3-thiazol-4-yl)-8-({3-methyl-4-[(2R)-2-methylmorpholin-4-yl]phenyl}amino)-1,2-dihydro-2,7-naphthyridin-1-one; 8-[(4-{2-[(2S)-2-(hydroxymethyl)pyrrolidin-1-yl]ethyl}phenyl)amino]-6-(2-methyl-1,3-thiazol-4-yl)-1,2-dihydro-2,7-naphthyridin-1-one; 6-(2-methyl-1,3-thiazol-4-yl)-8-({[4-(morpholin-4-yl)phenyl]methyl}amino)-1,2-dihydro-2,7-naphthyridin-1-one; 8-{[4-(piperidin-4-yl)phenyl]amino}-6-{[2-(propane-2-sulfonyl)phenyl]amino}-1,2-dihydro-2,7-naphthyridin-1-one; 6-(4-methyl-1,3-thiazol-2-yl)-8-{[4-(morpholin-4-yl)phenyl]amino}-1,2-dihydro-2,7-naphthyridin-1-one; 6-{[2-(methylsulfanyl)phenyl]amino}-8-{[4-(piperidin-4-yl)phenyl]amino}-1,2-dihydro-2,7-naphthyridin-1-one; 6-(3-methylpyridin-2-yl)-8-{[4-(morpholin-4-yl)phenyl]amino}-1,2-dihydro-2,7-naphthyridin-1-one; 6-[(3-phenoxyphenyl)amino]-8-{[4-(piperidin-4-yl)phenyl]amino}-1,2-dihydro-2,7-naphthyridin-1-one; 8-[(4-{2-[4-(2-methoxyethyl)piperazin-1-yl]ethyl}phenyl)amino]-6-(6-methylpyridin-2-yl)-1,2-dihydro-2,7-naphthyridin-1-one; 6-(6-methylpyridin-2-yl)-8-[(4-{2-[4-(pyrrolidin-1-yl)piperidin-1-yl]ethyl}phenyl)amino]-1,2-dihydro-2,7-naphthyridin-1-one; 6-[(2-ethoxyphenyl)amino]-8-{[4-(piperidin-4-yl)phenyl]amino}-1,2-dihydro-2,7-naphthyridin-1-one; 6-(6-methoxypyrazin-2-yl)-8-[(3-methyl-1H-indazol-6-yl)amino]-1,2-dihydro-2,7-naphthyridin-1-one; 6-(2-methoxypyrimidin-5-yl)-8-[(3-methyl-1H-indazol-6-yl)amino]-1,2-dihydro-2,7-naphthyridin-1-one; 8-[(3-methyl-1H-indazol-6-yl)amino]-6-(6-methylpyridin-2-yl)-1,2-dihydro-2,7-naphthyridin-1-one; 8-[(3-methyl-1H-indazol-6-yl)amino]-6-(pyrimidin-5-yl)-1,2-dihydro-2,7-naphthyridin-1-one; 6-[6-(4-methyl-1H-imidazol-1-yl)pyridin-2-yl]-8-({3-methyl-4-[(2R)-2-methylmorpholin-4-yl]phenyl}amino)-1,2-dihydro-2,7-naphthyridin-1-one; 8-({3-methyl-4-[(2R)-2-methylmorpholin-4-yl]phenyl}amino)-6-[6-(morpholin-4-yl)pyridin-2-yl]-1,2-dihydro-2,7-naphthyridin-1-one; 6-[6-(dimethylamino)pyridin-2-yl]-8-({3-methyl-4-[(2R)-2-methylmorpholin-4-yl]phenyl}amino)-1,2-dihydro-2,7-naphthyridin-1-one; 6-(2-methoxypyrimidin-5-yl)-8-{[3-methyl-4-(1- methylpiperidin-4-yl)phenyl]amino}-1,2-dihydro-2,7-naphthyridin-1-one; 8-{[3-methyl-4-(piperidin-4-yl)phenyl]amino}-6-(pyrimidin-5-yl)-1,2-dihydro-2,7-naphthyridin-1-one; 6-(2-methoxypyrimidin-5-yl)-8-{[3-methyl-4-(piperidin-4-yl)phenyl]amino}-1,2-dihydro-2,7-naphthyridin-1-one; 6-(3-methoxypyrazin-2-yl)-8-{[3-methyl-4-(1-methylpiperidin-4-yl)phenyl]amino}-1,2-dihydro-2,7-naphthyridin-1-one; 6-(6-methoxypyrazin-2-yl)-8-{[3-methyl-4-(piperidin-4-yl)phenyl]amino}-1,2-dihydro-2,7-naphthyridin-1-one; 6-(6-methoxypyrazin-2-yl)-8-{[3-methyl-4-(1-methylpiperidin-4-yl)phenyl]amino}-1,2-dihydro-2,7-naphthyridin-1-one; 8-({4-[(4-ethylpiperazin-1-yl)methyl]phenyl}amino)-6-[(5-methoxy-2-methylphenyl)amino]-1,2-dihydro-2,7-naphthyridin-1-one; 8-({4-[(4-ethylpiperazin-1-yl)methyl]phenyl}amino)-6-{[2-(trifluoromethoxy)phenyl]amino}-1,2-dihydro-2,7-naphthyridin-1-one; 8-({4-[(4-ethylpiperazin-1-yl)methyl]phenyl}amino)-6-{[2-methoxy-5-(trifluoromethyl)phenyl]amino}-1,2-dihydro-2,7-naphthyridin-1-one; 8-({4-[(4-ethylpiperazin-1-yl)methyl]phenyl}amino)-6-(1H-indazol-6-ylamino)-1,2-dihydro-2,7-naphthyridin-1-one; 8-({4-[(4-ethylpiperazin-1-yl)methyl]phenyl}amino)-6-[(2-methoxy-5-methylphenyl)amino]-1,2-dihydro-2,7-naphthyridin-1-one; N-(3-{[1-({4-[(4-ethylpiperazin-1-yl)methyl]phenyl}amino)-8-oxo-7,8-dihydro-2,7-naphthyridin-3-yl]amino}-4-methoxyphenyl)acetamide 8-({4-[(4-ethylpiperazin-1-yl)methyl]phenyl}amino)-6-{[2-methoxy-4-(phenylamino)phenyl]amino}-1,2-dihydro-2,7-naphthyridin-1-one; 6-[(5-chloro-2-methoxyphenyl)amino]-8-({4-[(4-ethylpiperazin-1-yl)methyl]phenyl}amino)-1,2-dihydro-2,7-naphthyridin-1-one; 8-({4-[(4-ethylpiperazin-1-yl)methyl]phenyl}amino)-6-[(2-methoxy-5-nitrophenyl)amino]-1,2-dihydro-2,7-naphthyridin-1-one; 8-{[4-(piperidin-4-yl)phenyl]amino}-6-{[3-(trifluoromethoxy)phenyl]amino}-1,2-dihydro-2,7-naphthyridin-1-one; 6-[(3-methoxy-4-phenylphenyl)amino]-8-{[4-(piperidin-4-yl)phenyl]amino}-1,2-dihydro-2,7-naphthyridin-1-one; 8-({4-[(4-ethylpiperazin-1-yl)methyl]phenyl}amino)-6-[(3-methoxy-4-phenylphenyl)amino]-1,2-dihydro-2,7-naphthyridin-1-one; 8-[(2,3-dimethyl-2H-indazol-6-yl)amino]-6-(6-methoxypyrazin-2-yl)-1,2-dihydro-2,7-naphthyridin-1-one; 6-(6-methoxypyrazin-2-yl)-8-[(2-methyl-2H-indazol-6-yl)amino]-1,2-dihydro-2,7-naphthyridin-1-one; 6-(6-methoxypyrazin-2-yl)-8-({4-[1-(3,3,3-trifluoro-2-hydroxypropyl)piperidin-4-yl]phenyl}amino)-1,2-dihydro-2,7-naphthyridin-1-one; 6-(6-methoxypyrazin-2-yl)-8-{[6-(oxan-4-yl)pyridin-3-yl]amino}-1,2-dihydro-2,7-naphthyridin-1-one; 8-[(2,3-dimethyl-2H-indazol-6-yl)amino]-6-(3-methoxypyrazin-2-yl)-1,2-dihydro-2,7-naphthyridin-1-one; 6-(2,4-dimethoxypyrimidin-5-yl)-8-[(2,3-dimethyl-2H-indazol-6-yl)amino]-1,2-dihydro-2,7-naphthyridin-1-one; 6-(2,4-dimethoxypyrimidin-5-yl)-8-{[3-methyl-4-(2-methylmorpholin-4-yl)phenyl]amino}-1,2-dihydro-2,7-naphthyridin-1-one; 6-(5-amino-6-methylpyrazin-2-yl)-8-[(2,3-dimethyl-2H-indazol-6-yl)amino]-1,2-dihydro-2,7-naphthyridin-1-one; 6-(2-aminopyrimidin-5-yl)-2-methyl-8-{[3-methyl-4-(2-methylmorpholin-4-yl)phenyl]amino}-1,2-dihydro-2,7-naphthyridin-1-one; 6-(5-amino-6-methoxypyrazin-2-yl)-2-methyl-8-{[4-(morpholin-4-yl)phenyl]amino}-1,2-dihydro-2,7-naphthyridin-1-one; 6-(5-amino-6-methoxypyrazin-2-yl)-8-({3-methyl-4-[2-(pyrrolidin-1-yl)ethoxy]phenyl}amino)-1,2-dihydro-2,7-naphthyridin-1-one; 8-({3-methyl-4-[(2R)-2-methylmorpholin-4-yl]phenyl}amino)-6-{6-[2-(pyrrolidin-1-yl)ethoxy]pyridin-2-yl}-1,2-dihydro-2,7-naphthyridin-1-one; 6-(5-amino-6-methoxypyrazin-2-yl)-8-({3-methyl-4-[(2S)-2-methylmorpholin-4-yl]phenyl}amino)-1,2-dihydro-2,7-naphthyridin-1-one; 8-[(4-{2-[4-(dimethylamino)piperidin-1-yl]ethyl}phenyl)amino]-6-(pyrimidin-5-yl)-1,2-dihydro-2,7-naphthyridin-1-one; 8-[(4-{2-[(2S)-2-(hydroxymethyl)pyrrolidin-1-yl]ethyl}phenyl)amino]-6-(pyrimidin-5-yl)-1,2-dihydro-2,7-naphthyridin-1-one; 8-[(4-{2-[4-(2-methoxyethyl)piperazin-1-yl]ethyl}phenyl)amino]-6-(pyrimidin-5-yl)-1,2-dihydro-2,7-naphthyridin-1-one; 8-({4-[(1-methylpiperidin-4-yl)oxy]phenyl}amino)-6-(pyrimidin-5-yl)-1,2-dihydro-2,7-naphthyridin-1-one; 8-{[4-(oxan-4-yloxy)phenyl]amino}-6-(pyrimidin-5-yl)-1,2-dihydro-2,7-naphthyridin-1-one; N-{4-[1-({3-methyl-4-[(2R)-2-methylmorpholin-4-yl]phenyl}amino)-8-oxo-7,8-dihydro-2,7-naphthyridin-3-yl]phenyl}acetamide 8-({2-[(2R)-2-methylmorpholin-4-yl]pyrimidin-5-yl}amino)-6-(pyrimidin-5-yl)-1,2-dihydro-2,7-naphthyridin-1-one; 8-[(4-{2-[(2S)-2-(hydroxymethyl)pyrrolidin-1-yl]ethyl}phenyl)amino]-6-(6-methylpyridin-2-yl)-1,2-dihydro-2,7-naphthyridin-1-one; 8-[(4-{2-[4-(2-methoxyethyl)piperazin-1-yl]ethyl}phenyl)amino]-6-(2-methyl-1,3-thiazol-4-yl)-1,2-dihydro-2,7-naphthyridin-1-one; 8-[(4-{2-[4-(dimethylamino)piperidin-1-yl]ethyl}phenyl)amino]-6-(2-methyl-1,3-thiazol-4-yl)-1,2-dihydro-2,7-naphthyridin-1-one; 6-(2-methyl-1,3-thiazol-4-yl)-8-[(4-{2-[4-(pyrrolidin-1-yl)piperidin-1-yl]ethyl}phenyl)amino]-1,2-dihydro-2,7-naphthyridin-1-one; 8-({3-methyl-4-[1-(propan-2-yl)piperidin-4-yl]phenyl}amino)-6-(pyrimidin-5-yl)-1,2-dihydro-2,7-naphthyridin-1-one; 6-(5-amino-6-methoxypyrazin-2-yl)-8-({6-[(2S)-2-methylmorpholin-4-yl]pyridin-3-yl}amino)-1,2-dihydro-2,7-naphthyridin-1-one; 8-{[3-methyl-4-(1,2,3,6-tetrahydropyridin-4-yl)phenyl]amino}-6-(pyrimidin-5-yl)-1,2-dihydro-2,7-naphthyridin-1-one; 8-({3-methyl-4-[6-(piperazin-1-yl)pyridin-3-yl]phenyl}amino)-6-(pyrimidin-5-yl)-1,2-dihydro-2,7-naphthyridin-1-one; 8-({4-[1-(piperidin-4-yl)-1H-pyrazol-4-yl]phenyl}amino)-6-(pyrimidin-5-yl)-1,2-dihydro-2,7-naphthyridin-1-one; 8-({3-methyl-4-[1-(piperidin-4-yl)-1H-pyrazol-4-yl]phenyl}amino)-6-(pyrimidin-5-yl)-1,2-dihydro-2,7-naphthyridin-1-one; 8-({4-[2-(morpholin-4-yl)ethyl]phenyl}amino)-6-(pyrimidin-5-yl)-1,2-dihydro-2,7-naphthyridin-1-one; 8-[(4-{2-[4-(morpholin-4-yl)piperidin-1-yl]ethyl}phenyl)amino]-6-(pyrimidin-5-yl)-1,2-dihydro-2,7-naphthyridin-1-one; 8-({4-[2-(4-hydroxypiperidin-1-yl)ethyl]phenyl}amino)-6-(pyrimidin-5-yl)-1,2-dihydro-2,7-naphthyridin-1-one; 8-({3-methyl-4-[(1-methylpiperidin-4-yl)oxy]phenyl}amino)-6-(pyrimidin-5-yl)-1,2-dihydro-2,7-naphthyridin-1-one; 8-({4-[1-(3-fluoropropyl)piperidin-4-yl]phenyl}amino)-6-(6-methoxypyrazin-2-yl)-1,2-dihydro-2,7-naphthyridin-1-one; 8-({4-[1-(3-fluoropropyl)piperidin-4-yl]-3-methylphenyl}amino)-6-(6-methoxypyrazin-2-yl)-1,2-dihydro-2,7-naphthyridin-1-one; 8-({4-[1-(2-methoxyethyl)piperidin-4-yl]-3-methylphenyl}amino)-6-(6-methoxypyrazin-2-yl)-1,2-dihydro-2,7-naphthyridin-1-one; 6-(6-methoxypyrazin-2-yl)-8-{[3-methyl-4-(oxan-4-yl)phenyl]amino}-1,2-dihydro-2,7-naphthyridin-1-one; 6-(6-methoxypyrazin-2-yl)-8-({3-methyl-4-[(1-methylpiperidin-4-yl)oxy]phenyl}amino)-1,2-dihydro-2,7-naphthyridin-1-one; 6-(2-aminopyrimidin-5-yl)-8-({4-[1-(3-fluoropropyl)piperidin-4-yl]-3-methylphenyl}amino)-2-methyl-1,2-dihydro-2,7-naphthyridin-1-one; 6-(6-methoxypyrazin-2-yl)-8-({3-methyl-4-[1-(piperidin-4-yl)-1H-pyrazol-4-yl]phenyl}amino)-1,2-dihydro-2,7-naphthyridin-1-one; 6-(6-methylpyridin-2-yl)-8-[(4-{2-[4-(morpholin-4-yl)piperidin-1-yl]ethyl}phenyl)amino]-1,2-dihydro-2,7-naphthyridin-1-one; 6-(6-methylpyridin-2-yl)-8-({4-[2-(morpholin-4-yl)ethyl]phenyl}amino)-1,2-dihydro-2,7-naphthyridin-1-one;

6-(6-methylpyridin-2-yl)-8-({4-[1-(3,3,3-trifluoro-2-hydroxypropyl)piperidin-4-yl]phenyl}amino)-1,2-dihydro-2,7-naphthyridin-1-one; 8-({4-[2-(4-hydroxypiperidin-1-yl)ethyl]phenyl}amino)-6-(6-methylpyridin-2-yl)-1,2-dihydro-2,7-naphthyridin-1-one; 6-(2-methyl-1,3-thiazol-4-yl)-8-[(4-{2-[4-(morpholin-4-yl)piperidin-1-yl]ethyl}phenyl)amino]-1,2-dihydro-2,7-naphthyridin-1-one; 6-(2-methyl-1,3-thiazol-4-yl)-8-({4-[2-(morpholin-4-yl)ethyl]phenyl}amino)-1,2-dihydro-2,7-naphthyridin-1-one; 6-(2-methyl-1,3-thiazol-4-yl)-8-[(2-methyl-2H-indazol-6-yl)amino]-1,2-dihydro-2,7-naphthyridin-1-one; 6-(2-methyl-1,3-thiazol-4-yl)-8-({4-[1-(3,3,3-trifluoro-2-hydroxypropyl)piperidin-4-yl]phenyl}amino)-1,2-dihydro-2,7-naphthyridin-1-one; 8-({4-[2-(4-hydroxypiperidin-1-yl)ethyl]phenyl}amino)-6-(2-methyl-1,3-thiazol-4-yl)-1,2-dihydro-2,7-naphthyridin-1-one; 6,8-bis(phenylsulfanyl)-1,2-dihydro-2,7-naphthyridin-1-one; 6-(2-methoxypyrimidin-5-yl)-8-({4-[1-(3,3,3-trifluoro-2-hydroxypropyl)piperidin-4-yl]phenyl}amino)-1,2-dihydro-2,7-naphthyridin-1-one; 8-({4-[2-(4-hydroxypiperidin-1-yl)ethyl]phenyl}amino)-6-(2-methoxypyrimidin-5-yl)-1,2-dihydro-2,7-naphthyridin-1-one; 6-(2-methoxypyrimidin-5-yl)-8-({4-[2-(morpholin-4-yl)ethyl]phenyl}amino)-1,2-dihydro-2,7-naphthyridin-1-one; 8-({3-fluoro-4-[2-(pyrrolidin-1-yl)ethoxy]phenyl}amino)-6-(2-methoxypyrimidin-5-yl)-1,2-dihydro-2,7-naphthyridin-1-one; 8-({3-fluoro-4-[2-(pyrrolidin-1-yl)ethoxy]phenyl}amino)-6-(pyrimidin-5-yl)-1,2-dihydro-2,7-naphthyridin-1-one; 8-{[4-(1-cyclopropylpiperidin-4-yl)phenyl]amino}-6-(pyrimidin-5-yl)-1,2-dihydro-2,7-naphthyridin-1-one; 8-[(4-{1-[2-(morpholin-4-yl)ethyl]-1H-pyrazol-4-yl}phenyl)amino]-6-(pyrimidin-5-yl)-1,2-dihydro-2,7-naphthyridin-1-one; 8-[(3-methyl-4-{1-[2-(morpholin-4-yl)ethyl]-1H-pyrazol-4-yl}phenyl)amino]-6-(pyrimidin-5-yl)-1,2-dihydro-2,7-naphthyridin-1-one; 8-({4-[2-(4-hydroxypiperidin-1-yl)ethyl]phenyl}amino)-6-[2-(methylamino)pyrimidin-5-yl]-1,2-dihydro-2,7-naphthyridin-1-one; 8-[(4-{2-[4-(dimethylamino)piperidin-1-yl]ethyl}phenyl)amino]-6-[2-(methylamino)pyrimidin-5-yl]-1,2-dihydro-2,7-naphthyridin-1-one; 8-[(4-{2-[(2S)-2-(hydroxymethyl)pyrrolidin-1-yl]ethyl}phenyl)amino]-6-[2-(methylamino)pyrimidin-5-yl]-1,2-dihydro-2,7-naphthyridin-1-one; 8-[(4-{2-[4-(2-methoxyethyl)piperazin-1-yl]ethyl}phenyl)amino]-6-[2-(methylamino)pyrimidin-5-yl]-1,2-dihydro-2,7-naphthyridin-1-one; 6-[2-(methylamino)pyrimidin-5-yl]-8-[(4-{2-[4-(pyrrolidin-1-yl)piperidin-1-yl]ethyl}phenyl)amino]-1,2-dihydro-2,7-naphthyridin-1-one; 8-({4-[1-(3-fluoropropyl)piperidin-4-yl]phenyl}amino)-6-[2-(methylamino)pyrimidin-5-yl]-1,2-dihydro-2,7-naphthyridin-1-one; 8-{[4-(piperazin-1-yl)-3-(trifluoromethyl)phenyl]amino}-6-(pyrimidin-5-yl)-1,2-dihydro-2,7-naphthyridin-1-one; 6-(2-methylpyrimidin-5-yl)-8-{[4-(piperazin-1-yl)-3-(trifluoromethyl)phenyl]amino}-1,2-dihydro-2,7-naphthyridin-1-one; 6-(6-amino-5-methylpyridin-3-yl)-8-{[3-methyl-4-(oxan-4-yl)phenyl]amino}-1,2-dihydro-2,7-naphthyridin-1-one; 6-(2-aminopyrimidin-5-yl)-2-methyl-8-({2-methyl-5-[2-(morpholin-4-yl)ethoxy]phenyl}amino)-1,2-dihydro-2,7-naphthyridin-1-one; 6-(2-aminopyrimidin-5-yl)-8-({2-methyl-5-[2-(morpholin-4-yl)ethoxy]phenyl}amino)-1,2-dihydro-2,7-naphthyridin-1-one; 4-{[3-(6-methoxypyrazin-2-yl)-8-oxo-7,8-dihydro-2,7-naphthyridin-1-yl]amino}-N,2-dimethylbenzamide; 8-[(4-{2-[4-(2-methoxyethyl)piperazin-1-yl]ethyl}phenyl)amino]-6-(6-methoxypyrazin-2-yl)-1,2-dihydro-2,7-naphthyridin-1-one; 6-(6-methoxypyrazin-2-yl)-8-[(4-{1-[2-(morpholin-4-yl)ethyl]-1H-pyrazol-4-yl}phenyl)amino]-1,2-dihydro-2,7-naphthyridin-1-one; 8-{[2-methoxy-4-(4-methylpiperazin- 1-yl)phenyl]amino}-6-(6-methoxypyrazin-2-yl)-1,2-dihydro-2,7-naphthyridin-1-one; 8-{[4-(morpholin-4-yl)phenyl]amino}-6-{2H,3H,4H-pyrido[3,2-b][1,4]oxazin-7-yl}-1,2-dihydro-2,7-naphthyridin-1-one; 6-(2-methyl-1,3-thiazol-4-yl)-8-({4-[(1-methylpiperidin-4-yl)oxy]phenyl}amino)-1,2-dihydro-2,7-naphthyridin-1-one; 6-(2-methyl-1,3-thiazol-4-yl)-8-{[4-(oxan-4-yloxy)phenyl]amino}-1,2-dihydro-2,7-naphthyridin-1-one; 8-({4-[1-(3-fluoropropyl)piperidin-4-yl]phenyl}amino)-6-(2-methyl-1,3-thiazol-4-yl)-1,2-dihydro-2,7-naphthyridin-1-one; 8-({4-[(1-methylpiperidin-4-yl)oxy]phenyl}amino)-6-(6-methylpyridin-2-yl)-1,2-dihydro-2,7-naphthyridin-1-one; 6-(6-methylpyridin-2-yl)-8-{[4-(oxan-4-yloxy)phenyl]amino}-1,2-dihydro-2,7-naphthyridin-1-one; 8-({4-[1-(3-fluoropropyl)piperidin-4-yl]phenyl}amino)-6-(6-methylpyridin-2-yl)-1,2-dihydro-2,7-naphthyridin-1-one; 6-(4-methyl-1,3-thiazol-2-yl)-8-({4-[(1-methylpiperidin-4-yl)oxy]phenyl}amino)-1,2-dihydro-2,7-naphthyridin-1-one; 6-(4-methyl-1,3-thiazol-2-yl)-8-{[4-(oxan-4-yloxy)phenyl]amino}-1,2-dihydro-2,7-naphthyridin-1-one; 8-({4-[2-(4-hydroxypiperidin-1-yl)ethyl]phenyl}amino)-6-(4-methyl-1,3-thiazol-2-yl)-1,2-dihydro-2,7-naphthyridin-1-one; 6-(4-methyl-1,3-thiazol-2-yl)-8-({4-[1-(3,3,3-trifluoro-2-hydroxypropyl)piperidin-4-yl]phenyl}amino)-1,2-dihydro-2,7-naphthyridin-1-one; 6-(4-methyl-1,3-thiazol-2-yl)-8-({2-[(2R)-2-methylmorpholin-4-yl]pyrimidin-5-yl}amino)-1,2-dihydro-2,7-naphthyridin-1-one; 8-[{2-fluoro-5-methyl-4-(1-methylpiperidin-4-yl)phenyl]amino}-6-(pyrimidin-5-yl)-1,2-dihydro-2,7-naphthyridin-1-one; 8-{[2-fluoro-5-methyl-4-(1-methylpiperidin-4-yl)phenyl]amino}-6-(2-methoxypyrimidin-5-yl)-1,2-dihydro-2,7-naphthyridin-1-one; 8-{[3-fluoro-4-(1-methylpiperidin-4-yl)phenyl]amino}-6-(pyrimidin-5-yl)-1,2-dihydro-2,7-naphthyridin-1-one; 8-{[3-fluoro-4-(1-methylpiperidin-4-yl)phenyl]amino}-6-(2-methoxypyrimidin-5-yl)-1,2-dihydro-2,7-naphthyridin-1-one; 8-{[6-(1-methylpiperidin-4-yl)pyridin-3-yl]amino}-6-(pyrimidin-5-yl)-1,2-dihydro-2,7-naphthyridin-1-one; 6-(2-methoxypyrimidin-5-yl)-8-{[6-(1-methylpiperidin-4-yl)pyridin-3-yl]amino}-1,2-dihydro-2,7-naphthyridin-1-one; 6-(2,6-dimethylphenyl)-8-{[4-(piperidin-4-yl)phenyl]amino}-1,2-dihydro-2,7-naphthyridin-1-one; tert-butyl 4-(4-{[3-(2-butoxyphenyl)-8-oxo-7,8-dihydro-2,7-naphthyridin-1-yl]amino}phenyl)piperidine-1-carboxylate; 6-(2-butoxyphenyl)-8-{[4-(piperidin-4-yl)phenyl]amino}-1,2-dihydro-2,7-naphthyridin-1-one; tert-butyl 4-(4-{[3-(2-ethoxy-5-methylphenyl)-8-oxo-7,8-dihydro-2,7-naphthyridin-1-yl]amino}phenyl)piperidine-1-carboxylate; 6-(2-ethoxy-5-methylphenyl)-8-{[4-(piperidin-4-yl)phenyl]amino}-1,2-dihydro-2,7-naphthyridin-1-one; tert-butyl 4-(4-{[8-oxo-3-(2-propoxyphenyl)-7,8-dihydro-2,7-naphthyridin-1-yl]amino}phenyl)piperidine-1-carboxylate; 8-{[4-(piperidin-4-yl)phenyl]amino}-6-(2-propoxyphenyl)-1,2-dihydro-2,7-naphthyridin-1-one; tert-butyl 4-[4-({8-oxo-3-[2-(propan-2-yloxy)phenyl]-7,8-dihydro-2,7-naphthyridin-1-yl}amino)phenyl]piperidine-1-carboxylate; 8-{[4-(piperidin-4-yl)phenyl]amino}-6-[2-(propan-2-yloxy)phenyl]-1,2-dihydro-2,7-naphthyridin-1-one; tert-butyl 4-(4-{[8-oxo-3-(2-phenoxyphenyl)-7,8-dihydro-2,7-naphthyridin-1-yl]amino}phenyl)piperidine-1-carboxylate; 6-(2-phenoxyphenyl)-8-{[4-(piperidin-4-yl)phenyl]amino}-1,2-dihydro-2,7-naphthyridin-1-one; 6-[2-(methylamino)pyrimidin-5-yl]-8-[(4-{1-[2-(morpholin-4-yl)ethyl]-1H-pyrazol-4-yl}phenyl)amino]-1,2-dihydro-2,7-naphthyridin-1-one; 8-[(3-methyl-4-{1-[2-(morpholin-4-yl)ethyl]-1H-pyrazol-4-yl}phenyl)amino]-6-[2-(methylamino)pyrimidin-5-yl]-1,2-dihydro-2,7-naphthyridin-1-one; 6-(5-amino-6- methoxypyrazin-2-yl)-8-({4-[2-(morpholin-4-yl)ethyl]phenyl}amino)-1,2-dihydro-2,7-naphthyridin-1-one; 6-(6-methylpyrazin-2-yl)-8-{[4-(morpholin-4-yl)phenyl]amino}-1,2-dihydro-2,7-naphthyridin-1-one; 6-(5-amino-6-methoxypyrazin-2-yl)-8-({3-methyl-4-[(1-methylpiperidin-4-yl)oxy]phenyl}amino)-1,2-dihydro-2,7-naphthyridin-1-one; 6-(5-amino-6-methoxypyrazin-2-yl)-8-({3-methyl-4-[1-(piperidin-4-yl)-1H-pyrazol-4-yl]phenyl}amino)-1,2-dihydro-2,7-naphthyridin-1-one; 6-(5-amino-6-methoxypyrazin-2-yl)-8-[(3-methyl-4-{1-[2-(morpholin-4-yl)ethyl]-1H-pyrazol-4-yl}phenyl)amino]-1,2-dihydro-2,7-naphthyridin-1-one; 6-(2-aminopyrimidin-5-yl)-2-(2-methanesulfonylethyl)-8-{[4-(morpholin-4-yl)phenyl]amino}-1,2-dihydro-2,7-naphthyridin-1-one; 6-(6-methoxypyrazin-2-yl)-8-({6-[(2R)-2-methylmorpholin-4-yl]pyridin-3-yl}amino)-1,2-dihydro-2,7-naphthyridin-1-one; 6-(6-methoxypyrazin-2-yl)-8-({6-[(2S)-2-methylmorpholin-4-yl]pyridin-3-yl}amino)-1,2-dihydro-2,7-naphthyridin-1-one; 8-({3-fluoro-4-[(2R)-2-methylmorpholin-4-yl]phenyl}amino)-6-(6-methoxypyrazin-2-yl)-1,2-dihydro-2,7-naphthyridin-1-one; 4-{[3-(6-methoxypyrazin-2-yl)-8-oxo-7,8-dihydro-2,7-naphthyridin-1-yl]amino}-N-propylbenzamide; 8-({4-[1-(2,3-dihydroxypropyl)piperidin-4-yl]phenyl}amino)-6-(6-methylpyridin-2-yl)-1,2-dihydro-2,7-naphthyridin-1-one; 6-(6-methylpyridin-2-yl)-8-[(4-{1-[2-(morpholin-4-yl)ethyl]-1H-pyrazol-4-yl}phenyl)amino]-1,2-dihydro-2,7-naphthyridin-1-one; 8-[(3-methyl-4-{1-[2-(morpholin-4-yl)ethyl]-1H-pyrazol-4-yl}phenyl)amino]-6-(6-methylpyridin-2-yl)-1,2-dihydro-2,7-naphthyridin-1-one; N,2-dimethyl-4-{[3-(6-methylpyridin-2-yl)-8-oxo-7,8-dihydro-2,7-naphthyridin-1-yl]amino}benzamide; 6-(2-aminopyrimidin-5-yl)-8-[(3-chlorophenyl)amino]-2-(2-methoxyethyl)-1,2-dihydro-2,7-naphthyridin-1-one; 6-(2-aminopyrimidin-5-yl)-2-(2-methoxyethyl)-8-[(3-methylphenyl)amino]-1,2-dihydro-2,7-naphthyridin-1-one; 6-(5-amino-6-methoxypyrazin-2-yl)-2-(2-methoxyethyl)-8-{[4-(morpholin-4-yl)phenyl]amino}-1,2-dihydro-2,7-naphthyridin-1-one; 6-(2-aminopyrimidin-5-yl)-8-[(3-methoxyphenyl)amino]-2-[2-(morpholin-4-yl)ethyl]-1,2-dihydro-2,7-naphthyridin-1-one; 6-(2-aminopyrimidin-5-yl)-8-[(3-methylphenyl)amino]-2-[2-(morpholin-4-yl)ethyl]-1,2-dihydro-2,7-naphthyridin-1-one; 6-(2-aminopyrimidin-5-yl)-8-[(3-chlorophenyl)amino]-2-[2-(morpholin-4-yl)ethyl]-1,2-dihydro-2,7-naphthyridin-1-one; 8-[(1-methyl-1H-pyrazol-4-yl)amino]-6-(pyrimidin-5-yl)-1,2-dihydro-2,7-naphthyridin-1-one; 8-[(2-methanesulfonyl-1,2,3,4-tetrahydro isoquinolin-6-yl)amino]-6-(pyrimidin-5-yl)-1,2-dihydro-2,7-naphthyridin-1-one; 8-[(2-methanesulfonyl-1,2,3,4-tetrahydroisoquinolin-6-yl)amino]-6-(pyrimidin-5-yl)-1,2-dihydro-2,7-naphthyridin-1-one; 8-{[4-(2,2-dimethylmorpholin-4-yl)-3-methylphenyl]amino}-6-(pyrimidin-5-yl)-1,2-dihydro-2,7-naphthyridin-1-one; 8-{[4-(2,2-dimethylmorpholin-4-yl)-3-methylphenyl]amino}-6-(2-methoxypyrimidin-5-yl)-1,2-dihydro-2,7-naphthyridin-1-one; 6-(2,4-dimethoxypyrimidin-5-yl)-8-({4-[1-(2-methoxyethyl)piperidin-4-yl]phenyl}amino)-1,2-dihydro-2,7-naphthyridin-1-one; 8-({4-[1-(2-methoxyethyl)piperidin-4-yl]phenyl}amino)-6-(6-methoxypyrazin-2-yl)-1,2-dihydro-2,7-naphthyridin-1-one; 6-(6-methoxypyrazin-2-yl)-8-[(3-methyl-4-{1-[2-(morpholin-4-yl)ethyl]-1H-pyrazol-4-yl)phenyl]amino}-1,2-dihydro-2,7-naphthyridin-1-one; 6-(6-methoxypyrazin-2-yl)-8-{[4-(pyrrolidin-3-yl)phenyl]amino}-1,2-dihydro-2,7-naphthyridin-1-one; 6-(2,4-dimethoxypyrimidin-5-yl)-8-({4-[1-(2-methoxyethyl)pyrrolidin-3-yl]phenyl}amino)-1,2-dihydro-2,7-naphthyridin-1-one; 8-({4-[1-(2-methoxyethyl)pyrrolidin-3-yl]phenyl}amino)-6-(6-methoxypyrazin-2-yl)-1,2-dihydro-2,7-naphthyridin-1-one; 8-{[6-(oxan-4-yl)pyridin-3-yl]amino}-6-{2H,3H,4H-pyrido[3,2-b][1,4]oxazin-7-yl}-1,2-dihydro-2,7-naphthyridin-1-one; 6-(6-methoxypyrazin-2-yl)-8-({4-[1-(4,4,4-trifluorobutyl)piperidin-4-yl]phenyl}amino)-1,2-dihydro-2,7-naphthyridin-1-one; 6-(6-methoxypyrazin-2-yl)-8-{[4-(piperidin-4-yl)phenyl]amino}-1,2-dihydro-2,7-naphthyridin-1-one; 8-{[4-(1-ethylpyrrolidin-3-yl)phenyl]amino}-6-(6-methoxypyrazin-2-yl)-1,2-dihydro-2,7-naphthyridin-1-one; 4-(4-methoxyphenyl)-8-{[4-(morpholin-4-yl)phenyl]amino}-1,2-dihydro-2,7-naphthyridin-1-one; N-methyl-4-(8-{[4-(morpholin-4-yl)phenyl]amino}-1-oxo-1,2-dihydro-2,7-naphthyridin-4-yl)benzamide; 8-{[4-(morpholin-4-yl)phenyl]amino}-4-[3-(trifluoromethyl)phenyl]-1,2-dihydro-2,7-naphthyridin-1-one; 4-[3-(dimethylamino)phenyl]-8-{[4-(morpholin-4-yl)phenyl]amino}-1,2-dihydro-2,7-naphthyridin-1-one; 4-(4-chlorophenyl)-8-{[4-(morpholin-4-yl)phenyl]amino}-1,2-dihydro-2,7-naphthyridin-1-one; 8-{[4-(morpholin-4-yl)phenyl]amino}-4-[4-(trifluoromethyl)phenyl]-1,2-dihydro-2,7-naphthyridin-1-one; 6-(2-aminopyrimidin-5-yl)-2-ethyl-8-{[4-(1-ethylpyrrolidin-3-yl)phenyl]amino}-1,2-dihydro-2,7-naphthyridin-1-one; 6-(2,6-dimethoxyphenyl)-8-{[4-(piperidin-4-yl)phenyl]amino}-1,2-dihydro-2,7-naphthyridin-1-one; tert-butyl 4-(4-{[3-(2,6-dimethoxyphenyl)-8-oxo-7,8-dihydro-2,7-naphthyridin-1-yl]amino}phenyl)piperidine-1-carboxylate; 8-{[2-(3-methylbutoxy)phenyl]amino}-6-(phenylamino)-1,2-dihydro-2,7-naphthyridin-1-one; 6-({4-[(4-ethylpiperazin-1-yl)methyl]phenyl}amino)-8-{[2-(3-methylbutoxy)phenyl]amino}-1,2-dihydro-2,7-naphthyridin-1-one; 8-{[2-(3-methylbutoxy)phenyl]amino}-6-{[2-(propane-2-sulfonyl)phenyl]amino}-1,2-dihydro-2,7-naphthyridin-1-one; 8-{[2-(3-methylbutoxy)phenyl]amino}-6-(pyridin-3-ylamino)-1,2-dihydro-2,7-naphthyridin-1-one; 8-{[2-(3-methylbutoxy)phenyl]amino}-6-{[3-(piperidin-1-ylmethyl)phenyl]amino}-1,2-dihydro-2,7-naphthyridin-1-one; 6-[(2-methoxy-5-phenoxyphenyl)amino]-8-{[2-(3-methylbutoxy)phenyl]amino}-1,2-dihydro-2,7-naphthyridin-1-one; 8-{[2-(3-methylbutoxy)phenyl]amino}-6-{[3-(morpholin-4-yl)phenyl]amino}-1,2-dihydro-2,7-naphthyridin-1-one; 8-{[2-(3-methylbutoxy)phenyl]amino}-6-{[2-(methylsulfanyl)phenyl]amino}-1,2-dihydro-2,7-naphthyridin-1-one; 8-{[2-(3-methylbutoxy)phenyl]amino}-6-[3-(pyrrolidin-1-yl)phenyl]-1,2-dihydro-2,7-naphthyridin-1-one; 5-(1-{[2-(3-methylbutoxy)phenyl]amino}-8-oxo-7,8-dihydro-2,7-naphthyridin-3-yl)pyridine-3-carbonitrile 6-{2-[(dimethylamino)methyl]phenyl}-8-{[2-(3-methylbutoxy)phenyl]amino}-1,2-dihydro-2,7-naphthyridin-1-one; 8-{[2-(3-methylbutoxy)phenyl]amino}-6-[3-(morpholin-4-ylcarbonyl)phenyl]-1,2-dihydro-2,7-naphthyridin-1-one; 4-methoxy-3-(1-{[2-(3-methylbutoxy)phenyl]amino}-8-oxo-7,8-dihydro-2,7-naphthyridin-3-yl)benzaldehyde 6-(2,6-dimethoxyphenyl)-8-{[2-(3-methylbutoxy)phenyl]amino}-1,2-dihydro-2,7-naphthyridin-1-one; 6-(2-ethoxypyridin-3-yl)-8-{[2-(3-methylbutoxy)phenyl]amino}-1,2-dihydro-2,7-naphthyridin-1-one; 3-methoxy-2-(1-{[2-(3-methylbutoxy)phenyl]amino}-8-oxo-7,8-dihydro-2,7-naphthyridin-3-yl)benzonitrile 3-methoxy-2-(1-{[2-(3-methylbutoxy)phenyl]amino}-8-oxo-7,8-dihydro-2,7-naphthyridin-3-yl)benzamide; 2-methyl-5-[(1-{[4-(morpholin-4-yl)phenyl]amino}-8-oxo-7,8-dihydro-2,7-naphthyridin-3-yl)amino]benzene-1-sulfonamide; 3-[(1-{[4-(morpholin-4-yl)phenyl]amino}-8-oxo-7,8-dihydro-2,7-naphthyridin-3-yl)amino]benzene-1-sulfonamide; 8-{[2-(3-methylbutoxy)phenyl]amino}-6-[1-(piperidin-4-yl)-1H- pyrazol-4-yl]-1,2-dihydro-2,7-naphthyridin-1-one; 8-{[2-(3-methylbutoxy)phenyl]amino}-6-[4-(piperazin-1-yl)phenyl]-1,2-dihydro-2,7-naphthyridin-1-one; 6-{[4-(4-aminopiperidin-1-yl)pyridin-3-yl]amino}-8-{[2-(3-methylbutoxy)phenyl]amino}-1,2-dihydro-2,7-naphthyridin-1-one; 8-{[2-(3-methylbutoxy)phenyl]amino}-6-{[4-(piperidin-4-yl)phenyl]amino}-1,2-dihydro-2,7-naphthyridin-1-one; 3-methoxy-2-(8-oxo-1-{[4-(piperidin-4-yl)phenyl]amino}-7,8-dihydro-2,7-naphthyridin-3-yl) benzamide; 6-{2-[(dimethylamino)methyl]phenyl}-8-{[4-(piperidin-4-yl)phenyl]amino}-1,2-dihydro-2,7-naphthyridin-1-one; 6-(2-chloro-6-methoxyphenyl)-8-{[4-(piperidin-4-yl)phenyl]amino}-1,2-dihydro-2,7-naphthyridin-1-one; 6-(2-aminopyrimidin-5-yl)-8-[(1-methyl-1H-pyrazol-4-yl)amino]-1,2-dihydro-2,7-naphthyridin-1-one; 6-(2-methoxypyrimidin-5-yl)-8-[(1-methyl-1H-pyrazol-4-yl)amino]-1,2-dihydro-2,7-naphthyridin-1-one; 6-(2-aminopyrimidin-5-yl)-8-[(3-methyl-4-{1-[2-(morpholin-4-yl)ethyl]-1H-pyrazol-4-yl}phenyl)amino]-1,2-dihydro-2,7-naphthyridin-1-one; 6-(2-methoxypyrimidin-5-yl)-8-[(3-methyl-4-{1-[2-(morpholin-4-yl)ethyl]-1H-pyrazol-4-yl}phenyl)amino]-1,2-dihydro-2,7-naphthyridin-1-one; 6-(6-methoxypyridin-2-yl)-8-[(3-methyl-4-{1-[2-(morpholin-4-yl)ethyl]-1H-pyrazol-4-yl}phenyl)amino]-1,2-dihydro-2,7-naphthyridin-1-one; 6-(5-amino-4-methylpyridin-2-yl)-8-[(3-methyl-4-{1-[2-(morpholin-4-yl)ethyl]-1H-pyrazol-4-yl}phenyl)amino]-1,2-dihydro-2,7-naphthyridin-1-one; 1-[2-(4-{[8-oxo-3-(pyrimidin-5-yl)-7,8-dihydro-2,7-naphthyridin-1-yl]amino}phenyl)ethyl]piperidine-3-carboxylic acid 8-{[1-(piperidin-4-yl)-1H-pyrazol-4-yl]amino}-6-(pyrimidin-5-yl)-1,2-dihydro-2,7-naphthyridin-1-one; 1-[2-(4-{[3-(2-methoxypyrimidin-5-yl)-8-oxo-7,8-dihydro-2,7-naphthyridin-1-yl]amino}phenyl)ethyl]piperidine-3-carboxylic acid 6-(6-amino-5-methylpyridin-3-yl)-8-({4-[1-(2-methoxyethyl)piperidin-4-yl]phenyl}amino)-1,2-dihydro-2,7-naphthyridin-1-one; 8-({4-[1-(2-methoxyethyl)piperidin-4-yl]phenyl}amino)-6-(pyrimidin-5-yl)-1,2-dihydro-2,7-naphthyridin-1-one; 8-({4-[1-(2-methoxyethyl)piperidin-4-yl]phenyl}amino)-6-(2-methylpyrimidin-5-yl)-1,2-dihydro-2,7-naphthyridin-1-one; 8-{[4-(1-cyclopropylpiperidin-4-yl)-3-methylphenyl]amino}-6-(pyrimidin-5-yl)-1,2-dihydro-2,7-naphthyridin-1-one; 8-{[4-(1-cyclopropylpiperidin-4-yl)-3-methylphenyl]amino}-6-(2-methoxypyrimidin-5-yl)-1,2-dihydro-2,7-naphthyridin-1-one; 4-(1-methyl-1H-pyrazol-4-yl)-8-{[4-(morpholin-4-yl)phenyl]amino}-1,2-dihydro-2,7-naphthyridin-1-one; 4-[2-methyl-4-(trifluoromethyl)phenyl]-8-{[4-(morpholin-4-yl)phenyl]amino}-1,2-dihydro-2,7-naphthyridin-1-one; 4-(4-methoxy-2-methylphenyl)-8-{[4-(morpholin-4-yl)phenyl]amino}-1,2-dihydro-2,7-naphthyridin-1-one; 4-(5-methoxypyridin-3-yl)-8-{[4-(morpholin-4-yl)phenyl]amino}-1,2-dihydro-2,7-naphthyridin-1-one; 8-{[3-methyl-4-(1-methylpiperidin-4-yl)phenyl]amino}-6-[6-(pyrrolidin-1-ylmethyl)pyridin-3-yl]-1,2-dihydro-2,7-naphthyridin-1-one; 8-({3-methyl-4-[(2R)-2-methylmorpholin-4-yl]phenyl}amino)-6-[6-(pyrrolidin-1-ylmethyl)pyridin-3-yl]-1,2-dihydro-2,7-naphthyridin-1-one; 6-(6-methylpyridin-3-yl)-8-{[4-(piperidin-4-yl)-3-(trifluoromethyl)phenyl]amino}-1,2-dihydro-2,7-naphthyridin-1-one; 6-(2-methoxypyrimidin-5-yl)-8-{[4-(piperidin-4-yl)-3-(trifluoromethyl)phenyl]amino}-1,2-dihydro-2,7-naphthyridin-1-one; 8-{[4-(1-cyclopropylpiperidin-4-yl)-3-methylphenyl]amino}-6-(6-methylpyridin-3-yl)-1,2-dihydro-2,7-naphthyridin-1-one; 8-({6-[(2R)-2-methylmorpholin-4-yl]pyridin-3-yl}amino)-6-(6-methylpyridin-3-yl)-1,2-dihydro-2,7-naphthyridin-1-one; 8-{[4-(2,2-dimethylmorpholin-4-yl)-3-methylphenyl]amino}-6-(6-methylpyridin-3-yl)-1,2-dihydro-2,7-naphthyridin-1-one; 8-({4-[1-(2-methanesulfonylethyl)piperidin-4-yl]-3-methylphenyl}amino)-6-(pyrimidin-5-yl)-1,2-dihydro-2,7-naphthyridin-1-one; 8-{[4-(1-methylpiperidin-4-yl)-3-(trifluoromethyl)phenyl]amino}-6-(6-methylpyridin-3-yl)-1,2-dihydro-2,7-naphthyridin-1-one; 1-[2-(4-{[8-oxo-3-(pyrimidin-5-yl)-7,8-dihydro-2,7-naphthyridin-1-yl]amino}phenyl)ethyl]piperidine-4-carboxylic acid 1-[2-(4-{[3-(2-methoxypyrimidin-5-yl)-8-oxo-7,8-dihydro-2,7-naphthyridin-1-yl]amino}phenyl)ethyl]piperidine-4-carboxylic acid 8-({6-[1-(2-methoxyethyl)piperidin-4-yl]pyridin-3-yl}amino)-6-(6-methoxypyrazin-2-yl)-1,2-dihydro-2,7-naphthyridin-1-one; 6-(2-methoxypyrimidin-5-yl)-8-{[1-(piperidin-4-yl)-1H-pyrazol-4-yl]amino}-1,2-dihydro-2,7-naphthyridin-1-one; 8-({6-[1-(2-methoxyethyl)piperidin-4-yl]pyridin-3-yl}amino)-6-(pyrimidin-5-yl)-1,2-dihydro-2,7-naphthyridin-1-one; 6-(2-hydroxypyrimidin-5-yl)-8-{[1-(piperidin-4-yl)-1H-pyrazol-4-yl]amino}-1,2-dihydro-2,7-naphthyridin-1-one; 6-(6-amino-5-methylpyridin-3-yl)-8-{[6-(oxan-4-yl)pyridin-3-yl]amino}-1,2-dihydro-2,7-naphthyridin-1-one; 6-(2-aminopyrimidin-5-yl)-2-methyl-8-[(3-methyl-4-{1-[2-(morpholin-4-yl)ethyl]-1H-pyrazol-4-yl}phenyl)amino]-1,2-dihydro-2,7-naphthyridin-1-one; 8-{[(3-fluorophenyl)methyl]amino}-6-{[4-(morpholin-4-yl)phenyl]amino}-1,2-dihydro-2,7-naphthyridin-1-one; 6-(2-aminopyrimidin-5-yl)-8-[(1-methyl-1H-pyrazol-4-yl)amino]-2-[2-(morpholin-4-yl)ethyl]-1,2-dihydro-2,7-naphthyridin-1-one; 8-[(3-methyl-4-{1-[2-(morpholin-4-yl)ethyl]-1H-pyrazol-4-yl}phenyl)amino]-6-[1-(2-methylpropyl)-1H-pyrazol-4-yl]-1,2-dihydro-2,7-naphthyridin-1-one; 3-[4-(2-methyl-4-{[8-oxo-3-(pyrimidin-5-yl)-7,8-dihydro-2,7-naphthyridin-1-yl]amino}phenyl)piperidin-1-yl]propanenitrile 6-(2-aminopyrimidin-5-yl)-8-[(3-methoxyphenyl)amino]-2-methyl-1,2-dihydro-2,7-naphthyridin-1-one; 4-(3-chloro-2-methylphenyl)-8-{[4-(morpholin-4-yl)phenyl]amino}-1,2-dihydro-2,7-naphthyridin-1-one; 8-({4-[2-(oxan-4-yl)-1,3-thiazol-4-yl]phenyl}amino)-6-(pyrimidin-5-yl)-1,2-dihydro-2,7-naphthyridin-1-one; 8-({4-[2-(piperidin-3-yl)-1,3-thiazol-4-yl]phenyl}amino)-6-(pyrimidin-5-yl)-1,2-dihydro-2,7-naphthyridin-1-one; 8-({4-[2-(2-aminoethyl)-1,3-thiazol-4-yl]phenyl}amino)-6-(pyrimidin-5-yl)-1,2-dihydro-2,7-naphthyridin-1-one; 8-({4-[2-(pyridin-3-yl)-1,3-thiazol-4-yl]phenyl}amino)-6-(pyrimidin-5-yl)-1,2-dihydro-2,7-naphthyridin-1-one; 8-({3-methyl-4-[1-(piperidin-4-yl)-1H-pyrazol-4-yl]phenyl}amino)-6-(6-methylpyridin-2-yl)-1,2-dihydro-2,7-naphthyridin-1-one; 8-({3-methyl-4-[6-(piperazin-1-yl)pyridin-3-yl]phenyl}amino)-6-(6-methylpyridin-2-yl)-1,2-dihydro-2,7-naphthyridin-1-one; 8-{[4-(piperidin-4-yl)-3-(trifluoromethyl)phenyl]amino}-6-(pyrimidin-5-yl)-1,2-dihydro-2,7-naphthyridin-1-one; 8-{[4-(1-acetylpiperidin-4-yl)-3-methylphenyl]amino}-6-(pyrimidin-5-yl)-1,2-dihydro-2,7-naphthyridin-1-one; 8-{[4-(1-acetylpiperidin-4-yl)-3-methylphenyl]amino}-6-(2-methoxypyrimidin-5-yl)-1,2-dihydro-2,7-naphthyridin-1-one; 8-{[4-(1-methylpiperidin-4-yl)-3-(trifluoromethyl)phenyl]amino}-6-(pyrimidin-5-yl)-1,2-dihydro-2,7-naphthyridin-1-one; 5-[1-({3-methyl-4-[(2R)-2-methylmorpholin-4-yl]phenyl}amino)-8-oxo-7,8-dihydro-2,7-naphthyridin-3-yl]pyridine-2-carbonitrile 6-(6-methoxypyridin-2-yl)-8-({4-[1-(4,4,4-trifluorobutyl)piperidin-4-yl]phenyl}amino)-1,2-dihydro-2,7-naphthyridin-1-one; 8-({4-[1-(2-methoxyethyl)piperidin-4-yl]-3-methylphenyl}amino)-6-(6-methoxypyridin-2-yl)-1,2-dihydro-2,7-naphthyridin-1-one; 8-({4-[1-(2-methoxyethyl)piperidin-4-yl]-3-methylphenyl}amino)-6-(5- methoxypyridin-3-yl)-1,2-dihydro-2,7-naphthyridin-1-one; 2-(2-amino ethyl)-6-(2-aminopyrimidin-5-yl)-8-{[4-(morpholin-4-yl)phenyl]amino}-1,2-dihydro-2,7-naphthyridin-1-one; 8-({4-[1-(2-methoxyethyl)piperidin-4-yl]phenyl}amino)-6-2H,3H,4H-pyrido[3,2-b][1,4]oxazin-7-yl)-1,2-dihydro-2,7-naphthyridin-1-one; 8-({4-[1-(2-methoxyethyl)piperidin-4-yl]phenyl}amino)-6-(6-methoxypyridin-2-yl)-1,2-dihydro-2,7-naphthyridin-1-one; 6-(5-amino-6-methylpyrazin-2-yl)-8-({4-[1-(2-methoxyethyl)piperidin-4-yl]-3-methylphenyl}amino)-1,2-dihydro-2,7-naphthyridin-1-one; 8-[(4-{1-[2-(dimethylamino)acetyl]pyrrolidin-3-yl}phenyl)amino]-6-(6-methoxypyrazin-2-yl)-1,2-dihydro-2,7-naphthyridin-1-one; 6-(6-methoxypyrimidin-4-yl)-8-{[4-(morpholin-4-yl)phenyl]amino}-1,2-dihydro-2,7-naphthyridin-1-one; 6-(6-methoxypyridin-2-yl)-8-({3-methyl-4-[3-(4-methylpiperazin-1-yl)propoxy]phenyl}amino)-1,2-dihydro-2,7-naphthyridin-1-one; 4-phenyl-8-[(4-{2-[4-(pyrrolidin-1-yl)piperidin-1-yl]ethyl}phenyl)amino]-1,2-dihydro-2,7-naphthyridin-1-one; 4-(4-methoxyphenyl)-8-[(4-{2-[4-(pyrrolidin-1-yl)piperidin-1-yl]ethyl}phenyl)amino]-1,2-dihydro-2,7-naphthyridin-1-one; 4-(4-chlorophenyl)-8-[(4-{2-[4-(pyrrolidin-1-yl)piperidin-1-yl]ethyl}phenyl)amino]-1,2-dihydro-2,7-naphthyridin-1-one; 8-[(4-{2-[4-(pyrrolidin-1-yl)piperidin-1-yl]ethyl}phenyl)amino]-4-[4-(trifluoromethyl)phenyl]-1,2-dihydro-2,7-naphthyridin-1-one; 8-[(4-{2-[4-(pyrrolidin-1-yl)piperidin-1-yl]ethyl}phenyl)amino]-4-[3-(trifluoromethyl)phenyl]-1,2-dihydro-2,7-naphthyridin-1-one; 4-[3-(dimethylamino)phenyl]-8-[(4-{2-[4-(pyrrolidin-1-yl)piperidin-1-yl]ethyl}phenyl)amino]-1,2-dihydro-2,7-naphthyridin-1-one; 4-(4-methoxy-2-methylphenyl)-8-[(4-{2-[4-(pyrrolidin-1-yl)piperidin-1-yl]ethyl}phenyl)amino]-1,2-dihydro-2,7-naphthyridin-1-one; 4-[2-methyl-4-(trifluoromethyl)phenyl]-8-[(4-{2-[4-(pyrrolidin-1-yl)piperidin-1-yl]ethyl}phenyl)amino]-1,2-dihydro-2,7-naphthyridin-1-one; 4-(1-methyl-1H-pyrazol-4-yl)-8-[(4-{2-[4-(pyrrolidin-1-yl)piperidin-1-yl]ethyl}phenyl)amino]-1,2-dihydro-2,7-naphthyridin-1-one; 4-(5-methoxypyridin-3-yl)-8-[(4-{2-[4-(pyrrolidin-1-yl)piperidin-1-yl]ethyl}phenyl)amino]-1,2-dihydro-2,7-naphthyridin-1-one; 8-amino-2-methyl-6-(pyrimidin-4-ylamino)-1,2-dihydro-2,7-naphthyridin-1-one; 8-({4-[1-(2-methanesulfonylethyl)piperidin-4-yl]-3-methylphenyl}amino)-6-(6-methylpyridin-3-yl)-1,2-dihydro-2,7-naphthyridin-1-one; 8-({4-[1-(2-methanesulfonylethyl)piperidin-4-yl]-3-methylphenyl}amino)-6-(2-methoxypyrimidin-5-yl)-1,2-dihydro-2,7-naphthyridin-1-one; 6-(1-methyl-1H-pyrazol-4-yl)-8-[(3-methyl-4-{1-[2-(morpholin-4-yl)ethyl]-1H-pyrazol-4-yl}phenyl)amino]-1,2-dihydro-2,7-naphthyridin-1-one; 3-[4-(4-{[3-(2-methoxypyrimidin-5-yl)-8-oxo-7,8-dihydro-2,7-naphthyridin-1-yl]amino}-2-methylphenyl)piperidin-1-yl]propanenitrile 6-(2-aminopyrimidin-5-yl)-2-(2-hydroxy-3-methoxypropyl)-8-[(3-methoxyphenyl)amino]-1,2-dihydro-2,7-naphthyridin-1-one; 6-(2-aminopyrimidin-5-yl)-2-[3-(dimethylamino)propyl]-8-[(3-methoxyphenyl)amino]-1,2-dihydro-2,7-naphthyridin-1-one; 2-[4-(2-methyl-4-{[8-oxo-3-(pyrimidin-5-yl)-7,8-dihydro-2,7-naphthyridin-1-yl]amino}phenyl)piperidin-1-yl]acetonitrile 2-[4-(2-methyl-4-{[8-oxo-3-(pyrimidin-5-yl)-7,8-dihydro-2,7-naphthyridin-1-yl]amino}phenyl)piperidin-1-yl]acetamide 8-({4-[1-(2-hydroxy-3-methoxypropyl)piperidin-4-yl]-3-methylphenyl}amino)-6-(pyrimidin-5-yl)-1,2-dihydro-2,7-naphthyridin-1-one; 6-(2-aminopyrimidin-5-yl)-8-[({3-methoxyphenyl]amino}-2-(3-methoxypropyl)-1,2-dihydro-2,7-naphthyridin-1-one; 6-(2-aminopyrimidin-5-yl)-8-[(3,5-dimethoxyphenyl)amino]-1,2-dihydro-2,7-naphthyridin-1-one; 6-(2-aminopyrimidin-5-yl)-8-[(3,4-dimethoxyphenyl)amino]-1,2-dihydro-2,7-naphthyridin-1-one; 6-(2-aminopyrimidin-5-yl)-8-[(3,5-dimethoxyphenyl)amino]-2-methyl-1,2-dihydro-2,7-naphthyridin-1-one; 6-(2-aminopyrimidin-5-yl)-8-[(3,4,5-trimethoxyphenyl)amino]-1,2-dihydro-2,7-naphthyridin-1-one; 6-[6-(hydroxymethyl)pyridin-3-yl]-8-{[4-(morpholin-4-yl)phenyl]amino}-1,2-dihydro-2,7-naphthyridin-1-one; 6-[6-(hydroxymethyl)pyridin-3-yl]-8-({3-methyl-4-[(2R)-2-methylmorpholin-4-yl]phenyl}amino)-1,2-dihydro-2,7-naphthyridin-1-one; 8-{[4-(1,2-dimethylpiperidin-4-yl)-3-fluorophenyl]amino}-6-(2-methoxypyrimidin-5-yl)-1,2-dihydro-2,7-naphthyridin-1-one; 8-[(2-methylphenyl)amino]-6-[3-(pyrrolidin-1-yl)phenyl]-1,2-dihydro-2,7-naphthyridin-1-one; 8-[(2-methoxyphenyl)amino]-6-[3-(pyrrolidin-1-yl)phenyl]-1,2-dihydro-2,7-naphthyridin-1-one; 8-[(2-ethoxyphenyl)amino]-6-[3-(pyrrolidin-1-yl)phenyl]-1,2-dihydro-2,7-naphthyridin-1-one; 8-{[2-(propan-2-yloxy)phenyl]amino}-6-[3-(pyrrolidin-1-yl)phenyl]-1,2-dihydro-2,7-naphthyridin-1-one; 6-(2-aminopyrimidin-5-yl)-8-[(3,5-dimethoxyphenyl)amino]-2-(2-methoxyethyl)-1,2-dihydro-2,7-naphthyridin-1-one; 6-(2-aminopyrimidin-5-yl)-8-[(3,5-dimethoxyphenyl)amino]-2-[2-(dimethylamino)ethyl]-1,2-dihydro-2,7-naphthyridin-1-one; 8-({1-[1-(2-methoxyethyl)piperidin-4-yl]-1H-pyrazol-4-yl}amino)-6-(pyrimidin-5-yl)-1,2-dihydro-2,7-naphthyridin-1-one; 8-({1-[1-(2-methanesulfonylethyl)piperidin-4-yl]-1H-pyrazol-4-yl}amino)-6-(pyrimidin-5-yl)-1,2-dihydro-2,7-naphthyridin-1-one; 6-(2-aminopyrimidin-5-yl)-2-methyl-8-[(1-methyl-1H-pyrazol-4-yl)amino]-1,2-dihydro-2,7-naphthyridin-1-one; 6-(2-aminopyrimidin-5-yl)-8-[(3,4-dimethoxyphenyl)amino]-2-methyl-1,2-dihydro-2,7-naphthyridin-1-one; 6-(2-aminopyrimidin-5-yl)-2-methyl-8-[(3,4,5-trimethoxyphenyl)amino]-1,2-dihydro-2,7-naphthyridin-1-one; 4-[6-(4-ethylpiperazin-1-yl)-8-{[4-(morpholin-4-yl)phenyl]amino}-1-oxo-1,2-dihydro-2,7-naphthyridin-4-yl]-N-methylbenzamide; 6-(4-ethylpiperazin-1-yl)-4-(4-methoxyphenyl)-8-{[4-(morpholin-4-yl)phenyl]amino}-1,2-dihydro-2,7-naphthyridin-1-one; 4-(4-chlorophenyl)-6-(4-ethylpiperazin-1-yl)-8-{[4-(morpholin-4-yl)phenyl]amino}-1,2-dihydro-2,7-naphthyridin-1-one; 6-(4-ethylpiperazin-1-yl)-8-{[4-(morpholin-4-yl)phenyl]amino}-4-[4-(trifluoromethyl)phenyl]-1,2-dihydro-2,7-naphthyridin-1-one; 6-(4-ethylpiperazin-1-yl)-8-{[4-(morpholin-4-yl)phenyl]amino}-4-[3-(trifluoromethyl)phenyl]-1,2-dihydro-2,7-naphthyridin-1-one; 4-[3-(dimethylamino)phenyl]-6-(4-ethylpiperazin-1-yl)-8-{[4-(morpholin-4-yl)phenyl]amino}-1,2-dihydro-2,7-naphthyridin-1-one; 6-(4-ethylpiperazin-1-yl)-4-(4-methoxy-2-methylphenyl)-8-{[4-(morpholin-4-yl)phenyl]amino}-1,2-dihydro-2,7-naphthyridin-1-one; 6-(4-ethylpiperazin-1-yl)-4-[2-methyl-4-(trifluoromethyl)phenyl]-8-{[4-(morpholin-4-yl)phenyl]amino}-1,2-dihydro-2,7-naphthyridin-1-one; 6-(4-ethylpiperazin-1-yl)-4-(1-methyl-1H-pyrazol-4-yl)-8-{[4-(morpholin-4-yl)phenyl]amino}-1,2-dihydro-2,7-naphthyridin-1-one; 6-(4-ethylpiperazin-1-yl)-4-(5-methoxypyridin-3-yl)-8-{[4-(morpholin-4-yl)phenyl]amino}-1,2-dihydro-2,7-naphthyridin-1-one; 8-amino-2-methyl-6-(pyridin-2-ylamino)-1,2-dihydro-2,7-naphthyridin-1-one; 8-[(4-{1-[2-(dimethylamino)acetyl]piperidin-4-yl}phenyl)amino]-6-(pyrimidin-5-yl)-1,2-dihydro-2,7-naphthyridin-1-one; 8-[(4-{1-[2-(dimethylamino)acetyl]piperidin-4-yl}phenyl)amino]-6-(6-methoxypyrazin-2-yl)-1,2-dihydro-2,7-naphthyridin-1-one; 8-[(4-{1-[2-(ethylamino)acetyl]piperidin-4-yl}phenyl)amino]-6-(pyrimidin-5-yl)-1,2-dihydro-2,7-naphthyridin-1-one; 8-[(4-{1-[2-(ethylamino)

acetyl]piperidin-4-yl}phenyl)amino]-6-(6-methoxypyrazin-2-yl)-1,2-dihydro-2,7-naphthyridin-1-one; N-[3-(2-aminopyrimidin-5-yl)-8-oxo-7,8-dihydro-2,7-naphthyridin-1-yl]-4-fluorobenzamide; 4-fluoro-N-[3-(6-methoxypyrazin-2-yl)-8-oxo-7,8-dihydro-2,7-naphthyridin-1-yl]benzamide; 6-(2-amino-6-methylpyrimidin-4-yl)-8-({4-[1-(2-methoxyethyl)piperidin-4-yl]phenyl}amino)-1,2-dihydro-2,7-naphthyridin-1-one; 6-(2-aminopyrimidin-5-yl)-2-(2-hydroxyethyl)-8-{[4-(morpholin-4-yl)phenyl] amino}-1,2-dihydro-2,7-naphthyridin-1-one; 8-({3-[(dimethylamino)methyl]-1H-indazol-6-yl}amino)-6-(pyrimidin-5-yl)-1,2-dihydro-2,7-naphthyridin-1-one; 8-({3-[(dimethylamino)methyl]-1H-indazol-6-yl}amino)-6-(2-methoxypyrimidin-5-yl)-1,2-dihydro-2,7-naphthyridin-1-one; 8-({3-[(dimethylamino)methyl]-1H-indazol-6-yl}amino)-6-(6-methylpyridin-3-yl)-1,2-dihydro-2,7-naphthyridin-1-one; 8-[(2-methanesulfonyl-1,2,3,4-tetrahydroisoquinolin-6-yl)amino]-6-(6-methylpyridin-3-yl)-1,2-dihydro-2,7-naphthyridin-1-one; 8-[(2-methanesulfonyl-1,2,3,4-tetrahydroisoquinolin-6-yl) amino]-6-(2-methoxypyrimidin-5-yl)-1,2-dihydro-2,7-naphthyridin-1-one; 8-amino-2-methyl-6-[(5-methylpyridin-2-yl)amino]-1,2-dihydro-2,7-naphthyridin-1-one; 8-amino-2-methyl-6-[(3-methylpyridin-2-yl)amino]-1,2-dihydro-2,7-naphthyridin-1-one; 6-[(1-amino-7-methyl-8-oxo-7,8-dihydro-2,7-naphthyridin-3-yl)amino]pyridine-3-carbonitrile 6-[(1-amino-7-methyl-8-oxo-7,8-dihydro-2,7-naphthyridin-3-yl)amino]pyridine-3-carboxamide 8-amino-2-methyl-6-[(1-methyl-1H-pyrazol-3-yl)amino]-1,2-dihydro-2,7-naphthyridin-1-one; 8-amino-2-methyl-6-(1,3-thiazol-2-ylamino)-1,2-dihydro-2,7-naphthyridin-1-one; 8-amino-2-methyl-6-(pyridazin-3-ylamino)-1,2-dihydro-2,7-naphthyridin-1-one; 8-amino-2-methyl-6-(pyrazin-2-ylamino)-1,2-dihydro-2,7-naphthyridin-1-one; 8-amino-2-benzyl-6-(pyrimidin-2-ylamino)-1,2-dihydro-2,7-naphthyridin-1-one; 8-amino-2-methyl-6-(pyrimidin-2-ylamino)-1,2-dihydro-2,7-naphthyridin-1-one; 2-[4-(4-{[8-oxo-3-(pyrimidin-5-yl)-7,8-dihydro-2,7-naphthyridin-1-yl] amino}-1H-pyrazol-1-yl)piperidin-1-yl]acetonitrile 8-({4-[1-(2,3-dihydroxypropyl)piperidin-4-yl]phenyl}amino)-6-(pyrimidin-5-yl)-1,2-dihydro-2,7-naphthyridin-1-one; 8-({4-[1-(2,3-dihydroxypropyl)piperidin-4-yl] phenyl}amino)-6-(2-methoxypyrimidin-5-yl)-1,2-dihydro-2,7-naphthyridin-1-one; 8-({4-[1-(2-methoxyethyl)-1H-pyrazol-4-yl]phenyl}amino)-6-(pyrimidin-5-yl)-1,2-dihydro-2,7-naphthyridin-1-one; 8-({4-[1-(2-methoxyethyl)-1H-pyrazol-4-yl]phenyl}amino)-6-(2-methoxypyrimidin-5-yl)-1,2-dihydro-2,7-naphthyridin-1-one; 8-({1-[2-(morpholin-4-yl)ethyl]-1H-pyrazol-4-yl}amino)-6-(pyrimidin-5-yl)-1,2-dihydro-2,7-naphthyridin-1-one; 6-(2-methoxypyrimidin-5-yl)-8-({1-[2-(morpholin-4-yl)ethyl]-1H-pyrazol-4-yl}amino)-1,2-dihydro-2,7-naphthyridin-1-one; 6-(2-aminopyrimidin-5-yl)-8-[(3,4-dimethoxyphenyl)amino]-2-(2-methoxyethyl)-1,2-dihydro-2,7-naphthyridin-1-one; 2-[6-(2-aminopyrimidin-5-yl)-8-[(3,4-dimethoxyphenyl)amino]-1-oxo-1,2-dihydro-2,7-naphthyridin-2-yl]acetonitrile 8-{[4-(1-methyl-1H-pyrazol-4-yl)phenyl]amino}-6-(pyrimidin-5-yl)-1,2-dihydro-2,7-naphthyridin-1-one; 6-(2-methoxypyrimidin-5-yl)-8-{[4-(1-methyl-1H-pyrazol-4-yl)phenyl]amino}-1,2-dihydro-2,7-naphthyridin-1-one; 6-(2-aminopyrimidin-5-yl)-8-({4-[1-(2-methoxyethyl)-1H-pyrazol-4-yl] phenyl}amino)-1,2-dihydro-2,7-naphthyridin-1-one; 6-(2-aminopyrimidin-5-yl)-8-[(3,4-dimethoxyphenyl)amino]-2-[2-(dimethylamino)ethyl]-1,2-dihydro-2,7-naphthyridin-1-one; 6-(2-aminopyrimidin-5-yl)-8-[(3,4-dimethoxyphenyl) amino]-2-(2-hydroxy-3-methoxypropyl)-1,2-dihydro-2,7-naphthyridin-1-one; 6-(2-aminopyrimidin-5-yl)-8-({1-[2-(morpholin-4-yl)ethyl]-1H-pyrazol-4-yl}amino)-1,2-dihydro-2,7-naphthyridin-1-one; 6-(2-aminopyrimidin-5-yl)-8-{[4-(1-methyl-1H-pyrazol-4-yl)phenyl]amino}-1,2-dihydro-2,7-naphthyridin-1-one; 6-(2-aminopyrimidin-5-yl)-8-({4-[1-(2-methoxyethyl)-1H-pyrazol-4-yl] phenyl}amino)-2-methyl-1,2-dihydro-2,7-naphthyridin-1-one; 6-(2-aminopyrimidin-5-yl)-8-({4-[1-(2-methoxyethyl)-1H-pyrazol-4-yl]phenyl}amino)-2-[2-(morpholin-4-yl) ethyl]-1,2-dihydro-2,7-naphthyridin-1-one; 6-(2-aminopyrimidin-5-yl)-2-methyl-8-({1-[2-(morpholin-4-yl) ethyl]-1H-pyrazol-4-yl}amino)-1,2-dihydro-2,7-naphthyridin-1-one; 6-(2-aminopyrimidin-5-yl)-2-methyl-8-{[4-(1-methyl-1H-pyrazol-4-yl)phenyl]amino}-1,2-dihydro-2,7-naphthyridin-1-one; 6-(2-aminopyrimidin-5-yl)-8-{[4-(1-methyl-1H-pyrazol-4-yl)phenyl]amino}-2-[2-(morpholin-4-yl)ethyl]-1,2-dihydro-2,7-naphthyridin-1-one; N-methyl-2-[4-(2-methyl-4-{[8-oxo-3-(pyrimidin-5-yl)-7,8-dihydro-2,7-naphthyridin-1-yl]amino}phenyl) piperidin-1-yl]acetamide 8-[(2-acetyl-1,2,3,4-tetrahydro isoquinolin-6-yl)amino]-6-(pyrimidin-5-yl)-1,2-dihydro-2,7-naphthyridin-1-one; 8-{[2-(2-methoxyethyl)-1,2,3,4-tetrahydroisoquinolin-6-yl]amino}-6-(pyrimidin-5-yl)-1,2-dihydro-2,7-naphthyridin-1-one; 6-(pyrimidin-5-yl)-8-{[3-(1,2,3,6-tetrahydropyridin-4-yl)-1H-indazol-6-yl]amino}-1,2-dihydro-2,7-naphthyridin-1-one; 6-{imidazo[1,2-a] pyrimidin-6-yl}-2-methyl-8-{[4-(morpholin-4-yl)phenyl] amino}-1,2-dihydro-2,7-naphthyridin-1-one; 6-{8-methylimidazo[1,2-a]pyrazin-6-yl}-8-{[4-(morpholin-4-yl) phenyl]amino}-1,2-dihydro-2,7-naphthyridin-1-one; 6-{imidazo[1,2-a]pyrimidin-6-yl}-8-{[4-(morpholin-4-yl) phenyl]amino}-1,2-dihydro-2,7-naphthyridin-1-one; 2-({1-[(4-{1-[2-(dimethylamino)acetyl]piperidin-4-yl}-3-methylphenyl)amino]-8-oxo-7,8-dihydro-2,7-naphthyridin-3-yl}amino)-6-methylbenzene-1-sulfonamide; 2-{[1-({4-[1-(2-methoxyethyl)piperidin-4-yl]-3-methylphenyl}amino)-8-oxo-7,8-dihydro-2,7-naphthyridin-3-yl]amino}-6-methylbenzene-1-sulfonamide; 8-[(4-{1-[2-(dimethylamino)acetyl]piperidin-4-yl}-3-methylphenyl) amino]-6-(pyrimidin-5-yl)-1,2-dihydro-2,7-naphthyridin-1-one; 8-[(4-{1-[2-(dimethylamino)acetyl]piperidin-4-yl}-3-methylphenyl)amino]-6-(6-methoxypyrazin-2-yl)-1,2-dihydro-2,7-naphthyridin-1-one; 8-[(4-{1-[2-(ethylamino) acetyl]piperidin-4-yl}-3-methylphenyl)amino]-6-(pyrimidin-5-yl)-1,2-dihydro-2,7-naphthyridin-1-one; 8-[(4-{1-[2-(ethylamino)acetyl]piperidin-4-yl}-3-methylphenyl) amino]-6-(6-methoxypyrazin-2-yl)-1,2-dihydro-2,7-naphthyridin-1-one; 8-[(6-{1-[2-(dimethylamino)acetyl] piperidin-4-yl}pyridin-3-yl)amino]-6-(pyrimidin-5-yl)-1,2-dihydro-2,7-naphthyridin-1-one; 6-(6-methoxypyrazin-2-yl)-8-({4-[2-(4-methylpiperazin-1-yl)ethyl]phenyl}amino)-1,2-dihydro-2,7-naphthyridin-1-one; 6-[6-(2-hydroxypropan-2-yl)pyridin-3-yl]-2-methyl-8-(propan-2-ylamino)-1,2-dihydro-2,7-naphthyridin-1-one; 6-(2-aminopyrimidin-5-yl)-2-methyl-8-(propan-2-ylamino)-1,2-dihydro-2,7-naphthyridin-1-one; 8-amino-2-benzyl-6-(pyrimidin-4-ylamino)-1,2-dihydro-2,7-naphthyridin-1-one; 8-amino-2-benzyl-6-(pyridin-2-ylamino)-1,2-dihydro-2,7-naphthyridin-1-one; 8-amino-2-benzyl-6-[(5-methylpyridin-2-yl)amino]-1,2-dihydro-2,7-naphthyridin-1-one; 8-amino-2-benzyl-6-[(3-methylpyridin-2-yl)amino]-1,2-dihydro-2,7-naphthyridin-1-one; 8-amino-2-benzyl-6-(pyridazin-3-ylamino)-1,2-dihydro-2,7-naphthyridin-1-one; 4-{6-[(2-methoxyethyl)amino]-8-{[4-(morpholin-4-yl)phenyl] amino}-1-oxo-1,2-dihydro-2,7-naphthyridin-4-yl}-N-methylbenzamide; 6-[(2-methoxyethyl)amino]-4-(4-methoxyphenyl)-8-{[4-(morpholin-4-yl)phenyl]amino}-1, 2-dihydro-2,7-naphthyridin-1-one; 8-amino-2-benzyl-6-[(1-methyl-1H-pyrazol-3-yl)amino]-1,2-dihydro-2,7-naphthyridin-1-one; 6-[(2-methoxyethyl)amino]-4-(5-methoxypyridin-3-yl)-8-{[4-(morpholin-4-yl)phenyl]amino}-1,2-dihydro-2,7-naphthyridin-1-one; 6-{8-methylimidazo pyridin-6-yl}-8-{[4-(morpholin-4-yl)phenyl]amino}-1,2-dihydro-2,7-naphthyridin-1-one; 8-amino-2-benzyl-6-(pyrazin-2-ylamino)-1,2-dihydro-2,7-naphthyridin-1-one, and 8-{[4-(morpholin-4-yl)phenyl]amino}-6-{1H,2H,3H-pyrrolo[2,3-b]pyridin-5-yl}-1,2-dihydro-2,7-naphthyridin-1-one.

In another aspect, the present invention provides pharmaceutical compositions comprising a therapeutically effective amount of a compound of Formulas (I), (Ia), (Ib), (Ic), I(d) or I(e), and a pharmaceutically acceptable carrier. In certain embodiments, such pharmaceutical compositions are formulated for intravenous, oral administration, rectal administration inhalation, nasal administration, topical administration, ophthalmic administration or optic administration. In other embodiments, such pharmaceutical composition are formulated as tablets, a pills, capsules, a liquid, an inhalant, a nasal spray solution, a suppository, a solution, an emulsion, an ointment, eye drops or ear drops.

In another aspect, the present invention provides a medicament for treating a Syk-mediated disease or condition in a patient comprising a therapeutically effective amount of a compound of Formulas (I), (Ia), (Ib), (Ic), I(d) or I(e).

In another aspect, the present invention provides the use of a compound of Formulas (I), (Ia), (Ib), (Ic), I(d) or I(e) in the manufacture of a medicament for treating a Syk-mediated disease or condition.

In another aspect, the present invention provides methods for modulating a protein kinase, comprising administering to a system or a subject in need thereof, a therapeutically effective amount of a compound of Formulas (I), (Ia), (Ib), (Ic), I(d) or I(e), or pharmaceutically acceptable salts or pharmaceutical compositions thereof, thereby modulating the protein kinase. In certain embodiments, the protein kinase is Syk, ZAP70, KDR, FMS, FLT3, c-Kit, RET, IGR-1R, Alk, c-FMS, TrkA, TrkB, TrkC kinases, or a combination thereof. In other embodiments the protein kinase is Syk. In certain embodiments of such methods, the compounds of Formulas (I), (Ia), (Ib), (Ic), I(d) or I(e), or pharmaceutically acceptable salts or pharmaceutical compositions thereof, inhibit protein kinases. In certain embodiments, the protein kinases inhibited by compounds of Formulas (I), (Ia), (Ib), (Ic), I(d) or I(e), or pharmaceutically acceptable salts or pharmaceutical compositions thereof are Syk, ZAP70, KDR, FMS, FLT3, c-Kit, RET, IGR-1R, Alk, c-FMS, TrkA, TrkB, TrkC kinases, or a combination thereof. In other embodiments the Syk.protein kinase is inhibited by compounds of Formulas (I), (Ia), (Ib), (Ic), I(d) or I(e), or pharmaceutically acceptable salts or pharmaceutical compositions thereof.

In another aspect, the present invention provides methods for modulating a protein kinase, comprising administering to a system or a subject in need thereof, a therapeutically effective amount of a compound of Formulas (I), (Ia), (Ib), (Ic), I(d) or I(e), or pharmaceutically acceptable salts, pharmaceutical compositions or medicaments thereof, thereby modulating the protein kinase. In certain embodiments, the protein kinase is Syk, ZAP70, KDR, FMS, FLT3, c-Kit, RET, IGR-1R, Alk, c-FMS, TrkA, TrkB, TrkC kinases, or a combination thereof. In other embodiments the protein kinase is Syk. In certain embodiments of such methods, the compound of Formulas (I), (Ia), (Ib), (Ic), I(d) or I(e), or pharmaceutically acceptable salts, pharmaceutical compositions or medicaments thereof, inhibit protein kinases. In certain embodiments, the protein kinases inhibited by compounds of Formulas (I), (Ia), (Ib), (Ic), I(d) or I(e), or pharmaceutically acceptable salts, pharmaceutical compositions or medicaments thereof are Syk, ZAP70, KDR, FMS, FLT3, c-Kit, RET, IGR-1R, Alk, c-FMS, TrkA, TrkB, TrkC kinases, or a combination thereof. In other embodiments the Syk.protein kinase is inhibited by compounds of Formulas (I), (Ia), (Ib), (Ic), I(d) or I(e), or pharmaceutically acceptable salts, pharmaceutical compositions or medicaments thereof.

In another aspect, the present invention provides methods for treating a Syk mediated disease or condition comprising administering to a system or a subject in need of such treatment a therapeutically effective amount of a compound of Formulas (I), (Ia), (Ib), (Ic), I(d) or I(e), or pharmaceutically acceptable salts, pharmaceutical compositions or medicaments thereof, thereby treating such Syk mediated diseases or conditions. In certain embodiments such Syk mediated diseases or conditions are inflammatory diseases or conditions, respiratory diseases or autoimmune diseases or conditions. In certain embodiments such Syk mediated diseases or conditions are asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, multiple sclerosis, cancer, breast cancer, HIV or lupus.

In another aspect, the present invention provides methods for treating a Syk mediated disease or condition comprising administering to a system or a subject in need of such treatment a therapeutically effective amount of a compound of Formulas (I), (Ia), (Ib), (Ic), I(d) or I(e), or pharmaceutically acceptable salts, pharmaceutical compositions or medicaments thereof in combination with a second therapeutic agent, thereby treating such Syk mediated diseases or conditions. In certain embodiments such Syk mediated diseases or conditions are inflammatory diseases or conditions, respiratory diseases or autoimmune diseases or conditions. In certain embodiments such Syk mediated diseases or conditions are asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, multiple sclerosis, cancer, breast cancer, HIV or lupus.

In the above methods for using the compounds of the invention, a compound of Formulas (I), (Ia), (Ib), (Ic), I(d) or I(e), or pharmaceutically acceptable salts, pharmaceutical compositions or medicaments thereof is administered to a system comprising cells or tissues. In certain embodiments, a compound of Formulas (I), (Ia), (Ib), (Ic), I(d) or I(e), or pharmaceutically acceptable salts, pharmaceutical compositions or medicaments thereof is administered to a human or animal subject.

In another aspect, the present invention provides methods for treating a cell-proliferative disease or condition comprising administering to a system or a subject in need of such treatment a therapeutically effective amount of a compound of Formulas (I), (Ia), (Ib), (Ic), I(d) or I(e), or pharmaceutically acceptable salts, pharmaceutical compositions or medicaments thereof, wherein the cell-proliferative disease or condition is lymphoma, osteosarcoma, melanoma, breast cancer, renal cancer, prostate cancer, colorectal cancer, thyroid cancer, ovarian cancer, pancreatic cancer, neuronal cancer, lung cancer, uterine cancer or gastrointestinal cancer.

In another aspect, the present invention provides a compound having the structure

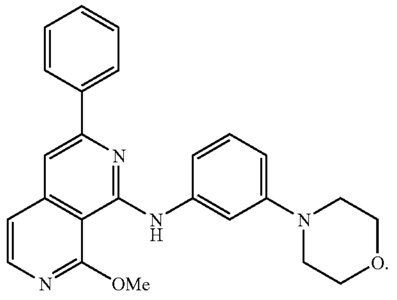 [SMILES: COc1nccc2cc(-c3ccccc3)nc(Nc3cccc(N4CCOCC4)c3)c12]

In another aspect, the present invention provides a compound having the structure

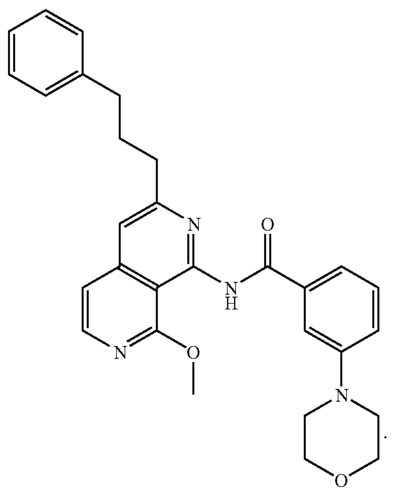 [SMILES: COc1nccc2cc(CCCc3ccccc3)nc(NC(=O)c3cccc(N4CCOCC4)c3)c12]

In another aspect, the present invention provides a compound having the structure

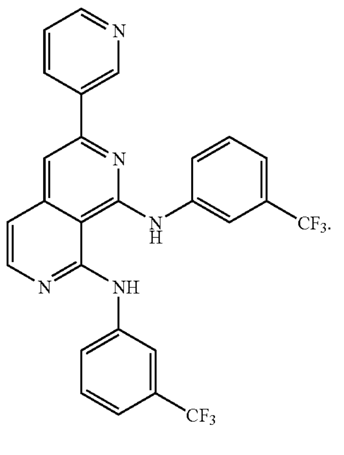 [SMILES: FC(F)(F)c1cccc(Nc2nccc3cc(-c4cccnc4)nc(Nc4cccc(C(F)(F)F)c4)c23)c1]

In another aspect, the present invention provides a compound having the structure

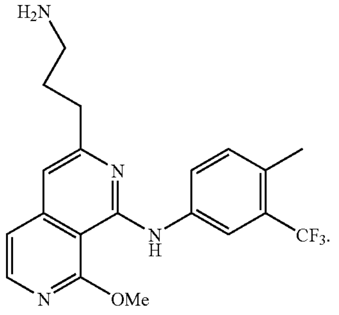 [SMILES: COc1nccc2cc(CCCN)nc(Nc3ccc(C)c(C(F)(F)F)c3)c12]

In another aspect, the present invention provides a compound having the structure

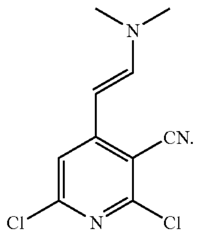

DETAILED DESCRIPTION OF THE INVENTION

Definitions

The term "alkenyl", as used herein, refers to a partially unsaturated branched or straight chain hydrocarbon having at least one carbon-carbon double bond. Atoms oriented about the double bond are in either the cis (Z) or trans (E) conformation. As used herein, the terms "$C_2$-$C_4$alkenyl", "$C_2$-$C_5$alkenyl", "$C_2$-$C_6$alkenyl", "$C_2$-$C_7$alkenyl", and "$C_2$-$C_8$alkenyl" refer to an alkyenyl group containing at least 2, and at most 4, 5, 6, 7 or 8 carbon atoms, respectively. Non-limiting examples of alkenyl groups, as used herein, include ethenyl, propenyl, allyl (2-propenyl), butenyl, pentenyl, hexenyl, heptenyl, octenyl, nonenyl, decenyl and the like.

The term "alkyl", as used herein, refers to a saturated branched or straight chain hydrocarbon. As used herein, the terms "$C_1$-$C_3$alkyl", "$C_1$-$C_4$alkyl", "$C_1$-$C_5$alkyl", "$C_1$-$C_6$alkyl", "$C_1$-$C_7$ alkyl" and "$C_1$-$C_8$alkyl" refer to an alkyl group containing at least 1, and at most 3, 4, 5, 6, 7 or 8 carbon atoms, respectively. Non-limiting examples of alkyl groups as used herein include methyl, ethyl, n-propyl, isopropyl, n-butyl, isobutyl, sec-butyl, t-butyl, n-pentyl, isopentyl, hexyl, heptyl, octyl, nonyl, decyl and the like.

The term "alkylene", as used herein, refers to a saturated branched or straight chain divalent hydrocarbon radical, wherein the radical is derived by the removal of one hydrogen atom from each of two carbon atoms. As used herein, the terms "$C_1$-$C_3$ alkylene", "$C_1$-$C_4$alkylene", "$C_1$-$C_5$alkylene", and "$C_1$-$C_6$alkylene" refer to an alkylene group containing at least 1, and at most 3, 4, 5 or 6 carbon atoms respectively. Non-limiting examples of alkylene groups as used herein include, methylene, ethylene, n-propylene, isopropylene, n-butylene, isobutylene, sec-butylene, t-butylene, n-pentylene, isopentylene, hexylene and the like.

The term "alkynyl", as used herein, refers to a partially unsaturated branched or straight chain hydrocarbon radical having at least one carbon-carbon triple bond. As used herein, the terms "$C_2$-$C_4$alkynyl", "$C_2$-$C_5$alkynyl", "$C_2$-$C_6$alkynyl", "$C_2$-$C_7$alkynyl", and "$C_2$-$C_8$alkynyl" refer to an alkynyl group containing at least 2, and at most 4, 5, 6, 7 or 8 carbon atoms, respectively. Non-limiting examples of alkynyl groups, as used herein, include ethynyl, propynyl, butynyl, pentynyl, hexynyl, heptynyl, octynyl, nonynyl, decynyl and the like.

The term "alkoxy", as used herein, refers to the group —$OR_a$, where $R_a$ is an alkyl group as defined herein. As used herein, the terms "$C_1$-$C_3$ alkoxy", "$C_1$-$C_4$alkoxy", "$C_1$-$C_5$ alkoxy", "$C_1$-$C_6$alkoxy", "$C_1$-$C_7$alkoxy" and "$C_1$-$C_8$alkoxy" refer to an alkoxy group wherein the alkyl moiety contains at least 1, and at most 3, 4, 5, 6, 7 or 8, carbon atoms. Non-limiting examples of alkoxy groups, as used herein, include methoxy, ethoxy, n-propoxy, isopropoxy, n-butoxy, t-butoxy, pentoxy, hexoxy, heptoxy, and the like.

The term "aryl", as used herein, refers to monocyclic, bicyclic, and tricyclic ring systems having a total of five to fourteen ring members, wherein at least one ring in the system is aromatic and wherein each ring in the system contains 3 to 7 ring members. An aryl group may contain one or more substituents and thus may be "optionally substituted". Unless otherwise defined herein, suitable substituents on the unsaturated carbon atom of an aryl group are generally selected from halogen; —R, —OR, —SR, —$NO_2$, —CN, —$N(R)_2$, —NRC(O)R, —NRC(S)R, —NRC(O)$N(R)_2$, —NRC(S)N$(R)_2$, —$NRCO_2R$, —NRNRC(O)R, —NRNRC(O)$N(R)_2$, —$NRNRCO_2R$, —C(O)C(O)R, —C(O)$CH_2$C(O)R, —$CO_2R$, —C(O)$R^o$, —C(S)R, —C(O)$N(R)_2$, —C(S)$N(R)_2$, —OC(O)$N(R)_2$, —OC(O)R, —C(O)N(OR)R, —C(NOR)R, —$S(O)_2R$, —$S(O)_3R$, —$SO_2N(R)_2$, —S(O)R, —$NRSO_2N(R)_2$, —$NRSO_2R$, —N(OR)R, —C(═NH)—$N(R)_2$, —$P(O)_2R$, —$PO(R)_2$, —$OPO(R)_2$, —$(CH_2)_{0-2}$NHC(O)R, phenyl (Ph) optionally substituted with R, —O(Ph) optionally substituted with R, —$(CH_2)_{1-2}$(Ph), optionally substituted with R, or —CH═CH(Ph), optionally substituted with R, wherein each independent occurrence of R is selected from hydrogen, optionally substituted $C_1$-$C_6$alkyl, optionally substituted $C_1$-$C_6$alkoxy, an unsubstituted 5-6 membered heteroaryl, phenyl, —O(Ph), or —$CH_2$(Ph), or two independent occurrences of R, on the same substituent or different substituents, taken together with the atom(s) to which each R is bound, to form an optionally substituted 3-12 membered saturated, partially unsaturated, or fully unsaturated monocyclic or bicyclic ring having 0-4 heteroatoms independently selected from nitrogen, oxygen, or sulfur. Non-limiting examples of aryl groups, as used herein, include phenyl, naphthyl, fluorenyl, indenyl, azulenyl, anthracenyl and the like.

The term "arylene", as used means a divalent radical derived from an aryl group.

The term "cyano", as used herein, refers to a —CN group.

The term "cycloalkyl", as used herein, refers to a saturated or partially unsaturated, monocyclic, fused bicyclic, fused tricyclic or bridged polycyclic ring assembly. As used herein, the terms "$C_3$-$C_5$ cycloalkyl", "$C_3$-$C_6$ cycloalkyl", "$C_3$-$C_7$ cycloalkyl", "$C_3$-$C_8$ cycloalkyl, "$C_3$-$C_9$ cycloalkyl and "$C_3$-$C_{10}$ cycloalkyl refer to a cycloalkyl group wherein the saturated or partially unsaturated, monocyclic, fused bicyclic or bridged polycyclic ring assembly contain at least 3, and at most 5, 6, 7, 8, 9 or 10, carbon atoms. Non-limiting examples of cycloalkyl groups, as used herein, include cyclopropyl, cyclobutyl, cyclopentyl, cyclohexyl, cycloheptyl, cyclooctyl, cyclononyl, cyclodecyl, cyclopentenyl, cyclohexenyl, decahydronaphthalenyl, 2,3,4,5,6,7-hexahydro-1H-indenyl and the like.

The term "cyclic heterodionyl", as used herein, refers to a heteroaryl compound bearing two carbonyl substituents. Non-limiting examples of cyclic heterodionyl, as used herein, include thiazolidinyl diones, oxazolidinyl diones and pyrrolidinyl diones.

The term "halogen", as used herein, refers to fluorine (F), chlorine (Cl), bromine (Br), or iodine (I).

The term "halo", as used herein, refers to the halogen radicals: fluoro (—F), chloro (—Cl), bromo (—Br), and iodo (—I).

The terms "haloalkyl" or "halo-substituted alkyl", as used herein, refers to an alkyl group as defined herein, substituted with at least one halo group or combinations thereof. Non-limiting examples of such branched or straight chained haloalkyl groups, as used herein, include methyl, ethyl, propyl, isopropyl, isobutyl and n-butyl substituted with one or more halo groups or combinations thereof, including, but not limited to, trifluoromethyl, pentafluoroethyl, and the like.

The term "halo-substituted alkenyl", as used herein, refers to an alkenyl group as defined above, substituted with at least one halo group or combinations thereof. Non-limiting examples of such branched or straight chained haloalkenyl groups, as used herein, include ethenyl, propenyl, allyl (2-propenyl), butenyl, pentenyl, hexenyl, heptenyl, octenyl, nonenyl, decenyl and the like substituted with one or more halo groups or combinations thereof.

The term "halo-substituted alkynyl", as used herein, refers to an alkynyl group as defined above, substituted with at least one halo group or combinations thereof. Non-limiting examples of such branched or straight chained haloalkynyl groups, as used herein, include ethynyl, propynyl, butynyl, pentynyl, hexynyl, heptynyl, octynyl, nonynyl, decynyl and the like substituted with one or more halo groups or combinations thereof.

The term "haloalkoxy", as used herein, refers to an alkoxy group as defined above, substituted with one or more halo group or combinations thereof. Non-limiting examples of such branched or straight chained haloalkynyl groups, as used herein, include methoxy, ethoxy, n-propoxy, isopropoxy, n-butoxy, t-butoxy, pentoxy, hexoxy, heptoxy and the like substituted with one or more groups or combinations thereof.

The term "heteroalkyl", as used herein, refers to refers to an alkyl group as defined herein wherein one or more carbon atoms are independently replaced by one or more of oxygen, sulfur, nitrogen, or combinations thereof.

The term "heteroaryl", as used herein, refers to monocyclic, bicyclic, and tricyclic ring systems having a total of five to fourteen ring members, wherein at least one ring in the system is aromatic, at least one ring in the system contains one or more heteroatoms selected from nitrogen, oxygen and sulfur, and wherein each ring in the system contains 3 to 7 ring members. Unless otherwise defined above and herein, suitable substituents on the unsaturated carbon atom of a heteroaryl group are generally selected from halogen; —R, —OR, —SR, —$NO_2$, —CN, —$N(R)_2$, —NRC(O)R, —NRC(S)R, —NRC(O)$N(R)_2$, —NRC(S)$N(R)_2$, —$NRCO_2R$, —NRNRC(O)R, —NRNRC(O)$N(R)_2$, —$NRNRCO_2R$, —C(O)C(O)R, —C(O)$CH_2$C(O)R, —$CO_2R$, —C(O)$R^o$, —C(S)R, —C(O)$N(R)_2$, —C(S)$N(R)_2$, —OC(O)$N(R)_2$, —OC(O)R, —C(O)N(OR)R, —C(NOR)R, —$S(O)_2R$, —$S(O)_3R$, —$SO_2N(R)_2$, —S(O)R, —$NRSO_2N(R)_2$, —$NRSO_2R$, —N(OR)R, —C(═NH)—$N(R)_2$, —$P(O)_2R$, —$PO(R)_2$, —$OPO(R)_2$, —$(CH_2)_{0-2}$NHC(O)R, phenyl (Ph) optionally substituted with R, —O(Ph) optionally substituted with R, $—(CH_2)_{1-2}(Ph)$, optionally substituted with R, or —CH═CH(Ph), optionally substituted with R, wherein each independent occurrence of R is selected from hydrogen, optionally substituted $C_1$-$C_6$alkyl, optionally substituted $C_1$-$C_6$alkoxy, an unsubstituted 5-6 membered heteroaryl, phenyl, —O(Ph), or $—CH_2(Ph)$, or two independent occurrences of R, on the same substituent or different substituents, taken together with the atom(s) to which each R is bound, to form an optionally substituted 3-12 membered saturated, partially unsaturated, or fully unsaturated monocyclic or bicyclic ring having 0-4 heteroatoms independently selected from nitrogen, oxygen, or sulfur. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl, triazolyl and tetrazolyl.

The term “heterocycloalkyl”, as used herein, refers to a cycloalkyl, as defined herein, wherein one or more of the ring carbons are replaced by a moiety selected from —O—, —N═, —NR—, —C(O)—, —S—, —S(O)— or $—S(O)_2—$, wherein R is hydrogen, $C_1$-$C_8$alkyl or a nitrogen protecting group, with the proviso that the ring of said group does not contain two adjacent O or S atoms. Non-limiting examples of heterocycloalkyl groups, as used herein, include morpholino, pyrrolidinyl, pyrrolidinyl-2-one, piperazinyl, piperidinyl, piperidinylone, 1,4-dioxa-8-aza-spiro[4.5]dec-8-yl, 2H-pyrrolyl, 2-pyrrolinyl, 3-pyrrolinyl, 1,3-dioxolanyl, 2-imidazolinyl, imidazolidinyl, 2-pyrazolinyl, pyrazolidinyl, 1,4-dioxanyl, 1,4-dithianyl, thiomorpholinyl, azepanyl, hexahydro-1,4-diazepinyl, tetrahydrofuranyl, dihydrofuranyl, tetrahydrothienyl, tetrahydropyranyl, dihydropyranyl, tetrahydrothiopyranyl, thioxanyl, azetidinyl, oxetanyl, thietanyl, oxepanyl, thiepanyl, 1,2,3,6-tetrahydropyridinyl, 2H-pyranyl, 4H-pyranyl, dioxanyl, 1,3-dioxolanyl, dithianyl, dithiolanyl, dihydropyranyl, dihydrothienyl, dihydrofuranyl, imidazolinyl, imidazolidinyl, 3-azabicyclo[3.1.0]hexanyl, and 3-azabicyclo[4.1.0]heptanyl.

The term “heteroatom”, as used herein, refers to one or more of oxygen, sulfur, nitrogen, phosphorus, or silicon.

The term “hydroxyl”, as used herein, refers to the group —OH.

The term “hydroxyalkyl”, as used herein refers to an alkyl group as defined herein substituted with at least one hydroxyl, hydroxyl being as defined herein. Non-limiting examples of branched or straight chained “$C_1$-$C_6$ hydroxyalkyl groups as used herein include methyl, ethyl, propyl, isopropyl, isobutyl and n-butyl substituted independently with one or more hydroxyl groups.

The term “isocyanato”, as used herein, refers to a —N═C═O group.

The term “isothiocyanato”, as used herein, refers to a —N═C═S group.

The term “mercaptyl”, as used herein, refers to an (alkyl) S— group.

The term “optionally substituted”, as used herein, means that the referenced group may or may not be substituted with one or more additional group(s) individually and independently selected from alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof. Non-limiting examples of optional substituents include, halo, —CN—, —OR, —C(O)R, $^-$OC(O)R, —C(O)OR, OC(O)NHR, $—C(O)N(R)_2$, —SR—, —S(═O)R, $—S(═O)_2R$, —NHR, $—N(R)_2$, —NHC(O)—, NHC(O)O—, —C(O)NH—, $S(═O)_2NHR$, $—S(O)_2N(R)_2$, $—NHS(═O)_2$, $—NHS(O)_2R$, $C_1$-$C_6$ alkyl, $C_1$-$C_6$ alkoxy, aryl, heteroaryl, cycloalkyl, heterocycloalkyl, halo-substituted $C_1$-$C_6$alkyl, halo-substituted $C_1$-$C_6$alkoxy, where each R is independently selected from H, halo, $C_1$-$C_6$ alkyl, $C_1$-$C_6$ alkoxy, aryl, heteroaryl, cycloalkyl, heterocycloalkyl, halo-substituted $C_1$-$C_6$alkyl, halo-substituted $C_1$-$C_6$alkoxy.

The term “solvate”, as used herein, refers to a complex of variable stoichiometry formed by a solute (in this invention, a compound of Formula (I), or a salt thereof) and a solvent. Such solvents for the purpose of the invention may not interfere with the biological activity of the solute. Non-limiting examples of suitable solvents include water, acetone, methanol, ethanol and acetic acid. Preferably the solvent used is a pharmaceutically acceptable solvent. Non-limiting examples of suitable pharmaceutically acceptable solvents include water, ethanol and acetic acid.

The term “acceptable” with respect to a formulation, composition or ingredient, as used herein, means having no persistent detrimental effect on the general health of the subject being treated.

The term “administration” or “administering” of the subject compound means providing a compound of the invention and prodrugs thereof to a subject in need of treatment.

The term “bone disease,” as used herein, refers to a disease or condition of the bone, including, but not limited to, inapproriate bone remodeling, loss or gain, osteopenia, osteomalacia, osteofibrosis, and Paget’s disease.

The term “cardiovascular disease,” as used herein refers to diseases affecting the heart or blood vessels or both, including but not limited to: arrhythmia; atherosclerosis and its sequelae; angina; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

The term “cancer,” as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

The term “carrier,” as used herein, refers to chemical compounds or agents that facilitate the incorporation of a compound described herein into cells or tissues.

The terms “co-administration” or “combined administration” or the like as used herein are meant to encompass administration of the selected therapeutic agents to a single patient, and are intended to include treatment regimens in which the agents are not necessarily administered by the same route of administration or at the same time.

The term “dermatological disorder,” as used herein refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, and urticaria.

The term "diluent" as used herein, refers to chemical compounds that are used to dilute a compound described herein prior to delivery. Diluents can also be used to stabilize compounds described herein.

The terms "effective amount" or "therapeutically effective amount," as used herein, refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis.

The term "iatrogenic", as used herein, means a condition, disorder, or disease created or worsened by medical or surgical therapy.

The term "inflammatory disorders", as used herein, refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporarl arteritis); joints (arthritis: crystalline, osteo-, psoriatic, reactive, rheumatoid, Reiter's); gastrointestinal tract (Disease,); skin (dermatitis); or multiple organs and tissues (systemic lupus erythematosus).

The term "Kinase Panel", as used herein, refers to is a list of kinases including but not limited to Abl(human), Abl (T3151), JAK2, JAK3, ALK, JNK1α1, ALK4, KDR, Aurora-A, Lck, Blk, MAPK1, Bmx, MAPKAP-K2, BRK, MEK1, CaMKII(rat), Met, CDK1/cyclinB, p70S6K, CHK2, PAK2, CK1, PDGFRα, CK2, PDK1, c-Kit, Pim-2, C-Raf, PKA(h), CSK, PKBα, Src, PKCα, DYRK2, Plk3, EGFR, ROCK-I, Fes, Ron, FGFR-3, Ros, Flt3, SAPK2α, Fms, SGK, Fyn, SIK, GSK3β, Syk, IGFR, Tie-2, IKKβ, TrkB, IR, WNK3, IRAK4, ZAP-70, ITK, AMPK(rat), LIMK1, Rsk2, Axl, LKB1, SAPK2β, BrSK2, Lyn (h), SAPK3, BTK, MAPKAP-K3, SAPK4, CaMKIV, MARK1, Snk, CDK2/cyclinA, MINK, SRPK1, CDK3/cyclinE, MKK4(m), TAK1, CDK5/p25, MKK6(h), TBK1, CDK6/cyclinD3, MLCK, TrkA, CDK7/cyclinH/MAT1, MRCKß3, TSSK1, CHK1, MSK1, Yes, CK1d, MST2, ZIPK, c-Kit (D816V), MuSK, DAPK2, NEK2, DDR2, NEK6, DMPK, PAK-4, DRAK1, PAR-1Bα, EphA1, PDGFRβ, EphA2, Pim-1, EphA5, PKBβ, EphB2, PKCβI, EphB4, PKCδ, FGFR1, PKCη, FGFR2, PKCθ, FGFR4, PKD2, Fgr, PKG1β, Flt1, PRK2, Hck, PYK2, HIPK2, Ret, IKKα, RIPK2, IRR, ROCK-II(human), JNK2α2, Rse, JNK3, Rsk1(h), PI3 Kγ, PI3 Kδ and PI3-Kβ.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The terms "neurogenerative disease" or "nervous system disorder," as used herein, refers to conditions that alter the structure or function of the brain, spinal cord or peripheral nervous system, including but not limited to Alzheimer's Disease, cerebral edema, cerebral ischemia, multiple sclerosis, neuropathies, Parkinson's Disease, those found after blunt or surgical trauma (including post-surgical cognitive dysfunction and spinal cord or brain stem injury), as well as the neurological aspects of disorders such as degenerative disk disease and sciatica. The acronym "CNS" refers to disorders of the central nervous system (brain and spinal cord).

The terms "ocular disease" or "ophthalmic disease," as used herein, refer to diseases which affect the eye or eyes and potentially the surrounding tissues as well. Ocular or ophthalmic diseases include, but are not limited to, conjunctivitis, retinitis, scleritis, uveitis, allergic conjuctivitis, vernal conjunctivitis, pappillary conjunctivitis.

The term "pharmaceutically acceptable," as used herein, refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

The term "pharmaceutically acceptable salt", as used herein, refers to a formulation of a compound that does not cause significant irritation to an organism to which it is administered and does not abrogate the biological activity and properties of the compounds described herein.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a coagent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The term "pharmaceutical composition", as used herein, refers to a mixture of a compound described herein with other chemical components, such as carriers, stabilizers, diluents, dispersing agents, suspending agents, thickening agents, and/or excipients.

The term "prodrug", as used herein, refers to an agent that is converted into the parent drug in vivo. Prodrugs are often useful because, in some situations, they may be easier to administer than the parent drug. Prodrugs are bioavailable by oral administration whereas the parent is not. Prodrugs improve solubility in pharmaceutical compositions over the parent drug. A non-limiting example of a prodrug of the compounds described herein is a compound described herein administered as an ester which is then metabolically hydrolyzed to a carboxylic acid, the active entity, once inside the cell. A further example of a prodrug is a short peptide bonded to an acid group where the peptide is metabolized to reveal the active moiety.

The term "respiratory disease," as used herein, refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "subject" or "patient", as used herein, encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

The term "Syk inhibitor", as used herein, refers to a compound which inhibits the Syk receptor.

The term "Syk mediated disease" or a "disorder or disease or condition mediated by inappropriate Syk activity", as used herein, refers to any disease state mediated or modulated by Syk kinase mechanisms. Such disease states include, but are not limited to, inflammatory, respiratory diseases and autoimmune diseases, such as, by way of example only, asthma, chronic obstructive pulmonary disease (COPD), adult respiratory distress syndrome (ARDS), ulcerative colitis, Crohns disease, bronchitis, dermatitis, allergic rhinitis, psorasis, scleroderma, urticaria, rheumatoid arthritis, multiple sclerosis, cancer, HIV and lupus.

The term "therapeutically effective amount", as used herein, refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The terms "treat", "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

The compound names provided herein were obtained using ChemDraw Ultra 10.0 (CambridgeSoft®) or JChem version 5.0.3 (ChemAxon).

Other objects, features and advantages of the methods and compositions described herein will become apparent from the following detailed description. It should be understood, however, that the detailed description and the specific examples, while indicating specific embodiments, are given by way of illustration only.

Description of the Preferred Embodiments

The present invention provides compounds and pharmaceutical compositions thereof, which are protein kinase inhibitors. The present invention provides compounds, pharmaceutical compositions and methods for the treatment and/or prevention of protein kinase related diseases or conditions/disorders, including disease or conditions/disorders associated with abnormal or deregulated protein kinase activity. In certain embodiments, such protein kinases are Syk, ZAP70, KDR, FMS, FLT3, c-Kit, RET, TrkA, TrkB, TrkC, IGR-1R, Alk and/or c-FMS. In certain embodiments the compounds and pharmaceutical compositions of the present invention are inhibitors of Syk, ZAP70, KDR, FMS, FLT3, c-Kit and/or RET protein kinases. In other embodiments, the compounds and pharmaceutical compositions of the present invention are used to treat and/or prevent diseases and conditions related to, or mediated by, Syk, ZAP70, KDR, FMS, FLT3, c-Kit, RET or a combination thereof. In certain embodiments the compounds and pharmaceutical compositions of the present invention are inhibitors of Syk, TrkA, TrkB, TrkC, IGR-1R, Alk and/or c-FMS protein kinases. In other embodiments, the compounds and pharmaceutical compositions of the present invention are used to treat and/or prevent diseases and conditions related to, or mediated by, Syk, TrkA, TrkB, TrkC, IGR-1R, Alk, c-FMS or a combination thereof.

The protein kinase inhibitors of the present invention are compounds having Formula (I), and pharmaceutically acceptable salts, solvates, N-oxides, prodrugs and isomers thereof:

(I)

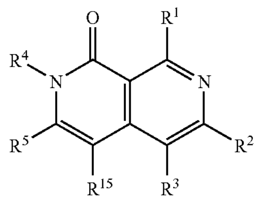

wherein:

$R^1$ is —$NR^6R^7$, $(CH_2)_nR^{19}$, $L^3R^{19}$, $R^{20}$, $C_6$-$C_{14}$aryl, $C_3$-$C_8$cycloalkyl, $C_2$-$C_{14}$heterocycloalkyl or $C_3$-$C_{13}$heteroaryl, wherein the $C_6$-$C_{14}$aryl, $C_3$-$C_8$cycloalkyl, $C_2$-$C_{14}$heterocycloalkyl and $C_3$-$C_{13}$heteroaryl of $R^1$ is optionally substituted with 1 to 3 substituents independently selected from halogen, nitro, cyano, $C_1$-$C_6$alkyl, $C_1$-$C_6$alkoxy, $C_1$-$C_6$alkylthio, hydroxyl-$C_1$-$C_6$alkyl, halo-substituted-$C_1$-$C_6$alkyl, halo-substituted-$C_1$-$C_6$alkoxy, $C_3$-$C_{12}$cycloalkyl, $C_2$-$C_{14}$heterocycloalkyl, $C_6$-$C_{14}$aryl, $C_3$-$C_{13}$heteroaryl, —$X^2S(O)_{0-2}R^{17}$, —$X^2S(O)_{0-2}X^2R^{19}$, —$X^2NR^{17}R^{17}$, —$X^2NR^{17}C(O)R^{17}$, —$X^2C(O)NR^{17}R^{17}$, —$X^2NR^{17}C(O)R^{19}$, —$X^2C(O)NR^{17}R^{19}$, —$X^2C(O)R^{19}$, —$X^2NR^{17}X^2R^{19}$ and —$X^2OX^2R^{19}$; wherein, $X^2$ is a bond or $C_1$-$C_4$alkylene;

$L^3$ is a bond, $C_1$-$C_6$alkyl or $C_1$-$C_6$alkoxy; wherein the $C_1$-$C_6$alkyl and $C_1$-$C_6$alkoxy groups of $L^3$ are optionally substituted with 1 to 3 substituents independently selected from halogen, —CN, —$C_1$-$C_6$alkyl, $C_1$-$C_6$alkoxy, —$OR^{13}$, —$C(O)R^{13}$, $OC(O)R^{13}$, —$C(O)OR^{13}$, —$N(R^{12})_2$, —$C(O)N(R^{12})_2$, —$N(R^{12})C(O)R^{13}$, $C_2$-$C_{14}$heterocycloalkyl, —$S(O)_2R^{13}$, —$S(O)_2$ $N(R^{12})_2$, $R^{13}$, —$(C(R^{12})_2)_nR^{13}$, —$(C(R^{12})_2)_nR^{14}$, halo-substituted $C_1$-$C_6$alkyl and halo-substituted $C_1$-$C_6$alkoxy;

$R^{17}$ is H or $C_1$-$C_6$alkyl; and $R^{19}$ is $R^{20}$, $C_3$-$C_{12}$cycloalkyl, $C_2$-$C_{14}$heterocycloalkyl, $C_6$-$C_{14}$aryl or $C_3$-$C_{13}$heteroaryl, wherein the $C_6$-$C_{14}$aryl, $C_3$-$C_{13}$heteroaryl, $C_3$-$C_{12}$cycloalkyl and $C_2$-$C_{14}$heterocycloalkyl of $R^{19}$ are optionally substituted with 1 to 3 radicals independently selected from halogen, nitro, cyano, $C_1$-$C_6$alkyl, $C_1$-$C_6$alkoxy, $C_1$-$C_6$alkylthio, hydroxyl-$C_1$-$C_6$alkyl, halo-substituted-$C_1$-$C_6$alkyl, and halo-substituted-$C_1$-$C_6$alkoxy;

$R^2$ and $R^3$ are independently selected from H, $(CH_2)_nR^{11}$, —$C(O)R^{12}$, —$CR^{12}$═$NOCR^{12}$, —$NR^8R^{10}$, halogen, $R^{20}$, $C_1$-$C_6$alkyl, $C_2$-$C_6$alkenyl, $C_2$-$C_6$alkynyl, $C_1$-$C_6$alkoxy, $C_1$-$C_6$alkylthio, hydroxyl-$C_1$-$C_6$alkyl, halo-substituted-$C_1$-$C_6$alkyl, and halo-substituted-$C_1$-$C_6$alkoxy, $C_6$-$C_{14}$aryl, $C_3$-$C_{13}$heteroaryl and $C_2$-$C_{14}$heterocycloalkyl, wherein the $C_6$-$C_{14}$aryl, $C_2$-$C_6$alkenyl, $C_2$-$C_6$alkynyl, $C_3$-$C_{13}$heteroaryl, and $C_2$-$C_{14}$heterocycloalkyl of $R^2$ and $R^3$ are optionally substituted with 1 to 3 substituents independently selected from halogen, —CN, —$NO_2$, —$OR^{12}$, —$OR^{10}$, ═O, —$C(O)R^{12}$, —$OC(O)R^{12}$, —$C(O)OR^{12}$, —$N(R^{11})_2$, —$N(R^{12})_2$, —$N(R^{12}R^{10}$, —$N(R^{12}R^{11})$, —$NR^{12}C(O)N(R^{12})_2$, —$NHS(O)_2R^{13}$, —$(CR^{12}R^{12})_nR^{11}$, —$SR^8$, —$C(O)N(R^{12}R^{10})$, —$N(R^{12})C(O)R^{13}$, —$C(O)N(R^{12})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, $^-OC(O)R^{13}$, —$C(O)OR^{13}$, —$S(O)_2R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl and halo-substituted $C_1$-$C_6$alkoxy;

$R^4$ is H, $C_1$-$C_6$alkyl or —$(CR^{12}R^{12})_nR^{11}$;

$R^5$ is H or $C_1$-$C_6$alkyl;

$R^6$ is $C_6$-$C_{14}$aryl, $C_3$-$C_{13}$heteroaryl, $C_2$-$C_{14}$heterocycloalkyl, $C_1$-$C_6$alkyl, $C_3$-$C_8$cycloalkyl, halo-substituted $C_1$-$C_6$alkyl, —$(CH_2)_nR^9$, $R^{20}$, -$L^3R^9$ or —$Y^1$-$L^1$-$R^{14}$, wherein, $Y^1$ is arylene, heteroarylene or heterocycloalkylene, and $L^1$- is a bond, —O—, —C(O)—, —$C(O)N(R^{11})$—, —$(C(R^{12})_2)_n$— or —$O(CH_2)_n$—;

and wherein the $C_6$-$C_{14}$aryl, $C_3$-$C_{13}$heteroaryl, $C_1$-$C_6$alkyl, halo-substituted $C_1$-$C_6$alkyl, $C_2$-$C_{14}$heterocycloalkyl and $C_3$-$C_8$cycloalkyl of $R^6$ and $Y^1$ are optionally substituted with 1 to 3 substituents independently selected from, halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$(CR^{12}R^{12})_nR^{11}$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, $^-OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

$R^7$ is H or $C_1$-$C_6$ alkyl;

$R^8$ is H or $C_1$-$C_6$ alkyl;

$R^9$ is $R^{20}$, $C_6$-$C_{14}$aryl, $C_3$-$C_{13}$heteroaryl, $C_2$-$C_{14}$heterocycloalkyl, $C_3$-$C_8$cycloalkyl or $Y^2$-$L^2$-$R^{14}$, wherein, $Y^2$ is bond, arylene, heteroarylene or heterocycloalkylene, and $L^2$- is a bond, —O—, or —$O(CH_2)_n$—;

and wherein the $C_6$-$C_{14}$aryl, $C_3$-$C_{13}$heteroaryl, $C_3$-$C_8$cycloalkyl and $C_2$-$C_{14}$heterocycloalkyl of $R^9$ and $Y^2$ are optionally substituted with 1 to 3 substituents independently selected from halogen, —CN, ═O, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, $N(R^{12}R^{11})$, —$(CR^{12}R^{12})_nR^{11}$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

$R^{10}$ is halo-substituted $C_1$-$C_6$alkyl, $C_6$-$C_{14}$aryl, $C_3$-$C_{13}$heteroaryl, $C_2$-$C_{14}$heterocycloalkyl, $C_3$-$C_8$cycloalkyl or —$(CH_2)_nR^{11}$, wherein the $C_6$-$C_{14}$aryl, $C_3$-$C_{13}$heteroaryl, $C_2$-$C_{14}$heterocycloalkyl and $C_3$-$C_8$cycloalkyl of $R^{10}$ are optionally substituted with 1 to 3 substituents independently selected from halogen, —CN, hydroxyl, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$(CR^{12}R^{12})_nR^{11}$, —$SR^8$, —$NR^{12}C(O)N(R^{12})_2$, —$C(O)N(R^{12}R^{10})$, —$N(R^{12})C(O)$—$R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, $^-OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

$R^{11}$ is —$N(R^{12})_2$, —$OR^{13}$, $R^{20}$, —$C(O)N(R^{12})_2$, —$S(O)_2R^{13}$, —$S(O)^2$ $N(R^{12})_2$, $C_6$-$C_{14}$aryl, $C_3$-$C_{13}$heteroaryl, $C_1$-$C_6$alkyl, $C_3$-$C_8$cycloalkyl, or $C_2$-$C_{14}$heterocycloalkyl, wherein the $C_6$-$C_{14}$aryl, $C_3$-$C_{13}$heteroaryl, $C_1$-$C_6$alkyl, $C_3$-$C_8$cycloalkyl and $C_2$-$C_{14}$heterocycloalkyl of $R^{11}$ are optionally substituted with 1 to 3 substituents independently selected from halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10}$, —$N(R^{12}R^{11})$, —$(CR^{12}R^{12})_nR^{11}$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})^2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $OR^{13}$, —$C(O)R^{13}$, $^{-}OC(O)R^{13}$, —$C(O)OR^{13}$, —$S(O)_2R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

each $R^{u}$ is independently selected from H, $C_1$-$C_6$alkyl, $C_2$-$C_6$alkene, halo-substituted $C_1$-$C_6$alkyl and $C_3$-$C_8$cycloalkyl, or each $R^{12}$ is independently a $C_1$-$C_6$alkyl that together with N they are attached to form a heterocycloalkyl;

$R^{13}$ is H, $C_1$-$C_6$ alkyl, $C_3$-$C_8$cycloalkyl, halo-substituted $C_1$-$C_6$ alkyl or $C_2$-$C_{14}$heterocycloalkyl;

$R^{14}$ is H, halogen, $OR^{13}$, $R^{20}$, —CN, —$S(O)_2N(R^{12})_2$, —$S(O)_2R^{13}$, —$C(O)N(R^{12})_2$, $N(R^{12})_2$, $C_1$-$C_6$alkyl, halo-substituted $C_1$-$C_6$alkyl, $C_6$-$C_{14}$aryl, heteroaryl or $C_2$-$C_{14}$heterocycloalkyl, wherein the $C_2$-$C_{14}$heterocycloalkyl, $C_6$-$C_{14}$aryl and $C_3$-$C_{13}$heteroaryl are optionally substituted with 1-3 substituents independently selected from halogen, —CN, $C_1$-$C_6$alkyl, $C_1$-$C_6$alkoxy, $C_3$-$C_8$cycloalkyl, —$OR^{13}$, —$C(O)R^{13}$, $^{-}OC(O)R^{13}$, —$C(O)OR^{13}$, —$N(R^{12})_2$, —$C(O)(C(R^{12})_2)_nR^{16}$, —$C(O)N(R^{12})_2$, heterocycloalkyl, —$S(O)_2R^{13}$, —$S(O)_2$ $N(R^{12})_2$, —$NHS(O)_2R^{13}$, $R^{13}$, $R^{10}$, —$(CH_2)_nR^{12}$, —$(CH_2)_nR^{13}$, —$O(CH_2)_nR^{13}$, —$(C(R^{12})_2)_nR^{16}$, halo-substituted $C_1$-$C_6$alkyl and halo-substituted $C_1$-$C_6$alkoxy;

$R^{15}$ is H, $C_1$-$C_6$alkyl, $C_2$-$C_6$alkenyl, —CN, halogen, $R^{10}$, $R^{16}$ is H, halogen, $OR^{13}$, —$C(O)R^{13}$, —$OC(O)R^{13}$, —$C(O)OR^{13}$, —$N(R^{12})_2$, —CN, —$S(O)_2N(R^{12})_2$, —$S(O)_2R^{13}$, $C(O)N(R^{12})_2$, —$NR^{12}C(O)(R^{12})$, halo-substituted $C_1$-$C_6$alkyl, or $C_2$-$C_{14}$heterocycloalkyl;

$R^{20}$ is

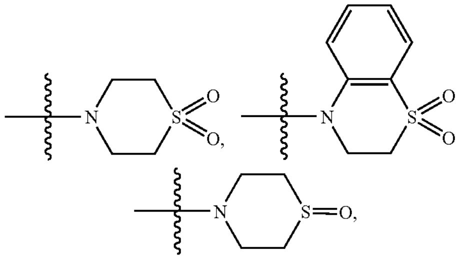

or and each n is independently 1, 2, 3, 4, 5 or 6.

In certain embodiments such compounds, pharmaceutically acceptable salts, isomers and pharmaceutically acceptable solvates thereof have the structure of Formula (Ia), Formula (Ib), Formula (Ic), Formula (Id) or Formula (Ie), wherein $R^1$-$R^{21}$, m, n, and p are as described herein:

(Ia)

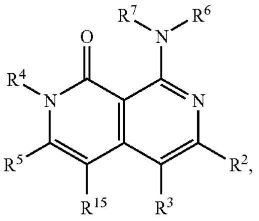

-continued (Ib)

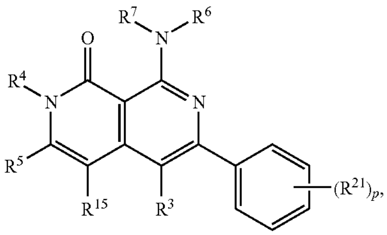

(Ic)

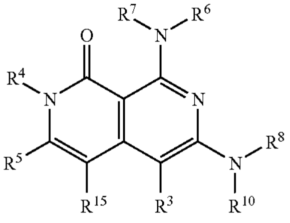

(Id)

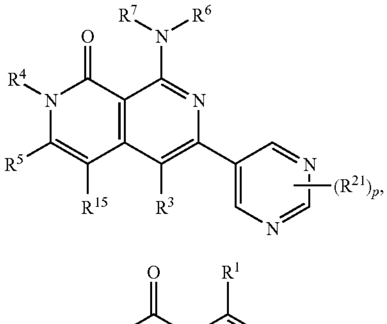

(Ie)

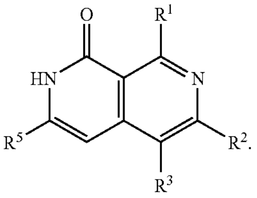

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as $^{2}H$, $^{3}H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations of the compounds of the invention and pharmaceutically acceptable salts thereof, for example, those in which a radioactive isotope such as $^{3}H$ or $^{14}C$ is incorporated, are useful in drug and/or substrate tissue distribution studies. In particular examples, $^{3}H$ and $^{14}C$ isotopes may be used for their ease of preparation and detectability. In other examples, substitution with isotopes such as $^{2}H$ may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents.

These compounds and pharmaceutical compositions of the present invention are useful for treating or preventing a variety of disorders, including, but not limited to, heart disease, diabetes, Alzheimer's disease, immunodeficiency disorders, inflammatory diseases, neurological inflammation, chronic arthritis inflammation, hypertension, respiratory diseases, autoimmune diseases, destructive bone disorders such as osteoporosis, proliferative disorders, infectious diseases, immunologically-mediated diseases, and viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. The compositions are especially useful for disorders such as chronic myelogenous leukemia (CML), acute myeloid leukemia (AML), acute promyelocytic leukemia (APL), rheumatoid arthritis, asthma, osteoarthritis, ischemia, cancer (including, but not limited to, prostate cancer, ovarian cancer, breast cancer and endometrial cancer), liver disease including hepatic ischemia, heart disease such as myocardial infarction and congestive heart failure, pathologic immune conditions involving T cell activation, and neurodegenerative disorders.

Pharmacology and Utility

Protein kinases (PTK) play a central role in the regulation of a wide variety of cellular processes and maintaining control over cellular function. Protein kinases catalyze and regulate the process of phosphorylation, whereby the kinases covalently attach phosphate groups to proteins or lipid targets in response to a variety of extracellular signals. Examples of such stimuli include hormones, neurotransmitters, growth and differentiation factors, cell cycle events, environmental stresses and nutritional stresses. An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events. These diseases include, but are not limited to, autoimmune diseases, inflammatory diseases, bone diseases, metabolic diseases, neurological and neurodegenerative diseases, cancer, cardiovascular diseases, respiratory diseases, allergies and asthma, Alzheimer's disease, and hormone-related diseases.

Examples of protein-tyrosine kinases include, but are not limited to, (a) tyrosine kinases such as Irk, IGFR-1, Zap-70, Bmx, Btk, CHK (Csk homologous kinase), CSK (C-terminal Src Kinase), Itk-1, Src (c-Src, Lyn, Fyn, Lck, Syk, Hck, Yes, Blk, Fgr and Frk), Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met-I or c-MET), PDGFR (.alpha. and .beta.), Tie-1, Tie-2 (also Tek-1 or Tek), VEGFR1 (also FLT-1), VEGFR2 (also KDR), FLT-3, FLT-4, c-KIT, JAK1, JAK2, JAK3, TYK2, LOK, RET, TRKA, PYK2, ALK (Anaplastic Lymphoma Kinase), EPHA (1-8), EPHB (1-6), RON, Fes, Fer or EPHB4 (also EPHB4-1), and (b) and serine/threonine kinases such as Aurora, c-RAF, SGK, MAP kinases (e.g., MKK4, MKK6, etc.), SAPK2α, SAPK2β, Ark, ATM (1-3), CamK (1-IV), CamKK, Chk1 and 2 (Checkpoint kinases), CK1, CK2, Erk, IKK-I (also IKK-ALPHA or CHUK), IKK-2 (also IKK-BETA), Ilk, Ink (1-3), LimK (1 and 2), MLK3Raf (A, B, and C), CDK (1-10), PKC (including all PKC subtypes), P1k (1-3), NIX, Pak (1-3), PDK1, PKR, RhoK, RIP, RIP-2, GSK3 (α and β), PKA, P38, Erk (1-3), PKB (including all PKB subtypes) (also AKT-1, AKT-2, AKT-3 or AKT3-1), IRAK1, FRK, SGK, TAK1 and Tpl-2 (also COT).

Phosphorylation modulates or regulates a variety of cellular processes such as proliferation, growth, differentiation, metabolism, apoptosis, motility, transcription, translation and other signaling processes. Aberrant or excessive PTK activity has been observed in many disease states including, but not limited to, benign and malignant proliferative disorders, diseases resulting from inappropriate activation of the immune system and diseases resulting from inappropriate activation of the nervous systems. Specific diseases and disease conditions include, but are not limited to, autoimmune disorders, allograft rejection, graft vs. host disease, diabetic retinopathy, choroidal neovascularization due to age-related macular degeneration, psoriasis, arthritis, osteoarthritis, rheumatoid arthritis, synovial pannus invasion in arthritis, multiple sclerosis, myasthenia gravis, diabetes mellitus, diabetic angiopathy, retinopathy of prematurity, infantile hemangiomas, non-small cell lung, bladder and head and neck cancers, prostate cancer, breast cancer, ovarian cancer, gastric and pancreatic cancer, psoriasis, fibrosis, rheumatoid arthritis, atherosclerosis, restenosis, auto-immune disease, allergy, respiratory diseases, asthma, transplantation rejection, inflammation, thrombosis, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, ocular diseases, viral infections, heart disease, lung or pulmonary diseases or kidney or renal diseases and bronchitis.

Tyrosine kinases can be broadly classified as receptor-type (having extracellular, transmembrane and intracellular domains) or the non-receptor type (being wholly intracellular) protein tyrosine kinases. Inappropriate or uncontrolled activation of many of these kinase (aberrant protein tyrosine kinase activity), for example by over-expression or mutation, results in uncontrolled cell growth. Many of the protein tyrosine kinases, whether a receptor or non-receptor tyrosine kinase have been found to be involved in cellular signaling pathways involved in numerous pathogenic conditions, including, but not limited to, immunomodulation, inflammation, or proliferative disorders such as cancer.

Compounds of the invention are screened against the kinase panel (wild type and/or mutation thereof) and modulate the activity of at least one panel kinase panel member. Examples of kinases that are inhibited by the compounds and compositions of the invention and against which the methods described herein are useful, include, but are not limited to Syk, ZAP70, KDR, FMS, FLT3, c-Kit, RET, TrkA, TrkB, TrkC, IGR-1R, Alk, c-FMS kinases, and mutant forms thereof. As such, the compounds and compositions of the invention are useful for treating diseases or disorders in which such kinases contribute to the pathology and/or symptomology of a disease or disorder associated with such kinases. Such diseases or disorders include, but are not limited to, pancreatic cancer, papillary thyroid carcinoma, ovarian carcinoma, human adenoid cystic carcinoma, non small cell lung cancer, secretory breast carcinoma, congenital fibrosarcoma, congenital mesoblastic nephroma, acute myelogenous leukemia, psoriasis, metastasis, cancer-related pain and neuroblastoma.

Receptor Tyrosine Kinases (RTKs).

The Receptor Tyrosine Kinases (RTKs) comprise a large family of transmembrane receptors with diverse biological activities. A number of distinct RTK subfamilies have been identified including, but not limited to, EGF receptor family, the Insulin receptor family, the PDGF receptor family, the FGF receptor family, the VEGF receptor family, the HGF receptor family, the Trk receptor family), the EPH receptor family, the AXL receptor family, the LTK receptor family, the TIE receptor family), the ROR receptor family, the DDR receptor family, the RET receptor family, the KLG receptor family, the RYK receptor family and the MuSK receptor family.

Receptor tyrosine kinases have been shown to be not only key regulators of normal cellular processes but also to have a critical role in the development and progression of many types of cancer. The receptor tyrosine kinase (RTK) family includes receptors that are crucial for the growth and differentiation of a variety of cell types. The intrinsic function of RTK mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response such as, by way of example only, cell division, differentiation, metabolic effects, and changes in the extracellular microenvironment.

Tropomyosin-Receptor-Kinase (Trk) Family

The Trk family receptor tyrosine kinases, TrkA (NTRK1), TrkB (NTRK2), and TrkC (NTRK3), are the signaling receptors that mediate the biological actions of the peptide hormones of the neurotrophin family. Trk receptors are membrane-bound receptor that, through several signal cascades, controls neuronal growth and survival, and differentiation, migration and metastasis of tumor cells. The neurotrophin family of growth factors includes nerve growth factor (NGF), brain-derived neurotrophic factor (BDNF), and two neurotrophins (NT), NT-3, and NT-4. Neurotrophins are critical to the functioning of the nervous system, and the activation of Trk receptors by neurotrophin binding leads to activation of signal cascades resulting in promoting survival and other functional regulation of cells. Each type of neurotrophin has a different binding affinity toward its corresponding Trk receptor, and upon neurotrophin binding, the Trk receptors phosphorylates themselves and members of the MAPK pathway. The differences in the signaling initiated by these distinct types of receptors are important for generating diverse biological responses.

The Trk receptors are implicated in the development and progression of cancer, possibly by upregulation of either the receptor, their ligand (NGF), BDNF, NT-3, and NT-4), or both. In many cases high Trk expression is associated with aggressive tumor behavior, poor prognosis and metastasis. Thus, diseases and disorders related to Trk receptors result from 1) expression of a Trk receptor(s) in cells which normally do not express such a receptor(s); 2) expression of a Trk receptor(s) by cells which normally do not express such a receptor(s); 3) increased expression of Trk receptor(s) leading to unwanted cell proliferation; 4) increased expression of Trk receptor(s) leading to adhesion independent cell survival; 5) mutations leading to constitutive activation of Trk receptor(s); 6) over stimulation of Trk receptor(s) due to abnormally high amount of, or mutations in, Trk receptor(s), and/or 7) abnormally high amount of Trk receptor(s) activity due to abnormally high amount of, or mutations in, Trk receptor(s).

Genetic abnormalities, i.e. point mutations and chromosomal rearrangements involving both the genes expressing TrkB and TrkC have been found in a variety of cancer types. In a kinome-wide approach to identify point mutants in tyrosine kinases, mutations in the genes expressing TrkB and TrkC were found in cell lines and primary samples from patients with colorectal cancer. In addition, chromosomal translocations involving the genes expressing TrkA and TrkB have been found in several different types of tumors. Gene rearrangements involving the genes expressing TrkA and a set of different fusion partners (TPM3, TPR, TFG) are a hallmark of a subset of papillary thyroid cancers. Moreover, secretary breast cancer, infant fibrosarcoma and congenital mesoblastic nephroma have been shown to be associated with a chromosomal rearrangement t(12;15) generating a ETV6-NTRK3 fusion gene that was shown to have constitutive kinase activity and transforming potential in several different cell lines including fibroblasts, hematopoietic cells and breast epithelial cells.

TrkA has the highest affinity to the binding nerve growth factor (NGF). NGF is important in both local and nuclear actions, regulating growth cones, motility, and expression of genes encoding the biosynthesis enzymes for neurotransmitters. Nocireceptive sensory neurons express mostly trkA and not trkB or trkC.

TrkB serves as a receptor for both BDNF and NT-4, and is expressed in neuroendocrine-type cells in the small intestine and the colon, in the alpha cells of the pancreas, in the monocytes and macrophages of the lymph nodes and of the spleen, and in the granular layers of the epidermis. TrkB is also expressed in cancerous prostate cells but not in normal cells.

The binding of BDNF to TrkB receptor causes activation of intercellular cascades which regulate neuronal development and plasticity, long-term potentiation, and apoptosis. BDNF promotes the proliferation, differentiation and growth and survival of normal neural components such as retinal cells and glial cells. In addition, TrkB activation is a potent and specific suppressor of anchorage independent cell death (anoikis), which is apoptosis induced by loss of attachment of a cell to its matrix. By way of example, activation of the Phosphatidylinositol-3kinase/Protein Kinase B signaling axis by TrkB promotes the survival of non-transformed epithelial cells in 3-dimensional cultures and induces tumor formation and metastasis of those cells in immuno-compromised mice. Anchorage independent cell survival is a metastatic process allowing tumor cells to migrate through the systemic circulation and grow at distant organs. Agonism of TrkB results in the failure of induced cell death by cancer treatments. Thus, TrkB modulation is a target for treatment of benign and malignant proliferative diseases, especially tumor diseases.

Diseases and disorders related to the TrkB receptor include, but are not limited to, cancers, such as, by way of example only, neuroblastoma progression, Wilm's tumor progression, breast cancer, pancreatic cancer, colon cancer, prostate cancer, and lung cancer. The TrkB receptor has been shown to be associated with Alzheimer's disease.

TrkC is activated by binding with NT-3 and is expressed by proprioceptive sensory neurons. The axons of these proprioceptive sensory neurons are much thicker than those of nocireceptive sensory neurons, which express TrkA. Signalling through TrkC leads to cell differentiation and development of proprioceptive neurons that sense body position. Mutations in this gene expressing TrkC is associated with medulloblastomas, secretory breast carcinomas and other cancers. In addition, high expression of TrkC is a hallmark of melanoma, especially in cases with brain metastasis.

Compounds described herein are also used for the treatment of diseases which respond to an inhibition of the Trk receptor tyrosine kinases (TrkA, TrkB, and TrkC). Compounds described herein inhibit Trk receptor tyrosine kinases (TrkA, TrkB, and TrkC) activity and are, therefore, suitable for the treatment of diseases, such as, neuroblastoma, Wilm's tumor, breast cancer, pancreatic cancer, colon cancer, prostate cancer, and lung cancer.

Platelet-Derived Growth Factor (PDGF) Receptor Family

PDGF (Platelet-derived Growth Factor) is a very commonly occurring growth factor, which plays an important role both in normal growth and also in pathological cell proliferation, such as is seen in carcinogenesis and in diseases of the smooth-muscle cells of blood vessels, for example in atherosclerosis and thrombosis. The PDGF growth factor family consists of PDGF-A, PDGF-B, PDGF-C and PDGF-D, which form either homo- or heterodimers (AA, AB, BB, CC, DD) that bind to the protein tyrosine kinase receptors PDGFR-$\alpha$ and PDGFR-$\beta$. Dimerization of the growth factors is a prerequisite for activation of the kinase, as the monomeric forms are inactive. The two receptor isoforms dimerize upon binding resulting in three possible receptor combinations, PDGFR-$\alpha\alpha$, PDGFR-$\beta\beta$ and PDGFR-$\alpha\beta$. Growth factor AA binds only to -$\alpha\alpha$, growth factor BB can bind with -$\alpha\alpha$, -$\beta\beta$ and -$\alpha\beta$, growth factors CC and AB specifically interact with -$\alpha\alpha$ and -$\alpha\beta$, and growth factor DD binds to -$\beta\beta$.

Key downstream mediators of PDGFR signaling are Ras/mitogen-activated protein kinase (MAPK), PI-3 kinase and phospholipase-$\gamma$ (PLC$\gamma$) pathways. MAPK family members regulate various biological functions by phosphorylation of target molecules (transcription factors and other kinases) and thus contribute to regulation of cellular processes such as proliferation, differentiation, apoptosis and immunoresponses. PI-3 kinase activation generated PIP3 which functions as a second messenger to activate downstream tyrosine kinases Btk and Itk, the Ser/Thr kinases PDK1 and Akt (PKB). Akt activation is involved in survival, proliferation and cell growth. After activation PLC$\gamma$ hydrolyses its substrate, PtdIns(4,5)P2, and forms two secondary messengers, diacylglycerol and Ins(1,4,5)P3 which stimulates intracellular processes such as proliferation, angiogenesis and cell motility. The PDGF-receptor plays an important role in the maintenance, growth and development of hematopoietic and non-hematopoietic cells.

PDGFR is expressed on early stem cells, mast cells, myeloid cells, mesenchymal cells and smooth muscle cells. Only PDGFR-$\beta$ is implicated in myeloid leukemias-usually as a translocation partner with Tel, Huntingtin interacting protein (HIP1) or Rabaptin5. Activation mutations in PDGFR-$\alpha$ kinase domain are associated with gastrointestinal stromal tumors (GIST).

Vascular Endothelial Growth Factor (VEGF) Receptor Family

VEGF, also known as fms-related tyrosine kinase-1 (FLT1), is an important signaling protein involved in both vasculogenesis (formation of embryonic circulatory system) and angiogenesis (growth of blood vessels from pre-existing vasculature). Structurally VEGF belongs to the PDGF family of cytokine-knot growth factors. The VEGF sub-family of growth factors includes VEGF-A, VEGF-B, VEGF-C and VEGF-D. VEGF-A binds to receptor VEGFR-1 (Flt-1) and to VEGFR-2 (KDR/Flk-1). VEGF-C and VEGF-D bind to receptor VEGFR-3 and mediate lymphangiogenesis. The VGFR receptors mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, and infantile hemangiomas).

Fms-Like Tyrosine Kinase

The fms-like tyrosine kinase-3 (FLT3) ligand (FLT3L) is one of the cytokines that affects the development of multiple hematopoietic lineages. These effects occur through the binding of FLT3L to the FLT3 receptor, also referred to as fetal liver tkinase-2 (flk-2) and STK-1, a receptor tyrosine kinase (RTK) expressed on hematopoietic stem and progenitor cells. FLT3 is a member of the type III receptor tyrosine kinase (RTK) family The ligand for FLT3 is expressed by the marrow stromal cells and other cells and synergizes with other growth factors to stimulate proliferation of stem cells, progenitor cells, dendritic cells, and natural killer cells. Flt3 plays an important role in the maintenance, growth and development of hematopoietic and non-hematopoietic cells.

The FLT3 gene encodes a membrane-bound RTK that plays an important role in proliferation, differentiation and apoptosis of cells during normal hematopoiesis. The FLT3 gene is mainly expressed by early myeloid and lymphoid progenitor cells. Hematopoietic disorders are pre-malignant disorders and include, for instance, the myeloproliferative disorders, such as thrombocythemia, essential thrombocytosis (ET), angiogenic myeloid metaplasia, myelofibrosis (MF), myelofibrosis with myeloid metaplasia (MMM), chronic idiopathic myelofibrosis (IMF), and polycythemia vera (PV), the cytopenias, and pre-malignant myelodysplastic syndromes. Hematological malignancies include leukemias, lymphomas (non-Hodgkin's lymphoma), Hodgkin's disease (also called Hodgkin's lymphoma), and myeloma—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM) and myeloid sarcoma.

Aberrant expression of the Flt3 gene has been documented in both adult and childhood leukemias including acute myeloid leukemia (AML), AML with trilineage myelodysplasia (AML/TMDS), acute lymphoblastic leukemia (ALL), and myelodysplastic syndrome (MDS). Activating mutations of the Flt3 receptor have been found in about 35% of patients with acute myeloblastic leukemia (AML), and are associated with a poor prognosis. The most common mutation involves in-frame duplication within the juxtamembrane domain, with an additional 5-10% of patients having a point mutation at asparagine 835. Both of these mutations are associated with constitutive activation of the tyrosine kinase activity of Flt3, and result in proliferation and viability signals in the absence of ligand. Patients expressing the mutant form of the receptor have been shown to have a decreased chance for cure. Thus, there is accumulating evidence for a role for hyper-activated (mutated) Flt3 kinase activity in human leukemias and myelodysplastic syndrome.

FLT-3 and c-Kit regulate maintenance of stem cell/early progenitor pools as well the development of mature lymphoid and myeloid cells. Both receptors contain an intrinsic kinase domain that is activated upon ligand-mediated dimerization of the receptors. Upon activation, the kinase domain induces autophosphorylation of the receptor as well as the phosphorylation of various cytoplasmic proteins that help propogate the activation signal leading to growth, differentiation and survival. Some of the downstream regulators of FLT-3 and c-Kit receptor signaling include, PLCγ, PI3-kinase, Grb-2, SHIP and Src related kinases. Both receptor tyrosine kinases have been shown to play a role in a variety of hematopoietic and non-hematopoietic malignancies. Mutations that induce ligand independent activation of FLT-3 and c-Kit have been implicated acute-myelogenous leukemia (AML), acute lymphocytic leukemia (ALL), mastocytosis and gastrointestinal stromal tumor (GIST). These mutations include single amino acid changes in the kinase domain or internal tandem duplications, point mutations or in-frame deletions of the juxtamembrane region of the receptors. In addition to activating mutations, ligand dependent (autocrine or paracrine) stimulation of over-expressed wild-type FLT-3 or c-Kit can contribute to the malignant phenotype.

c-Fms encodes for macrophage colony stimulating factor receptor (M-CSF-1R) which is expressed predominately in the monocytes/macrophage lineage. MCSF-1R and its ligand regulate macrophage lineage growth and differentiation. Like the other family members, MCSF-1R contains an intrinsic kinase domain that is activated upon ligand-induced dimerization of the receptor. MCSF-1R is also expressed in non-hematopoietic cells including mammary gland epithelial cells and neurons. Mutations in this receptor are potentially linked to myeloid leukemias and its expression is correlated with metastatic breast, ovarian and endometrial carcinomas. Another possible indication for antagonists of MCSF-1R is osteoporosis.

Compounds described herein are inhibitors of FLT-3 and c-kit and are used for the treatment of diseases which respond to an inhibition of the FLT-3 c-kit receptors.

Insulin-Like Growth Factor 1 (IGF-1) Receptor

The Insulin-like Growth Factor 1 (IGF-1) Receptor is a transmembrane receptor that is activated by IGF-1 and by the related growth factor IGF-2. IGF-1R mediates the effects of IGF-1, which is a polypeptide protein hormone similar in molecular structure to insulin. IGF-1 plays an important role in survival and proliferation in mitosis-competent cells, and growth (hypertrophy) in tissues such as skeletal muscle and cardiac muscle. The IGFR signalling pathway is of critical importance during normal development of mammary gland tissue during pregnancy and lactation. During pregnancy, there is intense proliferation of epithelial cells which form the duct and gland tissue. Following weaning, the cells undergo apoptosis and all the tissue is destroyed. Several growth factors and hormones are involved in this overall process, and IGF-1R is believed to have roles in the differentiation of the cells and a key role in inhibiting apoptosis until weaning is complete.

The IGF-1R is implicated in several cancers including, but not limited to, breast cancer. In some instances its anti-apoptotic properties allow cancerous cells to resist the cytotoxic properties of chemotherapeutic drugs or radiotherapy. It is further implicated in breast cancer by increasing the metastatic potential of the original tumour by inferring the ability to promote vascularisation.

RET Receptor Family

The RET proto-oncogene encodes a receptor tyrosine kinase for members of the glial cell line derived neurotrophic factor (GDNF) family of extracellular signalling molecules. RET loss of function mutations are associated with the development of Hirschsprung's disease, while gain of function mutations are associated with development of various types of cancer, including medullar thyroid carcinoma and multiple endocrine neoplasias type II and III.

RET is the receptor for members of the glial cell line derived neurotrophic factor (GDNF) family of extracellular signalling molecules (GFL's). There are three different isoforms, RET51, RET43 and RETS, containing 51, 43 and 9 amino acids in their C-terminal tail, respectively. RET signal transduction is key to the development of normal kidneys and the enteric nervous system.

In order to activate RET GFLs first need to form a complex with a glycosylphosphatidylinositol (GPI)-anchored co-receptor. The co-receptors themselves are classified as members of the GDNF receptor-α (GFRα) protein family. Different members of the GFRα family (GFRα1-GFRα4) exhibit a specific binding activity for a specific GFLs. Upon GFL-GFRα complex formation, the complex then brings together two molecules of RET, triggering trans-autophosphorylation of specific tyrosine residues within the tyrosine kinase domain of each RET molecule. Tyr900 and Tyr905 within the activation loop (A-loop) of the kinase domain have been shown to be autophosphorylation sites by mass spectrometry. Phosphorylation of Tyr905 stabilizes the active conformation of the kinase which in turn results in the autophosphorylation of other tyrosine residues mainly located in the C-terminal tail region of the molecule.

c-Kit Receptor

The compounds of the present invention also inhibit cellular processes involving stem-cell factor (SCF, also known as the c-kit ligand or steel factor), such as inhibiting SCF receptor (kit) autophosphorylation and SCF-stimulated activation of MAPK kinase (mitogen-activated protein kinase). MO7e cells are a human promegakaryocytic leukemia cell line, which depends on SCF for proliferation.

c-Kit has a substantial homology to the PDGF receptor and to the CSF-1 receptor (c-Fms). Investigations on various erythroid and myeloid cell lines indicate an expression of the c-Kit gene in early stages of differentiation. Certain tumors such as glioblastoma cells likewise exhibit a pronounced expression of the c-Kit gene.

Anaplastic Lymphoma Kinase (Ki-1 or ALK)

ALK is a novel receptor protein-tyrosine kinase having a putative transmembrane domain and an extracellular domain. ALK plays an important role in the development of the brain and exerts its effects on specific neurons in the nervous system.

Anaplastic lymphoma kinase (ALK), a member of the insulin receptor superfamily of receptor tyrosine kinases, has been implicated in oncogenesis in hematopoietic and non-hematopoietic tumors. The aberrant expression of full-length ALK receptor proteins has been reported in neuroblastomas and glioblastomas; and ALK fusion proteins have occurred in anaplastic large cell lymphoma.

Non-Receptor Tyrosine Kinases.

Non-receptor tyrosine kinases represent a collection of cellular enzymes that lack extracellular and transmembrane sequences. Over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. The Src subfamily of non-receptor tyrosine kinases is comprised of the largest number of PTKs and includes Src, Yes, Fyn, Lyn, Lck, Blk, Hck, Fgr and Yrk. The Src subfamily of enzymes has been linked to oncogenesis and immune responses.

The Src family of kinases is implicated in cancer, immune system dysfunction osteopetrosis, and bone remodeling diseases, and therefore Src kinases are considered as potential therapeutic targets for various human diseases. Src expression is linked to cancers such as colon, breast, hepatic and pancreatic cancer, certain B-cell leukemias and lymphomas.

In addition, antisense Src expressed in ovarian and colon tumor cells inhibits tumor growth.

Csk, or C-terminal Src kinase, phosphorylates and thereby inhibits Src catalytic activity. Suppression of arthritic bone destruction has been achieved by the overexpression of Csk in rheumatoid synoviocytes and osteoclasts. This implies that Src inhibition may prevent joint destruction that is characteristic in patients suffering from rheumatoid arthritis. Src also plays a role in the replication of hepatitis B virus. The virally encoded transcription factor HBx activates Src in a step required for propagation of the virus.

Other Src family kinases are also potential therapeutic targets. Lck plays a role in T-cell signaling, and mice that lack the Lck gene have a poor ability to develop thymocytes. The function of Lck as a positive activator of T-cell signaling suggests that Lck inhibitors may be useful for treating autoimmune disease such as rheumatoid arthritis. Hck, Fgr and Lyn are important mediators of integrin signaling in myeloid leukocytes Inhibition of these kinase mediators may therefore be useful for treating inflammation.

Spleen Tyrosine Kinase (Syk)

Spleen tyrosine kinase (SYK) and Zap-70 are members of the Syk family of tyrosine kinases. These non-receptor cytoplasmic tyrosine kinases share a characteristic by a carboxy terminal kinase domain and a dual SH2 domain separated by a linker domain. Syk is a non-receptor linked protein tyrosine kinase which plays a critical role in mediator of immunoreceptor signalling in a host of inflammatory cells including mast cells, B-cells, macrophages and neutrophils. These immunoreceptors, including Fc receptors (such as FcϵRI) and the B-cell receptor, are important for both allergic diseases and antibody-mediated autoimmune diseases. Syk also plays a role in FcϵRI mediated mast cell degranulation and eosiniphil activation. Accordingly, Syk kinase is implicated in various allergic disorders, in particular asthma.

Inhibition of eosinophil apoptosis has been proposed as key mechanisms for the development of blood and tissue eosinophilia in asthma. IL-5 and GM-CSF are upregulated in asthma and are proposed to cause blood and tissue eosinophilia by inhibition of eosinophil apoptosis Inhibition of eosinophil apoptosis has been proposed as a key mechanism for the development of blood and tissue eosinophilia in asthma. Syk kinase is required for the prevention of eosinophil apoptosis by cytokines.

While Syk and Zap-70 are primarily expressed in hematopoietic tissues, Syk is also expressed in a variety of other tissues. Within B and T cells respectively, Syk and Zap-70 transmit signals from the B-cell receptor and T-cell receptor. Syk plays a similar role in transmitting signals from a variety of cell surface receptors including CD74, Fc Receptor, and integrins.

Abnormal function of Syk has been implicated in several instances of hematopoeitic malignancies including translocations involving Itk and Tel. Constitutive Syk activity can transform B cells. Several transforming viruses contain "Immunoreceptor Tyrosine Activation Motifs" (ITAMs) which lead to activation of Syk including Epstein Barr virus, bovine leukemia virus, and mouse mammary tumor virus.

Syk kinase is known to play a critical role in other signaling cascades. For example, Syk kinase is an effector of B-cell receptor (BCR) signaling and is an essential component of integrin beta(1), beta(2) and beta(3) signaling in neutrophils.

Syk kinase is important in transducing the downstream cellular signals associated with cross-linking Fc epsilon RI (Fcer1) and or Fc epsilon RI (Fcer1) receptors, and is positioned early in the signalling cascade. In mast cells, for example, the early sequence of Fc epsilon RI (Fcer1) signalling following allergen cross-linking of receptor-IgE complexes involves first Lyn (a Src family tyrosine kinase) and then Syk. Inhibitors of Syk activity would therefore be expected to inhibit all downstream signalling cascades thereby alleviating the immediate allergic response and adverse events initiated by the release of pro-inflammatory mediators and spasmogens.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE (Fc epsilon RI) and IgG (Fc epsilon.RI) become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesised lipid mediators including prostaglandins and leukotrienes.

Rheumatoid Arthritis (RA) is an auto-immune disease affecting approximately 1% of the population. It is characterised by inflammation of articular joints leading to debilitating destruction of bone and cartilage. Targeting B cell function is a therapeutic strategy in auto-immune diseases such as RA, with B cell function and auto-antibody production being central to the ongoing pathology in the disease.

Studies using cells from mice deficient in the Spleen Tyrosine Kinase (Syk) have demonstrated a non-redundant role of this kinase in B cell function. The deficiency in Syk is characterised by a block in B cell development. These studies, along with studies on mature B cells deficient in Syk, demonstrate that Syk is required for the differentiation and activation of B cells. Hence, inhibition of Syk in RA patients is likely to block B cell function and thereby reduce Rheumatoid Factor production. In addition to the role of Syk in B cell function, and of further relevance to the treatment of RA, is the requirement for Syk activity in Fc receptor (FcR) signalling. FcR activation by immune complexes in RA has been suggested to contribute to the release of multiple pro-inflammatory mediators.

Syk also plays a role in FcγR dependent and independent response in bone marrow derived macrophages. Syk deficient macrophages are defective in phagocytosis induced by FcγR, but have normal phagocytosis in response to complement. Aerosolized Syk antisense suppresses Syk expression and mediator release from macrophages.

Loss of Syk was found in childhood pro-B cell ALL. Syk is an important suppressor of breast cancer cell growth and metastasis. Tel-Syk fusion protein was found in patients with atypical myelodysplastic syndrome and constitutively activates PI3-K/Akt, MAPK and Jak2 independent STATS signaling. Overexpression of Tel-Syk fusion protein causes B-cell lymphoma in mice (differentiation defect in pre-B-cells). ITK-Syk fusion protein was found in 17% of patients with unspecified peripheral T-cell lymphomas. Syk overexpression is associated with mantle cell lymphoma and Waldenstroem's makroglobulinaemia.

The compounds described herein are inhibitors of Syk kinase activity and have therapeutic benefit in the treatment of disorders associated with inappropriate Syk activity, in particular in the treatment and prevention of disease states mediated by Syk. Such disease states include inflammatory, allergic and autoimmune diseases, by way of example only, asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, multiple sclerosis, cancer, breast cancer, HIV and lupus Furthermore, the compounds, compositions and methods of the present invention provides methods of regulating, and in particular inhibiting, signal transduction cascades in which Syk plays a role. The method generally involves contacting a Syk-dependent receptor or a cell expressing a Syk-dependent receptor with an amount of a compound described herein, or prodrug a compound described herein, or an acceptable salt, hydrate, solvate, N-oxide and/or composition thereof, effective to regulate or inhibit the signal transduction cascade. The methods are used to regulate, and in particular inhibit, downstream processes or cellular responses elicited by activation of the particular Syk-dependent signal transduction cascade. The methods are practiced to regulate any signal transduction cascade where Syk is not known or later discovered to play a role. The methods are practiced in in-vitro contexts or in in-vivo contexts as a therapeutic approach towards the treatment or prevention of diseases characterized by, caused by or associated with activation of the Syk-dependent signal transduction cascade. Non-limited examples of such diseases include those described above.

The compounds, compositions and methods of the present invention are inhibitors of Syk kinase, and therefore regulate, and in particular inhibit, any signaling cascade where Syk plays a role, such as, fore example, the Fc receptor, BCR and integrin signaling cascades, as well as the cellular responses elicited through these signaling cascades. The particular cellular response regulated or inhibited will depend, in part, on the specific cell type and receptor signaling cascade. Non-limiting examples of cellular responses that may be regulated or inhibited with the compounds described herein include a respiratory burst, cellular adhesion, cellular degranulation, cell spreading, cell migration, phagocytosis (e.g., in macrophages), calcium ion flux (e.g., in mast, basophil, neutrophil, eosinophil and B-cells), platelet aggregation, and cell maturation (e.g., in B-cells).

Zeta-Chain-Associated Protein Kinase 70 (ZAP70) Kinase

ZAP-70 is normally expressed in T cells and natural killer cells and has a critical role in the initiation of T-cell signaling. ZAP-70 in B cells is used as a prognostic marker in identifying different forms of chronic lymphocytic leukemia (CLL).

T lymphocytes are activated by engagement of the T cell receptor with processed antigen fragments presented by professional antigen presenting cells (e.g. macrophages, dendritic cells and B cells). Upon this activation, the tyrosine kinase Lck becomes activated and phosphorylates the intracellular portions of the CD3 complex (called ITAMs). The most important member of the CD3 family is CD3-zeta to which ZAP-70 binds. The tandem SH2-domains of ZAP-70 are engaged by the doubly phosphorylated ITAMs of CD3-zeta, which positions ZAP-70 to phosphorylate the transmembrane protein LAT (Linker of Activated T cells). Phosphorylated LAT in turn serves as a docking site to which a number of signaling proteins bind. The final outcome of T cell activation is the transcription of several gene products which allow the T cells to differentiate, proliferate and secrete a number of cytokines.

In accordance with the foregoing, the present invention further provides a method for preventing or treating any of the diseases or disorders described above in a subject in need of such treatment, which method comprises administering to said subject a therapeutically effective amount (See, "*Administration and Pharmaceutical Compositions*", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

For the therapeutic uses of compounds provided herein, including compounds of Formula (I), or pharmaceutically acceptable salts, solvates, N-oxides, prodrugs and isomers thereof, such compounds are administered in therapeutically effective amounts either alone or as part of a pharmaceutical composition. Accordingly, provided herein are pharmaceutical compositions, which comprise at least one compound provided herein, including at least one compound of Formulas (I), pharmaceutically acceptable salts and/or solvates thereof, and one or more pharmaceutically acceptable carriers, diluents, adjuvant or excipients. In addition, such compounds and compositions are administered singly or in combination with one or more additional therapeutic agents. The method of administration of such compounds and compositions include, but are not limited to, oral administration, rectal administration, parenteral, intravenous administration, intravitreal administration, subcutaneous administration, intramuscular administration, inhalation, intranasal administration, dermal administration, topical administration, ophthalmic administration or buccal administration, tracheal administration, bronchial administration, sublingual administration or otic administration.

The therapeutically effective amount will vary depending on, among others, the disease indicated, the severity of the disease, the age and relative health of the subject, the potency of the compound administered, the mode of administration and the treatment desired. In certain embodiments, the daily dosage of a compound of Formula (I), satisfactory results are indicated to be obtained systemically at daily dosages of from about 0.03 to 2.5 mg/kg per body weight. In certain embodiments, the daily dosage of a compound of Formula (I), administered by inhalation, is in the range from 0.05 micrograms per kilogram body weight (μg/kg) to 100 micrograms per kilogram body weight (μg/kg). In other embodiments, the daily dosage of a compound of Formula (I), administered orally, is in the range from 0.01 micrograms per kilogram body weight (μg/kg) to 100 milligrams per kilogram body weight (mg/kg). An indicated daily dosage in the larger mammal, e.g. humans, is in the range from about 0.5 mg to about 100 mg of a compound of Formula (I), conveniently administered, e.g. in divided doses up to four times a day or in controlled release form. In certain embodiment, unit dosage forms for oral administration comprise from about 1 to 50 mg of a compound of Formula (I).

In certain embodiments, compounds of the invention, and salts and solvates thereof, are administered as the raw chemical, while in other embodiments the compounds of the invention, and salts and solvates thereof, are administered as a pharmaceutical composition. Accordingly, provided herein are pharmaceutical compositions, which comprise at least one compound of Formulas (I), salts and/or solvates thereof, and one or more pharmaceutically acceptable carriers, diluents, or excipients. Furthermore, another aspect provided herein is a process for the preparation of such pharmaceutical composition including admixing a compound of the Formula (I) described herein, and salts and solvates thereof, with one or more pharmaceutically acceptable carriers, diluents or excipients. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. The compositions may be sterilized and/or contain adjuvants, such as preserving, stabilizing, wetting or emulsifying agents, solution promoters, salts for regulating the osmotic pressure and/or buffers.

Compounds of the invention, and salts and solvates thereof, can be administered as pharmaceutical compositions by any conventional route including, but not limited to, intravenous administration (parenteral), oral administration, rectal administration, inhalation, nasal administration, topical administration, ophthalmic administration or otic administration.

Compounds provided herein are administered alone, or are administered by way of known pharmaceutical formulations, including tablets, capsules or elixirs for oral administration, suppositories for rectal administration, sterile solutions or suspensions for parenteral or intramuscular administration, lotions, gels, ointments or creams for topical administration, and the like.

Other aspects provided herein are processes for the preparation of pharmaceutical composition which comprise at least one compound of Formulas (I), or pharmaceutically acceptable salts and/or solvates thereof. In certain embodiments, such processes include admixing a compound of the Formula (I), and pharmaceutically acceptable salts and solvates thereof, with one or more pharmaceutically acceptable carriers, diluents or excipients. In certain embodiments, the pharmaceutical compositions comprising a compound of Formula (I) in free form or in a pharmaceutically acceptable salt or solvate form, in association with at least one pharmaceutically acceptable carrier, diluent or excipient are manufactured by mixing, granulating and/or coating methods. In other embodiments, such compositions optionally contain excipients, such as adjuvants, preserving, stabilizing, wetting or emulsifying agents, solution promoters, salts for regulating the osmotic pressure and/or buffers. In other embodiments, such compositions are sterilized.

In certain embodiments, pharmaceutical formulations (pharmaceutical compositions) provided herein include those in which the active ingredient is present in at least 1% by weight. In certain embodiments, pharmaceutical formulations (pharmaceutical compositions) provided herein include those in which the active ingredient is present in at least 5% by weight. In certain embodiments, pharmaceutical formulations (pharmaceutical compositions) provided herein include those in which the active ingredient is present in at least 10% by weight. In certain embodiments, pharmaceutical formulations (pharmaceutical compositions) provided herein include those in which the active ingredient is present in at least 20% by weight. In certain embodiments, pharmaceutical formulations (pharmaceutical compositions) provided herein include those in which the active ingredient is present in at least 20% by weight. In certain embodiments, pharmaceutical formulations (pharmaceutical compositions) provided herein include those in which the active ingredient is present in at least 40% by weight. In certain embodiments, pharmaceutical formulations (pharmaceutical compositions) provided herein include those in which the active ingredient is present in at least 50% by weight. That is, the ratio of active ingredient to the other components (by way of example, the addition of adjuvant, diluent and carrier) of the pharmaceutical composition is at least 1:99, 5:95, 10:90, 20:80, 30:70, 40:60 or at least 50:50 by weight.

Oral Dosage Forms

In certain embodiments, the pharmaceutical compositions containing at least one compound of Formula (I) are administered orally as discrete dosage forms, wherein such dosage forms include, but are not limited to, capsules, gelatin capsules, caplets, tablets, chewable tablets, powders, granules, syrups, flavored syrups, solutions or suspensions in aqueous or non-aqueous liquids, edible foams or whips, and oil-in-water liquid emulsions or water-in-oil liquid emulsions.

The capsules, gelatin capsules, caplets, tablets, chewable tablets, powders or granules, used for the oral administration of at least one compound of Formula (I) are prepared by admixing at least one compound of Formula (I) (active ingredient) together with at least one excipient using conventional pharmaceutical compounding techniques. Non-limiting examples of excipients used in oral dosage forms described herein include, but are not limited to, binders, fillers, disintegrants, lubricants, absorbents, colorants, flavors, preservatives and sweeteners.

Non-limiting examples of such binders include, but are not limited to, corn starch, potato starch, starch paste, pre-gelatinized starch, or other starches, sugars, gelatin, natural and synthetic gums such as acacia, sodium alginate, alginic acid, other alginates, tragacanth, guar gum, cellulose and its derivatives (by way of example only, ethyl cellulose, cellulose acetate, carboxymethyl cellulose calcium, sodium carboxymethylcellulose, methyl cellulose, hydroxypropyl methylcellulose and microcrystalline cellulose), magnesium aluminum silicate, polyvinyl pyrrolidone and combinations thereof.

Non-limiting examples of such fillers include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein are present in from about 50 to about 99 weight percent of the pharmaceutical composition or dosage form.

Non-limiting examples of such disintegrants include, but are not limited to, agar-agar, alginic acid, sodium alginate, calcium carbonate, sodium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and combinations thereof. In certain embodiments, the amount of disintegrant used in the pharmaceutical compositions provided herein is from about 0.5 to about 15 weight percent of disintegrant, while in other embodiments the amount is from about 1 to about 5 weight percent of disintegrant.

Non-limiting examples of such lubricants include, but are not limited to, sodium stearate, calcium stearate, magnesium stearate, stearic acid, mineral oil, light mineral oil, glycerin, sorbitol, mannitol, polyethylene glycol, other glycols, sodium lauryl sulfate, talc, hydrogenated vegetable oil (by way of example only, peanut oil, cottonseed oil, sunflower oil, sesame oil, olive oil, corn oil, and soybean oil), zinc stearate, sodium oleate, ethyl oleate, ethyl laureate, agar, silica, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.) and combinations thereof. In certain embodiments, the amount of lubricants used in the pharmaceutical compositions provided herein is in an amount of less than about 1 weight percent of the pharmaceutical compositions or dosage forms.

Non-limiting examples of such diluents include, but are not limited to, lactose, dextrose, sucrose, mannitol, sorbitol, cellulose, glycine or combinations thereof.

In certain embodiments, tablets and capsules are prepared by uniformly admixing at least one compound of Formula (I) (active ingredients) with liquid carriers, finely divided solid carriers, or both, and then shaping the product into the desired presentation if necessary. In certain embodiments, tablets are prepared by compression. In other embodiments, tablets are prepared by molding.

In certain embodiments, at least one compound of Formula (I) is orally administered as a controlled release dosage form. Such dosage forms are used to provide slow or controlled-release of one or more compounds of Formula (I). Controlled release is obtained using, for example, hydroxypropylmethyl cellulose, other polymer matrices, gels, permeable membranes, osmotic systems, multilayer coatings, microparticles, liposomes, microspheres, or a combination thereof. In certain embodiments, controlled-release dosage forms are used to extend activity of the compound of Formula (I), reduce dosage frequency, and increase patient compliance.

Administration of compounds of Formula (I) as oral fluids such as solution, syrups and elixirs are prepared in unit dosage forms such that a given quantity of solution, syrups or elixirs contains a predetermined amount of a compound of Formula (I). Syrups are prepared by dissolving the compound in a suitably flavored aqueous solution, while elixirs are prepared through the use of a non-toxic alcoholic vehicle. Suspensions are formulated by dispersing the compound in a non-toxic vehicle. Non-limiting examples of excipients used in as oral fluids for oral administration include, but are not limited to, solubilizers, emulsifiers, flavoring agents, preservatives, and coloring agents. Non-limiting examples of solubilizers and emulsifiers include, but are not limited to, water, glycols, oils, alcohols, ethoxylated isostearyl alcohols and polyoxy ethylene sorbitol ethers. Non-limiting examples of preservatives include, but are not limited to, sodium benzoate. Non-limiting examples of flavoring agents include, but are not limited to, peppermint oil or natural sweeteners or saccharin or other artificial sweeteners.

Parenteral Dosage Forms

In certain embodiments pharmaceutical compositions containing at least one compound of Formula (I) are administered parenterally by various routes including, but not limited to, subcutaneous, intravenous (including bolus injection), intramuscular, and intraarterial.

Such parenteral dosage forms are administered in the form of sterile or sterilizable injectable solutions, suspensions, dry and/or lyophylized products ready to be dissolved or suspended in a pharmaceutically acceptable vehicle for injection (reconstitutable powders) and emulsions. Vehicles used in such dosage forms include, but are not limited to, Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Transdermal Dosage Forms

In certain embodiments pharmaceutical compositions containing at least one compound of Formula (I) are administered transdermally. Such transdermal dosage forms include "reservoir type" or "matrix type" patches, which are applied to the skin and worn for a specific period of time to permit the penetration of a desired amount of a compound of Formula (I). By way of example only, such transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. In other embodiments, matrix transdermal formulations are used.

Formulations for transdermal delivery of a compound of Formula (I) include an effective amount of a compound of Formula (I), a carrier and an optional diluent. A carrier includes, but is not limited to, absorbable pharmacologically acceptable solvents to assist passage through the skin of the host, such as water, acetone, ethanol, ethylene glycol, propylene glycol, butane-1,3-diol, isopropyl myristate, isopropyl palmitate, mineral oil, and combinations thereof.

In certain embodiments, such transdermal delivery systems include penetration enhancers to assist in delivering one or more compounds of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In other embodiments, the pH of such a transdermal pharmaceutical composition or dosage form, or of the tissue to which the pharmaceutical composition or dosage form is applied, is adjusted to improve delivery of one or more compounds of Formula (I). In other embodiments, the polarity of a solvent carrier, its ionic strength, or tonicity are adjusted to improve delivery. In other embodiments, compounds such as stearates are added to advantageously alter the hydrophilicity or lipophilicity of one or more compounds of Formula (I) so as to improve delivery. In certain embodiments, such stearates serve as a lipid vehicle for the formulation, as an emulsifying agent or surfactant, and as a delivery-enhancing or penetration-enhancing agent. In other embodiments, different salts, hydrates or solvates of the compounds of Formula (I) are used to further adjust the properties of the resulting composition.

Topical Dosage Forms

In certain embodiments at least one compound of Formula (I) is administered by topical application of pharmaceutical composition containing at least one compound of Formula (I) in the form of lotions, gels, ointments solutions, emulsions, suspensions or creams. Suitable formulations for topical application to the skin are aqueous solutions, ointments, creams or gels, while formulations for ophthalmic administration are aqueous solutions. Such formulations optionally contain solubilizers, stabilizers, tonicity enhancing agents, buffers and preservatives.

Such topical formulations include at least one carrier, and optionally at least one diluent. Such carriers and diluents include, but are not limited to, water, acetone, ethanol, ethylene glycol, propylene glycol, butane-1,3-diol, isopropyl myristate, isopropyl palmitate, mineral oil, and combinations thereof.

In certain embodiments, such topical formulations include penetration enhancers to assist in delivering one or more compounds of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In certain embodiments pharmaceutical compositions containing at least one compound of Formula (I) are administered by inhalation. Dosage forms for inhaled administration are formulated as aerosols or dry powders. Aerosol formulations for inhalation administration comprise a solution or fine suspension of at least one compound of Formula (I) in a pharmaceutically acceptable aqueous or non-aqueous solvent. In addition, such pharmaceutical compositions optionally comprise a powder base such as lactose, glucose, trehalose, mannitol or starch, and optionally a performance modifier such as L-leucine or another amino acid, and/or metals salts of stearic acid such as magnesium or calcium stearate.

In certain embodiments, compounds of Formula (I) are be administered directly to the lung by inhalation using a Metered Dose Inhaler ("MDI"), which utilizes canisters that contain a suitable low boiling propellant, e.g., dichlorodifluoromethane, trichlorofluoromethane, dichlorotetrafluoroethane, carbon dioxide or other suitable gas, or a Dry Powder Inhaler (DPI) device which uses a burst of gas to create a cloud of dry powder inside a container, which is then be inhaled by the patient. In certain embodiments, capsules and cartridges of gelatin for use in an inhaler or insufflator are formulated containing a powder mixture of a compound of Formula (I) and a powder base such as lactose or starch. In certain embodiments, compounds of Formula (I) are delivered to the lung using a liquid spray device, wherein such devices use extremely small nozzle holes to aerosolize liquid drug formulations that can then be directly inhaled into the lung. In other embodiments, compounds of Formula (I) are delivered to the lung using a nebulizer device, wherein a nebulizers creates an aerosols of liquid drug formulations by using ultrasonic energy to form fine particles that can be readily inhaled. In other embodiments, compounds of Formula (I) are delivered to the lung using an electrohydrodynamic ("EHD") aerosol device wherein such EHD aerosol devices use electrical energy to aerosolize liquid drug solutions or suspensions.

In certain embodiments, the pharmaceutical composition containing at least one compound of Formula (I), or pharmaceutically acceptable salts and solvates thereof, described herein, also contain one or more absorption enhancers. In certain embodiments, such absorption enhancers include, but are not limited to, sodium glycocholate, sodium caprate, N-lauryl-β-D-maltopyranoside, EDTA, and mixed micelles.

In certain embodiments pharmaceutical compositions containing at least one compound of Formula (I) are administered nasally. The dosage forms for nasal administration are formulated as aerosols, solutions, drops, gels or dry powders.

In certain embodiments pharmaceutical compositions containing at least one compound of Formula (I) are administered rectally in the form of suppositories, enemas, ointment, creams rectal foams or rectal gels. In certain embodiments such suppositories are prepared from fatty emulsions or suspensions, cocoa butter or other glycerides.

In certain embodiments pharmaceutical compositions containing at least one compound of Formula (I) are administered opthamically as eye drops. Such formulations are aqueous solutions that optionally contain solubilizers, stabilizers, tonicity enhancing agents, buffers and preservatives.

In certain embodiments pharmaceutical compositions containing at least one compound of Formula (I) are administered otically as ear drops. Such formulations are aqueous solutions that optionally contain solubilizers, stabilizers, tonicity enhancing agents, buffers and preservatives.

In certain embodiments pharmaceutical compositions containing at least one compound of Formula (I) are formulated as a depot preparation. Such long acting formulations are administered by implantation (for example subcutaneously or intramuscularly) or by intramuscular injection. In certain embodiments, such formulations include polymeric or hydrophobic materials (for example, as an emulsion in an acceptable oil) or ion exchange resins, or as sparingly soluble derivatives, for example, as a sparingly soluble salt.

In other embodiments, a compound of Formula (I) described herein, or a pharmaceutically acceptable salt, N-oxide, isomer or solvate thereof, or a pharmaceutical composition containing such compounds of Formula (I), is administered to a patient who has not previously undergone or is not currently undergoing treatment with another therapeutic agent.

In certain embodiments pharmaceutical compositions containing at least one compound of Formula (I) are administered in the form of liposome delivery systems, such as small unilamellar vesicles, large unilamellar vesicles and multilamellar vesicles. Liposomes are formed from a variety of phospholipids, such as cholesterol, stearylamine or phosphatidylcholines.

The invention provides compounds of Formula (I) and salts, solvates and pharmaceutical compositions thereof for use in modulating Syk activity, including inhibiting Syk activity. The invention provides compounds of Formula (I) and salts, solvates and pharmaceutical compositions thereof for use in the treatment of diseases and conditions mediated by inappropriate Syk activity. By way of example only, this inappropriate Syk activity is any Syk activity that deviates from the normal Syk activity expected in a particular mammalian subject. Inappropriate Syk activity may take the form of, for instance, an abnormal increase in activity, or an aberration in the timing and or control of Syk activity. Such inappropriate activity may result then, for example, from overexpression or mutation of the protein kinase leading to inappropriate or uncontrolled activation.

In a further embodiment, the present invention is directed to methods of regulating, modulating, or inhibiting Syk, using compounds of Formula (I) or a pharmaceutically acceptable salt or solvate thereof, for the prevention and/or treatment of disorders related to unregulated Syk activity.

In a further embodiment, the present invention provides a method of treatment of a mammal suffering from a disorder mediated by Syk activity, which includes administering to said subject an effective amount of a compound of Formula (I) or a pharmaceutically acceptable salt, solvate, or a physiologically functional derivative thereof.

In a further embodiment, the present invention provides for the use of a compound of Formula (I), or a pharmaceutically acceptable salt or solvate thereof, in the preparation of a medicament for the treatment of a disease or condition/disorder mediated by Syk activity.

In a further embodiment, the disease or condition mediated by inappropriate Syk activity is rheumatoid arthritis. In a further embodiment, the disease or condition mediated by inappropriate Syk activity is allergic rhinitis. In a further embodiment, the disease or condition mediated by inappropriate Syk activity is chronic obstructive pulmonary disease (COPD). In a further embodiment, the disease or condition mediated by inappropriate Syk activity is adult respiratory distress syndrome (ARDS).

In a further embodiment, the present invention provides a pharmaceutical composition comprising at least one compound of Formula (I) adapted for administration by the oral route, for treating, for example, rheumatoid arthritis. In a further embodiment, the present invention provides a pharmaceutical composition comprising at least one compound of Formula (I) adapted for administration by the nasal route, for treating, for example, allergic rhinitis. In a further embodiment, the present invention provides a pharmaceutical composition comprising at least one compound of Formula (I) adapted for administration by the inhaled route, for treating, for example, COPD or ARDS.

Combination Therapies

In certain embodiments, a compound of Formula (I) is used in combination with a second therapeutic agent, for ameliorating a condition mediated by a protein kinase, such as a Syk-mediated condition. In certain embodiments, the compounds of the invention are used in combination with a chemotherapeutic agent to treat a cell proliferative disorder, including but not limited to, lymphoma, osteosarcoma, melanoma, or a tumor of breast, renal, prostate, colorectal, thyroid, ovarian, pancreatic, neuronal, lung, uterine or gastrointestinal tumor. In certain embodiments, the compounds of the invention are used in combination with an agent to treat respiratory diseases.

In certain embodiments, compounds of the present invention, and their salts and solvates thereof, are administered alone or in combination with other therapeutic agents (pharmaceutical combinations) for the treatment of diseases and conditions associated with inappropriate Syk activity. In certain embodiment, the compounds and pharmaceutically acceptable compositions of the invention are administered concurrently with one or more other desired therapeutics or medical procedures. In other embodiment, the compounds and pharmaceutically acceptable compositions of the invention are administered prior to one or more other desired therapeutics or medical procedures. In certain embodiment, the compounds and pharmaceutically acceptable compositions of the invention are administered subsequent to one or more other desired therapeutics or medical procedures.

Chemotherapeutic agents or other anti-proliferative agents used in combination with the compounds of the invention to treat proliferative diseases and cancer include, but are not limited to, surgery, radiotherapy (gamma.-radiation, neutron beam radiotherapy, electron beam radiotherapy, proton therapy, brachytherapy, and systemic radioactive isotopes), endocrine therapy, biologic response modifiers (interferons, interleukins, and tumor necrosis factor (TNF)), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), GLEEVEC™ adriamycin, dexamethasone, and cyclophosphamide.

Other chemotherapeutic agents which are used in the compositions and methods of the invention include but are not limited to anthracyclines, alkylating agents (e.g., mitomycin C), alkyl sulfonates, aziridines, ethylenimines, methylmelamines, nitrogen mustards, nitrosoureas, antibiotics, antimetabolites, folic acid analogs (e.g., dihydrofolate reductase inhibitors such as methotrexate), purine analogs, pyrimidine analogs, enzymes, podophyllotoxins, platinum-containing agents, interferons, and interleukins Particular examples of known chemotherapeutic agents which may be used in the compositions and methods of the invention include, but are not limited to, busulfan, improsulfan, piposulfan, benzodepa, carboquone, meturedepa, uredepa, altretamine, triethylenemelamine, triethylenephosphoramide, triethylenethiophosphoramide, trimethylolomelamine, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, fluorouracil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, elformithine, elliptinium acetate, etoglucid, etoposide, flutamide, gallium nitrate, hydroxyurea, interferon-alpha, interferon-beta, interferon-gamma, interleukin-2, lentinan, lonidamine, mitoguazone, mitoxantrone, mopidamol, nitracrine, pentostatin, phenamet, pirarubicin, podophyllinic acid, 2-ethylhydrazide, procarbazine, razoxane, sizofuran, spirogermanium, paclitaxel, tamoxifen, teniposide, tenuazonic acid, triaziquone, 2,2',2"-trichlorotriethylamine, urethane, vinblastine, vincristine, and vindesine.

Other agents used in combination with the compounds of the invention include, but are not limited to: treatments for Alzheimer's Disease such as ARRICEPT™ and EXCELON™; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., AVONEX™ and REBIF™), COPAXONE™, and mitoxantrone; treatments for asthma such as albuterol and SINGULAIR™; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Other agents having synergic effects when used in combination with the compounds include, but are not limited to, immunomodulatory or anti-inflammatory substances, for example cyclosporin, rapamycin, or ascomycin, or immunosuppressant analogues thereof, for example cyclosporin A (CsA), cyclosporin G, FK-506, rapamycin, or comparable compounds, cortico steroids, cyclophosphamide, azathioprine, methotrexate, brequinar, leflunomide, mizoribine, mycophenolic acid, mycophenolate mofetil, 15deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA41g. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

Processes for Making Compounds of the Invention

General procedures for preparing compounds of the invention are described in the Examples, infra. In the reactions described, reactive functional groups, for example hydroxy, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry", John Wiley and Sons, 1991).

In certain embodiments compounds of the invention are prepared as a pharmaceutically acceptable acid addition salt by reacting the free base form of the compound with a pharmaceutically acceptable inorganic or organic acid. In other embodiments, a pharmaceutically acceptable base addition salt of a compound of the invention is prepared by reacting the free acid form of the compound with a pharmaceutically acceptable inorganic or organic base. Alternatively, the salt forms of the compounds of the invention are prepared using salts of the starting materials or intermediates. In certain embodiments, the compounds of the invention are in the form of other salts including, but not limited to, oxalates or trifluoroacetates.

A pharmaceutically acceptable acid addition salt is formed by reaction of the free base form a compound of Formula (I) with a suitable inorganic or organic acid including, but not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid. A pharmaceutically acceptable acid addition salt of a compound of formula (I) can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

The free acid or free base forms of the compounds of the invention may be prepared from the corresponding base addition salt or acid addition salt from, respectively. For example a compound of the invention in an acid addition salt form may be converted to the corresponding free base by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention may be prepared by methods known to those of ordinary skill in the art (e.g., for further details see Saulnier et al., (1994), Bioorganic and Medicinal Chemistry Letters, Vol. 4, p. 1985). For example, appropriate prodrugs may be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention may be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention may be conveniently prepared or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds of the invention may be prepared as their individual stereoisomers by reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubility, reactivity, etc.) and may be readily separated by taking advantage of these dissimilarities. The diastereomers may be separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

Compounds of Formula (I) are made by processes described herein and in the Examples. In certain embodiments, compounds of Formula (I) are made by:

(a) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

One of skill in the art will appreciate that the above transformations are only representative of methods for preparation of the compounds of the present invention, and that other well known methods can similarly be used.

The synthesis of certain compounds of Formula (I) is illustrated in scheme (I), scheme (II), scheme (III) and scheme (IV).
Scheme (I)
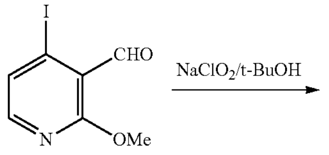
1
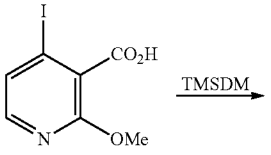
2
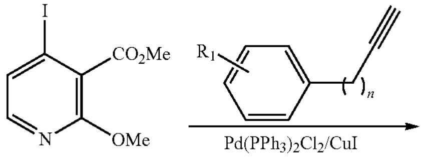
3
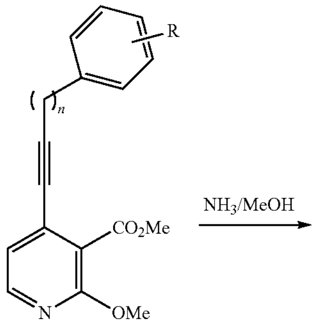
4
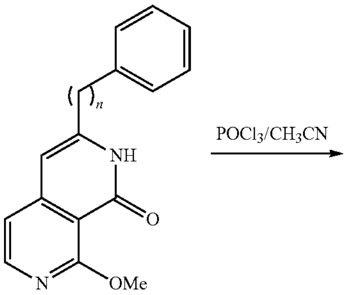
5
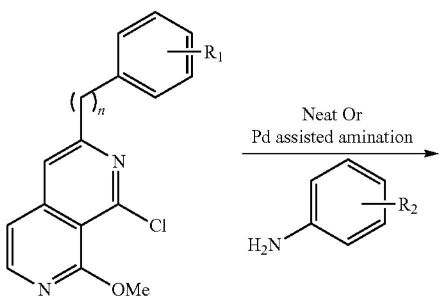
6
-continued
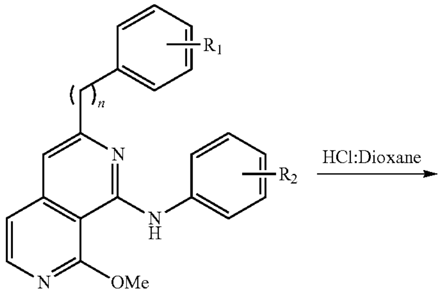
7
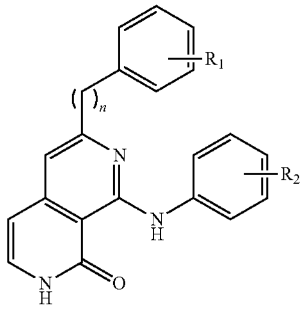
8
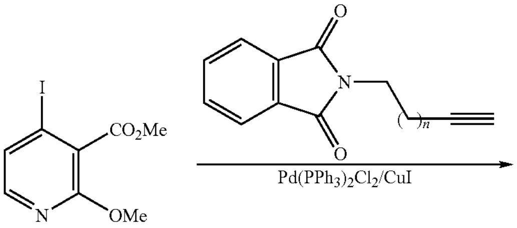
3
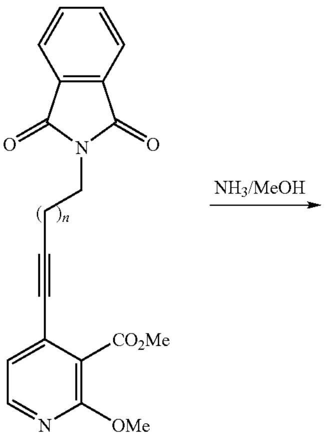
9

-continued
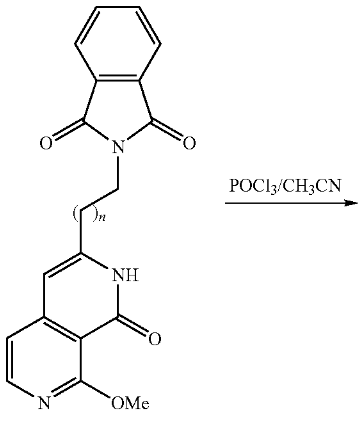
10
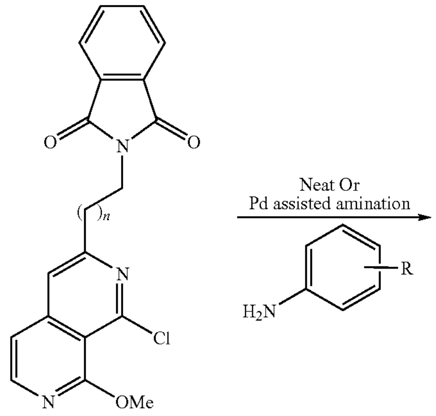
11
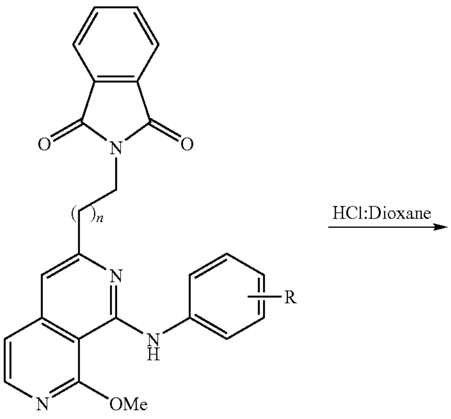
12
-continued
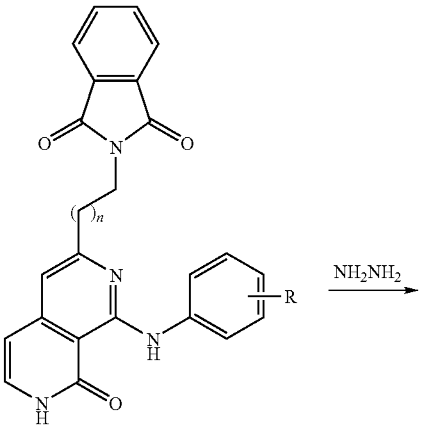
13
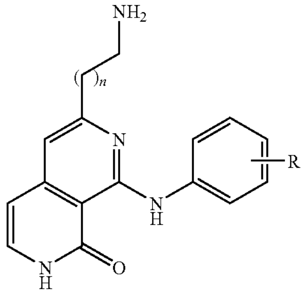
14
Scheme (III)
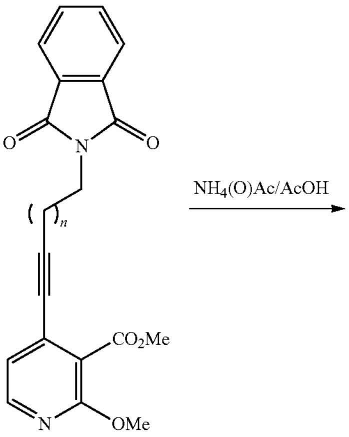
9

-continued
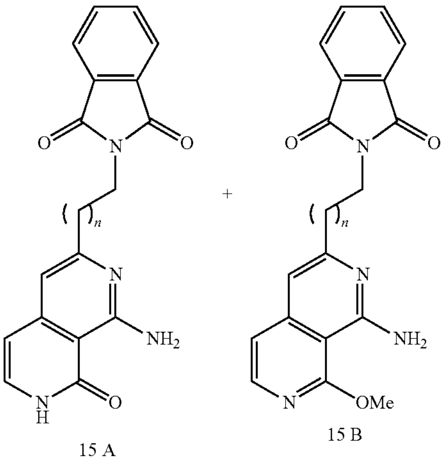
15 A 15 B
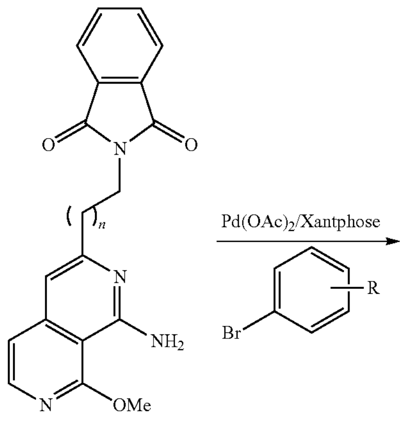
15 B
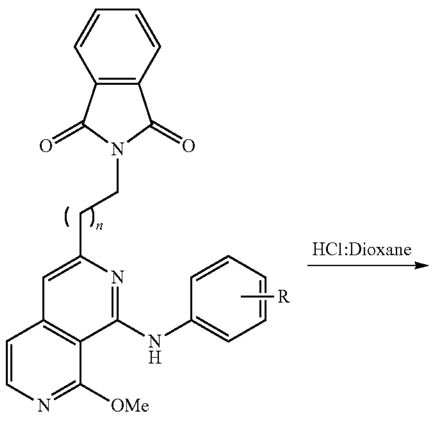
12
-continued
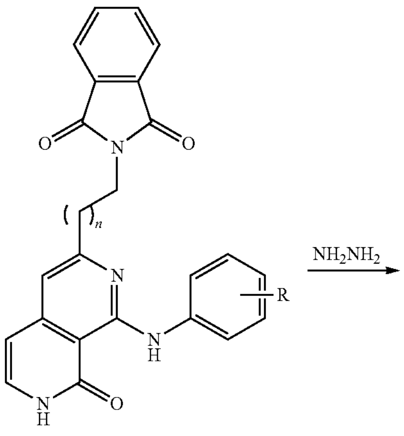
13
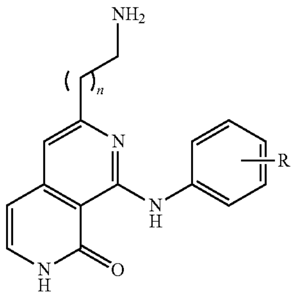
14
Scheme (IV)
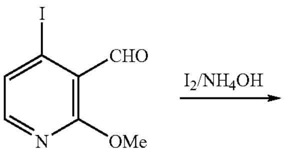
1
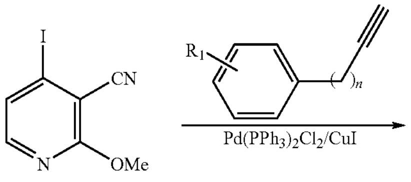
16
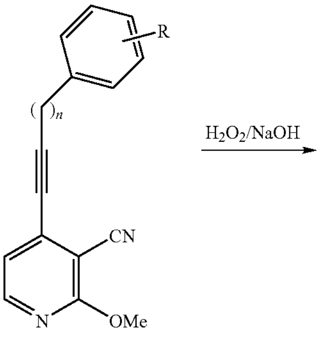
17

-continued

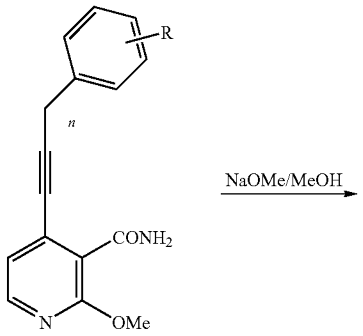

18

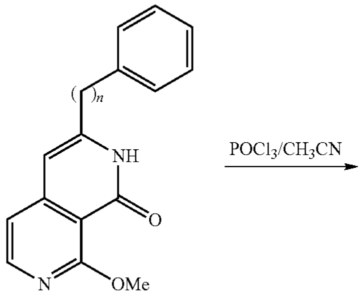

5

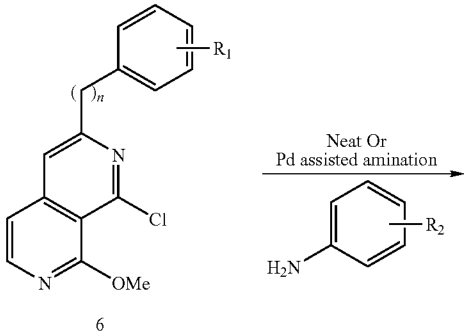

6

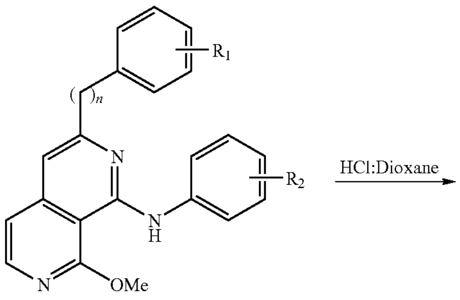

7

-continued

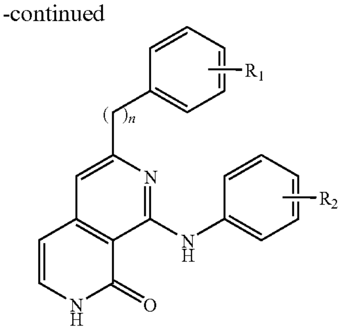

8

In certain compounds of Formula (I), the $R^1$ and $R^2$ of schemes (I) and scheme (IV) are optionally selected from halogen, —CN, $C_1$-$C_6$ alkyl, $C_1$-$C_6$ alkoxy, —$OR^{13}$, —C(O)$R^{13}$, $^{-}OC(O)R^{13}$, —$C(O)OR^{13}$, —$N(R^{12})_2$, —$C(O)N(R^{12})_2$, $C_2$-$C_{14}$heterocycloalkyl, —$S(O)_2R^{13}$, —$S(O)_2$ $N(R^{12})_2$, —$(CH_2)_nR^{13}$, —$(CH_2)_nR^{14}$ halo-substituted $C_1$-$C_6$ alkyl and halo-substituted $C_1$-$C_6$ alkoxy, and each n is independently 1, 2, 3, 4, 5 or 6. $R^{12}$ and $R^{13}$ are as described herein.

In certain compounds of Formula (I), the R groups of schemes (II) and scheme (III) are optionally selected from halogen, —CN, $C_1$-$C_6$ alkyl, $C_1$-$C_6$ alkoxy, —$OR^{13}$, —C(O)$R^{13}$, —$OC(O)R^{13}$, —$C(O)OR^{13}$, —$N(R^{12})_2$, —C(O)N$(R^{12})_2$, $C_2$-$C_{14}$heterocycloalkyl, —$S(O)_2R^{13}$, —$S(O)_2$ $N(R^{12})_2$, —$(CH_2)_nR^{13}$, —$(CH_2)_nR^{14}$ halo-substituted $C_1$-$C_6$ alkyl and halo-substituted $C_1$-$C_6$ alkoxy, and each n is independently 1, 2, 3, 4, 5 or 6. $R^{12}$ and $R^{13}$ are as described herein.

The synthesis of certain intermediates used in the synthesis of compounds of Formula (I) is illustrated in scheme (V) and scheme (VI).

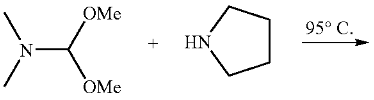

19

20

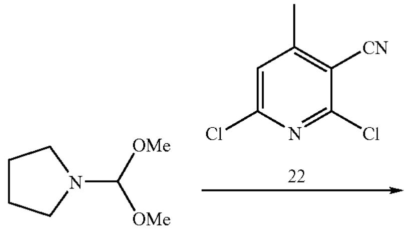

22

21

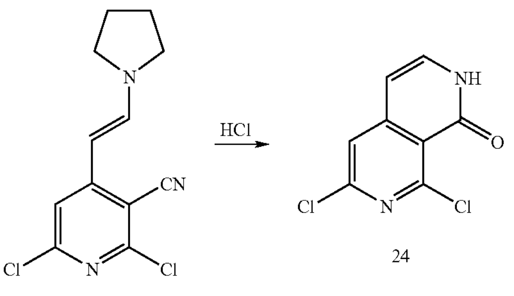

24

23

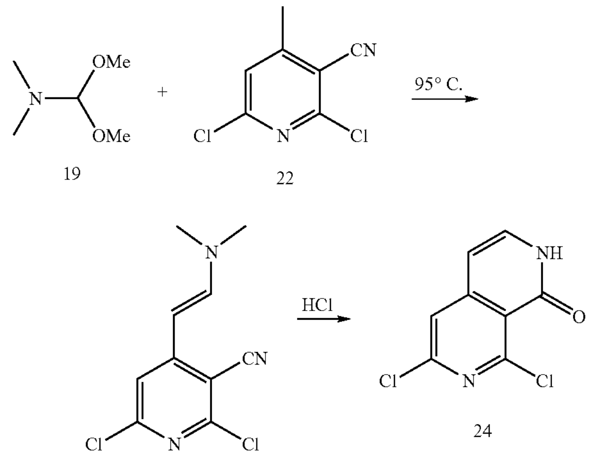
19 22 25 24
The synthesis of certain compounds of Formula (I) using the 6,8-dichloro-2,7-naphthyridin-1(2H)-one (24) intermediate compound is illustrated in scheme (VII) and scheme (VIII).
Scheme (VII)
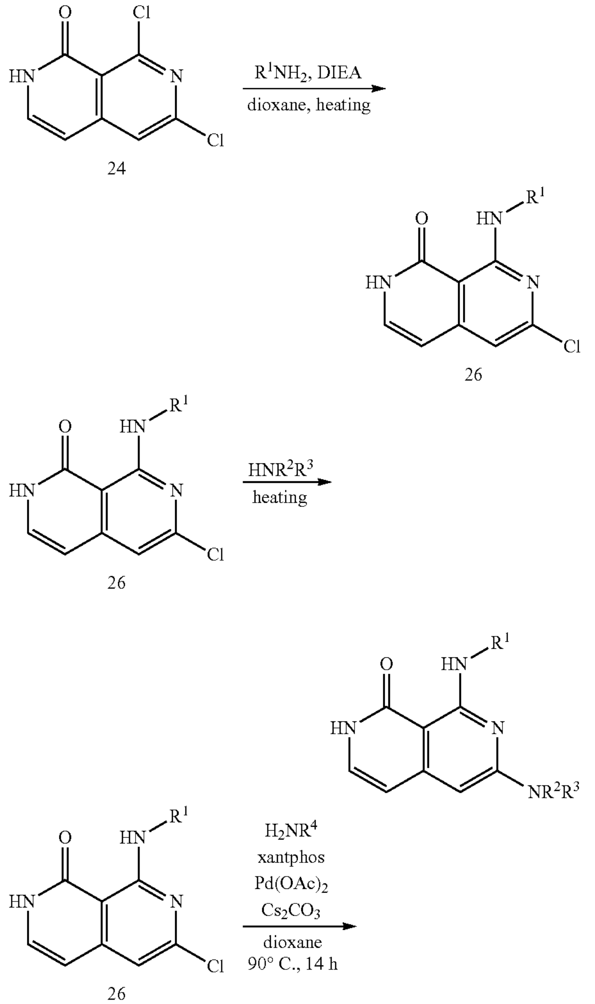
24 26 26 26
-continued
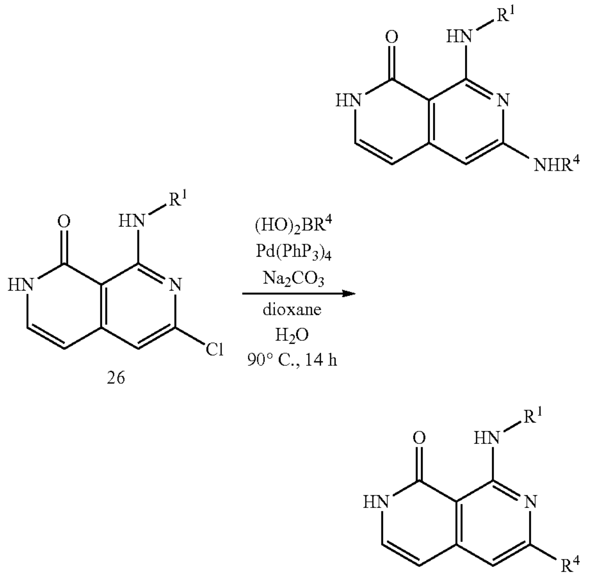
26
Scheme (VIII)
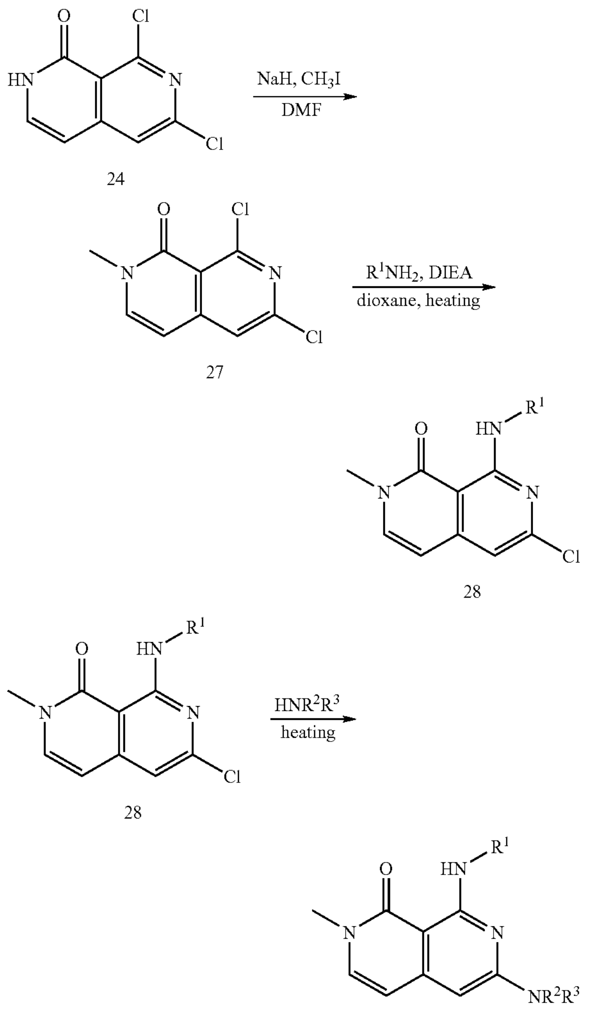
24 27 28 28

-continued

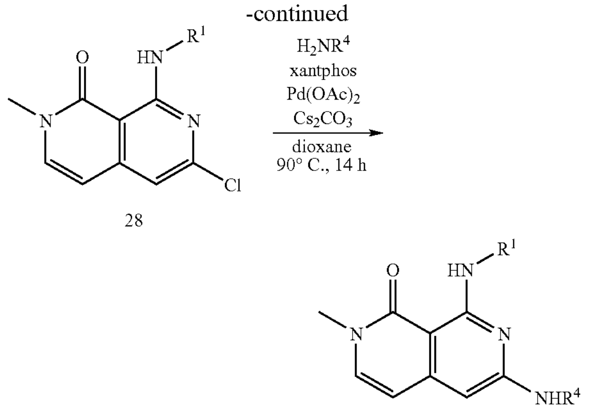

28

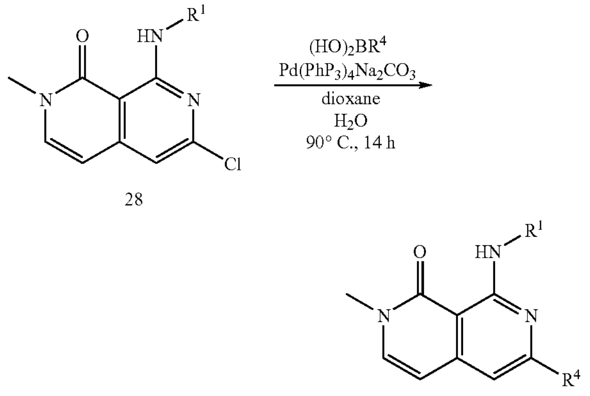

28

In certain compounds of Formula (I), the $R^1$ of scheme (VII) and scheme (VIII) is $C_6$-$C_{14}$aryl, $C_3$-$C_{13}$hetero aryl, $C_2$-$C_{14}$hetero cyclo alkyl, $C_1$-$C_6$alkyl, $C_3$-$C_8$cyclo alkyl, halo-substituted $C_1$-$C_6$alkyl, —$(CH_2)_n R^9$, -$L^3R^9$ or —$Y^1$-$L^1$-$R^{14}$, wherein, $Y^1$ is arylene, heteroarylene or heterocycloalkylene, and is a bond, —O—, —C(O)—, —C(O)N$(R^{11})$—, —$(C(R^{12})_2)_n$— or —$O(CH_2)_n$— and wherein the $C_6$-$C_{14}$aryl, $C_3$-$C_{13}$heteroaryl, $C_1$-$C_6$alkyl, halo-substituted $C_1$-$C_6$alkyl, $C_2$-$C_{14}$heterocycloalkyl and $C_3$-$C_8$cycloalkyl and $Y^1$ are optionally substituted with 1 to 3 substituents independently selected from halogen, —CN, —$C_1$-$C_6$ alkyl, $C_1$-$C_6$alkoxy, —$OR^{13}$, —C(O)$R^{13}$, $^-$OC(O)$R^{13}$, —C(O)$OR^{13}$, —$N(R^{12})_2$, —C(O)$N(R^{12})_2$, $C_2$-$C_{14}$heterocycloalkyl, —$S(O)_2R^{13}$, —$S(O)_2$ $N(R^{12})_2$, $R^{13}$, —$(CH_2)_nR^{13}$, —$(CH_2)_nR^{14}$, halo-substituted $C_1$-$C_6$ alkyl and halo-substituted $C_1$-$C_6$alkoxy, and each n is independently 1, 2, 3, 4, 5 or 6.

In certain compounds of Formula (I), the $R^1$ of scheme (VII) and scheme (VIII) is $C_6$-$C_{14}$aryl, $C_3$-$C_{13}$heteroaryl, $C_2$-$C_{14}$heterocycloalkyl, $C_3$-$C_8$cycloalkyl or $Y^2$-$L^2$-$R^{14}$, wherein, $Y^2$ is bond, arylene, heteroarylene or heterocycloalkylene, and $L^2$- is a bond, —O—, or —$O(CH_2)_n$—, and wherein the $C_6$-$C_{14}$aryl, $C_3$-$C_{13}$heteroaryl, $C_3$-$C_8$cycloalkyl and $C_2$-$C_{14}$heterocycloalkyl and $Y^2$ are optionally substituted with 1 to 3 substituents independently selected from halogen, —CN, =O, $C_1$-$C_6$alkyl, $C_1$-$C_6$alkoxy, —$OR^{13}$, —C(O)$R^{13}$, —OC(O)$R^{13}$, —C(O)$OR^{13}$, —$N(R^{12})_2$, —C(O)$N(R^{12})_2$, $C_2$-$C_{14}$heterocycloalkyl, —$S(O)_2R^{13}$, —$NR^{12}S(O)_2R^{13}$, —$S(O)_2$ $N(R^{12})_2$, $R^{13}$, —$(CH_2)_nR^{12}$, —$(CH_2)_nR^{14}$, halo-substituted $C_1$-$C_6$alkyl and halo-substituted $C_1$-$C_6$alkoxy.

In certain compounds of Formula (I), the $R^2$ of scheme (VII) and scheme (VIII) is H or $C_1$-$C_6$ alkyl, and the $R^3$ is halo-substituted $C_1$-$C_6$alkyl, $C_6$-$C_{14}$aryl, $C_3$-$C_{13}$heteroaryl, $C_2$-$C_{14}$heterocycloalkyl, $C_3$-$C_8$cycloalkyl or —$(CH_2)_nR^{11}$, wherein the $C_6$-$C_{14}$aryl, $C_3$-$C_{13}$heteroaryl, $C_2$-$C_{14}$heterocycloalkyl or $C_3$-$C_8$cycloalkyl are optionally substituted with 1 to 3 substituents independently selected from halogen, —CN, $C_1$-$C_6$alkyl, hydroxyl-$C_1$-$C_6$alkyl, $C_1$-$C_6$alkoxy, $C_3$-$C_8$cycloalkyl, —$OR^{13}$, —C(O)$R^{13}$, $^-$OC(O)$R^{13}$, —C(O)$OR^{13}$, —$N(R^{12})_2$, —C(O)$N(R^{12})_2$, $C_2$-$C_{14}$heterocycloalkyl, —$S(O)_2R^{13}$, —$S(O)_2N(R^{12})_2$, —$NHS(O)_2R^{13}$, $R^{13}$, —$(CH_2)_nR^{12}$, —$(CH_2)_nR^{14}$, halo-substituted $C_1$-$C_6$alkyl and halo-substituted $C_1$-$C_6$alkoxy.

In certain compounds of Formula (I), the $R^4$ of scheme (VII) and scheme (VIII) is halogen, $C_1$-$C_6$alkyl, $C_1$-$C_6$alkoxy, $C_1$-$C_6$alkylthio, hydroxyl-$C_1$-$C_6$alkyl, halo-substituted-$C_1$-$C_6$alkyl, and halo-substituted-$C_1$-$C_6$alkoxy, $C_6$-$C_{14}$aryl, $C_3$-$C_{13}$heteroaryl and $C_2$-$C_{14}$heterocycloalkyl, wherein the $C_6$-$C_{14}$aryl, $C_3$-$C_{13}$heteroaryl, and $C_2$-$C_{14}$heterocycloalkyl of $R^2$ and $R^3$ are optionally substituted with 1 to 3 substituents independently selected from halogen, —CN, —$NO_2$, —$OR^{12}$, —$OR^{10}$, =O, —C(O)$R^{12}$, —OC(O)$R^{12}$, —C(O)$OR^{12}$, —$N(R^{11})_2$, —$N(R^{12})_2$, —$NR^{12}C(O)N(R^{12})_2$, —C(O)$N(R^{12}R^{10})$, —$N(R^{12})C(O)R^{13}$, —C(O)$N(R^{11})_2$, —C(O)$N(R^{12})_2$, —$(CR^{12}R^{12})_nR^{11}$, —$(CH_2)_nR^{12}$, —$(CH_2)_nR^{13}$, $(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, $C_2$-$C_{14}$heterocycloalkyl, $C_1$-$C_6$alkyl, $C_1$-$C_6$alkoxy, hydroxyl-$C_1$-$C_6$alkyl, halo-substituted $C_1$-$C_6$alkyl and halo-substituted $C_1$-$C_6$alkoxy.

In certain embodiments of the $R^1$, $R^2$, $R^3$ and $R^4$ groups of scheme (VII) and scheme (VIII) presented above, $R^{11}$ is —$N(R^{12})_2$, —$OR^{13}$, —C(O)$N(R^{12})_2$, —$S(O)_2R^{13}$, —$S(O)_2$ $N(R^{12})_2$, $C_6$-$C_{14}$aryl, $C_3$-$C_{13}$heteroaryl, $C_1$-$C_6$alkyl, $C_3$-$C_8$cycloalkyl, or $C_2$-$C_{14}$heterocycloalkyl, wherein the $C_6$-$C_{14}$aryl, $C_3$-$C_{13}$heteroaryl, $C_1$-$C_6$alkyl, $C_3$-$C_8$cycloalkyl and $C_2$-$C_{14}$heterocycloalkyl of $R^{11}$ are optionally substituted with 1 to 3 substituents independently selected from halogen, —CN, $C_1$-$C_6$ alkyl, $C_1$-$C_6$ alkoxy, $C_3$-$C_8$cycloalkyl, —$OR^{13}$, —C(O)$R^{13}$, $^-$OC(O)$R^{13}$, —C(O)$OR^{13}$, —$N(R^{12})_2$, —C(O)$N(R^{12})_2$, $C_6$-$C_{14}$aryl, $C_3$-$C_{13}$heteroaryl, $C_2$-$C_{14}$heterocycloalkyl, —$S(O)_2R^{13}$, —$S(O)_2N(R^{12})_2$, —$NHS(O)_2R^{13}$, $R^{13}$, —$(CH_2)_nR^{12}$, —$(CH_2)_nR^{14}$, halo-substituted $C_1$-$C_6$alkyl and halo-substituted $C_1$-$C_6$alkoxy, and each n is independently 1, 2, 3, 4, 5 or 6.

In certain embodiments of the $R^1$, $R^2$, $R^3$ and $R^4$ groups of scheme (VII) and scheme (VIII) presented above, each $R^{12}$ is independently selected from H, $C_1$-$C_6$alkyl, $C_2$-$C_6$alkene, halo-substituted $C_1$-$C_6$alkyl and $C_3$-$C_8$cycloalkyl, or each $R^{12}$ is independently a $C_1$-$C_6$alkyl that together with N they are attached to form a heterocycloalkyl group.

In certain embodiments of the $R^1$, $R^2$, $R^3$ and $R^4$ groups of scheme (XIV) and scheme (VIII) presented above, $R^{13}$ is H, $C_1$-$C_6$ alkyl, $C_3$-$C_8$cycloalkyl, halo-substituted $C_1$-$C_6$ alkyl or $C_2$-$C_{14}$heterocycloalkyl.

In certain embodiments of the $R^1$, $R^2$, $R^3$ and $R^4$ groups of scheme (XIV) and scheme (VIII) presented above, $R^{14}$ is H, halogen, $OR^{13}$, —CN, —$S(O)_2N(R^{12})_2$, —$S(O)_2R^{13}$, —C(O)$N(R^{12})_2$, $N(R^{12})_2$, $C_1$-$C_6$alkyl, halo-substituted $C_1$-$C_6$alkyl, $C_6$-$C_{14}$aryl, heteroaryl or $C_2$-$C_{14}$heterocycloalkyl, wherein the $C_2$-$C_{14}$heterocycloalkyl, $C_6$-$C_{14}$aryl and $C_3$-$C_{13}$heteroaryl are optionally substituted with 1-3 substituents independently selected from halogen, —CN, $C_1$-$C_6$alkyl, $C_1$-$C_6$alkoxy, $C_3$-$C_8$cycloalkyl, —$OR^{13}$, —C(O)$R^{13}$, $^-$OC(O)$R^{13}$, —C(O)$OR^{13}$, —$N(R^{12})_2$, —C(O)$(C(R^{12})_2)_nR^{16}$, —C(O)$N(R^{12})_2$, heterocycloalkyl, —$S(O)_2R^{13}$, —$S(O)_2N(R^{12})_2$, —$NHS(O)_2R^{13}$, $R^{13}$, $R^{10}$, —$(CH_2)_nR^{12}$, —$(CH_2)_nR^{13}$, —$(C(R^{12})_2)_nR^{16}$, halo substituted $C_1$-$C_6$alkyl and halo-substituted $C_1$-$C_6$alkoxy and each n is independently 1, 2, 3, 4, 5 or 6.

In certain embodiments of scheme (VII) the NH moiety of 6,8-dichloro-2,7-naphthyridin-1(2H)-one (24) is protected with appropriated amine protecting groups prior to subsequent reactions and then deprotected to give the final product.

EXAMPLES

The present invention is further exemplified, but not limited, by the following examples that illustrate the preparation of compounds of Formula (I) according to the invention.

Example 1

Synthesis of 6-phenyl-8-(3-(trifluoromethyl)phenylamino)-2,7-naphthyridin-1(2H)-one

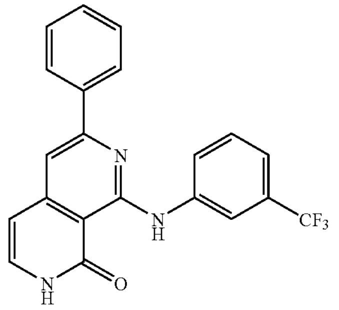 [SMILES: O=c1[nH]ccc2cc(-c3ccccc3)nc(Nc3cccc(C(F)(F)F)c3)c12]

Example 1a

4-Iodo-2-methoxynicotinic acid

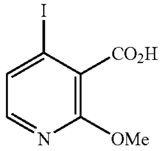 [SMILES: COc1nccc(I)c1C(=O)O]

To a solution of 4-iodo-2-methoxynicotinaldehyde (1 g, 3.58 mmol) in t-BuOH (6 mL), cooled at 25° C., is added 2-methyl-2-butene (6 mL, 2 M solution), $Na_2HPO_4$ (1.2 g) and water (3 mL). The reaction mixture is stirred for 5 minutes and sodium chlorite (800 mg, 8.9 mmol) is added slowly. Stirring of the mixture is continued until the aldehyde is completely consumed (3 hours, monitored by LCMS). The reaction is quenched with aq. formic acid. The mixture is partitioned between ethyl acetate (100 mL) and the organic extracts are washed with brine, dried over $Na_2SO_4$, filtered and concentrated. The white powder was used for the next reaction without any further purification. $^1H$ NMR 400 MHz (DMSO-$d_6$) δ 10.06 (s, 1H), 7.89 (d, 1H, J=5.6 Hz), 7.48 (d, 1H, J=5.6 Hz), 3.87 (s, 1H); MS m/z 294.1 (M+1). MS m/z 280.01 (M+1).

Example 1b

Methyl 4-iodo-2-methoxynicotinate

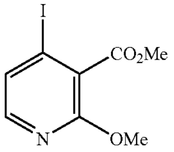 [SMILES: COC(=O)c1c(I)ccnc1OC]

4-Iodo-2-methoxynicotinic acid (800 mg, 2.87 mmol) is dissolved in MeOH (7 mL) and cooled at 0° C. Trimethylsilyldiazomethane (9 mL, 2M in hexane, 4.5 mmol) is added slowly over 20 minutes. The reaction mixture is brought to room temperature and stirred for 16 hours. The reaction mixture is concentrated and purified by silica gel column chromatography using hexane:ethyl acetate as eluent to afford the desired compound. $^1H$ NMR 400 MHz (DMSO-$d_6$) δ 7.88 (d, 1H, J=5.6 Hz), 7.34 (d, 1H, J=5.6 Hz), 4.12 (s, 3H), 3.84 (s, 1H); MS m/z 294.1 (M+1).

Example 1c

Methyl 2-methoxy-4-(phenylethynyl)nicotinate

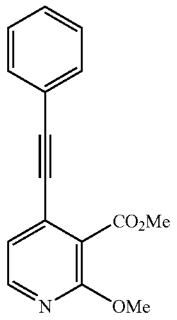 [SMILES: COC(=O)c1c(C#Cc2ccccc2)ccnc1OC]

A mixture of methyl 4-iodo-2-methoxynicotinate (400 mg, 1.36 mmol), ethynylbenzene (167 mg, 1.63 mmol), $Pd(PPh_3)_2Cl_2$ (47 mg, 0.068 mmol), CuI (7.7 mg, 0.04 mmol) and triethylamine (400 uL) is stirred at room temperature for 20 hours. The mixture is diluted with water, made alkaline with $K_2CO_3$ and extracted with $CHCl_3$. The organic layer is washed with brine, water and concentrated under vacuum. The title compound is purified by silica gel column chromatography using hexane/ethyl acetate as eluent. MS m/z 268.1 (M+1).

Example 1d 8-methoxy-3-phenyl-2,7-naphthyridin-1(2H)-one

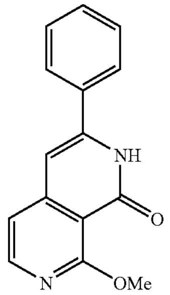 [SMILES: COc1nccc2cc(-c3ccccc3)[nH]c(=O)c12]

Methyl 2-methoxy-4-(phenylethynyl)nicotinate (100 mg, 0.37 mmol) is dissolved in 7% $NH_3$ in MeOH (3 mL) and heated at 115° C. in a sealed tube for 24 hours. The reaction mixture is cooled to 0° C. and the cyclized product is crystallized out. The compound is collected by filtration and dried after washing with hexanes. MS m/z 253.1 (M+1).

Example 1e

1-Chloro-8-methoxy-3-phenyl-2,7-naphthyridine

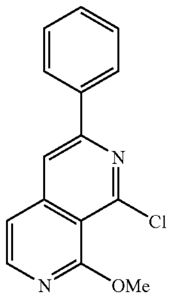 [SMILES: COc1nccc2cc(-c3ccccc3)nc(Cl)c12]

8-Methoxy-3-phenyl-2,7-naphthyridin-1(2H)-one (80 mg, 0.32 mmol) is dissolved in $CH_3CN$ (2 mL) and $POCl_3$ (59 uL, 0.64 mmol) The mixture is stirred at 80° C. for 3 hours. $POCl_3$ is removed and neutralized with sat. $NaHCO_3$. The compound is extracted with $CHCl_3$ and the organic layer is dried ($Na_2SO_4$) and evaporated to yield the crude compound and used for the next step without any further purification. MS m/z 271.1 (M+1).

Example 1f

6-Phenyl-8-(3-(trifluoromethyl)phenylamino)-2,7-naphthyridin-1(2H)-one

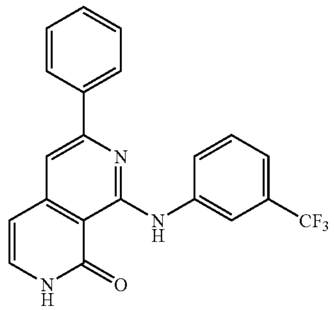 [SMILES: O=c1[nH]ccc2cc(-c3ccccc3)nc(Nc3cccc(C(F)(F)F)c3)c12]

A mixture of 1-chloro-8-methoxy-3-phenyl-2,7-naphthyridine (30 mg, 0.11 mmol) and 3-(trifluoromethyllaniline in sec-BuOH (200 uL) is irradiated in a microwave at 120° C. for 30 minutes. HCl (50 uL, 6N in dioxane) is added and stirred at room temperature for 2 hours. The reaction mixture is directly subjected to prep-HPLC to afford the title compound as a TFA salt. $^1$H NMR 400 MHz (DMSO-$d_6$) δ 12.09 (s, 1H), 10.70, (s, 1H), 10.55 (s, 1H), 8.84 (s, 1H), 8.29 (s, 1H), 8.19 (s, 1H), 8.03-7.97 9 (m, 2H), 7.69 (d, 1H, J=7.6 Hz), 7.57-7.49 (m, 3H), 7.40 (d, 1H, J=7.6 Hz), 6.72 (dd, 1H, J=3.2, 1.6 Hz); MS m/z 382.1 (M+1).

Example 2

Synthesis of 6-(3-aminopropyl)-8-(3-(trifluoromethyl)phenylamino)-2,7-naphthyridin-1(2H)-one

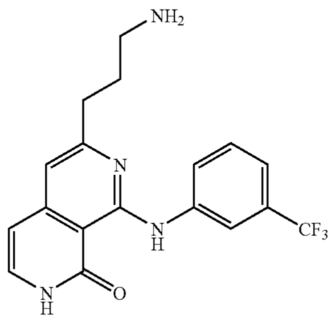 [SMILES: NCCCc1cc2cc[nH]c(=O)c2c(Nc2cccc(C(F)(F)F)c2)n1]

Example 2a

Methyl 4-(5-(1,3-dioxoisoindolin-2-yl)pent-1-ynyl)-2-methoxynicotinate

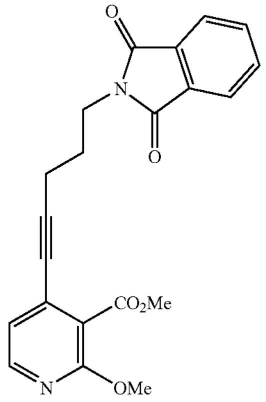 [SMILES: COC(=O)c1c(C#CCCCN2C(=O)c3ccccc3C2=O)ccnc1OC]

A mixture of methyl 4-iodo-2-methoxynicotinate (400 mg, 1.36 mmol), 2-(pent-4-ynyl)isoindoline-1,3-dione (318 mg, 1.5 mmol), $Pd(PPh_3)_2Cl_2$ (47 mg, 0.068 mmol), CuI (7.7 mg, 0.04 mmol) and triethylamine (400 uL) is stirred at room temperature for 20 hours. The mixture is diluted with water, made alkaline with $K_2CO_3$ and extracted with $CHCl_3$. The organic layer is washed with brine, water and concentrated under vacuum. The title compound is purified by silica gel column chromatography using hexane/ethyl acetate as eluent. MS m/z 379.1 (M+1).

Example 2b 2-(3-(8-Methoxy-1-oxo-1,2-dihydro-2,7-naphthyridin-3-yl)propyl)isoindoline-1,3-dione

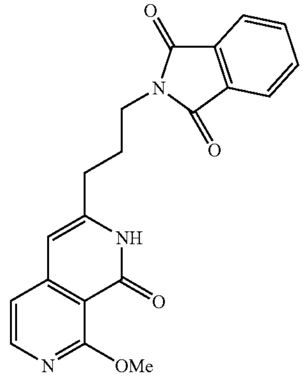 [SMILES: COc1nccc2cc(CCCN3C(=O)c4ccccc4C3=O)[nH]c(=O)c12]

Methyl 4-(5-(1,3-dioxoisoindolin-2-yl)pent-1-ynyl)-2-methoxynicotinate (100 mg, 0.26 mmol) is dissolved in 7% $NH_3$ in MeOH (3 mL) and heated at 115° C. in a sealed tube for 24 hours. The reaction mixture is cooled and the solvents are removed by evaporation. The cyclized product is separated using silica gel column chromatography using hexan: ethyl acetate as solvent. MS m/z 364.1 (M+1).

Example 2c 2-(3-(1-chloro-8-methoxy-2,7-naphthyridin-3-yl)propyl)isoindoline-1,3-dione

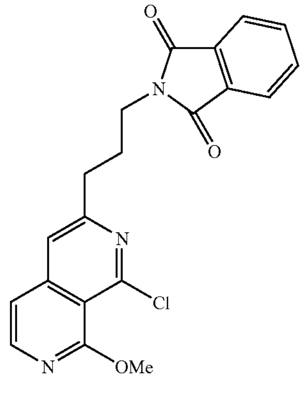 [SMILES: COc1nccc2cc(CCCN3C(=O)c4ccccc4C3=O)nc(Cl)c12]

2-(3-(8-Methoxy-1-oxo-1,2-dihydro-2,7-naphthyridin-3-yl)propyl)isoindoline-1,3-dione (200 mg, 0.55 mmol) is dissolved in $CH_3CN$ (2 mL) and $POCl_3$ (59 uL, 0.64 mmol) The mixture is stirred at 80° C. for 3 hours. $POCl_3$ is removed and neutralized with sat. $NaHCO_3$. The compound is extracted with $CHCl_3$ and the organic layer is dried ($Na_2SO_4$) and evaporated to yield the crude compound, which is used in the next step without any further purification. MS m/z 382.1 (M+1).

Example 2d 6-(3-aminopropyl)-8-(3-(trifluoromethyl)phenylamino)-2,7-naphthyridin-1(2H)-one

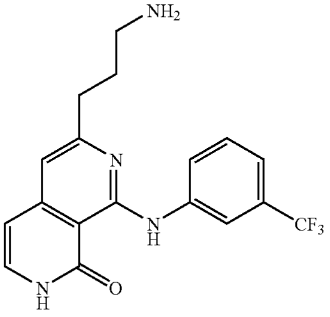 [SMILES: NCCCc1cc2cc[nH]c(=O)c2c(Nc2cccc(C(F)(F)F)c2)n1]

A mixture of 2-(3-(1-chloro-8-methoxy-2,7-naphthyridin-3-yl)propyl)isoindoline-1,3-dione (60 mg, 0.14 mmol) and 3-(trifluoromethyl)aniline (24.8 mg, 0.15 mmol) in sec-BuOH (200 uL) is irradiated in a microwave at 120° C. for 30 minutes. HCl (50 uL, 6N in dioxane) is added and stirred at room temperature for 2 hours. The solvent is completely removed and the mixture is dried. The mixture is then dissolved in EtOH (1 mL) and hydrazine (6.4 mg, 0.2 mmol) is added. The mixture is stirred at 60° C. for 2 hours. The reaction mixture is directly subjected to prep-HPLC to afford the title compound as a TFA salt. $^1H$ NMR (400 MHz, MeOD-$d_4$) δ 8.42 (s, 1H), 7.74 (d, 1H), 7.29 (t, 1H), 7.12 (d, 1H), 6.43 (d, 1H), 6.00 (d, 1H), 5.42 (s, 1H), 3.99 (t, 2H), 3.60 (m, 3H), 2.93 (t, 2H); MS m/z 363.20 (M+1).

Example 3

Synthesis of 6-(2-aminoethylamino)-8-(3-(trifluoromethyl)phenylamino)-2,7-naphthyridin-1(2H)-one

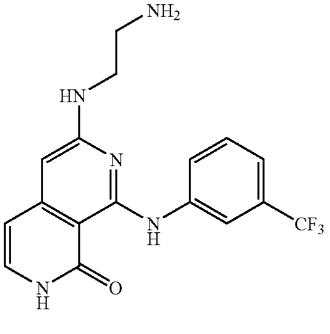 [SMILES: NCCNc1cc2cc[nH]c(=O)c2c(Nc2cccc(C(F)(F)F)c2)n1]

Example 3a (E)-2,6-dichloro-4-(2-(pyrrolidin-1-yl)vinyl)nicotinonitrile

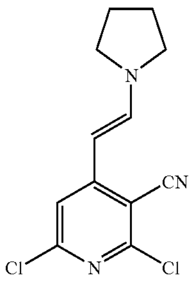 [SMILES: N#Cc1c(/C=C/N2CCCC2)cc(Cl)nc1Cl]

A mixture of dimethylformamide dimethylacetal (20 mL, 0.149 mol) and pyrrolidine (18.7 mL, 0.224 mol) is stirred at 95° C. for 2 hours under $N_2$ and then the reaction mixture is distilled at atmospheric pressure under $N_2$ to remove volatiles. Then the reaction mixture is distilled under reduced pressure. The fraction is distilled at approximately 100° C. (bp) at 100 mbar while the heating bath temperature is gradually raised to 150° C. 12 g of the condensation product is collected as a colorless oil. A suspension of the above condensation product (6 g, 0.032 mol) in 10 mL of isopropanol is treated with 3-cyano-4-methylpyridine (10.1 g, 0.016 mol) and is stirred at 90° C. for 2 hours and the precipitate is filtered to give 2,6-dichloro-4-(2-(pyrrolidin-1-yl)vinyl)nicotinonitrile as a brick red solid.

Example 3b 6,8-dichloro-2,7-naphthyridin-1(2H)-one

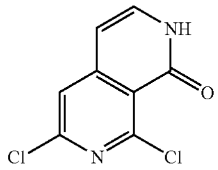 [SMILES: O=c1[nH]ccc2cc(Cl)nc(Cl)c12]

A suspension 2,6-dichloro-4-(2-(pyrrolidin-1-yl)vinyl) nicotinonitrile (2 g, 7.457 mmol) in 6 mL of conc-HCl is stirred at 60° C. for 6 hours and stirred at room temperature for 1 hour. The reaction mixture is added to 50 mL of water and the precipitate is collected by filtration and washed with water and ether to give 1.4 g of 6,8-dichloro-2,7-naphthyridin-1(2H)-one as a crude product (pale yellow solid). The dichloro compound was used for the reaction transformations without any further purification.

Example 3c 6-(2-aminoethylamino)-8-(3-(trifluoromethyl)phenylamino)-2,7-naphthyridin-1(2H)-one

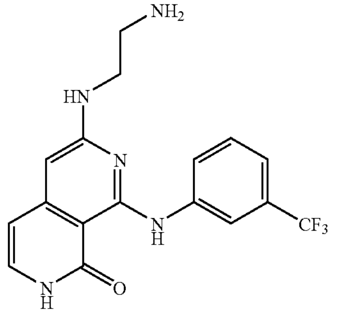 [SMILES: NCCNc1cc2cc[nH]c(=O)c2c(Nc2cccc(C(F)(F)F)c2)n1]

A suspension of 6,8-dichloro-2,7-naphthyridin-1(2H)-one (50 mg, 0.23 mmol) and 3-trifluoromethylaniline (37.6 mg, 0.23 mmol) in 0.1 mL NMP is irradiated by microwave at 130° C. for 45 minutes. LCMS shows the quantitative conversion and the crude product is used for the next amination reaction step without any further purification.

Ethane-1,2-diamine (15 mg, 0.25 mmol) is added to the above reaction mixture and is then irradiated by microwave at 155° C. for 45 minutes. The mixture is directly subjected to prep-HPLC to afford the title compound. $^1$H NMR (400 MHz, MeOD-$d_4$) δ 8.40 (s, 1H), 7.63 (d, 1H), 7.39 (t, 1H), 7.17 (d, 1H), 7.11 (d, 1H), 6.12 (d, 1H), 5.80 (s, 1H), 3.56 (t, 2H), 3.37 (s, 3H), 3.03 (t, 2H); MS m/z 376.15 (M+1).

Example 4

Synthesis of 6-(2-aminoethylamino)-8-(3-(trifluoromethyl)phenylamino)-2,7-naphthyridin-1(2H)-one

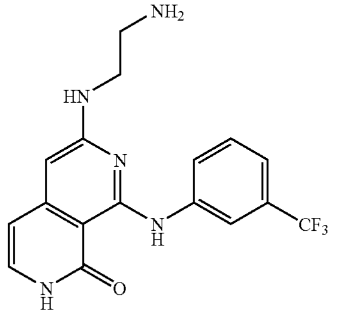 [SMILES: NCCNc1cc2cc[nH]c(=O)c2c(Nc2cccc(C(F)(F)F)c2)n1]

Example 4a (E)-2,6-Dichloro-4-(2-(dimethylamino)vinyl)nicotinonitrile

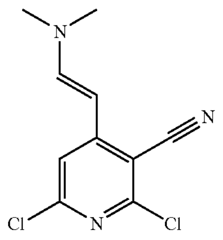

To 2,6-dichloro-4-methylnicotinonitrile (20.3 g, 0.108 mol) in 200 mL of isopropyl alcohol is added N,N-dimethylformamide dimethylacetal (14.4 mL, 0.108 mol) and the reaction is stirred at 65° C. for 18 hrs. After the reaction is cooled to ambient temperature, the precipitate is collected by filtration, washed with 50 mL of isopropyl alcohol, and air dried giving (E)-2,6-Dichloro-4-(2-(dimethylamino)vinyl)nicotinonitrile as a yellow solid. MS ($ES_+$) calcd. 242.02. found 242.10 ($MH_+$). H-NMR (600 MHz, DMSO-$d_6$) 2.90 (br.s, 3H), 3.17 (br.s, 3H), 5.05 (d, J=12.6 Hz, 1H), 7.61 (s, 1H), 8.09 (d, J=12.6 Hz, 1H).

Example 4b 6,8-dichloro-2,7-naphthyridin-1(2H)-one

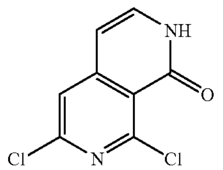 [SMILES: O=c1[nH]ccc2cc(Cl)nc(Cl)c12]

To (E)-2,6-dichloro-4-(2-(dimethylamino)vinyl)nicotinonitrile (2.00 g, 8.26 mmol) in a 40 ml glass vial is added 8 mL of conc. HCl and the vial is sealed. The reaction is stirred at a temperature of 43° C. to 45° C. for 18 hrs. After cooling to ambient temperature 10 g of ice water is added to the resulting heavy yellow slurry. The precipitate is collected by filtration, washed successively with cold water (10 mL), ether (10 mL), and ethyl acetate (20 mL), and dried under vacuum, giving 6,8-dichloro-2,7-naphthyridin-1(2H)-one as a slightly yellow solid. MS ($ES_+$) calcd. 214.97. found 215.00 ($MH_+$). H-NMR (600 MHz, DMSO-$d_6$) 6.53 (d, J=6.6 Hz, 1H), 7.51 (t, J=6.6 Hz, 1H), 7.78 (s, 1H), 11.77 (br.s, 1H).

Example 4c 6-(2-aminoethylamino)-8-(3-(trifluoromethyl)phenylamino)-2,7-naphthyridin-1(2H)-one

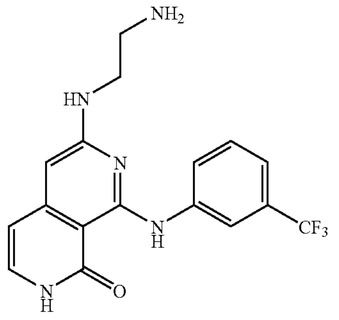 [SMILES: NCCNc1cc2cc[nH]c(=O)c2c(Nc2cccc(C(F)(F)F)c2)n1]

A suspension of 6,8-dichloro-2,7-naphthyridin-1(2H)-one (50 mg, 0.23 mmol) and 3-trifluoromethylaniline (37.6 mg, 0.23 mmol) in 0.1 mL NMP is irradiated by microwave at 130° C. for 45 minutes. LC/MS shows quantitative conversion and the crude product is used for the next amination reaction step without further purification.

Ethane-1,2-diamine (15 mg, 0.25 mmol) is added to the above reaction mixture and is then irradiated by microwave at 155° C. for 45 minutes. The mixture is directly subjected to prep-HPLC to give 6-(2-aminoethylamino)-8-(3-(trifluoromethyl)phenylamino)-2,7-naphthyridin-1(2H)-one. $^1H$ NMR (400 MHz, MeOD-$d_4$) δ 8.40 (s, 1H), 7.63 (d, 1H), 7.39 (t, 1H), 7.17 (d, 1H), 7.11 (d, 1H), 6.12 (d, 1H), 5.80 (s, 1H), 3.56 (t, 2H), 3.37 (s, 3H), 3.03 (t, 2H); MS m/z 376.15 (M+1).

Example 5

Synthesis of 8-(3-methyl-4-((R)-2-methylmorpholino)phenylamino)-6-(pyrimidin-5-yl)-2,7-naphthyridin-1(2H)-one

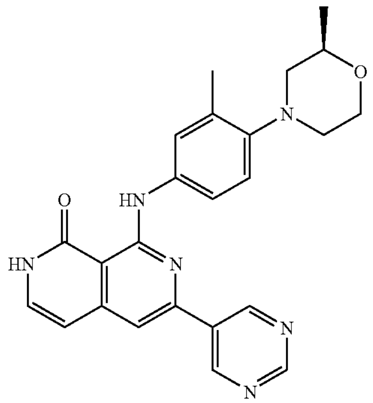 [SMILES: Cc1cc(Nc2nc(-c3cncnc3)cc3cc[nH]c(=O)c23)ccc1N1CCO[C@H](C)C1]

Example 5a

(R)-2-methylmorpholine hydrochloride

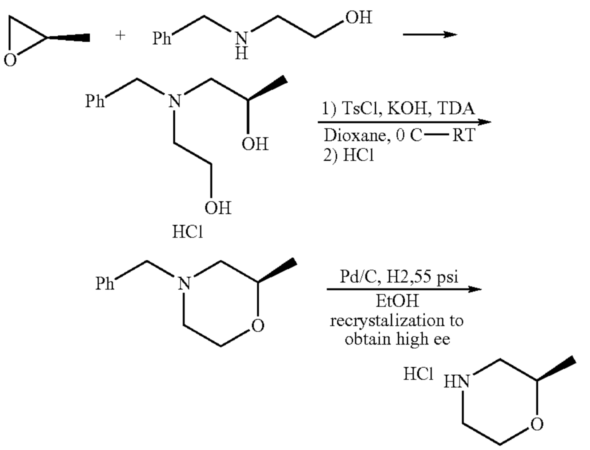

TDA: tris(3,6-dioxaheptyl)amine

N-Benzylethanolamine (39.8 g, 250 mmol) was stirred with (R)-(+)-propylene oxide (17.6 g, 99%, 300 mmol) in a sealed tube at 45° C. overnight (17 h). Evaporation of the excess of propylene oxide in vacuo gave the diol residue which was used directly for the next step. The diol (270 mmol) was dissolved in dioxane (250 mL, anhydrous). KOH (52 g, 810 mmole, powder) and tris(3,6-dioxaheptyl)amine (0.91 mL, 2.7 mmole) were added and the mixture was cooled to 0° C. after which tosyl chloride (51.5 g, 270 mmol, in 250 mL anhydrous dioxane) was added dropwise. The reaction mixture was allowed to stir at 0° C. for 45 minutes after which it was warmed to room temperature and stirred overnight. The reaction mixture was filtered (to remove insolubles, KCl, KOH) and the filtrate was evaporated in vacuo. HCl (2 N, 400 mL) was added to the product and the resulting acidic aqueous solution was washed with ethyl acetate (200 mL×2), the solution cooled to 0° C. and neutralized by adding NaOH (pH monitored with pH paper). The mixture was then extracted with ethyl acetate. The organic phase was washed with brine, then dried over $Na_2SO_4$. The crude was purified by chromatography on silica gel (5~20% ethyl acetate in DCM) to give the cyclized product.

The free base is converted to the HCl salt and recrystallized as follows: The free base obtained above was treated with HCl (2 M in ether, 50 mL) and subject to evaporation to yield the HCl salt. The salt was mixed with ethyl acetate (120 mL) and heated to reflux. EtOH was added dropwise cautiously until the entire solid just dissolved. Then it was cooled to room temperature and kept in the refrigerator overnight. The precipitate obtained was filtered to give pure product.

A solution of the recrystallized salt (6.28 g, 27.6 mmole) in ethanol (30 mL) was hydrogenated over 10% Pd/C (0.63 g) under pressure (55 psi) at room temperature overnight. The mixture was filtered through celite (washed with EtOH) and the filtrate was evaporated to give an oil. Addition of ether and subsequent evaporation gave R-2-methylmorpholine hydrochloride (>99% ee) as a hygroscopic solid.

Example 5b

(R)-3-methyl-4-(2-methylmorpholino)aniline

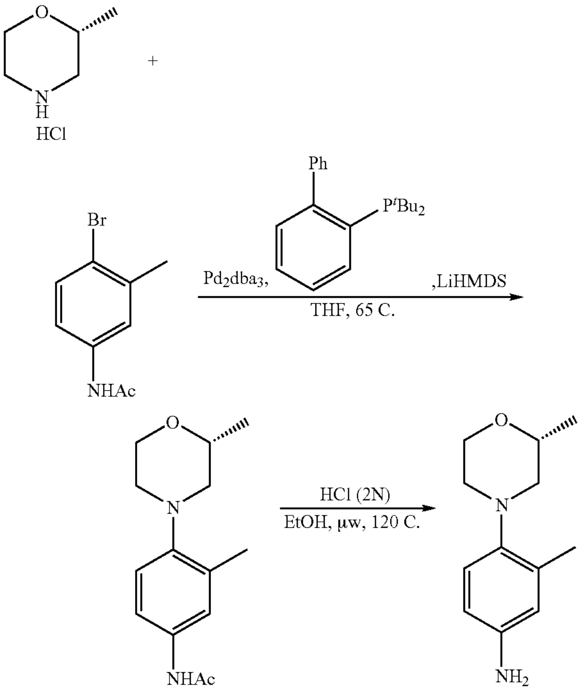

Under $N_2$ atmosphere, to a mixture of (R)-2-methylmorpholine HCl salt (1.1 g, 8 mmol), N-(4-bromo-3-methylphenyl)acetamide (1.7 g, 7.45 mmol), Pd2 dba3 (92 mg, 0.1 mmol) and 2-(di-t-butylphosphino)biphenyl (72 mg, 0.24 mmol) was added LiHMDS (28 mmol, 28 mL, 1 M in THF). The resulting mixture was stirred at 65° C. overnight. THF was removed under reduced pressure. The residue was treated with HCl (1N), basified with NaHCO3, and then extracted with EtOAc. The combined organics was washed with brine and dried over $Na_2SO_4$. The crude was purified by flash chromatography on silica gel (40-100% EtOAc in hexanes) to afford the product as a yellow solid.

A solution of the product obtained above (693 mg) in EtOH—HCl(2N) (1:1, 14 mL) was heated for 30 minutes in a microwave. The mixture was cooled to room temperature, and EtOH was removed by rotavapor. The residue was dissolved in EtOAc, washed with NaHCO3, brine, then dried over $Na_2SO_4$. Upon removal of solvent, the product was obtained as a brown oil which was used in next step without further purification.

Example 5c 8-(3-methyl-4-((R)-2-methylmorpholino)phenylamino)-6-(pyrimidin-5-yl)-2,7-naphthyridin-1(2H)-one

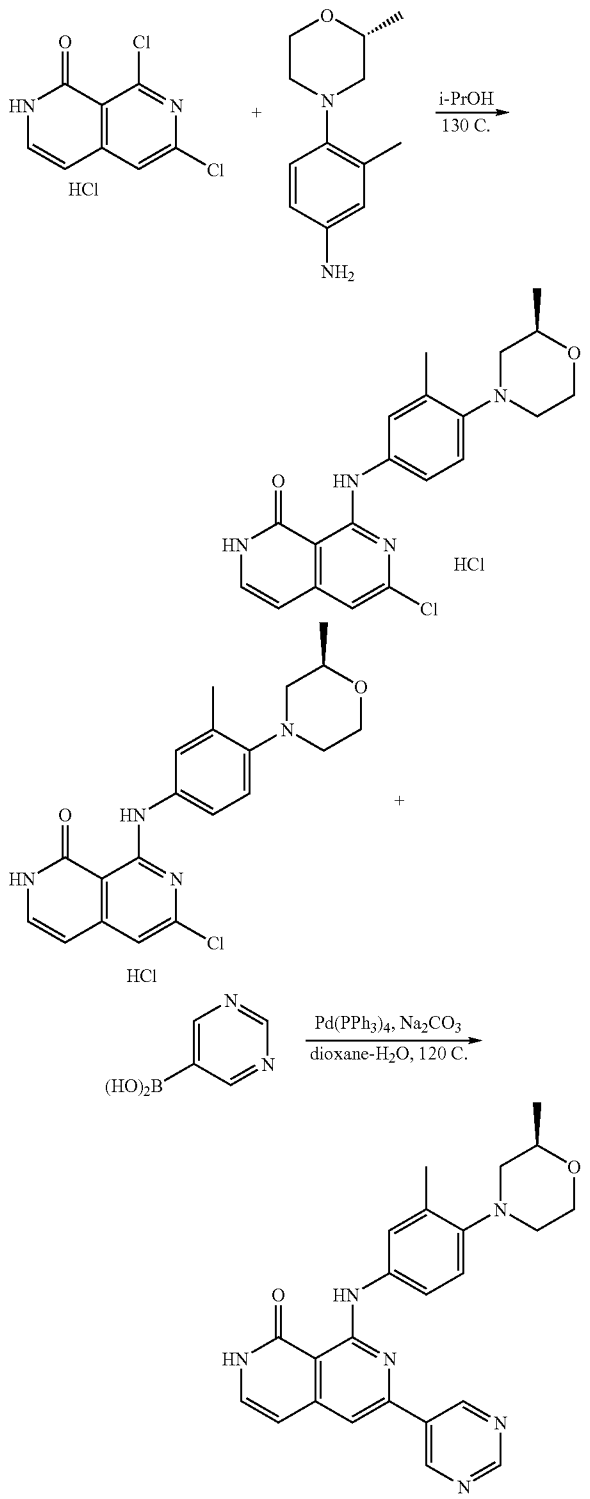

A mixture of dichloro compound (691 mg, 2.75 mmol) and aniline compound (567 mg, 2.75 mmol) in i-PrOH (10 mL) was heated at 130° C. for 2 days in a sealed tube. The solid was collected by filtration (960 mg). To a mixture of the monochloro compound (211 mg, 0.5 mmol), pyrimidin-5-ylboronic acid (124 mg, 1 mmol) and $Pd(PPh_3)_4$ (29 mg, 0.025 mmol) in dioxane (10 mL) was added $Na_2CO_3$ (1M, 2 mL) and water (2 mL). The reaction mixture was heated at 120° C. for 30 minutes in a microwave. The mixture was extracted with DCM (30 mL×3), the combined organics was washed with brine, then dried over $Na_2SO_4$. The solvent was removed, and the residue was subjected to flash chromatography on silica gel (0-10% MeOH in DCM) to afford the product 8-(3-methyl-4-((R)-2-methylmorpholino)phenylamino)-6-(pyrimidin-5-yl)-2,7-naphthyridin-1(2H)-one as a yellow solid. $^1$H NMR (400 MHz, $CDCl_3$) δ 11.44 (s, 1H), 9.80 (s, 1H), 9.40 (s, 2H), 9.27 (s, 1H, br), 7.76 (dd, J=8.4, 2.4 Hz, 1H), 7.58 (d, J=2.4 Hz, 1H), 7.24 (d, J=6.4 Hz, 1H), 7.12 (s, 1H), 7.07 (d, J=8.4 Hz, 1H), 6.49 (d, J=6.4 Hz, 1H), 4.03-3.95 (m, 1H), 3.90-3.77 (m, 2H), 3.03-2.81 (m, 3H), 2.55 (dd, J=11.2, 9.6 Hz, 1H), 2.37 (s, 3H), 1.23 (d, J=6.4 Hz, 3H).

Example 6

Synthesis of (R)-8-(3-methyl-4-(2-methylmorpholino)phenylamino)-6-(6-methylpyridin-3-yl)-2,7-naphthyridin-1(2H)-one

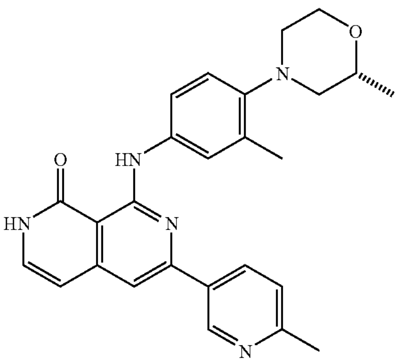 [SMILES: Cc1ccc(-c2cc3cc[nH]c(=O)c3c(Nc3ccc(N4CCO[C@H](C)C4)c(C)c3)n2)cn1]

A mixture of (R)-6-chloro-8-(3-methyl-4-(2-methylmorpholino)phenylamino)-2,7-naphthyridin-1(2H)-one (770 mg, 2.0 mmol), 2-methyl-5-(4,4,5,5-tetramethyl-1,3,2-dioxaborolan-2-yl)pyridine (0.8 g, 3.65 mmol), $Pd(PPh_3)_4$ (200.0 mg, 0.173 mmol) and $Na_2CO_3$ (1.0 g, 9.45 mmol) in a mixed solvent of dioxane (16.0 mL) and $H_2O$ (4.0 mL) was purged with $N_2$, heated at 90° C. for 16 hours, evaporated to result in a residue which was subjected to chromatography with gradient mixed solvents from DCM/MeOH/28% aqueous $NH_4OH$ (49:10:1) to (19:10:1) afforded a product which was then recrystallized in toluene to afford the title compound. $^1$H NMR (DMSO-$d_6$) δ 1.12 (d, J=6.4 Hz, 3H, $CH_3$), 2.31 (s, 3H, $CH_3$), 2.42 (m, 1H), 2.55 (s, 3H, $CH_3$), 2.70 (m, 1H), 2.85-2.95 (2H), 3.65-3.73 (2H), 3.85 (m, 1H), 6.53 (d, J=7.2 Hz, 1H), 7.07 (d, J=8.4 Hz, 1H), 7.42 (d, J=8.4 Hz, 1H), 7.43 (d, J=7.2 Hz, 1H), 7.48 (s, 1H), 7.66 (d, J=2.4 Hz, 1H), 7.74 (dd, J=8.0, 2.4 Hz, 1H), 8.35 (dd, J=8.8, 2.4 Hz, 1H), 9.20 (s, 1H), 11.77 (br s, 1H, NH), 11.92 (br s, 1H, NH); ESI-MS ink 442.2 ($MH^+$); Anal. Calcd for $C_{26}H_{27}N_5O_2$: C, 70.73; H, 6.16; N, 15.86. Found: C, 70.73; H, 6.13; N, 15.83.

Example 7

Synthesis of 6-(6-methoxypyrazin-2-yl)-8-(4-morpholinophenylamino)-2,7-naphthyridin-1(2H)-one

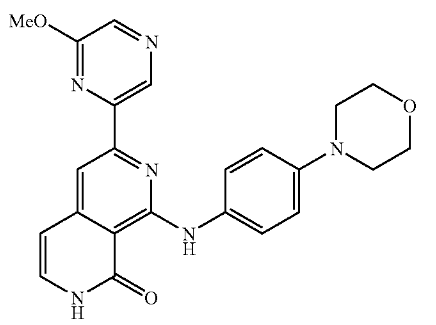 [SMILES: COc1cncc(-c2cc3cc[nH]c(=O)c3c(Nc3ccc(N4CCOCC4)cc3)n2)n1]

6-chloro-8-(4-morpholinophenylamino)-2,7-naphthyridin-1(2H)-one (30 mg, 0.084 mmol) was dissolved in DMF (1 mL) in a microwave vial and 2-methoxy-6-(tributylstannyl)pyrazine (40 mg, 0.1 mmol) was added followed by $PdCl_2dppf$ (6.1 mg, 0.0084 mmol) at room temperature. The vial was flushed with nitrogen and closed the cap and subjected to microwave irradiation at 135 C for 60 minutes. The reaction mixture was diluted with DMSO and purified by prep HPLC. The compound was isolated as a TFA salt. $^1H$ NMR (400 MHz, DMSO-$d_6$) δ 11.14 (s, 1H), 8.96 (s, 1H), 8.33 (s, 1H), 7.68 (s, 1H), 7.67 (d, 2H, J=8.8 Hz), 7.38 (m, 1H), 6.95 (d, 2H, J=8.8 Hz), 6.57 (d, 1H, J=7.2 Hz), 4.0 (s, 3H), 3.69 (t, 4H, J=4.8 Hz), 3.04 (t, 4H, J=4.8 Hz); MS m/z 431.2 (M+1).

Example 8

Synthesis of 8-(Alkylamino)-6-aryl-2-methyl-2,7-naphthyridin-1(2H)-ones

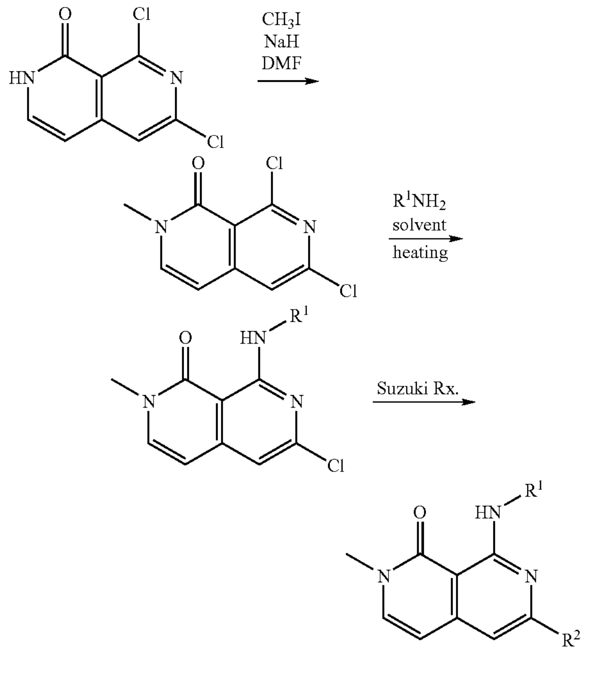

Example 8a 6,8-Dichloro-2-methyl-2,7-naphthyridin-1(2H)-one

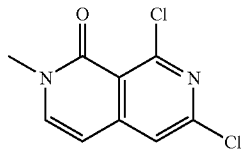

To a solution of 6,8-dichloro-2,7-naphthyridin-1(2H)-one (215.0 mg, 1.0 mmol) in dry DMF (10 mL) was added NaH (100 mg, 60% in mineral oil, 2.5 mmol) at 0° C. under $N_2$. After the reaction mixture was allowed to be warmed to room temperature and stirred for 20 minutes, $CH_3I$ (0.25 mL, 568.08 mg, 4.0 mmol) was added via syringe. The reaction mixture was stirred at room temperature for 18 hours and concentrated under reduced pressure. The residue was diluted with EtOAc (100 mL), washed with saturated $NH_4Cl$ solution (2×50 mL), water (30 mL) and brine (20 mL), and concentrated to afford the crude title compound. ESI-MS m/z 229.0 ($MH^+$).

Example 8b

6-Chloro-2-methyl-8-(methylamino)-2,7-naphthyridin-1(2H)-one

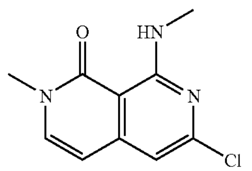

A mixture of 6,8-dichloro-2-methyl-2,7-naphthyridin-1(2H)-one (46 mg, 0.2 mmol) and $CH_3NH_2$ solution in THF (2.0 M, 2.5 mL) was heated at 95° C. for 5 hours and evaporated to afford the crude title compound. ESI-MS m/z 224.0 ($MH^+$).

Example 8c

2-Methyl-8-(methylamino)-6-(pyrimidin-5-yl)-2,7-naphthyridin-1(2H)-one

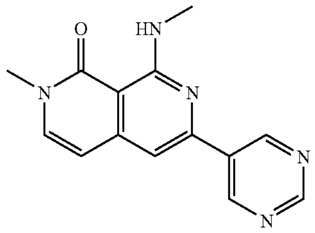 [SMILES: CNc1nc(-c2cncnc2)cc2ccn(C)c(=O)c12]

A mixture of crude 6-chloro-2-methyl-8-(methylamino)-2,7-naphthyridin-1(2H)-one (6 mg, ~0.025 mmol), pyrimidin-5-ylboronic acid (6.2 mg, 0.05 mmol), $Pd(PPh_3)_4$ (2.5 mg, 0.002 mmol) and $Na_2CO_3$ (10.6 mg, 0.1 mol) in a mixed solvent of dioxane (1.5 mL) and $H_2O$ (0.5 mL) was purged with $N_2$, heated at 90° C. for 16 hours and evaporated to result in a residue that was subjected to HPLC purification to afford TFA salt of the title compound. ESI-MS m/z 268.1 ($MH^+$).

By repeating the procedures described in the above examples, using appropriate starting materials, the following compounds of Formula I, as identified in Table 1, are obtained.

TABLE 1

| No | Structure | Physical Data $^1H$ NMR 400 MHz (DMSO-$d_6$) and/or MS (m/z) |
|---|---|---|
| 1 | 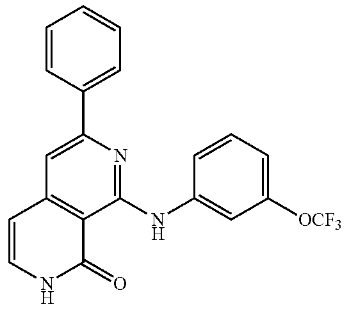 [SMILES: O=c1[nH]ccc2cc(-c3ccccc3)nc(Nc3cccc(OC(F)(F)F)c3)c12] | MS m/z 398.1 (M + 1). |
| 2 | 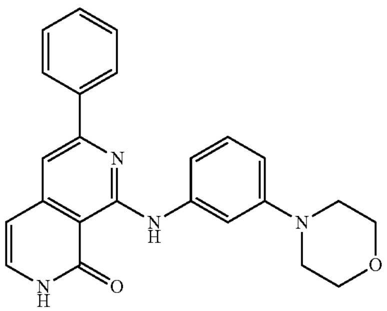 [SMILES: O=c1[nH]ccc2cc(-c3ccccc3)nc(Nc3cccc(N4CCOCC4)c3)c12] | MS m/z 399.1 (M + 1). |
| 3 | 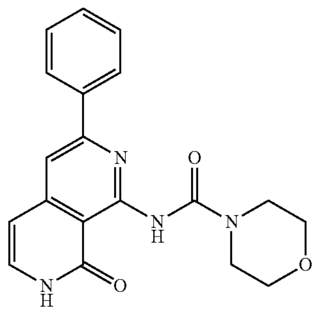 [SMILES: O=C(Nc1nc(-c2ccccc2)cc2cc[nH]c(=O)c12)N1CCOCC1] | MS m/z 351.1 (M + 1). |
| 4 | 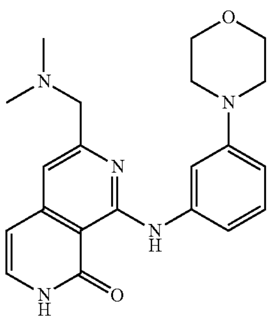 [SMILES: CN(C)Cc1cc2cc[nH]c(=O)c2c(Nc2cccc(N3CCOCC3)c2)n1] | MS m/z 380.2 (M + 1). |

TABLE 1-continued
| No | Structure | Physical Data $^1H$ NMR 400 MHz (DMSO-$d_6$) and/or MS (m/z) |
|---|---|---|
| 5 | 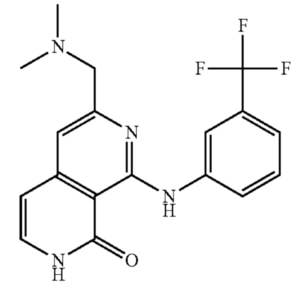 [SMILES: CN(C)Cc1cc2cc[nH]c(=O)c2c(Nc2cccc(C(F)(F)F)c2)n1] | MS m/z 363.1 (M + 1). |
| 6 | 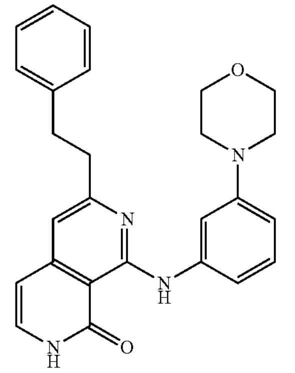 [SMILES: O=c1[nH]ccc2cc(CCc3ccccc3)nc(Nc3cccc(N4CCOCC4)c3)c12] | MS m/z 427.1 (M + 1). |
| 7 | 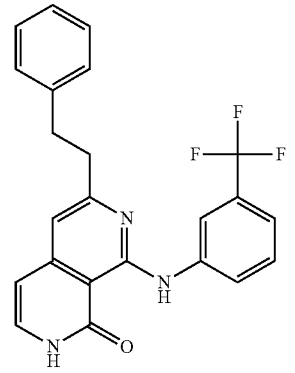 [SMILES: O=c1[nH]ccc2cc(CCc3ccccc3)nc(Nc3cccc(C(F)(F)F)c3)c12] | MS m/z 410.1 (M + 1). |
| 8 | 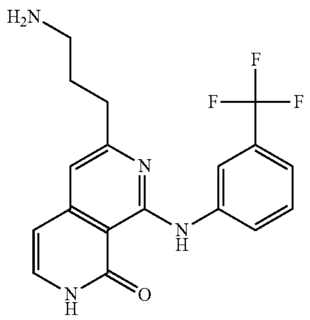 [SMILES: NCCCc1cc2cc[nH]c(=O)c2c(Nc2cccc(C(F)(F)F)c2)n1] | MS m/z 363.14 (M + 1). |

TABLE 1-continued
| No | Structure | Physical Data $^1H$ NMR 400 MHz (DMSO-$d_6$) and/or MS (m/z) |
|---|---|---|
| 9 | 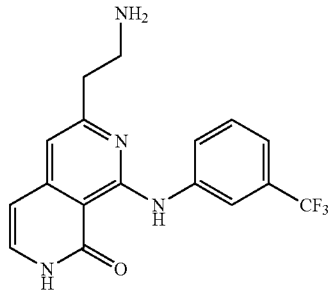 [SMILES: NCCc1cc2cc[nH]c(=O)c2c(Nc2cccc(C(F)(F)F)c2)n1] | MS m/z 349.1 (M + 1). |
| 10 | 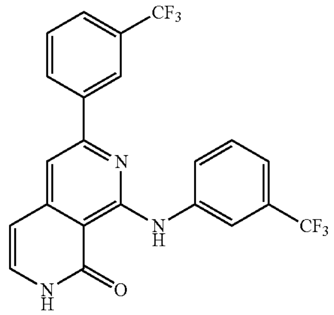 [SMILES: O=c1[nH]ccc2cc(-c3cccc(C(F)(F)F)c3)nc(Nc3cccc(C(F)(F)F)c3)c12] | MS m/z 450.1 (M + 1). |
| 11 | 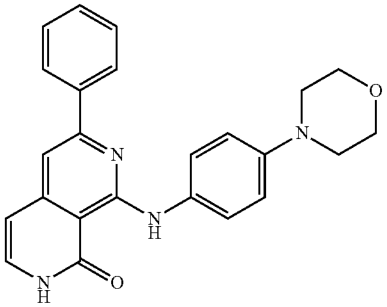 [SMILES: O=c1[nH]ccc2cc(-c3ccccc3)nc(Nc3ccc(N4CCOCC4)cc3)c12] | MS m/z 399.1 (M + 1). |
| 12 | 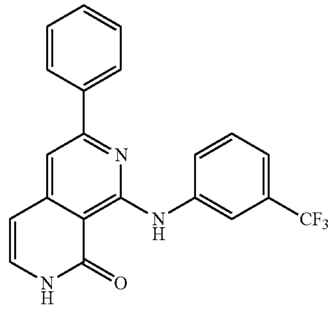 [SMILES: O=c1[nH]ccc2cc(-c3ccccc3)nc(Nc3cccc(C(F)(F)F)c3)c12] | MS m/z 382.1 (M + 1). |
| 13 | 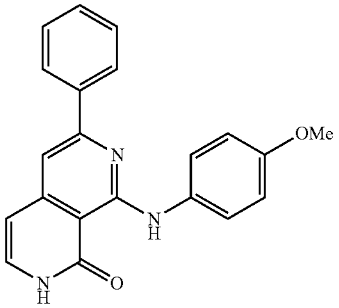 [SMILES: COc1ccc(Nc2nc(-c3ccccc3)cc3cc[nH]c(=O)c23)cc1] | MS m/z 344.2 (M + 1). |

TABLE 1-continued
| No | Structure | Physical Data $^1H$ NMR 400 MHz ($DMSO-d_6$) and/or MS (m/z) |
|---|---|---|
| 14 | 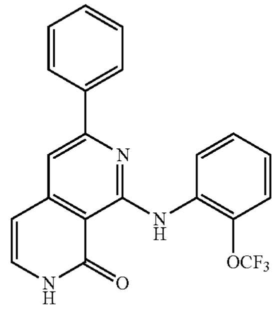 [SMILES: O=c1[nH]ccc2cc(-c3ccccc3)nc(Nc3ccccc3OC(F)(F)F)c12] | MS m/z 398.1 (M + 1). |
| 15 | 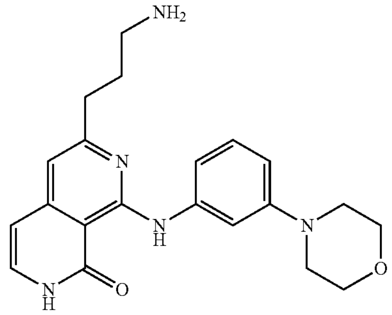 [SMILES: NCCCc1cc2cc[nH]c(=O)c2c(Nc2cccc(N3CCOCC3)c2)n1] | MS m/z 380.1 (M + 1). |
| 16 | 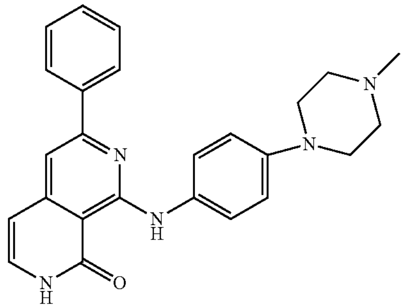 [SMILES: CN1CCN(c2ccc(Nc3nc(-c4ccccc4)cc4cc[nH]c(=O)c34)cc2)CC1] | MS m/z 412.2 (M + 1). |
| 17 | 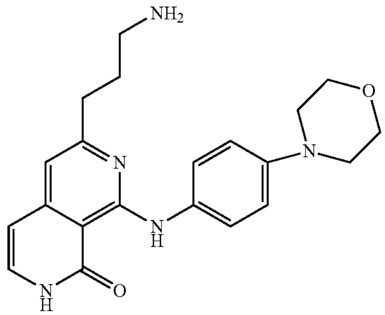 [SMILES: NCCCc1cc2cc[nH]c(=O)c2c(Nc2ccc(N3CCOCC3)cc2)n1] | MS m/z 380.2 (M + 1). |

TABLE 1-continued
| No | Structure | Physical Data $^1H$ NMR 400 MHz ($DMSO-d_6$) and/or MS (m/z) |
|---|---|---|
| 18 | 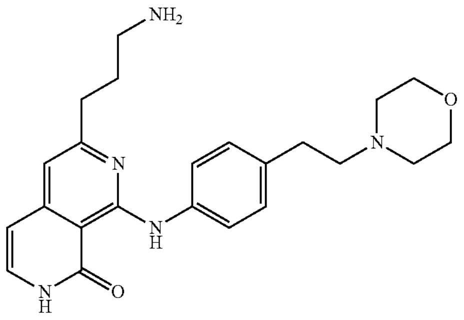 [SMILES: NCCCc1cc2cc[nH]c(=O)c2c(Nc2ccc(CCN3CCOCC3)cc2)n1] | MS m/z 408.2 (M + 1). |
| 19 | 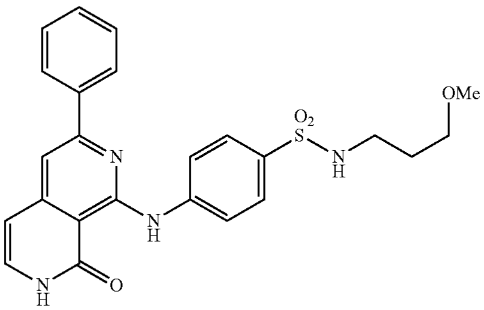 [SMILES: COCCCNS(=O)(=O)c1ccc(Nc2nc(-c3ccccc3)cc3cc[nH]c(=O)c23)cc1] | MS m/z 465.1 (M + 1). |
| 20 | 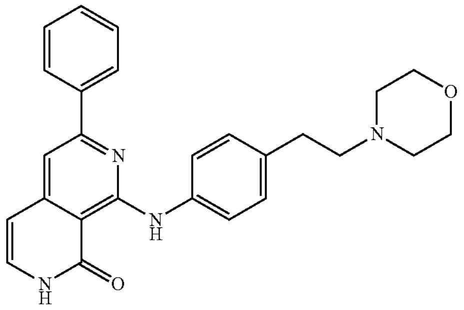 [SMILES: O=c1[nH]ccc2cc(-c3ccccc3)nc(Nc3ccc(CCN4CCOCC4)cc3)c12] | MS m/z 427.1 (M + 1). |
| 21 | 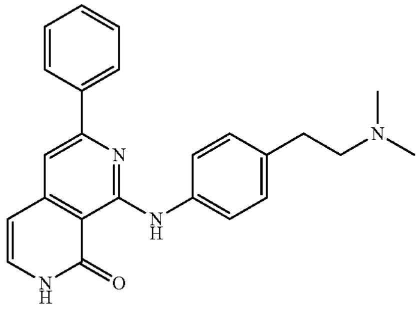 [SMILES: CN(C)CCc1ccc(Nc2nc(-c3ccccc3)cc3cc[nH]c(=O)c23)cc1] | MS m/z 385.2 (M + 1). |

TABLE 1-continued
| No | Structure | Physical Data $^1H$ NMR 400 MHz (DMSO-$d_6$) and/or MS (m/z) |
|---|---|---|
| 22 | 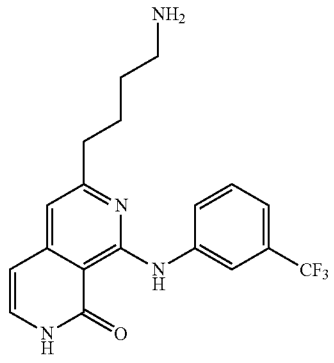 [SMILES: NCCCCc1cc2cc[nH]c(=O)c2c(Nc2cccc(C(F)(F)F)c2)n1] | MS m/z 377.1 (M + 1). |
| 23 | 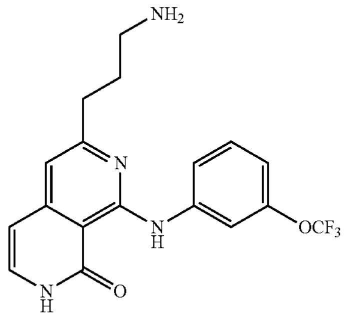 [SMILES: NCCCc1cc2cc[nH]c(=O)c2c(Nc2cccc(OC(F)(F)F)c2)n1] | MS m/z 379.2 (M + 1). |
| 24 | 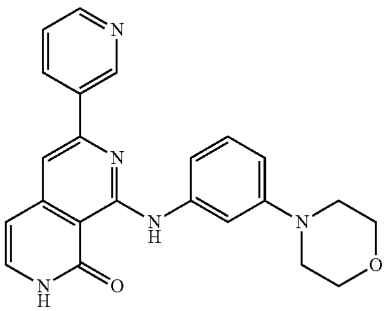 [SMILES: O=c1[nH]ccc2cc(-c3cccnc3)nc(Nc3cccc(N4CCOCC4)c3)c12] | MS m/z 400.1 (M + 1). |
| 25 | 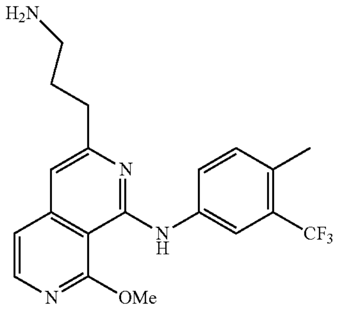 [SMILES: COc1nccc2cc(CCCN)nc(Nc3ccc(C)c(C(F)(F)F)c3)c12] | MS m/z 391.17 (M + 1). |

TABLE 1-continued
| No | Structure | Physical Data $^1$H NMR 400 MHz (DMSO-$d_6$) and/or MS (m/z) |
|---|---|---|
| 26 | 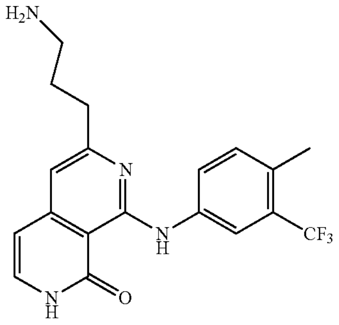 [SMILES: Cc1ccc(Nc2nc(CCCN)cc3cc[nH]c(=O)c23)cc1C(F)(F)F] | MS m/z 377.2 (M + 1). |
| 27 | 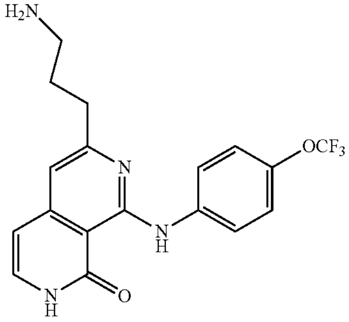 [SMILES: NCCCc1cc2cc[nH]c(=O)c2c(Nc2ccc(OC(F)(F)F)cc2)n1] | MS m/z 379.21 (M + 1). |
| 28 | 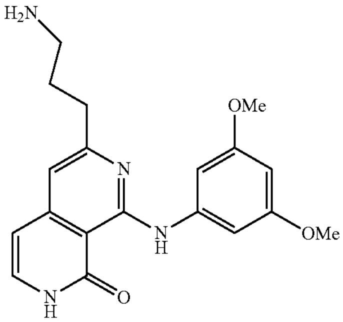 [SMILES: COc1cc(Nc2nc(CCCN)cc3cc[nH]c(=O)c23)cc(OC)c1] | MS m/z 355.1 (M + 1). |
| 29 | 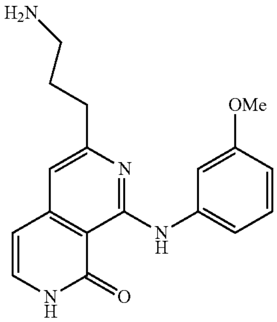 [SMILES: COc1cccc(Nc2nc(CCCN)cc3cc[nH]c(=O)c23)c1] | MS m/z 325.21 (M + 1). |

TABLE 1-continued
| No | Structure | Physical Data $^1H$ NMR 400 MHz ($DMSO-d_6$) and/or MS (m/z) |
|---|---|---|
| 30 | 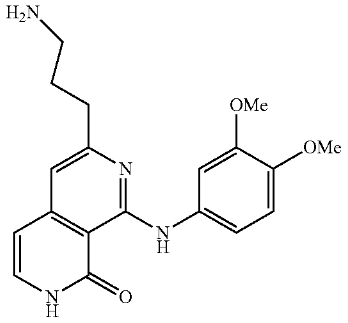 [SMILES: COc1ccc(Nc2nc(CCCN)cc3cc[nH]c(=O)c23)cc1OC] | MS m/z 355.1 (M + 1). |
| 31 | 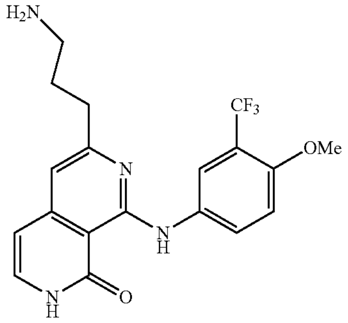 [SMILES: COc1ccc(Nc2nc(CCCN)cc3cc[nH]c(=O)c23)cc1C(F)(F)F] | MS m/z 393.1 (M + 1). |
| 32 | 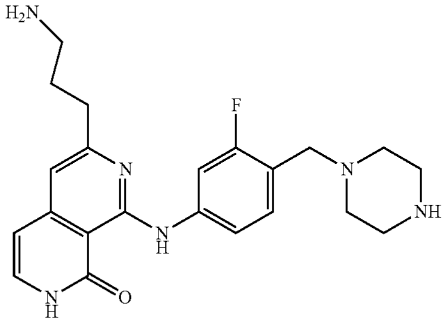 [SMILES: NCCCc1cc2cc[nH]c(=O)c2c(Nc2ccc(CN3CCNCC3)c(F)c2)n1] | MS m/z 411.22 (M + 1). |
| 33 | 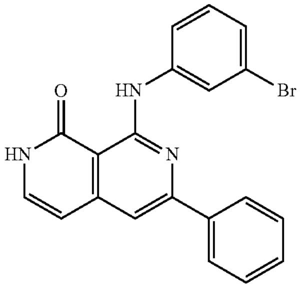 [SMILES: O=c1[nH]ccc2cc(-c3ccccc3)nc(Nc3cccc(Br)c3)c12] | MS m/z 392.2 (M + 1). |
| 34 | 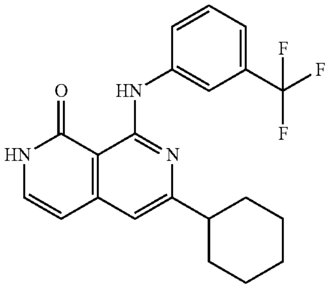 [SMILES: O=c1[nH]ccc2cc(C3CCCCC3)nc(Nc3cccc(C(F)(F)F)c3)c12] | MS m/z 388.1 (M + 1). |

TABLE 1-continued
| No | Structure | Physical Data $^1H$ NMR 400 MHz (DMSO-$d_6$) and/or MS (m/z) |
|---|---|---|
| 35 | 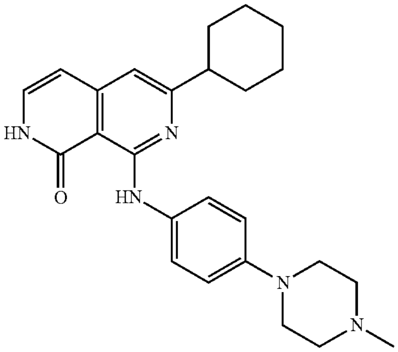 [SMILES: CN1CCN(c2ccc(Nc3nc(C4CCCCC4)cc4cc[nH]c(=O)c34)cc2)CC1] | MS m/z 418.25 (M + 1). |
| 36 | 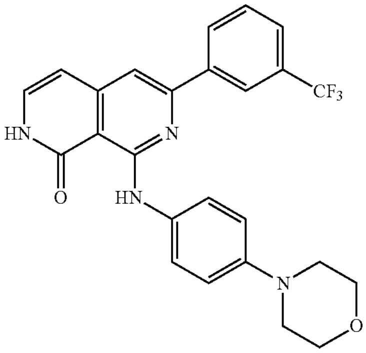 [SMILES: O=c1[nH]ccc2cc(-c3cccc(C(F)(F)F)c3)nc(Nc3ccc(N4CCOCC4)cc3)c12] | MS m/z 467.16 (M + 1). |
| 37 | 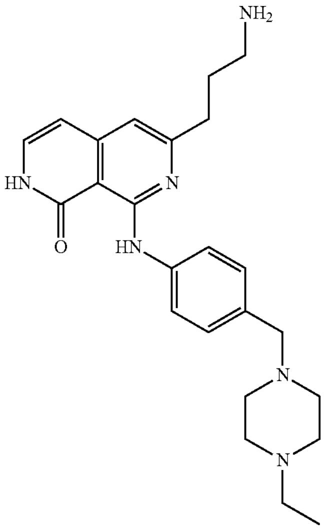 [SMILES: CCN1CCN(Cc2ccc(Nc3nc(CCCN)cc4cc[nH]c(=O)c34)cc2)CC1] | MS m/z 421.26 (M + 1). |
| 38 | 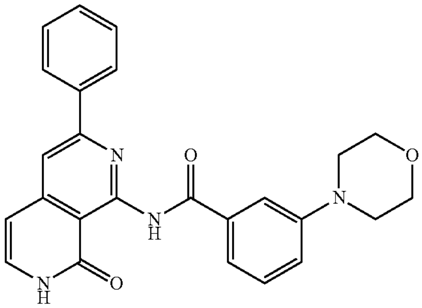 [SMILES: O=C(Nc1nc(-c2ccccc2)cc2cc[nH]c(=O)c12)c1cccc(N2CCOCC2)c1] | MS m/z 427.21 (M + 1). |

TABLE 1-continued
| No | Structure | Physical Data $^1H$ NMR 400 MHz ($DMSO-d_6$) and/or MS (m/z) |
|---|---|---|
| 39 | 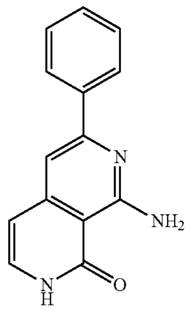 [SMILES: Nc1nc(-c2ccccc2)cc2cc[nH]c(=O)c12] | MS m/z 238.1 (M + 1). |
| 40 | 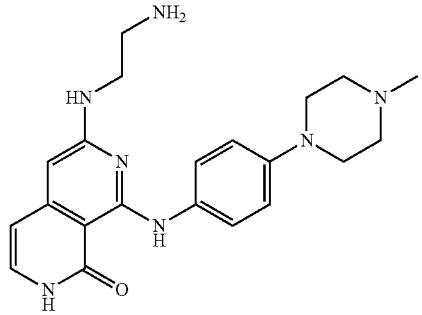 [SMILES: CN1CCN(c2ccc(Nc3nc(NCCN)cc4cc[nH]c(=O)c34)cc2)CC1] | MS m/z 394.23 (M + 1). |
| 41 | 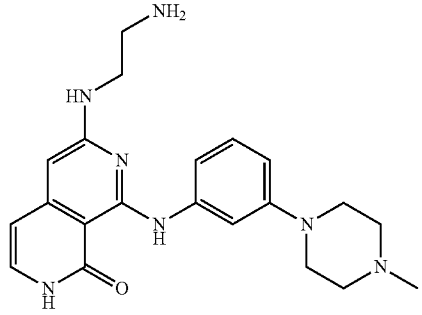 [SMILES: CN1CCN(c2cccc(Nc3nc(NCCN)cc4cc[nH]c(=O)c34)c2)CC1] | MS m/z 394.23 (M + 1). |
| 42 | 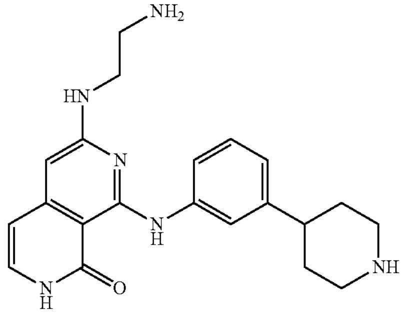 [SMILES: NCCNc1cc2cc[nH]c(=O)c2c(Nc2cccc(C3CCNCC3)c2)n1] | MS m/z 379.22 (M + 1). |

TABLE 1-continued
| No | Structure | Physical Data $^1H$ NMR 400 MHz ($DMSO-d_6$) and/or MS (m/z) |
|---|---|---|
| 43 | 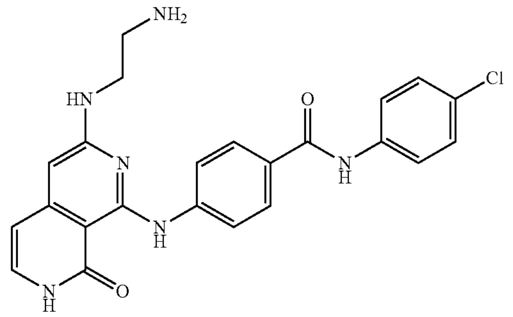 [SMILES: NCCNc1cc2cc[nH]c(=O)c2c(Nc2ccc(C(=O)Nc3ccc(Cl)cc3)cc2)n1] | MS m/z 449.14 (M + 1). |
| 44 | 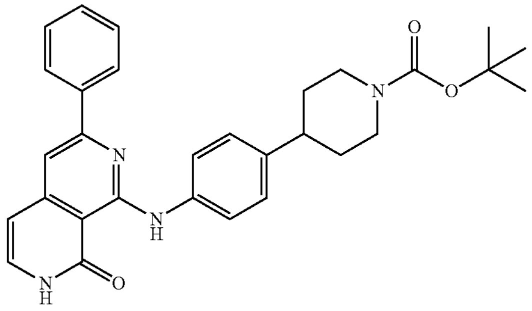 [SMILES: CC(C)(C)OC(=O)N1CCC(c2ccc(Nc3nc(-c4ccccc4)cc4cc[nH]c(=O)c34)cc2)CC1] | MS m/z 497.21 (M + 1). |
| 45 | 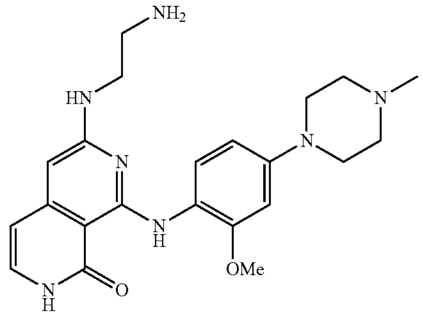 [SMILES: COc1cc(N2CCN(C)CC2)ccc1Nc1nc(NCCN)cc2cc[nH]c(=O)c12] | MS m/z 424.24 (M + 1). |
| 46 | 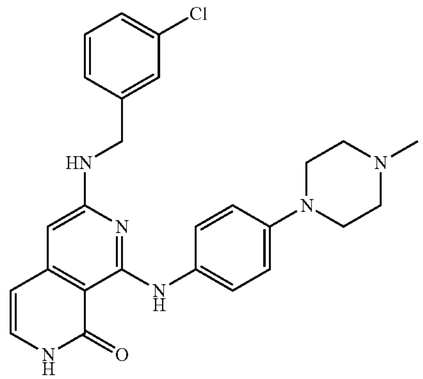 [SMILES: CN1CCN(c2ccc(Nc3nc(NCc4cccc(Cl)c4)cc4cc[nH]c(=O)c34)cc2)CC1] | MS m/z 475.19 (M + 1). |

TABLE 1-continued
| No | Structure | Physical Data $^1$H NMR 400 MHz (DMSO-$d_6$) and/or MS (m/z) |
|---|---|---|
| 47 | 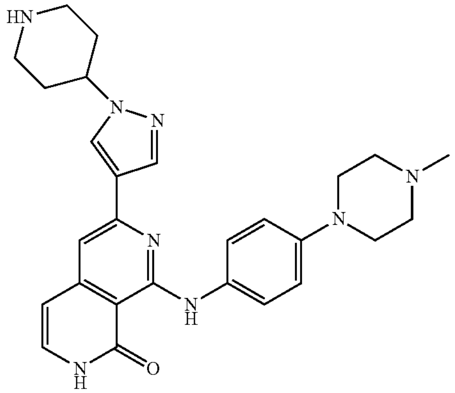 [SMILES: CN1CCN(c2ccc(Nc3nc(-c4cnn(C5CCNCC5)c4)cc4cc[nH]c(=O)c34)cc2)CC1] | MS m/z 485.2 (M + 1). |
| 48 | 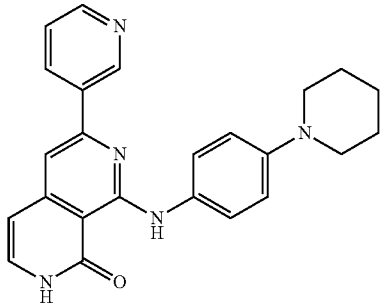 [SMILES: O=c1[nH]ccc2cc(-c3cccnc3)nc(Nc3ccc(N4CCCCC4)cc3)c12] | MS m/z 398.19 (M + 1). |
| 49 | 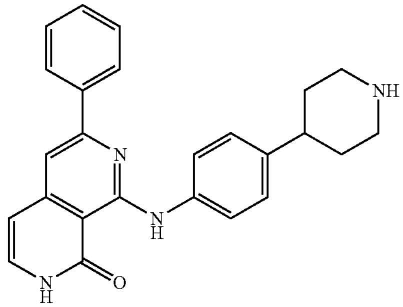 [SMILES: O=c1[nH]ccc2cc(-c3ccccc3)nc(Nc3ccc(C4CCNCC4)cc3)c12] | MS m/z 397.2 (M + 1). |
| 50 | 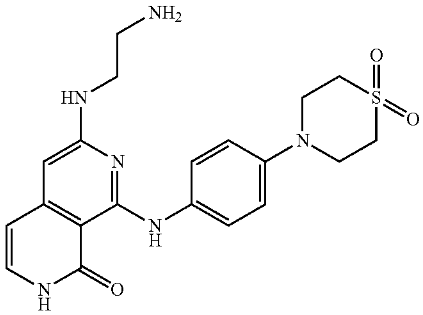 [SMILES: NCCNc1cc2cc[nH]c(=O)c2c(Nc2ccc(N3CCS(=O)(=O)CC3)cc2)n1] | MS m/z 429.16 (M + 1). |

TABLE 1-continued
| No | Structure | Physical Data $^1H$ NMR 400 MHz (DMSO-$d_6$) and/or MS (m/z) |
|---|---|---|
| 51 | 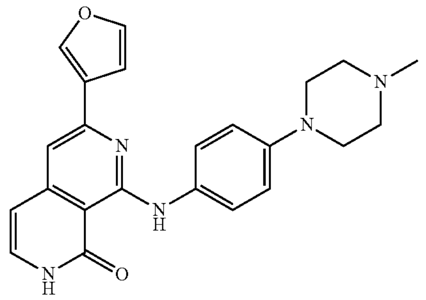 [SMILES: CN1CCN(c2ccc(Nc3nc(-c4ccoc4)cc4cc[nH]c(=O)c34)cc2)CC1] | MS m/z 402.2 (M + 1). |
| 52 | 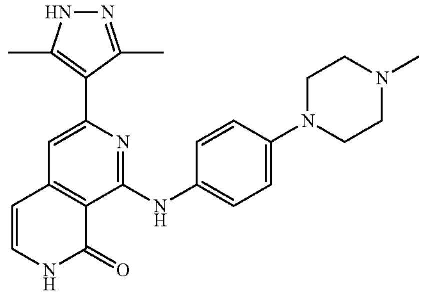 | MS m/z 413.33 (M + 1). |
| 53 | 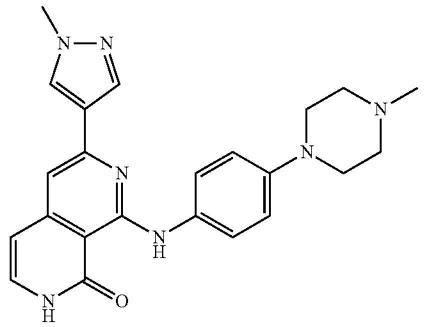 [SMILES: CN1CCN(c2ccc(Nc3nc(-c4cnn(C)c4)cc4cc[nH]c(=O)c34)cc2)CC1] | MS m/z 416.2 (M + 1). |
| 54 | 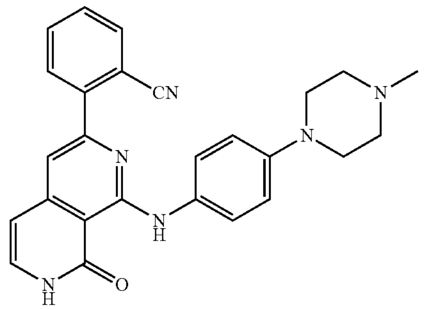 [SMILES: CN1CCN(c2ccc(Nc3nc(-c4ccccc4C#N)cc4cc[nH]c(=O)c34)cc2)CC1] | MS m/z 437.21 (M + 1). |
| 55 | 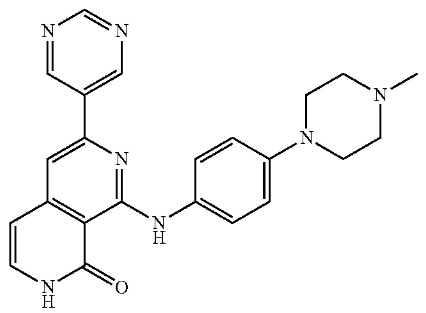 [SMILES: CN1CCN(c2ccc(Nc3nc(-c4cncnc4)cc4cc[nH]c(=O)c34)cc2)CC1] | MS m/z 414.2 (M + 1). |

TABLE 1-continued
| No | Structure | Physical Data $^1H$ NMR 400 MHz (DMSO-$d_6$) and/or MS (m/z) |
|---|---|---|
| 56 | 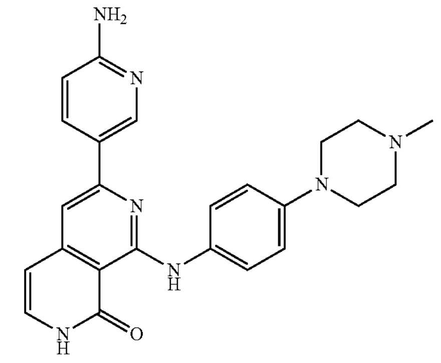 [SMILES: CN1CCN(c2ccc(Nc3nc(-c4ccc(N)nc4)cc4cc[nH]c(=O)c34)cc2)CC1] | MS m/z 428.21 (M + 1). |
| 57 | 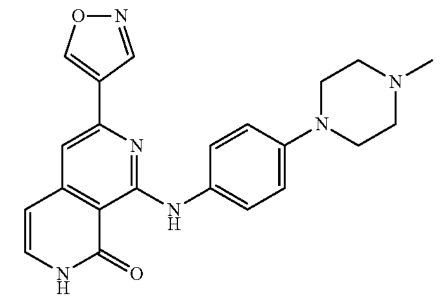 [SMILES: CN1CCN(c2ccc(Nc3nc(-c4cnoc4)cc4cc[nH]c(=O)c34)cc2)CC1] | MS m/z 403.21 (M + 1). |
| 58 | 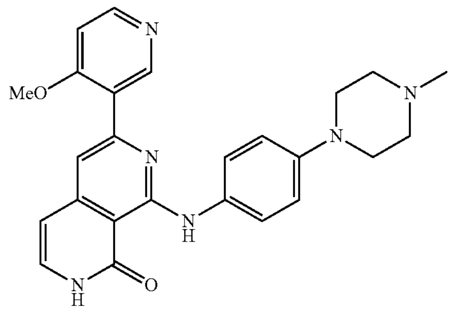 [SMILES: COc1ccncc1-c1cc2cc[nH]c(=O)c2c(Nc2ccc(N3CCN(C)CC3)cc2)n1] | MS m/z 443.21 (M + 1). |
| 59 | 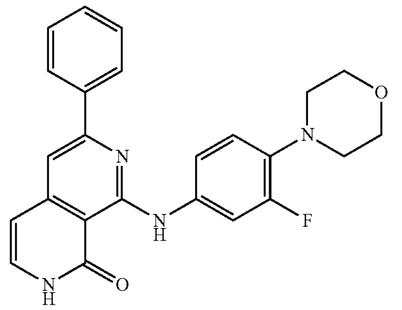 [SMILES: O=c1[nH]ccc2cc(-c3ccccc3)nc(Nc3ccc(N4CCOCC4)c(F)c3)c12] | MS m/z 417.1 (M + 1). |

TABLE 1-continued
| No | Structure | Physical Data $^1H$ NMR 400 MHz (DMSO-$d_6$) and/or MS (m/z) |
| --- | --- | --- |
| 60 | 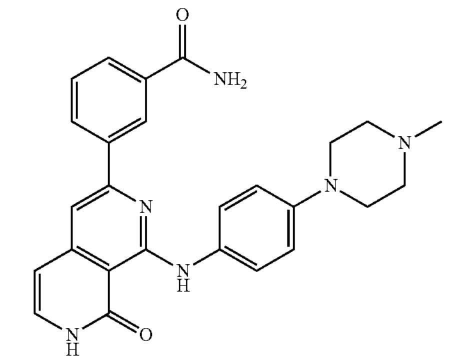 [SMILES: CN1CCN(c2ccc(Nc3nc(-c4cccc(C(N)=O)c4)cc4cc[nH]c(=O)c34)cc2)CC1] | MS m/z 455.2 (M + 1). |
| 61 | 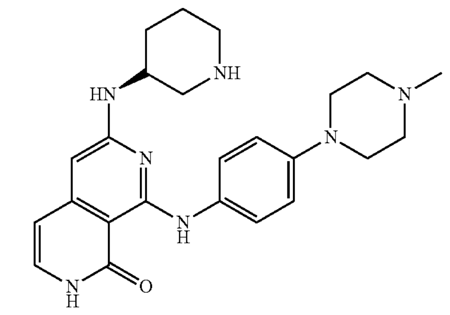 | MS m/z 434.1 (M + 1). |
| 62 | 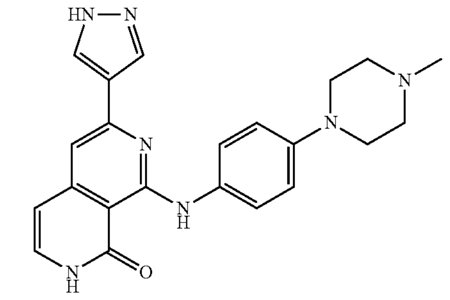 [SMILES: CN1CCN(c2ccc(Nc3nc(-c4cn[nH]c4)cc4cc[nH]c(=O)c34)cc2)CC1] | MS m/z 402.2 (M + 1). |
| 63 | 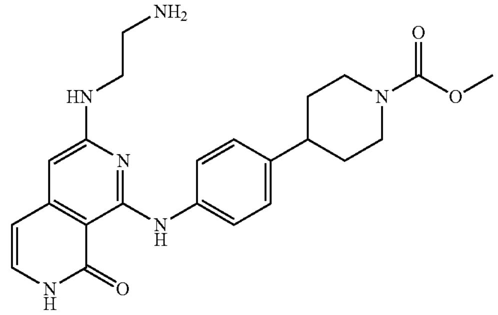 | MS m/z 479.21 (M + 1). |

TABLE 1-continued
| No | Structure | Physical Data $^1H$ NMR 400 MHz (DMSO-$d_6$) and/or MS (m/z) |
|---|---|---|
| 64 | 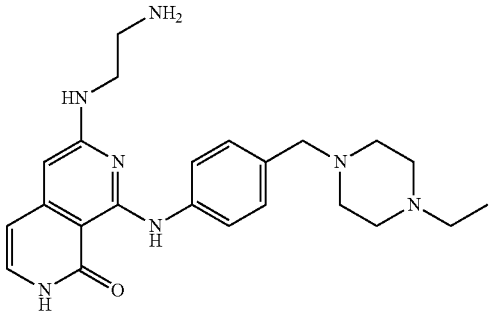 [SMILES: CCN1CCN(Cc2ccc(Nc3nc(NCCN)cc4cc[nH]c(=O)c34)cc2)CC1] | MS m/z 422.26 (M + 1). |
| 65 | 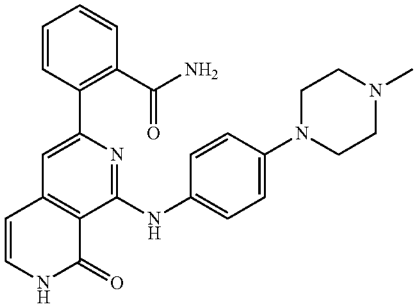 [SMILES: CN1CCN(c2ccc(Nc3nc(-c4ccccc4C(N)=O)cc4cc[nH]c(=O)c34)cc2)CC1] | MS m/z 455.21 (M + 1). |
| 66 | 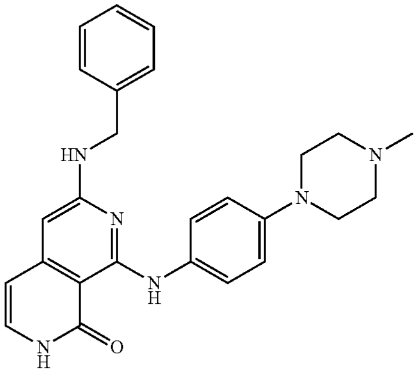 [SMILES: CN1CCN(c2ccc(Nc3nc(NCc4ccccc4)cc4cc[nH]c(=O)c34)cc2)CC1] | MS m/z 441.23 (M + 1). |
| 67 | 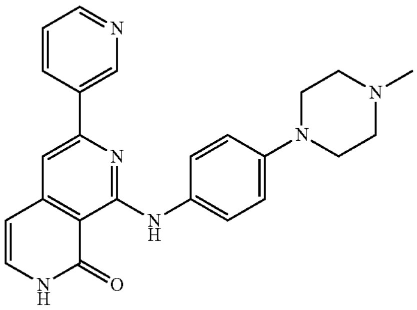 [SMILES: CN1CCN(c2ccc(Nc3nc(-c4cccnc4)cc4cc[nH]c(=O)c34)cc2)CC1] | MS m/z 413.2 (M + 1). |

TABLE 1-continued
| No | Structure | Physical Data $^1H$ NMR 400 MHz (DMSO-$d_6$) and/or MS (m/z) |
|---|---|---|
| 68 | 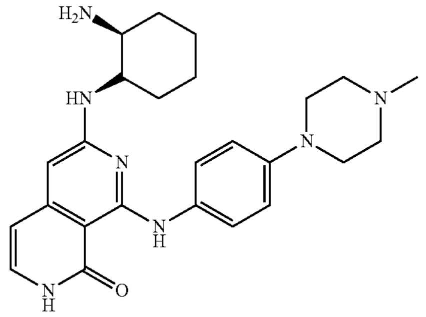 | MS m/z 448.1 (M + 1). |
| 69 | 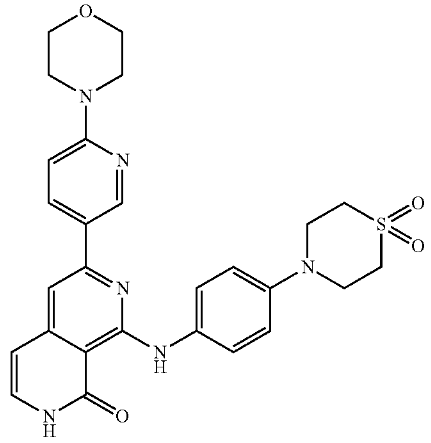 [SMILES: O=c1[nH]ccc2cc(-c3ccc(N4CCOCC4)nc3)nc(Nc3ccc(N4CCS(=O)(=O)CC4)cc3)c12] | MS m/z 533.2 (M + 1). |
| 70 | 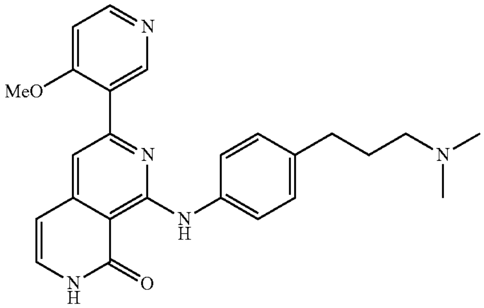 [SMILES: COc1ccncc1-c1cc2cc[nH]c(=O)c2c(Nc2ccc(CCCN(C)C)cc2)n1] | MS m/z 430.1 (M + 1). |
| 71 | 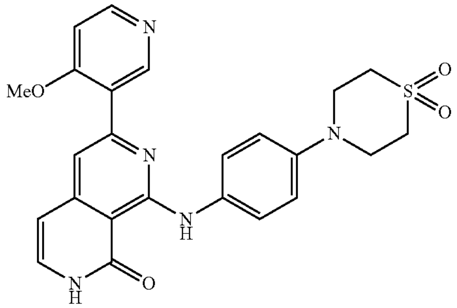 [SMILES: COc1ccncc1-c1cc2cc[nH]c(=O)c2c(Nc2ccc(N3CCS(=O)(=O)CC3)cc2)n1] | MS m/z 478.2 (M + 1). |

TABLE 1-continued
| No | Structure | Physical Data $^{1}H$ NMR 400 MHz (DMSO-$d_6$) and/or MS (m/z) |
|---|---|---|
| 72 | 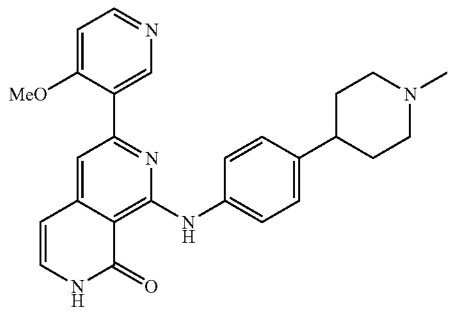 [SMILES: COc1ccncc1-c1cc2cc[nH]c(=O)c2c(Nc2ccc(C3CCN(C)CC3)cc2)n1] | MS m/z 442.1 (M + 1). |
| 73 | 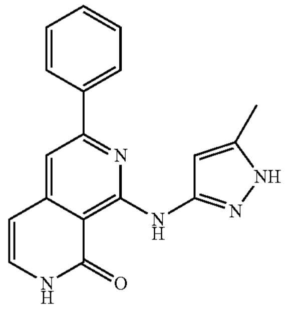 [SMILES: Cc1cc(Nc2nc(-c3ccccc3)cc3cc[nH]c(=O)c23)n[nH]1] | MS m/z 318.1 (M + 1). |
| 74 | 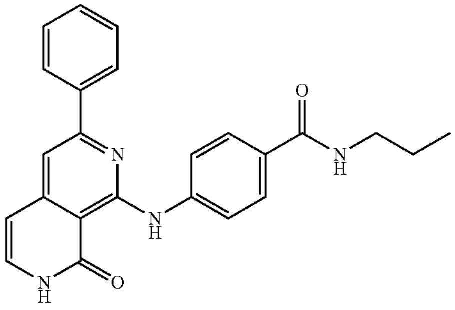 [SMILES: CCCNC(=O)c1ccc(Nc2nc(-c3ccccc3)cc3cc[nH]c(=O)c23)cc1] | MS m/z 399.0 (M + 1). |
| 75 | 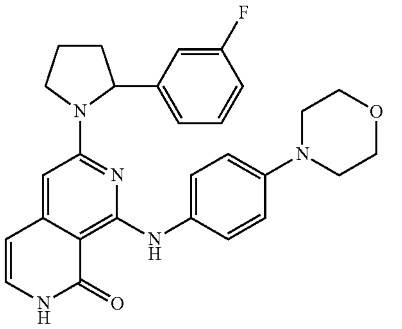 [SMILES: O=c1[nH]ccc2cc(N3CCCC3c3cccc(F)c3)nc(Nc3ccc(N4CCOCC4)cc3)c12] | MS m/z 486.2 (M + 1). |

TABLE 1-continued
| No | Structure | Physical Data $^1H$ NMR 400 MHz (DMSO-$d_6$) and/or MS (m/z) |
|---|---|---|
| 76 | 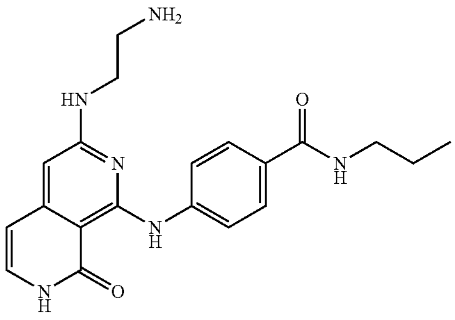 [SMILES: CCCNC(=O)c1ccc(Nc2nc(NCCN)cc3cc[nH]c(=O)c23)cc1] | MS m/z 381.1 (M + 1). |
| 77 | 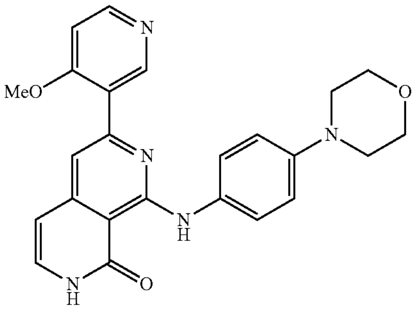 [SMILES: COc1ccncc1-c1cc2cc[nH]c(=O)c2c(Nc2ccc(N3CCOCC3)cc2)n1] | MS m/z 430.1 (M + 1). |
| 78 | 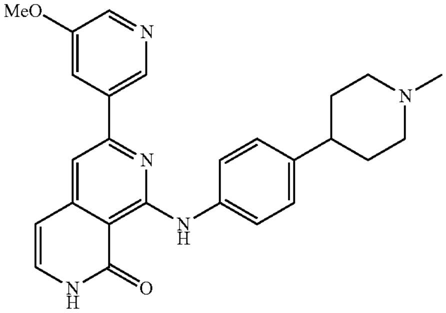 [SMILES: COc1cncc(-c2cc3cc[nH]c(=O)c3c(Nc3ccc(C4CCN(C)CC4)cc3)n2)c1] | MS m/z 441.0 (M + 1). |
| 79 | 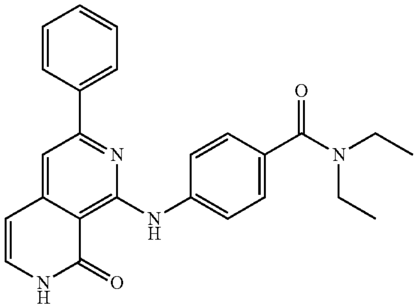 [SMILES: CCN(CC)C(=O)c1ccc(Nc2nc(-c3ccccc3)cc3cc[nH]c(=O)c23)cc1] | MS m/z 413.1 (M + 1). |

TABLE 1-continued
| No | Structure | Physical Data $^1H$ NMR 400 MHz (DMSO-$d_6$) and/or MS (m/z) |
|---|---|---|
| 80 | 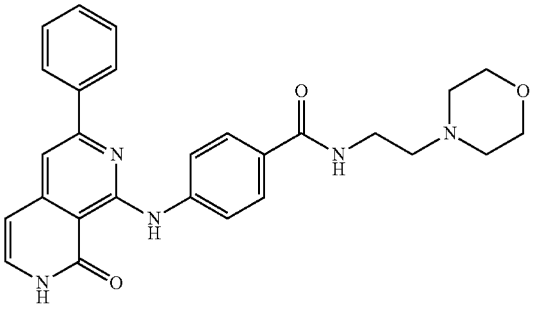 [SMILES: O=C(NCCN1CCOCC1)c1ccc(Nc2nc(-c3ccccc3)cc3cc[nH]c(=O)c23)cc1] | MS m/z 470.1 (M + 1). |
| 81 | 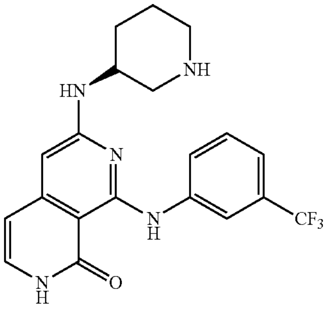 | MS m/z 404.16 (M + 1). |
| 82 | 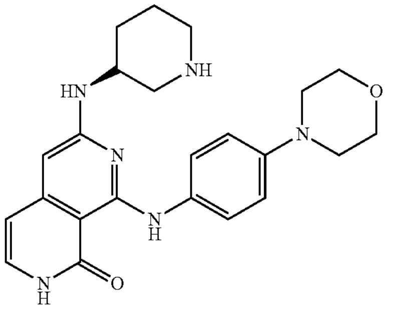 | MS m/z 421.23 (M + 1). |
| 83 | 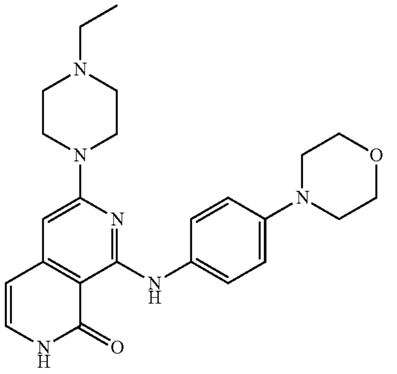 [SMILES: CCN1CCN(c2cc3cc[nH]c(=O)c3c(Nc3ccc(N4CCOCC4)cc3)n2)CC1] | MS m/z 435.25 (M + 1). |

TABLE 1-continued
| No | Structure | Physical Data $^1$H NMR 400 MHz (DMSO-$d_6$) and/or MS (m/z) |
|---|---|---|
| 84 | 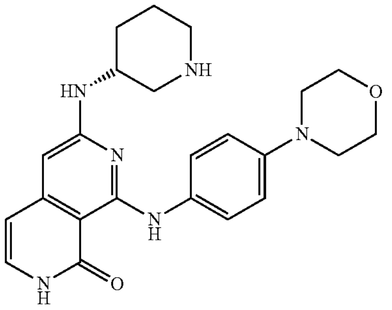 | MS m/z 421.2 (M + 1). |
| 85 | 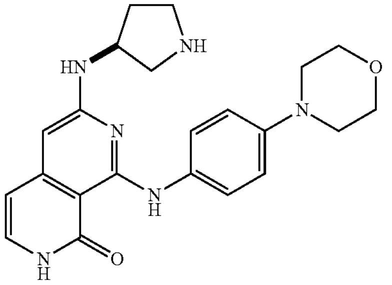 | MS m/z 407.21 (M + 1). |
| 86 | 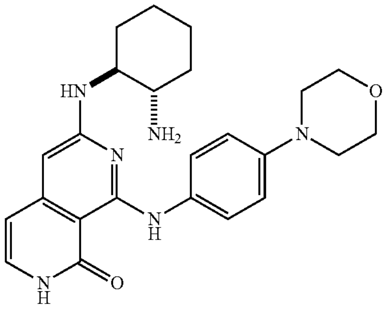 | MS m/z 435.24 (M + 1). |
| 87 | 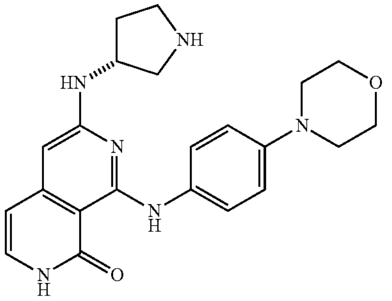 | MS m/z 407.12 (M + 1). |
| 88 | 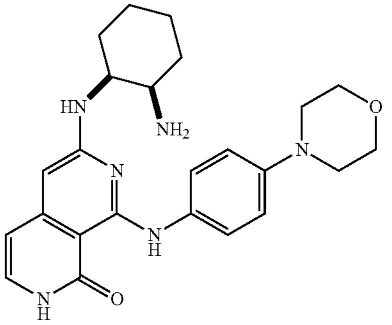 | MS m/z 435.32 (M + 1). |

TABLE 1-continued
| No | Structure | Physical Data $^1$H NMR 400 MHz (DMSO-$d_6$) and/or MS (m/z) |
|---|---|---|
| 89 | 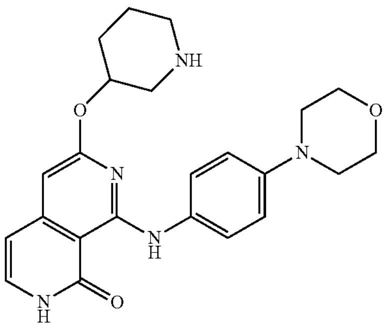 [SMILES: O=c1[nH]ccc2cc(OC3CCCNC3)nc(Nc3ccc(N4CCOCC4)cc3)c12] | MS m/z 422.21 (M + 1). |
| 90 | 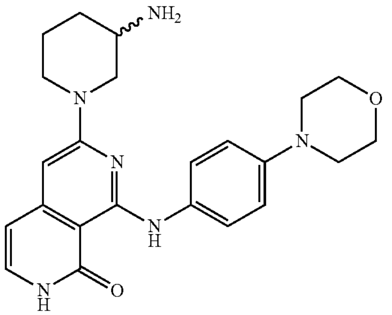 [SMILES: NC1CCCN(c2cc3cc[nH]c(=O)c3c(Nc3ccc(N4CCOCC4)cc3)n2)C1] | MS m/z 421.23 (M + 1). |
| 91 | 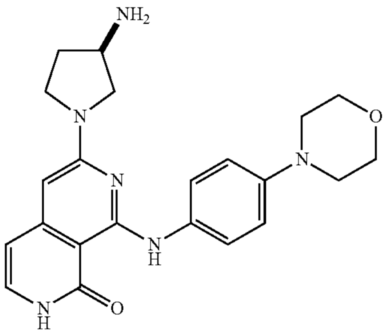 [SMILES: N[C@@H]1CCN(c2cc3cc[nH]c(=O)c3c(Nc3ccc(N4CCOCC4)cc3)n2)C1] | MS m/z 407.21 (M + 1). |
| 92 | 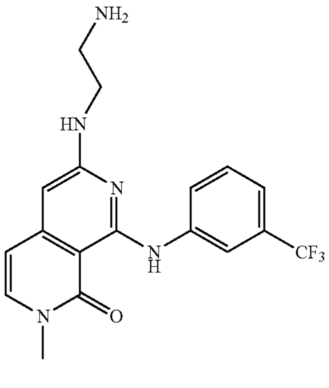 [SMILES: Cn1ccc2cc(NCCN)nc(Nc3cccc(C(F)(F)F)c3)c2c1=O] | $^1$H NMR (400 MHz, MeOD-$d_4$) δ 8.40 (s, 1H), 7.63 (d, 1H), 7.39 (t, 1H), 7.17 (d, 1H), 7.11 (d, 1H), 6.12 (d, 1H), 5.80 (s, 1H), 3.56 (t, 2H), 3.37 (s, 3H), 3.03 (t, 2H); MS m/z 376.15 (M + 1). |

TABLE 1-continued
| No | Structure | Physical Data $^1H$ NMR 400 MHz (DMSO-$d_6$) and/or MS (m/z) |
|---|---|---|
| 93 | 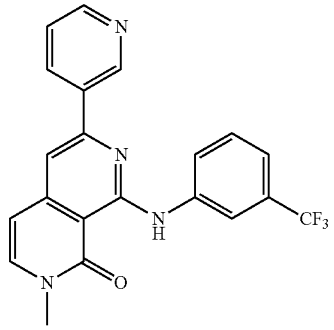 [SMILES: Cn1ccc2cc(-c3cccnc3)nc(Nc3cccc(C(F)(F)F)c3)c2c1=O] | MS m/z 397.12 (M + 1). |
| 94 | 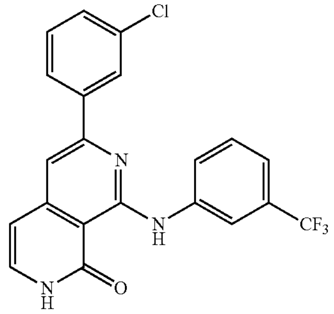 [SMILES: O=c1[nH]ccc2cc(-c3cccc(Cl)c3)nc(Nc3cccc(C(F)(F)F)c3)c12] | MS m/z 416.2 (M + 1). |
| 95 | 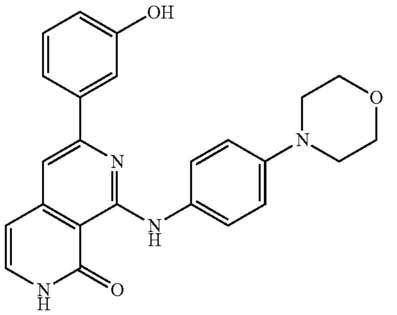 [SMILES: O=c1[nH]ccc2cc(-c3cccc(O)c3)nc(Nc3ccc(N4CCOCC4)cc3)c12] | MS m/z 415.17 (M + 1). |
| 96 | 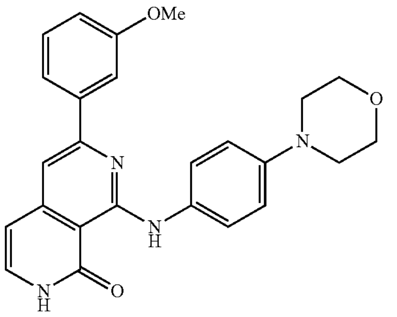 [SMILES: COc1cccc(-c2cc3cc[nH]c(=O)c3c(Nc3ccc(N4CCOCC4)cc3)n2)c1] | MS m/z 429.16 (M + 1). |

TABLE 1-continued
| No | Structure | Physical Data $^1$H NMR 400 MHz (DMSO-$d_6$) and/or MS (m/z) |
|---|---|---|
| 97 | 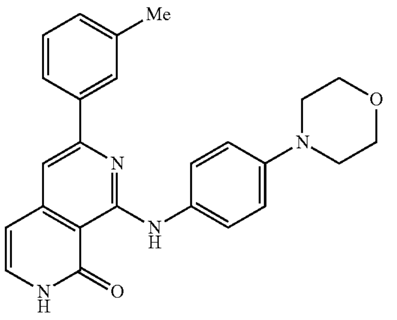 [SMILES: Cc1cccc(-c2cc3cc[nH]c(=O)c3c(Nc3ccc(N4CCOCC4)cc3)n2)c1] | MS m/z 413.19 (M + 1). |
| 98 | 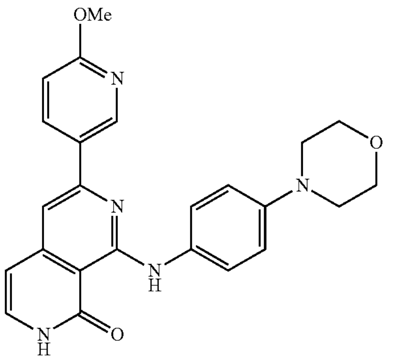 [SMILES: COc1ccc(-c2cc3cc[nH]c(=O)c3c(Nc3ccc(N4CCOCC4)cc3)n2)cn1] | MS m/z 430.4 (M + 1). |
| 99 | 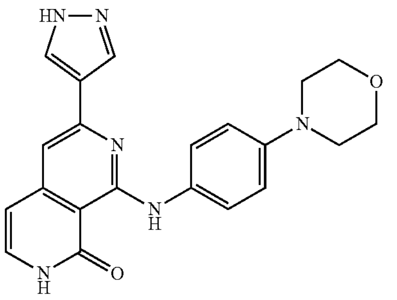 [SMILES: O=c1[nH]ccc2cc(-c3cn[nH]c3)nc(Nc3ccc(N4CCOCC4)cc3)c12] | MS m/z 389.14 (M + 1). |
| 100 | 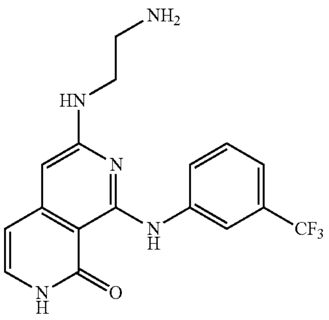 [SMILES: NCCNc1cc2cc[nH]c(=O)c2c(Nc2cccc(C(F)(F)F)c2)n1] | $^1$H NMR (400 MHz, MeOD-$d_4$) δ 8.40 (s, 1H), 7.65 (d, 1H), 7.38 (t, 1H), 7.15 (d, 1H), 6.90 (d, 1H), 6.10 (d, 1H), 5.79 (s, 1H), 3.49 (t, 2H), 2.90 (t, 2H); MS m/z 364.22 (M + l), |

TABLE 1-continued
| No | Structure | Physical Data $^1H$ NMR 400 MHz (DMSO-$d_6$) and/or MS (m/z) |
|---|---|---|
| 101 | 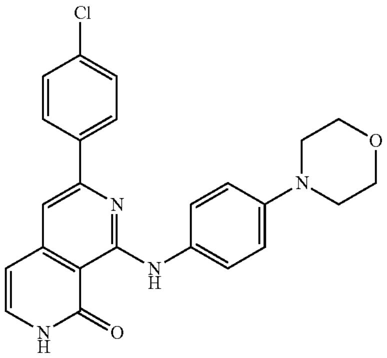 [SMILES: O=c1[nH]ccc2cc(-c3ccc(Cl)cc3)nc(Nc3ccc(N4CCOCC4)cc3)c12] | MS m/z 433.11 (M + 1). |
| 102 | 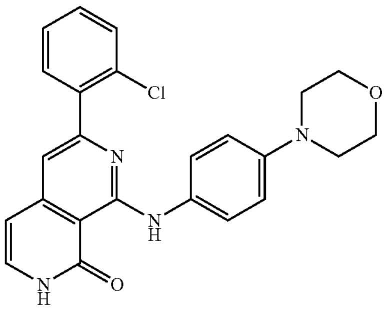 [SMILES: O=c1[nH]ccc2cc(-c3ccccc3Cl)nc(Nc3ccc(N4CCOCC4)cc3)c12] | MS m/z 433.02 (M + 1). |
| 103 | 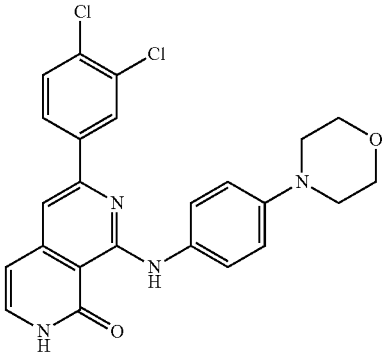 [SMILES: O=c1[nH]ccc2cc(-c3ccc(Cl)c(Cl)c3)nc(Nc3ccc(N4CCOCC4)cc3)c12] | MS m/z 467.12 (M + 1). |
| 104 | 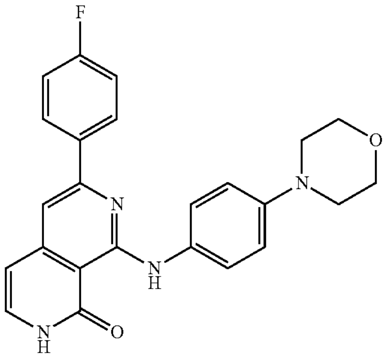 [SMILES: O=c1[nH]ccc2cc(-c3ccc(F)cc3)nc(Nc3ccc(N4CCOCC4)cc3)c12] | MS m/z 417.16 (M + 1). |

TABLE 1-continued
| No | Structure | Physical Data $^1H$ NMR 400 MHz (DMSO-$d_6$) and/or MS (m/z) |
|---|---|---|
| 105 | 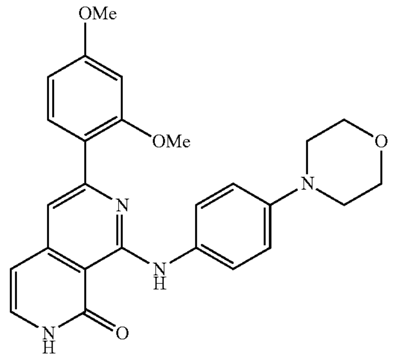 [SMILES: COc1ccc(-c2cc3cc[nH]c(=O)c3c(Nc3ccc(N4CCOCC4)cc3)n2)c(OC)c1] | MS m/z 459.23 (M + 1). |
| 106 | 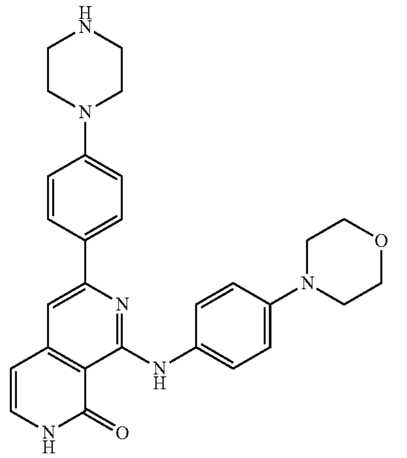 [SMILES: O=c1[nH]ccc2cc(-c3ccc(N4CCNCC4)cc3)nc(Nc3ccc(N4CCOCC4)cc3)c12] | MS m/z 483.23 (M + 1). |
| 107 | 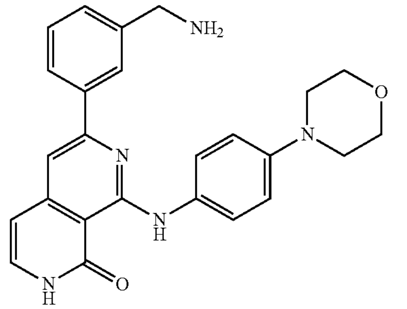 [SMILES: NCc1cccc(-c2cc3cc[nH]c(=O)c3c(Nc3ccc(N4CCOCC4)cc3)n2)c1] | $^1H$ NMR (400 MHz, MeOD-$d_4$) δ 8.07 (m, 2H), 7.71 (d, 2H), 7.45 (m, 2H), 7.21 (d, 2H), 6.93 (dd, 2H), 6.47 (d, 1H), 4.04 (s, 2H), 3.76 (t, 4H), 3.03 (dd, 4H); MS m/z 428.21 (M + 1). |
| 108 | 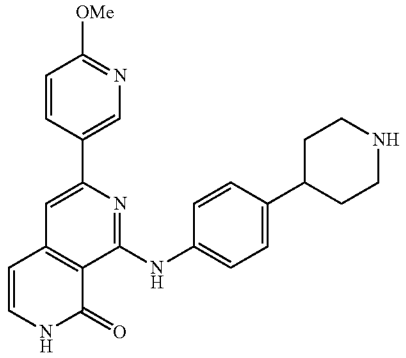 | MS m/z 428.31 (M + 1). |

TABLE 1-continued
| No | Structure | Physical Data $^1H$ NMR 400 MHz (DMSO-$d_6$) and/or MS (m/z) |
|---|---|---|
| 109 | 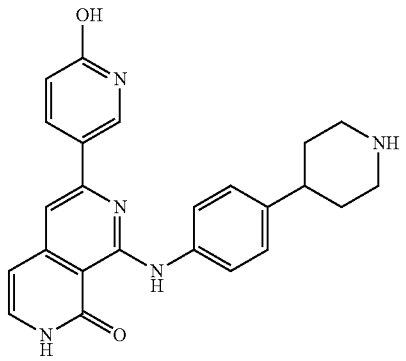 [SMILES: O=c1[nH]ccc2cc(-c3ccc(O)nc3)nc(Nc3ccc(C4CCNCC4)cc3)c12] | MS m/z 413.20 (M + 1). |
| 110 | 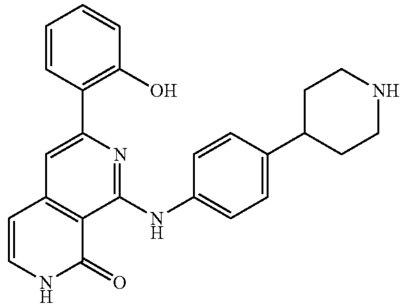 [SMILES: O=c1[nH]ccc2cc(-c3ccccc3O)nc(Nc3ccc(C4CCNCC4)cc3)c12] | MS m/z 413.20 (M + 1). |
| 111 | 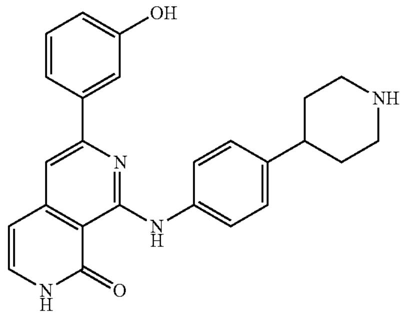 [SMILES: O=c1[nH]ccc2cc(-c3cccc(O)c3)nc(Nc3ccc(C4CCNCC4)cc3)c12] | $^1H$ NMR (400 MHz, MeOD-$d_4$) δ 7.82 (m, 2H), 7.49 (m, 2H), 7.19 (m, 5H), 6.77 (m, 1H), 6.48 (d, 1H), 3.29 (m, 2H), 2.93 (m, 2H), 2.72 (m, 1H), 1.94 (m, 2H), 1.77 (m, 2H); MS m/z 413.13 (M + 1). |
| 112 | 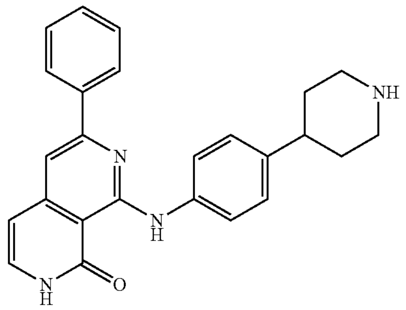 [SMILES: O=c1[nH]ccc2cc(-c3ccccc3)nc(Nc3ccc(C4CCNCC4)cc3)c12] | MS m/z 397.2 (M + 1). |

TABLE 1-continued
| No | Structure | Physical Data $^1H$ NMR 400 MHz (DMSO-$d_6$) and/or MS (m/z) |
| --- | --- | --- |
| 113 | 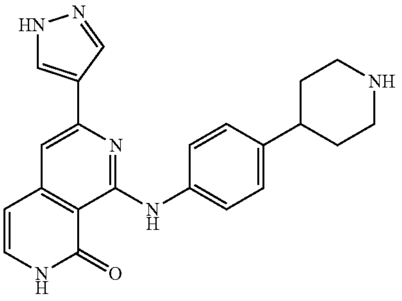 [SMILES: O=c1[nH]ccc2cc(-c3cn[nH]c3)nc(Nc3ccc(C4CCNCC4)cc3)c12] | MS m/z 401.1 (M + 1). |
| 114 | 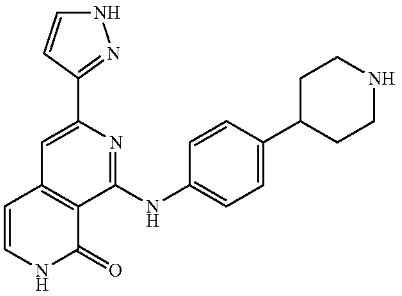 [SMILES: O=c1[nH]ccc2cc(-c3cc[nH]n3)nc(Nc3ccc(C4CCNCC4)cc3)c12] | $^1H$ NMR (400 MHz, MeOD-$d_4$) δ 8.07 (s, 1H), 7.94 (s, 1H), 7.75 (dd, 1H), 7.16 (dd, 1H), 6.93 (s, 1H), 6.39 (d, 1H), 6.12 (d, 1H), 3.88 (s, 3H), 3.22 (m, 2H), 2.88 (m, 2H), 2.71 (m, 1H), 1.90 (m, 2H), 1.73 (m, 2H); MS m/z 387.21 (M + 1). |
| 115 | 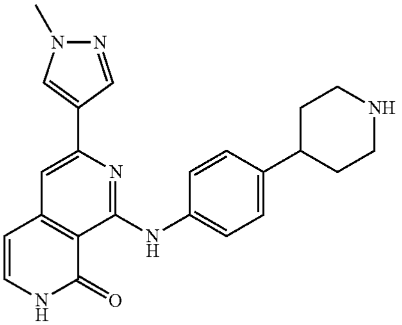 [SMILES: Cn1cc(-c2cc3cc[nH]c(=O)c3c(Nc3ccc(C4CCNCC4)cc3)n2)cn1] | MS m/z 401.1 (M + 1). |
| 116 | 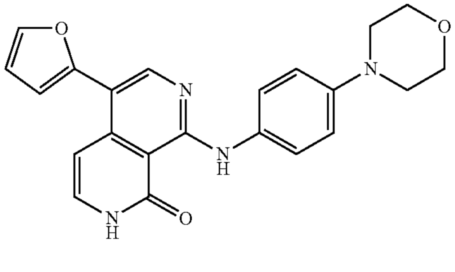 [SMILES: O=c1[nH]ccc2c(-c3ccco3)cnc(Nc3ccc(N4CCOCC4)cc3)c12] | MS m/z 389.1 (M + 1). |
| 117 | 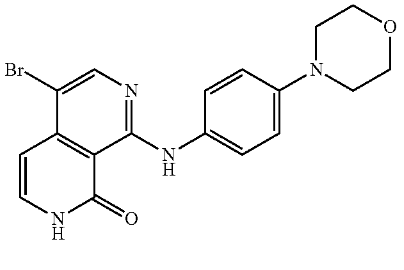 [SMILES: O=c1[nH]ccc2c(Br)cnc(Nc3ccc(N4CCOCC4)cc3)c12] | MS m/z 401.2 (M + 1). |

TABLE 1-continued
| No | Structure | Physical Data $^1H$ NMR 400 MHz (DMSO-$d_6$) and/or MS (m/z) |
|---|---|---|
| 118 | 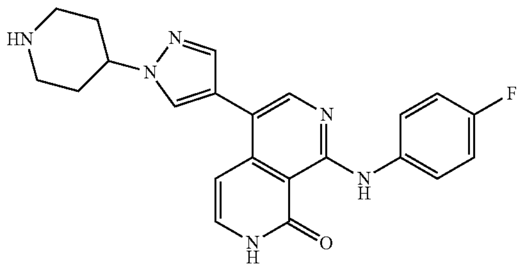 [SMILES: O=c1[nH]ccc2c(-c3cnn(C4CCNCC4)c3)cnc(Nc3ccc(F)cc3)c12] | MS m/z 404.1 (M + 1). |
| 119 | 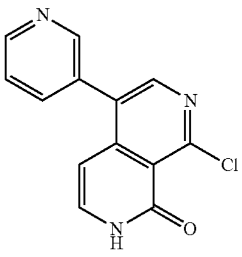 [SMILES: O=c1[nH]ccc2c(-c3cccnc3)cnc(Cl)c12] | MS m/z 258.1 (M + 1). |
| 120 | 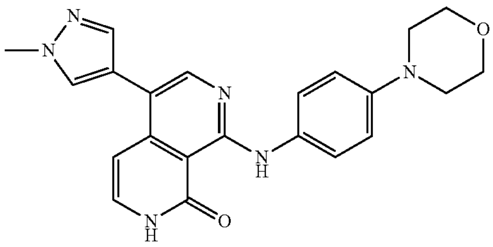 [SMILES: Cn1cc(-c2cnc(Nc3ccc(N4CCOCC4)cc3)c3c(=O)[nH]ccc23)cn1] | MS m/z 403.1 (M + 1). |
| 121 | 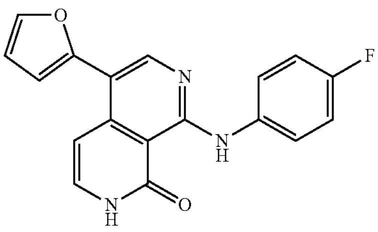 [SMILES: O=c1[nH]ccc2c(-c3ccco3)cnc(Nc3ccc(F)cc3)c12] | MS m/z 322.1 (M + 1). |
| 122 | 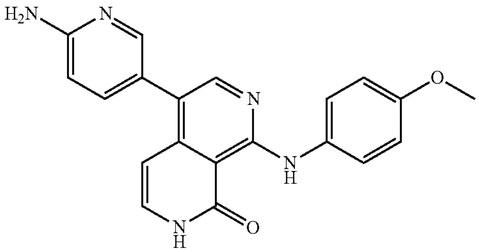 [SMILES: COc1ccc(Nc2ncc(-c3ccc(N)nc3)c3cc[nH]c(=O)c23)cc1] | MS m/z 360.1 (M + 1). |
| 123 | 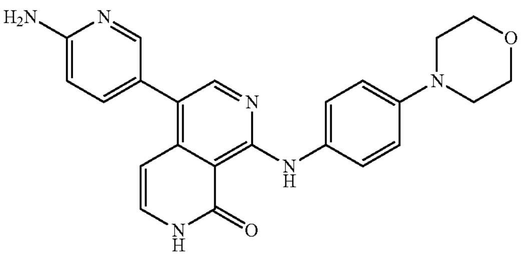 [SMILES: Nc1ccc(-c2cnc(Nc3ccc(N4CCOCC4)cc3)c3c(=O)[nH]ccc23)cn1] | MS m/z 415.2 (M + 1). |

TABLE 1-continued
| No | Structure | Physical Data $^1H$ NMR 400 MHz (DMSO-$d_6$) and/or MS (m/z) |
|---|---|---|
| 124 | 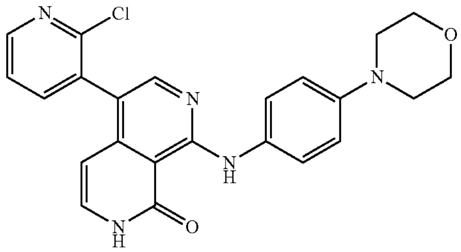 [SMILES: O=c1[nH]ccc2c(-c3cccnc3Cl)cnc(Nc3ccc(N4CCOCC4)cc3)c12] | MS m/z 434.0 (M + 1). |
| 125 | 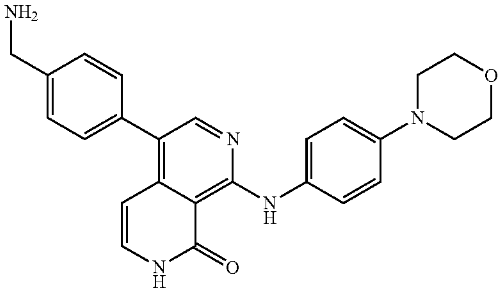 [SMILES: NCc1ccc(-c2cnc(Nc3ccc(N4CCOCC4)cc3)c3c(=O)[nH]ccc23)cc1] | MS m/z 428.1 (M + 1). |
| 126 | 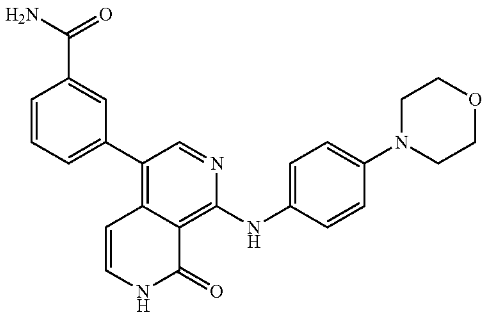 [SMILES: NC(=O)c1cccc(-c2cnc(Nc3ccc(N4CCOCC4)cc3)c3c(=O)[nH]ccc23)c1] | MS m/z 442.1 (M + 1). |
| 127 | 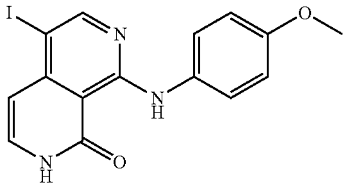 [SMILES: COc1ccc(Nc2ncc(I)c3cc[nH]c(=O)c23)cc1] | MS m/z 394.0 (M + 1). |
| 128 | 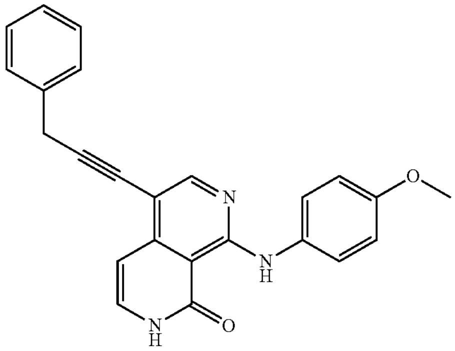 [SMILES: COc1ccc(Nc2ncc(C#CCc3ccccc3)c3cc[nH]c(=O)c23)cc1] | MS m/z 382.2 (M + 1). |

TABLE 1-continued
| No | Structure | Physical Data $^1$H NMR 400 MHz (DMSO-$d_6$) and/or MS (m/z) |
|---|---|---|
| 129 | 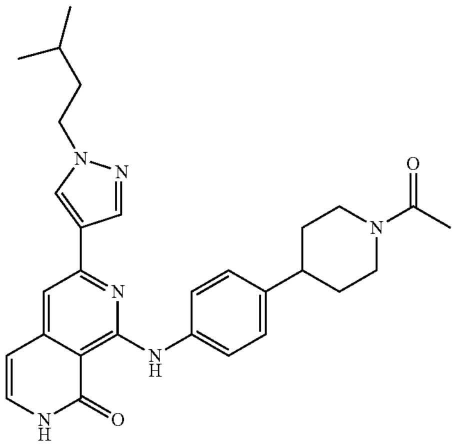 [SMILES: CC(=O)N1CCC(c2ccc(Nc3nc(-c4cnn(CCC(C)C)c4)cc4cc[nH]c(=O)c34)cc2)CC1] | MS m/z 499.2 (M + 1). |
| 130 | 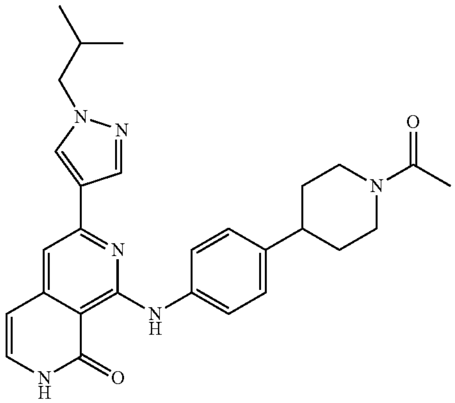 [SMILES: CC(=O)N1CCC(c2ccc(Nc3nc(-c4cnn(CC(C)C)c4)cc4cc[nH]c(=O)c34)cc2)CC1] | MS m/z 485.0 (M + 1). |
| 131 | 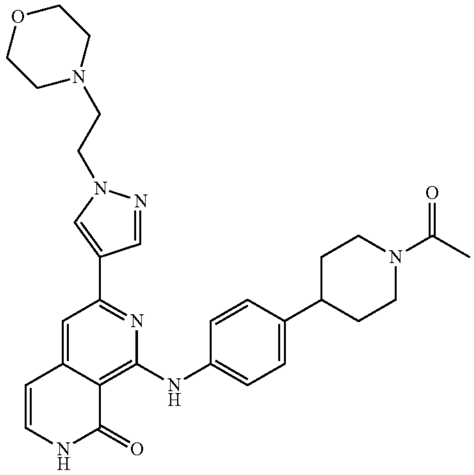 [SMILES: CC(=O)N1CCC(c2ccc(Nc3nc(-c4cnn(CCN5CCOCC5)c4)cc4cc[nH]c(=O)c34)cc2)CC1] | MS m/z 541.1 (M + 1). |

TABLE 1-continued
| No | Structure | Physical Data $^1H$ NMR 400 MHz (DMSO-$d_6$) and/or MS (m/z) |
|---|---|---|
| 132 | 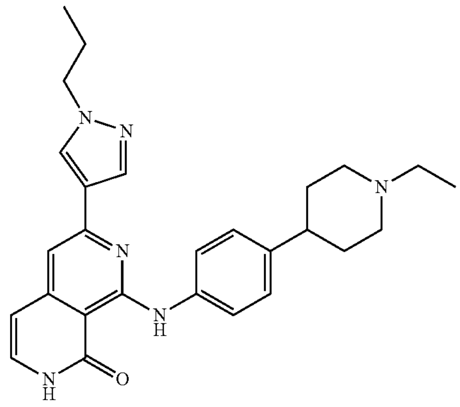 [SMILES: CCCn1cc(-c2cc3cc[nH]c(=O)c3c(Nc3ccc(C4CCN(CC)CC4)cc3)n2)cn1] | MS m/z 457.1 (M + 1). |
| 133 | 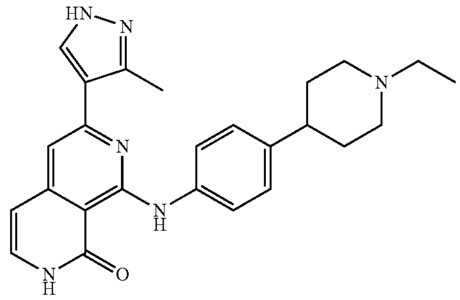 [SMILES: CCN1CCC(c2ccc(Nc3nc(-c4c[nH]nc4C)cc4cc[nH]c(=O)c34)cc2)CC1] | MS m/z 429.3 (M + 1). |
| 134 | 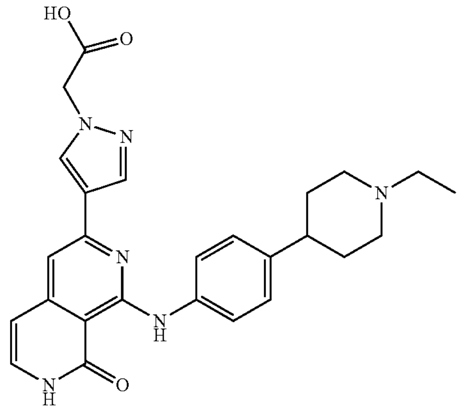 [SMILES: CCN1CCC(c2ccc(Nc3nc(-c4cnn(CC(=O)O)c4)cc4cc[nH]c(=O)c34)cc2)CC1] | MS m/z 473.1 (M + 1). |
| 135 | 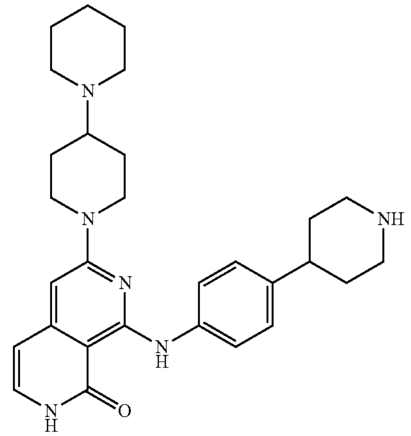 [SMILES: O=c1[nH]ccc2cc(N3CCC(N4CCCCC4)CC3)nc(Nc3ccc(C4CCNCC4)cc3)c12] | MS m/z 486.1 (M + 1). |

TABLE 1-continued
| No | Structure | Physical Data $^1H$ NMR 400 MHz (DMSO-$d_6$) and/or MS (m/z) |
|---|---|---|
| 136 | 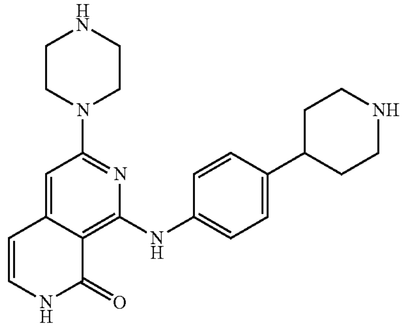 [SMILES: O=c1[nH]ccc2cc(N3CCNCC3)nc(Nc3ccc(C4CCNCC4)cc3)c12] | MS m/z 405.2 (M + 1). |
| 137 | 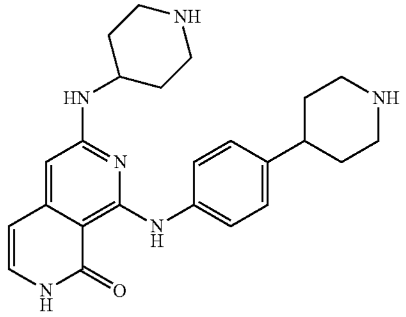 [SMILES: O=c1[nH]ccc2cc(NC3CCNCC3)nc(Nc3ccc(C4CCNCC4)cc3)c12] | MS m/z 419.2 (M + 1). |
| 138 | 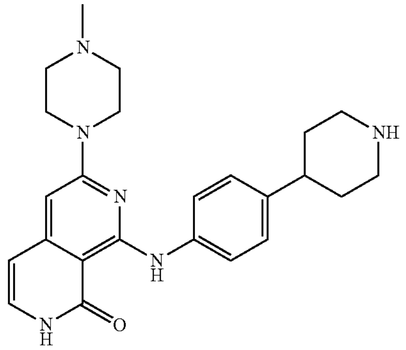 [SMILES: CN1CCN(c2cc3cc[nH]c(=O)c3c(Nc3ccc(C4CCNCC4)cc3)n2)CC1] | MS m/z 419.1 (M + 1). |
| 139 | 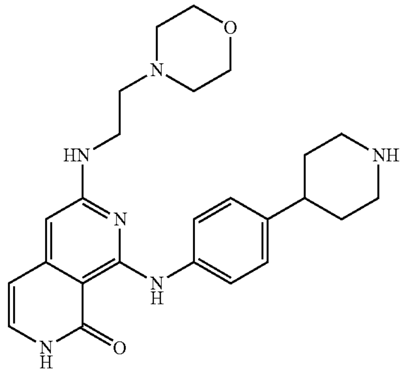 [SMILES: O=c1[nH]ccc2cc(NCCN3CCOCC3)nc(Nc3ccc(C4CCNCC4)cc3)c12] | MS m/z 449.1 (M + 1). |

TABLE 1-continued
| No | Structure | Physical Data $^1H$ NMR 400 MHz (DMSO-$d_6$) and/or MS (m/z) |
|---|---|---|
| 140 | 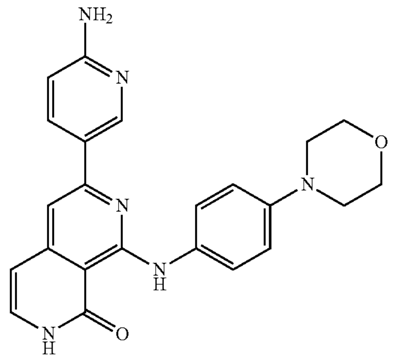 [SMILES: Nc1ccc(-c2cc3cc[nH]c(=O)c3c(Nc3ccc(N4CCOCC4)cc3)n2)cn1] | MS m/z 415.1 (M + 1). |
| 141 | 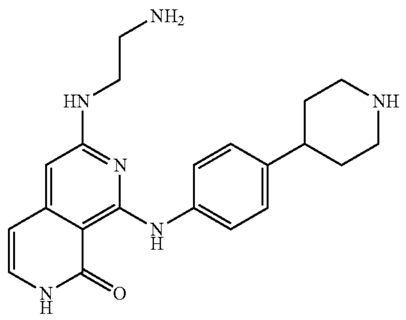 [SMILES: NCCNc1cc2cc[nH]c(=O)c2c(Nc2ccc(C3CCNCC3)cc2)n1] | MS m/z 379.1 (M + 1). |
| 142 | 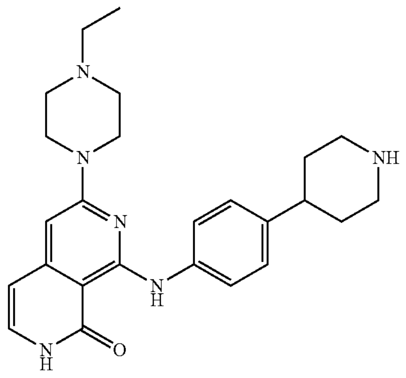 [SMILES: CCN1CCN(c2cc3cc[nH]c(=O)c3c(Nc3ccc(C4CCNCC4)cc3)n2)CC1] | MS m/z 433.1 (M + 1). |
| 143 | 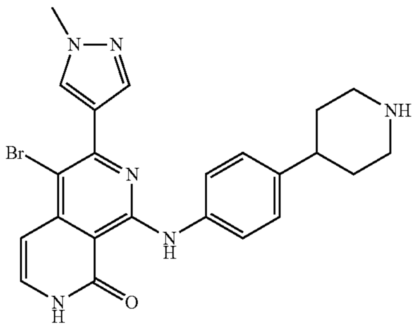 [SMILES: Cn1cc(-c2nc(Nc3ccc(C4CCNCC4)cc3)c3c(=O)[nH]ccc3c2Br)cn1] | MS m/z 479.2 (M + 1). ($MH^+$); Anal. Calcd for $C_{26}H_{27}N_5O_2$: C, 70.73; H, 6.16; N, 15.86. Found: C, 70.73; H, 6.13; N, 15.83. |

TABLE 1-continued
| No | Structure | Physical Data $^1$H NMR 400 MHz (DMSO-$d_6$) and/or MS (m/z) |
|---|---|---|
| 144 | 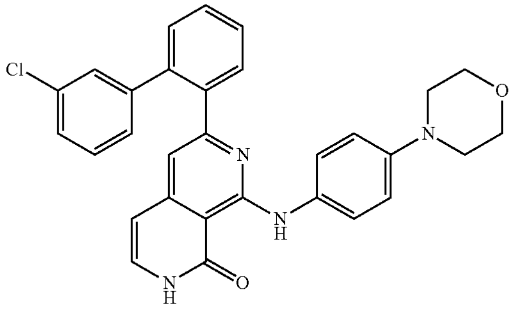 [SMILES: O=c1[nH]ccc2cc(-c3ccccc3-c3cccc(Cl)c3)nc(Nc3ccc(N4CCOCC4)cc3)c12] | MS m/z 509.1 (M + 1). |
| 145 | 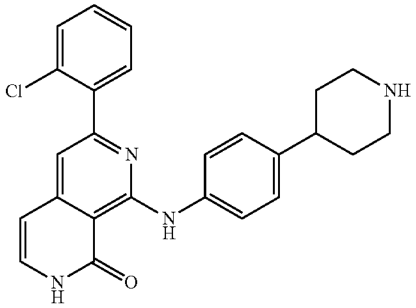 [SMILES: O=c1[nH]ccc2cc(-c3ccccc3Cl)nc(Nc3ccc(C4CCNCC4)cc3)c12] | MS m/z 431.1 (M + 1). |
| 146 | 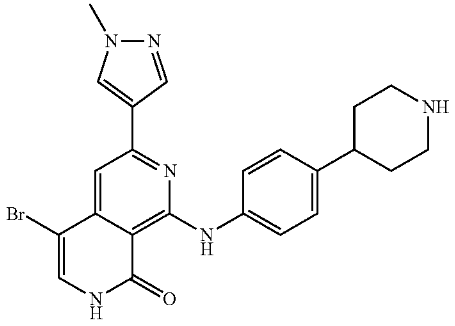 [SMILES: Cn1cc(-c2cc3c(Br)c[nH]c(=O)c3c(Nc3ccc(C4CCNCC4)cc3)n2)cn1] | MS m/z 479.1 (M + 1). |
| 147 | 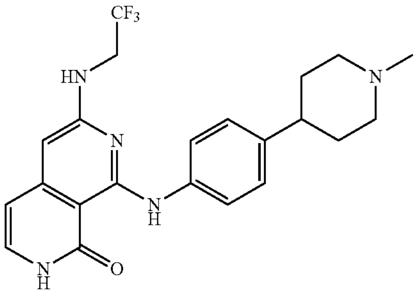 [SMILES: CN1CCC(c2ccc(Nc3nc(NCC(F)(F)F)cc4cc[nH]c(=O)c34)cc2)CC1] | MS m/z 432.1 (M + 1). |
| 148 | 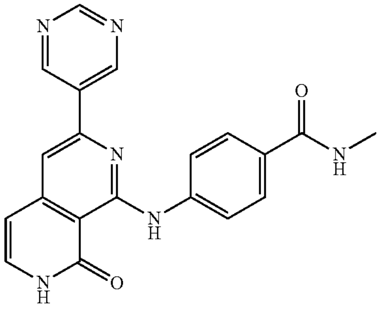 [SMILES: CNC(=O)c1ccc(Nc2nc(-c3cncnc3)cc3cc[nH]c(=O)c23)cc1] | $^1$H NMR (400 MHz, DMSO-$d_6$) δ 12.29 (s, 1H), 11.29 (s, 1H), 9.5 (s, 1H), 9.30 (s, 1H), 7.95 (d, 2H, J = 8.4 Hz), 7.90 (d, 2H, J = 8.4 Hz), 7.76 (s, 1H), 7.52 (d, 1H, J = 7.2 Hz), 6.59 (d, 1H, J = 6.8 Hz), 2.79 (d, 1H, J = 4.8 Hz); MS m/z 373.2 (M + 1). |

TABLE 1-continued
| No | Structure | Physical Data $^1H$ NMR 400 MHz (DMSO-$d_6$) and/or MS (m/z) |
|---|---|---|
| 149 | 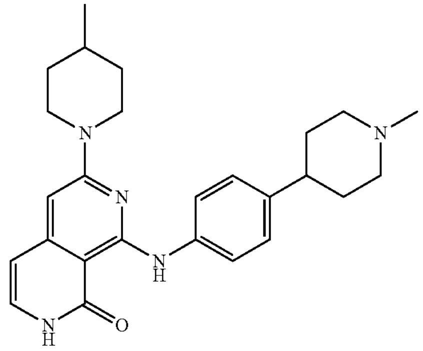 [SMILES: CC1CCN(c2cc3cc[nH]c(=O)c3c(Nc3ccc(C4CCN(C)CC4)cc3)n2)CC1] | MS m/z 432.14 (M + 1). |
| 150 | 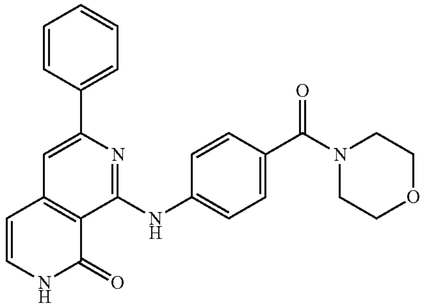 [SMILES: O=C(c1ccc(Nc2nc(-c3ccccc3)cc3cc[nH]c(=O)c23)cc1)N1CCOCC1] | MS m/z 427.21 (M + 1). |
| 151 | 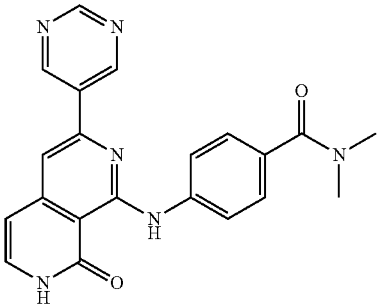 [SMILES: CN(C)C(=O)c1ccc(Nc2nc(-c3cncnc3)cc3cc[nH]c(=O)c23)cc1] | $^1H$ NMR (400 MHz, DMSO-d6) δ 12.17 (s, 1H), 9.41 (s, 1H), 9.23 (s, 1H), 7.84 (d, 2H, J = 8.4 Hz), 7.66 (s, 1H), 7.46 (s, 1H), 7.43 (d, 2H, J = 8.4 Hz), 7.41 (m, 1H), 6.52 (d, 1H, J = 7.2 Hz), 3.2 (s, 3H), 2.9 (s, 3H) MS m/z 387.11 (M + 1). |
| 152 | 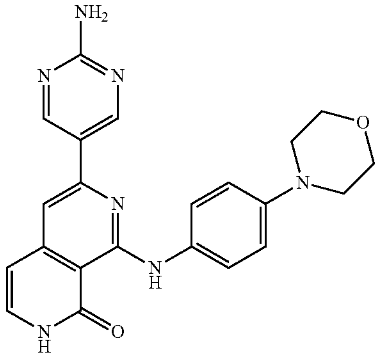 [SMILES: Nc1ncc(-c2cc3cc[nH]c(=O)c3c(Nc3ccc(N4CCOCC4)cc3)n2)cn1] | $^1H$ NMR (400 MHz, DMSO-d6) δ δ 12.14 (s, 1H), 9.43(s, 1H), 9.25 (s, 1H), 7.85 (d, 2H, J = 8.8 Hz), 7.15 (s, 1H), 6.94 (d, 2H, J = 8.8 Hz), 6.90 (d, 1H, J = 5.2 Hz), 6.31 (d, 1H, J = 6.8 Hz), 3.81 (m, 4H), 3.25 (m, 4H); MS m/z 416.18 (M + 1). |

TABLE 1-continued
| No | Structure | Physical Data $^1H$ NMR 400 MHz ($DMSO-d_6$) and/or MS (m/z) |
|---|---|---|
| 153 | 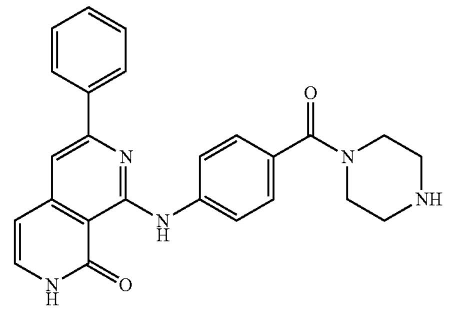 [SMILES: O=C(c1ccc(Nc2nc(-c3ccccc3)cc3cc[nH]c(=O)c23)cc1)N1CCNCC1] | MS m/z 426.13 (M + 1). |
| 154 | 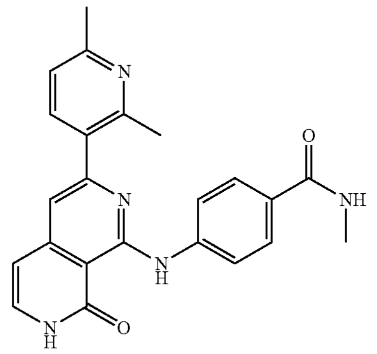 [SMILES: CNC(=O)c1ccc(Nc2nc(-c3ccc(C)nc3C)cc3cc[nH]c(=O)c23)cc1] | $^1H$ NMR (400 MHz, $DMSO-d_6$) δ 12.35 (s, 1H), 8.33 (d, 1H, J = 4.4 Hz), 7.95 (d, 2H, J = 8.8 Hz), 7.87 (d, 2H, J = 8.8 Hz), 7.54 (d, 1H, J = 6.8 Hz), 7.29 (d, 1H, J = 6.8 Hz), 7.19 (s, 1H), 6.66 (d, 2H, J = 6.8 Hz), 3.4 (s, 3H), 2.6 (s, 3H), 2.53 (s, 3H); MS m/z 400.1 (M + 1). |
| 155 | 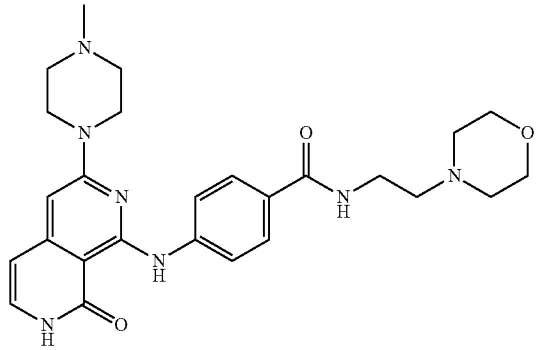 [SMILES: CN1CCN(c2cc3cc[nH]c(=O)c3c(Nc3ccc(C(=O)NCCN4CCOCC4)cc3)n2)CC1] | MS m/z 492.26 (M + 1). |
| 156 | 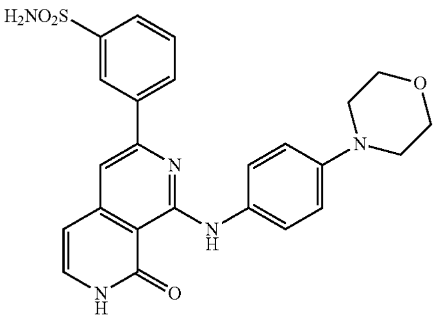 [SMILES: NS(=O)(=O)c1cccc(-c2cc3cc[nH]c(=O)c3c(Nc3ccc(N4CCOCC4)cc3)n2)c1] | $^1H$ NMR (400 MHz, DMSO-d6) δ 11.73 (s, 1H), 8.57 (s, 1H), 8.25 (m, 1H), 7.84 (m, 2H)), 7.70 (d, 2H, J = 8.8 Hz), 7.75 (d, 2H, J = 8.8 Hz), 7.44 (t, 1H, J = 6.8 Hz), 7.36 (d, 1H, J = 6.8 Hz), 6.92 (d, 2H, J = 8.8 Hz), 6.52 (d, 1H, J = 6.8 Hz), 3.69 (m, 4H), 3.09 (m, 4H); MS m/z 478.31 (M + 1). |

TABLE 1-continued
| No | Structure | Physical Data $^1$H NMR 400 MHz (DMSO-$d_6$) and/or MS (m/z) |
|---|---|---|
| 157 | 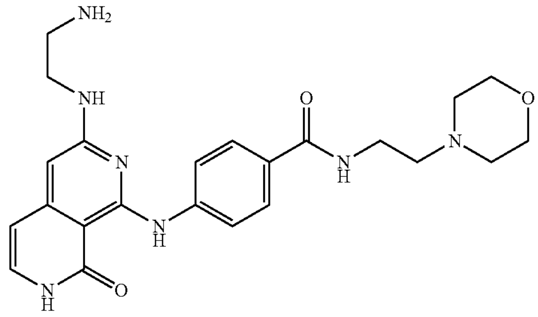 [SMILES: NCCNc1cc2cc[nH]c(=O)c2c(Nc2ccc(C(=O)NCCN3CCOCC3)cc2)n1] | MS m/z 452.2 (M + 1). |
| 158 | 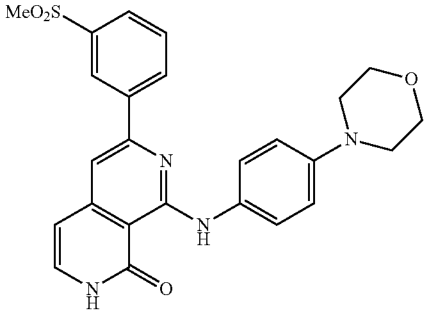 [SMILES: CS(=O)(=O)c1cccc(-c2cc3cc[nH]c(=O)c3c(Nc3ccc(N4CCOCC4)cc3)n2)c1] | $^1$H NMR (400 MHz, DMSO-d6) δ 11.87(s, 1H), 8.68 (s, 1H), 8.46 (d, 1H, J = 4.8 Hz), 8.03 (d, 1H, J = 4.8 Hz), 7.83 (d, 2H, J = 8.8 Hz), 7.75 (d, 2H, J = 8.8 Hz), 7.46 (t, 1H, J = 6.8 Hz), 7.35 (d, 1H, J = 5.2 Hz), 6.61 (d, 1H, J = 6.8 Hz), 3.80 (m, 4H), 3.3 (s, 3H), 3.23 (m, 4H); MS m/z 477.2 (M + 1). |
| 159 | 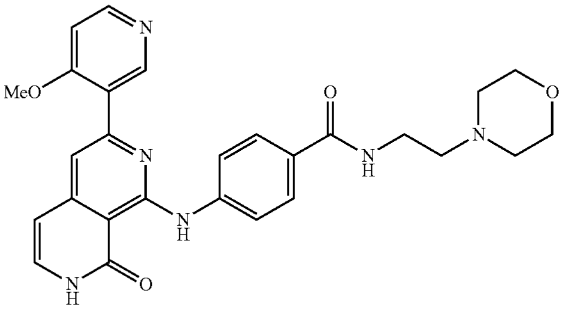 [SMILES: COc1ccncc1-c1cc2cc[nH]c(=O)c2c(Nc2ccc(C(=O)NCCN3CCOCC3)cc2)n1] | MS m/z 501.12 (M + 1). |
| 160 | 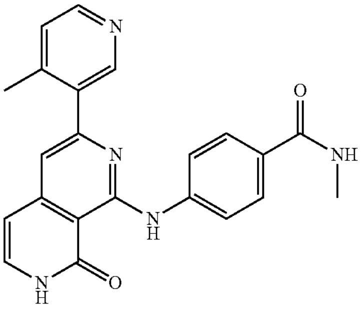 [SMILES: CNC(=O)c1ccc(Nc2nc(-c3cnccc3C)cc3cc[nH]c(=O)c23)cc1] | $^1$H NMR (400 MHz, DMSO-d6) δ 12.24 (s, 1H), 11.86 (d, 1H, J = 6 Hz), 8.63 (s, 1H), 8.46 (d, 1H, J = 4.8 Hz), 8.22 (J, 1H, J = 4.8 Hz), 7.82 (d, 2H, J = 8.8 Hz), 7.66 (t, 1H, J = 7.6), 7.41 (s, 1H), (d, 2H, J = 8.8 Hz), 7.44 (t, 1H, J = 6.8 Hz), 7.35 (d, 1H, J = 5.2 Hz), 7.13 (s, 1H), 6.55 (d, 1H, J = 6.8 Hz), 2.70 (d, 3H, J = 4.8 Hz), 2.40 (s, 3H); MS m/z 386.17 (M + l). |

TABLE 1-continued
| No | Structure | Physical Data $^1H$ NMR 400 MHz ($DMSO-d_6$) and/or MS (m/z) |
|---|---|---|
| 161 | 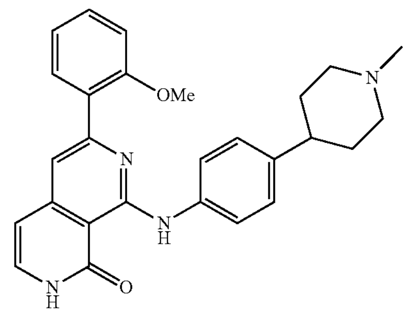 [SMILES: COc1ccccc1-c1cc2cc[nH]c(=O)c2c(Nc2ccc(C3CCN(C)CC3)cc2)n1] | MS m/z 441.1 (M + 1). |
| 162 | 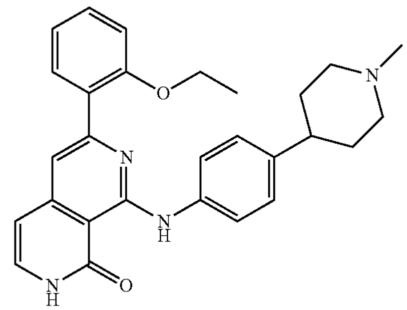 [SMILES: CCOc1ccccc1-c1cc2cc[nH]c(=O)c2c(Nc2ccc(C3CCN(C)CC3)cc2)n1] | MS m/z 455.1 (M + 1). |
| 163 | 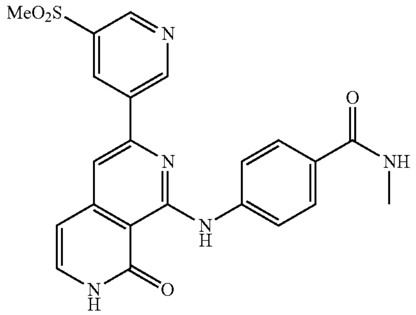 [SMILES: CNC(=O)c1ccc(Nc2nc(-c3cncc(S(C)(=O)=O)c3)cc3cc[nH]c(=O)c23)cc1] | $^1H$ NMR (400 MHz, DMSO-d6) δ 12.23 (s, 1H), 9.57 (d, 1H, J = 2.0 Hz), 9.12 (d, 1H, J = 2 Hz), 8.31 (m, 1H), 7.90 (d, 2H, J = 8.8 Hz), 7.82 (d, 2H, J = 8.8 Hz), 7.78 (s, 1H), 7.46 (d, 1H, J = 6.8 Hz), 6.58 (d, 1H, J = 6.8 Hz), 3.37 (s, 3H), 2.72 (d, 3H, J= 4.4 Hz); MS m/z 450.03 (M + 1). |
| 164 | 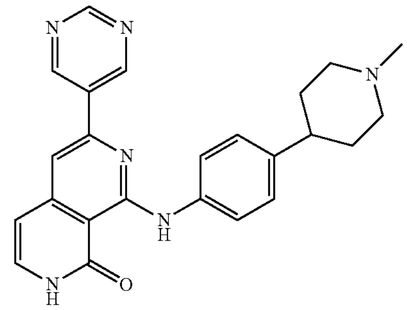 [SMILES: CN1CCC(c2ccc(Nc3nc(-c4cncnc4)cc4cc[nH]c(=O)c34)cc2)CC1] | $^1H$ NMR (400 MHz, $DMSO-d_6$) δ 12.02 (s, 1H), 11.92 (s, 1H), 9.90 (brs, 1H), 9.47 (s, 1H), 9.29 (s, 1H), 7.82 (d, 2H, J = 8.4 Hz), 7.67 (s, 1H), 7.49 (m, 1H), 7.28 (d, 2H, J = 8.4 Hz), 6.56 (d, 1H, J = 6.8 Hz), 3.48 (m, 3H), 2.93 (m, 4H, 2.72 (m, 1H), 2.04 (m, 2H), 1.94 (m, 2H); MS m/z 413.2 (M + 1). |

TABLE 1-continued
| No | Structure | Physical Data $^1$H NMR 400 MHz (DMSO-$d_6$) and/or MS (m/z) |
|---|---|---|
| 165 | 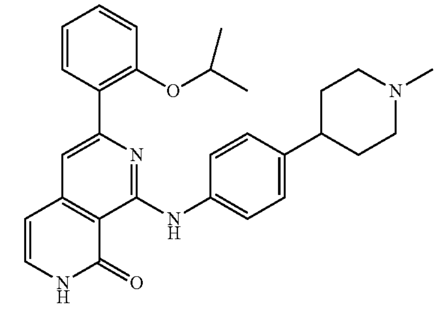 [SMILES: CC(C)Oc1ccccc1-c1cc2cc[nH]c(=O)c2c(Nc2ccc(C3CCN(C)CC3)cc2)n1] | MS m/z 469.2 (M + 1). |
| 166 | 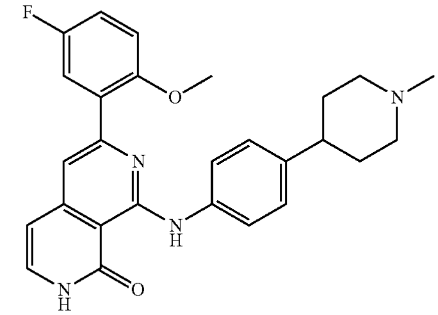 [SMILES: COc1ccc(F)cc1-c1cc2cc[nH]c(=O)c2c(Nc2ccc(C3CCN(C)CC3)cc2)n1] | MS m/z 459.31 (M + 1). |
| 167 | 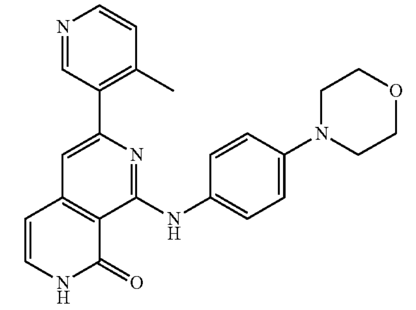 [SMILES: Cc1ccncc1-c1cc2cc[nH]c(=O)c2c(Nc2ccc(N3CCOCC3)cc2)n1] | $^1$H NMR (400 MHz, DMSO-d6) δ δ 12.08 (s, 1H), 9.06 (s, 1H), 8.89 (m, 1H), 8.08 (m, 1H), 7.78 (d, 2H, J = 8.8 Hz), 7.59 (m, 1H), 7.26 (d, 2H, J = 8.8 Hz), 6.65 (d, 1H, J = 6.8 Hz), 3.91 (s, 4H), 3.30 (m, 4H), 2.72 (s, 3H); MS m/z 414.2 (M + 1). |
| 168 | 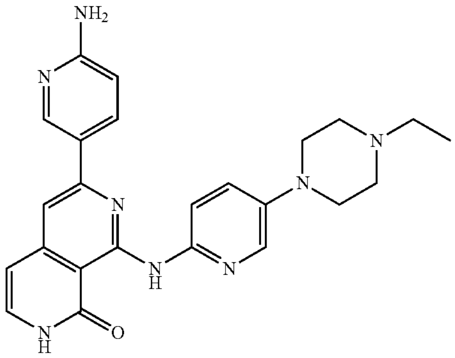 [SMILES: CCN1CCN(c2ccc(Nc3nc(-c4ccc(N)nc4)cc4cc[nH]c(=O)c34)nc2)CC1] | MS m/z 443.1 (M + 1). |

TABLE 1-continued
| No | Structure | Physical Data $^1H$ NMR 400 MHz ($DMSO-d_6$) and/or MS (m/z) |
|---|---|---|
| 169 | 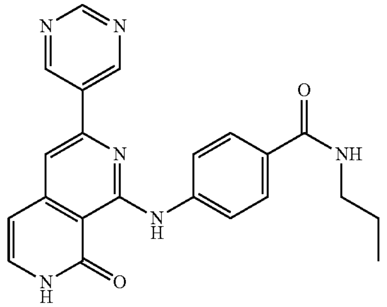 [SMILES: CCCNC(=O)c1ccc(Nc2nc(-c3cncnc3)cc3cc[nH]c(=O)c23)cc1] | $^1H$ NMR (400 MHz, $DMSO-d_6$) δ 12.21 (s, 1H), 11.94 (s, 1H), 9.43 (s, 1H), 9.24 (s, 1H), 7.87 (d, 2H, J = 8.4 Hz), 7.90 (d, 2H, J = 8.4 Hz), 7.76 (s, 1H), 7.52 (d, 1H, J = 7.2 Hz), 6.59 (d, 1H, J = 6.8 Hz), 3.16 (m, 2H), 1.47 (m, 2H), 0.84 (t, 3H, J = 7.2 Hz); MS m/z 401.2 (M + 1). |
| 170 | 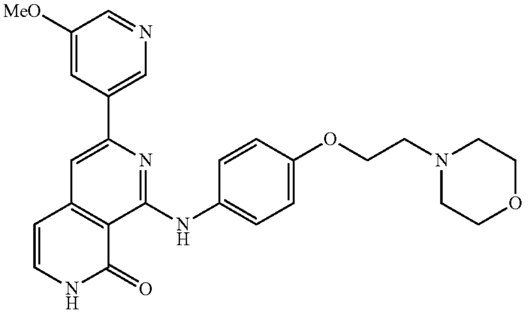 [SMILES: COc1cncc(-c2cc3cc[nH]c(=O)c3c(Nc3ccc(OCCN4CCOCC4)cc3)n2)c1] | MS m/z 474.2 (M + 1). |
| 171 | 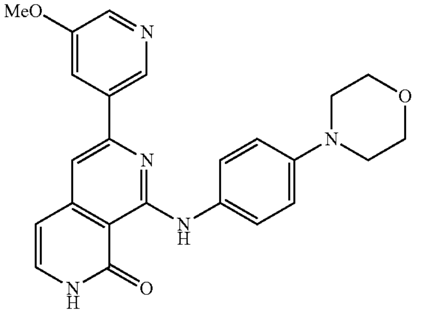 [SMILES: COc1cncc(-c2cc3cc[nH]c(=O)c3c(Nc3ccc(N4CCOCC4)cc3)n2)c1] | MS m/z 430.21 (M + 1). |
| 172 | 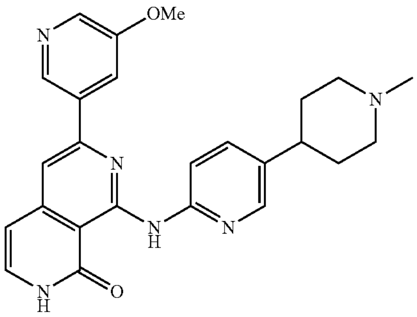 | $^1H$ NMR (400 MHz, DMSO-d6) δ 11.82 (s, 1H), 8.92 (s, 1H), 7.65 (d, 2H, J = 8.4 Hz), 7.35 (s, 1H), 7.12 (d, 2H, J = 8.4 Hz), 6.47 (d, 1H, J = 6.8 Hz), 4.01 (s, 1H), 3.92 (s, 3H), 3.27 (s, 3H), 2.88 (m, 4H), 2.22 (m, 1H), 1.72-1.58 (m, 4H); MS m/z 473.1 (M + 1). |

TABLE 1-continued
| No | Structure | Physical Data $^1H$ NMR 400 MHz (DMSO-$d_6$) and/or MS (m/z) |
|---|---|---|
| 173 | 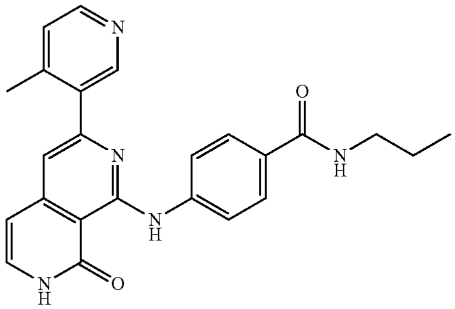 [SMILES: CCCNC(=O)c1ccc(Nc2nc(-c3cnccc3C)cc3cc[nH]c(=O)c23)cc1] | MS m/z 414.1 (M + 1). |
| 174 | 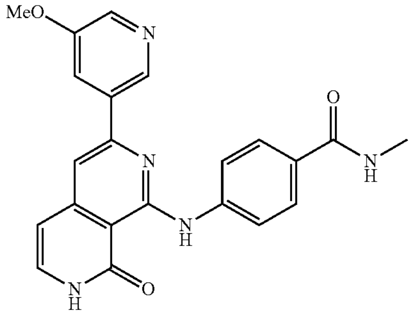 [SMILES: CNC(=O)c1ccc(Nc2nc(-c3cncc(OC)c3)cc3cc[nH]c(=O)c23)cc1] | MS m/z 402.12 (M + 1). |
| 175 | 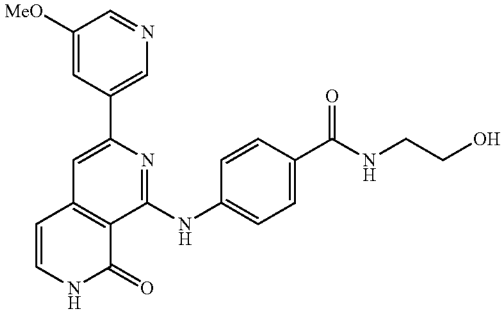 [SMILES: COc1cncc(-c2cc3cc[nH]c(=O)c3c(Nc3ccc(C(=O)NCCO)cc3)n2)c1] | MS m/z 432.2 (M + 1). |
| 176 | 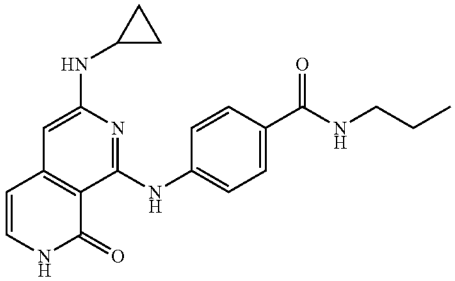 [SMILES: CCCNC(=O)c1ccc(Nc2nc(NC3CC3)cc3cc[nH]c(=O)c23)cc1] | MS m/z 378.2 (M + 1). |
| 177 | 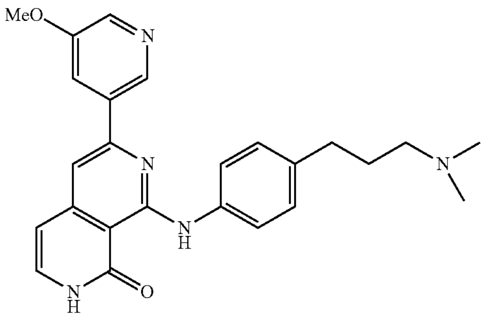 [SMILES: COc1cncc(-c2cc3cc[nH]c(=O)c3c(Nc3ccc(CCCN(C)C)cc3)n2)c1] | MS m/z 430.32 (M + 1). |

TABLE 1-continued
| No | Structure | Physical Data $^1H$ NMR 400 MHz (DMSO-$d_6$) and/or MS (m/z) |
|---|---|---|
| 178 | 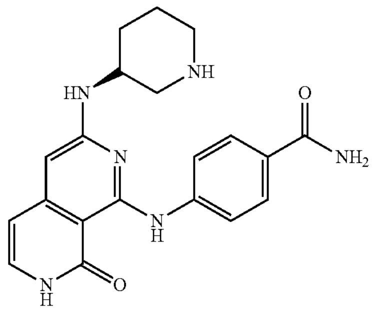 | MS m/z 379.12 (M + 1). |
| 179 | 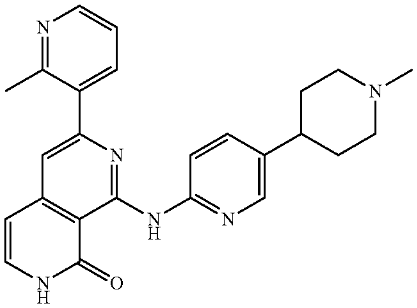 [SMILES: Cc1ncccc1-c1cc2cc[nH]c(=O)c2c(Nc2ccc(C3CCN(C)CC3)cn2)n1] | MS m/z 426.3 (M + 1). |
| 180 | 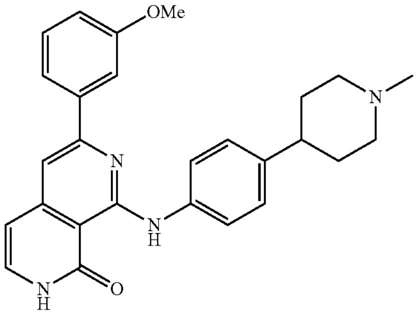 [SMILES: COc1cccc(-c2cc3cc[nH]c(=O)c3c(Nc3ccc(C4CCN(C)CC4)cc3)n2)c1] | MS m/z 441.2 (M + 1). |
| 181 | 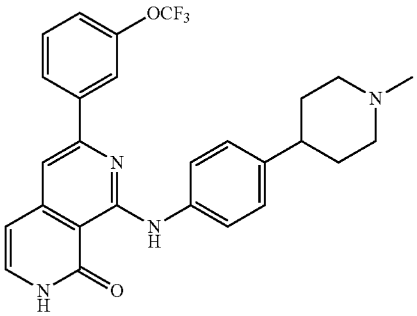 [SMILES: CN1CCC(c2ccc(Nc3nc(-c4cccc(OC(F)(F)F)c4)cc4cc[nH]c(=O)c34)cc2)CC1] | MS m/z 495.2 (M + 1). |

TABLE 1-continued
| No | Structure | Physical Data $^1$H NMR 400 MHz (DMSO-$d_6$) and/or MS (m/z) |
|---|---|---|
| 182 | 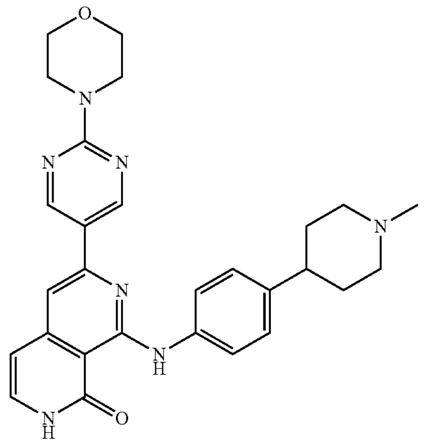 [SMILES: CN1CCC(c2ccc(Nc3nc(-c4cnc(N5CCOCC5)nc4)cc4cc[nH]c(=O)c34)cc2)CC1] | MS m/z 498.06 (M + 1). |
| 183 | 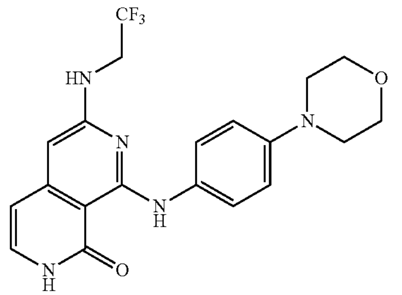 [SMILES: O=c1[nH]ccc2cc(NCC(F)(F)F)nc(Nc3ccc(N4CCOCC4)cc3)c12] | MS m/z 420.1 (M + 1). |
| 184 | 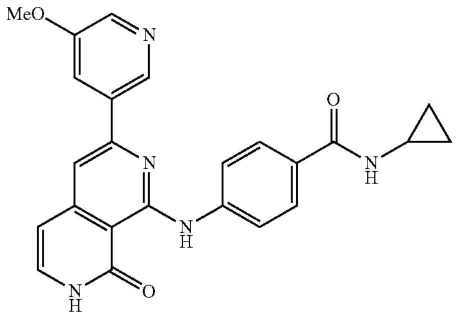 [SMILES: COc1cncc(-c2cc3cc[nH]c(=O)c3c(Nc3ccc(C(=O)NC4CC4)cc3)n2)c1] | MS m/z 428.16 (M + 1). |
| 185 | 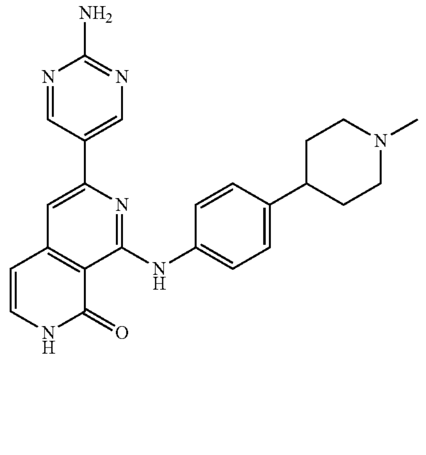 [SMILES: CN1CCC(c2ccc(Nc3nc(-c4cnc(N)nc4)cc4cc[nH]c(=O)c34)cc2)CC1] | MS m/z 428.11 (M + 1). |

TABLE 1-continued
| No | Structure | Physical Data $^1$H NMR 400 MHz (DMSO-$d_6$) and/or MS (m/z) |
|---|---|---|
| 186 | 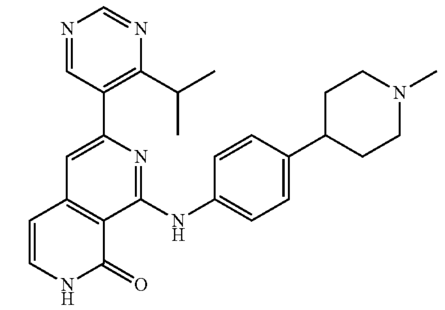 [SMILES: CC(C)c1ncncc1-c1cc2cc[nH]c(=O)c2c(Nc2ccc(C3CCN(C)CC3)cc2)n1] | MS m/z 455.12 (M + 1). |
| 187 | 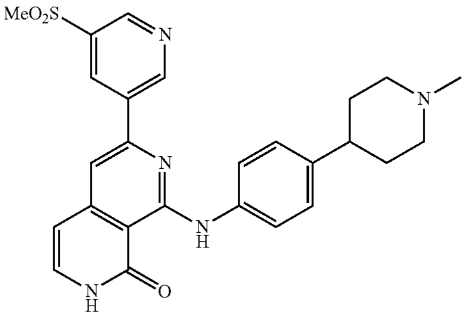 | MS m/z 490.1 (M + 1). |
| 188 | 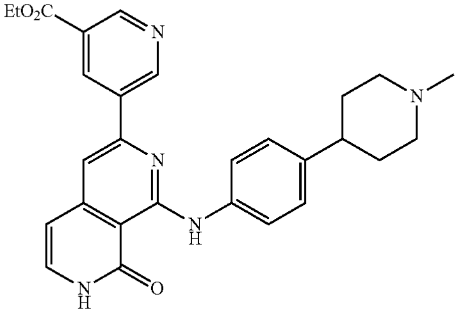 [SMILES: CCOC(=O)c1cncc(-c2cc3cc[nH]c(=O)c3c(Nc3ccc(C4CCN(C)CC4)cc3)n2)c1] | MS m/z 484.22 (M + 1). |
| 189 | 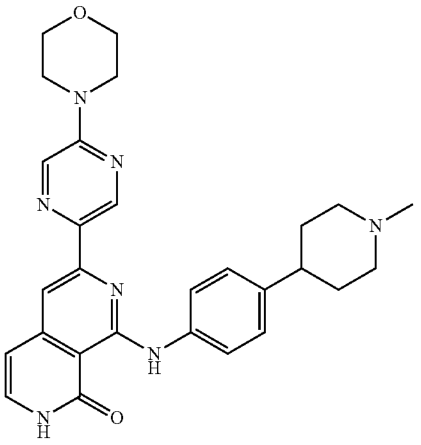 [SMILES: CN1CCC(c2ccc(Nc3nc(-c4cnc(N5CCOCC5)cn4)cc4cc[nH]c(=O)c34)cc2)CC1] | MS m/z 498.2 (M + 1). |

TABLE 1-continued
| No | Structure | Physical Data $^1H$ NMR 400 MHz (DMSO-$d_6$) and/or MS (m/z) |
|---|---|---|
| 190 | 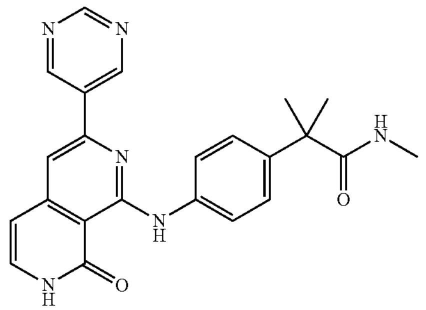 [SMILES: CNC(=O)C(C)(C)c1ccc(Nc2nc(-c3cncnc3)cc3cc[nH]c(=O)c23)cc1] | MS m/z 415.16 (M + 1). |
| 191 | 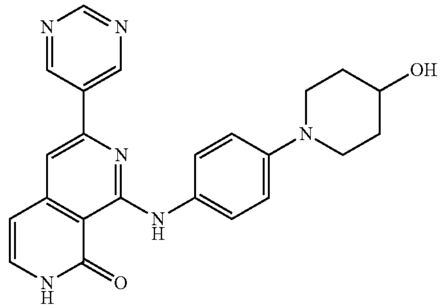 [SMILES: O=c1[nH]ccc2cc(-c3cncnc3)nc(Nc3ccc(N4CCC(O)CC4)cc3)c12] | MS m/z 427.1 (M + 1). |
| 192 | 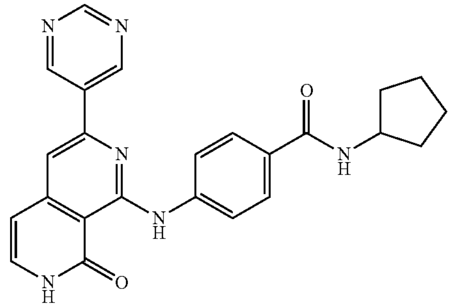 [SMILES: O=C(NC1CCCC1)c1ccc(Nc2nc(-c3cncnc3)cc3cc[nH]c(=O)c23)cc1] | MS m/z 470.1 (M + 1). |
| 193 | 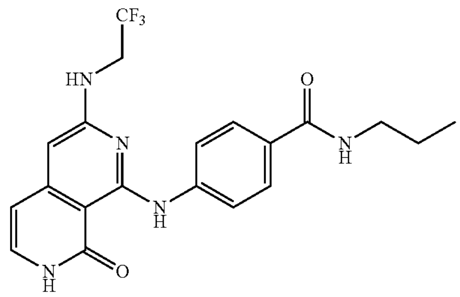 [SMILES: CCCNC(=O)c1ccc(Nc2nc(NCC(F)(F)F)cc3cc[nH]c(=O)c23)cc1] | MS m/z 420.1 (M + 1). |
| 194 | 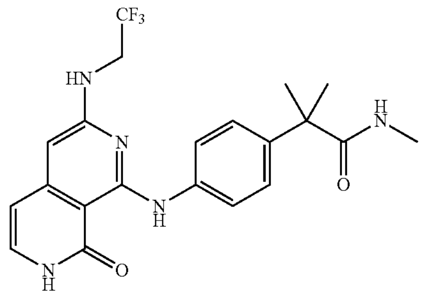 [SMILES: CNC(=O)C(C)(C)c1ccc(Nc2nc(NCC(F)(F)F)cc3cc[nH]c(=O)c23)cc1] | MS m/z 434.01 (M + 1). |

TABLE 1-continued
| No | Structure | Physical Data $^1H$ NMR 400 MHz (DMSO-$d_6$) and/or MS (m/z) |
|---|---|---|
| 195 | 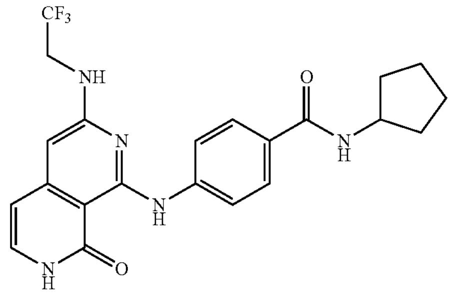 [SMILES: O=C(NC1CCCC1)c1ccc(Nc2nc(NCC(F)(F)F)cc3cc[nH]c(=O)c23)cc1] | MS m/z 446.23 (M + 1). |
| 196 | 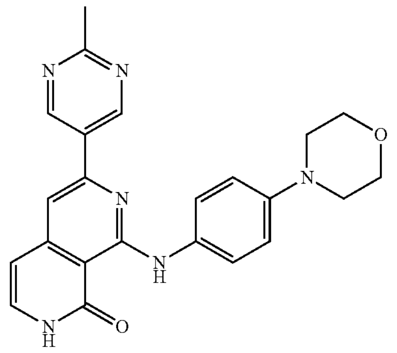 [SMILES: Cc1ncc(-c2cc3cc[nH]c(=O)c3c(Nc3ccc(N4CCOCC4)cc3)n2)cn1] | MS m/z 415.14 (M + 1). |
| 197 | 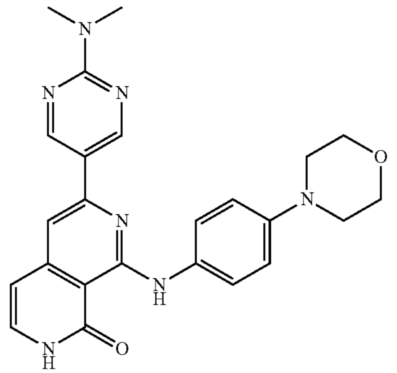 [SMILES: CN(C)c1ncc(-c2cc3cc[nH]c(=O)c3c(Nc3ccc(N4CCOCC4)cc3)n2)cn1] | MS m/z 444.1 (M + 1). |
| 198 | 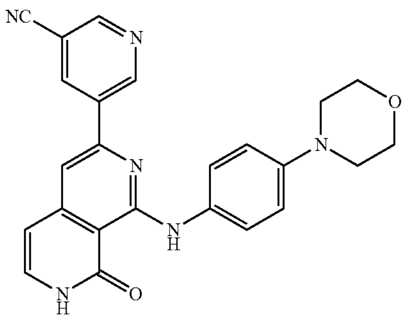 [SMILES: N#Cc1cncc(-c2cc3cc[nH]c(=O)c3c(Nc3ccc(N4CCOCC4)cc3)n2)c1] | MS m/z 425.1 (M + 1). |

TABLE 1-continued
| No | Structure | Physical Data $^1H$ NMR 400 MHz (DMSO-$d_6$) and/or MS (m/z) |
|---|---|---|
| 199 | 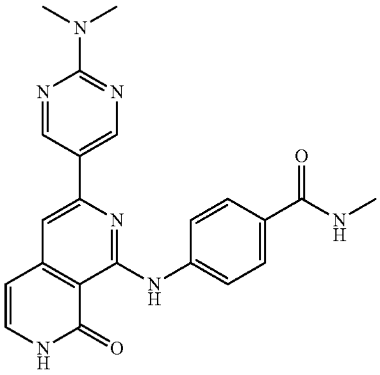 [SMILES: CNC(=O)c1ccc(Nc2nc(-c3cnc(N(C)C)nc3)cc3cc[nH]c(=O)c23)cc1] | MS m/z 416.08 (M + 1). |
| 200 | 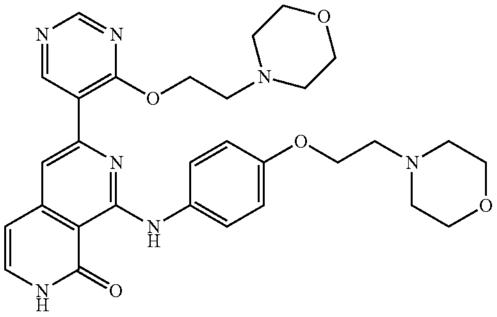 [SMILES: O=c1[nH]ccc2cc(-c3cncnc3OCCN3CCOCC3)nc(Nc3ccc(OCCN4CCOCC4)cc3)c12] | MS m/z 487.1 (M + 1). |
| 201 | 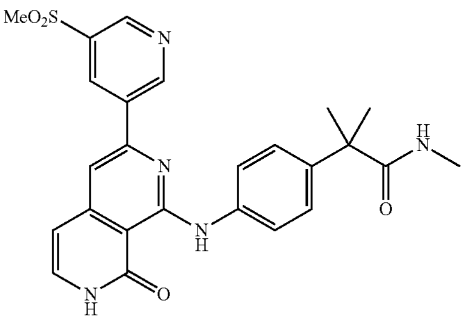 [SMILES: CNC(=O)C(C)(C)c1ccc(Nc2nc(-c3cncc(S(C)(=O)=O)c3)cc3cc[nH]c(=O)c23)cc1] | MS m/z 492.23 (M + 1). |
| 202 | 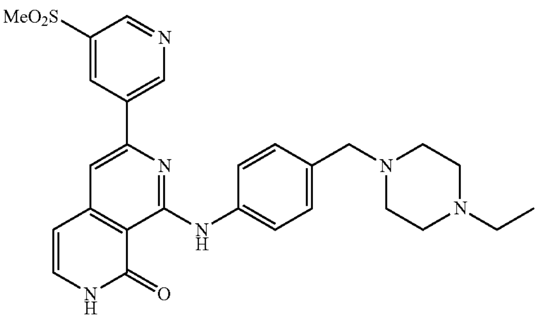 [SMILES: CCN1CCN(Cc2ccc(Nc3nc(-c4cncc(S(C)(=O)=O)c4)cc4cc[nH]c(=O)c34)cc2)CC1] | MS m/z 519.21 (M + 1). |

TABLE 1-continued
| No | Structure | Physical Data $^1$H NMR 400 MHz (DMSO-$d_6$) and/or MS (m/z) |
|---|---|---|
| 203 | 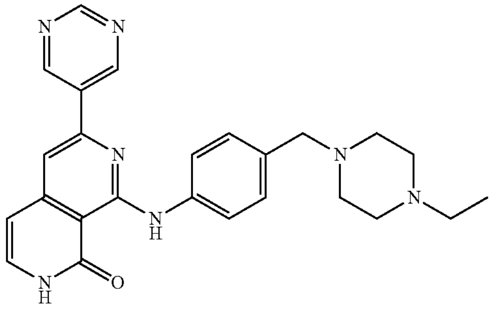 [SMILES: CCN1CCN(Cc2ccc(Nc3nc(-c4cncnc4)cc4cc[nH]c(=O)c34)cc2)CC1] | MS m/z 442.01 (M + 1). |
| 204 | 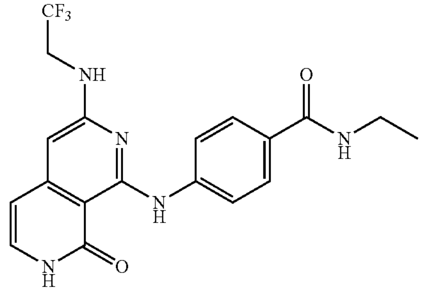 | MS m/z 392.4 (M + 1). |
| 205 | 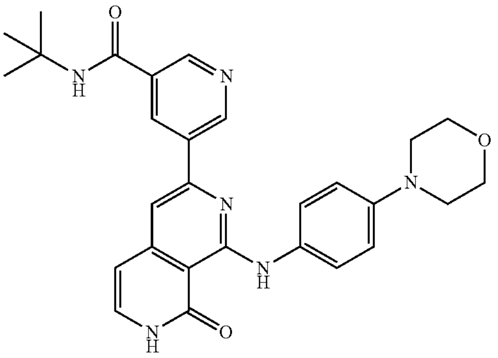 [SMILES: CC(C)(C)NC(=O)c1cncc(-c2cc3cc[nH]c(=O)c3c(Nc3ccc(N4CCOCC4)cc3)n2)c1] | MS m/z 499.13 (M + 1). |
| 206 | 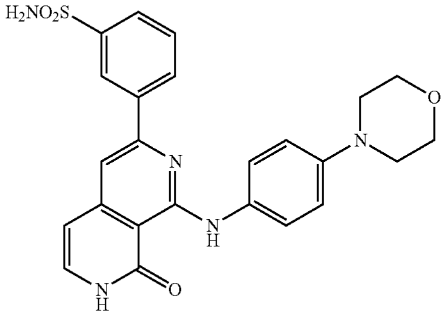 [SMILES: NS(=O)(=O)c1cccc(-c2cc3cc[nH]c(=O)c3c(Nc3ccc(N4CCOCC4)cc3)n2)c1] | MS m/z 493.11 (M + 1). |

TABLE 1-continued
| No | Structure | Physical Data $^1H$ NMR 400 MHz (DMSO-$d_6$) and/or MS (m/z) |
|---|---|---|
| 207 | 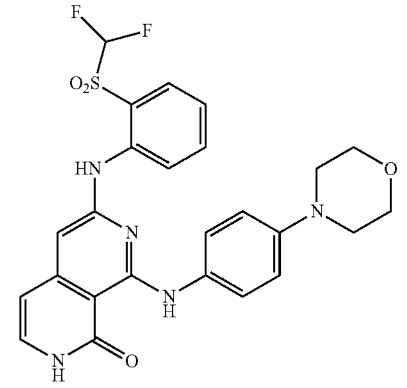 | MS m/z 526.1 (M + 1). |
| 208 | 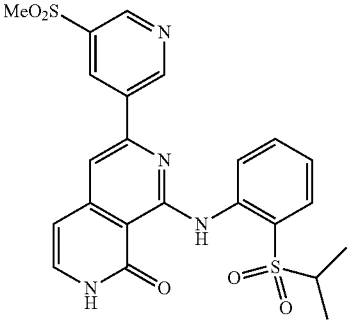 | MS m/z 451.13 (M + 1). |
| 209 | 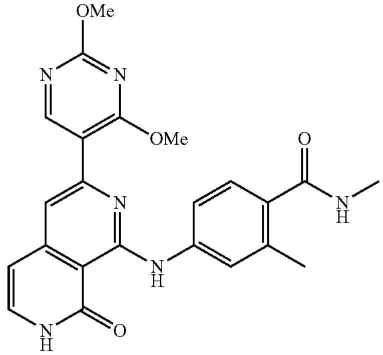 | MS m/z 447.2 (M + 1). |
| 210 | 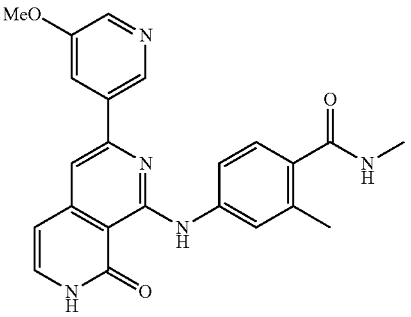 | MS m/z 416.12 (M + 1). |

TABLE 1-continued
| No | Structure | Physical Data $^1H$ NMR 400 MHz (DMSO-$d_6$) and/or MS (m/z) |
|---|---|---|
| 211 | 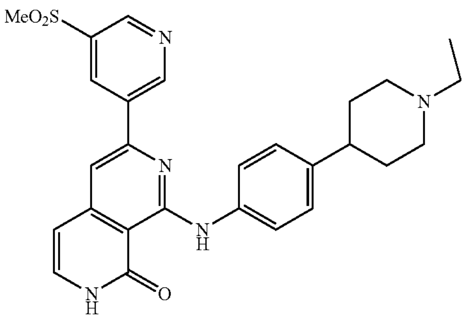 | MS m/z 504.1 (M + 1). |
| 212 | 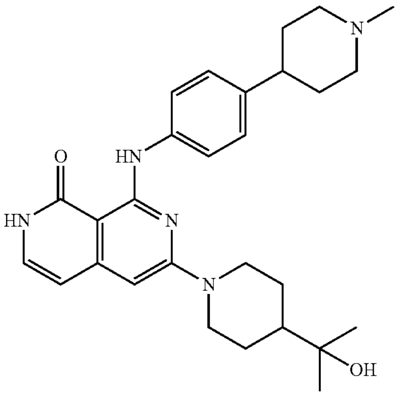 [SMILES: CN1CCC(c2ccc(Nc3nc(N4CCC(C(C)(C)O)CC4)cc4cc[nH]c(=O)c34)cc2)CC1] | MS m/z 476.3 (M + 1). |
| 213 | 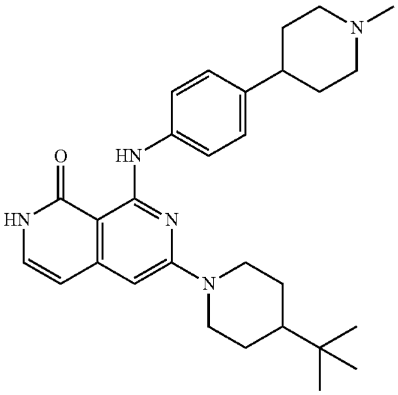 [SMILES: CN1CCC(c2ccc(Nc3nc(N4CCC(C(C)(C)C)CC4)cc4cc[nH]c(=O)c34)cc2)CC1] | MS m/z 474.3 (M + 1). |
| 214 | 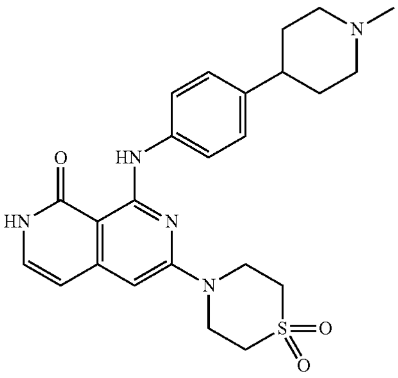 [SMILES: CN1CCC(c2ccc(Nc3nc(N4CCS(=O)(=O)CC4)cc4cc[nH]c(=O)c34)cc2)CC1] | MS m/z 468.2 (M + 1). |

TABLE 1-continued
| No | Structure | Physical Data $^1H$ NMR 400 MHz (DMSO-$d_6$) and/or MS (m/z) |
|---|---|---|
| 215 | 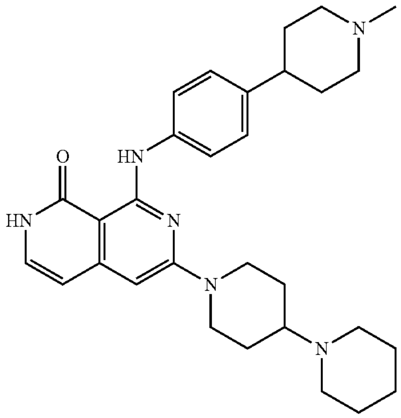 [SMILES: CN1CCC(c2ccc(Nc3nc(N4CCC(N5CCCCC5)CC4)cc4cc[nH]c(=O)c34)cc2)CC1] | MS m/z 501.3 (M + 1). |
| 216 | 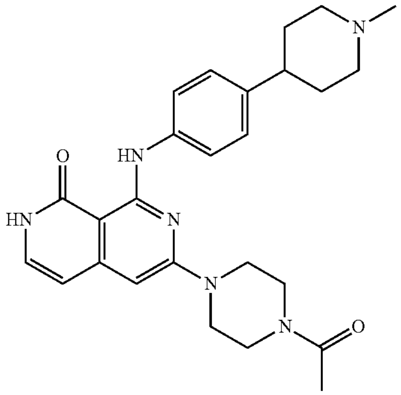 [SMILES: CC(=O)N1CCN(c2cc3cc[nH]c(=O)c3c(Nc3ccc(C4CCN(C)CC4)cc3)n2)CC1] | MS m/z 461.3 (M + 1). |
| 217 | 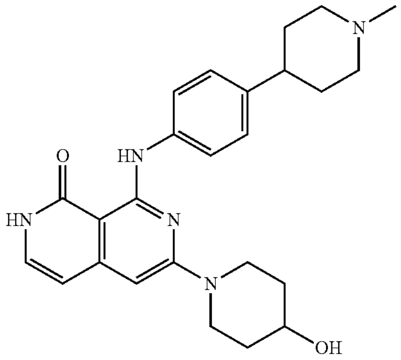 [SMILES: CN1CCC(c2ccc(Nc3nc(N4CCC(O)CC4)cc4cc[nH]c(=O)c34)cc2)CC1] | MS m/z 434.2 (M + 1). |

TABLE 1-continued
| No | Structure | Physical Data $^1H$ NMR 400 MHz ($DMSO-d_6$) and/or MS (m/z) |
|---|---|---|
| 218 | 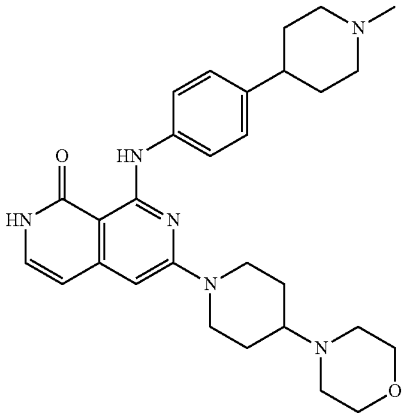 [SMILES: CN1CCC(c2ccc(Nc3nc(N4CCC(N5CCOCC5)CC4)cc4cc[nH]c(=O)c34)cc2)CC1] | MS m/z 503.3 (M + 1). |
| 219 | 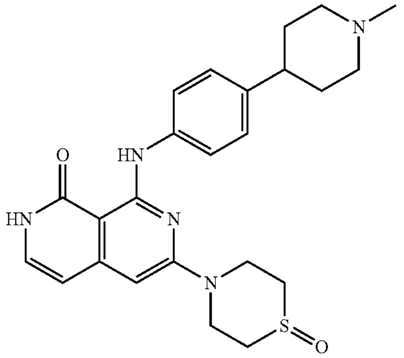 [SMILES: CN1CCC(c2ccc(Nc3nc(N4CCS(=O)CC4)cc4cc[nH]c(=O)c34)cc2)CC1] | MS m/z 452.2 (M + 1). |
| 220 | 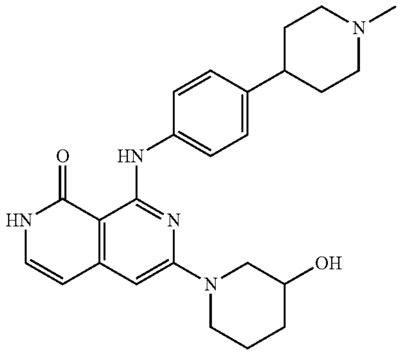 [SMILES: CN1CCC(c2ccc(Nc3nc(N4CCCC(O)C4)cc4cc[nH]c(=O)c34)cc2)CC1] | MS m/z 434.2 (M + 1). |
| 221 | 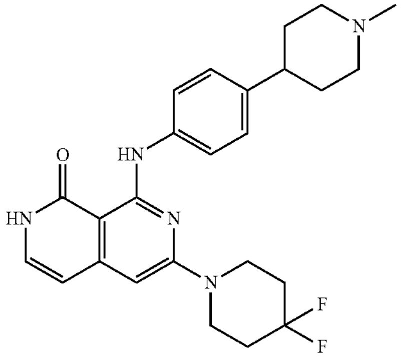 [SMILES: CN1CCC(c2ccc(Nc3nc(N4CCC(F)(F)CC4)cc4cc[nH]c(=O)c34)cc2)CC1] | MS m/z 454.2 (M + 1). |

TABLE 1-continued
| No | Structure | Physical Data $^1$H NMR 400 MHz (DMSO-$d_6$) and/or MS (m/z) |
|---|---|---|
| 222 | 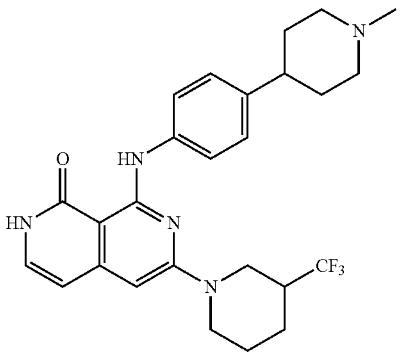 [SMILES: CN1CCC(c2ccc(Nc3nc(N4CCCC(C(F)(F)F)C4)cc4cc[nH]c(=O)c34)cc2)CC1] | MS m/z 486.2 (M + 1). |
| 223 | 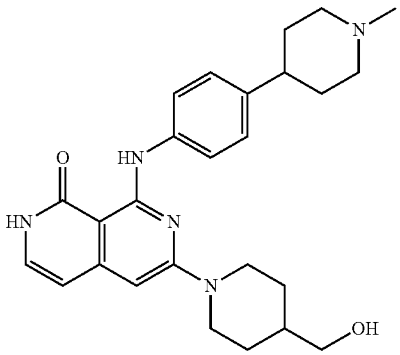 [SMILES: CN1CCC(c2ccc(Nc3nc(N4CCC(CO)CC4)cc4cc[nH]c(=O)c34)cc2)CC1] | MS m/z 448.3 (M + 1). |
| 224 | 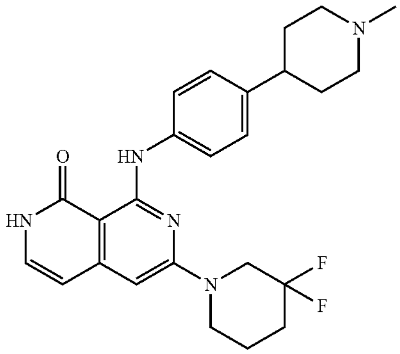 [SMILES: CN1CCC(c2ccc(Nc3nc(N4CCCC(F)(F)C4)cc4cc[nH]c(=O)c34)cc2)CC1] | MS m/z 454.2 (M + 1). |
| 225 | 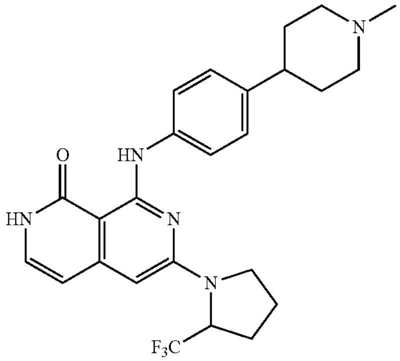 [SMILES: CN1CCC(c2ccc(Nc3nc(N4CCCC4C(F)(F)F)cc4cc[nH]c(=O)c34)cc2)CC1] | MS m/z 472.2 (M + 1). |

TABLE 1-continued
| No | Structure | Physical Data $^1H$ NMR 400 MHz (DMSO-$d_6$) and/or MS (m/z) |
|---|---|---|
| 226 | 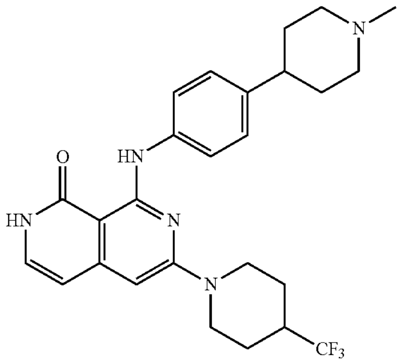 [SMILES: CN1CCC(c2ccc(Nc3nc(N4CCC(C(F)(F)F)CC4)cc4cc[nH]c(=O)c34)cc2)CC1] | MS m/z 486.2 (M + 1). |
| 227 | 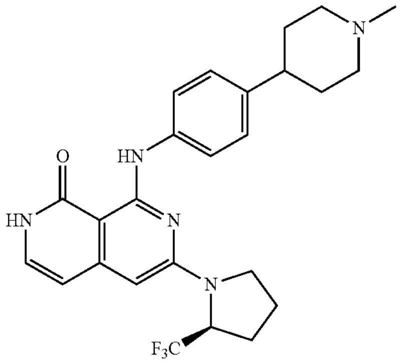 [SMILES: CN1CCC(c2ccc(Nc3nc(N4CCC[C@H]4C(F)(F)F)cc4cc[nH]c(=O)c34)cc2)CC1] | MS m/z 472.2 (M + 1). |
| 228 | 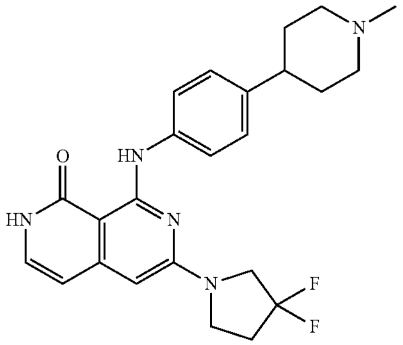 [SMILES: CN1CCC(c2ccc(Nc3nc(N4CCC(F)(F)C4)cc4cc[nH]c(=O)c34)cc2)CC1] | MS m/z 440.2 (M + 1). |
| 229 | 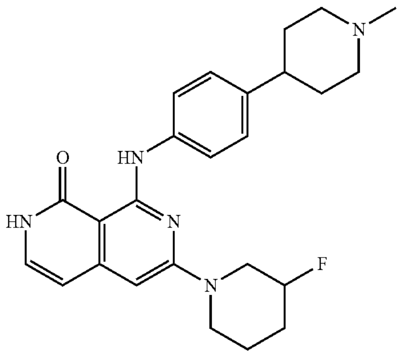 [SMILES: CN1CCC(c2ccc(Nc3nc(N4CCCC(F)C4)cc4cc[nH]c(=O)c34)cc2)CC1] | MS m/z 436.2 (M + 1). |

TABLE 1-continued
| No | Structure | Physical Data $^1$H NMR 400 MHz (DMSO-$d_6$) and/or MS (m/z) |
|---|---|---|
| 230 | 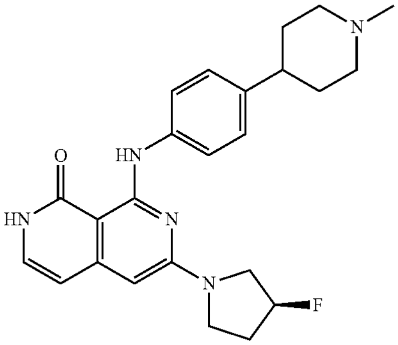 [SMILES: CN1CCC(c2ccc(Nc3nc(N4CC[C@H](F)C4)cc4cc[nH]c(=O)c34)cc2)CC1] | MS m/z 422.2 (M + 1). |
| 231 | 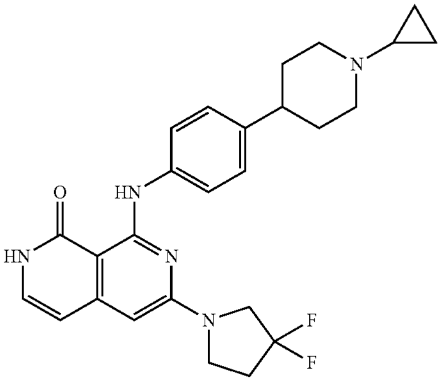 [SMILES: O=c1[nH]ccc2cc(N3CCC(F)(F)C3)nc(Nc3ccc(C4CCN(C5CC5)CC4)cc3)c12] | MS m/z 466.2 (M + 1). |
| 232 | 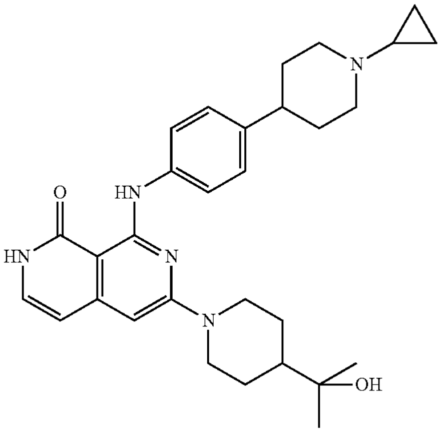 [SMILES: CC(C)(O)C1CCN(c2cc3cc[nH]c(=O)c3c(Nc3ccc(C4CCN(C5CC5)CC4)cc3)n2)CC1] | MS m/z 502.3 (M + 1). |
| 233 | 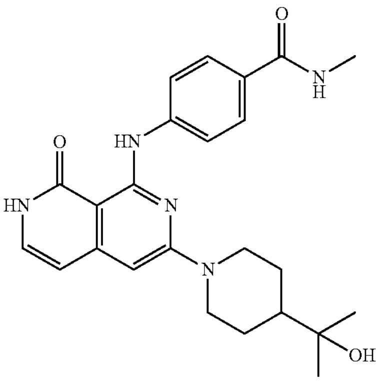 [SMILES: CNC(=O)c1ccc(Nc2nc(N3CCC(C(C)(C)O)CC3)cc3cc[nH]c(=O)c23)cc1] | MS m/z 436.2 (M + 1). |

TABLE 1-continued
| No | Structure | Physical Data $^1H$ NMR 400 MHz (DMSO-$d_6$) and/or MS (m/z) |
|---|---|---|
| 234 | 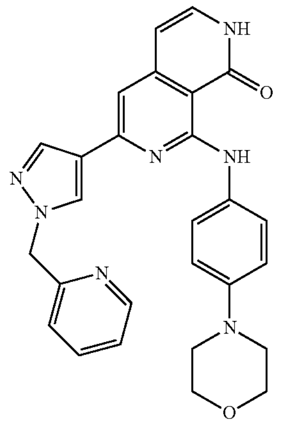 [SMILES: O=c1[nH]ccc2cc(-c3cnn(Cc4ccccn4)c3)nc(Nc3ccc(N4CCOCC4)cc3)c12] | ESI-MS m/z 480.2 (MH+). |
| 235 | 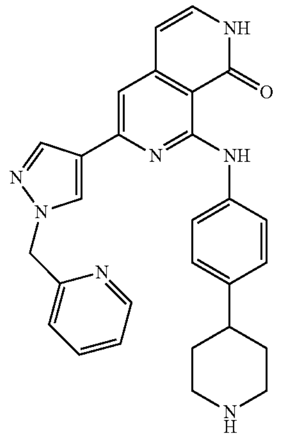 [SMILES: O=c1[nH]ccc2cc(-c3cnn(Cc4ccccn4)c3)nc(Nc3ccc(C4CCNCC4)cc3)c12] | ESI-MS m/z 478.2 (MH+). |
| 236 | 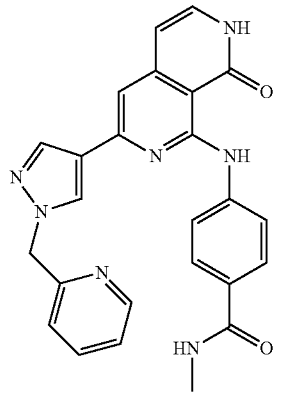 [SMILES: CNC(=O)c1ccc(Nc2nc(-c3cnn(Cc4ccccn4)c3)cc3cc[nH]c(=O)c23)cc1] | ESI-MS m/z 452.2 (MH+). |

TABLE 1-continued
| No | Structure | Physical Data $^1H$ NMR 400 MHz ($DMSO-d_6$) and/or MS (m/z) |
|---|---|---|
| 237 | 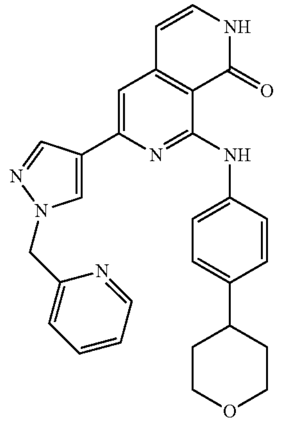 [SMILES: O=c1[nH]ccc2cc(-c3cnn(Cc4ccccn4)c3)nc(Nc3ccc(C4CCOCC4)cc3)c12] | $^1H$ NMR ($MeOD-d_4$) δ 1.79 (m, 4H), 2.79 (m, 1H), 3.58 (m, 2H), 4.06 (d, J = 10.8 Hz, 2H), 5.55 (s, 2H), 6.49 (d, J = 6.8 Hz, 1H), 7.06 (s, 1H), 7.24 (dd, J = 7.2, 11.2 Hz, 4H), 7.37 (dd, J = 5.2, 6.8 Hz, 1H), 7.82 (d, J = 8.8 Hz, 2H), 7.84 (dd, J = 1.6, 7.6 Hz, 1H), 1H), 8.13 (s, 1H), 8.37 (s, 1H), 8.55 (d, J = 4.8 Hz, 1H), 11.72 (s, 1H); ESI-MS m/z 479.2 ($MH^+$). |
| 238 | 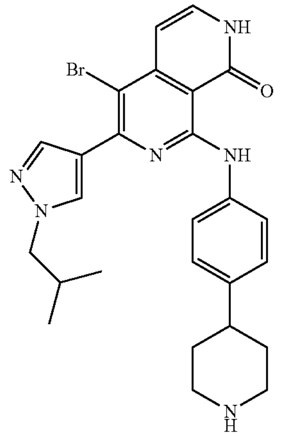 [SMILES: CC(C)Cn1cc(-c2nc(Nc3ccc(C4CCNCC4)cc3)c3c(=O)[nH]ccc3c2Br)cn1] | ESI-MS m/z 522.2 ($MH^+$). |
| 239 | 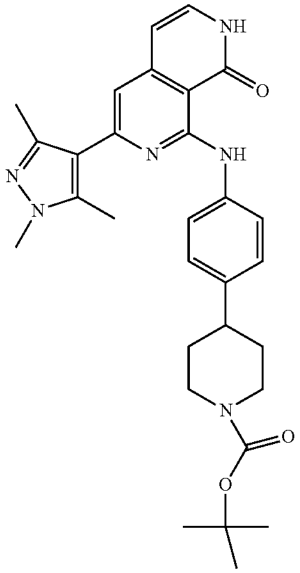 [SMILES: Cc1nn(C)c(C)c1-c1cc2cc[nH]c(=O)c2c(Nc2ccc(C3CCN(C(=O)OC(C)(C)C)CC3)cc2)n1] | ESI-MS m/z 528.2 ($MH^+$). |

TABLE 1-continued
| No | Structure | Physical Data $^1$H NMR 400 MHz (DMSO-$d_6$) and/or MS (m/z) |
|---|---|---|
| 240 | 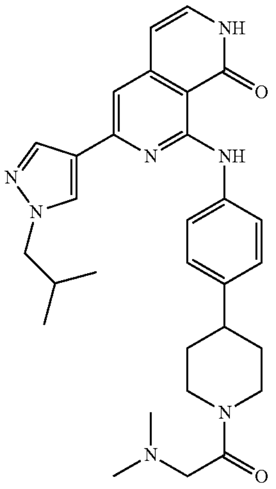 [SMILES: CC(C)Cn1cc(-c2cc3cc[nH]c(=O)c3c(Nc3ccc(C4CCN(C(=O)CN(C)C)CC4)cc3)n2)cn1] | ESI-MS m/z 529.2 (MH$^+$). |
| 241 | 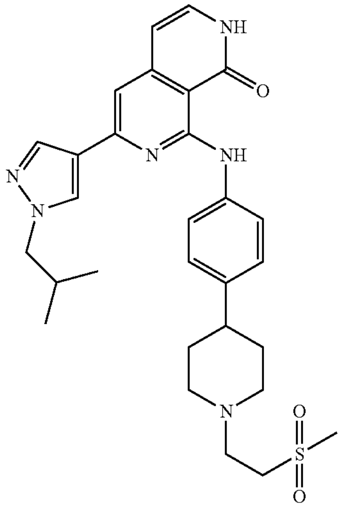 [SMILES: CC(C)Cn1cc(-c2cc3cc[nH]c(=O)c3c(Nc3ccc(C4CCN(CCS(C)(=O)=O)CC4)cc3)n2)cn1] | ESI-MS m/z 549.2 (MH$^+$). |
| 242 | 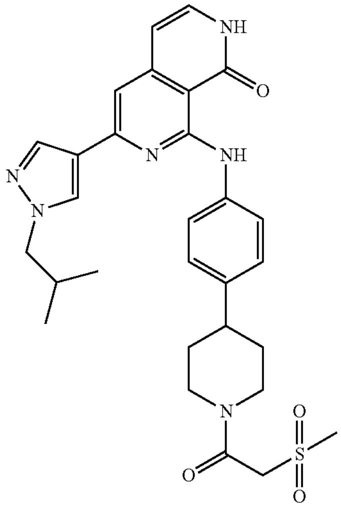 [SMILES: CC(C)Cn1cc(-c2cc3cc[nH]c(=O)c3c(Nc3ccc(C4CCN(C(=O)CS(C)(=O)=O)CC4)cc3)n2)cn1] | ESI-MS m/z 563.2 (MH$^+$). |

TABLE 1-continued
| No | Structure | Physical Data $^1H$ NMR 400 MHz ($DMSO-d_6$) and/or MS (m/z) |
| --- | --- | --- |
| 243 | 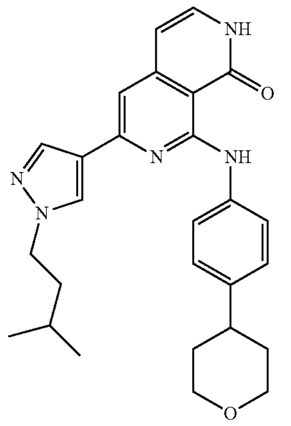 [SMILES: CC(C)CCn1cc(-c2cc3cc[nH]c(=O)c3c(Nc3ccc(C4CCOCC4)cc3)n2)cn1] | ESI-MS m/z 458.2 ($MH^+$). |
| 244 | 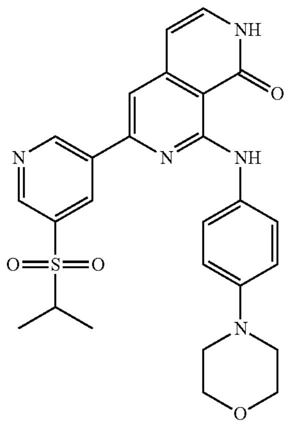 [SMILES: CC(C)S(=O)(=O)c1cncc(-c2cc3cc[nH]c(=O)c3c(Nc3ccc(N4CCOCC4)cc3)n2)c1] | ESI-MS m/z 506.2 ($MH^+$). |
| 245 | 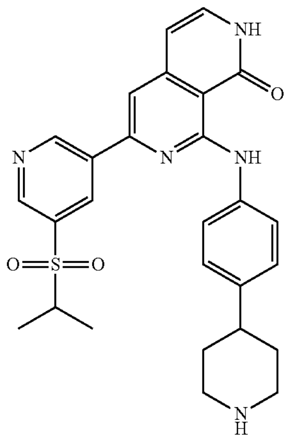 [SMILES: CC(C)S(=O)(=O)c1cncc(-c2cc3cc[nH]c(=O)c3c(Nc3ccc(C4CCNCC4)cc3)n2)c1] | ESI-MS m/z 504.2 ($MH^+$). |

TABLE 1-continued
| No | Structure | Physical Data $^1$H NMR 400 MHz (DMSO-$d_6$) and/or MS (m/z) |
|---|---|---|
| 246 | 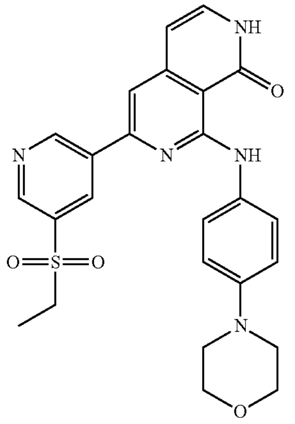 | $^1$H NMR (DMSO-$d_6$) δ 1.19 (t, J = 7.2 Hz, 3H), 3.09 (t, J = 4.8 Hz, 4H), 3.50 (dd, J = 7.2, 14.8 Hz, 2H), 3.76 (t, J = 4.4 Hz, 4H), 6.57 (d, J = 7.2 Hz, 1H), 6.98 (d, J = 9.2 Hz, 2H), 7.48 (t, J = 6.8 Hz, 1H), 1H), 7.68 (s, 1H), 7.72 (d, J = 8.8 Hz, 2H), 8.88 (t, J = 2.4 Hz, 1H), 9.09 (d, J = 2.0 Hz, 1H), 9.60 (d, J = 2.0 Hz, 1H), 11.82 (s, 1H), 11.87 (bs, 1H); ESI-MS m/z 492.2 (MH$^+$). |
| 247 | 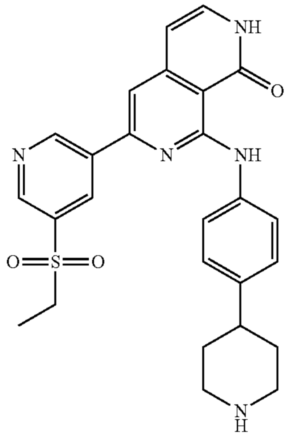 [SMILES: CCS(=O)(=O)c1cncc(-c2cc3cc[nH]c(=O)c3c(Nc3ccc(C4CCNCC4)cc3)n2)c1] | ESI-MS m/z 490.2 (MH$^+$). |
| 248 | 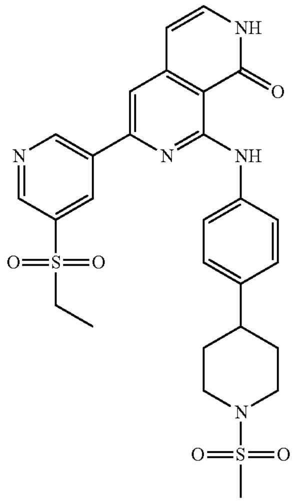 [SMILES: CCS(=O)(=O)c1cncc(-c2cc3cc[nH]c(=O)c3c(Nc3ccc(C4CCN(S(C)(=O)=O)CC4)cc3)n2)c1] | ESI-MS m/z 568.2 (MH$^+$). |

TABLE 1-continued
| No | Structure | Physical Data $^1H$ NMR 400 MHz (DMSO-$d_6$) and/or MS (m/z) |
|---|---|---|
| 249 | 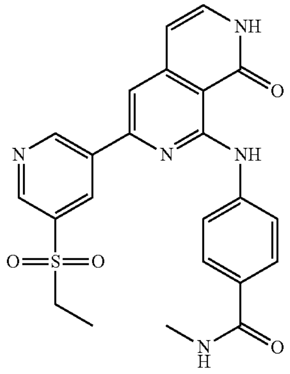 [SMILES: CCS(=O)(=O)c1cncc(-c2cc3cc[nH]c(=O)c3c(Nc3ccc(C(=O)NC)cc3)n2)c1] | $^1H$ NMR (DMSO-$d_6$) δ 1.21 (t, J = 7.2 Hz, 3H), 2.79 (d, J = 4.8 Hz, 3H), 3.52 (dd, J = 7.2, 14.8 Hz, 2H), 6.64 (d, J = 6.8 Hz, 1H), 7.54 (d, J = 6.8 Hz, 1H), 7.85 (s, 1H), 7.92 (dd, J = 8.8, 34.0 Hz, 4H), 8.38 (d, J = 4.4 Hz, 1H), 8.92 (t, J = 2.0 Hz, 1H), 9.13 (d, J = 2.0 Hz, 1H), 9.65 (d, J = 2.0 Hz, 1H), 12.01 (s, 1H), 12.36 (s, 1H); ESI-MS m/z 464.2 ($MH^+$). |
| 250 | 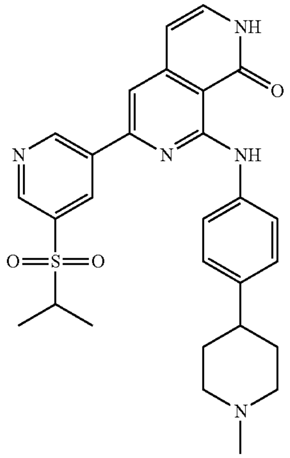 [SMILES: CC(C)S(=O)(=O)c1cncc(-c2cc3cc[nH]c(=O)c3c(Nc3ccc(C4CCN(C)CC4)cc3)n2)c1] | ESI-MS m/z 518.2 ($MH^+$). |
| 251 | 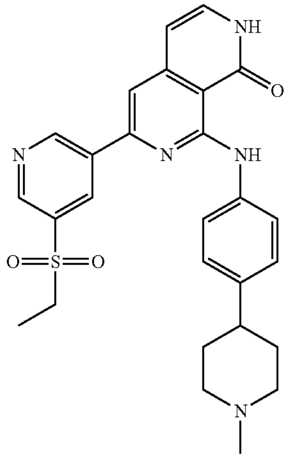 [SMILES: CCS(=O)(=O)c1cncc(-c2cc3cc[nH]c(=O)c3c(Nc3ccc(C4CCN(C)CC4)cc3)n2)c1] | ESI-MS m/z 504.2 ($MH^+$). |

TABLE 1-continued
| No | Structure | Physical Data $^1H$ NMR 400 MHz ($DMSO-d_6$) and/or MS (m/z) |
|---|---|---|
| 252 | 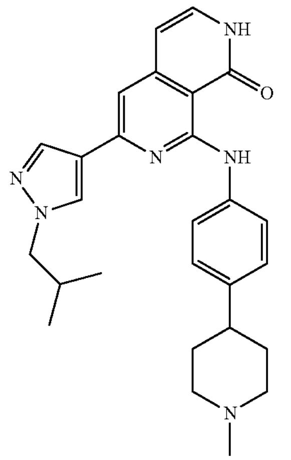 [SMILES: CC(C)Cn1cc(-c2cc3cc[nH]c(=O)c3c(Nc3ccc(C4CCN(C)CC4)cc3)n2)cn1] | $^1H$ NMR ($CDCl_3$ + $MeOD-d_4$) δ 0.96 (d, J = 6.8 Hz, 6H), 1.90 (m, 4H), 2.24 (m, 1H), 2.54 (t, J = 10.4 Hz, H) 2.67 (m, 1H), 3.24 (d, 12.0 Hz, 2H), 4.01 (d, J = 7.2 Hz, 2H), 6.45 (d, J = 6.8 Hz, 1H), 6.98 (s, 1H), 7.21 (d, J = 6.8 Hz, 1H), 7.24 (d, J= 8.4 Hz, 2H), 7.84 (dd, J= 1.6, 8.4 Hz, 2H), 8.04 (s, 1H), 8.11 (s, 1H), 11.70 (s, 1H); ESI-MS m/z 457.2 ($MH^+$). |
| 253 | 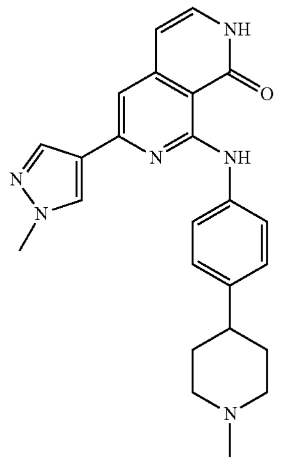 [SMILES: CN1CCC(c2ccc(Nc3nc(-c4cnn(C)c4)cc4cc[nH]c(=O)c34)cc2)CC1] | ESI-MS m/z 415.2 ($MH^+$). |
| 254 | 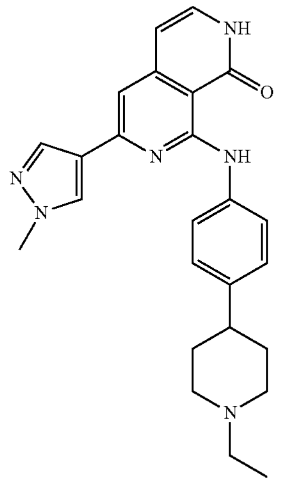 [SMILES: CCN1CCC(c2ccc(Nc3nc(-c4cnn(C)c4)cc4cc[nH]c(=O)c34)cc2)CC1] | ESI-MS m/z 429.2 ($MH^+$). |

TABLE 1-continued
| No | Structure | Physical Data $^1H$ NMR 400 MHz (DMSO-$d_6$) and/or MS (m/z) |
|---|---|---|
| 255 | 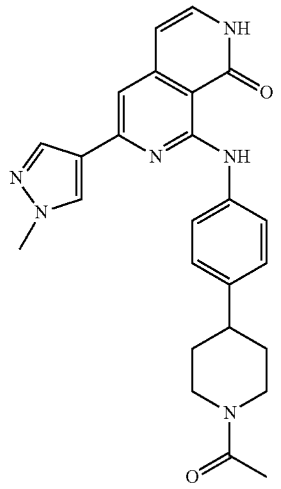 [SMILES: CC(=O)N1CCC(c2ccc(Nc3nc(-c4cnn(C)c4)cc4cc[nH]c(=O)c34)cc2)CC1] | ESI-MS m/z 443.2 ($MH^+$). |
| 256 | 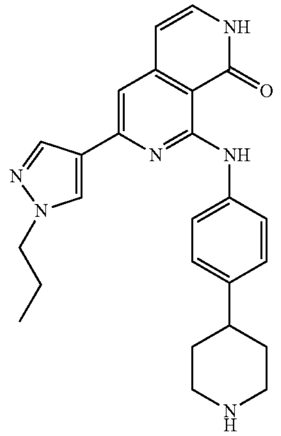 [SMILES: CCCn1cc(-c2cc3cc[nH]c(=O)c3c(Nc3ccc(C4CCNCC4)cc3)n2)cn1] | ESI-MS m/z 429.2 ($MH^+$). |
| 257 | 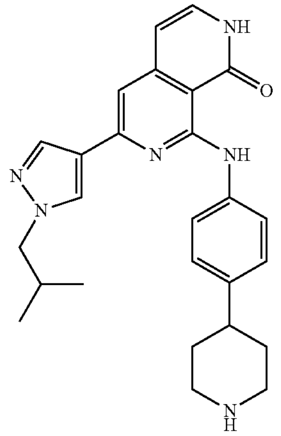 [SMILES: CC(C)Cn1cc(-c2cc3cc[nH]c(=O)c3c(Nc3ccc(C4CCNCC4)cc3)n2)cn1] | $^1H$ NMR (MeOD-$d_4$)□ 0.85 (d, J = 6.8 Hz, 6H), 1.68 (m, 2H), 1.72 (d, J = 12.8 Hz, 2H), 2.13 (m, 1H) 2.64 (m, 1H), 2.78 (m, 2H), 3.93 (d, J = 7.2 Hz, 2H), 6.39 (d, J = 6.8 Hz, 1H), 6.94 (s, 1H), 7.16 (dd, J = 4.8, 8.4 Hz, 1H), 7.74 (d, J = 8.4 Hz, 1H), 7.97 (s, 1H), 8.09 (s, 1H); ESI-MS m/z 443.2 ($MH^+$). |

TABLE 1-continued
| No | Structure | Physical Data $^1$H NMR 400 MHz (DMSO-$d_6$) and/or MS (m/z) |
|---|---|---|
| 258 | 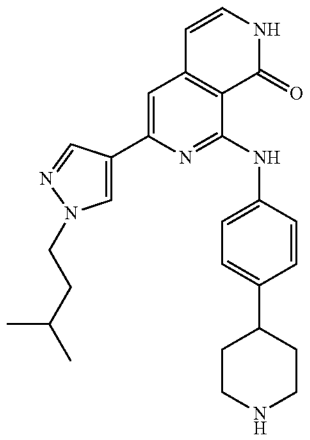 [SMILES: CC(C)CCn1cc(-c2cc3cc[nH]c(=O)c3c(Nc3ccc(C4CCNCC4)cc3)n2)cn1] | ESI-MS m/z 457.2 ($MH^+$). |
| 259 | 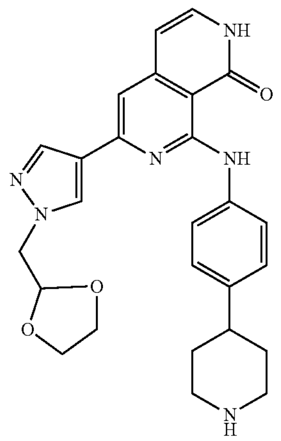 [SMILES: O=c1[nH]ccc2cc(-c3cnn(CC4OCCO4)c3)nc(Nc3ccc(C4CCNCC4)cc3)c12] | ESI-MS m/z 473.2 ($MH^+$). |
| 260 | 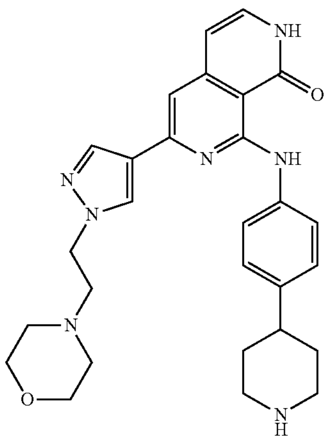 [SMILES: O=c1[nH]ccc2cc(-c3cnn(CCN4CCOCC4)c3)nc(Nc3ccc(C4CCNCC4)cc3)c12] | ESI-MS m/z 500.2 ($MH^+$). |

TABLE 1-continued
| No | Structure | Physical Data $^1$H NMR 400 MHz (DMSO-$d_6$) and/or MS (m/z) |
|---|---|---|
| 261 | 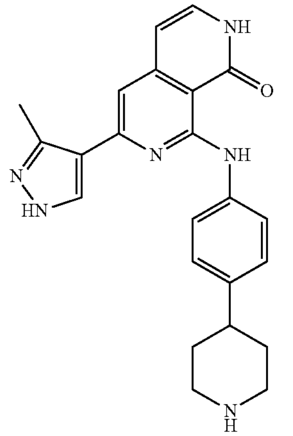 [SMILES: Cc1n[nH]cc1-c1cc2cc[nH]c(=O)c2c(Nc2ccc(C3CCNCC3)cc2)n1] | $^1$H NMR (MeOD-$d_4$) 1.87 (m, 2H), 2.01 (d, J = 14.0 Hz, 2H), 2.47 (s, 3H), 2.81 (m, 1H), 3.04 (m, 2H), 3.39 (m, 2H), 6.45 (d, J = 6.8 Hz, 1H), 6.90 (s, 1H), 7.19 (dd, J = 4.8, 7.2 Hz, 1H), 7.70 (dd, J = 2.0, 6.4 Hz, 1H), 7.95 (s, 1H); ESI-MS m/z 401.2 (MH$^+$). |
| 262 | 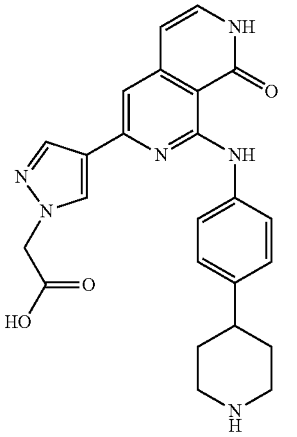 [SMILES: O=C(O)Cn1cc(-c2cc3cc[nH]c(=O)c3c(Nc3ccc(C4CCNCC4)cc3)n2)cn1] | $^1$H NMR (MeOD-$d_4$) 1.92 (m, 2H), 2.12 (d, J = 14.0 Hz, 2H), 2.91 (m, 1H), 3.14 (m, 2H), 3.50 (m, 2H), 5.07 (s, 2H), 6.51 (d, J = 6.8 Hz, 1H), 7.06 (s, 1H), 7.28 (t, J = 8.4 Hz, 1H), 7.88 (d, J = 8.4 Hz, 1H), 8.14 (s, 1H), 8.27 (s, 1H); ESI-MS m/z 445.2 (MH$^+$). |
| 263 | 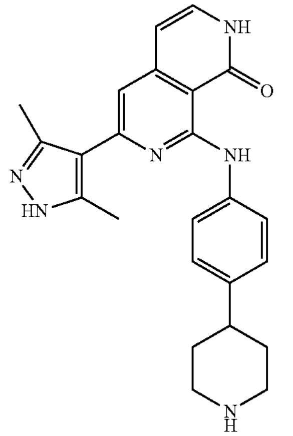 [SMILES: Cc1n[nH]c(C)c1-c1cc2cc[nH]c(=O)c2c(Nc2ccc(C3CCNCC3)cc2)n1] | ESI-MS m/z 415.2 (MH$^+$). |

TABLE 1-continued
| No | Structure | Physical Data $^1H$ NMR 400 MHz (DMSO-$d_6$) and/or MS (m/z) |
| --- | --- | --- |
| 264 | 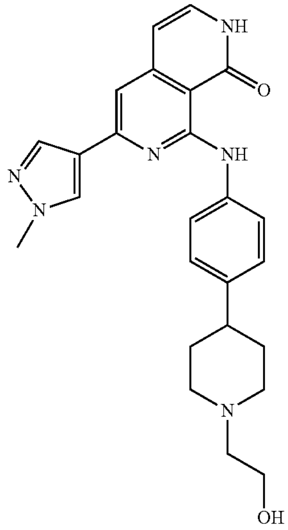 [SMILES: Cn1cc(-c2cc3cc[nH]c(=O)c3c(Nc3ccc(C4CCN(CCO)CC4)cc3)n2)cn1] | ESI-MS m/z 445.2 ($MH^+$). |
| 265 | 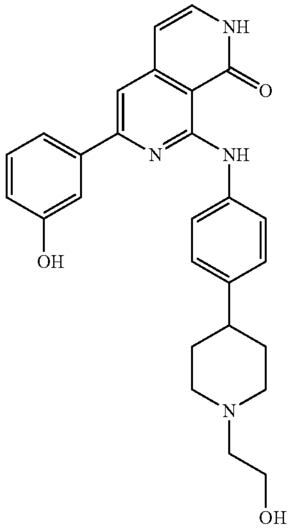 [SMILES: O=c1[nH]ccc2cc(-c3cccc(O)c3)nc(Nc3ccc(C4CCN(CCO)CC4)cc3)c12] | ESI-MS m/z 457.2 ($MH^+$). |
| 266 | 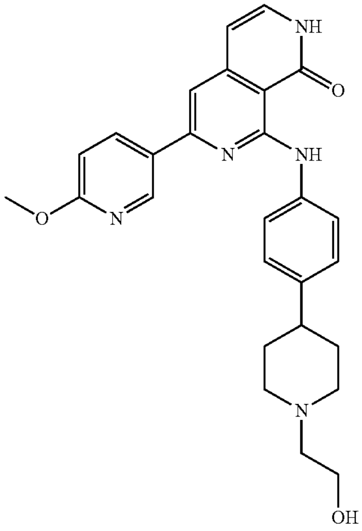 [SMILES: COc1ccc(-c2cc3cc[nH]c(=O)c3c(Nc3ccc(C4CCN(CCO)CC4)cc3)n2)cn1] | ESI-MS m/z 472.2 ($MH^+$). |

TABLE 1-continued
| No | Structure | Physical Data $^1H$ NMR 400 MHz (DMSO-$d_6$) and/or MS (m/z) |
| --- | --- | --- |
| 267 | 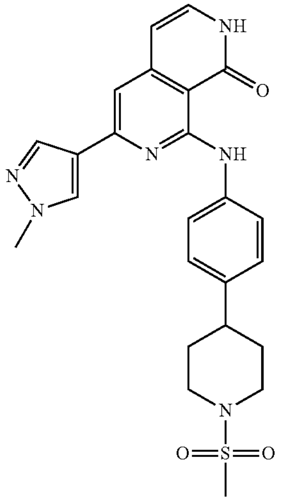 | ESI-MS m/z 415.2 ($MH^+$). |
| 268 | 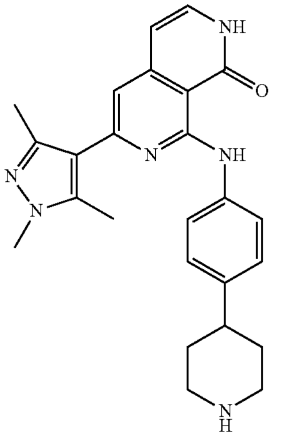 [SMILES: Cc1nn(C)c(C)c1-c1cc2cc[nH]c(=O)c2c(Nc2ccc(C3CCNCC3)cc2)n1] | ESI-MS m/z 429.2 ($MH^+$). |
| 269 | 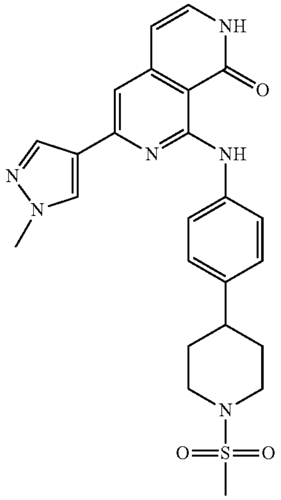 [SMILES: Cn1cc(-c2cc3cc[nH]c(=O)c3c(Nc3ccc(C4CCN(S(C)(=O)=O)CC4)cc3)n2)cn1] | ESI-MS m/z 479.2 ($MH^+$). |

TABLE 1-continued
| No | Structure | Physical Data $^1H$ NMR 400 MHz (DMSO-$d_6$) and/or MS (m/z) |
|---|---|---|
| 270 | 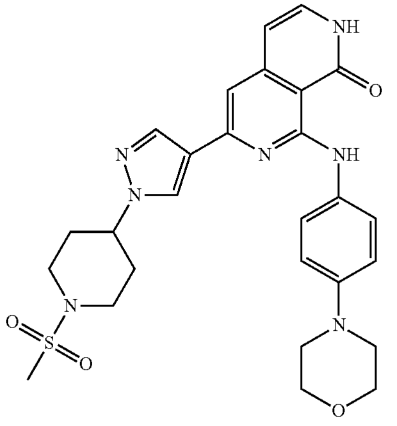 [SMILES: CS(=O)(=O)N1CCC(n2cc(-c3cc4cc[nH]c(=O)c4c(Nc4ccc(N5CCOCC5)cc4)n3)cn2)CC1] | ESI-MS m/z 550.2 ($MH^+$). |
| 271 | 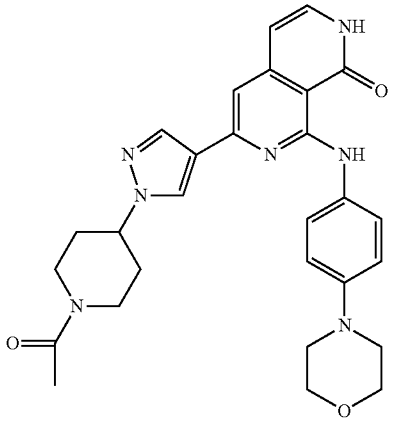 [SMILES: CC(=O)N1CCC(n2cc(-c3cc4cc[nH]c(=O)c4c(Nc4ccc(N5CCOCC5)cc4)n3)cn2)CC1] | ESI-MS m/z 514.2 ($MH^+$). |
| 272 | 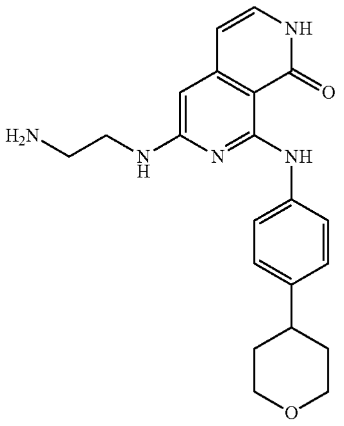 [SMILES: NCCNc1cc2cc[nH]c(=O)c2c(Nc2ccc(C3CCOCC3)cc2)n1] | ESI-MS m/z 380.2 ($MH^+$). |

TABLE 1-continued
| No | Structure | Physical Data $^1H$ NMR 400 MHz (DMSO-$d_6$) and/or MS (m/z) |
|---|---|---|
| 273 | 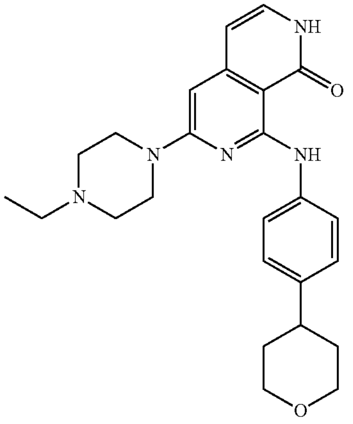 [SMILES: CCN1CCN(c2cc3cc[nH]c(=O)c3c(Nc3ccc(C4CCOCC4)cc3)n2)CC1] | ESI-MS m/z 434.2 (MH$^+$). |
| 274 | 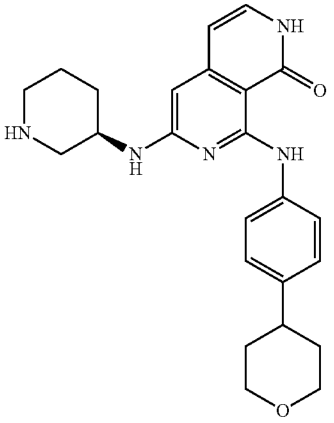 [SMILES: O=c1[nH]ccc2cc(N[C@@H]3CCCNC3)nc(Nc3ccc(C4CCOCC4)cc3)c12] | ESI-MS m/z 420.2 (MH$^+$). |
| 275 | 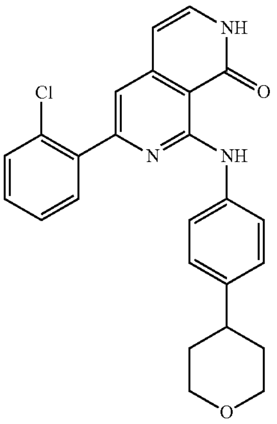 [SMILES: O=c1[nH]ccc2cc(-c3ccccc3Cl)nc(Nc3ccc(C4CCOCC4)cc3)c12] | ESI-MS m/z 432.2 (MH$^+$). |

TABLE 1-continued
| No | Structure | Physical Data $^1H$ NMR 400 MHz ($DMSO-d_6$) and/or MS (m/z) |
|---|---|---|
| 276 | 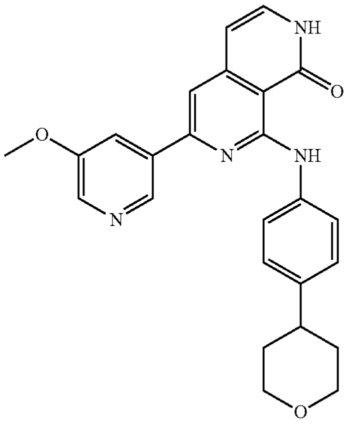 [SMILES: COc1cncc(-c2cc3cc[nH]c(=O)c3c(Nc3ccc(C4CCOCC4)cc3)n2)c1] | ESI-MS m/z 429.2 ($MH^+$). |
| 277 | 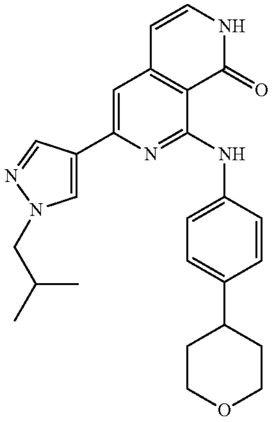 [SMILES: CC(C)Cn1cc(-c2cc3cc[nH]c(=O)c3c(Nc3ccc(C4CCOCC4)cc3)n2)cn1] | $^1H$ NMR ($MeOD-d_4$)Γ 0.96 (d, J = 6.8 Hz, 6H), 1.82 (dd, J = 3.6, 8.4 Hz, 4H), 2.25 (m, 1H), 2.81 (m, 1H), 3.60 (m, 2H), 4.02 (d, 7.2 Hz, 2H), 4.09 (dd, J = 3.2, 11.2 Hz, 2H), 6.47 (d, J = 7.2 Hz, 1H), 7.00 (s, 1H), 7.22 (d, J = 7.2 Hz, 1H), 7.26 (d, J = 8.4 Hz, 2H), 7.84 (dd, J = 1.6, 8.4 Hz, 2H), 8.06 (s, 1H), 8.13 (s, 1H); (ESI-MS m/z 444.2 ($MH^+$). |
| 278 | 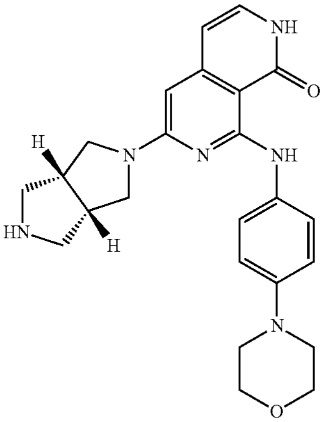 [SMILES: O=c1[nH]ccc2cc(N3C[C@H]4CNC[C@H]4C3)nc(Nc3ccc(N4CCOCC4)cc3)c12] | ESI-MS m/z 433.2 ($MH^+$). |

TABLE 1-continued
| No | Structure | Physical Data $^1H$ NMR 400 MHz ($DMSO-d_6$) and/or MS (m/z) |
|---|---|---|
| 279 | 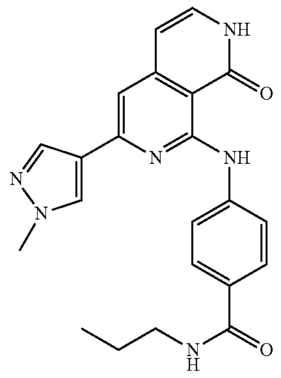 [SMILES: CCCNC(=O)c1ccc(Nc2nc(-c3cnn(C)c3)cc3cc[nH]c(=O)c23)cc1] | ESI-MS m/z 403.2 ($MH^+$). |
| 280 | 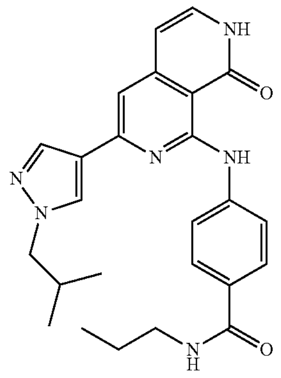 [SMILES: CCCNC(=O)c1ccc(Nc2nc(-c3cnn(CC(C)C)c3)cc3cc[nH]c(=O)c23)cc1] | ESI-MS m/z 445.2 ($MH^+$). |
| 281 | 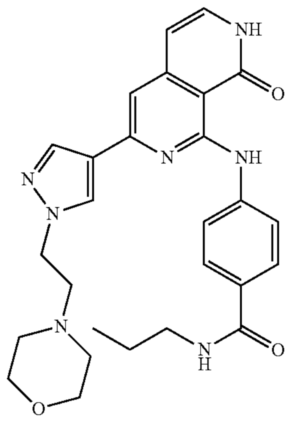 [SMILES: CCCNC(=O)c1ccc(Nc2nc(-c3cnn(CCN4CCOCC4)c3)cc3cc[nH]c(=O)c23)cc1] | $^1H$ NMR ($MeOD-d_4$): 1.00 (t, J = 7.6 Hz, 3H), 1.66 (m, 2H), 2.53 (t, J = 4.8 Hz, 4H), 2.86 (t, J = 6.4 Hz, 2H), 3.36 (t, J = 6.8 Hz, 2H), 3.68 (t, J = 4.8 Hz, 4H), 4.37 (t, J = 6.4 Hz, 2H), 6.50 (d, J = 7.2 Hz, 1H), 7.10 (s, 1H), 7.25 (d, J = 7.2 Hz, 1H), 7.85 (d, J = 8.8 Hz, 2H), 8.00 (d, J = 8.8 Hz, 2H), 8.07 (s, 1H), 8.27 (s, 1H); ESI-MS m/z 502.2 ($MH^+$). |
| 282 | 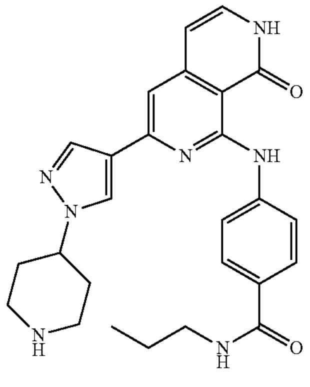 [SMILES: CCCNC(=O)c1ccc(Nc2nc(-c3cnn(C4CCNCC4)c3)cc3cc[nH]c(=O)c23)cc1] | ESI-MS m/z 472.2 ($MH^+$). |

TABLE 1-continued
| No | Structure | Physical Data $^1$H NMR 400 MHz (DMSO-$d_6$) and/or MS (m/z) |
|---|---|---|
| 283 | 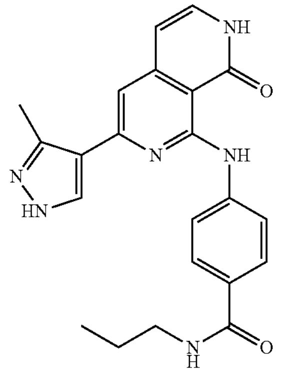 [SMILES: CCCNC(=O)c1ccc(Nc2nc(-c3c[nH]nc3C)cc3cc[nH]c(=O)c23)cc1] | ESI-MS m/z 403.2 (MH$^+$). |
| 284 | 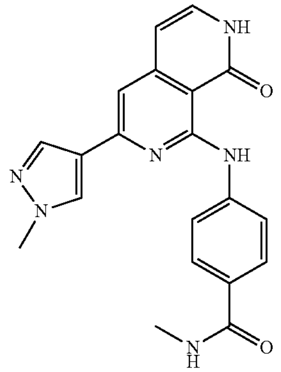 [SMILES: CNC(=O)c1ccc(Nc2nc(-c3cnn(C)c3)cc3cc[nH]c(=O)c23)cc1] | ESI-MS m/z 375.2 (MH$^+$). |
| 285 | 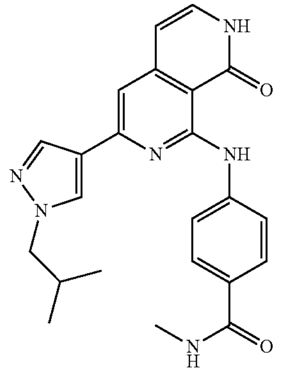 [SMILES: CNC(=O)c1ccc(Nc2nc(-c3cnn(CC(C)C)c3)cc3cc[nH]c(=O)c23)cc1] | $^1$H NMR (MeOD-$d_4$)⊦ 0.97 (d, J = 6.8 Hz, 6H), 2.26 (m, 1H (, 4.04 (d, J = 7.2 Hz, 2H), 6.51 (d, J = 7.2 Hz, 1H), 7.12 (s, 1H), 7.29 (d, J = 6.8 Hz, 1H), 7.86 (dd, J = 2.0. 9.2 Hz, 2H), 8.02 (dd, J = 2.0, 6.8 Hz, 2H), 8.09 (s, 1H), 8.22 (s, 1H); ESI-MS m/z 417.2 (MH$^+$). |
| 286 | 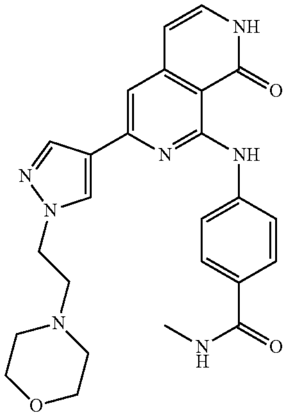 [SMILES: CNC(=O)c1ccc(Nc2nc(-c3cnn(CCN4CCOCC4)c3)cc3cc[nH]c(=O)c23)cc1] | $^1$H NMR (MeOD-$d_4$)⊊ 2.54 (t, J = 4.4 Hz, 4H), 2.87 (t, J = 6.4 Hz, 2H), 2.94 (s, 3H), 3.68 (t, J = 4.4 Hz, 4H), 4.37 (t, J = 6.4 Hz, 2H), 6.49 (d, J = 7.2 Hz, 1H), 7.09 (s, 1H), 7.28 (d, J = 7.2 Hz, 1H), 7.85 (dd, J = 2.0, 7.2 Hz, 2H), 8.01 (d, J = 8.8 Hz, 2H), 8.07 (s, 1H), 8.27 (s, 1H); ESI-MS m/z 474.2 (MH$^+$). |

TABLE 1-continued
| No | Structure | Physical Data $^1H$ NMR 400 MHz (DMSO-$d_6$) and/or MS (m/z) |
|---|---|---|
| 287 | 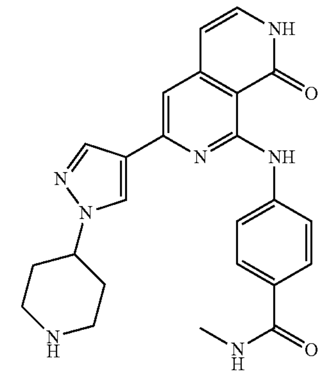 [SMILES: CNC(=O)c1ccc(Nc2nc(-c3cnn(C4CCNCC4)c3)cc3cc[nH]c(=O)c23)cc1] | ESI-MS m/z 444.2 ($MH^+$). |
| 288 | 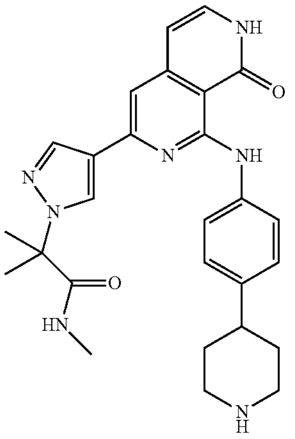 [SMILES: CNC(=O)C(C)(C)n1cc(-c2cc3cc[nH]c(=O)c3c(Nc3ccc(C4CCNCC4)cc3)n2)cn1] | ESI-MS m/z 486.2 ($MH^+$). |
| 289 | 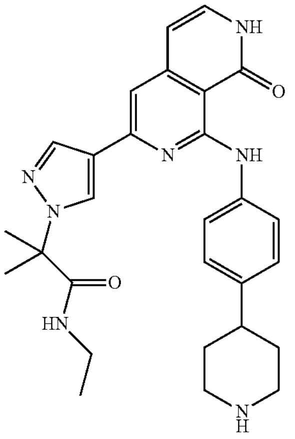 [SMILES: CCNC(=O)C(C)(C)n1cc(-c2cc3cc[nH]c(=O)c3c(Nc3ccc(C4CCNCC4)cc3)n2)cn1] | ESI-MS m/z 500.2 ($MH^+$). |

TABLE 1-continued
| No | Structure | Physical Data $^1$H NMR 400 MHz (DMSO-$d_6$) and/or MS (m/z) |
|---|---|---|
| 290 | 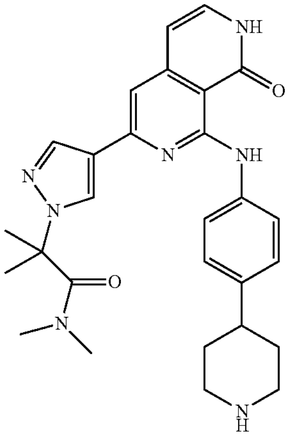 [SMILES: CN(C)C(=O)C(C)(C)n1cc(-c2cc3cc[nH]c(=O)c3c(Nc3ccc(C4CCNCC4)cc3)n2)cn1] | ESI-MS m/z 500.2 ($MH^+$). |
| 291 | 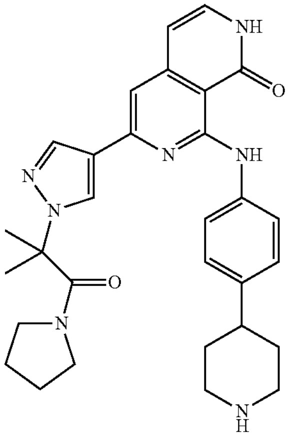 [SMILES: CC(C)(C(=O)N1CCCC1)n1cc(-c2cc3cc[nH]c(=O)c3c(Nc3ccc(C4CCNCC4)cc3)n2)cn1] | ESI-MS m/z 526.2 ($MH^+$). |
| 292 | 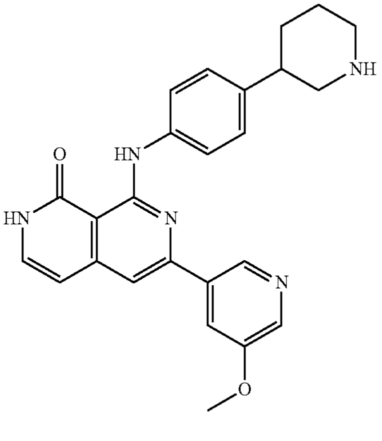 [SMILES: COc1cncc(-c2cc3cc[nH]c(=O)c3c(Nc3ccc(C4CCCNC4)cc3)n2)c1] | ESI-MS m/z 428.2 ($MH^+$) |

TABLE 1-continued
| No | Structure | Physical Data $^1H$ NMR 400 MHz (DMSO-$d_6$) and/or MS (m/z) |
|---|---|---|
| 293 | 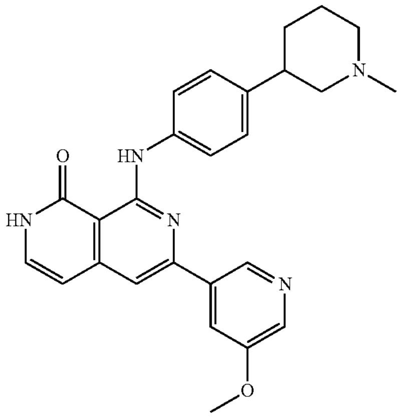 [SMILES: COc1cncc(-c2cc3cc[nH]c(=O)c3c(Nc3ccc(C4CCCN(C)C4)cc3)n2)c1] | $^1H$ NMR (DMSO-$d_6$) δ 1.60-1.99 (6H), 2.81 (d, J = 4.4 Hz, 3H), 2.93-2.99 (2H), 3.11 (m, 1H), 3.96 (s, 3H), 6.58 (d, J = 6.8 Hz, 1H), 7.31 (d, J = 8.4 Hz, 2H), 7.48 (dd, J = 6.8 and 6.0 Hz, 1H), 7.65 (s, 1H), 7.88 (d, J = 8.8 Hz, 2H), 8.04 (br, 1H), 8.41 (br, 1H), 8.95 (s, 1H); ESI-MS m/z 441.2 ($MH^+$) |
| 294 | 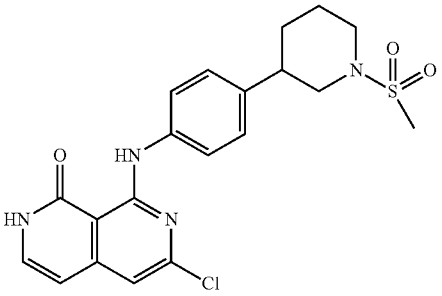 [SMILES: CS(=O)(=O)N1CCCC(c2ccc(Nc3nc(Cl)cc4cc[nH]c(=O)c34)cc2)C1] | ESI-MS m/z 433.1 ($MH^+$). |
| 295 | 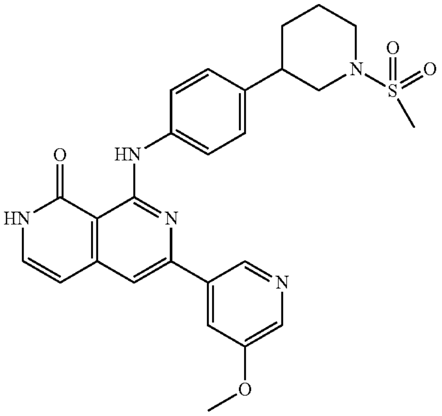 [SMILES: COc1cncc(-c2cc3cc[nH]c(=O)c3c(Nc3ccc(C4CCCN(S(C)(=O)=O)C4)cc3)n2)c1] | ESI-MS m/z 506.2 ($MH^+$) |
| 296 | 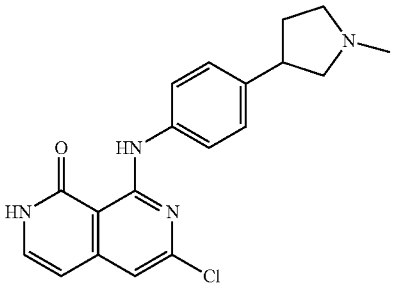 [SMILES: CN1CCC(c2ccc(Nc3nc(Cl)cc4cc[nH]c(=O)c34)cc2)C1] | ESI-MS m/z 355.1 ($MH^+$) |

TABLE 1-continued
| No | Structure | Physical Data $^1H$ NMR 400 MHz ($DMSO-d_6$) and/or MS (m/z) |
|---|---|---|
| 297 | 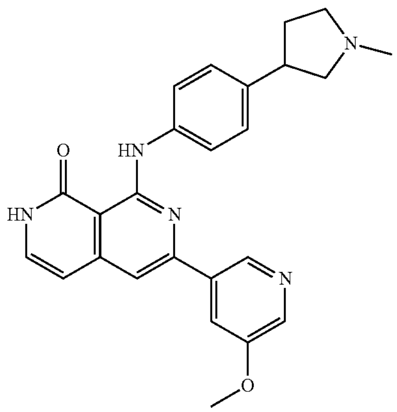 [SMILES: COc1cncc(-c2cc3cc[nH]c(=O)c3c(Nc3ccc(C4CCN(C)C4)cc3)n2)c1] | ESI-MS m/z 428.2 ($MH^+$) |
| 298 | 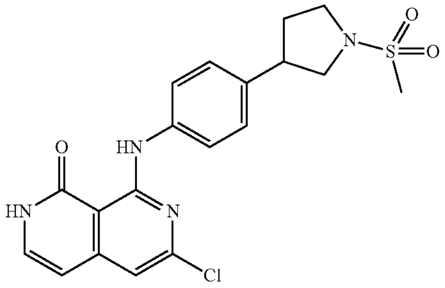 [SMILES: CS(=O)(=O)N1CCC(c2ccc(Nc3nc(Cl)cc4cc[nH]c(=O)c34)cc2)C1] | ESI-MS m/z 419.1 ($MH^+$) |
| 299 | 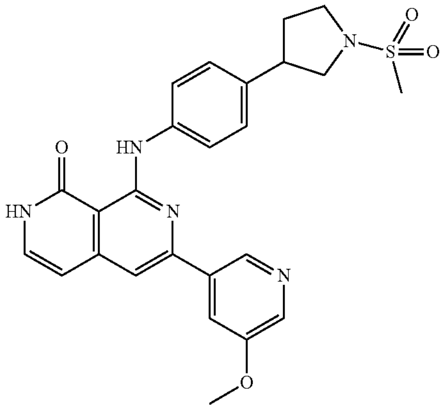 [SMILES: COc1cncc(-c2cc3cc[nH]c(=O)c3c(Nc3ccc(C4CCN(S(C)(=O)=O)C4)cc3)n2)c1] | ESI-MS m/z 492.2 ($MH^+$) |
| 300 | 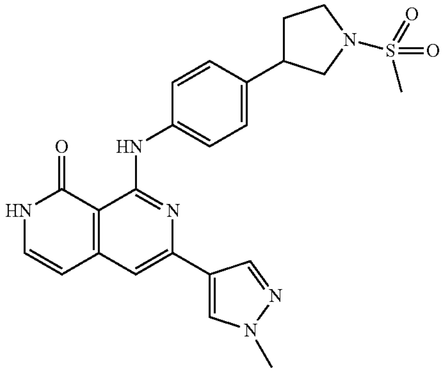 [SMILES: Cn1cc(-c2cc3cc[nH]c(=O)c3c(Nc3ccc(C4CCN(S(C)(=O)=O)C4)cc3)n2)cn1] | ESI-MS m/z 465.2 ($MH^+$) |

TABLE 1-continued
| No | Structure | Physical Data $^1H$ NMR 400 MHz (DMSO-$d_6$) and/or MS (m/z) |
|---|---|---|
| 301 | 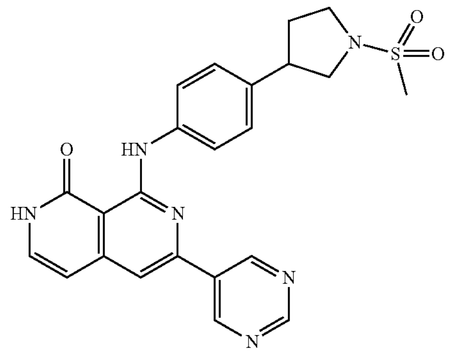 [SMILES: CS(=O)(=O)N1CCC(c2ccc(Nc3nc(-c4cncnc4)cc4cc[nH]c(=O)c34)cc2)C1] | ESI-MS m/z 463.2 (MH$^+$) |
| 302 | 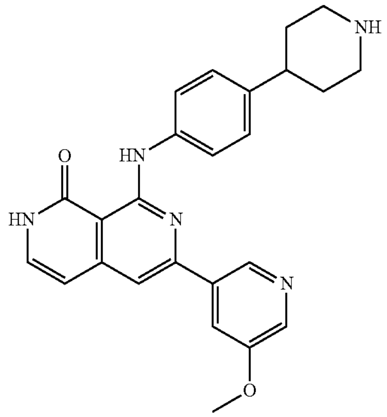 [SMILES: COc1cncc(-c2cc3cc[nH]c(=O)c3c(Nc3ccc(C4CCNCC4)cc3)n2)c1] | ESI-MS m/z 428.2 (MH$^+$) |
| 303 | 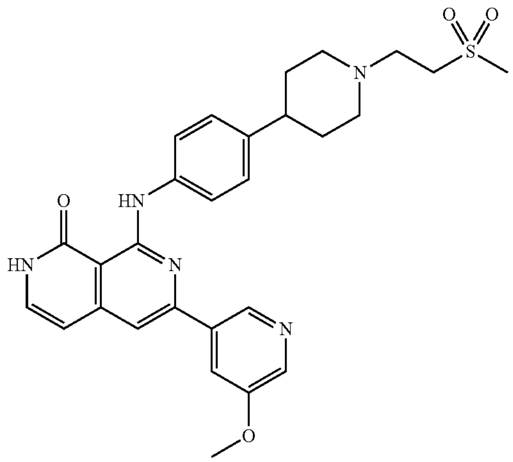 [SMILES: COc1cncc(-c2cc3cc[nH]c(=O)c3c(Nc3ccc(C4CCN(CCS(C)(=O)=O)CC4)cc3)n2)c1] | ESI-MS m/z 534.2 (MH$^+$) |

TABLE 1-continued
| No | Structure | Physical Data $^1H$ NMR 400 MHz (DMSO-$d_6$) and/or MS (m/z) |
|---|---|---|
| 304 | 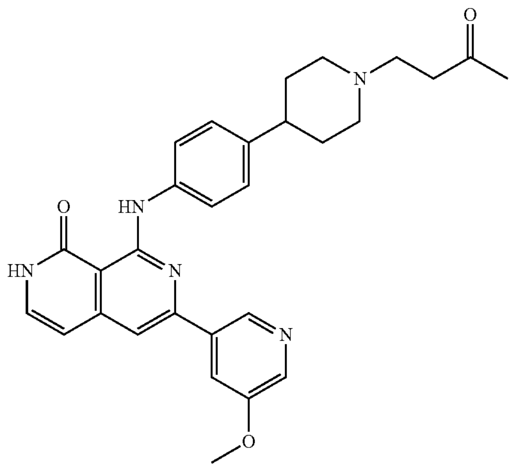 [SMILES: COc1cncc(-c2cc3cc[nH]c(=O)c3c(Nc3ccc(C4CCN(CCC(C)=O)CC4)cc3)n2)c1] | $^1H$ NMR (DMSO-$d_6$) δ 1.81-2.04 (4H), 2.19 (s, 3H), 2.81 (m, 1H), 2.96-3.12 (4H), 3.27-3.32 (2H), 3.54-3.60 (2H), 3.96 (s, 3H), 6.56 (d, J = 6.8 Hz, 1H), 7.26 (d, J = 8.8 Hz, 2H), 7.48 (dd, J = 6.8 and 6.4 Hz, 1H), 7.84 (d, J = 8.8 Hz, 2H), 8.05 (br, 1H), 8.41 (br, 1H), 8.94 (br, 1H); ESI-MS m/z 498.2 ($MH^+$) |
| 305 | 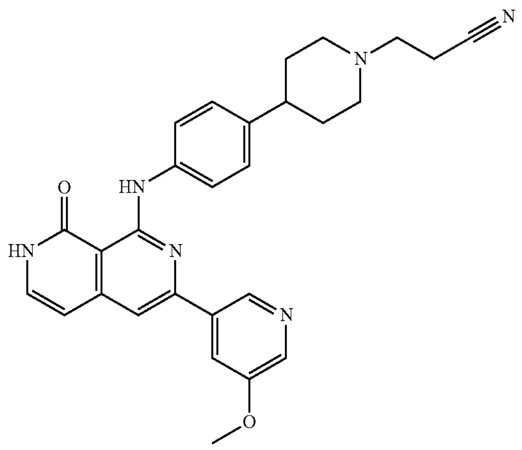 [SMILES: COc1cncc(-c2cc3cc[nH]c(=O)c3c(Nc3ccc(C4CCN(CCC#N)CC4)cc3)n2)c1] | ESI-MS m/z 480.2 ($MH^+$) |
| 306 | 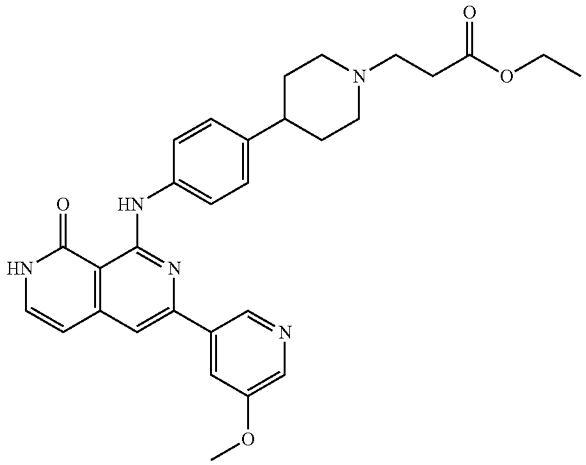 [SMILES: CCOC(=O)CCN1CCC(c2ccc(Nc3nc(-c4cncc(OC)c4)cc4cc[nH]c(=O)c34)cc2)CC1] | ESI-MS m/z 528.2 ($MH^+$) |

TABLE 1-continued
| No | Structure | Physical Data $^1H$ NMR 400 MHz (DMSO-$d_6$) and/or MS (m/z) |
|---|---|---|
| 307 | 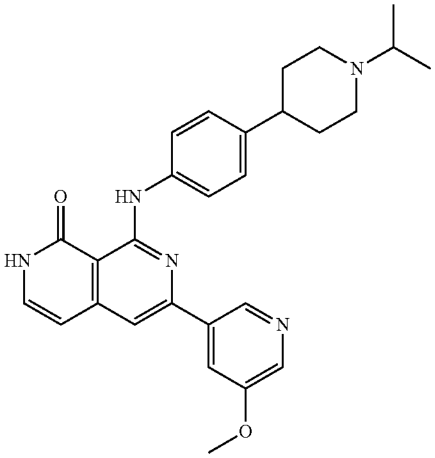 [SMILES: COc1cncc(-c2cc3cc[nH]c(=O)c3c(Nc3ccc(C4CCN(C(C)C)CC4)cc3)n2)c1] | ESI-MS m/z 470.3 ($MH^+$) |
| 308 | 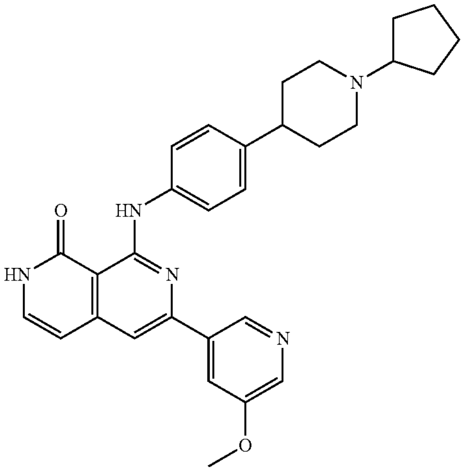 [SMILES: COc1cncc(-c2cc3cc[nH]c(=O)c3c(Nc3ccc(C4CCN(C5CCCC5)CC4)cc3)n2)c1] | ESI-MS m/z 496.3 ($MH^+$) |
| 309 | 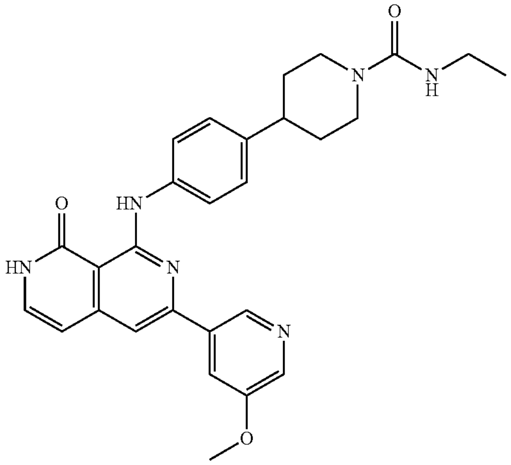 [SMILES: CCNC(=O)N1CCC(c2ccc(Nc3nc(-c4cncc(OC)c4)cc4cc[nH]c(=O)c34)cc2)CC1] | ESI-MS m/z 499.2 ($MH^+$) |

TABLE 1-continued
| No | Structure | Physical Data $^1H$ NMR 400 MHz (DMSO-$d_6$) and/or MS (m/z) |
|---|---|---|
| 310 | 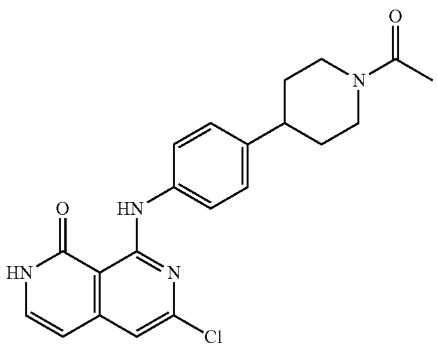 [SMILES: CC(=O)N1CCC(c2ccc(Nc3nc(Cl)cc4cc[nH]c(=O)c34)cc2)CC1] | ESI-MS m/z 397.1 ($MH^+$) |
| 311 | 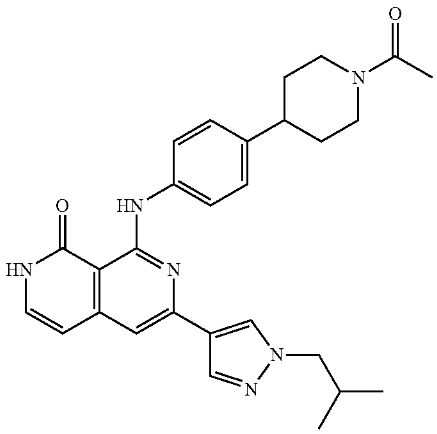 [SMILES: CC(=O)N1CCC(c2ccc(Nc3nc(-c4cnn(CC(C)C)c4)cc4cc[nH]c(=O)c34)cc2)CC1] | ESI-MS m/z 485.3 ($MH^+$) |
| 312 | 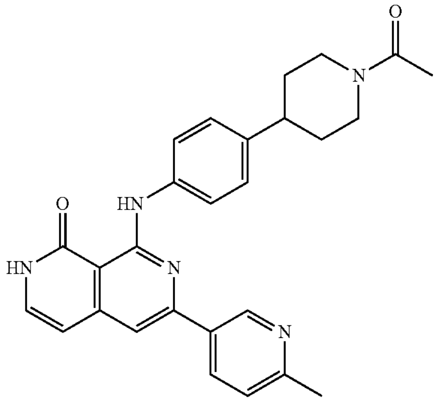 [SMILES: CC(=O)N1CCC(c2ccc(Nc3nc(-c4ccc(C)nc4)cc4cc[nH]c(=O)c34)cc2)CC1] | ESI-MS m/z 454.2 ($MH^+$) |

TABLE 1-continued
| No | Structure | Physical Data $^1H$ NMR 400 MHz (DMSO-$d_6$) and/or MS (m/z) |
| --- | --- | --- |
| 313 | 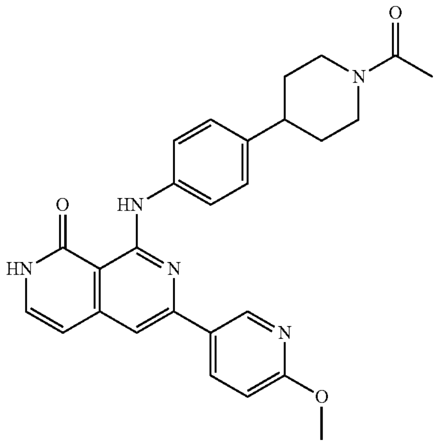 [SMILES: COc1ccc(-c2cc3cc[nH]c(=O)c3c(Nc3ccc(C4CCN(C(C)=O)CC4)cc3)n2)cn1] | ESI-MS m/z 470.2 ($MH^+$) |
| 314 | 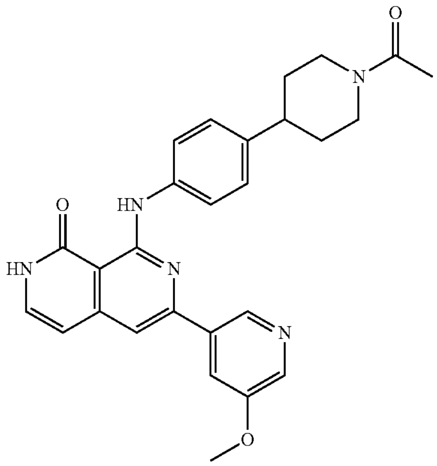 [SMILES: COc1cncc(-c2cc3cc[nH]c(=O)c3c(Nc3ccc(C4CCN(C(C)=O)CC4)cc3)n2)c1] | ESI-MS m/z 470.2 ($MH^+$) |
| 315 | 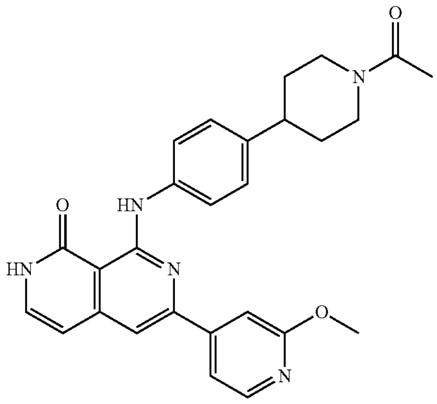 [SMILES: COc1cc(-c2cc3cc[nH]c(=O)c3c(Nc3ccc(C4CCN(C(C)=O)CC4)cc3)n2)ccn1] | ESI-MS m/z 470.2 ($MH^+$) |

TABLE 1-continued
| No | Structure | Physical Data $^1$H NMR 400 MHz (DMSO-$d_6$) and/or MS (m/z) |
|---|---|---|
| 316 | 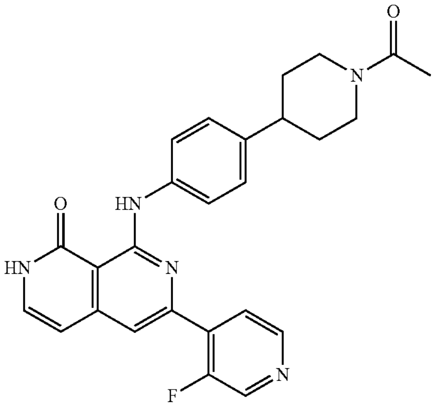 [SMILES: CC(=O)N1CCC(c2ccc(Nc3nc(-c4ccncc4F)cc4cc[nH]c(=O)c34)cc2)CC1] | ESI-MS m/z 458.2 ($MH^+$) |
| 317 | 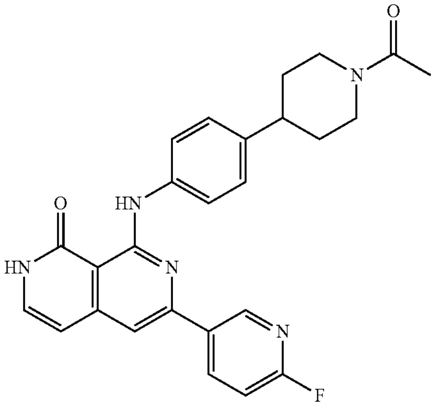 [SMILES: CC(=O)N1CCC(c2ccc(Nc3nc(-c4ccc(F)nc4)cc4cc[nH]c(=O)c34)cc2)CC1] | ESI-MS m/z 458.2 ($MH^+$) |
| 318 | 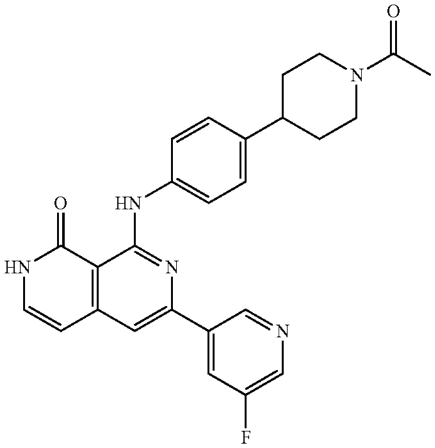 [SMILES: CC(=O)N1CCC(c2ccc(Nc3nc(-c4cncc(F)c4)cc4cc[nH]c(=O)c34)cc2)CC1] | $^1$H NMR (DMSO-$d_6$) δ 1.44 (m, 1H), 1.61 (m, 1H), 1.77-1.85 (2H), 2.04 (s, 3H), 2.59 (m, 1H), 2.77 (m, 1H), 3.14 (m, 1H), 3.92 (m, 1H), 4.53 (m, 1H), 6.56 (d, J = 7.2 Hz, 1H), 7.29 (d, J = 8.8 Hz, 2H), 7.47 (dd, J = 6.8 and 6.0 Hz, 1H), 7.64 (s, 1H), 7.77 (d, J = 8.8 Hz, 2H), 8.32 (m, 1H), 8.69 (d, J = 2.8 Hz, 1H), 9.20 (m, 1H); ESI-MS m/z 458.2 ($MH^+$) |

TABLE 1-continued
| No | Structure | Physical Data $^1$H NMR 400 MHz (DMSO-$d_6$) and/or MS (m/z) |
|---|---|---|
| 319 | 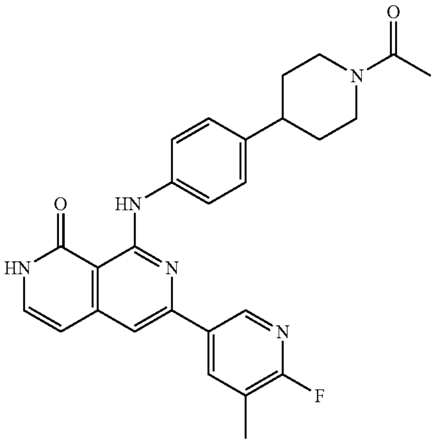 [SMILES: CC(=O)N1CCC(c2ccc(Nc3nc(-c4cnc(F)c(C)c4)cc4cc[nH]c(=O)c34)cc2)CC1] | ESI-MS m/z 472.2 ($MH^+$) |
| 320 | 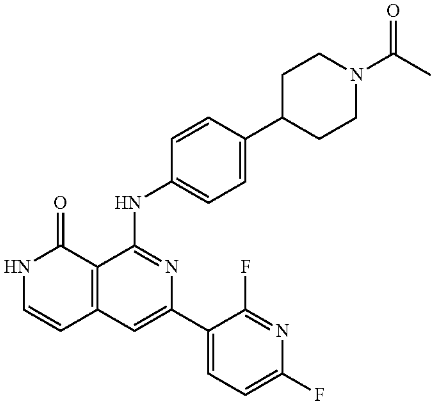 [SMILES: CC(=O)N1CCC(c2ccc(Nc3nc(-c4ccc(F)nc4F)cc4cc[nH]c(=O)c34)cc2)CC1] | ESI-MS m/z 476.2 ($MH^+$) |
| 321 | 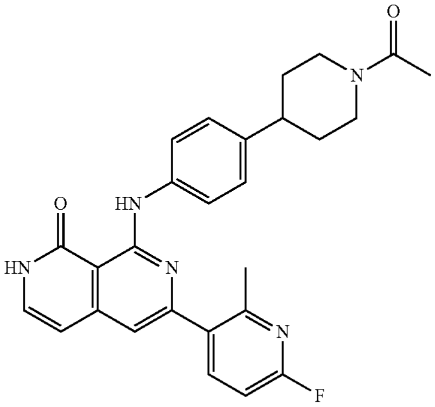 [SMILES: CC(=O)N1CCC(c2ccc(Nc3nc(-c4ccc(F)nc4C)cc4cc[nH]c(=O)c34)cc2)CC1] | ESI-MS m/z 472.2 ($MH^+$) |

TABLE 1-continued
| No | Structure | Physical Data $^1H$ NMR 400 MHz (DMSO-$d_6$) and/or MS (m/z) |
|---|---|---|
| 322 | 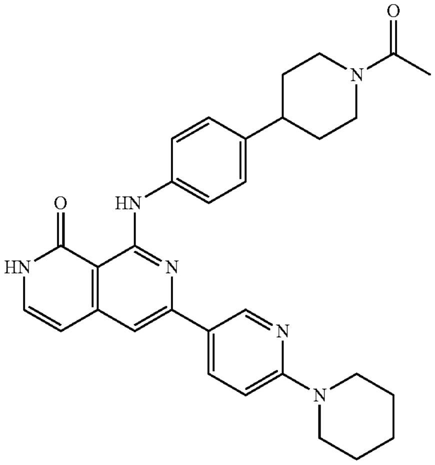 [SMILES: CC(=O)N1CCC(c2ccc(Nc3nc(-c4ccc(N5CCCCC5)nc4)cc4cc[nH]c(=O)c34)cc2)CC1] | ESI-MS m/z 523.3 ($MH^+$) |
| 323 | 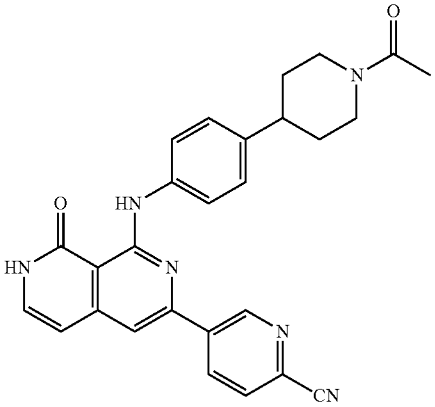 [SMILES: CC(=O)N1CCC(c2ccc(Nc3nc(-c4ccc(C#N)nc4)cc4cc[nH]c(=O)c34)cc2)CC1] | ESI-MS m/z 465.2 ($MH^+$) |
| 324 | 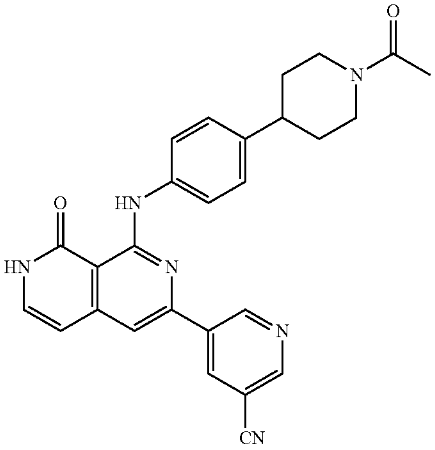 [SMILES: CC(=O)N1CCC(c2ccc(Nc3nc(-c4cncc(C#N)c4)cc4cc[nH]c(=O)c34)cc2)CC1] | ESI-MS m/z 465.2 ($MH^+$) |

TABLE 1-continued
| No | Structure | Physical Data $^1H$ NMR 400 MHz (DMSO-$d_6$) and/or MS (m/z) |
|---|---|---|
| 325 | 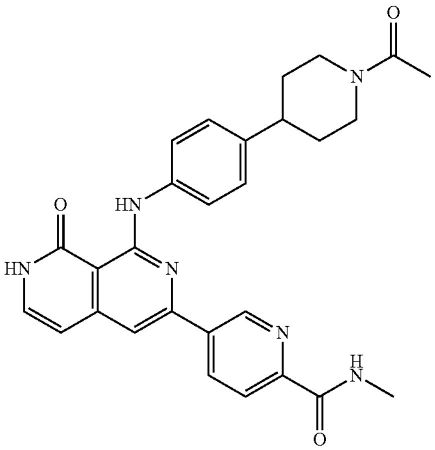 [SMILES: CNC(=O)c1ccc(-c2cc3cc[nH]c(=O)c3c(Nc3ccc(C4CCN(C(C)=O)CC4)cc3)n2)cn1] | $^1H$ NMR (DMSO-$d_6$) δ 1.50 (m, 1H), 1.66 (m, 1H), 1.83-1.92 (2H), 2.10 (s, 3H), 2.65 (m, 1H), 2.83 (m, 1H), 2.92 (d, J = 4.8 Hz, 3H), 3.19 (m, 1H), 3.99 (m, 1H), 4.60 (m, 1H), 6.65 (d, J = 7.2 Hz, 1H), 7.33 (d, J = 8.8 Hz, 2H), 7.53 (dd, J = 6.8 and 6.0 Hz, 1H), 7.71 (s, 1H), 7.86 (d, J = 8.8 Hz, 2H), 8.23 (d, J = 8.4 Hz, 1H), 8.70 (d, J = 8.4 Hz, 1H), 8.95 (br, 1H); ESI-MS m/z 497.2 ($MH^+$) |
| 326 | 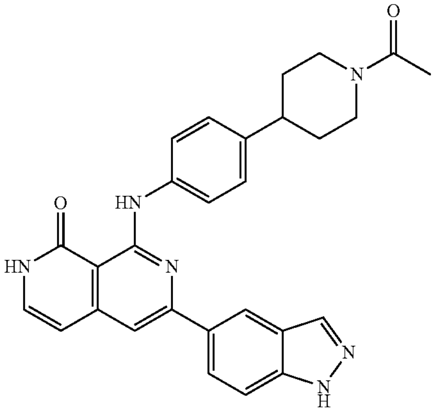 [SMILES: CC(=O)N1CCC(c2ccc(Nc3nc(-c4ccc5[nH]ncc5c4)cc4cc[nH]c(=O)c34)cc2)CC1] | ESI-MS m/z 479.2 ($MH^+$) |
| 327 | 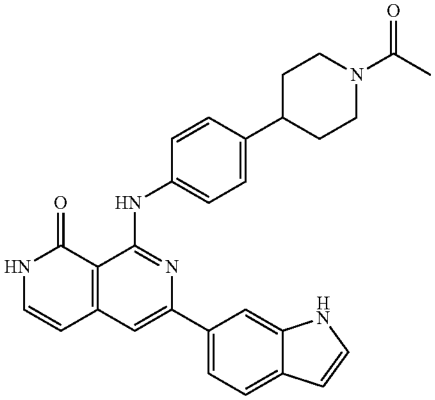 [SMILES: CC(=O)N1CCC(c2ccc(Nc3nc(-c4ccc5cc[nH]c5c4)cc4cc[nH]c(=O)c34)cc2)CC1] | ESI-MS m/z 478.2 ($MH^+$) |

TABLE 1-continued
| No | Structure | Physical Data $^1H$ NMR 400 MHz (DMSO-$d_6$) and/or MS (m/z) |
|---|---|---|
| 328 | 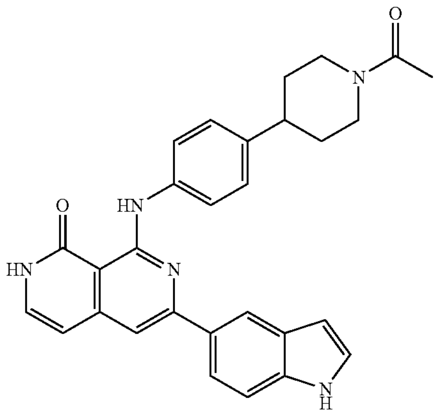 [SMILES: CC(=O)N1CCC(c2ccc(Nc3nc(-c4ccc5[nH]ccc5c4)cc4cc[nH]c(=O)c34)cc2)CC1] | ESI-MS m/z 478.2 ($MH^+$) |
| 329 | 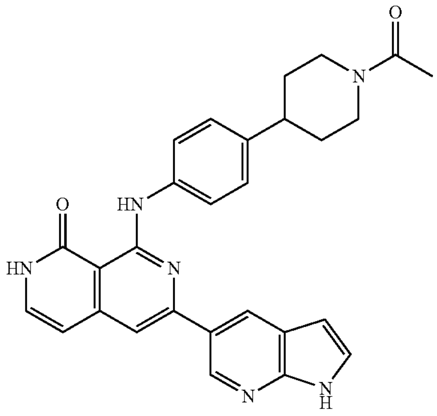 [SMILES: CC(=O)N1CCC(c2ccc(Nc3nc(-c4cnc5[nH]ccc5c4)cc4cc[nH]c(=O)c34)cc2)CC1] | ESI-MS m/z 479.2 ($MH^+$) |
| 330 | 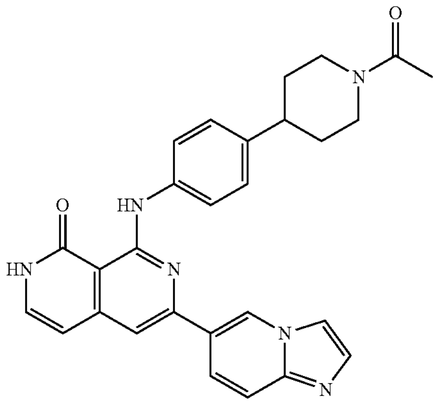 [SMILES: CC(=O)N1CCC(c2ccc(Nc3nc(-c4ccc5nccn5c4)cc4cc[nH]c(=O)c34)cc2)CC1] | ESI-MS m/z 479.2 ($MH^+$) |

TABLE 1-continued
| No | Structure | Physical Data $^1H$ NMR 400 MHz ($DMSO-d_6$) and/or MS (m/z) |
|---|---|---|
| 331 | 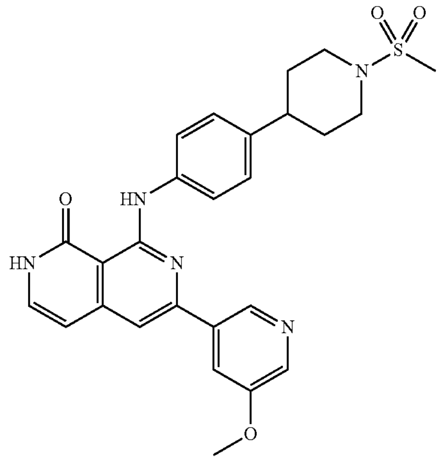 [SMILES: COc1cncc(-c2cc3cc[nH]c(=O)c3c(Nc3ccc(C4CCN(S(C)(=O)=O)CC4)cc3)n2)c1] | ESI-MS m/z 506.2 ($MH^+$) |
| 332 | 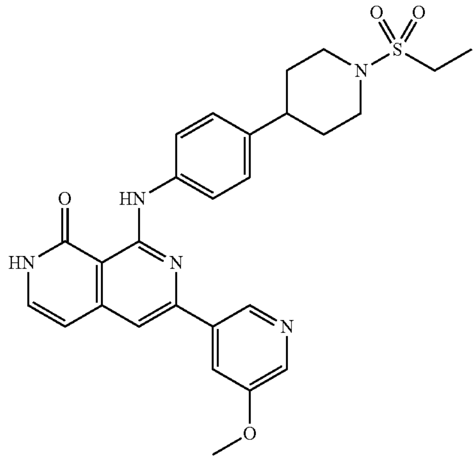 [SMILES: CCS(=O)(=O)N1CCC(c2ccc(Nc3nc(-c4cncc(OC)c4)cc4cc[nH]c(=O)c34)cc2)CC1] | ESI-MS m/z 520.2 ($MH^+$) |
| 333 | 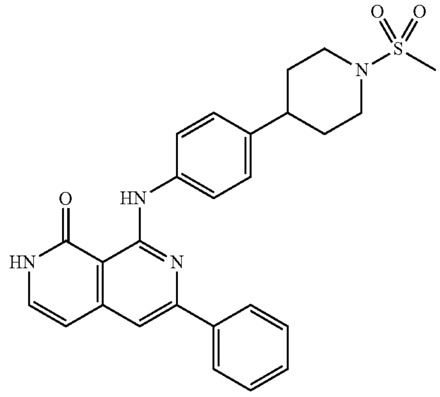 [SMILES: CS(=O)(=O)N1CCC(c2ccc(Nc3nc(-c4ccccc4)cc4cc[nH]c(=O)c34)cc2)CC1] | ESI-MS m/z 475.2 ($MH^+$) |

TABLE 1-continued
| No | Structure | Physical Data $^1$H NMR 400 MHz (DMSO-$d_6$) and/or MS (m/z) |
|---|---|---|
| 334 | 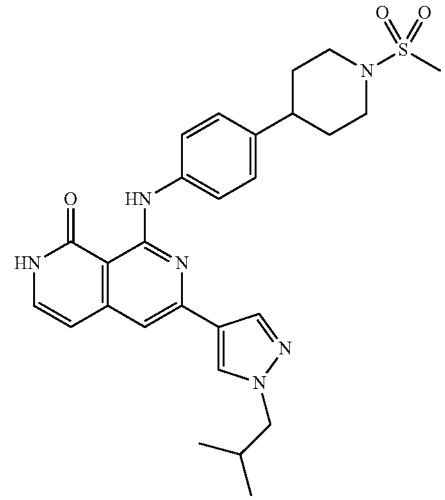 [SMILES: CC(C)Cn1cc(-c2cc3cc[nH]c(=O)c3c(Nc3ccc(C4CCN(S(C)(=O)=O)CC4)cc3)n2)cn1] | ESI-MS m/z 521.2 ($MH^+$) |
| 335 | 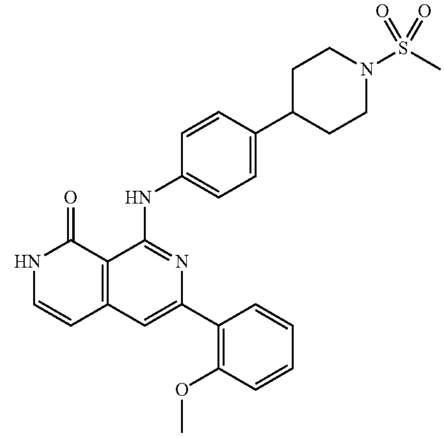 [SMILES: COc1ccccc1-c1cc2cc[nH]c(=O)c2c(Nc2ccc(C3CCN(S(C)(=O)=O)CC3)cc2)n1] | ESI-MS m/z 505.2 ($MH^+$) |
| 336 | 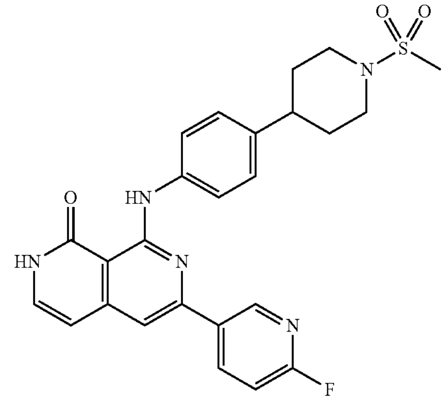 [SMILES: CS(=O)(=O)N1CCC(c2ccc(Nc3nc(-c4ccc(F)nc4)cc4cc[nH]c(=O)c34)cc2)CC1] | ESI-MS m/z 493.2 ($MH^+$) |

TABLE 1-continued
| No | Structure | Physical Data $^1H$ NMR 400 MHz (DMSO-$d_6$) and/or MS (m/z) |
|---|---|---|
| 337 | 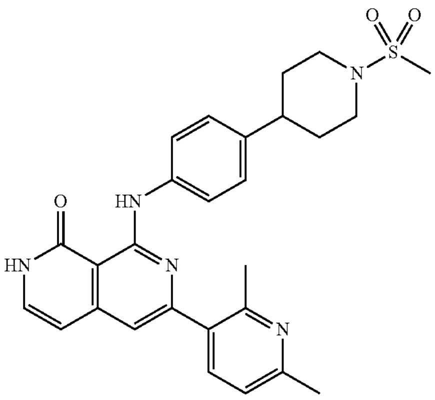 [SMILES: Cc1ccc(-c2cc3cc[nH]c(=O)c3c(Nc3ccc(C4CCN(S(C)(=O)=O)CC4)cc3)n2)c(C)n1] | $^1H$ NMR (DMSO-$d_6$) δ 1.60-1.69 (2H), 1.82-1.88 (2H), 2.59 (m, 1H), 2.66 (s, 3H), 2.69 (s, 3H), 2.76-2.83 (2H), 2.89 (s, 3H), 3.60-3.67 (2H), 6.57 (d, J= 7.2 Hz, 1H), 7.10 (s, 1H), 7.21 (d, J = 8.8 Hz, 2H), 7.48 (dd, J = 6.6 and 6.2 Hz, 1H), 7.61 (br, 1H), 7.70 (d, J = 8.8 Hz, 2H), 8.25 (br, 1H); ESI-MS m/z 504.2 ($MH^+$) |
| 338 | 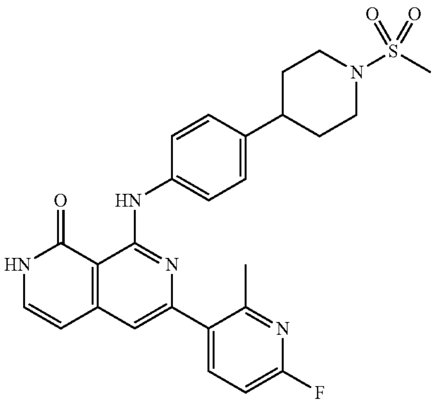 [SMILES: Cc1nc(F)ccc1-c1cc2cc[nH]c(=O)c2c(Nc2ccc(C3CCN(S(C)(=O)=O)CC3)cc2)n1] | ESI-MS m/z 508.2 ($MH^+$) |
| 339 | 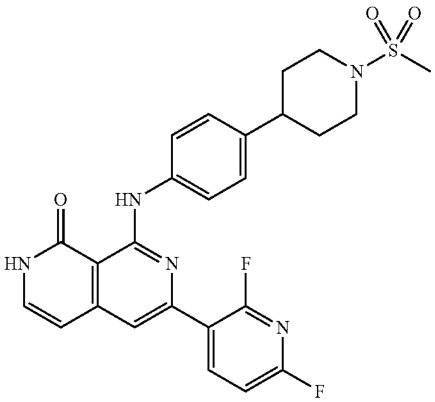 [SMILES: CS(=O)(=O)N1CCC(c2ccc(Nc3nc(-c4ccc(F)nc4F)cc4cc[nH]c(=O)c34)cc2)CC1] | $^1H$ NMR (DMSO-$d_6$) δ 1.56-1.65 (2H), 1.79-1.85 (2H), 2.55 (m, 1H), 2.72-2.78 (2H), 2.83 (s, 3H), 3.58-3.63 (2H), 6.56 (d, J = 6.8 Hz, 1H), 7.20 (d, J = 8.4 Hz, 2H), 7.28 (s, 1H), 7.33 (m, 1H), 7.40 (d, J = 6.8 Hz, 1H), 7.69 (d, J = 8.4 Hz, 2H), 8.67 (m, 1H); ESI-MS m/z 512.1 ($MH^+$) |

TABLE 1-continued
| No | Structure | Physical Data $^1H$ NMR 400 MHz (DMSO-$d_6$) and/or MS (m/z) |
|---|---|---|
| 340 | 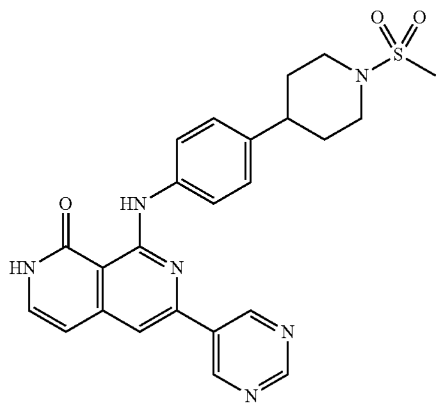 [SMILES: CS(=O)(=O)N1CCC(c2ccc(Nc3nc(-c4cncnc4)cc4cc[nH]c(=O)c34)cc2)CC1] | ESI-MS m/z 477.2 ($MH^+$) |
| 341 | 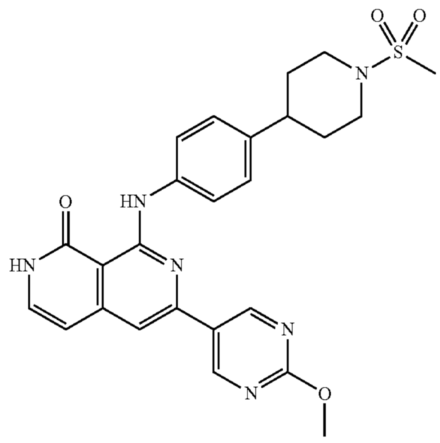 [SMILES: COc1ncc(-c2cc3cc[nH]c(=O)c3c(Nc3ccc(C4CCN(S(C)(=O)=O)CC4)cc3)n2)cn1] | ESI-MS m/z 507.2 ($MH^+$) |
| 342 | 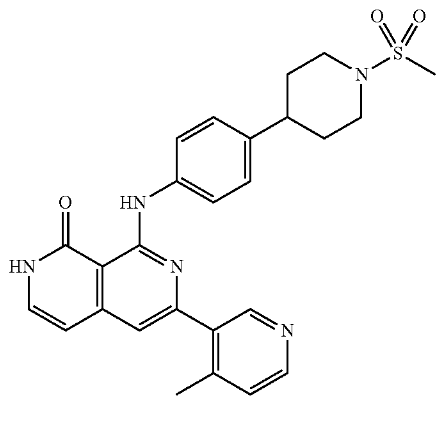 [SMILES: Cc1ccncc1-c1cc2cc[nH]c(=O)c2c(Nc2ccc(C3CCN(S(C)(=O)=O)CC3)cc2)n1] | $^1H$ NMR (DMSO-$d_6$) δ 1.60-1.70 (2H), 1.83-1.88 (2H), 2.54 (s, 3H), 2.58 (m, 1H), 2.76-2.83 (2H), 2.89 (s, 3H), 3.63-3.67 (2H), 6.58 (d, J = 6.8 Hz, 1H), 7.12 (s, 1H), 7.22 (d, J = 8.8 Hz, 2H), 7.48 (dd, J = 6.8 and 6.0 Hz, 1H), 7.67 (d, J = 5.4 Hz, 1H), 7.70 (d, J = 8.8 Hz, 2H), 8.64 (d, J = 5.4 Hz, 1H), 8.80 (s, 1H); ESI-MS m/z 490.2 ($MH^+$) |

TABLE 1-continued
| No | Structure | Physical Data $^1H$ NMR 400 MHz ($DMSO-d_6$) and/or MS (m/z) |
|---|---|---|
| 343 | 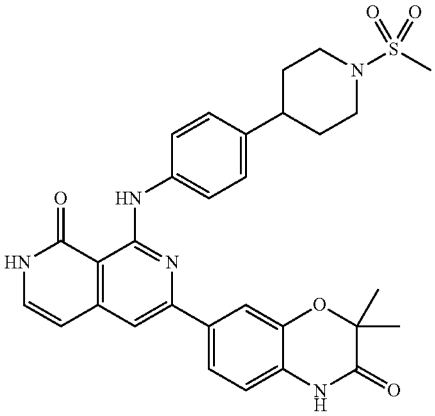 [SMILES: CC1(C)Oc2cc(-c3cc4cc[nH]c(=O)c4c(Nc4ccc(C5CCN(S(C)(=O)=O)CC5)cc4)n3)ccc2NC1=O] | ESI-MS m/z 575.2 ($MH^+$) |
| 344 | 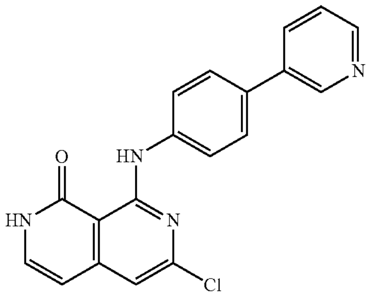 [SMILES: O=c1[nH]ccc2cc(Cl)nc(Nc3ccc(-c4cccnc4)cc3)c12] | ESI-MS m/z 349.1 ($MH^+$) |
| 345 | 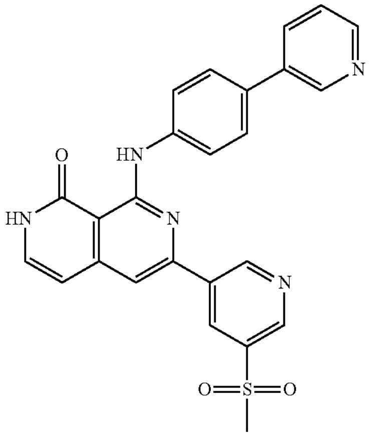 [SMILES: CS(=O)(=O)c1cncc(-c2cc3cc[nH]c(=O)c3c(Nc3ccc(-c4cccnc4)cc3)n2)c1] | ESI-MS m/z 470.1 ($MH^+$) |
| 346 | 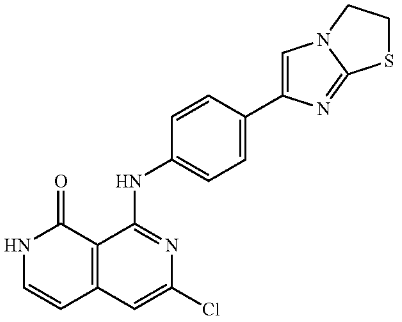 [SMILES: O=c1[nH]ccc2cc(Cl)nc(Nc3ccc(-c4cn5c(n4)SCC5)cc3)c12] | ESI-MS m/z 396.1 ($MH^+$) |

TABLE 1-continued
| No | Structure | Physical Data $^1H$ NMR 400 MHz ($DMSO-d_6$) and/or MS (m/z) |
|---|---|---|
| 347 | 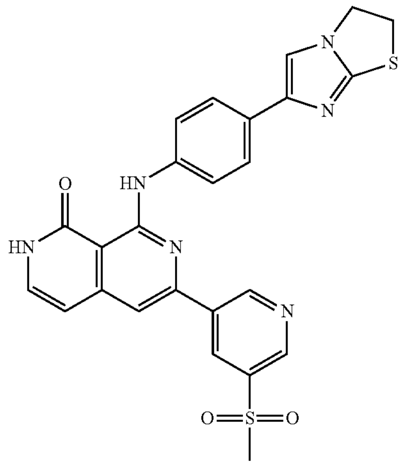 [SMILES: CS(=O)(=O)c1cncc(-c2cc3cc[nH]c(=O)c3c(Nc3ccc(-c4cn5c(n4)SCC5)cc3)n2)c1] | ESI-MS m/z 517.1 ($MH^+$) |
| 348 | 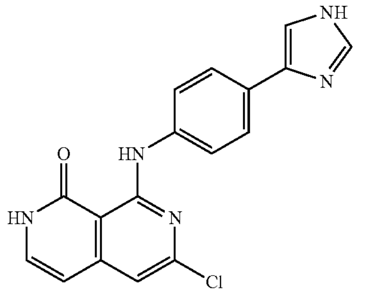 [SMILES: O=c1[nH]ccc2cc(Cl)nc(Nc3ccc(-c4c[nH]cn4)cc3)c12] | ESI-MS m/z 338.1 ($MH^+$) |
| 349 | 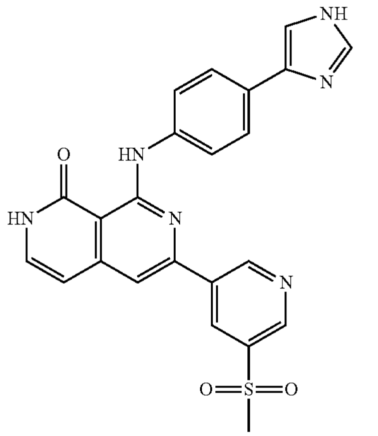 [SMILES: CS(=O)(=O)c1cncc(-c2cc3cc[nH]c(=O)c3c(Nc3ccc(-c4c[nH]cn4)cc3)n2)c1] | $^1H$ NMR ($DMSO-d_6$) δ 2.54 (s, 3H), 6.65 (d, J = 6.8 Hz, 1H), 7.53 (dd, J = 6.8 and 6.4 Hz, 1H), 7.83 (s, 1H), 7.84 (d, J = 8.6 Hz, 2H), 8.03 (d, J = 8.6 Hz, 2H), 8.04 (s, 1H), 8.86 (s, 1H), 8.99 (s, 1H), 9.18 (s, 1H), 9.64 (s, 1H); ESI-MS m/z 459.1 ($MH^+$) |
| 350 | 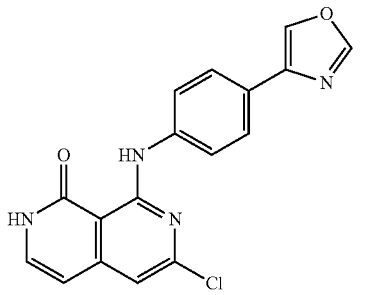 [SMILES: O=c1[nH]ccc2cc(Cl)nc(Nc3ccc(-c4cocn4)cc3)c12] | ESI-MS m/z 339.1 ($MH^+$) |

TABLE 1-continued
| No | Structure | Physical Data $^1H$ NMR 400 MHz (DMSO-$d_6$) and/or MS (m/z) |
|---|---|---|
| 351 | 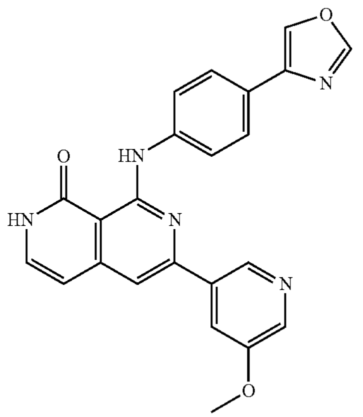 [SMILES: COc1cncc(-c2cc3cc[nH]c(=O)c3c(Nc3ccc(-c4cocn4)cc3)n2)c1] | $^1H$ NMR (DMSO-$d_6$) δ 3.97 (s, 3H), 6.59 (d, J = 6.8 Hz, 1H), 7.49 (dd, J = 6.8 and 6.4 Hz, 1H), 7.63 (s, 1H), 7.69 (s, 1H), 7.76 (d, J = 8.8 Hz, 2H), 8.02 (d, J = 8.8 Hz, 2H), 8.07 (br, 1H), 8.41 (s, 1H), 8.42 (s, 1H), 8.96 (s, 1H); ESI-MS m/z 412.1 (MH$^+$) |
| 352 | 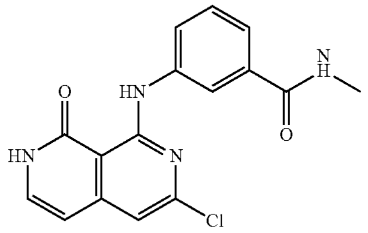 [SMILES: CNC(=O)c1cccc(Nc2nc(Cl)cc3cc[nH]c(=O)c23)c1] | ESI-MS m/z 329.1 (MH$^+$) |
| 353 | 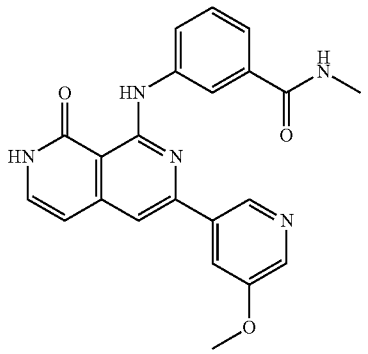 [SMILES: CNC(=O)c1cccc(Nc2nc(-c3cncc(OC)c3)cc3cc[nH]c(=O)c23)c1] | ESI-MS m/z 402.2 (MH$^+$) |
| 354 | 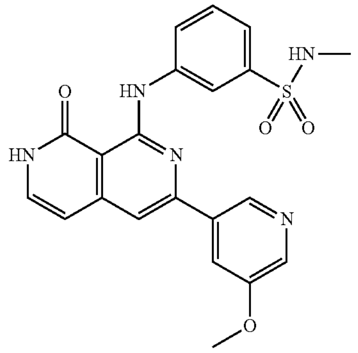 [SMILES: CNS(=O)(=O)c1cccc(Nc2nc(-c3cncc(OC)c3)cc3cc[nH]c(=O)c23)c1] | ESI-MS m/z 438.1 (MH$^+$) |

TABLE 1-continued
| No | Structure | Physical Data $^1H$ NMR 400 MHz (DMSO-$d_6$) and/or MS (m/z) |
|---|---|---|
| 355 | 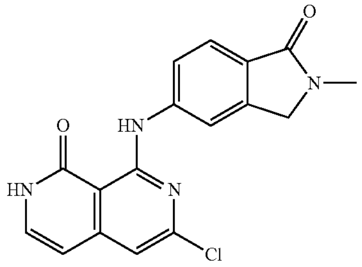 [SMILES: CN1Cc2cc(Nc3nc(Cl)cc4cc[nH]c(=O)c34)ccc2C1=O] | ESI-MS m/z 341.1 ($MH^+$) |
| 356 | 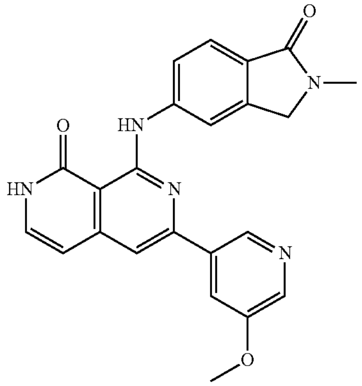 [SMILES: COc1cncc(-c2cc3cc[nH]c(=O)c3c(Nc3ccc4c(c3)CN(C)C4=O)n2)c1] | ESI-MS m/z 414.2 ($MH^+$) |
| 357 | 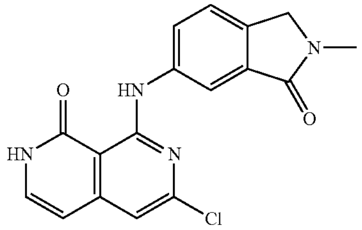 [SMILES: CN1Cc2ccc(Nc3nc(Cl)cc4cc[nH]c(=O)c34)cc2C1=O] | ESI-MS m/z 341.1 ($MH^+$) |
| 358 | 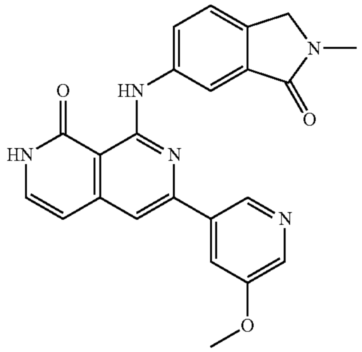 [SMILES: COc1cncc(-c2cc3cc[nH]c(=O)c3c(Nc3ccc4c(c3)C(=O)N(C)C4)n2)c1] | ESI-MS m/z 414.2 ($MH^+$) |
| 359 | 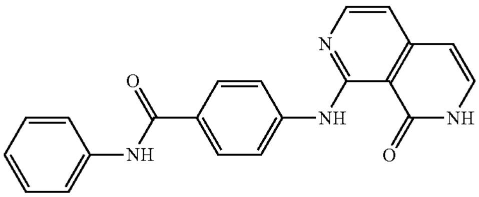 [SMILES: O=C(Nc1ccccc1)c1ccc(Nc2nccc3cc[nH]c(=O)c23)cc1] | ESI-MS m/z 357.1 ($MH^+$). |

TABLE 1-continued
| No | Structure | Physical Data $^1H$ NMR 400 MHz (DMSO-$d_6$) and/or MS (m/z) |
|---|---|---|
| 360 | 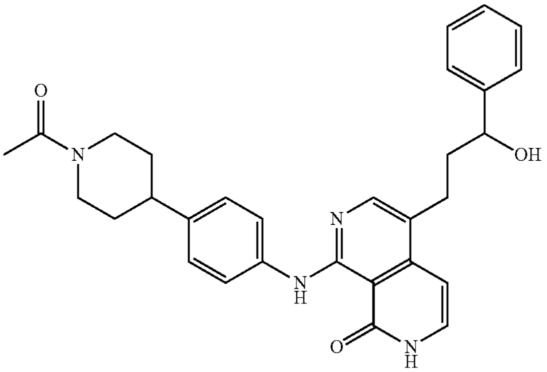 [SMILES: CC(=O)N1CCC(c2ccc(Nc3ncc(CCC(O)c4ccccc4)c4cc[nH]c(=O)c34)cc2)CC1] | ESI-MS m/z 497.3 ($MH^+$). |
| 361 | 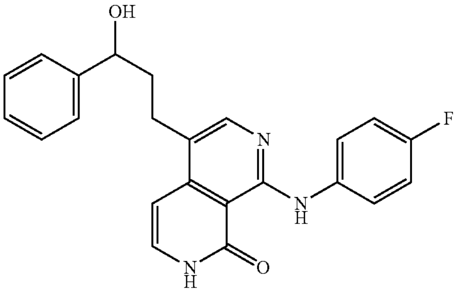 | ESI-MS m/z 390.2 ($MH^+$). |
| 362 | 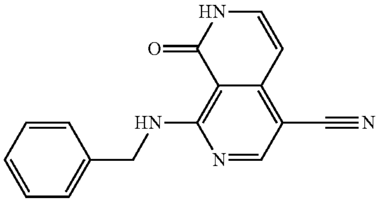 [SMILES: N#Cc1cnc(NCc2ccccc2)c2c(=O)[nH]ccc12] | ESI-MS m/z 277.1 ($MH^+$). |
| 363 | 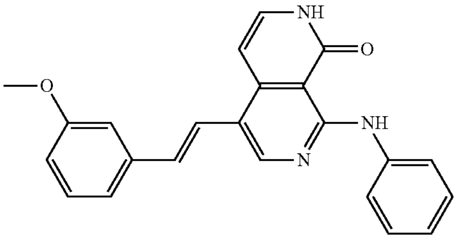 [SMILES: COc1cccc(/C=C/c2cnc(Nc3ccccc3)c3c(=O)[nH]ccc23)c1] | ESI-MS m/z 370.1 ($MH^+$). |
| 364 | 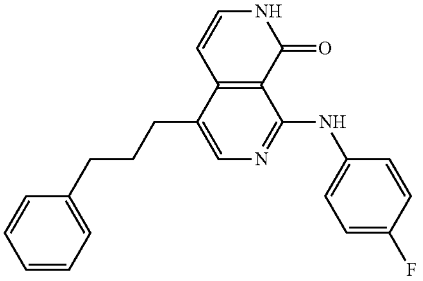 [SMILES: O=c1[nH]ccc2c(CCCc3ccccc3)cnc(Nc3ccc(F)cc3)c12] | ESI-MS m/z 374.2 ($MH^+$). |

TABLE 1-continued
| No | Structure | Physical Data $^1H$ NMR 400 MHz (DMSO-$d_6$) and/or MS (m/z) |
|---|---|---|
| 365 | 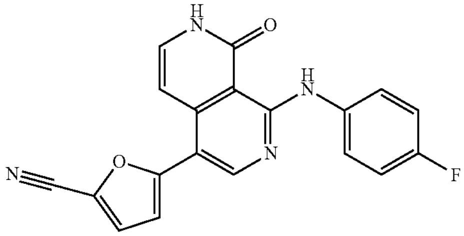 [SMILES: N#Cc1ccc(-c2cnc(Nc3ccc(F)cc3)c3c(=O)[nH]ccc23)o1] | ESI-MS m/z 374.1 (MH$^+$). |
| 366 | 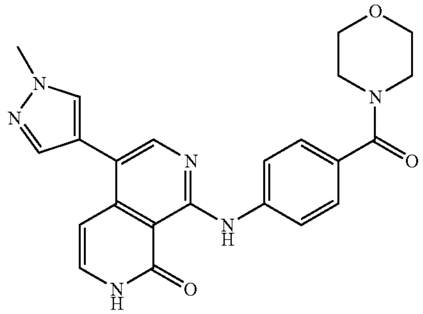 | ESI-MS m/z 431.2 (MH$^+$). |
| 367 | 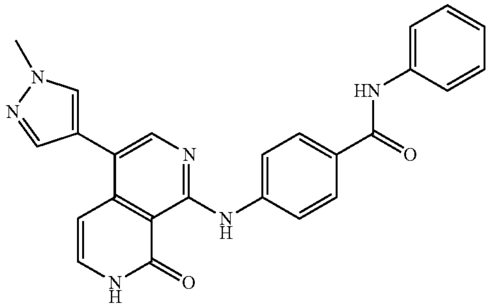 | ESI-MS m/z 437.2 (MH$^+$). |
| 368 | 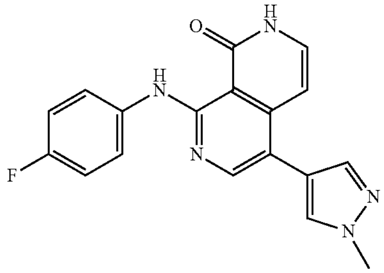 [SMILES: Cn1cc(-c2cnc(Nc3ccc(F)cc3)c3c(=O)[nH]ccc23)cn1] | ESI-MS m/z 336.1 (MH$^+$). |
| 369 | 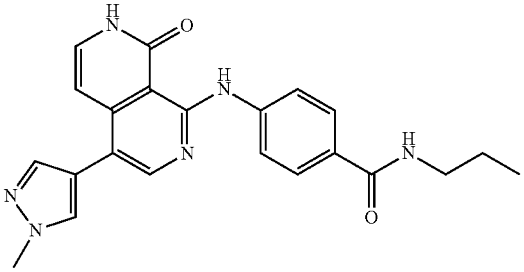 [SMILES: CCCNC(=O)c1ccc(Nc2ncc(-c3cnn(C)c3)c3cc[nH]c(=O)c23)cc1] | ESI-MS m/z 403.2 (MH$^+$). |

TABLE 1-continued
| No | Structure | Physical Data $^1H$ NMR 400 MHz (DMSO-$d_6$) and/or MS (m/z) |
|---|---|---|
| 370 | 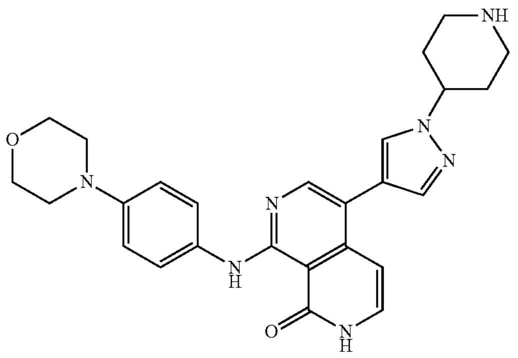 [SMILES: O=c1[nH]ccc2c(-c3cnn(C4CCNCC4)c3)cnc(Nc3ccc(N4CCOCC4)cc3)c12] | ESI-MS m/z 472.2 ($MH^+$). |
| 373 | 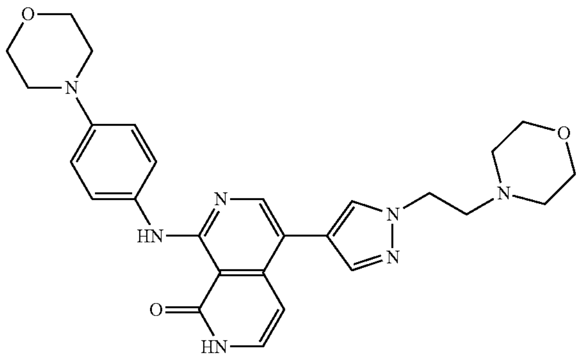 [SMILES: O=c1[nH]ccc2c(-c3cnn(CCN4CCOCC4)c3)cnc(Nc3ccc(N4CCOCC4)cc3)c12] | ESI-MS m/z 502.2 ($MH^+$). |
| 372 | 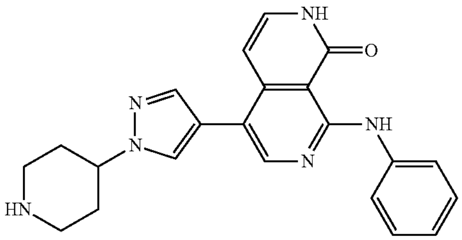 [SMILES: O=c1[nH]ccc2c(-c3cnn(C4CCNCC4)c3)cnc(Nc3ccccc3)c12] | ESI-MS m/z 387.3 ($MH^+$). |
| 373 | 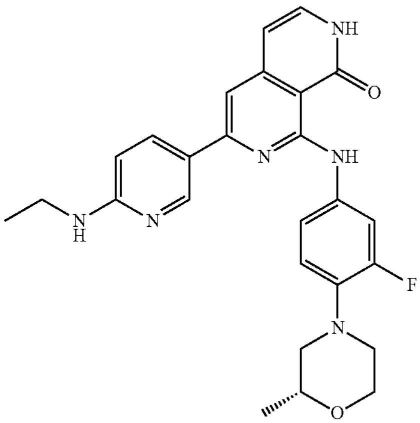 | ESI-MS m/z 450.3 ($MH^+$). |

TABLE 1-continued
| No | Structure | Physical Data $^1H$ NMR 400 MHz (DMSO-$d_6$) and/or MS (m/z) |
|---|---|---|
| 374 | 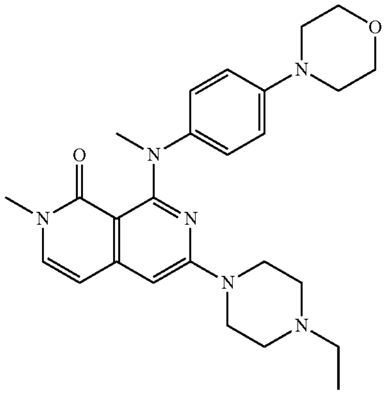 [SMILES: CCN1CCN(c2cc3ccn(C)c(=O)c3c(N(C)c3ccc(N4CCOCC4)cc3)n2)CC1] | ESI-MS m/z 463.3 (MH$^+$). |
| 375 | 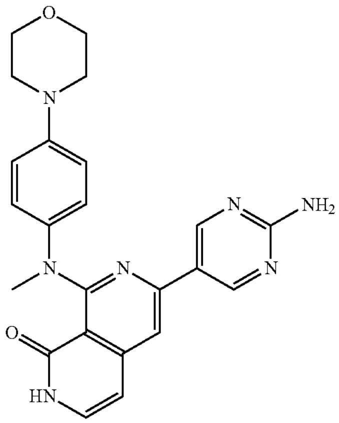 | ESI-MS m/z 340.2 (MH$^+$). |
| 376 | 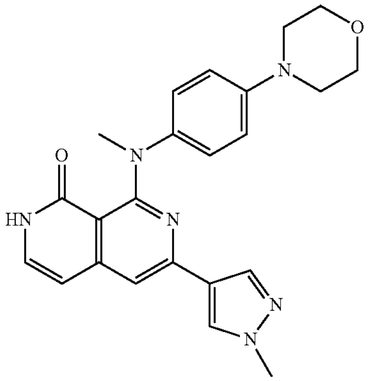 [SMILES: CN(c1ccc(N2CCOCC2)cc1)c1nc(-c2cnn(C)c2)cc2cc[nH]c(=O)c12] | ESI-MS m/z 417.2 (MH$^+$). |

TABLE 1-continued
| No | Structure | Physical Data $^1H$ NMR 400 MHz (DMSO-$d_6$) and/or MS (m/z) |
|---|---|---|
| 377 | 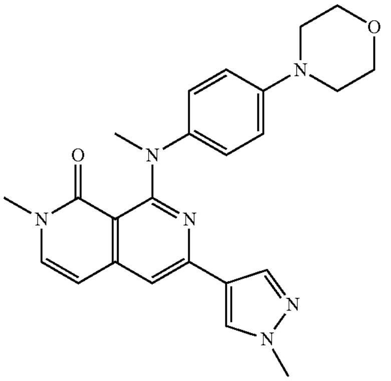 [SMILES: CN(c1ccc(N2CCOCC2)cc1)c1nc(-c2cnn(C)c2)cc2ccn(C)c(=O)c12] | ESI-MS m/z 431.2 ($MH^+$). |
| 378 | 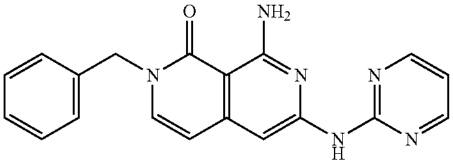 [SMILES: Nc1nc(Nc2ncccn2)cc2ccn(Cc3ccccc3)c(=O)c12] | ESI-MS m/z 345.2 ($MH^+$). |
| 379 | 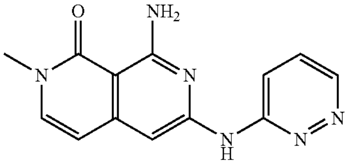 [SMILES: Cn1ccc2cc(Nc3cccnn3)nc(N)c2c1=O] | ESI-MS m/z 269.1 ($MH^+$). |
| 380 | 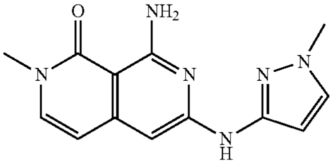 [SMILES: Cn1ccc(Nc2cc3ccn(C)c(=O)c3c(N)n2)n1] | ESI-MS m/z 271.20 ($MH^+$). |
| 383 | 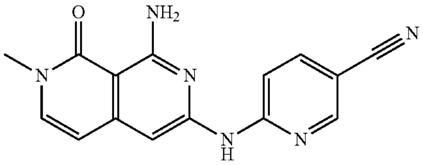 [SMILES: Cn1ccc2cc(Nc3ccc(C#N)cn3)nc(N)c2c1=O] | ESI-MS m/z 293.2 ($MH^+$). |
| 382 | 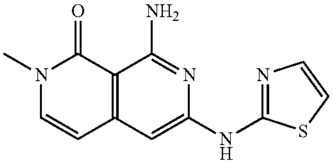 [SMILES: Cn1ccc2cc(Nc3nccs3)nc(N)c2c1=O] | ESI-MS m/z 274.1 ($MH^+$). |
| 383 | 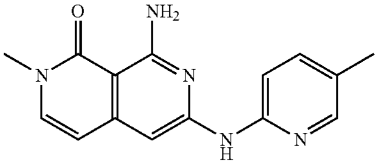 | ESI-MS m/z 282.20 ($MH^+$). |

TABLE 1-continued
| No | Structure | Physical Data $^1H$ NMR 400 MHz (DMSO-$d_6$) and/or MS (m/z) |
|---|---|---|
| 384 | 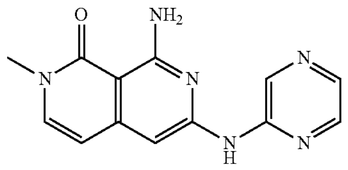 [SMILES: Cn1ccc2cc(Nc3cnccn3)nc(N)c2c1=O] | ESI-MS m/z 269.1 ($MH^+$). |
| 385 | 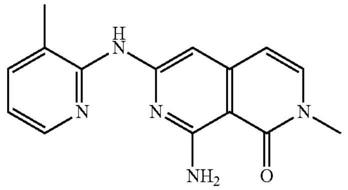 [SMILES: Cc1cccnc1Nc1cc2ccn(C)c(=O)c2c(N)n1] | ESI-MS m/z 282.20 ($MH^+$). |
| 386 | 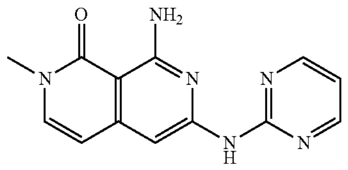 [SMILES: Cn1ccc2cc(Nc3ncccn3)nc(N)c2c1=O] | ESI-MS m/z 269.2 ($MH^+$). |
| 387 | 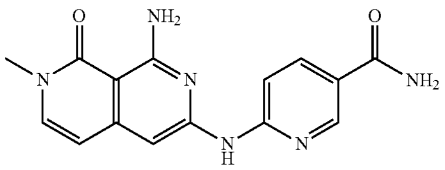 [SMILES: Cn1ccc2cc(Nc3ccc(C(N)=O)cn3)nc(N)c2c1=O] | ESI-MS m/z 311.1 ($MH^+$). |
| 388 | 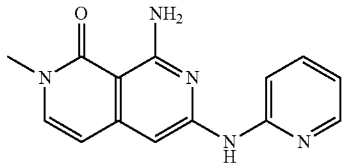 [SMILES: Cn1ccc2cc(Nc3ccccn3)nc(N)c2c1=O] | ESI-MS m/z 268.20 (MH+). |
| 389 | 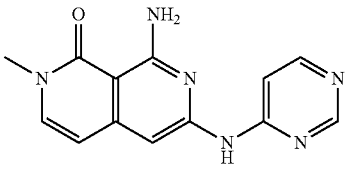 [SMILES: Cn1ccc2cc(Nc3ccncn3)nc(N)c2c1=O] | ESI-MS m/z 269.1 (MH+). |
| 390 | 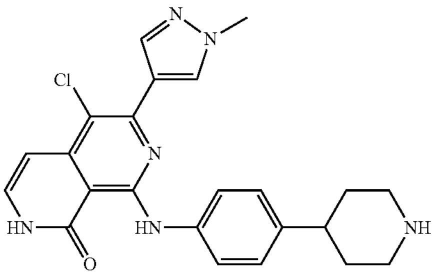 [SMILES: Cn1cc(-c2nc(Nc3ccc(C4CCNCC4)cc3)c3c(=O)[nH]ccc3c2Cl)cn1] | ESI-MS m/z 435.2 ($MH^+$). |

TABLE 1-continued
| No | Structure | Physical Data $^1H$ NMR 400 MHz (DMSO-$d_6$) and/or MS (m/z) |
|---|---|---|
| 393 | 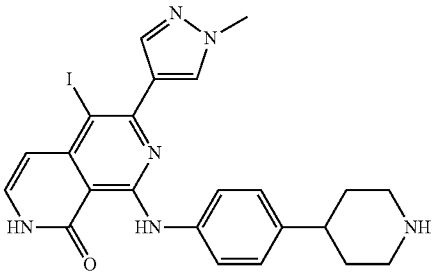 [SMILES: Cn1cc(-c2nc(Nc3ccc(C4CCNCC4)cc3)c3c(=O)[nH]ccc3c2I)cn1] | ESI-MS m/z 527.1 (MH$^+$). |
| 392 | 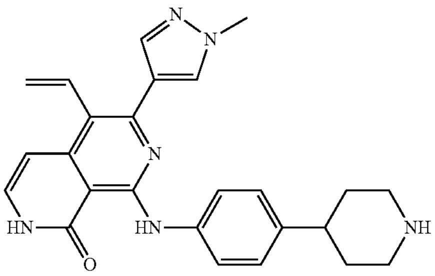 [SMILES: C=Cc1c(-c2cnn(C)c2)nc(Nc2ccc(C3CCNCC3)cc2)c2c(=O)[nH]ccc12] | ESI-MS m/z 427.2 (MH$^+$). |
| 393 | 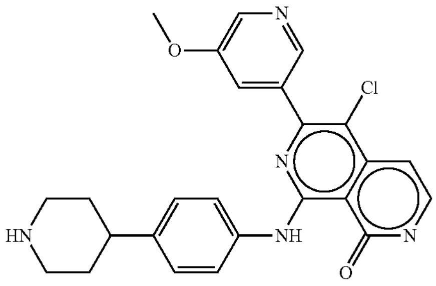 | ESI-MS m/z 461.2 (MH$^+$). |
| 394 | 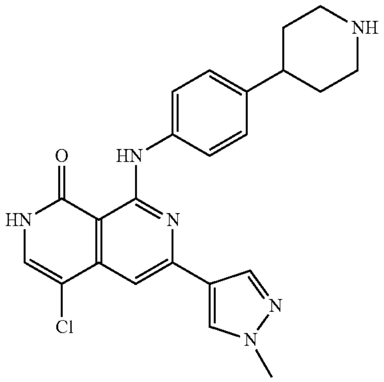 [SMILES: Cn1cc(-c2cc3c(Cl)c[nH]c(=O)c3c(Nc3ccc(C4CCNCC4)cc3)n2)cn1] | ESI-MS m/z 435.2 (MH$^+$). |
| 395 | 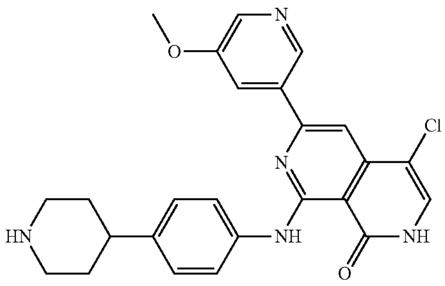 [SMILES: COc1cncc(-c2cc3c(Cl)c[nH]c(=O)c3c(Nc3ccc(C4CCNCC4)cc3)n2)c1] | ESI-MS m/z 462.2 (MH$^+$). |

TABLE 1-continued
| No | Structure | Physical Data $^1H$ NMR 400 MHz ($DMSO-d_6$) and/or MS (m/z) |
|---|---|---|
| 396 | 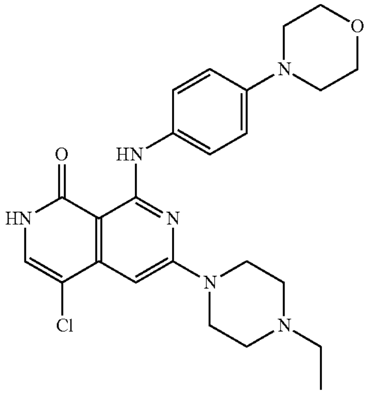 [SMILES: CCN1CCN(c2cc3c(Cl)c[nH]c(=O)c3c(Nc3ccc(N4CCOCC4)cc3)n2)CC1] | ESI-MS m/z 469.2 ($MH^+$). |
| 397 | 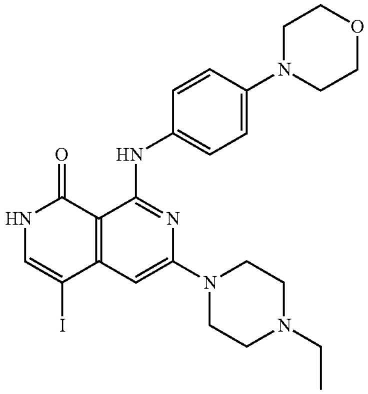 [SMILES: CCN1CCN(c2cc3c(I)c[nH]c(=O)c3c(Nc3ccc(N4CCOCC4)cc3)n2)CC1] | ESI-MS m/z 561.1 ($MH^+$). |
| 398 | 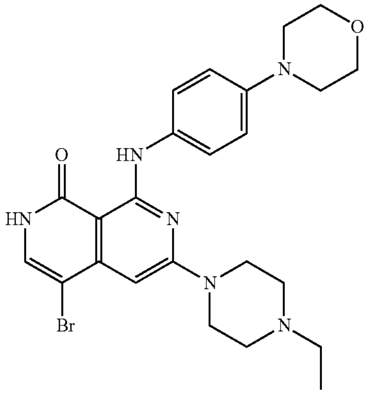 [SMILES: CCN1CCN(c2cc3c(Br)c[nH]c(=O)c3c(Nc3ccc(N4CCOCC4)cc3)n2)CC1] | ESI-MS m/z 513.1 ($MH^+$). |

TABLE 1-continued
| No | Structure | Physical Data $^1H$ NMR 400 MHz (DMSO-$d_6$) and/or MS (m/z) |
|---|---|---|
| 399 | 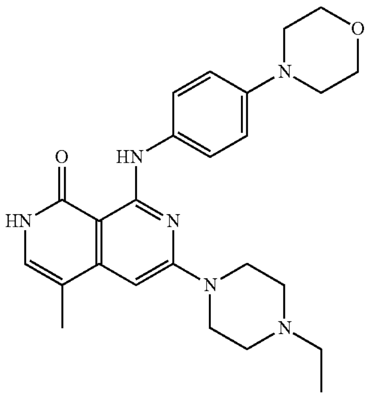 [SMILES: CCN1CCN(c2cc3c(C)c[nH]c(=O)c3c(Nc3ccc(N4CCOCC4)cc3)n2)CC1] | ESI-MS m/z 449.3 ($MH^+$). |
| 400 | 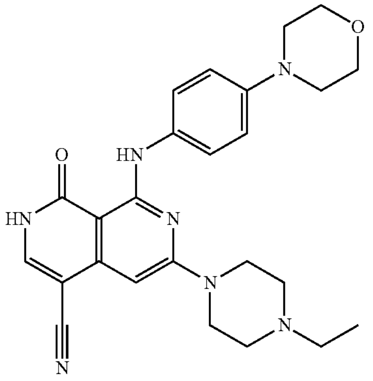 [SMILES: CCN1CCN(c2cc3c(C#N)c[nH]c(=O)c3c(Nc3ccc(N4CCOCC4)cc3)n2)CC1] | ESI-MS m/z 460.2 ($MH^+$). |
| 401 | 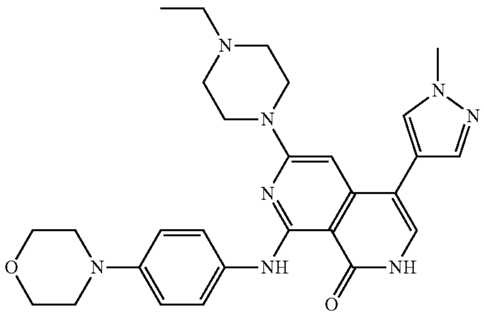 [SMILES: CCN1CCN(c2cc3c(-c4cnn(C)c4)c[nH]c(=O)c3c(Nc3ccc(N4CCOCC4)cc3)n2)CC1] | ESI-MS m/z 514.3 ($MH^+$). |
| 402 | 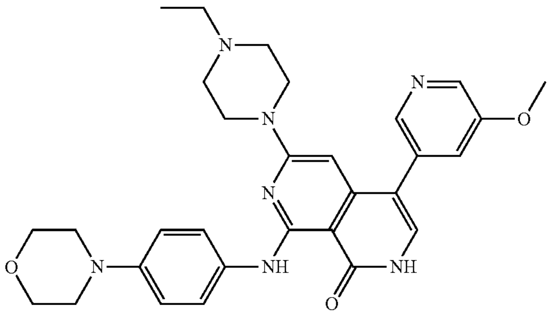 [SMILES: CCN1CCN(c2cc3c(-c4cncc(OC)c4)c[nH]c(=O)c3c(Nc3ccc(N4CCOCC4)cc3)n2)CC1] | ESI-MS m/z 541.3 ($MH^+$). |

TABLE 1-continued
| No | Structure | Physical Data $^1$H NMR 400 MHz (DMSO-$d_6$) and/or MS (m/z) |
|---|---|---|
| 403 | 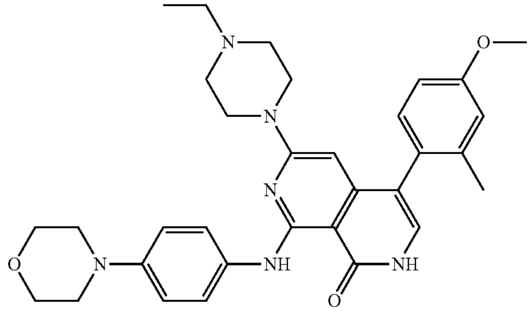 [SMILES: CCN1CCN(c2cc3c(-c4ccc(OC)cc4C)c[nH]c(=O)c3c(Nc3ccc(N4CCOCC4)cc3)n2)CC1] | ESI-MS m/z 554.3 (MH$^+$). |
| 404 | 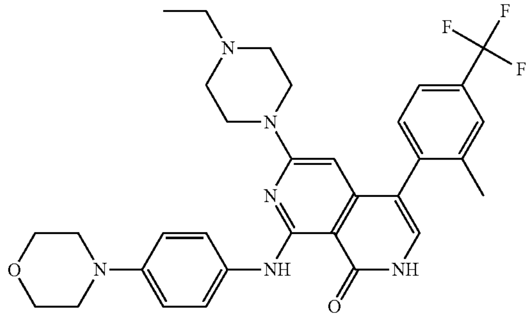 | ESI-MS m/z 592.3 (MH+). |
| 405 | 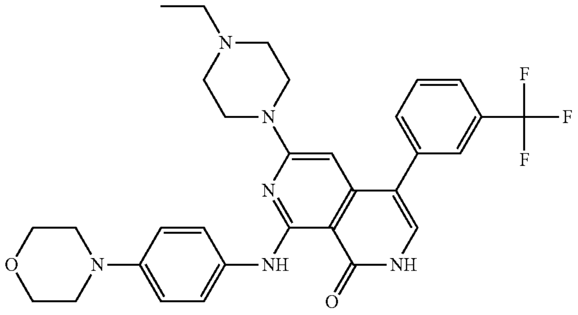 [SMILES: CCN1CCN(c2cc3c(-c4cccc(C(F)(F)F)c4)c[nH]c(=O)c3c(Nc3ccc(N4CCOCC4)cc3)n2)CC1] | ESI-MS m/z 579.3 (MH+). |
| 406 | 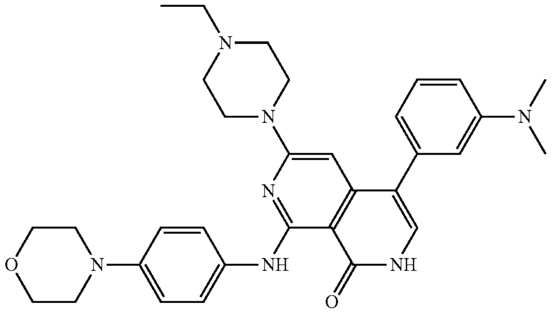 [SMILES: CCN1CCN(c2cc3c(-c4cccc(N(C)C)c4)c[nH]c(=O)c3c(Nc3ccc(N4CCOCC4)cc3)n2)CC1] | ESI-MS m/z 554.3 (MH+). |

TABLE 1-continued
| No | Structure | Physical Data $^1$H NMR 400 MHz (DMSO-$d_6$) and/or MS (m/z) |
|---|---|---|
| 407 | 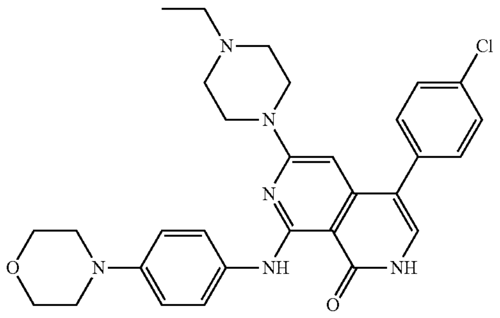 [SMILES: CCN1CCN(c2cc3c(-c4ccc(Cl)cc4)c[nH]c(=O)c3c(Nc3ccc(N4CCOCC4)cc3)n2)CC1] | ESI-MS m/z 545.3 (MH+). |
| 408 | 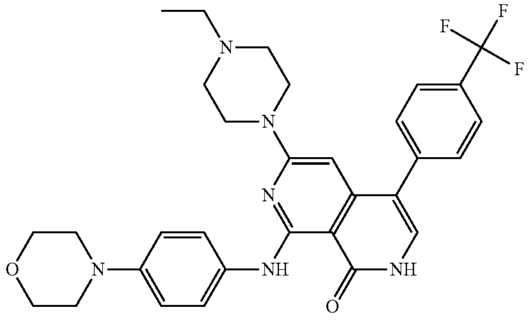 [SMILES: CCN1CCN(c2cc3c(-c4ccc(C(F)(F)F)cc4)c[nH]c(=O)c3c(Nc3ccc(N4CCOCC4)cc3)n2)CC1] | ESI-MS m/z 579.3 (MH+). |
| 409 | 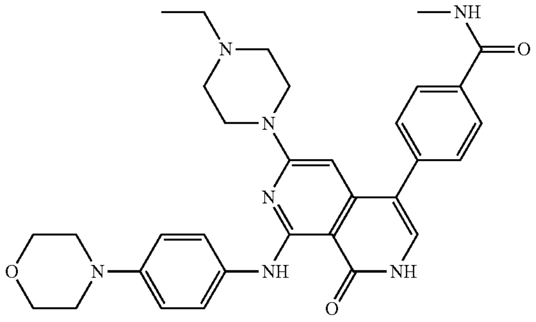 [SMILES: CCN1CCN(c2cc3c(-c4ccc(C(=O)NC)cc4)c[nH]c(=O)c3c(Nc3ccc(N4CCOCC4)cc3)n2)CC1] | ESI-MS m/z 568.3 (MH+). |
| 410 | 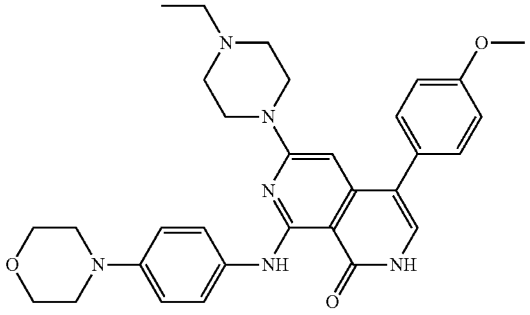 [SMILES: CCN1CCN(c2cc3c(-c4ccc(OC)cc4)c[nH]c(=O)c3c(Nc3ccc(N4CCOCC4)cc3)n2)CC1] | ESI-MS m/z 541.30 (MH+). |

TABLE 1-continued
| No | Structure | Physical Data $^1$H NMR 400 MHz (DMSO-$d_6$) and/or MS (m/z) |
|---|---|---|
| 411 | 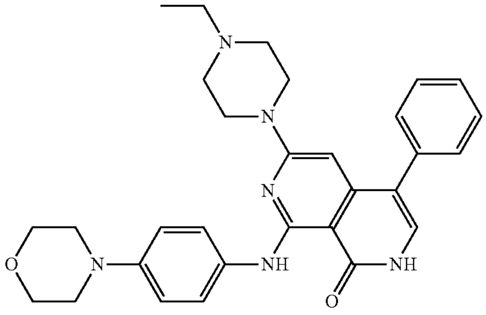 [SMILES: CCN1CCN(c2cc3c(-c4ccccc4)c[nH]c(=O)c3c(Nc3ccc(N4CCOCC4)cc3)n2)CC1] | ESI-MS m/z 511.30 (MH+). |
| 412 | 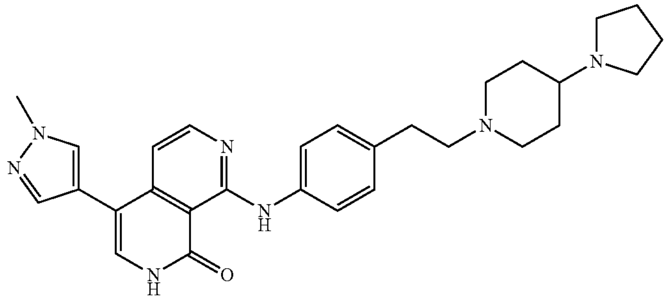 [SMILES: Cn1cc(-c2c[nH]c(=O)c3c(Nc4ccc(CCN5CCC(N6CCCC6)CC5)cc4)nccc23)cn1] | ESI-MS m/z 498.3 (MH+). |
| 413 | 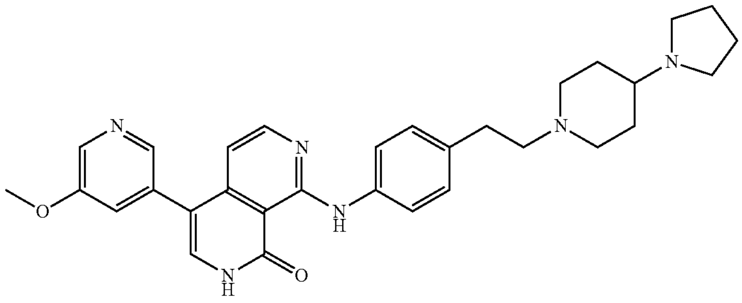 [SMILES: COc1cncc(-c2c[nH]c(=O)c3c(Nc4ccc(CCN5CCC(N6CCCC6)CC5)cc4)nccc23)c1] | ESI-MS m/z 525.3 (MH+). |
| 414 | 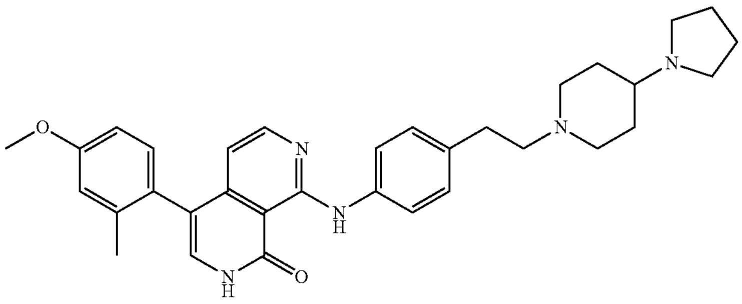 [SMILES: COc1ccc(-c2c[nH]c(=O)c3c(Nc4ccc(CCN5CCC(N6CCCC6)CC5)cc4)nccc23)c(C)c1] | ESI-MS m/z 538.3 (MH+). |
| 415 | 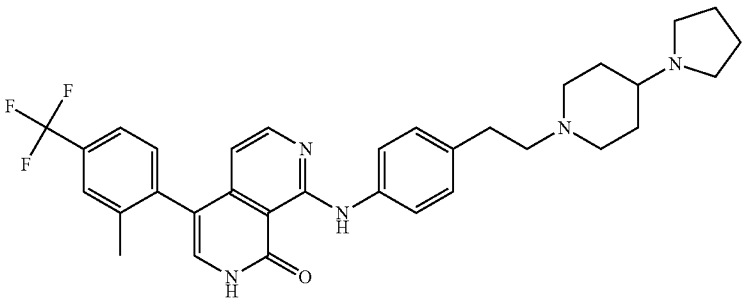 [SMILES: Cc1cc(C(F)(F)F)ccc1-c1c[nH]c(=O)c2c(Nc3ccc(CCN4CCC(N5CCCC5)CC4)cc3)nccc12] | ESI-MS m/z 576.3 (MH+). |

TABLE 1-continued
| No | Structure | Physical Data $^1$H NMR 400 MHz (DMSO-d$_6$) and/or MS (m/z) |
|---|---|---|
| 416 | 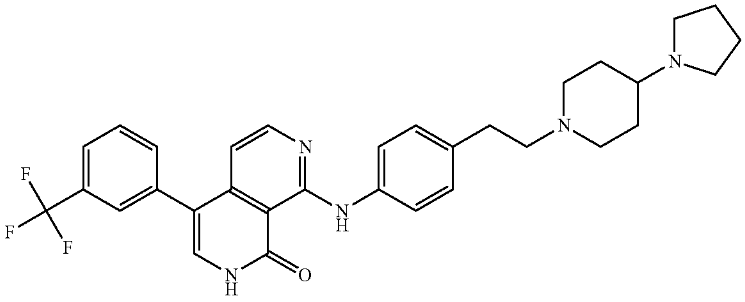 [SMILES: O=c1[nH]cc(-c2cccc(C(F)(F)F)c2)c2ccnc(Nc3ccc(CCN4CCC(N5CCCC5)CC4)cc3)c12] | ESI-MS m/z 562.3 (MH+). |
| 417 | 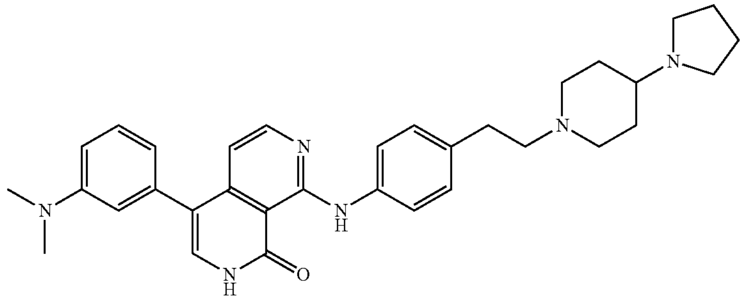 [SMILES: CN(C)c1cccc(-c2c[nH]c(=O)c3c(Nc4ccc(CCN5CCC(N6CCCC6)CC5)cc4)nccc23)c1] | ESI-MS m/z 537.3 (MH+). |
| 418 | 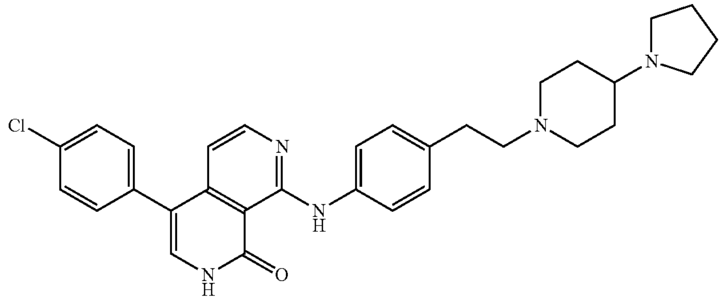 [SMILES: O=c1[nH]cc(-c2ccc(Cl)cc2)c2ccnc(Nc3ccc(CCN4CCC(N5CCCC5)CC4)cc3)c12] | ESI-MS m/z 528.3 (MH+). |
| 419 | 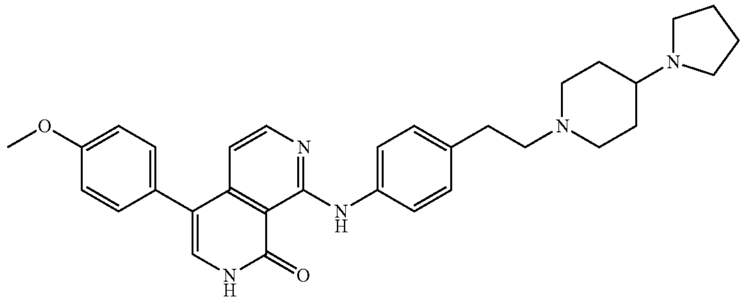 [SMILES: COc1ccc(-c2c[nH]c(=O)c3c(Nc4ccc(CCN5CCC(N6CCCC6)CC5)cc4)nccc23)cc1] | ESI-MS m/z 524.3 (MH+). |
| 420 | 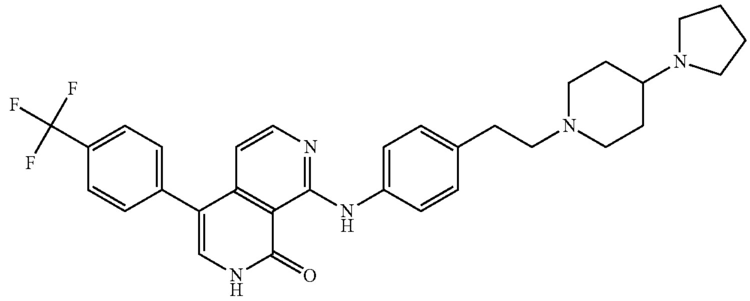 [SMILES: O=c1[nH]cc(-c2ccc(C(F)(F)F)cc2)c2ccnc(Nc3ccc(CCN4CCC(N5CCCC5)CC4)cc3)c12] | ESI-MS m/z 562.3 (MH+). |

TABLE 1-continued
| No | Structure | Physical Data $^1H$ NMR 400 MHz (DMSO-$d_6$) and/or MS (m/z) |
|---|---|---|
| 421 | 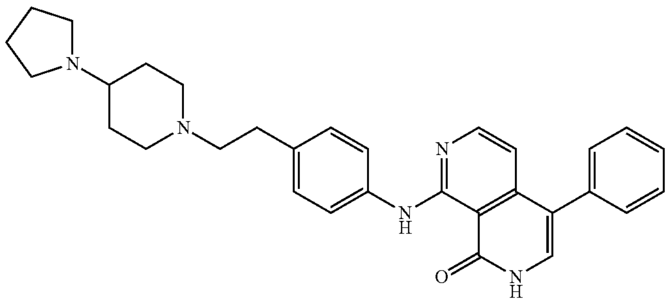 [SMILES: O=c1[nH]cc(-c2ccccc2)c2ccnc(Nc3ccc(CCN4CCC(N5CCCC5)CC4)cc3)c12] | ESI-MS m/z 494.3 (MH+). |
| 424 | 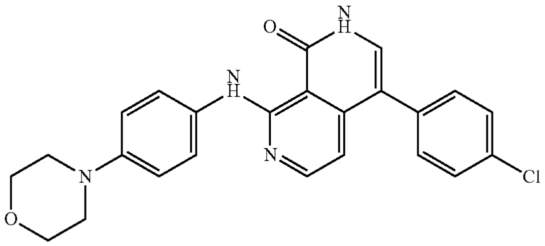 [SMILES: O=c1[nH]cc(-c2ccc(Cl)cc2)c2ccnc(Nc3ccc(N4CCOCC4)cc3)c12] | ESI-MS m/z 433.1 (MH+). |
| 423 | 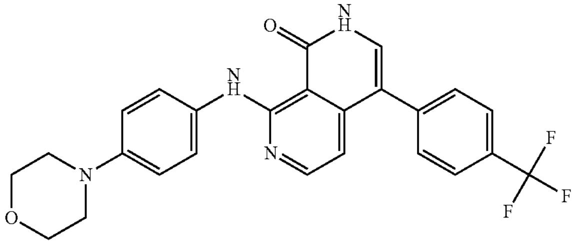 [SMILES: O=c1[nH]cc(-c2ccc(C(F)(F)F)cc2)c2ccnc(Nc3ccc(N4CCOCC4)cc3)c12] | ESI-MS m/z 467.2 (MH+). |
| 424 | 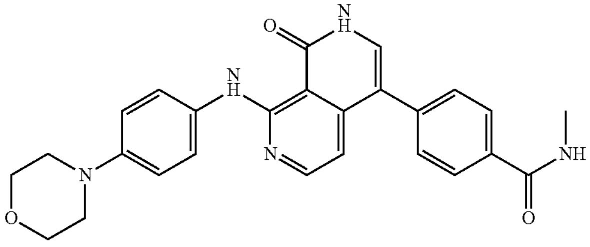 [SMILES: CNC(=O)c1ccc(-c2c[nH]c(=O)c3c(Nc4ccc(N5CCOCC5)cc4)nccc23)cc1] | ESI-MS m/z 456.2 (MH+). |
| 425 | 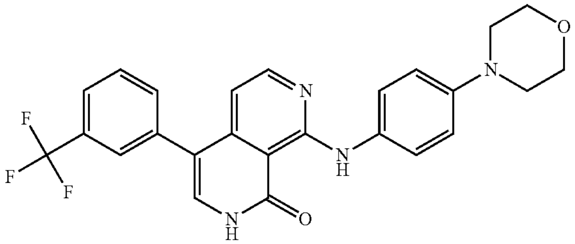 [SMILES: O=c1[nH]cc(-c2cccc(C(F)(F)F)c2)c2ccnc(Nc3ccc(N4CCOCC4)cc3)c12] | ESI-MS m/z 467.2 (MH+). |
| 426 | 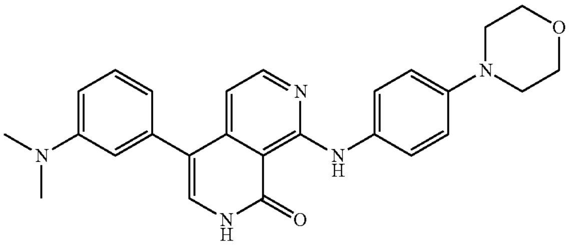 [SMILES: CN(C)c1cccc(-c2c[nH]c(=O)c3c(Nc4ccc(N5CCOCC5)cc4)nccc23)c1] | ESI-MS m/z 442.2 (MH+). |

TABLE 1-continued
| No | Structure | Physical Data $^1H$ NMR 400 MHz (DMSO-$d_6$) and/or MS (m/z) |
|---|---|---|
| 427 | 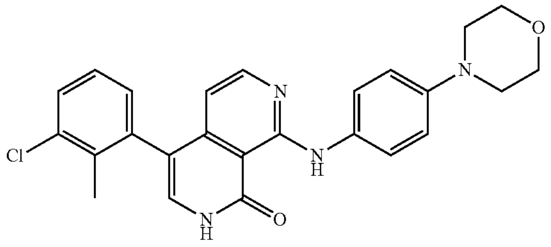 [SMILES: Cc1c(Cl)cccc1-c1c[nH]c(=O)c2c(Nc3ccc(N4CCOCC4)cc3)nccc12] | ESI-MS m/z 446.2 (MH+). |
| 428 | 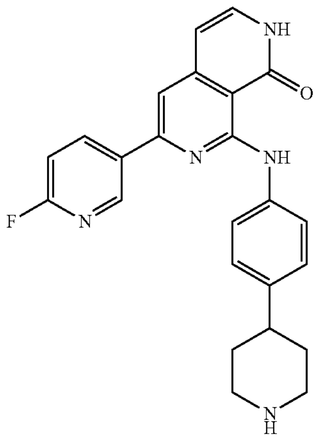 [SMILES: O=c1[nH]ccc2cc(-c3ccc(F)nc3)nc(Nc3ccc(C4CCNCC4)cc3)c12] | ESI-MS m/z 443.2 (MH+). |
| 429 | 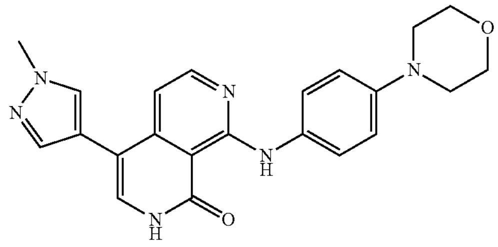 [SMILES: Cn1cc(-c2c[nH]c(=O)c3c(Nc4ccc(N5CCOCC5)cc4)nccc23)cn1] | ESI-MS m/z 403.2 (MH+). |
| 430 | 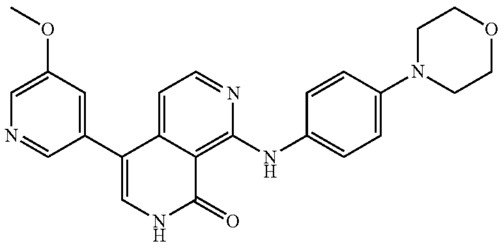 [SMILES: COc1cncc(-c2c[nH]c(=O)c3c(Nc4ccc(N5CCOCC5)cc4)nccc23)c1] | ESI-MS m/z 430.2 (MH+). |
| 431 | 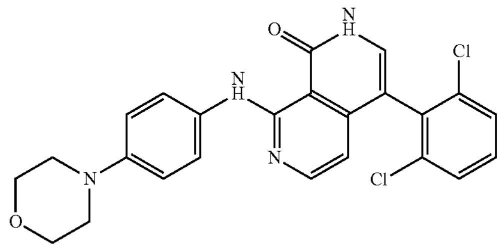 [SMILES: O=c1[nH]cc(-c2c(Cl)cccc2Cl)c2ccnc(Nc3ccc(N4CCOCC4)cc3)c12] | ESI-MS m/z 467.1 (MH+). |

TABLE 1-continued
| No | Structure | Physical Data $^1$H NMR 400 MHz (DMSO-$d_6$) and/or MS (m/z) |
|---|---|---|
| 432 | 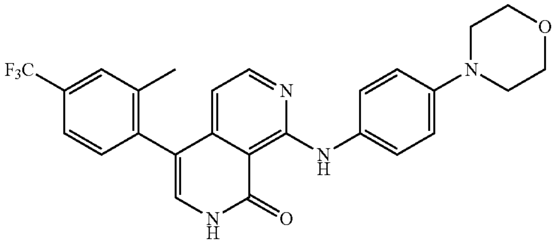 [SMILES: Cc1cc(C(F)(F)F)ccc1-c1c[nH]c(=O)c2c(Nc3ccc(N4CCOCC4)cc3)nccc12] | ESI-MS m/z 481.2 (MH+). |
| 433 | 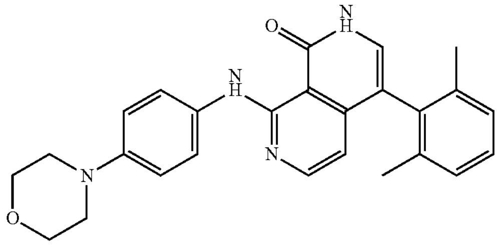 [SMILES: Cc1cccc(C)c1-c1c[nH]c(=O)c2c(Nc3ccc(N4CCOCC4)cc3)nccc12] | ESI-MS m/z 427.2 (MH+). |
| 434 | 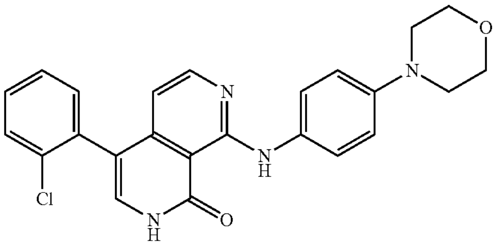 [SMILES: O=c1[nH]cc(-c2ccccc2Cl)c2ccnc(Nc3ccc(N4CCOCC4)cc3)c12] | ESI-MS m/z 433.2 (MH+). |
| 435 | 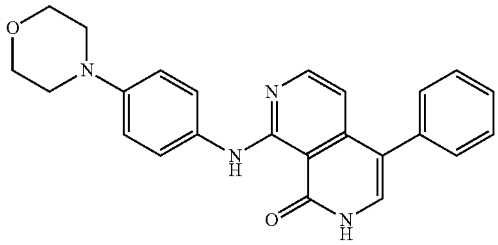 [SMILES: O=c1[nH]cc(-c2ccccc2)c2ccnc(Nc3ccc(N4CCOCC4)cc3)c12] | ESI-MS m/z 399.2 (MH+). |
| 436 | 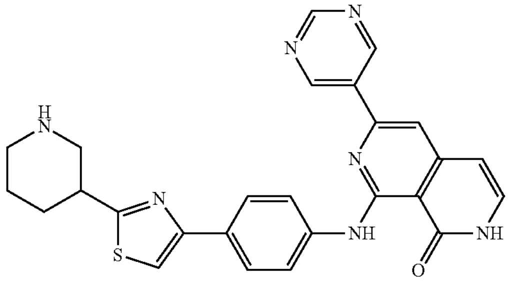 [SMILES: O=c1[nH]ccc2cc(-c3cncnc3)nc(Nc3ccc(-c4csc(C5CCCNC5)n4)cc3)c12] | ESI-MS m/z 482.2 (MH+). |

TABLE 1-continued
| No | Structure | Physical Data $^1H$ NMR 400 MHz (DMSO-$d_6$) and/or MS (m/z) |
|---|---|---|
| 437 | 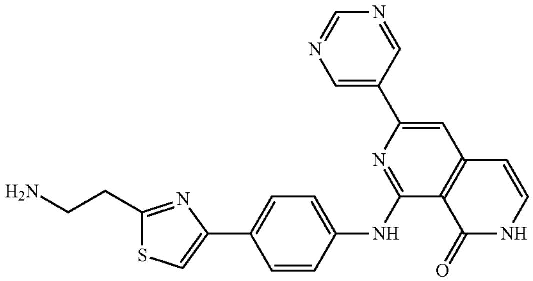 [SMILES: NCCc1nc(-c2ccc(Nc3nc(-c4cncnc4)cc4cc[nH]c(=O)c34)cc2)cs1] | ESI-MS m/z 442.1 (MH+). |
| 438 | 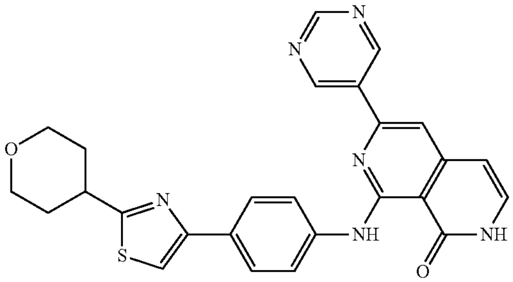 [SMILES: O=c1[nH]ccc2cc(-c3cncnc3)nc(Nc3ccc(-c4csc(C5CCOCC5)n4)cc3)c12] | ESI-MS m/z 483.2 (MH+). |
| 439 | 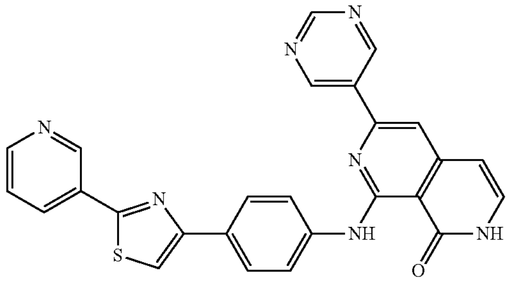 [SMILES: O=c1[nH]ccc2cc(-c3cncnc3)nc(Nc3ccc(-c4csc(-c5cccnc5)n4)cc3)c12] | ESI-MS m/z 476.1 (MH+). |
| 440 | 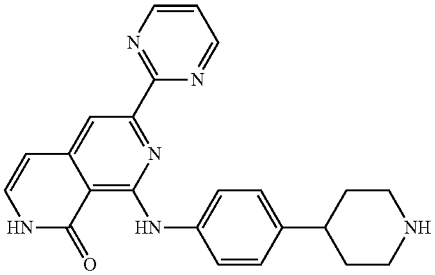 [SMILES: O=c1[nH]ccc2cc(-c3ncccn3)nc(Nc3ccc(C4CCNCC4)cc3)c12] | ESI-MS m/z 399.2 (MH+). |
| 441 | 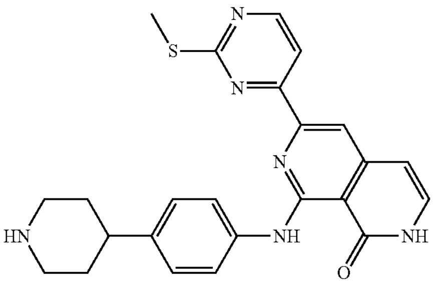 [SMILES: CSc1nccc(-c2cc3cc[nH]c(=O)c3c(Nc3ccc(C4CCNCC4)cc3)n2)n1] | ESI-MS m/z 445.2 (MH+). |

TABLE 1-continued
| No | Structure | Physical Data $^1$H NMR 400 MHz (DMSO-$d_6$) and/or MS (m/z) |
|---|---|---|
| 442 | 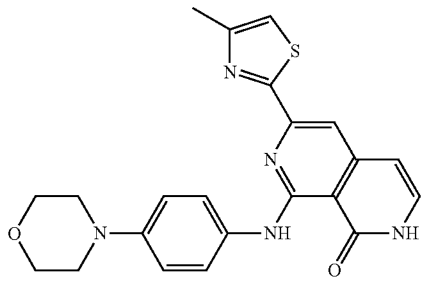 [SMILES: Cc1csc(-c2cc3cc[nH]c(=O)c3c(Nc3ccc(N4CCOCC4)cc3)n2)n1] | ESI-MS m/z 420.1 (MH+). |
| 443 | 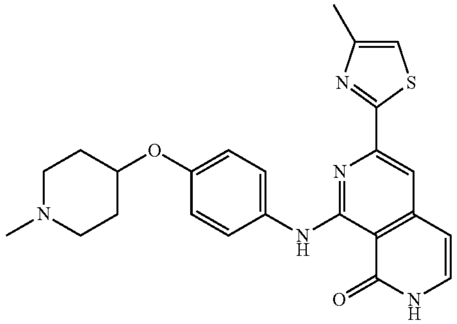 [SMILES: Cc1csc(-c2cc3cc[nH]c(=O)c3c(Nc3ccc(OC4CCN(C)CC4)cc3)n2)n1] | ESI-MS m/z 447.2 (MH+). |
| 444 | 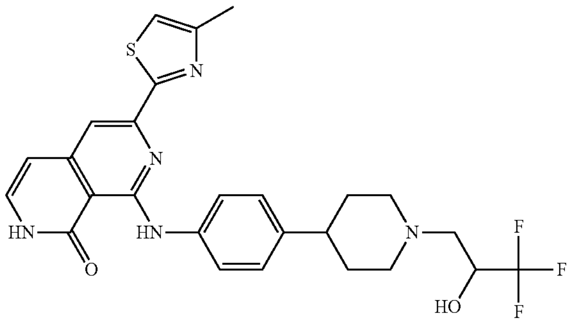 [SMILES: Cc1csc(-c2cc3cc[nH]c(=O)c3c(Nc3ccc(C4CCN(CC(O)C(F)(F)F)CC4)cc3)n2)n1] | ESI-MS m/z 530.2 (MH+). |
| 445 | 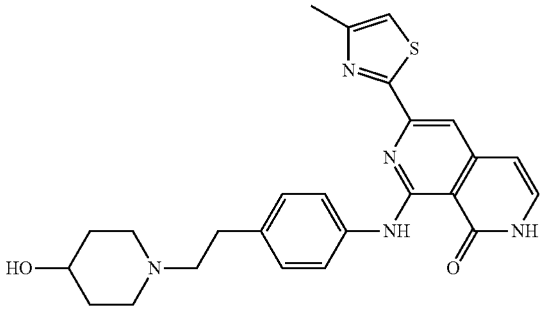 [SMILES: Cc1csc(-c2cc3cc[nH]c(=O)c3c(Nc3ccc(CCN4CCC(O)CC4)cc3)n2)n1] | ESI-MS m/z 462.2 (MH+). |
| 446 | 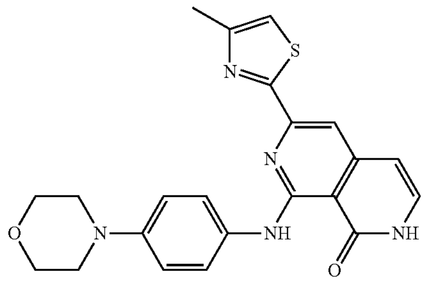 [SMILES: Cc1csc(-c2cc3cc[nH]c(=O)c3c(Nc3ccc(N4CCOCC4)cc3)n2)n1] | ESI-MS m/z 420.1 (MH+). |

TABLE 1-continued
| No | Structure | Physical Data $^1H$ NMR 400 MHz ($DMSO-d_6$) and/or MS (m/z) |
|---|---|---|
| 447 | 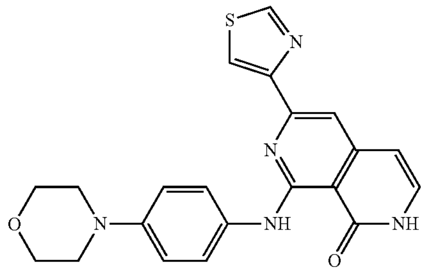 [SMILES: O=c1[nH]ccc2cc(-c3cscn3)nc(Nc3ccc(N4CCOCC4)cc3)c12] | ESI-MS m/z 406.2 (MH+). |
| 448 | 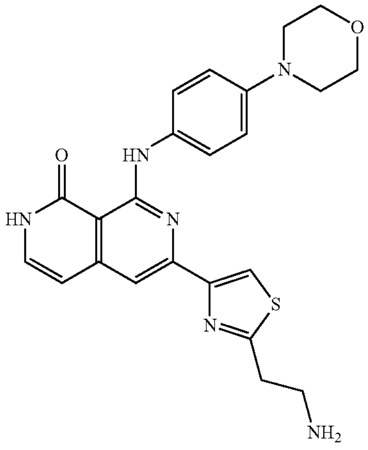 [SMILES: NCCc1nc(-c2cc3cc[nH]c(=O)c3c(Nc3ccc(N4CCOCC4)cc3)n2)cs1] | ESI-MS m/z 449.2 (MH+). |
| 449 | 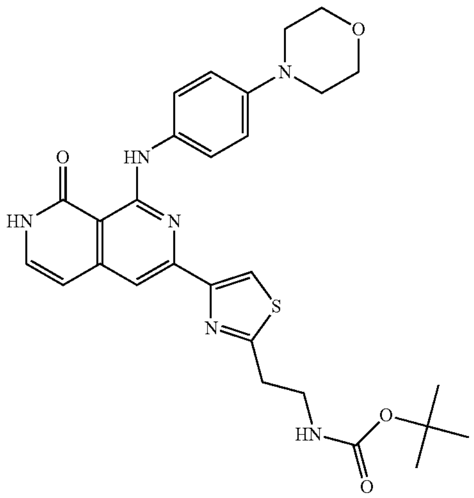 [SMILES: CC(C)(C)OC(=O)NCCc1nc(-c2cc3cc[nH]c(=O)c3c(Nc3ccc(N4CCOCC4)cc3)n2)cs1] | ESI-MS m/z 549.2 (MH+). |

TABLE 1-continued
| No | Structure | Physical Data $^1H$ NMR 400 MHz ($DMSO-d_6$) and/or MS (m/z) |
|---|---|---|
| 450 | 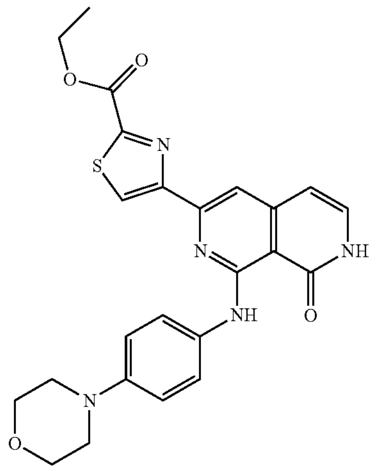 [SMILES: CCOC(=O)c1nc(-c2cc3cc[nH]c(=O)c3c(Nc3ccc(N4CCOCC4)cc3)n2)cs1] | ESI-MS m/z 478.1 (MH+). |
| 451 | 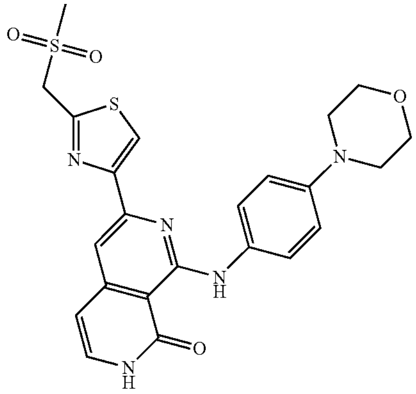 [SMILES: CS(=O)(=O)Cc1nc(-c2cc3cc[nH]c(=O)c3c(Nc3ccc(N4CCOCC4)cc3)n2)cs1] | ESI-MS m/z 498.1 (MH+). |
| 452 | 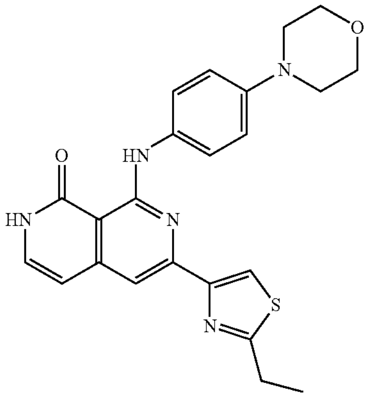 [SMILES: CCc1nc(-c2cc3cc[nH]c(=O)c3c(Nc3ccc(N4CCOCC4)cc3)n2)cs1] | ESI-MS m/z 434.2 (MH+). |

TABLE 1-continued
| No | Structure | Physical Data $^1$H NMR 400 MHz (DMSO-$d_6$) and/or MS (m/z) |
|---|---|---|
| 453 | 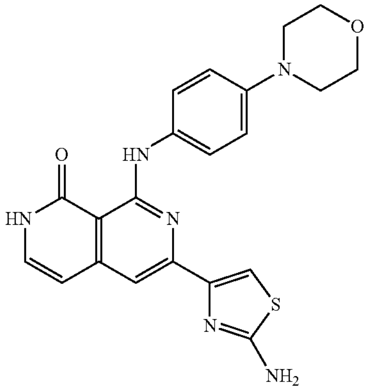 [SMILES: Nc1nc(-c2cc3cc[nH]c(=O)c3c(Nc3ccc(N4CCOCC4)cc3)n2)cs1] | ESI-MS m/z 421.1 (MH+). |
| 454 | 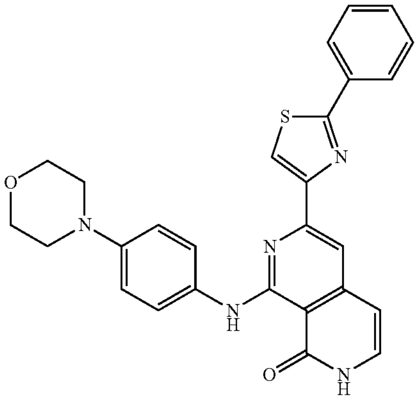 [SMILES: O=c1[nH]ccc2cc(-c3csc(-c4ccccc4)n3)nc(Nc3ccc(N4CCOCC4)cc3)c12] | ESI-MS m/z 482.2 (MH+). |
| 455 | 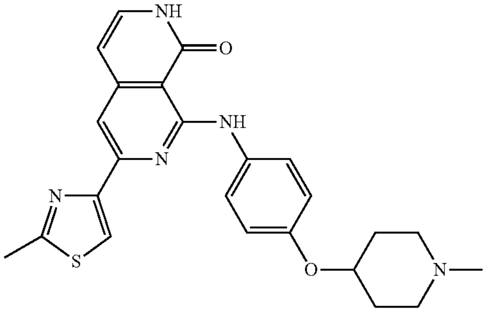 | ESI-MS m/z 448.2 (MH+). |
| 456 | 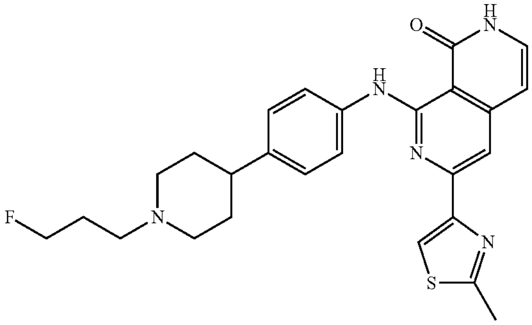 [SMILES: Cc1nc(-c2cc3cc[nH]c(=O)c3c(Nc3ccc(C4CCN(CCCF)CC4)cc3)n2)cs1] | ESI-MS m/z 478.2 (MH+). |

TABLE 1-continued
| No | Structure | Physical Data $^1H$ NMR 400 MHz (DMSO-$d_6$) and/or MS (m/z) |
|---|---|---|
| 457 | 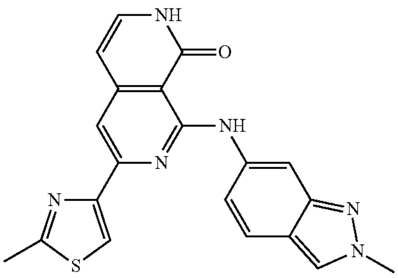 | ESI-MS m/z 389.1 (MH+). |
| 458 | 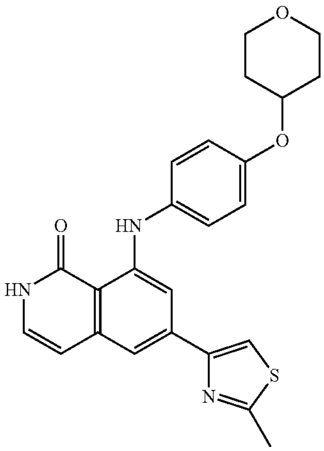 [SMILES: Cc1nc(-c2cc(Nc3ccc(OC4CCOCC4)cc3)c3c(=O)[nH]ccc3c2)cs1] | ESI-MS m/z 435.1 (MH+). |
| 459 | 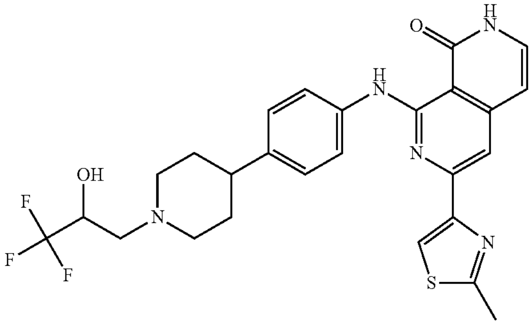 [SMILES: Cc1nc(-c2cc3cc[nH]c(=O)c3c(Nc3ccc(C4CCN(CC(O)C(F)(F)F)CC4)cc3)n2)cs1] | ESI-MS m/z 530.2 (MH+). |
| 460 | 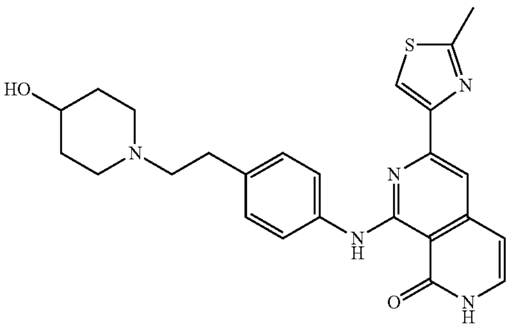 [SMILES: Cc1nc(-c2cc3cc[nH]c(=O)c3c(Nc3ccc(CCN4CCC(O)CC4)cc3)n2)cs1] | ESI-MS m/z 462.2 (MH+). |

TABLE 1-continued
| No | Structure | Physical Data $^1H$ NMR 400 MHz (DMSO-$d_6$) and/or MS (m/z) |
|---|---|---|
| 461 | 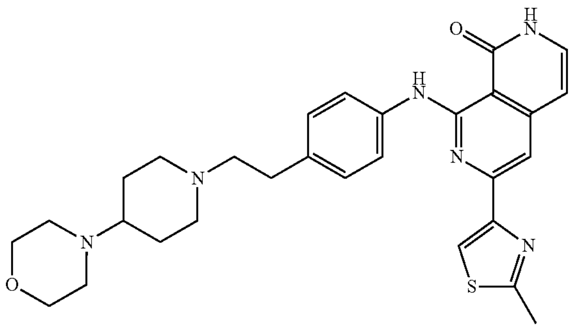 [SMILES: Cc1nc(-c2cc3cc[nH]c(=O)c3c(Nc3ccc(CCN4CCC(N5CCOCC5)CC4)cc3)n2)cs1] | ESI-MS m/z 531.3 (MH+). |
| 462 | 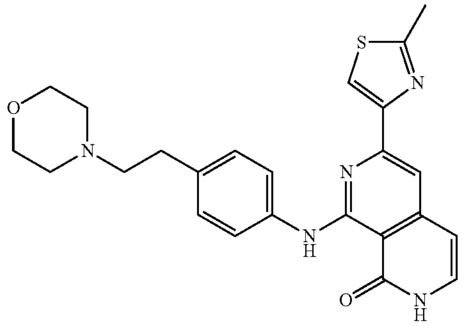 [SMILES: Cc1nc(-c2cc3cc[nH]c(=O)c3c(Nc3ccc(CCN4CCOCC4)cc3)n2)cs1] | ESI-MS m/z 448.2 (MH+). |
| 463 | 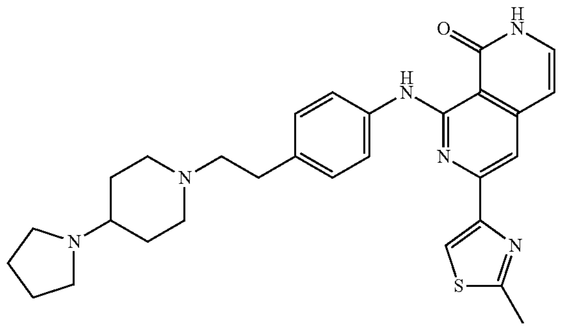 [SMILES: Cc1nc(-c2cc3cc[nH]c(=O)c3c(Nc3ccc(CCN4CCC(N5CCCC5)CC4)cc3)n2)cs1] | ESI-MS m/z 515.3 (MH+). |
| 464 | 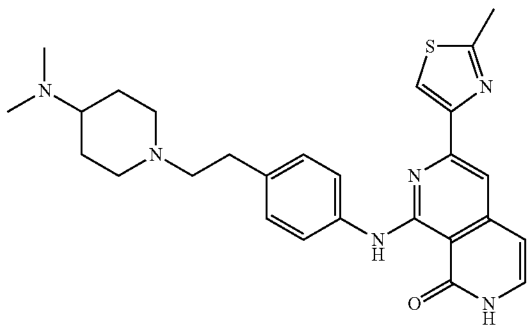 [SMILES: Cc1nc(-c2cc3cc[nH]c(=O)c3c(Nc3ccc(CCN4CCC(N(C)C)CC4)cc3)n2)cs1] | ESI-MS m/z 489.2 (MH+). |

TABLE 1-continued
| No | Structure | Physical Data $^1$H NMR 400 MHz (DMSO-d$_6$) and/or MS (m/z) |
|---|---|---|
| 465 | 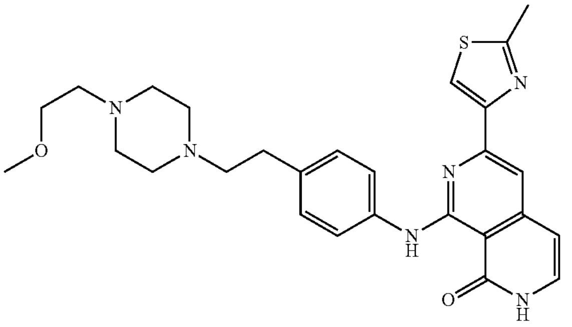 [SMILES: COCCN1CCN(CCc2ccc(Nc3nc(-c4csc(C)n4)cc4cc[nH]c(=O)c34)cc2)CC1] | ESI-MS m/z 505.2 (MH+). |
| 466 | 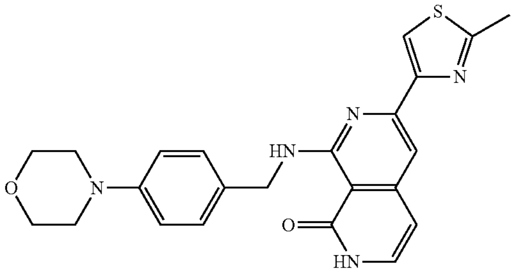 [SMILES: Cc1nc(-c2cc3cc[nH]c(=O)c3c(NCc3ccc(N4CCOCC4)cc3)n2)cs1] | ESI-MS m/z 434.2 (MH+). |
| 467 | 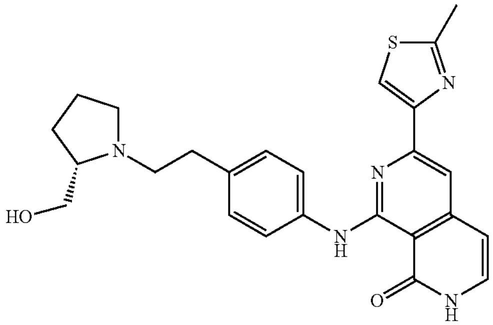 [SMILES: Cc1nc(-c2cc3cc[nH]c(=O)c3c(Nc3ccc(CCN4CCC[C@H]4CO)cc3)n2)cs1] | ESI-MS m/z 462.2 (MH+). |
| 468 | 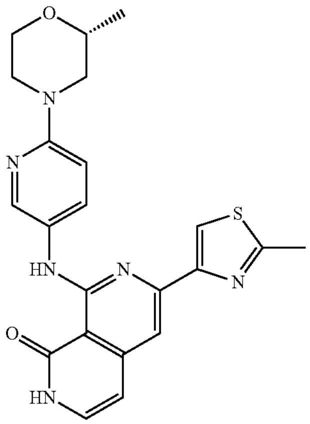 [SMILES: Cc1nc(-c2cc3cc[nH]c(=O)c3c(Nc3ccc(N4CCO[C@H](C)C4)nc3)n2)cs1] | ESI-MS m/z 435.2 (MH+). |

TABLE 1-continued
| No | Structure | Physical Data $^1$H NMR 400 MHz (DMSO-$d_6$) and/or MS (m/z) |
|---|---|---|
| 469 | 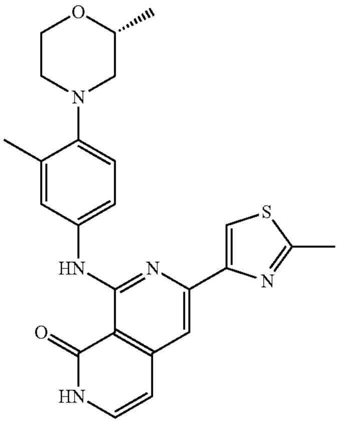 | ESI-MS m/z 448.2 (MH+). |
| 470 | 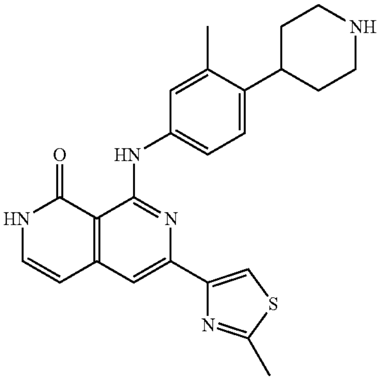 [SMILES: Cc1nc(-c2cc3cc[nH]c(=O)c3c(Nc3ccc(C4CCNCC4)c(C)c3)n2)cs1] | ESI-MS m/z 432.2 (MH+). |
| 471 | 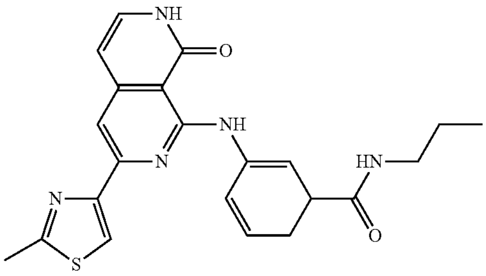 [SMILES: CCCNC(=O)C1C=C(Nc2nc(-c3csc(C)n3)cc3cc[nH]c(=O)c23)C=CC1] | ESI-MS m/z 420.2 (MH+). |
| 472 | 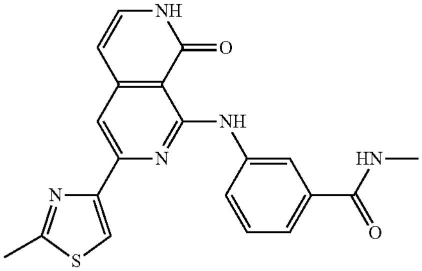 | ESI-MS m/z 392.1 (MH+). |

TABLE 1-continued
| No | Structure | Physical Data $^1$H NMR 400 MHz (DMSO-$d_6$) and/or MS (m/z) |
|---|---|---|
| 473 | 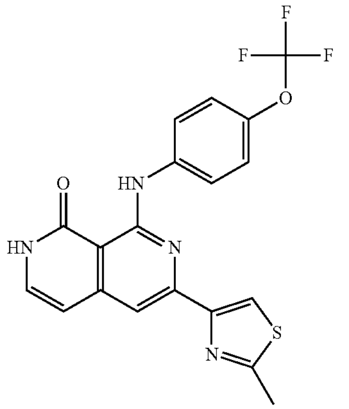 [SMILES: Cc1nc(-c2cc3cc[nH]c(=O)c3c(Nc3ccc(OC(F)(F)F)cc3)n2)cs1] | ESI-MS m/z 419.1 (MH+). |
| 474 | 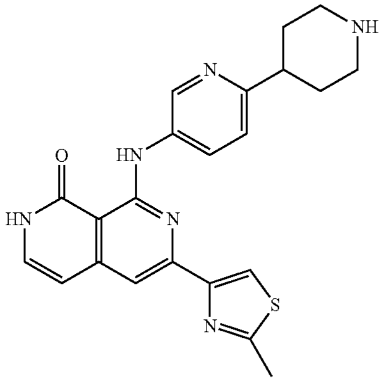 [SMILES: Cc1nc(-c2cc3cc[nH]c(=O)c3c(Nc3ccc(C4CCNCC4)nc3)n2)cs1] | ESI-MS m/z 419.1 (MH+). |
| 475 | 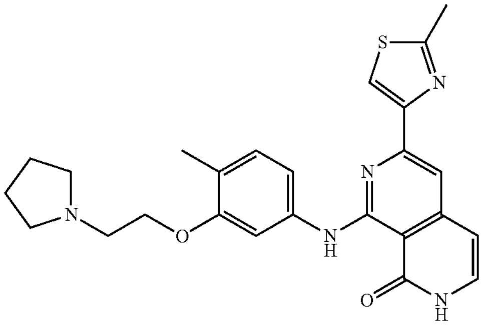 [SMILES: Cc1nc(-c2cc3cc[nH]c(=O)c3c(Nc3ccc(C)c(OCCN4CCCC4)c3)n2)cs1] | ESI-MS m/z 462.2 (MH+). |
| 476 | 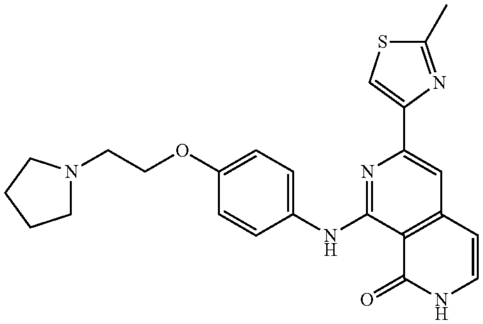 [SMILES: Cc1nc(-c2cc3cc[nH]c(=O)c3c(Nc3ccc(OCCN4CCCC4)cc3)n2)cs1] | ESI-MS m/z 448.2 (MH+). |

TABLE 1-continued
| No | Structure | Physical Data $^1H$ NMR 400 MHz (DMSO-$d_6$) and/or MS (m/z) |
|---|---|---|
| 478 | 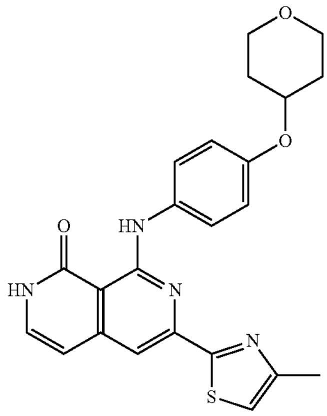 | ESI-MS m/z 462.2 (MH+). |
| 479 | 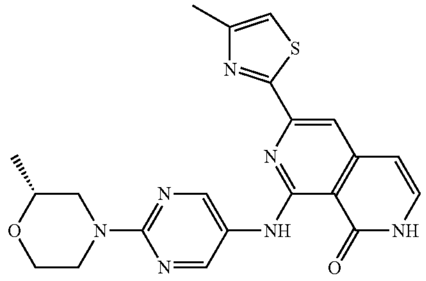 [SMILES: Cc1csc(-c2cc3cc[nH]c(=O)c3c(Nc3cnc(N4CCO[C@H](C)C4)nc3)n2)n1] | ESI-MS m/z 435.2 (MH+). |
| 480 | 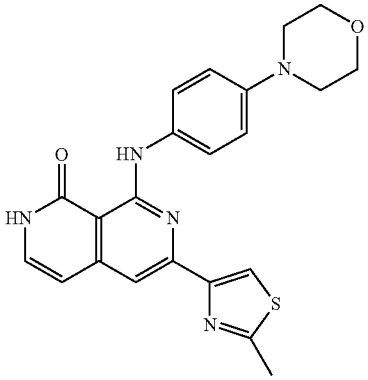 [SMILES: Cc1nc(-c2cc3cc[nH]c(=O)c3c(Nc3ccc(N4CCOCC4)cc3)n2)cs1] | ESI-MS m/z 420.1 (MH+). |
| 481 | 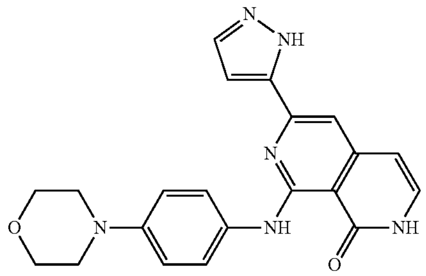 [SMILES: O=c1[nH]ccc2cc(-c3ccn[nH]3)nc(Nc3ccc(N4CCOCC4)cc3)c12] | ESI-MS m/z 389.2 (MH+). |

TABLE 1-continued
| No | Structure | Physical Data $^1H$ NMR 400 MHz (DMSO-$d_6$) and/or MS (m/z) |
|---|---|---|
| 482 | 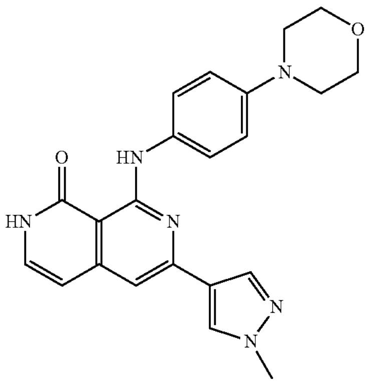 [SMILES: Cn1cc(-c2cc3cc[nH]c(=O)c3c(Nc3ccc(N4CCOCC4)cc3)n2)cn1] | ESI-MS m/z 403.2 (MH+). |
| 483 | 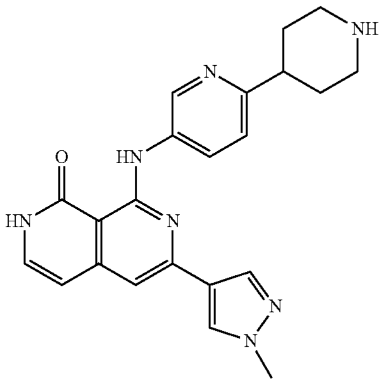 [SMILES: Cn1cc(-c2cc3cc[nH]c(=O)c3c(Nc3ccc(C4CCNCC4)nc3)n2)cn1] | ESI-MS m/z 402.2 (MH+). |
| 484 | 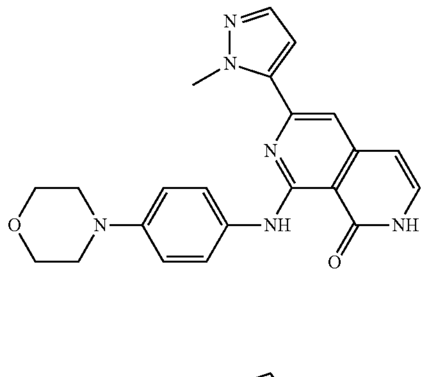 | ESI-MS m/z 403.2 (MH+). |
| 485 | 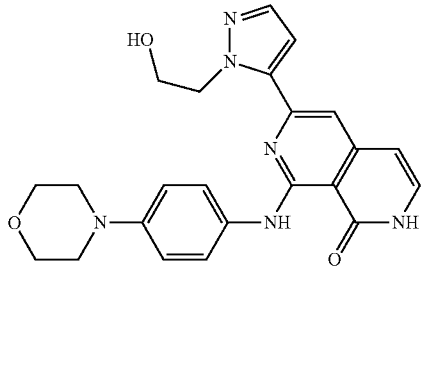 [SMILES: O=c1[nH]ccc2cc(-c3ccnn3CCO)nc(Nc3ccc(N4CCOCC4)cc3)c12] | ESI-MS m/z 433.2 (MH+). |

TABLE 1-continued
| No | Structure | Physical Data $^1H$ NMR 400 MHz (DMSO-$d_6$) and/or MS (m/z) |
|---|---|---|
| 486 | 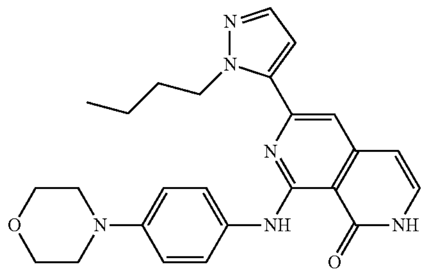 [SMILES: CCCCn1nccc1-c1cc2cc[nH]c(=O)c2c(Nc2ccc(N3CCOCC3)cc2)n1] | ESI-MS m/z 445.2 (MH+). |
| 487 | 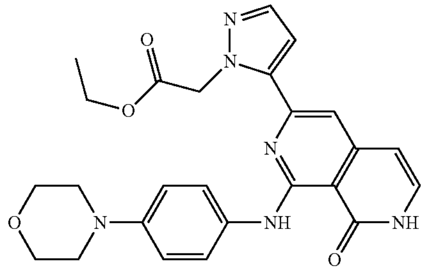 [SMILES: CCOC(=O)Cn1nccc1-c1cc2cc[nH]c(=O)c2c(Nc2ccc(N3CCOCC3)cc2)n1] | ESI-MS m/z 475.2 (MH+). |
| 488 | 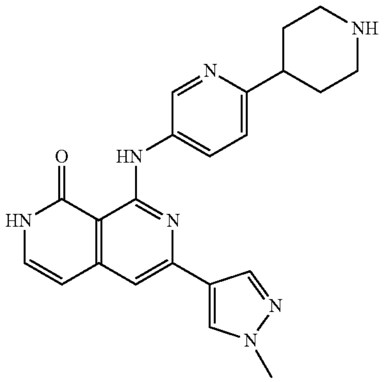 [SMILES: Cn1cc(-c2cc3cc[nH]c(=O)c3c(Nc3ccc(C4CCNCC4)nc3)n2)cn1] | ESI-MS m/z 402.2 (MH+). |
| 489 | 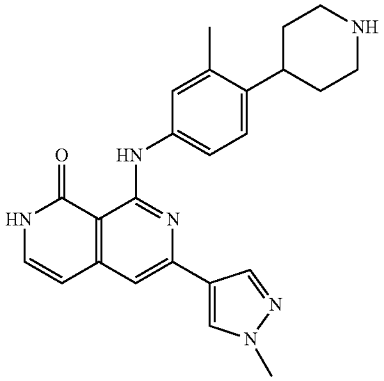 [SMILES: Cc1cc(Nc2nc(-c3cnn(C)c3)cc3cc[nH]c(=O)c23)ccc1C1CCNCC1] | ESI-MS m/z 415.2 (MH+). |

TABLE 1-continued
| No | Structure | Physical Data $^1H$ NMR 400 MHz ($DMSO-d_6$) and/or MS (m/z) |
|---|---|---|
| 490 | 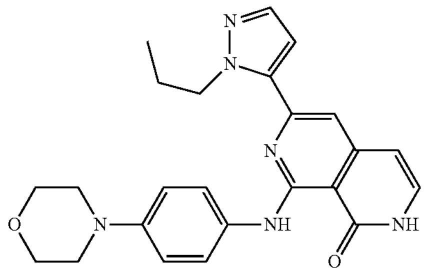 [SMILES: CCCn1nccc1-c1cc2cc[nH]c(=O)c2c(Nc2ccc(N3CCOCC3)cc2)n1] | ESI-MS m/z 431.2 (MH+). |
| 491 | 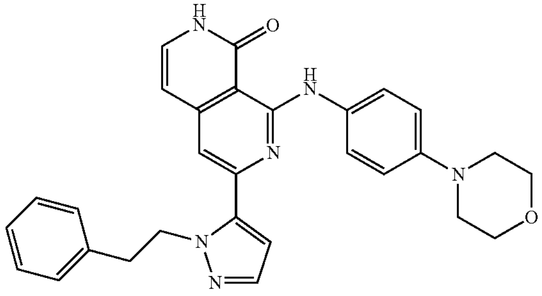 [SMILES: O=c1[nH]ccc2cc(-c3ccnn3CCc3ccccc3)nc(Nc3ccc(N4CCOCC4)cc3)c12] | ESI-MS m/z 493.2 (MH+). |
| 492 | 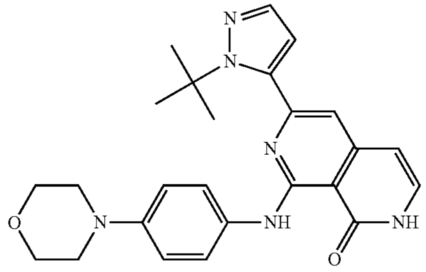 [SMILES: CC(C)(C)n1nccc1-c1cc2cc[nH]c(=O)c2c(Nc2ccc(N3CCOCC3)cc2)n1] | ESI-MS m/z 445.2 (MH+). |
| 493 | 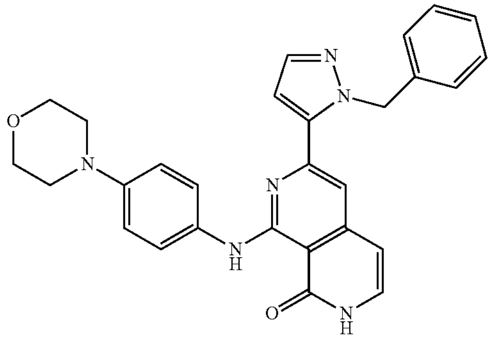 [SMILES: O=c1[nH]ccc2cc(-c3ccnn3Cc3ccccc3)nc(Nc3ccc(N4CCOCC4)cc3)c12] | ESI-MS m/z 479.2 (MH+). |
| 494 | 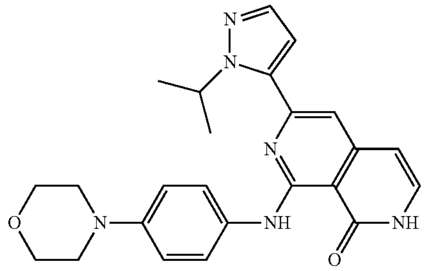 [SMILES: CC(C)n1nccc1-c1cc2cc[nH]c(=O)c2c(Nc2ccc(N3CCOCC3)cc2)n1] | ESI-MS m/z 431.2 (MH+). |

TABLE 1-continued
| No | Structure | Physical Data $^1$H NMR 400 MHz (DMSO-$d_6$) and/or MS (m/z) |
|---|---|---|
| 495 | 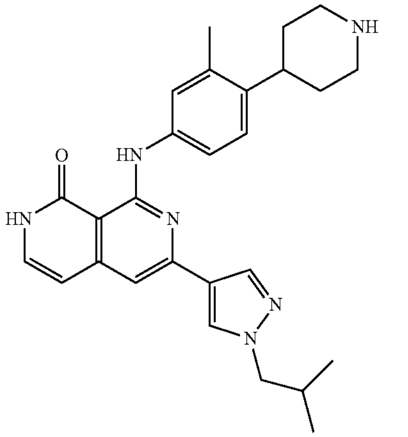 [SMILES: Cc1cc(Nc2nc(-c3cnn(CC(C)C)c3)cc3cc[nH]c(=O)c23)ccc1C1CCNCC1] | ESI-MS m/z 457.3 (MH+). |
| 496 | 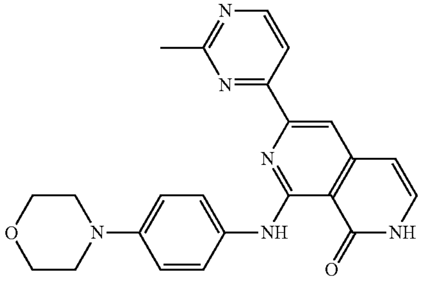 [SMILES: Cc1nccc(-c2cc3cc[nH]c(=O)c3c(Nc3ccc(N4CCOCC4)cc3)n2)n1] | ESI-MS m/z 415.2 (MH+). |
| 497 | 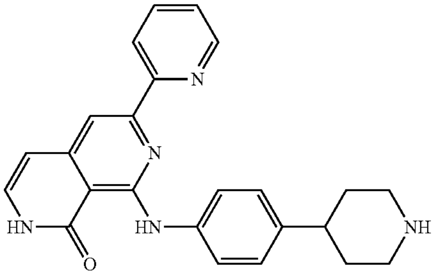 | ESI-MS m/z 398.2 (MH+). |
| 498 | 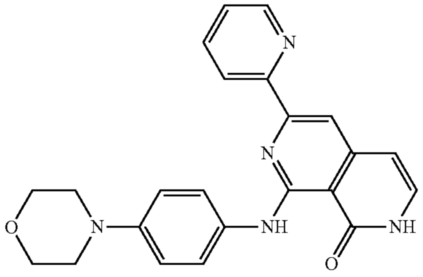 [SMILES: O=c1[nH]ccc2cc(-c3ccccn3)nc(Nc3ccc(N4CCOCC4)cc3)c12] | ESI-MS m/z 400.2 (MH+). |
| 499 | 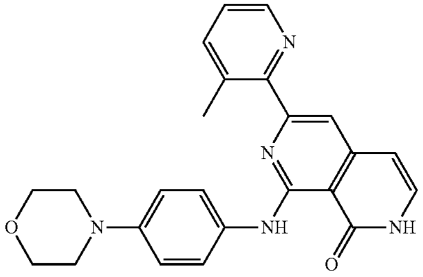 [SMILES: Cc1cccnc1-c1cc2cc[nH]c(=O)c2c(Nc2ccc(N3CCOCC3)cc2)n1] | ESI-MS m/z 412.2 (MH+). |

TABLE 1-continued
| No | Structure | Physical Data $^1$H NMR 400 MHz (DMSO-$d_6$) and/or MS (m/z) |
|---|---|---|
| 500 | 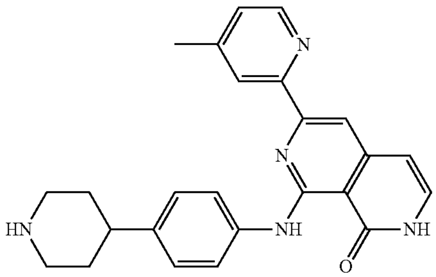 [SMILES: Cc1ccnc(-c2cc3cc[nH]c(=O)c3c(Nc3ccc(C4CCNCC4)cc3)n2)c1] | ESI-MS m/z 412.2 (MH+). |
| 501 | 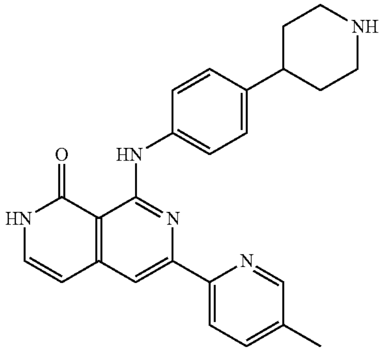 [SMILES: Cc1ccc(-c2cc3cc[nH]c(=O)c3c(Nc3ccc(C4CCNCC4)cc3)n2)nc1] | ESI-MS m/z 412.2 (MH+). |
| 502 | 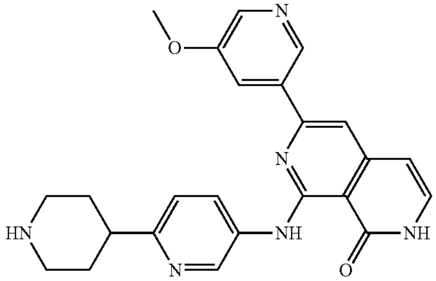 [SMILES: COc1cncc(-c2cc3cc[nH]c(=O)c3c(Nc3ccc(C4CCNCC4)nc3)n2)c1] | ESI-MS m/z 429.2 (MH+). |
| 503 | 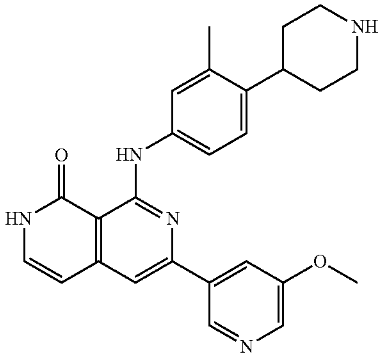 [SMILES: COc1cncc(-c2cc3cc[nH]c(=O)c3c(Nc3ccc(C4CCNCC4)c(C)c3)n2)c1] | ESI-MS m/z 442.2 (MH+). |
| 504 | 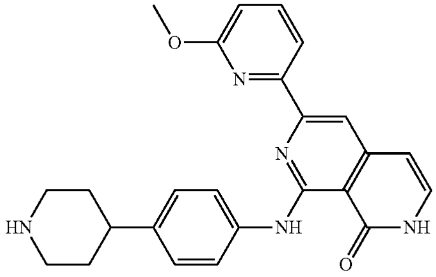 [SMILES: COc1cccc(-c2cc3cc[nH]c(=O)c3c(Nc3ccc(C4CCNCC4)cc3)n2)n1] | ESI-MS m/z 429.2 (MH+). |

TABLE 1-continued
| No | Structure | Physical Data $^1H$ NMR 400 MHz (DMSO-$d_6$) and/or MS (m/z) |
|---|---|---|
| 505 | 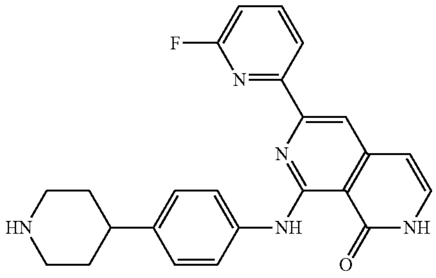 [SMILES: O=c1[nH]ccc2cc(-c3cccc(F)n3)nc(Nc3ccc(C4CCNCC4)cc3)c12] | ESI-MS m/z 415.2 (MH+). |
| 506 | 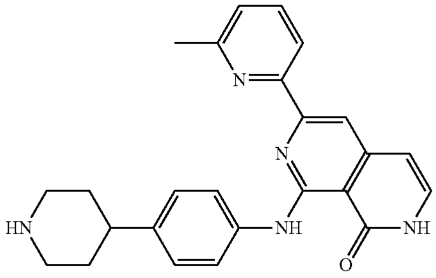 | ESI-MS m/z 412.2 (MH+). |
| 507 | 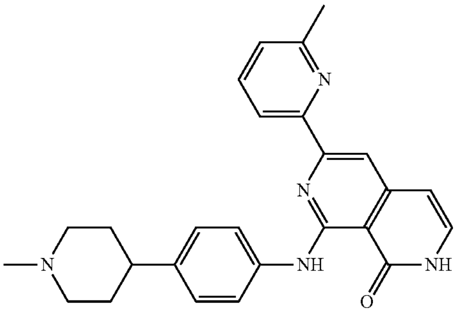 [SMILES: Cc1cccc(-c2cc3cc[nH]c(=O)c3c(Nc3ccc(C4CCN(C)CC4)cc3)n2)n1] | ESI-MS m/z 426.2 (MH+). |
| 508 | 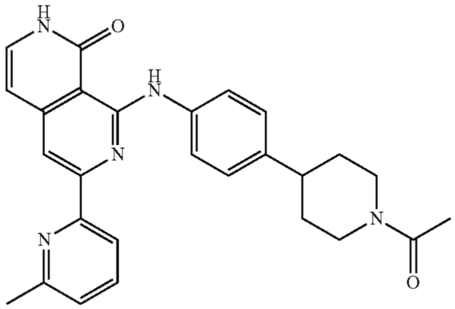 [SMILES: CC(=O)N1CCC(c2ccc(Nc3nc(-c4cccc(C)n4)cc4cc[nH]c(=O)c34)cc2)CC1] | ESI-MS m/z 454.2 (MH+). |
| 509 | 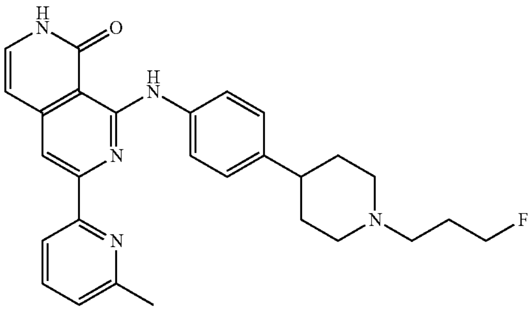 [SMILES: Cc1cccc(-c2cc3cc[nH]c(=O)c3c(Nc3ccc(C4CCN(CCCF)CC4)cc3)n2)n1] | ESI-MS m/z 472.2 (MH+). |

TABLE 1-continued
| No | Structure | Physical Data $^1H$ NMR 400 MHz (DMSO-$d_6$) and/or MS (m/z) |
|---|---|---|
| 510 | 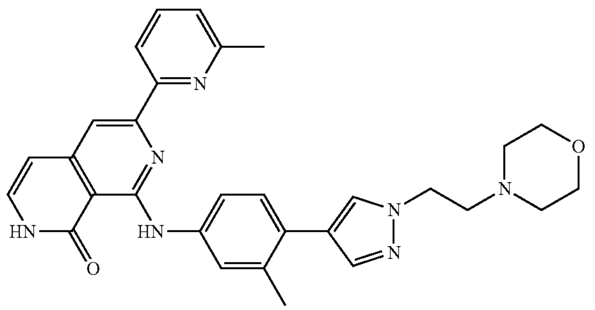 [SMILES: Cc1cccc(-c2cc3cc[nH]c(=O)c3c(Nc3ccc(-c4cnn(CCN5CCOCC5)c4)c(C)c3)n2)n1] | ESI-MS m/z 522.3 (MH+). |
| 511 | 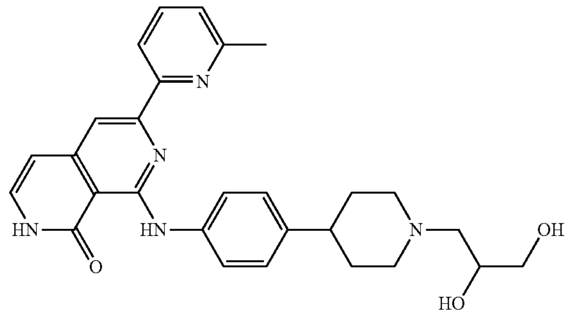 [SMILES: Cc1cccc(-c2cc3cc[nH]c(=O)c3c(Nc3ccc(C4CCN(CC(O)CO)CC4)cc3)n2)n1] | ESI-MS m/z 486.2 (MH+). |
| 512 | 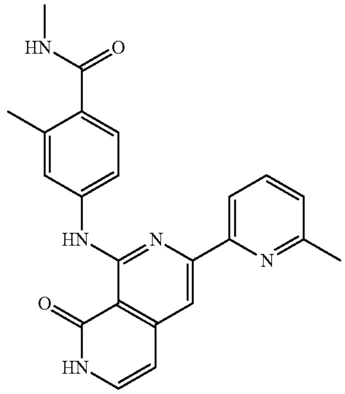 | ESI-MS m/z 400.2 (MH+). |
| 513 | 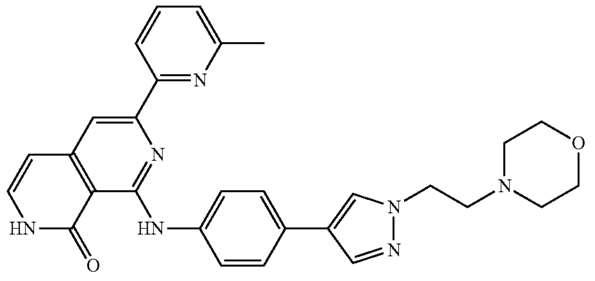 [SMILES: Cc1cccc(-c2cc3cc[nH]c(=O)c3c(Nc3ccc(-c4cnn(CCN5CCOCC5)c4)cc3)n2)n1] | ESI-MS m/z 508.2 (MH+). |

TABLE 1-continued
| No | Structure | Physical Data $^1H$ NMR 400 MHz (DMSO-$d_6$) and/or MS (m/z) |
|---|---|---|
| 514 | 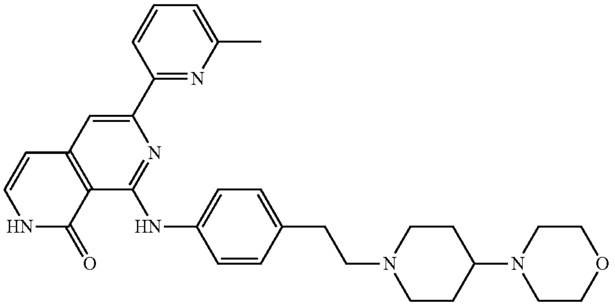 [SMILES: Cc1cccc(-c2cc3cc[nH]c(=O)c3c(Nc3ccc(CCN4CCC(N5CCOCC5)CC4)cc3)n2)n1] | ESI-MS m/z 525.6 (MH+). |
| 515 | 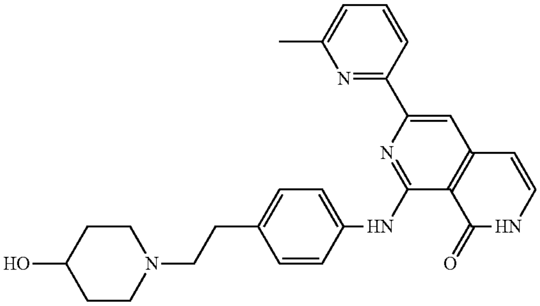 [SMILES: Cc1cccc(-c2cc3cc[nH]c(=O)c3c(Nc3ccc(CCN4CCC(O)CC4)cc3)n2)n1] | ESI-MS m/z 456.2 (MH+). |
| 516 | 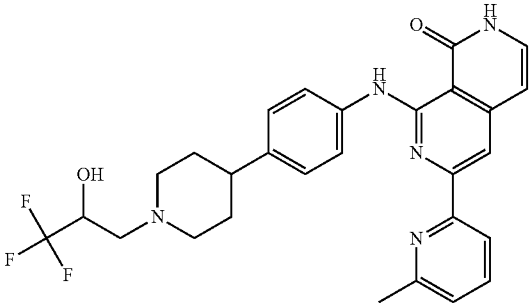 [SMILES: Cc1cccc(-c2cc3cc[nH]c(=O)c3c(Nc3ccc(C4CCN(CC(O)C(F)(F)F)CC4)cc3)n2)n1] | ESI-MS m/z 524.2 (MH+). |
| 517 | 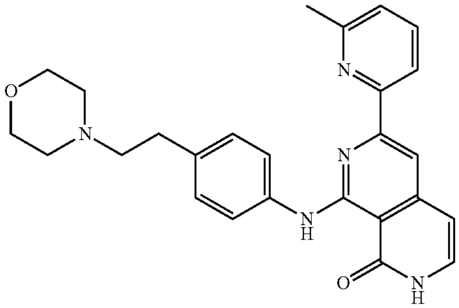 [SMILES: Cc1cccc(-c2cc3cc[nH]c(=O)c3c(Nc3ccc(CCN4CCOCC4)cc3)n2)n1] | ESI-MS m/z 442.2 (MH+). |
| 518 | 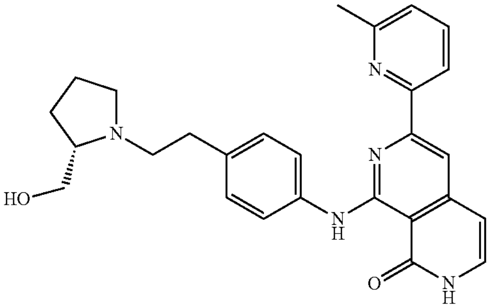 [SMILES: Cc1cccc(-c2cc3cc[nH]c(=O)c3c(Nc3ccc(CCN4CCC[C@H]4CO)cc3)n2)n1] | ESI-MS m/z 456.2 (MH+). |

TABLE 1-continued
| No | Structure | Physical Data $^1$H NMR 400 MHz (DMSO-$d_6$) and/or MS (m/z) |
|---|---|---|
| 519 | 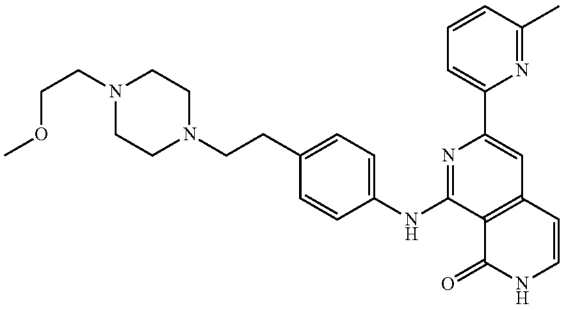 | ESI-MS m/z 499.3 (MH+). |
| 520 | 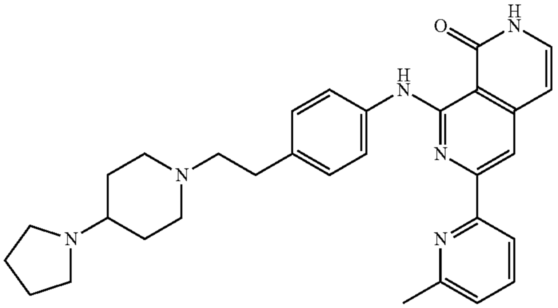 [SMILES: Cc1cccc(-c2cc3cc[nH]c(=O)c3c(Nc3ccc(CCN4CCC(N5CCCC5)CC4)cc3)n2)n1] | ESI-MS m/z 509.3 (MH+). |
| 521 | 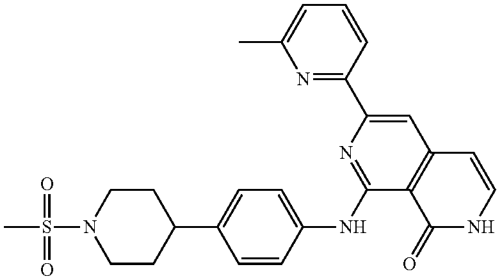 [SMILES: Cc1cccc(-c2cc3cc[nH]c(=O)c3c(Nc3ccc(C4CCN(S(C)(=O)=O)CC4)cc3)n2)n1] | ESI-MS m/z 490.2 (MH+). |
| 522 | 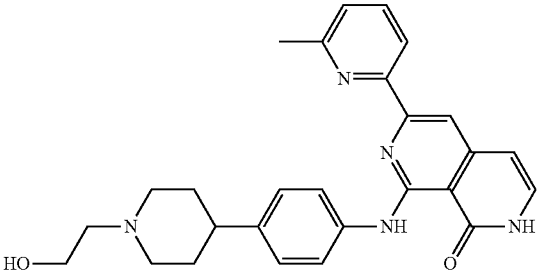 [SMILES: Cc1cccc(-c2cc3cc[nH]c(=O)c3c(Nc3ccc(C4CCN(CCO)CC4)cc3)n2)n1] | ESI-MS m/z 456.2 (MH+). |
| 523 | 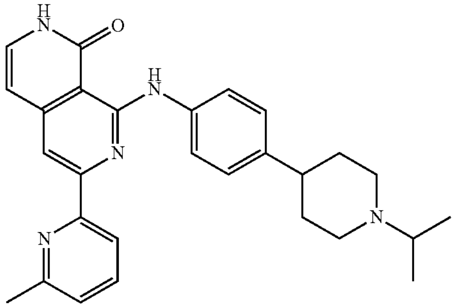 [SMILES: Cc1cccc(-c2cc3cc[nH]c(=O)c3c(Nc3ccc(C4CCN(C(C)C)CC4)cc3)n2)n1] | ESI-MS m/z 454.3 (MH+). |

TABLE 1-continued
| No | Structure | Physical Data $^1$H NMR 400 MHz (DMSO-$d_6$) and/or MS (m/z) |
|---|---|---|
| 524 | 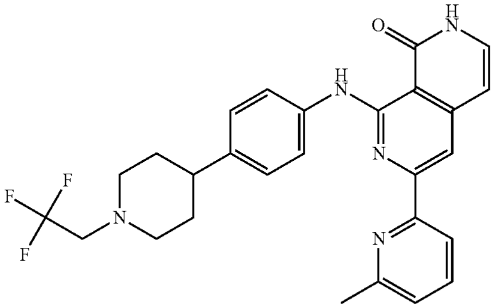 [SMILES: Cc1cccc(-c2cc3cc[nH]c(=O)c3c(Nc3ccc(C4CCN(CC(F)(F)F)CC4)cc3)n2)n1] | ESI-MS m/z 494.2 (MH+). |
| 525 | 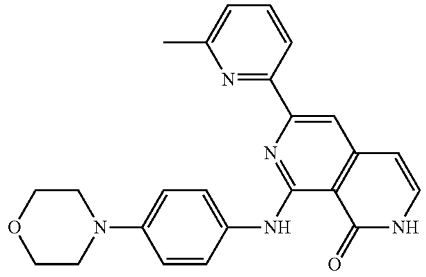 [SMILES: Cc1cccc(-c2cc3cc[nH]c(=O)c3c(Nc3ccc(N4CCOCC4)cc3)n2)n1] | ESI-MS m/z 414.2 (MH+). |
| 526 | 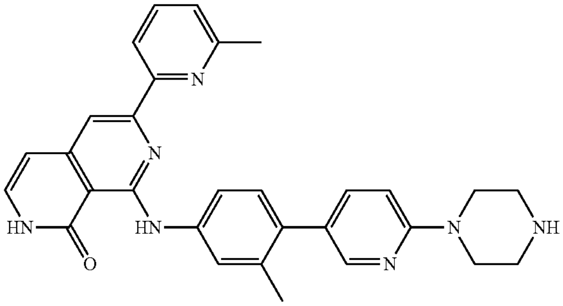 [SMILES: Cc1cccc(-c2cc3cc[nH]c(=O)c3c(Nc3ccc(-c4ccc(N5CCNCC5)nc4)c(C)c3)n2)n1] | ESI-MS m/z 504.2 (MH+). |
| 527 | 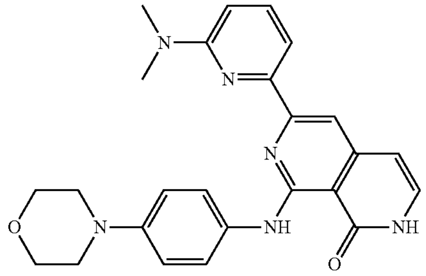 [SMILES: CN(C)c1cccc(-c2cc3cc[nH]c(=O)c3c(Nc3ccc(N4CCOCC4)cc3)n2)n1] | ESI-MS m/z 443.2 (MH+). |
| 528 | 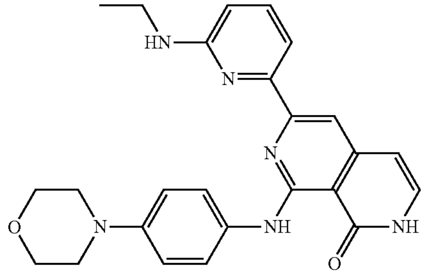 [SMILES: CCNc1cccc(-c2cc3cc[nH]c(=O)c3c(Nc3ccc(N4CCOCC4)cc3)n2)n1] | ESI-MS m/z 443.2 (MH+). |

TABLE 1-continued
| No | Structure | Physical Data $^1H$ NMR 400 MHz (DMSO-$d_6$) and/or MS (m/z) |
|---|---|---|
| 529 | 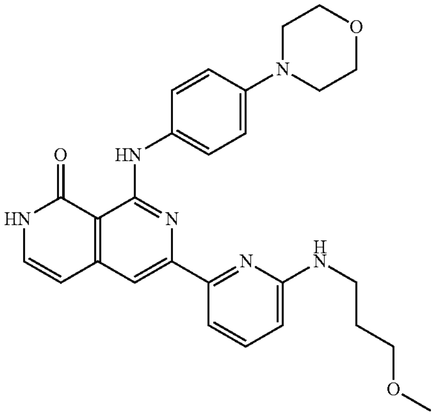 | ESI-MS m/z 457.2 (MH+). |
| 530 | 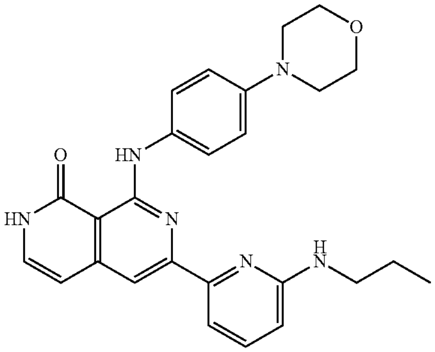 [SMILES: CCCNc1cccc(-c2cc3cc[nH]c(=O)c3c(Nc3ccc(N4CCOCC4)cc3)n2)n1] | ESI-MS m/z 456.2 (MH+). |
| 531 | 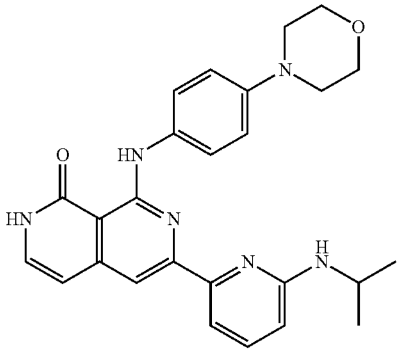 [SMILES: CC(C)Nc1cccc(-c2cc3cc[nH]c(=O)c3c(Nc3ccc(N4CCOCC4)cc3)n2)n1] | ESI-MS m/z 457.2 (MH+). |
| 532 | 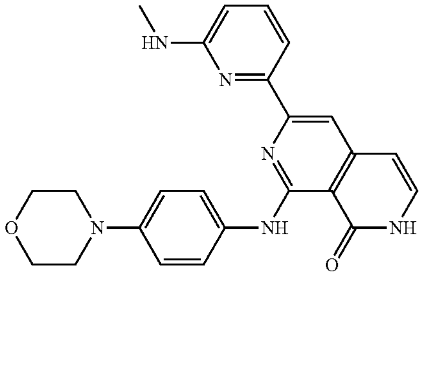 [SMILES: CNc1cccc(-c2cc3cc[nH]c(=O)c3c(Nc3ccc(N4CCOCC4)cc3)n2)n1] | ESI-MS m/z 429.2 (MH+). |

TABLE 1-continued
| No | Structure | Physical Data $^1H$ NMR 400 MHz (DMSO-$d_6$) and/or MS (m/z) |
|---|---|---|
| 533 | 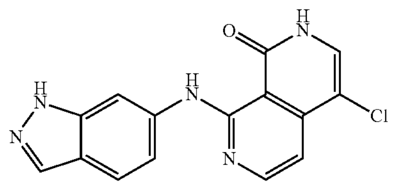 [SMILES: O=c1[nH]cc(Cl)c2ccnc(Nc3ccc4cn[nH]c4c3)c12] | ESI-MS m/z 312.0 (MH+). |
| 534 | 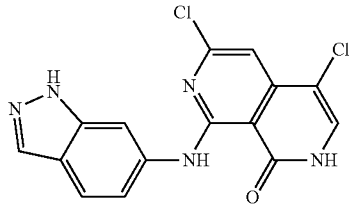 [SMILES: O=c1[nH]cc(Cl)c2cc(Cl)nc(Nc3ccc4cn[nH]c4c3)c12] | ESI-MS m/z 346.0 (MH+). |
| 535 | 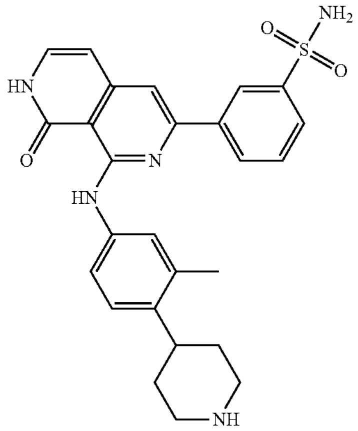 [SMILES: Cc1cc(Nc2nc(-c3cccc(S(N)(=O)=O)c3)cc3cc[nH]c(=O)c23)ccc1C1CCNCC1] | ESI-MS m/z 490.2 (MH+). |
| 536 | 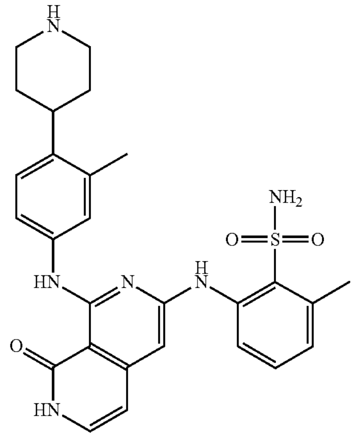 [SMILES: Cc1cc(Nc2nc(Nc3cccc(C)c3S(N)(=O)=O)cc3cc[nH]c(=O)c23)ccc1C1CCNCC1] | ESI-MS m/z 519.2 (MH+). |

TABLE 1-continued
| No | Structure | Physical Data $^1H$ NMR 400 MHz ($DMSO-d_6$) and/or MS (m/z) |
|---|---|---|
| 537 | 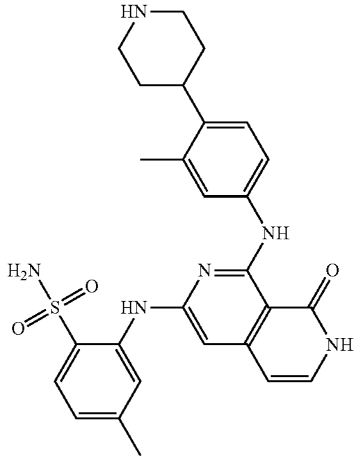 [SMILES: Cc1ccc(S(N)(=O)=O)c(Nc2cc3cc[nH]c(=O)c3c(Nc3ccc(C4CCNCC4)c(C)c3)n2)c1] | ESI-MS m/z 519.2 (MH+). |
| 538 | 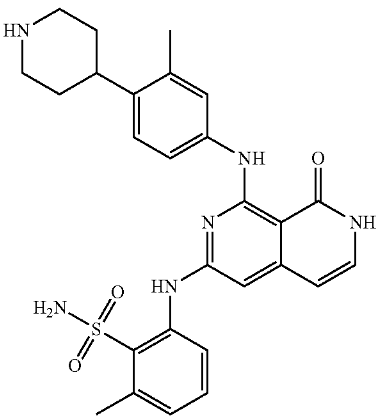 [SMILES: Cc1cc(Nc2nc(Nc3cccc(C)c3S(N)(=O)=O)cc3cc[nH]c(=O)c23)ccc1C1CCNCC1] | ESI-MS m/z 519.2 (MH+). |
| 539 | 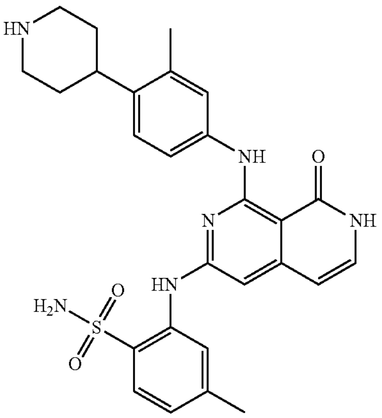 [SMILES: Cc1ccc(S(N)(=O)=O)c(Nc2cc3cc[nH]c(=O)c3c(Nc3ccc(C4CCNCC4)c(C)c3)n2)c1] | ESI-MS m/z 519.2 (MH+). |
| 540 | 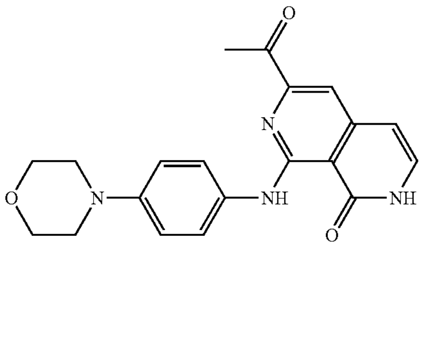 [SMILES: CC(=O)c1cc2cc[nH]c(=O)c2c(Nc2ccc(N3CCOCC3)cc2)n1] | ESI-MS m/z 365.2 (MH+). |

TABLE 1-continued
| No | Structure | Physical Data $^1$H NMR 400 MHz (DMSO-$d_6$) and/or MS (m/z) |
|---|---|---|
| 541 | 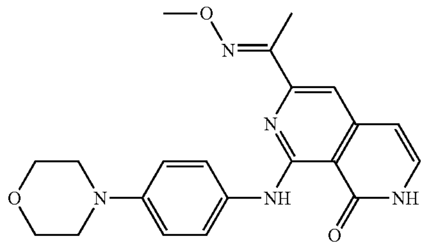 [SMILES: CO/N=C(\C)c1cc2cc[nH]c(=O)c2c(Nc2ccc(N3CCOCC3)cc2)n1] | ESI-MS m/z 394.2 (MH+). |
| 542 | 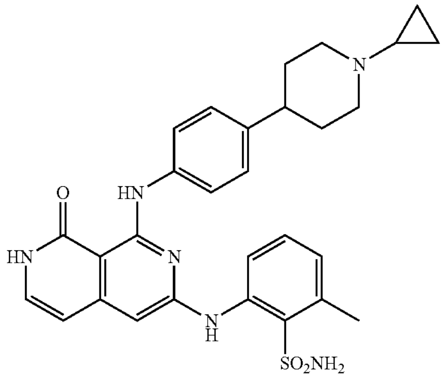 [SMILES: Cc1cccc(Nc2cc3cc[nH]c(=O)c3c(Nc3ccc(C4CCN(C5CC5)CC4)cc3)n2)c1S(N)(=O)=O] | MS m/z 545.2 (M + 1). |
| 543 | 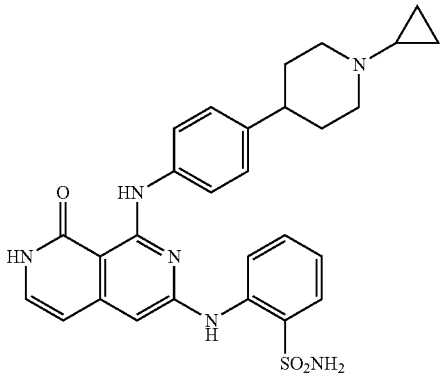 [SMILES: NS(=O)(=O)c1ccccc1Nc1cc2cc[nH]c(=O)c2c(Nc2ccc(C3CCN(C4CC4)CC3)cc2)n1] | MS m/z 531.2 (M + 1). |
| 544 | 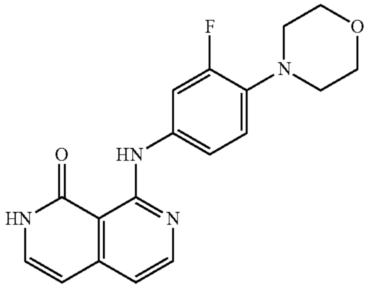 | MS m/z 431.1 (M + 1). |

TABLE 1-continued
| No | Structure | Physical Data $^1$H NMR 400 MHz (DMSO-$d_6$) and/or MS (m/z) |
|---|---|---|
| 545 | 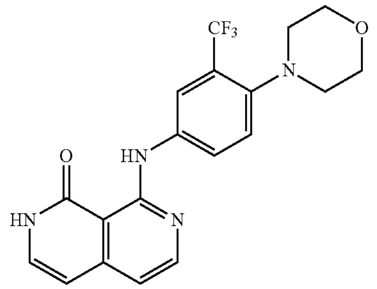 | MS m/z 391.1 (M + 1). |
| 546 | 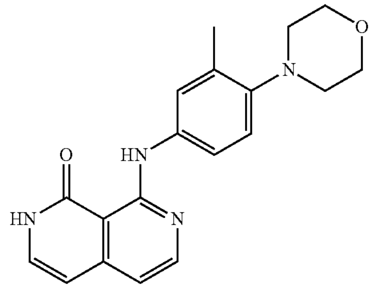 | MS m/z 337.2 (M + 1). |
| 547 | 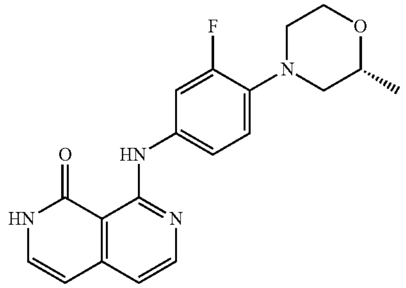 [SMILES: C[C@@H]1CN(c2ccc(Nc3nccc4cc[nH]c(=O)c34)cc2F)CCO1] | MS m/z 355.2 (M + 1). |
| 548 | 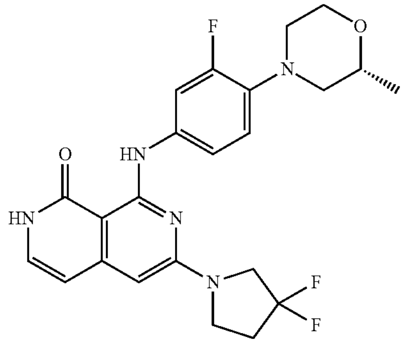 [SMILES: C[C@@H]1CN(c2ccc(Nc3nc(N4CCC(F)(F)C4)cc4cc[nH]c(=O)c34)cc2F)CCO1] | MS m/z 460.2 (M + 1). |
| 549 | 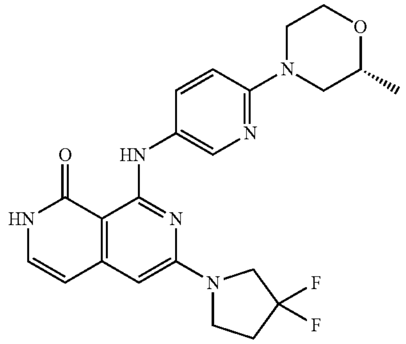 [SMILES: C[C@@H]1CN(c2ccc(Nc3nc(N4CCC(F)(F)C4)cc4cc[nH]c(=O)c34)cn2)CCO1] | MS m/z 443.2 (M + 1). |

TABLE 1-continued
| No | Structure | Physical Data $^1H$ NMR 400 MHz ($DMSO-d_6$) and/or MS (m/z) |
|---|---|---|
| 550 | 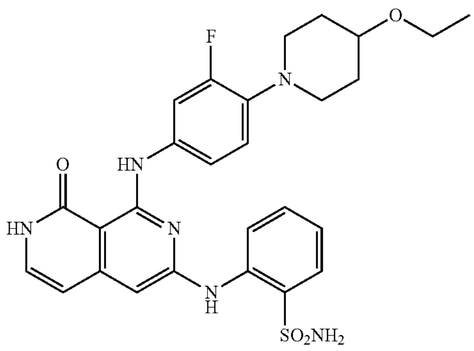 [SMILES: CCOC1CCN(c2ccc(Nc3nc(Nc4ccccc4S(N)(=O)=O)cc4cc[nH]c(=O)c34)cc2F)CC1] | MS m/z 553.2 (M + 1). |
| 551 | 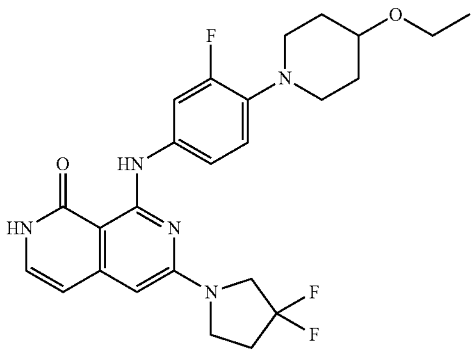 [SMILES: CCOC1CCN(c2ccc(Nc3nc(N4CCC(F)(F)C4)cc4cc[nH]c(=O)c34)cc2F)CC1] | MS m/z 488.2 (M + 1). |
| 552 | 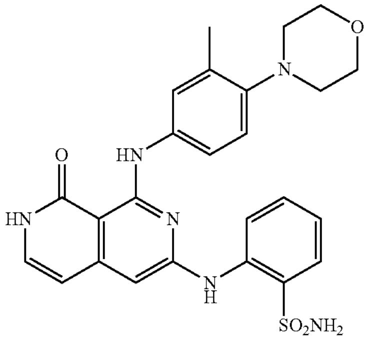 [SMILES: Cc1cc(Nc2nc(Nc3ccccc3S(N)(=O)=O)cc3cc[nH]c(=O)c23)ccc1N1CCOCC1] | MS m/z 507.2 (M + 1). |
| 553 | 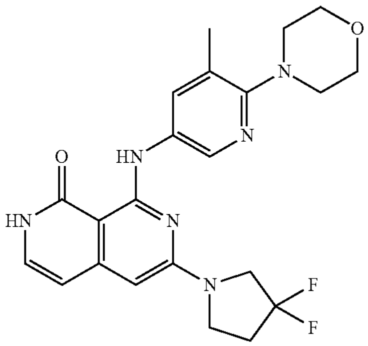 [SMILES: Cc1cc(Nc2nc(N3CCC(F)(F)C3)cc3cc[nH]c(=O)c23)cnc1N1CCOCC1] | MS m/z 443.2 (M + 1). |

TABLE 1-continued
| No | Structure | Physical Data $^1H$ NMR 400 MHz (DMSO-$d_6$) and/or MS (m/z) |
| --- | --- | --- |
| 554 | 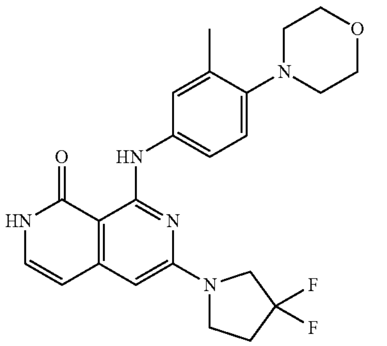 [SMILES: Cc1cc(Nc2nc(N3CCC(F)(F)C3)cc3cc[nH]c(=O)c23)ccc1N1CCOCC1] | MS m/z 442.2 (M + 1). |
| 555 | 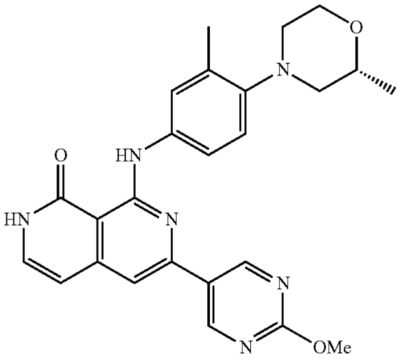 [SMILES: COc1ncc(-c2cc3cc[nH]c(=O)c3c(Nc3ccc(N4CCO[C@H](C)C4)c(C)c3)n2)cn1] | MS m/z 459.2 (M + 1). |
| 556 | 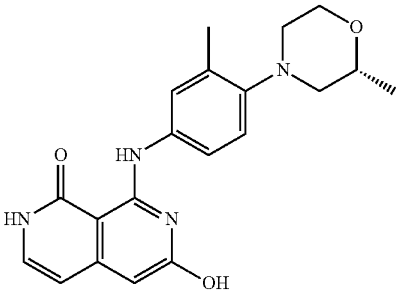 [SMILES: Cc1cc(Nc2nc(O)cc3cc[nH]c(=O)c23)ccc1N1CCO[C@H](C)C1] | MS m/z 367.2 (M + 1). |
| 557 | 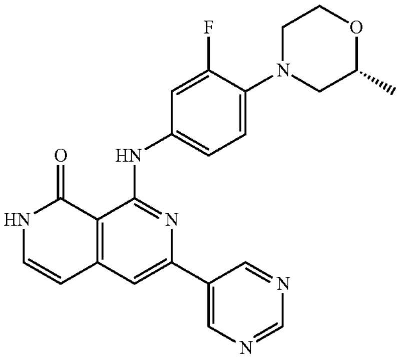 | MS m/z 433.2 (M + 1). |

TABLE 1-continued
| No | Structure | Physical Data $^1H$ NMR 400 MHz (DMSO-$d_6$) and/or MS (m/z) |
|---|---|---|
| 558 | 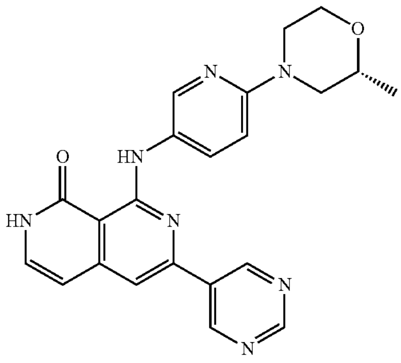 [SMILES: C[C@@H]1CN(c2ccc(Nc3nc(-c4cncnc4)cc4cc[nH]c(=O)c34)cn2)CCO1] | MS m/z 416.2 (M + 1). |
| 559 | 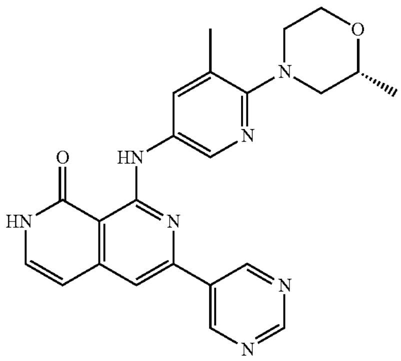 [SMILES: Cc1cc(Nc2nc(-c3cncnc3)cc3cc[nH]c(=O)c23)cnc1N1CCO[C@H](C)C1] | MS m/z 430.2 (M + 1). |
| 560 | 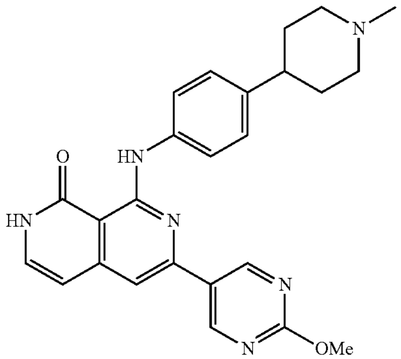 [SMILES: COc1ncc(-c2cc3cc[nH]c(=O)c3c(Nc3ccc(C4CCN(C)CC4)cc3)n2)cn1] | MS m/z 443.2 (M + 1). |
| 561 | 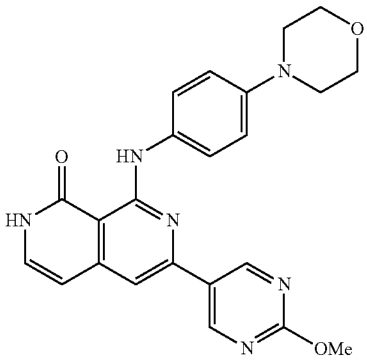 [SMILES: COc1ncc(-c2cc3cc[nH]c(=O)c3c(Nc3ccc(N4CCOCC4)cc3)n2)cn1] | MS m/z 431.2 (M + 1). |

TABLE 1-continued
| No | Structure | Physical Data $^1H$ NMR 400 MHz (DMSO-$d_6$) and/or MS (m/z) |
|---|---|---|
| 562 | 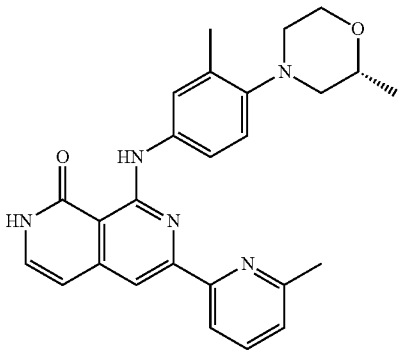 [SMILES: Cc1cccc(-c2cc3cc[nH]c(=O)c3c(Nc3ccc(N4CCO[C@H](C)C4)c(C)c3)n2)n1] | MS m/z 442.2 (M + 1). |
| 563 | 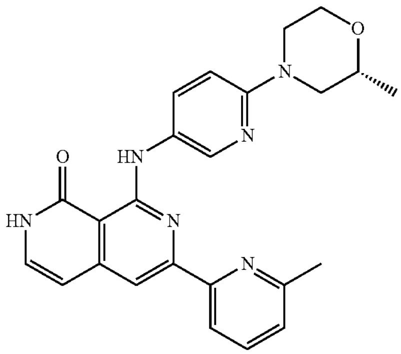 [SMILES: Cc1cccc(-c2cc3cc[nH]c(=O)c3c(Nc3ccc(N4CCO[C@H](C)C4)nc3)n2)n1] | MS m/z 429.2 (M + 1). |
| 564 | 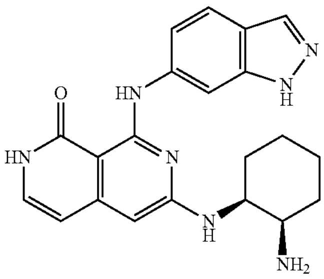 [SMILES: N[C@@H]1CCCC[C@@H]1Nc1cc2cc[nH]c(=O)c2c(Nc2ccc3cn[nH]c3c2)n1] | MS m/z 390.2 (M + 1). |
| 565 | 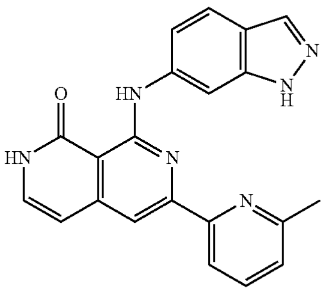 [SMILES: Cc1cccc(-c2cc3cc[nH]c(=O)c3c(Nc3ccc4cn[nH]c4c3)n2)n1] | MS m/z 369.1 (M + 1). |

TABLE 1-continued
| No | Structure | Physical Data $^1H$ NMR 400 MHz (DMSO-$d_6$) and/or MS (m/z) |
|---|---|---|
| 566 | 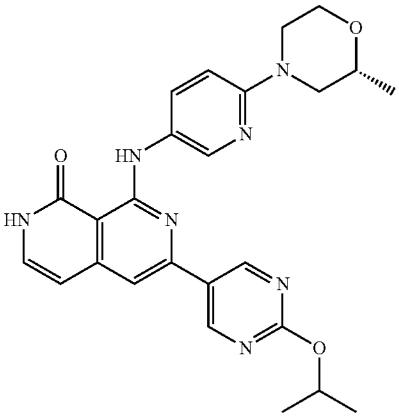 [SMILES: CC(C)Oc1ncc(-c2cc3cc[nH]c(=O)c3c(Nc3ccc(N4CCO[C@H](C)C4)nc3)n2)cn1] | MS m/z 474.2 (M + 1). |
| 567 | 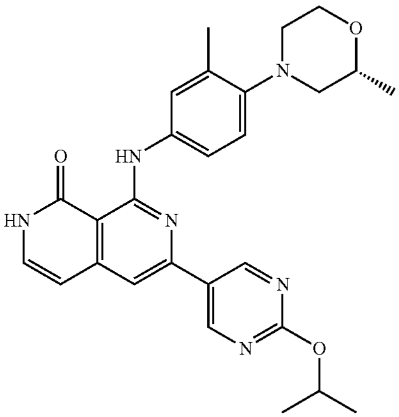 [SMILES: Cc1cc(Nc2nc(-c3cnc(OC(C)C)nc3)cc3cc[nH]c(=O)c23)ccc1N1CCO[C@H](C)C1] | MS m/z 489.2 (M + 1). |
| 568 | 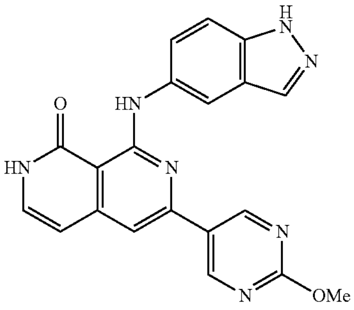 [SMILES: COc1ncc(-c2cc3cc[nH]c(=O)c3c(Nc3ccc4[nH]ncc4c3)n2)cn1] | MS m/z 386.1 (M + 1). |
| 569 | 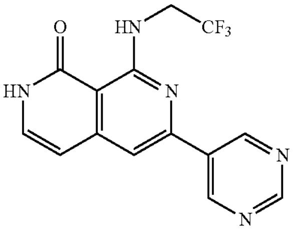 [SMILES: O=c1[nH]ccc2cc(-c3cncnc3)nc(NCC(F)(F)F)c12] | MS m/z 322.1 (M + 1). |

TABLE 1-continued
| No | Structure | Physical Data $^1H$ NMR 400 MHz (DMSO-$d_6$) and/or MS (m/z) |
|---|---|---|
| 570 | 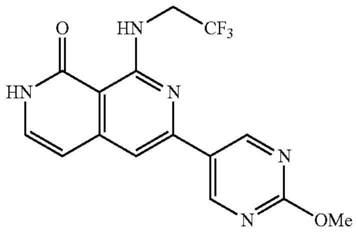 [SMILES: COc1ncc(-c2cc3cc[nH]c(=O)c3c(NCC(F)(F)F)n2)cn1] | MS m/z 352.1 (M + 1). |
| 571 | 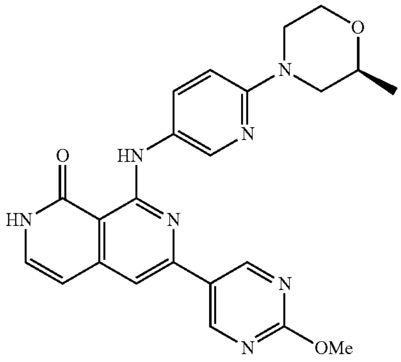 [SMILES: COc1ncc(-c2cc3cc[nH]c(=O)c3c(Nc3ccc(N4CCO[C@@H](C)C4)nc3)n2)cn1] | MS m/z 446.2 (M + 1). |
| 572 | 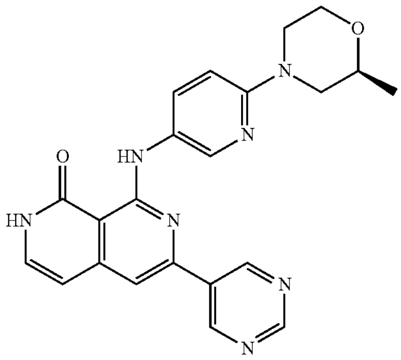 [SMILES: C[C@H]1CN(c2ccc(Nc3nc(-c4cncnc4)cc4cc[nH]c(=O)c34)cn2)CCO1] | MS m/z 416.2 (M + 1). |
| 573 | 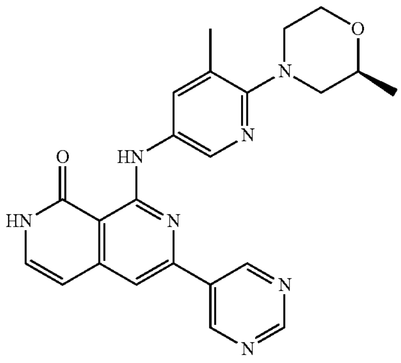 [SMILES: Cc1cc(Nc2nc(-c3cncnc3)cc3cc[nH]c(=O)c23)cnc1N1CCO[C@@H](C)C1] | MS m/z 429.2 (M + 1). |

TABLE 1-continued
| No | Structure | Physical Data $^1H$ NMR 400 MHz (DMSO-$d_6$) and/or MS (m/z) |
|---|---|---|
| 574 | 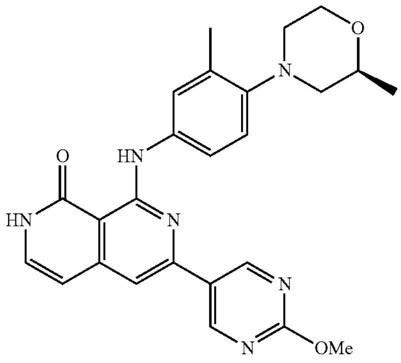 [SMILES: COc1ncc(-c2cc3cc[nH]c(=O)c3c(Nc3ccc(N4CCO[C@@H](C)C4)c(C)c3)n2)cn1] | MS m/z 459.2 (M + 1). |
| 575 | 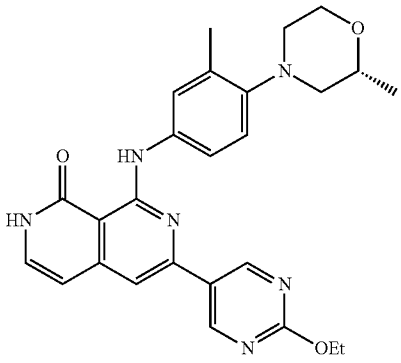 [SMILES: CCOc1ncc(-c2cc3cc[nH]c(=O)c3c(Nc3ccc(N4CCO[C@H](C)C4)c(C)c3)n2)cn1] | MS m/z 473.2 (M + 1). |
| 576 | 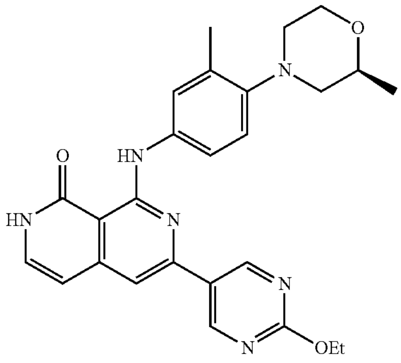 [SMILES: CCOc1ncc(-c2cc3cc[nH]c(=O)c3c(Nc3ccc(N4CCO[C@@H](C)C4)c(C)c3)n2)cn1] | MS m/z 473.2 (M + 1). |
| 578 | 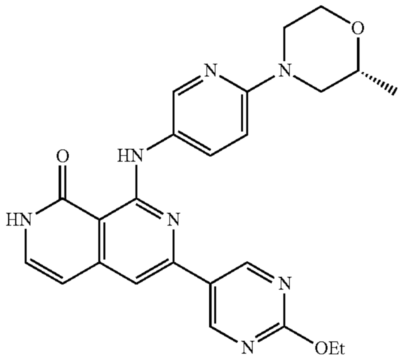 [SMILES: CCOc1ncc(-c2cc3cc[nH]c(=O)c3c(Nc3ccc(N4CCO[C@H](C)C4)nc3)n2)cn1] | MS m/z 460.2 (M + 1). |

TABLE 1-continued
| No | Structure | Physical Data $^1$H NMR 400 MHz (DMSO-$d_6$) and/or MS (m/z) |
|---|---|---|
| 579 | 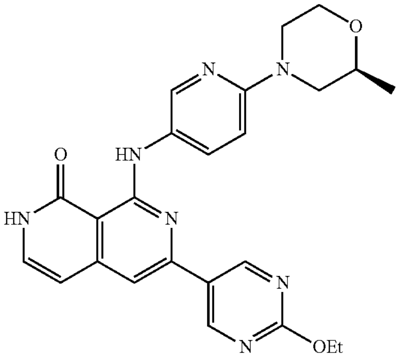 [SMILES: CCOc1ncc(-c2cc3cc[nH]c(=O)c3c(Nc3ccc(N4CCO[C@@H](C)C4)nc3)n2)cn1] | MS m/z 460.2 (M + 1). |
| 580 | 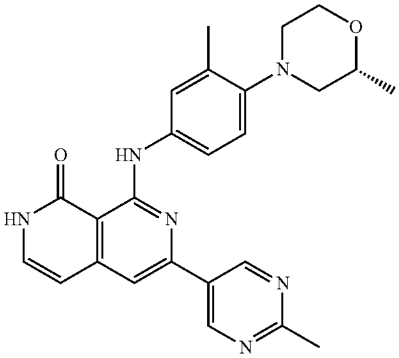 [SMILES: Cc1ncc(-c2cc3cc[nH]c(=O)c3c(Nc3ccc(N4CCO[C@H](C)C4)c(C)c3)n2)cn1] | MS m/z 443.2 (M + 1). |
| 581 | 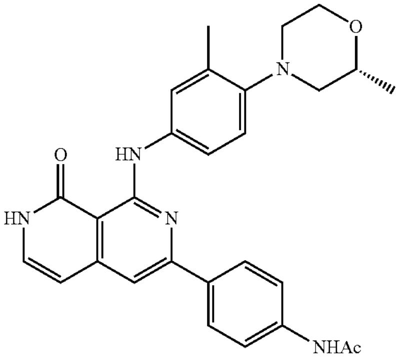 [SMILES: CC(=O)Nc1ccc(-c2cc3cc[nH]c(=O)c3c(Nc3ccc(N4CCO[C@H](C)C4)c(C)c3)n2)cc1] | MS m/z 484.2 (M + 1). |
| 582 | 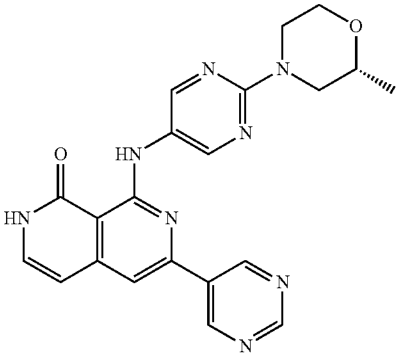 [SMILES: C[C@@H]1CN(c2ncc(Nc3nc(-c4cncnc4)cc4cc[nH]c(=O)c34)cn2)CCO1] | MS m/z 417.2 (M + 1). |

TABLE 1-continued
| No | Structure | Physical Data $^1H$ NMR 400 MHz (DMSO-$d_6$) and/or MS (m/z) |
|---|---|---|
| 583 | 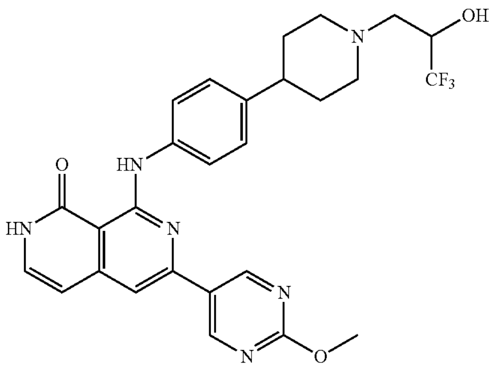 [SMILES: COc1ncc(-c2cc3cc[nH]c(=O)c3c(Nc3ccc(C4CCN(CC(O)C(F)(F)F)CC4)cc3)n2)cn1] | MS m/z 541.2 (M + 1). |
| 584 | 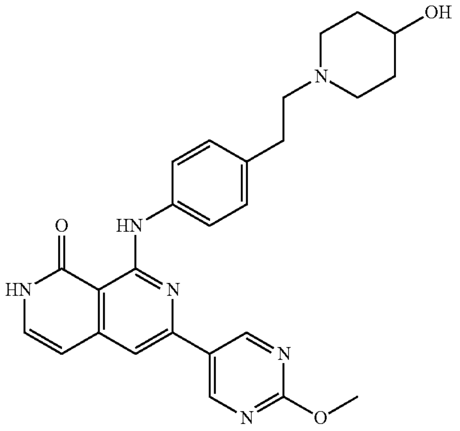 [SMILES: COc1ncc(-c2cc3cc[nH]c(=O)c3c(Nc3ccc(CCN4CCC(O)CC4)cc3)n2)cn1] | MS m/z 473.2 (M + 1). |
| 585 | 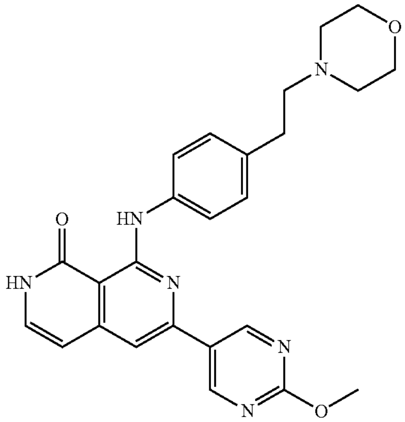 [SMILES: COc1ncc(-c2cc3cc[nH]c(=O)c3c(Nc3ccc(CCN4CCOCC4)cc3)n2)cn1] | MS m/z 459.2 (M + 1). |

TABLE 1-continued
| No | Structure | Physical Data $^1H$ NMR 400 MHz ($DMSO-d_6$) and/or MS (m/z) |
|---|---|---|
| 586 | 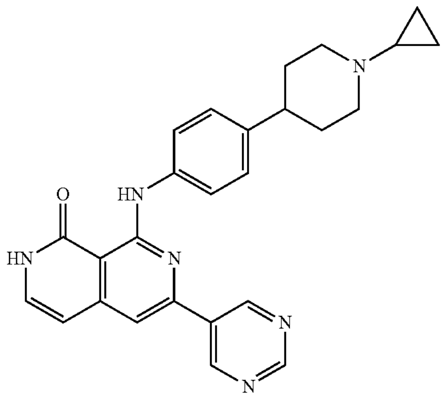 [SMILES: O=c1[nH]ccc2cc(-c3cncnc3)nc(Nc3ccc(C4CCN(C5CC5)CC4)cc3)c12] | MS m/z 439.2 (M + 1). |
| 587 | 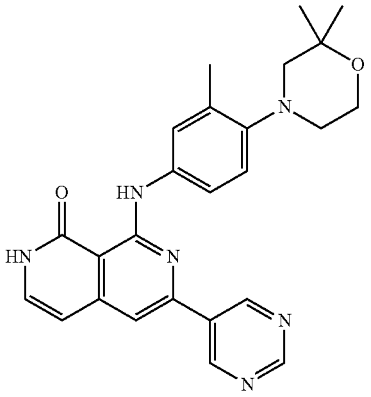 [SMILES: Cc1cc(Nc2nc(-c3cncnc3)cc3cc[nH]c(=O)c23)ccc1N1CCOC(C)(C)C1] | MS m/z 443.2 (M + 1). |
| 588 | 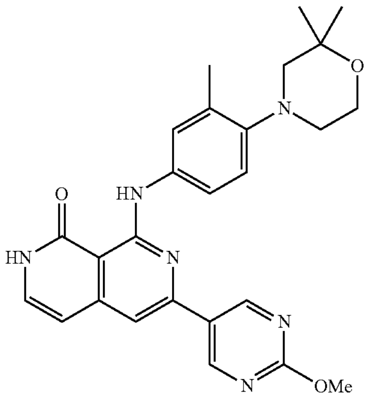 [SMILES: COc1ncc(-c2cc3cc[nH]c(=O)c3c(Nc3ccc(N4CCOC(C)(C)C4)c(C)c3)n2)cn1] | MS m/z 473.2 (M + 1). |

TABLE 1-continued
| No | Structure | Physical Data $^1H$ NMR 400 MHz (DMSO-$d_6$) and/or MS (m/z) |
| --- | --- | --- |
| 589 | 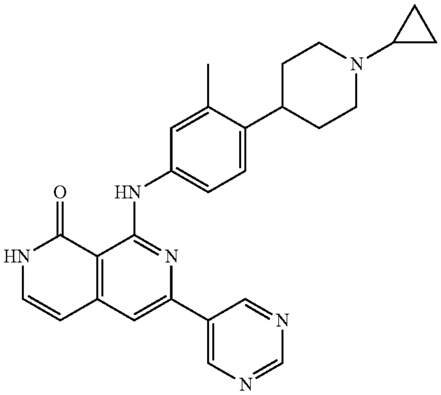 [SMILES: Cc1cc(Nc2nc(-c3cncnc3)cc3cc[nH]c(=O)c23)ccc1C1CCN(C2CC2)CC1] | MS m/z 453.2 (M + 1). |
| 590 | 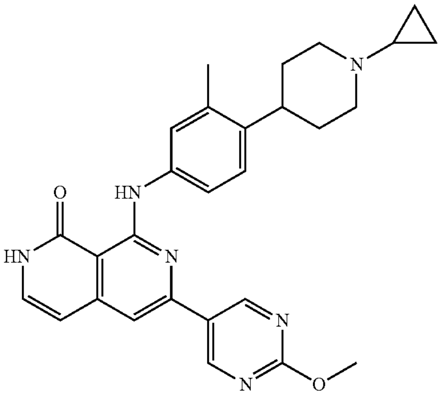 [SMILES: COc1ncc(-c2cc3cc[nH]c(=O)c3c(Nc3ccc(C4CCN(C5CC5)CC4)c(C)c3)n2)cn1] | MS m/z 483.2 (M + 1). |
| 591 | 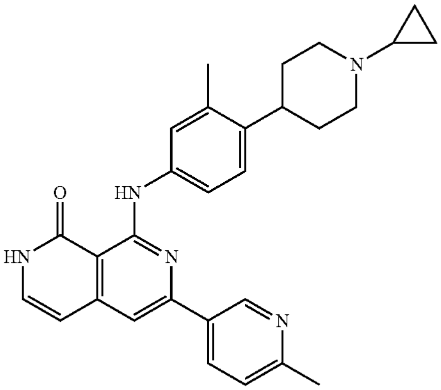 [SMILES: Cc1ccc(-c2cc3cc[nH]c(=O)c3c(Nc3ccc(C4CCN(C5CC5)CC4)c(C)c3)n2)cn1] | MS m/z 466.2 (M + 1). |
| 592 | 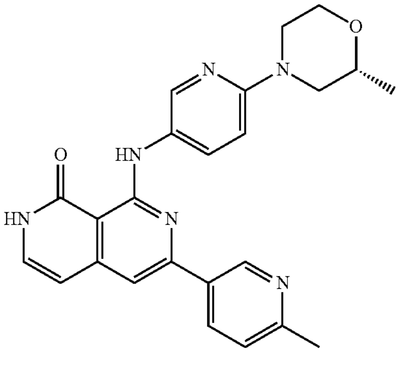 [SMILES: Cc1ccc(-c2cc3cc[nH]c(=O)c3c(Nc3ccc(N4CCO[C@H](C)C4)nc3)n2)cn1] | MS m/z 429.2 (M + 1). |

TABLE 1-continued
| No | Structure | Physical Data $^1H$ NMR 400 MHz (DMSO-$d_6$) and/or MS (m/z) |
|---|---|---|
| 593 | 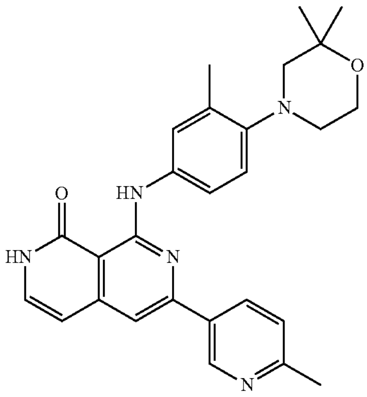 [SMILES: Cc1ccc(-c2cc3cc[nH]c(=O)c3c(Nc3ccc(N4CCOC(C)(C)C4)c(C)c3)n2)cn1] | MS m/z 456.2 (M + 1). |
| 594 | 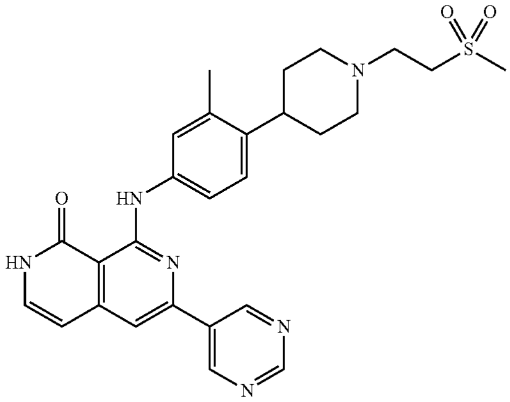 [SMILES: Cc1cc(Nc2nc(-c3cncnc3)cc3cc[nH]c(=O)c23)ccc1C1CCN(CCS(C)(=O)=O)CC1] | MS m/z 519.2 (M + 1). |
| 595 | 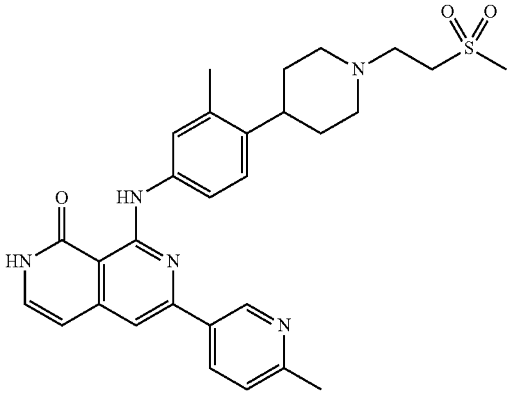 [SMILES: Cc1ccc(-c2cc3cc[nH]c(=O)c3c(Nc3ccc(C4CCN(CCS(C)(=O)=O)CC4)c(C)c3)n2)cn1] | MS m/z 532.2 (M + 1). |

TABLE 1-continued
| No | Structure | Physical Data $^1H$ NMR 400 MHz ($DMSO-d_6$) and/or MS (m/z) |
|---|---|---|
| 596 | 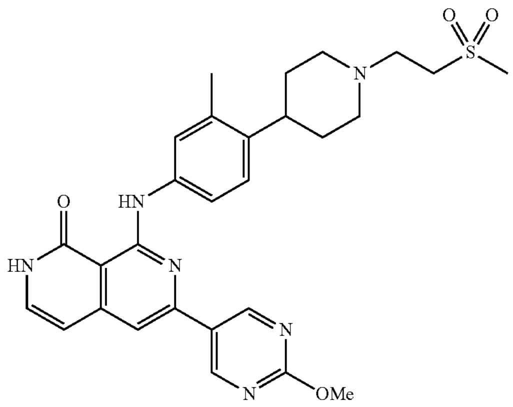 [SMILES: COc1ncc(-c2cc3cc[nH]c(=O)c3c(Nc3ccc(C4CCN(CCS(C)(=O)=O)CC4)c(C)c3)n2)cn1] | MS m/z 549.2 (M + 1). |
| 597 | 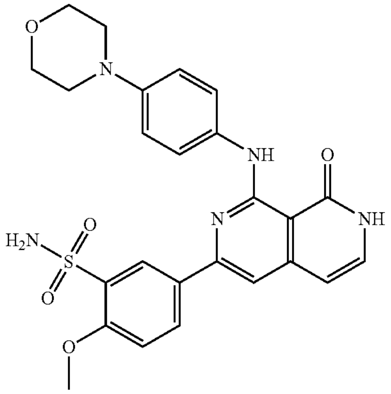 [SMILES: COc1ccc(-c2cc3cc[nH]c(=O)c3c(Nc3ccc(N4CCOCC4)cc3)n2)cc1S(N)(=O)=O] | MS m/z 508.3 (M + 1). |
| 598 | 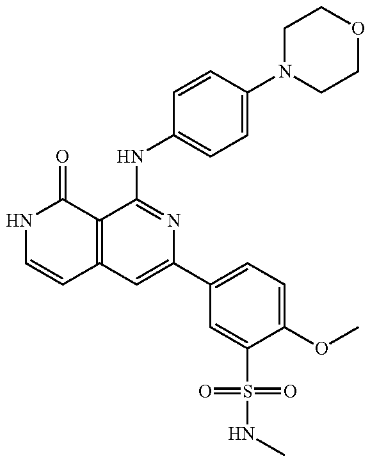 [SMILES: CNS(=O)(=O)c1cc(-c2cc3cc[nH]c(=O)c3c(Nc3ccc(N4CCOCC4)cc3)n2)ccc1OC] | MS m/z 522.3 (M + 1). |

TABLE 1-continued
| No | Structure | Physical Data $^1H$ NMR 400 MHz (DMSO-$d_6$) and/or MS (m/z) |
|---|---|---|
| 599 | 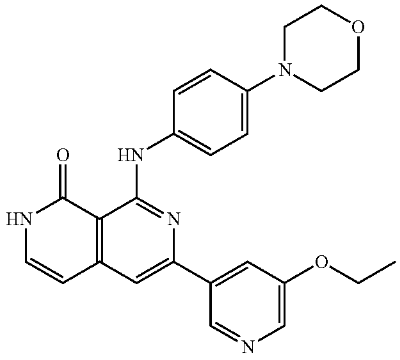 [SMILES: CCOc1cncc(-c2cc3cc[nH]c(=O)c3c(Nc3ccc(N4CCOCC4)cc3)n2)c1] | MS m/z 444.2 (M + 1). |
| 600 | 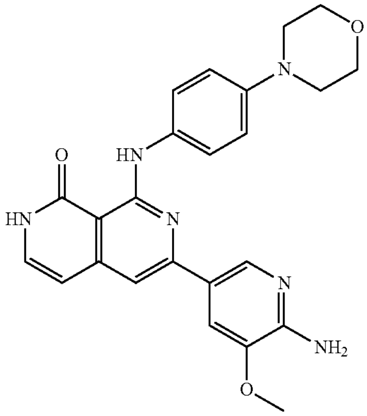 [SMILES: COc1cc(-c2cc3cc[nH]c(=O)c3c(Nc3ccc(N4CCOCC4)cc3)n2)cnc1N] | MS m/z 445.2 (M + 1). |
| 601 | 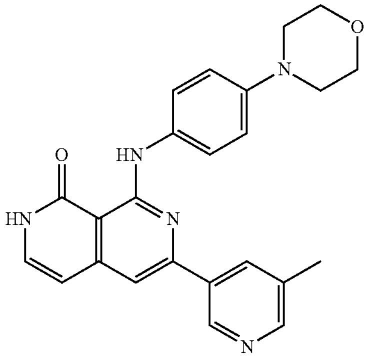 [SMILES: Cc1cncc(-c2cc3cc[nH]c(=O)c3c(Nc3ccc(N4CCOCC4)cc3)n2)c1] | MS m/z 414.2 (M + 1). |
| 602 | 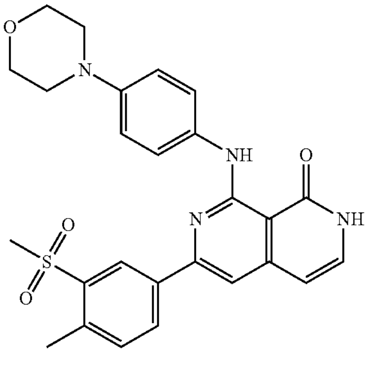 [SMILES: Cc1ccc(-c2cc3cc[nH]c(=O)c3c(Nc3ccc(N4CCOCC4)cc3)n2)cc1S(C)(=O)=O] | MS m/z 491.3 (M + 1). |

TABLE 1-continued
| No | Structure | Physical Data $^1H$ NMR 400 MHz (DMSO-$d_6$) and/or MS (m/z) |
|---|---|---|
| 603 | 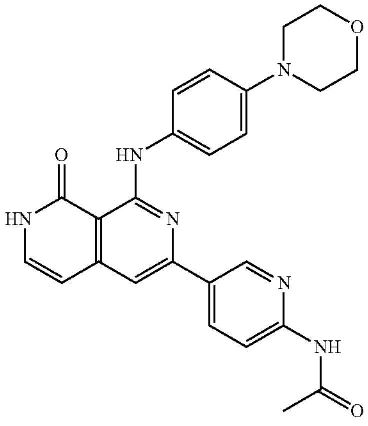 [SMILES: CC(=O)Nc1ccc(-c2cc3cc[nH]c(=O)c3c(Nc3ccc(N4CCOCC4)cc3)n2)cn1] | MS m/z 456.2 (M + 1). |
| 604 | 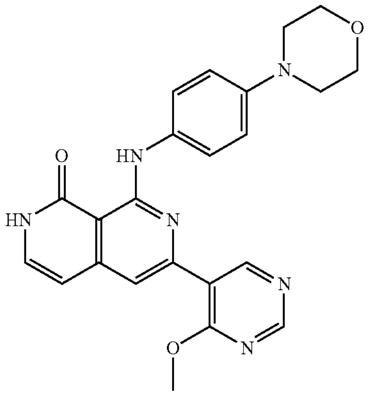 [SMILES: COc1ncncc1-c1cc2cc[nH]c(=O)c2c(Nc2ccc(N3CCOCC3)cc2)n1] | MS m/z 431.2 (M + 1). |
| 605 | 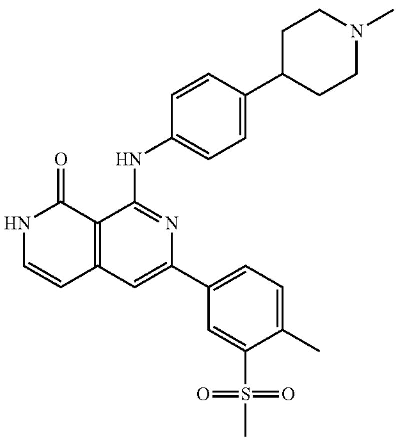 [SMILES: Cc1ccc(-c2cc3cc[nH]c(=O)c3c(Nc3ccc(C4CCN(C)CC4)cc3)n2)cc1S(C)(=O)=O] | MS m/z 503.3 (M + 1). |

TABLE 1-continued
| No | Structure | Physical Data $^1H$ NMR 400 MHz (DMSO-$d_6$) and/or MS (m/z) |
|---|---|---|
| 606 | 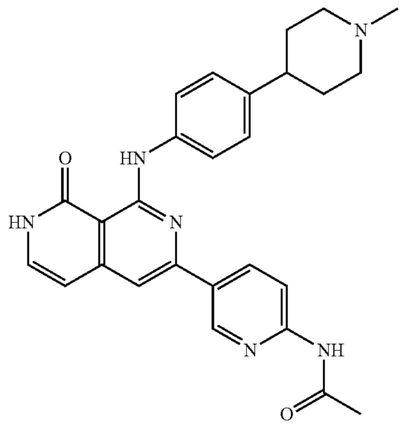 [SMILES: CC(=O)Nc1ccc(-c2cc3cc[nH]c(=O)c3c(Nc3ccc(C4CCN(C)CC4)cc3)n2)cn1] | MS m/z 469.2 (M + 1). |
| 607 | 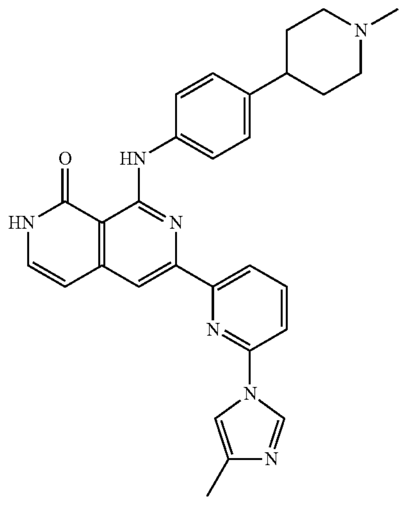 [SMILES: Cc1cn(-c2cccc(-c3cc4cc[nH]c(=O)c4c(Nc4ccc(C5CCN(C)CC5)cc4)n3)n2)cn1] | MS m/z 492.3 (M + 1). |
| 608 | 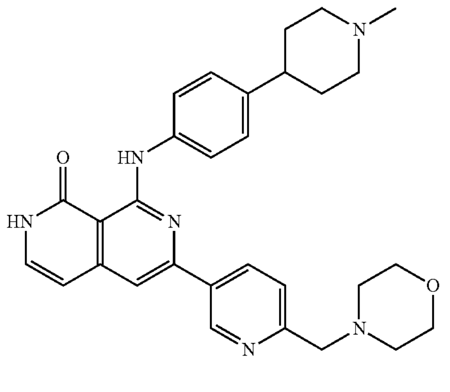 [SMILES: CN1CCC(c2ccc(Nc3nc(-c4ccc(CN5CCOCC5)nc4)cc4cc[nH]c(=O)c34)cc2)CC1] | MS m/z 511.3 (M + 1). |

TABLE 1-continued
| No | Structure | Physical Data $^1$H NMR 400 MHz (DMSO-$d_6$) and/or MS (m/z) |
|---|---|---|
| 609 | 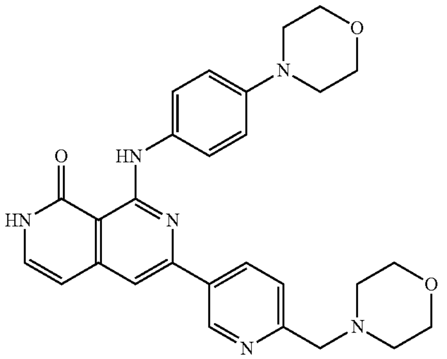 [SMILES: O=c1[nH]ccc2cc(-c3ccc(CN4CCOCC4)nc3)nc(Nc3ccc(N4CCOCC4)cc3)c12] | MS m/z 499.3 (M + 1). |
| 610 | 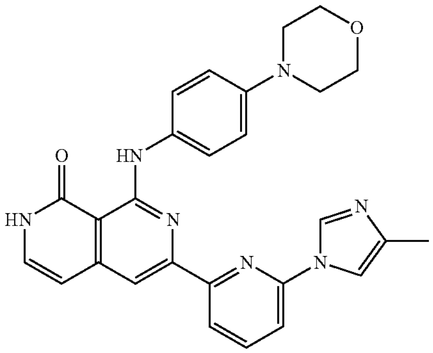 [SMILES: Cc1cn(-c2cccc(-c3cc4cc[nH]c(=O)c4c(Nc4ccc(N5CCOCC5)cc4)n3)n2)cn1] | MS m/z 480.2 (M + 1). |
| 611 | 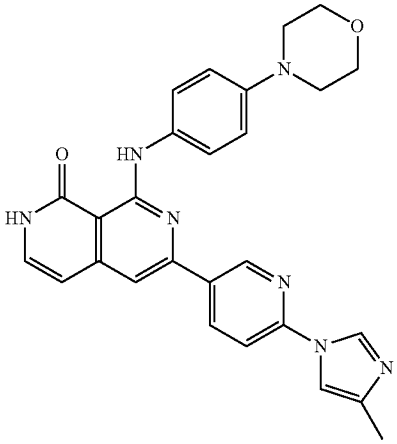 [SMILES: Cc1cn(-c2ccc(-c3cc4cc[nH]c(=O)c4c(Nc4ccc(N5CCOCC5)cc4)n3)cn2)cn1] | MS m/z 480.2 (M + 1). |
| 612 | 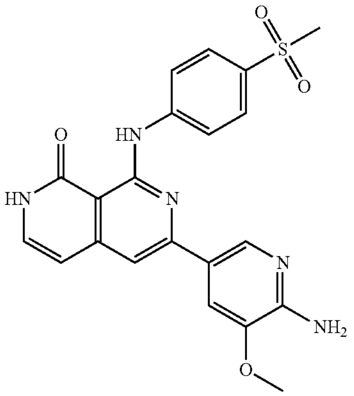 [SMILES: COc1cc(-c2cc3cc[nH]c(=O)c3c(Nc3ccc(S(C)(=O)=O)cc3)n2)cnc1N] | MS m/z 438.2 (M + 1). |

TABLE 1-continued
| No | Structure | Physical Data $^1H$ NMR 400 MHz (DMSO-$d_6$) and/or MS (m/z) |
|---|---|---|
| 613 | 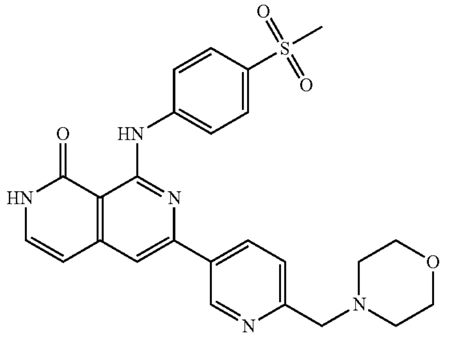 [SMILES: CS(=O)(=O)c1ccc(Nc2nc(-c3ccc(CN4CCOCC4)nc3)cc3cc[nH]c(=O)c23)cc1] | MS m/z 492.2 (M + 1). |
| 614 | 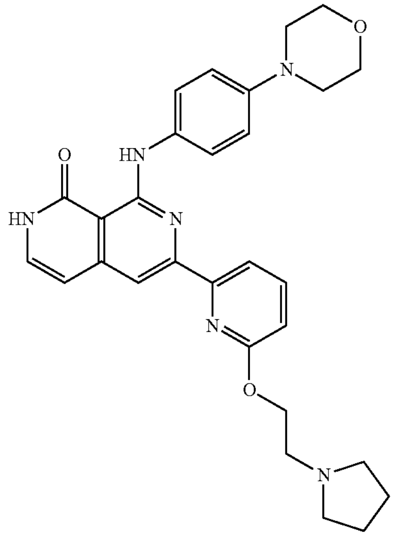 [SMILES: O=c1[nH]ccc2cc(-c3cccc(OCCN4CCCC4)n3)nc(Nc3ccc(N4CCOCC4)cc3)c12] | MS m/z 513.3 (M + 1). |
| 615 | 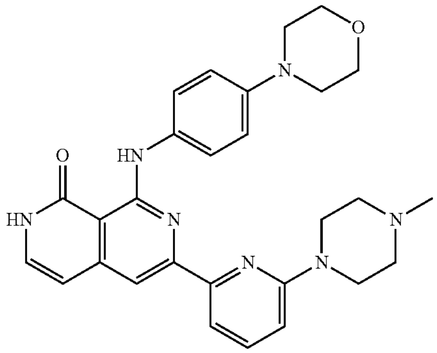 [SMILES: CN1CCN(c2cccc(-c3cc4cc[nH]c(=O)c4c(Nc4ccc(N5CCOCC5)cc4)n3)n2)CC1] | MS m/z 498.2 (M + 1). |

TABLE 1-continued
| No | Structure | Physical Data $^1H$ NMR 400 MHz ($DMSO-d_6$) and/or MS (m/z) |
|---|---|---|
| 616 | 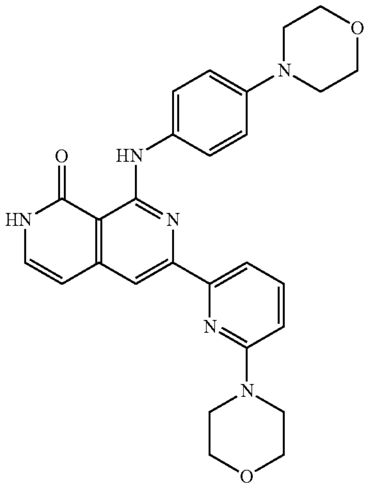 [SMILES: O=c1[nH]ccc2cc(-c3cccc(N4CCOCC4)n3)nc(Nc3ccc(N4CCOCC4)cc3)c12] | MS m/z 485.2 (M + 1). |
| 617 | 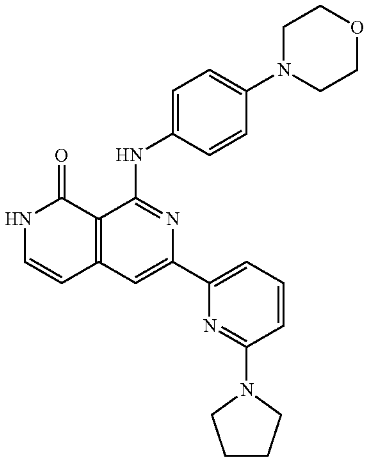 [SMILES: O=c1[nH]ccc2cc(-c3cccc(N4CCCC4)n3)nc(Nc3ccc(N4CCOCC4)cc3)c12] | MS m/z 469.2 (M + 1). |
| 618 | 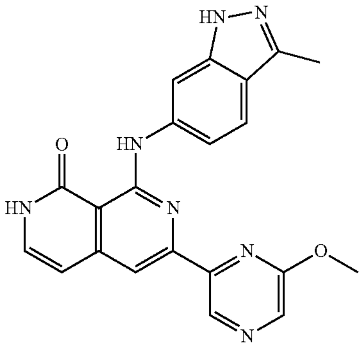 [SMILES: COc1cncc(-c2cc3cc[nH]c(=O)c3c(Nc3ccc4c(C)n[nH]c4c3)n2)n1] | MS m/z 400.2 (M + 1). |

TABLE 1-continued
| No | Structure | Physical Data $^1$H NMR 400 MHz (DMSO-$d_6$) and/or MS (m/z) |
|---|---|---|
| 619 | 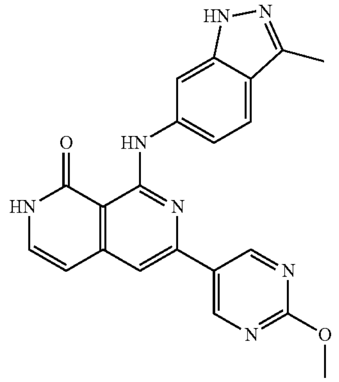 [SMILES: COc1ncc(-c2cc3cc[nH]c(=O)c3c(Nc3ccc4c(C)n[nH]c4c3)n2)cn1] | MS m/z 400.2 (M + 1). |
| 620 | 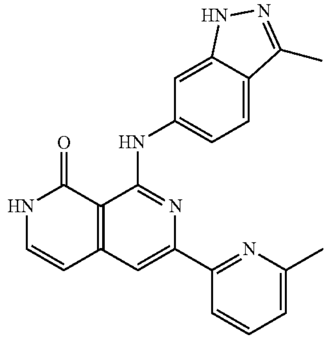 [SMILES: Cc1cccc(-c2cc3cc[nH]c(=O)c3c(Nc3ccc4c(C)n[nH]c4c3)n2)n1] | MS m/z 383.2 (M + 1). |
| 621 | 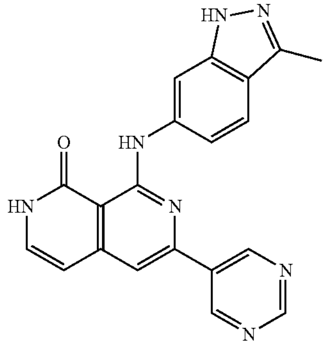 [SMILES: Cc1n[nH]c2cc(Nc3nc(-c4cncnc4)cc4cc[nH]c(=O)c34)ccc12] | MS m/z 370.2 (M + 1). |
| 622 | 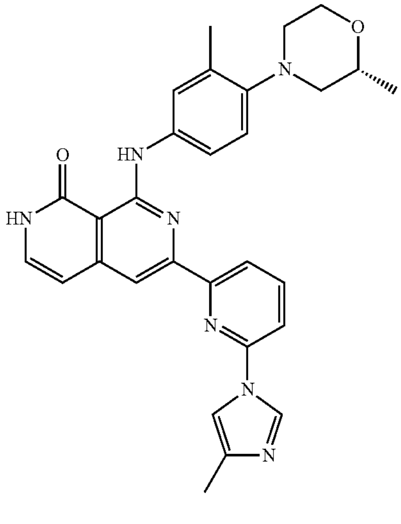 [SMILES: Cc1cn(-c2cccc(-c3cc4cc[nH]c(=O)c4c(Nc4ccc(N5CCO[C@H](C)C5)c(C)c4)n3)n2)cn1] | MS m/z 508.3 (M + 1). |

TABLE 1-continued
| No | Structure | Physical Data $^1H$ NMR 400 MHz (DMSO-$d_6$) and/or MS (m/z) |
|---|---|---|
| 623 | 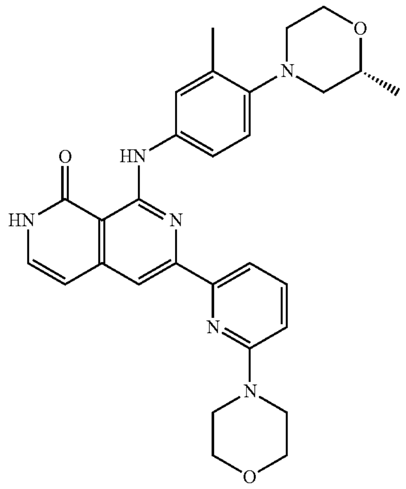 [SMILES: Cc1cc(Nc2nc(-c3cccc(N4CCOCC4)n3)cc3cc[nH]c(=O)c23)ccc1N1CCO[C@H](C)C1] | MS m/z 513.3 (M + 1). |
| 624 | 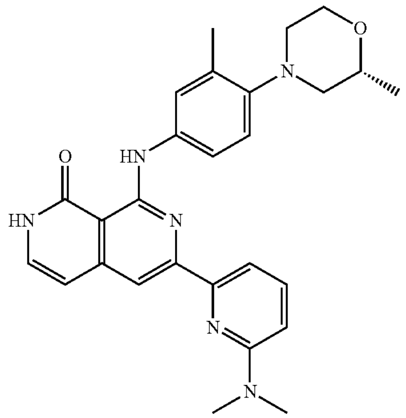 [SMILES: Cc1cc(Nc2nc(-c3cccc(N(C)C)n3)cc3cc[nH]c(=O)c23)ccc1N1CCO[C@H](C)C1] | MS m/z 471.2 (M + 1). |
| 625 | 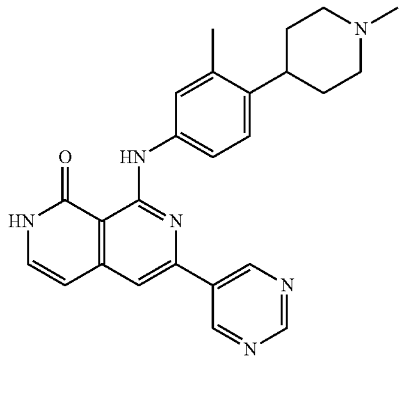 [SMILES: Cc1cc(Nc2nc(-c3cncnc3)cc3cc[nH]c(=O)c23)ccc1C1CCN(C)CC1] | MS m/z 427.2 (M + 1). |

TABLE 1-continued
| No | Structure | Physical Data $^1H$ NMR 400 MHz (DMSO-$d_6$) and/or MS (m/z) |
| --- | --- | --- |
| 626 | 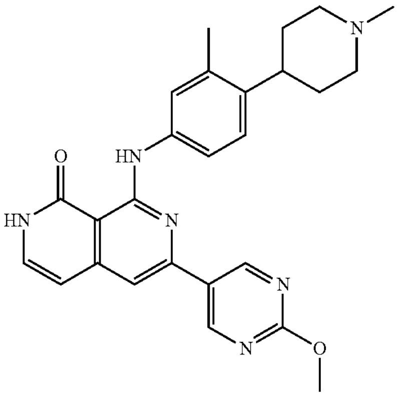 [SMILES: COc1ncc(-c2cc3cc[nH]c(=O)c3c(Nc3ccc(C4CCN(C)CC4)c(C)c3)n2)cn1] | MS m/z 457.2 (M + 1). |
| 627 | 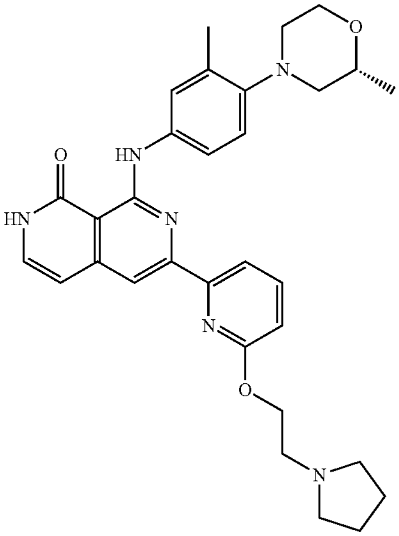 [SMILES: Cc1cc(Nc2nc(-c3cccc(OCCN4CCCC4)n3)cc3cc[nH]c(=O)c23)ccc1N1CCO[C@H](C)C1] | MS m/z 541.3 (M + 1). |
| 628 | 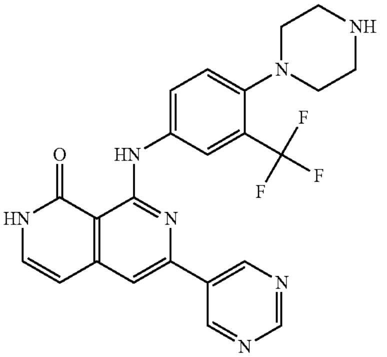 [SMILES: O=c1[nH]ccc2cc(-c3cncnc3)nc(Nc3ccc(N4CCNCC4)c(C(F)(F)F)c3)c12] | MS m/z 468.2 (M + 1). |

TABLE 1-continued
| No | Structure | Physical Data $^1H$ NMR 400 MHz ($DMSO-d_6$) and/or MS (m/z) |
|---|---|---|
| 629 | 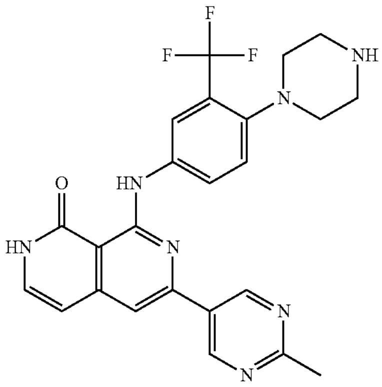 [SMILES: Cc1ncc(-c2cc3cc[nH]c(=O)c3c(Nc3ccc(N4CCNCC4)c(C(F)(F)F)c3)n2)cn1] | MS m/z 482.3 (M + 1). |
| 630 | 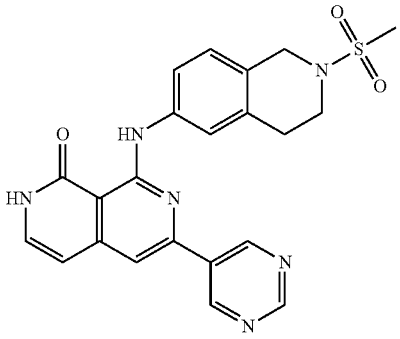 [SMILES: CS(=O)(=O)N1CCc2cc(Nc3nc(-c4cncnc4)cc4cc[nH]c(=O)c34)ccc2C1] | MS m/z 449.2 (M + 1). |
| 631 | 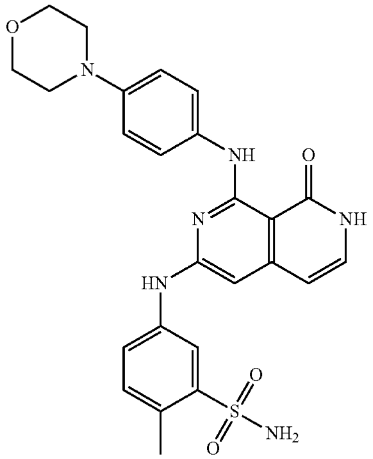 [SMILES: Cc1ccc(Nc2cc3cc[nH]c(=O)c3c(Nc3ccc(N4CCOCC4)cc3)n2)cc1S(N)(=O)=O] | MS m/z 507.2 (M + 1). |

TABLE 1-continued
| No | Structure | Physical Data $^1H$ NMR 400 MHz (DMSO-$d_6$) and/or MS (m/z) |
|---|---|---|
| 632 | 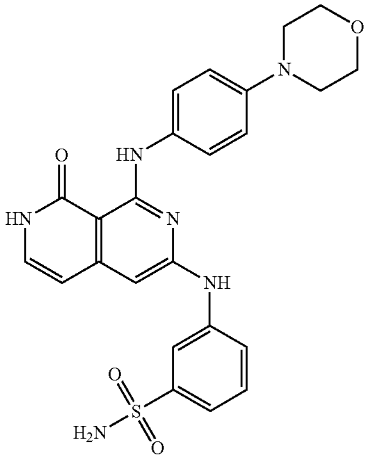 [SMILES: NS(=O)(=O)c1cccc(Nc2cc3cc[nH]c(=O)c3c(Nc3ccc(N4CCOCC4)cc3)n2)c1] | MS m/z 493.2 (M + 1). |
| 633 | 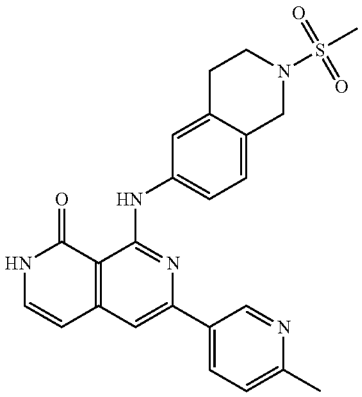 [SMILES: Cc1ccc(-c2cc3cc[nH]c(=O)c3c(Nc3ccc4c(c3)CCN(S(C)(=O)=O)C4)n2)cn1] | MS m/z 462.2 (M + 1). |
| 634 | 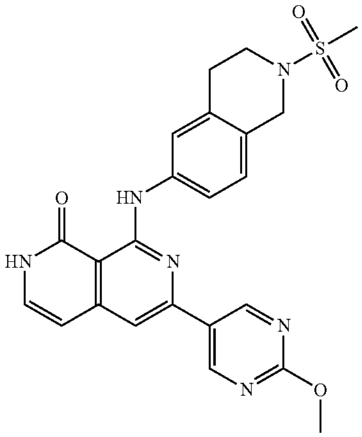 [SMILES: COc1ncc(-c2cc3cc[nH]c(=O)c3c(Nc3ccc4c(c3)CCN(S(C)(=O)=O)C4)n2)cn1] | MS m/z 479.2 (M + 1). |

TABLE 1-continued
| No | Structure | Physical Data $^1H$ NMR 400 MHz (DMSO-$d_6$) and/or MS (m/z) |
|---|---|---|
| 635 | 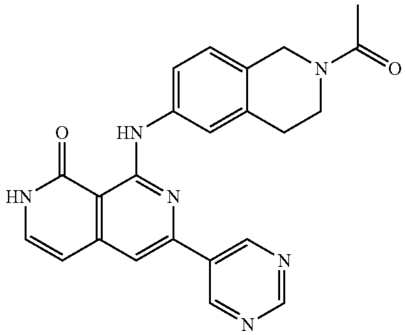 [SMILES: CC(=O)N1CCc2cc(Nc3nc(-c4cncnc4)cc4cc[nH]c(=O)c34)ccc2C1] | MS m/z 413.2 (M + 1). |
| 636 | 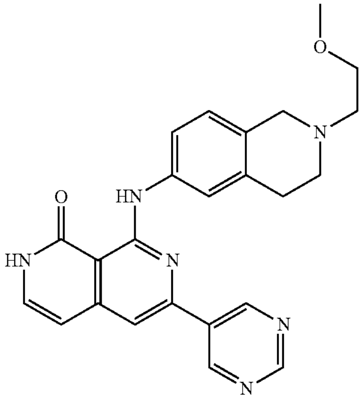 [SMILES: COCCN1CCc2cc(Nc3nc(-c4cncnc4)cc4cc[nH]c(=O)c34)ccc2C1] | MS m/z 429.2 (M + 1). |
| 637 | 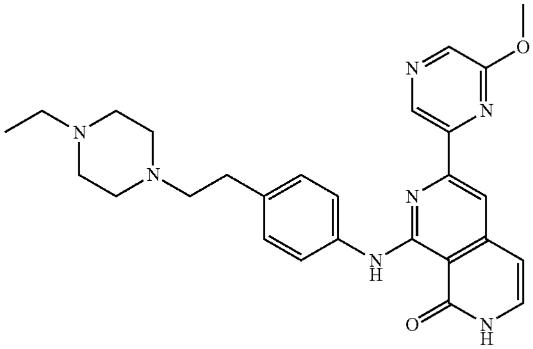 [SMILES: CCN1CCN(CCc2ccc(Nc3nc(-c4cncc(OC)n4)cc4cc[nH]c(=O)c34)cc2)CC1] | $^1H$ NMR (400 MHz, DMSO-d6) δ 12.03 (s, 1H), 9.06 (s, 1H), 7.84 (d, 2H, J = 8.8 Hz), 7.85 (s, 1H), 7.49 (t, 1H, J = 6.4 Hz), 7.36 (d, 2H, J = 8.8 Hz), 6.69 (d, 1H, J = 6.8 Hz), 4.08 (s, 3H), 3.43-3.40 (m, 2H), 3.32-3.31 (m, 2H), 3.09 (q, 2H, J = 7.2 Hz), 2.50 (brs, 8H), 1.28 (t, 3H, J = 7.2 Hz); MS m/z 486.2 (M + l). |
| 638 | 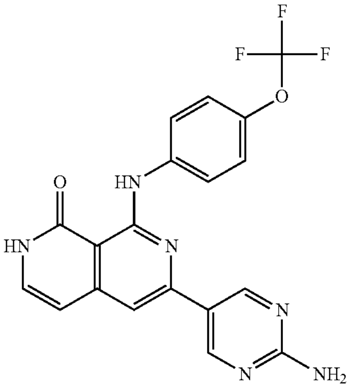 [SMILES: Nc1ncc(-c2cc3cc[nH]c(=O)c3c(Nc3ccc(OC(F)(F)F)cc3)n2)cn1] | $^1H$ NMR (400 MHz, DMSO-d6) δ 12.12 (s, 1H), 9.42 (s, 1H), 9.26 (s, 1H), 7.86 (d, 2H, J = 8.8 Hz), 7.15 (s, 1H), 6.96 (d, 2H, J = 8.8 Hz), 6.90 (d, 1H, J = 5.2 Hz), 6.31 (d, 1H, J = 6.8 Hz); MS m/z 414.03 (M + 1). |

TABLE 1-continued
| No | Structure | Physical Data $^1$H NMR 400 MHz (DMSO-$d_6$) and/or MS (m/z) |
|---|---|---|
| 639 | 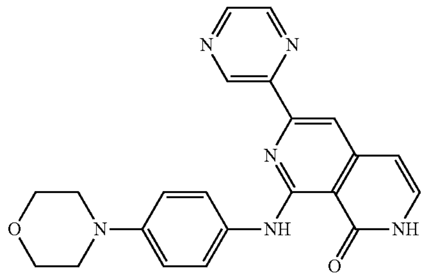 [SMILES: O=c1[nH]ccc2cc(-c3cnccn3)nc(Nc3ccc(N4CCOCC4)cc3)c12] | $^1$H NMR (400 MHz, DMSO-d6) δ 12.16 (s, 1H), 8.99 (s, 1H), 8.97 (s, 1H), 7.84 (d, 2H, J = 8.4 Hz), 7.66 (s, 1H), 7.46 (s, 1H), 7.43 (d, 2H, J = 8.4 Hz), 7.41 (m, 1H), 6.52 (d, 1H, J = 7.2 Hz), 3.71 (t, 4H, J = 4.8 Hz), 3.05 (t, 4H, J = 4.8 Hz); MS m/z 401.2 (M + 1), |
| 640 | 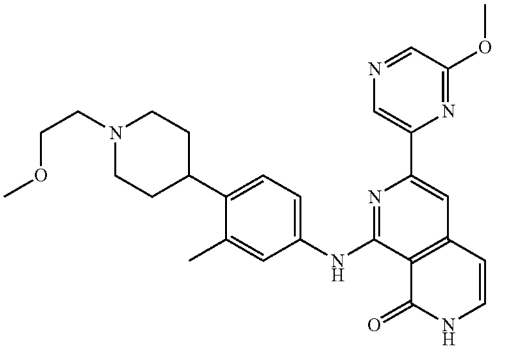 | $^1$H NMR (400 MHz, DMSO-d6) δ 12.02 (s, 1H), 9.01 (s, 1H), 8.40 (s, 1H), 7.81 (s, 1H), 7.72 (dd, 1H, J = 3.8, 2 Hz), 7.65 (d, 1H, J = 2 Hz), 7.48 (t, 1H, J = 6.4 Hz), 7.24 (d, 1H, J = 8.8 Hz), 6.63 (d, 1H, J = 6.8 Hz), 3.92 (s, 3H), 3.72-3.30 (m, 2H), 3.59-3.58 (m, 2H), 3.35 (s, 3H), 3.30-3.27 (m, 2H), 3.14-3.06 (m, 2H), 2.82- 2.76 (m, 1H, 2.72 (s, 3H), 2.14 (m, 2H), 1.97 (m, 2H); MS m/z 501.2 (M + 1). |
| 641 | 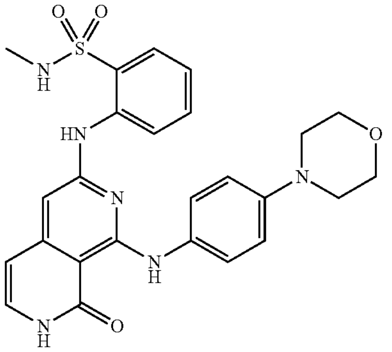 [SMILES: CNS(=O)(=O)c1ccccc1Nc1cc2cc[nH]c(=O)c2c(Nc2ccc(N3CCOCC3)cc2)n1] | MS m/z 507.2 (M + 1). |
| 642 | 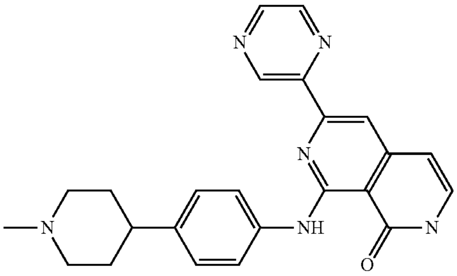 [SMILES: CN1CCC(c2ccc(Nc3nc(-c4cnccn4)cc4cc[nH]c(=O)c34)cc2)CC1] | $^1$H NMR (400 MHz, DMSO-d6) δ 12.17 (s, 1H), 8.98 (s, 1H), 8.96 (s, 1H), 7.80 (d, 2H, J = 8.4 Hz), 7.66 (s, 1H), 7.46 (s, 1H), 7.39 (d, 2H, J = 8.4 Hz), 7.32 (m, 1H), 6.52 (d, 1H, J = 7.2 Hz), 3.48 (s, 3H), 2.93 (m, 4H), 2.72 (m, 1H), 2.04 (m, 2H), 1.94 (m, 2H); MS m/z 413.2 (M + 1). |

TABLE 1-continued

| No | Structure | Physical Data $^1H$ NMR 400 MHz (DMSO-$d_6$) and/or MS (m/z) |
|---|---|---|
| 643 | 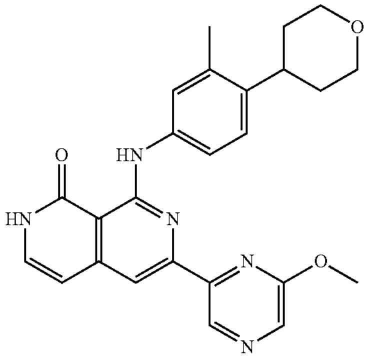 [SMILES: COc1cncc(-c2cc3cc[nH]c(=O)c3c(Nc3ccc(C4CCOCC4)c(C)c3)n2)n1] | $^1H$ NMR (400 MHz, DMSO-d6) δ 11.95 (s, 1H), 9.08 (s, 1H), 8.42 (s, 1H), 7.82 (s, 1H), 7.77 (dd, 1H, J = 3.8, 2 Hz), 7.64 (d, 1H, J = 2 Hz), 7.47 (t, 1H, J = 6.4 Hz), 7.27 (d, 1H, J = 8.8 Hz), 6.68 (d, 1H, J = 6.8 Hz), 4.08 (s, 3H), 3.98-3.95 (m, 2H), 3.51-3.45 (m, 2H), 2.98-2.93 (m, 1H), 2.38 (s, 3H), 1.72-1.62 (m, 4H); MS m/z 444.1 (M + 1). |
| 644 | 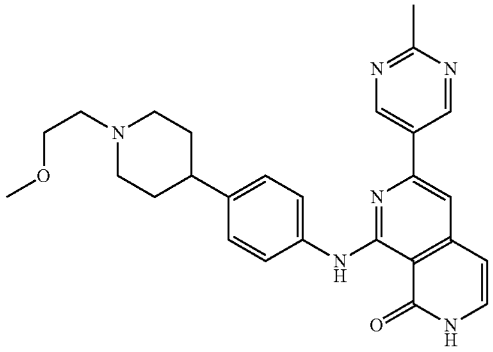 | $^1H$ NMR (400 MHz, DMSO-d6) δ 11.97 (s, 1H), 9.34 (s, 2H), 7.79 (d, 2H, J = 8.8 Hz), 7.58 (s, 1H), 7.47-7.44 (m, 1H), 7.26 (d, 2H, J = 8.8 Hz), 6.53 (d, 1H, J = 7.2 Hz), 3.58-3.55 (m, 2H), 3.32 (s, 3H), 3.30-3.28 (m, 3H), 3.14-3.06 (m, 2H), (m, 3H), 2.82-2.76 (m, 4H), 2.71 (s, 3H), 2.14 (m, 2H), 1.98 (m, 2H); MS m/z 431.2 (M + 1). |
| 645 | 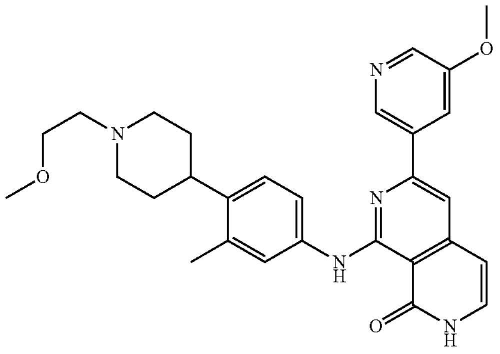 | $^1H$ NMR (400 MHz, DMSO-d6) δ 11.97 (s, 1H), 8.95 (d, 1H, J = 2.0 Hz), 8.41 (d, 1H, J = 2.8 Hz), 8.0 (brs, 1H), 7.77-7.75 (m, 1H), 7.71 (d, 1H, J = 2.4 Hz), 7.64 (s, 1H), 7.46 (t, 1H, J = 6.8 Hz), 7.17 (d, 1H, J = 8.4 Hz), 6.58 (dd, 1H, J = 7.2, 1.2 Hz), 3.97 (s, 3H), 3.72-3.30 (m, 2H), 3.59-3.58 (m, 2H), 3.35 (s, 3H), 3.30-3.28 (m, 2H), 3.14-3.06 (m, 2H), 2.82-2.76 (m, 1H), 2.71 (s, 3H), 2.14 (m, 2H), 1.98 (m, 2H); MS m/z 500.1 (M + 1). |
| 646 | 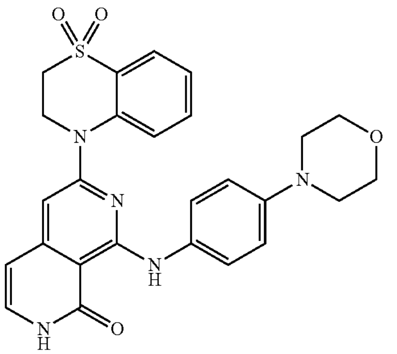 [SMILES: O=c1[nH]ccc2cc(N3CCS(=O)(=O)c4ccccc43)nc(Nc3ccc(N4CCOCC4)cc3)c12] | MS m/z 504.1 (M + 1) |

TABLE 1-continued
| No | Structure | Physical Data $^1$H NMR 400 MHz (DMSO-$d_6$) and/or MS (m/z) |
|---|---|---|
| 647 | 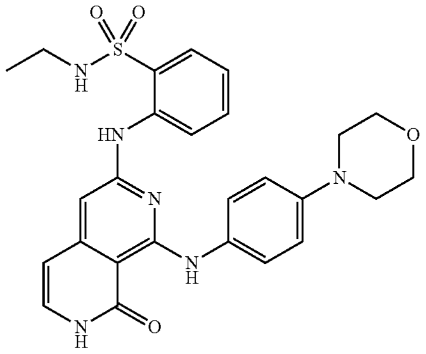 [SMILES: CCNS(=O)(=O)c1ccccc1Nc1cc2cc[nH]c(=O)c2c(Nc2ccc(N3CCOCC3)cc2)n1] | MS m/z 521.14 (M + 1). |
| 648 | 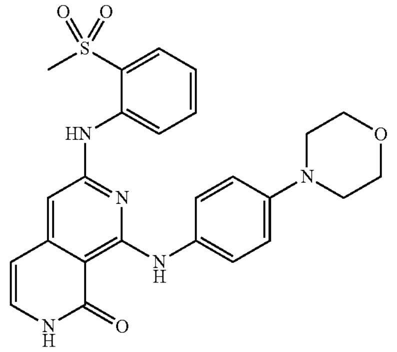 [SMILES: CS(=O)(=O)c1ccccc1Nc1cc2cc[nH]c(=O)c2c(Nc2ccc(N3CCOCC3)cc2)n1] | MS m/z 492.18 (M + 1). |
| 649 | 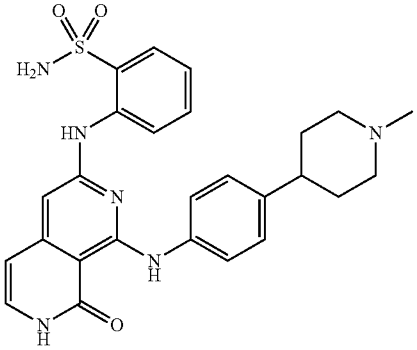 [SMILES: CN1CCC(c2ccc(Nc3nc(Nc4ccccc4S(N)(=O)=O)cc4cc[nH]c(=O)c34)cc2)CC1] | MS m/z 505.2 (M + 1). |
| 650 | 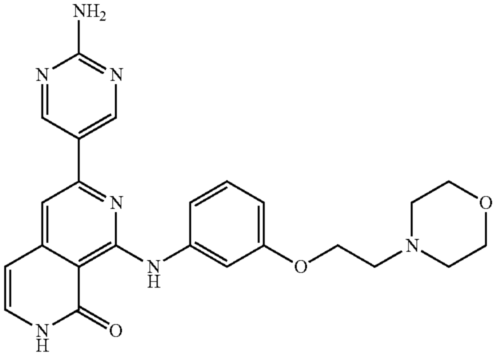 [SMILES: Nc1ncc(-c2cc3cc[nH]c(=O)c3c(Nc3cccc(OCCN4CCOCC4)c3)n2)cn1] | MS m/z 460.1 (M + 1). |

TABLE 1-continued
| No | Structure | Physical Data $^1H$ NMR 400 MHz (DMSO-$d_6$) and/or MS (m/z) |
|---|---|---|
| 651 | 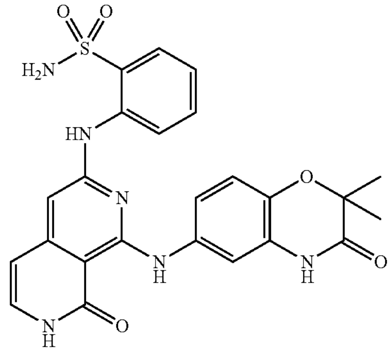 [SMILES: CC1(C)Oc2ccc(Nc3nc(Nc4ccccc4S(N)(=O)=O)cc4cc[nH]c(=O)c34)cc2NC1=O] | MS m/z 507.13 (M + 1). |
| 652 | 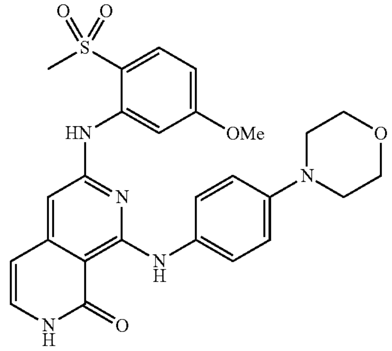 [SMILES: COc1ccc(S(C)(=O)=O)c(Nc2cc3cc[nH]c(=O)c3c(Nc3ccc(N4CCOCC4)cc3)n2)c1] | MS m/z 522.1 (M + 1). |
| 653 | 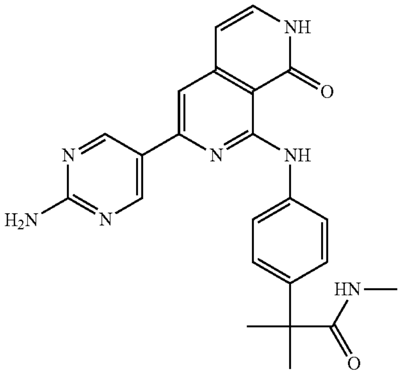 [SMILES: CNC(=O)C(C)(C)c1ccc(Nc2nc(-c3cnc(N)nc3)cc3cc[nH]c(=O)c23)cc1] | MS m/z 430.16 (M + 1). |
| 654 | 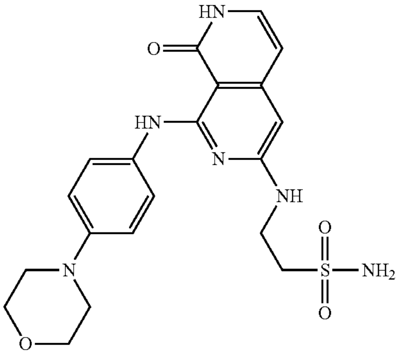 [SMILES: NS(=O)(=O)CCNc1cc2cc[nH]c(=O)c2c(Nc2ccc(N3CCOCC3)cc2)n1] | MS m/z 445.1 (M + 1). |

TABLE 1-continued
| No | Structure | Physical Data $^{1}H$ NMR 400 MHz (DMSO-$d_6$) and/or MS (m/z) |
|---|---|---|
| 655 | 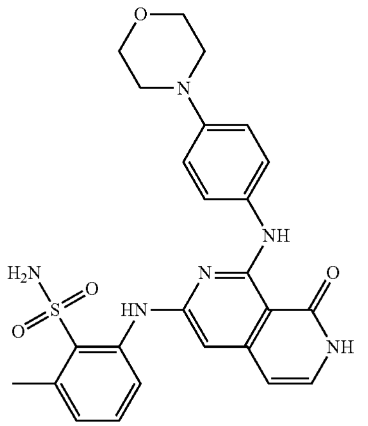 [SMILES: Cc1cccc(Nc2cc3cc[nH]c(=O)c3c(Nc3ccc(N4CCOCC4)cc3)n2)c1S(N)(=O)=O] | MS m/z 507.1 (M + 1). |
| 656 | 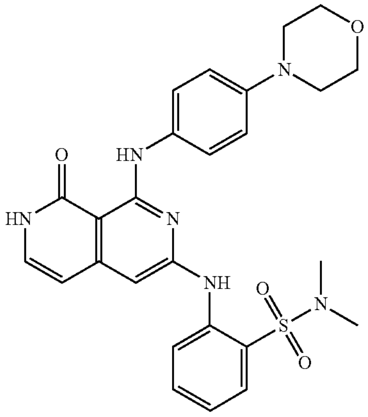 [SMILES: CN(C)S(=O)(=O)c1ccccc1Nc1cc2cc[nH]c(=O)c2c(Nc2ccc(N3CCOCC3)cc2)n1] | MS m/z 521.2 (M + 1). |
| 657 | 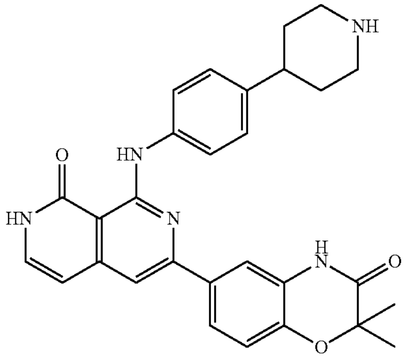 [SMILES: CC1(C)Oc2ccc(-c3cc4cc[nH]c(=O)c4c(Nc4ccc(C5CCNCC5)cc4)n3)cc2NC1=O] | MS m/z 496.12 (M + 1). |

TABLE 1-continued
| No | Structure | Physical Data $^1H$ NMR 400 MHz (DMSO-$d_6$) and/or MS (m/z) |
|---|---|---|
| 658 | 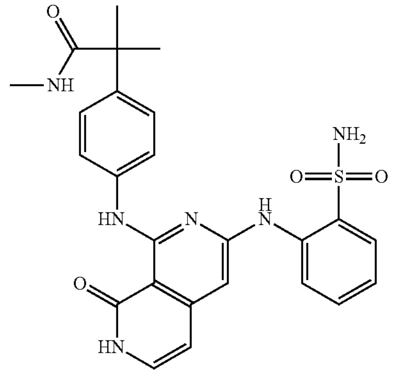 [SMILES: CNC(=O)C(C)(C)c1ccc(Nc2nc(Nc3ccccc3S(N)(=O)=O)cc3cc[nH]c(=O)c23)cc1] | MS m/z 507.1 (M + 1). |
| 659 | 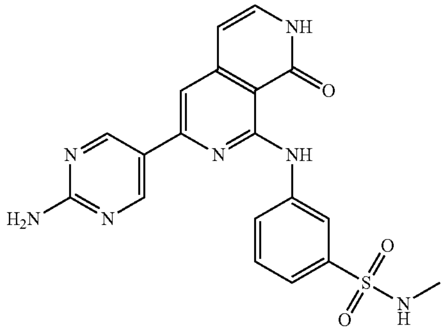 [SMILES: CNS(=O)(=O)c1cccc(Nc2nc(-c3cnc(N)nc3)cc3cc[nH]c(=O)c23)c1] | MS m/z 424.2 (M + 1). |
| 660 | 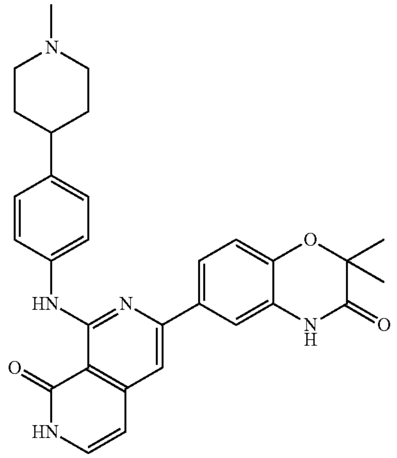 [SMILES: CN1CCC(c2ccc(Nc3nc(-c4ccc5c(c4)NC(=O)C(C)(C)O5)cc4cc[nH]c(=O)c34)cc2)CC1] | MS m/z 510.2 (M + 1). |

TABLE 1-continued
| No | Structure | Physical Data $^1H$ NMR 400 MHz (DMSO-$d_6$) and/or MS (m/z) |
|---|---|---|
| 661 | 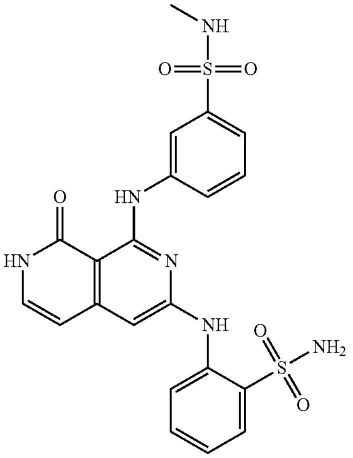 [SMILES: CNS(=O)(=O)c1cccc(Nc2nc(Nc3ccccc3S(N)(=O)=O)cc3cc[nH]c(=O)c23)c1] | MS m/z 501.2 (M + 1). |
| 662 | 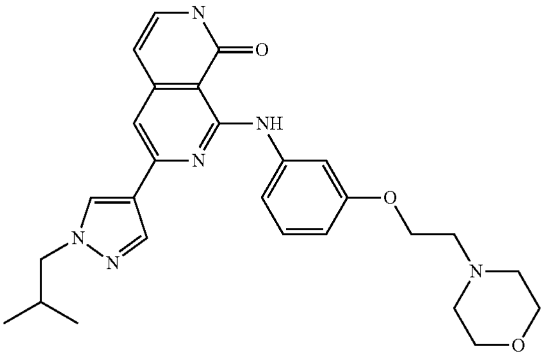 [SMILES: CC(C)Cn1cc(-c2cc3cc[nH]c(=O)c3c(Nc3cccc(OCCN4CCOCC4)c3)n2)cn1] | MS m/z 489.12 (M + 1). |
| 663 | 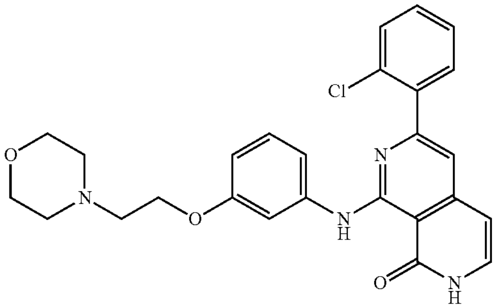 [SMILES: O=c1[nH]ccc2cc(-c3ccccc3Cl)nc(Nc3cccc(OCCN4CCOCC4)c3)c12] | MS m/z 477.1 (M + 1). |
| 664 | 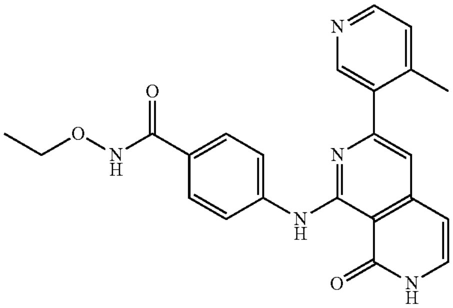 [SMILES: CCONC(=O)c1ccc(Nc2nc(-c3cnccc3C)cc3cc[nH]c(=O)c23)cc1] | MS m/z 416.2 (M + 1). |

TABLE 1-continued
| No | Structure | Physical Data $^1H$ NMR 400 MHz (DMSO-$d_6$) and/or MS (m/z) |
|---|---|---|
| 665 | 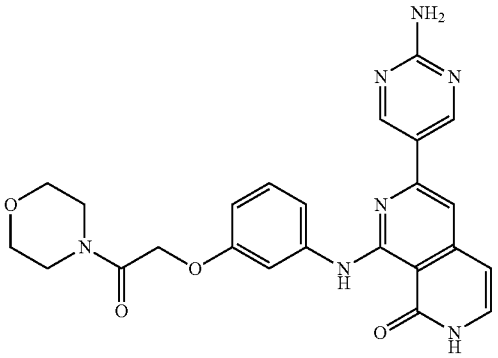 [SMILES: Nc1ncc(-c2cc3cc[nH]c(=O)c3c(Nc3cccc(OCC(=O)N4CCOCC4)c3)n2)cn1] | MS m/z 474.2 (M + 1). |
| 666 | 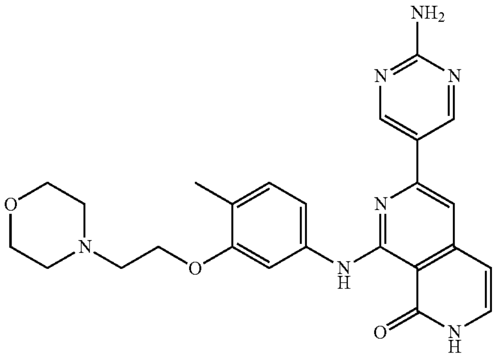 [SMILES: Cc1ccc(Nc2nc(-c3cnc(N)nc3)cc3cc[nH]c(=O)c23)cc1OCCN1CCOCC1] | MS m/z 474.2 (M + 1). |
| 667 | 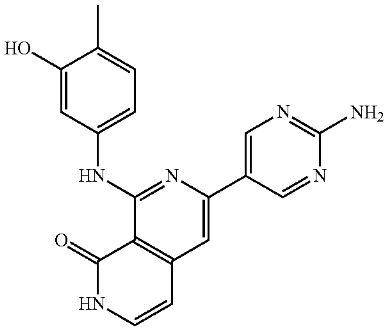 [SMILES: Cc1ccc(Nc2nc(-c3cnc(N)nc3)cc3cc[nH]c(=O)c23)cc1O] | MS m/z 361.1 (M + 1). |
| 668 | 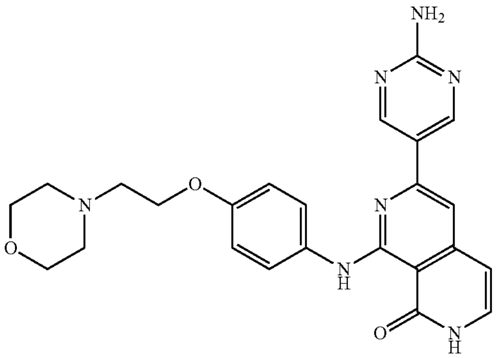 [SMILES: Nc1ncc(-c2cc3cc[nH]c(=O)c3c(Nc3ccc(OCCN4CCOCC4)cc3)n2)cn1] | MS m/z 460.1 (M + 1). |

TABLE 1-continued
| No | Structure | Physical Data $^1$H NMR 400 MHz (DMSO-$d_6$) and/or MS (m/z) |
|---|---|---|
| 669 | 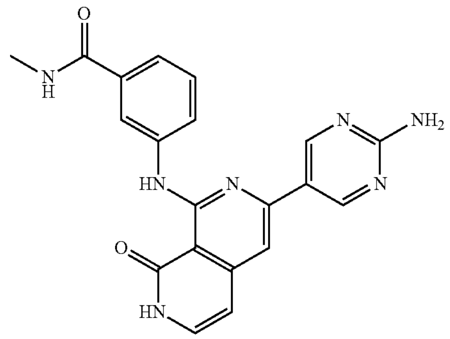 [SMILES: CNC(=O)c1cccc(Nc2nc(-c3cnc(N)nc3)cc3cc[nH]c(=O)c23)c1] | MS m/z 388.12 (M + 1). |
| 670 | 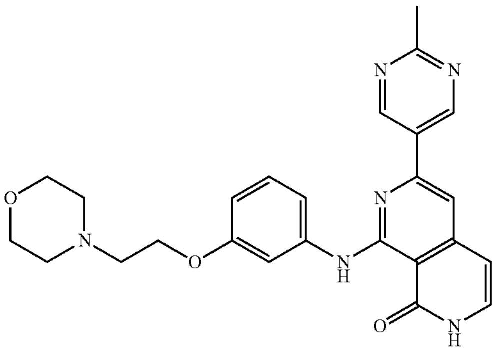 [SMILES: Cc1ncc(-c2cc3cc[nH]c(=O)c3c(Nc3cccc(OCCN4CCOCC4)c3)n2)cn1] | MS m/z 459.2 (M + 1). |
| 671 | 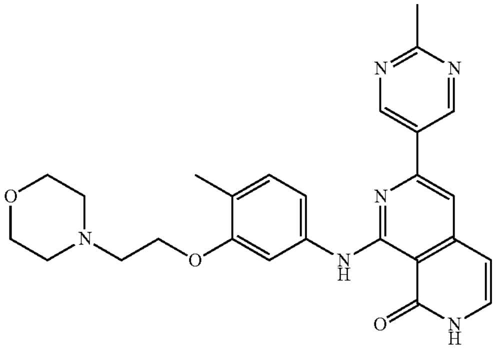 [SMILES: Cc1ncc(-c2cc3cc[nH]c(=O)c3c(Nc3ccc(C)c(OCCN4CCOCC4)c3)n2)cn1] | MS m/z 473.2 (M + 1). |
| 672 | 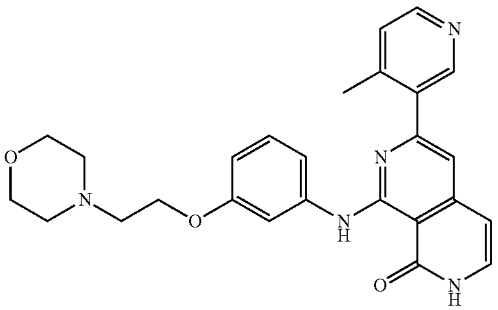 [SMILES: Cc1ccncc1-c1cc2cc[nH]c(=O)c2c(Nc2cccc(OCCN3CCOCC3)c2)n1] | MS m/z 458.2 (M + 1). |

TABLE 1-continued
| No | Structure | Physical Data $^1H$ NMR 400 MHz ($DMSO-d_6$) and/or MS (m/z) |
|---|---|---|
| 673 | 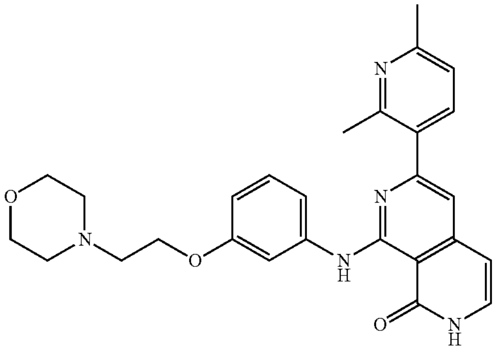 [SMILES: Cc1ccc(-c2cc3cc[nH]c(=O)c3c(Nc3cccc(OCCN4CCOCC4)c3)n2)c(C)n1] | MS m/z 472.2 (M + 1). |
| 674 | 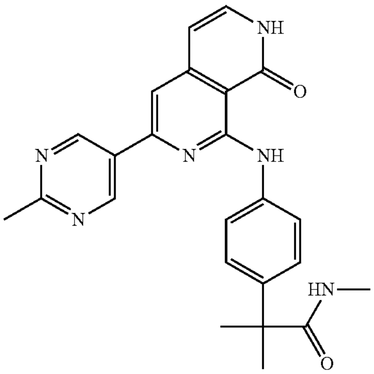 | MS m/z 429.2 (M + 1). |
| 675 | 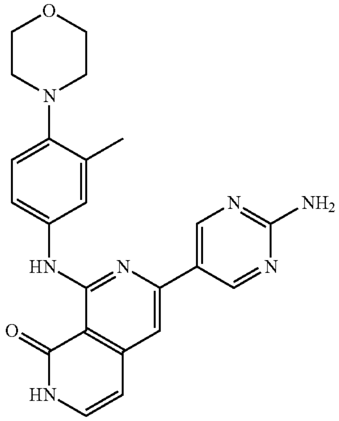 [SMILES: Cc1cc(Nc2nc(-c3cnc(N)nc3)cc3cc[nH]c(=O)c23)ccc1N1CCOCC1] | MS m/z 430.2 (M + 1). |
| 676 | 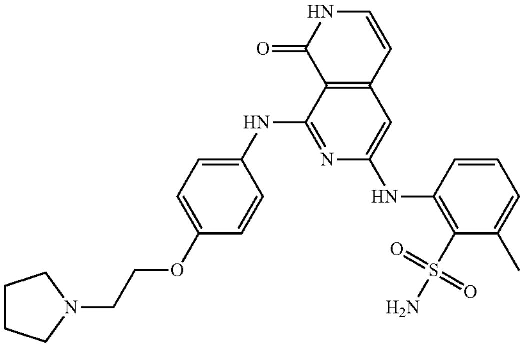 [SMILES: Cc1cccc(Nc2cc3cc[nH]c(=O)c3c(Nc3ccc(OCCN4CCCC4)cc3)n2)c1S(N)(=O)=O] | MS m/z 535.2 (M + 1). |

TABLE 1-continued
| No | Structure | Physical Data $^1$H NMR 400 MHz (DMSO-$d_6$) and/or MS (m/z) |
|---|---|---|
| 678 | 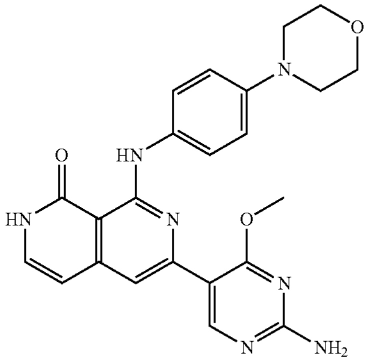 [SMILES: COc1nc(N)ncc1-c1cc2cc[nH]c(=O)c2c(Nc2ccc(N3CCOCC3)cc2)n1] | MS m/z 446.2 (M + 1). |
| 679 | 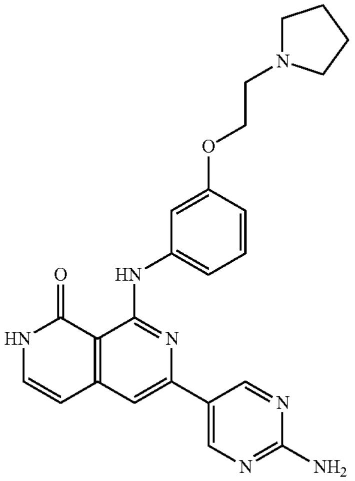 [SMILES: Nc1ncc(-c2cc3cc[nH]c(=O)c3c(Nc3cccc(OCCN4CCCC4)c3)n2)cn1] | MS m/z 444.2 (M + 1). |
| 680 | 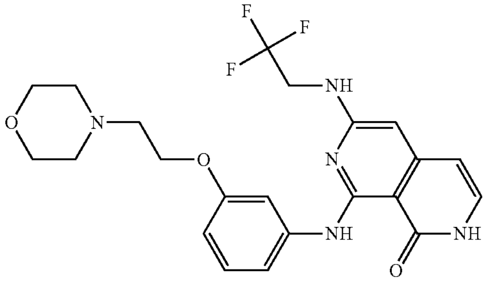 [SMILES: O=c1[nH]ccc2cc(NCC(F)(F)F)nc(Nc3cccc(OCCN4CCOCC4)c3)c12] | MS m/z 464.2 (M + 1). |
| 681 | 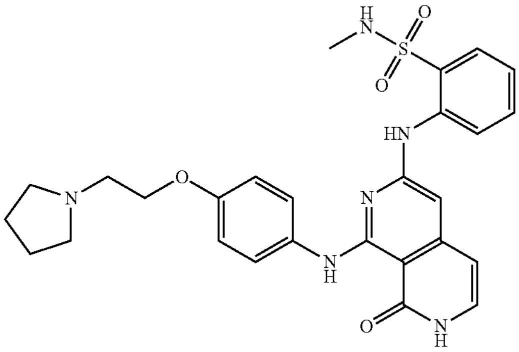 [SMILES: CNS(=O)(=O)c1ccccc1Nc1cc2cc[nH]c(=O)c2c(Nc2ccc(OCCN3CCCC3)cc2)n1] | MS m/z 535.2 (M + 1). |

TABLE 1-continued
| No | Structure | Physical Data $^1H$ NMR 400 MHz (DMSO-$d_6$) and/or MS (m/z) |
|---|---|---|
| 682 | 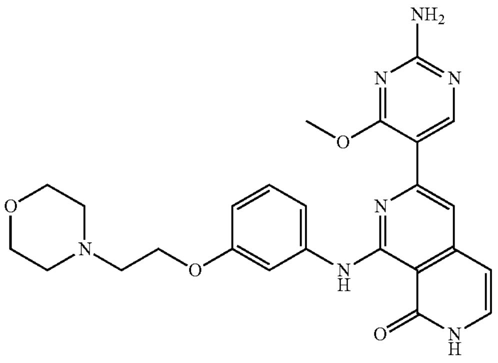 [SMILES: COc1nc(N)ncc1-c1cc2cc[nH]c(=O)c2c(Nc2cccc(OCCN3CCOCC3)c2)n1] | MS m/z 490.2 (M + 1). |
| 683 | 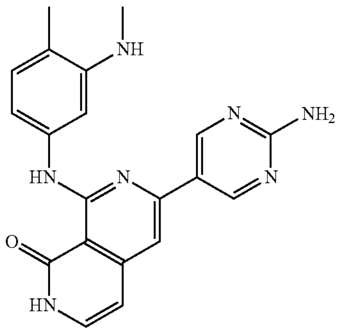 [SMILES: CNc1cc(Nc2nc(-c3cnc(N)nc3)cc3cc[nH]c(=O)c23)ccc1C] | MS m/z 374.2 (M + 1). |
| 684 | 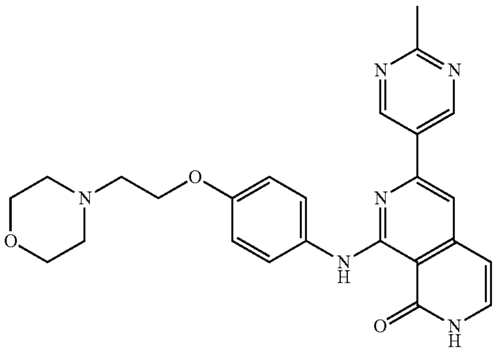 [SMILES: Cc1ncc(-c2cc3cc[nH]c(=O)c3c(Nc3ccc(OCCN4CCOCC4)cc3)n2)cn1] | MS m/z 459.2 (M + 1). |
| 685 | 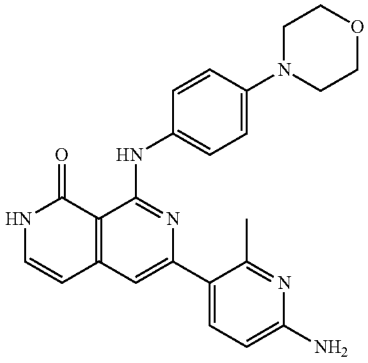 [SMILES: Cc1nc(N)ccc1-c1cc2cc[nH]c(=O)c2c(Nc2ccc(N3CCOCC3)cc2)n1] | MS m/z 429.2 (M + 1). |

TABLE 1-continued
| No | Structure | Physical Data $^1$H NMR 400 MHz (DMSO-$d_6$) and/or MS (m/z) |
|---|---|---|
| 686 | 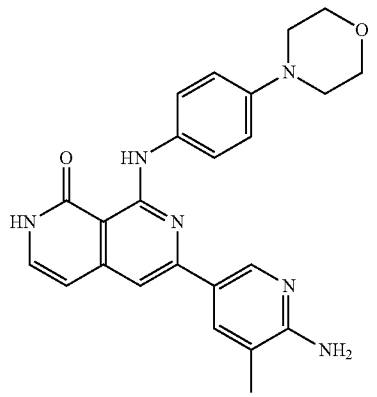 [SMILES: Cc1cc(-c2cc3cc[nH]c(=O)c3c(Nc3ccc(N4CCOCC4)cc3)n2)cnc1N] | MS m/z 429.2 (M + 1). |
| 687 | 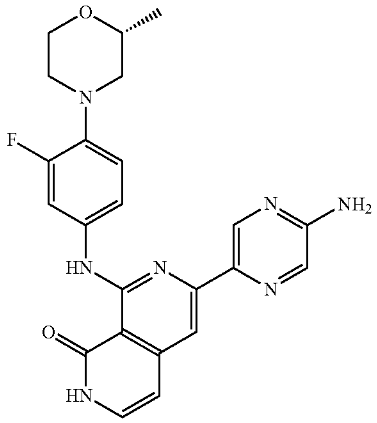 [SMILES: C[C@@H]1CN(c2ccc(Nc3nc(-c4cnc(N)cn4)cc4cc[nH]c(=O)c34)cc2F)CCO1] | MS m/z 448.2 (M + 1). |
| 688 | 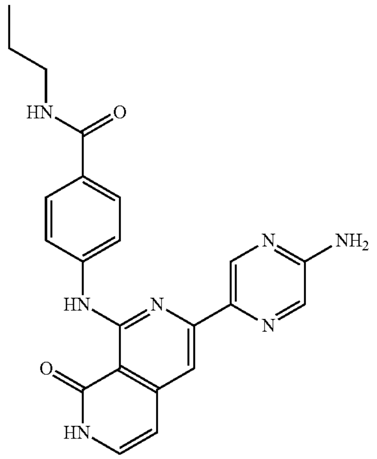 [SMILES: CCCNC(=O)c1ccc(Nc2nc(-c3cnc(N)cn3)cc3cc[nH]c(=O)c23)cc1] | MS m/z 416.2 (M + 1). |
| 689 | 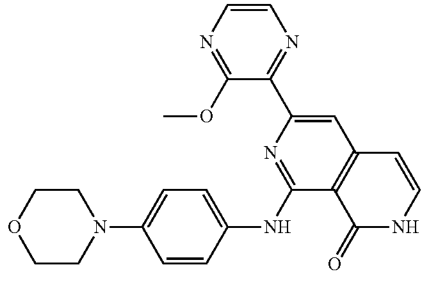 [SMILES: COc1nccnc1-c1cc2cc[nH]c(=O)c2c(Nc2ccc(N3CCOCC3)cc2)n1] | MS m/z 431.2 (M + 1). |

TABLE 1-continued
| No | Structure | Physical Data $^1$H NMR 400 MHz (DMSO-$d_6$) and/or MS (m/z) |
|---|---|---|
| 690 | 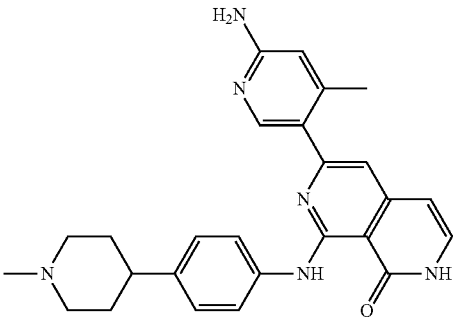 [SMILES: Cc1cc(N)ncc1-c1cc2cc[nH]c(=O)c2c(Nc2ccc(C3CCN(C)CC3)cc2)n1] | MS m/z 441.2 (M + 1). |
| 691 | 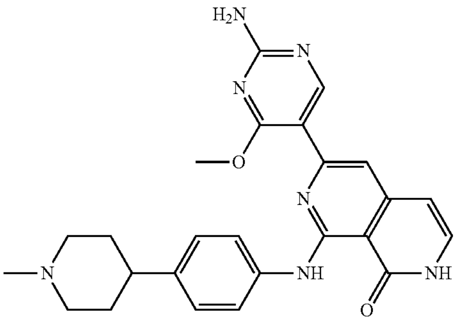 [SMILES: COc1nc(N)ncc1-c1cc2cc[nH]c(=O)c2c(Nc2ccc(C3CCN(C)CC3)cc2)n1] | MS m/z 458.2 (M + 1). |
| 692 | 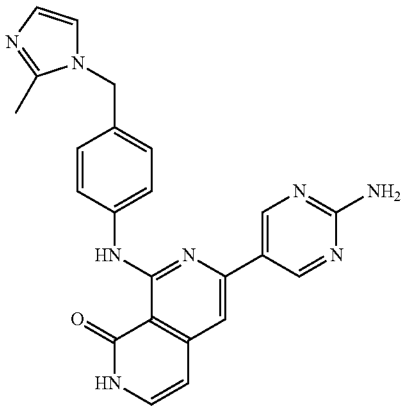 [SMILES: Cc1nccn1Cc1ccc(Nc2nc(-c3cnc(N)nc3)cc3cc[nH]c(=O)c23)cc1] | MS m/z 425.2 (M + 1). |
| 693 | 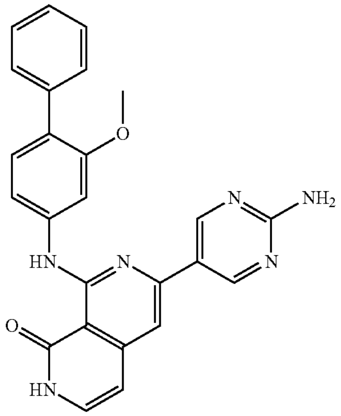 [SMILES: COc1cc(Nc2nc(-c3cnc(N)nc3)cc3cc[nH]c(=O)c23)ccc1-c1ccccc1] | MS m/z 437.2 (M + 1). |

TABLE 1-continued
| No | Structure | Physical Data $^1H$ NMR 400 MHz (DMSO-$d_6$) and/or MS (m/z) |
|---|---|---|
| 694 | 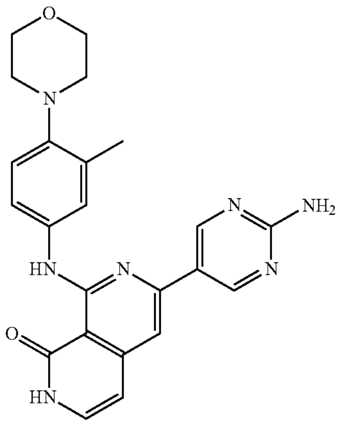 [SMILES: Cc1cc(Nc2nc(-c3cnc(N)nc3)cc3cc[nH]c(=O)c23)ccc1N1CCOCC1] | MS m/z 430.2 (M + 1). |
| 695 | 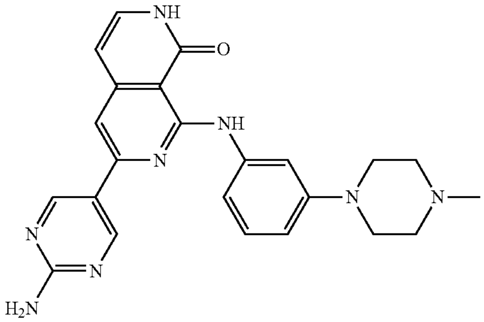 [SMILES: CN1CCN(c2cccc(Nc3nc(-c4cnc(N)nc4)cc4cc[nH]c(=O)c34)c2)CC1] | MS m/z 429.2 (M + 1). |
| 696 | 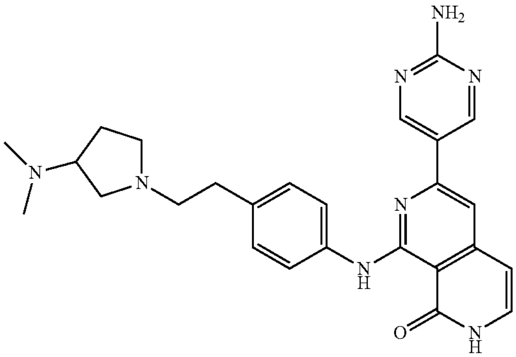 [SMILES: CN(C)C1CCN(CCc2ccc(Nc3nc(-c4cnc(N)nc4)cc4cc[nH]c(=O)c34)cc2)C1] | MS m/z 471.2 (M + 1). |
| 697 | 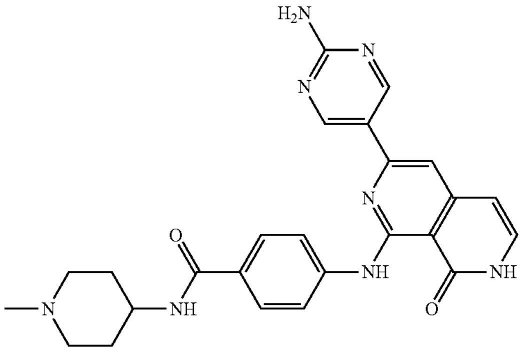 [SMILES: CN1CCC(NC(=O)c2ccc(Nc3nc(-c4cnc(N)nc4)cc4cc[nH]c(=O)c34)cc2)CC1] | MS m/z 471.2 (M + 1). |

TABLE 1-continued
| No | Structure | Physical Data $^1H$ NMR 400 MHz (DMSO-$d_6$) and/or MS (m/z) |
|---|---|---|
| 698 | 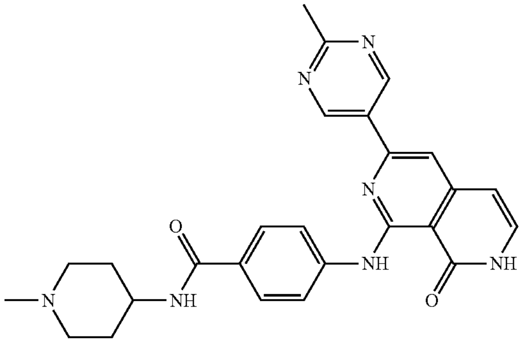 [SMILES: Cc1ncc(-c2cc3cc[nH]c(=O)c3c(Nc3ccc(C(=O)NC4CCN(C)CC4)cc3)n2)cn1] | MS m/z 470.2 (M + 1). |
| 699 | 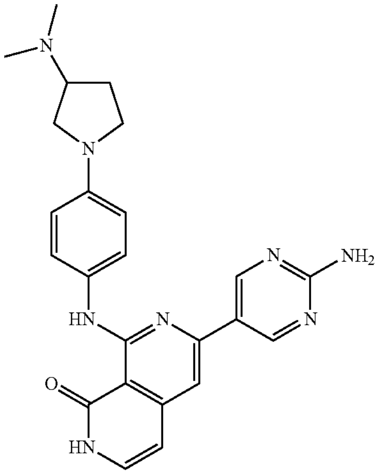 [SMILES: CN(C)C1CCN(c2ccc(Nc3nc(-c4cnc(N)nc4)cc4cc[nH]c(=O)c34)cc2)C1] | MS m/z 443.2 (M + 1). |
| 700 | 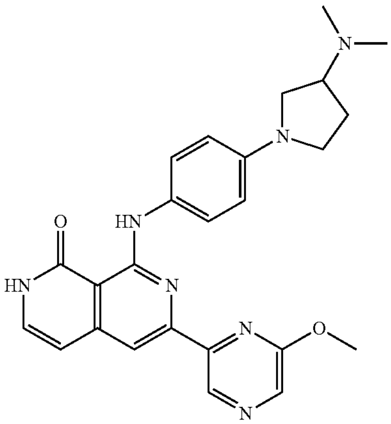 [SMILES: COc1cncc(-c2cc3cc[nH]c(=O)c3c(Nc3ccc(N4CCC(N(C)C)C4)cc3)n2)n1] | MS m/z 458.2 (M + 1). |

TABLE 1-continued
| No | Structure | Physical Data $^1H$ NMR 400 MHz (DMSO-$d_6$) and/or MS (m/z) |
|---|---|---|
| 701 | 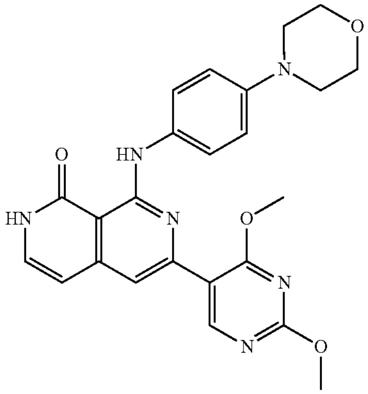 [SMILES: COc1ncc(-c2cc3cc[nH]c(=O)c3c(Nc3ccc(N4CCOCC4)cc3)n2)c(OC)n1] | MS m/z 461.2 (M + 1). |
| 702 | 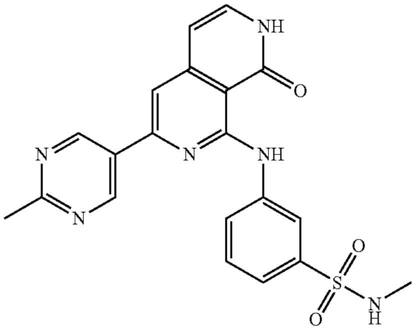 | MS m/z 423.2 (M + 1). |
| 703 | 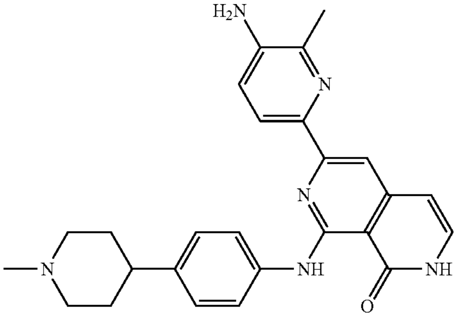 [SMILES: Cc1nc(-c2cc3cc[nH]c(=O)c3c(Nc3ccc(C4CCN(C)CC4)cc3)n2)ccc1N] | MS m/z 441.2 (M + 1). |
| 704 | 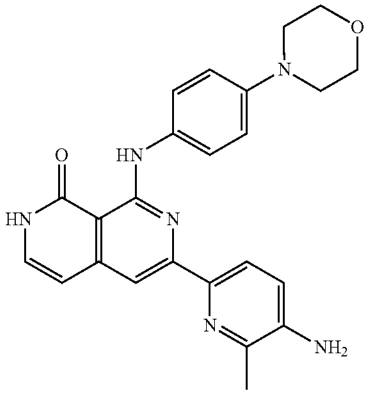 [SMILES: Cc1nc(-c2cc3cc[nH]c(=O)c3c(Nc3ccc(N4CCOCC4)cc3)n2)ccc1N] | MS m/z 429.2 (M + 1). |

TABLE 1-continued
| No | Structure | Physical Data $^1$H NMR 400 MHz (DMSO-$d_6$) and/or MS (m/z) |
|---|---|---|
| 705 | 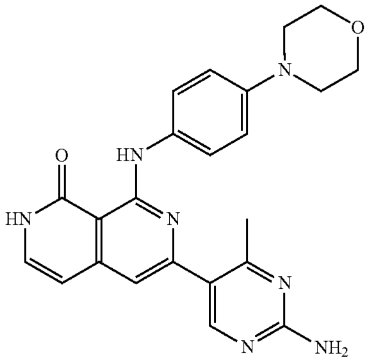 [SMILES: Cc1nc(N)ncc1-c1cc2cc[nH]c(=O)c2c(Nc2ccc(N3CCOCC3)cc2)n1] | MS m/z 430.2 (M + 1). |
| 706 | 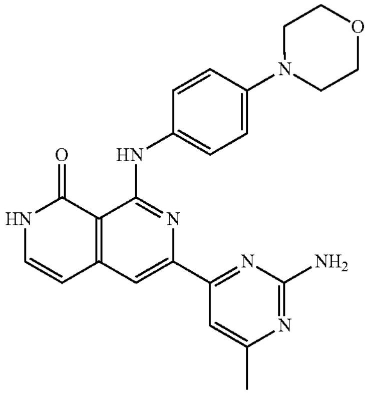 [SMILES: Cc1cc(-c2cc3cc[nH]c(=O)c3c(Nc3ccc(N4CCOCC4)cc3)n2)nc(N)n1] | MS m/z 430.2 (M + 1). |
| 707 | 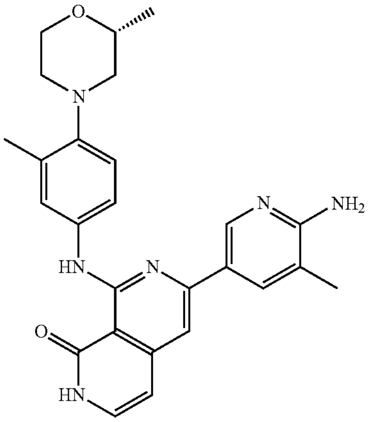 | MS m/z 457.2 (M + 1). |
| 708 | 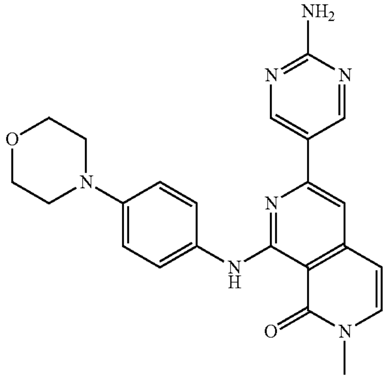 [SMILES: Cn1ccc2cc(-c3cnc(N)nc3)nc(Nc3ccc(N4CCOCC4)cc3)c2c1=O] | MS m/z 430.2 (M + 1). |

TABLE 1-continued
| No | Structure | Physical Data $^1H$ NMR 400 MHz ($DMSO-d_6$) and/or MS (m/z) |
|---|---|---|
| 709 | 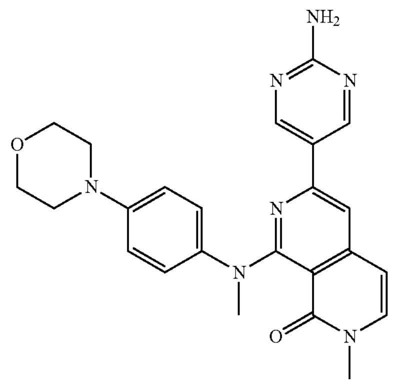 [SMILES: CN(c1ccc(N2CCOCC2)cc1)c1nc(-c2cnc(N)nc2)cc2ccn(C)c(=O)c12] | MS m/z 444.2 (M + 1). |
| 710 | 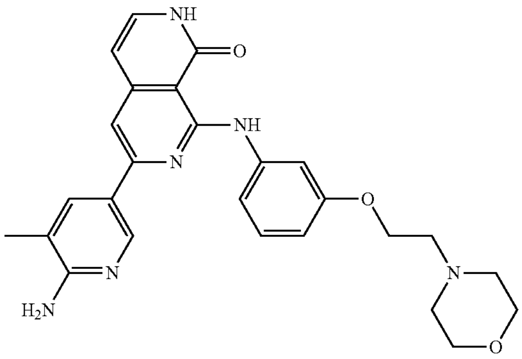 [SMILES: Cc1cc(-c2cc3cc[nH]c(=O)c3c(Nc3cccc(OCCN4CCOCC4)c3)n2)cnc1N] | MS m/z 473.2 (M + 1). |
| 711 | 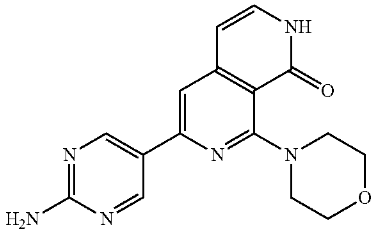 [SMILES: Nc1ncc(-c2cc3cc[nH]c(=O)c3c(N3CCOCC3)n2)cn1] | MS m/z 325.2 (M + 1). |
| 712 | 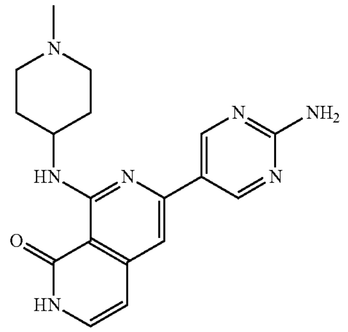 [SMILES: CN1CCC(Nc2nc(-c3cnc(N)nc3)cc3cc[nH]c(=O)c23)CC1] | MS m/z 352.2 (M + 1). |

TABLE 1-continued
| No | Structure | Physical Data $^1$H NMR 400 MHz (DMSO-$d_6$) and/or MS (m/z) |
|---|---|---|
| 713 | 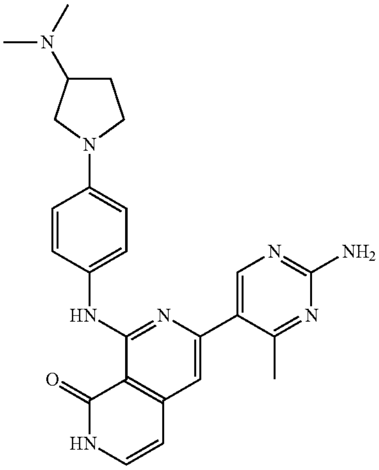 [SMILES: Cc1nc(N)ncc1-c1cc2cc[nH]c(=O)c2c(Nc2ccc(N3CCC(N(C)C)C3)cc2)n1] | MS m/z 456.2 (M + 1). |
| 714 | 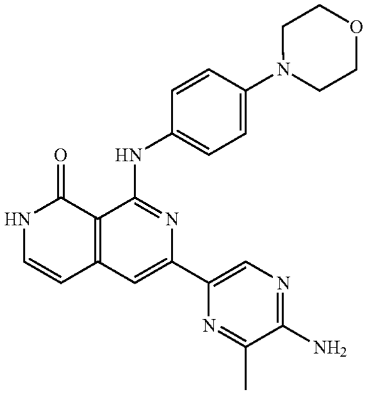 [SMILES: Cc1nc(-c2cc3cc[nH]c(=O)c3c(Nc3ccc(N4CCOCC4)cc3)n2)cnc1N] | MS m/z 430.2 (M + 1). |
| 715 | 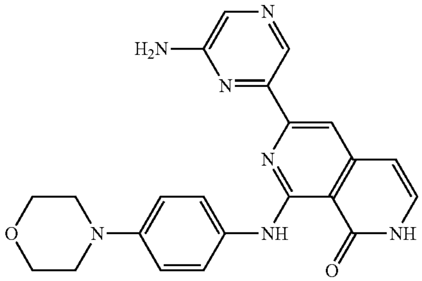 [SMILES: Nc1cncc(-c2cc3cc[nH]c(=O)c3c(Nc3ccc(N4CCOCC4)cc3)n2)n1] | MS m/z 416.2 (M + 1). |
| 716 | 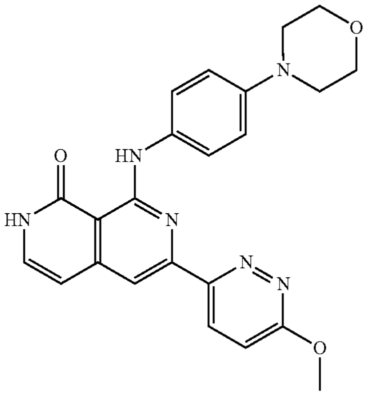 [SMILES: COc1ccc(-c2cc3cc[nH]c(=O)c3c(Nc3ccc(N4CCOCC4)cc3)n2)nn1] | MS m/z 431.2 (M + 1). |

TABLE 1-continued
| No | Structure | Physical Data $^1H$ NMR 400 MHz ($DMSO-d_6$) and/or MS (m/z) |
|---|---|---|
| 717 | 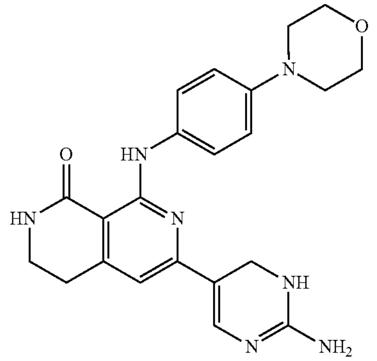 [SMILES: NC1=NC=C(c2cc3c(c(Nc4ccc(N5CCOCC5)cc4)n2)C(=O)NCC3)CN1] | MS m/z 420.2 (M + 1). |
| 718 | 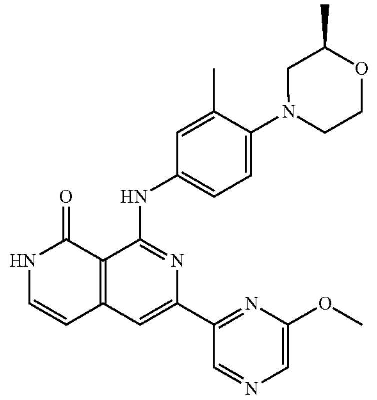 [SMILES: COc1cncc(-c2cc3cc[nH]c(=O)c3c(Nc3ccc(N4CCO[C@H](C)C4)c(C)c3)n2)n1] | MS m/z 459.2 (M + 1). |
| 719 | 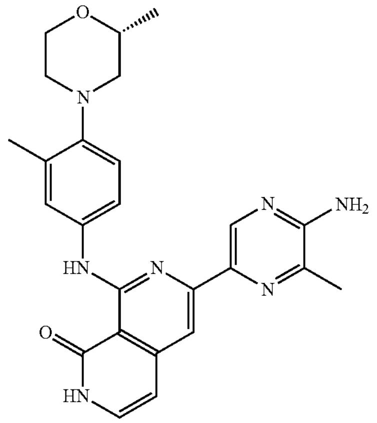 | MS m/z 458.2 (M + 1). |
| 720 | 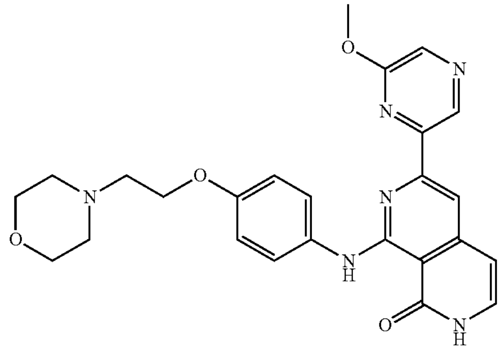 [SMILES: COc1cncc(-c2cc3cc[nH]c(=O)c3c(Nc3ccc(OCCN4CCOCC4)cc3)n2)n1] | MS m/z 475.2 (M + 1). |

TABLE 1-continued
| No | Structure | Physical Data $^1H$ NMR 400 MHz (DMSO-$d_6$) and/or MS (m/z) |
| --- | --- | --- |
| 721 | 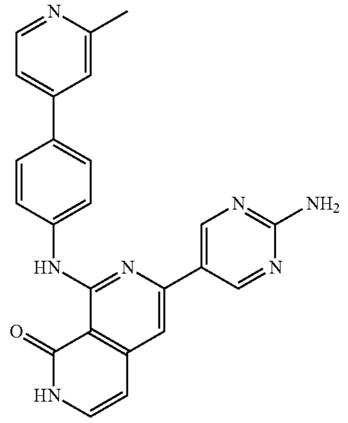 [SMILES: Cc1cc(-c2ccc(Nc3nc(-c4cnc(N)nc4)cc4cc[nH]c(=O)c34)cc2)ccn1] | MS m/z 422.2 (M + 1). |
| 722 | 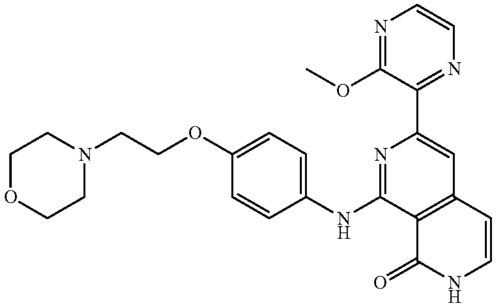 [SMILES: COc1nccnc1-c1cc2cc[nH]c(=O)c2c(Nc2ccc(OCCN3CCOCC3)cc2)n1] | MS m/z 475.2 (M + 1). |
| 723 | 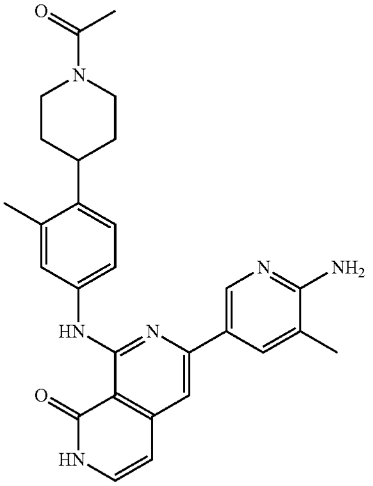 | MS m/z 483.2 (M + 1). |
| 724 | 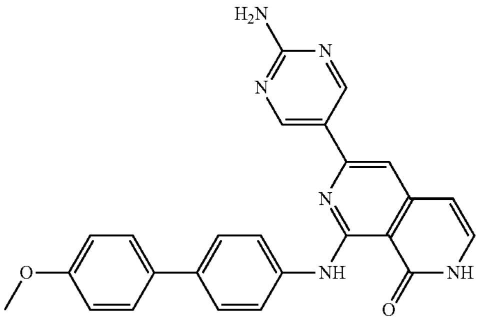 [SMILES: COc1ccc(-c2ccc(Nc3nc(-c4cnc(N)nc4)cc4cc[nH]c(=O)c34)cc2)cc1] | MS m/z 437.2 (M + 1). |

TABLE 1-continued
| No | Structure | Physical Data $^1H$ NMR 400 MHz (DMSO-$d_6$) and/or MS (m/z) |
|---|---|---|
| 725 | 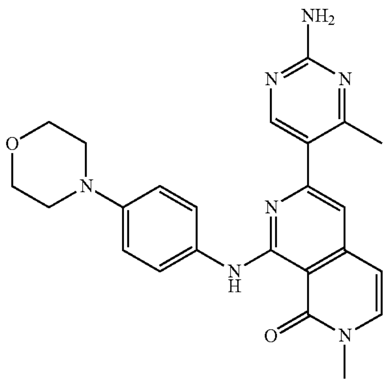 [SMILES: Cc1nc(N)ncc1-c1cc2ccn(C)c(=O)c2c(Nc2ccc(N3CCOCC3)cc2)n1] | MS m/z 444.2 (M + 1). |
| 726 | 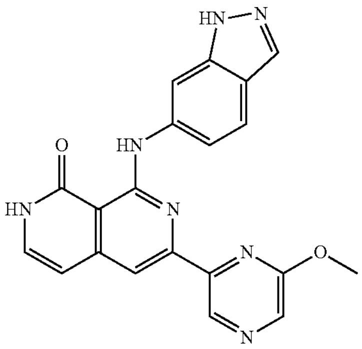 [SMILES: COc1cncc(-c2cc3cc[nH]c(=O)c3c(Nc3ccc4cn[nH]c4c3)n2)n1] | MS m/z 386.2 (M + 1). |
| 727 | 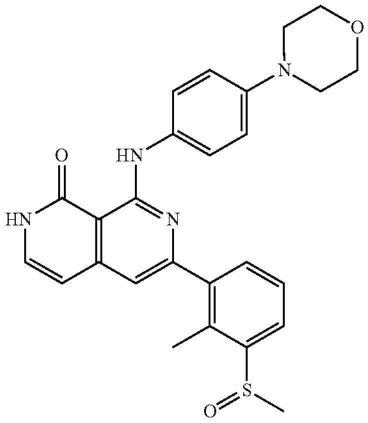 [SMILES: Cc1c(-c2cc3cc[nH]c(=O)c3c(Nc3ccc(N4CCOCC4)cc3)n2)cccc1S(C)=O] | MS m/z 475.2 (M + 1). |

TABLE 1-continued
| No | Structure | Physical Data $^1$H NMR 400 MHz (DMSO-$d_6$) and/or MS (m/z) |
|---|---|---|
| 728 | 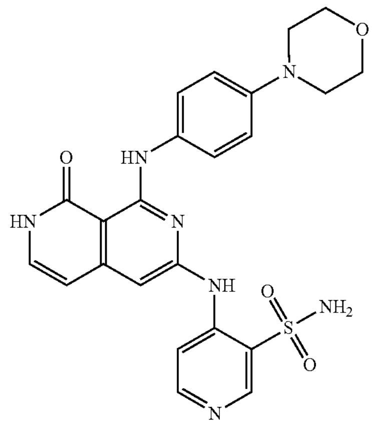 [SMILES: NS(=O)(=O)c1cnccc1Nc1cc2cc[nH]c(=O)c2c(Nc2ccc(N3CCOCC3)cc2)n1] | MS m/z 494.2 (M + 1). |
| 729 | 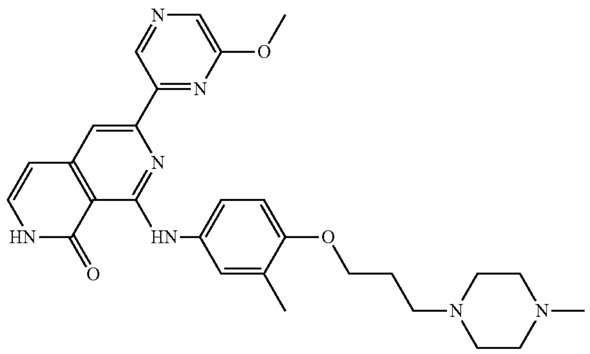 [SMILES: COc1cncc(-c2cc3cc[nH]c(=O)c3c(Nc3ccc(OCCCN4CCN(C)CC4)c(C)c3)n2)n1] | MS m/z 516.2 (M + 1). |
| 730 | 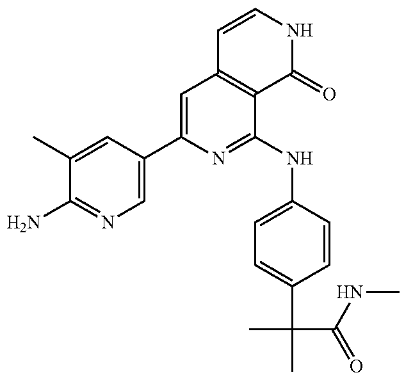 | MS m/z 443.2 (M + 1). |
| 731 | 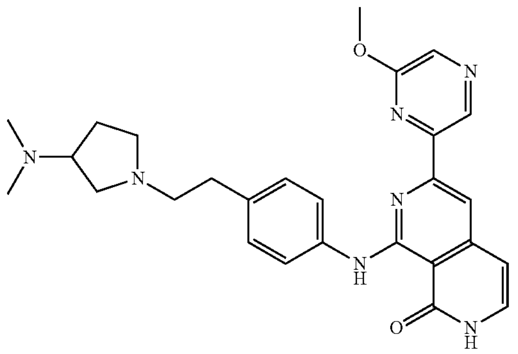 [SMILES: COc1cncc(-c2cc3cc[nH]c(=O)c3c(Nc3ccc(CCN4CCC(N(C)C)C4)cc3)n2)n1] | MS m/z 486.2 (M + 1). |

TABLE 1-continued
| No | Structure | Physical Data $^1H$ NMR 400 MHz (DMSO-$d_6$) and/or MS (m/z) |
|---|---|---|
| 732 | 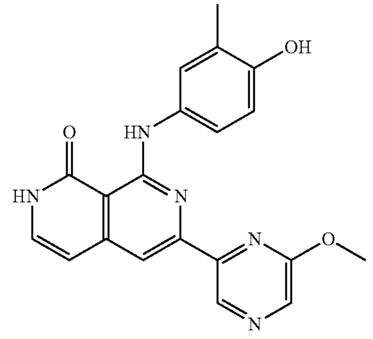 [SMILES: COc1cncc(-c2cc3cc[nH]c(=O)c3c(Nc3ccc(O)c(C)c3)n2)n1] | MS m/z 376.2 (M + 1). |
| 733 | 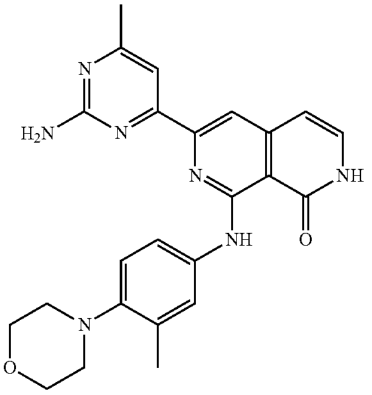 [SMILES: Cc1cc(-c2cc3cc[nH]c(=O)c3c(Nc3ccc(N4CCOCC4)c(C)c3)n2)nc(N)n1] | MS m/z 444.2 (M + 1). |
| 734 | 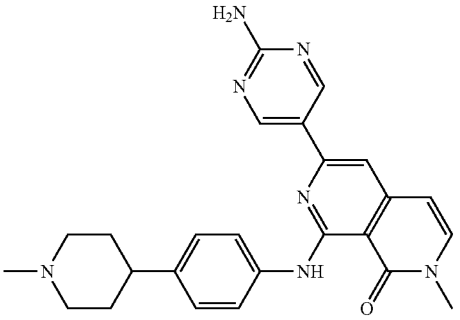 | MS m/z 442.2 (M + 1). |
| 735 | 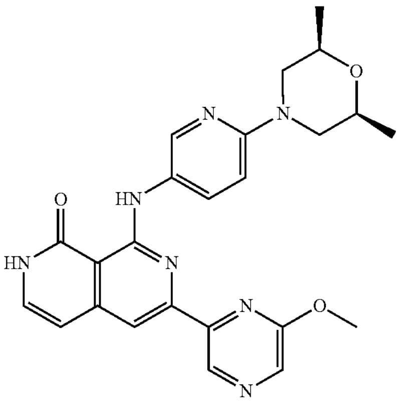 [SMILES: COc1cncc(-c2cc3cc[nH]c(=O)c3c(Nc3ccc(N4C[C@@H](C)O[C@@H](C)C4)nc3)n2)n1] | MS m/z 460.2 (M + 1). |

TABLE 1-continued
| No | Structure | Physical Data $^1H$ NMR 400 MHz (DMSO-$d_6$) and/or MS (m/z) |
|---|---|---|
| 736 | 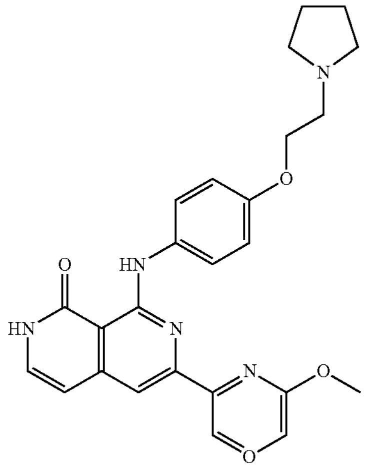 | MS m/z 459.2 (M + 1). |
| 737 | 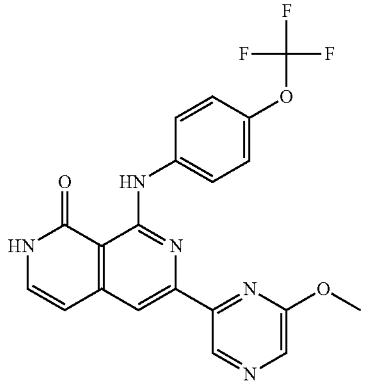 [SMILES: COc1cncc(-c2cc3cc[nH]c(=O)c3c(Nc3ccc(OC(F)(F)F)cc3)n2)n1] | MS m/z 430.2 (M + 1). |
| 738 | 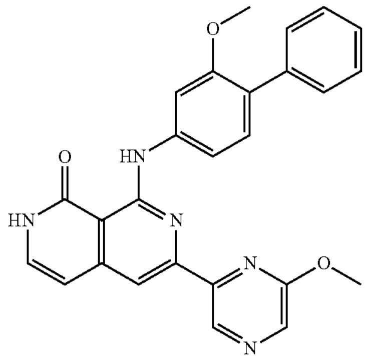 [SMILES: COc1cncc(-c2cc3cc[nH]c(=O)c3c(Nc3ccc(-c4ccccc4)c(OC)c3)n2)n1] | MS m/z 452.2 (M + 1). |

TABLE 1-continued
| No | Structure | Physical Data $^1H$ NMR 400 MHz (DMSO-$d_6$) and/or MS (m/z) |
|---|---|---|
| 739 | 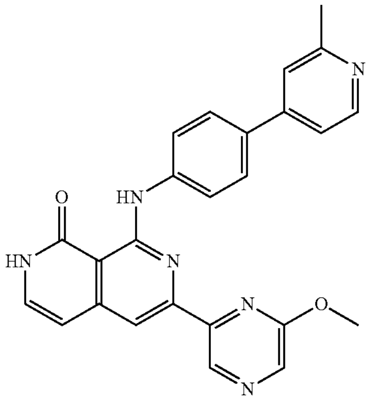 [SMILES: COc1cncc(-c2cc3cc[nH]c(=O)c3c(Nc3ccc(-c4ccnc(C)c4)cc3)n2)n1] | MS m/z 437.2 (M + 1). |
| 740 | 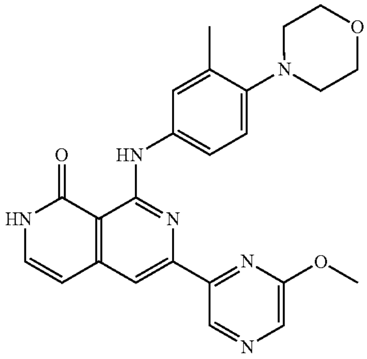 | MS m/z 445.2 (M + 1). |
| 741 | 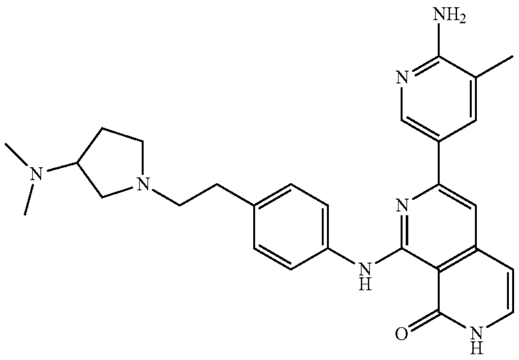 | MS m/z 484.1 (M + 1). |
| 742 | 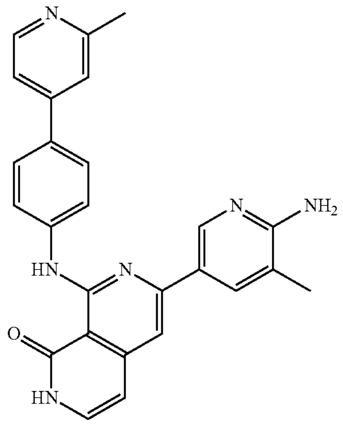 [SMILES: Cc1cc(-c2ccc(Nc3nc(-c4cnc(N)c(C)c4)cc4cc[nH]c(=O)c34)cc2)ccn1] | MS m/z 435.12 (M + 1). |

TABLE 1-continued
| No | Structure | Physical Data $^1$H NMR 400 MHz (DMSO-$d_6$) and/or MS (m/z) |
|---|---|---|
| 743 | 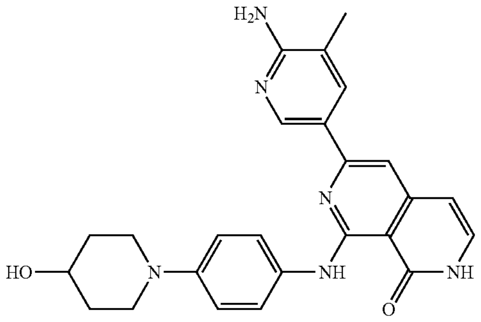 [SMILES: Cc1cc(-c2cc3cc[nH]c(=O)c3c(Nc3ccc(N4CCC(O)CC4)cc3)n2)cnc1N] | MS m/z 443.22 (M + 1). |
| 744 | 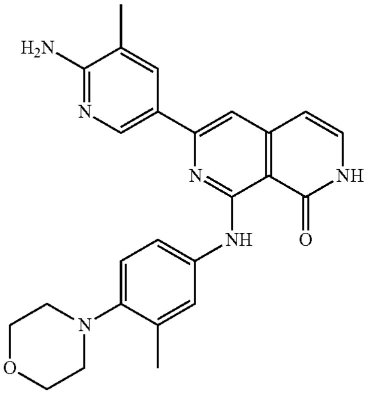 | MS m/z 443.1 (M + 1). |
| 745 | 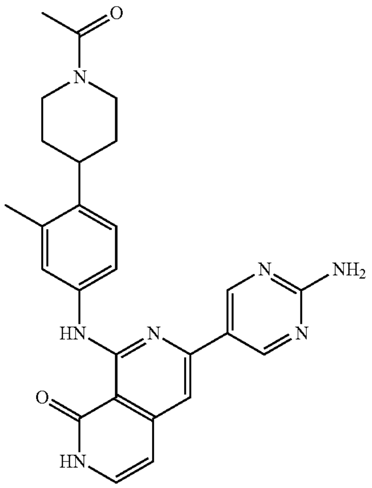 [SMILES: CC(=O)N1CCC(c2ccc(Nc3nc(-c4cnc(N)nc4)cc4cc[nH]c(=O)c34)cc2C)CC1] | MS m/z 470.1 (M + 1). |
| 746 | 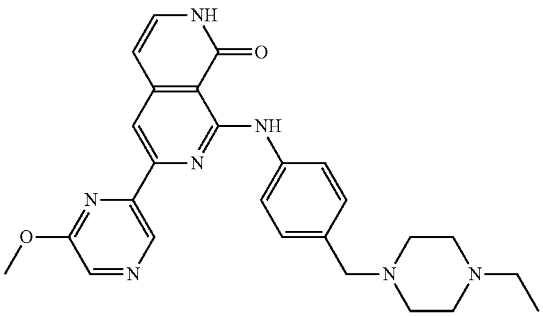 [SMILES: CCN1CCN(Cc2ccc(Nc3nc(-c4cncc(OC)n4)cc4cc[nH]c(=O)c34)cc2)CC1] | MS m/z 472.1 (M + 1). |

TABLE 1-continued
| No | Structure | Physical Data $^1H$ NMR 400 MHz (DMSO-$d_6$) and/or MS (m/z) |
| --- | --- | --- |
| 747 | 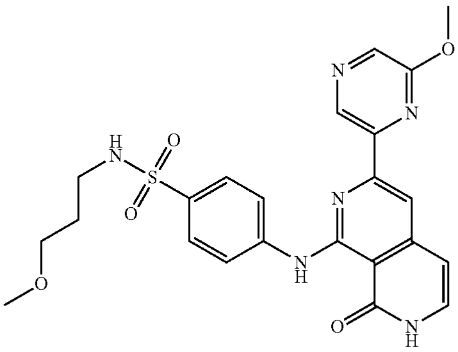 | MS m/z 497.1 (M + 1). |
| 748 | 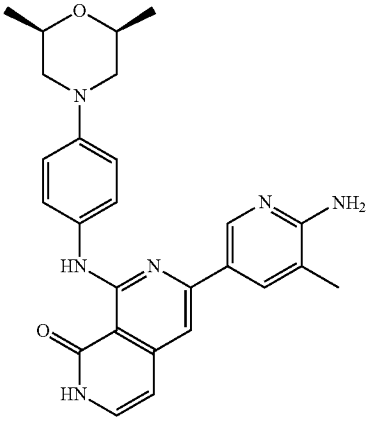 | MS m/z 457.2 (M + 1). |
| 749 | 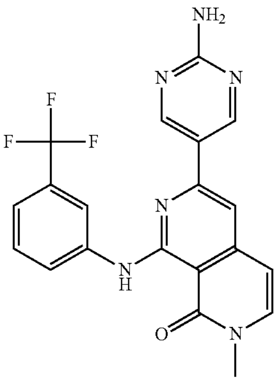 [SMILES: Cn1ccc2cc(-c3cnc(N)nc3)nc(Nc3cccc(C(F)(F)F)c3)c2c1=O] | MS m/z 413.2 (M + 1). |
| 750 | 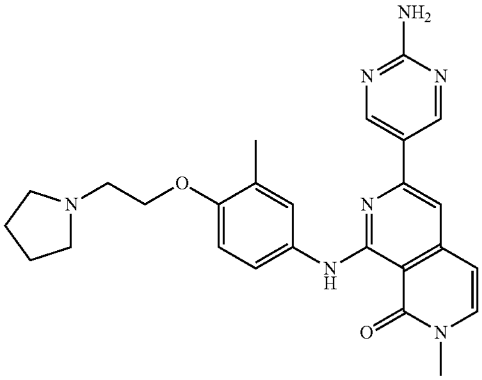 [SMILES: Cc1cc(Nc2nc(-c3cnc(N)nc3)cc3ccn(C)c(=O)c23)ccc1OCCN1CCCC1] | MS m/z 472.1 (M + 1). |

TABLE 1-continued
| No | Structure | Physical Data $^1H$ NMR 400 MHz (DMSO-$d_6$) and/or MS (m/z) |
|---|---|---|
| 751 | 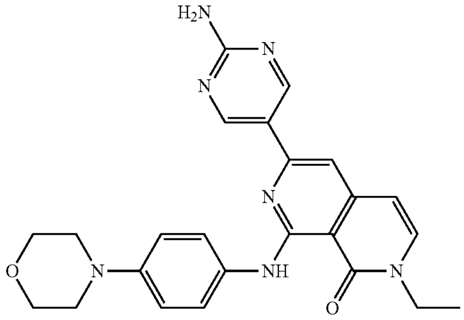 [SMILES: CCn1ccc2cc(-c3cnc(N)nc3)nc(Nc3ccc(N4CCOCC4)cc3)c2c1=O] | MS m/z 444.2 (M + 1). |
| 752 | 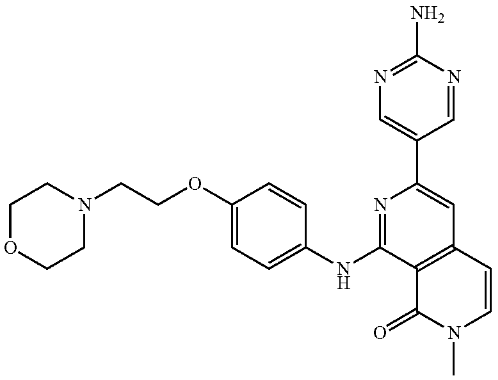 [SMILES: Cn1ccc2cc(-c3cnc(N)nc3)nc(Nc3ccc(OCCN4CCOCC4)cc3)c2c1=O] | MS m/z 474.2 (M + 1). |
| 753 | 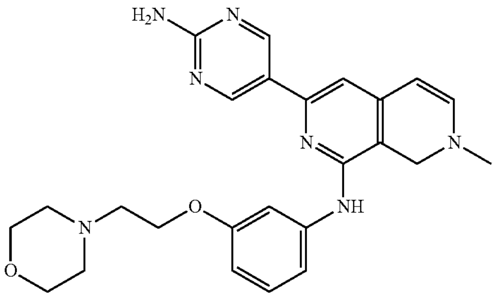 | MS m/z 474.1 (M + 1). |
| 754 | 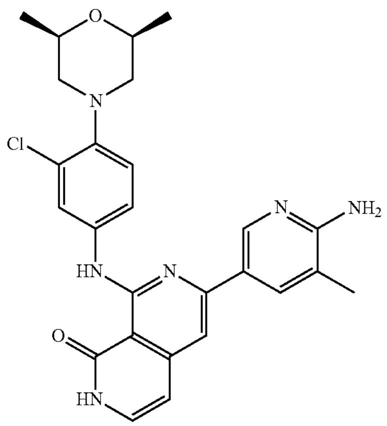 [SMILES: Cc1cc(-c2cc3cc[nH]c(=O)c3c(Nc3ccc(N4C[C@@H](C)O[C@@H](C)C4)c(Cl)c3)n2)cnc1N] | MS m/z 491.2 (M + 1). |

TABLE 1-continued
| No | Structure | Physical Data $^1H$ NMR 400 MHz (DMSO-$d_6$) and/or MS (m/z) |
| --- | --- | --- |
| 755 | 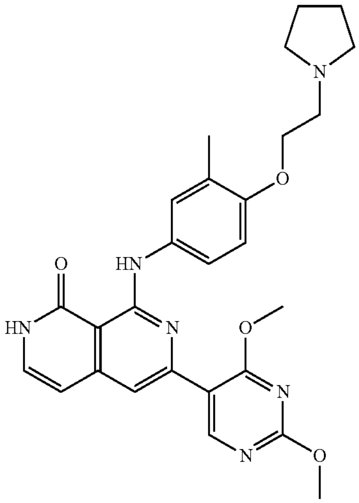 [SMILES: COc1ncc(-c2cc3cc[nH]c(=O)c3c(Nc3ccc(OCCN4CCCC4)c(C)c3)n2)c(OC)n1] | MS m/z 503.3 (M + 1). |
| 756 | 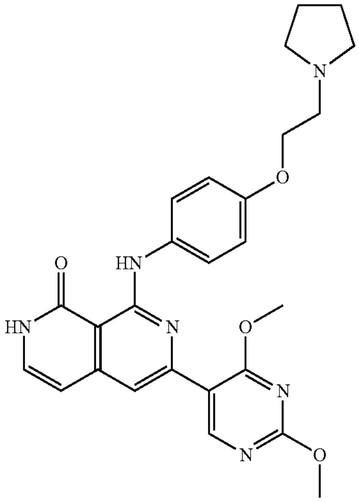 [SMILES: COc1ncc(-c2cc3cc[nH]c(=O)c3c(Nc3ccc(OCCN4CCCC4)cc3)n2)c(OC)n1] | MS m/z 489.2 (M + 1). |
| 757 | 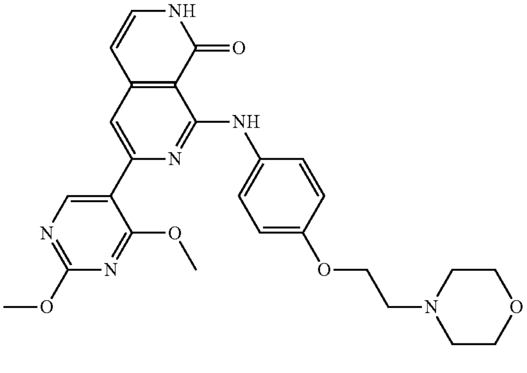 [SMILES: COc1ncc(-c2cc3cc[nH]c(=O)c3c(Nc3ccc(OCCN4CCOCC4)cc3)n2)c(OC)n1] | MS m/z 504.1 (M + 1). |

TABLE 1-continued
| No | Structure | Physical Data $^1H$ NMR 400 MHz (DMSO-$d_6$) and/or MS (m/z) |
|---|---|---|
| 758 | 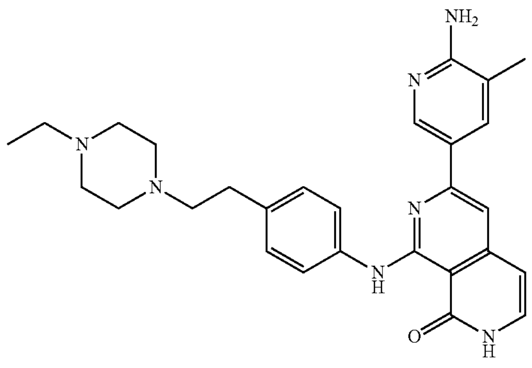 [SMILES: CCN1CCN(CCc2ccc(Nc3nc(-c4cnc(N)c(C)c4)cc4cc[nH]c(=O)c34)cc2)CC1] | MS m/z 484.2 (M + 1). |
| 759 | 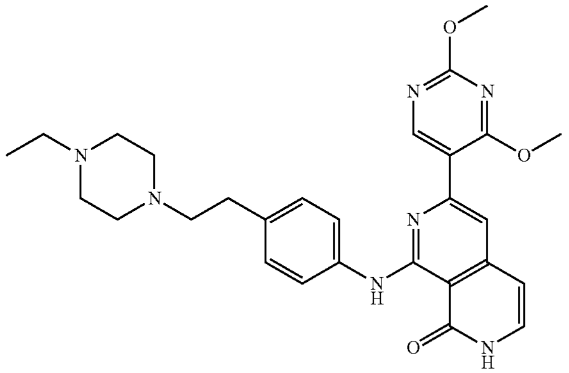 [SMILES: CCN1CCN(CCc2ccc(Nc3nc(-c4cnc(OC)nc4OC)cc4cc[nH]c(=O)c34)cc2)CC1] | MS m/z 516.11 (M + 1). |
| 760 | 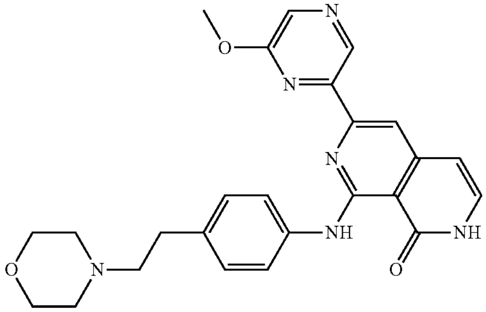 [SMILES: COc1cncc(-c2cc3cc[nH]c(=O)c3c(Nc3ccc(CCN4CCOCC4)cc3)n2)n1] | MS m/z 459.3 (M + 1). |
| 761 | 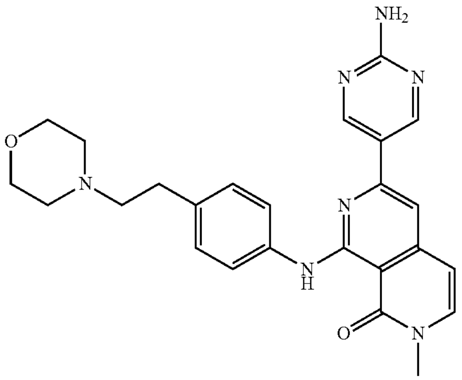 [SMILES: Cn1ccc2cc(-c3cnc(N)nc3)nc(Nc3ccc(CCN4CCOCC4)cc3)c2c1=O] | MS m/z 457.2 (M + 1). |

TABLE 1-continued
| No | Structure | Physical Data $^1H$ NMR 400 MHz (DMSO-$d_6$) and/or MS (m/z) |
|---|---|---|
| 762 | 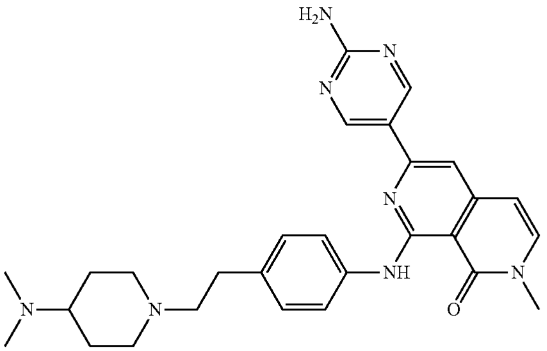 | MS m/z 499.1 (M + 1). |
| 763 | 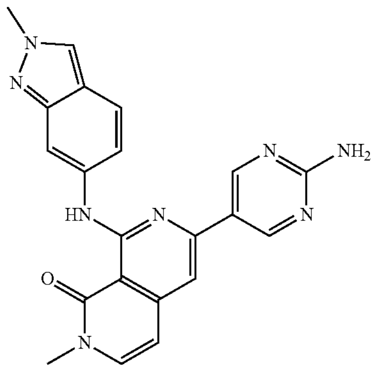 [SMILES: Cn1cc2ccc(Nc3nc(-c4cnc(N)nc4)cc4ccn(C)c(=O)c34)cc2n1] | MS m/z 399.1 (M + 1). |
| 764 | 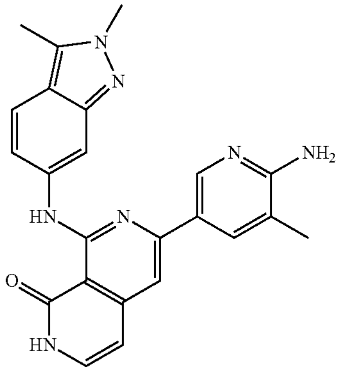 [SMILES: Cc1cc(-c2cc3cc[nH]c(=O)c3c(Nc3ccc4c(C)n(C)nc4c3)n2)cnc1N] | MS m/z 412.2 (M + 1). |
| 765 | 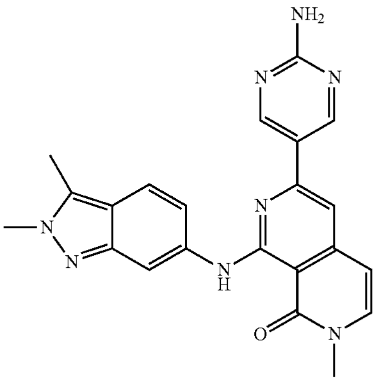 [SMILES: Cc1c2ccc(Nc3nc(-c4cnc(N)nc4)cc4ccn(C)c(=O)c34)cc2nn1C] | MS m/z 413.1 (M + 1). |

TABLE 1-continued
| No | Structure | Physical Data $^1H$ NMR 400 MHz (DMSO-$d_6$) and/or MS (m/z) |
|---|---|---|
| 766 | 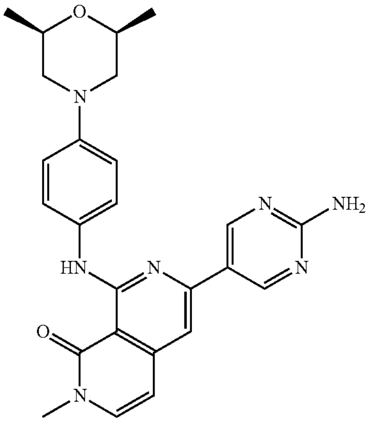 [SMILES: C[C@@H]1CN(c2ccc(Nc3nc(-c4cnc(N)nc4)cc4ccn(C)c(=O)c34)cc2)C[C@H](C)O1] | MS m/z 458.2 (M + 1). |
| 767 | 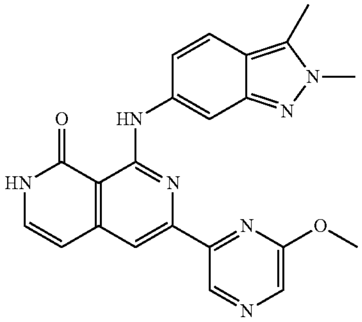 [SMILES: COc1cncc(-c2cc3cc[nH]c(=O)c3c(Nc3ccc4c(C)n(C)nc4c3)n2)n1] | MS m/z 414.3 (M + 1). |
| 768 | 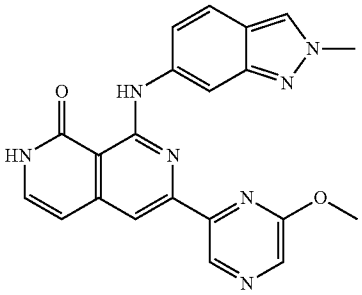 [SMILES: COc1cncc(-c2cc3cc[nH]c(=O)c3c(Nc3ccc4cn(C)nc4c3)n2)n1] | MS m/z 400.2 (M + 1). |
| 769 | 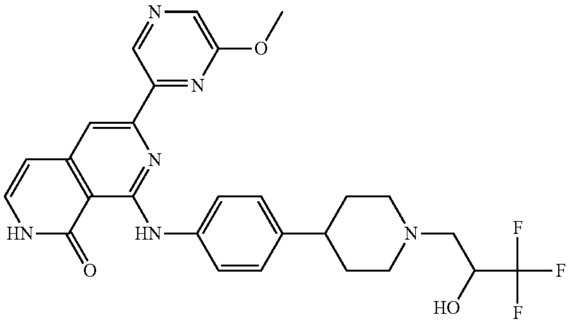 [SMILES: COc1cncc(-c2cc3cc[nH]c(=O)c3c(Nc3ccc(C4CCN(CC(O)C(F)(F)F)CC4)cc3)n2)n1] | MS m/z 541.13 (M + 1). |

TABLE 1-continued
| No | Structure | Physical Data $^1H$ NMR 400 MHz ($DMSO-d_6$) and/or MS (m/z) |
|---|---|---|
| 770 | 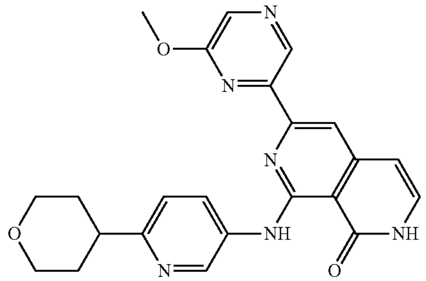 [SMILES: COc1cncc(-c2cc3cc[nH]c(=O)c3c(Nc3ccc(C4CCOCC4)nc3)n2)n1] | MS m/z 431.23 (M + 1). |
| 771 | 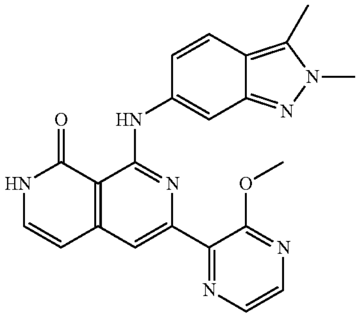 [SMILES: COc1nccnc1-c1cc2cc[nH]c(=O)c2c(Nc2ccc3c(C)n(C)nc3c2)n1] | MS m/z 414.12 (M + 1). |
| 772 | 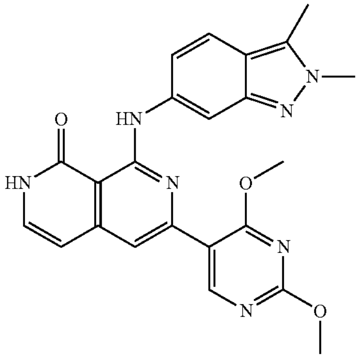 [SMILES: COc1ncc(-c2cc3cc[nH]c(=O)c3c(Nc3ccc4c(C)n(C)nc4c3)n2)c(OC)n1] | MS m/z 444.2 (M + 1). |
| 773 | 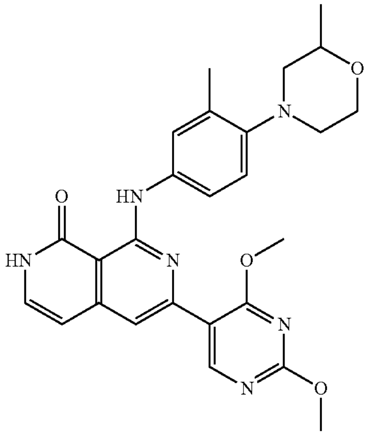 [SMILES: COc1ncc(-c2cc3cc[nH]c(=O)c3c(Nc3ccc(N4CCOC(C)C4)c(C)c3)n2)c(OC)n1] | MS m/z 489.21 (M + 1). |

TABLE 1-continued
| No | Structure | Physical Data $^1H$ NMR 400 MHz (DMSO-$d_6$) and/or MS (m/z) |
|---|---|---|
| 774 | 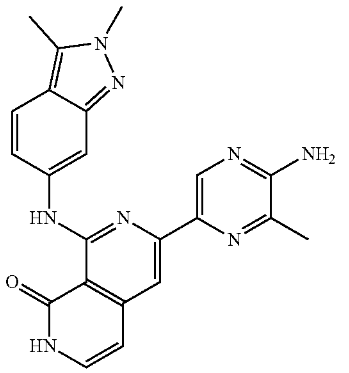 [SMILES: Cc1nc(-c2cc3cc[nH]c(=O)c3c(Nc3ccc4c(C)n(C)nc4c3)n2)cnc1N] | MS m/z 413.2 (M + 1). |
| 775 | 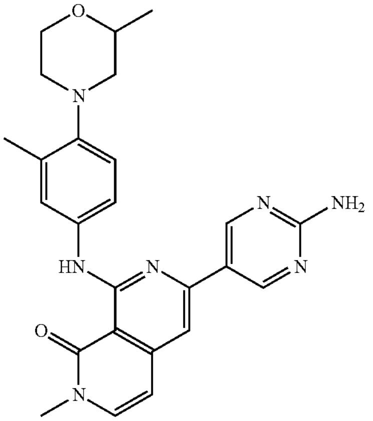 [SMILES: Cc1cc(Nc2nc(-c3cnc(N)nc3)cc3ccn(C)c(=O)c23)ccc1N1CCOC(C)C1] | MS m/z 458.2 (M + 1). |
| 776 | 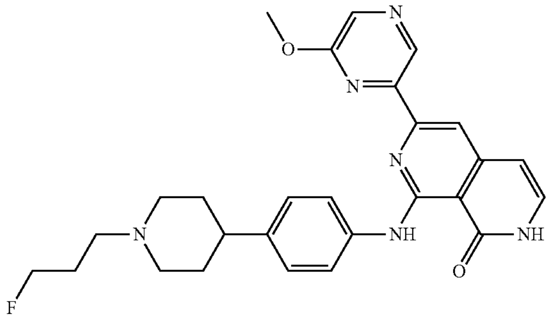 | MS m/z 489.1 (M + 1). |
| 778 | 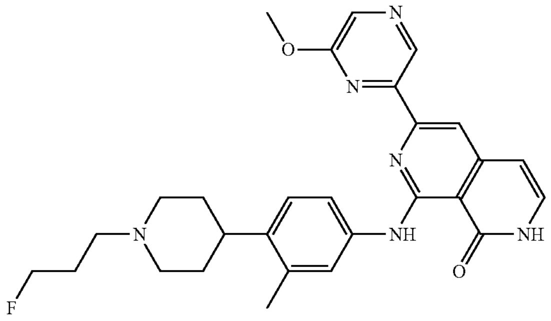 [SMILES: COc1cncc(-c2cc3cc[nH]c(=O)c3c(Nc3ccc(C4CCN(CCCF)CC4)c(C)c3)n2)n1] | MS m/z 503.1 (M + 1). |

TABLE 1-continued
| No | Structure | Physical Data $^1$H NMR 400 MHz (DMSO-$d_6$) and/or MS (m/z) |
|---|---|---|
| 779 | 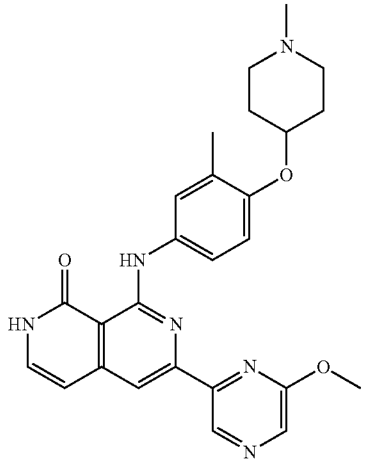 [SMILES: COc1cncc(-c2cc3cc[nH]c(=O)c3c(Nc3ccc(OC4CCN(C)CC4)c(C)c3)n2)n1] | MS m/z 473.2 (M + 1). |
| 780 | 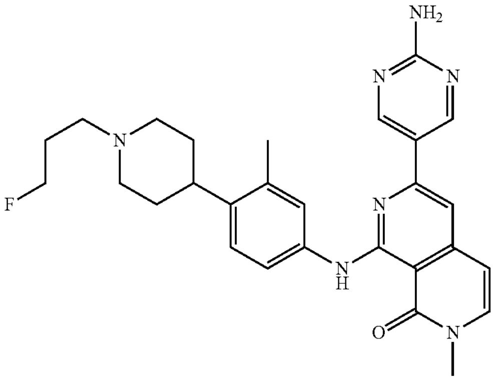 [SMILES: Cc1cc(Nc2nc(-c3cnc(N)nc3)cc3ccn(C)c(=O)c23)ccc1C1CCN(CCCF)CC1] | MS m/z 502.11 (M + 1). |
| 781 | 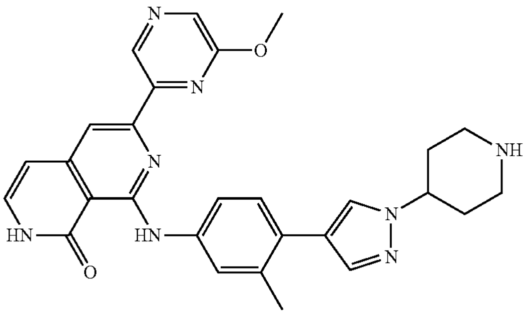 [SMILES: COc1cncc(-c2cc3cc[nH]c(=O)c3c(Nc3ccc(-c4cnn(C5CCNCC5)c4)c(C)c3)n2)n1] | MS m/z 509.2 (M + 1). |
| 782 | 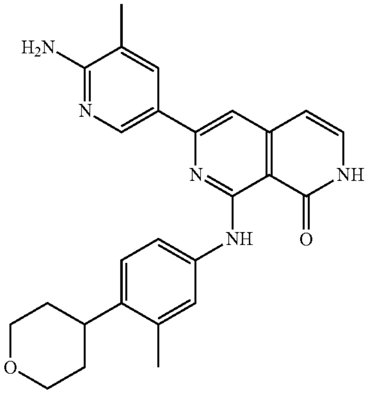 | MS m/z 442.21 (M + 1). |

TABLE 1-continued
| No | Structure | Physical Data $^1H$ NMR 400 MHz (DMSO-$d_6$) and/or MS (m/z) |
|---|---|---|
| 783 | 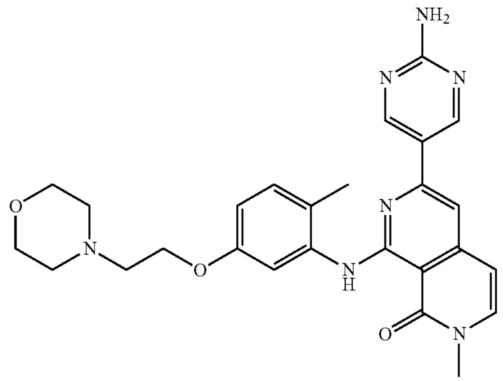 [SMILES: Cc1ccc(OCCN2CCOCC2)cc1Nc1nc(-c2cnc(N)nc2)cc2ccn(C)c(=O)c12] | MS m/z 488.32 (M + 1). |
| 784 | 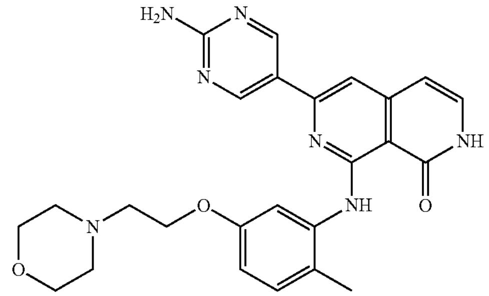 [SMILES: Cc1ccc(OCCN2CCOCC2)cc1Nc1nc(-c2cnc(N)nc2)cc2cc[nH]c(=O)c12] | MS m/z 474.1 (M + 1). |
| 785 | 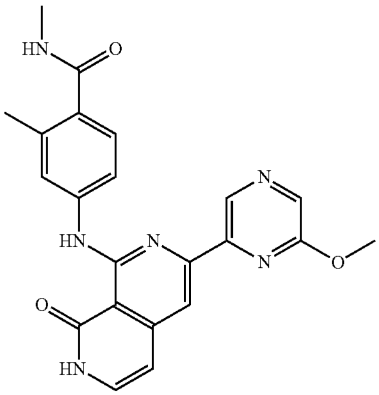 | MS m/z 417.1 (M + 1). |
| 786 | 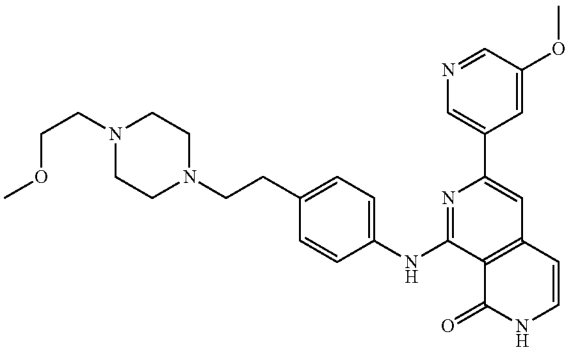 | MS m/z 516.1 (M + 1). |

TABLE 1-continued
| No | Structure | Physical Data $^1H$ NMR 400 MHz (DMSO-$d_6$) and/or MS (m/z) |
|---|---|---|
| 787 | 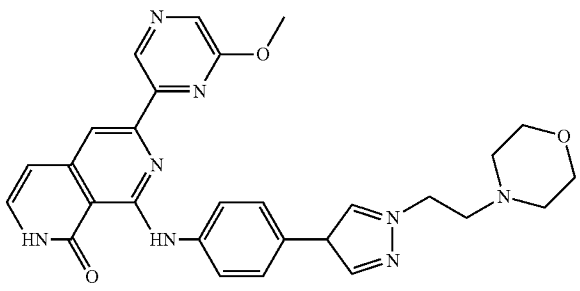 | MS m/z 525.2 (M + 1). |
| 788 | 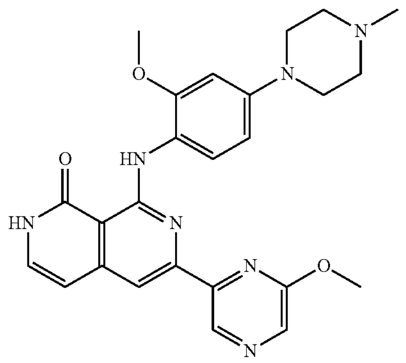 [SMILES: COc1cncc(-c2cc3cc[nH]c(=O)c3c(Nc3ccc(N4CCN(C)CC4)cc3OC)n2)n1] | MS m/z 474.2 (M + 1). |
| 789 | 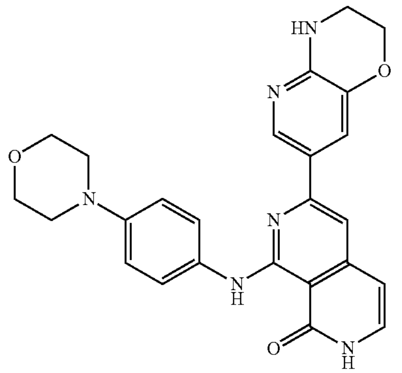 | MS m/z 457.3 (M + 1). |
| 790 | 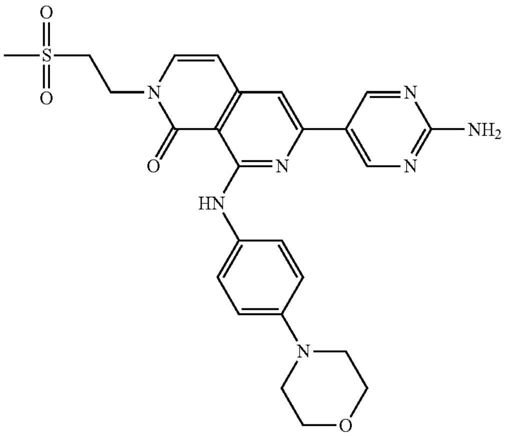 [SMILES: CS(=O)(=O)CCn1ccc2cc(-c3cnc(N)nc3)nc(Nc3ccc(N4CCOCC4)cc3)c2c1=O] | MS m/z 522.2 (M + 1). |

TABLE 1-continued
| No | Structure | Physical Data $^1H$ NMR 400 MHz (DMSO-$d_6$) and/or MS (m/z) |
|---|---|---|
| 791 | 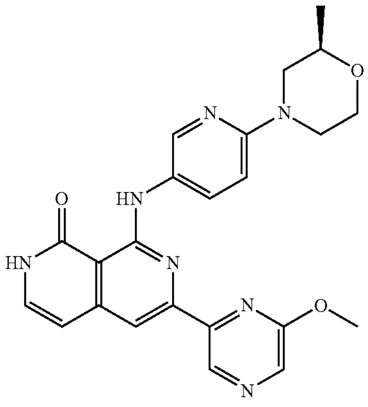 [SMILES: COc1cncc(-c2cc3cc[nH]c(=O)c3c(Nc3ccc(N4CCO[C@H](C)C4)nc3)n2)n1] | MS m/z 446.1 (M + 1). |
| 792 | 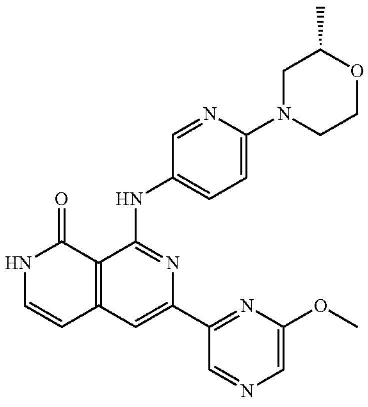 [SMILES: COc1cncc(-c2cc3cc[nH]c(=O)c3c(Nc3ccc(N4CCO[C@@H](C)C4)nc3)n2)n1] | MS m/z 446.11 (M + 1). |
| 793 | 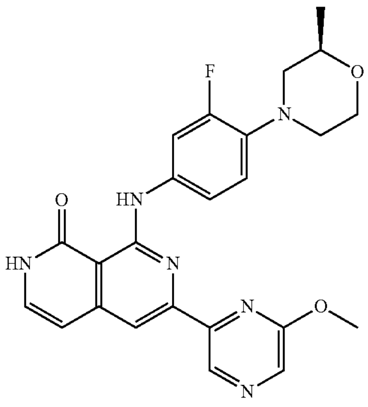 [SMILES: COc1cncc(-c2cc3cc[nH]c(=O)c3c(Nc3ccc(N4CCO[C@H](C)C4)c(F)c3)n2)n1] | MS m/z 463.12 (M + 1). |

TABLE 1-continued
| No | Structure | Physical Data $^1$H NMR 400 MHz (DMSO-$d_6$) and/or MS (m/z) |
|---|---|---|
| 794 | 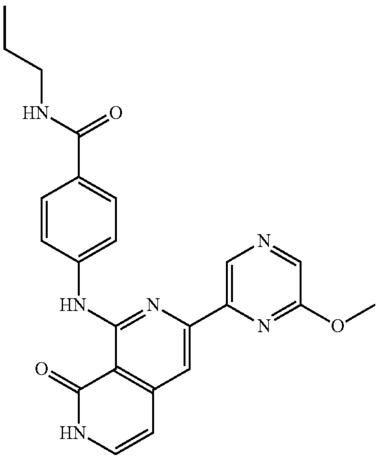 [SMILES: CCCNC(=O)c1ccc(Nc2nc(-c3cncc(OC)n3)cc3cc[nH]c(=O)c23)cc1] | MS m/z 431.24 (M + 1). |
| 795 | 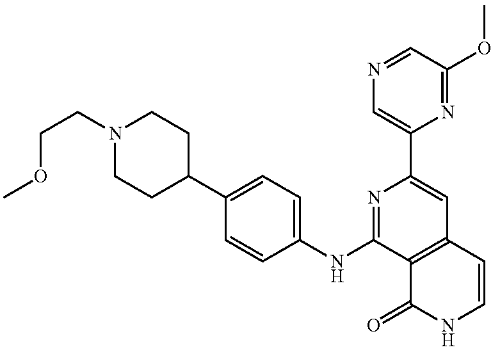 | MS m/z 487.23 (M + 1). |
| 796 | 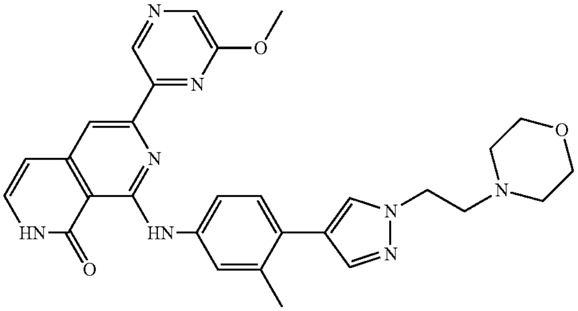 [SMILES: COc1cncc(-c2cc3cc[nH]c(=O)c3c(Nc3ccc(-c4cnn(CCN5CCOCC5)c4)c(C)c3)n2)n1] | MS m/z 539.1 (M + 1). |
| 797 | 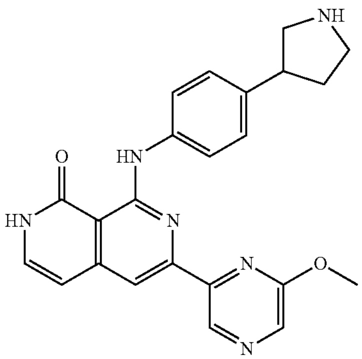 [SMILES: COc1cncc(-c2cc3cc[nH]c(=O)c3c(Nc3ccc(C4CCNC4)cc3)n2)n1] | MS m/z 415.1 (M + 1). |

TABLE 1-continued
| No | Structure | Physical Data $^1H$ NMR 400 MHz (DMSO-$d_6$) and/or MS (m/z) |
|---|---|---|
| 798 | 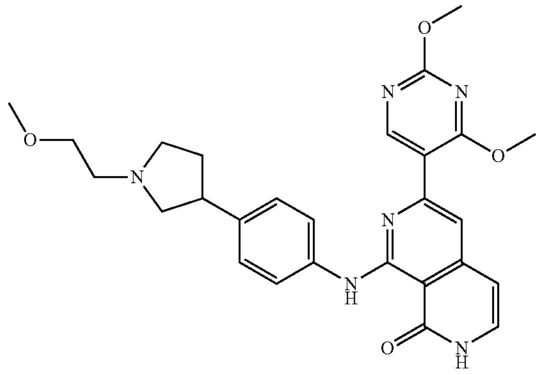 | MS m/z 503.2 (M + 1). |
| 799 | 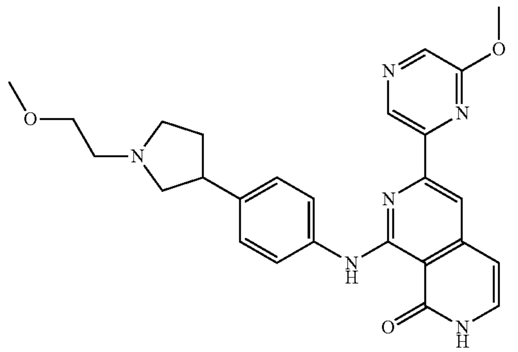 | MS m/z 473.2 (M + 1). |
| 800 | 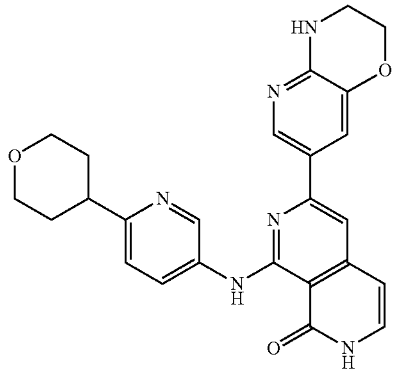 [SMILES: O=c1[nH]ccc2cc(-c3cnc4c(c3)OCCN4)nc(Nc3ccc(C4CCOCC4)nc3)c12] | MS m/z 457.1 (M + 1). |
| 801 | 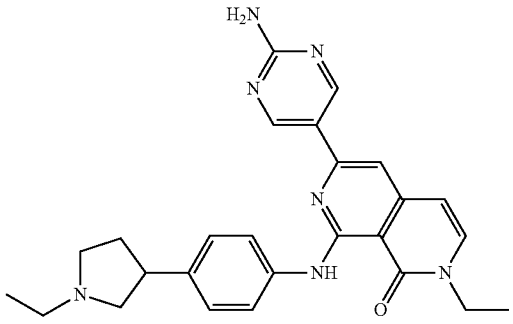 [SMILES: CCN1CCC(c2ccc(Nc3nc(-c4cnc(N)nc4)cc4ccn(CC)c(=O)c34)cc2)C1] | MS m/z 456.12 (M + 1). |

TABLE 1-continued
| No | Structure | Physical Data<br>$^1$H NMR 400 MHz<br>(DMSO-$d_6$) and/or MS (m/z) |
|---|---|---|
| 802 | 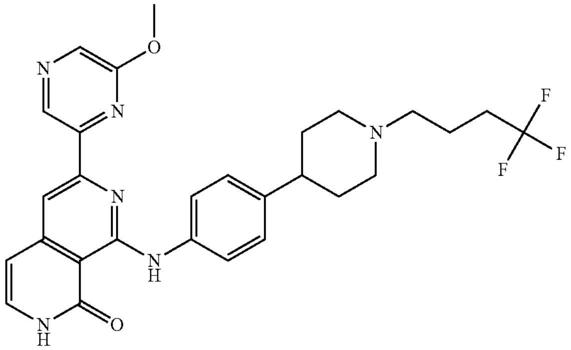 [SMILES: COc1cncc(-c2cc3cc[nH]c(=O)c3c(Nc3ccc(C4CCN(CCCC(F)(F)F)CC4)cc3)n2)n1] | MS m/z 439.2 (M + 1). |
| 803 | 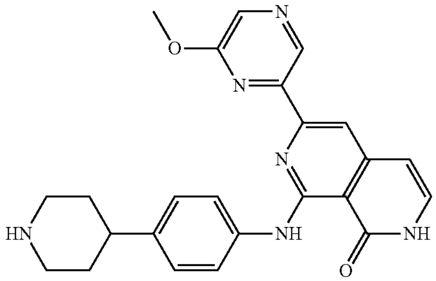 | MS m/z 429.1 (M + 1). |
| 804 | 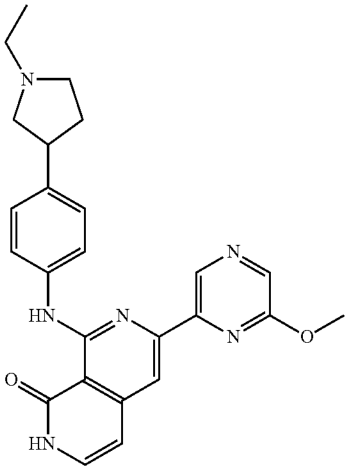 [SMILES: CCN1CCC(c2ccc(Nc3nc(-c4cncc(OC)n4)cc4cc[nH]c(=O)c34)cc2)C1] | MS m/z 443.1 (M + 1). |
| 805 | 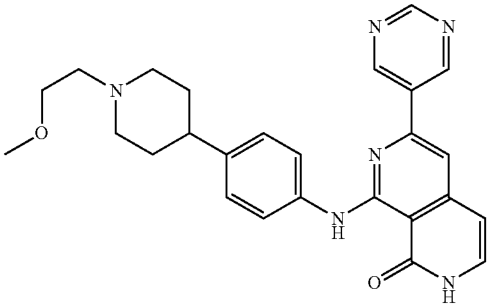 [SMILES: COCCN1CCC(c2ccc(Nc3nc(-c4cncnc4)cc4cc[nH]c(=O)c34)cc2)CC1] | MS m/z 457.1 (M + 1). |

TABLE 1-continued
| No | Structure | Physical Data $^1H$ NMR 400 MHz (DMSO-$d_6$) and/or MS (m/z) |
| --- | --- | --- |
| 806 | 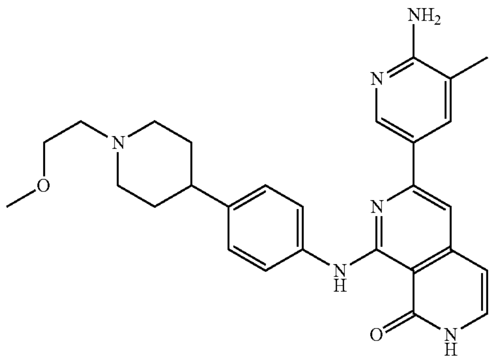 | MS m/z 485.1 (M + 1). |
| 807 | 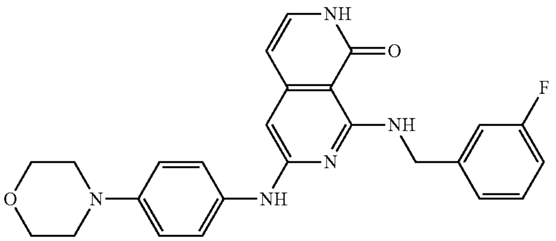 [SMILES: O=c1[nH]ccc2cc(Nc3ccc(N4CCOCC4)cc3)nc(NCc3cccc(F)c3)c12] | MS m/z 446.2 (M + 1). |
| 808 | 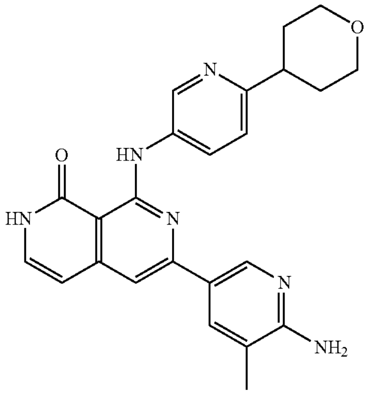 [SMILES: Cc1cc(-c2cc3cc[nH]c(=O)c3c(Nc3ccc(C4CCOCC4)nc3)n2)cnc1N] | MS m/z 429.3 (M + 1). |
| 809 | 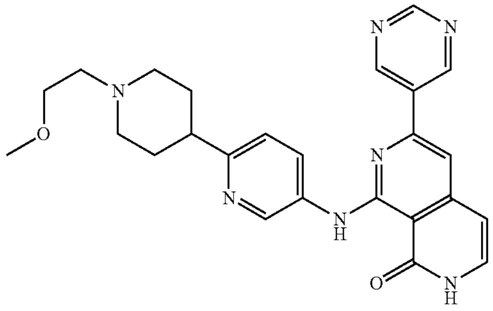 [SMILES: COCCN1CCC(c2ccc(Nc3nc(-c4cncnc4)cc4cc[nH]c(=O)c34)cn2)CC1] | MS m/z 458.1 (M + 1). |

TABLE 1-continued
| No | Structure | Physical Data $^1H$ NMR 400 MHz (DMSO-$d_6$) and/or MS (m/z) |
|---|---|---|
| 810 | 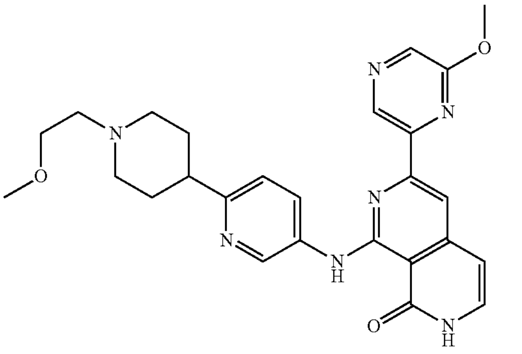 | MS m/z 488.1 (M + 1). |
| 811 | 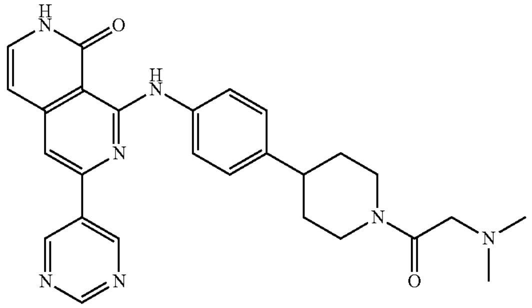 [SMILES: CN(C)CC(=O)N1CCC(c2ccc(Nc3nc(-c4cncnc4)cc4cc[nH]c(=O)c34)cc2)CC1] | MS m/z 484.1 (M + 1). |
| 812 | 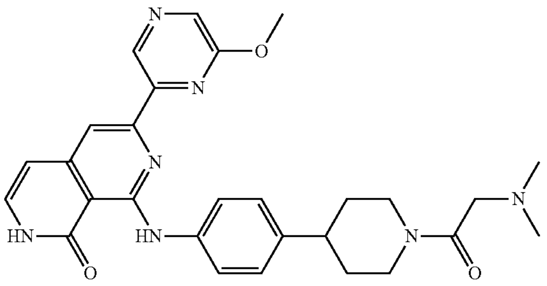 [SMILES: COc1cncc(-c2cc3cc[nH]c(=O)c3c(Nc3ccc(C4CCN(C(=O)CN(C)C)CC4)cc3)n2)n1] | MS m/z 514.2 (M + 1). |
| 813 | 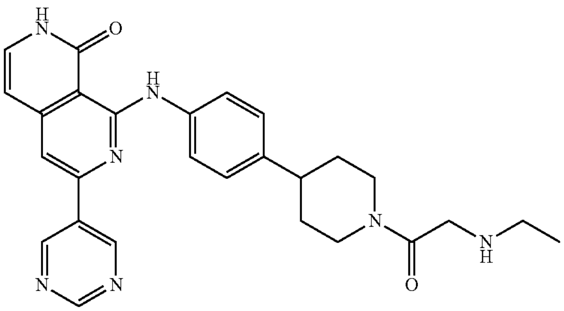 [SMILES: CCNCC(=O)N1CCC(c2ccc(Nc3nc(-c4cncnc4)cc4cc[nH]c(=O)c34)cc2)CC1] | MS m/z 484.1 (M + 1). |

TABLE 1-continued
| No | Structure | Physical Data $^1$H NMR 400 MHz (DMSO-$d_6$) and/or MS (m/z) |
|---|---|---|
| 814 | 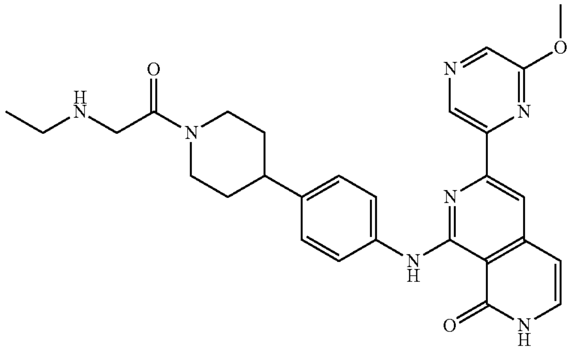 [SMILES: CCNCC(=O)N1CCC(c2ccc(Nc3nc(-c4cncc(OC)n4)cc4cc[nH]c(=O)c34)cc2)CC1] | MS m/z 514.12 (M + 1). |
| 815 | 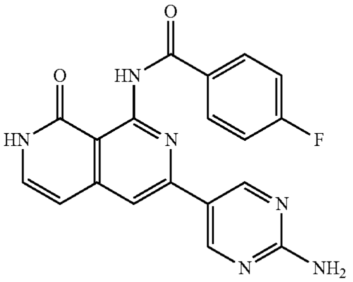 [SMILES: Nc1ncc(-c2cc3cc[nH]c(=O)c3c(NC(=O)c3ccc(F)cc3)n2)cn1] | MS m/z 377.11 (M + 1). |
| 816 | 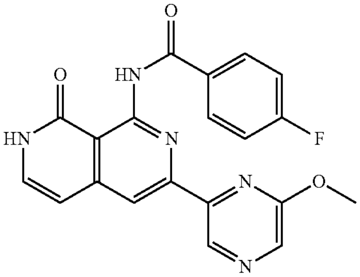 [SMILES: COc1cncc(-c2cc3cc[nH]c(=O)c3c(NC(=O)c3ccc(F)cc3)n2)n1] | MS m/z 392.2 (M + 1). |
| 817 | 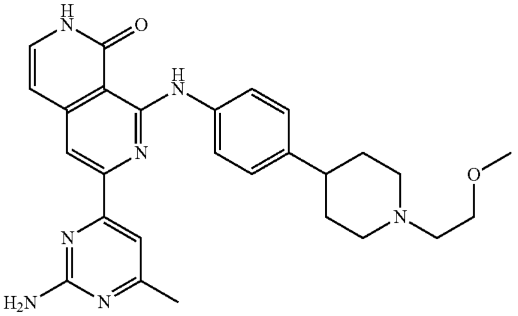 [SMILES: COCCN1CCC(c2ccc(Nc3nc(-c4cc(C)nc(N)n4)cc4cc[nH]c(=O)c34)cc2)CC1] | MS m/z 486.2 (M + 1). |

TABLE 1-continued
| No | Structure | Physical Data $^1H$ NMR 400 MHz (DMSO-$d_6$) and/or MS (m/z) |
|---|---|---|
| 818 | 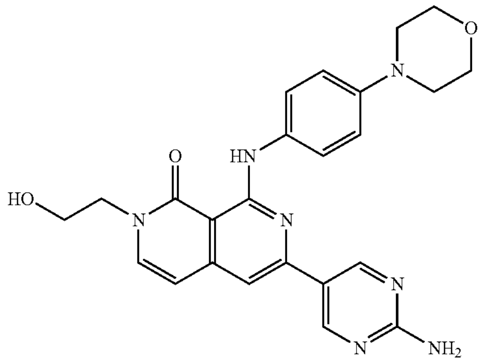 [SMILES: Nc1ncc(-c2cc3ccn(CCO)c(=O)c3c(Nc3ccc(N4CCOCC4)cc3)n2)cn1] | MS m/z 460.3 (M + 1). |
| 819 | 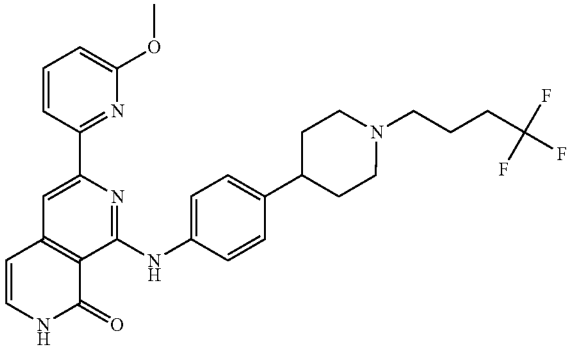 | MS m/z 438.1 (M + 1). |
| 820 | 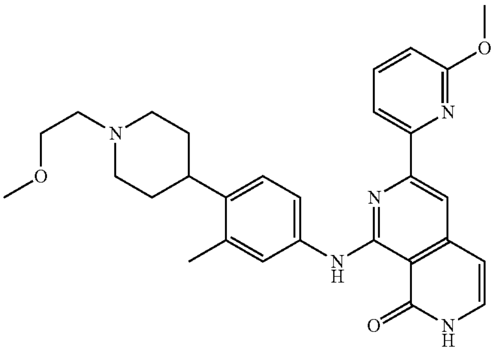 | MS m/z 500.2 (M + 1). |
| 821 | 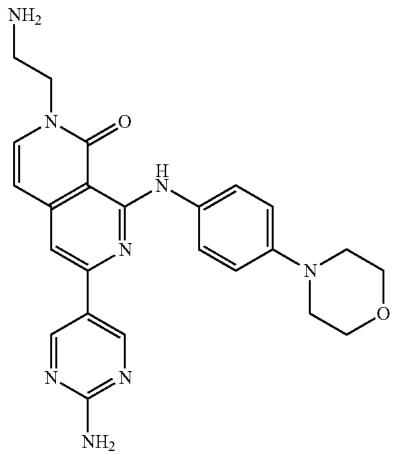 [SMILES: NCCn1ccc2cc(-c3cnc(N)nc3)nc(Nc3ccc(N4CCOCC4)cc3)c2c1=O] | MS m/z 459.2 (M + 1). |

TABLE 1-continued
| No | Structure | Physical Data $^1H$ NMR 400 MHz (DMSO-$d_6$) and/or MS (m/z) |
|---|---|---|
| 822 | 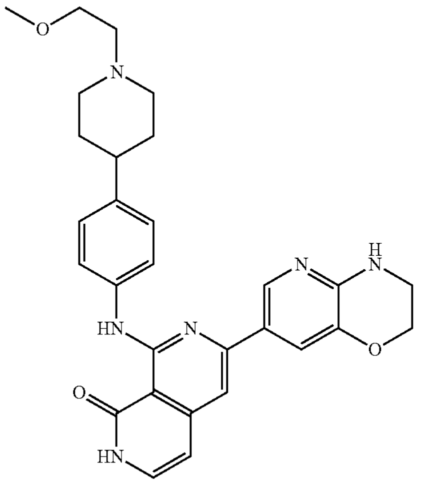 [SMILES: COCCN1CCC(c2ccc(Nc3nc(-c4cnc5c(c4)OCCN5)cc4cc[nH]c(=O)c34)cc2)CC1] | MS m/z 513.1 (M + 1). |
| 823 | 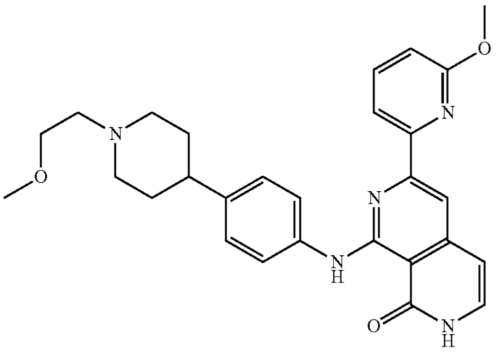 | MS m/z 489.2 (M + 1). |
| 824 | 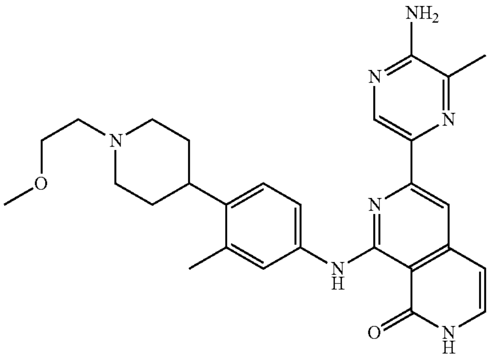 | MS m/z 500.1 (M + 1). |
| 825 | 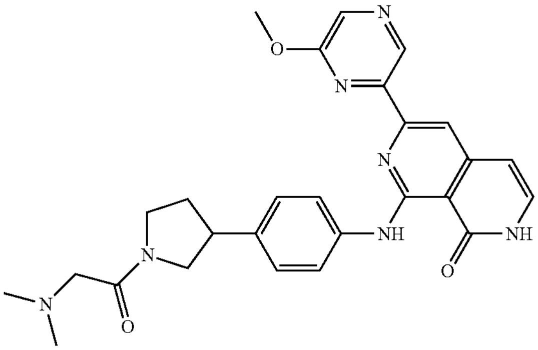 [SMILES: COc1cncc(-c2cc3cc[nH]c(=O)c3c(Nc3ccc(C4CCN(C(=O)CN(C)C)C4)cc3)n2)n1] | MS m/z 500.1 (M + 1). |

TABLE 1-continued
| No | Structure | Physical Data $^1H$ NMR 400 MHz (DMSO-$d_6$) and/or MS (m/z) |
| --- | --- | --- |
| 826 | 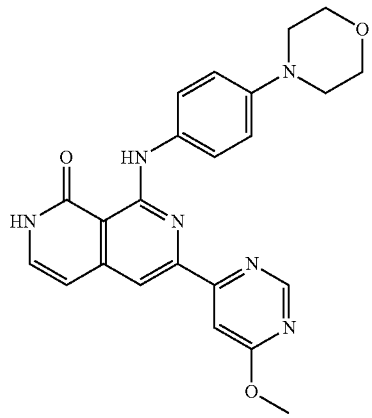 [SMILES: COc1cc(-c2cc3cc[nH]c(=O)c3c(Nc3ccc(N4CCOCC4)cc3)n2)ncn1] | MS m/z 431.4 (M + 1). |
| 827 | 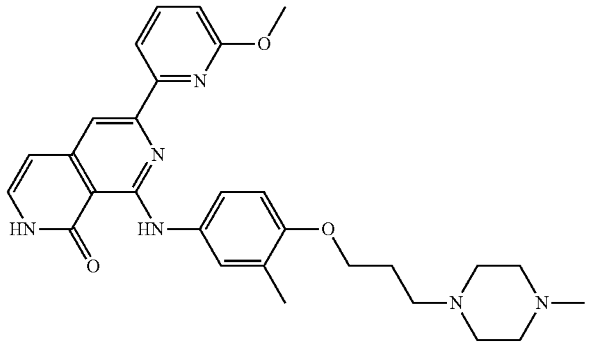 [SMILES: COc1cccc(-c2cc3cc[nH]c(=O)c3c(Nc3ccc(OCCCN4CCN(C)CC4)c(C)c3)n2)n1] | MS m/z 515.1 (M + 1). |
| 828 | 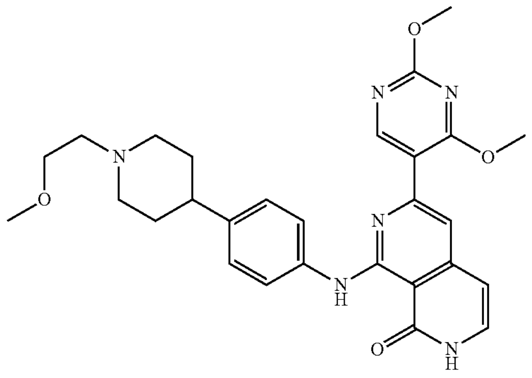 | MS m/z 517.2 (M + 1). |
| 829 | 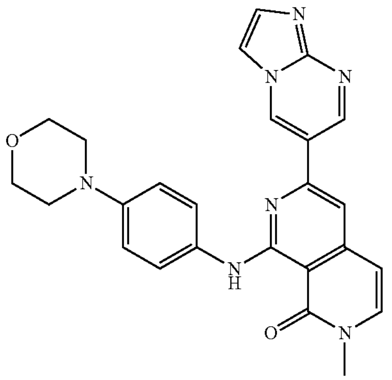 [SMILES: Cn1ccc2cc(-c3cnc4nccn4c3)nc(Nc3ccc(N4CCOCC4)cc3)c2c1=O] | MS m/z 454.1 (M + 1). |

TABLE 1-continued
| No | Structure | Physical Data $^1$H NMR 400 MHz (DMSO-d$_6$) and/or MS (m/z) |
|---|---|---|
| 830 | 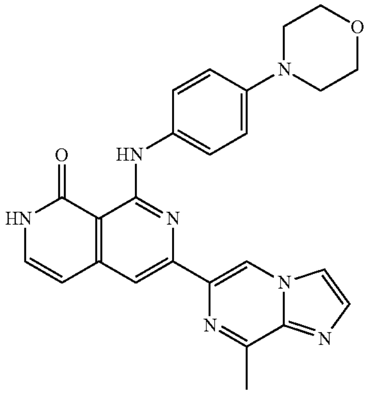 [SMILES: Cc1nc(-c2cc3cc[nH]c(=O)c3c(Nc3ccc(N4CCOCC4)cc3)n2)cn2ccnc12] | MS m/z 454.1 (M + 1). |
| 831 | 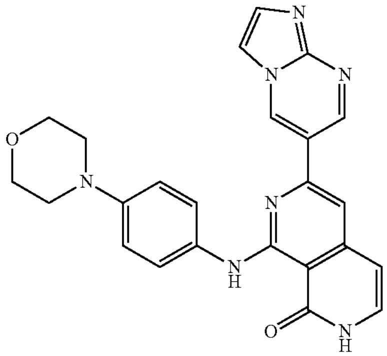 [SMILES: O=c1[nH]ccc2cc(-c3cnc4nccn4c3)nc(Nc3ccc(N4CCOCC4)cc3)c12] | MS m/z 440.2 (M + 1). |
| 832 | 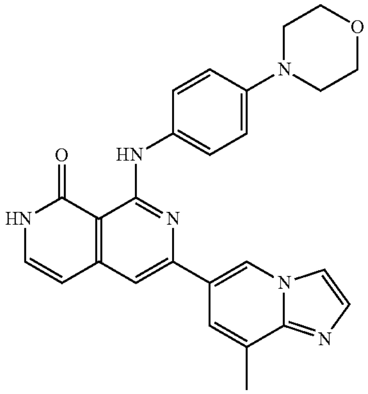 [SMILES: Cc1cc(-c2cc3cc[nH]c(=O)c3c(Nc3ccc(N4CCOCC4)cc3)n2)cn2ccnc12] | MS m/z 453.1 (M + 1). |
| 833 | 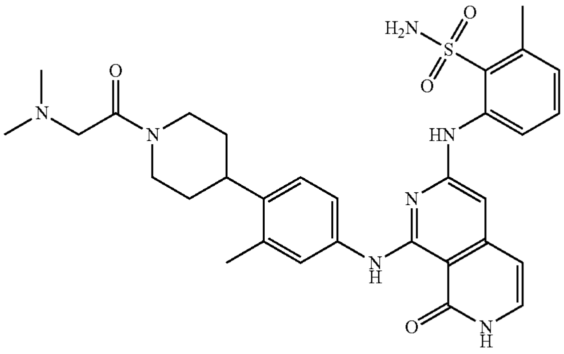 [SMILES: Cc1cc(Nc2nc(Nc3cccc(C)c3S(N)(=O)=O)cc3cc[nH]c(=O)c23)ccc1C1CCN(C(=O)CN(C)C)CC1] | MS m/z 604.1 (M + 1). |

TABLE 1-continued
| No | Structure | Physical Data $^1H$ NMR 400 MHz (DMSO-$d_6$) and/or MS (m/z) |
|---|---|---|
| 834 | 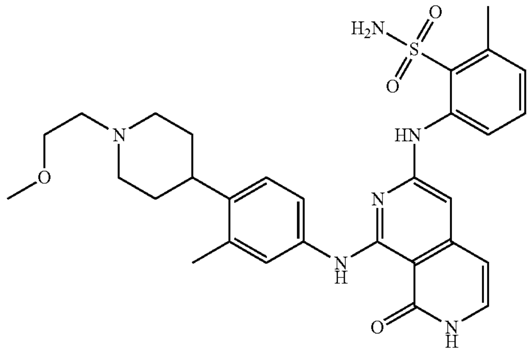 [SMILES: COCCN1CCC(c2ccc(Nc3nc(Nc4cccc(C)c4S(N)(=O)=O)cc4cc[nH]c(=O)c34)cc2C)CC1] | MS m/z 577.1 (M + 1). |
| 835 | 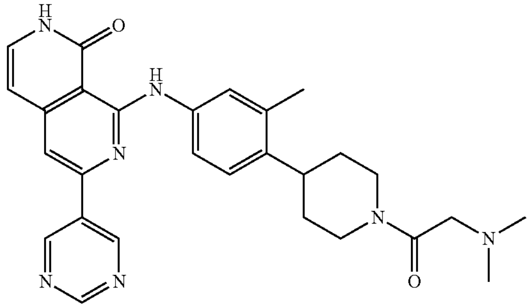 [SMILES: Cc1cc(Nc2nc(-c3cncnc3)cc3cc[nH]c(=O)c23)ccc1C1CCN(C(=O)CN(C)C)CC1] | MS m/z 498.2 (M + 1). |
| 836 | 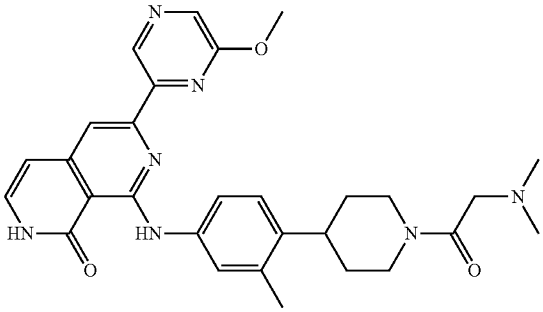 [SMILES: COc1cncc(-c2cc3cc[nH]c(=O)c3c(Nc3ccc(C4CCN(C(=O)CN(C)C)CC4)c(C)c3)n2)n1] | MS m/z 528.1 (M + 1). |
| 837 | 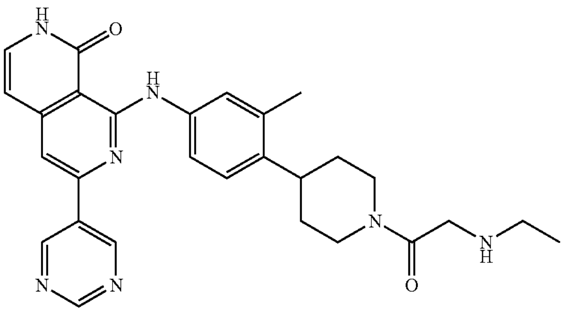 [SMILES: CCNCC(=O)N1CCC(c2ccc(Nc3nc(-c4cncnc4)cc4cc[nH]c(=O)c34)cc2C)CC1] | MS m/z 498.2 (M + 1). |

TABLE 1-continued
| No | Structure | Physical Data $^1H$ NMR 400 MHz (DMSO-$d_6$) and/or MS (m/z) |
|---|---|---|
| 838 | 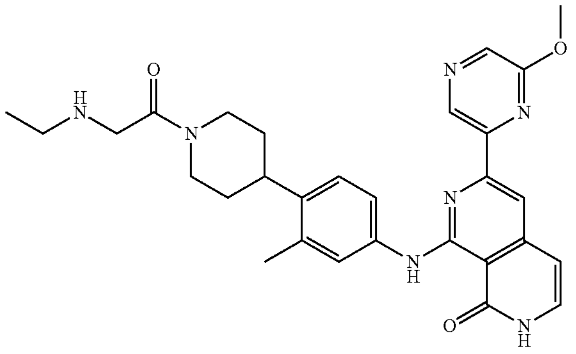 [SMILES: CCNCC(=O)N1CCC(c2ccc(Nc3nc(-c4cncc(OC)n4)cc4cc[nH]c(=O)c34)cc2C)CC1] | MS m/z 528.2 (M + 1). |
| 839 | 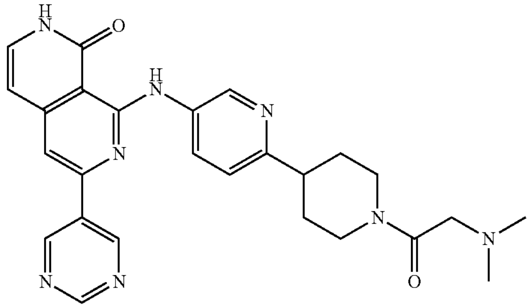 | MS m/z 489.2 (M + 1). |
| 840 | 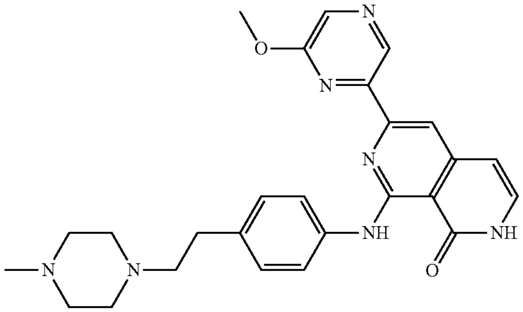 [SMILES: COc1cncc(-c2cc3cc[nH]c(=O)c3c(Nc3ccc(CCN4CCN(C)CC4)cc3)n2)n1] | MS m/z 472.12 (M + 1). |
| 841 | 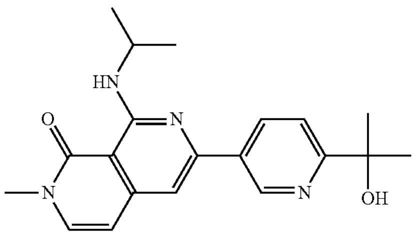 [SMILES: CC(C)Nc1nc(-c2ccc(C(C)(C)O)nc2)cc2ccn(C)c(=O)c12] | MS m/z 353.1 (M + 1). |
| 842 | 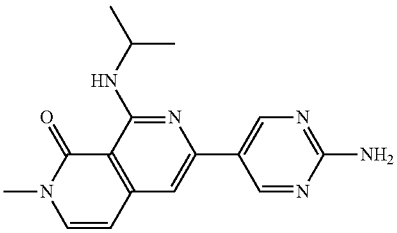 [SMILES: CC(C)Nc1nc(-c2cnc(N)nc2)cc2ccn(C)c(=O)c12] | MS m/z 311.2 (M + 1). |

TABLE 1-continued
| No | Structure | Physical Data $^1$H NMR 400 MHz (DMSO-$d_6$) and/or MS (m/z) |
|---|---|---|
| 843 | 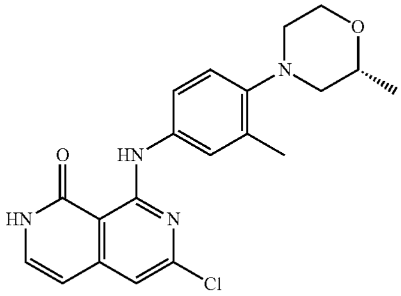 [SMILES: Cc1cc(Nc2nc(Cl)cc3cc[nH]c(=O)c23)ccc1N1CCO[C@H](C)C1] | ESI-MS m/z 385.1 (MH$^+$) |
| 844 | 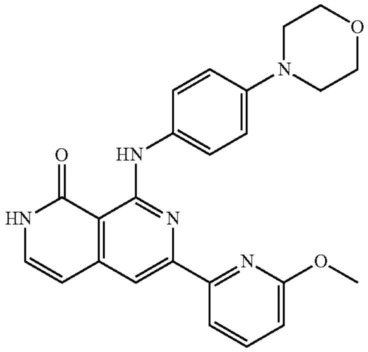 [SMILES: COc1cccc(-c2cc3cc[nH]c(=O)c3c(Nc3ccc(N4CCOCC4)cc3)n2)n1] | $^1$H NMR (DMSO-$d_6$) δ 3.09 (t, J = 4.8 Hz, 4H), 3.75 (t, J = 4.8 Hz, 4H), 4.01 (s, 3H, $CH_3$), 6.63 (d, J = 7.4 Hz, 1H), 6.92 (d, J = 7.4 Hz, 1H), 7.01 (d, J = 9.0 Hz, 2H), 7.41 (br m, 1H), 7.76 (d, J = 9.0 Hz, 2H), 7.79 (s, 1H), 7.88 (dd, J = 8.0, 7.2 Hz, 1H), 7.95 (d, J = 7.2 Hz, 1H); ESI-MS m/z 430.2 (MH$^+$); Anal. Calcd for $C_{24}H_{23}N_5O_3$: C, 67.12; H, 5.40; N, 16.31. Found: C, 66.85; H, 5.32; N, 16.30. |
| 845 | 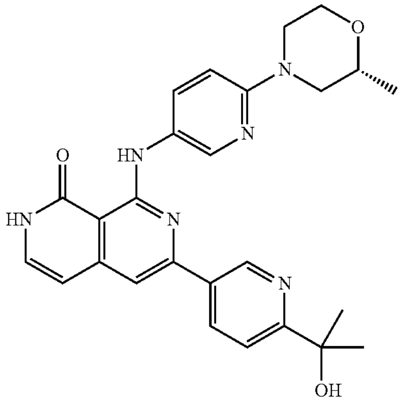 [SMILES: C[C@@H]1CN(c2ccc(Nc3nc(-c4ccc(C(C)(C)O)nc4)cc4cc[nH]c(=O)c34)cn2)CCO1] | ESI-MS m/z 473.2 (MH$^+$) |
| 846 | 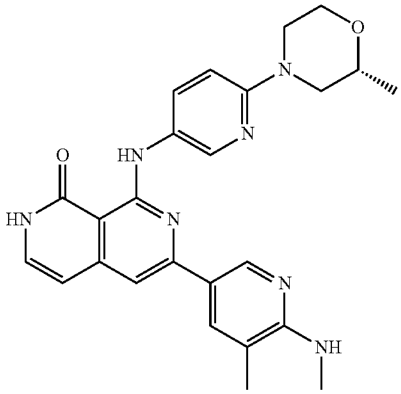 [SMILES: CNc1ncc(-c2cc3cc[nH]c(=O)c3c(Nc3ccc(N4CCO[C@H](C)C4)nc3)n2)cc1C] | ESI-MS m/z 458.2 (MH$^+$) |

TABLE 1-continued
| No | Structure | Physical Data $^1H$ NMR 400 MHz (DMSO-$d_6$) and/or MS (m/z) |
|---|---|---|
| 847 | 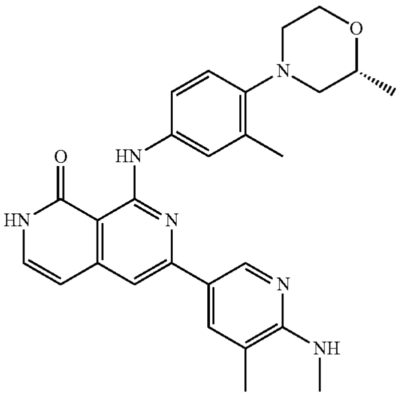 | ESI-MS m/z 471.2 ($MH^+$) |
| 848 | 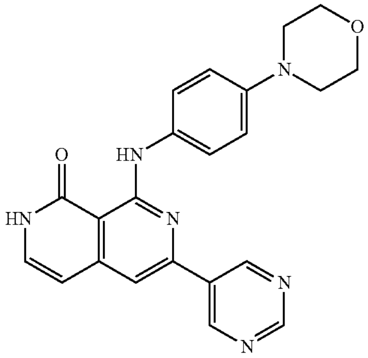 [SMILES: O=c1[nH]ccc2cc(-c3cncnc3)nc(Nc3ccc(N4CCOCC4)cc3)c12] | ESI-MS m/z 401.2 ($MH^+$) |
| 849 | 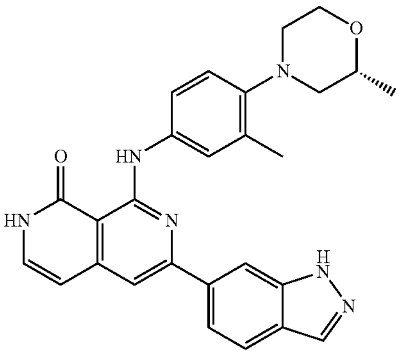 [SMILES: Cc1cc(Nc2nc(-c3ccc4cn[nH]c4c3)cc3cc[nH]c(=O)c23)ccc1N1CCO[C@H](C)C1] | ESI-MS m/z 467.2 ($MH^+$) |
| 850 | 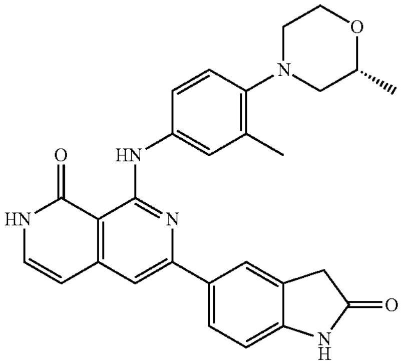 [SMILES: Cc1cc(Nc2nc(-c3ccc4c(c3)CC(=O)N4)cc3cc[nH]c(=O)c23)ccc1N1CCO[C@H](C)C1] | ESI-MS m/z 482.2 ($MH^+$) |

TABLE 1-continued
| No | Structure | Physical Data $^1H$ NMR 400 MHz (DMSO-$d_6$) and/or MS (m/z) |
|---|---|---|
| 851 | 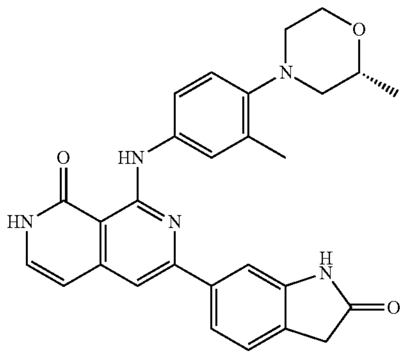 [SMILES: Cc1cc(Nc2nc(-c3ccc4c(c3)NC(=O)C4)cc3cc[nH]c(=O)c23)ccc1N1CCO[C@H](C)C1] | ESI-MS m/z 482.2 ($MH^+$) |
| 852 | 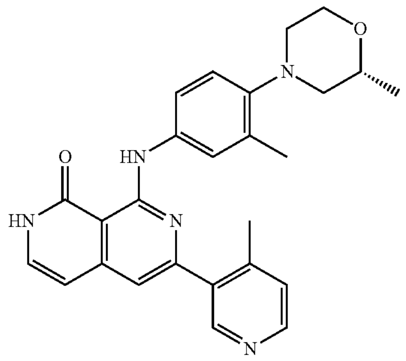 [SMILES: Cc1ccncc1-c1cc2cc[nH]c(=O)c2c(Nc2ccc(N3CCO[C@H](C)C3)c(C)c2)n1] | ESI-MS m/z 442.2 ($MH^+$) |
| 853 | 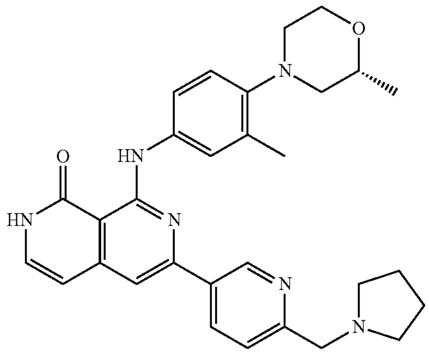 [SMILES: Cc1cc(Nc2nc(-c3ccc(CN4CCCC4)nc3)cc3cc[nH]c(=O)c23)ccc1N1CCO[C@H](C)C1] | ESI-MS m/z 511.3 ($MH^+$) |
| 854 | 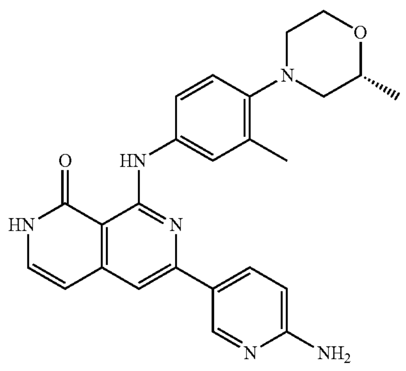 [SMILES: Cc1cc(Nc2nc(-c3ccc(N)nc3)cc3cc[nH]c(=O)c23)ccc1N1CCO[C@H](C)C1] | ESI-MS m/z 443.2 ($MH^+$) |

TABLE 1-continued
| No | Structure | Physical Data $^1H$ NMR 400 MHz (DMSO-$d_6$) and/or MS (m/z) |
|---|---|---|
| 855 | 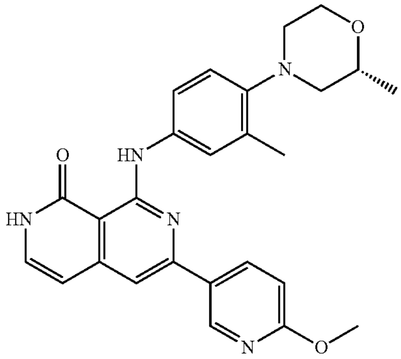 [SMILES: COc1ccc(-c2cc3cc[nH]c(=O)c3c(Nc3ccc(N4CCO[C@H](C)C4)c(C)c3)n2)cn1] | ESI-MS m/z 458.2 (MH$^+$) |
| 856 | 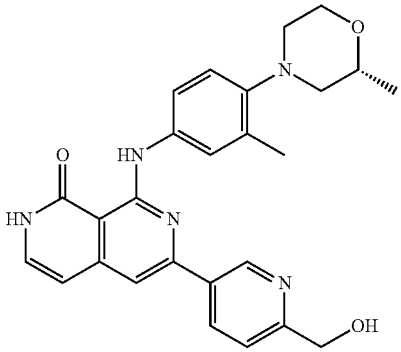 [SMILES: Cc1cc(Nc2nc(-c3ccc(CO)nc3)cc3cc[nH]c(=O)c23)ccc1N1CCO[C@H](C)C1] | ESI-MS m/z 458.2 (MH$^+$) |
| 857 | 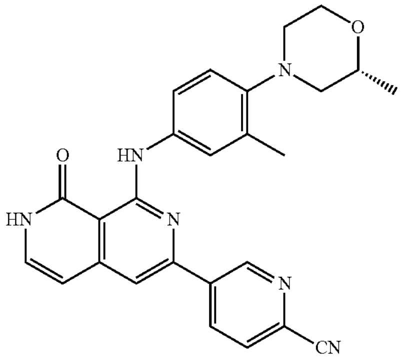 [SMILES: Cc1cc(Nc2nc(-c3ccc(C#N)nc3)cc3cc[nH]c(=O)c23)ccc1N1CCO[C@H](C)C1] | ESI-MS m/z 453.2 (MH$^+$) |
| 858 | 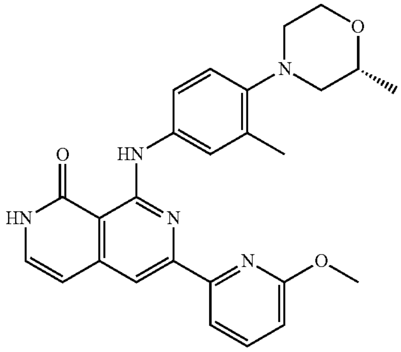 [SMILES: COc1cccc(-c2cc3cc[nH]c(=O)c3c(Nc3ccc(N4CCO[C@H](C)C4)c(C)c3)n2)n1] | ESI-MS m/z 458.2 (MH$^+$) |

TABLE 1-continued
| No | Structure | Physical Data $^1H$ NMR 400 MHz (DMSO-$d_6$) and/or MS (m/z) |
|---|---|---|
| 859 | 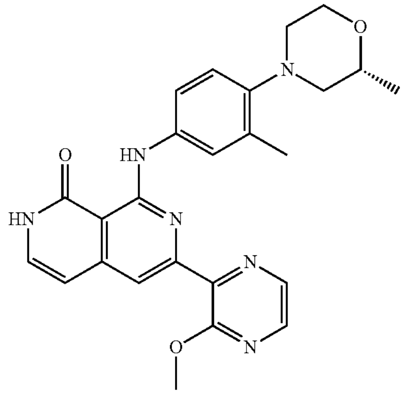 [SMILES: COc1nccnc1-c1cc2cc[nH]c(=O)c2c(Nc2ccc(N3CCO[C@H](C)C3)c(C)c2)n1] | ESI-MS m/z 459.2 ($MH^+$) |
| 860 | 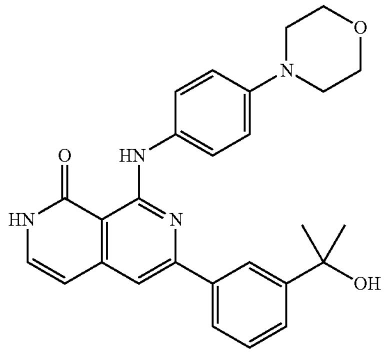 [SMILES: CC(C)(O)c1cccc(-c2cc3cc[nH]c(=O)c3c(Nc3ccc(N4CCOCC4)cc3)n2)c1] | ESI-MS m/z 457.2 ($MH^+$) |
| 861 | 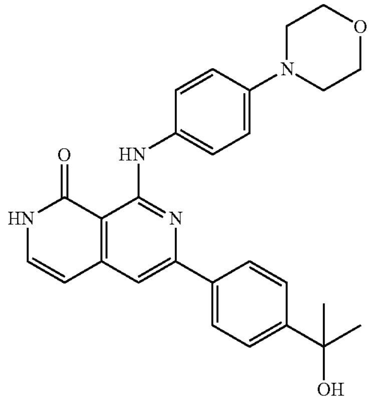 [SMILES: CC(C)(O)c1ccc(-c2cc3cc[nH]c(=O)c3c(Nc3ccc(N4CCOCC4)cc3)n2)cc1] | ESI-MS m/z 457.2 ($MH^+$) |
| 862 | 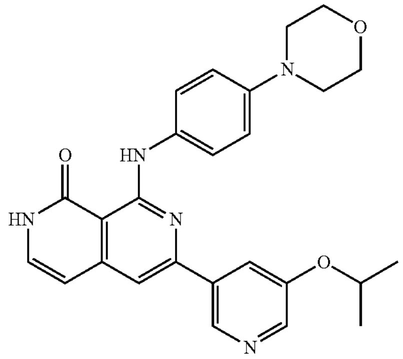 [SMILES: CC(C)Oc1cncc(-c2cc3cc[nH]c(=O)c3c(Nc3ccc(N4CCOCC4)cc3)n2)c1] | ESI-MS m/z 458.2 ($MH^+$) |

TABLE 1-continued
| No | Structure | Physical Data $^1H$ NMR 400 MHz (DMSO-$d_6$) and/or MS (m/z) |
|---|---|---|
| 863 | 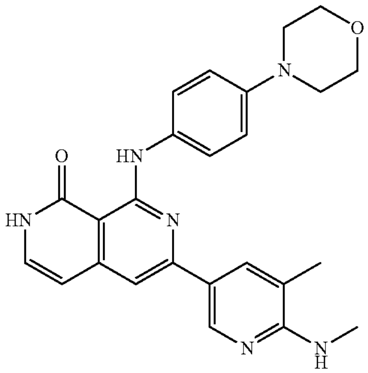 [SMILES: CNc1ncc(-c2cc3cc[nH]c(=O)c3c(Nc3ccc(N4CCOCC4)cc3)n2)cc1C] | ESI-MS m/z 443.2 (MH$^+$) |
| 864 | 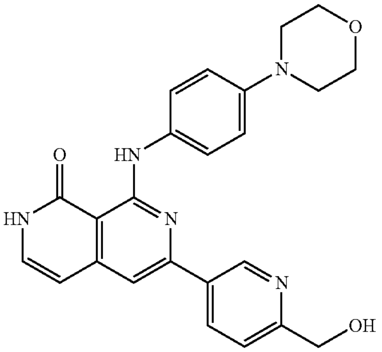 [SMILES: O=c1[nH]ccc2cc(-c3ccc(CO)nc3)nc(Nc3ccc(N4CCOCC4)cc3)c12] | ESI-MS m/z 430.2 (MH$^+$) |
| 865 | 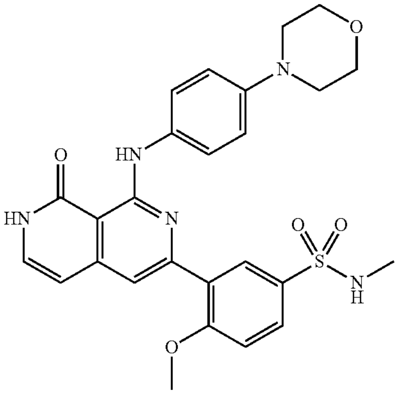 [SMILES: CNS(=O)(=O)c1ccc(OC)c(-c2cc3cc[nH]c(=O)c3c(Nc3ccc(N4CCOCC4)cc3)n2)c1] | ESI-MS m/z 522.2 (MH$^+$) |
| 866 | 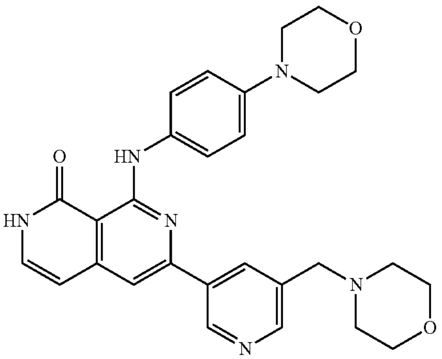 [SMILES: O=c1[nH]ccc2cc(-c3cncc(CN4CCOCC4)c3)nc(Nc3ccc(N4CCOCC4)cc3)c12] | ESI-MS m/z 499.2 (MH$^+$) |

TABLE 1-continued
| No | Structure | Physical Data $^1$H NMR 400 MHz (DMSO-$d_6$) and/or MS (m/z) |
|---|---|---|
| 867 | 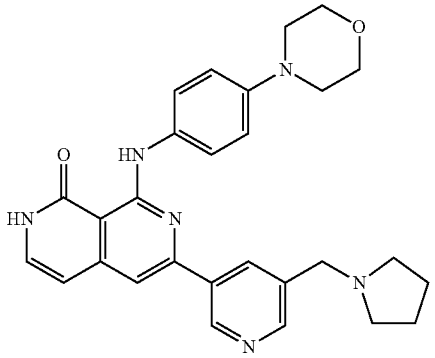 [SMILES: O=c1[nH]ccc2cc(-c3cncc(CN4CCCC4)c3)nc(Nc3ccc(N4CCOCC4)cc3)c12] | ESI-MS m/z 483.2 (MH$^+$) |
| 868 | 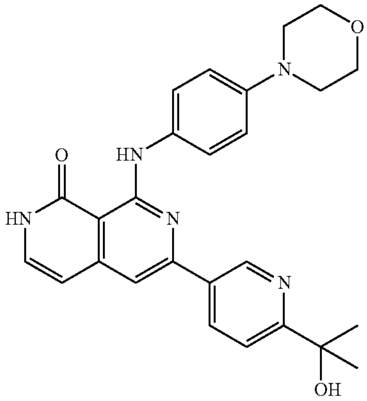 [SMILES: CC(C)(O)c1ccc(-c2cc3cc[nH]c(=O)c3c(Nc3ccc(N4CCOCC4)cc3)n2)cn1] | ESI-MS m/z 458.2 (MH$^+$) |
| 869 | 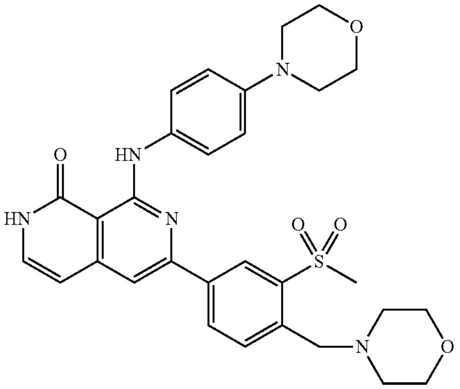 [SMILES: CS(=O)(=O)c1cc(-c2cc3cc[nH]c(=O)c3c(Nc3ccc(N4CCOCC4)cc3)n2)ccc1CN1CCOCC1] | ESI-MS m/z 576.2 (MH$^+$) |
| 870 | 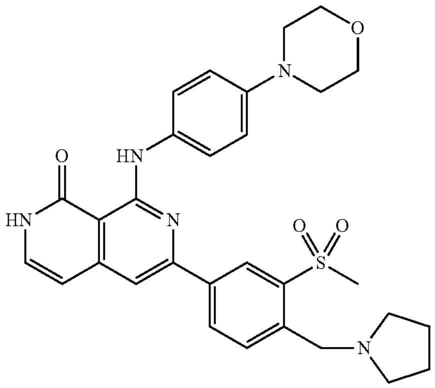 [SMILES: CS(=O)(=O)c1cc(-c2cc3cc[nH]c(=O)c3c(Nc3ccc(N4CCOCC4)cc3)n2)ccc1CN1CCCC1] | ESI-MS m/z 560.2 (MH$^+$) |

TABLE 1-continued
| No | Structure | Physical Data $^1$H NMR 400 MHz (DMSO-$d_6$) and/or MS (m/z) |
|---|---|---|
| 871 | 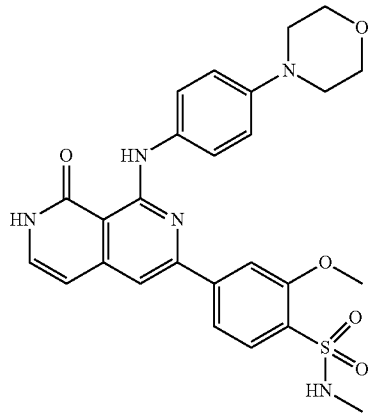 [SMILES: CNS(=O)(=O)c1ccc(-c2cc3cc[nH]c(=O)c3c(Nc3ccc(N4CCOCC4)cc3)n2)cc1OC] | ESI-MS m/z 522.2 (MH$^+$) |
| 872 | 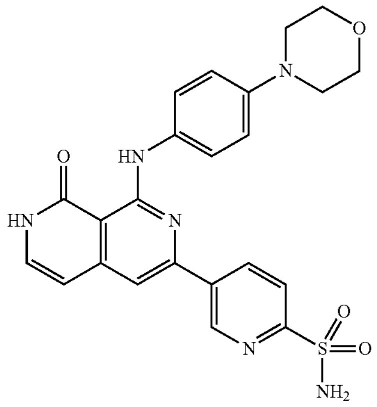 [SMILES: NS(=O)(=O)c1ccc(-c2cc3cc[nH]c(=O)c3c(Nc3ccc(N4CCOCC4)cc3)n2)cn1] | ESI-MS m/z 479.1 (MH$^+$) |
| 873 | 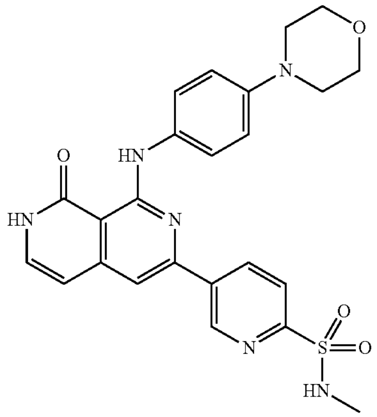 [SMILES: CNS(=O)(=O)c1ccc(-c2cc3cc[nH]c(=O)c3c(Nc3ccc(N4CCOCC4)cc3)n2)cn1] | ESI-MS m/z 493.2 (MH$^+$) |

TABLE 1-continued
| No | Structure | Physical Data $^1$H NMR 400 MHz (DMSO-$d_6$) and/or MS (m/z) |
|---|---|---|
| 874 | 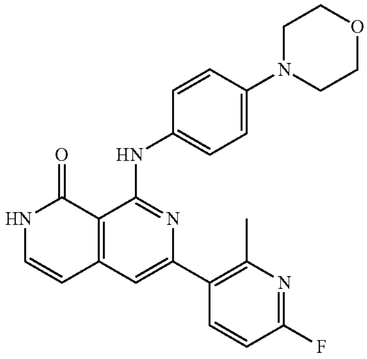 [SMILES: Cc1nc(F)ccc1-c1cc2cc[nH]c(=O)c2c(Nc2ccc(N3CCOCC3)cc2)n1] | ESI-MS m/z 432.2 ($MH^+$) |
| 875 | 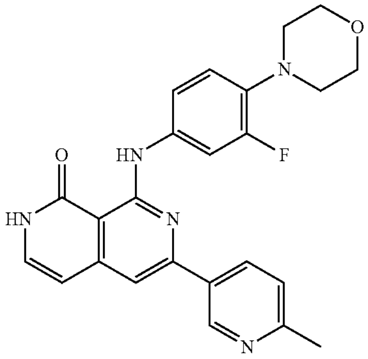 [SMILES: Cc1ccc(-c2cc3cc[nH]c(=O)c3c(Nc3ccc(N4CCOCC4)c(F)c3)n2)cn1] | ESI-MS m/z 432.2 ($MH^+$) |
| 876 | 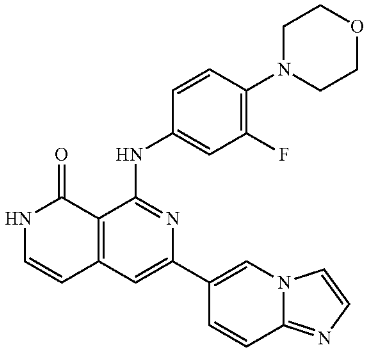 [SMILES: O=c1[nH]ccc2cc(-c3ccc4nccn4c3)nc(Nc3ccc(N4CCOCC4)c(F)c3)c12] | ESI-MS m/z 457.2 ($MH^+$) |
| 878 | 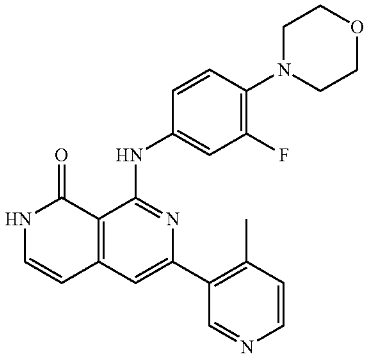 [SMILES: Cc1ccncc1-c1cc2cc[nH]c(=O)c2c(Nc2ccc(N3CCOCC3)c(F)c2)n1] | ESI-MS m/z 432.2 ($MH^+$) |

TABLE 1-continued
| No | Structure | Physical Data $^1$H NMR 400 MHz (DMSO-$d_6$) and/or MS (m/z) |
|---|---|---|
| 879 | 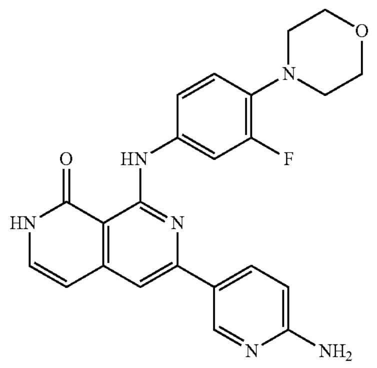 [SMILES: Nc1ccc(-c2cc3cc[nH]c(=O)c3c(Nc3ccc(N4CCOCC4)c(F)c3)n2)cn1] | ESI-MS m/z 433.2 (MH$^+$) |
| 880 | 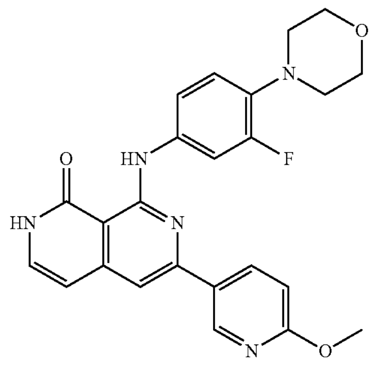 [SMILES: COc1ccc(-c2cc3cc[nH]c(=O)c3c(Nc3ccc(N4CCOCC4)c(F)c3)n2)cn1] | ESI-MS m/z 448.2 (MH$^+$) |
| 881 | 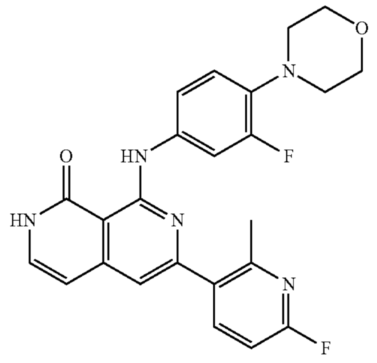 [SMILES: Cc1nc(F)ccc1-c1cc2cc[nH]c(=O)c2c(Nc2ccc(N3CCOCC3)c(F)c2)n1] | ESI-MS m/z 450.2 (MH$^+$) |
| 882 | 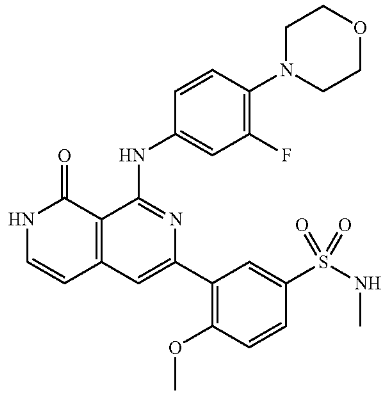 [SMILES: CNS(=O)(=O)c1ccc(OC)c(-c2cc3cc[nH]c(=O)c3c(Nc3ccc(N4CCOCC4)c(F)c3)n2)c1] | ESI-MS m/z 540.2 (MH$^+$) |

TABLE 1-continued
| No | Structure | Physical Data $^1H$ NMR 400 MHz (DMSO-$d_6$) and/or MS (m/z) |
|---|---|---|
| 883 | 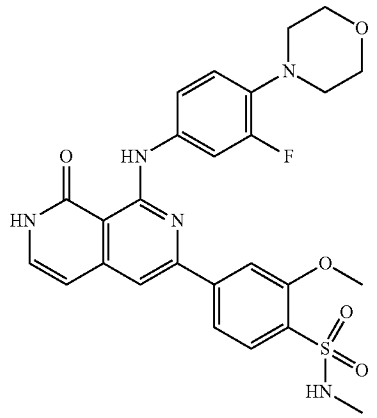 [SMILES: CNS(=O)(=O)c1ccc(-c2cc3cc[nH]c(=O)c3c(Nc3ccc(N4CCOCC4)c(F)c3)n2)cc1OC] | ESI-MS m/z 540.2 (MH$^+$) |
| 884 | 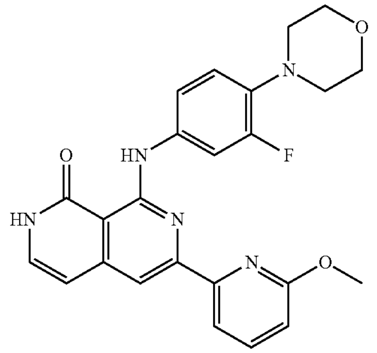 [SMILES: COc1cccc(-c2cc3cc[nH]c(=O)c3c(Nc3ccc(N4CCOCC4)c(F)c3)n2)n1] | ESI-MS m/z 448.2 (MH$^+$) |
| 885 | 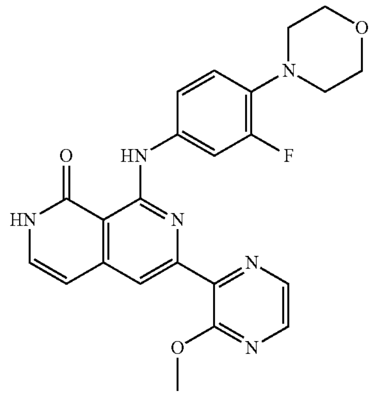 [SMILES: COc1nccnc1-c1cc2cc[nH]c(=O)c2c(Nc2ccc(N3CCOCC3)c(F)c2)n1] | ESI-MS m/z 449.2 (MH$^+$) |
| 886 | 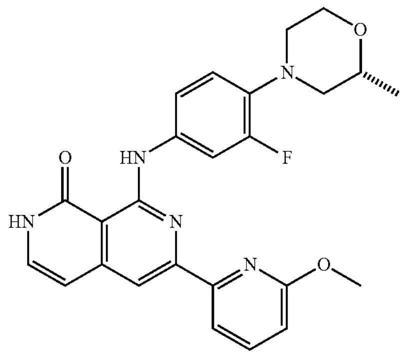 [SMILES: COc1cccc(-c2cc3cc[nH]c(=O)c3c(Nc3ccc(N4CCO[C@H](C)C4)c(F)c3)n2)n1] | ESI-MS m/z 462.2 (MH$^+$) |

TABLE 1-continued
| No | Structure | Physical Data $^{1}H$ NMR 400 MHz (DMSO-$d_6$) and/or MS (m/z) |
|---|---|---|
| 887 | 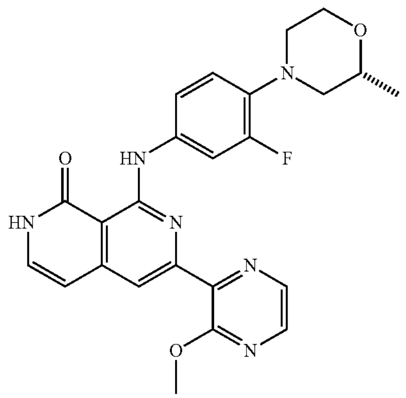 [SMILES: COc1nccnc1-c1cc2cc[nH]c(=O)c2c(Nc2ccc(N3CCO[C@H](C)C3)c(F)c2)n1] | ESI-MS m/z 463.2 ($MH^+$) |
| 888 | 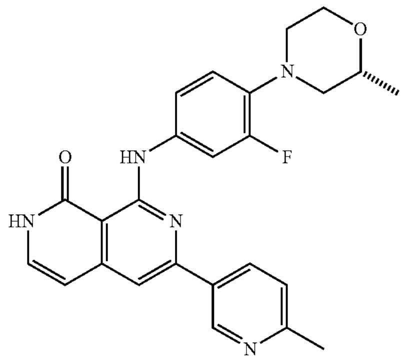 [SMILES: Cc1ccc(-c2cc3cc[nH]c(=O)c3c(Nc3ccc(N4CCO[C@H](C)C4)c(F)c3)n2)cn1] | ESI-MS m/z 446.2 ($MH^+$) |
| 889 | 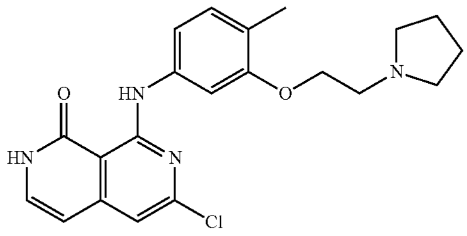 [SMILES: Cc1ccc(Nc2nc(Cl)cc3cc[nH]c(=O)c23)cc1OCCN1CCCC1] | ESI-MS m/z 399.2 ($MH^+$) |
| 890 | 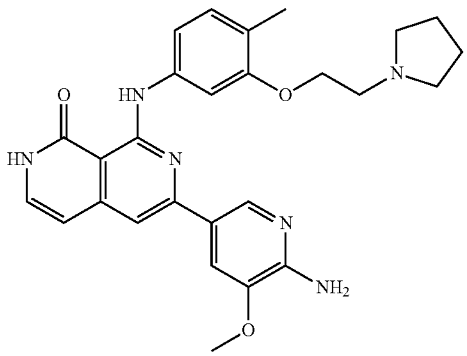 [SMILES: COc1cc(-c2cc3cc[nH]c(=O)c3c(Nc3ccc(C)c(OCCN4CCCC4)c3)n2)cnc1N] | ESI-MS m/z 487.2 ($MH^+$) |

TABLE 1-continued
| No | Structure | Physical Data $^1H$ NMR 400 MHz ($DMSO-d_6$) and/or MS (m/z) |
|---|---|---|
| 891 | 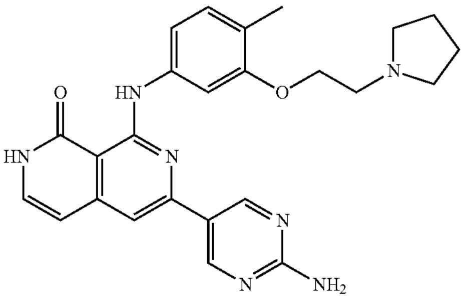 [SMILES: Cc1ccc(Nc2nc(-c3cnc(N)nc3)cc3cc[nH]c(=O)c23)cc1OCCN1CCCC1] | ESI-MS m/z 458.2 ($MH^+$) |
| 892 | 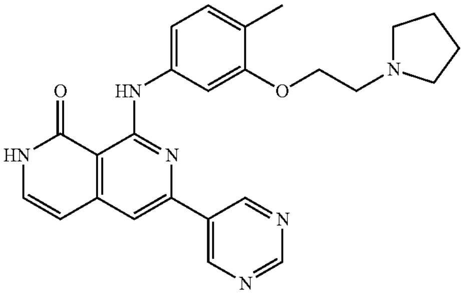 [SMILES: Cc1ccc(Nc2nc(-c3cncnc3)cc3cc[nH]c(=O)c23)cc1OCCN1CCCC1] | ESI-MS m/z 443.2 ($MH^+$) |
| 893 | 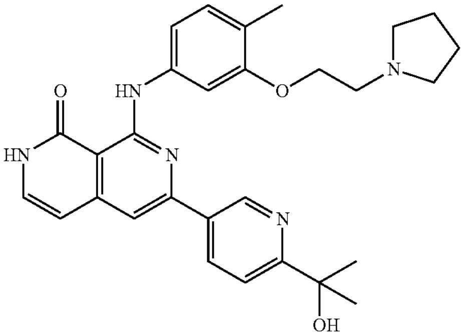 [SMILES: Cc1ccc(Nc2nc(-c3ccc(C(C)(C)O)nc3)cc3cc[nH]c(=O)c23)cc1OCCN1CCCC1] | ESI-MS m/z 500.3 ($MH^+$) |
| 894 | 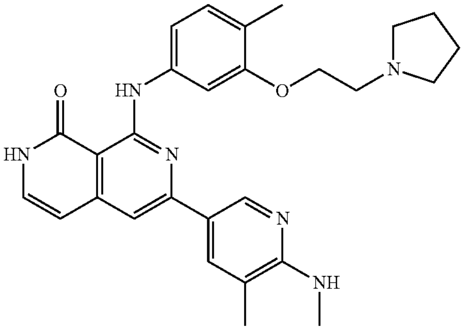 [SMILES: CNc1ncc(-c2cc3cc[nH]c(=O)c3c(Nc3ccc(C)c(OCCN4CCCC4)c3)n2)cc1C] | ESI-MS m/z 485.3 ($MH^+$) |
| 895 | 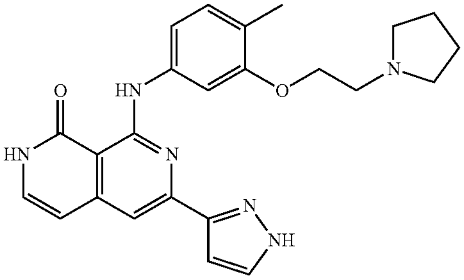 [SMILES: Cc1ccc(Nc2nc(-c3cc[nH]n3)cc3cc[nH]c(=O)c23)cc1OCCN1CCCC1] | ESI-MS m/z 431.2 ($MH^+$) |

TABLE 1-continued
| No | Structure | Physical Data $^1H$ NMR 400 MHz (DMSO-$d_6$) and/or MS (m/z) |
|---|---|---|
| 896 | 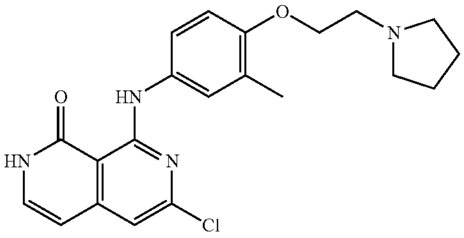 [SMILES: Cc1cc(Nc2nc(Cl)cc3cc[nH]c(=O)c23)ccc1OCCN1CCCC1] | ESI-MS m/z 399.2 (MH$^+$) |
| 897 | 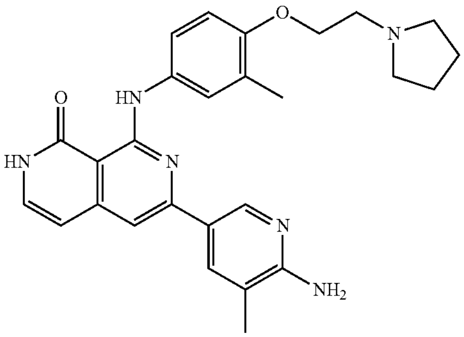 [SMILES: Cc1cc(Nc2nc(-c3cnc(N)c(C)c3)cc3cc[nH]c(=O)c23)ccc1OCCN1CCCC1] | ESI-MS m/z 471.2 (MH$^+$) |
| 898 | 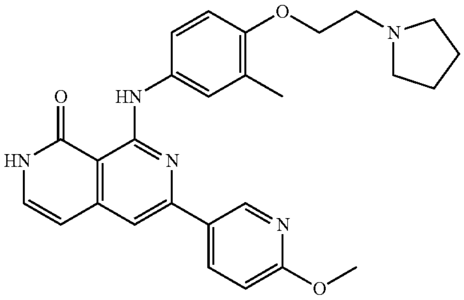 [SMILES: COc1ccc(-c2cc3cc[nH]c(=O)c3c(Nc3ccc(OCCN4CCCC4)c(C)c3)n2)cn1] | ESI-MS m/z 472.2 (MH$^+$) |
| 899 | 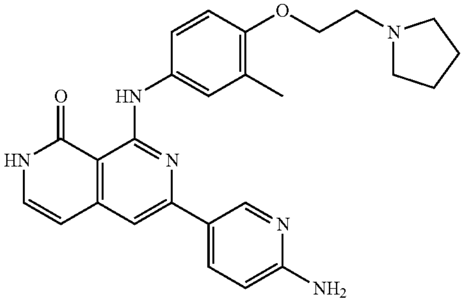 | ESI-MS m/z 457.2 (MH$^+$) |
| 900 | 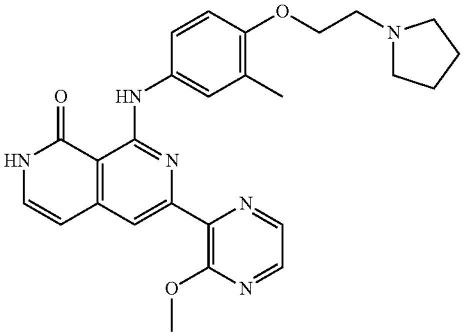 [SMILES: COc1nccnc1-c1cc2cc[nH]c(=O)c2c(Nc2ccc(OCCN3CCCC3)c(C)c2)n1] | ESI-MS m/z 473.2 (MH$^+$) |

TABLE 1-continued
| No | Structure | Physical Data $^1H$ NMR 400 MHz (DMSO-$d_6$) and/or MS (m/z) |
|---|---|---|
| 901 | 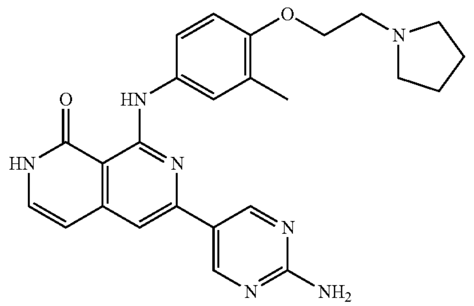 [SMILES: Cc1cc(Nc2nc(-c3cnc(N)nc3)cc3cc[nH]c(=O)c23)ccc1OCCN1CCCC1] | ESI-MS m/z 458.2 ($MH^+$) |
| 902 | 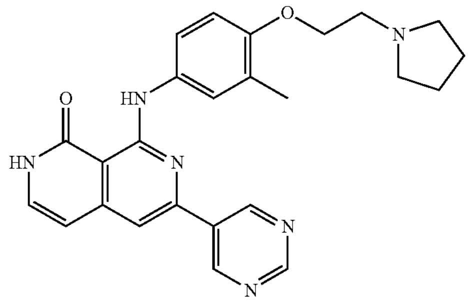 [SMILES: Cc1cc(Nc2nc(-c3cncnc3)cc3cc[nH]c(=O)c23)ccc1OCCN1CCCC1] | ESI-MS m/z 443.2 ($MH^+$) |
| 903 | 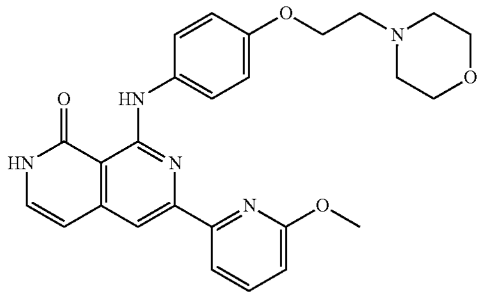 [SMILES: COc1cccc(-c2cc3cc[nH]c(=O)c3c(Nc3ccc(OCCN4CCOCC4)cc3)n2)n1] | ESI-MS m/z 474.2 ($MH^+$) |
| 904 | 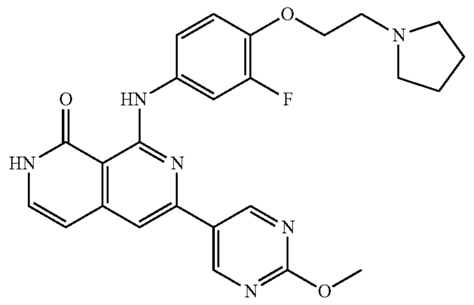 [SMILES: COc1ncc(-c2cc3cc[nH]c(=O)c3c(Nc3ccc(OCCN4CCCC4)c(F)c3)n2)cn1] | ESI-MS m/z 477.2 ($MH^+$) |
| 905 | 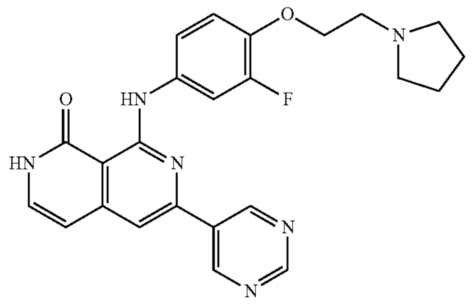 [SMILES: O=c1[nH]ccc2cc(-c3cncnc3)nc(Nc3ccc(OCCN4CCCC4)c(F)c3)c12] | ESI-MS m/z 447.2 ($MH^+$) |

TABLE 1-continued
| No | Structure | Physical Data $^{1}H$ NMR 400 MHz (DMSO-$d_6$) and/or MS (m/z) |
| --- | --- | --- |
| 906 | 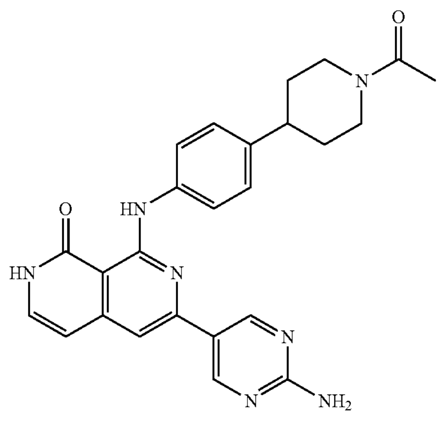 [SMILES: CC(=O)N1CCC(c2ccc(Nc3nc(-c4cnc(N)nc4)cc4cc[nH]c(=O)c34)cc2)CC1] | ESI-MS m/z 456.2 ($MH^+$) |
| 907 | 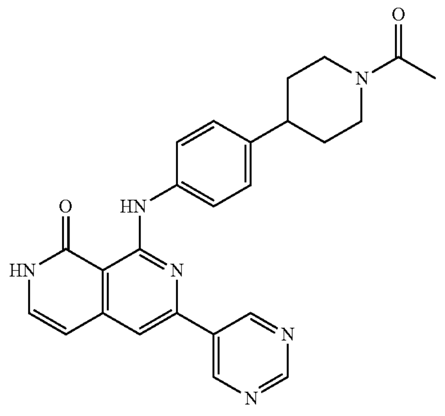 [SMILES: CC(=O)N1CCC(c2ccc(Nc3nc(-c4cncnc4)cc4cc[nH]c(=O)c34)cc2)CC1] | ESI-MS m/z 441.2 ($MH^+$) |
| 908 | 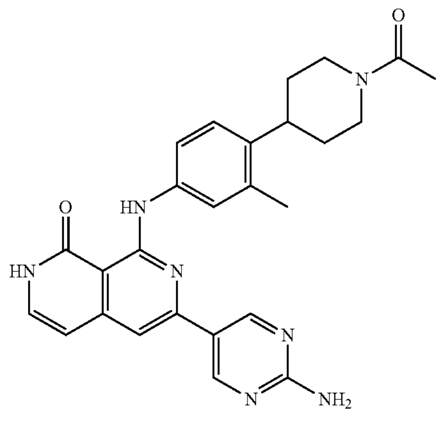 [SMILES: CC(=O)N1CCC(c2ccc(Nc3nc(-c4cnc(N)nc4)cc4cc[nH]c(=O)c34)cc2C)CC1] | ESI-MS m/z 470.2 ($MH^+$) |

TABLE 1-continued
| No | Structure | Physical Data $^1H$ NMR 400 MHz (DMSO-$d_6$) and/or MS (m/z) |
|---|---|---|
| 909 | 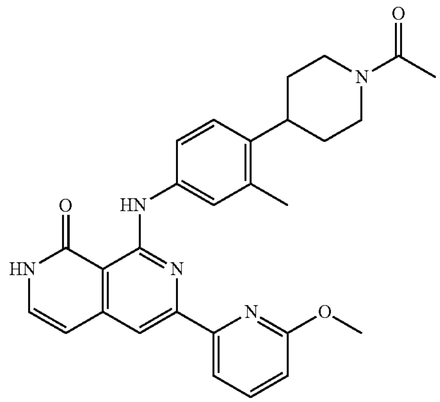 [SMILES: COc1cccc(-c2cc3cc[nH]c(=O)c3c(Nc3ccc(C4CCN(C(C)=O)CC4)c(C)c3)n2)n1] | ESI-MS m/z 484.2 MH$^+$) |
| 910 | 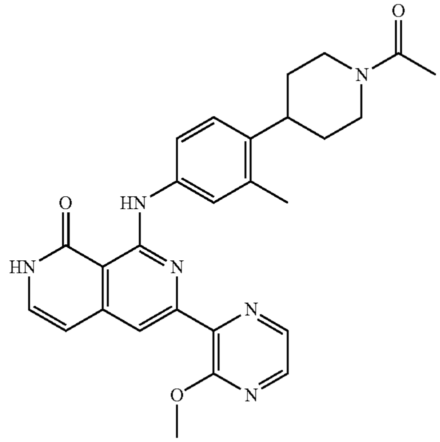 [SMILES: COc1nccnc1-c1cc2cc[nH]c(=O)c2c(Nc2ccc(C3CCN(C(C)=O)CC3)c(C)c2)n1] | ESI-MS m/z 485.2 MH$^+$) |
| 911 | 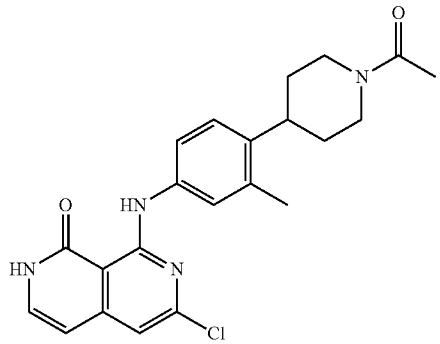 [SMILES: CC(=O)N1CCC(c2ccc(Nc3nc(Cl)cc4cc[nH]c(=O)c34)cc2C)CC1] | ESI-MS m/z 411.2 (MH$^+$) |

TABLE 1-continued
| No | Structure | Physical Data $^1H$ NMR 400 MHz (DMSO-$d_6$) and/or MS (m/z) |
|---|---|---|
| 912 | 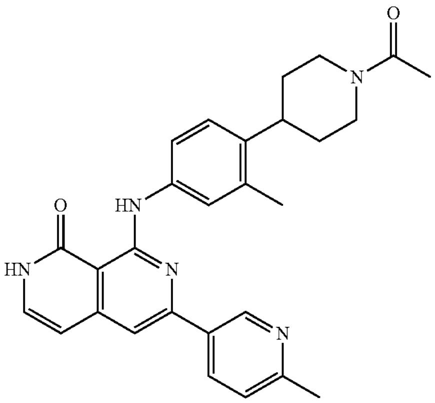 [SMILES: CC(=O)N1CCC(c2ccc(Nc3nc(-c4ccc(C)nc4)cc4cc[nH]c(=O)c34)cc2C)CC1] | ESI-MS m/z 468 ($MH^+$) |
| 913 | 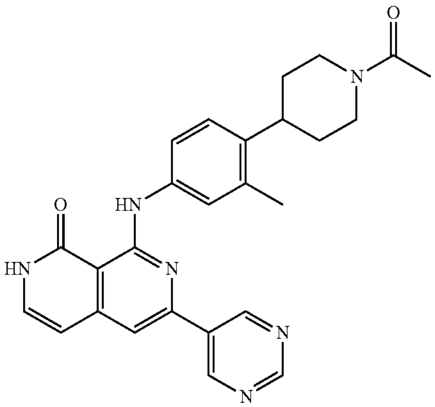 [SMILES: CC(=O)N1CCC(c2ccc(Nc3nc(-c4cncnc4)cc4cc[nH]c(=O)c34)cc2C)CC1] | ESI-MS m/z 455.2 $MH^+$) |
| 914 | 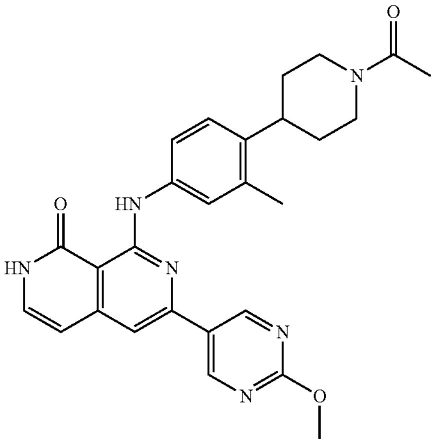 [SMILES: COc1ncc(-c2cc3cc[nH]c(=O)c3c(Nc3ccc(C4CCN(C(C)=O)CC4)c(C)c3)n2)cn1] | ESI-MS m/z 485.2 ($MH^+$) |

TABLE 1-continued
| No | Structure | Physical Data $^1H$ NMR 400 MHz ($DMSO-d_6$) and/or MS (m/z) |
|---|---|---|
| 915 | 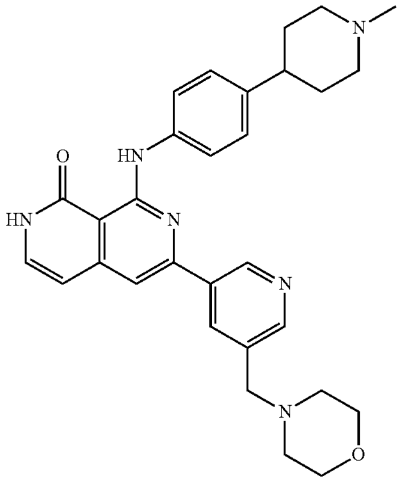 [SMILES: CN1CCC(c2ccc(Nc3nc(-c4cncc(CN5CCOCC5)c4)cc4cc[nH]c(=O)c34)cc2)CC1] | ESI-MS m/z 511.3 ($MH^+$) |
| 916 | 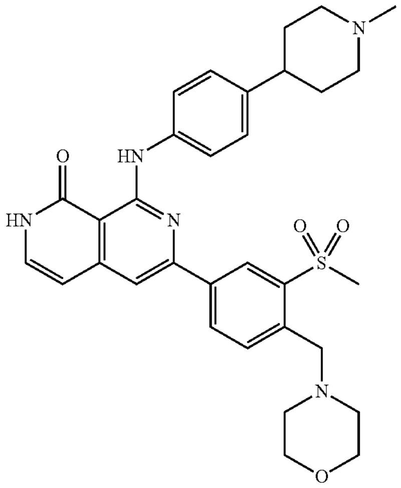 [SMILES: CN1CCC(c2ccc(Nc3nc(-c4ccc(CN5CCOCC5)c(S(C)(=O)=O)c4)cc4cc[nH]c(=O)c34)cc2)CC1] | ESI-MS m/z 588.3 ($MH^+$) |
| 917 | 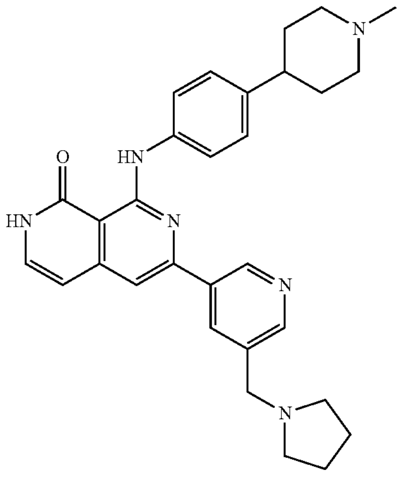 [SMILES: CN1CCC(c2ccc(Nc3nc(-c4cncc(CN5CCCC5)c4)cc4cc[nH]c(=O)c34)cc2)CC1] | ESI-MS m/z 495.3 ($MH^+$) |

TABLE 1-continued
| No | Structure | Physical Data $^1H$ NMR 400 MHz (DMSO-$d_6$) and/or MS (m/z) |
|---|---|---|
| 918 | 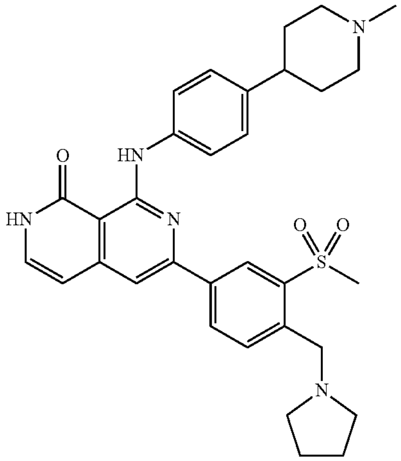 [SMILES: CN1CCC(c2ccc(Nc3nc(-c4ccc(CN5CCCC5)c(S(C)(=O)=O)c4)cc4cc[nH]c(=O)c34)cc2)CC1] | ESI-MS m/z 572.3 ($MH^+$) |
| 919 | 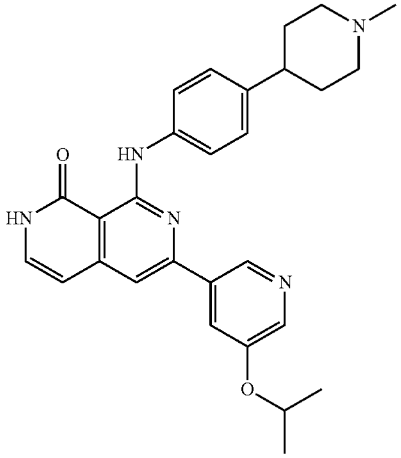 [SMILES: CC(C)Oc1cncc(-c2cc3cc[nH]c(=O)c3c(Nc3ccc(C4CCN(C)CC4)cc3)n2)c1] | ESI-MS m/z 470.2 ($MH^+$) |
| 920 | 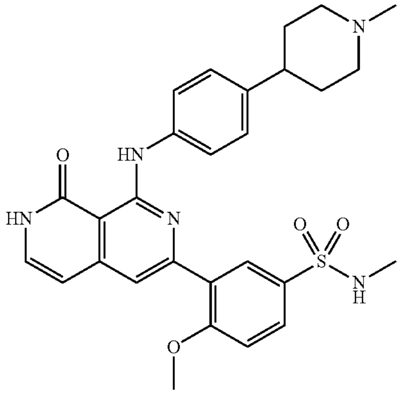 [SMILES: CNS(=O)(=O)c1ccc(OC)c(-c2cc3cc[nH]c(=O)c3c(Nc3ccc(C4CCN(C)CC4)cc3)n2)c1] | ESI-MS m/z 534.2 ($MH^+$) |

TABLE 1-continued
| No | Structure | Physical Data $^1H$ NMR 400 MHz (DMSO-$d_6$) and/or MS (m/z) |
|---|---|---|
| 921 | 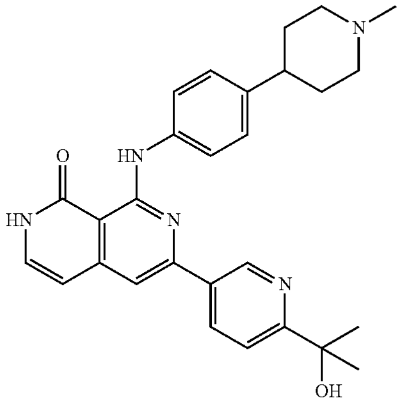 [SMILES: CN1CCC(c2ccc(Nc3nc(-c4ccc(C(C)(C)O)nc4)cc4cc[nH]c(=O)c34)cc2)CC1] | ESI-MS m/z 470.2 ($MH^+$) |
| 922 | 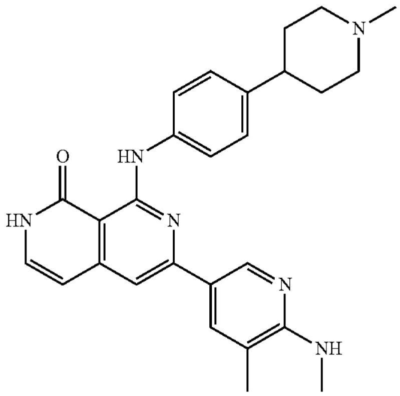 [SMILES: CNc1ncc(-c2cc3cc[nH]c(=O)c3c(Nc3ccc(C4CCN(C)CC4)cc3)n2)cc1C] | ESI-MS m/z 455.2 ($MH^+$) |
| 923 | 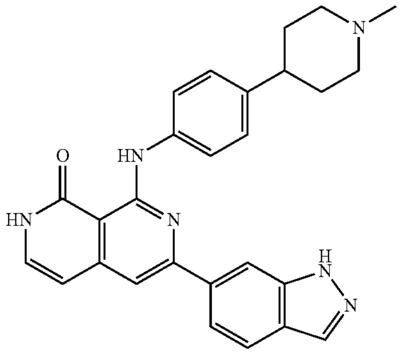 [SMILES: CN1CCC(c2ccc(Nc3nc(-c4ccc5cn[nH]c5c4)cc4cc[nH]c(=O)c34)cc2)CC1] | ESI-MS m/z 451.2 ($MH^+$) |
| 924 | 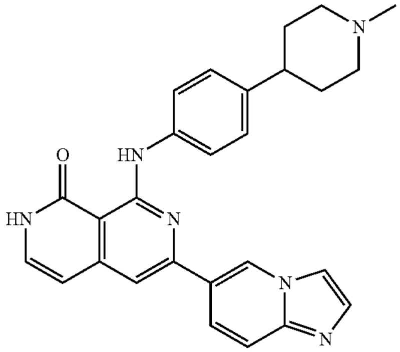 [SMILES: CN1CCC(c2ccc(Nc3nc(-c4ccc5nccn5c4)cc4cc[nH]c(=O)c34)cc2)CC1] | ESI-MS m/z 451.2 ($MH^+$) |

TABLE 1-continued
| No | Structure | Physical Data $^1H$ NMR 400 MHz ($DMSO-d_6$) and/or MS (m/z) |
|---|---|---|
| 925 | 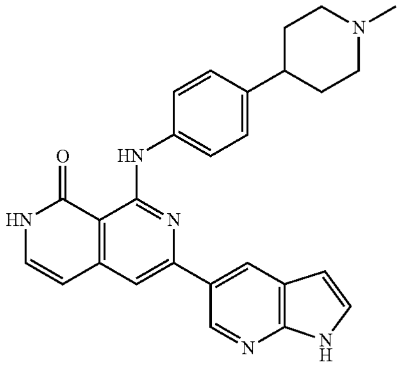 [SMILES: CN1CCC(c2ccc(Nc3nc(-c4cnc5[nH]ccc5c4)cc4cc[nH]c(=O)c34)cc2)CC1] | ESI-MS m/z 451.2 ($MH^+$) |
| 926 | 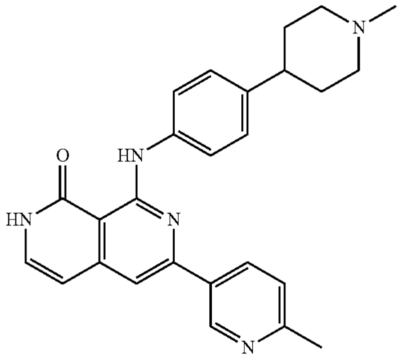 [SMILES: Cc1ccc(-c2cc3cc[nH]c(=O)c3c(Nc3ccc(C4CCN(C)CC4)cc3)n2)cn1] | ESI-MS m/z 426.2 ($MH^+$) |
| 927 | 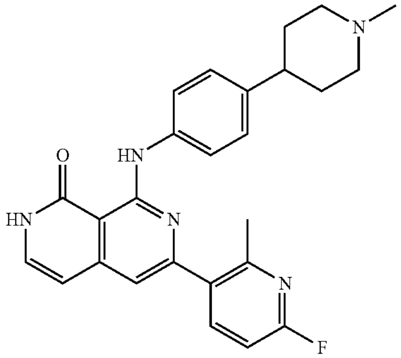 [SMILES: Cc1nc(F)ccc1-c1cc2cc[nH]c(=O)c2c(Nc2ccc(C3CCN(C)CC3)cc2)n1] | ESI-MS m/z 444.2 ($MH^+$) |
| 928 | 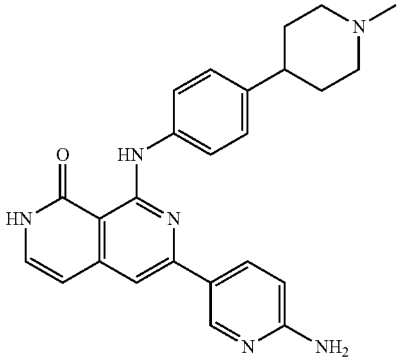 [SMILES: CN1CCC(c2ccc(Nc3nc(-c4ccc(N)nc4)cc4cc[nH]c(=O)c34)cc2)CC1] | ESI-MS m/z 427.2 ($MH^+$) |

TABLE 1-continued
| No | Structure | Physical Data $^1$H NMR 400 MHz (DMSO-$d_6$) and/or MS (m/z) |
|---|---|---|
| 929 | 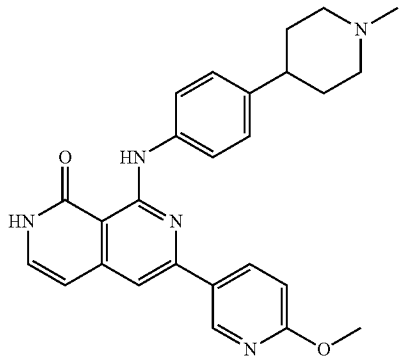 [SMILES: COc1ccc(-c2cc3cc[nH]c(=O)c3c(Nc3ccc(C4CCN(C)CC4)cc3)n2)cn1] | ESI-MS m/z 442.2 (MH$^+$) |
| 930 | 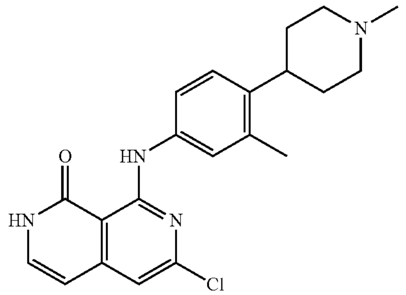 [SMILES: Cc1cc(Nc2nc(Cl)cc3cc[nH]c(=O)c23)ccc1C1CCN(C)CC1] | ESI-MS m/z 383.2 (MH$^+$) |
| 931 | 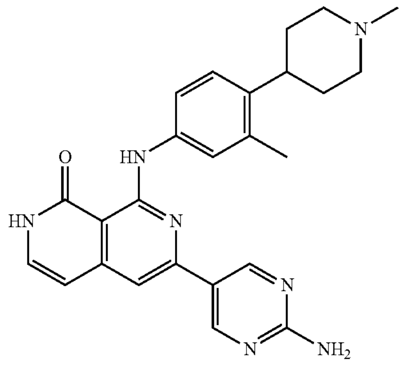 [SMILES: Cc1cc(Nc2nc(-c3cnc(N)nc3)cc3cc[nH]c(=O)c23)ccc1C1CCN(C)CC1] | ESI-MS m/z 442.2 (MH$^+$) |
| 932 | 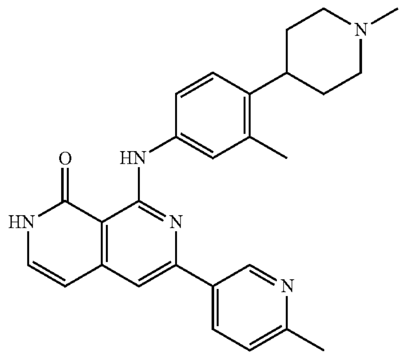 [SMILES: Cc1ccc(-c2cc3cc[nH]c(=O)c3c(Nc3ccc(C4CCN(C)CC4)c(C)c3)n2)cn1] | ESI-MS m/z 440.2 (MH$^+$) |

TABLE 1-continued
| No | Structure | Physical Data $^1H$ NMR 400 MHz (DMSO-$d_6$) and/or MS (m/z) |
|---|---|---|
| 933 | 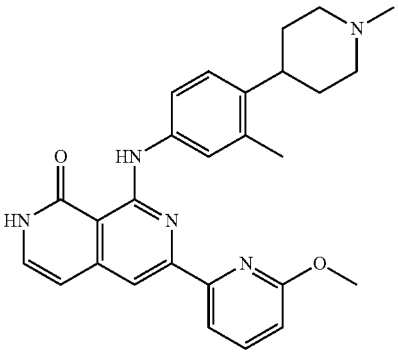 [SMILES: COc1cccc(-c2cc3cc[nH]c(=O)c3c(Nc3ccc(C4CCN(C)CC4)c(C)c3)n2)n1] | ESI-MS m/z 456.2 (MH$^+$) |
| 934 | 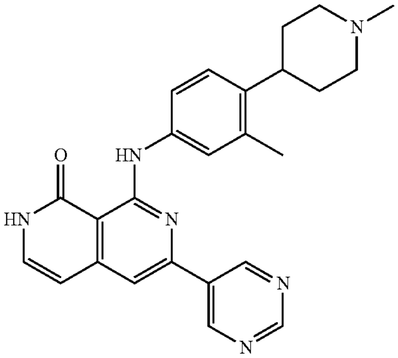 [SMILES: Cc1cc(Nc2nc(-c3cncnc3)cc3cc[nH]c(=O)c23)ccc1C1CCN(C)CC1] | ESI-MS m/z 427.2 (MH$^+$) |
| 935 | 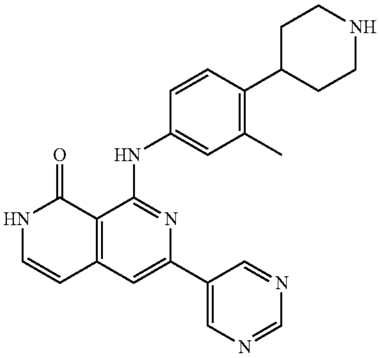 [SMILES: Cc1cc(Nc2nc(-c3cncnc3)cc3cc[nH]c(=O)c23)ccc1C1CCNCC1] | ESI-MS m/z 413.2 (MH$^+$) |
| 936 | 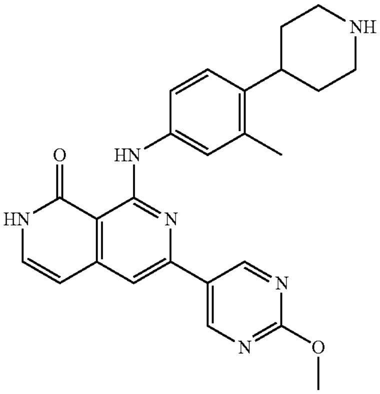 [SMILES: COc1ncc(-c2cc3cc[nH]c(=O)c3c(Nc3ccc(C4CCNCC4)c(C)c3)n2)cn1] | ESI-MS m/z 443.2 (MH$^+$) |

TABLE 1-continued
| No | Structure | Physical Data $^1H$ NMR 400 MHz (DMSO-$d_6$) and/or MS (m/z) |
| --- | --- | --- |
| 937 | 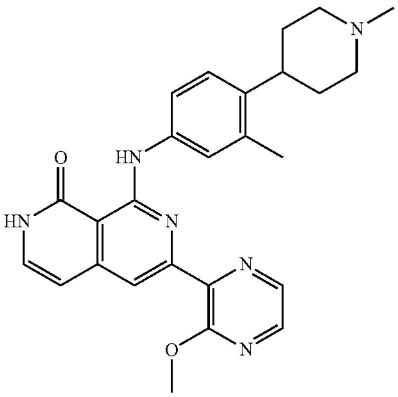 [SMILES: COc1nccnc1-c1cc2cc[nH]c(=O)c2c(Nc2ccc(C3CCN(C)CC3)c(C)c2)n1] | ESI-MS m/z 457.2 ($MH^+$) |
| 938 | 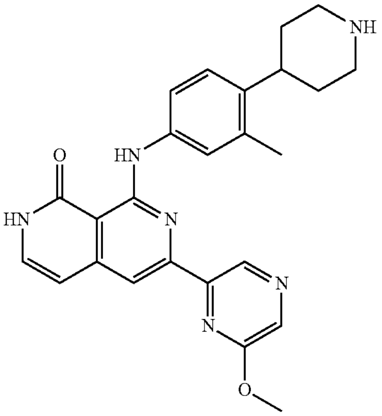 [SMILES: COc1cncc(-c2cc3cc[nH]c(=O)c3c(Nc3ccc(C4CCNCC4)c(C)c3)n2)n1] | ESI-MS m/z 443.2 ($MH^+$) |
| 939 | 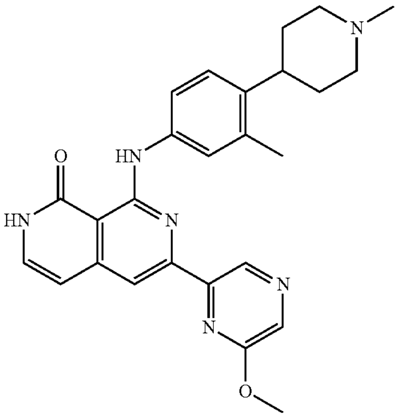 [SMILES: COc1cncc(-c2cc3cc[nH]c(=O)c3c(Nc3ccc(C4CCN(C)CC4)c(C)c3)n2)n1] | ESI-MS m/z 457.2 ($MH^+$) |

TABLE 1-continued
| No | Structure | Physical Data $^1H$ NMR 400 MHz (DMSO-$d_6$) and/or MS (m/z) |
|---|---|---|
| 940 | 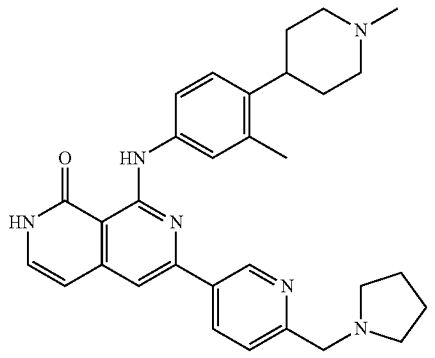 [SMILES: Cc1cc(Nc2nc(-c3ccc(CN4CCCC4)nc3)cc3cc[nH]c(=O)c23)ccc1C1CCN(C)CC1] | ESI-MS m/z 509.3 (MH$^+$) |
| 941 | 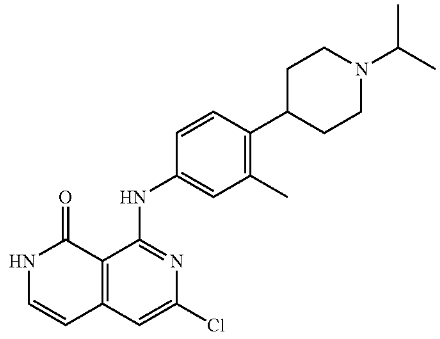 [SMILES: Cc1cc(Nc2nc(Cl)cc3cc[nH]c(=O)c23)ccc1C1CCN(C(C)C)CC1] | ESI-MS m/z 411.2 (MH$^+$) |
| 942 | 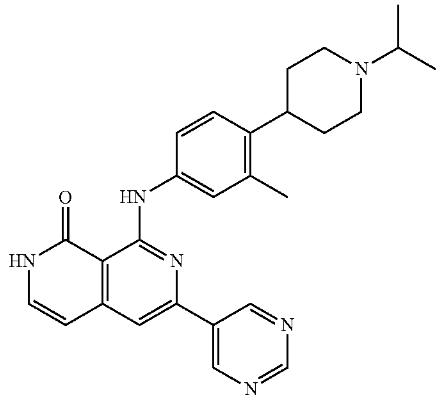 [SMILES: Cc1cc(Nc2nc(-c3cncnc3)cc3cc[nH]c(=O)c23)ccc1C1CCN(C(C)C)CC1] | ESI-MS m/z 455.2 (MH$^+$) |
| 943 | 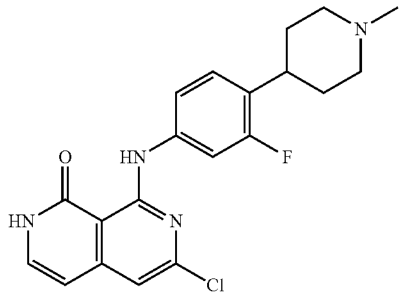 [SMILES: CN1CCC(c2ccc(Nc3nc(Cl)cc4cc[nH]c(=O)c34)cc2F)CC1] | ESI-MS m/z 387.1 (MH$^+$) |

TABLE 1-continued
| No | Structure | Physical Data $^1H$ NMR 400 MHz (DMSO-$d_6$) and/or MS (m/z) |
|---|---|---|
| 944 | 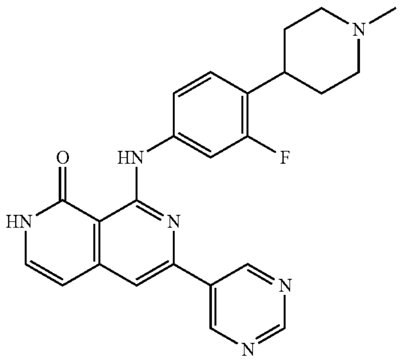 [SMILES: CN1CCC(c2ccc(Nc3nc(-c4cncnc4)cc4cc[nH]c(=O)c34)cc2F)CC1] | ESI-MS m/z 431.2 ($MH^+$) |
| 945 | 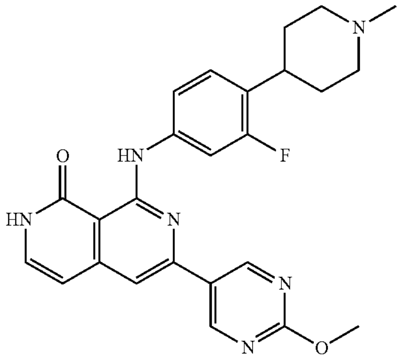 [SMILES: COc1ncc(-c2cc3cc[nH]c(=O)c3c(Nc3ccc(C4CCN(C)CC4)c(F)c3)n2)cn1] | ESI-MS m/z 461.2 ($MH^+$) |
| 946 | 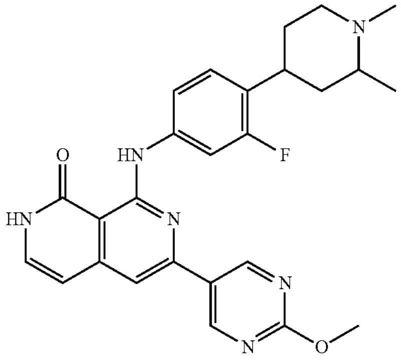 [SMILES: COc1ncc(-c2cc3cc[nH]c(=O)c3c(Nc3ccc(C4CCN(C)C(C)C4)c(F)c3)n2)cn1] | ESI-MS m/z 475.2 ($MH^+$) |
| 947 | 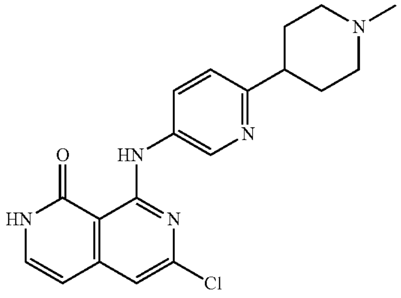 [SMILES: CN1CCC(c2ccc(Nc3nc(Cl)cc4cc[nH]c(=O)c34)cn2)CC1] | ESI-MS m/z 370.1 ($MH^+$) |

TABLE 1-continued
| No | Structure | Physical Data $^1H$ NMR 400 MHz (DMSO-$d_6$) and/or MS (m/z) |
|---|---|---|
| 948 | 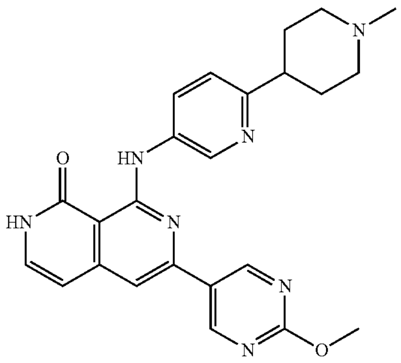 [SMILES: COc1ncc(-c2cc3cc[nH]c(=O)c3c(Nc3ccc(C4CCN(C)CC4)nc3)n2)cn1] | ESI-MS m/z 444.2 ($MH^+$) |
| 949 | 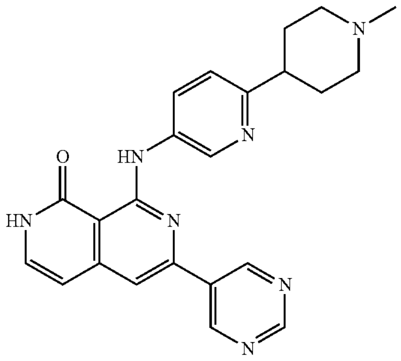 [SMILES: CN1CCC(c2ccc(Nc3nc(-c4cncnc4)cc4cc[nH]c(=O)c34)cn2)CC1] | ESI-MS m/z 414.2 ($MH^+$) |
| 950 | 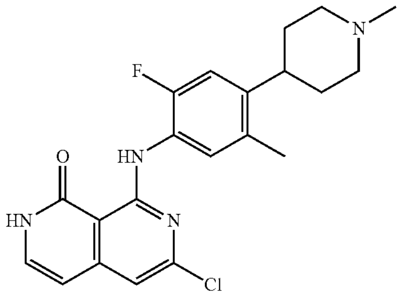 [SMILES: Cc1cc(Nc2nc(Cl)cc3cc[nH]c(=O)c23)c(F)cc1C1CCN(C)CC1] | ESI-MS m/z 401.1 ($MH^+$) |
| 951 | 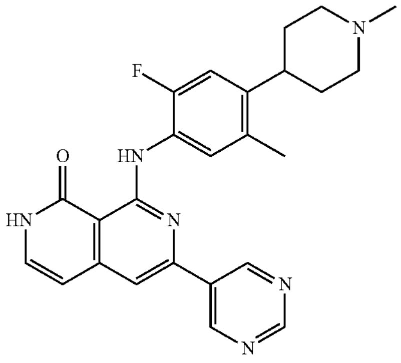 [SMILES: Cc1cc(Nc2nc(-c3cncnc3)cc3cc[nH]c(=O)c23)c(F)cc1C1CCN(C)CC1] | ESI-MS m/z 445.2 ($MH^+$) |

TABLE 1-continued
| No | Structure | Physical Data $^1H$ NMR 400 MHz (DMSO-$d_6$) and/or MS (m/z) |
|---|---|---|
| 952 | 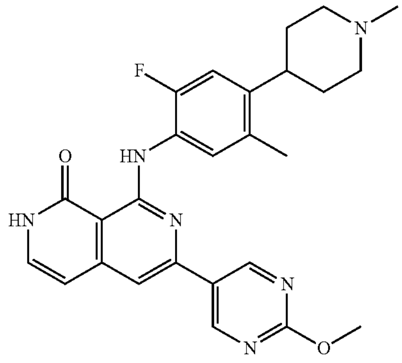 [SMILES: COc1ncc(-c2cc3cc[nH]c(=O)c3c(Nc3cc(C)c(C4CCN(C)CC4)cc3F)n2)cn1] | ESI-MS m/z 475.2 ($MH^+$) |
| 953 | 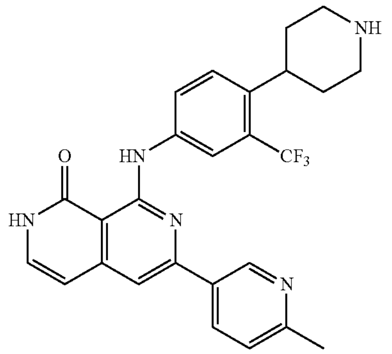 [SMILES: Cc1ccc(-c2cc3cc[nH]c(=O)c3c(Nc3ccc(C4CCNCC4)c(C(F)(F)F)c3)n2)cn1] | ESI-MS m/z 480.2 ($MH^+$) |
| 954 | 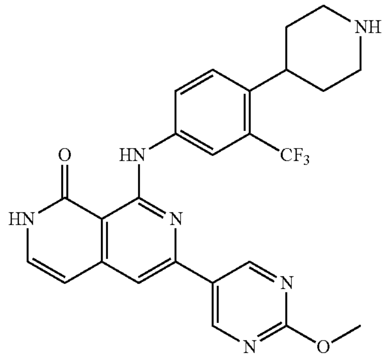 [SMILES: COc1ncc(-c2cc3cc[nH]c(=O)c3c(Nc3ccc(C4CCNCC4)c(C(F)(F)F)c3)n2)cn1] | ESI-MS m/z 497.2 ($MH^+$) |
| 955 | 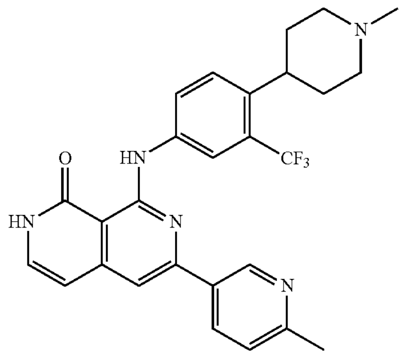 [SMILES: Cc1ccc(-c2cc3cc[nH]c(=O)c3c(Nc3ccc(C4CCN(C)CC4)c(C(F)(F)F)c3)n2)cn1] | ESI-MS m/z 494.2 ($MH^+$) |

TABLE 1-continued
| No | Structure | Physical Data $^1$H NMR 400 MHz (DMSO-$d_6$) and/or MS (m/z) |
|---|---|---|
| 956 | 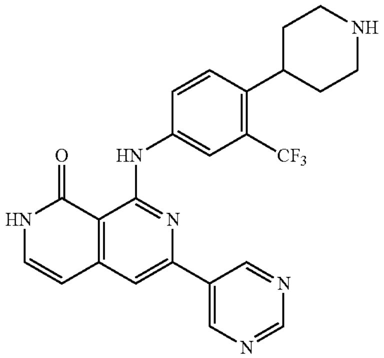 [SMILES: O=c1[nH]ccc2cc(-c3cncnc3)nc(Nc3ccc(C4CCNCC4)c(C(F)(F)F)c3)c12] | ESI-MS m/z 494.2 (MH$^+$) |
| 957 | 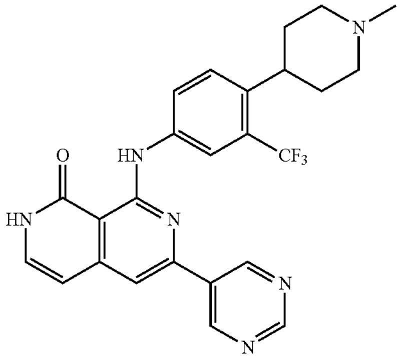 [SMILES: CN1CCC(c2ccc(Nc3nc(-c4cncnc4)cc4cc[nH]c(=O)c34)cc2C(F)(F)F)CC1] | ESI-MS m/z 481.2 (MH$^+$) |
| 958 | 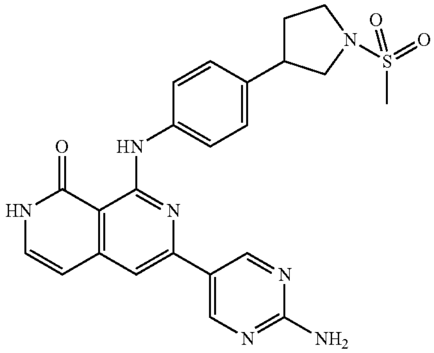 [SMILES: CS(=O)(=O)N1CCC(c2ccc(Nc3nc(-c4cnc(N)nc4)cc4cc[nH]c(=O)c34)cc2)C1] | ESI-MS m/z 478.2 (MH$^+$) |
| 959 | 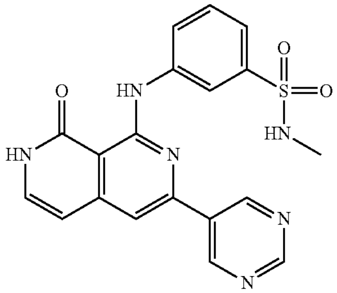 [SMILES: CNS(=O)(=O)c1cccc(Nc2nc(-c3cncnc3)cc3cc[nH]c(=O)c23)c1] | ESI-MS m/z 409.1 (MH$^+$) |

TABLE 1-continued
| No | Structure | Physical Data $^1$H NMR 400 MHz (DMSO-$d_6$) and/or MS (m/z) |
|---|---|---|
| 960 | 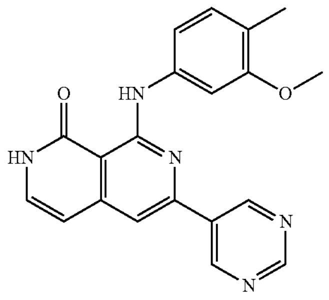 [SMILES: COc1cc(Nc2nc(-c3cncnc3)cc3cc[nH]c(=O)c23)ccc1C] | ESI-MS m/z 360.1 (MH$^+$) |
| 961 | 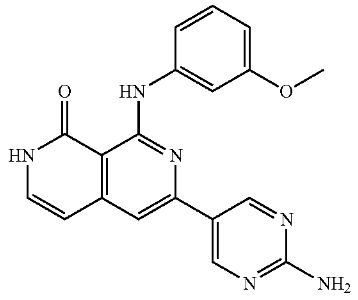 [SMILES: COc1cccc(Nc2nc(-c3cnc(N)nc3)cc3cc[nH]c(=O)c23)c1] | ESI-MS m/z 361.1 (MH$^+$) |
| 962 | 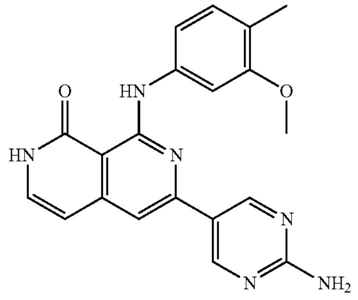 [SMILES: COc1cc(Nc2nc(-c3cnc(N)nc3)cc3cc[nH]c(=O)c23)ccc1C] | ESI-MS m/z 375.1 (MH$^+$) |
| 963 | 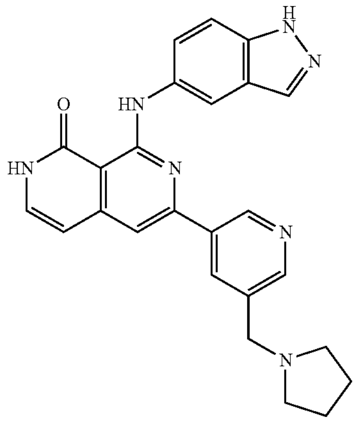 [SMILES: O=c1[nH]ccc2cc(-c3cncc(CN4CCCC4)c3)nc(Nc3ccc4[nH]ncc4c3)c12] | ESI-MS m/z 438.2 (MH$^+$) |

TABLE 1-continued
| No | Structure | Physical Data $^1H$ NMR 400 MHz ($DMSO-d_6$) and/or MS (m/z) |
|---|---|---|
| 964 | 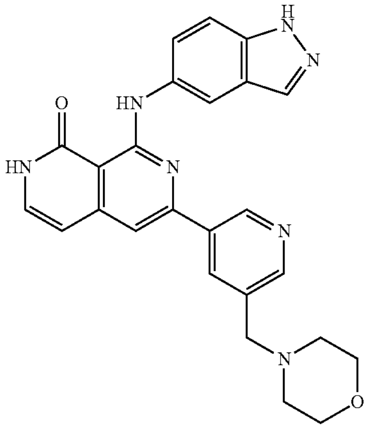 [SMILES: O=c1[nH]ccc2cc(-c3cncc(CN4CCOCC4)c3)nc(Nc3ccc4[nH]ncc4c3)c12] | ESI-MS m/z 454.2 ($MH^+$) |
| 965 | 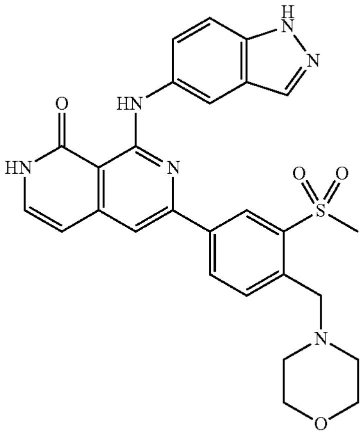 [SMILES: CS(=O)(=O)c1cc(-c2cc3cc[nH]c(=O)c3c(Nc3ccc4[nH]ncc4c3)n2)ccc1CN1CCOCC1] | ESI-MS m/z 531.2 ($MH^+$) |
| 966 | 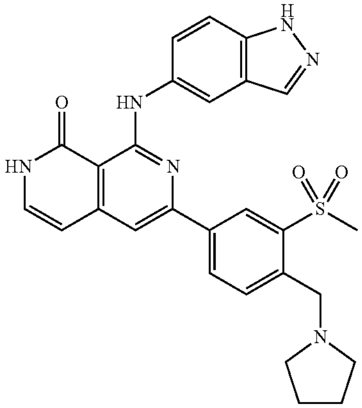 [SMILES: CS(=O)(=O)c1cc(-c2cc3cc[nH]c(=O)c3c(Nc3ccc4[nH]ncc4c3)n2)ccc1CN1CCCC1] | ESI-MS m/z 515.2 ($MH^+$) |

TABLE 1-continued
| No | Structure | Physical Data $^1H$ NMR 400 MHz (DMSO-$d_6$) and/or MS (m/z) |
|---|---|---|
| 967 | 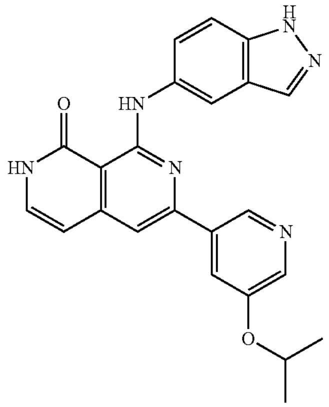 [SMILES: CC(C)Oc1cncc(-c2cc3cc[nH]c(=O)c3c(Nc3ccc4[nH]ncc4c3)n2)c1] | ESI-MS m/z 413.2 ($MH^+$) |
| 968 | 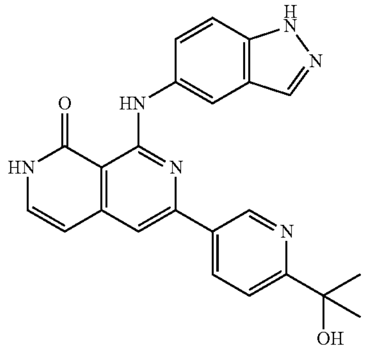 [SMILES: CC(C)(O)c1ccc(-c2cc3cc[nH]c(=O)c3c(Nc3ccc4[nH]ncc4c3)n2)cn1] | ESI-MS m/z 413.2 ($MH^+$) |
| 969 | 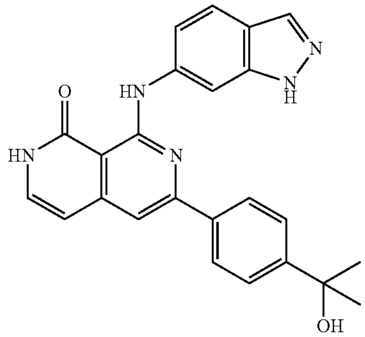 [SMILES: CC(C)(O)c1ccc(-c2cc3cc[nH]c(=O)c3c(Nc3ccc4cn[nH]c4c3)n2)cc1] | ESI-MS m/z 412.2 ($MH^+$) |
| 970 | 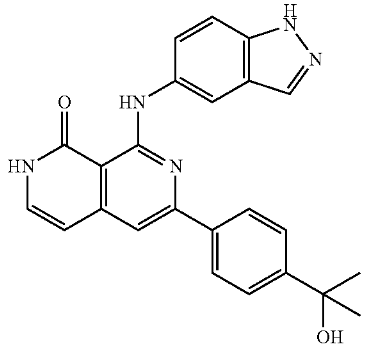 [SMILES: CC(C)(O)c1ccc(-c2cc3cc[nH]c(=O)c3c(Nc3ccc4[nH]ncc4c3)n2)cc1] | ESI-MS m/z 412.2 ($MH^+$) |

TABLE 1-continued
| No | Structure | Physical Data $^1H$ NMR 400 MHz (DMSO-$d_6$) and/or MS (m/z) |
|---|---|---|
| 971 | 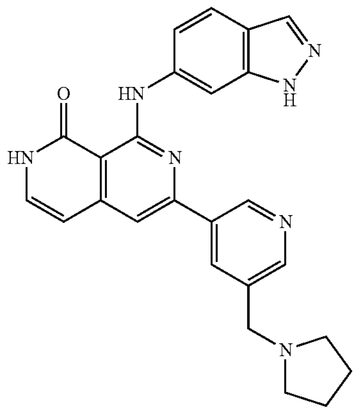 [SMILES: O=c1[nH]ccc2cc(-c3cncc(CN4CCCC4)c3)nc(Nc3ccc4cn[nH]c4c3)c12] | ESI-MS m/z 438.2 ($MH^+$) |
| 972 | 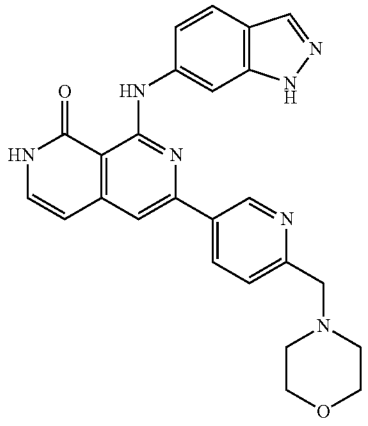 [SMILES: O=c1[nH]ccc2cc(-c3ccc(CN4CCOCC4)nc3)nc(Nc3ccc4cn[nH]c4c3)c12] | ESI-MS m/z 534.2 ($MH^+$) |
| 973 | 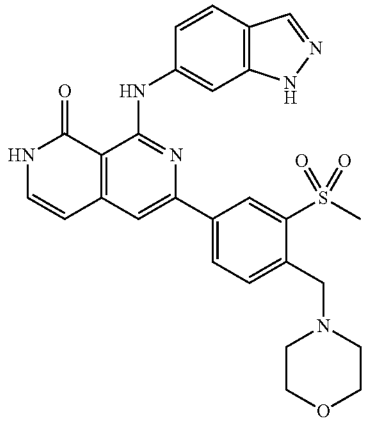 [SMILES: CS(=O)(=O)c1cc(-c2cc3cc[nH]c(=O)c3c(Nc3ccc4cn[nH]c4c3)n2)ccc1CN1CCOCC1] | ESI-MS m/z 531.2 ($MH^+$) |

TABLE 1-continued
| No | Structure | Physical Data $^1H$ NMR 400 MHz (DMSO-$d_6$) and/or MS (m/z) |
|---|---|---|
| 974 | 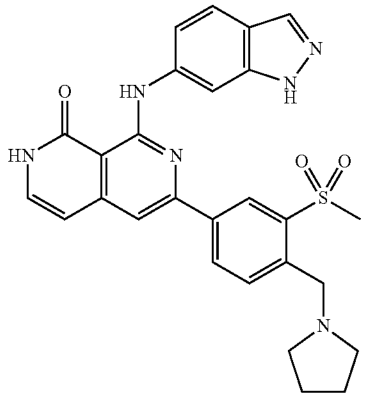 [SMILES: CS(=O)(=O)c1cc(-c2cc3cc[nH]c(=O)c3c(Nc3ccc4cn[nH]c4c3)n2)ccc1CN1CCCC1] | ESI-MS m/z 515.2 ($MH^+$) |
| 975 | 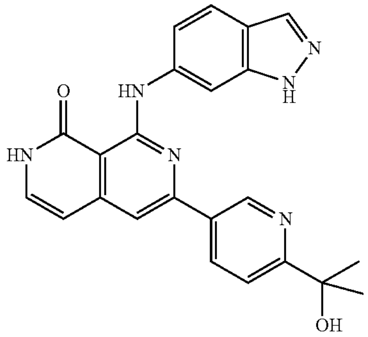 [SMILES: CC(C)(O)c1ccc(-c2cc3cc[nH]c(=O)c3c(Nc3ccc4cn[nH]c4c3)n2)cn1] | ESI-MS m/z 413.2 ($MH^+$) |
| 976 | 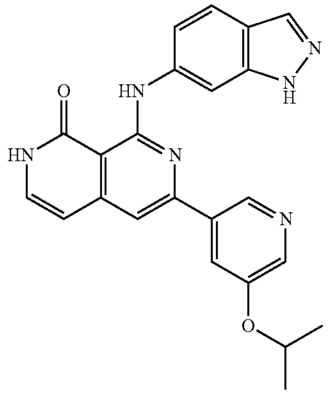 [SMILES: CC(C)Oc1cncc(-c2cc3cc[nH]c(=O)c3c(Nc3ccc4cn[nH]c4c3)n2)c1] | ESI-MS m/z 412.2 ($MH^+$) |
| 978 | 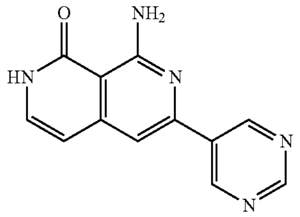 [SMILES: Nc1nc(-c2cncnc2)cc2cc[nH]c(=O)c12] | ESI-MS m/z 240.1 ($MH^+$) |

TABLE 1-continued
| No | Structure | Physical Data $^1H$ NMR 400 MHz (DMSO-$d_6$) and/or MS (m/z) |
|---|---|---|
| 979 | 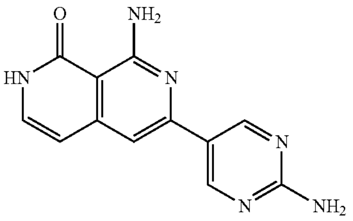 [SMILES: Nc1ncc(-c2cc3cc[nH]c(=O)c3c(N)n2)cn1] | ESI-MS m/z 255.1 ($MH^+$) |
| 980 | 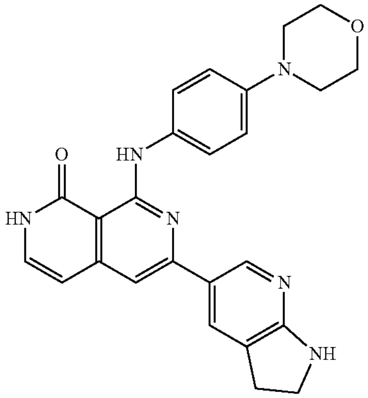 [SMILES: O=c1[nH]ccc2cc(-c3cnc4c(c3)CCN4)nc(Nc3ccc(N4CCOCC4)cc3)c12] | ESI-MS m/z 441.2 ($MH^+$) |
| 981 | 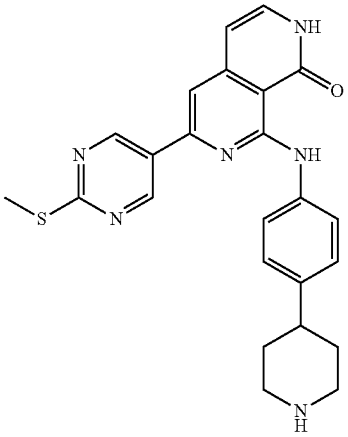 [SMILES: CSc1ncc(-c2cc3cc[nH]c(=O)c3c(Nc3ccc(C4CCNCC4)cc3)n2)cn1] | ESI-MS m/z 445.2 ($MH^+$). |
| 982 | 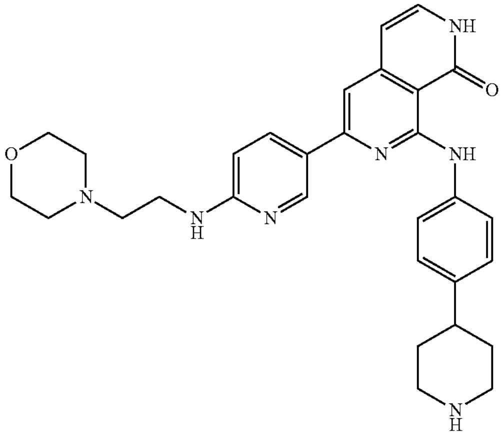 [SMILES: O=c1[nH]ccc2cc(-c3ccc(NCCN4CCOCC4)nc3)nc(Nc3ccc(C4CCNCC4)cc3)c12] | ESI-MS m/z 526.2 ($MH^+$). |

TABLE 1-continued
| No | Structure | Physical Data $^1H$ NMR 400 MHz (DMSO-$d_6$) and/or MS (m/z) |
|---|---|---|
| 983 | | |
| 984 | 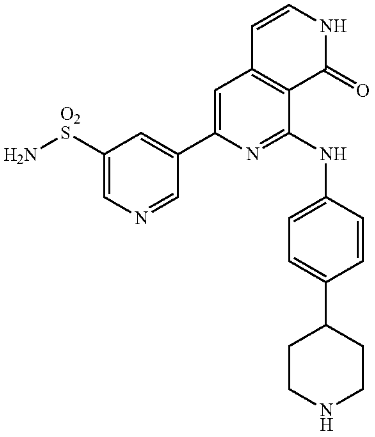 [SMILES: NS(=O)(=O)c1cncc(-c2cc3cc[nH]c(=O)c3c(Nc3ccc(C4CCNCC4)cc3)n2)c1] | ESI-MS m/z 477.2 (MH$^+$). |
| 985 | 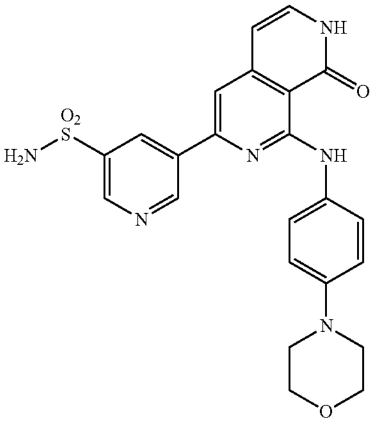 [SMILES: NS(=O)(=O)c1cncc(-c2cc3cc[nH]c(=O)c3c(Nc3ccc(N4CCOCC4)cc3)n2)c1] | ESI-MS m/z 479.2 (MH$^+$). |
| 986 | 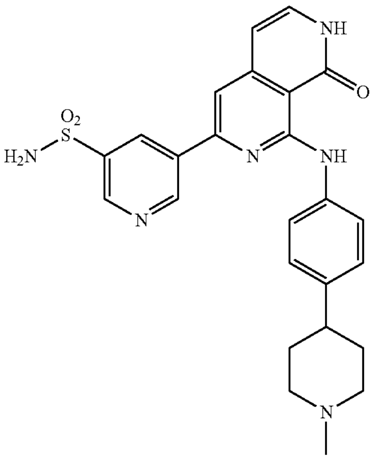 [SMILES: CN1CCC(c2ccc(Nc3nc(-c4cncc(S(N)(=O)=O)c4)cc4cc[nH]c(=O)c34)cc2)CC1] | ESI-MS m/z 491.2 (MH$^+$). |

TABLE 1-continued
| No | Structure | Physical Data $^1H$ NMR 400 MHz (DMSO-$d_6$) and/or MS (m/z) |
|---|---|---|
| 987 | 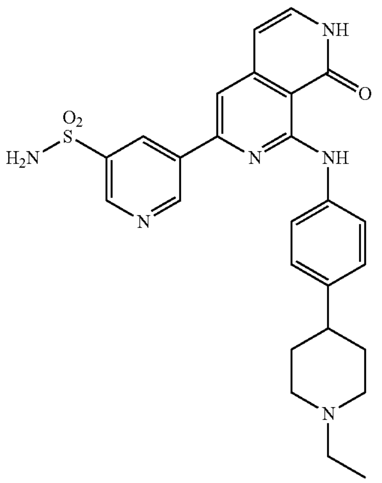 [SMILES: CCN1CCC(c2ccc(Nc3nc(-c4cncc(S(N)(=O)=O)c4)cc4cc[nH]c(=O)c34)cc2)CC1] | ESI-MS m/z 505.2 ($MH^+$). |
| 988 | 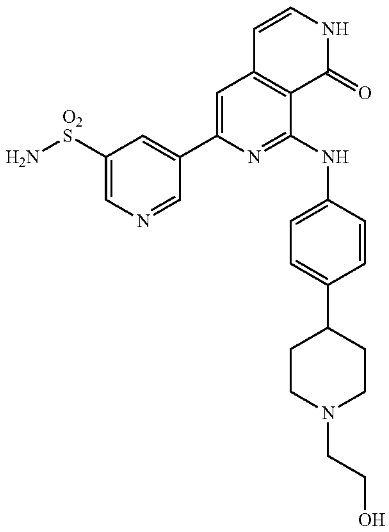 [SMILES: NS(=O)(=O)c1cncc(-c2cc3cc[nH]c(=O)c3c(Nc3ccc(C4CCN(CCO)CC4)cc3)n2)c1] | ESI-MS m/z 512.2 ($MH^+$). |
| 989 | 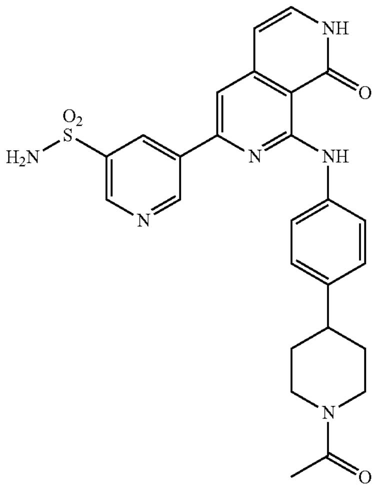 [SMILES: CC(=O)N1CCC(c2ccc(Nc3nc(-c4cncc(S(N)(=O)=O)c4)cc4cc[nH]c(=O)c34)cc2)CC1] | ESI-MS m/z 519.2 ($MH^+$). |

TABLE 1-continued
| No | Structure | Physical Data $^1H$ NMR 400 MHz (DMSO-$d_6$) and/or MS (m/z) |
|---|---|---|
| 990 | 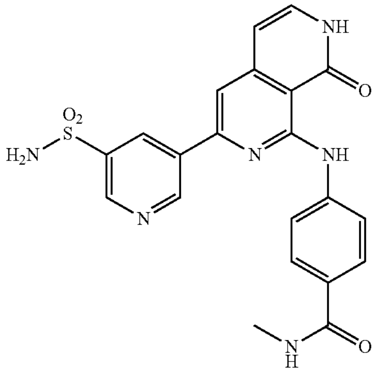 [SMILES: CNC(=O)c1ccc(Nc2nc(-c3cncc(S(N)(=O)=O)c3)cc3cc[nH]c(=O)c23)cc1] | ESI-MS m/z 451.2 ($MH^+$). |
| 991 | 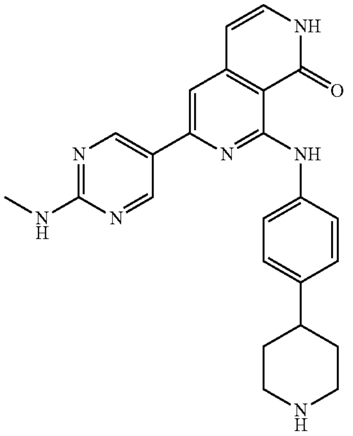 [SMILES: CNc1ncc(-c2cc3cc[nH]c(=O)c3c(Nc3ccc(C4CCNCC4)cc3)n2)cn1] | ESI-MS m/z 428.2 ($MH^+$). |
| 992 | 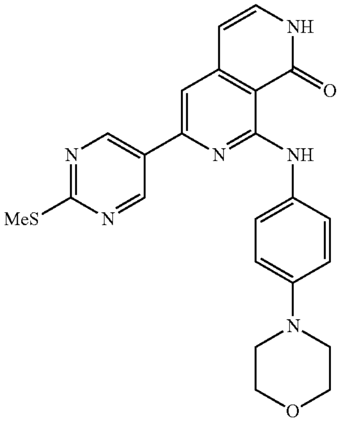 [SMILES: CSc1ncc(-c2cc3cc[nH]c(=O)c3c(Nc3ccc(N4CCOCC4)cc3)n2)cn1] | ESI-MS m/z 447.2 ($MH^+$). |

TABLE 1-continued
| No | Structure | Physical Data $^1H$ NMR 400 MHz (DMSO-$d_6$) and/or MS (m/z) |
|---|---|---|
| 993 | 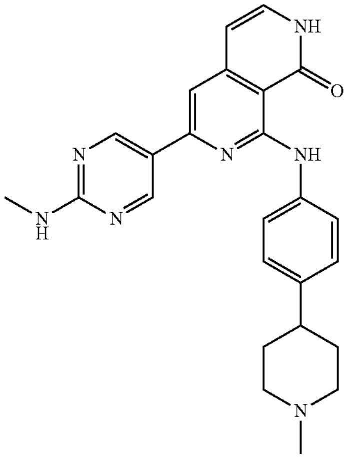 [SMILES: CNc1ncc(-c2cc3cc[nH]c(=O)c3c(Nc3ccc(C4CCN(C)CC4)cc3)n2)cn1] | ESI-MS m/z 442.2 ($MH^+$). |
| 994 | 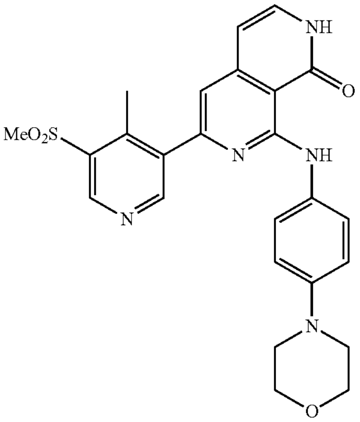 [SMILES: Cc1c(-c2cc3cc[nH]c(=O)c3c(Nc3ccc(N4CCOCC4)cc3)n2)cncc1S(C)(=O)=O] | $^1H$ NMR (MeOD-$d_4$) δ 2.70 (s, 3H), 3.04 (t, J = 4.8 Hz, 4H), 3.41 (s, 3H), 3.72 (t, J = 4.8 Hz, 4H), 6.52 (d, J = 7.2 Hz, 1H), 6.91 (d, J = 8.8 Hz, 2H), 7.01 (s, 1H), 7.47 (d, J = 6.8 Hz, 1H), 7.60 (d, J = 8.8 Hz, 1H), 8.87 (s, 1H), 9.04 (s, 1H), 11.86 (bs, 1H), 11.90 (s, 1H); ESI-MS m/z 492.2 ($MH^+$). |
| 995 | 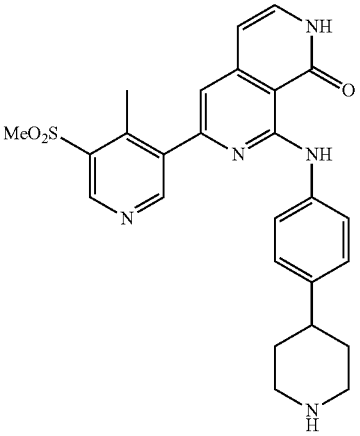 [SMILES: Cc1c(-c2cc3cc[nH]c(=O)c3c(Nc3ccc(C4CCNCC4)cc3)n2)cncc1S(C)(=O)=O] | ESI-MS m/z 490.2 ($MH^+$). |

TABLE 1-continued
| No | Structure | Physical Data $^1H$ NMR 400 MHz (DMSO-$d_6$) and/or MS (m/z) |
|---|---|---|
| 996 | 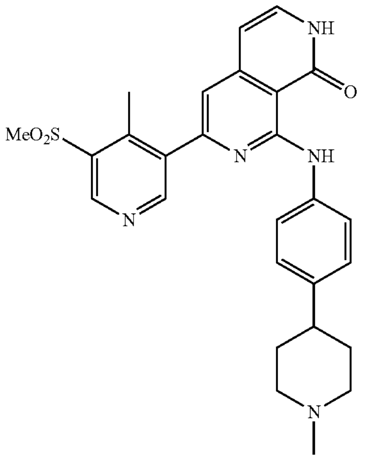 [SMILES: Cc1c(-c2cc3cc[nH]c(=O)c3c(Nc3ccc(C4CCN(C)CC4)cc3)n2)cncc1S(C)(=O)=O] | ESI-MS m/z 504.2 ($MH^+$). |
| 997 | 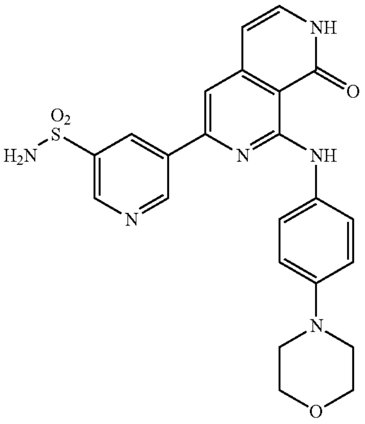 [SMILES: NS(=O)(=O)c1cncc(-c2cc3cc[nH]c(=O)c3c(Nc3ccc(N4CCOCC4)cc3)n2)c1] | ESI-MS m/z 479.2 ($MH^+$). |
| 998 | 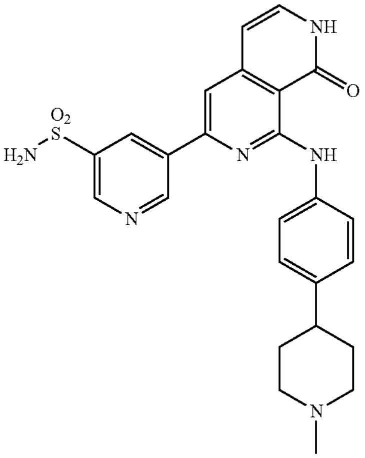 [SMILES: CN1CCC(c2ccc(Nc3nc(-c4cncc(S(N)(=O)=O)c4)cc4cc[nH]c(=O)c34)cc2)CC1] | ESI-MS m/z 491.2 ($MH^+$). |

TABLE 1-continued
| No | Structure | Physical Data $^1H$ NMR 400 MHz (DMSO-$d_6$) and/or MS (m/z) |
|---|---|---|
| 999 | 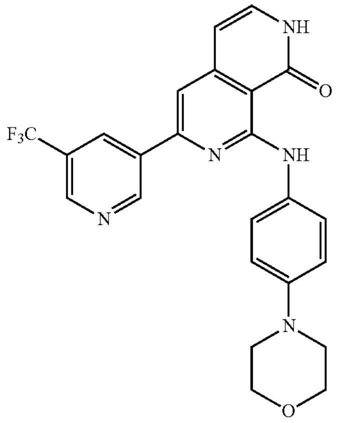 [SMILES: O=c1[nH]ccc2cc(-c3cncc(C(F)(F)F)c3)nc(Nc3ccc(N4CCOCC4)cc3)c12] | ESI-MS m/z 468.2 ($MH^+$). |
| 1000 | 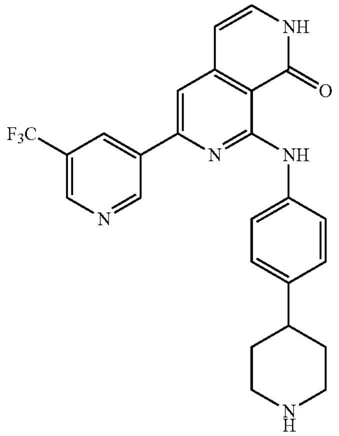 [SMILES: O=c1[nH]ccc2cc(-c3cncc(C(F)(F)F)c3)nc(Nc3ccc(C4CCNCC4)cc3)c12] | ESI-MS m/z 466.2 ($MH^+$). |
| 1001 | 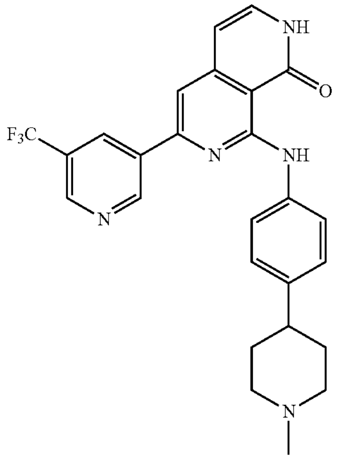 [SMILES: CN1CCC(c2ccc(Nc3nc(-c4cncc(C(F)(F)F)c4)cc4cc[nH]c(=O)c34)cc2)CC1] | ESI-MS m/z 480.2 ($MH^+$). |

TABLE 1-continued
| No | Structure | Physical Data $^1$H NMR 400 MHz (DMSO-$d_6$) and/or MS (m/z) |
|---|---|---|
| 1002 | 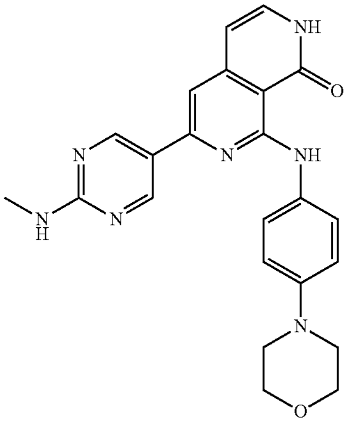 [SMILES: CNc1ncc(-c2cc3cc[nH]c(=O)c3c(Nc3ccc(N4CCOCC4)cc3)n2)cn1] | ESI-MS m/z 430.2 ($MH^+$). |
| 1003 | 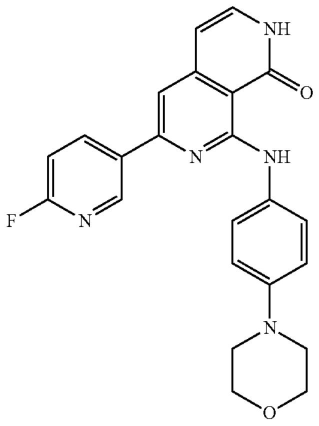 [SMILES: O=c1[nH]ccc2cc(-c3ccc(F)nc3)nc(Nc3ccc(N4CCOCC4)cc3)c12] | $^1$H NMR (MeOD-$d_4$) δ 3.28 (bs, 4H), 3.86 (s, 4H), 6.55 (dd, J = 1.2, 7.2 Hz, 1H), 7.23 (bs, 2H), 7.36 (dd, J = 2.8. 8.4 Hz, 1H), 7.45 (dd, J = 6.0, 6.8 Hz, 1H), 7.54 (s, 1H), 7.81 (d, J = 8.8 Hz, 2H), 8.64 (dt, J = 2.4, 8.4 Hz, 1H), 8.96 (d, J = 2.8 Hz, 1H), 11.85 (d, J = 5.6 Hz, 1H), 11.94 (s, 1H); ESI-MS m/z 418.2 ($MH^+$). |
| 1004 | 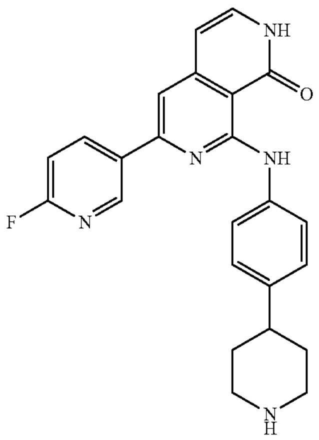 [SMILES: O=c1[nH]ccc2cc(-c3ccc(F)nc3)nc(Nc3ccc(C4CCNCC4)cc3)c12] | ESI-MS m/z 416.2 ($MH^+$). |

TABLE 1-continued
| No | Structure | Physical Data $^1H$ NMR 400 MHz (DMSO-$d_6$) and/or MS (m/z) |
|---|---|---|
| 1005 | 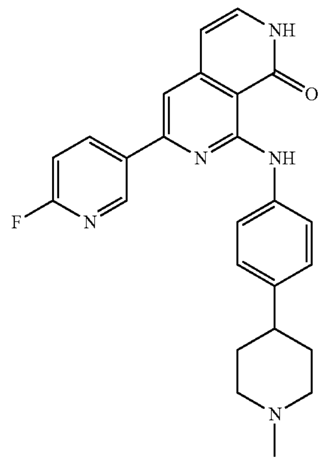 [SMILES: CN1CCC(c2ccc(Nc3nc(-c4ccc(F)nc4)cc4cc[nH]c(=O)c34)cc2)CC1] | ESI-MS m/z 430.2 (MH$^+$). |
| 1006 | 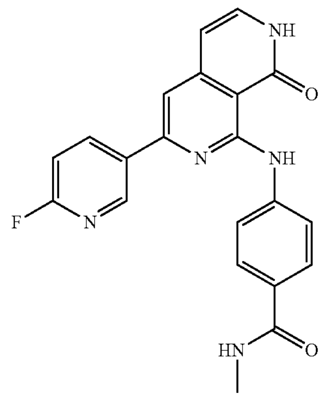 [SMILES: CNC(=O)c1ccc(Nc2nc(-c3ccc(F)nc3)cc3cc[nH]c(=O)c23)cc1] | ESI-MS m/z 390.2 (MH$^+$). |
| 1007 | 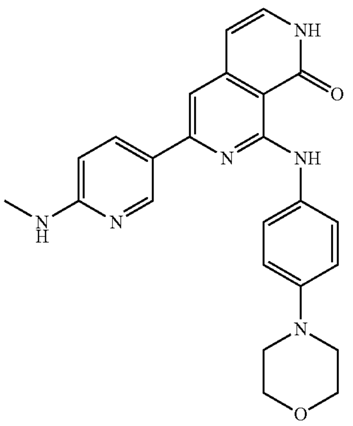 [SMILES: CNc1ccc(-c2cc3cc[nH]c(=O)c3c(Nc3ccc(N4CCOCC4)cc3)n2)cn1] | ESI-MS m/z 429.2 (MH$^+$). |

TABLE 1-continued
| No | Structure | Physical Data $^1H$ NMR 400 MHz ($DMSO-d_6$) and/or MS (m/z) |
|---|---|---|
| 1008 | 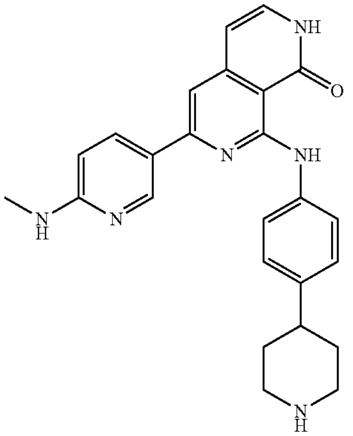 [SMILES: CNc1ccc(-c2cc3cc[nH]c(=O)c3c(Nc3ccc(C4CCNCC4)cc3)n2)cn1] | ESI-MS m/z 427.2 ($MH^+$). |
| 1009 | 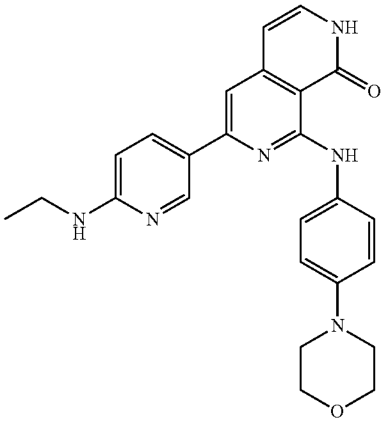 [SMILES: CCNc1ccc(-c2cc3cc[nH]c(=O)c3c(Nc3ccc(N4CCOCC4)cc3)n2)cn1] | $^1H$ NMR ($MeOD-d_4$) δ 1.40 (t, 3H), 3.50 (q, 2H), 3.69 (bs, 4H), 4.12 (bs, 4H), 6.60 (d, J = 6.4 Hz, 1H), 7.16 (d, J = 8.8 Hz, 1H), 7.38 (d, J = 6.4 Hz, 2H), 7.70 (bs, 1H), 8.03 (bs, 2H), 8.57 (d, J = 9.6 Hz, 1H), 8.60 (s, 1H); ESI-MS m/z 443.2 ($MH^+$). |
| 1010 | 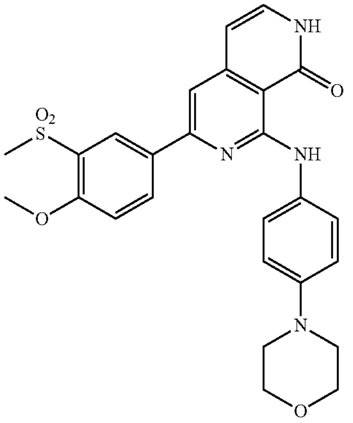 [SMILES: COc1ccc(-c2cc3cc[nH]c(=O)c3c(Nc3ccc(N4CCOCC4)cc3)n2)cc1S(C)(=O)=O] | ESI-MS m/z 507.2 ($MH^+$). |

TABLE 1-continued
| No | Structure | Physical Data $^1H$ NMR 400 MHz (DMSO-$d_6$) and/or MS (m/z) |
|---|---|---|
| 1011 | 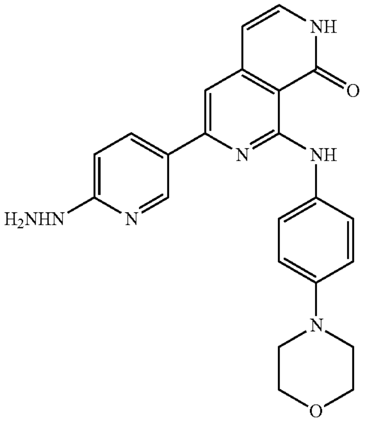 | ESI-MS m/z 430.2 ($MH^+$). |
| 1012 | 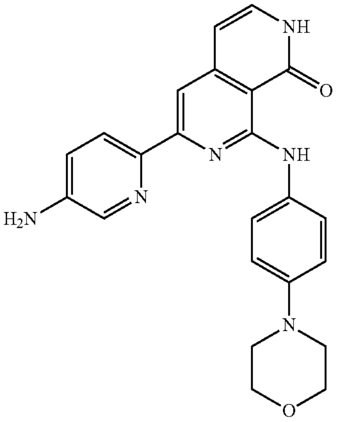 [SMILES: Nc1ccc(-c2cc3cc[nH]c(=O)c3c(Nc3ccc(N4CCOCC4)cc3)n2)nc1] | ESI-MS m/z 415.2 ($MH^+$). |
| 1013 | 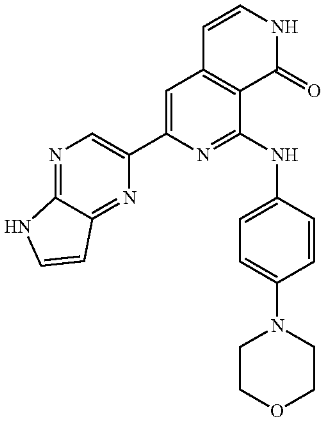 [SMILES: O=c1[nH]ccc2cc(-c3cnc4[nH]ccc4n3)nc(Nc3ccc(N4CCOCC4)cc3)c12] | ESI-MS m/z 440.2 ($MH^+$). |

TABLE 1-continued
| No | Structure | Physical Data $^1H$ NMR 400 MHz (DMSO-$d_6$) and/or MS (m/z) |
|---|---|---|
| 1014 | 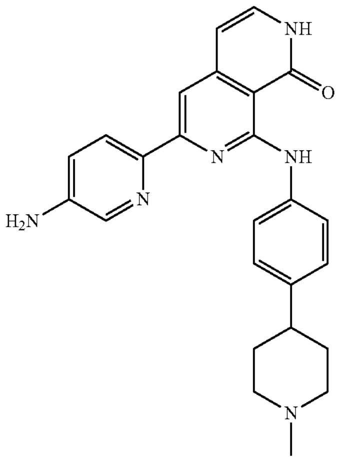 [SMILES: CN1CCC(c2ccc(Nc3nc(-c4ccc(N)cn4)cc4cc[nH]c(=O)c34)cc2)CC1] | ESI-MS m/z 427.2 ($MH^+$). |
| 1015 | 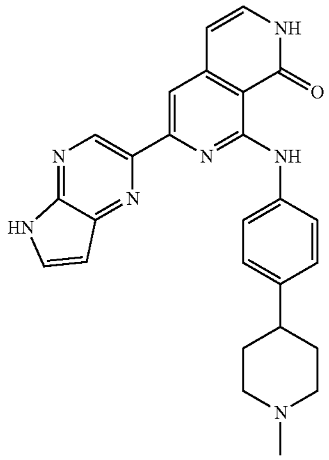 [SMILES: CN1CCC(c2ccc(Nc3nc(-c4cnc5[nH]ccc5n4)cc4cc[nH]c(=O)c34)cc2)CC1] | ESI-MS m/z 452.2 ($MH^+$). |
| 1016 | 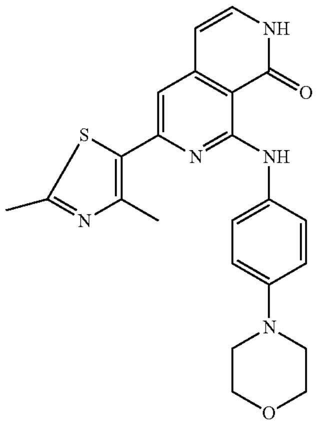 [SMILES: Cc1nc(C)c(-c2cc3cc[nH]c(=O)c3c(Nc3ccc(N4CCOCC4)cc3)n2)s1] | ESI-MS m/z 434.2 ($MH^+$). |

TABLE 1-continued
| No | Structure | Physical Data $^1H$ NMR 400 MHz ($DMSO-d_6$) and/or MS (m/z) |
|---|---|---|
| 1017 | 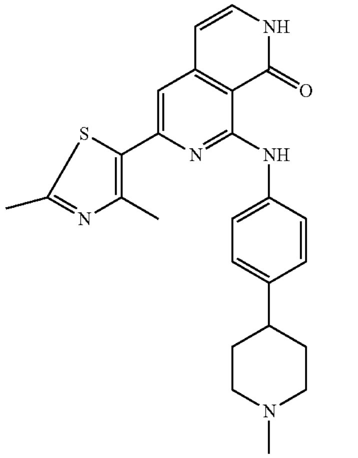 [SMILES: Cc1nc(C)c(-c2cc3cc[nH]c(=O)c3c(Nc3ccc(C4CCN(C)CC4)cc3)n2)s1] | ESI-MS m/z 446.2 ($MH^+$). |
| 1018 | 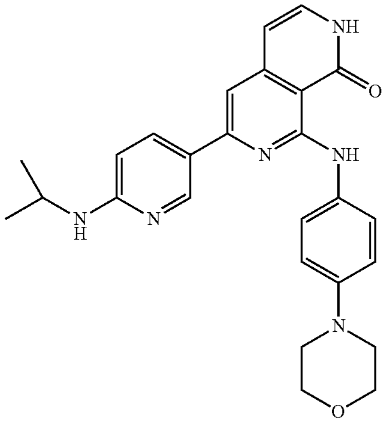 [SMILES: CC(C)Nc1ccc(-c2cc3cc[nH]c(=O)c3c(Nc3ccc(N4CCOCC4)cc3)n2)cn1] | ESI-MS m/z 457.2 ($MH^+$). |
| 1019 | 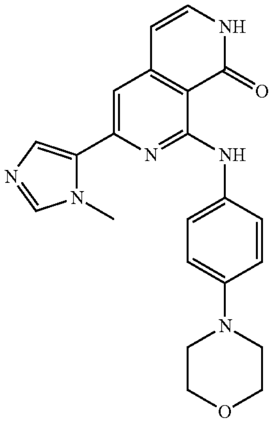 [SMILES: Cn1cncc1-c1cc2cc[nH]c(=O)c2c(Nc2ccc(N3CCOCC3)cc2)n1] | ESI-MS m/z 403.2 ($MH^+$). |

TABLE 1-continued
| No | Structure | Physical Data $^1H$ NMR 400 MHz (DMSO-$d_6$) and/or MS (m/z) |
|---|---|---|
| 1020 | 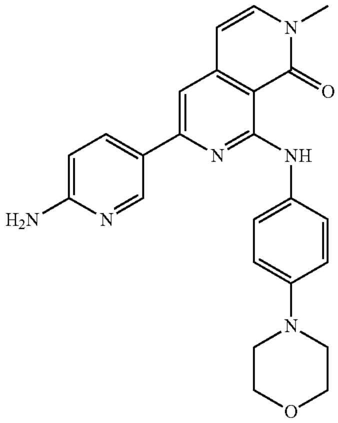 [SMILES: Cn1ccc2cc(-c3ccc(N)nc3)nc(Nc3ccc(N4CCOCC4)cc3)c2c1=O] | ESI-MS m/z 429.2 ($MH^+$). |
| 1021 | 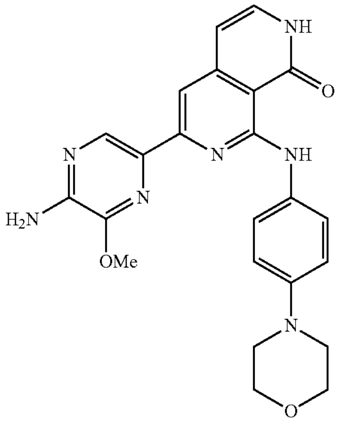 [SMILES: COc1nc(-c2cc3cc[nH]c(=O)c3c(Nc3ccc(N4CCOCC4)cc3)n2)cnc1N] | $^1H$ NMR (MeOD-$d_4$) δ 3.64 (bs, 4H), 4.09 (t, J = 4.4 Hz, 4H), 4.16 (s, 3H), 6.69 (d, J = 7.2 Hz, 1H), 7.51 (d, J = 6.8 Hz, 2H), 7.70 (s, 1H), 7.94 (d, J = 8.0 Hz, 2H), 8.28 (s, 1H); ESI-MS m/z 446.2 ($MH^+$). |
| 1022 | 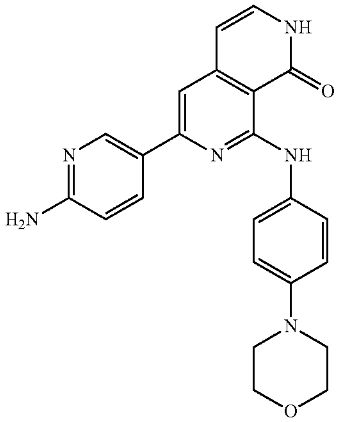 [SMILES: Nc1ccc(-c2cc3cc[nH]c(=O)c3c(Nc3ccc(N4CCOCC4)cc3)n2)cn1] | ESI-MS m/z 415.2 ($MH^+$). |

TABLE 1-continued
| No | Structure | Physical Data $^1$H NMR 400 MHz (DMSO-$d_6$) and/or MS (m/z) |
|---|---|---|
| 1023 | 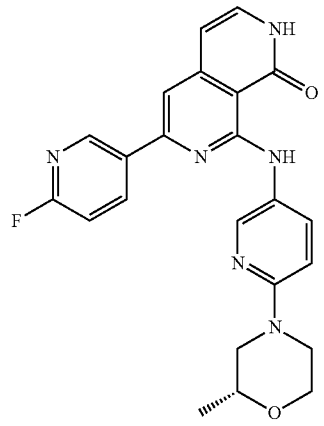 [SMILES: C[C@@H]1CN(c2ccc(Nc3nc(-c4ccc(F)nc4)cc4cc[nH]c(=O)c34)cn2)CCO1] | ESI-MS m/z 433.2 (MH$^+$). |
| 1024 | 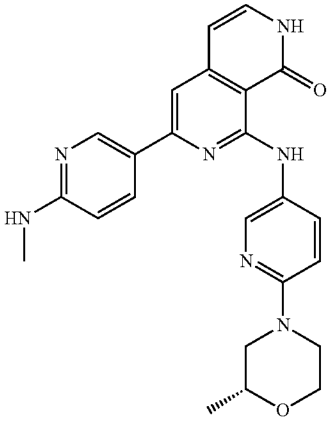 [SMILES: CNc1ccc(-c2cc3cc[nH]c(=O)c3c(Nc3ccc(N4CCO[C@H](C)C4)nc3)n2)cn1] | ESI-MS m/z 444.2 (MH$^+$). |
| 1025 | 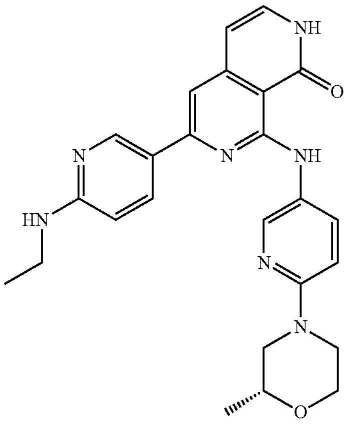 | ESI-MS m/z 430.2 (MH$^+$). |

TABLE 1-continued
| No | Structure | Physical Data $^1H$ NMR 400 MHz ($DMSO-d_6$) and/or MS (m/z) |
|---|---|---|
| 1026 | 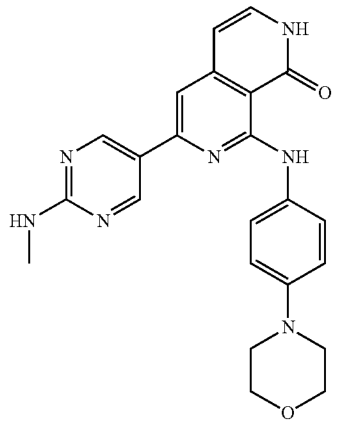 | ESI-MS m/z 468.2 ($MH^+$). |
| 1027 | 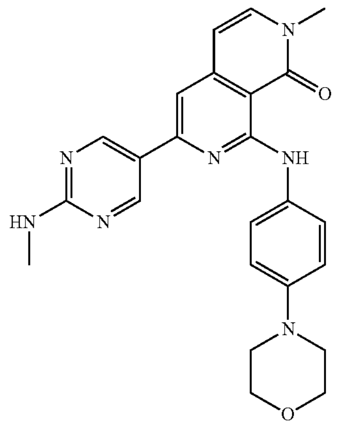 [SMILES: CNc1ncc(-c2cc3ccn(C)c(=O)c3c(Nc3ccc(N4CCOCC4)cc3)n2)cn1] | ESI-MS m/z 444.2 ($MH^+$). |
| 1028 | 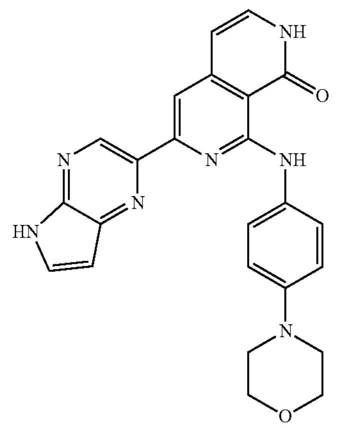 [SMILES: O=c1[nH]ccc2cc(-c3cnc4[nH]ccc4n3)nc(Nc3ccc(N4CCOCC4)cc3)c12] | ESI-MS m/z 440.2 ($MH^+$). |

TABLE 1-continued
| No | Structure | Physical Data $^1H$ NMR 400 MHz (DMSO-$d_6$) and/or MS (m/z) |
|---|---|---|
| 1029 | 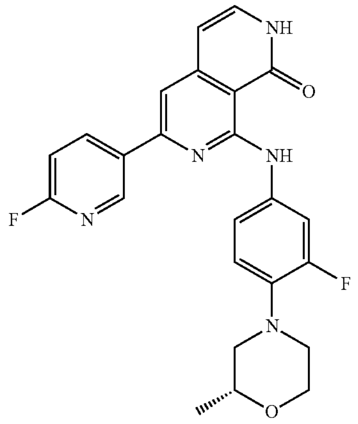 [SMILES: C[C@@H]1CN(c2ccc(Nc3nc(-c4ccc(F)nc4)cc4cc[nH]c(=O)c34)cc2F)CCO1] | $^1H$ NMR (DMSO-$d_6$) δ 1.13 (d, J = 6.4 Hz, 3H), 2.43 (t, J = 10.8 Hz, 1H), 2.74 (t, J = 9.6 Hz, 1H), 3.19 (dd, J = 11.2, 24.0 Hz, 2H), 3.70 (m, 2H), 3.87 (d, J = 10.4 Hz, 1H), 6.53 (d, J = 6.8 Hz, 1H), 7.06 (t, J = 9.2 Hz, 1H), 7.38 (t, J = 7.6 Hz, 2H), 7.45 (d, J = 6.4 Hz, 1H), 7.53 (s, 1H), 8.61 (t, J = 7.2 Hz, 1H), 8.94 (s, 1H), 11.85 (bs, 1H), 12.02 (s, 1H); ESI-MS m/z 450.2 ($MH^+$). |
| 1030 | 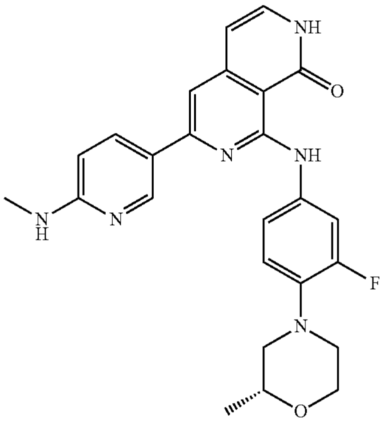 [SMILES: CNc1ccc(-c2cc3cc[nH]c(=O)c3c(Nc3ccc(N4CCO[C@H](C)C4)c(F)c3)n2)cn1] | ESI-MS m/z 461.2 ($MH^+$). |
| 1031 | 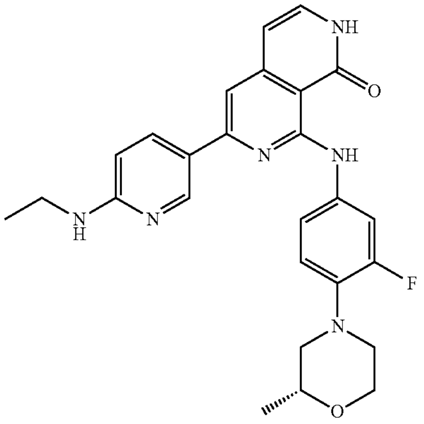 [SMILES: CCNc1ccc(-c2cc3cc[nH]c(=O)c3c(Nc3ccc(N4CCO[C@H](C)C4)c(F)c3)n2)cn1] | ESI-MS m/z 475.2 ($MH^+$). |

TABLE 1-continued
| No | Structure | Physical Data $^1H$ NMR 400 MHz (DMSO-$d_6$) and/or MS (m/z) |
|---|---|---|
| 1032 | 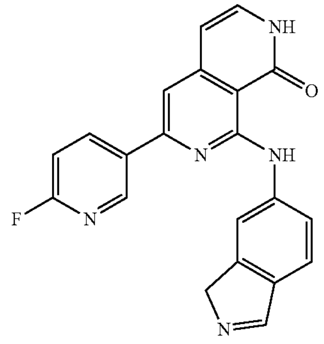 [SMILES: O=c1[nH]ccc2cc(-c3ccc(F)nc3)nc(Nc3ccc4c(c3)CN=C4)c12] | ESI-MS m/z 373.2 ($MH^+$). |
| 1033 | 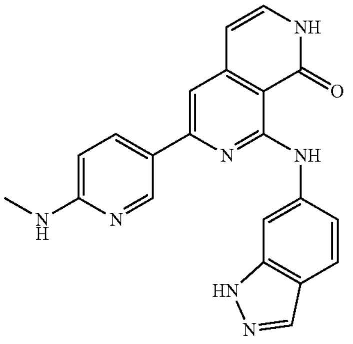 [SMILES: CNc1ccc(-c2cc3cc[nH]c(=O)c3c(Nc3ccc4cn[nH]c4c3)n2)cn1] | ESI-MS m/z 384.2 ($MH^+$). |
| 1034 | 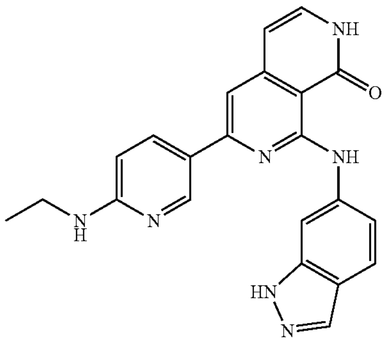 [SMILES: CCNc1ccc(-c2cc3cc[nH]c(=O)c3c(Nc3ccc4cn[nH]c4c3)n2)cn1] | ESI-MS m/z 398.2 ($MH^+$). |
| 1035 | 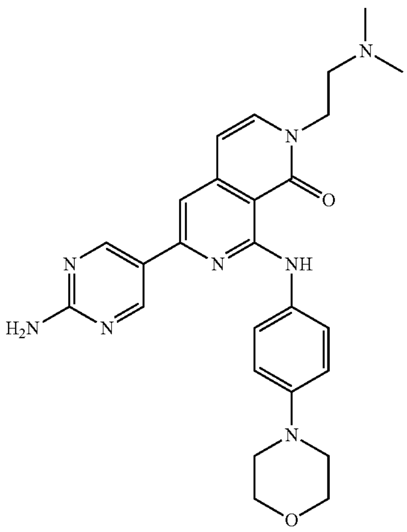 [SMILES: CN(C)CCn1ccc2cc(-c3cnc(N)nc3)nc(Nc3ccc(N4CCOCC4)cc3)c2c1=O] | $^1H$ NMR (MeOD-$d_4$) δ 3.08 (s, 6H), 3.64 (t, J = 6.4 Hz, 2H), 3.74 (t, J = 5.2 Hz, 4H), 4.16 (t, J = 4.8 Hz, 4H), 4.49 (t, J = 6.0 Hz, 2H), 6.74 (d, J = 7.2 Hz, 1H), 7.50 (s, 1H), 7.70 (d, J = 7.6 Hz, 1H), 7.78 (d, J = 9.2 Hz, 2H), 8.08 (d, J = 8.8 Hz, 2H), 9.26 (s, 2H); ESI-MS m/z 487.2 ($MH^+$). |

| No | Structure | Physical Data $^1$H NMR 400 MHz (DMSO-$d_6$) and/or MS (m/z) |
|---|---|---|
| 1036 | 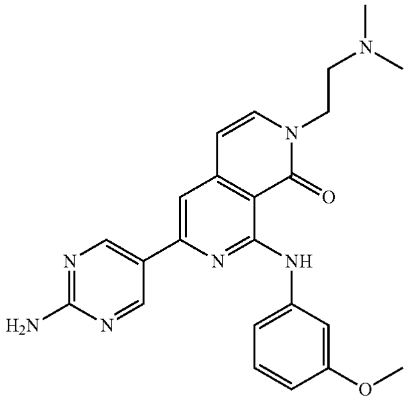 [SMILES: COc1cccc(Nc2nc(-c3cnc(N)nc3)cc3ccn(CCN(C)C)c(=O)c23)c1] | ESI-MS m/z 432.2 (MH$^+$). |
| 1037 | 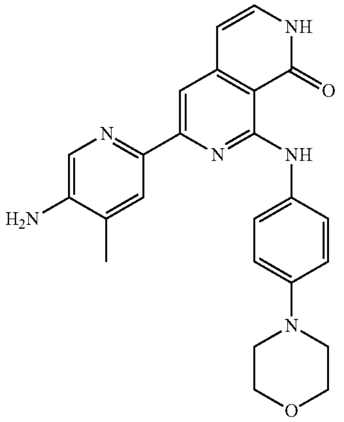 [SMILES: Cc1cc(-c2cc3cc[nH]c(=O)c3c(Nc3ccc(N4CCOCC4)cc3)n2)ncc1N] | ESI-MS m/z 429.2 (MH$^+$). |
| 1038 | 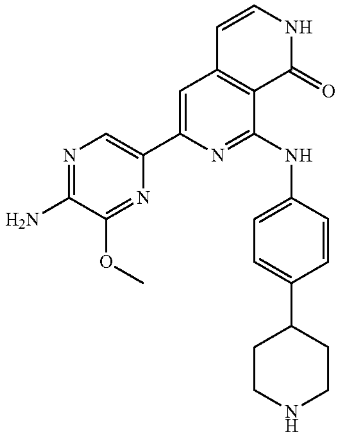 [SMILES: COc1nc(-c2cc3cc[nH]c(=O)c3c(Nc3ccc(C4CCNCC4)cc3)n2)cnc1N] | ESI-MS m/z 444.2 (MH$^+$). |

TABLE 1-continued
| No | Structure | Physical Data $^1H$ NMR 400 MHz ($DMSO-d_6$) and/or MS (m/z) |
|---|---|---|
| 1039 | 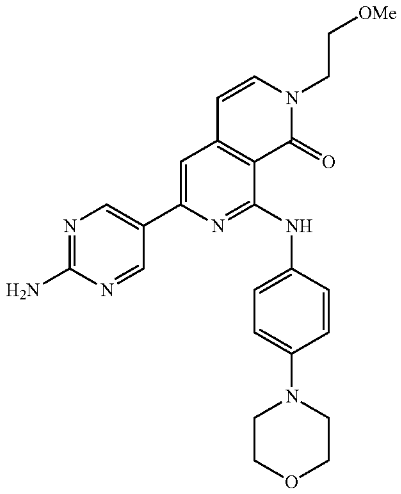 [SMILES: COCCn1ccc2cc(-c3cnc(N)nc3)nc(Nc3ccc(N4CCOCC4)cc3)c2c1=O] | $^1H$ NMR ($DMSO-d_6$) δ 3.09 (t, J = 4.8 Hz, 4H), 3.27 (s, 3H), 3.65 (t, J = 5.2 Hz, 2H), 3.75 (t, J = 4.8 Hz, 4H), 4.15 (t, J = 5.2 Hz, 2H), 6.49 (d, J = 7.2 Hz, 1H), 7.00 (d, J = 9.2 Hz, 2H), 7.08 (s, 1H), 7.29 (s, 1H), 7.60 (d, J = 7.2 Hz, 1H), 7.69 (d, J = 9.2 Hz, 1H), 8.95 (s, 2H), 11.76 (s, 1H); ESI-MS m/z 474.2 ($MH^+$). |
| 1040 | 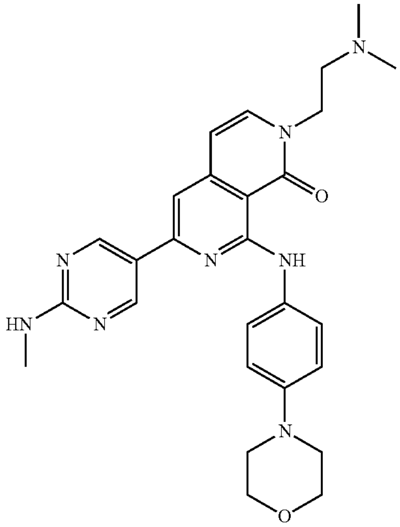 [SMILES: CNc1ncc(-c2cc3ccn(CCN(C)C)c(=O)c3c(Nc3ccc(N4CCOCC4)cc3)n2)cn1] | ESI-MS m/z 501.2 ($MH^+$). |
| 1041 | 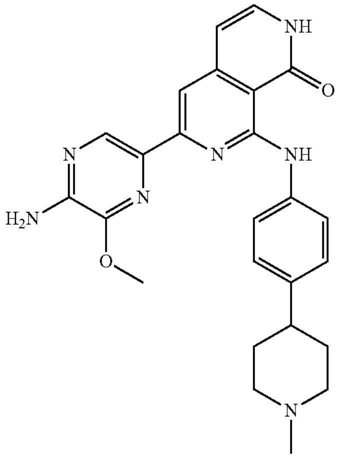 [SMILES: COc1nc(-c2cc3cc[nH]c(=O)c3c(Nc3ccc(C4CCN(C)CC4)cc3)n2)cnc1N] | ESI-MS m/z 458.2 ($MH^+$). |

TABLE 1-continued
| No | Structure | Physical Data $^1$H NMR 400 MHz (DMSO-$d_6$) and/or MS (m/z) |
|---|---|---|
| 1042 | 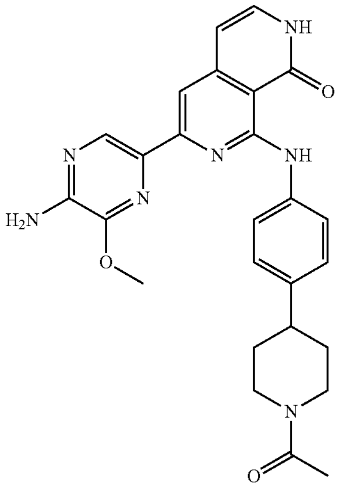 [SMILES: COc1nc(-c2cc3cc[nH]c(=O)c3c(Nc3ccc(C4CCN(C(C)=O)CC4)cc3)n2)cnc1N] | ESI-MS m/z 486.2 (MH$^+$). |
| 1043 | 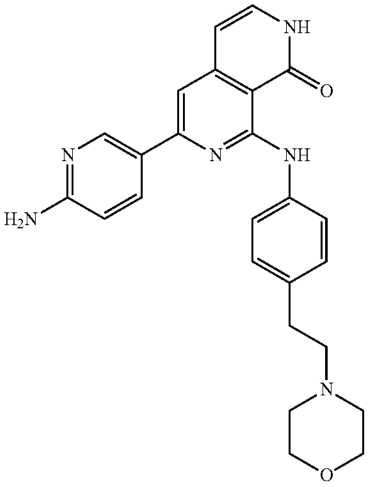 [SMILES: Nc1ccc(-c2cc3cc[nH]c(=O)c3c(Nc3ccc(CCN4CCOCC4)cc3)n2)cn1] | ESI-MS m/z 443.2 (MH$^+$). |
| 1044 | 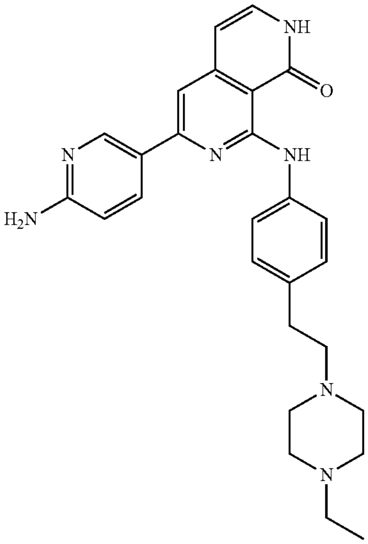 [SMILES: CCN1CCN(CCc2ccc(Nc3nc(-c4ccc(N)nc4)cc4cc[nH]c(=O)c34)cc2)CC1] | ESI-MS m/z 470.2 (MH$^+$). |

TABLE 1-continued
| No | Structure | Physical Data $^1H$ NMR 400 MHz (DMSO-$d_6$) and/or MS (m/z) |
|---|---|---|
| 1045 | 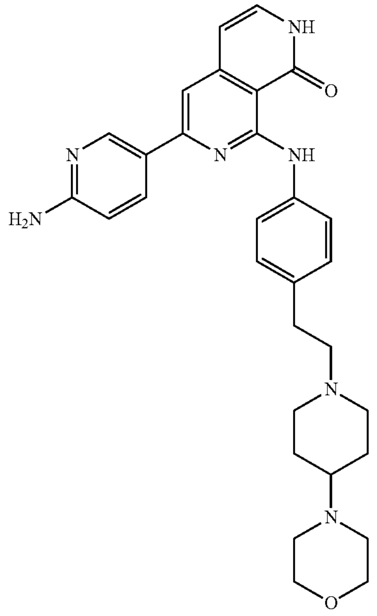 [SMILES: Nc1ccc(-c2cc3cc[nH]c(=O)c3c(Nc3ccc(CCN4CCC(N5CCOCC5)CC4)cc3)n2)cn1] | ESI-MS m/z 526.2 (MH$^+$). |
| 1046 | 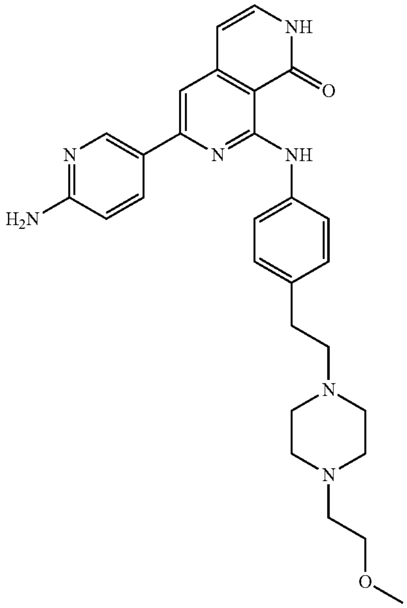 [SMILES: COCCN1CCN(CCc2ccc(Nc3nc(-c4ccc(N)nc4)cc4cc[nH]c(=O)c34)cc2)CC1] | ESI-MS m/z 500.2 (MH$^+$). |
| 1047 | 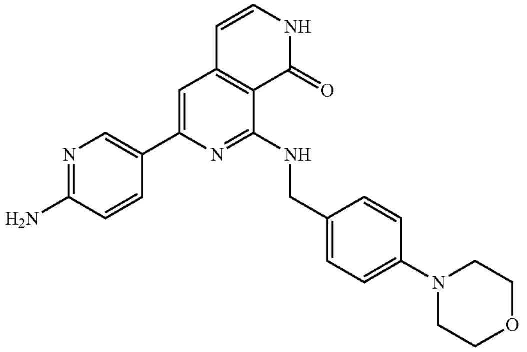 [SMILES: Nc1ccc(-c2cc3cc[nH]c(=O)c3c(NCc3ccc(N4CCOCC4)cc3)n2)cn1] | ESI-MS m/z 429.2 (MH$^+$). |

TABLE 1-continued
| No | Structure | Physical Data $^1$H NMR 400 MHz (DMSO-$d_6$) and/or MS (m/z) |
| --- | --- | --- |
| 1048 | 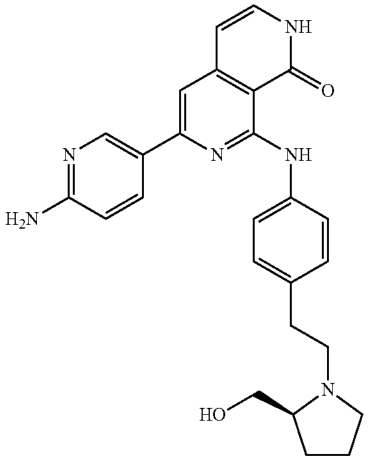 [SMILES: Nc1ccc(-c2cc3cc[nH]c(=O)c3c(Nc3ccc(CCN4CCC[C@H]4CO)cc3)n2)cn1] | ESI-MS m/z 457.2 ($MH^+$). |
| 1049 | 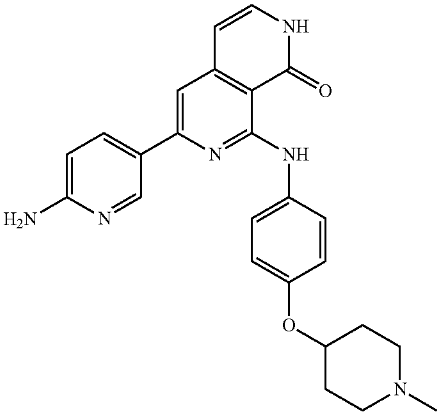 [SMILES: CN1CCC(Oc2ccc(Nc3nc(-c4ccc(N)nc4)cc4cc[nH]c(=O)c34)cc2)CC1] | ESI-MS m/z 443.2 ($MH^+$). |
| 1050 | 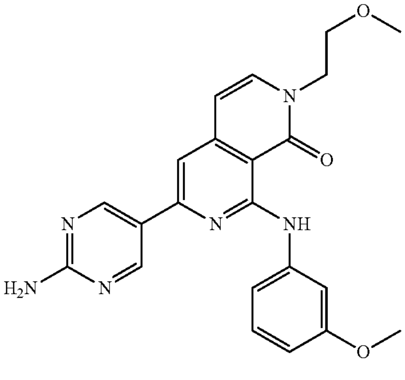 [SMILES: COCCn1ccc2cc(-c3cnc(N)nc3)nc(Nc3cccc(OC)c3)c2c1=O] | ESI-MS m/z 419.2 ($MH^+$). |

TABLE 1-continued
| No | Structure | Physical Data $^1$H NMR 400 MHz (DMSO-d$_6$) and/or MS (m/z) |
|---|---|---|
| 1051 | 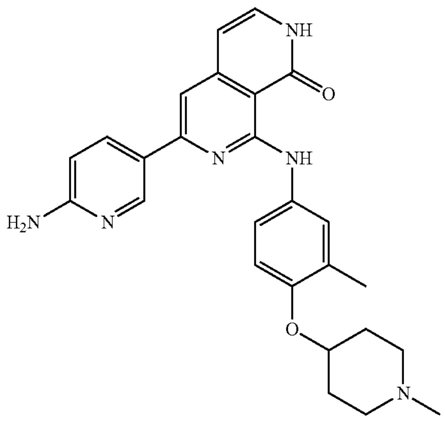 [SMILES: Cc1cc(Nc2nc(-c3ccc(N)nc3)cc3cc[nH]c(=O)c23)ccc1OC1CCN(C)CC1] | ESI-MS m/z 457.2 (MH$^+$). |
| 1052 | 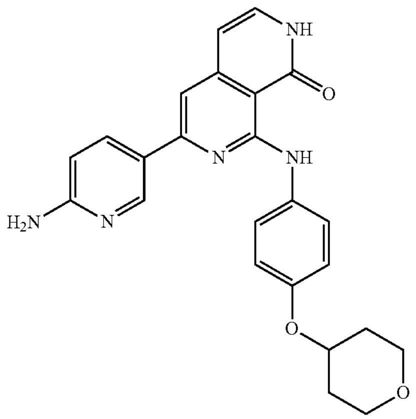 [SMILES: Nc1ccc(-c2cc3cc[nH]c(=O)c3c(Nc3ccc(OC4CCOCC4)cc3)n2)cn1] | ESI-MS m/z 430.2 (MH$^+$). |
| 1053 | 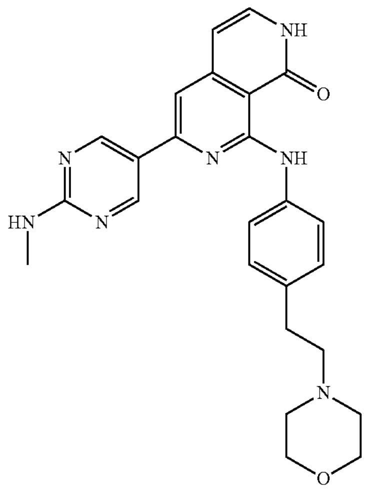 [SMILES: CNc1ncc(-c2cc3cc[nH]c(=O)c3c(Nc3ccc(CCN4CCOCC4)cc3)n2)cn1] | ESI-MS m/z 458.2 (MH$^+$). |

TABLE 1-continued
| No | Structure | Physical Data $^{1}H$ NMR 400 MHz (DMSO-$d_6$) and/or MS (m/z) |
|---|---|---|
| 1054 | 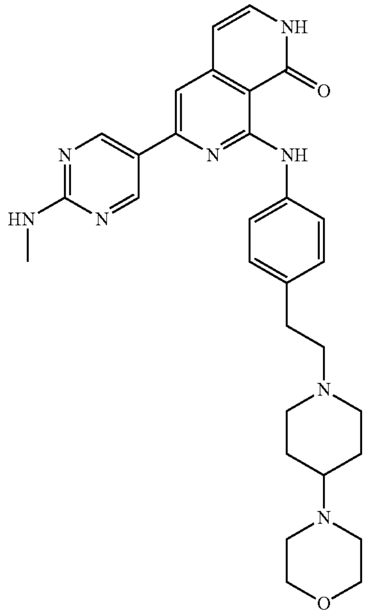 [SMILES: CNc1ncc(-c2cc3cc[nH]c(=O)c3c(Nc3ccc(CCN4CCC(N5CCOCC5)CC4)cc3)n2)cn1] | ESI-MS m/z 541.2 ($MH^+$). |
| 1055 | 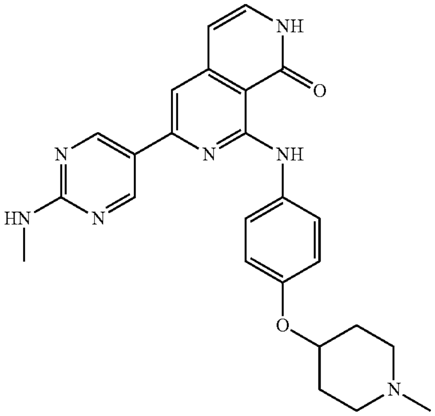 [SMILES: CNc1ncc(-c2cc3cc[nH]c(=O)c3c(Nc3ccc(OC4CCN(C)CC4)cc3)n2)cn1] | $^{1}H$ NMR (DMSO-$d_6$) δ 1.59 (m, 2H), 1.98 (m, 2H), 2.88 (d, J = 4.8 Hz, 3H), 3.49 (m, 2H), 3.87 (m, 2H), 4.55 (m, 1H), 6.45 (d, J = 7.2 Hz, 1H), 7.03 (d, J = 8.8 Hz, 2H), 7.31 (s, 1H), 7.37 (d, J = 6.8 Hz, 1H), 7.55 (d, J = 4.9 Hz, 1H), 7.71 (d, J = 8.8 Hz, 2H), 9.00 (bs, 2H), 11.66 (bs, 1H), 11.81 (s, 1H); ESI-MS m/z 458.2 ($MH^+$). |
| 1056 | 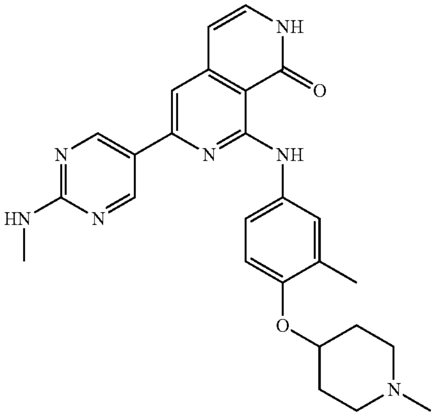 [SMILES: CNc1ncc(-c2cc3cc[nH]c(=O)c3c(Nc3ccc(OC4CCN(C)CC4)c(C)c3)n2)cn1] | ESI-MS m/z 472.2 ($MH^+$). |

TABLE 1-continued
| No | Structure | Physical Data $^1H$ NMR 400 MHz (DMSO-$d_6$) and/or MS (m/z) |
|---|---|---|
| 1057 | 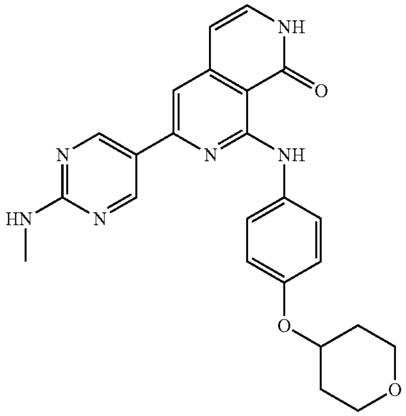 [SMILES: CNc1ncc(-c2cc3cc[nH]c(=O)c3c(Nc3ccc(OC4CCOCC4)cc3)n2)cn1] | ESI-MS m/z 445.2 (MH$^+$). |
| 1058 | 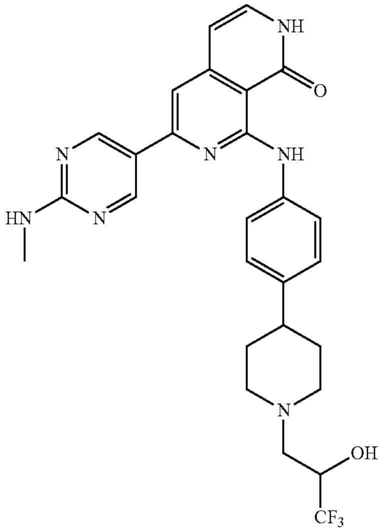 [SMILES: CNc1ncc(-c2cc3cc[nH]c(=O)c3c(Nc3ccc(C4CCN(CC(O)C(F)(F)F)CC4)cc3)n2)cn1] | ESI-MS m/z 540.2 (MH$^+$). |
| 1059 | 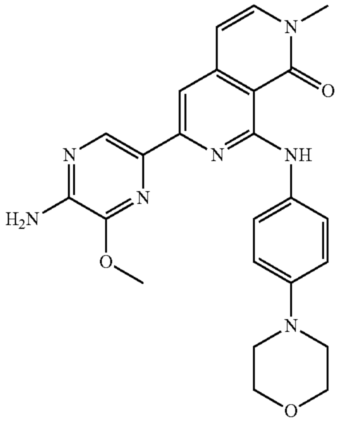 [SMILES: COc1nc(-c2cc3ccn(C)c(=O)c3c(Nc3ccc(N4CCOCC4)cc3)n2)cnc1N] | ESI-MS m/z 460.2 (MH$^+$). |

TABLE 1-continued
| No | Structure | Physical Data $^1H$ NMR 400 MHz (DMSO-$d_6$) and/or MS (m/z) |
|---|---|---|
| 1060 | 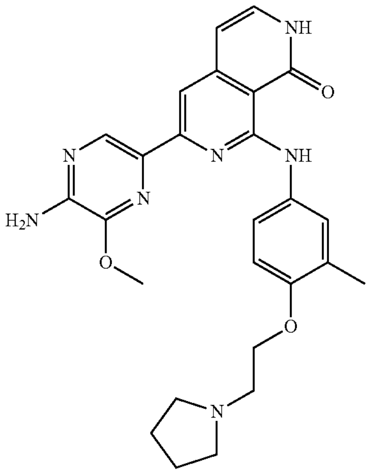 [SMILES: COc1nc(-c2cc3cc[nH]c(=O)c3c(Nc3ccc(OCCN4CCCC4)c(C)c3)n2)cnc1N] | ESI-MS m/z 488.2 ($MH^+$). |
| 1061 | 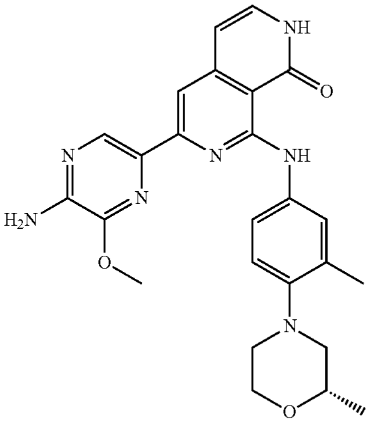 [SMILES: COc1nc(-c2cc3cc[nH]c(=O)c3c(Nc3ccc(N4CCO[C@@H](C)C4)c(C)c3)n2)cnc1N] | ESI-MS m/z 474.2 ($MH^+$). |
| 1062 | 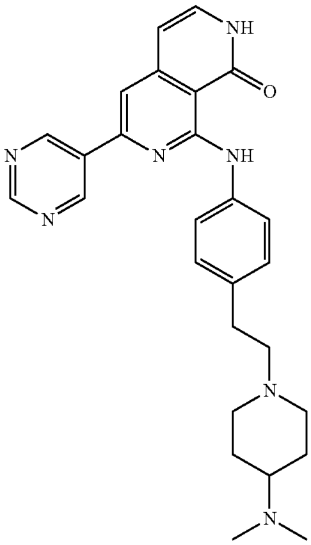 [SMILES: CN(C)C1CCN(CCc2ccc(Nc3nc(-c4cncnc4)cc4cc[nH]c(=O)c34)cc2)CC1] | $^1H$ NMR (DMSO-$d_6$) δ 1.35 (m, 2H), 1.71 (d, J = 12.0 Hz, 2H), 1.92 (t, J = 12.0 Hz, 2H), 2.00 (m, 1H), 2.15 (s, 6H), 2.49 (m, 2H), 2.71 (t, J = 7.2 Hz, 2H), 2.96 (d, J = 11.6 Hz, 2H), 6.49 (d, J = 6.4 Hz, 1H), 7.23 (d, J = 8.4 Hz, 2H), 7.53 (d, J = 6.8 Hz, 1H), 7.58 (s, 1H), 7.75 (d, J = 8.4 Hz, 2H), 9.27 (s, 1H), 9.45 (s, 2H), 12.44 (s, 1H); ESI-MS m/z 470.2 ($MH^+$). |

TABLE 1-continued
| No | Structure | Physical Data $^1H$ NMR 400 MHz (DMSO-$d_6$) and/or MS (m/z) |
|---|---|---|
| 1063 | 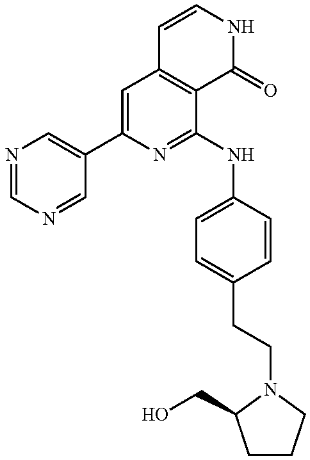 [SMILES: O=c1[nH]ccc2cc(-c3cncnc3)nc(Nc3ccc(CCN4CCC[C@H]4CO)cc3)c12] | ESI-MS m/z 443.2 ($MH^+$). |
| 1064 | 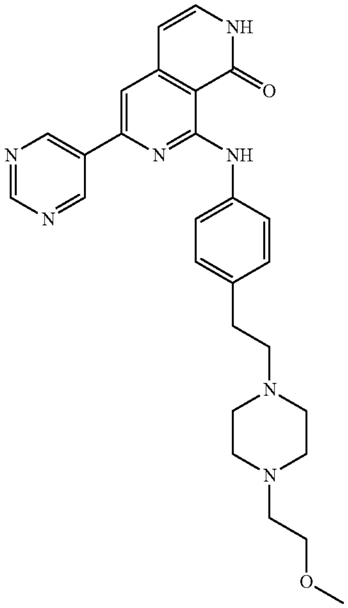 [SMILES: COCCN1CCN(CCc2ccc(Nc3nc(-c4cncnc4)cc4cc[nH]c(=O)c34)cc2)CC1] | ESI-MS m/z 486.2 ($MH^+$). |
| 1065 | 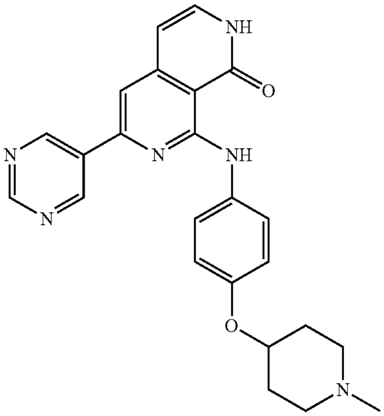 [SMILES: CN1CCC(Oc2ccc(Nc3nc(-c4cncnc4)cc4cc[nH]c(=O)c34)cc2)CC1] | ESI-MS m/z 429.2 ($MH^+$). |

TABLE 1-continued
| No | Structure | Physical Data $^1H$ NMR 400 MHz (DMSO-$d_6$) and/or MS (m/z) |
| --- | --- | --- |
| 1066 | 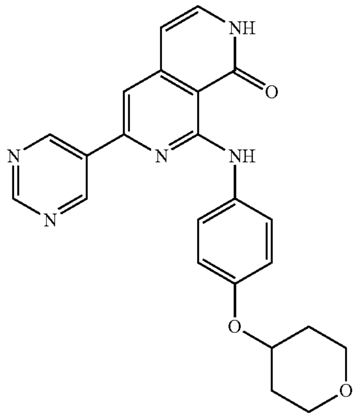 [SMILES: O=c1[nH]ccc2cc(-c3cncnc3)nc(Nc3ccc(OC4CCOCC4)cc3)c12] | ESI-MS m/z 416.2 (MH$^+$). |
| 1067 | 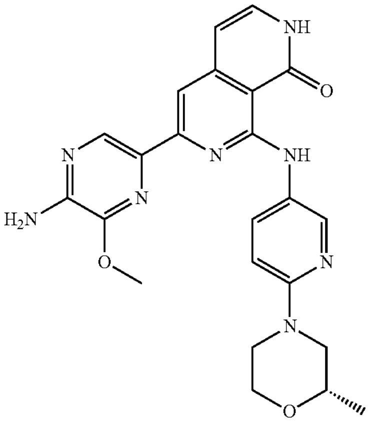 [SMILES: COc1nc(-c2cc3cc[nH]c(=O)c3c(Nc3ccc(N4CCO[C@@H](C)C4)nc3)n2)cnc1N] | ESI-MS m/z 461.2 (MH$^+$). |
| 1068 | 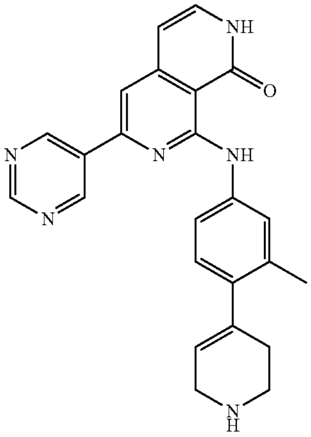 [SMILES: Cc1cc(Nc2nc(-c3cncnc3)cc3cc[nH]c(=O)c23)ccc1C1=CCNCC1] | ESI-MS m/z 411.2 (MH$^+$). |

TABLE 1-continued
| No | Structure | Physical Data $^1$H NMR 400 MHz (DMSO-$d_6$) and/or MS (m/z) |
|---|---|---|
| 1069 | 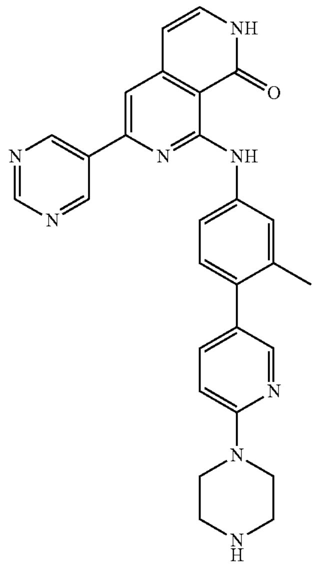 [SMILES: Cc1cc(Nc2nc(-c3cncnc3)cc3cc[nH]c(=O)c23)ccc1-c1ccc(N2CCNCC2)nc1] | ESI-MS m/z 491.2 ($MH^+$). |
| 1070 | 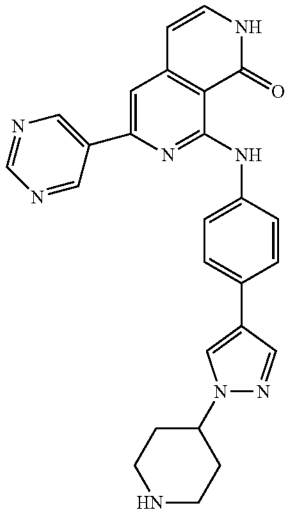 [SMILES: O=c1[nH]ccc2cc(-c3cncnc3)nc(Nc3ccc(-c4cnn(C5CCNCC5)c4)cc3)c12] | ESI-MS m/z 465.2 ($MH^+$). |

TABLE 1-continued
| No | Structure | Physical Data $^1$H NMR 400 MHz (DMSO-$d_6$) and/or MS (m/z) |
|---|---|---|
| 1071 | 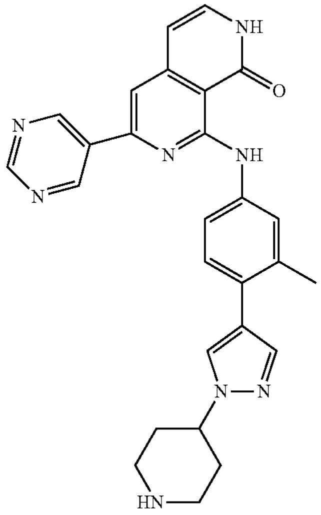 [SMILES: Cc1cc(Nc2nc(-c3cncnc3)cc3cc[nH]c(=O)c23)ccc1-c1cnn(C2CCNCC2)c1] | ESI-MS m/z 479.2 (MH$^+$). |
| 1072 | 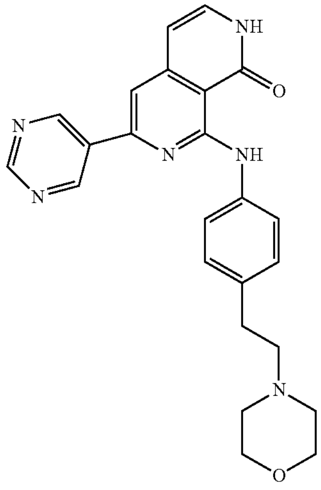 [SMILES: O=c1[nH]ccc2cc(-c3cncnc3)nc(Nc3ccc(CCN4CCOCC4)cc3)c12] | ESI-MS m/z 429.2 (MH$^+$). |

TABLE 1-continued
| No | Structure | Physical Data $^1H$ NMR 400 MHz ($DMSO-d_6$) and/or MS (m/z) |
|---|---|---|
| 1073 | 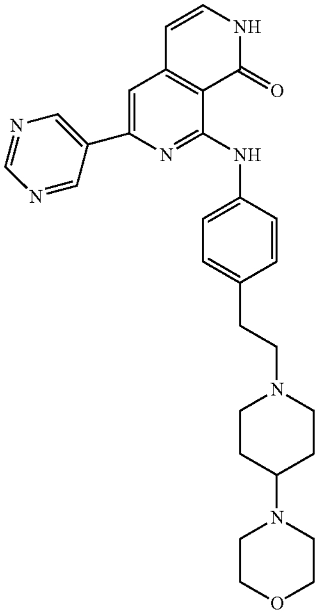 [SMILES: O=c1[nH]ccc2cc(-c3cncnc3)nc(Nc3ccc(CCN4CCC(N5CCOCC5)CC4)cc3)c12] | ESI-MS m/z 512.2 ($MH^+$). |
| 1074 | 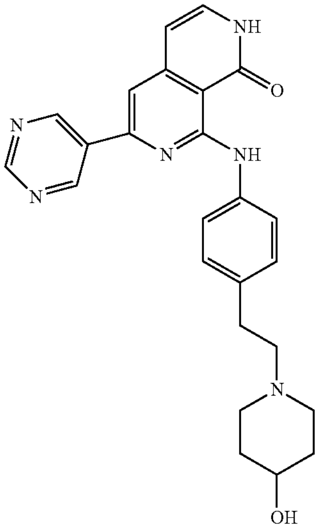 [SMILES: O=c1[nH]ccc2cc(-c3cncnc3)nc(Nc3ccc(CCN4CCC(O)CC4)cc3)c12] | ESI-MS m/z 443.2 ($MH^+$). |
| 1075 | 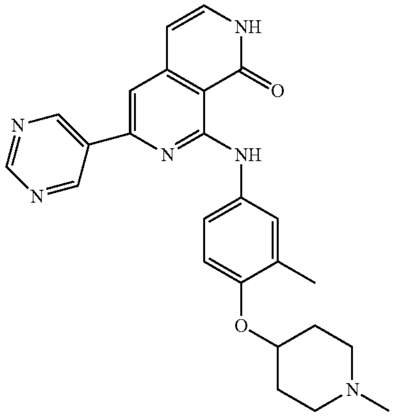 [SMILES: Cc1cc(Nc2nc(-c3cncnc3)cc3cc[nH]c(=O)c23)ccc1OC1CCN(C)CC1] | ESI-MS m/z 443.2 ($MH^+$). |

TABLE 1-continued
| No | Structure | Physical Data $^1$H NMR 400 MHz (DMSO-$d_6$) and/or MS (m/z) |
|---|---|---|
| 1076 | 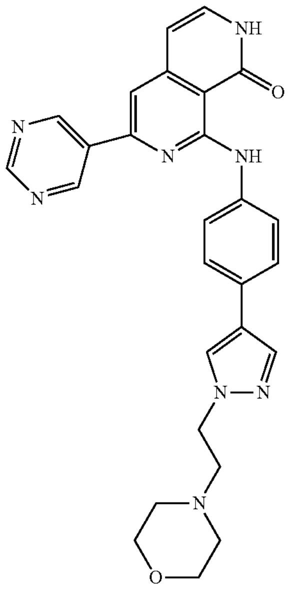 [SMILES: O=c1[nH]ccc2cc(-c3cncnc3)nc(Nc3ccc(-c4cnn(CCN5CCOCC5)c4)cc3)c12] | ESI-MS m/z 495.2 (MH$^+$). |
| 1077 | 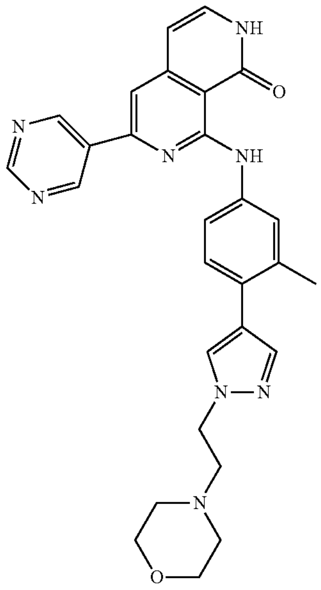 [SMILES: Cc1cc(Nc2nc(-c3cncnc3)cc3cc[nH]c(=O)c23)ccc1-c1cnn(CCN2CCOCC2)c1] | ESI-MS m/z 509.2 (MH$^+$). |

TABLE 1-continued
| No | Structure | Physical Data $^1H$ NMR 400 MHz ($DMSO-d_6$) and/or MS (m/z) |
|---|---|---|
| 1078 | 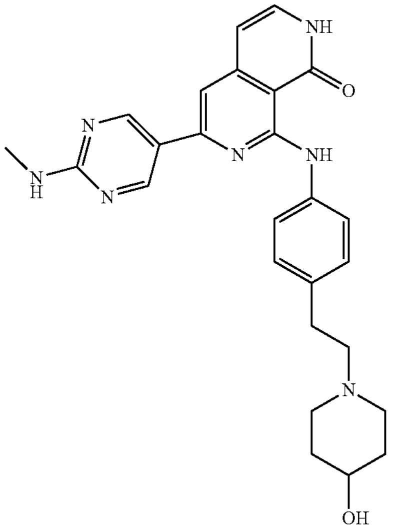 [SMILES: CNc1ncc(-c2cc3cc[nH]c(=O)c3c(Nc3ccc(CCN4CCC(O)CC4)cc3)n2)cn1] | ESI-MS m/z 472.2 ($MH^+$). |
| 1079 | 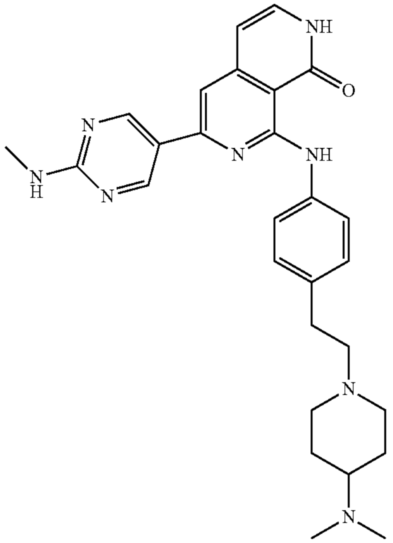 | ESI-MS m/z 499.2 ($MH^+$). |
| 1080 | 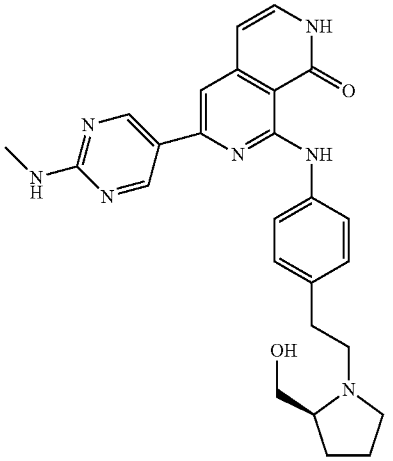 [SMILES: CNc1ncc(-c2cc3cc[nH]c(=O)c3c(Nc3ccc(CCN4CCC[C@H]4CO)cc3)n2)cn1] | ESI-MS m/z 472.2 ($MH^+$). |

TABLE 1-continued
| No | Structure | Physical Data $^1H$ NMR 400 MHz ($DMSO-d_6$) and/or MS (m/z) |
|---|---|---|
| 1081 | 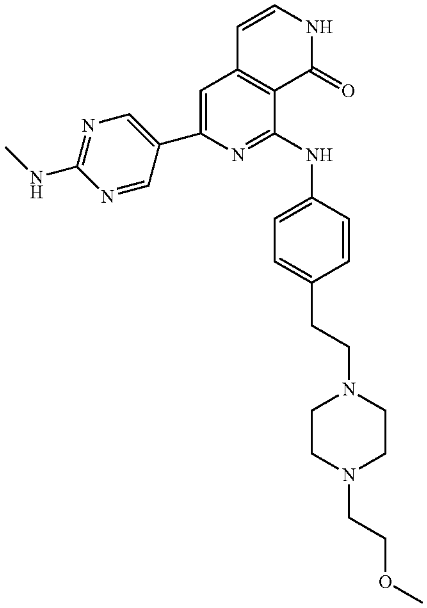 | ESI-MS m/z 415.2 ($MH^+$). |
| 1082 | 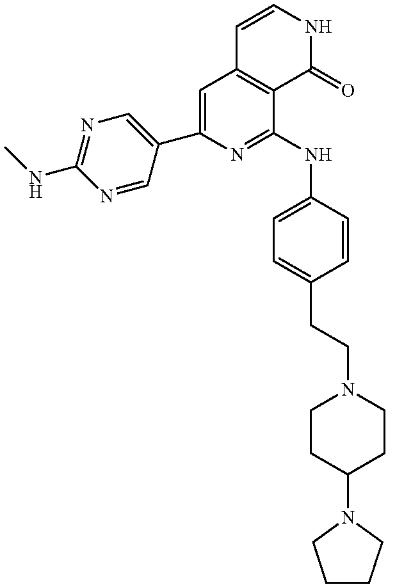 [SMILES: CNc1ncc(-c2cc3cc[nH]c(=O)c3c(Nc3ccc(CCN4CCC(N5CCCC5)CC4)cc3)n2)cn1] | ESI-MS m/z 525.2 ($MH^+$). |

TABLE 1-continued
| No | Structure | Physical Data $^1H$ NMR 400 MHz (DMSO-$d_6$) and/or MS (m/z) |
|---|---|---|
| 1083 | 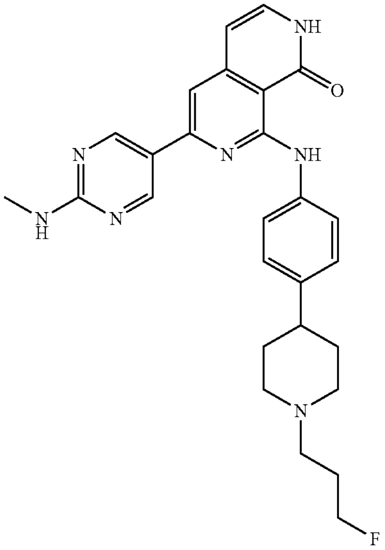 [SMILES: CNc1ncc(-c2cc3cc[nH]c(=O)c3c(Nc3ccc(C4CCN(CCCF)CC4)cc3)n2)cn1] | ESI-MS m/z 488.2 (MH+). |
| 1084 | 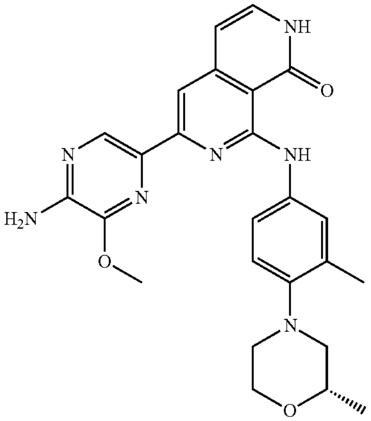 [SMILES: COc1nc(-c2cc3cc[nH]c(=O)c3c(Nc3ccc(N4CCO[C@@H](C)C4)c(C)c3)n2)cnc1N] | ESI-MS m/z 474.2 (MH+). |
| 1085 | 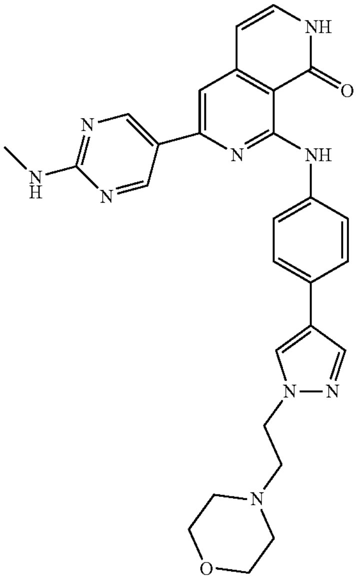 [SMILES: CNc1ncc(-c2cc3cc[nH]c(=O)c3c(Nc3ccc(-c4cnn(CCN5CCOCC5)c4)cc3)n2)cn1] | ESI-MS m/z 524.2 (MH+). |

TABLE 1-continued
| No | Structure | Physical Data $^1H$ NMR 400 MHz (DMSO-$d_6$) and/or MS (m/z) |
| --- | --- | --- |
| 1086 | 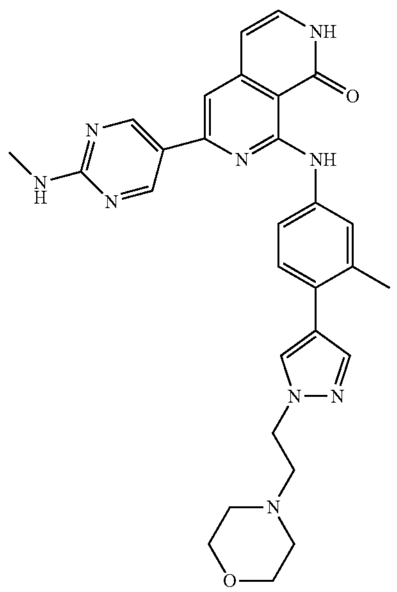 | ESI-MS m/z 538.2 (MH$^+$). |
| 1087 | 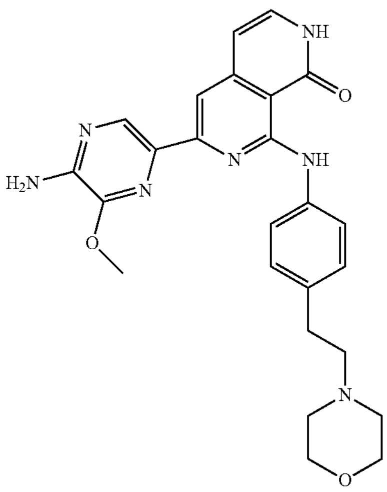 [SMILES: COc1nc(-c2cc3cc[nH]c(=O)c3c(Nc3ccc(CCN4CCOCC4)cc3)n2)cnc1N] | ESI-MS m/z 474.2 (MH$^+$). |
| 1088 | 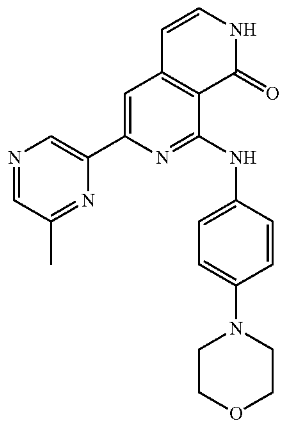 [SMILES: Cc1cncc(-c2cc3cc[nH]c(=O)c3c(Nc3ccc(N4CCOCC4)cc3)n2)n1] | ESI-MS m/z 415.2 (MH$^+$). |

TABLE 1-continued
| No | Structure | Physical Data $^1$H NMR 400 MHz (DMSO-$d_6$) and/or MS (m/z) |
|---|---|---|
| 1089 | 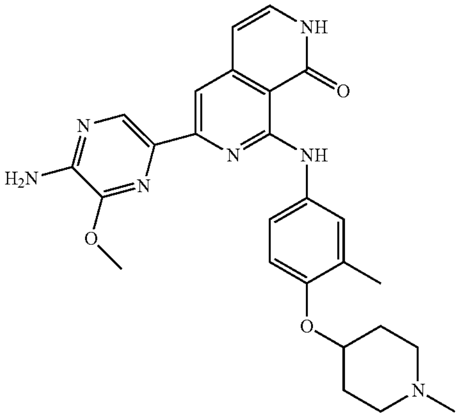 [SMILES: COc1nc(-c2cc3cc[nH]c(=O)c3c(Nc3ccc(OC4CCN(C)CC4)c(C)c3)n2)cnc1N] | ESI-MS m/z 488.2 (MH$^+$). |
| 1090 | 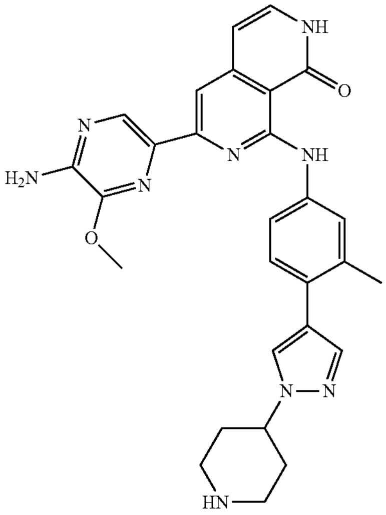 [SMILES: COc1nc(-c2cc3cc[nH]c(=O)c3c(Nc3ccc(-c4cnn(C5CCNCC5)c4)c(C)c3)n2)cnc1N] | ESI-MS m/z 524.2 (MH$^+$). |
| 1091 | 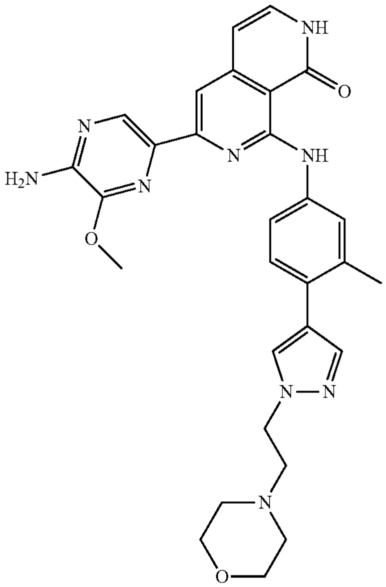 [SMILES: COc1nc(-c2cc3cc[nH]c(=O)c3c(Nc3ccc(-c4cnn(CCN5CCOCC5)c4)c(C)c3)n2)cnc1N] | ESI-MS m/z 554.2 (MH$^+$). |

TABLE 1-continued
| No | Structure | Physical Data $^1H$ NMR 400 MHz (DMSO-$d_6$) and/or MS (m/z) |
|---|---|---|
| 1092 | 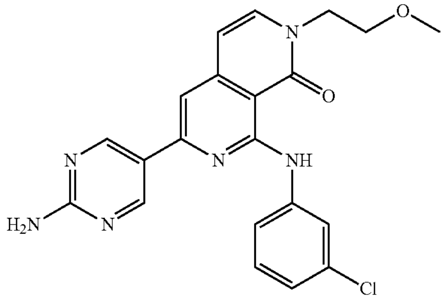 [SMILES: COCCn1ccc2cc(-c3cnc(N)nc3)nc(Nc3cccc(Cl)c3)c2c1=O] | ESI-MS m/z 423.2 (MH$^+$). |
| 1093 | 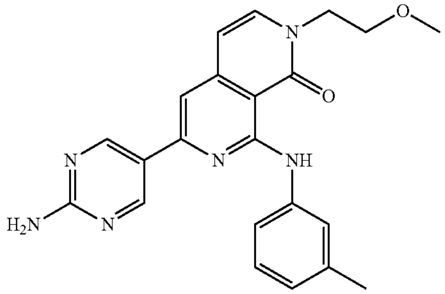 [SMILES: COCCn1ccc2cc(-c3cnc(N)nc3)nc(Nc3cccc(C)c3)c2c1=O] | ESI-MS m/z 403.2 (MH$^+$). |
| 1094 | 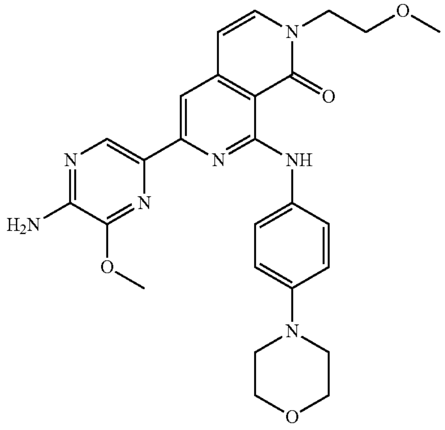 [SMILES: COCCn1ccc2cc(-c3cnc(N)c(OC)n3)nc(Nc3ccc(N4CCOCC4)cc3)c2c1=O] | ESI-MS m/z 503.2 (MH$^+$). |
| 1095 | 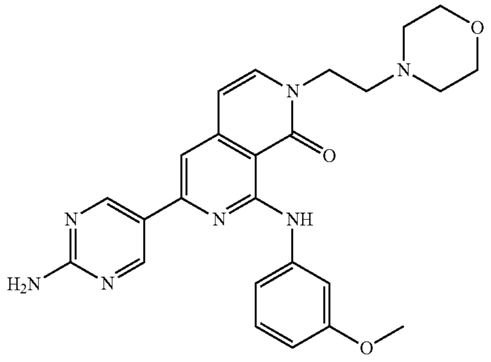 [SMILES: COc1cccc(Nc2nc(-c3cnc(N)nc3)cc3ccn(CCN4CCOCC4)c(=O)c23)c1] | ESI-MS m/z 474.2 (MH$^+$). |

TABLE 1-continued
| No | Structure | Physical Data $^1H$ NMR 400 MHz (DMSO-$d_6$) and/or MS (m/z) |
|---|---|---|
| 1096 | 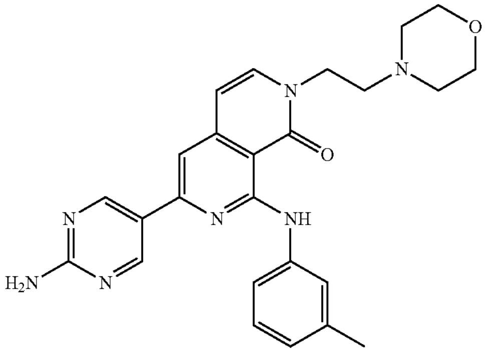 [SMILES: Cc1cccc(Nc2nc(-c3cnc(N)nc3)cc3ccn(CCN4CCOCC4)c(=O)c23)c1] | ESI-MS m/z 458.2 (MH+). |
| 1097 | 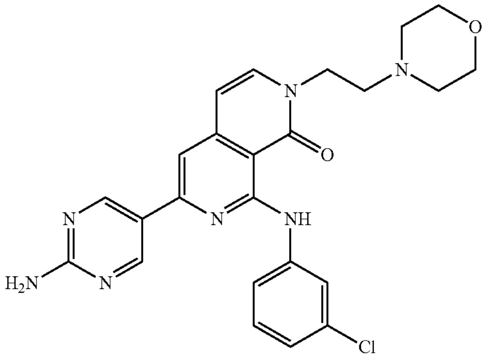 [SMILES: Nc1ncc(-c2cc3ccn(CCN4CCOCC4)c(=O)c3c(Nc3cccc(Cl)c3)n2)cn1] | ESI-MS m/z 478.2 (MH+). |
| 1098 | 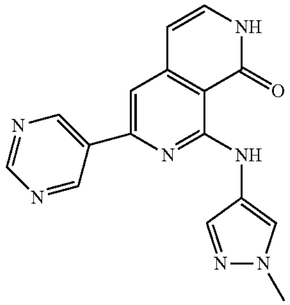 [SMILES: Cn1cc(Nc2nc(-c3cncnc3)cc3cc[nH]c(=O)c23)cn1] | ESI-MS m/z 320.2 (MH+). |
| 1099 | 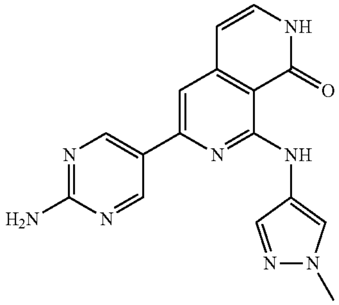 [SMILES: Cn1cc(Nc2nc(-c3cnc(N)nc3)cc3cc[nH]c(=O)c23)cn1] | ESI-MS m/z 335.2 (MH+). |

TABLE 1-continued
| No | Structure | Physical Data $^1H$ NMR 400 MHz (DMSO-$d_6$) and/or MS (m/z) |
|---|---|---|
| 1100 | 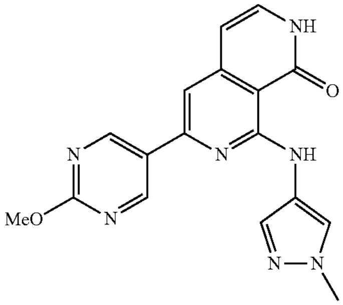 [SMILES: COc1ncc(-c2cc3cc[nH]c(=O)c3c(Nc3cnn(C)c3)n2)cn1] | $^1H$ NMR (DMSO-$d_6$) δ 3.87 (s, 3H), 4.02 (s, 3H), 6.44 (d, J = 6.8 Hz, 1H), 7.36 (s, 1H), 7.45 (d, J = 6.8 Hz, 2H), 7.68 (s, 1H), 8.14 (s, 1H), 9.26 (s, 2H), 11.85 (s, 1H); ESI-MS m/z 350.2 ($MH^+$). |
| 1101 | 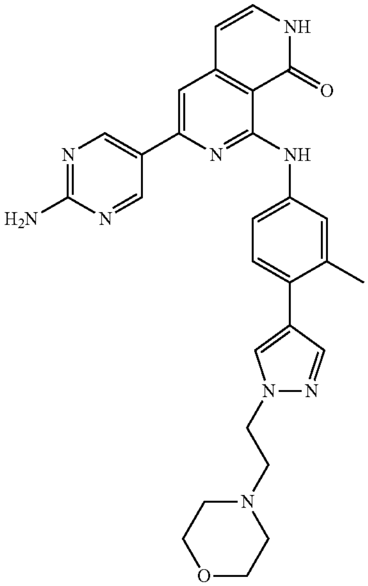 [SMILES: Cc1cc(Nc2nc(-c3cnc(N)nc3)cc3cc[nH]c(=O)c23)ccc1-c1cnn(CCN2CCOCC2)c1] | ESI-MS m/z 524.2 ($MH^+$). |
| 1102 | 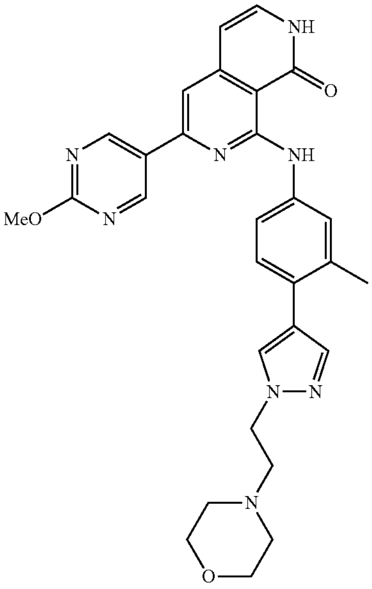 [SMILES: COc1ncc(-c2cc3cc[nH]c(=O)c3c(Nc3ccc(-c4cnn(CCN5CCOCC5)c4)c(C)c3)n2)cn1] | ESI-MS m/z 539.2 ($MH^+$). |

TABLE 1-continued
| No | Structure | Physical Data $^1$H NMR 400 MHz (DMSO-$d_6$) and/or MS (m/z) |
|---|---|---|
| 1103 | 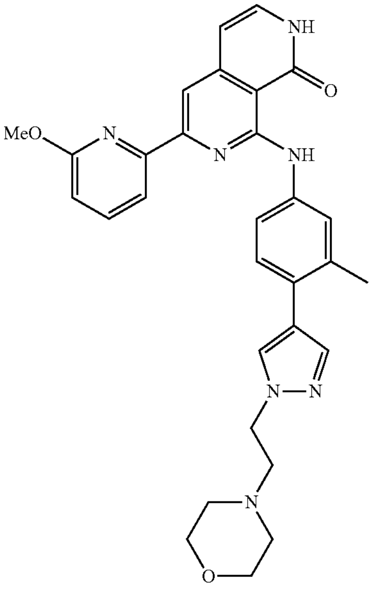 [SMILES: COc1cccc(-c2cc3cc[nH]c(=O)c3c(Nc3ccc(-c4cnn(CCN5CCOCC5)c4)c(C)c3)n2)n1] | ESI-MS m/z 538.2 (MH$^+$). |
| 1104 | 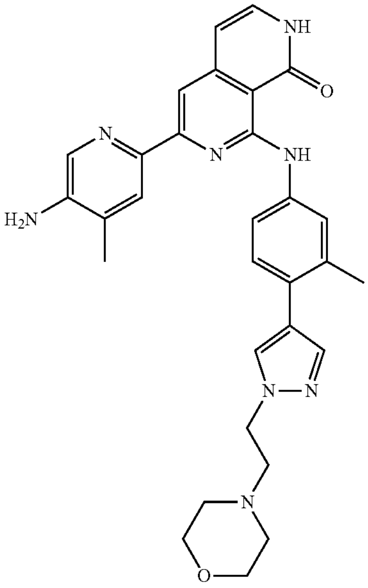 [SMILES: Cc1cc(-c2cc3cc[nH]c(=O)c3c(Nc3ccc(-c4cnn(CCN5CCOCC5)c4)c(C)c3)n2)ncc1N] | ESI-MS m/z 537.2 (MH$^+$). |

TABLE 1-continued
| No | Structure | Physical Data $^1H$ NMR 400 MHz (DMSO-$d_6$) and/or MS (m/z) |
|---|---|---|
| 1105 | 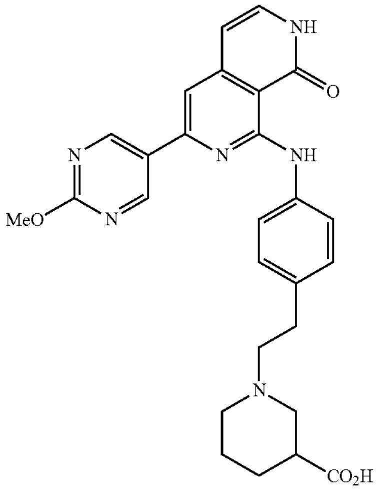 [SMILES: COc1ncc(-c2cc3cc[nH]c(=O)c3c(Nc3ccc(CCN4CCCC(C(=O)O)C4)cc3)n2)cn1] | ESI-MS m/z 471.2 (MH$^+$). |
| 1106 | 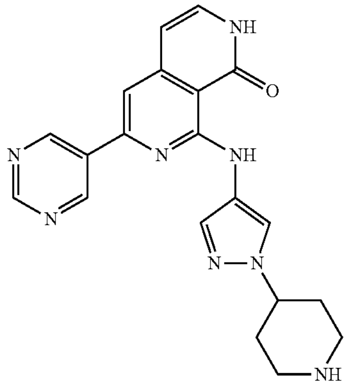 [SMILES: O=c1[nH]ccc2cc(-c3cncnc3)nc(Nc3cnn(C4CCNCC4)c3)c12] | ESI-MS m/z 389.2 (MH$^+$). |
| 1107 | 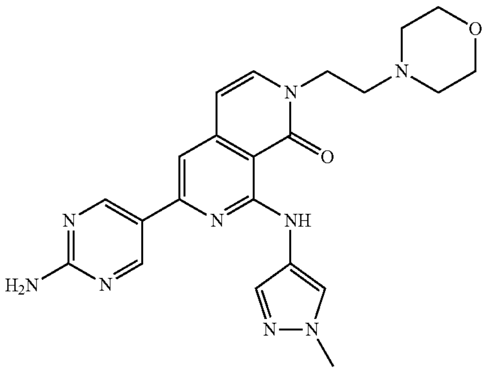 | ESI-MS m/z 335.2 (MH$^+$). |

TABLE 1-continued
| No | Structure | Physical Data $^1H$ NMR 400 MHz ($DMSO-d_6$) and/or MS (m/z) |
|---|---|---|
| 1108 | 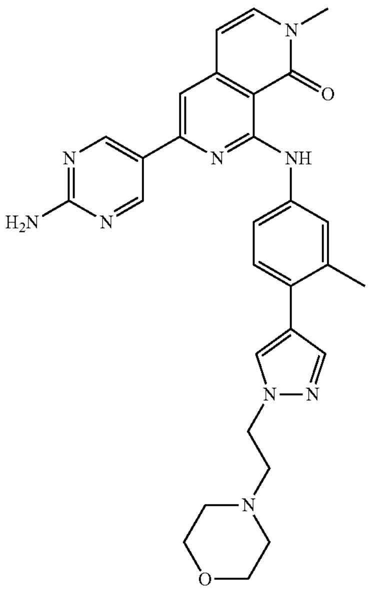 | ESI-MS m/z 524.2 ($MH^+$). |
| 1109 | 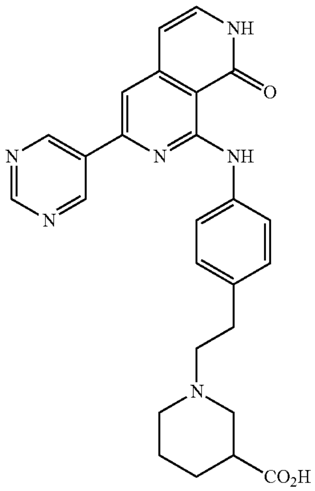 [SMILES: O=C(O)C1CCCN(CCc2ccc(Nc3nc(-c4cncnc4)cc4cc[nH]c(=O)c34)cc2)C1] | ESI-MS m/z 471.2 ($MH^+$). |

TABLE 1-continued
| No | Structure | Physical Data $^1H$ NMR 400 MHz (DMSO-$d_6$) and/or MS (m/z) |
|---|---|---|
| 1110 | 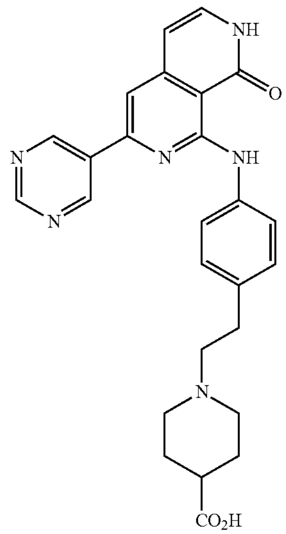 [SMILES: O=C(O)C1CCN(CCc2ccc(Nc3nc(-c4cncnc4)cc4cc[nH]c(=O)c34)cc2)CC1] | ESI-MS m/z 471.2 ($MH^+$). |
| 1111 | 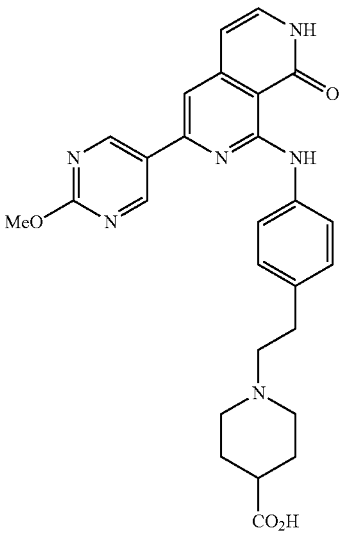 [SMILES: COc1ncc(-c2cc3cc[nH]c(=O)c3c(Nc3ccc(CCN4CCC(C(=O)O)CC4)cc3)n2)cn1] | ESI-MS m/z 501.2 ($MH^+$). |
| 1112 | 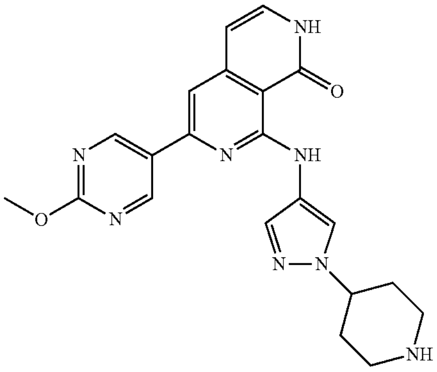 [SMILES: COc1ncc(-c2cc3cc[nH]c(=O)c3c(Nc3cnn(C4CCNCC4)c3)n2)cn1] | ESI-MS m/z 419.2 ($MH^+$). |

TABLE 1-continued
| No | Structure | Physical Data $^1$H NMR 400 MHz (DMSO-$d_6$) and/or MS (m/z) |
|---|---|---|
| 1113 | 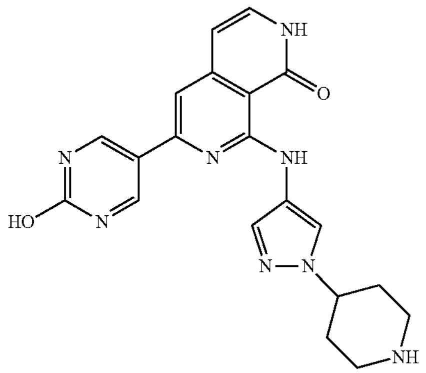 [SMILES: O=c1[nH]ccc2cc(-c3cnc(O)nc3)nc(Nc3cnn(C4CCNCC4)c3)c12] | ESI-MS m/z 405.2 (MH$^+$). |
| 1114 | 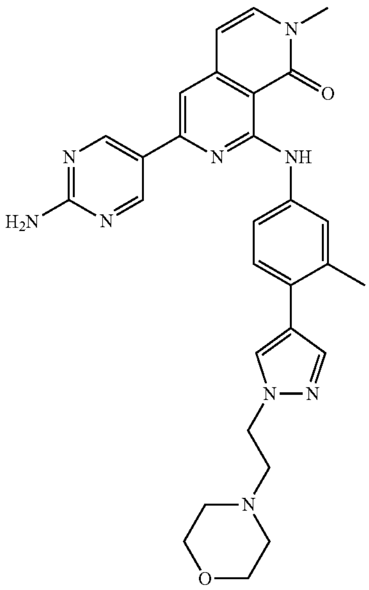 [SMILES: Cc1cc(Nc2nc(-c3cnc(N)nc3)cc3ccn(C)c(=O)c23)ccc1-c1cnn(CCN2CCOCC2)c1] | ESI-MS m/z 538.2 (MH$^+$). |
| 1115 | 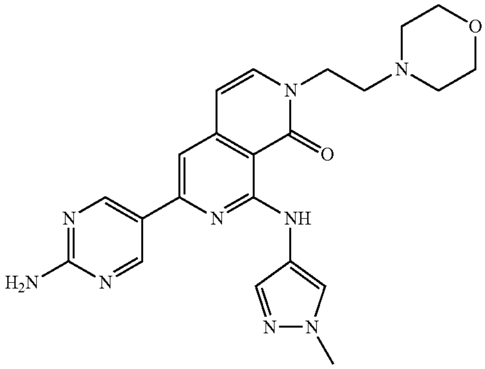 [SMILES: Cn1cc(Nc2nc(-c3cnc(N)nc3)cc3ccn(CCN4CCOCC4)c(=O)c23)cn1] | $^1$H NMR (DMSO-$d_6$) δ 2.45 (bs, 4H), 2.62 (t, J = 6.0 Hz, 2H), 3.55 (t, J = 4.4 Hz, 4H), 3.86 (s, 3H), 4.08 (t, J = 6.4 Hz, 2H), 6.50 (d, J = 7.2 Hz, 1H), 7.09 (s, 2H), 7.24 (s, 1H), 7.64 (d, J = 7.2 Hz, 1H), 7.72 (s, 1H), 8.14 (s, 1H), 8.96 (s, 2H), 11.57 (s, 1H); ESI-MS m/z 448.2 (MH$^+$). |

TABLE 1-continued
| No | Structure | Physical Data $^1$H NMR 400 MHz (DMSO-$d_6$) and/or MS (m/z) |
|---|---|---|
| 1116 | 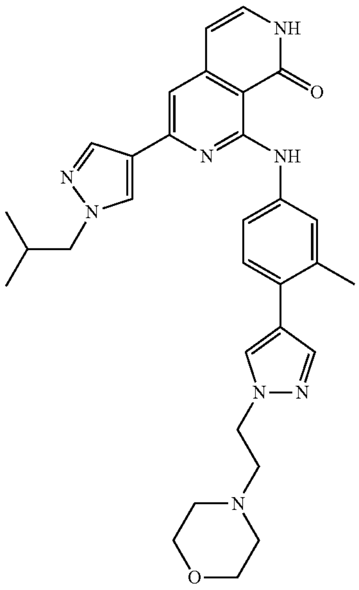 [SMILES: Cc1cc(Nc2nc(-c3cnn(CC(C)C)c3)cc3cc[nH]c(=O)c23)ccc1-c1cnn(CCN2CCOCC2)c1] | $^1$H NMR (DMSO-$d_6$) δ 0.88 (d, J = 6.4 Hz, 4H), 2.17 (m, 1H), 2.44 (s, 3H), 2.51 (m, 3H), 3.12 (bs, 2H), 3.36 (d, J= 11.6 Hz, 2H), 3.65 (t, J = 6.4 Hz, 2H), 3.88 (m, 4H), 4.01 (d, J = 7.2 Hz, 2H), 4.72 (t, J = 6.8 Hz, 2H), 6.44 (d, J = 7.2 Hz, 1H), 7.15 (s, 1H), 7.37 (m, 1H), 7.43 (d, J = 8.0 Hz, 1H), 7.81 (m, 3H), 8.06 (s, 1H), 8.12 (s, 1H), 8.31 (s, 1H), 11.70 (d, J = 5.6 Hz, 1H), 11.82 (bs, 1H), 12.02 (s, 1H); ESI-MS m/z 553.2 ($MH^+$). |
| 1117 | 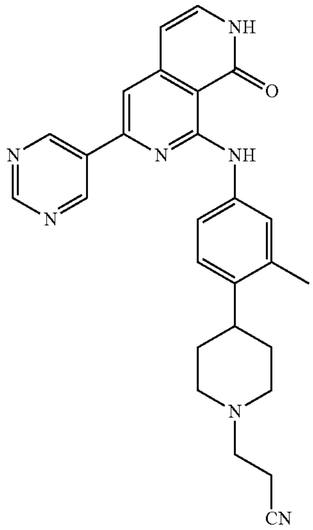 [SMILES: Cc1cc(Nc2nc(-c3cncnc3)cc3cc[nH]c(=O)c23)ccc1C1CCN(CCC#N)CC1] | ESI-MS m/z 466.2 ($MH^+$). |
| 1118 | 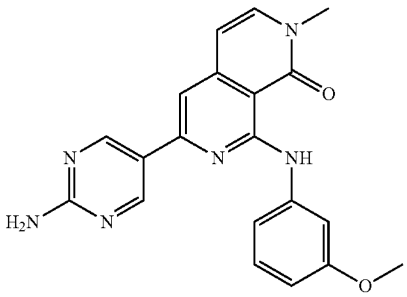 [SMILES: COc1cccc(Nc2nc(-c3cnc(N)nc3)cc3ccn(C)c(=O)c23)c1] | $^1$H NMR (DMSO-$d_6$) δ 3.53 (s, 3H), 3.81 (s, 3H), 6.53 (d, J = 7.2 Hz, 1H), 6.61 (dd, J = 1.6, 8.0 Hz, 1H), 7.14 (s, 2H), 7.15 (s, 1H), 7.27 (t, J = 8.0 Hz, 1H), 7.37 (s, 1H), 7.70 (d, J = 7.2 Hz, 1H), 7.84 (t, J = 2.0 Hz, 1H), 8.99 (s, 2H), 12.12 (s, 1H); ESI-MS m/z 375.2 ($MH^+$). |

TABLE 1-continued
| No | Structure | Physical Data $^1$H NMR 400 MHz (DMSO-$d_6$) and/or MS (m/z) |
|---|---|---|
| 1119 | 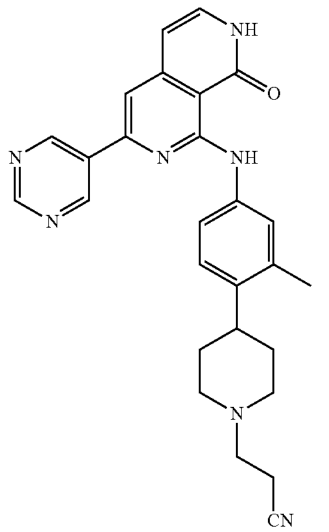 [SMILES: Cc1cc(Nc2nc(-c3cncnc3)cc3cc[nH]c(=O)c23)ccc1C1CCN(CCC#N)CC1] | ESI-MS m/z 448.2 (MH$^+$). |
| 1120 | 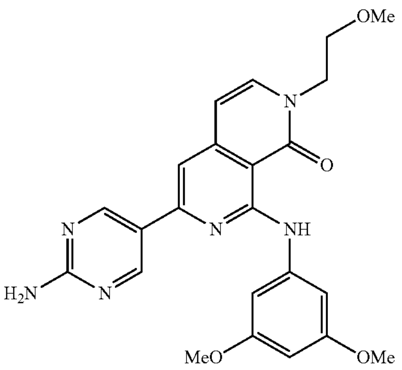 [SMILES: COCCn1ccc2cc(-c3cnc(N)nc3)nc(Nc3cc(OC)cc(OC)c3)c2c1=O] | ESI-MS m/z 449.2 (MH$^+$). |
| 1121 | 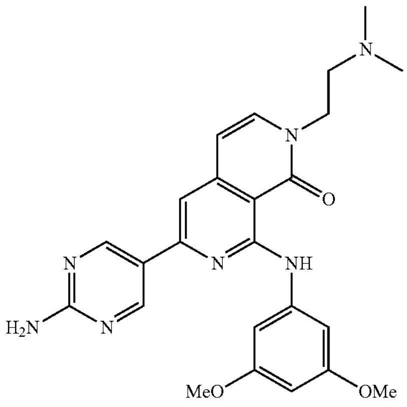 [SMILES: COc1cc(Nc2nc(-c3cnc(N)nc3)cc3ccn(CCN(C)C)c(=O)c23)cc(OC)c1] | ESI-MS m/z 462.2 (MH$^+$). |

TABLE 1-continued
| No | Structure | Physical Data $^1H$ NMR 400 MHz (DMSO-$d_6$) and/or MS (m/z) |
|---|---|---|
| 1122 | 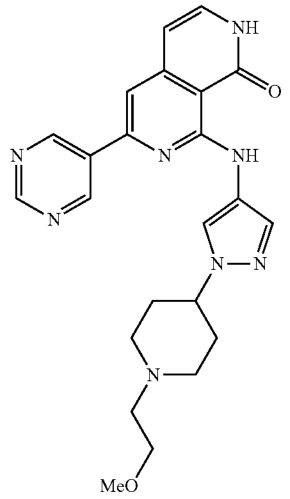 [SMILES: COCCN1CCC(n2cc(Nc3nc(-c4cncnc4)cc4cc[nH]c(=O)c34)cn2)CC1] | ESI-MS m/z 447.2 (MH+). |
| 1123 | 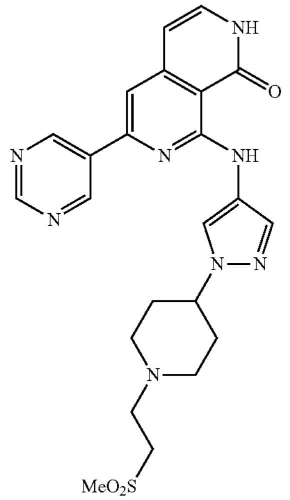 [SMILES: CS(=O)(=O)CCN1CCC(n2cc(Nc3nc(-c4cncnc4)cc4cc[nH]c(=O)c34)cn2)CC1] | ESI-MS m/z 494.2 (MH+). |
| 1124 | 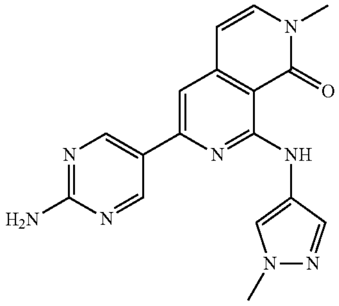 [SMILES: Cn1cc(Nc2nc(-c3cnc(N)nc3)cc3ccn(C)c(=O)c23)cn1] | ESI-MS m/z 349.2 (MH+). |

TABLE 1-continued
| No | Structure | Physical Data $^1H$ NMR 400 MHz (DMSO-$d_6$) and/or MS (m/z) |
|---|---|---|
| 1125 | 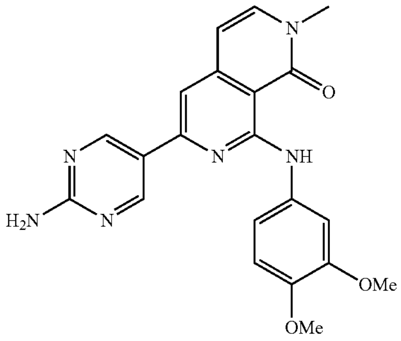 [SMILES: COc1ccc(Nc2nc(-c3cnc(N)nc3)cc3ccn(C)c(=O)c23)cc1OC] | ESI-MS m/z 405.2 (MH$^+$). |
| 1126 | 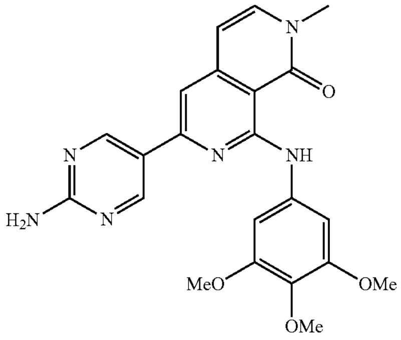 [SMILES: COc1cc(Nc2nc(-c3cnc(N)nc3)cc3ccn(C)c(=O)c23)cc(OC)c1OC] | ESI-MS m/z 435.2 (MH$^+$). |
| 1127 | 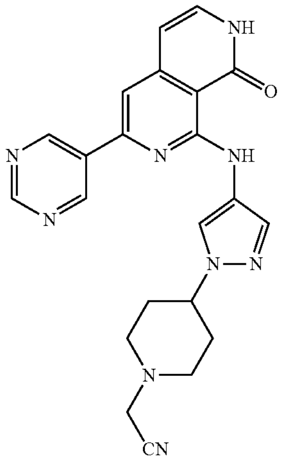 [SMILES: N#CCN1CCC(n2cc(Nc3nc(-c4cncnc4)cc4cc[nH]c(=O)c34)cn2)CC1] | ESI-MS m/z 428.2 (MH$^+$). |

TABLE 1-continued
| No | Structure | Physical Data $^1$H NMR 400 MHz (DMSO-$d_6$) and/or MS (m/z) |
|---|---|---|
| 1128 | 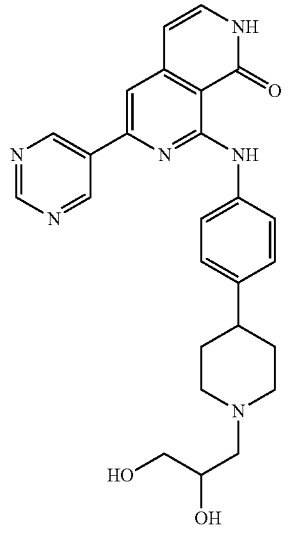 [SMILES: O=c1[nH]ccc2cc(-c3cncnc3)nc(Nc3ccc(C4CCN(CC(O)CO)CC4)cc3)c12] | ESI-MS m/z 473.2 (MH$^+$). |
| 1129 | 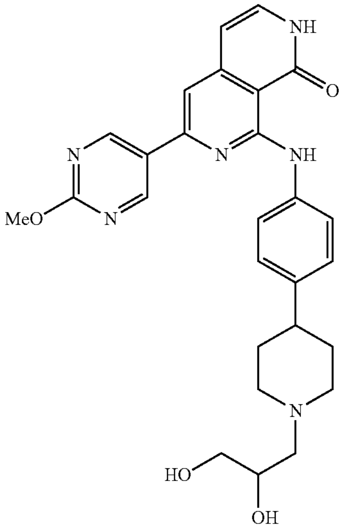 [SMILES: COc1ncc(-c2cc3cc[nH]c(=O)c3c(Nc3ccc(C4CCN(CC(O)CO)CC4)cc3)n2)cn1] | ESI-MS m/z 503.2 (MH$^+$). |
| 1130 | 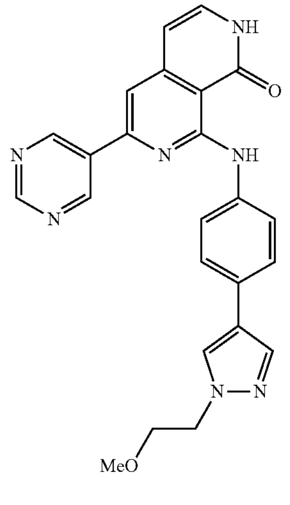 [SMILES: COCCn1cc(-c2ccc(Nc3nc(-c4cncnc4)cc4cc[nH]c(=O)c34)cc2)cn1] | ESI-MS m/z 440.2 (MH$^+$). |

TABLE 1-continued
| No | Structure | Physical Data $^1H$ NMR 400 MHz (DMSO-$d_6$) and/or MS (m/z) |
| --- | --- | --- |
| 1131 | 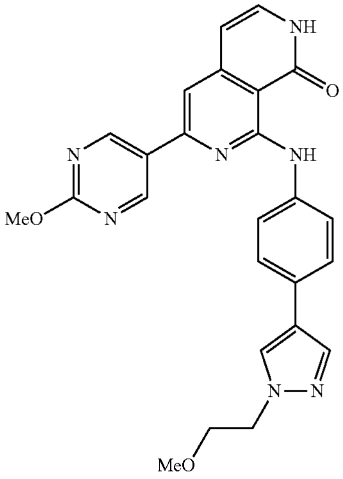 | ESI-MS m/z 470.2 (MH$^+$). |
| 1132 | 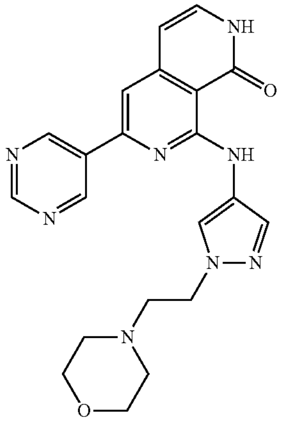 [SMILES: O=c1[nH]ccc2cc(-c3cncnc3)nc(Nc3cnn(CCN4CCOCC4)c3)c12] | ESI-MS m/z 419.2 (MH$^+$). |
| 1133 | 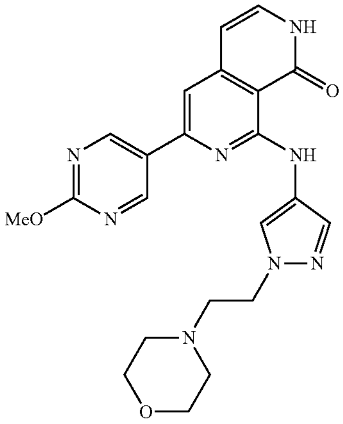 [SMILES: COc1ncc(-c2cc3cc[nH]c(=O)c3c(Nc3cnn(CCN4CCOCC4)c3)n2)cn1] | ESI-MS m/z 449.2 (MH$^+$). |

TABLE 1-continued
| No | Structure | Physical Data $^1H$ NMR 400 MHz ($DMSO-d_6$) and/or MS (m/z) |
|---|---|---|
| 1134 | 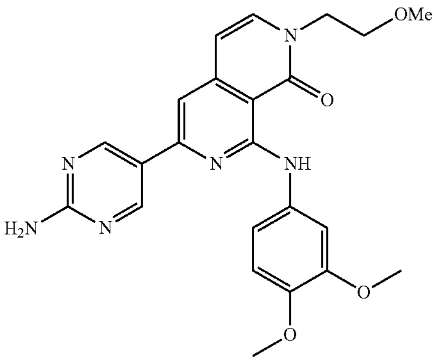 [SMILES: COCCn1ccc2cc(-c3cnc(N)nc3)nc(Nc3ccc(OC)c(OC)c3)c2c1=O] | ESI-MS m/z 449.2 ($MH^+$). |
| 1135 | 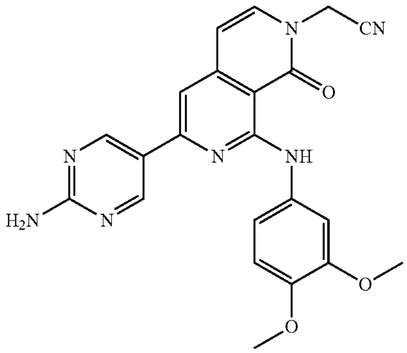 [SMILES: COc1ccc(Nc2nc(-c3cnc(N)nc3)cc3ccn(CC#N)c(=O)c23)cc1OC] | ESI-MS m/z 430.2 ($MH^+$). |
| 1136 | 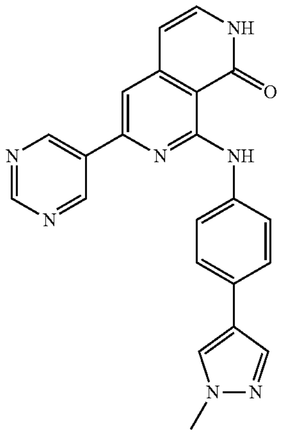 [SMILES: Cn1cc(-c2ccc(Nc3nc(-c4cncnc4)cc4cc[nH]c(=O)c34)cc2)cn1] | ESI-MS m/z 396.2 ($MH^+$). |

TABLE 1-continued

| No | Structure | Physical Data $^{1}H$ NMR 400 MHz ($DMSO-d_6$) and/or MS (m/z) |
|---|---|---|
| 1137 | 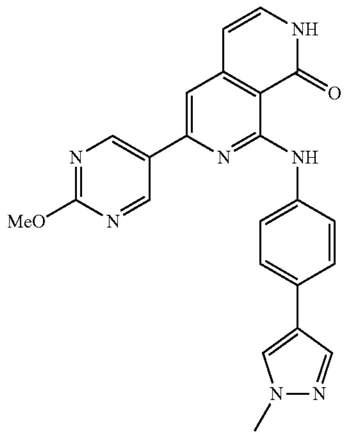 [SMILES: COc1ncc(-c2cc3cc[nH]c(=O)c3c(Nc3ccc(-c4cnn(C)c4)cc3)n2)cn1] | ESI-MS m/z 426.2 ($MH^+$). |
| 1138 | 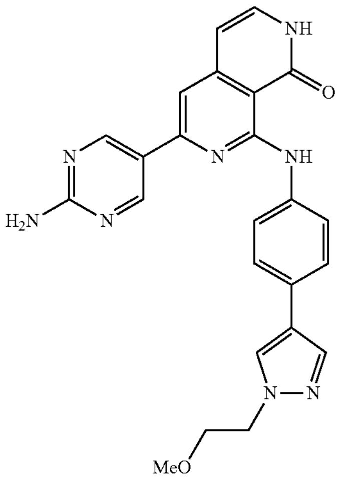 [SMILES: COCCn1cc(-c2ccc(Nc3nc(-c4cnc(N)nc4)cc4cc[nH]c(=O)c34)cc2)cn1] | ESI-MS m/z 455.2 ($MH^+$). |
| 1139 | 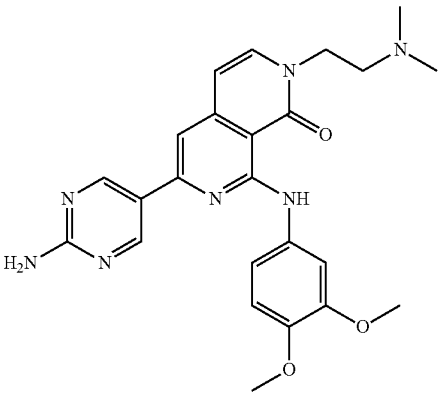 [SMILES: COc1ccc(Nc2nc(-c3cnc(N)nc3)cc3ccn(CCN(C)C)c(=O)c23)cc1OC] | ESI-MS m/z 462.2 ($MH^+$). |

Assays

Compounds of the present invention are assayed to measure their capacity to inhibit a kinase panel, including but not limited to Syk, ZAP70, KDR, FMS, FLT3, c-Kit, RET, TrkA, TrkB, TrkC, IGR-1R, Alk and c-FMS kinases.

Inhibition of Cellular Syk, Zap70 and KDR Dependent Proliferation

Compounds of the present invention are assayed to measure their capacity to selectively inhibit cell proliferation of Ba/F3 cells expressing activated Syk, Zap70 and KDR through fusion to the dimerization domain of Tel (ETV6) transcription factor compared with parental BaF3 cells. Luciferase expressing Ba/F3 murine pro-B cells are transformed with Tel-Syk, Tel-Zap70 or Tel-KDR. Cells are maintained in RPMI/10% fetal calf serum (RPMI/FCS) supplemented with penicillin 50 μg/mL, streptomycin 50 μg/mL and L-glutamine 200 mM. Untransformed Ba/F3 cells are similarly maintained with the addition of murine recombinant IL3. Cells are dispensed into 384-well format plate at 5000 cell/well in 50 μL of culture medium. Compounds of the invention are dissolved and diluted in dimethylsufoxide (DMSO). Twelve points 1:3 serial dilutions are made into DMSO to create concentrations gradient ranging from 10 mM to 0.05 μM. Cells are added with 50 nL of diluted compounds and incubated for 48 hours in cell culture incubator. Luminiscent signal is measured following the addition of Bright Glo® (Promega) luciferase substrate. $IC_{50}$ values are calculated by linear regression analysis of the percentage inhibition of each compound at 12 concentrations.

Inhibition of Enzymatic Syk and Zap70 Kinase Activity

Purified recombinant hSyk (full length) and Zap70 (kinase domain) diluted in assay buffer are dispensed in 384 well proxi-plates. Compounds of the invention are dissolved and diluted in dimethylsufoxide (DMSO). Twelve points 1:3 serial dilutions are made into DMSO to create concentrations gradient ranging from 10 mM to 0.05 μM. 50 mL of diluted compounds are added to the enzyme solutions and incubated for 30 mM at room temperature, after which ATP and biotynilated peptide substrate are added. Substrate phosphorylation is a function of the HTRF signal measured following the addition of Cisbio-HTRF reagents. $IC_{50}$ values are calculated by linear regression analysis of the percentage inhibition of each compound at 12 concentrations Inhibition of Cellular TrkA, TrkB or TrkC Dependent Proliferation The cell line used is the Ba/F3 murine hematopoietic progenitor cell line transformed with human Tel-TrkA, Tel-TrkB or Tel-TrkC cDNAs (Ba/F3 EN AB/C). These cells are maintained in RPMI/10% fetal bovine serum (RPMI/F B S) supplemented with penicillin 50 mg/mL, streptomycin 50 mg/mL and L-glutamine 200 mM. Untransformed Ba/F3 cells are similarly maintained with the addition 5 ng/ml of murine recombinant IL3.

50 μl of a Ba/F3 or Ba/F3 EN A/B/C cell suspension are plated in Greiner 384 well microplates (white) at a density of 2000 cells per well. 50 nl of serially diluted test compound (1 0-0.0001 mM in DMSO solution) is added to each well. The cells are incubated for 48 hours at 37° C., 5% CO2. 25 μl of Bright glow is added to each well. The emitted luminiscence is quantified using the ACQUEST™ luminescence system (Molecular Devices).

Effect on Proliferation of Various Kinases Dependent Cells

Compounds of the invention are tested for their antiproliferative effect on Ba/F3 cells expressing either Tel-TrkA, Tel-TrkB or Tel-TrkC and an additional panel of 34 selected diverse kinases activated by fusion to the dimerizing partners Bcr or Tel (Abl, AlK, BMX, EphA3, EphB2, FGFR2, FGFR3, FGFR4, FGR, FLT1, FLT3, FLT4, FMS, IGF1R, InsR, JAK1, JAK2, JAK3, KDR, Kit, Lck, Lyn, MER, MET, PDGFRb, RET, RON, Ros-1, Src, Syk, TIE2, TYK2, Tie1, ZAP70). The antiproliferative effect of these compounds on the different cell lines and on the non transformed cells were tested at 12 different concentrations of 3-fold serially diluted compounds in 384 well plates as described above (in media lacking IL3). The IC50 values of the compounds the different cell lines were determined from the dose response curves obtained as describe above.

FLT-3 (Enzymatic Assay)

Kinase activity assay with purified FLT-3 (Upstate) is carried out in a final volume of 10 μL containing 0.25 μg/mL of enzyme in kinase buffer (30 mM Tris-HCl pH7.5, 15 mM $MgCl_2$, 4.5 mM $MnCl_2$, 15 μM $Na_3VO_4$ and 50 μg/mL BSA), and substrates (5 μg/mL biotin-poly-EY(Glu, Tyr) (CIS-US, Inc.) and 3 μM ATP). Two solutions are made: the first solution of 5 μl contains the FLT-3 enzyme in kinase buffer was first dispensed into 384-well format ProxiPlate® (Perkin-Elmer) followed by adding 50 nL of compounds dissolved in DMSO, then 5 μl of second solution contains the substrate (poly-EY) and ATP in kinase buffer was added to each wells. The reactions are incubated at room temperature for one hour, stopped by adding 10 μL of HTRF detection mixture, which contains 30 mM Tris-HCl pH 7.5, 0.5 M KF, 50 mM ETDA, 0.2 mg/mL BSA, 15 μg/mL streptavidin-XL665 (CIS-US, Inc.) and 150 ng/mL cryptate conjugated anti-phosphotyrosine antibody (CIS-US, Inc.). After one hour of room temperature incubation to allow for streptavidin-biotin interaction, time resolved florescent signals are read on Analyst GT (Molecular Devices Corp.). $IC_{50}$ values are calculated by linear regression analysis of the percentage inhibition of each compound at 12 concentrations (1:3 dilution from 50 μM to 0.28 nM). In this assay, compounds of the invention have an $IC_{50}$ in the range of 10 nM to 2 μM.

FLT-3 (Cellular Assay)

Compounds of the invention are tested for their ability to inhibit transformed Ba/F3-FLT3-ITD cell proliferation, which is depended on FLT-3 cellular kinase activity. Ba/F3-FLT3-ITD are cultured up to 800,000 cells/mL in suspension, with RPMI 1640 supplemented with 10% fetal bovine serum as the culture medium. Cells are dispensed into 384-well format plate at 5000 cell/well in 50 μL culture medium. Compounds of the invention are dissolved and diluted in dimethylsulfoxide (DMSO). Twelve points 1:3 serial dilutions are made into DMSO to create concentrations gradient ranging typically from 10 mM to 0.05 μM. Cells are added with 50 nL of diluted compounds and incubated for 48 hours in cell culture incubator. AlamarBlue® (TREK Diagnostic Systems), which can be used to monitor the reducing environment created by proliferating cells, are added to cells at final concentration of 10%. After additional four hours of incubation in a 37° C. cell culture incubator, fluorescence signals from reduced AlamarBlue® (Excitation at 530 nm, Emission at 580 nm) are quantified on Analyst GT (Molecular Devices Corp.). $IC_{50}$ values are calculated by linear regression analysis of the percentage inhibition of each compound at 12 concentrations c-Kit—Proliferation Assay Compounds were tested for their ability to inhibit the proliferation of wt Ba/F3 cells and Ba/F3 cells transformed with Tel c-Kit fused tyrosine kinases. Untransformed Ba/F3 cells are maintained in media containing recombinant IL3. Cells are plated into 384 well TC plates at 5,000 cells in 50 ul media per well and test compound at 0.06 nM to 10 μM is added. The cells are then incubated for 48 hours at 37° C., 5% $CO_2$. After incubating the cells, 25 μL of BRIGHT GLO® (Promega) is added to each well following manufacturer's instructions and the plates are read using Analyst GT—Luminescence mode—50000 integration time in RLU. IC50 values, the concentration of compound required for 50% inhibition, are determined from a dose response curve.

cKit—Mo7e Assay

The compounds described herein are tested for inhibition of SCF dependent proliferation using Mo7e cells which endogenously express c-kit in a 96 well format. Briefly, two-fold serially diluted test compounds (Cmax=10 μM) are evaluated for their antiproliferative activity of Mo7e cells stimulated with human recombinant SCF. After 48 hours of incubation at 37° C., cell viability is measured by using a MTT colorimetric assay from Promega.

Upstate KinaseProfiler™—Radio-Enzymatic Filter Binding Assay

Certain compounds of the invention are assessed for their ability to inhibit individual members of a panel of kinases (a partial, non-limiting list of kinases includes: Syk, ZAP70, KDR, FMS, FLT3, c-Kit, RET, TrkA, TrkB, TrkC, IGR-1R, Alk and c-FMS kinases). The compounds are tested in duplicates at a final concentration of 10 μM following this generic protocol. Note that the kinase buffer composition and the substrates vary for the different kinases included in the "Upstate KinaseProfile™" panel. Kinase buffer (2.5 μL, 10×-containing $MnCl_2$ when required), active kinase (0.001-0.01 Units; 2.5 μL), specific or Poly(Glu-4-Tyr) peptide (5-500 μM or 0.01 mg/ml) in kinase buffer and kinase buffer (50 μM; 5 μL) are mixed in an eppendorf on ice. A Mg/ATP mix (10 μL; 67.5 (or 33.75) mM $MgCl_2$, 450 (or 225) μM ATP and 1 μCi/μl [γ-$^{32}$P]-ATP (3000 Ci/mmol)) is added and the reaction is incubated at about 30° C. for about 10 minutes. The reaction mixture is spotted (20 μL) onto a 2 cm×2 cm P81 (phosphocellulose, for positively charged peptide substrates) or Whatman No. 1 (for Poly (Glu4-Tyr) peptide substrate) paper square. The assay squares are washed 4 times, for 5 minutes each, with 0.75% phosphoric acid and washed once with acetone for 5 minutes. The assay squares are transferred to a scintillation vial, 5 ml scintillation cocktail are added and $^{32}$P incorporation (cpm) to the peptide substrate is quantified with a Beckman scintillation counter. Percentage inhibition is calculated for each reaction.

In addition, compounds of Formula (I) were assessed for their ability to inhibit individual kinases utilizing Caliper Life Sciences' proprietary LabChip™ technology. A partial, non-limiting list of kinases includes: Syk, ZAP70, KDR, FMS, FLT3, c-Kit, RET, TrkA, TrkB, TrkC, IGR-1R, Alk and c-FMS kinases. The off-chip incubation mobility-shift kinase assay uses a microfluidic chip to measure the conversion of a fluorescent peptide substrate to a phosphorylated product. The reaction mixture, from a microtiter plate well, is introduced through a capillary sipper onto the chip, where the nonphosphorylated substrate and phosphorylated product are separated by electrophoresis and detected via laser induced fluorescence. The signature of the fluorescence signal over time reveals the extent of the reaction. The phosphorylated product migrates through the chip faster than the non-phosphorylated substrate, and signals from the two forms of the peptide appear as distinct peaks. Caliper's data analysis software (HTSWA) determines peak heights, from which the ratio of product to the peak sum P/(P+S) and percent (%) conversion is calculated. This value is used to compare compound wells to control wells present on the plate, and thereby determine the % inhibition values for the compound. The formula used to calculate % inhibition is as follows, where $C_{100\%}$ is the average % conversion of the 100% activity wells and $C_{0\%}$ is the average % conversion of the 0% activity wells: $(1-(\%\ \text{conversionofsample}-C_{0\%})/(C_{100\%}-C_{0\%}))*100$.

Compounds (10 mM stocks in 100% DMSO) are diluted to a final concentration of 5 μM for single point inhibition experiments, and a series dilution of 10, 3, 1, 0.3, 0.1, 0.03, 0.01, 0.003, 0.001, 0.0003, 0.0001, 0.00003 μM were made for $IC_{50}$ determination. Generally, 12 μL of enzyme buffer containing purified kinase (various amount; various suppliers), 100 mM HEPES, pH 7.5, 1 mM DTT (Calbiochem, 2333153), 10 mM $MgCl_2$ (Sigma, M-1028) or 10 mM $MnCl_2$ (Sigma, M-1787) (assay specific), and 0.002% Brij-35 (Sigma, B4184) are added to each well. Compound and enzyme are allowed to pre-incubate for 15 minutes. 12 μL of peptide/ATP buffer containing 100 mM HEPES, pH 7.5, 1.5 μM fluorescein-labeled peptide (specific to kinase of interest), ATP (at $K_M$ apparent, Sigma, A9187), and 0.002% Brij-35 is then added to each well to initiate the reaction. The final concentration of DMSO in the well is 4%. Generally, reactions are incubated for 1 to 1.5 hours at room temperature to obtain adequate conversion of peptide to phosphorylated product in the linear range of the reaction. Reactions are terminated with the addition of 45 μL of Stop Buffer (containing 20 mM EDTA). Plates are then read on the LabChip 3000 using a 12-sipper LabChip. % conversion values and % inhibition values are obtained as described and $IC_{50}$ curves of compounds are generated using GraphPad Prism Version 4 or 5.01, or XLfit Version 4.3.2. When using GraphPad Prism, a nonlinear curve fit using the sigmoidal dose response—variable slope fit was used to graph $IC_{50}$ curves and determine $IC_{50}$ values and hillslopes. When using XLfit, Fit Model 205 (4-Parameter Logistic Model) is used to generate and fit the $IC_{50}$ curve.

In certain embodiments, compounds of Formula (I) in free form or in pharmaceutically acceptable salt form, exhibit valuable pharmacological properties, for example, as indicated by the in vitro tests described in this application. The $IC_{50}$ value in those experiments is given as that concentration of the test compound in question that results in a cell count that is 50% lower than that obtained using the control without inhibitor. In general, compounds of the invention have $IC_{50}$ values from 1 nM to 10 μM. In some examples, compounds of the invention have $IC_{50}$ values from 0.01 μM to 5 μM. In other examples, compounds of the invention have $IC_{50}$ values from 0.01 μM to 1 μM, or more particularly from 1 nM to 1 μM. In yet other examples, compounds of the invention have $IC_{50}$ values of less than 1 nM or more than 10 μM. In certain embodiments, compounds of Formula (I) exhibit a percentage inhibition of greater than 50%, or in other embodiments compounds of Formula (I) exhibit a percentage inhibition greater than about 70%, against one or more of the following kinases at 10 μM: Syk, ZAP70, KDR, FMS, FLT3, c-Kit, RET, TrkA, TrkB, TrkC, IGR-1R, Alk and c-FMS kinases.

Ceratin Assay Results

By way of example only, the compound 8-(4-morpholinophenylamino)-6-phenyl-2,7-naphthyridin-1(2H)-one (see table 1, compound 11) has an $IC_{50}$ of 0.06 μM and 50 μM in Syk and Zap70 enzymatic assay respectively. In addition, 8-(4-morpholinophenylamino)-6-phenyl-2,7-naphthyridin-1(2H)-one has an $IC_{50}$ of 0.15 μM, 0.27 μM, 0.02 μM, 0.02 μM, 0.07 μM and in $BaF_3$/Tel-Syk, $BaF_3$/Tel-KDR, $BaF_3$/Tel-FMS, $BaF_3$/Tel-KIT and $BaF_3$/Tel-TRKA cellular assays, respectively. At a concentration of 5 μM, 8-(4-morpholinophenylamino)-6-phenyl-2,7-naphthyridin-1(2H)-one inhibits the following kinases by the percentage shown in brackets (for example, 100% means complete inhibition, 0% means no inhibition): Abl (100%), CHK2 (94%), FLT3 (100%), FMS (84%), JAK2 (96%), KDR (96%), RET (99%), TRKA (74%).

By way of example only, the compound 8-(4-morpholinophenylamino)-6-(4-ethylpiperazin-1-yl)-2,7-naphthyridin-1(2H)-one (see table 1, compound 83) has an $IC_{50}$ of 0.01 μM and 3.54 μM in Syk and Zap70 enzymatic assays, respectively. In addition, 8-(4-morpholinophenylamino)-6-(4-ethylpiperazin-1-yl)-2,7-naphthyridin-1(2H)-one has an $IC_{50}$ of 0.12 μM, 5.0 μM, 0.50 μM, 1.22 μM, 0.49 μM and 0.53 μM in $BaF_3$/Tel-Syk, $BaF_3$/Tel-KDR, $BaF_3$/Tel-FMS, $BaF_3$/Tel-KIT, $BaF_3$/Tel-TRKA and $BaF_3$/Tel-FLT3 cellular assays, respectively.

By way of example only, the $IC_{50}$ for Syk inhibition by other compounds of Formula (I) are listed in Table 2 below. The compound No. corresponds to the compounds listed in Table 1.

TABLE 2

| Compound No. | Syk HTRF |
|---|---|
| 11 | 0.058 |
| 17 | 0.001 |
| 83 | 0.009 |
| 102 | 0.475 |
| 655 | 0.324 |
| 83 | 0.003 |
| 100 | 0.398 |
| 117 | 0.277 |
| 120 | 0.421 |
| 130 | 0.044 |
| 151 | 0.078 |
| 164 | 0.002 |
| 167 | 0.109 |
| 183 | 0.024 |
| 190 | 0.008 |
| 276 | 0.237 |
| 304 | 0.008 |
| 443 | 0.115 |
| 1124 | 0.048 |
| 580 | 0.22 |
| 589 | 0.079 |
| 610 | 0.292 |
| 643 | 0.031 |
| 637 | 0.046 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula (Ia), or a pharmaceutically acceptable salt, thereof:

(Ia)

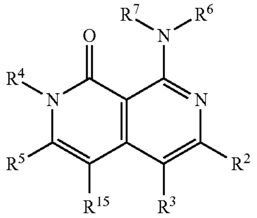

wherein:

$R^2$ and $R^3$ are independently selected from H, $(CH_2)_nR^{11}$, —$C(O)R^{12}$, —$CR^{12}$═$NOCR^{12}$, —$NR^8R^{10}$, halogen, $R^{20}$, $C_2$-$C_6$alkenyl, $C_2$-$C_6$alkynyl, $C_1$-$C_6$alkoxy, $C_1$-$C_6$alkylthio, hydroxyl-$C_1$-$C_6$alkyl, halo-substituted-$C_1$-$C_6$alkyl, halo-substituted-$C_1$-$C_6$alkoxy, $C_6$-$C_{14}$aryl, $C_3$-$C_{13}$heteroaryl and $C_2$-$C_{14}$heterocycloalkyl, wherein the $C_6$-$C_{14}$aryl, $C_2$-$C_6$alkenyl, $C_2$-$C_6$alkynyl, $C_3$-$C_{13}$heteroaryl, and $C_2$-$C_{14}$heterocycloalkyl of $R^2$ and $R^3$ are optionally substituted with 1 to 3 substituents independently selected from halogen, —CN, —$NO_2$, —$OR^{12}$, —$OR^{10}$, ═O, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$NR^{12}C(O)N(R^{12})_2$, —$NHS(O)_2R^{13}$—$SR^8$, —$C(O)N(R^{12}R^{10})$, —$N(R^{12})C(O)R^{13}$, —$C(O)N(R^{11})_2$, —$C(O)N(R^{12})_2$, —$(CR^{12}$—$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl and halo-substituted $C_1$-$C_6$alkoxy;

$R^4$ is H, $C_1$-$C_6$alkyl or —$(CR^{12}R^{12})_nR^{11}$;

$R^5$ is H or $C_1$-$C_6$alkyl;

$R^6$ is $C_6$-$C_{14}$aryl, $C_3$-$C_{13}$heteroaryl, $C_2$-$C_{14}$heterocycloalkyl, $C_1$-$C_6$alkyl, $C_3$-$C_8$cycloalkyl, halo-substituted $C_1$-$C_6$alkyl, —$(CH_2)_nR^9$, $R^{20}$, -$L^3R^9$ or —$Y^1$-$L^1$-$R^{14}$, wherein, $Y^1$ is arylene, heteroarylene or heterocycloalkylene, and $L^1$- is a bond, —O—, —C(O)—, —$C(O)N(R^{11})$—, —$(C(R^{12})_2)_n$— or —$O(CH_2)_n$—;

$L^3$ is a bond, $C_1$-$C_6$alkyl or $C_1$-$C_6$alkoxy; wherein the $C_1$-$C_6$alkyl and $C_1$-$C_6$alkoxy groups of $L^3$ are optionally substituted with 1 to 3 substituents independently selected from halogen, —CN, —$C_1$-$C_6$alkyl, $C_1$-$C_6$alkoxy, —$OR^{13}$, —$C(O)R^{13}$, —$OC(O)R^{13}$, —$C(O)OR^{13}$, —$N(R^{12})_2$, —$C(O)_n(R^{12})_2$, —$N(R^{12})C(O)R^{13}$, $C_2$-$C_{14}$heterocycloalkyl, —$S(O)_2R^{13}$, —$S(O)_2N(R^{12})_2$, $R^{13}$, —$(C(R^{12})_2)_nR^{13}$, —$(C(R^{12})_2)_nR^{14}$, halo-substituted $C_1$-$C_6$alkyl and halo-substituted $C_1$-$C_6$alkoxy;

and wherein the $C_6$-$C_{14}$aryl, $C_3$-$C_{13}$heteroaryl, $C_1$-$C_6$alkyl, halo-substituted $C_1$-$C_6$alkyl, $C_2$-$C_{14}$heterocycloalkyl and $C_3$-$C_8$cycloalkyl of $R^6$ and $Y^1$ are optionally substituted with 1 to 3 substituents independently selected from, halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_2R^{11}$, $(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

$R^7$ is H or $C_1$-$C_6$ alkyl;

$R^8$ is H or $C_1$-$C_6$ alkyl;

$R^9$ is $R^{20}$, $C_6$-$C_{14}$aryl, $C_3$-$C_{13}$heteroaryl, $C_2$-$C_{14}$heterocycloalkyl, $C_3$-$C_8$cycloalkyl or $Y^2$-$L^2$-$R^{14}$, wherein, $Y^2$ is bond, arylene, heteroarylene or heterocycloalkylene, and $L^2$- is a bond, —O—, or —$O(CH_2)_n$—;

and wherein the $C_6$-$C_{14}$aryl, $C_3$-$C_{13}$heteroaryl, $C_3$-$C_8$cycloalkyl and $C_2$-$C_{14}$heterocycloalkyl of $R^9$ and $Y^2$ are optionally substituted with 1 to 3 substituents independently selected from halogen, —CN, ═O, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, ¯$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

$R^{10}$ is halo-substituted $C_1$-$C_6$alkyl, $C_6$-$C_{14}$aryl, $C_3$-$C_{13}$heteroaryl, $C_2$-$C_{14}$heterocycloalkyl, $C_3$-$C_8$cycloalkyl or —$(CH_2)_nR^{11}$, wherein the $C_6$-$C_{14}$aryl, $C_3$-$C_{13}$heteroaryl, $C_2$-$C_{14}$heterocycloalkyl and $C_3$-$C_8$cycloalkyl of $R^{10}$ are optionally substituted with 1 to 3 substituents independently selected from halogen, —CN, hydroxl, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, —$OR^{13}$, —$C(O)R^{13}$, $^-OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

$R^{11}$ is —$N(R^{12})_2$, —$OR^{13}$, $R^{20}$, —$C(O)N(R^{12})_2$, —$S(O)_2R^{13}$, —$S(O)_2N(R^{12})_2$, $C_6$-$C_{14}$aryl, $C_3$-$C_{13}$heteroaryl, $C_3$-$C_8$cycloalkyl, or $C_2$-$C_{14}$heterocycloalkyl, wherein the $C_6$-$C_{14}$aryl, $C_3$-$C_{13}$heteroaryl, $C_3$-$C_8$cycloalkyl and $C_2$-$C_{14}$heterocycloalkyl of $R^{11}$ are optionally substituted with 1 to 3 substituents independently selected from halogen, —CN, —$OR^{12}$, —$OR^{10}$, —$C(O)R^{12}$, —$OC(O)R^{12}$, —$C(O)OR^{12}$, —$N(R^{12})_2$, —$N(R^{12}R^{10})$, —$SR^8$, —$NR^{12}C(O)N(R^{12})_2$, —$C(O)N(R^{12}R^{10})$, —$N(R^{12})C(O)R^{13}$, —$C(O)N(R^{12})_2$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{12})_2$, $R^{12}$, $R^{10}$, —$OR^{13}$, —$C(O)R^{13}$, $^-OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

each $R^{12}$ is independently selected from H, $C_1$-$C_6$alkyl, $C_2$-$C_6$alkene, halo-substituted $C_1$-$C_6$alkyl and $C_3$-$C_8$cycloalkyl, or each $R^{12}$ is independently a $C_1$-$C_6$alkyl that together with N they are attached to form a heterocycloalkyl;

$R^{13}$ is H, $C_1$-$C_6$ alkyl, $C_3$-$C_8$cycloalkyl, halo-substituted $C_1$-$C_6$ alkyl or $C_2$-$C_{14}$heterocycloalkyl;

$R^{14}$ is H, halogen, $OR^{13}$, $R^{20}$, —CN, —$S(O)_2N(R^{12})_2$, —$S(O)_2R^{13}$, —$C(O)N(R^{12})_2$, $N(R^{12})_2$, $C_1$-$C_6$alkyl, halo-substituted $C_1$-$C_6$alkyl, $C_6$-$C_{14}$aryl, heteroaryl or $C_2$-$C_{14}$heterocycloalkyl, wherein the $C_2$-$C_{14}$heterocycloalkyl, $C_6$-$C_{14}$aryl and $C_3$-$C_{13}$heteroaryl are optionally substituted with 1-3 substituents independently selected from halogen, —CN, $C_1$-$C_6$alkyl, $C_1$-$C_6$alkoxy, $C_3$-$C_8$cycloalkyl, —$OR^{13}$, —$C(O)R^{13}$, $^-OC(O)R^{13}$, —$C(O)OR^{13}$, —$N(R^{12})_2$, —$C(O)(C(R^{12})_2)_nR^{16}$, —$C(O)N(R^{12})_2$, heterocycloalkyl, —$S(O)_2R^{13}$, —$S(O)_2N(R^{12})_2$, —$NHS(O)_2R^{13}$, $R^{13}$, $R^{10}$, —$(CH_2)_nR^{12}$, —$(CH_2)_nR^{13}$, —$O(CH_2)_nR^{13}$, —$(C(R^{12})_2)_nR^{16}$, halo-substituted $C_1$-$C_6$alkyl and halo-substituted $C_1$-$C_6$alkoxy;

$R^{15}$ is H, $C_1$-$C_6$alkyl, $C_2$-$C_6$alkenyl, —CN, halogen, $R^{10}$, $R^{16}$ is H, halogen, $OR^{13}$, —$C(O)R^{13}$, —$OC(O)R^{13}$, —$C(O)OR^{13}$, —$N(R^{12})_2$, —CN, —$S(O)_2N(R^{12})_2$, —$S(O)_2R^{13}$, $C(O)N(R^{12})_2$, —$NR^{12}C(O)(R^{12})$, halo-substituted $C_1$-$C_6$alkyl, or $C_2$-$C_{14}$heterocycloalkyl;

$R^{20}$ is

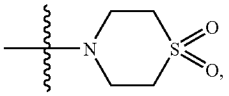
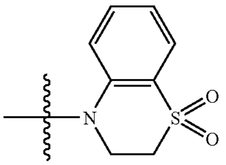
or
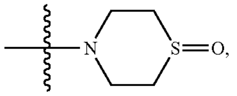

and each n is independently 1, 2, 3, 4, 5 or 6.

2. The compound of claim 1, wherein $R^2$ is H, halogen, $R^{20}$,

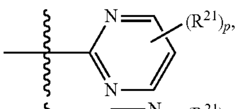
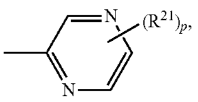
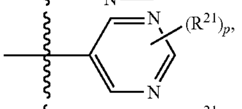
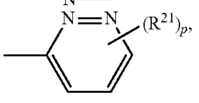
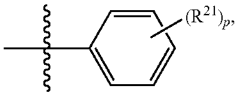
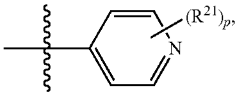
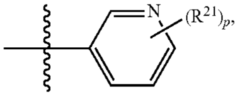
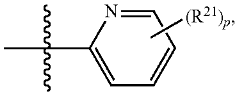
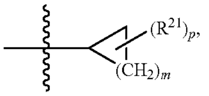
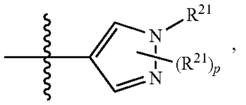
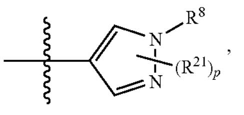
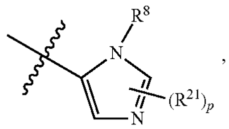
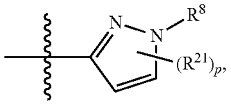
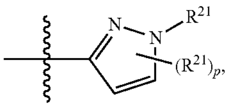
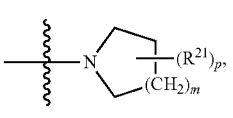
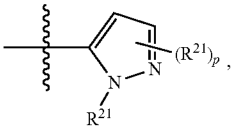
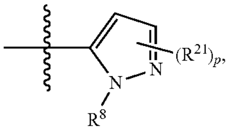
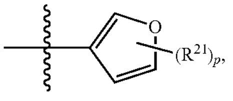
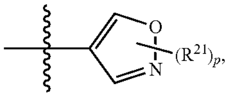
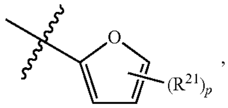
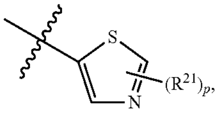
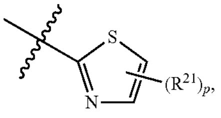

-continued

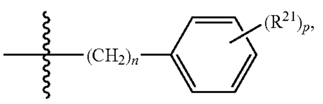
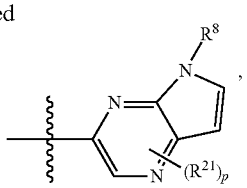
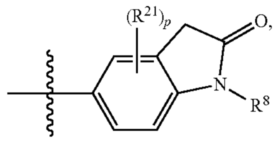
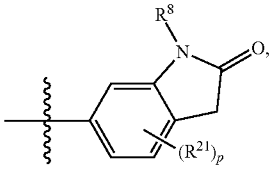
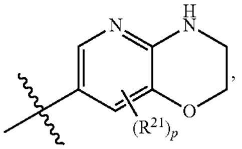
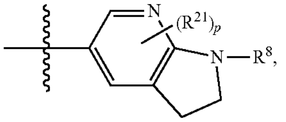
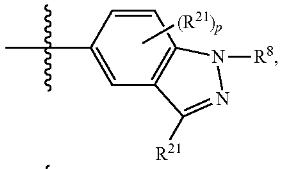
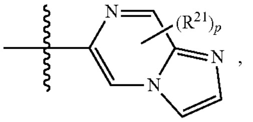
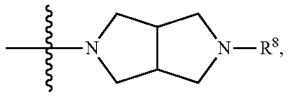
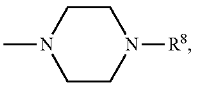
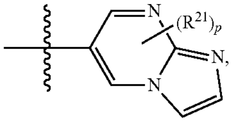
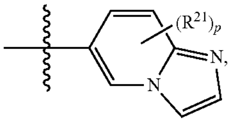
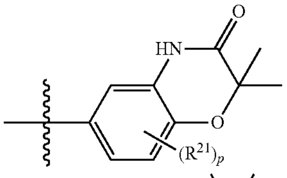

or

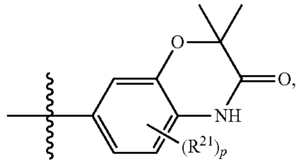

wherein:

$R^{21}$ is halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

n is 1, 2, 3 or 4;

m is 1, 2, or 3 and p is 0, 1, 2 or 3.

3. The compound of claim 1, wherein the compound of Formula (Ia) is a compound of Formula (Ib), Formula (Ic) or Formula (Id):

(Ib)

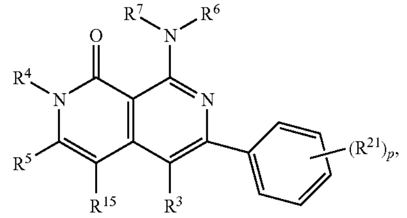

(Ic)

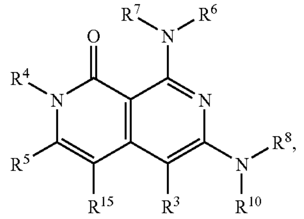

(Id)

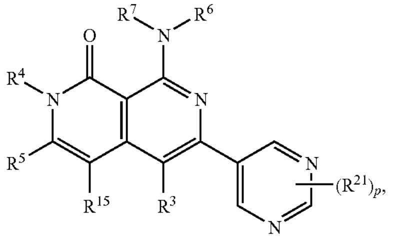

wherein, $R^{21}$ is halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

n is 1, 2, 3 or 4, and p is 0, 1, 2 or 3.

4. The compound of claim 1, wherein $R^6$ is $C_6$-$C_{14}$aryl, $C_3$-$C_{13}$heteroaryl, or $C_2$-$C_{14}$heterocycloalkyl, wherein the $C_6$-$C_{14}$aryl, $C_3$-$C_{13}$heteroaryl, and $C_2$-$C_{14}$heterocycloalkyl are optionally substituted with 1 to 3 substituents independently selected from halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, $^-OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy and n is 1, 2, 3 or 4.

5. The compound of claim 4, wherein $R^6$ is
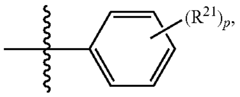,
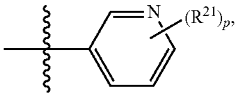,
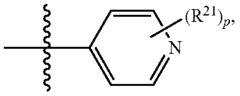,
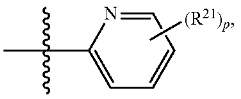,
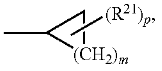,
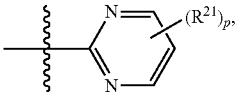,
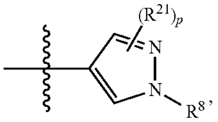,
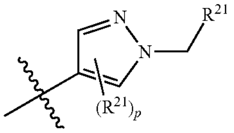,
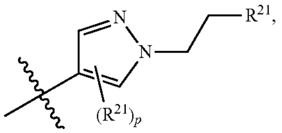,
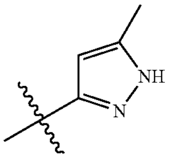,
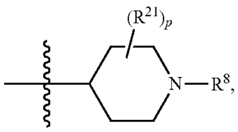,
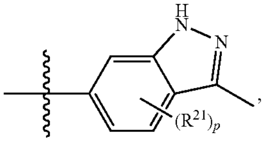,
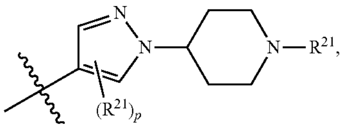,
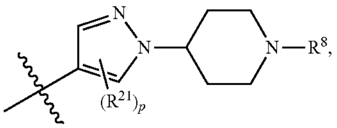,
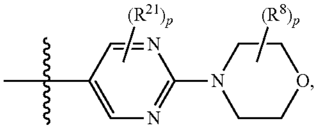,
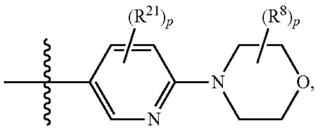,
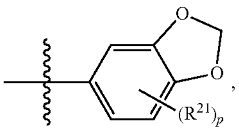,
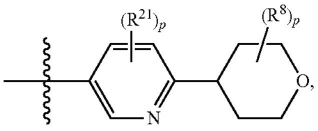,
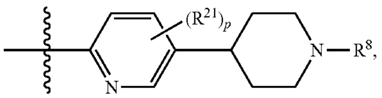,
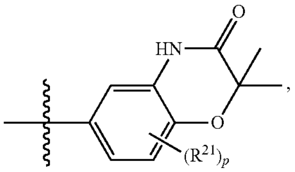,
-continued
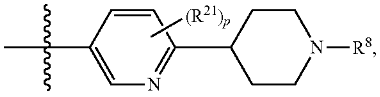,
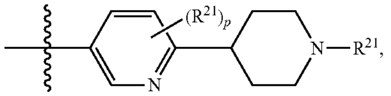,
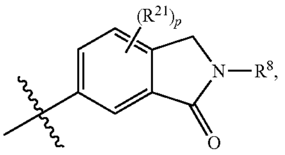,
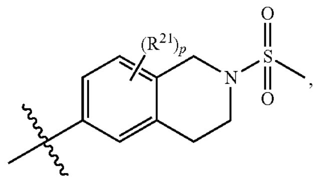,
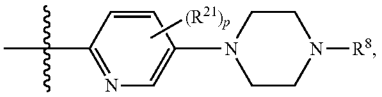,
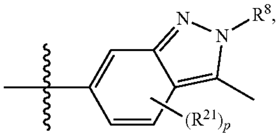,
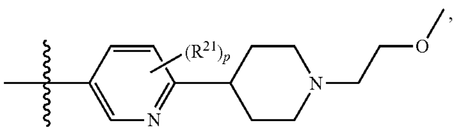,
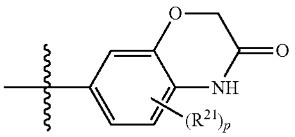,
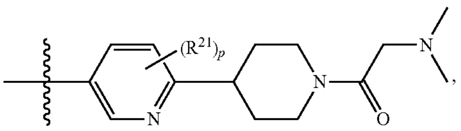,
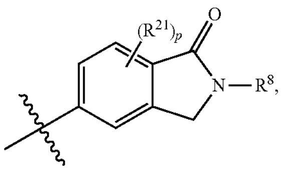,
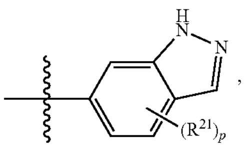,
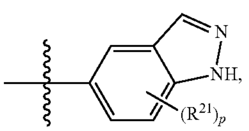,
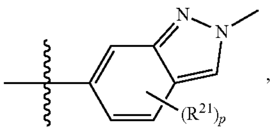,
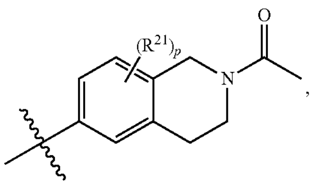,
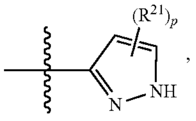, -continued

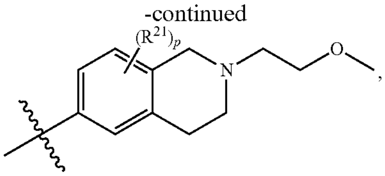,

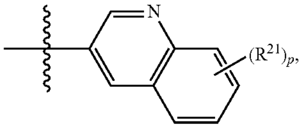

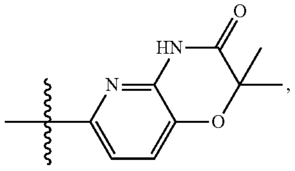, or

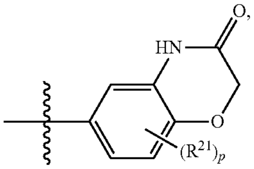

wherein:

$R^{21}$ is halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, $^-OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

$R^8$ is H or $C_1$-$C_6$ alkyl;

n is 1, 2, 3 or 4, and p is 0, 1, 2 or 3.

6. The compound of claim 1, wherein $R^6$ is —$(CH_2)_nR^9$ or -$L^3R^9$, wherein:

$R^9$ is $C_6$-$C_{14}$aryl, $C_3$-$C_{13}$heteroaryl or $C_2$-$C_{14}$heterocycloalkyl, wherein the $C_6$-$C_{14}$aryl, $C_3$-$C_{13}$heteroaryl and $C_2$-$C_{14}$heterocycloalkyl are optionally substituted with 1 to 3 substituents independently selected from halogen, —CN, —$OR^{12}$, —$OR^{10}$, —$C(O)R^{12}$, —$OC(O)R^{12}$, —$C(O)OR^{12}$, $N(R^{11})_2$, —$N(R^{12})_2$, —$N(R^{12}R^{10})$, —$N(R^{12}R^{11})$, $SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, $^-OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

$L^3$ is a $C_1$-$C_6$alkyl or $C_1$-$C_6$alkoxy; wherein the $C_1$-$C_6$alkyl and $C_1$-$C_6$alkoxy groups of $L^3$ are optionally substituted with 1 to 3 substituents independently selected from halogen, —$C_1$-$C_6$alkyl, —$OR^{13}$, —$N(R^{12})_2$, halo-substituted $C_1$-$C_6$alkyl and halo-substituted $C_1$-$C_6$alkoxy, and n is 1, 2, 3 or 4.

7. The compound of claim 6, wherein $R^{13}$ is H or $C_1$-$C_6$ alkyl.

8. The compound of claim 7, wherein $R^9$ is

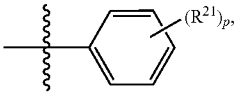, 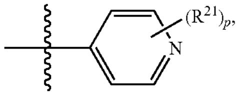,

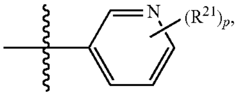, 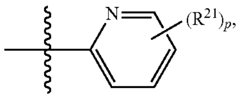,

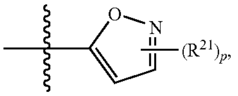, 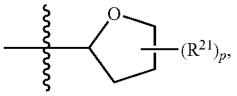,

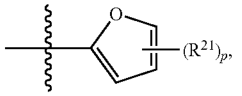, 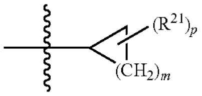,

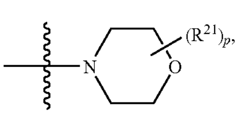, 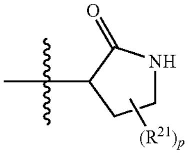 or

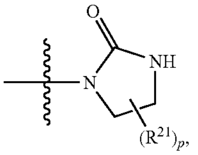, wherein:

$R^{21}$ is halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, $^-OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

n is 1, 2, 3 or 4;

m is 1, 2, 3 or 4, and p is 0, 1, 2 or 3.

9. The compound of claim 1, wherein $R^6$ is —$Y^1$-$L^1$-$R^{14}$, wherein $Y^1$ is phenylene and $R^{14}$ is heterocycloalkyl optionally substituted with 1-3 substituents independently selected from halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy and n is 1, 2, 3 or 4.

10. The compound of claim 1, wherein $R^6$ is —$(CH_2)_nR^9$ and $R^9$ is $Y^2$-$L^2$-$R^{14}$, wherein $Y^2$ is phenylene and $R^{14}$ is $C_2$-$C_{14}$heterocycloalkyl optionally substituted with 1-3 substituents independently selected from halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$- $C_6$alkyl, halo-substituted $C_1$-$C_6$alkyl or halo-substituted $C_1$-$C_6$alkoxy and n is 1, 2, 3 or 4.

11. The compound of claim 1, wherein $R^6$ is $C_1$-$C_6$alkyl or halo-substituted $C_1$-$C_6$alkyl, wherein the $C_1$-$C_6$alkyl and halo-substituted $C_1$-$C_6$alkyl of $R^6$ are optionally substituted with 1 to 3 substituents independently selected from halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy and n is 1, 2, 3 or 4.

12. The compound of claim 3, wherein, $R^{10}$ is $C_6$-$C_{14}$aryl, $C_3$-$C_{13}$heteroaryl, $C_2$-$C_{14}$heterocycloalkyl, $C_3$-$C_8$cycloalkyl or —$(CH_2)_nR^{11}$, wherein the $C_6$-$C_{14}$aryl, $C_3$-$C_{13}$heteroaryl, $C_2$-$C_{14}$heterocycloalkyl and $C_3$-$C_8$cycloalkyl of $R^{10}$ are optionally substituted with 1 to 3 substituents independently selected from halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy and n is 1, 2, 3 or 4.

13. The compound of claim 12, wherein, $R^{10}$ is

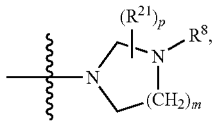

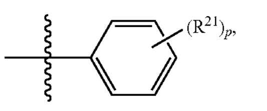

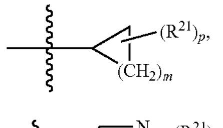

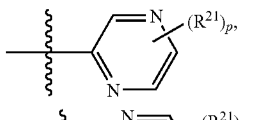

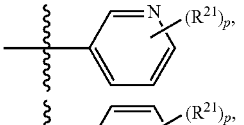

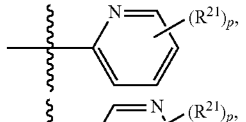

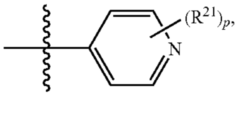

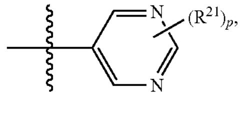

-continued

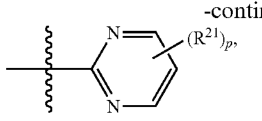

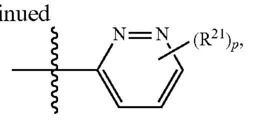

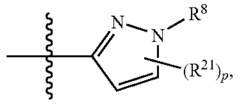

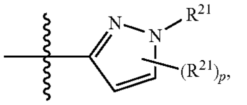

or

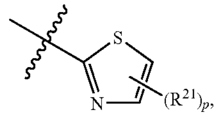

wherein:

$R^{21}$ is halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

n is 1, 2, 3 or 4;

m is 1, 2, or 3 and p is 0, 1, 2 or 3.

14. The compound of claim 3, wherein $R^{10}$ is —$(CH_2)_nR^{11}$.

15. The compound of claim 14, wherein $R^{11}$ is —$N(R^{12})_2$, —$OR^{13}$, —$C(O)N(R^{12})_2$, $C_6$-$C_{14}$aryl, $C_3$-$C_{13}$heteroaryl, $C_3$-$C_8$cycloalkyl, or $C_2$-$C_{14}$heterocycloalkyl, wherein the $C_6$-$C_{14}$aryl, $C_3$-$C_{13}$heteroaryl, $C_2$-$C_{14}$heterocycloalkyl and $C_3$-$C_8$cycloalkyl of $R^{11}$ are optionally substituted with 1 to 3 substituents independently selected from halogen, —CN, —$OR^{12}$, —$OR^{10}$, —$C(O)R^{12}$, —$OC(O)R^{12}$, —$C(O)OR^{12}$, —$N(R^{12})_2$, —$N(R^{12}R^{10})$, —$SR^8$, —$NR^{12}C(O)N(R^{12})_2$, —$C(O)N(R^{12}R^{10})$, —$N(R^{12})C(O)R^{13}$, —$C(O)N(R^{12})_2$—$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy, and n is 1, 2, 3 or 4.

16. The compound of claim 15, wherein $R^{11}$ is —$N(R^{12})_2$,

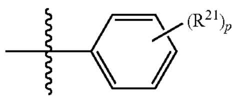

or

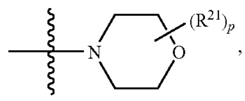

, wherein:

$R^{21}$ is halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

n is 1, 2, 3 or 4, and p is 0, 1, 2 or 3.

17. The compound of claim 1, wherein $R^{15}$ is H, halogen, $C_2$-$C_6$alkenyl, —CN,

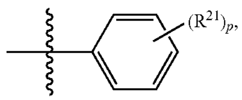

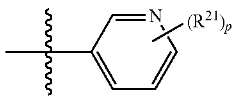

or

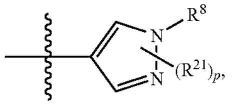

wherein:

$R^{21}$ is halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$SR^8$, —$NR^{12}C(O)N(R^{12})_2$, —$C(O)N(R^{12}R^{10})$, —$N(R^{12})C(O)R^{13}$, —$NHS(O)_2R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, $^{-}OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy, and p is 0, 1, 2 or 3.

18. The compound of claim 1, wherein $R^3$ is H, —CN, halogen, $C_2$-$C_6$ alkenyl,

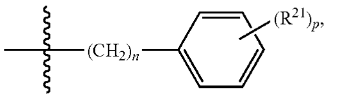

,

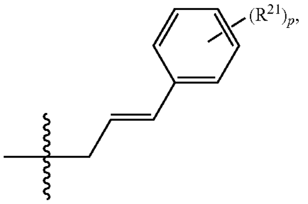

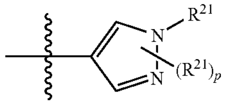

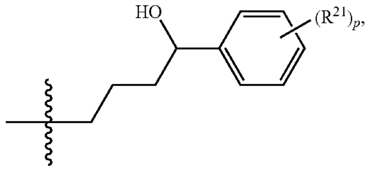

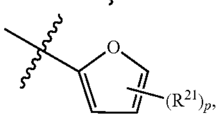

or

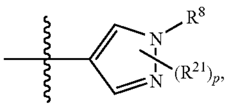

wherein:

$R^{21}$ is halogen, —CN, —$OR^{12}$, —$OR^{10}$, —$C(O)R^{12}$, —$OC(O)R^{12}$, —$C(O)OR^{12}$, —$N(R^{11})_2$, —$N(R^{12})_2$, —$N(R^{12}R^{10})$, —$N(R^{12}R^{11})$, —$SR^8$, —$NR^{12}C(O)N(R^{12})_2$, —$C(O)N(R^{12}R^{10})$, —$N(R^{12})C(O)R^{13}$, —$C(O)N(R^{11})_2$, —$C(O)N(R^{12})_2$, —$(CR^{12}R^{12})_nR^{11}$, —$(CH_2)_nR^{12}$, —$(CH_2)_nR^{13}$, —$O(CH_2)_nR^{13}$, $(CH_2)_nR^{14}$, —$O(CH_2)_nR^{14}$, $(CH_2)_nR^{16}$, —$S(O)_2R^{12}$, —$S(O)_2N(R^{11})_2$, —$S(O)_2N(R^{12})_2$, $R^{12}$, $R^{10}$, —$OR^{13}$, —$C(O)R^{13}$, —$OC(O)R^{13}$, —$C(O)OR^{13}$, —$S(O)_2R^{13}$, —$R^{13}$, $C_2$-$C_{14}$ heterocycloalkyl, $C_1$-$C_6$alkyl, $C_1$-$C_6$alkoxy, hydroxyl-$C_1$-$C_6$alkyl, halo-substituted $C_1$-$C_6$alkyl or halo-substituted $C_1$-$C_6$alkoxy;

n is 1, 2, 3 or 4, and p is 0, 2 or 3.

19. The compound of claim 1, wherein $R^{15}$, $R^4$, $R^3$, $R^7$, $R^5$ and $R^8$ are H.

20. The compound of claim 1 selected from:

3-(morpholin-4-yl)-N-(8-oxo-3-phenyl-7,8-dihydro-2,7-naphthyridin-1-yl)benzamide;

8-amino-6-phenyl-1,2-dihydro-2,7-naphthyridin-1-one;

8-{[3-(morpholin-4-yl)phenyl]amino}-6-phenyl-1,2-dihydro-2,7-naphthyridin-1-one;

N-(8-oxo-3-phenyl-7,8-dihydro-2,7-naphthyridin-1-yl)oxane-4-carboxamide;

6-[(dimethylamino)methyl]-8-{[3-(trifluoromethyl)phenyl]amino}-1,2-dihydro-2,7-naphthyridin-1-one;

6-[(dimethylamino)methyl]-8-{[3-(morpholin-4-yl)phenyl]amino}-1,2-dihydro-2,7-naphthyridin-1-one;

6-(2-phenylethyl)-8-{[3-(trifluoromethyl)phenyl]amino}-1,2-dihydro-2,7-naphthyridin-1-one;

8-{[3-(morpholin-4-yl)phenyl]amino}-6-(2-phenylethyl)-1,2-dihydro-2,7-naphthyridin-1-one;

6-[3-(trifluoromethyl)phenyl]-8-{[3-(trifluoromethyl)phenyl]amino}-1,2-dihydro-2,7-naphthyridin-1-one;

6-(2-aminoethyl)-8-{[3-(trifluoromethyl)phenyl]amino}-1,2-dihydro-2,7-naphthyridin-1-one;

6-(3-aminopropyl)-8-{[3-(trifluoromethyl)phenyl]amino}-1,2-dihydro-2,7-naphthyridin-1-one;

6-phenyl-8-{[3-(trifluoromethyl)phenyl]amino}-1,2-dihydro-2,7-naphthyridin-1-one;

8-{[4-(morpholin-4-yl)phenyl]amino}-6-phenyl-1,2-dihydro-2,7-naphthyridin-1-one;

6-(pyridin-3-yl)-8-{[3-(trifluoromethyl)phenyl]amino}-1,2-dihydro-2,7-naphthyridin-1-one;

2-[2-(8-amino-1-oxo-1,2-dihydro-2,7-naphthyridin-3-yl)ethyl]-2,3-dihydro-1H-isoindole-1,3-dione;

6-(3-aminopropyl)-8-{[4-(morpholin-4-yl)phenyl]amino}-1,2-dihydro-2,7-naphthyridin-1-one;

6-(3-aminopropyl)-8-{[3-(morpholin-4-yl)phenyl]amino}-1,2-dihydro-2,7-naphthyridin-1-one;

8-{[4-(4-methylpiperazin-1-yl)phenyl]amino}-6-phenyl-1,2-dihydro-2,7-naphthyridin-1-one;

8-({4-[3-(dimethylamino)propyl]phenyl}amino)-6-phenyl-1,2-dihydro-2,7-naphthyridin-1-one;

8-({4-[2-(morpholin-4-yl)ethyl]phenyl}amino)-6-phenyl-1,2-dihydro-2,7-naphthyridin-1-one;

N-(3-methoxypropyl)-4-[(8-oxo-3-phenyl-7,8-dihydro-2,7-naphthyridin-1-yl)amino]benzene-1-sulfonamide;

6-phenyl-8-{[3-(trifluoromethoxy)phenyl]amino}-1,2-dihydro-2,7-naphthyridin-1-one;

6-(3-aminopropyl)-8-({4-[2-(morpholin-4-yl)ethyl]phenyl}amino)-1,2-dihydro-2,7-naphthyridin-1-one;

8-amino-3-(2-aminoethyl)-1,2-dihydro-2,7-naphthyridin-1-one;

6-(4-aminobutyl)-8-{[3-(trifluoromethyl)phenyl]amino}-1,2-dihydro-2,7-naphthyridin-1-one;

6-(4-aminobutyl)-8-{[3-(trifluoromethoxy)phenyl]amino}-1,2-dihydro-2,7-naphthyridin-1-one;

6-(3-aminopropyl)-8-{[4-methyl-3-(trifluoromethyl)phenyl]amino}-1,2-dihydro-2,7-naphthyridin-1-one;

8-{[3-(morpholin-4-yl)phenyl]amino}-6-(pyridin-3-yl)-1,2-dihydro-2,7-naphthyridin-1-one;

8-amino-3-(3-aminopropyl)-1,2-dihydro-2,7-naphthyridin-1-one;

6-phenyl-8-{[4-(trifluoromethoxy)phenyl]amino}-1,2-dihydro-2,7-naphthyridin-1-one;

6-(3-aminopropyl)-8-{[4-methoxy-3-(trifluoromethyl)phenyl]amino}-1,2-dihydro-2,7-naphthyridin-1-one;

6-(3-aminopropyl)-8-[(3,5-dimethoxyphenyl)amino]-1,2-dihydro-2,7-naphthyridin-1-one;

6-(3-aminopropyl)-8-[(3,4-dimethoxyphenyl)amino]-1,2-dihydro-2,7-naphthyridin-1-one;

6-(3-aminopropyl)-8-[(3-methoxyphenyl)amino]-1,2-dihydro-2,7-naphthyridin-1-one;

6-(3-aminopropyl)-8-{[3-fluoro-4-(piperazin-1-ylmethyl)phenyl]amino}-1,2-dihydro-2,7-naphthyridin-1-one;

8-[(3-bromophenyl)amino]-6-phenyl-1,2-dihydro-2,7-naphthyridin-1-one;

6-cyclohexyl-8-{[3-(trifluoromethyl)phenyl]amino}-1,2-dihydro-2,7-naphthyridin-1-one;

6-cyclohexyl-8-{[4-(4-methylpiperazin-1-yl)phenyl]amino}-1,2-dihydro-2,7-naphthyridin-1-one;

8-[(4-methoxyphenyl)amino]-6-phenyl-1,2-dihydro-2,7-naphthyridin-1-one;

6-phenyl-8-{[2-(trifluoromethoxy)phenyl]amino}-1,2-dihydro-2,7-naphthyridin-1-one;

8-{[4-(morpholin-4-yl)phenyl]amino}-6-[3-(trifluoromethyl)phenyl]-1,2-dihydro-2,7-naphthyridin-1-one;

6-[(2-aminoethyl)amino]-8-{[3-(trifluoromethyl)phenyl]amino}-1,2-dihydro-2,7-naphthyridin-1-one;

6-[(2-aminoethyl)amino]-8-{[4-(morpholin-4-yl)phenyl]amino}-1,2-dihydro-2,7-naphthyridin-1-one;

6-(3-aminopropyl)-8-{[4-(4-ethylpiperazin-1-yl)phenyl]amino}-1,2-dihydro-2,7-naphthyridin-1-one;

6-[(3R)-piperidin-3-ylamino]-8-{[3-(trifluoromethyl)phenyl]amino}-1,2-dihydro-2,7-naphthyridin-1-one;

8-{[4-(morpholin-4-yl)phenyl]amino}-6-[(3R)-piperidin-3-ylamino]-1,2-dihydro-2,7-naphthyridin-1-one;

6-(4-ethylpiperazin-1-yl)-8-{[4-(morpholin-4-yl)phenyl]amino}-1,2-dihydro-2,7-naphthyridin-1-one;

8-{[4-(morpholin-4-yl)phenyl]amino}-6-[(3S)-piperidin-3-ylamino]-1,2-dihydro-2,7-naphthyridin-1-one;

8-{[4-(morpholin-4-yl)phenyl]amino}-6-[(3S)-pyrrolidin-3-ylamino]-1,2-dihydro-2,7-naphthyridin-1-one;

6-{[(1S,2S)-2-aminocyclohexyl]amino}-8-{[4-(morpholin-4-yl)phenyl]amino}-1,2-dihydro-2,7-naphthyridin-1-one;

8-{[4-(morpholin-4-yl)phenyl]amino}-6-[(3R)-pyrrolidin-3-ylamino]-1,2-dihydro-2,7-naphthyridin-1-one;

6-{[(1S,2R)-2-aminocyclohexyl]amino}-8-{[4-(morpholin-4-yl)phenyl]amino}-1,2-dihydro-2,7-naphthyridin-1-one;

8-{[4-(morpholin-4-yl)phenyl]amino}-6-(piperidin-3-yloxy)-1,2-dihydro-2,7-naphthyridin-1-one;

6-[(2-aminoethyl)amino]-8-{[4-(4-methylpiperazin-1-yl)phenyl]amino}-1,2-dihydro-2,7-naphthyridin-1-one;

8-{[4-(4-methylpiperazin-1-yl)phenyl]amino}-6-[(3S)-piperidin-3-ylamino]-1,2-dihydro-2,7-naphthyridin-1-one;

6-(benzylamino)-8-{[4-(4-methylpiperazin-1-yl)phenyl]amino}-1,2-dihydro-2,7-naphthyridin-1-one;

6-[(2-aminoethyl)amino]-8-{[4-(piperidin-4-yl)phenyl]amino}-1,2-dihydro-2,7-naphthyridin-1-one;

tert-butyl 4-[4-({3-[(2-aminoethyl)amino]-8-oxo-7,8-dihydro-2,7-naphthyridin-1-yl}amino)phenyl]piperidine-1-carboxylate;

6-[(2-aminoethyl)amino]-8-({4-[(4-ethylpiperazin-1-yl)methyl]phenyl}amino)-1,2-dihydro-2,7-naphthyridin-1-one;

8-{[4-(4-methylpiperazin-1-yl)phenyl]amino}-6-(pyridin-3-yl)-1,2-dihydro-2,7-naphthyridin-1-one;

2-(1-{[4-(4-methylpiperazin-1-yl)phenyl]amino}-8-oxo-7,8-dihydro-2,7-naphthyridin-3-yl)benzamide;

8-{[4-(4-methylpiperazin-1-yl)phenyl]amino}-6-(1H-pyrazol-4-yl)-1,2-dihydro-2,7-naphthyridin-1-one;

6-{[(1S,2S)-2-aminocyclohexyl]amino}-8-{[4-(4-methylpiperazin-1-yl)phenyl]amino}-1,2-dihydro-2,7-naphthyridin-1-one;

6-{[(2-aminoethyl]amino}-8-{[3-(4-methylpiperazin-1-yl)phenyl]amino}-1,2-dihydro-2,7-naphthyridin-1-one;

6-(3-aminopiperidin-1-yl)-8-{[4-(morpholin-4-yl)phenyl]amino}-1,2-dihydro-2,7-naphthyridin-1-one;

6-{[(3-chlorophenyl)methyl]amino}-8-{[4-(4-methylpiperazin-1-yl)phenyl]amino}-1,2-dihydro-2,7-naphthyridin-1-one;

6-[(3R)-3-aminopyrrolidin-1-yl]-8-{[4-(morpholin-4-yl)phenyl]amino}-1,2-dihydro-2,7-naphthyridin-1-one;

8-{[4-(piperidin-1-yl)phenyl]amino}-6-(pyridin-3-yl)-1,2-dihydro-2,7-naphthyridin-1-one;

6-[(2-aminoethyl)amino]-2-methyl-8-{[3-(trifluoromethyl)phenyl]amino}-1,2-dihydro-2,7-naphthyridin-1-one;

8-{[4-(morpholin-4-yl)phenyl]amino}-6-(pyridin-3-yl)-1,2-dihydro-2,7-naphthyridin-1-one;

8-{[4-(4-methylpiperazin-1-yl)phenyl]amino}-6-[1-(piperidin-4-yl)-1H-pyrazol-4-yl]-1,2-dihydro-2,7-naphthyridin-1-one;

6-(3-chlorophenyl)-8-{[4-(morpholin-4-yl)phenyl]amino}-1,2-dihydro-2,7-naphthyridin-1-one;

4-({3-[(2-aminoethyl)amino]-8-oxo-7,8-dihydro-2,7-naphthyridin-1-yl}amino)-N-(4-chlorophenyl)benzamide;

6-(3-methylphenyl)-8-{[4-(morpholin-4-yl)phenyl]amino}-1,2-dihydro-2,7-naphthyridin-1-one;

tert-butyl 4-{4-[(8-oxo-3-phenyl-7,8-dihydro-2,7-naphthyridin-1-yl)amino]phenyl}piperidine-1-carboxylate;

6-phenyl-8-{[4-(piperidin-4-yl)phenyl]amino}-1,2-dihydro-2,7-naphthyridin-1-one;

6-(3-hydroxyphenyl)-8-{[4-(morpholin-4-yl)phenyl]amino}-1,2-dihydro-2,7-naphthyridin-1-one;

6-(3-methoxyphenyl)-8-{[4-(morpholin-4-yl)phenyl]amino}-1,2-dihydro-2,7-naphthyridin-1-one;

6-[(2-aminoethyl)amino]-8-{[2-methoxy-4-(4-methylpiperazin-1-yl)phenyl]amino}-1,2-dihydro-2,7-naphthyridin-1-one;

6-(6-methoxypyridin-3-yl)-8-{[4-(morpholin-4-yl)phenyl]amino}-1,2-dihydro-2,7-naphthyridin-1-one;

8-{[4-(morpholin-4-yl)phenyl]amino}-6-(1H-pyrazol-4-yl)-1,2-dihydro-2,7-naphthyridin-1-one;

6-(3,5-dimethyl-1H-pyrazol-4-yl)-8-{[4-(4-methylpiperazin-1-yl)phenyl]amino}-1,2-dihydro-2,7-naphthyridin-1-one;

2-(1-{[4-(4-methylpiperazin-1-yl)phenyl]amino}-8-oxo-7,8-dihydro-2,7-naphthyridin-3-yl)benzonitrile 6-(4-methoxypyridin-3-yl)-8-{[4-(4-methylpiperazin-1-yl)phenyl]amino}-1,2-dihydro-2,7-naphthyridin-1-one;

6-(6-aminopyridin-3-yl)-8-{[4-(4-methylpiperazin-1-yl)phenyl]amino}-1,2-dihydro-2,7-naphthyridin-1-one;

3-(1-{[4-(4-methylpiperazin-1-yl)phenyl]amino}-8-oxo-7,8-dihydro-2,7-naphthyridin-3-yl)benzamide;

8-{[4-(4-methylpiperazin-1-yl)phenyl]amino}-6-(pyrimidin-5-yl)-1,2-dihydro-2,7-naphthyridin-1-one;

6-(3,5-dimethyl-1,2-oxazol-4-yl)-8-{[4-(4-methylpiperazin-1-yl)phenyl]amino}-1,2-dihydro-2,7-naphthyridin-1-one;

6-(furan-3-yl)-8-{[4-(4-methylpiperazin-1-yl)phenyl]amino}-1,2-dihydro-2,7-naphthyridin-1-one;

6-(1-methyl-1H-pyrazol-4-yl)-8-{[4-(4-methylpiperazin-1-yl)phenyl]amino}-1,2-dihydro-2,7-naphthyridin-1-one;

4-[4-({3-[(2-aminoethyl)amino]-8-oxo-7,8-dihydro-2,7-naphthyridin-1-yl}amino)phenyl]-1,4-thiomorpholine-1,1-dione;

8-{[3-fluoro-4-(morpholin-4-yl)phenyl]amino}-6-phenyl-1,2-dihydro-2,7-naphthyridin-1-one;

4-{4-[(8-oxo-3-phenyl-7,8-dihydro-2,7-naphthyridin-1-yl)amino]phenyl}-1,4-thiomorpholine-1,1-dione;

6-(4-chlorophenyl)-8-{[4-(morpholin-4-yl)phenyl]amino}-1,2-dihydro-2,7-naphthyridin-1-one;

6-(2-chlorophenyl)-8-{[4-(morpholin-4-yl)phenyl]amino}-1,2-dihydro-2,7-naphthyridin-1-one;

6-(3,4-dichlorophenyl)-8-{[4-(morpholin-4-yl)phenyl]amino}-1,2-dihydro-2,7-naphthyridin-1-one;

6-(4-fluorophenyl)-8-{[4-(morpholin-4-yl)phenyl]amino}-1,2-dihydro-2,7-naphthyridin-1-one;

6-(2,4-dimethoxyphenyl)-8-{[4-(morpholin-4-yl)phenyl]amino}-1,2-dihydro-2,7-naphthyridin-1-one;

6-[3-(aminomethyl)phenyl]-8-{[4-(morpholin-4-yl)phenyl]amino}-1,2-dihydro-2,7-naphthyridin-1-one;

8-{[4-(morpholin-4-yl)phenyl]amino}-6-[4-(piperazin-1-yl)phenyl]-1,2-dihydro-2,7-naphthyridin-1-one;

8-{[4-(piperidin-4-yl)phenyl]amino}-6-(1H-pyrazol-4-yl)-1,2-dihydro-2,7-naphthyridin-1-one;

6-(1-methyl-1H-pyrazol-4-yl)-8-{[4-(piperidin-4-yl)phenyl]amino}-1,2-dihydro-2,7-naphthyridin-1-one;

8-{[4-(piperidin-4-yl)phenyl]amino}-6-(1H-pyrazol-3-yl)-1,2-dihydro-2,7-naphthyridin-1-one;

6-(3-hydroxyphenyl)-8-{[4-(piperidin-4-yl)phenyl]amino}-1,2-dihydro-2,7-naphthyridin-1-one;

6-(2-hydroxyphenyl)-8-{[4-(piperidin-4-yl)phenyl]amino}-1,2-dihydro-2,7-naphthyridin-1-one;

6-(6-hydroxypyridin-3-yl)-8-{[4-(piperidin-4-yl)phenyl]amino}-1,2-dihydro-2,7-naphthyridin-1-one;

6-(6-methoxypyridin-3-yl)-8-{[4-(piperidin-4-yl)phenyl]amino}-1,2-dihydro-2,7-naphthyridin-1-one;

8-{[4-(piperidin-4-yl)phenyl]amino}-6-(1-propyl-1H-pyrazol-4-yl)-1,2-dihydro-2,7-naphthyridin-1-one;

6-[1-(2-methylpropyl)-1H-pyrazol-4-yl]-8-{[4-(piperidin-4-yl)phenyl]amino}-1,2-dihydro-2,7-naphthyridin-1-one;

6-[1-(3-methylbutyl)-1H-pyrazol-4-yl]-8-{[4-(piperidin-4-yl)phenyl]amino}-1,2-dihydro-2,7-naphthyridin-1-one;

6-[1-(1,3-dioxolan-2-ylmethyl)-1H-pyrazol-4-yl]-8-{[4-(piperidin-4-yl)phenyl]amino}-1,2-dihydro-2,7-naphthyridin-1-one;

6-{1-[2-(morpholin-4-yl)ethyl]-1H-pyrazol-4-yl}-8-{[4-(piperidin-4-yl)phenyl]amino}-1,2-dihydro-2,7-naphthyridin-1-one;

6-(3-methyl-1H-pyrazol-4-yl)-8-{[4-(piperidin-4-yl)phenyl]amino}-1,2-dihydro-2,7-naphthyridin-1-one;

2-[4-(8-oxo-1-{[4-(piperidin-4-yl)phenyl]amino}-7,8-dihydro-2,7-naphthyridin-3-yl)-1H-pyrazol-1-yl]acetic acid 6-(3,5-dimethyl-1H-pyrazol-4-yl)-8-{[4-(piperidin-4-yl)phenyl]amino}-1,2-dihydro-2,7-naphthyridin-1-one;

8-({4-[1-(2-hydroxyethyl)piperidin-4-yl]phenyl}amino)-6-(1-methyl-1H-pyrazol-4-yl)-1,2-dihydro-2,7-naphthyridin-1-one;

8-({4-[1-(2-hydroxyethyl)piperidin-4-yl]phenyl}amino)-6-(3-hydroxyphenyl)-1,2-dihydro-2,7-naphthyridin-1-one;

8-({4-[1-(2-hydroxyethyl)piperidin-4-yl]phenyl}amino)-6-(6-methoxypyridin-3-yl)-1,2-dihydro-2,7-naphthyridin-1-one;

6-(1H-pyrazol-4-yl)-8-{[3-(trifluoromethyl)phenyl]amino}-1,2-dihydro-2,7-naphthyridin-1-one;

8-{[3-fluoro-4-(morpholin-4-yl)phenyl]amino}-6-[1-(piperidin-4-yl)-1H-pyrazol-4-yl]-1,2-dihydro-2,7-naphthyridin-1-one;

6-(1-benzyl-1H-pyrazol-4-yl)-8-{[3-fluoro-4-(morpholin-4-yl)phenyl]amino}-1,2-dihydro-2,7-naphthyridin-1-one;

8-[(4-fluorophenyl)amino]-5-[1-(piperidin-4-yl)-1H-pyrazol-4-yl]-1,2-dihydro-2,7-naphthyridin-1-one;

5-(1-methyl-1H-pyrazol-4-yl)-8-{[4-(morpholin-4-yl)phenyl]amino}-1,2-dihydro-2,7-naphthyridin-1-one;

8-[(4-fluorophenyl)amino]-5-(1-methyl-1H-pyrazol-4-yl)-1,2-dihydro-2,7-naphthyridin-1-one;

5-bromo-8-{[4-(morpholin-4-yl)phenyl]amino}-1,2-dihydro-2,7-naphthyridin-1-one;

8-{[4-(morpholin-4-yl)phenyl]amino}-1,2-dihydro-2,7-naphthyridin-1-one;

8-chloro-5-(pyridin-3-yl)-1,2-dihydro-2,7-naphthyridin-1-one;

6-(3,5-dimethyl-1H-pyrazol-4-yl)-8-{[4-(morpholin-4-yl)phenyl]amino}-1,2-dihydro-2,7-naphthyridin-1-one;

2-(1-{[4-(morpholin-4-yl)phenyl]amino}-8-oxo-7,8-dihydro-2,7-naphthyridin-3-yl)benzonitrile 5-(furan-3-yl)-8-{[4-(morpholin-4-yl)phenyl]amino}-1,2-dihydro-2,7-naphthyridin-1-one;

4-[(8-oxo-3-phenyl-7,8-dihydro-2,7-naphthyridin-1-yl)amino]-N-propylbenzamide;

4-({3-[(2-aminoethyl)amino]-8-oxo-7,8-dihydro-2,7-naphthyridin-1-yl}amino)-N-propylbenzamide;

4-(4-{[3-(4-methoxypyridin-3-yl)-8-oxo-7,8-dihydro-2,7-naphthyridin-1-yl]amino}phenyl)-1,4-thiomorpholine-1,1-dione;

6-[2-(3-fluorophenyl)pyrrolidin-1-yl]-8-{[4-(morpholin-4-yl)phenyl]amino}-1,2-dihydro-2,7-naphthyridin-1-one;

6-(4-methoxypyridin-3-yl)-8-{[4-(1-methylpiperidin-4-yl)phenyl]amino}-1,2-dihydro-2,7-naphthyridin-1-one;

4-[4-({3-[6-(morpholin-4-yl)pyridin-3-yl]-8-oxo-7,8-dihydro-2,7-naphthyridin-1-yl}amino)phenyl]-1,4-thiomorpholine-1,1-dione;

6-(4-methoxypyridin-3-yl)-8-{[4-(piperidin-1-yl)phenyl]amino}-1,2-dihydro-2,7-naphthyridin-1-one;

8-({4-[3-(dimethylamino)propyl]phenyl}amino)-6-(4-methoxypyridin-3-yl)-1,2-dihydro-2,7-naphthyridin-1-one;

8-{[4-(1-ethylpiperidin-4-yl)phenyl]amino}-6-(1-propyl-1H-pyrazol-4-yl)-1,2-dihydro-2,7-naphthyridin-1-one;

8-{[4-(1-ethylpiperidin-4-yl)phenyl]amino}-6-(3-methyl-1H-pyrazol-4-yl)-1,2-dihydro-2,7-naphthyridin-1-one;

6-[2-(3-fluorophenyl)pyrrolidin-1-yl]-8-{[4-(1-methylpiperidin-4-yl)phenyl]amino}-1,2-dihydro-2,7-naphthyridin-1-one;

2-[4-(1-{[4-(1-ethylpiperidin-4-yl)phenyl]amino}-8-oxo-7,8-dihydro-2,7-naphthyridin-3-yl)-1H-pyrazol-1-yl]acetic acid 8-{[4-(1-acetylpiperidin-4-yl)phenyl]amino}-6-[1-(2-methylpropyl)-1H-pyrazol-4-yl]-1,2-dihydro-2,7-naphthyridin-1-one;

8-[(5-methyl-1H-pyrazol-3-yl)amino]-6-phenyl-1,2-dihydro-2,7-naphthyridin-1-one;

8-{[4-(1-acetylpiperidin-4-yl)phenyl]amino}-6-[1-(3-methylbutyl)-1H-pyrazol-4-yl]-1,2-dihydro-2,7-naphthyridin-1-one;

8-{[4-(1-acetylpiperidin-4-yl)phenyl]amino}-6-{1-[2-(morpholin-4-yl)ethyl]-1H-pyrazol-4-yl}-1,2-dihydro-2,7-naphthyridin-1-one;

6-(6-aminopyridin-3-yl)-8-{[4-(morpholin-4-yl)phenyl]amino}-1,2-dihydro-2,7-naphthyridin-1-one;

6-(4-ethylpiperazin-1-yl)-8-{[4-(piperidin-4-yl)phenyl]amino}-1,2-dihydro-2,7-naphthyridin-1-one;

6-(piperazin-1-yl)-8-{[4-(piperidin-4-yl)phenyl]amino}-1,2-dihydro-2,7-naphthyridin-1-one;

6-(4-methylpiperazin-1-yl)-8-{[4-(piperidin-4-yl)phenyl]amino}-1,2-dihydro-2,7-naphthyridin-1-one;

8-{[4-(piperidin-4-yl)phenyl]amino}-6-(piperidin-4-ylamino)-1,2-dihydro-2,7-naphthyridin-1-one;

6-[4-(piperidin-1-yl)piperidin-1-yl]-8-{[4-(piperidin-4-yl)phenyl]amino}-1,2-dihydro-2,7-naphthyridin-1-one;

6-{[2-(morpholin-4-yl)ethyl]amino}-8-{[4-(piperidin-4-yl)phenyl]amino}-1,2-dihydro-2,7-naphthyridin-1-one;

6-(5-methoxypyridin-3-yl)-8-{[4-(1-methylpiperidin-4-yl)phenyl]amino}-1,2-dihydro-2,7-naphthyridin-1-one;

5-(6-aminopyridin-3-yl)-8-[(4-methoxyphenyl)amino]-1,2-dihydro-2,7-naphthyridin-1-one;

5-(6-aminopyridin-3-yl)-8-{[4-(morpholin-4-yl)phenyl]amino}-1,2-dihydro-2,7-naphthyridin-1-one;

5-(2-chloropyridin-3-yl)-8-{[4-(morpholin-4-yl)phenyl]amino}-1,2-dihydro-2,7-naphthyridin-1-one;

5-[4-(aminomethyl)phenyl]-8-{[4-(morpholin-4-yl)phenyl]amino}-1,2-dihydro-2,7-naphthyridin-1-one;

3-(1-{[4-(morpholin-4-yl)phenyl]amino}-8-oxo-7,8-dihydro-2,7-naphthyridin-4-yl)benzamide;

5-iodo-8-[(4-methoxyphenyl)amino]-1,2-dihydro-2,7-naphthyridin-1-one;

8-[(4-methoxyphenyl)amino]-5-(3-phenylprop-1-yn-1-yl)-1,2-dihydro-2,7-naphthyridin-1-one;

5-phenyl-8-(phenylamino)-1,2-dihydro-2,7-naphthyridin-1-one;

5-(2-chlorophenyl)-8-(phenylamino)-1,2-dihydro-2,7-naphthyridin-1-one;

5-(3-chlorophenyl)-8-(phenylamino)-1,2-dihydro-2,7-naphthyridin-1-one;

5-(4-chlorophenyl)-8-(phenylamino)-1,2-dihydro-2,7-naphthyridin-1-one;

5-(2-methoxyphenyl)-8-(phenylamino)-1,2-dihydro-2,7-naphthyridin-1-one;

5-(3-methoxyphenyl)-8-(phenylamino)-1,2-dihydro-2,7-naphthyridin-1-one;

5-(4-methoxyphenyl)-8-(phenylamino)-1,2-dihydro-2,7-naphthyridin-1-one;

5-(1-benzyl-1H-pyrazol-4-yl)-8-{[4-(morpholin-4-yl)phenyl]amino}-1,2-dihydro-2,7-naphthyridin-1-one;

8-(phenylamino)-5-[1-(piperidin-4-yl)-1H-pyrazol-4-yl]-1,2-dihydro-2,7-naphthyridin-1-one;

5-(1-benzyl-1H-pyrazol-4-yl)-8-(phenylamino)-1,2-dihydro-2,7-naphthyridin-1-one;

5-{1-[2-(morpholin-4-yl)ethyl]-1H-pyrazol-4-yl}-8-(phenylamino)-1,2-dihydro-2,7-naphthyridin-1-one;

5-[1-(1,3-dioxolan-2-ylmethyl)-1H-pyrazol-4-yl]-8-(phenylamino)-1,2-dihydro-2,7-naphthyridin-1-one;

5-(1-methyl-1H-pyrazol-4-yl)-8-(phenylamino)-1,2-dihydro-2,7-naphthyridin-1-one;

5-(furan-3-yl)-8-(phenylamino)-1,2-dihydro-2,7-naphthyridin-1-one;

5-[8-oxo-1-(phenylamino)-7,8-dihydro-2,7-naphthyridin-4-yl]furan-2-carb aldehyde 8-(phenylamino)-5-(pyridin-3-yl)-1,2-dihydro-2,7-naphthyridin-1-one;

6-[2-(2-chlorophenyl)phenyl]-8-{[4-(morpholin-4-yl)phenyl]amino}-1,2-dihydro-2,7-naphthyridin-1-one;

6-(2-chlorophenyl)-8-{[4-(piperidin-4-yl)phenyl]amino}-1,2-dihydro-2,7-naphthyridin-1-one;

N-[2-(morpholin-4-yl)ethyl]-4-[(8-oxo-3-phenyl-7,8-dihydro-2,7-naphthyridin-1-yl)amino]benzamide;

N,N-diethyl-4-[(8-oxo-3-phenyl-7,8-dihydro-2,7-naphthyridin-1-yl)amino]benzamide;

6-(1-methyl-1H-pyrazol-4-yl)-8-{[4-(1-methylpiperidin-4-yl)phenyl]amino}-1,2-dihydro-2,7-naphthyridin-1-one;

8-{[4-(1-ethylpiperidin-4-yl)phenyl]amino}-6-(1-methyl-1H-pyrazol-4-yl)-1,2-dihydro-2,7-naphthyridin-1-one;

8-{[4-(1-acetylpiperidin-4-yl)phenyl]amino}-6-(1-methyl-1H-pyrazol-4-yl)-1,2-dihydro-2,7-naphthyridin-1-one;

8-(phenylamino)-5-[3-(trifluoromethyl)phenyl]-1,2-dihydro-2,7-naphthyridin-1-one;

8-(phenylamino)-5-[4-(trifluoromethyl)phenyl]-1,2-dihydro-2,7-naphthyridin-1-one;

5-(6-aminopyridin-3-yl)-8-(phenylamino)-1,2-dihydro-2,7-naphthyridin-1-one;

5-[6-(morpholin-4-yl)pyridin-3-yl]-8-(phenylamino)-1,2-dihydro-2,7-naphthyridin-1-one;

8-(phenylamino)-5-[6-(piperazin-1-yl)pyridin-3-yl]-1,2-dihydro-2,7-naphthyridin-1-one;

5-[6-(4-methylpiperazin-1-yl)pyridin-3-yl]-8-(phenylamino)-1,2-dihydro-2,7-naphthyridin-1-one;

5-(3-aminophenyl)-8-(phenylamino)-1,2-dihydro-2,7-naphthyridin-1-one;

5-(4-aminophenyl)-8-(phenylamino)-1,2-dihydro-2,7-naphthyridin-1-one;

5-(3-fluorophenyl)-8-(phenylamino)-1,2-dihydro-2,7-naphthyridin-1-one;

5-(4-fluorophenyl)-8-(phenylamino)-1,2-dihydro-2,7-naphthyridin-1-one;

4-[8-oxo-1-(phenylamino)-7,8-dihydro-2,7-naphthyridin-4-yl]benzamide;

8-(phenylamino)-5-[(1E)-3-phenylprop-1-en-1-yl]-1,2-dihydro-2,7-naphthyridin-1-one;

5-[(E)-2-(2,4-difluorophenyl)ethenyl]-8-(phenylamino)-1,2-dihydro-2,7-naphthyridin-1-one;

5-[(E)-2-cyclohexylethenyl]-8-(phenylamino)-1,2-dihydro-2,7-naphthyridin-1-one;

8-(phenylamino)-5-[(E)-2-[3-(trifluoromethyl)phenyl]ethenyl]-1,2-dihydro-2,7-naphthyridin-1-one;

6-(4-tert-butylpiperidin-1-yl)-8-{[4-(1-methylpiperidin-4-yl)phenyl]amino}-1,2-dihydro-2,7-naphthyridin-1-one;

6-[4-(2-hydroxypropan-2-yl)piperidin-1-yl]-8-{[4-(1-methylpiperidin-4-yl)phenyl]amino}-1,2-dihydro-2,7-naphthyridin-1-one;

3-[8-oxo-1-(phenylamino)-7,8-dihydro-2,7-naphthyridin-4-yl]benzonitrile

8-{[4-(1-methylpiperidin-4-yl)phenyl]amino}-6-[(2,2,2-trifluoroethyl)amino]-1,2-dihydro-2,7-naphthyridin-1-one;

6-(4-methylpiperidin-1-yl)-8-{[4-(1-methylpiperidin-4-yl)phenyl]amino}-1,2-dihydro-2,7-naphthyridin-1-one;

8-{[4-(morpholin-4-ylcarbonyl)phenyl]amino}-6-phenyl-1,2-dihydro-2,7-naphthyridin-1-one;
6-phenyl-8-{[4-(piperazin-1-ylcarbonyl)phenyl]amino}-1,2-dihydro-2,7-naphthyridin-1-one;
4-{[3-(4-methylpiperazin-1-yl)-8-oxo-7,8-dihydro-2,7-naphthyridin-1-yl]amino}-N-[2-(morpholin-4-yl)ethyl]benzamide;
4-({3-[(2-aminoethyl)amino]-8-oxo-7,8-dihydro-2,7-naphthyridin-1-yl}amino)-N-[2-(morpholin-4-yl)ethyl]benzamide;
4-{[3-(4-methoxypyridin-3-yl)-8-oxo-7,8-dihydro-2,7-naphthyridin-1-yl]amino}-N-[2-(morpholin-4-yl)ethyl]benzamide;
6-(2-methoxyphenyl)-8-{[4-(1-methylpiperidin-4-yl)phenyl]amino}-1,2-dihydro-2,7-naphthyridin-1-one;
6-(2-ethoxyphenyl)-8-{[4-(1-methylpiperidin-4-yl)phenyl]amino}-1,2-dihydro-2,7-naphthyridin-1-one;
8-{[4-(1-methylpiperidin-4-yl)phenyl]amino}-6-[2-(propan-2-yloxy)phenyl]-1,2-dihydro-2,7-naphthyridin-1-one;
6-(5-fluoro-2-methoxyphenyl)-8-{[4-(1-methylpiperidin-4-yl)phenyl]amino}-1,2-dihydro-2,7-naphthyridin-1-one;
6-(6-aminopyridin-3-yl)-8-{[5-(4-ethylpiperazin-1-yl)pyridin-2-yl]amino}-1,2-dihydro-2,7-naphthyridin-1-one;
6-(5-methoxypyridin-3-yl)-8-{[4-(piperidin-4-yl)phenyl]amino}-1,2-dihydro-2,7-naphthyridin-1-one;
6-(5-methoxypyridin-3-yl)-8-{[4-(piperidin-3-yl)phenyl]amino}-1,2-dihydro-2,7-naphthyridin-1-one;
6-(5-methoxypyridin-3-yl)-8-{[4-(1-methylpiperidin-3-yl)phenyl]amino}-1,2-dihydro-2,7-naphthyridin-1-one;
8-{[4-(1-methanesulfonylpiperidin-4-yl)phenyl]amino}-6-(5-methoxypyridin-3-yl)-1,2-dihydro-2,7-naphthyridin-1-one;
8-{[4-(1-acetylpiperidin-4-yl)phenyl]amino}-6-(5-methoxypyridin-3-yl)-1,2-dihydro-2,7-naphthyridin-1-one;
6-(3-aminopropyl)-8-({4-[(4-ethylpiperazin-1-yl)methyl]phenyl}amino)-1,2-dihydro-2,7-naphthyridin-1-one;
6-(5-methoxypyridin-3-yl)-8-({4-[2-(morpholin-4-yl)ethoxy]phenyl}amino)-1,2-dihydro-2,7-naphthyridin-1-one;
8-{[4-(morpholin-4-yl)phenyl]amino}-5-[1-(piperidin-4-yl)-1H-pyrazol-4-yl]-1,2-dihydro-2,7-naphthyridin-1-one;
5-{1-[2-(morpholin-4-yl)ethyl]-1H-pyrazol-4-yl}-8-{[4-(morpholin-4-yl)phenyl]amino}-1,2-dihydro-2,7-naphthyridin-1-one;
5-[(E)-2-(3-methoxyphenyl)ethenyl]-8-(phenylamino)-1,2-dihydro-2,7-naphthyridin-1-one;
4-(1-{[4-(1-methylpiperidin-4-yl)phenyl]amino}-8-oxo-7,8-dihydro-2,7-naphthyridin-3-yl)-1,4-thiomorpholine-1,1-dione;
6-(4-acetylpiperazin-1-yl)-8-{[4-(1-methylpiperidin-4-yl)phenyl]amino}-1,2-dihydro-2,7-naphthyridin-1-one;
8-{[4-(1-methylpiperidin-4-yl)phenyl]amino}-6-[4-(piperidin-1-yl)piperidin-1-yl]-1,2-dihydro-2,7-naphthyridin-1-one;
6-(4-hydroxypiperidin-1-yl)-8-{[4-(1-methylpiperidin-4-yl)phenyl]amino}-1,2-dihydro-2,7-naphthyridin-1-one;
8-{[4-(1-methylpiperidin-4-yl)phenyl]amino}-6-[4-(morpholin-4-yl)piperidin-1-yl]-1,2-dihydro-2,7-naphthyridin-1-one;
4-(1-{[4-(1-methylpiperidin-4-yl)phenyl]amino}-8-oxo-7,8-dihydro-2,7-naphthyridin-3-yl)-1,4-thiomorpholin-1-one;
6-(2-methoxypyridin-3-yl)-8-{[4-(1-methylpiperidin-4-yl)phenyl]amino}-1,2-dihydro-2,7-naphthyridin-1-one;
N-ethyl-4-(4-{[3-(5-methoxypyridin-3-yl)-8-oxo-7,8-dihydro-2,7-naphthyridin-1-yl]amino}phenyl)piperidine-1-carboxamide
6-(5-methoxypyridin-3-yl)-8-({4-[1-(propan-2-yl)piperidin-4-yl]phenyl}amino)-1,2-dihydro-2,7-naphthyridin-1-one;
8-{[4-(1-cyclopentylpiperidin-4-yl)phenyl]amino}-6-(5-methoxypyridin-3-yl)-1,2-dihydro-2,7-naphthyridin-1-one;
8-({4-[1-(2-methanesulfonylethyl)piperidin-4-yl]phenyl}amino)-6-(5-methoxypyridin-3-yl)-1,2-dihydro-2,7-naphthyridin-1-one;
6-(5-methoxypyridin-3-yl)-8-({4-[1-(3-oxobutyl)piperidin-4-yl]phenyl}amino)-1,2-dihydro-2,7-naphthyridin-1-one;
3-[4-(4-{[3-(5-methoxypyridin-3-yl)-8-oxo-7,8-dihydro-2,7-naphthyridin-1-yl]amino}phenyl)piperidin-1-yl]propanenitrile
4-[(8-oxo-7,8-dihydro-2,7-naphthyridin-1-yl)amino]-N-phenylbenzamide;
4-{[4-(1-methyl-1H-pyrazol-4-yl)-8-oxo-7,8-dihydro-2,7-naphthyridin-1-yl]amino}-N-phenylbenzamide;
4-{[4-(1-methyl-1H-pyrazol-4-yl)-8-oxo-7,8-dihydro-2,7-naphthyridin-1-yl]amino}-N-propylbenzamide;
4-{[3-(4-methylpyridin-3-yl)-8-oxo-7,8-dihydro-2,7-naphthyridin-1-yl]amino}-N-propylbenzamide;
4-{[3-(5-methoxypyridin-3-yl)-8-oxo-7,8-dihydro-2,7-naphthyridin-1-yl]amino}-N-methylbenzamide;
N-(2-hydroxyethyl)-4-{[3-(5-methoxypyridin-3-yl)-8-oxo-7,8-dihydro-2,7-naphthyridin-1-yl]amino}benzamide;
4-{[3-(cyclopropylamino)-8-oxo-7,8-dihydro-2,7-naphthyridin-1-yl]amino}-N-propylbenzamide;
8-({4-[3-(dimethylamino)propyl]phenyl}amino)-6-(5-methoxypyridin-3-yl)-1,2-dihydro-2,7-naphthyridin-1-one;
8-[(4-fluorophenyl)amino]-5-(furan-3-yl)-1,2-dihydro-2,7-naphthyridin-1-one;
8-{[4-(morpholin-4-yl)phenyl]amino}-6-[(2,2,2-trifluoroethyl)amino]-1,2-dihydro-2,7-naphthyridin-1-one;
N-cyclopropyl-4-{[3-(5-methoxypyridin-3-yl)-8-oxo-7,8-dihydro-2,7-naphthyridin-1-yl]amino}benzamide;
8-{[4-(1-acetylpiperidin-4-yl)phenyl]amino}-6-chloro-1,2-dihydro-2,7-naphthyridin-1-one;
8-{[4-(1-acetylpiperidin-4-yl)phenyl]amino}-6-(1H-indazol-5-yl)-1,2-dihydro-2,7-naphthyridin-1-one;
8-{[4-(1-acetylpiperidin-4-yl)phenyl]amino}-6-(1H-indol-6-yl)-1,2-dihydro-2,7-naphthyridin-1-one;
8-{[4-(1-acetylpiperidin-4-yl)phenyl]amino}-6-(1H-indol-5-yl)-1,2-dihydro-2,7-naphthyridin-1-one;
8-{[4-(1-acetylpiperidin-4-yl)phenyl]amino}-6-(3-fluoropyridin-4-yl)-1,2-dihydro-2,7-naphthyridin-1-one;
8-{[4-(1-acetylpiperidin-4-yl)phenyl]amino}-6-(6-fluoropyridin-3-yl)-1,2-dihydro-2,7-naphthyridin-1-one;
8-{[4-(1-acetylpiperidin-4-yl)phenyl]amino}-6-(2-methoxypyridin-4-yl)-1,2-dihydro-2,7-naphthyridin-1-one;
8-{[4-(1-acetylpiperidin-4-yl)phenyl]amino}-6-(6-fluoro-5-methylpyridin-3-yl)-1,2-dihydro-2,7-naphthyridin-1-one;

5-bromo-6-(1-methyl-1H-pyrazol-4-yl)-8-{[4-(piperidin-4-yl)phenyl]amino}-1,2-dihydro-2,7-naphthyridin-1-one;

6-(3-hydroxypiperidin-1-yl)-8-{[4-(1-methylpiperidin-4-yl)phenyl]amino}-1,2-dihydro-2,7-naphthyridin-1-one;

6-(4,4-difluoropiperidin-1-yl)-8-{[4-(1-methylpiperidin-4-yl)phenyl]amino}-1,2-dihydro-2,7-naphthyridin-1-one;

8-{[4-(1-methylpiperidin-4-yl)phenyl]amino}-6-[3-(trifluoromethyl)piperidin-1-yl]-1,2-dihydro-2,7-naphthyridin-1-one;

6-[4-(hydroxymethyl)piperidin-1-yl]-8-{[4-(1-methylpiperidin-4-yl)phenyl]amino}-1,2-dihydro-2,7-naphthyridin-1-one;

4-({8-oxo-3-[(3R)-piperidin-3-ylamino]-7,8-dihydro-2,7-naphthyridin-1-yl}amino)benzamide;

6-(3-methoxyphenyl)-8-{[4-(1-methylpiperidin-4-yl)phenyl]amino}-1,2-dihydro-2,7-naphthyridin-1-one;

8-{[4-(1-methylpiperidin-4-yl)phenyl]amino}-6-[3-(trifluoromethoxy)phenyl]-1,2-dihydro-2,7-naphthyridin-1-one;

8-{[4-(1-methylpiperidin-4-yl)phenyl]amino}-6-[2-(morpholin-4-yl)pyrimidin-5-yl]-1,2-dihydro-2,7-naphthyridin-1-one;

8-{[4-(1-methylpiperidin-4-yl)phenyl]amino}-6-(pyrimidin-5-yl)-1,2-dihydro-2,7-naphthyridin-1-one;

8-({4-[1-(ethanesulfonyl)piperidin-4-yl]phenyl}amino)-6-(5-methoxypyridin-3-yl)-1,2-dihydro-2,7-naphthyridin-1-one;

ethyl 3-[4-(4-{[3-(5-methoxypyridin-3-yl)-8-oxo-7,8-dihydro-2,7-naphthyridin-1-yl]amino}phenyl)piperidin-1-yl]propanoate 6-(3,3-difluoropiperidin-1-yl)-8-{[4-(1-methylpiperidin-4-yl)phenyl]amino}-1,2-dihydro-2,7-naphthyridin-1-one;

8-{[4-(1-methylpiperidin-4-yl)phenyl]amino}-6-[2-(trifluoromethyl)pyrrolidin-1-yl]-1,2-dihydro-2,7-naphthyridin-1-one;

8-{[4-(1-methylpiperidin-4-yl)phenyl]amino}-6-[4-(trifluoromethyl)piperidin-1-yl]-1,2-dihydro-2,7-naphthyridin-1-one;

8-{[4-(1-methylpiperidin-4-yl)phenyl]amino}-6-[(2S)-2-(trifluoromethyl)pyrrolidin-1-yl]-1,2-dihydro-2,7-naphthyridin-1-one;

6-(3,3-difluoropyrrolidin-1-yl)-8-{[4-(1-methylpiperidin-4-yl)phenyl]amino}-1,2-dihydro-2,7-naphthyridin-1-one;

6-(3-fluoropiperidin-1-yl)-8-{[4-(1-methylpiperidin-4-yl)phenyl]amino}-1,2-dihydro-2,7-naphthyridin-1-one;

4-bromo-6-(4-ethylpiperazin-1-yl)-8-{[4-(morpholin-4-yl)phenyl]amino}-1,2-dihydro-2,7-naphthyridin-1-one;

6-[(3S)-3-fluoropyrrolidin-1-yl]-8-{[4-(1-methylpiperidin-4-yl)phenyl]amino}-1,2-dihydro-2,7-naphthyridin-1-one;

4-chloro-6-(4-ethylpiperazin-1-yl)-8-{[4-(morpholin-4-yl)phenyl]amino}-1,2-dihydro-2,7-naphthyridin-1-one;

6-(4-ethylpiperazin-1-yl)-4-iodo-8-{[4-(morpholin-4-yl)phenyl]amino}-1,2-dihydro-2,7-naphthyridin-1-one;

5-(1-methyl-1H-pyrazol-4-yl)-8-{[4-(morpholin-4-ylcarbonyl)phenyl]amino}-1,2-dihydro-2,7-naphthyridin-1-one;

5-iodo-6-(1-methyl-1H-pyrazol-4-yl)-8-{[4-(piperidin-4-yl)phenyl]amino}-1,2-dihydro-2,7-naphthyridin-1-one;

5-chloro-6-(1-methyl-1H-pyrazol-4-yl)-8-{[4-(piperidin-4-yl)phenyl]amino}-1,2-dihydro-2,7-naphthyridin-1-one;

5-{1-[(4-fluorophenyl)amino]-8-oxo-7,8-dihydro-2,7-naphthyridin-4-yl}furan-2-carbonitrile 6-(2-aminopyrimidin-5-yl)-8-{[4-(1-methylpiperidin-4-yl)phenyl]amino}-1,2-dihydro-2,7-naphthyridin-1-one;

6-(2,4-dimethoxypyrimidin-5-yl)-8-{[4-(1-methylpiperidin-4-yl)phenyl]amino}-1,2-dihydro-2,7-naphthyridin-1-one;

8-{[4-(1-methylpiperidin-4-yl)phenyl]amino}-6-[4-(propan-2-yl)pyrimidin-5-yl]-1,2-dihydro-2,7-naphthyridin-1-one;

6-(5-methanesulfonylpyridin-3-yl)-8-{[4-(1-methylpiperidin-4-yl)phenyl]amino}-1,2-dihydro-2,7-naphthyridin-1-one;

ethyl 5-(1-{[4-(1-methylpiperidin-4-yl)phenyl]amino}-8-oxo-7,8-dihydro-2,7-naphthyridin-3-yl)pyridine-3-carboxylate;

8-{[4-(1-methylpiperidin-4-yl)phenyl]amino}-6-[5-(morpholin-4-yl)pyrazin-2-yl]-1,2-dihydro-2,7-naphthyridin-1-one;

8-{[4-(1-methylpiperidin-4-yl)phenyl]amino}-6-(4-methylpyridin-3-yl)-1,2-dihydro-2,7-naphthyridin-1-one;

8-{[4-(1-methanesulfonylpiperidin-4-yl)phenyl]amino}-6-[1-(2-methylpropyl)-1H-pyrazol-4-yl]-1,2-dihydro-2,7-naphthyridin-1-one;

8-{[4-(1-methanesulfonylpiperidin-4-yl)phenyl]amino}-6-(2-methoxyphenyl)-1,2-dihydro-2,7-naphthyridin-1-one;

8-{[4-(1-methanesulfonylpiperidin-4-yl)phenyl]amino}-6-phenyl-1,2-dihydro-2,7-naphthyridin-1-one;

6-(6-fluoropyridin-3-yl)-8-{[4-(1-methanesulfonylpiperidin-4-yl)phenyl]amino}-1,2-dihydro-2,7-naphthyridin-1-one;

8-{[4-(piperidin-4-yl)phenyl]amino}-6-(1,3,5-trimethyl-1H-pyrazol-4-yl)-1,2-dihydro-2,7-naphthyridin-1-one;

8-{[4-(1-methanesulfonylpiperidin-4-yl)phenyl]amino}-6-(1-methyl-1H-pyrazol-4-yl)-1,2-dihydro-2,7-naphthyridin-1-one;

6-[1-(1-methanesulfonylpiperidin-4-yl)-1H-pyrazol-4-yl]-8-{[4-(morpholin-4-yl)phenyl]amino}-1,2-dihydro-2,7-naphthyridin-1-one;

6-[1-(1-acetylpiperidin-4-yl)-1H-pyrazol-4-yl]-8-{[4-(morpholin-4-yl)phenyl]amino}-1,2-dihydro-2,7-naphthyridin-1-one;

N,2-dimethyl-2-(4-{[8-oxo-3-(pyrimidin-5-yl)-7,8-dihydro-2,7-naphthyridin-1-yl]amino}phenyl)propanamide 4-{[8-oxo-3-(pyrimidin-5-yl)-7,8-dihydro-2,7-naphthyridin-1-yl]amino}-N-propylbenzamide;

8-{[4-(4-hydroxypiperidin-1-yl)phenyl]amino}-6-(pyrimidin-5-yl)-1,2-dihydro-2,7-naphthyridin-1-one;

N-cyclopentyl-4-{[8-oxo-3-(pyrimidin-5-yl)-7,8-dihydro-2,7-naphthyridin-1-yl]amino}benzamide;

4-({8-oxo-3-[(2,2,2-trifluoroethyl)amino]-7,8-dihydro-2,7-naphthyridin-1-yl}amino)-N-propylbenzamide;

N,2-dimethyl-2-[4-({8-oxo-3-[(2,2,2-trifluoroethyl)amino]-7,8-dihydro-2,7-naphthyridin-1-yl}amino)phenyl]propanamide 8-[(4-fluorophenyl)amino]-5-(3-phenylpropyl)-1,2-dihydro-2,7-naphthyridin-1-one;

6-(4-ethylpiperazin-1-yl)-8-{[4-(morpholin-4-yl)phenyl]amino}-1-oxo-1,2-dihydro-2,7-naphthyridine-4-carbonitrile 1-(benzylamino)-8-oxo-7,8-dihydro-2,7-naphthyridine-4-carbonitrile 6-(4-methylpyridin-3-yl)-8-{[4-(morpholin-4-yl)phenyl]amino}-1,2-dihydro-2,7-naphthyridin-1-one;

6-chloro-8-{[4-(pyridin-3-yl)phenyl]amino}-1,2-dihydro-2,7-naphthyridin-1-one;

6-chloro-8-[(4-{2H,3H-imidazo[2,1-b][1,3]thiazol-6-yl}phenyl)amino]-1,2-dihydro-2,7-naphthyridin-1-one;

6-chloro-8-{[4-(1H-imidazol-4-yl)phenyl]amino}-1,2-dihydro-2,7-naphthyridin-1-one;

6-chloro-8-{[4-(1,3-oxazol-4-yl)phenyl]amino}-1,2-dihydro-2,7-naphthyridin-1-one;

6-(5-methanesulfonylpyridin-3-yl)-8-{[4-(pyridin-3-yl)phenyl]amino}-1,2-dihydro-2,7-naphthyridin-1-one;

8-[(4-{2H,3H-imidazo[2,1-b][1,3]thiazol-6-yl}phenyl)amino]-6-(5-methanesulfonylpyridin-3-yl)-1,2-dihydro-2,7-naphthyridin-1-one;

8-{[4-(1H-imidazol-4-yl)phenyl]amino}-6-(5-methanesulfonylpyridin-3-yl)-1,2-dihydro-2,7-naphthyridin-1-one;

8-{[4-(1-acetylpiperidin-4-yl)phenyl]amino}-6-(6-methoxypyridin-3-yl)-1,2-dihydro-2,7-naphthyridin-1-one;

5-(1-{[4-(1-acetylpiperidin-4-yl)phenyl]amino}-8-oxo-7,8-dihydro-2,7-naphthyridin-3-yl)pyridine-3-carbonitrile 8-{[4-(1-acetylpiperidin-4-yl)phenyl]amino}-6-(6-methylpyridin-3-yl)-1,2-dihydro-2,7-naphthyridin-1-one;

8-{[4-(1-acetylpiperidin-4-yl)phenyl]amino}-6-[6-(piperidin-1-yl)pyridin-3-yl]-1,2-dihydro-2,7-naphthyridin-1-one;

6-[(2-aminoethyl)amino]-8-{[4-(oxan-4-yl)phenyl]amino}-1,2-dihydro-2,7-naphthyridin-1-one;

6-(4-ethylpiperazin-1-yl)-8-{[4-(oxan-4-yl)phenyl]amino}-1,2-dihydro-2,7-naphthyridin-1-one;

8-{[4-(oxan-4-yl)phenyl]amino}-6-[(3R)-piperidin-3-ylamino]-1,2-dihydro-2,7-naphthyridin-1-one;

6-(2-chlorophenyl)-8-{[4-(oxan-4-yl)phenyl]amino}-1,2-dihydro-2,7-naphthyridin-1-one;

6-(5-methoxypyridin-3-yl)-8-{[4-(oxan-4-yl)phenyl]amino}-1,2-dihydro-2,7-naphthyridin-1-one;

6-[1-(2-methylpropyl)-1H-pyrazol-4-yl]-8-{[4-(oxan-4-yl)phenyl]amino}-1,2-dihydro-2,7-naphthyridin-1-one;

6-[(3aS,6aS)-octahydropyrrolo[3,4-c]pyrrol-2-yl]-8-{[4-(morpholin-4-yl)phenyl]amino}-1,2-dihydro-2,7-naphthyridin-1-one;

6-(4-ethylpiperazin-1-yl)-4-methyl-8-{[4-(morpholin-4-yl)phenyl]amino}-1,2-dihydro-2,7-naphthyridin-1-one;

8-[(4-fluorophenyl)amino]-5-(3-hydroxy-3-phenylpropyl)-1,2-dihydro-2,7-naphthyridin-1-one;

8-{[4-(1-cyclopropylpiperidin-4-yl)phenyl]amino}-6-(3,3-difluoropyrrolidin-1-yl)-1,2-dihydro-2,7-naphthyridin-1-one;

8-{[4-(1-cyclopropylpiperidin-4-yl)phenyl]amino}-6-[4-(2-hydroxypropan-2-yl)piperidin-1-yl]-1,2-dihydro-2,7-naphthyridin-1-one;

N-cyclopentyl-4-({8-oxo-3-[(2,2,2-trifluoroethyl)amino]-7,8-dihydro-2,7-naphthyridin-1-yl}amino)benzamide;

6-(2-methylpyrimidin-5-yl)-8-{[4-(morpholin-4-yl)phenyl]amino}-1,2-dihydro-2,7-naphthyridin-1-one;

6-[2-(dimethylamino)pyrimidin-5-yl]-8-{[4-(morpholin-4-yl)phenyl]amino}-1,2-dihydro-2,7-naphthyridin-1-one;

5-(1-{[4-(morpholin-4-yl)phenyl]amino}-8-oxo-7,8-dihydro-2,7-naphthyridin-3-yl)pyridine-3-carbonitrile N-methyl-4-{[8-oxo-3-(pyrimidin-5-yl)-7,8-dihydro-2,7-naphthyridin-1-yl]amino}benzamide;

4-{[3-(2,6-dimethylpyridin-3-yl)-8-oxo-7,8-dihydro-2,7-naphthyridin-1-yl]amino}-N-methylbenzamide;

4-({3-[2-(dimethylamino)pyrimidin-5-yl]-8-oxo-7,8-dihydro-2,7-naphthyridin-1-yl}amino)-N-methylbenzamide;

8-({4-[2-(morpholin-4-yl)ethoxy]phenyl}amino)-6-[4-(propan-2-yl)pyrimidin-5-yl]-1,2-dihydro-2,7-naphthyridin-1-one;

2-(4-{[3-(5-methanesulfonylpyridin-3-yl)-8-oxo-7,8-dihydro-2,7-naphthyridin-1-yl]amino}phenyl)-N,2-dimethylpropanamide 8-{[4-(1-acetylpiperidin-4-yl)phenyl]amino}-6-(3,3-difluoropyrrolidin-1-yl)-1,2-dihydro-2,7-naphthyridin-1-one;

6-chloro-8-[(2-methyl-1-oxo-2,3-dihydro-1H-isoindol-5-yl)amino]-1,2-dihydro-2,7-naphthyridin-1-one;

6-chloro-8-[(2-methyl-3-oxo-2,3-dihydro-1H-isoindol-5-yl)amino]-1,2-dihydro-2,7-naphthyridin-1-one;

6-(5-methoxypyridin-3-yl)-8-[(2-methyl-1-oxo-2,3-dihydro-1H-isoindol-5-yl)amino]-1,2-dihydro-2,7-naphthyridin-1-one;

6-(5-methoxypyridin-3-yl)-8-[(2-methyl-3-oxo-2,3-dihydro-1H-isoindol-5-yl)amino]-1,2-dihydro-2,7-naphthyridin-1-one;

3-{[3-(5-methoxypyridin-3-yl)-8-oxo-7,8-dihydro-2,7-naphthyridin-1-yl]amino}-N-methylbenzamide;

8-{[4-(1-acetylpiperidin-4-yl)phenyl]amino}-6-(2,6-difluoropyridin-3-yl)-1,2-dihydro-2,7-naphthyridin-1-one;

8-{[4-(1-acetylpiperidin-4-yl)phenyl]amino}-6-{imidazo[1,2-a]pyridin-6-yl}-1,2-dihydro-2,7-naphthyridin-1-one;

8-{[4-(1-acetylpiperidin-4-yl)phenyl]amino}-6-(5-fluoropyridin-3-yl)-1,2-dihydro-2,7-naphthyridin-1-one;

3-[(3-chloro-8-oxo-7,8-dihydro-2,7-naphthyridin-1-yl)amino]-N-methylbenzamide;

8-{[4-(1-acetylpiperidin-4-yl)phenyl]amino}-6-(6-fluoro-2-methylpyridin-3-yl)-1,2-dihydro-2,7-naphthyridin-1-one;

6-(5-methoxypyridin-3-yl)-8-{[4-(1,3-oxazol-4-yl)phenyl]amino}-1,2-dihydro-2,7-naphthyridin-1-one;

8-{[4-(1-acetylpiperidin-4-yl)phenyl]amino}-6-{1H-pyrrolo[2,3-b]pyridin-5-yl}-1,2-dihydro-2,7-naphthyridin-1-one;

5-(1-{[4-(1-acetylpiperidin-4-yl)phenyl]amino}-8-oxo-7,8-dihydro-2,7-naphthyridin-3-yl)pyridine-2-carbonitrile 6-(6-fluoro-2-methylpyridin-3-yl)-8-{[4-(1-methanesulfonylpiperidin-4-yl)phenyl]amino}-1,2-dihydro-2,7-naphthyridin-1-one;

6-(2,6-difluoropyridin-3-yl)-8-{[4-(1-methanesulfonylpiperidin-4-yl)phenyl]amino}-1,2-dihydro-2,7-naphthyridin-1-one;

5-(1-{[4-(1-acetylpiperidin-4-yl)phenyl]amino}-8-oxo-7,8-dihydro-2,7-naphthyridin-3-yl)-N-methylpyridine-2-carboxamide 6-chloro-8-{[4-(1-methanesulfonylpiperidin-3-yl)phenyl]amino}-1,2-dihydro-2,7-naphthyridin-1-one;

6-chloro-8-{[4-(1-methanesulfonylpyrrolidin-3-yl)phenyl]amino}-1,2-dihydro-2,7-naphthyridin-1-one;

6-chloro-8-{[4-(1-methylpyrrolidin-3-yl)phenyl]amino}-1,2-dihydro-2,7-naphthyridin-1-one;

4-chloro-6-(1-methyl-1H-pyrazol-4-yl)-8-{[4-(piperidin-4-yl)phenyl]amino}-1,2-dihydro-2,7-naphthyridin-1-one;

4-chloro-6-(5-methoxypyridin-3-yl)-8-{[4-(piperidin-4-yl)phenyl]amino}-1,2-dihydro-2,7-naphthyridin-1-one;

6-(3,3-difluoropyrrolidin-1-yl)-8-{[4-(1-methanesulfonylpiperidin-4-yl)phenyl]amino}-1,2-dihydro-2,7-naphthyridin-1-one;

4-({3-[4-(2-hydroxypropan-2-yl)piperidin-1-yl]-8-oxo-7,8-dihydro-2,7-naphthyridin-1-yl}amino)-N-methylbenzamide;

4-{[3-(1-methyl-1H-pyrazol-4-yl)-8-oxo-7,8-dihydro-2,7-naphthyridin-1-yl]amino}-N-propylbenzamide;

4-({3-[1-(2-methylpropyl)-1H-pyrazol-4-yl]-8-oxo-7,8-dihydro-2,7-naphthyridin-1-yl}amino)-N-propylbenzamide;

4-[(3-{1-[2-(morpholin-4-yl)ethyl]-1H-pyrazol-4-yl}-8-oxo-7,8-dihydro-2,7-naphthyridin-1-yl)amino]-N-propylbenzamide;

4-({8-oxo-3-[1-(piperidin-4-yl)-1H-pyrazol-4-yl]-7,8-dihydro-2,7-naphthyridin-1-yl}amino)-N-propylbenzamide;

4-{[3-(3-methyl-1H-pyrazol-4-yl)-8-oxo-7,8-dihydro-2,7-naphthyridin-1-yl]amino}-N-propylbenzamide;

N-methyl-4-{[3-(1-methyl-1H-pyrazol-4-yl)-8-oxo-7,8-dihydro-2,7-naphthyridin-1-yl]amino}benzamide;

N-methyl-4-({3-[1-(2-methylpropyl)-1H-pyrazol-4-yl]-8-oxo-7,8-dihydro-2,7-naphthyridin-1-yl}amino)benzamide;

N-methyl-4-[(3-{1-[2-(morpholin-4-yl)ethyl]-1H-pyrazol-4-yl}-8-oxo-7,8-dihydro-2,7-naphthyridin-1-yl)amino]benzamide;

N-methyl-4-({8-oxo-3-[1-(piperidin-4-yl)-1H-pyrazol-4-yl]-7,8-dihydro-2,7-naphthyridin-1-yl}amino)benzamide;

N,2-dimethyl-2-[4-(8-oxo-1-{[4-(piperidin-4-yl)phenyl]amino}-7,8-dihydro-2,7-naphthyridin-3-yl)-1H-pyrazol-1-yl]propanamide N-ethyl-2-methyl-2-[4-(8-oxo-1-{[4-(piperidin-4-yl)phenyl]amino}-7,8-dihydro-2,7-naphthyridin-3-yl)-1H-pyrazol-1-yl]propanamide N,N,2-trimethyl-2-[4-(8-oxo-1-{[4-(piperidin-4-yl)phenyl]amino}-7,8-dihydro-2,7-naphthyridin-3-yl)-1H-pyrazol-1-yl]propanamide 6-{1-[2-methyl-1-oxo-1-(pyrrolidin-1-yl)propan-2-yl]-1H-pyrazol-4-yl}-8-{[4-(piperidin-4-yl)phenyl]amino}-1,2-dihydro-2,7-naphthyridin-1-one;

8-({4-[(4-ethylpiperazin-1-yl)methyl]phenyl}amino)-6-(5-methanesulfonylpyridin-3-yl)-1,2-dihydro-2,7-naphthyridin-1-one;

8-({4-[(4-ethylpiperazin-1-yl)methyl]phenyl}amino)-6-(pyrimidin-5-yl)-1,2-dihydro-2,7-naphthyridin-1-one;

N-methyl-4-({8-oxo-3-[(2,2,2-trifluoroethyl)amino]-7,8-dihydro-2,7-naphthyridin-1-yl}amino)benzamide;

N,N-dimethyl-4-{[8-oxo-3-(pyrimidin-5-yl)-7,8-dihydro-2,7-naphthyridin-1-yl]amino}benzamide;

4-{[3-(5-methanesulfonylpyridin-3-yl)-8-oxo-7,8-dihydro-2,7-naphthyridin-1-yl]amino}-N-methylbenzamide;

6-(2-aminopyrimidin-5-yl)-8-{[4-(morpholin-4-yl)phenyl]amino}-1,2-dihydro-2,7-naphthyridin-1-one;

6-(3-methanesulfonylphenyl)-8-{[4-(morpholin-4-yl)phenyl]amino}-1,2-dihydro-2,7-naphthyridin-1-one;

3-(1-{[4-(morpholin-4-yl)phenyl]amino}-8-oxo-7,8-dihydro-2,7-naphthyridin-3-yl)benzene-1-sulfonamide;

N-methyl-4-{[3-(4-methylpyridin-3-yl)-8-oxo-7,8-dihydro-2,7-naphthyridin-1-yl]amino}benzamide;

N-tert-butyl-5-(1-{[4-(morpholin-4-yl)phenyl]amino}-8-oxo-7,8-dihydro-2,7-naphthyridin-3-yl)pyridine-3-carboxamide N-tert-butyl-5-(1-{[4-(morpholin-4-yl)phenyl]amino}-8-oxo-7,8-dihydro-2,7-naphthyridin-3-yl)pyridine-3-carboxamide 8-{[4-(1-methanesulfonylpiperidin-4-yl)phenyl]amino}-6-(pyrimidin-5-yl)-1,2-dihydro-2,7-naphthyridin-1-one;

8-{[4-(1-methanesulfonylpiperidin-4-yl)phenyl]amino}-6-(2-methoxypyrimidin-5-yl)-1,2-dihydro-2,7-naphthyridin-1-one;

8-{[4-(1-methanesulfonylpiperidin-4-yl)phenyl]amino}-6-(4-methylpyridin-3-yl)-1,2-dihydro-2,7-naphthyridin-1-one;

8-{[4-(1-methanesulfonylpyrrolidin-3-yl)phenyl]amino}-6-(5-methoxypyridin-3-yl)-1,2-dihydro-2,7-naphthyridin-1-one;

6-(5-methoxypyridin-3-yl)-8-{[4-(1-methylpyrrolidin-3-yl)phenyl]amino}-1,2-dihydro-2,7-naphthyridin-1-one;

6-(2,6-dimethylpyridin-3-yl)-8-{[4-(1-methanesulfonylpiperidin-4-yl)phenyl]amino}-1,2-dihydro-2,7-naphthyridin-1-one;

8-{[4-(1-methanesulfonylpiperidin-4-yl)phenyl]amino}-6-{1-[2-(morpholin-4-yl)ethyl]-1H-pyrazol-4-yl}-1,2-dihydro-2,7-naphthyridin-1-one;

5-bromo-6-[1-(2-methylpropyl)-1H-pyrazol-4-yl]-8-{[4-(piperidin-4-yl)phenyl]amino}-1,2-dihydro-2,7-naphthyridin-1-one;

8-{[4-(1-acetylpiperidin-4-yl)phenyl]amino}-5-(3-hydroxy-3-phenylpropyl)-1,2-dihydro-2,7-naphthyridin-1-one;

N-methyl-4-{[8-oxo-3-(2-oxopyrrolidin-1-yl)-7,8-dihydro-2,7-naphthyridin-1-yl]amino}benzamide;

N-methyl-4-{[8-oxo-3-(2-oxopiperidin-1-yl)-7,8-dihydro-2,7-naphthyridin-1-yl]amino}benzamide;

8-{[4-(1-cyclopropylpiperidin-4-yl)phenyl]amino}-6-(2-oxopyrrolidin-1-yl)-1,2-dihydro-2,7-naphthyridin-1-one;

2-[(1-{[4-(morpholin-4-yl)phenyl]amino}-8-oxo-7,8-dihydro-2,7-naphthyridin-3-yl)amino]benzene-1-sulfonamide;

6-{[2-(difluoromethane)sulfonylphenyl]amino}-8-{[4-(morpholin-4-yl)phenyl]amino}-1,2-dihydro-2,7-naphthyridin-1-one;

6-(5-methoxypyridin-3-yl)-8-{[2-(propane-2-sulfonyl)phenyl]amino}-1,2-dihydro-2,7-naphthyridin-1-one;

4-{[3-(2,4-dimethoxypyrimidin-5-yl)-8-oxo-7,8-dihydro-2,7-naphthyridin-1-yl]amino}-N,2-dimethylbenzamide;

4-{[3-(5-methoxypyridin-3-yl)-8-oxo-7,8-dihydro-2,7-naphthyridin-1-yl]amino}-N,2-dimethylbenzamide;

8-{[4-(1-ethylpiperidin-4-yl)phenyl]amino}-6-(5-methanesulfonylpyridin-3-yl)-1,2-dihydro-2,7-naphthyridin-1-one;

8-{[4-(1-methanesulfonylpiperidin-3-yl)phenyl]amino}-6-(5-methoxypyridin-3-yl)-1,2-dihydro-2,7-naphthyridin-1-one;

5-chloro-6-(5-methoxypyridin-3-yl)-8-{[4-(piperidin-4-yl)phenyl]amino}-1,2-dihydro-2,7-naphthyridin-1-one;

8-[(4-{1-[2-(dimethylamino)acetyl]piperidin-4-yl}phenyl]amino}-6-[1-(2-methylpropyl)-1H-pyrazol-4-yl]-1,2-dihydro-2,7-naphthyridin-1-one;

8-{[4-(morpholin-4-yl)phenyl]amino}-6-[1-(pyridin-2-ylmethyl)-1H-pyrazol-4-yl]-1,2-dihydro-2,7-naphthyridin-1-one;

8-{[4-(piperidin-4-yl)phenyl]amino}-6-[1-(pyridin-2-ylmethyl)-1H-pyrazol-4-yl]-1,2-dihydro-2,7-naphthyridin-1-one;

N-methyl-4-({8-oxo-3-[1-(pyridin-2-ylmethyl)-1H-pyrazol-4-yl]-7,8-dihydro-2,7-naphthyridin-1-yl}amino)benzamide;

8-{[4-(oxan-4-yl)phenyl]amino}-6-[1-(pyridin-2-ylmethyl)-1H-pyrazol-4-yl]-1,2-dihydro-2,7-naphthyridin-1-one;

8-({4-[1-(2-methanesulfonylethyl)piperidin-4-yl]phenyl}amino)-6-[1-(2-methylpropyl)-1H-pyrazol-4-yl]-1,2-dihydro-2,7-naphthyridin-1-one;

6-(3,3-difluoropiperidin-1-yl)-8-{[4-(oxan-4-yl)phenyl]amino}-1,2-dihydro-2,7-naphthyridin-1-one;

8-{[4-(1-methanesulfonylpyrrolidin-3-yl)phenyl]amino}-6-(1-methyl-1H-pyrazol-4-yl)-1,2-dihydro-2,7-naphthyridin-1-one;

8-({4-[1-(2-methanesulfonylacetyl)piperidin-4-yl]phenyl}amino)-6-[1-(2-methylpropyl)-1H-pyrazol-4-yl]-1,2-dihydro-2,7-naphthyridin-1-one;

6-[1-(3-methylbutyl)-1H-pyrazol-4-yl]-8-{[4-(oxan-4-yl)phenyl]amino}-1,2-dihydro-2,7-naphthyridin-1-one;

8-{[4-(morpholin-4-yl)phenyl]amino}-6-[5-(propane-2-sulfonyl)pyridin-3-yl]-1,2-dihydro-2,7-naphthyridin-1-one;

8-{[4-(piperidin-4-yl)phenyl]amino}-6-[5-(propane-2-sulfonyl)pyridin-3-yl]-1,2-dihydro-2,7-naphthyridin-1-one;

N-methyl-4-{[8-oxo-3-(2-oxoazepan-1-yl)-7,8-dihydro-2,7-naphthyridin-1-yl]amino}benzamide;

6-(3,3-difluoropyrrolidin-1-yl)-8-{[4-(oxan-4-yl)phenyl]amino}-1,2-dihydro-2,7-naphthyridin-1-one;

8-{[4-(1-cyclopropylpiperidin-4-yl)phenyl]amino}-6-(3-methanesulfonylphenyl)-1,2-dihydro-2,7-naphthyridin-1-one;

8-({6-[(2R,6S)-2,6-dimethylmorpholin-4-yl]pyridin-3-yl}amino)-6-(3-methanesulfonylphenyl)-1,2-dihydro-2,7-naphthyridin-1-one;

2-{[1-({6-[(2R,6S)-2,6-dimethylmorpholin-4-yl]pyridin-3-yl}amino)-8-oxo-7,8-dihydro-2,7-naphthyridin-3-yl]amino}benzene-1-sulfonamide;

4-({8-oxo-3-[(2-sulfamoylphenyl)amino]-7,8-dihydro-2,7-naphthyridin-1-yl}amino)-N-propylbenzamide;

N,2-dimethyl-4-({8-oxo-3-[(2-sulfamoylphenyl)amino]-7,8-dihydro-2,7-naphthyridin-1-yl}amino)benzamide;

2-[(8-oxo-1-{[4-(piperidin-4-yl)phenyl]amino}-7,8-dihydro-2,7-naphthyridin-3-yl)amino]benzene-1-sulfonamide;

2-[(1-{[4-(morpholin-4-yl)phenyl]amino}-8-oxo-7,8-dihydro-2,7-naphthyridin-3-yl)amino]benzamide;

6-[(4-fluoro-2-methylphenyl)amino]-8-{[4-(morpholin-4-yl)phenyl]amino}-1,2-dihydro-2,7-naphthyridin-1-one;

8-{[4-(morpholin-4-yl)phenyl]amino}-6-{[2-(propane-2-sulfonyl)phenyl]amino}-1,2-dihydro-2,7-naphthyridin-1-one;

6-(3-methanesulfonylphenyl)-8-{[4-(piperidin-4-yl)phenyl]amino}-1,2-dihydro-2,7-naphthyridin-1-one;

4-{[3-(3-methanesulfonylphenyl)-8-oxo-7,8-dihydro-2,7-naphthyridin-1-yl]amino}-N-propylbenzamide;

N-ethyl-3-(1-{[4-(morpholin-4-yl)phenyl]amino}-8-oxo-7,8-dihydro-2,7-naphthyridin-3-yl)benzene-1-sulfonamide;

8-{[4-(1-methanesulfonylpyrrolidin-3-yl)phenyl]amino}-6-(pyrimidin-5-yl)-1,2-dihydro-2,7-naphthyridin-1-one;

{[3-(5-methoxypyridin-3-yl)-8-oxo-7,8-dihydro-2,7-naphthyridin-1-yl]amino}-N-methylbenzene-1-sulfonamide;

6-[5-(ethanesulfonyl)pyridin-3-yl]-8-{[4-(morpholin-4-yl)phenyl]amino}-1,2-dihydro-2,7-naphthyridin-1-one;

6-[5-(ethanesulfonyl)pyridin-3-yl]-8-{[4-(piperidin-4-yl)phenyl]amino}-1,2-dihydro-2,7-naphthyridin-1-one;

6-[5-(ethanesulfonyl)pyridin-3-yl]-8-{[4-(1-methanesulfonylpiperidin-4-yl)phenyl]amino}-1,2-dihydro-2,7-naphthyridin-1-one;

4-({3-[5-(ethanesulfonyl)pyridin-3-yl]-8-oxo-7,8-dihydro-2,7-naphthyridin-1-yl}amino)-N-methylbenzamide;

8-{[4-(1-methylpiperidin-4-yl)phenyl]amino}-6-[5-(propane-2-sulfonyl)pyridin-3-yl]-1,2-dihydro-2,7-naphthyridin-1-one;

6-[5-(ethanesulfonyl)pyridin-3-yl]-8-{[4-(1-methylpiperidin-4-yl)phenyl]amino}-1,2-dihydro-2,7-naphthyridin-1-one;

8-{[4-(1-methylpiperidin-4-yl)phenyl]amino}-6-[1-(2-methylpropyl)-1H-pyrazol-4-yl]-1,2-dihydro-2,7-naphthyridin-1-one;

2,2-dimethyl-6-(1-{[4-(morpholin-4-yl)phenyl]amino}-8-oxo-7,8-dihydro-2,7-naphthyridin-3-yl)-3,4-dihydro-2H-1,4-benzoxazin-3-one;

2,2-dimethyl-7-(1-{[4-(morpholin-4-yl)phenyl]amino}-8-oxo-7,8-dihydro-2,7-naphthyridin-3-yl)-3,4-dihydro-2H-1,4-benzoxazin-3-one;

7-[(1-{[4-(morpholin-4-yl)phenyl]amino}-8-oxo-7,8-dihydro-2,7-naphthyridin-3-yl)amino]-3,4-dihydro-2H-1,4-benzoxazin-3-one;

2,2-dimethyl-6-[(1-{[4-(morpholin-4-yl)phenyl]amino}-8-oxo-7,8-dihydro-2,7-naphthyridin-3-yl)amino]-3,4-dihydro-2H-1,4-benzoxazin-3-one;

N-methyl-2-[(1-{[4-(morpholin-4-yl)phenyl]amino}-8-oxo-7,8-dihydro-2,7-naphthyridin-3-yl)amino]benzamide;

8-{[4-(1-methylpiperidin-4-yl)phenyl]amino}-6-(2-methylpyrimidin-5-yl)-1,2-dihydro-2,7-naphthyridin-1-one;

6-(2,3-dihydro-1H-indol-1-yl)-8-{[4-(morpholin-4-yl)phenyl]amino}-1,2-dihydro-2,7-naphthyridin-1-one;

6-(1-methyl-1H-pyrazol-4-yl)-8-{[3-methyl-4-(piperidin-4-yl)phenyl]amino}-1,2-dihydro-2,7-naphthyridin-1-one;

8-{[3-methyl-4-(piperidin-4-yl)phenyl]amino}-6-[1-(2-methylpropyl)-1H-pyrazol-4-yl]-1,2-dihydro-2,7-naphthyridin-1-one;

6-(5-methoxypyridin-3-yl)-8-{[3-methyl-4-(piperidin-4-yl)phenyl]amino}-1,2-dihydro-2,7-naphthyridin-1-one;

3-(1-{[3-methyl-4-(piperidin-4-yl)phenyl]amino}-8-oxo-7,8-dihydro-2,7-naphthyridin-3-yl)benzene-1-sulfonamide;

6-[2-(methylsulfanyl)pyrimidin-5-yl]-8-{[4-(piperidin-4-yl)phenyl]amino}-1,2-dihydro-2,7-naphthyridin-1-one;

6-(6-{[2-(morpholin-4-yl)ethyl]amino}pyridin-3-yl)-8-{[4-(piperidin-4-yl)phenyl]amino}-1,2-dihydro-2,7-naphthyridin-1-one;

6-(1-methyl-1H-pyrazol-4-yl)-8-{[6-(piperidin-4-yl)pyridin-3-yl]amino}-1,2-dihydro-2,7-naphthyridin-1-one;

6-(5-methoxypyridin-3-yl)-8-{[6-(piperidin-4-yl)pyridin-3-yl]amino}-1,2-dihydro-2,7-naphthyridin-1-one;

6-acetyl-8-{[4-(morpholin-4-yl)phenyl]amino}-1,2-dihydro-2,7-naphthyridin-1-one;

6-[(1E)-1-(methoxyimino)ethyl]-8-{[4-(morpholin-4-yl)phenyl]amino}-1,2-dihydro-2,7-naphthyridin-1-one;

2-[(1-{[4-(1-acetylpiperidin-4-yl)phenyl]amino}-8-oxo-7,8-dihydro-2,7-naphthyridin-3-yl)amino]benzene-1-sulfonamide;

2-[(1-{[4-(oxan-4-yl)phenyl]amino}-8-oxo-7,8-dihydro-2,7-naphthyridin-3-yl)amino]benzene-1-sulfonamide;

2-[(1-{[4-(1-methanesulfonylpiperidin-4-yl)phenyl]amino}-8-oxo-7,8-dihydro-2,7-naphthyridin-3-yl)amino]benzene-1-sulfonamide;

2-{[1-({4-[2-(morpholin-4-yl)ethoxy]phenyl}amino)-8-oxo-7,8-dihydro-2,7-naphthyridin-3-yl]amino}benzene-1-sulfonamide;

tert-butyl 4-(4-{[8-oxo-3-(1,3,5-trimethyl-1H-pyrazol-4-yl)-7,8-dihydro-2,7-naphthyridin-1-yl]amino}phenyl)piperidine-1-carboxylate;

5-(8-oxo-1-{[4-(piperidin-4-yl)phenyl]amino}-7,8-dihydro-2,7-naphthyridin-3-yl)pyridine-3-sulfonamide;

5-(1-{[4-(morpholin-4-yl)phenyl]amino}-8-oxo-7,8-dihydro-2,7-naphthyridin-3-yl)pyridine-3-sulfonamide;

5-(1-{[4-(1-ethylpiperidin-4-yl)phenyl]amino}-8-oxo-7,8-dihydro-2,7-naphthyridin-3-yl)pyridine-3-sulfonamide;

5-[1-({4-[1-(2-hydroxyethyl)piperidin-4-yl]phenyl}amino)-8-oxo-7,8-dihydro-2,7-naphthyridin-3-yl]pyridine-3-sulfonamide;

5-(1-{[4-(1-acetylpiperidin-4-yl)phenyl]amino}-8-oxo-7,8-dihydro-2,7-naphthyridin-3-yl)pyridine-3-sulfonamide;

N-methyl-4-{[8-oxo-3-(5-sulfamoylpyridin-3-yl)-7,8-dihydro-2,7-naphthyridin-1-yl]amino}benzamide;

6-[2-(methylamino)pyrimidin-5-yl]-8-{[4-(piperidin-4-yl)phenyl]amino}-1,2-dihydro-2,7-naphthyridin-1-one;

6-(6-methylpyridin-2-yl)-8-{[4-(morpholin-4-yl)phenyl]amino}-1,2-dihydro-2,7-naphthyridin-1-one;

5-ethenyl-6-(1-methyl-1H-pyrazol-4-yl)-8-{[4-(piperidin-4-yl)phenyl]amino}-1,2-dihydro-2,7-naphthyridin-1-one;

6-(6-methylpyridin-2-yl)-8-{[4-(piperidin-4-yl)phenyl]amino}-1,2-dihydro-2,7-naphthyridin-1-one;

8-{[4-(piperidin-4-yl)phenyl]amino}-6-(pyridin-2-yl)-1,2-dihydro-2,7-naphthyridin-1-one;

4-(1-{[4-(morpholin-4-yl)phenyl]amino}-8-oxo-7,8-dihydro-2,7-naphthyridin-3-yl)-3,4-dihydro-2H-1,4-benzothiazine-1,1-dione;

N-methyl-2-[(1-{[4-(morpholin-4-yl)phenyl]amino}-8-oxo-7,8-dihydro-2,7-naphthyridin-3-yl)amino]benzene-1-sulfonamide;

N-ethyl-2-[(1-{[4-(morpholin-4-yl)phenyl]amino}-8-oxo-7,8-dihydro-2,7-naphthyridin-3-yl)amino]benzene-1-sulfonamide;

6-[(2-methanesulfonylphenyl)amino]-8-{[4-(morpholin-4-yl)phenyl]amino}-1,2-dihydro-2,7-naphthyridin-1-one;

2-[(1-{[4-(1-methylpiperidin-4-yl)phenyl]amino}-8-oxo-7,8-dihydro-2,7-naphthyridin-3-yl)amino]benzene-1-sulfonamide;

6-(2-aminopyrimidin-5-yl)-8-({3-[2-(morpholin-4-yl)ethoxy]phenyl}amino)-1,2-dihydro-2,7-naphthyridin-1-one;

2-({1-[(2,2-dimethyl-3-oxo-3,4-dihydro-2H-1,4-benzoxazin-6-yl)amino]-8-oxo-7,8-dihydro-2,7-naphthyridin-3-yl}amino)benzene-1-sulfonamide;

4-methoxy-2-[(1-{[4-(morpholin-4-yl)phenyl]amino}-8-oxo-7,8-dihydro-2,7-naphthyridin-3-yl)amino]benzene-1-sulfonamide;

N,N,2-trimethyl-5-(1-{[4-(morpholin-4-yl)phenyl]amino}-8-oxo-7,8-dihydro-2,7-naphthyridin-3-yl)benzene-1-sulfonamide;

3-(1-{[4-(morpholin-4-yl)phenyl]amino}-8-oxo-7,8-dihydro-2,7-naphthyridin-3-yl)-N-(propan-2-yl)benzene-1-sulfonamide;

N-cyclopropyl-3-(1-{[4-(morpholin-4-yl)phenyl]amino}-8-oxo-7,8-dihydro-2,7-naphthyridin-3-yl)benzene-1-sulfonamide;

8-{[4-(1-acetylpiperidin-4-yl)phenyl]amino}-6-(3-methanesulfonylphenyl)-1,2-dihydro-2,7-naphthyridin-1-one;

8-{[4-(1-ethylpiperidin-4-yl)phenyl]amino}-6-(3-methanesulfonylphenyl)-1,2-dihydro-2,7-naphthyridin-1-one;

6-(3-methanesulfonylphenyl)-8-{[4-(oxan-4-yl)phenyl]amino}-1,2-dihydro-2,7-naphthyridin-1-one;

N-[3-(1-{[2-methoxy-5-methyl-4-(piperidin-4-yl)phenyl]amino}-8-oxo-7,8-dihydro-2,7-naphthyridin-3-yl)phenyl]methanesulfonamide;

2-hydroxy-N-[3-(1-{[4-(morpholin-4-yl)phenyl]amino}-8-oxo-7,8-dihydro-2,7-naphthyridin-3-yl)phenyl]ethane-1-sulfonamido 8-{[2-methoxy-5-methyl-4-(piperidin-4-yl)phenyl]amino}-6-(2-methoxypyridin-3-yl)-1,2-dihydro-2,7-naphthyridin-1-one;

6-(2,6-dimethoxypyridin-3-yl)-8-{[2-methoxy-5-methyl-4-(piperidin-4-yl)phenyl]amino}-1,2-dihydro-2,7-naphthyridin-1-one;

6-(4-methanesulfonylphenyl)-8-{[2-methoxy-5-methyl-4-(piperidin-4-yl)phenyl]amino}-1,2-dihydro-2,7-naphthyridin-1-one;

6-[2-(methylsulfanyl)pyrimidin-5-yl]-8-{[4-(morpholin-4-yl)phenyl]amino}-1,2-dihydro-2,7-naphthyridin-1-one;

6-[2-(methylamino)pyrimidin-5-yl]-8-{[4-(1-methylpiperidin-4-yl)phenyl]amino}-1,2-dihydro-2,7-naphthyridin-1-one;

6-(6-methoxypyridin-2-yl)-8-{[4-(piperidin-4-yl)phenyl]amino}-1,2-dihydro-2,7-naphthyridin-1-one;

6-(6-fluoropyridin-2-yl)-8-{[4-(piperidin-4-yl)phenyl]amino}-1,2-dihydro-2,7-naphthyridin-1-one;

8-{[4-(piperidin-4-yl)phenyl]amino}-6-(pyrimidin-2-yl)-1,2-dihydro-2,7-naphthyridin-1-one;

6-(2-ethyl-1,3-thiazol-4-yl)-8-{[4-(morpholin-4-yl)phenyl]amino}-1,2-dihydro-2,7-naphthyridin-1-one;

6-(5-methylpyridin-2-yl)-8-{[4-(piperidin-4-yl)phenyl]amino}-1,2-dihydro-2,7-naphthyridin-1-one;

6-(4-methylpyridin-2-yl)-8-{[4-(piperidin-4-yl)phenyl]amino}-1,2-dihydro-2,7-naphthyridin-1-one;

6-[2-(methylsulfanyl)pyrimidin-4-yl]-8-{[4-(piperidin-4-yl)phenyl]amino}-1,2-dihydro-2,7-naphthyridin-1-one;

2-(4-{[3-(2-aminopyrimidin-5-yl)-8-oxo-7,8-dihydro-2,7-naphthyridin-1-yl]amino}phenyl)-N,2-dimethylpropanamide 2-[(1-{[4-(morpholin-4-yl)phenyl]amino}-8-oxo-7,8-dihydro-2,7-naphthyridin-3-yl)amino]ethane-1-sulfonamide;

2-methyl-6-[(1-{[4-(morpholin-4-yl)phenyl]amino}-8-oxo-7,8-dihydro-2,7-naphthyridin-3-yl)amino]benzene-1-sulfonamide;

N,N-dimethyl-2-[(1-{[4-(morpholin-4-yl)phenyl]amino}-8-oxo-7,8-dihydro-2,7-naphthyridin-3-yl)amino]benzene-1-sulfonamide;

2,2-dimethyl-6-(8-oxo-1-{[4-(piperidin-4-yl)phenyl]amino}-7,8-dihydro-2,7-naphthyridin-3-yl)-3,4-dihydro-2H-1,4-benzoxazin-3-one;

N,2-dimethyl-2-[4-({8-oxo-3-[(2-sulfamoylphenyl)amino}-7,8-dihydro-2,7-naphthyridin-1-yl]amino)phenyl]propanamide 2-[(1-{[4-(1-cyclopropylpiperidin-4-yl)phenyl]amino}-8-oxo-7,8-dihydro-2,7-naphthyridin-3-yl)amino]-6-methylbenzene-1-sulfonamide;

6-(2-aminopyrimidin-5-yl)-8-{[4-(trifluoromethoxy)phenyl]amino}-1,2-dihydro-2,7-naphthyridin-1-one;

3-{[3-(2-aminopyrimidin-5-yl)-8-oxo-7,8-dihydro-2,7-naphthyridin-1-yl]amino}-N-methylbenzene-1-sulfonamide;

2,2-dimethyl-6-(1-{[4-(1-methylpiperidin-4-yl)phenyl]amino}-8-oxo-7,8-dihydro-2,7-naphthyridin-3-yl)-3,4-dihydro-2H-1,4-benzoxazin-3-one;

N-methyl-3-({8-oxo-3-[(2-sulfamoylphenyl)amino]-7,8-dihydro-2,7-naphthyridin-1-yl}amino)benzene-1-sulfonamide;

6-[1-(2-methylpropyl)-1H-pyrazol-4-yl]-8-({3-[2-(morpholin-4-yl)ethoxy]phenyl}amino)-1,2-dihydro-2,7-naphthyridin-1-one;

6-(2-chlorophenyl)-8-({3-[2-(morpholin-4-yl)ethoxy]phenyl}amino)-1,2-dihydro-2,7-naphthyridin-1-one;

N-ethoxy-4-{[3-(4-methylpyridin-3-yl)-8-oxo-7,8-dihydro-2,7-naphthyridin-1-yl]amino}benzamide;

2-[(1-{[4-(1-cyclopropylpiperidin-4-yl)phenyl]amino}-8-oxo-7,8-dihydro-2,7-naphthyridin-3-yl)amino]benzene-1-sulfonamide;

2-methyl-6-[(1-{[3-methyl-4-(piperidin-4-yl)phenyl]amino}-8-oxo-7,8-dihydro-2,7-naphthyridin-3-yl)amino]benzene-1-sulfonamide;

4-methyl-2-[(1-{[3-methyl-4-(piperidin-4-yl)phenyl]amino}-8-oxo-7,8-dihydro-2,7-naphthyridin-3-yl)amino]benzene-1-sulfonamide;

6-(1-methyl-1H-pyrazol-5-yl)-8-{[4-(morpholin-4-yl)phenyl]amino}-1,2-dihydro-2,7-naphthyridin-1-one;

6-(1-methyl-1H-pyrazol-3-yl)-8-{[4-(morpholin-4-yl)phenyl]amino}-1,2-dihydro-2,7-naphthyridin-1-one;

2-methoxy-5-(1-{[4-(morpholin-4-yl)phenyl]amino}-8-oxo-7,8-dihydro-2,7-naphthyridin-3-yl)benzene-1-sulfonamide;

2-methoxy-N-methyl-5-(1-{[4-(morpholin-4-yl)phenyl]amino}-8-oxo-7,8-dihydro-2,7-naphthyridin-3-yl)benzene-1-sulfonamide;

tert-butyl 3-(4-{[3-(4-methanesulfonylphenyl)-8-oxo-7,8-dihydro-2,7-naphthyridin-1-yl]amino}phenyl)pyrrolidine-1-carboxylate;

6-(4-methanesulfonylphenyl)-8-{[4-(pyrrolidin-3-yl)phenyl]amino}-1,2-dihydro-2,7-naphthyridin-1-one;

tert-butyl 4-(4-{[3-(4-methanesulfonylphenyl)-8-oxo-7,8-dihydro-2,7-naphthyridin-1-yl]amino}phenyl)piperidine-1-carboxylate;

6-(4-methanesulfonylphenyl)-8-{[4-(piperidin-4-yl)phenyl]amino}-1,2-dihydro-2,7-naphthyridin-1-one;

6-(2-methyl-1,3-thiazol-4-yl)-8-{[4-(morpholin-4-yl)phenyl]amino}-1,2-dihydro-2,7-naphthyridin-1-one;

6-(2-aminopyrimidin-5-yl)-8-({3-[2-(morpholin-4-yl)-2-oxoethoxy]phenyl}amino)-1,2-dihydro-2,7-naphthyridin-1-one;

6-(2-aminopyrimidin-5-yl)-8-({4-methyl-3-[2-(morpholin-4-yl)ethoxy]phenyl}amino)-1,2-dihydro-2,7-naphthyridin-1-one;

6-(2-aminopyrimidin-5-yl)-8-[(3-hydroxy-4-methylphenyl)amino]-1,2-dihydro-2,7-naphthyridin-1-one;

6-(2-aminopyrimidin-5-yl)-8-({4-[2-(morpholin-4-yl)ethoxy]phenyl}amino)-1,2-dihydro-2,7-naphthyridin-1-one;

3-{[3-(2-aminopyrimidin-5-yl)-8-oxo-7,8-dihydro-2,7-naphthyridin-1-yl]amino}-N-methylbenzamide;

6-(2-methylpyrimidin-5-yl)-8-({3-[2-(morpholin-4-yl)ethoxy]phenyl}amino)-1,2-dihydro-2,7-naphthyridin-1-one;

8-({4-methyl-3-[2-(morpholin-4-yl)ethoxy]phenyl}amino)-6-(2-methylpyrimidin-5-yl)-1,2-dihydro-2,7-naphthyridin-1-one;

6-(4-methylpyridin-3-yl)-8-({3-[2-(morpholin-4-yl)ethoxy]phenyl}amino)-1,2-dihydro-2,7-naphthyridin-1-one;

6-(2,6-dimethylpyridin-3-yl)-8-({3-[2-(morpholin-4-yl)ethoxy]phenyl}amino)-1,2-dihydro-2,7-naphthyridin-1-one;

8-{[4-(morpholin-4-yl)phenyl]amino}-6-(2-phenyl-1,3-thiazol-4-yl)-1,2-dihydro-2,7-naphthyridin-1-one;

6-(5-methanesulfonyl-4-methylpyridin-3-yl)-8-{[4-(morpholin-4-yl)phenyl]amino}-1,2-dihydro-2,7-naphthyridin-1-one;

6-(5-methanesulfonyl-4-methylpyridin-3-yl)-8-{[4-(morpholin-4-yl)phenyl]amino}-1,2-dihydro-2,7-naphthyridin-1-one;

6-(5-methanesulfonyl-4-methylpyridin-3-yl)-8-{[4-(piperidin-4-yl)phenyl]amino}-1,2-dihydro-2,7-naphthyridin-1-one;

6-(5-methanesulfonyl-4-methylpyridin-3-yl)-8-{[4-(1-methylpiperidin-4-yl)phenyl]amino}-1,2-dihydro-2,7-naphthyridin-1-one;

6-[3-(2-hydroxypropan-2-yl)phenyl]-8-{[4-(morpholin-4-yl)phenyl]amino}-1,2-dihydro-2,7-naphthyridin-1-one;

6-[4-(2-hydroxypropan-2-yl)phenyl]-8-{[4-(morpholin-4-yl)phenyl]amino}-1,2-dihydro-2,7-naphthyridin-1-one;

6-[3-methanesulfonyl-4-(morpholin-4-ylmethyl)phenyl]-8-{[4-(morpholin-4-yl)phenyl]amino}-1,2-dihydro-2,7-naphthyridin-1-one;

6-[3-methanesulfonyl-4-(pyrrolidin-1-ylmethyl)phenyl]-8-{[4-(morpholin-4-yl)phenyl]amino}-1,2-dihydro-2,7-naphthyridin-1-one;

6-(5-ethoxypyridin-3-yl)-8-{[4-(morpholin-4-yl)phenyl]amino}-1,2-dihydro-2,7-naphthyridin-1-one;

6-(6-amino-5-methoxypyridin-3-yl)-8-{[4-(morpholin-4-yl)phenyl]amino}-1,2-dihydro-2,7-naphthyridin-1-one;

6-(5-methylpyridin-3-yl)-8-{[4-(morpholin-4-yl)phenyl]amino}-1,2-dihydro-2,7-naphthyridin-1-one;

6-(3-methanesulfonyl-4-methylphenyl)-8-{[4-(morpholin-4-yl)phenyl]amino}-1,2-dihydro-2,7-naphthyridin-1-one;

N-[5-(1-{[4-(morpholin-4-yl)phenyl]amino}-8-oxo-7,8-dihydro-2,7-naphthyridin-3-yl)pyridin-2-yl]acetamide 6-(4-methoxypyrimidin-5-yl)-8-{[4-(morpholin-4-yl)phenyl]amino}-1,2-dihydro-2,7-naphthyridin-1-one;

6-(6-amino-4-methylpyridin-3-yl)-8-{[4-(morpholin-4-yl)phenyl]amino}-1,2-dihydro-2,7-naphthyridin-1-one;

6-(6-amino-4-methylpyridin-3-yl)-8-{[4-(1-methylpiperidin-4-yl)phenyl]amino}-1,2-dihydro-2,7-naphthyridin-1-one;

6-(6-amino-5-methylpyridin-3-yl)-8-{[4-(morpholin-4-yl)phenyl]amino}-1,2-dihydro-2,7-naphthyridin-1-one;
6-(2-aminopyrimidin-5-yl)-8-({4-[2-(pyrrolidin-1-yl)ethoxy]phenyl}amino)-1,2-dihydro-2,7-naphthyridin-1-one;
2-methyl-6-[(1-{[4-(1-methylpiperidin-4-yl)phenyl]amino}-8-oxo-7,8-dihydro-2,7-naphthyridin-3-yl)amino]benzene-1-sulfonamide;
N-methyl-2-[(1-{[4-(1-methylpiperidin-4-yl)phenyl]amino}-8-oxo-7,8-dihydro-2,7-naphthyridin-3-yl)amino]benzene-1-sulfonamide;
8-{[4-(1-ethylpiperidin-4-yl)phenyl]amino}-6-(4-methanesulfonylphenyl)-1,2-dihydro-2,7-naphthyridin-1-one;
8-{[4-(morpholin-4-yl)phenyl]amino}-6-(1H-pyrazol-5-yl)-1,2-dihydro-2,7-naphthyridin-1-one;
4-chloro-8-(1H-indazol-6-ylamino)-1,2-dihydro-2,7-naphthyridin-1-one;
4,6-dichloro-8-(1H-indazol-6-ylamino)-1,2-dihydro-2,7-naphthyridin-1-one;
8-{[4-(morpholin-4-yl)phenyl]amino}-6-(pyridin-2-yl)-1,2-dihydro-2,7-naphthyridin-1-one;
8-{[4-(morpholin-4-yl)phenyl]amino}-6-[5-(propan-2-yloxy)pyridin-3-yl]-1,2-dihydro-2,7-naphthyridin-1-one;
6-[5-methyl-6-(methylamino)pyridin-3-yl]-8-{[4-(morpholin-4-yl)phenyl]amino}-1,2-dihydro-2,7-naphthyridin-1-one;
4-methoxy-N-methyl-3-(1-{[4-(morpholin-4-yl)phenyl]amino}-8-oxo-7,8-dihydro-2,7-naphthyridin-3-yl)benzene-1-sulfonamide;
8-{[4-(morpholin-4-yl)phenyl]amino}-6-(1-propyl-1H-pyrazol-5-yl)-1,2-dihydro-2,7-naphthyridin-1-one;
8-{[4-(morpholin-4-yl)phenyl]amino}-6-[1-(2-phenylethyl)-1H-pyrazol-5-yl]-1,2-dihydro-2,7-naphthyridin-1-one;
8-{[4-(morpholin-4-yl)phenyl]amino}-6-[1-(propan-2-yl)-1H-pyrazol-5-yl]-1,2-dihydro-2,7-naphthyridin-1-one;
6-(1-benzyl-1H-pyrazol-5-yl)-8-{[4-(morpholin-4-yl)phenyl]amino}-1,2-dihydro-2,7-naphthyridin-1-one;
6-(1-tert-butyl-1H-pyrazol-5-yl)-8-{[4-(morpholin-4-yl)phenyl]amino}-1,2-dihydro-2,7-naphthyridin-1-one;
5-(1-{[4-(1-methylpiperidin-4-yl)phenyl]amino}-8-oxo-7,8-dihydro-2,7-naphthyridin-3-yl)pyridine-3-sulfonamide;
8-{[4-(morpholin-4-yl)phenyl]amino}-6-[5-(trifluoromethyl)pyridin-3-yl]-1,2-dihydro-2,7-naphthyridin-1-one;
8-{[4-(piperidin-4-yl)phenyl]amino}-6-[5-(trifluoromethyl)pyridin-3-yl]-1,2-dihydro-2,7-naphthyridin-1-one;
8-{[4-(1-methylpiperidin-4-yl)phenyl]amino}-6-[5-(trifluoromethyl)pyridin-3-yl]-1,2-dihydro-2,7-naphthyridin-1-one;
6-[2-(methylamino)pyrimidin-5-yl]-8-{[4-(morpholin-4-yl)phenyl]amino}-1,2-dihydro-2,7-naphthyridin-1-one;
6-(6-fluoropyridin-3-yl)-8-{[4-(morpholin-4-yl)phenyl]amino}-1,2-dihydro-2,7-naphthyridin-1-one;
6-(6-fluoropyridin-3-yl)-8-{[4-(piperidin-4-yl)phenyl]amino}-1,2-dihydro-2,7-naphthyridin-1-one;
6-[6-(methylamino)pyridin-3-yl]-8-{[4-(morpholin-4-yl)phenyl]amino}-1,2-dihydro-2,7-naphthyridin-1-one;
8-{[3-fluoro-4-(morpholin-4-yl)phenyl]amino}-1,2-dihydro-2,7-naphthyridin-1-one;
8-{[4-(morpholin-4-yl)-3-(trifluoromethyl)phenyl]amino}-1,2-dihydro-2,7-naphthyridin-1-one;
8-{[3-methyl-4-(morpholin-4-yl)phenyl]amino}-1,2-dihydro-2,7-naphthyridin-1-one;
6-(3,3-difluoropyrrolidin-1-yl)-8-({3-fluoro-4-[(2R)-2-methylmorpholin-4-yl]phenyl}amino)-1,2-dihydro-2,7-naphthyridin-1-one;
8-({3-fluoro-4-[(2R)-2-methylmorpholin-4-yl]phenyl}amino)-1,2-dihydro-2,7-naphthyridin-1-one;
6-(2-aminopyrimidin-5-yl)-8-({3-[2-(pyrrolidin-1-yl)ethoxy]phenyl}amino)-1,2-dihydro-2,7-naphthyridin-1-one;
6-(2-amino-4-methoxypyrimidin-5-yl)-8-{[4-(morpholin-4-yl)phenyl]amino}-1,2-dihydro-2,7-naphthyridin-1-one;
6-(2-aminopyrimidin-5-yl)-8-{[3-methyl-4-(morpholin-4-yl)phenyl]amino}-1,2-dihydro-2,7-naphthyridin-1-one;
N,2-dimethyl-2-(4-{[3-(2-methylpyrimidin-5-yl)-8-oxo-7,8-dihydro-2,7-naphthyridin-1-yl]amino}phenyl)propanamide
2-methyl-6-{[8-oxo-1-({4-[2-(pyrrolidin-1-yl)ethoxy]phenyl}amino)-7,8-dihydro-2,7-naphthyridin-3-yl]amino}benzene-1-sulfonamide;
8-{[4-(morpholin-4-yl)phenyl]amino}-6-[5-(morpholin-4-ylmethyl)pyridin-3-yl]-1,2-dihydro-2,7-naphthyridin-1-one;
8-{[4-(morpholin-4-yl)phenyl]amino}-6-[5-(pyrrolidin-1-ylmethyl)pyridin-3-yl]-1,2-dihydro-2,7-naphthyridin-1-one;
6-(6-fluoropyridin-3-yl)-8-{[4-(1-methylpiperidin-4-yl)phenyl]amino}-1,2-dihydro-2,7-naphthyridin-1-one;
4-{[3-(6-fluoropyridin-3-yl)-8-oxo-7,8-dihydro-2,7-naphthyridin-1-yl]amino}-N-methylbenzamide;
6-[6-(methylamino)pyridin-3-yl]-8-{[4-(piperidin-4-yl)phenyl]amino}-1,2-dihydro-2,7-naphthyridin-1-one;
6-[6-(ethylamino)pyridin-3-yl]-8-{[4-(morpholin-4-yl)phenyl]amino}-1,2-dihydro-2,7-naphthyridin-1-one;
6-(3-methanesulfonyl-4-methoxyphenyl)-8-{[4-(morpholin-4-yl)phenyl]amino}-1,2-dihydro-2,7-naphthyridin-1-one;
6-(3-methanesulfonyl-4-methylphenyl)-8-{[4-(1-methylpiperidin-4-yl)phenyl]amino}-1,2-dihydro-2,7-naphthyridin-1-one;
N-[5-(1-{[4-(1-methylpiperidin-4-yl)phenyl]amino}-8-oxo-7,8-dihydro-2,7-naphthyridin-3-yl)pyridin-2-yl]acetamide
8-({3-[2-(morpholin-4-yl)ethoxy]phenyl}amino)-6-[(2,2,2-trifluoroethyl)amino]-1,2-dihydro-2,7-naphthyridin-1-one;
N-methyl-2-{[8-oxo-1-({4-[2-(pyrrolidin-1-yl)ethoxy]phenyl}amino)-7,8-dihydro-2,7-naphthyridin-3-yl]amino}benzene-1-sulfonamide;
6-(2-amino-4-methoxypyrimidin-5-yl)-8-({3-[2-(morpholin-4-yl)ethoxy]phenyl}amino)-1,2-dihydro-2,7-naphthyridin-1-one;
6-(2-aminopyrimidin-5-yl)-8-{[4-methyl-3-(methylamino)phenyl]amino}-1,2-dihydro-2,7-naphthyridin-1-one;
6-(2-methylpyrimidin-5-yl)-8-({4-[2-(morpholin-4-yl)ethoxy]phenyl}amino)-1,2-dihydro-2,7-naphthyridin-1-one;
8-{[4-(morpholin-4-yl)phenyl]amino}-6-(pyrazin-2-yl)-1,2-dihydro-2,7-naphthyridin-1-one;
6-(5-aminopyrazin-2-yl)-8-{[4-(morpholin-4-yl)phenyl]amino}-1,2-dihydro-2,7-naphthyridin-1-one;

6-(6-amino-2-methylpyridin-3-yl)-8-{[4-(morpholin-4-yl)phenyl]amino}-1,2-dihydro-2,7-naphthyridin-1-one;

2-[(1-{[4-(4-ethoxypiperidin-1-yl)-3-fluorophenyl]amino}-8-oxo-7,8-dihydro-2,7-naphthyridin-3-yl)amino]benzene-1-sulfonamide;

6-(3,3-difluoropyrrolidin-1-yl)-8-{[4-(4-ethoxypiperidin-1-yl)-3-fluorophenyl]amino}-1,2-dihydro-2,7-naphthyridin-1-one;

8-{[4-(1-methylpiperidin-4-yl)phenyl]amino}-6-(6-methylpyridin-2-yl)-1,2-dihydro-2,7-naphthyridin-1-one;

8-{[4-(1-acetylpiperidin-4-yl)phenyl]amino}-6-(6-methylpyridin-2-yl)-1,2-dihydro-2,7-naphthyridin-1-one;

6-(3,3-difluoropyrrolidin-1-yl)-8-({6-[(2R)-2-methylmorpholin-4-yl]pyridin-3-yl}amino)-1,2-dihydro-2,7-naphthyridin-1-one;

2-[(1-{[3-methyl-4-(morpholin-4-yl)phenyl]amino}-8-oxo-7,8-dihydro-2,7-naphthyridin-3-yl)amino]benzene-1-sulfonamide;

6-(3,3-difluoropyrrolidin-1-yl)-8-{[5-methyl-6-(morpholin-4-yl)pyridin-3-yl]amino}-1,2-dihydro-2,7-naphthyridin-1-one;

6-(3,3-difluoropyrrolidin-1-yl)-8-{[3-methyl-4-(morpholin-4-yl)phenyl]amino}-1,2-dihydro-2,7-naphthyridin-1-one;

8-{[4-(1-methylpiperidin-4-yl)phenyl]amino}-6-(pyrazin-2-yl)-1,2-dihydro-2,7-naphthyridin-1-one;

6-(5-aminopyrazin-2-yl)-8-({3-fluoro-4-[(2R)-2-methylmorpholin-4-yl]phenyl}amino)-1,2-dihydro-2,7-naphthyridin-1-one;

4-{[3-(5-aminopyrazin-2-yl)-8-oxo-7,8-dihydro-2,7-naphthyridin-1-yl]amino}-N-propylbenzamide;

6-(6-methoxypyrazin-2-yl)-8-{[4-(morpholin-4-yl)phenyl]amino}-1,2-dihydro-2,7-naphthyridin-1-one;

6-(3-methoxypyrazin-2-yl)-8-{[4-(morpholin-4-yl)phenyl]amino}-1,2-dihydro-2,7-naphthyridin-1-one;

6-(2-amino-4-methoxypyrimidin-5-yl)-8-{[4-(1-methylpiperidin-4-yl)phenyl]amino}-1,2-dihydro-2,7-naphthyridin-1-one;

6-(2-aminopyrimidin-5-yl)-8-({4-[(2-methyl-1H-imidazol-1-yl)methyl]phenyl}amino)-1,2-dihydro-2,7-naphthyridin-1-one;

6-(2-aminopyrimidin-5-yl)-8-[(3-methoxy-4-phenylphenyl)amino]-1,2-dihydro-2,7-naphthyridin-1-one;

6-(2-aminopyrimidin-5-yl)-8-{[3-(4-methylpiperazin-1-yl)phenyl]amino}-1,2-dihydro-2,7-naphthyridin-1-one;

6-(2-aminopyrimidin-5-yl)-8-[(4-{2-[3-(dimethylamino)pyrrolidin-1-yl]ethyl}phenyl)amino]-1,2-dihydro-2,7-naphthyridin-1-one;

6-(1-butyl-1H-pyrazol-5-yl)-8-{[4-(morpholin-4-yl)phenyl]amino}-1,2-dihydro-2,7-naphthyridin-1-one;

6-[1-(2-hydroxyethyl)-1H-pyrazol-5-yl]-8-{[4-(morpholin-4-yl)phenyl]amino}-1,2-dihydro-2,7-naphthyridin-1-one;

ethyl 2-[5-(1-{[4-(morpholin-4-yl)phenyl]amino}-8-oxo-7,8-dihydro-2,7-naphthyridin-3-yl)-1H-pyrazol-1-yl]acetate 6-(2-methylpyrimidin-4-yl)-8-{[4-(morpholin-4-yl)phenyl]amino}-1,2-dihydro-2,7-naphthyridin-1-one;

6-(6-methylpyridin-2-yl)-8-({4-[1-(2,2,2-trifluoroethyl)piperidin-4-yl]phenyl}amino)-1,2-dihydro-2,7-naphthyridin-1-one;

8-({4-[1-(2-hydroxyethyl)piperidin-4-yl]phenyl}amino)-6-(6-methylpyridin-2-yl)-1,2-dihydro-2,7-naphthyridin-1-one;

6-(6-methylpyridin-2-yl)-8-({4-[1-(propan-2-yl)piperidin-4-yl]phenyl}amino)-1,2-dihydro-2,7-naphthyridin-1-one;

8-{[4-(1-methanesulfonylpiperidin-4-yl)phenyl]amino}-6-(6-methylpyridin-2-yl)-1,2-dihydro-2,7-naphthyridin-1-one;

6-(2-amino-1,3-thiazol-4-yl)-8-{[4-(morpholin-4-yl)phenyl]amino}-1,2-dihydro-2,7-naphthyridin-1-one;

6-[2-(methylamino)-1,3-thiazol-4-yl]-8-{[4-(morpholin-4-yl)phenyl]amino}-1,2-dihydro-2,7-naphthyridin-1-one;

6-[6-(2-hydroxypropan-2-yl)pyridin-3-yl]-8-{[4-(morpholin-4-yl)phenyl]amino}-1,2-dihydro-2,7-naphthyridin-1-one;

6-(6-amino-5-methoxypyridin-3-yl)-8-({4-methyl-3-[2-(pyrrolidin-1-yl)ethoxy]phenyl}amino)-1,2-dihydro-2,7-naphthyridin-1-one;

6-(2-aminopyrimidin-5-yl)-8-({4-methyl-3-[2-(pyrrolidin-1-yl)ethoxy]phenyl}amino)-1,2-dihydro-2,7-naphthyridin-1-one;

8-({4-methyl-3-[2-(pyrrolidin-1-yl)ethoxy]phenyl}amino)-6-(pyrimidin-5-yl)-1,2-dihydro-2,7-naphthyridin-1-one;

6-[6-(2-hydroxypropan-2-yl)pyridin-3-yl]-8-({4-methyl-3-[2-(pyrrolidin-1-yl)ethoxy]phenyl}amino)-1,2-dihydro-2,7-naphthyridin-1-one;

8-({4-methyl-3-[2-(pyrrolidin-1-yl)ethoxy]phenyl}amino)-6-(1H-pyrazol-3-yl)-1,2-dihydro-2,7-naphthyridin-1-one;

8-({4-methyl-3-[2-(pyrrolidin-1-yl)ethoxy]phenyl}amino)-6-[5-methyl-6-(methylamino)pyridin-3-yl]-1,2-dihydro-2,7-naphthyridin-1-one;

6-(2-methoxypyrimidin-5-yl)-8-({6-[(2R)-2-methylmorpholin-4-yl]pyridin-3-yl}amino)-1,2-dihydro-2,7-naphthyridin-1-one;

8-{[3-fluoro-4-(morpholin-4-yl)phenyl]amino}-6-(2-methoxypyrimidin-5-yl)-1,2-dihydro-2,7-naphthyridin-1-one;

8-(1H-indazol-6-ylamino)-6-(2-methoxypyrimidin-5-yl)-1,2-dihydro-2,7-naphthyridin-1-one;

8-({3-fluoro-4-[(2R)-2-methylmorpholin-4-yl]phenyl}amino)-6-(2-methoxypyrimidin-5-yl)-1,2-dihydro-2,7-naphthyridin-1-one;

6-(2-methoxypyrimidin-5-yl)-8-({5-methyl-6-[(2R)-2-methylmorpholin-4-yl]pyridin-3-yl}amino)-1,2-dihydro-2,7-naphthyridin-1-one;

8-{[4-(4-ethoxypiperidin-1-yl)-3-fluorophenyl]amino}-6-(2-methoxypyrimidin-5-yl)-1,2-dihydro-2,7-naphthyridin-1-one;

8-({6-[(2R)-2-methylmorpholin-4-yl]pyridin-3-yl}amino)-6-(pyrimidin-5-yl)-1,2-dihydro-2,7-naphthyridin-1-one;

8-({3-methyl-4-[(2R)-2-methylmorpholin-4-yl]phenyl}amino)-6-(pyrimidin-5-yl)-1,2-dihydro-2,7-naphthyridin-1-one;

4-{[3-(2-aminopyrimidin-5-yl)-8-oxo-7,8-dihydro-2,7-naphthyridin-1-yl]amino}-N-(1-methylpiperidin-4-yl)benzamide;

N-(1-methylpiperidin-4-yl)-4-{[3-(2-methylpyrimidin-5-yl)-8-oxo-7,8-dihydro-2,7-naphthyridin-1-yl]amino}benzamide;

6-(2-aminopyrimidin-5-yl)-8-({4-[3-(dimethylamino)pyrrolidin-1-yl]phenyl}amino)-1,2-dihydro-2,7-naphthyridin-1-one;

8-({4-[3-(dimethylamino)pyrrolidin-1-yl]phenyl}amino)-6-(6-methoxypyrazin-2-yl)-1,2-dihydro-2,7-naphthyridin-1-one;

6-(2,4-dimethoxypyrimidin-5-yl)-8-{[4-(morpholin-4-yl)phenyl]amino}-1,2-dihydro-2,7-naphthyridin-1-one;

N-methyl-3-{[3-(2-methylpyrimidin-5-yl)-8-oxo-7,8-dihydro-2,7-naphthyridin-1-yl]amino}benzene-1-sulfonamide;

2-methoxy-N-methyl-4-(1-{[4-(morpholin-4-yl)phenyl]amino}-8-oxo-7,8-dihydro-2,7-naphthyridin-3-yl)benzene-1-sulfonamide;

6-(6-hydrazinylpyridin-3-yl)-8-{[4-(morpholin-4-yl)phenyl]amino}-1,2-dihydro-2,7-naphthyridin-1-one;

6-[6-(4-methyl-1H-imidazol-1-yl)pyridin-2-yl]-8-{[4-(1-methylpiperidin-4-yl)phenyl]amino}-1,2-dihydro-2,7-naphthyridin-1-one;

8-{[4-(1-methylpiperidin-4-yl)phenyl]amino}-6-[6-(morpholin-4-ylmethyl)pyridin-3-yl]-1,2-dihydro-2,7-naphthyridin-1-one;

8-{[4-(morpholin-4-yl)phenyl]amino}-6-[6-(morpholin-4-ylmethyl)pyridin-3-yl]-1,2-dihydro-2,7-naphthyridin-1-one;

6-(2-methoxypyrimidin-5-yl)-8-({3-methyl-4-[(2R)-2-methylmorpholin-4-yl]phenyl}amino)-1,2-dihydro-2,7-naphthyridin-1-one;

6-hydroxy-8-({3-methyl-4-[(2R)-2-methylmorpholin-4-yl]phenyl}amino)-1,2-dihydro-2,7-naphthyridin-1-one;

8-({3-fluoro-4-[(2R)-2-methylmorpholin-4-yl]phenyl}amino)-6-(pyrimidin-5-yl)-1,2-dihydro-2,7-naphthyridin-1-one;

8-({5-methyl-6-[(2R)-2-methylmorpholin-4-yl]pyridin-3-yl}amino)-6-(pyrimidin-5-yl)-1,2-dihydro-2,7-naphthyridin-1-one;

ethyl 4-(1-{[4-(morpholin-4-yl)phenyl]amino}-8-oxo-7,8-dihydro-2,7-naphthyridin-3-yl)-1,3-thiazole-2-carboxylate;

6-[2-(methanesulfonylmethyl)-1,3-thiazol-4-yl]-8-{[4-(morpholin-4-yl)phenyl]amino}-1,2-dihydro-2,7-naphthyridin-1-one;

tert-butyl N-{2-[4-(1-{[4-(morpholin-4-yl)phenyl]amino}-8-oxo-7,8-dihydro-2,7-naphthyridin-3-yl)-1,3-thiazol-2-yl]ethyl}carbamate 6-[2-(2-aminoethyl)-1,3-thiazol-4-yl]-8-{[4-(morpholin-4-yl)phenyl]amino}-1,2-dihydro-2,7-naphthyridin-1-one;

6-(5-amino-6-methylpyridin-2-yl)-8-{[4-(1-methylpiperidin-4-yl)phenyl]amino}-1,2-dihydro-2,7-naphthyridin-1-one;

6-(5-amino-6-methylpyridin-2-yl)-8-{[4-(morpholin-4-yl)phenyl]amino}-1,2-dihydro-2,7-naphthyridin-1-one;

6-(2-amino-4-methylpyrimidin-5-yl)-8-{[4-(morpholin-4-yl)phenyl]amino}-1,2-dihydro-2,7-naphthyridin-1-one;

6-(2-amino-6-methylpyrimidin-4-yl)-8-{[4-(morpholin-4-yl)phenyl]amino}-1,2-dihydro-2,7-naphthyridin-1-one;

6-(6-amino-5-methylpyridin-3-yl)-8-({3-methyl-4-[(2R)-2-methylmorpholin-4-yl]phenyl}amino)-1,2-dihydro-2,7-naphthyridin-1-one;

6-(2-aminopyrimidin-5-yl)-2-methyl-8-{[4-(morpholin-4-yl)phenyl]amino}-1,2-dihydro-2,7-naphthyridin-1-one;

6-(2-aminopyrimidin-5-yl)-2-methyl-8-{methyl[4-(morpholin-4-yl)phenyl]amino}-1,2-dihydro-2,7-naphthyridin-1-one;

6-(6-amino-5-methylpyridin-3-yl)-8-({3-[2-(morpholin-4-yl)ethoxy]phenyl}amino)-1,2-dihydro-2,7-naphthyridin-1-one;

6-(2-aminopyrimidin-5-yl)-8-(morpholin-4-yl)-1,2-dihydro-2,7-naphthyridin-1-one;

6-(2-aminopyrimidin-5-yl)-8-[(1-methylpiperidin-4-yl)amino]-1,2-dihydro-2,7-naphthyridin-1-one;

6-(2-amino-4-methylpyrimidin-5-yl)-8-({4-[3-(dimethylamino)pyrrolidin-1-yl]phenyl}amino)-1,2-dihydro-2,7-naphthyridin-1-one;

6-(5-aminopyridin-2-yl)-8-{[4-(morpholin-4-yl)phenyl]amino}-1,2-dihydro-2,7-naphthyridin-1-one;

8-{[4-(morpholin-4-yl)phenyl]amino}-6-{5H-pyrrolo[2,3-b]pyrazin-2-yl}-1,2-dihydro-2,7-naphthyridin-1-one;

6-(5-aminopyridin-2-yl)-8-{[4-(1-methylpiperidin-4-yl)phenyl]amino}-1,2-dihydro-2,7-naphthyridin-1-one;

8-{[4-(1-methylpiperidin-4-yl)phenyl]amino}-6-{5H-pyrrolo[2,3-b]pyrazin-2-yl}-1,2-dihydro-2,7-naphthyridin-1-one;

6-(2,4-dimethyl-1,3-thiazol-5-yl)-8-{[4-(morpholin-4-yl)phenyl]amino}-1,2-dihydro-2,7-naphthyridin-1-one;

6-(2,4-dimethyl-1,3-thiazol-5-yl)-8-{[4-(1-methylpiperidin-4-yl)phenyl]amino}-1,2-dihydro-2,7-naphthyridin-1-one;

8-{[4-(piperidin-4-yl)phenyl]amino}-6-[4-(propane-2-sulfonyl)phenyl]-1,2-dihydro-2,7-naphthyridin-1-one;

6-[6-(4-methyl-1H-imidazol-1-yl)pyridin-2-yl]-8-{[4-(morpholin-4-yl)phenyl]amino}-1,2-dihydro-2,7-naphthyridin-1-one;

N,N-dimethyl-4-(8-oxo-1-{[4-(piperidin-4-yl)phenyl]amino}-7,8-dihydro-2,7-naphthyridin-3-yl)benzene-1-sulfonamide;

tert-butyl 4-[4-({8-oxo-3-[4-(propane-2-sulfonyl)phenyl]-7,8-dihydro-2,7-naphthyridin-1-yl}amino)phenyl]piperidine-1-carboxylate;

tert-butyl 4-[4-({3-[4-(dimethylsulfamoyl)phenyl]-8-oxo-7,8-dihydro-2,7-naphthyridin-1-yl}amino)phenyl]piperidine-1-carboxylate;

tert-butyl 4-(4-{[3-(3-methanesulfonylphenyl)-8-oxo-7,8-dihydro-2,7-naphthyridin-1-yl]amino}phenyl)piperidine-1-carboxylate;

6-(5-amino-6-methylpyrazin-2-yl)-8-{[4-(morpholin-4-yl)phenyl]amino}-1,2-dihydro-2,7-naphthyridin-1-one;

6-(6-aminopyrazin-2-yl)-8-{[4-(morpholin-4-yl)phenyl]amino}-1,2-dihydro-2,7-naphthyridin-1-one;

6-(6-methoxypyridazin-3-yl)-8-{[4-(morpholin-4-yl)phenyl]amino}-1,2-dihydro-2,7-naphthyridin-1-one;

8-({4-[1-(2-methanesulfonylethyl)piperidin-4-yl]phenyl}amino)-6-(4-methanesulfonylphenyl)-1,2-dihydro-2,7-naphthyridin-1-one;

6-(2-methoxypyrimidin-5-yl)-8-{[4-(morpholin-4-yl)phenyl]amino}-1,2-dihydro-2,7-naphthyridin-1-one;

6-(2-methoxypyrimidin-5-yl)-8-{[4-(1-methylpiperidin-4-yl)phenyl]amino}-1,2-dihydro-2,7-naphthyridin-1-one;

6-(1-methyl-1H-pyrazol-4-yl)-8-{[4-(morpholin-4-yl)phenyl]amino}-1,2-dihydro-2,7-naphthyridin-1-one;

6-(4-ethylpiperazin-1-yl)-8-{[4-(morpholin-4-yl)phenyl]amino}-4-phenyl-1,2-dihydro-2,7-naphthyridin-1-one;

8-{[4-(morpholin-4-yl)phenyl]amino}-4-phenyl-1,2-dihydro-2,7-naphthyridin-1-one;

4-(2-chlorophenyl)-8-{[4-(morpholin-4-yl)phenyl]amino}-1,2-dihydro-2,7-naphthyridin-1-one;

6-(1-methyl-1H-pyrazol-4-yl)-8-{methyl[4-(morpholin-4-yl)phenyl]amino}-1,2-dihydro-2,7-naphthyridin-1-one;

8-{[4-(1-acetylpiperidin-4-yl)phenyl]amino}-6-(2-aminopyrimidin-5-yl)-1,2-dihydro-2,7-naphthyridin-1-one;

8-{[4-(1-acetylpiperidin-4-yl)phenyl]amino}-6-(pyrimidin-5-yl)-1,2-dihydro-2,7-naphthyridin-1-one;

6-(2-aminopyrimidin-5-yl)-8-{[4-(1-methanesulfonylpyrrolidin-3-yl)phenyl]amino}-1,2-dihydro-2,7-naphthyridin-1-one;

N-methyl-3-{[8-oxo-3-(pyrimidin-5-yl)-7,8-dihydro-2,7-naphthyridin-1-yl]amino}benzene-1-sulfonamide;

6-(2-aminopyrimidin-5-yl)-8-[(3-methoxyphenyl)amino]-1,2-dihydro-2,7-naphthyridin-1-one;

6-[6-(2-hydroxypropan-2-yl)pyridin-3-yl]-8-{[4-(1-methylpiperidin-4-yl)phenyl]amino}-1,2-dihydro-2,7-naphthyridin-1-one;

6-[5-methyl-6-(methylamino)pyridin-3-yl]-8-{[4-(1-methylpiperidin-4-yl)phenyl]amino}-1,2-dihydro-2,7-naphthyridin-1-one;

8-{[4-(1-methylpiperidin-4-yl)phenyl]amino}-6-[5-(propan-2-yloxy)pyridin-3-yl]-1,2-dihydro-2,7-naphthyridin-1-one;

4-methoxy-N-methyl-3-(1-{[4-(1-methylpiperidin-4-yl)phenyl]amino}-8-oxo-7,8-dihydro-2,7-naphthyridin-3-yl)benzene-1-sulfonamide;

6-[3-methanesulfonyl-4-(pyrrolidin-1-ylmethyl)phenyl]-8-{[4-(1-methylpiperidin-4-yl)phenyl]amino}-1,2-dihydro-2,7-naphthyridin-1-one;

6-[3-methanesulfonyl-4-(morpholin-4-ylmethyl)phenyl]-8-{[4-(1-methylpiperidin-4-yl)phenyl]amino}-1,2-dihydro-2,7-naphthyridin-1-one;

8-{[4-(1-methylpiperidin-4-yl)phenyl]amino}-6-[5-(morpholin-4-ylmethyl)pyridin-3-yl]-1,2-dihydro-2,7-naphthyridin-1-one;

8-{[4-(1-methylpiperidin-4-yl)phenyl]amino}-6-[5-(pyrrolidin-1-ylmethyl)pyridin-3-yl]-1,2-dihydro-2,7-naphthyridin-1-one;

8-{[4-(morpholin-4-yl)phenyl]amino}-6-[6-(propan-2-ylamino)pyridin-3-yl]-1,2-dihydro-2,7-naphthyridin-1-one;

6-(1-methyl-1H-imidazol-5-yl)-8-{[4-(morpholin-4-yl)phenyl]amino}-1,2-dihydro-2,7-naphthyridin-1-one;

6-(6-aminopyridin-3-yl)-2-methyl-8-{[4-(morpholin-4-yl)phenyl]amino}-1,2-dihydro-2,7-naphthyridin-1-one;

8-{[4-(morpholin-4-yl)phenyl]amino}-6-(1,3-thiazol-4-yl)-1,2-dihydro-2,7-naphthyridin-1-one;

tert-butyl 6-{[3-(4-methanesulfonylphenyl)-8-oxo-7,8-dihydro-2,7-naphthyridin-1-yl]amino}-1,2,3,4-tetrahydroisoquinoline-2-carboxylate;

6-(4-methanesulfonylphenyl)-8-(1,2,3,4-tetrahydroisoquinolin-6-ylamino)-1,2-dihydro-2,7-naphthyridin-1-one;

8-{[4-(1-ethylpiperidin-4-yl)phenyl]amino}-6-[4-(propane-2-sulfonyl)phenyl]-1,2-dihydro-2,7-naphthyridin-1-one;

4-(1-{[4-(1-ethylpiperidin-4-yl)phenyl]amino}-8-oxo-7,8-dihydro-2,7-naphthyridin-3-yl)-N,N-dimethylbenzene-1-sulfonamide;

6-[6-(4-methyl-1H-imidazol-1-yl)pyridin-3-yl]-8-{[4-(morpholin-4-yl)phenyl]amino}-1,2-dihydro-2,7-naphthyridin-1-one;

8-[(2-ethyl-1,2,3,4-tetrahydro isoquinolin-6-yl)amino]-6-(4-methanesulfonylphenyl)-1,2-dihydro-2,7-naphthyridin-1-one;

benzyl 4-{1-[(4-{1-[(tert-butoxy)carbonyl]piperidin-4-yl}phenyl)amino]-8-oxo-7,8-dihydro-2,7-naphthyridin-3-yl}piperazine-1-carboxylate;

8-({6-[(2R)-2-methylmorpholin-4-yl]pyridin-3-yl}amino)-6-(6-methylpyridin-2-yl)-1,2-dihydro-2,7-naphthyridin-1-one;

8-({3-methyl-4-[(2R)-2-methylmorpholin-4-yl]phenyl}amino)-6-(6-methylpyridin-2-yl)-1,2-dihydro-2,7-naphthyridin-1-one;

6-{[(1S,2R)-2-aminocyclohexyl]amino}-8-(1H-indazol-6-ylamino)-1,2-dihydro-2,7-naphthyridin-1-one;

6-(6-methoxypyrazin-2-yl)-8-({3-methyl-4-[(2R)-2-methylmorpholin-4-yl]phenyl}amino)-1,2-dihydro-2,7-naphthyridin-1-one;

6-(5-amino-6-methylpyrazin-2-yl)-8-({3-methyl-4-[(2R)-2-methylmorpholin-4-yl]phenyl}amino)-1,2-dihydro-2,7-naphthyridin-1-one;

6-(6-methoxypyrazin-2-yl)-8-({4-[2-(morpholin-4-yl)ethoxy]phenyl}amino)-1,2-dihydro-2,7-naphthyridin-1-one;

6-(2-aminopyrimidin-5-yl)-8-{[4-(2-methylpyridin-4-yl)phenyl]amino}-1,2-dihydro-2,7-naphthyridin-1-one;

8-{[4-(1-acetylpiperidin-4-yl)-3-methylphenyl]amino}-6-(6-amino-5-methylpyridin-3-yl)-1,2-dihydro-2,7-naphthyridin-1-one;

6-(2-aminopyrimidin-5-yl)-8-{[4-(4-methoxyphenyl)phenyl]amino}-1,2-dihydro-2,7-naphthyridin-1-one;

6-(2-amino-4-methylpyrimidin-5-yl)-2-methyl-8-{[4-(morpholin-4-yl)phenyl]amino}-1,2-dihydro-2,7-naphthyridin-1-one;

8-(1H-indazol-6-ylamino)-6-(6-methoxypyrazin-2-yl)-1,2-dihydro-2,7-naphthyridin-1-one;

6-(3-methanesulfinyl-2-methylphenyl)-8-{[4-(morpholin-4-yl)phenyl]amino}-1,2-dihydro-2,7-naphthyridin-1-one;

8-[(2-methanesulfonylethyl)({4-[1-(2-methanesulfonylethyl)piperidin-4-yl]phenyl})amino]-6-(4-methanesulfonylphenyl)-1,2-dihydro-2,7-naphthyridin-1-one;

8-{[4-(1-ethylpiperidin-4-yl)phenyl]amino}-6-(4-methanesulfonylpiperazin-1-yl)-1,2-dihydro-2,7-naphthyridin-1-one;

8-{[4-(1-ethylpiperidin-4-yl)-2-methoxy-5-methylphenyl]amino}-6-(4-methanesulfonylphenyl)-1,2-dihydro-2,7-naphthyridin-1-one;

8-{[4-(morpholin-4-yl)phenyl]amino}-6-(pyrimidin-5-yl)-1,2-dihydro-2,7-naphthyridin-1-one;

8-(1H-indazol-6-ylamino)-6-[5-(propan-2-yloxy)pyridin-3-yl]-1,2-dihydro-2,7-naphthyridin-1-one;

6-[6-(2-hydroxypropan-2-yl)pyridin-3-yl]-8-(1H-indazol-6-ylamino)-1,2-dihydro-2,7-naphthyridin-1-one;

8-(1H-indazol-6-ylamino)-6-[3-methanesulfonyl-4-(pyrrolidin-1-ylmethyl)phenyl]-1,2-dihydro-2,7-naphthyridin-1-one;

8-(1H-indazol-6-ylamino)-6-[3-methanesulfonyl-4-(morpholin-4-ylmethyl)phenyl]-1,2-dihydro-2,7-naphthyridin-1-one;

8-(1H-indazol-6-ylamino)-6-[6-(morpholin-4-ylmethyl)pyridin-3-yl]-1,2-dihydro-2,7-naphthyridin-1-one;

8-(1H-indazol-6-ylamino)-6-[5-(pyrrolidin-1-ylmethyl)pyridin-3-yl]-1,2-dihydro-2,7-naphthyridin-1-one;

3-(1-{[3-fluoro-4-(morpholin-4-yl)phenyl]amino}-8-oxo-7,8-dihydro-2,7-naphthyridin-3-yl)-4-methoxy-N-methylbenzene-1-sulfonamide;

4-(1-{[3-fluoro-4-(morpholin-4-yl)phenyl]amino}-8-oxo-7,8-dihydro-2,7-naphthyridin-3-yl)-2-methoxy-N-methylbenzene-1-sulfonamide;

6-[6-(2-hydroxypropan-2-yl)pyridin-3-yl]-8-({6-[(2R)-2-methylmorpholin-4-yl]pyridin-3-yl}amino)-1,2-dihydro-2,7-naphthyridin-1-one;

8-(1H-indazol-6-ylamino)-6-(6-methylpyridin-2-yl)-1,2-dihydro-2,7-naphthyridin-1-one;

6-[5-methyl-6-(methylamino)pyridin-3-yl]-8-({6-[(2R)-2-methylmorpholin-4-yl]pyridin-3-yl}amino)-1,2-dihydro-2,7-naphthyridin-1-one;

8-({6-[(2R)-2-methylmorpholin-4-yl]pyridin-3-yl}amino)-6-[2-(propan-2-yloxy)pyrimidin-5-yl]-1,2-dihydro-2,7-naphthyridin-1-one;

8-({3-methyl-4-[(2R)-2-methylmorpholin-4-yl]phenyl}amino)-6-[2-(propan-2-yloxy)pyrimidin-5-yl]-1,2-dihydro-2,7-naphthyridin-1-one;

8-({3-methyl-4-[(2R)-2-methylmorpholin-4-yl]phenyl}amino)-6-[5-methyl-6-(methylamino)pyridin-3-yl]-1,2-dihydro-2,7-naphthyridin-1-one;

6-(1H-indazol-6-yl)-8-({3-methyl-4-[(2R)-2-methylmorpholin-4-yl]phenyl}amino)-1,2-dihydro-2,7-naphthyridin-1-one;

8-amino-6-(pyrimidin-5-yl)-1,2-dihydro-2,7-naphthyridin-1-one;

8-amino-6-(2-aminopyrimidin-5-yl)-1,2-dihydro-2,7-naphthyridin-1-one;

6-(4-methanesulfonylpiperazin-1-yl)-8-{[4-(piperidin-4-yl)phenyl]amino}-1,2-dihydro-2,7-naphthyridin-1-one;

8-({3-methyl-4-[(2R)-2-methylmorpholin-4-yl]phenyl}amino)-6-(2-oxo-2,3-dihydro-1H-indol-5-yl)-1,2-dihydro-2,7-naphthyridin-1-one;

8-({3-methyl-4-[(2R)-2-methylmorpholin-4-yl]phenyl}amino)-6-(2-oxo-2,3-dihydro-1H-indol-6-yl)-1,2-dihydro-2,7-naphthyridin-1-one;

6-[6-(methylamino)pyridin-2-yl]-8-{[4-(morpholin-4-yl)phenyl]amino}-1,2-dihydro-2,7-naphthyridin-1-one;

8-{[4-(morpholin-4-yl)phenyl]amino}-6-[6-(propylamino)pyridin-2-yl]-1,2-dihydro-2,7-naphthyridin-1-one;

6-(5-amino-6-methoxypyrazin-2-yl)-8-{[4-(morpholin-4-yl)phenyl]amino}-1,2-dihydro-2,7-naphthyridin-1-one;

8-{[4-(morpholin-4-yl)phenyl]amino}-6-[6-(propan-2-ylamino)pyridin-2-yl]-1,2-dihydro-2,7-naphthyridin-1-one;

6-{6-[(3-methoxypropyl)amino]pyridin-2-yl}-8-{[4-(morpholin-4-yl)phenyl]amino}-1,2-dihydro-2,7-naphthyridin-1-one;

6-[6-(dimethylamino)pyridin-2-yl]-8-{[4-(morpholin-4-yl)phenyl]amino}-1,2-dihydro-2,7-naphthyridin-1-one;

6-(4-ethylpiperazin-1-yl)-8-{methyl[6-(morpholin-4-yl)pyridin-3-yl]amino}-1,2-dihydro-2,7-naphthyridin-1-one;

4-(2,6-dimethylphenyl)-8-{[4-(morpholin-4-yl)phenyl]amino}-1,2-dihydro-2,7-naphthyridin-1-one;

2-methyl-6-(1-methyl-1-pyrazol-4-yl)-8-{methyl[4-(morpholin-4-yl)phenyl]amino}-1,2-dihydro-2,7-naphthyridin-1-one;

6-(2-aminopyrimidin-5-yl)-8-{methyl[4-(morpholin-4-yl)phenyl]amino}-1,2-dihydro-2,7-naphthyridin-1-one;

6-(2-methyl-1,3-thiazol-4-yl)-8-({4-[2-(pyrrolidin-1-yl)ethoxy]phenyl}amino)-1,2-dihydro-2,7-naphthyridin-1-one;

6-(2-methyl-1,3-thiazol-4-yl)-8-({4-methyl-3-[2-(pyrrolidin-1-yl)ethoxy]phenyl}amino)-1,2-dihydro-2,7-naphthyridin-1-one;

4-[(1-{[4-(morpholin-4-yl)phenyl]amino}-8-oxo-7,8-dihydro-2,7-naphthyridin-3-yl)amino]pyridine-3-sulfonamide;

6-(6-methoxypyrazin-2-yl)-8-({3-methyl-4-[3-(4-methylpiperazin-1-yl)propoxy]phenyl}amino)-1,2-dihydro-2,7-naphthyridin-1-one;

2-(4-{[3-(6-amino-5-methylpyridin-3-yl)-8-oxo-7,8-dihydro-2,7-naphthyridin-1-yl]amino}phenyl)-N,2-dimethylpropanamide 8-[(4-{2-[3-(dimethylamino)pyrrolidin-1-yl]ethyl}phenyl)amino]-6-(6-methoxypyrazin-2-yl)-1,2-dihydro-2,7-naphthyridin-1-one;

8-[(4-hydroxy-3-methylphenyl)amino]-6-(6-methoxypyrazin-2-yl)-1,2-dihydro-2,7-naphthyridin-1-one;

6-(2-amino-6-methylpyrimidin-4-yl)-8-{[3-methyl-4-(morpholin-4-yl)phenyl]amino}-1,2-dihydro-2,7-naphthyridin-1-one;

6-(2-aminopyrimidin-5-yl)-2-methyl-8-{[4-(1-methylpiperidin-4-yl)phenyl]amino}-1,2-dihydro-2,7-naphthyridin-1-one;

4-(2,6-dichlorophenyl)-8-{[4-(morpholin-4-yl)phenyl]amino}-1,2-dihydro-2,7-naphthyridin-1-one;

6-(6-amino-5-methoxypyridin-3-yl)-8-[(4-methanesulfonylphenyl)amino]-1,2-dihydro-2,7-naphthyridin-1-one;

8-[(4-methanesulfonylphenyl)amino]-6-[6-(morpholin-4-ylmethyl)pyridin-3-yl]-1,2-dihydro-2,7-naphthyridin-1-one;

8-{[3-fluoro-4-(morpholin-4-yl)phenyl]amino}-6-{imidazo pyridin-6-yl}-1,2-dihydro-2,7-naphthyridin-1-one;

8-{[3-fluoro-4-(morpholin-4-yl)phenyl]amino}-6-(6-methylpyridin-3-yl)-1,2-dihydro-2,7-naphthyridin-1-one;

6-(1H-indazol-6-yl)-8-{[4-(1-methylpiperidin-4-yl)phenyl]amino}-1,2-dihydro-2,7-naphthyridin-1-one;

6-{imidazo[1,2-a]pyridin-6-yl}-8-{[4-(1-methylpiperidin-4-yl)phenyl]amino}-1,2-dihydro-2,7-naphthyridin-1-one;

8-{[4-(1-methylpiperidin-4-yl)phenyl]amino}-6-{1H-pyrrolo[2,3-b]pyridin-5-yl}-1,2-dihydro-2,7-naphthyridin-1-one;

8-{[4-(1-methylpiperidin-4-yl]phenyl}amino)-6-(6-methylpyridin-3-yl)-1,2-dihydro-2,7-naphthyridin-1-one;

8-({3-methyl-4-[(2R)-2-methylmorpholin-4-yl]phenyl}amino)-6-(6-methylpyridin-3-yl)-1,2-dihydro-2,7-naphthyridin-1-one;

6-(6-fluoro-2-methylpyridin-3-yl)-8-{[4-(morpholin-4-yl)phenyl]amino}-1,2-dihydro-2,7-naphthyridin-1-one;

6-(6-fluoro-2-methylpyridin-3-yl)-8-{[3-fluoro-4-(morpholin-4-yl)phenyl]amino}-1,2-dihydro-2,7-naphthyridin-1-one;

6-(6-fluoro-2-methylpyridin-3-yl)-8-{[4-(1-methylpiperidin-4-yl)phenyl]amino}-1,2-dihydro-2,7-naphthyridin-1-one;

8-{[3-fluoro-4-(morpholin-4-yl)phenyl]amino}-6-(4-methylpyridin-3-yl)-1,2-dihydro-2,7-naphthyridin-1-one;

8-({3-methyl-4-[(2R)-2-methylmorpholin-4-yl]phenyl}amino)-6-(4-methylpyridin-3-yl)-1,2-dihydro-2,7-naphthyridin-1-one;

6-(6-aminopyridin-3-yl)-8-({3-methyl-4-[(2R)-2-methylmorpholin-4-yl]phenyl}amino)-1,2-dihydro-2,7-naphthyridin-1-one;

6-(6-methoxypyridin-3-yl)-8-({3-methyl-4-[(2R)-2-methylmorpholin-4-yl]phenyl}amino)-1,2-dihydro-2,7-naphthyridin-1-one;

6-(6-aminopyridin-3-yl)-8-{[3-fluoro-4-(morpholin-4-yl)phenyl]amino}-1,2-dihydro-2,7-naphthyridin-1-one;

6-(6-aminopyridin-3-yl)-8-{[4-(1-methylpiperidin-4-yl)phenyl]amino}-1,2-dihydro-2,7-naphthyridin-1-one;

6-(6-methoxypyridin-3-yl)-8-{[4-(1-methylpiperidin-4-yl)phenyl]amino}-1,2-dihydro-2,7-naphthyridin-1-one;
6-(6-methoxypyridin-2-yl)-8-{[4-(morpholin-4-yl)phenyl]amino}-1,2-dihydro-2,7-naphthyridin-1-one;
6-(2-aminopyrimidin-5-yl)-8-({3-methyl-4-[2-(pyrrolidin-1-yl)ethoxy]phenyl}amino)-1,2-dihydro-2,7-naphthyridin-1-one;
8-({3-methyl-4-[2-(pyrrolidin-1-yl)ethoxy]phenyl}amino)-6-(pyrimidin-5-yl)-1,2-dihydro-2,7-naphthyridin-1-one;
6-(3-methoxypyrazin-2-yl)-8-({4-[2-(morpholin-4-yl)ethoxy]phenyl}amino)-1,2-dihydro-2,7-naphthyridin-1-one;
6-(6-aminopyridin-3-yl)-8-({3-methyl-4-[2-(pyrrolidin-1-yl)ethoxy]phenyl}amino)-1,2-dihydro-2,7-naphthyridin-1-one;
6-(6-methoxypyridin-3-yl)-8-({3-methyl-4-[2-(pyrrolidin-1-yl)ethoxy]phenyl}amino)-1,2-dihydro-2,7-naphthyridin-1-one;
6-(6-amino-5-methylpyridin-3-yl)-8-({3-methyl-4-[2-(pyrrolidin-1-yl)ethoxy]phenyl}amino)-1,2-dihydro-2,7-naphthyridin-1-one;
8-{[3-fluoro-4-(morpholin-4-yl)phenyl]amino}-6-(6-methoxypyridin-2-yl)-1,2-dihydro-2,7-naphthyridin-1-one;
6-[6-(ethylamino)pyridin-2-yl]-8-{[4-(morpholin-4-yl)phenyl]amino}-1,2-dihydro-2,7-naphthyridin-1-one;
6-(4-ethylpiperazin-1-yl)-2-methyl-8-{methyl[4-(morpholin-4-yl)phenyl]amino}-1,2-dihydro-2,7-naphthyridin-1-one;
8-{[4-(1-ethylpiperidin-4-yl)phenyl]amino}-6-(furan-3-yl)-1,2-dihydro-2,7-naphthyridin-1-one;
8-(1H-indazol-5-ylamino)-6-(2-methoxypyrimidin-5-yl)-1,2-dihydro-2,7-naphthyridin-1-one;
8-{[4-(1-ethylpiperidin-4-yl)phenyl]amino}-6-(4-hydroxyphenyl)-1,2-dihydro-2,7-naphthyridin-1-one;
6-[4-(dimethylamino)phenyl]-8-{[4-(1-ethylpiperidin-4-yl)phenyl]amino}-1,2-dihydro-2,7-naphthyridin-1-one;
8-{[4-(1-ethylpiperidin-4-yl)phenyl]amino}-6-(4-fluoro-2-methylphenyl)-1,2-dihydro-2,7-naphthyridin-1-one;
8-{[4-(1-ethylpiperidin-4-yl)phenyl]amino}-6-(4-fluoro-3-methoxyphenyl)-1,2-dihydro-2,7-naphthyridin-1-one;
6-[4-(benzyloxy)phenyl]-8-{[4-(1-ethylpiperidin-4-yl)phenyl]amino}-1,2-dihydro-2,7-naphthyridin-1-one;
6-(6-fluoropyridin-3-yl)-8-({6-[(2R)-2-methylmorpholin-4-yl]pyridin-3-yl}amino)-1,2-dihydro-2,7-naphthyridin-1-one;
6-[6-(methylamino)pyridin-3-yl]-8-({6-[(2R)-2-methylmorpholin-4-yl]pyridin-3-yl}amino)-1,2-dihydro-2,7-naphthyridin-1-one;
6-[6-(ethylamino)pyridin-3-yl]-8-({6-[(2R)-2-methylmorpholin-4-yl]pyridin-3-yl}amino)-1,2-dihydro-2,7-naphthyridin-1-one;
2-methyl-6-[2-(methylamino)pyrimidin-5-yl]-8-{[4-(morpholin-4-yl)phenyl]amino}-1,2-dihydro-2,7-naphthyridin-1-one;
8-({6-[(2R,6S)-2,6-dimethylmorpholin-4-yl]pyridin-3-yl}amino)-6-(6-methoxypyrazin-2-yl)-1,2-dihydro-2,7-naphthyridin-1-one;
6-(6-methoxypyrazin-2-yl)-8-({4-[2-(pyrrolidin-1-yl)ethoxy]phenyl}amino)-1,2-dihydro-2,7-naphthyridin-1-one;
6-(6-methoxypyrazin-2-yl)-8-{[4-(trifluoromethoxy)phenyl]amino}-1,2-dihydro-2,7-naphthyridin-1-one;
8-[(3-methoxy-4-phenylphenyl)amino]-6-(6-methoxypyrazin-2-yl)-1,2-dihydro-2,7-naphthyridin-1-one;
6-(6-methoxypyrazin-2-yl)-8-{[4-(2-methylpyridin-4-yl)phenyl]amino}-1,2-dihydro-2,7-naphthyridin-1-one;
6-(6-methoxypyrazin-2-yl)-8-{[3-methyl-4-(morpholin-4-yl)phenyl]amino}-1,2-dihydro-2,7-naphthyridin-1-one;
6-(6-amino-5-methylpyridin-3-yl)-8-[(4-{2-[3-(dimethylamino)pyrrolidin-1-yl]ethyl}phenyl)amino]-1,2-dihydro-2,7-naphthyridin-1-one;
6-(6-amino-5-methylpyridin-3-yl)-8-{[4-(2-methylpyridin-4-yl)phenyl]amino}-1,2-dihydro-2,7-naphthyridin-1-one;
6-(6-amino-5-methylpyridin-3-yl)-8-{[4-(4-hydroxypiperidin-1-yl)phenyl]amino}-1,2-dihydro-2,7-naphthyridin-1-one;
6-(6-amino-5-methylpyridin-3-yl)-8-{[3-methyl-4-(morpholin-4-yl)phenyl]amino}-1,2-dihydro-2,7-naphthyridin-1-one;
8-{[4-(1-acetylpiperidin-4-yl)-3-methylphenyl]amino}-6-(2-aminopyrimidin-5-yl)-1,2-dihydro-2,7-naphthyridin-1-one;
5-(1-{[4-(morpholin-4-yl)phenyl]amino}-8-oxo-7,8-dihydro-2,7-naphthyridin-3-yl)pyridine-2-sulfonamide;
N-methyl-5-(1-[{4-(morpholin-4-yl)phenyl]amino}-8-oxo-7,8-dihydro-2,7-naphthyridin-3-yl)pyridine-2-sulfonamide;
6-(3-methoxypyrazin-2-yl)-8-({3-methyl-4-[2-(pyrrolidin-1-yl)ethoxy]phenyl}amino)-1,2-dihydro-2,7-naphthyridin-1-one;
8-[(3-methoxy-4-methylphenyl)amino]-6-(pyrimidin-5-yl)-1,2-dihydro-2,7-naphthyridin-1-one;
8-amino-2-methyl-6-(pyrimidin-5-yl)-1,2-dihydro-2,7-naphthyridin-1-one;
2-methyl-8-(methylamino)-6-(pyrimidin-5-yl)-1,2-dihydro-2,7-naphthyridin-1-one;
8-amino-6-(2-aminopyrimidin-5-yl)-2-methyl-1,2-dihydro-2,7-naphthyridin-1-one;
6-(2-aminopyrimidin-5-yl)-2-methyl-8-(methylamino)-1,2-dihydro-2,7-naphthyridin-1-one;
8-{[4-(1-ethylpiperidin-4-yl)phenyl]amino}-6-(2-methanesulfonylphenyl)-1,2-dihydro-2,7-naphthyridin-1-one;
6-(4-methanesulfonylphenyl)-8-{[3-(morpholin-4-yl)phenyl]amino}-1,2-dihydro-2,7-naphthyridin-1-one;
8-{[4-(1-ethylpiperidin-4-yl)phenyl]amino}-6-[2-(methylsulfanyl)phenyl]-1,2-dihydro-2,7-naphthyridin-1-one;
8-({4-[(4-ethylpiperazin-1-yl)methyl]phenyl}amino)-6-[(2-methylphenyl)amino]-1,2-dihydro-2,7-naphthyridin-1-one;
8-({4-[(4-ethylpiperazin-1-yl)methyl]phenyl}amino)-6-(3-methanesulfonylphenyl)-1,2-dihydro-2,7-naphthyridin-1-one;
8-({4-[(4-ethylpiperazin-1-yl)methyl]phenyl}amino)-6-(4-methanesulfonylphenyl)-1,2-dihydro-2,7-naphthyridin-1-one;
6-(3-methanesulfonylphenyl)-8-{[3-(morpholin-4-yl)phenyl]amino}-1,2-dihydro-2,7-naphthyridin-1-one;
8-{[4-(1-ethylpiperidin-4-yl)phenyl]amino}-6-[(2-methylphenyl)amino]-1,2-dihydro-2,7-naphthyridin-1-one;
6-[4-(2-hydroxypropan-2-yl)phenyl]-8-(1H-indazol-5-ylamino)-1,2-dihydro-2,7-naphthyridin-1-one;
6-[6-(2-hydroxypropan-2-yl)pyridin-3-yl]-8-(1H-indazol-5-ylamino)-1,2-dihydro-2,7-naphthyridin-1-one;
8-(1H-indazol-5-ylamino)-6-[5-(propan-2-yloxy)pyridin-3-yl]-1,2-dihydro-2,7-naphthyridin-1-one;

6-(6-fluoropyridin-3-yl)-8-(1H-indazol-6-ylamino)-1,2-dihydro-2,7-naphthyridin-1-one;

8-(1H-indazol-6-ylamino)-6-[6-(methylamino)pyridin-3-yl]-1,2-dihydro-2,7-naphthyridin-1-one;

6-[6-(ethylamino)pyridin-3-yl]-8-(1H-indazol-6-ylamino)-1,2-dihydro-2,7-naphthyridin-1-one;

6-(2-aminopyrimidin-5-yl)-2-[2-(dimethylamino)ethyl]-8-{[4-(morpholin-4-yl)phenyl]amino}-1,2-dihydro-2,7-naphthyridin-1-one;

6-(2-methyl-1,3-thiazol-4-yl)-8-{[4-(trifluoromethoxy)phenyl]amino}-1,2-dihydro-2,7-naphthyridin-1-one;

N-methyl-3-{[3-(2-methyl-1,3-thiazol-4-yl)-8-oxo-7,8-dihydro-2,7-naphthyridin-1-yl]amino}benzamide;

3-{[3-(2-methyl-1,3-thiazol-4-yl)-8-oxo-7,8-dihydro-2,7-naphthyridin-1-yl]amino}-N-propylbenzamide;

6-(2-methyl-1,3-thiazol-4-yl)-8-{[6-(piperidin-4-yl)pyridin-3-yl]amino}-1,2-dihydro-2,7-naphthyridin-1-one;

6-(2-methyl-1,3-thiazol-4-yl)-8-{[3-methyl-4-(piperidin-4-yl)phenyl]amino}-1,2-dihydro-2,7-naphthyridin-1-one;

8-({4-[(4-ethylpiperazin-1-yl)methyl]phenyl}amino)-6-(6-methoxypyrazin-2-yl)-1,2-dihydro-2,7-naphthyridin-1-one;

N-(3-methoxypropyl)-4-{[3-(6-methoxypyrazin-2-yl)-8-oxo-7,8-dihydro-2,7-naphthyridin-1-yl]amino}benzene-1-sulfonamide;

6-(6-amino-5-methylpyridin-3-yl)-8-({4-[(2R,6S)-2,6-dimethylmorpholin-4-yl]phenyl}amino)-1,2-dihydro-2,7-naphthyridin-1-one;

6-(2-aminopyrimidin-5-yl)-2-methyl-8-{[3-(trifluoromethyl)phenyl]amino}-1,2-dihydro-2,7-naphthyridin-1-one;

6-(2-aminopyrimidin-5-yl)-2-methyl-8-({3-methyl-4-[2-(pyrrolidin-1-yl)ethoxy]phenyl}amino)-1,2-dihydro-2,7-naphthyridin-1-one;

6-(2-aminopyrimidin-5-yl)-2-ethyl-8-{[4-(morpholin-4-yl)phenyl]amino}-1,2-dihydro-2,7-naphthyridin-1-one;

6-(2-aminopyrimidin-5-yl)-2-methyl-8-({4-[2-(morpholin-4-yl)ethoxy]phenyl}amino)-1,2-dihydro-2,7-naphthyridin-1-one;

6-(2-aminopyrimidin-5-yl)-2-methyl-8-({3-[2-(morpholin-4-yl)ethoxy]phenyl}amino)-1,2-dihydro-2,7-naphthyridin-1-one;

6-(6-amino-5-methylpyridin-3-yl)-8-({3-chloro-4-[(2R,6S)-2,6-dimethylmorpholin-4-yl]phenyl}amino)-1,2-dihydro-2,7-naphthyridin-1-one;

8-({3-fluoro-4-[(2R)-2-methylmorpholin-4-yl]phenyl}amino)-6-(6-fluoropyridin-3-yl)-1,2-dihydro-2,7-naphthyridin-1-one;

8-({3-fluoro-4-[(2R)-2-methylmorpholin-4-yl]phenyl}amino)-6-[6-(methylamino)pyridin-3-yl]-1,2-dihydro-2,7-naphthyridin-1-one;

6-[6-(ethylamino)pyridin-3-yl]-8-({3-fluoro-4-[(2R)-2-methylmorpholin-4-yl]phenyl}amino)-1,2-dihydro-2,7-naphthyridin-1-one;

8-(1H-indazol-5-ylamino)-6-[3-methanesulfonyl-4-(pyrrolidin-1-ylmethyl)phenyl]-1,2-dihydro-2,7-naphthyridin-1-one;

8-(1H-indazol-5-ylamino)-6-[3-methanesulfonyl-4-(morpholin-4-ylmethyl)phenyl]-1,2-dihydro-2,7-naphthyridin-1-one;

8-(1H-indazol-5-ylamino)-6-[5-(morpholin-4-ylmethyl)pyridin-3-yl]-1,2-dihydro-2,7-naphthyridin-1-one;

8-(1H-indazol-5-ylamino)-6-[5-(pyrrolidin-1-ylmethyl)pyridin-3-yl]-1,2-dihydro-2,7-naphthyridin-1-one;

6-[4-(2-hydroxypropan-2-yl)phenyl]-8-(1H-indazol-6-ylamino)-1,2-dihydro-2,7-naphthyridin-1-one;

6-(2-aminopyrimidin-5-yl)-8-[(3-methoxy-4-methylphenyl)amino]-1,2-dihydro-2,7-naphthyridin-1-one;

2-(2-methanesulfonylethyl)-8-({4-[1-(2-methanesulfonylethyl)piperidin-4-yl]phenyl}amino)-6-(4-methanesulfonylphenyl)-1,2-dihydro-2,7-naphthyridin-1-one;

6-chloro-2-(2-methanesulfonylethyl)-8-({4-[1-(2-methanesulfonylethyl)piperidin-4-yl]phenyl}amino)-1,2-dihydro-2,7-naphthyridin-1-one;

6-chloro-8-{[4-(1-ethylpiperidin-4-yl)phenyl]amino}-2-(2-methanesulfonylethyl)-1,2-dihydro-2,7-naphthyridin-1-one;

8-{[4-(1-ethylpiperidin-4-yl)phenyl]amino}-2-(2-methanesulfonylethyl)-6-(4-methanesulfonylphenyl)-1,2-dihydro-2,7-naphthyridin-1-one;

2-(2-methanesulfonylethyl)-6-(4-methanesulfonylphenyl)-8-{[4-(piperidin-4-yl)phenyl]amino}-1,2-dihydro-2,7-naphthyridin-1-one;

6-chloro-2-(2-methanesulfonylethyl)-8-{[4-(piperidin-4-yl)phenyl]amino}-1,2-dihydro-2,7-naphthyridin-1-one;

tert-butyl 4-(4-{[7-(2-methanesulfonylethyl)-3-(4-methanesulfonylphenyl)-8-oxo-7,8-dihydro-2,7-naphthyridin-1-yl]amino}phenyl)piperidine-1-carboxylate;

tert-butyl 4-(4-{[3-chloro-7-(2-methanesulfonylethyl)-8-oxo-7,8-dihydro-2,7-naphthyridin-1-yl]amino}phenyl)piperidine-1-carboxylate;

6-(6-methoxypyridin-2-yl)-8-({3-methyl-4-[(2R)-2-methylmorpholin-4-yl]phenyl}amino)-1,2-dihydro-2,7-naphthyridin-1-one;

6-(6-methoxypyridin-2-yl)-8-({4-[2-(morpholin-4-yl)ethoxy]phenyl}amino)-1,2-dihydro-2,7-naphthyridin-1-one;

6-(3-methoxypyrazin-2-yl)-8-({3-methyl-4-[(2R)-2-methylmorpholin-4-yl]phenyl}amino)-1,2-dihydro-2,7-naphthyridin-1-one;

8-({3-fluoro-4-[(2R)-2-methylmorpholin-4-yl]phenyl}amino)-6-(6-methylpyridin-3-yl)-1,2-dihydro-2,7-naphthyridin-1-one;

8-({3-fluoro-4-[(2R)-2-methylmorpholin-4-yl]phenyl}amino)-6-(6-methoxypyridin-2-yl)-1,2-dihydro-2,7-naphthyridin-1-one;

8-({3-fluoro-4-[(2R)-2-methylmorpholin-4-yl]phenyl}amino)-6-(3-methoxypyrazin-2-yl)-1,2-dihydro-2,7-naphthyridin-1-one;

8-{[3-fluoro-4-(morpholin-4-yl)phenyl]amino}-6-(3-methoxypyrazin-2-yl)-1,2-dihydro-2,7-naphthyridin-1-one;

8-(1H-indazol-6-ylamino)-6-(pyrimidin-5-yl)-1,2-dihydro-2,7-naphthyridin-1-one;

6-(pyrimidin-5-yl)-8-[(2,2,2-trifluoroethyl)amino]-1,2-dihydro-2,7-naphthyridin-1-one;

6-(2-methoxypyrimidin-5-yl)-8-[(2,2,2-trifluoroethyl)amino]-1,2-dihydro-2,7-naphthyridin-1-one;

6-(2-aminopyrimidin-5-yl)-2-[2-(dimethylamino)ethyl]-8-[(3-methoxyphenyl)amino]-1,2-dihydro-2,7-naphthyridin-1-one;

6-(5-amino-4-methylpyridin-2-yl)-8-{[4-(morpholin-4-yl)phenyl]amino}-1,2-dihydro-2,7-naphthyridin-1-one;

6-(5-amino-6-methoxypyrazin-2-yl)-8-{[4-(piperidin-4-yl)phenyl]amino}-1,2-dihydro-2,7-naphthyridin-1-one;

6-(2-methoxypyrimidin-5-yl)-8-({6-[(2S)-2-methylmorpholin-4-yl]pyridin-3-yl}amino)-1,2-dihydro-2,7-naphthyridin-1-one;

8-({6-[(2S)-2-methylmorpholin-4-yl]pyridin-3-yl}amino)-6-(pyrimidin-5-yl)-1,2-dihydro-2,7-naphthyridin-1-one;

6-(2-aminopyrimidin-5-yl)-2-(2-methoxyethyl)-8-{[4-(morpholin-4-yl)phenyl]amino}-1,2-dihydro-2,7-naphthyridin-1-one;

2-[2-(dimethylamino)ethyl]-6-[2-(methylamino)pyrimidin-5-yl]-8-{[4-(morpholin-4-yl)phenyl]amino}-1,2-dihydro-2,7-naphthyridin-1-one;

8-{[4-(1-acetylpiperidin-4-yl)-3-methylphenyl]amino}-6-(2-aminopyrimidin-5-yl)-2-methyl-1,2-dihydro-2,7-naphthyridin-1-one;

6-(2-aminopyrimidin-5-yl)-8-{[3-methyl-4-(1-methylpiperidin-4-yl)phenyl]amino}-1,2-dihydro-2,7-naphthyridin-1-one;

8-{[3-methyl-4-(1-methylpiperidin-4-yl)phenyl]amino}-6-(6-methylpyridin-3-yl)-1,2-dihydro-2,7-naphthyridin-1-one;

6-(6-methoxypyridin-2-yl)-8-{[3-methyl-4-(1-methylpiperidin-4-yl)phenyl]amino}-1,2-dihydro-2,7-naphthyridin-1-one;

8-{[4-(1-acetylpiperidin-4-yl)-3-methylphenyl]amino}-6-(6-methoxypyridin-2-yl)-1,2-dihydro-2,7-naphthyridin-1-one;

8-{[4-(1-acetylpiperidin-4-yl)-3-methylphenyl]amino}-6-(3-methoxypyrazin-2-yl)-1,2-dihydro-2,7-naphthyridin-1-one;

8-{[4-(1-acetylpiperidin-4-yl)-3-methylphenyl]amino}-6-(6-methylpyridin-3-yl)-1,2-dihydro-2,7-naphthyridin-1-one;

6-(2,4-dimethoxypyrimidin-5-yl)-8-({3-methyl-4-[2-(pyrrolidin-1-yl)ethoxy]phenyl}amino)-1,2-dihydro-2,7-naphthyridin-1-one;

6-(2,4-dimethoxypyrimidin-5-yl)-8-({4-[2-(pyrrolidin-1-yl)ethoxy]phenyl}amino)-1,2-dihydro-2,7-naphthyridin-1-one;

6-(2,4-dimethoxypyrimidin-5-yl)-8-({4-[2-(morpholin-4-yl)ethoxy]phenyl}amino)-1,2-dihydro-2,7-naphthyridin-1-one;

6-(6-amino-5-methylpyridin-3-yl)-8-({4-[2-(4-ethylpiperazin-1-yl)ethyl]phenyl}amino)-1,2-dihydro-2,7-naphthyridin-1-one;

6-(2,4-dimethoxypyrimidin-5-yl)-8-({4-[2-(4-ethylpiperazin-1-yl)ethyl]phenyl}amino)-1,2-dihydro-2,7-naphthyridin-1-one;

8-({4-[2-(4-ethylpiperazin-1-yl)ethyl]phenyl}amino)-6-(6-methoxypyrazin-2-yl)-1,2-dihydro-2,7-naphthyridin-1-one;

6-(6-methoxypyrazin-2-yl)-8-({4-[2-(morpholin-4-yl)ethyl]phenyl}amino)-1,2-dihydro-2,7-naphthyridin-1-one;

6-(5-amino-6-methoxypyrazin-2-yl)-8-{[4-(1-methylpiperidin-4-yl)phenyl]amino}-1,2-dihydro-2,7-naphthyridin-1-one;

8-{[4-(1-acetylpiperidin-4-yl)phenyl]amino}-6-(5-amino-6-methoxypyrazin-2-yl)-1,2-dihydro-2,7-naphthyridin-1-one;

6-(6-aminopyridin-3-yl)-8-({4-[2-(morpholin-4-yl)ethyl]phenyl}amino)-1,2-dihydro-2,7-naphthyridin-1-one;

6-(6-aminopyridin-3-yl)-8-({4-[2-(4-ethylpiperazin-1-yl)ethyl]phenyl}amino)-1,2-dihydro-2,7-naphthyridin-1-one;

6-(6-aminopyridin-3-yl)-8-[(4-{2-[4-(morpholin-4-yl)piperidin-1-yl]ethyl}phenyl)amino]-1,2-dihydro-2,7-naphthyridin-1-one;

6-(6-aminopyridin-3-yl)-8-[(4-{2-[4-(2-methoxyethyl)piperazin-1-yl]ethyl}phenyl)amino]-1,2-dihydro-2,7-naphthyridin-1-one;

6-(6-aminopyridin-3-yl)-8-[(4-{2-[(2S)-2-(hydroxymethyl)pyrrolidin-1-yl]ethyl}phenyl)amino]-1,2-dihydro-2,7-naphthyridin-1-one;

6-(6-aminopyridin-3-yl)-8-({4-[(1-methylpiperidin-4-yl)oxy]phenyl}amino)-1,2-dihydro-2,7-naphthyridin-1-one;

8-({3-methyl-4-[(2S)-2-methylmorpholin-4-yl]phenyl}amino)-6-(pyrimidin-5-yl)-1,2-dihydro-2,7-naphthyridin-1-one;

6-(2-methoxypyrimidin-5-yl)-8-({3-methyl-4-[(2S)-2-methylmorpholin-4-yl]phenyl}amino)-1,2-dihydro-2,7-naphthyridin-1-one;

8-{[4-(morpholin-4-yl)phenyl]amino}-6-{6-[2-(pyrrolidin-1-yl)ethoxy]pyridin-2-yl}-1,2-dihydro-2,7-naphthyridin-1-one;

6-(2-ethoxypyrimidin-5-yl)-8-({3-methyl-4-[(2R)-2-methylmorpholin-4-yl]phenyl}amino)-1,2-dihydro-2,7-naphthyridin-1-one;

6-[6-(4-methylpiperazin-1-yl)pyridin-2-yl]-8-{[4-(morpholin-4-yl)phenyl]amino}-1,2-dihydro-2,7-naphthyridin-1-one;

8-{[4-(morpholin-4-yl)phenyl]amino}-6-[6-(morpholin-4-yl)pyridin-2-yl]-1,2-dihydro-2,7-naphthyridin-1-one;

8-{[4-(morpholin-4-yl)phenyl]amino}-6-[6-(pyrrolidin-1-yl)pyridin-2-yl]-1,2-dihydro-2,7-naphthyridin-1-one;

6-(2-ethoxypyrimidin-5-yl)-8-({6-[(2S)-2-methylmorpholin-4-yl]pyridin-3-yl}amino)-1,2-dihydro-2,7-naphthyridin-1-one;

6-(2-ethoxypyrimidin-5-yl)-8-({6-[(2R)-2-methylmorpholin-4-yl]pyridin-3-yl}amino)-1,2-dihydro-2,7-naphthyridin-1-one;

6-(2-ethoxypyrimidin-5-yl)-8-({3-methyl-4-[(2S)-2-methylmorpholin-4-yl]phenyl}amino)-1,2-dihydro-2,7-naphthyridin-1-one;

6-(6-aminopyridin-3-yl)-8-({[4-(morpholin-4-yl)phenyl]methyl}amino)-1,2-dihydro-2,7-naphthyridin-1-one;

8-{[3-methyl-4-(1-methylpiperidin-4-yl)phenyl]amino}-6-(pyrimidin-5-yl)-1,2-dihydro-2,7-naphthyridin-1-one;

6-(6-aminopyridin-3-yl)-8-({3-methyl-4-[(1-methylpiperidin-4-yl)oxy]phenyl}amino)-1,2-dihydro-2,7-naphthyridin-1-one;

6-(6-aminopyridin-3-yl)-8-{[4-(oxan-4-yloxy)phenyl]amino}-1,2-dihydro-2,7-naphthyridin-1-one;

6-[2-(methylamino)pyrimidin-5-yl]-8-({4-[2-(morpholin-4-yl)ethyl]phenyl}amino)-1,2-dihydro-2,7-naphthyridin-1-one;

6-[2-(methylamino)pyrimidin-5-yl]-8-[(4-{2-[4-(morpholin-4-yl)piperidin-1-yl]ethyl}phenyl)amino]-1,2-dihydro-2,7-naphthyridin-1-one;

6-[2-(methylamino)pyrimidin-5-yl]-8-({4-[(1-methylpiperidin-4-yl)oxy]phenyl}amino)-1,2-dihydro-2,7-naphthyridin-1-one;

8-({3-methyl-4-[(1-methylpiperidin-4-yl)oxy]phenyl}amino)-6-[2-(methylamino)pyrimidin-5-yl]-1,2-dihydro-2,7-naphthyridin-1-one;

6-[2-(methylamino)pyrimidin-5-yl]-8-{[4-(oxan-4-yloxy)phenyl]amino}-1,2-dihydro-2,7-naphthyridin-1-one;

6-[2-(methylamino)pyrimidin-5-yl]-8-({4-[1-(3,3,3-trifluoro-2-hydroxypropyl)piperidin-4-yl]phenyl}amino)-1,2-dihydro-2,7-naphthyridin-1-one;

6-(2-aminopyrimidin-5-yl)-2-(2-methoxyethyl)-8-[(3-methoxyphenyl)amino]-1,2-dihydro-2,7-naphthyridin-1-one;
6-(6-amino-5-methylpyridin-3-yl)-8-[(2,3-dimethyl-2H-indazol-6-yl)amino]-1,2-dihydro-2,7-naphthyridin-1-one;
6-(2-aminopyrimidin-5-yl)-8-[(2,3-dimethyl-2H-indazol-6-yl)amino]-2-methyl-1,2-dihydro-2,7-naphthyridin-1-one;
6-(2-aminopyrimidin-5-yl)-2-methyl-8-[(2-methyl-2H-indazol-6-yl)amino]-1,2-dihydro-2,7-naphthyridin-1-one;
6-(2-aminopyrimidin-5-yl)-8-({4-[(2R,6S)-2,6-dimethylmorpholin-4-yl]phenyl}amino)-2-methyl-1,2-dihydro-2,7-naphthyridin-1-one;
6-(2-aminopyrimidin-5-yl)-2-methyl-8-({4-[2-(morpholin-4-yl)ethyl]phenyl}amino)-1,2-dihydro-2,7-naphthyridin-1-one;
6-(2-aminopyrimidin-5-yl)-8-[(4-{2-[4-(dimethylamino)piperidin-1-yl]ethyl}phenyl)amino]-2-methyl-1,2-dihydro-2,7-naphthyridin-1-one;
8-({3-methyl-4-[(2R)-2-methylmorpholin-4-yl]phenyl}amino)-6-(2-methylpyrimidin-5-yl)-1,2-dihydro-2,7-naphthyridin-1-one;
6-(2-methyl-1,3-thiazol-4-yl)-8- ({6-[(2R)-2-methylmorpholin-4-yl]pyridin-3-yl}amino)-1,2-dihydro-2,7-naphthyridin-1-one;
6-(2-methyl-1,3-thiazol-4-yl)-8-({3-methyl-4-[(2R)-2-methylmorpholin-4-yl]phenyl}amino)-1,2-dihydro-2,7-naphthyridin-1-one;
8-[(4-{2-[(2S)-2-(hydroxymethyl)pyrrolidin-1-yl]ethyl}phenyl)amino]-6-(2-methyl-1,3-thiazol-4-yl)-1,2-dihydro-2,7-naphthyridin-1-one;
6-(2-methyl-1,3-thiazol-4-yl)-8-({[4-(morpholin-4-yl)phenyl]methyl}amino)-1,2-dihydro-2,7-naphthyridin-1-one;
8-{[4-(piperidin-4-yl)phenyl]amino}-6-{[2-(propane-2-sulfonyl)phenyl]amino}-1,2-dihydro-2,7-naphthyridin-1-one;
6-(4-methyl-1,3-thiazol-2-yl)-8-{[4-(morpholin-4-yl)phenyl]amino}-1,2-dihydro-2,7-naphthyridin-1-one;
6-{[2-(methylsulfanyl)phenyl]amino}-8-{[4-(piperidin-4-yl)phenyl]amino}-1,2-dihydro-2,7-naphthyridin-1-one;
6-(3-methylpyridin-2-yl)-8-{[4-(morpholin-4-yl)phenyl]amino}-1,2-dihydro-2,7-naphthyridin-1-one;
6-[(3-phenoxyphenyl)amino]-8-{[4-(piperidin-4-yl)phenyl]amino}-1,2-dihydro-2,7-naphthyridin-1-one;
8-[(4-{2-[4-(2-methoxyethyl)piperazin-1-yl]ethyl}phenyl)amino]-6-(6-methylpyridin-2-yl)-1,2-dihydro-2,7-naphthyridin-1-one;
6-(6-methylpyridin-2-yl)-8-[(4-{2-[4-(pyrrolidin-1-yl)piperidin-1-yl]ethyl}phenyl)amino]-1,2-dihydro-2,7-naphthyridin-1-one;
6-[(2-ethoxyphenyl)amino]-8-{[4-(piperidin-4-yl)phenyl]amino}-1,2-dihydro-2,7-naphthyridin-1-one;
6-(6-methoxypyrazin-2-yl)-8-[(3-methyl-1H-indazol-6-yl)amino]-1,2-dihydro-2,7-naphthyridin-1-one;
6-(2-methoxypyrimidin-5-yl)-8-[(3-methyl-1H-indazol-6-yl)amino]-1,2-dihydro-2,7-naphthyridin-1-one;
8-[(3-methyl-1H-indazol-6-yl)amino]-6-(6-methylpyridin-2-yl)-1,2-dihydro-2,7-naphthyridin-1-one;
8-[(3-methyl-1H-indazol-6-yl)amino]-6-(pyrimidin-5-yl)-1,2-dihydro-2,7-naphthyridin-1-one;
6-[6-(4-methyl-1H-imidazol-1-yl)pyridin-2-yl]-8-({3-methyl-4-[(2R)-2-methylmorpholin-4-yl]phenyl}amino)-1,2-dihydro-2,7-naphthyridin-1-one;
8-({3-methyl-4-[(2R)-2-methylmorpholin-4-yl]phenyl}amino)-6-[6-(morpholin-4-yl)pyridin-2-yl]-1,2-dihydro-2,7-naphthyridin-1-one;
6-[6-(dimethylamino)pyridin-2-yl]-8-({3-methyl-4-[(2R)-2-methylmorpholin-4-yl]phenyl}amino)-1,2-dihydro-2,7-naphthyridin-1-one;
6-(2-methoxypyrimidin-5-yl)-8-{[3-methyl-4-(1-methylpiperidin-4-yl)phenyl]amino}-1,2-dihydro-2,7-naphthyridin-1-one;
8-{[3-methyl-4-(piperidin-4-yl)phenyl]amino}-6-(pyrimidin-5-yl)-1,2-dihydro-2,7-naphthyridin-1-one;
6-(2-methoxypyrimidin-5-yl)-8-{[3-methyl-4-(piperidin-4-yl)phenyl]amino}-1,2-dihydro-2,7-naphthyridin-1-one;
6-(3-methoxypyrazin-2-yl)-8-{[3-methyl-4-(1-methylpiperidin-4-yl)phenyl]amino}-1,2-dihydro-2,7-naphthyridin-1-one;
6-(6-methoxypyrazin-2-yl)-8-{[3-methyl-4-(piperidin-4-yl)phenyl]amino}-1,2-dihydro-2,7-naphthyridin-1-one;
6-(6-methoxypyrazin-2-yl)-8-{[3-methyl-4-(1-methylpiperidin-4-yl)phenyl]amino}-1,2-dihydro-2,7-naphthyridin-1-one;
8-({4-[(4-ethylpiperazin-1-yl)methyl]phenyl}amino)-6-[(5-methoxy-2-methylphenyl)amino]-1,2-dihydro-2,7-naphthyridin-1-one;
8-({4-[(4-ethylpiperazin-1-yl)methyl]phenyl}amino)-6-{[2-(trifluoromethoxy)phenyl]amino}-1,2-dihydro-2,7-naphthyridin-1-one;
8-({4-[(4-ethylpiperazin-1-yl)methyl]phenyl}amino)-6-{[2-methoxy-5-(trifluoromethyl)phenyl]amino}-1,2-dihydro-2,7-naphthyridin-1-one;
8-({4-[(4-ethylpiperazin-1-yl)methyl]phenyl}amino)-6-(1H-indazol-6-ylamino)-1,2-dihydro-2,7-naphthyridin-1-one;
8-({4-[(4-ethylpiperazin-1-yl)methyl]phenyl}amino)-6-[(2-methoxy-5-methylphenyl)amino]-1,2-dihydro-2,7-naphthyridin-1-one;
N-(3-{[1-({4-[(4-ethylpiperazin-1-yl)methyl]phenyl}amino)-8-oxo-7,8-dihydro-2,7-naphthyridin-3-yl]amino}-4-methoxyphenyl)acetamide
8-({4-[(4-ethylpiperazin-1-yl)methyl]phenyl}amino)-6-{[2-methoxy-4-(phenylamino)phenyl]amino}-1,2-dihydro-2,7-naphthyridin-1-one;
6-[(5-chloro-2-methoxyphenyl)amino]-8-({4-[(4-ethylpiperazin-1-yl)methyl]phenyl}amino)-1,2-dihydro-2,7-naphthyridin-1-one;
8-({4-[(4-ethylpiperazin-1-yl)methyl]phenyl}amino)-6-[(2-methoxy-5-nitrophenyl)amino]-1,2-dihydro-2,7-naphthyridin-1-one;
8-{[4-(piperidin-4-yl)phenyl]amino}-6-{[3-(trifluoromethoxy)phenyl]amino}-1,2-dihydro-2,7-naphthyridin-1-one;
6-[(3-methoxy-4-phenylphenyl)amino]-8-{[4-(piperidin-4-yl)phenyl]amino}-1,2-dihydro-2,7-naphthyridin-1-one;
8-({4-[(4-ethylpiperazin-1-yl)methyl]phenyl}amino)-6-[(3-methoxy-4-phenylphenyl)amino]-1,2-dihydro-2,7-naphthyridin-1-one;
8-[(2,3-dimethyl-2H-indazol-6-yl)amino]-6-(6-methoxypyrazin-2-yl)-1,2-dihydro-2,7-naphthyridin-1-one;
6-(6-methoxypyrazin-2-yl)-8-[(2-methyl-2H-indazol-6-yl)amino]-1,2-dihydro-2,7-naphthyridin-1-one;
6-(6-methoxypyrazin-2-yl)-8-({4-[1-(3,3,3-trifluoro-2-hydroxypropyl)piperidin-4-yl]phenyl}amino)-1,2-dihydro-2,7-naphthyridin-1-one;

6-(6-methoxypyrazin-2-yl)-8-{[6-(oxan-4-yl)pyridin-3-yl]amino}-1,2-dihydro-2,7-naphthyridin-1-one;

8-[(2,3-dimethyl-2H-indazol-6-yl)amino]-6-(3-methoxypyrazin-2-yl)-1,2-dihydro-2,7-naphthyridin-1-one;

6-(2,4-dimethoxypyrimidin-5-yl)-8-[(2,3-dimethyl-2H-indazol-6-yl)amino]-1,2-dihydro-2,7-naphthyridin-1-one;

6-(2,4-dimethoxypyrimidin-5-yl)-8-{[3-methyl-4-(2-methylmorpholin-4-yl)phenyl]amino}-1,2-dihydro-2,7-naphthyridin-1-one;

6-(5-amino-6-methylpyrazin-2-yl)-8-[(2,3-dimethyl-2H-indazol-6-yl)amino]-1,2-dihydro-2,7-naphthyridin-1-one;

6-(2-aminopyrimidin-5-yl)-2-methyl-8-{[3-methyl-4-(2-methylmorpholin-4-yl)phenyl]amino}-1,2-dihydro-2,7-naphthyridin-1-one;

6-(5-amino-6-methoxypyrazin-2-yl)-2-methyl-8-{[4-(morpholin-4-yl)phenyl]amino}-1,2-dihydro-2,7-naphthyridin-1-one;

6-(5-amino-6-methoxypyrazin-2-yl)-8-({3-methyl-4-[2-(pyrrolidin-1-yl)ethoxy]phenyl}amino)-1,2-dihydro-2,7-naphthyridin-1-one;

8-({3-methyl-4-[(2R)-2-methylmorpholin-4-yl]phenyl}amino)-6-{6-[2-(pyrrolidin-1-yl)ethoxy]pyridin-2-yl}-1,2-dihydro-2,7-naphthyridin-1-one;

6-(5-amino-6-methoxypyrazin-2-yl)-8-({3-methyl-4-[(2S)-2-methylmorpholin-4-yl]phenyl}amino)-1,2-dihydro-2,7-naphthyridin-1-one;

8-[(4-{2-[4-(dimethylamino)piperidin-1-yl]ethyl}phenyl)amino]-6-(pyrimidin-5-yl)-1,2-dihydro-2,7-naphthyridin-1-one;

8-[(4-{2-[(2S)-2-(hydroxymethyl)pyrrolidin-1-yl]ethyl}phenyl)amino]-6-(pyrimidin-5-yl)-1,2-dihydro-2,7-naphthyridin-1-one;

8-[(4-{2-[4-(2-methoxyethyl)piperazin-1-yl]ethyl}phenyl)amino]-6-(pyrimidin-5-yl)-1,2-dihydro-2,7-naphthyridin-1-one;

8-({4-[(1-methylpiperidin-4-yl)oxy]phenyl}amino)-6-(pyrimidin-5-yl)-1,2-dihydro-2,7-naphthyridin-1-one;

8-{[4-(oxan-4-yloxy)phenyl]amino}-6-(pyrimidin-5-yl)-1,2-dihydro-2,7-naphthyridin-1-one;

N-{4-[1-({3-methyl-4-[(2R)-2-methylmorpholin-4-yl]phenyl}amino)-8-oxo-7,8-dihydro-2,7-naphthyridin-3-yl]phenyl}acetamide 8-({2-[(2R)-2-methylmorpholin-4-yl]pyrimidin-5-yl}amino)-6-(pyrimidin-5-yl)-1,2-dihydro-2,7-naphthyridin-1-one;

8-[(4-{2-[(2S)-2-(hydroxymethyl)pyrrolidin-1-yl]ethyl}phenyl)amino]-6-(6-methylpyridin-2-yl)-1,2-dihydro-2,7-naphthyridin-1-one;

8-[(4-{2-[4-(2-methoxyethyl)piperazin-1-yl]ethyl}phenyl)amino]-6-(2-methyl-1,3-thiazol-4-yl)-1,2-dihydro-2,7-naphthyridin-1-one;

8-[(4-{2-[4-(dimethylamino)piperidin-1-yl]ethyl}phenyl)amino]-6-(2-methyl-1,3-thiazol-4-yl)-1,2-dihydro-2,7-naphthyridin-1-one;

6-(2-methyl-1,3-thiazol-4-yl)-8-[(4-{2-[4-(pyrrolidin-1-yl)piperidin-1-yl]ethyl}phenyl)amino]-1,2-dihydro-2,7-naphthyridin-1-one;

8-({3-methyl-4-[1-(propan-2-yl)piperidin-4-yl]phenyl}amino)-6-(pyrimidin-5-yl)-1,2-dihydro-2,7-naphthyridin-1-one;

6-(5-amino-6-methoxypyrazin-2-yl)-8-({6-[(2S)-2-methylmorpholin-4-yl]pyridin-3-yl}amino)-1,2-dihydro-2,7-naphthyridin-1-one;

8-{[3-methyl-4-(1,2,3,6-tetrahydropyridin-4-yl)phenyl]amino}-6-(pyrimidin-5-yl)-1,2-dihydro-2,7-naphthyridin-1-one;

8-({3-methyl-4-[6-(piperazin-1-yl)pyridin-3-yl]phenyl}amino)-6-(pyrimidin-5-yl)-1,2-dihydro-2,7-naphthyridin-1-one;

8-({4-[1-(piperidin-4-yl)-1H-pyrazol-4-yl]phenyl}amino)-6-(pyrimidin-5-yl)-1,2-dihydro-2,7-naphthyridin-1-one;

8-({3-methyl-4-[1-(piperidin-4-yl)-1H-pyrazol-4-yl]phenyl}amino)-6-(pyrimidin-5-yl)-1,2-dihydro-2,7-naphthyridin-1-one;

8-({4-[2-(morpholin-4-yl)ethyl]phenyl}amino)-6-(pyrimidin-5-yl)-1,2-dihydro-2,7-naphthyridin-1-one;

8-[(4-{2-[4-(morpholin-4-yl)piperidin-1-yl]ethyl}phenyl)amino]-6-(pyrimidin-5-yl)-1,2-dihydro-2,7-naphthyridin-1-one;

8-({4-[2-(4-hydroxypiperidin-1-yl)ethyl]phenyl}amino)-6-(pyrimidin-5-yl)-1,2-dihydro-2,7-naphthyridin-1-one;

8-({3-methyl-4-[(1-methylpiperidin-4-yl)oxy]phenyl}amino)-6-(pyrimidin-5-yl)-1,2-dihydro-2,7-naphthyridin-1-one;

8-({4-[1-(3-fluoropropyl)piperidin-4-yl]phenyl}amino)-6-(6-methoxypyrazin-2-yl)-1,2-dihydro-2,7-naphthyridin-1-one;

8-({4-[1-(3-fluoropropyl)piperidin-4-yl]-3-methylphenyl}amino)-6-(6-methoxypyrazin-2-yl)-1,2-dihydro-2,7-naphthyridin-1-one;

8-({4-[1-(2-methoxyethyl)piperidin-4-yl]-3-methylphenyl}amino)-6-(6-methoxypyrazin-2-yl)-1,2-dihydro-2,7-naphthyridin-1-one;

6-(6-methoxypyrazin-2-yl)-8-{[3-methyl-4-(oxan-4-yl)phenyl]amino}-1,2-dihydro-2,7-naphthyridin-1-one;

6-(6-methoxypyrazin-2-yl)-8-({3-methyl-4-[(1-methylpiperidin-4-yl)oxy]phenyl}amino)-1,2-dihydro-2,7-naphthyridin-1-one;

6-(2-aminopyrimidin-5-yl)-8-({4-[1-(3-fluoropropyl)piperidin-4-yl]-3-methylphenyl}amino)-2-methyl-1,2-dihydro-2,7-naphthyridin-1-one;

6-(6-methoxypyrazin-2-yl)-8-({3-methyl-4-[1-(piperidin-4-yl)-1H-pyrazol-4-yl]phenyl}amino)-1,2-dihydro-2,7-naphthyridin-1-one;

6-(6-methylpyridin-2-yl)-8-[(4-{2-[4-(morpholin-4-yl)piperidin-1-yl]ethyl}phenyl)amino]-1,2-dihydro-2,7-naphthyridin-1-one;

6-(6-methylpyridin-2-yl)-8-({4-[2-(morpholin-4-yl)ethyl]phenyl}amino)-1,2-dihydro-2,7-naphthyridin-1-one;

6-(6-methylpyridin-2-yl)-8-({4-[1-(3,3,3-trifluoro-2-hydroxypropyl)piperidin-4-yl]phenyl}amino)-1,2-dihydro-2,7-naphthyridin-1-one;

8-({4-[2-(4-hydroxypiperidin-1-yl)ethyl]phenyl}amino)-6-(6-methylpyridin-2-yl)-1,2-dihydro-2,7-naphthyridin-1-one;

6-(2-methyl-1,3-thiazol-4-yl)-8-[(4-{2-[4-(morpholin-4-yl)piperidin-1-yl]ethyl}phenyl)amino]-1,2-dihydro-2,7-naphthyridin-1-one;

6-(2-methyl-1,3-thiazol-4-yl)-8-({4-[2-(morpholin-4-yl)ethyl]phenyl}amino)-1,2-dihydro-2,7-naphthyridin-1-one;

6-(2-methyl-1,3-thiazol-4-yl)-8-[(2-methyl-2H-indazol-6-yl)amino]-1,2-dihydro-2,7-naphthyridin-1-one;

6-(2-methyl-1,3-thiazol-4-yl)-8-({4-[1-(3,3,3-trifluoro-2-hydroxypropyl)piperidin-4-yl]phenyl}amino)-1,2-dihydro-2,7-naphthyridin-1-one;

8-({4-[2-(4-hydroxypiperidin-1-yl)ethyl]phenyl}amino)-6-(2-methyl-1,3-thiazol-4-yl)-1,2-dihydro-2,7-naphthyridin-1-one;

6-(2-methoxypyrimidin-5-yl)-8-({4-[1-(3,3,3-trifluoro-2-hydroxypropyl)piperidin-4-yl]phenyl}amino)-1,2-dihydro-2,7-naphthyridin-1-one;

8-({4-[2-(4-hydroxypiperidin-1-yl)ethyl]phenyl}amino)-6-(2-methoxypyrimidin-5-yl)-1,2-dihydro-2,7-naphthyridin-1-one;

6-(2-methoxypyrimidin-5-yl)-8-({4-[2-(morpholin-4-yl)ethyl]phenyl}amino)-1,2-dihydro-2,7-naphthyridin-1-one;

8-({3-fluoro-4-[2-(pyrrolidin-1-yl)ethoxy]phenyl}amino)-6-(2-methoxypyrimidin-5-yl)-1,2-dihydro-2,7-naphthyridin-1-one;

8-({3-fluoro-4-[2-(pyrrolidin-1-yl)ethoxy]phenyl}amino)-6-(pyrimidin-5-yl)-1,2-dihydro-2,7-naphthyridin-1-one;

8-{[4-(1-cyclopropylpiperidin-4-yl)phenyl]amino}-6-(pyrimidin-5-yl)-1,2-dihydro-2,7-naphthyridin-1-one;

8-[(4-{1-[2-(morpholin-4-yl)ethyl]-1H-pyrazol-4-yl}phenyl)amino]-6-(pyrimidin-5-yl)-1,2-dihydro-2,7-naphthyridin-1-one;

8-[(3-methyl-4-{1-[2-(morpholin-4-yl)ethyl]-1H-pyrazol-4-yl}phenyl)amino]-6-(pyrimidin-5-yl)-1,2-dihydro-2,7-naphthyridin-1-one;

8-({4-[2-(4-hydroxypiperidin-1-yl)ethyl]phenyl}amino)-6-[2-(methylamino)pyrimidin-5-yl]-1,2-dihydro-2,7-naphthyridin-1-one;

8-[(4-{2-[4-(dimethylamino)piperidin-1-yl]ethyl}phenyl)amino]-6-[2-(methylamino)pyrimidin-5-yl]-1,2-dihydro-2,7-naphthyridin-1-one;

8-[(4-{2-[(2S)-2-(hydroxymethyl)pyrrolidin-1-yl]ethyl}phenyl)amino]-6-[2-(methylamino)pyrimidin-5-yl]-1,2-dihydro-2,7-naphthyridin-1-one;

8-[(4-{2-[4-(2-methoxyethyl)piperazin-1-yl]ethyl}phenyl)amino]-6-[2-(methylamino)pyrimidin-5-yl]-1,2-dihydro-2,7-naphthyridin-1-one;

6-[2-(methylamino)pyrimidin-5-yl]-8-[(4-{2-[4-(pyrrolidin-1-yl)piperidin-1-yl]ethyl}phenyl)amino]-1,2-dihydro-2,7-naphthyridin-1-one;

8-({4-[1-(3-fluoropropyl)piperidin-4-yl]phenyl}amino)-6-[2-(methylamino)pyrimidin-5-yl]-1,2-dihydro-2,7-naphthyridin-1-one;

8-{[4-(piperazin-1-yl)-3-(trifluoromethyl)phenyl]amino}-6-(pyrimidin-5-yl)-1,2-dihydro-2,7-naphthyridin-1-one;

6-(2-methylpyrimidin-5-yl)-8-{[4-(piperazin-1-yl)-3-(trifluoromethyl)phenyl]amino}-1,2-dihydro-2,7-naphthyridin-1-one;

6-(6-amino-5-methylpyridin-3-yl)-8-{[3-methyl-4-(oxan-4-yl)phenyl]amino}-1,2-dihydro-2,7-naphthyridin-1-one;

6-(2-aminopyrimidin-5-yl)-2-methyl-8-({2-methyl-5-[2-(morpholin-4-yl)ethoxy]phenyl}amino)-1,2-dihydro-2,7-naphthyridin-1-one;

6-(2-aminopyrimidin-5-yl)-8-({2-methyl-5-[2-(morpholin-4-yl)ethoxy]phenyl}amino)-1,2-dihydro-2,7-naphthyridin-1-one;

4-{[3-(6-methoxypyrazin-2-yl)-8-oxo-7,8-dihydro-2,7-naphthyridin-1-yl]amino}-N,2-dimethylbenzamide;

8-[(4-{2-[4-(2-methoxyethyl)piperazin-1-yl]ethyl}phenyl)amino]-6-(6-methoxypyrazin-2-yl)-1,2-dihydro-2,7-naphthyridin-1-one;

6-(6-methoxypyrazin-2-yl)-8-[(4-{1-[2-(morpholin-4-yl)ethyl]-1H-pyrazol-4-yl}phenyl)amino]-1,2-dihydro-2,7-naphthyridin-1-one;

8-{[2-methoxy-4-(4-methylpiperazin-1-yl)phenyl]amino}-6-(6-methoxypyrazin-2-yl)-1,2-dihydro-2,7-naphthyridin-1-one;

8-{[4-(morpholin-4-yl)phenyl]amino}-6-{2H,3H,4H-pyrido[3,2-b][1,4]oxazin-7-yl}-1,2-dihydro-2,7-naphthyridin-1-one;

6-(2-methyl-1,3-thiazol-4-yl)-8-({4-[(1-methylpiperidin-4-yl)oxy]phenyl}amino)-1,2-dihydro-2,7-naphthyridin-1-one;

6-(2-methyl-1,3-thiazol-4-yl)-8-{[4-(oxan-4-yloxy)phenyl]amino}-1,2-dihydro-2,7-naphthyridin-1-one;

8-({4-[1-(3-fluoropropyl)piperidin-4-yl]phenyl}amino)-6-(2-methyl-1,3-thiazol-4-yl)-1,2-dihydro-2,7-naphthyridin-1-one;

8-({4-[(1-methylpiperidin-4-yl)oxy]phenyl}amino)-6-(6-methylpyridin-2-yl)-1,2-dihydro-2,7-naphthyridin-1-one;

6-(6-methylpyridin-2-yl)-8-{[4-(oxan-4-yloxy)phenyl]amino}-1,2-dihydro-2,7-naphthyridin-1-one;

8-({4-[1-(3-fluoropropyl)piperidin-4-yl]phenyl}amino)-6-(6-methylpyridin-2-yl)-1,2-dihydro-2,7-naphthyridin-1-one;

6-(4-methyl-1,3-thiazol-2-yl)-8-({4-[(1-methylpiperidin-4-yl)oxy]phenyl}amino)-1,2-dihydro-2,7-naphthyridin-1-one;

6-(4-methyl-1,3-thiazol-2-yl)-8-{[4-(oxan-4-yloxy)phenyl]amino}-1,2-dihydro-2,7-naphthyridin-1-one;

8-({4-[2-(4-hydroxypiperidin-1-yl)ethyl]phenyl}amino)-6-(4-methyl-1,3-thiazol-2-yl)-1,2-dihydro-2,7-naphthyridin-1-one;

6-(4-methyl-1,3-thiazol-2-yl)-8-({4-[1-(3,3,3-trifluoro-2-hydroxypropyl)piperidin-4-yl]phenyl}amino)-1,2-dihydro-2,7-naphthyridin-1-one;

6-(4-methyl-1,3-thiazol-2-yl)-8-({2-[(2R)-2-methylmorpholin-4-yl]pyrimidin-5-yl}amino)-1,2-dihydro-2,7-naphthyridin-1-one;

8-{[2-fluoro-5-methyl-4-(1-methylpiperidin-4-yl)phenyl]amino}-6-(pyrimidin-5-yl)-1,2-dihydro-2,7-naphthyridin-1-one;

8-{[2-fluoro-5-methyl-4-(1-methylpiperidin-4-yl)phenyl]amino}-6-(2-methoxypyrimidin-5-yl)-1,2-dihydro-2,7-naphthyridin-1-one;

8-{[3-fluoro-4-(1-methylpiperidin-4-yl)phenyl]amino}-6-(pyrimidin-5-yl)-1,2-dihydro-2,7-naphthyridin-1-one;

8-{[3-fluoro-4-(1-methylpiperidin-4-yl)phenyl]amino}-6-(2-methoxypyrimidin-5-yl)-1,2-dihydro-2,7-naphthyridin-1-one;

8-{[6-(1-methylpiperidin-4-yl)pyridin-3-yl]amino}-6-(pyrimidin-5-yl)-1,2-dihydro-2,7-naphthyridin-1-one;

6-(2-methoxypyrimidin-5-yl)-8-{[6-(1-methylpiperidin-4-yl)pyridin-3-yl]amino}-1,2-dihydro-2,7-naphthyridin-1-one;

6-(2,6-dimethylphenyl)-8-{[4-(piperidin-4-yl)phenyl]amino}-1,2-dihydro-2,7-naphthyridin-1-one;

tert-butyl 4-(4-{[3-(2-butoxyphenyl)-8-oxo-7,8-dihydro-2,7-naphthyridin-1-yl]amino}phenyl)piperidine-1-carboxylate;

6-(2-butoxyphenyl)-8-{[4-(piperidin-4-yl)phenyl]amino}-1,2-dihydro-2,7-naphthyridin-1-one;

tert-butyl 4-(4-{[3-(2-ethoxy-5-methylphenyl)-8-oxo-7,8-dihydro-2,7-naphthyridin-1-yl]amino}phenyl)piperidine-1-carboxylate;

6-(2-ethoxy-5-methylphenyl)-8-{[4-(piperidin-4-yl)phenyl]amino}-1,2-dihydro-2,7-naphthyridin-1-one;

tert-butyl 4-(4-{[8-oxo-3-(2-propoxyphenyl)-7,8-dihydro-2,7-naphthyridin-1-yl]amino}phenyl)piperidine-1-carboxylate;

8-{[4-(piperidin-4-yl)phenyl]amino}-6-(2-propoxyphenyl)-1,2-dihydro-2,7-naphthyridin-1-one;

tert-butyl 4-[4-({8-oxo-3-[2-(propan-2-yloxy)phenyl]-7,8-dihydro-2,7-naphthyridin-1-yl}amino)phenyl]piperidine-1-carboxylate;

8-{[4-(piperidin-4-yl)phenyl]amino}-6-[2-(propan-2-yloxy)phenyl]-1,2-dihydro-2,7-naphthyridin-1-one;

tert-butyl 4-(4-{[8-oxo-3-(2-phenoxyphenyl)-7,8-dihydro-2,7-naphthyridin-1-yl]amino}phenyl)piperidine-1-carboxylate;

6-(2-phenoxyphenyl)-8-{[4-(piperidin-4-yl)phenyl]amino}-1,2-dihydro-2,7-naphthyridin-1-one;

6-[2-(methylamino)pyrimidin-5-yl]-8-[(4-{1-[2-(morpholin-4-yl)ethyl]-1H-pyrazol-4-yl}phenyl)amino]-1,2-dihydro-2,7-naphthyridin-1-one;

8-[(3-methyl-4-{1-[2-(morpholin-4-yl)ethyl]-1H-pyrazol-4-yl}phenyl)amino]-6-[2-(methylamino)pyrimidin-5-yl]-1,2-dihydro-2,7-naphthyridin-1-one;

6-(5-amino-6-methoxypyrazin-2-yl)-8-({4-[2-(morpholin-4-yl)ethyl]phenyl}amino)-1,2-dihydro-2,7-naphthyridin-1-one;

6-(6-methylpyrazin-2-yl)-8-{[4-(morpholin-4-yl)phenyl]amino}-1,2-dihydro-2,7-naphthyridin-1-one;

6-(5-amino-6-methoxypyrazin-2-yl)-8-({3-methyl-4-[(1-methylpiperidin-4-yl)oxy]phenyl}amino)-1,2-dihydro-2,7-naphthyridin-1-one;

6-(5-amino-6-methoxypyrazin-2-yl)-8-({3-methyl-4-[1-(piperidin-4-yl)-1H-pyrazol-4-yl]phenyl}amino)-1,2-dihydro-2,7-naphthyridin-1-one;

6-(5-amino-6-methoxypyrazin-2-yl)-8-[(3-methyl-4-{1-[2-(morpholin-4-yl)ethyl]-1H-pyrazol-4-yl}phenyl)amino]-1,2-dihydro-2,7-naphthyridin-1-one;

6-(2-aminopyrimidin-5-yl)-2-(2-methanesulfonylethyl)-8-{[4-(morpholin-4-yl)phenyl]amino}-1,2-dihydro-2,7-naphthyridin-1-one;

6-(6-methoxypyrazin-2-yl)-8-({6-[(2R)-2-methylmorpholin-4-yl]pyridin-3-yl}amino)-1,2-dihydro-2,7-naphthyridin-1-one;

6-(6-methoxypyrazin-2-yl)-8-({6-[(2S)-2-methylmorpholin-4-yl]pyridin-3-yl}amino)-1,2-dihydro-2,7-naphthyridin-1-one;

8-({3-fluoro-4-[(2R)-2-methylmorpholin-4-yl]phenyl}amino)-6-(6-methoxypyrazin-2-yl)-1,2-dihydro-2,7-naphthyridin-1-one;

4-{[3-(6-methoxypyrazin-2-yl)-8-oxo-7,8-dihydro-2,7-naphthyridin-1-yl]amino}-N-propylbenzamide;

8-({4-[1-(2,3-dihydroxypropyl)piperidin-4-yl]phenyl}amino)-6-(6-methylpyridin-2-yl)-1,2-dihydro-2,7-naphthyridin-1-one;

6-(6-methylpyridin-2-yl)-8-[(4-{1-[2-(morpholin-4-yl)ethyl]-1H-pyrazol-4-yl}phenyl)amino]-1,2-dihydro-2,7-naphthyridin-1-one;

8-[(3-methyl-4-{1-[2-(morpholin-4-yl)ethyl]-1H-pyrazol-4-yl}phenyl)amino]-6-(6-methylpyridin-2-yl)-1,2-dihydro-2,7-naphthyridin-1-one;

N,2-dimethyl-4-{[3-(6-methylpyridin-2-yl)-8-oxo-7,8-dihydro-2,7-naphthyridin-1-yl]amino}benzamide;

6-(2-aminopyrimidin-5-yl)-8-[(3-chlorophenyl)amino]-2-(2-methoxyethyl)-1,2-dihydro-2,7-naphthyridin-1-one;

6-(2-aminopyrimidin-5-yl)-2-(2-methoxyethyl)-8-[(3-methylphenyl)amino]-1,2-dihydro-2,7-naphthyridin-1-one;

6-(5-amino-6-methoxypyrazin-2-yl)-2-(2-methoxyethyl)-8-{[4-(morpholin-4-yl)phenyl]amino}-1,2-dihydro-2,7-naphthyridin-1-one;

6-(2-aminopyrimidin-5-yl)-8-[(3-methoxyphenyl)amino]-2-[2-(morpholin-4-yl)ethyl]-1,2-dihydro-2,7-naphthyridin-1-one;

6-(2-aminopyrimidin-5-yl)-8-[(3-methylphenyl)amino]-2-[2-(morpholin-4-yl)ethyl]-1,2-dihydro-2,7-naphthyridin-1-one;

6-(2-aminopyrimidin-5-yl)-8-[(3-chlorophenyl)amino]-2-[2-(morpholin-4-yl)ethyl]-1,2-dihydro-2,7-naphthyridin-1-one;

8-[(1-methyl-1H-pyrazol-4-yl)amino]-6-(pyrimidin-5-yl)-1,2-dihydro-2,7-naphthyridin-1-one;

8-[(2-methanesulfonyl-1,2,3,4-tetrahydroisoquinolin-6-yl)amino]-6-(pyrimidin-5-yl)-1,2-dihydro-2,7-naphthyridin-1-one;

8-[(2-methanesulfonyl-1,2,3,4-tetrahydroisoquinolin-6-yl)amino]-6-(pyrimidin-5-yl)-1,2-dihydro-2,7-naphthyridin-1-one;

8-{[4-(2,2-dimethylmorpholin-4-yl)-3-methylphenyl]amino}-6-(pyrimidin-5-yl)-1,2-dihydro-2,7-naphthyridin-1-one;

8-{[4-(2,2-dimethylmorpholin-4-yl)-3-methylphenyl]amino}-6-(2-methoxypyrimidin-5-yl)-1,2-dihydro-2,7-naphthyridin-1-one;

6-(2,4-dimethoxypyrimidin-5-yl)-8-({4-[1-(2-methoxyethyl)piperidin-4-yl]phenyl}amino)-1,2-dihydro-2,7-naphthyridin-1-one;

8-({4-[1-(2-methoxyethyl)piperidin-4-yl]phenyl}amino)-6-(6-methoxypyrazin-2-yl)-1,2-dihydro-2,7-naphthyridin-1-one;

6-(6-methoxypyrazin-2-yl)-8-[(3-methyl-4-{1-[2-(morpholin-4-yl)ethyl]-1H-pyrazol-4-yl}phenyl)amino]-1,2-dihydro-2,7-naphthyridin-1-one;

6-(6-methoxypyrazin-2-yl)-8-{[4-(pyrrolidin-3-yl)phenyl]amino}-1,2-dihydro-2,7-naphthyridin-1-one;

6-(2,4-dimethoxypyrimidin-5-yl)-8-({4-[1-(2-methoxyethyl)pyrrolidin-3-yl]phenyl}amino)-1,2-dihydro-2,7-naphthyridin-1-one;

8-({4-[1-(2-methoxyethyl)pyrrolidin-3-yl]phenyl}amino)-6-(6-methoxypyrazin-2-yl)-1,2-dihydro-2,7-naphthyridin-1-one;

8-{[6-(oxan-4-yl)pyridin-3-yl]amino}-6-{2H,3H,4H-pyrido[3,2-b][1,4]oxazin-7-yl}-1,2-dihydro-2,7-naphthyridin-1-one;

6-(6-methoxypyrazin-2-yl)-8-({4-[1-(4,4,4-trifluorobutyl)piperidin-4-yl]phenyl}amino)-1,2-dihydro-2,7-naphthyridin-1-one;

6-(6-methoxypyrazin-2-yl)-8-{[4-(piperidin-4-yl)phenyl]amino}-1,2-dihydro-2,7-naphthyridin-1-one;

8-{[4-(1-ethylpyrrolidin-3-yl)phenyl]amino}-6-(6-methoxypyrazin-2-yl)-1,2-dihydro-2,7-naphthyridin-1-one;

4-(4-methoxyphenyl)-8-{[4-(morpholin-4-yl)phenyl]amino}-1,2-dihydro-2,7-naphthyridin-1-one;

N-methyl-4-(8-{[4-(morpholin-4-yl)phenyl]amino}-1-oxo-1,2-dihydro-2,7-naphthyridin-4-yl)benzamide;

8-{[4-(morpholin-4-yl)phenyl]amino}-4-[3-(trifluoromethyl)phenyl]-1,2-dihydro-2,7-naphthyridin-1-one;

4-[3-(dimethylamino)phenyl]-8-{[4-(morpholin-4-yl)phenyl]amino}-1,2-dihydro-2,7-naphthyridin-1-one;

4-(4-chlorophenyl)-8-{[4-(morpholin-4-yl)phenyl]amino}-1,2-dihydro-2,7-naphthyridin-1-one;

8-{[4-(morpholin-4-yl)phenyl]amino}-4-[4-(trifluoromethyl)phenyl]-1,2-dihydro-2,7-naphthyridin-1-one;

6-(2-aminopyrimidin-5-yl)-2-ethyl-8-{[4-(1-ethylpyrrolidin-3-yl)phenyl]amino}-1,2-dihydro-2,7-naphthyridin-1-one;
6-(2,6-dimethoxyphenyl)-8-{[4-(piperidin-4-yl)phenyl]amino}-1,2-dihydro-2,7-naphthyridin-1-one;
tert-butyl 4-(4-{[3-(2,6-dimethoxyphenyl)-8-oxo-7,8-dihydro-2,7-naphthyridin-1-yl}amino]phenyl)piperidine-1-carboxylate;
8-{[2-(3-methylbutoxy)phenyl]amino}-6-(phenylamino)-1,2-dihydro-2,7-naphthyridin-1-one;
6-({4-[(4-ethylpiperazin-1-yl)methyl]phenyl}amino)-8-{[2-(3-methylbutoxy)phenyl]amino}-1,2-dihydro-2,7-naphthyridin-1-one;
8-{[2-(3-methylbutoxy)phenyl]amino}-6-{[2-(propane-2-sulfonyl)phenyl]amino}-1,2-dihydro-2,7-naphthyridin-1-one;
8-{[2-(3-methylbutoxy)phenyl]amino}-6-(pyridin-3-ylamino)-1,2-dihydro-2,7-naphthyridin-1-one;
8-{[2-(3-methylbutoxy)phenyl]amino}-6-{[3-(piperidin-1-ylmethyl)phenyl]amino}-1,2-dihydro-2,7-naphthyridin-1-one;
6-[(2-methoxy-5-phenoxyphenyl)amino]-8-{[2-(3-methylbutoxy)phenyl]amino}-1,2-dihydro-2,7-naphthyridin-1-one;
8-{[2-(3-methylbutoxy)phenyl]amino}-6-{[3-(morpholin-4-yl)phenyl]amino}-1,2-dihydro-2,7-naphthyridin-1-one;
8-{[2-(3-methylbutoxy)phenyl]amino}-6-{[2-(methylsulfanyl)phenyl]amino}-1,2-dihydro-2,7-naphthyridin-1-one;
8-{[2-(3-methylbutoxy)phenyl]amino}-6-[3-(pyrrolidin-1-yl)phenyl]-1,2-dihydro-2,7-naphthyridin-1-one;
5-(1-{[2-(3-methylbutoxy)phenyl]amino}-8-oxo-7,8-dihydro-2,7-naphthyridin-3-yl)pyridine-3-carbonitrile
6-{2-[(dimethylamino)methyl]phenyl}-8-{[2-(3-methylbutoxy)phenyl]amino}-1,2-dihydro-2,7-naphthyridin-1-one;
8-{[2-(3-methylbutoxy)phenyl]amino}-6-[3-(morpholin-4-ylcarbonyl)phenyl]-1,2-dihydro-2,7-naphthyridin-1-one;
4-methoxy-3-(1-{[2-(3-methylbutoxy)phenyl]amino}-8-oxo-7,8-dihydro-2,7-naphthyridin-3-yl)benzaldehyde
6-(2,6-dimethoxyphenyl)-8-{[2-(3-methylbutoxy)phenyl]amino}-1,2-dihydro-2,7-naphthyridin-1-one;
6-(2-ethoxypyridin-3-yl)-8-{[2-(3-methylbutoxy)phenyl]amino}-1,2-dihydro-2,7-naphthyridin-1-one;
3-methoxy-2-(1-{[2-(3-methylbutoxy)phenyl]amino}-8-oxo-7,8-dihydro-2,7-naphthyridin-3-yl)benzonitrile
3-methoxy-2-(1-{[2-(3-methylbutoxy)phenyl]amino}-8-oxo-7,8-dihydro-2,7-naphthyridin-3-yl)benzamide;
2-methyl-5-[(1-{[4-(morpholin-4-yl)phenyl]amino}-8-oxo-7,8-dihydro-2,7-naphthyridin-3-yl)amino]benzene-1-sulfonamide;
3-[(1-{[4-(morpholin-4-yl)phenyl]amino}-8-oxo-7,8-dihydro-2,7-naphthyridin-3-yl)amino]benzene-1-sulfonamide;
8-{[2-(3-methylbutoxy)phenyl]amino}-6-[1-(piperidin-4-yl)-1H-pyrazol-4-yl]-1,2-dihydro-2,7-naphthyridin-1-one;
8-{[2-(3-methylbutoxy)phenyl]amino}-6-[4-(piperazin-1-yl)phenyl]-1,2-dihydro-2,7-naphthyridin-1-one;
6-{[4-(4-aminopiperidin-1-yl)pyridin-3-yl]amino}-8-{[2-(3-methylbutoxy)phenyl]amino}-1,2-dihydro-2,7-naphthyridin-1-one;
8-{[2-(3-methylbutoxy)phenyl]amino}-6-{[4-(piperidin-4-yl)phenyl]amino}-1,2-dihydro-2,7-naphthyridin-1-one;
3-methoxy-2-(8-oxo-1-{[4-(piperidin-4-yl)phenyl]amino}-7,8-dihydro-2,7-naphthyridin-3-yl)benzamide;
6-{2-[(dimethylamino)methyl]phenyl}-8-{[4-(piperidin-4-yl)phenyl]amino}-1,2-dihydro-2,7-naphthyridin-1-one;
6-(2-chloro-6-methoxyphenyl)-8-{[4-(piperidin-4-yl)phenyl]amino}-1,2-dihydro-2,7-naphthyridin-1-one;
6-(2-aminopyrimidin-5-yl)-8-[(1-methyl-1H-pyrazol-4-yl)amino]-1,2-dihydro-2,7-naphthyridin-1-one;
6-(2-methoxypyrimidin-5-yl)-8-[(1-methyl-1H-pyrazol-4-yl)amino]-1,2-dihydro-2,7-naphthyridin-1-one;
6-(2-aminopyrimidin-5-yl)-8-[(3-methyl-4-{1-[2-(morpholin-4-yl)ethyl]-1H-pyrazol-4-yl}phenyl)amino]-1,2-dihydro-2,7-naphthyridin-1-one;
6-(2-methoxypyrimidin-5-yl)-8-[(3-methyl-4-{1-[2-(morpholin-4-yl)ethyl]-1H-pyrazol-4-yl}phenyl)amino]-1,2-dihydro-2,7-naphthyridin-1-one;
6-(6-methoxypyridin-2-yl)-8-[(3-methyl-4-{1-[2-(morpholin-4-yl)ethyl]-1H-pyrazol-4-yl}phenyl)amino]-1,2-dihydro-2,7-naphthyridin-1-one;
6-(5-amino-4-methylpyridin-2-yl)-8-[(3-methyl-4-{1-[2-(morpholin-4-yl)ethyl]-1H-pyrazol-4-yl}phenyl)amino]-1,2-dihydro-2,7-naphthyridin-1-one;
1-[2-(4-{[8-oxo-3-(pyrimidin-5-yl)-7,8-dihydro-2,7-naphthyridin-1-yl]amino}phenyl)ethyl]piperidine-3-carboxylic acid
8-{[1-(piperidin-4-yl)-1H-pyrazol-4-yl]amino}-6-(pyrimidin-5-yl)-1,2-dihydro-2,7-naphthyridin-1-one;
1-[2-(4-{[3-(2-methoxypyrimidin-5-yl)-8-oxo-7,8-dihydro-2,7-naphthyridin-1-yl]amino}phenyl)ethyl]piperidine-3-carboxylic acid
6-(6-amino-5-methylpyridin-3-yl)-8-({4-[1-(2-methoxyethyl)piperidin-4-yl]phenyl}amino)-1,2-dihydro-2,7-naphthyridin-1-one;
8-({4-[1-(2-methoxyethyl)piperidin-4-yl]phenyl}amino)-6-(pyrimidin-5-yl)-1,2-dihydro-2,7-naphthyridin-1-one;
8-({4-[1-(2-methoxyethyl)piperidin-4-yl]phenyl}amino)-6-(2-methylpyrimidin-5-yl)-1,2-dihydro-2,7-naphthyridin-1-one;
8-{[4-(1-cyclopropylpiperidin-4-yl)-3-methylphenyl]amino}-6-(pyrimidin-5-yl)-1,2-dihydro-2,7-naphthyridin-1-one;
8-{[4-(1-cyclopropylpiperidin-4-yl)-3-methylphenyl]amino}-6-(2-methoxypyrimidin-5-yl)-1,2-dihydro-2,7-naphthyridin-1-one;
4-(1-methyl-1H-pyrazol-4-yl)-8-{[4-(morpholin-4-yl)phenyl]amino}-1,2-dihydro-2,7-naphthyridin-1-one;
4-[2-methyl-4-(trifluoromethyl)phenyl]-8-{[4-(morpholin-4-yl)phenyl]amino}-1,2-dihydro-2,7-naphthyridin-1-one;
4-(4-methoxy-2-methylphenyl)-8-{[4-(morpholin-4-yl)phenyl]amino}-1,2-dihydro-2,7-naphthyridin-1-one;
4-(5-methoxypyridin-3-yl)-8-{[4-(morpholin-4-yl)phenyl]amino}-1,2-dihydro-2,7-naphthyridin-1-one;
8-{[3-methyl-4-(1-methylpiperidin-4-yl)phenyl]amino}-6-[6-(pyrrolidin-1-ylmethyl)pyridin-3-yl]-1,2-dihydro-2,7-naphthyridin-1-one;
8-({3-methyl-4-[(2R)-2-methylmorpholin-4-yl]phenyl}amino)-6-[6-(pyrrolidin-1-ylmethyl)pyridin-3-yl]-1,2-dihydro-2,7-naphthyridin-1-one;
6-(6-methylpyridin-3-yl)-8-{[4-(piperidin-4-yl)-3-(trifluoromethyl)phenyl]amino}-1,2-dihydro-2,7-naphthyridin-1-one;
6-(2-methoxypyrimidin-5-yl)-8-{[4-(piperidin-4-yl)-3-(trifluoromethyl)phenyl]amino}-1,2-dihydro-2,7-naphthyridin-1-one;

8-{[4-(1-cyclopropylpiperidin-4-yl)-3-methylphenyl]amino}-6-(6-methylpyridin-3-yl)-1,2-dihydro-2,7-naphthyridin-1-one;

8-({6-[(2R)-2-methylmorpholin-4-yl]pyridin-3-yl}amino)-6-(6-methylpyridin-3-yl)-1,2-dihydro-2,7-naphthyridin-1-one;

8-{[4-(2,2-dimethylmorpholin-4-yl)-3-methylphenyl]amino}-6-(6-methylpyridin-3-yl)-1,2-dihydro-2,7-naphthyridin-1-one;

8-({4-[1-(2-methanesulfonylethyl)piperidin-4-yl]-3-methylphenyl}amino)-6-(pyrimidin-5-yl)-1,2-dihydro-2,7-naphthyridin-1-one;

8-{[4-(1-methylpiperidin-4-yl)-3-(trifluoromethyl)phenyl]amino}-6-(6-methylpyridin-3-yl)-1,2-dihydro-2,7-naphthyridin-1-one;

1-[2-(4-{[8-oxo-3-(pyrimidin-5-yl)-7,8-dihydro-2,7-naphthyridin-1-yl]amino}phenyl)ethyl]piperidine-4-carboxylic acid 1-[2-(4-{[3-(2-methoxypyrimidin-5-yl)-8-oxo-7,8-dihydro-2,7-naphthyridin-1-yl]amino}phenyl)ethyl]piperidine-4-carboxylic acid 8-({6-[1-(2-methoxyethyl)piperidin-4-yl]pyridin-3-yl}amino)-6-(6-methoxypyrazin-2-yl)-1,2-dihydro-2,7-naphthyridin-1-one;

6-(2-methoxypyrimidin-5-yl)-8-{[1-(piperidin-4-yl)-1H-pyrazol-4-yl]amino}-1,2-dihydro-2,7-naphthyridin-1-one;

8-({6-[1-(2-methoxyethyl)piperidin-4-yl]pyridin-3-yl}amino)-6-(pyrimidin-5-yl)-1,2-dihydro-2,7-naphthyridin-1-one;

6-(2-hydroxypyrimidin-5-yl)-8-{[1-(piperidin-4-yl)-1H-pyrazol-4-yl]amino}-1,2-dihydro-2,7-naphthyridin-1-one;

6-(6-amino-5-methylpyridin-3-yl)-8-{[6-(oxan-4-yl)pyridin-3-yl]amino}-1,2-dihydro-2,7-naphthyridin-1-one;

6-(2-aminopyrimidin-5-yl)-2-methyl-8-[(3-methyl-4-{1-[2-(morpholin-4-yl)ethyl]-1H-pyrazol-4-yl}phenyl)amino]-1,2-dihydro-2,7-naphthyridin-1-one;

8-{[(3-fluorophenyl)methyl]amino}-6-{[4-(morpholin-4-yl)phenyl]amino}-1,2-dihydro-2,7-naphthyridin-1-one;

6-(2-aminopyrimidin-5-yl)-8-[(1-methyl-1H-pyrazol-4-yl)amino]-2-[2-(morpholin-4-yl)ethyl]-1,2-dihydro-2,7-naphthyridin-1-one;

8-[(3-methyl-4-{1-[2-(morpholin-4-yl)ethyl]-1H-pyrazol-4-yl}phenyl)amino]-6-[1-(2-methylpropyl)-1H-pyrazol-4-yl]-1,2-dihydro-2,7-naphthyridin-1-one;

3-[4-(2-methyl-4-{[8-oxo-3-(pyrimidin-5-yl)-7,8-dihydro-2,7-naphthyridin-1-yl]amino}phenyl)piperidin-1-yl]propanenitrile 6-(2-aminopyrimidin-5-yl)-8-[(3-methoxyphenyl)amino]-2-methyl-1,2-dihydro-2,7-naphthyridin-1-one;

4-(3-chloro-2-methylphenyl)-8-{[4-(morpholin-4-yl)phenyl]amino}-1,2-dihydro-2,7-naphthyridin-1-one;

8-({4-[2-(oxan-4-yl)-1,3-thiazol-4-yl]phenyl}amino)-6-(pyrimidin-5-yl)-1,2-dihydro-2,7-naphthyridin-1-one;

8-({4-[2-(piperidin-3-yl)-1,3-thiazol-4-yl]phenyl}amino)-6-(pyrimidin-5-yl)-1,2-dihydro-2,7-naphthyridin-1-one;

8-({4-[2-(2-aminoethyl)-1,3-thiazol-4-yl]phenyl}amino)-6-(pyrimidin-5-yl)-1,2-dihydro-2,7-naphthyridin-1-one;

8-({4-[2-(pyridin-3-yl)-1,3-thiazol-4-yl]phenyl}amino)-6-(pyrimidin-5-yl)-1,2-dihydro-2,7-naphthyridin-1-one;

8-({3-methyl-4-[1-(piperidin-4-yl)-1H-pyrazol-4-yl]phenyl}amino)-6-(6-methylpyridin-2-yl)-1,2-dihydro-2,7-naphthyridin-1-one;

8-({3-methyl-4-[6-(piperazin-1-yl)pyridin-3-yl]phenyl}amino)-6-(6-methylpyridin-2-yl)-1,2-dihydro-2,7-naphthyridin-1-one;

8-{[4-(piperidin-4-yl)-3-(trifluoromethyl)phenyl]amino}-6-(pyrimidin-5-yl)-1,2-dihydro-2,7-naphthyridin-1-one;

8-{[4-(1-acetylpiperidin-4-yl)-3-methylphenyl]amino}-6-(pyrimidin-5-yl)-1,2-dihydro-2,7-naphthyridin-1-one;

8-{[4-(1-acetylpiperidin-4-yl)-3-methylphenyl]amino}-6-(2-methoxypyrimidin-5-yl)-1,2-dihydro-2,7-naphthyridin-1-one;

8-{[4-(1-methylpiperidin-4-yl)-3-(trifluoromethyl)phenyl]amino}-6-(pyrimidin-5-yl)-1,2-dihydro-2,7-naphthyridin-1-one;

5-[1-({3-methyl-4-[(2R)-2-methylmorpholin-4-yl]phenyl}amino)-8-oxo-7,8-dihydro-2,7-naphthyridin-3-yl]pyridine-2-carbonitrile 6-(6-methoxypyridin-2-yl)-8-({4-[1-(4,4,4-trifluorobutyl)piperidin-4-yl]phenyl}amino)-1,2-dihydro-2,7-naphthyridin-1-one;

8-({4-[1-(2-methoxyethyl)piperidin-4-yl]-3-methylphenyl}amino)-6-(6-methoxypyridin-2-yl)-1,2-dihydro-2,7-naphthyridin-1-one;

8-({4-[1-(2-methoxyethyl)piperidin-4-yl]-3-methylphenyl}amino)-6-(5-methoxypyridin-3-yl)-1,2-dihydro-2,7-naphthyridin-1-one;

2-(2-aminoethyl)-6-(2-aminopyrimidin-5-yl)-8-{[4-(morpholin-4-yl)phenyl]amino}-1,2-dihydro-2,7-naphthyridin-1-one;

8-({4-[1-(2-methoxyethyl)piperidin-4-yl]phenyl}amino)-6-{2H,3H,4H-pyrido[3,2-b][1,4]oxazin-7-yl}-1,2-dihydro-2,7-naphthyridin-1-one;

8-({4-[1-(2-methoxyethyl)piperidin-4-yl]phenyl}amino)-6-(6-methoxypyridin-2-yl)-1,2-dihydro-2,7-naphthyridin-1-one;

6-(5-amino-6-methylpyrazin-2-yl)-8-({4-[1-(2-methoxyethyl)piperidin-4-yl]-3-methylphenyl}amino)-1,2-dihydro-2,7-naphthyridin-1-one;

8-[(4-{1-[2-(dimethylamino)acetyl]pyrrolidin-3-yl}phenyl)amino]-6-(6-methoxypyrazin-2-yl)-1,2-dihydro-2,7-naphthyridin-1-one;

6-(6-methoxypyrimidin-4-yl)-8-{[4-(morpholin-4-yl)phenyl]amino}-1,2-dihydro-2,7-naphthyridin-1-one;

6-(6-methoxypyridin-2-yl)-8-({3-methyl-4-[3-(4-methylpiperazin-1-yl)propoxy]phenyl}amino)-1,2-dihydro-2,7-naphthyridin-1-one;

4-phenyl-8-[(4-{2-[4-(pyrrolidin-1-yl)piperidin-1-yl]ethyl}phenyl)amino]-1,2-dihydro-2,7-naphthyridin-1-one;

4-(4-methoxyphenyl)-8-[(4-{2-[4-(pyrrolidin-1-yl)piperidin-1-yl]ethyl}phenyl)amino]-1,2-dihydro-2,7-naphthyridin-1-one;

4-(4-chlorophenyl)-8-[(4-{2-[4-(pyrrolidin-1-yl)piperidin-1-yl]ethyl}phenyl)amino]-1,2-dihydro-2,7-naphthyridin-1-one;

8-[(4-{2-[4-(pyrrolidin-1-yl)piperidin-1-yl]ethyl}phenyl)amino]-4-[4-(trifluoromethyl)phenyl]-1,2-dihydro-2,7-naphthyridin-1-one;

8-[(4-{2-[4-(pyrrolidin-1-yl)piperidin-1-yl]ethyl}phenyl)amino]-4-[3-(trifluoromethyl)phenyl]-1,2-dihydro-2,7-naphthyridin-1-one;

4-[3-(dimethylamino)phenyl]-8-[(4-{2-[4-(pyrrolidin-1-yl)piperidin-1-yl]ethyl}phenyl)amino]-1,2-dihydro-2,7-naphthyridin-1-one;

4-(4-methoxy-2-methylphenyl)-8-[(4-{2-[4-(pyrrolidin-1-yl)piperidin-1-yl]ethyl}phenyl)amino]-1,2-dihydro-2,7-naphthyridin-1-one;

4-[2-methyl-4-(trifluoromethyl)phenyl]-8-[(4-{2-[4-(pyrrolidin-1-yl)piperidin-1-yl]ethyl}phenyl)amino]-1,2-dihydro-2,7-naphthyridin-1-one;

4-(1-methyl-1H-pyrazol-4-yl)-8-[(4-{2-[4-(pyrrolidin-1-yl)piperidin-1-yl]ethyl}phenyl)amino]-1,2-dihydro-2,7-naphthyridin-1-one;

4-(5-methoxypyridin-3-yl)-8-[(4-{2-[4-(pyrrolidin-1-yl)piperidin-1-yl]ethyl}phenyl)amino]-1,2-dihydro-2,7-naphthyridin-1-one;

8-amino-2-methyl-6-(pyrimidin-4-ylamino)-1,2-dihydro-2,7-naphthyridin-1-one;

8-({4-[1-(2-methanesulfonylethyl)piperidin-4-yl]-3-methylphenyl}amino)-6-(6-methylpyridin-3-yl)-1,2-dihydro-2,7-naphthyridin-1-one;

8-({4-[1-(2-methanesulfonylethyl)piperidin-4-yl]-3-methylphenyl}amino)-6-(2-methoxypyrimidin-5-yl)-1,2-dihydro-2,7-naphthyridin-1-one;

6-(1-methyl-1H-pyrazol-4-yl)-8-[(3-methyl-4-{1-[2-(morpholin-4-yl)ethyl]-1H-pyrazol-4-yl}phenyl)amino]-1,2-dihydro-2,7-naphthyridin-1-one;

3-[4-(4-{[3-(2-methoxypyrimidin-5-yl)-8-oxo-7,8-dihydro-2,7-naphthyridin-1-yl]amino}-2-methylphenyl)piperidin-1-yl]propanenitrile 6-(2-aminopyrimidin-5-yl)-2-(2-hydroxy-3-methoxypropyl)-8-[(3-methoxyphenyl)amino]-1,2-dihydro-2,7-naphthyridin-1-one;

6-(2-aminopyrimidin-5-yl)-2-[3-(dimethylamino)propyl]-8-[(3-methoxyphenyl)amino]-1,2-dihydro-2,7-naphthyridin-1-one;

2-[4-(2-methyl-4-{[8-oxo-3-(pyrimidin-5-yl)-7,8-dihydro-2,7-naphthyridin-1-yl]amino}phenyl)piperidin-1-yl]acetonitrile 2-[4-(2-methyl-4-{[8-oxo-3-(pyrimidin-5-yl)-7,8-dihydro-2,7-naphthyridin-1-yl]amino}phenyl)piperidin-1-yl]acetamide 8-({4-[1-(2-hydroxy-3-methoxypropyl)piperidin-4-yl]-3-methylphenyl}amino)-6-(pyrimidin-5-yl)-1,2-dihydro-2,7-naphthyridin-1-one;

6-(2-aminopyrimidin-5-yl)-8-[(3-methoxyphenyl)amino]-2-(3-methoxypropyl)-1,2-dihydro-2,7-naphthyridin-1-one;

6-(2-aminopyrimidin-5-yl)-8-[(3,5-dimethoxyphenyl)amino]-1,2-dihydro-2,7-naphthyridin-1-one;

6-(2-aminopyrimidin-5-yl)-8-[(3,4-dimethoxyphenyl)amino]-1,2-dihydro-2,7-naphthyridin-1-one;

6-(2-aminopyrimidin-5-yl)-8-[(3,5-dimethoxyphenyl)amino]-2-methyl-1,2-dihydro-2,7-naphthyridin-1-one;

6-(2-aminopyrimidin-5-yl)-8-[(3,4,5-trimethoxyphenyl)amino]-1,2-dihydro-2,7-naphthyridin-1-one;

6-[6-(hydroxymethyl)pyridin-3-yl]-8-{[4-(morpholin-4-yl)phenyl]amino}-1,2-dihydro-2,7-naphthyridin-1-one;

6-[6-(hydroxymethyl)pyridin-3-yl]-8-({3-methyl-4-[(2R)-2-methylmorpholin-4-yl]phenyl}amino)-1,2-dihydro-2,7-naphthyridin-1-one;

8-{[4-(1,2-dimethylpiperidin-4-yl)-3-fluorophenyl]amino}-6-(2-methoxypyrimidin-5-yl)-1,2-dihydro-2,7-naphthyridin-1-one;

8-[(2-methylphenyl)amino]-6-[3-(pyrrolidin-1-yl)phenyl]-1,2-dihydro-2,7-naphthyridin-1-one;

8-[(2-methoxyphenyl)amino]-6-[3-(pyrrolidin-1-yl)phenyl]-1,2-dihydro-2,7-naphthyridin-1-one;

8-[(2-ethoxyphenyl)amino]-6-[3-(pyrrolidin-1-yl)phenyl]-1,2-dihydro-2,7-naphthyridin-1-one;

8-{[2-(propan-2-yloxy)phenyl]amino}-6-[3-(pyrrolidin-1-yl)phenyl]-1,2-dihydro-2,7-naphthyridin-1-one;

6-(2-aminopyrimidin-5-yl)-8-[(3,5-dimethoxyphenyl)amino]-2-(2-methoxyethyl)-1,2-dihydro-2,7-naphthyridin-1-one;

6-(2-aminopyrimidin-5-yl)-8-[(3,5-dimethoxyphenyl)amino]-2-[2-(dimethylamino)ethyl]-1,2-dihydro-2,7-naphthyridin-1-one;

8-({1-[1-(2-methoxyethyl)piperidin-4-yl]-1H-pyrazol-4-yl}amino)-6-(pyrimidin-5-yl)-1,2-dihydro-2,7-naphthyridin-1-one;

8-({1-[1-(2-methanesulfonylethyl)piperidin-4-yl]-1H-pyrazol-4-yl}amino)-6-(pyrimidin-5-yl)-1,2-dihydro-2,7-naphthyridin-1-one;

6-(2-aminopyrimidin-5-yl)-2-methyl-8-[(1-methyl-1H-pyrazol-4-yl)amino]-1,2-dihydro-2,7-naphthyridin-1-one;

6-(2-aminopyrimidin-5-yl)-8-[(3,4-dimethoxyphenyl)amino]-2-methyl-1,2-dihydro-2,7-naphthyridin-1-one;

6-(2-aminopyrimidin-5-yl)-2-methyl-8-[(3,4,5-trimethoxyphenyl)amino]-1,2-dihydro-2,7-naphthyridin-1-one;

4-[6-(4-ethylpiperazin-1-yl)-8-{[4-(morpholin-4-yl)phenyl]amino}-1-oxo-1,2-dihydro-2,7-naphthyridin-4-yl]-N-methylbenzamide;

6-(4-ethylpiperazin-1-yl)-4-(4-methoxyphenyl)-8-{[4-(morpholin-4-yl)phenyl]amino}-1,2-dihydro-2,7-naphthyridin-1-one;

4-(4-chlorophenyl)-6-(4-ethylpiperazin-1-yl)-8-{[4-(morpholin-4-yl)phenyl]amino}-1,2-dihydro-2,7-naphthyridin-1-one;

6-(4-ethylpiperazin-1-yl)-8-{[4-(morpholin-4-yl)phenyl]amino}-4-[4-(trifluoromethyl)phenyl]-1,2-dihydro-2,7-naphthyridin-1-one;

6-(4-ethylpiperazin-1-yl)-8-{[4-(morpholin-4-yl)phenyl]amino}-4-[3-(trifluoromethyl)phenyl]-1,2-dihydro-2,7-naphthyridin-1-one;

4-[3-(dimethylamino)phenyl]-6-(4-ethylpiperazin-1-yl)-8-{[4-(morpholin-4-yl)phenyl]amino}-1,2-dihydro-2,7-naphthyridin-1-one;

6-(4-ethylpiperazin-1-yl)-4-(4-methoxy-2-methylphenyl)-8-{[4-(morpholin-4-yl)phenyl]amino}-1,2-dihydro-2,7-naphthyridin-1-one;

6-(4-ethylpiperazin-1-yl)-4-[2-methyl-4-(trifluoromethyl)phenyl]-8-{[4-(morpholin-4-yl)phenyl]amino}-1,2-dihydro-2,7-naphthyridin-1-one;

6-(4-ethylpiperazin-1-yl)-4-(1-methyl-1H-pyrazol-4-yl)-8-{[4-(morpholin-4-yl)phenyl]amino}-1,2-dihydro-2,7-naphthyridin-1-one;

6-(4-ethylpiperazin-1-yl)-4-(5-methoxypyridin-3-yl)-8-{[4-(morpholin-4-yl)phenyl]amino}-1,2-dihydro-2,7-naphthyridin-1-one;

8-amino-2-methyl-6-(pyridin-2-ylamino)-1,2-dihydro-2,7-naphthyridin-1-one;

8-[(4-{1-[2-(dimethylamino)acetyl]piperidin-4-yl}phenyl)amino]-6-(pyrimidin-5-yl)-1,2-dihydro-2,7-naphthyridin-1-one;

8-[(4-{1-[2-(dimethylamino)acetyl]piperidin-4-yl}-phenyl)amino]-6-(6-methoxypyrazin-2-yl)-1,2-dihydro-2,7-naphthyridin-1-one;

8-[(4-{1-[2-(ethylamino)acetyl]piperidin-4-yl}phenyl)amino]-6-(pyrimidin-5-yl)-1,2-dihydro-2,7-naphthyridin-1-one;

8-[(4-{1-[2-(ethylamino)acetyl]piperidin-4-yl}phenyl) amino]-6-(6-methoxypyrazin-2-yl)-1,2-dihydro-2,7-naphthyridin-1-one;

N-[3-(2-aminopyrimidin-5-yl)-8-oxo-7,8-dihydro-2,7-naphthyridin-1-yl]-4-fluorobenzamide;

4-fluoro-N-[3-(6-methoxypyrazin-2-yl)-8-oxo-7,8-dihydro-2,7-naphthyridin-1-yl]benzamide;

6-(2-amino-6-methylpyrimidin-4-yl)-8-({4-[1-(2-methoxyethyl)piperidin-4-yl]phenyl}amino)-1,2-dihydro-2,7-naphthyridin-1-one;

6-(2-aminopyrimidin-5-yl)-2-(2-hydroxyethyl)-8-{[4-(morpholin-4-yl)phenyl]amino}-1,2-dihydro-2,7-naphthyridin-1-one;

8-({3-[(dimethylamino)methyl]-1H-indazol-6-yl}amino)-6-(pyrimidin-5-yl)-1,2-dihydro-2,7-naphthyridin-1-one;

8-({3-[(dimethylamino)methyl]-1H-indazol-6-yl}amino)-6-(2-methoxypyrimidin-5-yl)-1,2-dihydro-2,7-naphthyridin-1-one;

8-({3-[(dimethylamino)methyl]-1H-indazol-6-yl}amino)-6-(6-methylpyridin-3-yl)-1,2-dihydro-2,7-naphthyridin-1-one;

8-[(2-methanesulfonyl-1,2,3,4-tetrahydroisoquinolin-6-yl)amino]-6-(6-methylpyridin-3-yl)-1,2-dihydro-2,7-naphthyridin-1-one;

8-[(2-methanesulfonyl-1,2,3,4-tetrahydroisoquinolin-6-yl)amino]-6-(2-methoxypyrimidin-5-yl)-1,2-dihydro-2,7-naphthyridin-1-one;

8-amino-2-methyl-6-[(5-methylpyridin-2-yl)amino]-1,2-dihydro-2,7-naphthyridin-1-one;

8-amino-2-methyl-6-[(3-methylpyridin-2-yl)amino]-1,2-dihydro-2,7-naphthyridin-1-one;

6-[(1-amino-7-methyl-8-oxo-7,8-dihydro-2,7-naphthyridin-3-yl)amino]pyridine-3-carbonitrile 6-[(1-amino-7-methyl-8-oxo-7,8-dihydro-2,7-naphthyridin-3-yl)amino]pyridine-3-carboxamide 8-amino-2-methyl-6-[(1-methyl-1H-pyrazol-3-yl)amino]-1,2-dihydro-2,7-naphthyridin-1-one;

8-amino-2-methyl-6-(1,3-thiazol-2-ylamino)-1,2-dihydro-2,7-naphthyridin-1-one;

8-amino-2-methyl-6-(pyridazin-3-ylamino)-1,2-dihydro-2,7-naphthyridin-1-one;

8-amino-2-methyl-6-(pyrazin-2-ylamino)-1,2-dihydro-2,7-naphthyridin-1-one;

8-amino-2-benzyl-6-(pyrimidin-2-ylamino)-1,2-dihydro-2,7-naphthyridin-1-one;

8-amino-2-methyl-6-(pyrimidin-2-ylamino)-1,2-dihydro-2,7-naphthyridin-1-one;

2-[4-(4-{[8-oxo-3-(pyrimidin-5-yl)-7,8-dihydro-2,7-naphthyridin-1-yl]amino}-1H-pyrazol-1-yl)piperidin-1-yl]acetonitrile 8-({4-[1-(2,3-dihydroxypropyl)piperidin-4-yl]phenyl}amino)-6-(pyrimidin-5-yl)-1,2-dihydro-2,7-naphthyridin-1-one;

8-({4-[1-(2,3-dihydroxypropyl)piperidin-4-yl]phenyl}amino)-6-(2-methoxypyrimidin-5-yl)-1,2-dihydro-2,7-naphthyridin-1-one;

8-({4-[1-(2-methoxyethyl)-1H-pyrazol-4-yl]phenyl}amino)-6-(pyrimidin-5-yl)-1,2-dihydro-2,7-naphthyridin-1-one;

8-({4-[1-(2-methoxyethyl)-1H-pyrazol-4-yl]phenyl}amino)-6-(2-methoxypyrimidin-5-yl)-1,2-dihydro-2,7-naphthyridin-1-one;

8-({1-[2-(morpholin-4-yl)ethyl]-1H-pyrazol-4-yl}amino)-6-(pyrimidin-5-yl)-1,2-dihydro-2,7-naphthyridin-1-one;

6-(2-methoxypyrimidin-5-yl)-8-({1-[2-(morpholin-4-yl)ethyl]-1H-pyrazol-4-yl}amino)-1,2-dihydro-2,7-naphthyridin-1-one;

6-(2-aminopyrimidin-5-yl)-8-[(3,4-dimethoxyphenyl)amino]-2-(2-methoxyethyl)-1,2-dihydro-2,7-naphthyridin-1-one;

2-[6-(2-aminopyrimidin-5-yl)-8-[(3,4-dimethoxyphenyl)amino]-1-oxo-1,2-dihydro-2,7-naphthyridin-2-yl]acetonitrile 8-{[4-(1-methyl-1H-pyrazol-4-yl)phenyl]amino}-6-(pyrimidin-5-yl)-1,2-dihydro-2,7-naphthyridin-1-one;

6-(2-methoxypyrimidin-5-yl)-8-{[4-(1-methyl-1H-pyrazol-4-yl)phenyl]amino}-1,2-dihydro-2,7-naphthyridin-1-one;

6-(2-aminopyrimidin-5-yl)-8-({4-[1-(2-methoxyethyl)-1H-pyrazol-4-yl]phenyl}amino)-1,2-dihydro-2,7-naphthyridin-1-one;

6-(2-aminopyrimidin-5-yl)-8-[(3,4-dimethoxyphenyl)amino]-2-[2-(dimethylamino)ethyl]-1,2-dihydro-2,7-naphthyridin-1-one;

6-(2-aminopyrimidin-5-yl)-8-[(3,4-dimethoxyphenyl)amino]-2-(2-hydroxy-3-methoxypropyl)-1,2-dihydro-2,7-naphthyridin-1-one;

6-(2-aminopyrimidin-5-yl)-8-({1-[2-(morpholin-4-yl)ethyl]-1H-pyrazol-4-yl}amino)-1,2-dihydro-2,7-naphthyridin-1-one;

6-(2-aminopyrimidin-5-yl)-8-{[4-(1-methyl-1H-pyrazol-4-yl)phenyl]amino}-1,2-dihydro-2,7-naphthyridin-1-one;

6-(2-aminopyrimidin-5-yl)-8-({4-[1-(2-methoxyethyl)-1H-pyrazol-4-yl]phenyl}amino)-2-methyl-1,2-dihydro-2,7-naphthyridin-1-one;

6-(2-aminopyrimidin-5-yl)-8-({4-[1-(2-methoxyethyl)-1H-pyrazol-4-yl]phenyl}amino)-2-[2-(morpholin-4-yl)ethyl]-1,2-dihydro-2,7-naphthyridin-1-one;

6-(2-aminopyrimidin-5-yl)-2-methyl-8-({1-[2-(morpholin-4-yl)ethyl]-1H-pyrazol-4-yl}amino)-1,2-dihydro-2,7-naphthyridin-1-one;

6-(2-aminopyrimidin-5-yl)-2-methyl-8-{[4-(1-methyl-1H-pyrazol-4-yl)phenyl]amino}-1,2-dihydro-2,7-naphthyridin-1-one;

6-(2-aminopyrimidin-5-yl)-8-{[4-(1-methyl-1H-pyrazol-4-yl)phenyl]amino}-2-[2-(morpholin-4-yl)ethyl]-1,2-dihydro-2,7-naphthyridin-1-one;

N-methyl-2-[4-(2-methyl-4-{[8-oxo-3-(pyrimidin-5-yl)-7,8-dihydro-2,7-naphthyridin-1-yl]amino}phenyl)piperidin-1-yl]acetamide 8-[(2-acetyl-1,2,3,4-tetrahydroisoquinolin-6-yl)amino]-6-(pyrimidin-5-yl)-1,2-dihydro-2,7-naphthyridin-1-one;

8-{[2-(2-methoxyethyl)-1,2,3,4-tetrahydroisoquinolin-6-yl]amino}-6-(pyrimidin-5-yl)-1,2-dihydro-2,7-naphthyridin-1-one;

6-(pyrimidin-5-yl)-8-{[3-(1,2,3,6-tetrahydropyridin-4-yl)-1H-indazol-6-yl]amino}-1,2-dihydro-2,7-naphthyridin-1-one;

6-{imidazo[1,2-a]pyrimidin-6-yl}-2-methyl-8-{[4-(morpholin-4-yl)phenyl]amino}-1,2-dihydro-2,7-naphthyridin-1-one;

6-{8-methylimidazo[1,2-a]pyrazin-6-yl}-8-{[4-(morpholin-4-yl)phenyl]amino}-1,2-dihydro-2,7-naphthyridin-1-one;

6-{imidazo[1,2-a]pyrimidin-6-yl}-8-{[4-(morpholin-4-yl)phenyl]amino}-1,2-dihydro-2,7-naphthyridin-1-one;

2-({1-[(4-{1-[2-(dimethylamino)acetyl]piperidin-4-yl}-3-methylphenyl)amino]-8-oxo-7,8-dihydro-2,7-naphthyridin-3-yl}amino)-6-methylbenzene-1-sulfonamide;

2-{[1-({4-[1-(2-methoxyethyl)piperidin-4-yl]-3-methylphenyl}amino)-8-oxo-7,8-dihydro-2,7-naphthyridin-3-yl]amino}-6-methylbenzene-1-sulfonamide;

8-[(4-{1-[2-(dimethylamino)acetyl]piperidin-4-yl}-3-methylphenyl)amino]-6-(pyrimidin-5-yl)-1,2-dihydro-2,7-naphthyridin-1-one;

8-[(4-{1-[2-(dimethylamino)acetyl]piperidin-4-yl}-3-methylphenyl)amino]-6-(6-methoxypyrazin-2-yl)-1,2-dihydro-2,7-naphthyridin-1-one;

8-[(4-{1-[2-(ethylamino)acetyl]piperidin-4-yl}-3-methylphenyl)amino]-6-(pyrimidin-5-yl)-1,2-dihydro-2,7-naphthyridin-1-one;

8-[(4-{1-[2-(ethylamino)acetyl]piperidin-4-yl}-3-methylphenyl)amino]-6-(6-methoxypyrazin-2-yl)-1,2-dihydro-2,7-naphthyridin-1-one;

8-[(6-{1-[2-(dimethylamino)acetyl]piperidin-4-yl}pyridin-3-yl)amino]-6-(pyrimidin-5-yl)-1,2-dihydro-2,7-naphthyridin-1-one;

6-(6-methoxypyrazin-2-yl)-8-({4-[2-(4-methylpiperazin-1-yl)ethyl]phenyl}amino)-1,2-dihydro-2,7-naphthyridin-1-one;

6-[6-(2-hydroxypropan-2-yl)pyridin-3-yl]-2-methyl-8-(propan-2-ylamino)-1,2-dihydro-2,7-naphthyridin-1-one;

6-(2-aminopyrimidin-5-yl)-2-methyl-8-(propan-2-ylamino)-1,2-dihydro-2,7-naphthyridin-1-one;

8-amino-2-benzyl-6-(pyrimidin-4-ylamino)-1,2-dihydro-2,7-naphthyridin-1-one;

8-amino-2-benzyl-6-(pyridin-2-ylamino)-1,2-dihydro-2,7-naphthyridin-1-one;

8-amino-2-benzyl-6-[(5-methylpyridin-2-yl)amino]-1,2-dihydro-2,7-naphthyridin-1-one;

8-amino-2-benzyl-6-[(3-methylpyridin-2-yl)amino]-1,2-dihydro-2,7-naphthyridin-1-one;

8-amino-2-benzyl-6-(pyridazin-3-ylamino)-1,2-dihydro-2,7-naphthyridin-1-one;

4-{6-[(2-methoxyethyl)amino]-8-{[4-(morpholin-4-yl)phenyl]amino}-1-oxo-1,2-dihydro-2,7-naphthyridin-4-yl}-N-methylbenzamide;

6-[(2-methoxyethyl)amino]-4-(4-methoxyphenyl)-8-{[4-(morpholin-4-yl)phenyl]amino}-1,2-dihydro-2,7-naphthyridin-1-one;

8-amino-2-benzyl-6-[(1-methyl-1H-pyrazol-3-yl)amino]-1,2-dihydro-2,7-naphthyridin-1-one;

6-[(2-methoxyethyl)amino]-4-(5-methoxypyridin-3-yl)-8-{[4-(morpholin-4-yl)phenyl]amino}-1,2-dihydro-2,7-naphthyridin-1-one;

6-{8-methylimidazo[1,2-a]pyridin-6-yl}-8-{[4-(morpholin-4-yl)phenyl]amino}-1,2-dihydro-2,7-naphthyridin-1-one;

8-amino-2-benzyl-6-(pyrazin-2-ylamino)-1,2-dihydro-2,7-naphthyridin-1-one, and

8-{[4-(morpholin-4-yl)phenyl]amino}-6-{1H,2H,3H-pyrrolo[2,3-b]pyridin-5-yl}-1,2-dihydro-2,7-naphthyridin-1-one.

21. A pharmaceutical composition comprising a therapeutically effective amount of a compound of claim 1 and a pharmaceutically acceptable carrier.

22. A method for inhibiting a kinase, comprising administering to a system or a subject in need thereof, a therapeutically effective amount of a compound of claim 1, or pharmaceutically acceptable salts or pharmaceutical compositions thereof, wherein the kinase is Syk.

23. A method for treating a Syk-mediated disease or condition, comprising administering to a system or subject in need of such treatment an effective amount of a compound of claim 1, or pharmaceutically acceptable salts or pharmaceutical compositions thereof.

24. The method of claim 23, wherein the disease or condition is an inflammatory disease, a respiratory disease, a cell-proliferative disease or an autoimmune disease.

25. The method of claim 24, wherein the disease or condition is asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, multiple sclerosis, cancer, or lupus.

* * * * *